(12) United States Patent
Yoon et al.

(10) Patent No.: US 10,730,863 B2
(45) Date of Patent: Aug. 4, 2020

(54) BRIDGED BICYCLIC COMPOUNDS AS FARNESOID X RECEPTOR MODULATORS

(71) Applicant: BRISTOL-MYERS SQUIBB COMPANY, Princeton, NJ (US)

(72) Inventors: David S. Yoon, Ambler, PA (US); Rushith Kumar Anumula, Bangalore (IN); Srinivas Cheruku, Bangalore (IN); Yanting Huang, Pennington, NJ (US); Elizabeth Anne Jurica, Robbinsville, NJ (US); Wei Meng, Pennington, NJ (US); Susheel Jethanand Nara, Bangalore (IN); Rishikesh Narayan, Mumbai (IN); Ramesh Kumar Sistla, Bangalore (IN); Ximao Wu, Princeton Junction, NJ (US); Guohua Zhao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/175,895

(22) Filed: Oct. 31, 2018

(65) Prior Publication Data
US 2019/0127358 A1    May 2, 2019

Related U.S. Application Data

(60) Provisional application No. 62/580,075, filed on Nov. 1, 2017.

(51) Int. Cl.
| | | |
|---|---|---|
| C07D 413/14 | (2006.01) |
| C07D 413/04 | (2006.01) |
| A61P 35/00 | (2006.01) |
| A61P 29/00 | (2006.01) |
| A61P 13/12 | (2006.01) |
| A61P 1/16 | (2006.01) |
| A61P 1/18 | (2006.01) |
| C07D 261/08 | (2006.01) |
| A61K 31/428 | (2006.01) |
| C07D 417/14 | (2006.01) |
| A61K 31/4245 | (2006.01) |
| C07D 471/04 | (2006.01) |
| A61K 31/429 | (2006.01) |
| A61K 31/422 | (2006.01) |
| C07D 417/12 | (2006.01) |

(52) U.S. Cl.
CPC .......... *C07D 413/14* (2013.01); *A61K 31/422* (2013.01); *A61K 31/428* (2013.01); *A61K 31/429* (2013.01); *A61K 31/4245* (2013.01); *A61P 1/16* (2018.01); *A61P 1/18* (2018.01); *A61P 13/12* (2018.01); *A61P 29/00* (2018.01); *A61P 35/00* (2018.01); *C07D 261/08* (2013.01); *C07D 413/04* (2013.01); *C07D 417/12* (2013.01); *C07D 417/14* (2013.01); *C07D 471/04* (2013.01)

(58) Field of Classification Search
CPC ....... C07D 413/14; C07D 413/04; A61P 1/16; A61P 1/18; A61P 13/12; A61P 29/00; A61P 35/00
USPC ........................................................ 514/318
See application file for complete search history.

(56) References Cited

U.S. PATENT DOCUMENTS

| | | | |
|---|---|---|---|
| 8,158,665 B2 | 4/2012 | Caldwell et al. |
| 8,907,095 B2 | 12/2014 | Xia et al. |
| 9,539,244 B2 | 1/2017 | Kinzel et al. |

(Continued)

FOREIGN PATENT DOCUMENTS

| | | | |
|---|---|---|---|
| CN | 106146483 A | 11/2016 |
| CN | 106632294 A | 5/2017 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

Primary Examiner — Kristin A Vajda
(74) Attorney, Agent, or Firm — Gary Greenblatt

(57) ABSTRACT

The present invention provides compounds of Formula (I):

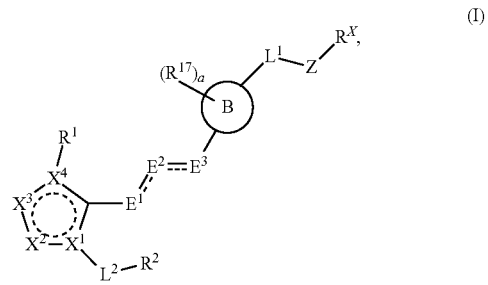

or stereoisomers, tautomers, or pharmaceutically acceptable salts or solvates thereof, wherein all the variables are as defined herein. These compounds modulate the activity of farnesoid X receptor (FXR), for example, as agonists. This invention also relates to pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

27 Claims, No Drawings

(56) References Cited

U.S. PATENT DOCUMENTS

| | | |
|---|---|---|
| 9,751,874 B2 | 9/2017 | Gege et al. |
| 2010/0152166 A1 | 6/2010 | Genin et al. |
| 2011/0034507 A1 | 2/2011 | Akwabi-Ameyaw et al. |
| 2015/0366856 A1 | 12/2015 | Tully et al. |
| 2016/0176861 A1 | 6/2016 | Gege et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2019/0002452 A1 | 1/2019 | Zhang et al. |

FOREIGN PATENT DOCUMENTS

| | | |
|---|---|---|
| CN | 107021958 A | 8/2017 |
| EP | 3401315 A1 | 11/2018 |
| WO | WO9313101 A1 | 7/1993 |
| WO | WO9817276 A1 | 4/1998 |
| WO | WO2006006490 A1 | 1/2006 |
| WO | WO2008094556 A2 | 8/2008 |
| WO | WO2009009059 A1 | 1/2009 |
| WO | WO2010058318 A1 | 5/2010 |
| WO | WO2011045292 A1 | 4/2011 |
| WO | WO2013186159 A1 | 12/2013 |
| WO | WO2014054053 A1 | 4/2014 |
| WO | WO2015172747 A1 | 11/2015 |
| WO | WO2017133521 A1 | 8/2017 |
| WO | WO2017145040 A1 | 8/2017 |
| WO | WO2017145041 A1 | 8/2017 |
| WO | WO2018059314 A1 | 4/2018 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Claudel, Thierry et al., "The Farnesoid X Receptor: A Novel Drug Target"?, Expert Opin. Investig. Drugs, vol. 13(9), pp. 1135-1148, (2004).

International Search Report for Application No. PCT/US2018/058326, dated Oct. 31, 2018.

Sepe, Valentina et al., "Farnesoid X Receptor Modulators 2014-present: A Patent Review, Expert Opinion on Therapeutic Patents", vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

* cited by examiner

BRIDGED BICYCLIC COMPOUNDS AS FARNESOID X RECEPTOR MODULATORS

CROSS REFERENCE

This application claims the benefit of U.S. Provisional Application Ser. No. 62/580,075 filed Nov. 1, 2017 which is incorporated herein in its entirety.

DESCRIPTION

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I), (IIa), and (IIb) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides a compound of Formula (I):

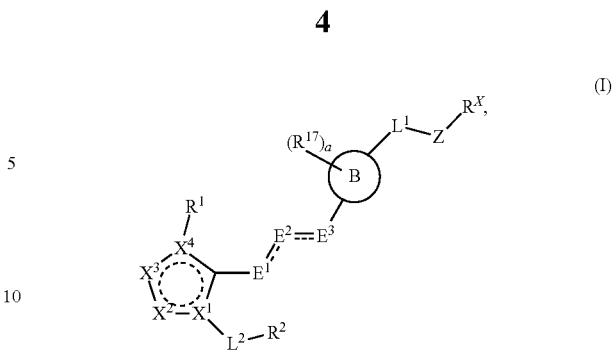

or a stereoisomer, a tautomer, or a pharmaceutically acceptable salt or solvate thereof;

wherein $X^1$ and $X^4$ are each independently C or N; $X^2$ and $X^3$ are each independently $CR^3$, N, $NR^4$, O, or S;

the dashed circle denotes an aromatic ring formed by $X^1$, $X^2$, $X^3$, $X^4$, and the carbon atom;

$E^1$ and $E^3$ are each independently a covalent bond, O, S, N, $NR^6$, $CR^5$, or $CR^{5a}R^{5b}$;

$E^2$ is O, S, N, $NR^8$, $CR^7$, or $CR^{7a}R^{7b}$; wherein ($E^1$ and $E^2$) or ($E^3$ and $E^2$) forms a single bond or double bond; provided that (1) the bonds between ($E^1$ and $E^2$) and ($E^3$ and $E^2$) are not both double bonds; and (2) not more than one of $E^1$, $E^2$, and $E^3$ is O, S, N, or $NR^8$;

the dashed line is an optional covalent bond; by "optional", it is meant a covalent bond that is either present or absent;

B ring is a 5- to 8-membered bridged cycloalkyl or cycloheteroalkyl; and the point of attachment to $L^1$ or Z is a carbon atom; and each of the cycloalkyl and cycloheteroalkyl independently includes, but is not limited to, mono-, bi-, poly-, and bridged ring systems;

$L^1$ is a covalent bond, O, S, $NR^{16}$, —C(S)NH—, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to 3 $R^9$; for example, the 5- to 6-membered heteroaryl includes, but is not limited to, oxadiazole, thiadiazole, triazole, pyrazole, imidazole, isothiazole, thiazole, oxazole, isoxazole, pyrrole, furan, thiophene, pyran, pyridine, pyridazine, pyrimidine, and pyrazine;

Z is 6- to 10-membered aryl, 5- to 10-membered heteroaryl, 3- to 10-membered carbocyclyl, or 4- to 10-membered heterocyclyl, wherein the aryl, heteroaryl carbocyclyl, and heterocyclyl are independently substituted with 0 to 5 $R^{10}$;

$L^2$ are each independently a covalent bond, O, S, $NR^{17}$, $C_{1-3}$ alkylene, or $C_{1-3}$ heteroalkylene, wherein the alkylene and heteroalkylene are independently substituted with 0 to 3 $R^{11}$;

$R^X$ is —$(CR^{12a}R^{12b})_e$—$R^Z$ or —$O(CR^{12a}R^{12b})_e$—$R^Z$;

e is 0 or 1;

$R^Z$ is selected from —CN, —OH, —C(O)$OR^{13}$, —C(O)$NR^{14a}R^{14b}$,

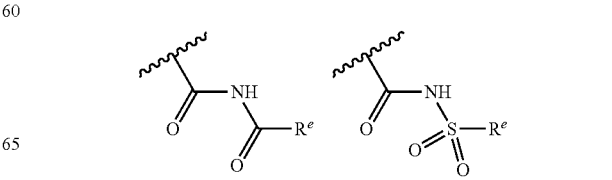

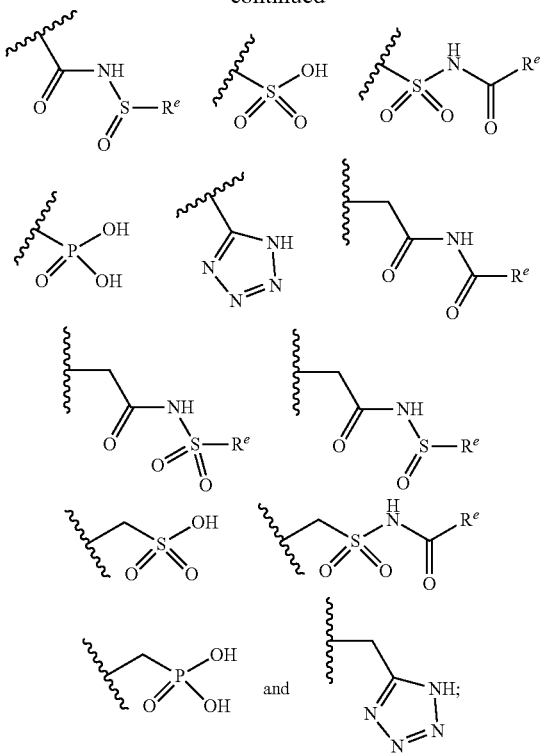

$R^e$ is $C_{1-6}$ alkyl, $C_{3-6}$ cycloalkyl, haloalkyl, hydroxyalkyl, aminoalkyl, alkoxyalkyl, haloalkoxyalkyl, or phenyl;

$R^1$ is $C_{1-6}$ alkyl, $C_{3-5}$ cycloalkyl, or $C_{4-6}$ heterocyclyl, wherein the alkyl, cycloalkyl, and heterocyclyl are each independently substituted with 0 to 3 $R^{15}$;

$R^2$ is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^{16}$;

$R^3$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; $R^4$, $R^6$, $R^8$, $R^{16}$ and $R^{17}$ are each independently hydrogen, $C_{1-6}$ alkyl, haloalkyl, hydroxyalkyl, aminoalkyl, alkoxyalkyl, or haloalkoxyalkyl;

$R^5$ is hydrogen, $C_{1-6}$ alkyl, haloalkyl, hydroxyalkyl, aminoalkyl, alkoxyalkyl, or haloalkoxyalkyl;

$R^{5a}$, $R^{5b}$, $R^{7a}$ and $R^{7b}$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^9$ and $R^{11}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

a is an integer of 0, 1, 2, or 3;

$R^{10}$ and $R^{16}$ are each independently halo, cyano, hydroxyl, amino, oxo, $—OR^a$, $—SR^a$, $=S$, $—NR^cR^c$, $=NH$, $=N—OH$, $=NR^a$, $=N—OR^a$, $—NO_2$, $—S(O)_2R^a$, $—S(O)_2NHR^b$, $—S(O)_2NR^cR^c$, $—S(O)_2OR^b$, $—OS(O)_2R^b$, $—OS(O)_2OR^b$, $—P(O)(OR^b)(OR^b)$, $—C(O)R^b$, $—C(NR^b)R^b$, $—C(O)OR^b$, $—C(O)NR^cR^c$, $—C(NR^b)NR^cR^c$, $—OC(O)R^b$, $—NR^bC(O)R^b$, $—OC(O)OR^b$, $—NR^bC(O)OR^b$, $—NR^bC(O)NR^cR^c$, $—NR^bC(NR^b)R^b$, $—NR^bC(NR^b)NR^cR^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$;

$R^a$ is selected from $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$ or alternatively, the two W are taken together with the nitrogen atom to which they are bonded form a 4-, 5-, 6- or 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, $—OR^a$, $—SR^a$, $=S$, $—NR^cR^c$, $=NH$, $=N—OH$, $=NR^a$, $=N—OR^a$, $—NO_2$, $—S(O)_2R^a$, $—S(O)_2NHR^b$, $—S(O)_2NR^cR^c$, $—S(O)_2OR^b$, $—OS(O)_2R^b$, $—OS(O)_2OR^b$, $—P(O)(OR^b)(OR^b)$, $—C(O)R^b$, $—C(NR^b)R^b$, $—C(O)OR^b$, $—C(O)NR^cR^c$, $—C(NR^b)NR^cR^c$, $—OC(O)R^b$, $—NR^bC(O)R^b$, $—OC(O)OR^b$, $—NR^bC(O)OR^b$, $—NR^bC(O)NR^cR^c$, $—NR^bC(NR^b)R^b$, and $—NR^bC(NR^b)NR^cR^c$;

$R^{12a}$ and $R^{12b}$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively, $R^{12a}$ and $R^{12b}$ together with the atom(s) to which they are attached, form a 3- or 4-membered carbocyclic or heterocyclic ring;

$R^{13}$ is hydrogen, $C_{1-10}$ alkyl, or glycosyl;

$R^{14a}$ and $R^{14b}$ are each independently hydrogen, $C_{1-6}$ alkyl, haloalkyl, hydroxyalkyl, aminoalkyl, alkoxyalkyl, haloalkoxyalkyl, alkoxy, or haloalkoxy; and $R^{15}$ is hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy.

In any of the preceding embodiments of Formula (I), $X^2$ is N or $NR^4$.

In any of the preceding embodiments of Formula (I), the point of attachment to $E^3$ or $E^2$ is also a carbon atom.

In any of the preceding embodiments of Formula (I), the B ring is a moiety selected from

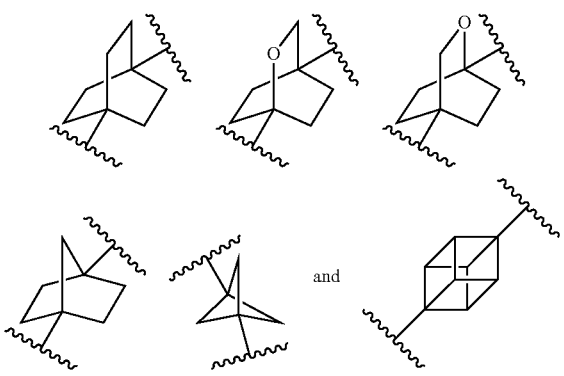

In any of the preceding embodiments of Formula (I), the

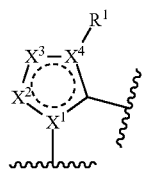

moiety is a ring moiety selected from

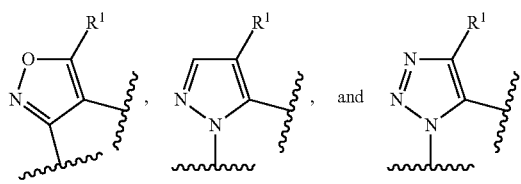

In any of the preceding embodiments of Formula (I), $E^1$, $E^2$ and $E^3$ together form a moiety selected from

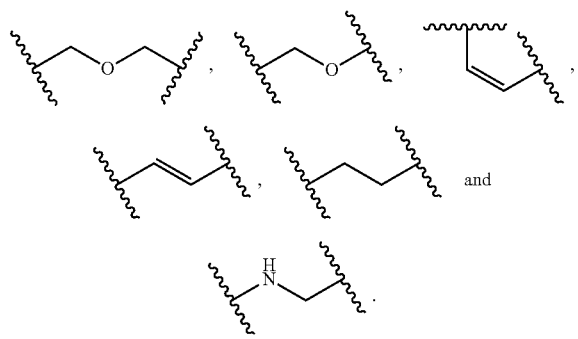

In any of the preceding embodiments of Formula (I), $L^1$ is a covalent bond,

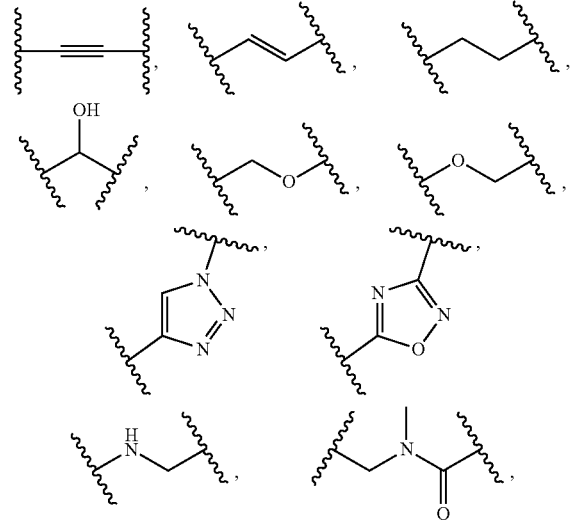

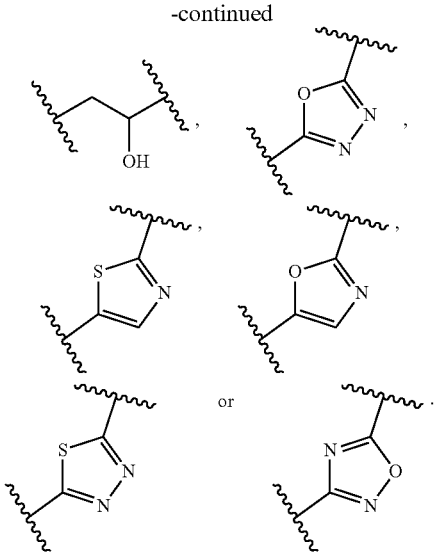

In any of the preceding embodiments of Formula (I), Z is phenyl, 3- to 7-membered cycloalkyl, 4- to 10-membered cycloheteroalkyl, or 5- to 10-membered heteroaryl, wherein the phenyl, cycloalkyl, cycloheteroalkyl, and heteroaryl are independently substituted with 0 to 5 $R^{10}$, wherein $R^8$ is the same as defined above.

In any of the preceding embodiments of Formula (I), —Z—$R^X$ is selected from

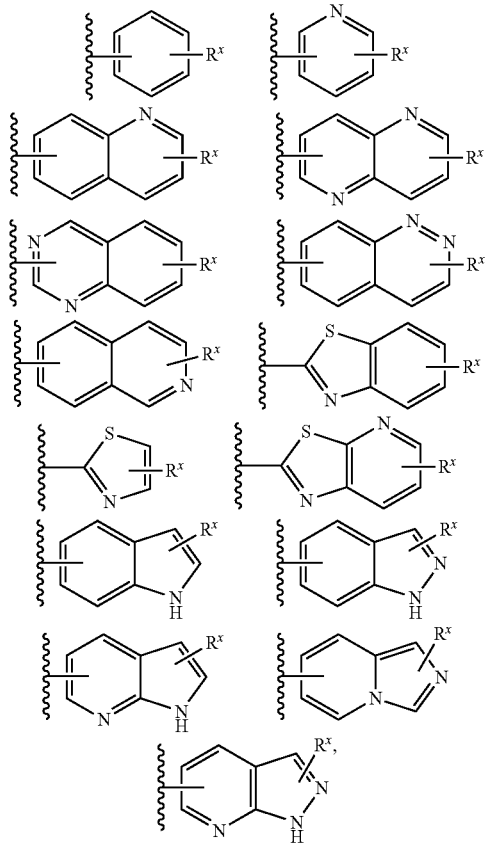

wherein the Z moiety is further substituted with 0 to 3 $R^{10}$, and $R^{10}$ is the same as defined above.

In any of the preceding embodiments of Formula (I), $R^1$ is $C_{1-3}$ alkyl or $C_{3-5}$ cycloalkyl.

In any of the preceding embodiments of Formula (I), $R^2$ is phenyl or 6-membered heteroaryl, wherein the phenyl and heteroaryl are independently substituted with 0 to 3 $R^{10}$.

In any of the preceding embodiments of Formula (I), $L^2$ is a covalent bond.

In any of the preceding embodiments of Formula (I), $R^X$ is —C(O)OH, —CH$_2$C(O)OH, —C(O)OCH$_3$, —CH$_2$C(O)OCH$_3$, —C(O)NH—S(O)$_2$—CH$_3$, or tetrazolyl.

In one embodiment the present invention, the compound of Formula (I) is represented by Formula (IIa) or (IIb):

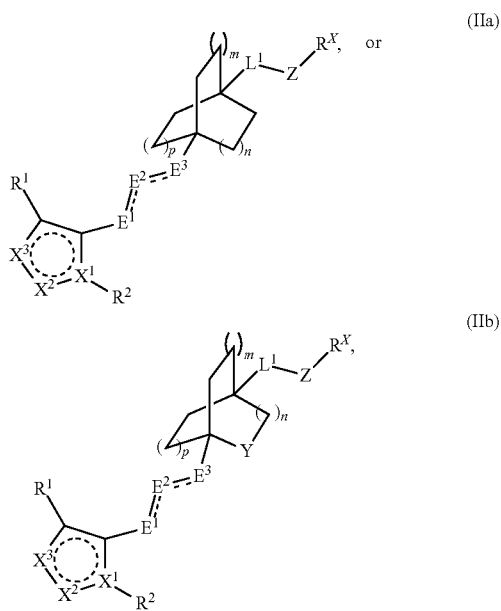

wherein
$X^1$ is C or N;
$X^2$ and $X^3$ are each independently CH, N, O, or S;
$E^1$ and $E^3$ are each independently a covalent bond, O, S, N, NH, CH, or CH$_2$;
$E^2$ is O, S, N, NH, CH, or CH$_2$; wherein ($E^1$ and $E^2$) or ($E^3$ and $E^2$) forms a single bond or double bond; provided that (1) the bonds between ($E^1$ and $E^2$) and ($E^3$ and $E^2$) are not both double bonds; and (2) at least one of $E^1$, $E^2$, and $E^3$ is not O, S, N, or NH;
Y is O, S, NH, or CH$_2$;
m, n, and p are each independently 0 or 1;
$L^1$ is a covalent bond, $C_{1-3}$ alkylene, $C_{1-3}$ heteroalkylene, $C_{2-4}$ alkenylene, $C_{2-4}$ alkynylene, or a 5- to 6-membered heteroaryl containing 1 to 3 heteroatoms independently selected from N, O, and S; wherein the alkylene, heteroalkylene, aryl, and heteroaryl are independently substituted with 0 to 3 $R^9$;
Z is phenyl, or 5- to 10-membered heteroaryl, wherein the phenyl and heteroaryl are independently substituted with 0 to 3 $R^{10}$;
$R^X$ is —C(O)OH;
$R^1$ is $C_{1-6}$ alkyl or $C_{3-5}$ cycloalkyl, wherein the alkyl or cycloalkyl is substituted with 0 to 3 $R^{15}$;
$R^2$ is phenyl or 6-membered heteroaryl, wherein the phenyl or heteroaryl is substituted with 0 to 3 $R^{16}$; and $R^9$, $R^{10}$, $R^{15}$, and $R^{16}$ are the same as defined above.

In any of the preceding embodiments of Formula (IIa) or (IIb), m, n, and p are 1; and Y is O or CH$_2$.

In any of the preceding embodiments of Formula (IIa) or (IIb), Y is CH$_2$; and $L^1$ is a 5- to 6-membered heteroaryl containing 1 to 3 heteroatoms independently selected from N, O, and S; and Z is phenyl or 6-membered heteroaryl; or alternatively $L^1$ is a covalent bond; and Z is 5- to 10-membered heteroaryl; or alternatively $L^1$ is $C_{1-3}$ alkylene, $C_{1-3}$ heteroalkylene or $C_{2-4}$ alkynylene; and Z is phenyl or 5- to 10-membered heteroaryl; wherein the phenyl and heteroaryl are each independently substituted by 0 to 3 $R^9$.

In any of the preceding embodiments of Formula (IIa) or (IIb), Y is O; and $L^1$ is a 5- to 6-membered heteroaryl containing 1 to 3 heteroatoms independently selected from N, O, and S; and Z is phenyl or 6-membered heteroaryl; or alternatively $L^1$ is a covalent bond; and Z is 5- to 10-membered heteroaryl; or alternatively $L^1$ is $C_{1-3}$ heteroalkylene or $C_{2-4}$ alkynylene; and Z is phenyl or 5- to 10-membered heteroaryl; wherein the phenyl and heteroaryl are each independently substituted by 0 to 3 $R^9$.

In any of the preceding embodiments of Formula (IIa) or (IIb), the

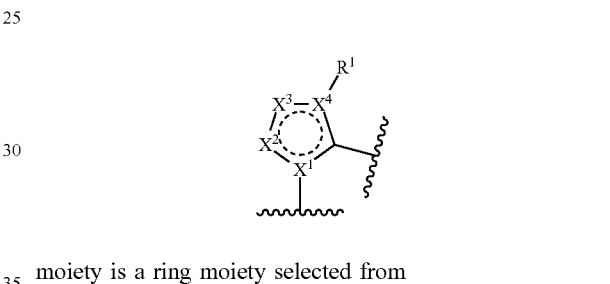

moiety is a ring moiety selected from

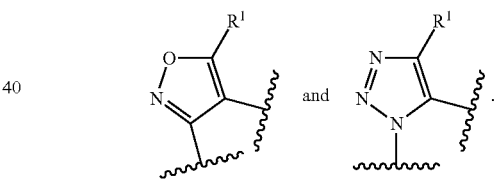

In any of the preceding embodiments of Formula (IIa) or (IIb), $E^1$, $E^2$ and $E^3$ together form a moiety selected from

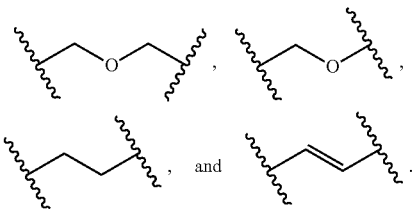

In any of the preceding embodiments of Formula (IIa) or (IIb), $L^1$ is a covalent bond, or

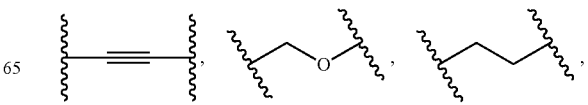

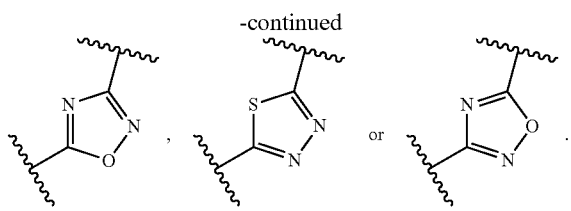

In any of the preceding embodiments of Formula (IIa) or (IIb), Z is phenyl, a 5- or 6-membered monocyclic heteroaryl, or 8- to 10-membered bicyclic heteroaryl, wherein the phenyl or heteroaryl is independently substituted with 0 to 3 $R^{10}$.

In one embodiment of Formula (I), Formula (IIa), or Formula (IIb), $X^1$ is C.

In one embodiment of Formula (I), Formula (IIa), or Formula (IIb), $X^2$ is N.

In one embodiment of Formula (I), Formula (IIa), or Formula (IIb), $X^3$ is O.

In one embodiment of Formula (I), $X^4$ is C.

In one embodiment of Formula (I), $X^1$ is C and $X^4$ is C.

In one embodiment of Formula (I), Formula (IIa), or Formula (IIb), one of $X^2$ and $X^3$ is N and the other of $X^2$ and $X^3$ is O.

In one embodiment of Formula (I), Formula (IIa), or Formula (IIb), $X^2$ is N and $X^3$ is O.

In one embodiment of Formula (I), Formula (IIa), or Formula (IIb), $X^2$ is O and $X^3$ is N.

In one embodiment of Formula (I), Formula (IIa), or Formula (IIb), $X^1$ is C; $X^2$ is N; and $X^3$ is O.

In one embodiment of Formula (I), $X^1$ is C; one of $X^2$ and $X^3$ is N and the other of $X^2$ and $X^3$ is O; and $X^4$ is C.

In one embodiment of Formula (I), $X^1$ is C; $X^2$ is N; $X^3$ is O; and $X^4$ is C.

In one embodiment of Formula (I), $X^1$ is C; $X^2$ is O; $X^3$ is N; and $X^4$ is C.

In one embodiment of Formula (I), Formula (IIa), or Formula (IIb), $X^1$ is N; $X^2$ is N; and $X^3$ is N.

In one embodiment of Formula (I), $E^1$, $E^2$, and $E^3$ together form a moiety selected from

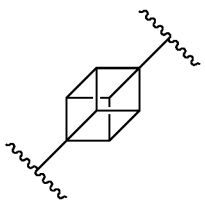

In one embodiment of Formula (I), $E^1$, $E^2$, and $E^3$ together form a moiety selected from

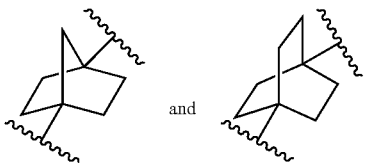

In one embodiment of Formula (I), Formula (IIa), or Formula (IIb), $R^1$ is cyclopropyl.

In one embodiment of Formula (I), Formula (IIa), or Formula (IIb), $R^2$ is phenyl or pyridinyl, each substituted with zero to 2 $R^{16}$.

In one embodiment of Formula (I), Formula (IIa), or Formula (IIb), $R^2$ is phenyl substituted with zero to 2 $R^{16}$.

In one embodiment of Formula (I), Formula (IIa), or Formula (IIb), $R^2$ is pyridinyl substituted with zero to 2 $R^{16}$.

In one embodiment of Formula (I), Formula (IIa), or Formula (IIb), each $R^{16}$ is independently F, Cl, —$CH_3$, —$CF_3$, —$OCH_3$, or —$OCF_3$.

In one embodiment of Formula (I), $L^2$ is a covalent bond.

In one embodiment of Formula (I), Formula (IIa), or Formula (IIb), the B ring is a moiety selected from

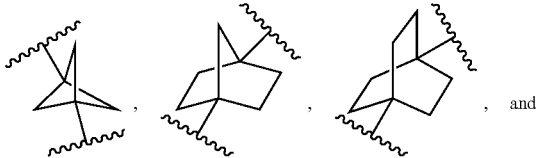

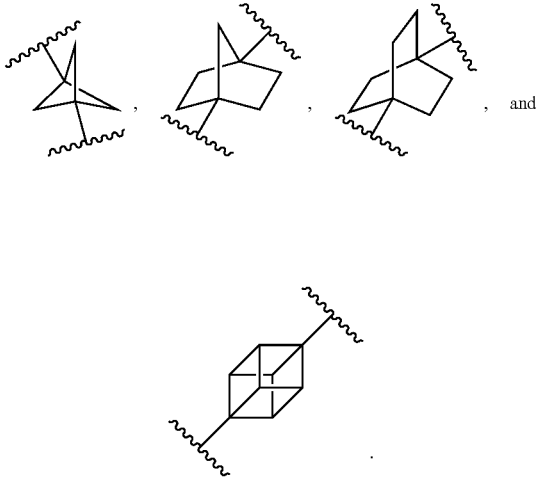

In one embodiment of Formula (I), Formula (IIa), or Formula (IIb), the B ring is a moiety selected from In one embodiment of Formula (I), Formula (IIa), or Formula (IIb), the B ring is In one embodiment of Formula (I), Formula (IIa), or Formula (IIb), the B ring is a moiety selected from In one embodiment of Formula (I), Formula (IIa), or Formula (IIb), the B ring is

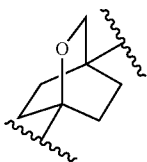

In one embodiment of Formula (I), Formula (IIa), or Formula (IIb), the B ring is

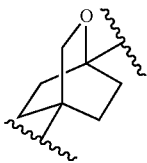

In one embodiment of Formula (I), Formula (IIa), or Formula (IIb), $L^1$ is a covalent bond,

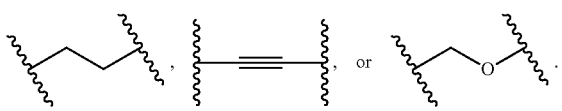

In one embodiment of Formula (I), Formula (IIa), or Formula (IIb), $L^1$ is a covalent bond.

In one embodiment of Formula (I), Formula (IIa), or (IIb), $L^1$ is:

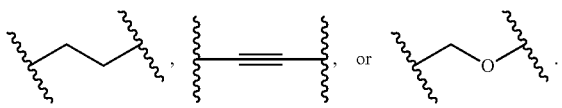

In one embodiment of Formula (I), Formula (IIa), or (IIb), $L^1$ is:

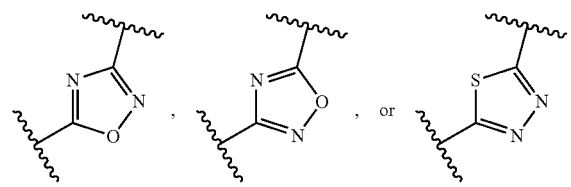

In one embodiment of Formula (I), Formula (IIa), or (IIb), Z is phenyl, pyrazolyl, thiazolyl, oxadiazolyl, pyridinyl, indolyl, indazolyl, benzo[d]thiazolyl, imidazo[1,2-a]pyridinyl, quinolinyl, or isoquinolinyl, each substituted with zero to 2 $R^{10}$.

In one embodiment of Formula (I), Formula (IIa), or (IIb), Z is phenyl, pyridinyl, benzo[d]thiazolyl, quinolinyl, or isoquinolinyl, each substituted with zero to 2 $R^{10}$.

In one embodiment of Formula (I), Formula (IIa), or (IIb), Z is phenyl substituted with zero to 2 $R^{10}$.

In one embodiment of Formula (I), Formula (IIa), or (IIb), Z is pyridinyl substituted with zero to 2 $R^{10}$.

In one embodiment of Formula (I), Formula (IIa), or (IIb), Z is benzo[d]thiazolyl substituted with zero to 2 $R^{10}$.

In one embodiment of Formula (I), Formula (IIa), or (IIb), Z is quinolinyl or isoquinolinyl, each substituted with zero to 2 $R^{10}$.

In one embodiment of Formula (I), Formula (IIa), or (IIb), Z is quinolinyl substituted with zero to 2 $R^{10}$.

In one embodiment of Formula (I), Formula (IIa), or (IIb), Z is isoquinolinyl substituted with zero to 2 $R^{10}$.

In one embodiment of Formula (I), Formula (IIa), or (IIb), each $R^{10}$ is independently F, Cl, —OH, —CN, —CH$_3$, —CH$_2$CH$_3$, —CH$_2$CH$_2$CH$_3$, —CH(CH$_3$)$_2$, —CHF$_2$, —CF$_3$, —CF$_2$CH$_3$, —CH$_2$OCH$_3$, —OCH$_3$, —OCH$_2$CH$_3$, —OCH(CH$_3$)$_2$, —OCHF$_2$, —OCF$_3$, —OCH$_2$CHF$_2$, —OCH$_2$CF$_3$, —OCH$_2$C(CH$_3$)$_2$OH, —OCH$_2$CH$_2$OCH$_3$, —OCH$_2$CH$_2$CH$_2$OCH$_3$, —OCH(CH$_2$Cl)(CH$_2$OH), —OCH$_2$CH(CH$_2$Cl)(CH$_2$OH), —O(C$_{3-5}$ cycloalkyl), —N(CH$_3$)$_2$, —S(O)$_2$CH$_3$, —CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), —OCH$_2$CH$_2$(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

In one embodiment of Formula (I), Formula (IIa), or (IIb), each $R^{10}$ is independently F, Cl, —OH, —CN, —CH$_3$, —CH$_2$CH$_3$, —CHF$_2$, —CF$_3$, —OCH$_3$, —OCH$_2$CH$_3$, —OCH(CH$_3$)$_2$, —OCHF$_2$, —OCF$_3$, —OCH$_2$CHF$_2$, —OCH$_2$CF$_3$, —O(C$_{3-5}$ cycloalkyl), —N(CH$_3$)$_2$, —S(O)$_2$CH$_3$, —CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

In one embodiment of Formula (I), Formula (IIa), or (IIb), each $R^{10}$ is independently —O(C$_{3-5}$ cycloalkyl), —CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), —OCH$_2$CH$_2$(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

In one embodiment of Formula (I), Formula (IIa), or (IIb), $R^x$ is —C(O)OH, —CH$_2$C(O)OH, or

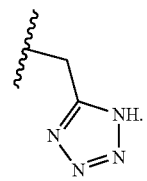 [SMILES: *Cc1nnn[nH]1]

In one embodiment of Formula (I), Formula (IIa), or (IIb), $R^x$ is —C(O)OH or —CH$_2$C(O)OH.

In one embodiment of Formula (I), Formula (IIa), or (IIb), $R^x$ is —C(O)OH.

In one embodiment of Formula (I), Formula (IIa), or (IIb), $R^x$ is

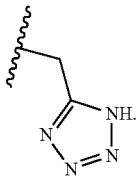

In one embodiment of Formula (I), a is zero or 1.
In one embodiment of Formula (I), a is zero.
In one embodiment of Formula (I), $X^1$ is C; $X^2$ is N; $X^3$ is O; $X^4$ is C; $R^1$ is cyclopropyl; $L^2$ is a covalent bond; $R^2$ is phenyl or pyridinyl, each substituted with zero to 2 $R^{16}$; $E^1$, $E^2$, and $E^3$ together form a moiety selected from

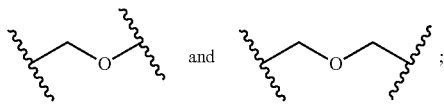

and the B ring is a moiety selected from

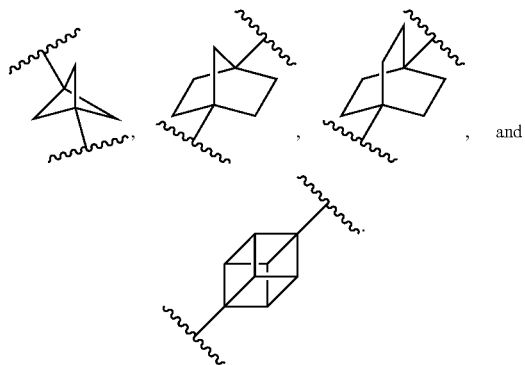

In one embodiment of Formula (I), Formula (IIa), or (IIb), $L^1$ is a covalent bond,

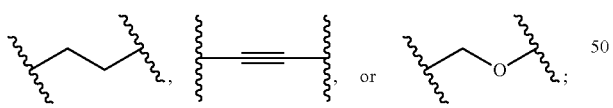

the B ring is

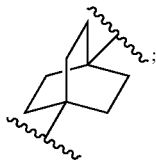 [SMILES: *C12CCC(*)(CC1)CC2]

and Z is phenyl, pyridinyl, benzo[d]thiazolyl, quinolinyl, or isoquinolinyl, each substituted with zero to 2 $R^{10}$; $R^x$ is —C(O)OH, —CH$_2$C(O)OH, or

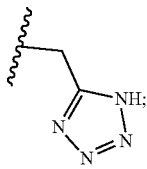

and each $R^{10}$ is independently F, Cl, —OH, —CN, CH$_3$, —CH$_2$CH$_3$, —CH$_2$CH$_2$CH$_3$, —CH(CH$_3$)$_2$, —CHF$_2$, —CF$_3$, —CF$_2$CH$_3$, —CH$_2$OCH$_3$, —OCH$_3$, —OCH$_2$CH$_3$, —OCH(CH$_3$)$_2$, —OCHF$_2$, —OCF$_3$, —OCH$_2$CHF$_2$, —OCH$_2$CF$_3$, —OCH$_2$C(CH$_3$)$_2$OH, —OCH$_2$CH$_2$OCH$_3$, —OCH$_2$CH$_2$CH$_2$OCH$_3$, —OCH(CH$_2$Cl)(CH$_2$OH), —OCH$_2$CH(CH$_2$Cl)(CH$_2$OH), —O(C$_{3-5}$ cycloalkyl), —N(CH$_3$)$_2$, —S(O)$_2$CH$_3$, CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), —OCH$_2$CH$_2$(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

One embodiment provides a compound of Formula (I), or a stereoisomer, a tautomer, or a pharmaceutically acceptable salt or solvate thereof; wherein:
$X^1$ is C; $X^2$ is N; $X^3$ is O; $X^4$ is C;
$R^1$ is cyclopropyl;
$L^2$ is a covalent bond;
$R^2$ is phenyl or pyridinyl, each substituted with zero to 2 $R^{16}$;
each $R^{16}$ is independently F, Cl, —CH$_3$, —CF$_3$, —OCH$_3$, or —OCF$_3$
$E^1$, $E^2$, and $E^3$ together form a moiety selected from

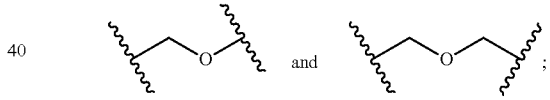

B ring is

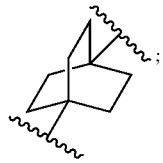 [SMILES: *C12CCC(*)(CC1)CC2]

a is 0;
$L^1$ is a covalent bond,

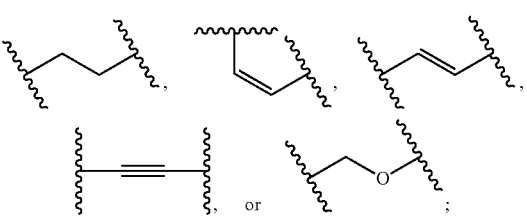

Z is phenyl, pyridinyl, benzo[d]thiazolyl, quinolinyl, or isoquinolinyl, each substituted with zero to 2 $R^{10}$;

$R^x$ is —C(O)OH, —CH$_2$C(O)OH, or

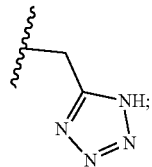 [SMILES: *Cc1nnn[nH]1]

and each $R^{10}$ is independently F, Cl, —OH, —CN, —CH$_3$, —CH$_2$CH$_3$, —CH$_2$CH$_2$CH$_3$, —CH(CH$_3$)$_2$, —CHF$_2$, —CF$_3$, —CF$_2$CH$_3$, —CH$_2$OCH$_3$, —OCH$_3$, —OH$_2$CH$_3$, —OCH(CH$_3$)$_2$, —OCHF$_2$, —OCF$_3$, —OCH$_2$CHF$_2$, —OCH$_2$CF$_3$, —OCH$_2$C(CH$_3$)$_2$OH, —OCH$_2$CH$_2$OCH$_3$, —OCH$_2$CH$_2$CH$_2$OCH$_3$, —OCH(CH$_2$C)(CH$_2$OH), —OCH$_2$CH(CH$_2$C)(CH$_2$OH), —O(C$_{3-5}$ cycloalkyl), —N(CH$_3$)$_2$, —S(O)$_2$CH$_3$, —CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), —OCH$_2$CH$_2$(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

One embodiment provides a compound of Formula (I), or a stereoisomer, a tautomer, or a pharmaceutically acceptable salt or solvate thereof; wherein:

$X^1$ is C; $X^2$ is N; $X^3$ is O; $X^4$ is C;

$R^1$ is cyclopropyl;

$L^2$ is a covalent bond;

$R^2$ is phenyl or pyridinyl, each substituted with zero to 2 $R^{16}$;

each $R^{16}$ is independently F, Cl, —CH$_3$, —CF$_3$, —OCH$_3$, or —OCF$_3$ $E^1$, $E^2$, and $E^3$ together form a moiety selected from

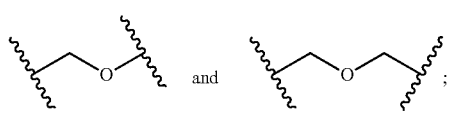

B ring is

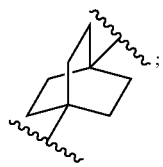

a is 0;

$L^1$ is a covalent bond,

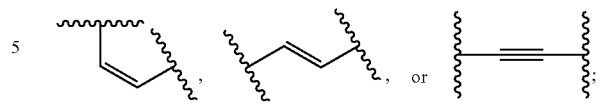

Z is phenyl, pyridinyl, benzo[d]thiazolyl, quinolinyl, or isoquinolinyl, each substituted with zero to 2 $R^{10}$;

$R^x$ is —C(O)OH, —CH$_2$C(O)OH, or

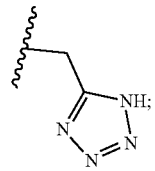

and each $R^{10}$ is independently F, Cl, —OH, —CN, —CH$_3$, —CH$_2$CH$_3$, —CH$_2$CH$_2$CH$_3$, —CH(CH$_3$)$_2$, —CHF$_2$, —CF$_3$, —CF$_2$CH$_3$, —CH$_2$OCH$_3$, —OCH$_3$, —OH$_2$CH$_3$, —OCH(CH$_3$)$_2$, —OCHF$_2$, —OCF$_3$, —OCH$_2$CHF$_2$, —OCH$_2$CF$_3$, —OCH$_2$C(CH$_3$)$_2$OH, —OCH$_2$CH$_2$OCH$_3$, —OCH$_2$CH$_2$CH$_2$OCH$_3$, —OCH(CH$_2$C)(CH$_2$OH), —OCH$_2$CH(CH$_2$C)(CH$_2$OH), —O(C$_{3-5}$ cycloalkyl), —N(CH$_3$)$_2$, —S(O)$_2$CH$_3$, —CH$_2$(cyclopropyl), —CH$_2$(oxetanyl), —OCH$_2$(cyclopropyl), —NH(cyclopropyl), —NH(phenyl), —O(oxetanyl), —O(tetrahydrofuranyl), —O(tetrahydropyranyl), —OCH$_2$(cyclopropyl), —OCH$_2$(cyclobutyl), —OCH$_2$(oxetanyl), —OCH$_2$CH$_2$(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

One embodiment provides a compound of Formula (I), or a stereoisomer, a tautomer, or a pharmaceutically acceptable salt or solvate thereof; wherein:

$X^1$ is C; $X^2$ is N; $X^3$ is O; $X^4$ is C;

$R^1$ is cyclopropyl;

$L^2$ is a covalent bond;

$R^2$ is phenyl or pyridinyl, each substituted with zero to 2 $R^{16}$;

each $R^{16}$ is independently F, Cl, —CH$_3$, —CF$_3$, —OCH$_3$, or —OCF$_3$ $E^1$, $E^2$, and $E^3$ together form a moiety selected from

B ring is

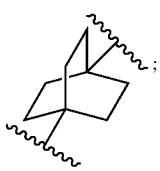 [SMILES: *C12CCC(*)(CC1)CC2]

a is 0;
L¹ is

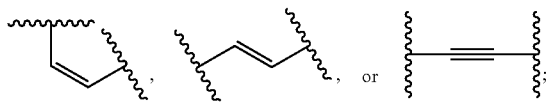

Z is phenyl, quinolinyl, or isoquinolinyl, each substituted with zero to 2 $R^{10}$;
$R^x$ is —C(O)OH; and
each $R^{10}$ is independently F, Cl, —OH, —CN, —CH₃, —CH₂CH₃, —CH₂CH₂CH₃, —CH(CH₃)₂, —CHF₂, —CF₃, —CF₂CH₃, —CH₂OCH₃, —OCH₃, —OCH₂CH₃, —OCH(CH₃)₂, —OCHF₂, —OCF₃, —OCH₂CHF₂, —OCH₂CF₃, —O(C₃₋₅ cycloalkyl), —N(CH₃)₂, —S(O)₂CH₃, —CH₂(cyclopropyl), —CH₂(oxetanyl), —OCH₂(cyclopropyl), —NH(cyclopropyl), —NH(phenyl), —O(oxetanyl), —O(tetrahydrofuranyl), —O(tetrahydropyranyl), —OCH₂(cyclopropyl), —OCH₂(cyclobutyl), —OCH₂(oxetanyl), —OCH₂CH₂(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

One embodiment provides a compound of Formula (I), or a stereoisomer, a tautomer, or a pharmaceutically acceptable salt or solvate thereof; wherein:
$X^1$ is C; $X^2$ is N; $X^3$ is O; $X^4$ is C;
$R^1$ is cyclopropyl;
$L^2$ is a covalent bond;
$R^2$ is pyridinyl, each substituted with zero to 2 $R^{16}$;
each $R^{16}$ is independently F, Cl, —CH₃, —CF₃, —OCH₃, or —OCF₃;
$E^1$, $E^2$, and $E^3$ together form a moiety selected from

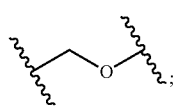 [SMILES: *CO*]

B ring is;

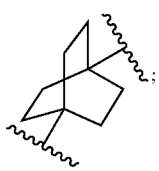 [SMILES: *C12CCC(*)(CC1)CC2]

a is 0;
L¹ is

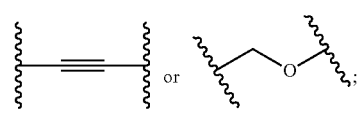

Z is phenyl, quinolinyl, or isoquinolinyl, each substituted with zero to 2 $R^{10}$;
$R^x$ is —C(O)OH; and
each $R^{10}$ is independently F, Cl, —OH, —CN, —CH₃, —CH₂CH₃, —CH₂CH₂CH₃, —CH(CH₃)₂, —CHF₂, —CF₃, —CF₂CH₃, —CH₂OCH₃, —OCH₃, —OCH₂CH₃, —OCH(CH₃)₂, —OCHF₂, —OCF₃, —OCH₂CHF₂, —OCH₂CF₃, —O(C₃₋₅ cycloalkyl), —N(CH₃)₂, —S(O)₂CH₃, —CH₂(cyclopropyl), —CH₂(oxetanyl), —OCH₂(cyclopropyl), —NH(cyclopropyl), —NH(phenyl), —O(oxetanyl), —O(tetrahydrofuranyl), —O(tetrahydropyranyl), —OCH₂(cyclopropyl), —OCH₂(cyclobutyl), —OCH₂(oxetanyl), —OCH₂CH₂(pyrrolidinyl), cyclopropyl, azetidinyl, (hydroxymethyl)azetidinyl, fluoroazetidinyl, (dimethylamino)azetidinyl, methoxyazetidinyl, hydroxyazetidinyl, morpholinyl, piperazinyl, methylpiperazinyl, hydroxypiperidinyl, pyrrolidinyl, or hydroxypyrrolidinyl.

One embodiment provides a compound of Formula (I), or a stereoisomer, a tautomer, or a pharmaceutically acceptable salt or solvate thereof; wherein said compound is selected from:

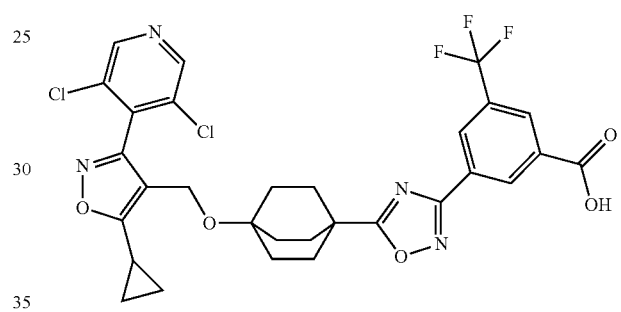

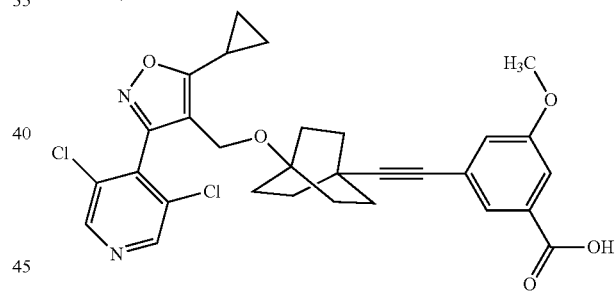

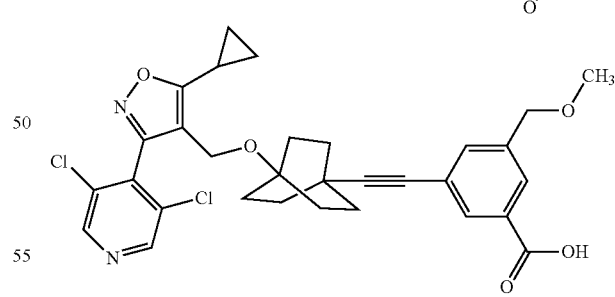

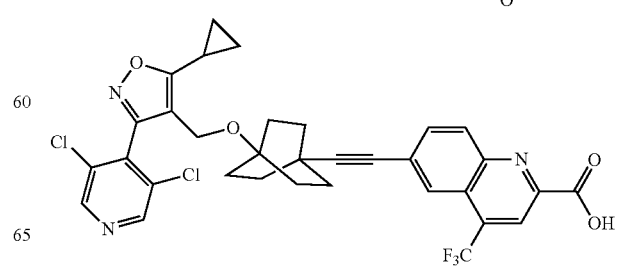

-continued

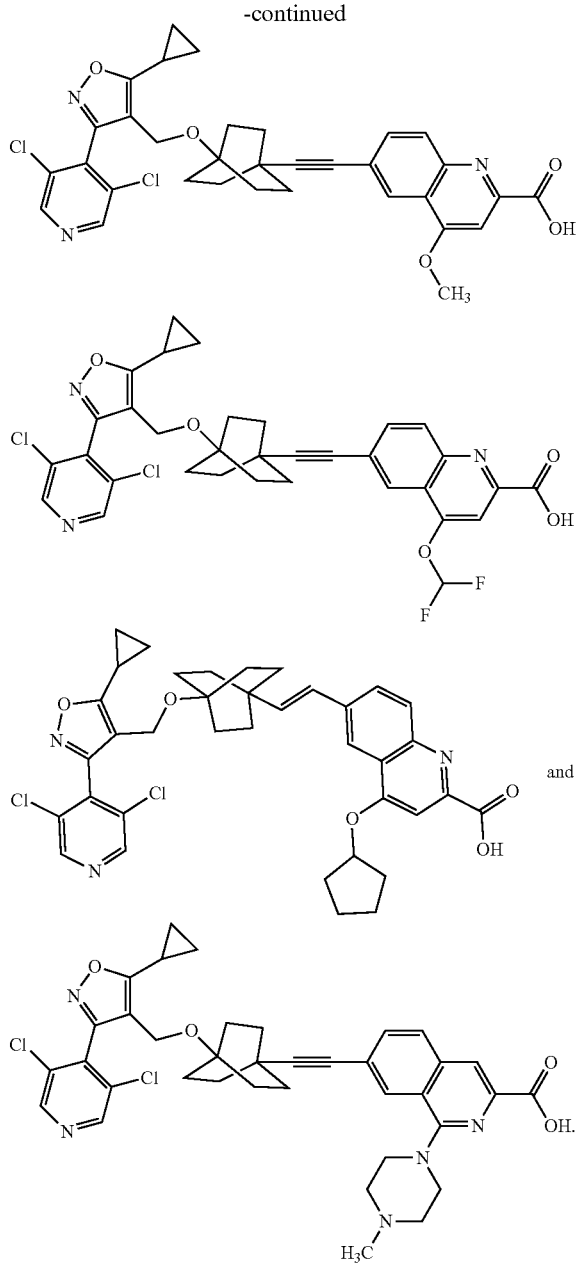

In one embodiment, the present invention provides, inter alia, compounds selected from any one of the Examples as described in the specification, or a stereoisomer, a tautomer, or a pharmaceutically acceptable salt or solvate thereof.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met(O$_2$)$^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDES) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), and (IIb), or stereoisomers, tautomers, or pharmaceutically acceptable salts or solvates thereof.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. While "alkenyl" denotes a monovalent radical, "alkenylene" denotes a bivalent radical. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. While "alkynyl" denotes a monovalent radical, "alkynylene" denotes a bivalent radical. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or spa carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulfur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by $—S(O)_2R'$, while sulfonamide may be represented by $—S(O)_2NR^cR^d$. R' is $C_1$ to $C_6$ alkyl; and $R^c$ and $R^d$ are the same as defined below for "amino".

The term "carbamate" as used herein alone or as part of another group refers to oxygen linked to an amido group. For example, carbamate may be represented by $N(R^cR^d)—C(O)—O—$, and $R^c$ and $R^d$ are the same as defined below for "amino".

The term "amido" as used herein alone or as part of another group refers to amino linked to a carbonyl group. For example, amido may be represented by $N(R^cR^d)—C(O)—$, and $R^c$ and $R^d$ are the same as defined below for "amino".

The term "amino" is defined as $—NR^{c1}R^{c2}$, wherein $R^{c1}$ and $R^{c2}$ are independently H or $C_{1-6}$ alkyl; or alternatively, $R^{c1}$ and $R^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When $R^{c1}$ or $R^{c2}$ (or both of them) is $C_{1-6}$ alkyl, the amino group can also be referred to as alkylamino. Examples of alkylamino group include, without limitation, $—NH_2$, methylamino, ethylamino, propylamino, isopropylamino and the like.

The term "aminoalkyl" refers to an alkyl group on which one of the hydrogen atoms is replaced by an amino group. For example, aminoalkyl may be represented by $N(R^{c1}R^{c2})$-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

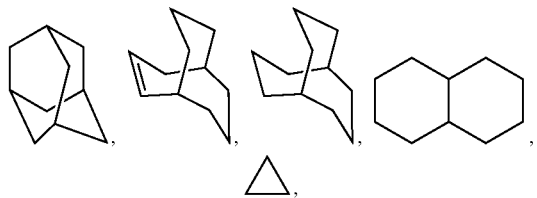

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, F, Cl, Br, I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

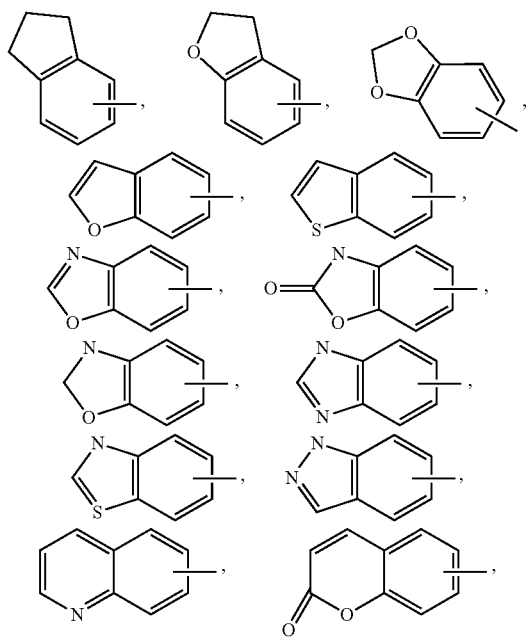

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkoxy, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, acylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy or squiggly bond in a structural formula, such as

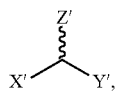

is used to depict a stereogenic center of the carbon atom to which X', Y', and Z' are attached and is intended to represent both enantiomers in a single FIGURE. That is, a structural formula with such as wavy bond denotes each of the enantiomers individually, such as

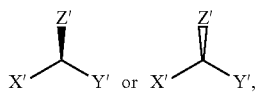

as well as a racemic mixture thereof. When a wavy or squiggly bond is attached to a double bond (such as C=C or C=N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

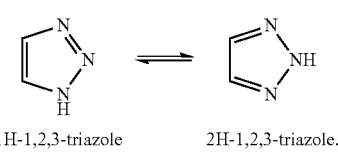

1H-1,2,3-triazole      2H-1,2,3-triazole.

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112: 309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);
Bundgaard, H. et al., *J. Pharm. Sci.*, 77:285 (1988); and
Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999); Rautio, J. et al., *Nature Review Drug Discovery*, 17, 559-587, (2018).

The present invention is intended to include all isotopes of atoms occurring in the present compounds. Isotopes include those atoms having the same atomic number but different mass numbers. By way of general example and without limitation, isotopes of hydrogen include deuterium (symbol D or $^2H$) and tritium (symbol T or $^3H$). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The term "glycosyl" means a monovalent free radical or substituent moiety obtained by removing the hemiacetal hydroxyl group from the cyclic form of a monosaccharide and, by extension, of a lower oligosaccharide. In one embodiment, the glycosyl group has the following structure:

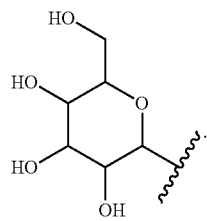

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

ABBREVIATIONS

The following abbreviations are employed in the Schemes, Examples and elsewhere herein:
AcOH=acetic acid
AIBN=azobisisobutyronitrile
BOP=(benzotriazol-1-yloxy)tris(dimethylamino)phosphonium hexafluorophosphate
CDI=1,1'-carbonyldiimidazole
Cs$_2$CO$_3$=cesium carbonate
DCE=dichloroethane
DCM=CH$_2$Cl$_2$=methylene chloride
DDQ=2,3-dichloro-5,6-dicyano-1,4-benzoquinone
DIBAL-H=diisobutylaluminium hydride
DIEA=Hunig's base=N,N-diisopropylethylamine
DMAP=4-dimethylaminopyridine
DME=1,2-dimethoxyethane
DMF=N,N-dimethylformamide
DMP=Dess-Martin periodinane
DMSO=dimethylsulfoxide
DPPA=diphenylphosphoryl azide
dppf=1,1'-bis(diphenylphosphino)ferrocene
EDC=1-ethyl-3-(3-dimethylaminopropyl)carbodiimide
EtOAc=ethyl acetate
EtOH=ethanol
HATU=1-[bis(dimethylamino)methylene]-1H-1,2,3-triazolo[4,5-b]pyridinium 3-oxide hexafluorophosphate
HBTU=N,N,N',N'-tetramethyl-O-(1H-benzotriazol-1-yl)uronium hexafluorophosphate
HCl=hydrochloric acid
HOBT=hydroxybenzotriazole
H$_2$SO$_4$=sulfuric acid
K$_2$CO$_3$=potassium carbonate
K$_2$HPO$_4$=potassium phosphate dibasic
KMnO$_4$=potassium permanganate
KOH=potassium hydroxide
KOtBu=potassium tert-butoxide
LAH=lithium aluminum hydride
mCPBA=meta-chloroperoxybenzoic acid
MeCN=acetonitrile
MeOH=methanol
MgSO$_4$=magnesium sulfate
Na$_2$CO$_3$=sodium carbonate
NaBH$_4$=sodium borohydride
NaHCO$_3$=sodium bicarbonate
NBS=N-bromosuccinimide
NCS=N-chlorosuccinimide
NH$_4$Cl=ammonium chloride
NMP=N-methyl-2-pyrrolidone
PCC=pyridinium chlorochromate
Pd$_2$(dba)$_3$=tris(dibenzylideneacetone)dipalladium(0)
Pd(dppf)Cl$_2$.CH$_2$Cl$_2$ adduct=[1,1'-bis(diphenylphosphino)ferrocene]dichloropalladium(ID, complex with dichloromethane
Pd(PPh$_3$)$_4$=tetrakis(triphenylphosphine)palladium(0)
PDC=pyridinium dichromate
PE=petroleum ether
Ph$_3$P=triphenylphosphine
PyBOP=(benzotriazol-1-yloxy)tripyrrolidinophosphonium hexafluorophosphate
SiO$_2$=silicon dioxide
T3P=propylphosphonic anhydride TBTU=O-(benzotriazol-1-yl)-N,N,N',N'-tetramethyluronium tetrafluoroborate
TEA=Et$_3$N=triethylamine
TFA=trifluoroacetic acid
THF=tetrahydrofuran
Xantphos=4,5-bis(diphenylphosphino)-9,9-dimethylxanthene IV. Methods of Preparation The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, VCH, New York (1989).

Generic Schemes

Compounds of the present invention, represented by Formula (I), Formula (IIa), Formula (IIb), or any subgenera or species thereof, can be prepared according to the general routes shown in SCHEMES 1 to 18 below.

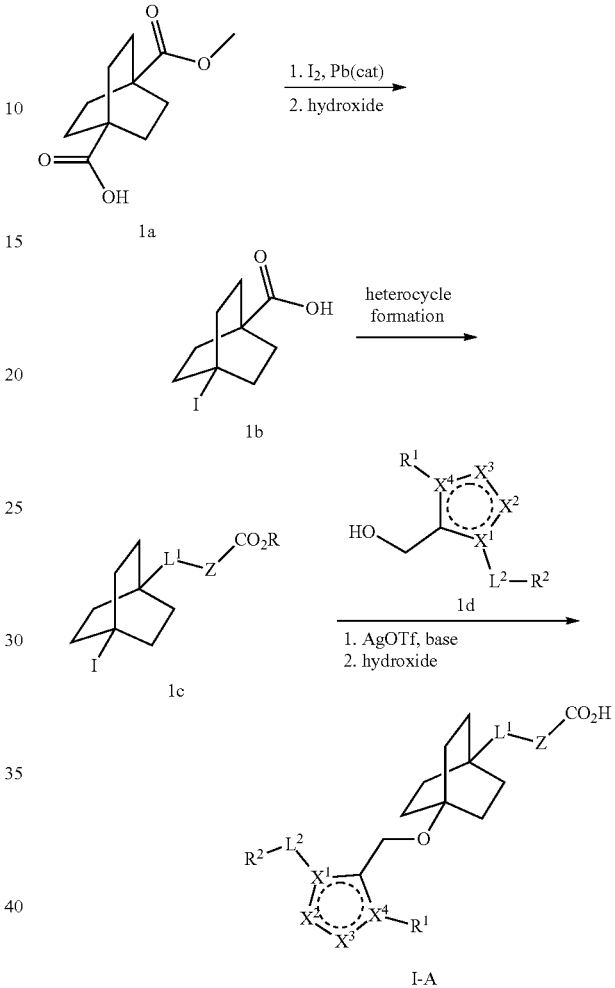

SCHEME 1

Scheme 1 describes the synthesis of compounds of Formula I-A (a subset of Formula I) wherein: L$^1$=5-membered heteroaryl ring. Z=6-membered aryl or 5- to 10-membered heteroaryl ring.

Heteroaryl methyl alcohol compound 1 d can be readily prepared by one of ordinary skill in the art using numerous and well established procedures, with representative examples found in WO 2012/087519 (Tully, D. C., et al.), WO 2009/012125 (Genin, M. J., et al.), and WO 2008/051942 (Navas, F. et al.).

Starting material 4-(methoxycarbonyl)bicyclo[2.2.2]octane-1-carboxylic acid 1a is available commercially, or can be prepared from known procedures by one of ordinary skill in the art (Kiesman W. F. et al. WO 2001/034610). Acid 1a can be iodinated via classical Hunsdieker reaction (Al Hussainy, R. et al. *J. Med. Chem.* 2011, 54, 3480-3491) or alternatively, via photochemistry applying methods described in *J. Am. Chem. Soc.* 1999, 121, 1936-1944 (See Kuduva, S. S., et al.; photochemical iodination of bridgehead cubane). Subsequent hydrolysis of the methyl ester with an alkali hydroxide base can provide acid 1b.

Heterocycle formation (L$^1$). The carboxylic acid moiety of compound 1b can be converted to various heterocycles ($L^1$) by one of ordinary skill in the art using numerous established methods, including but not limited to the following:

$L^1$=1,2,4-oxadiazole (Z=3-aryl or 3-heteroaryl) ($L^1$ attached to bicyclo[2.2.2]octane ring at 5-position of 1,2,4-oxadiazole). Acid 1b can be coupled with various aryl (or heteroaryl) amide oximes using a common amide bond coupling reagent (e.g. CDI, BOP, EDC) in a polar aprotic solvent (e.g. toluene, THF, 1,4-dioxane) at room temperature. The resultant acyclic intermediate can be subsequently cyclized to 1,2,4-oxadiazole at elevated temperatures (60° C. to 110° C.). Amide oximes can be synthesized from the corresponding aryl (or heteroaryl) nitriles by reaction with hydroxylamine (See Hirawat, S., et al. WO 2006/110483; general procedure for preparation of amide oxime).

$L^1$=1,3,4-oxadiazole (Z=5-aryl or 5-heteroaryl) or $L^1$=1,3,4-thiadiazole (Z=5-aryl or 5-heteroaryl) ($L^1$ attached to bicyclo[2.2.2]octane ring at 2-position of 1,3,4-oxa(thia)diazole). Acid 1b can be coupled with methyl 3-(hydrazinecarbonyl)benzoate (Bradner, J. E., et al. WO 2014/071247), using a typical amide bond coupling reagent (e.g. EDC, PyBOP, T3P) in a polar aprotic solvent (e.g. DMF, MeCN). The acyclic hydrazide intermediate can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or phosphorous pentasulfide (Yoshida, S., et al. *Org. Process Res. Dev.* 2013, 17, 1252-1260).

$L^1$=oxazole or thiazole (Z=2-aryl or 2-heteroaryl) ($L^1$ attached to bicyclo[2.2.2]octane ring at 4-position of oxazole or thiazole). Acid 1b can be activated for acylation by one of ordinary skill in the art using any number of reagents (e.g. thionyl chloride, oxalyl chloride), in a polar aprotic solvent (e.g. DCM, THF), at temperatures ranging between –30° C. to 25° C. The activated acid intermediate can be reacted with trimethylsilyldiazomethane in a polar aprotic solvent (e.g. diethyl ether, THF, DCM) at temperatures ranging between –5° C. to 5° C. The resultant diazoketone can be hydrolyzed under acidic conditions (HCl) to generate 2-chloroethanone intermediate. Cyclization to oxazole or thiazole can be accomplished by subsequent reaction of 2-chloroethanone moiety with aryl or heteroaryl primary carboxamide (or thiocarboxamide, respectively) in an ethereal solvent (1,4-dioxane) at elevated temperatures (175° C., sealed).

$L^1$=1H-imidazole (Z=2-aryl or 2-heteroaryl) ($L^1$ attached to bicyclo[2.2.2]octane ring at 4-position of 1H-imidazole). Cyclization to 1H-imidazole can be accomplished by reaction of aryl or heteroaryl amidine with the 2-chloroethanone intermediate described for the synthesis of $L^1$=oxazole or thiazole (supra). The coupling reaction can be conducted in an ethereal solvent (e.g. THF, 1,4-dioxane) at elevated temperatures (60° C. to 105° C.).

Aryl or heteroaryl amidines can be prepared by one of ordinary skill in the art using any one of numerous reported methods. One such method is by reaction of the corresponding aryl or heteroaryl nitrile with ammonia ("Preparation of amidine salts by reaction of nitriles with ammonium salts in the presence of ammonia." Schaefer, F. C. et al. *J. Org. Chem.* 1962, 27, 1255-1258).

Iodide 1c can be displaced with alcohol 1d in the presence of silver triflate and base (e.g. pyridine, 2,6-lutidene, 2,6-di-tert-butylpyridine). Hydrolysis of ester R (R=Me, Et, or other suitable alkyl substituent) using a typical alkali hydroxide base can provide compounds of Formula I-A.

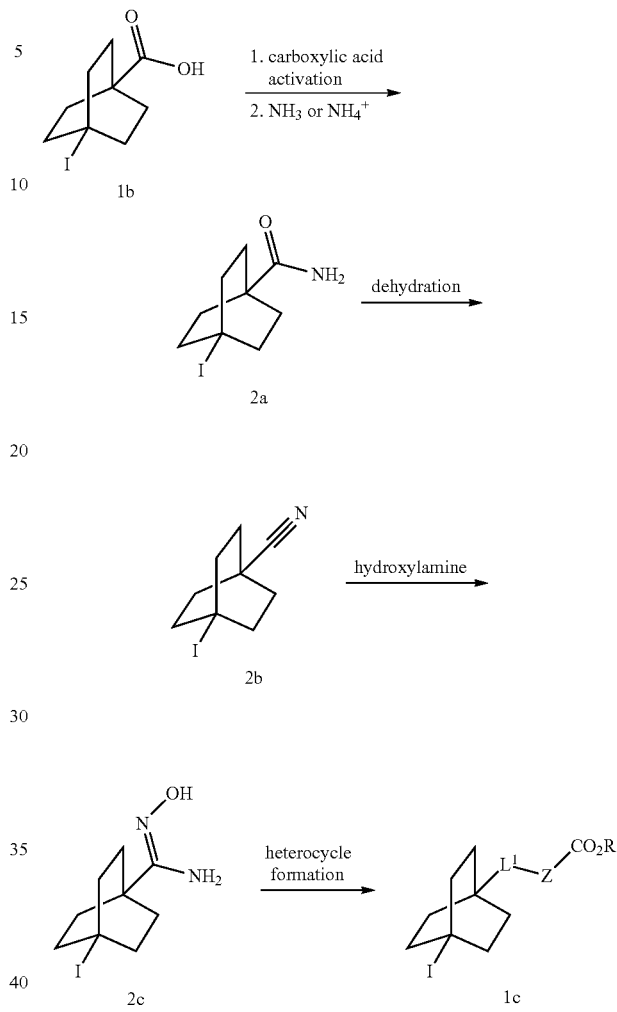

Scheme 2 describes an alternate synthesis of compound 1c (see Scheme 1), wherein: $L^1$=1,2,4-oxadiazole. Z=5-aryl or 5-heteroaryl. $L^1$ attached to bicyclo[2.2.2]octane ring at 3-position of 1,2,4-oxadiazole.

Acid 1b can be activated for acylation by one of ordinary skill in the art using any number of reagents (e.g. thionyl chloride, oxalyl chloride, methyl or ethylchloroformate), in a polar aprotic solvent (e.g. DCM, THF), at temperatures ranging between –30° C. to 0° C. The activated acid intermediate can be reacted with ammonia or ammonium (e.g. $NH_3(g)$, $NH_4Cl$) to generate primary amide 2a. Amide 2a can be converted to nitrile 2b using a dehydrating agent (e.g. phosphorous oxychloride, phosphorous pentoxide, trifluoroacetic anhydride). Nitrile 2b can be converted to the amide oxime 2c using hydroxylamine (See Hirawat, S., et al. WO 2006/110483; general procedure for conversion of nitriles to amide oximes), then coupled with various aryl or heteroaryl acids using a typical amide bond coupling reagent (e.g. CDI, BOP, EDC) in a polar aprotic solvent (e.g. toluene, THF, 1,4-dioxane). Cyclization can be conducted at elevated temperatures (60° C. to 100° C.) to form compound 1c. Methods described in Scheme 1 can be used to convert 1c to compounds of Formula I-A.

SCHEME 3

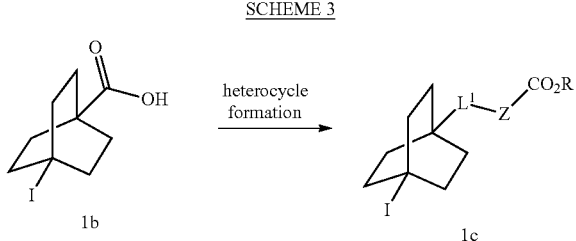

Scheme 4 describes an alternate synthesis of compound 1c (Scheme 1), wherein: $L^1$=covalent bond. Z=5- to 10-membered heteroaryl ring. Z attached to bicyclo[2.2.2] octane ring at 2-position of heteroaryl.

Heterocycle formation. The carboxylic acid moiety of compound 1b can be converted to various heterocycles by one of ordinary skill in the art using numerous known and well established methods, including but not limited to the following:

Benzothiazole. Method A: Acid 1b can be coupled with substituted 2-aminobenzenethiol (See generally Chedekel, M. R., et al. *Synth. Commun.* 1980, 10, 167-173; synthesis of various 2-aminobenzenethiols), using a common amide bond coupling reagent (e.g. BOP, T3P, EDC) in a polar aprotic solvent (e.g. DCE, THF). The coupling reaction can be conducted at elevated temperatures (60° C. to 80° C.) thereby accomplishing the in situ formation of the cyclized benzothiazole.

Method B: Alternatively, acid 1b can be coupled with substituted 2-chloroaniline (wide commercial availability) using a typical amide bond coupling reagent (e.g. T3P, BOP), or by activating the acid 1b for acylation using any number of common reagents (e.g. oxalyl chloride, thionyl chloride, phosphorus oxychloride). The resultant carboxamide can be treated with Lawesson's reagent at elevated temperature (120° C.) to affect the conversion of carboxamide to thiocarboxamide. Cyclization to benzothiazole can be accomplished by treatment with sodium hydride in a polar aprotic solvent (e.g. DMF, NMP) at elevated temperature (130° C.).

Benzoxazole. Acid 1b can be coupled with substituted 2-aminophenol (wide commercial availability) using a common amide bond coupling reagent (e.g. BOP, EDC), in a polar aprotic solvent (e.g. DMF, THF). Cyclization can be accomplished at elevated temperatures (115° C.) in the presence of a catalytic amount of acid (p-toluenesulfonic acid).

1H-Benzimidazole. Acid 1b can be coupled with ethyl 3,4-diaminobenzoate using a common amide bond coupling reagent (e.g. TBTU, T3P, PyBOP) in a polar aprotic solvent (e.g. DMF, NMP), then cyclized to benzimidazole under acidic conditions (AcOH neat) at elevated temperatures (115° C.).

Quinazoline. Acid 1b can be coupled with 4-amino-3-(aminomethyl)benzoate dihydrochloride (Pascal, R. et al. *Eur. J. Org. Chem.* 2000, 22, 3755-3761), using an amide bond coupling reagent (e.g. HBTU, EDC, PyBOP) in a polar aprotic solvent (e.g. MeCN, THF). Cyclization can be accomplished under acidic conditions (AcOH neat) at elevated temperatures (115° C.). The resultant dihydroquinazoline intermediate can be oxidized to quinazoline using an oxidizing agent such as DDQ.

Thiazole. Acid 1b can be activated for acylation by one of ordinary skill in the art using any number of reagents (e.g. thionyl chloride, oxalyl chloride, methyl or ethylchloroformate) in a polar aprotic solvent (e.g. THF, toluene), at temperatures ranging between −30° C. to 0° C. The activated acid intermediate can be reacted with ammonia or ammonium (e.g. $NH_3$(g), $NH_4Cl$) to generate the primary amide, which can be treated with Lawesson's reagent at elevated temperature (60° C. to 120° C.) to affect the conversion of carboxamide to thiocarboxamide. Thiocarboxamide can then be cyclized to thiazole by reaction with various electrophiles (e.g. 3-bromo-2-oxopropanoic acid, ethyl 2-chloroacetoacetate) at elevated temperatures (60° C. to 100° C.).

Compound 1c can be reacted with compound 1d using methods described in Scheme 1 to provide compounds of Formula I-A.

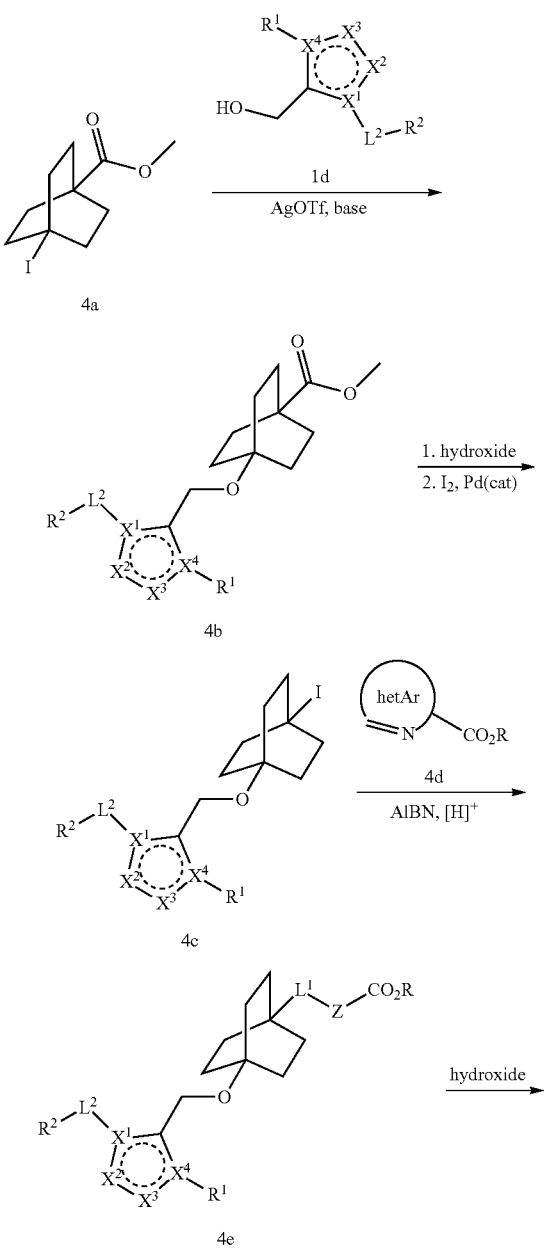

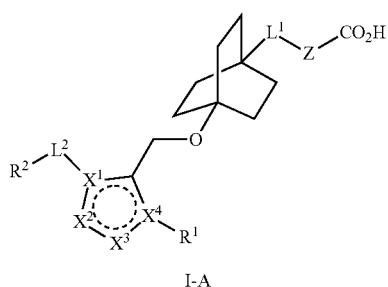

I-A

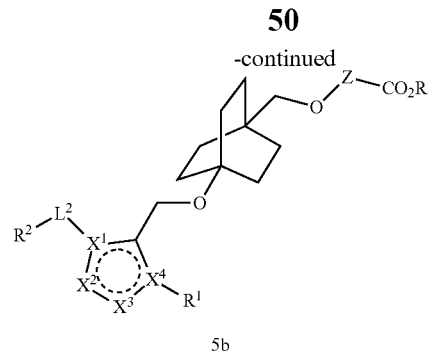

5b

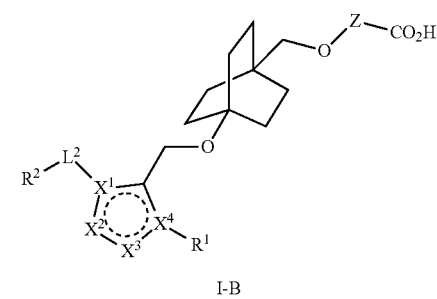

I-B

Scheme 4 describes an alternative synthetic route to obtain compounds of Formula I-A (a subset of Formula I), wherein: $L^1$=covalent bond. Z=9- to 10-membered heteroaryl ring.

Compound 4a can be synthesized according to methods described in Scheme 1. Displacement of iodide compound 4a with alcohol 1 d in the presence of silver triflate and base (e.g. pyridine, 2,6-lutidene, 2,6-di-tert-butylpyridine) can provide compound 4b. Ester 4b can be hydrolyzed using a typical alkali hydroxide base, and the resultant acid can be converted to iodo compound 4c by methods described in Scheme 1. Applying methods described by Togo, H. et al. ("Radical alkylation of heteroaromatic bases with polysilane compounds." *Bull. Chem. Soc. Jpn.* 1994, 67, 2522-2527), compound 4c can undergo radical substitution onto nitrogen-containing heteroaromatic compound 4d (e.g. substituted pyridine, quinoline, 1,5-naphthyridine etc.) in the presence of a radical initiator (AIBN) to provide compound 4e. Hydrolysis of ester R (R=Me, Et, or other suitable alkyl substituent) using a typical alkali hydroxide base can provide compounds of Formula I-A.

SCHEME 5

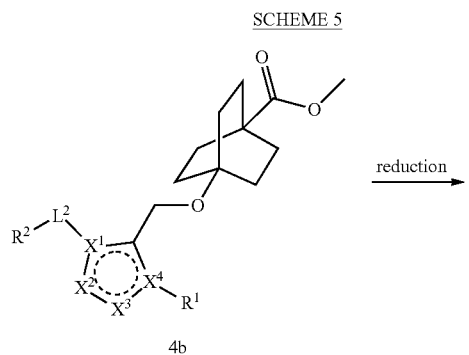

4b reduction

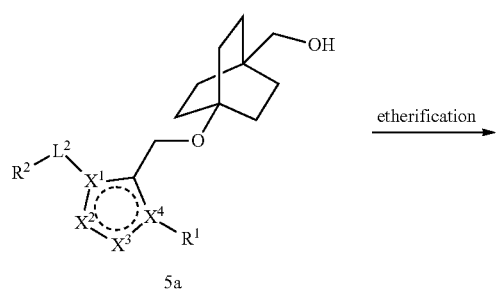

5a etherification

Scheme 7 describes the synthesis of compounds of Formula I-B (a subset of Formula I), wherein: Z=6- to 10-membered aryl, or 5- to 10-membered heteroaryl ring.

Carboxylic ester 4b can be readily converted to alcohol 5a by one of ordinary skill in the art with a common reducing agent (e.g. LAH, DIBAL-H, $NaBH_4$). Typical solvents for this transformation include chlorinated or ethereal solvents (e.g. DCM, ether, THF, 1,4-dioxane), and temperature can vary from −78° C. to 100° C.

Etherification. From alcohol 5a, many approaches exist to form the ether bond that will lead to compounds of Formula I-B, including but not limited the following methods:

SNAr reaction. Alcohol 5a can undergo a SNAr reaction with 2-halogen substituted pyridine (or other nitrogen containing heterocycles). This transformation is typically conducted under basic conditions with bases such as carbonate, amine, hydride, silazide, alkoxide, and alkyl lithium. Aprotic solvents such as chlorinated or ethereal solvents (e.g. DCM, THF, 1,4-dioxane) are used and temperature can vary from −78° C. to 120° C.

$SN_2$ reaction. Additionally, alcohol 5a can be converted to a halide. Typical reagents used for halogenation include $PPh_3$/carbon tetrabromide, bromine, phosphorus tribromide, phosphorus trichloride, and methanesulfonyl chloride. Aprotic chlorinated or ethereal solvents are commonly used (e.g. DCM, carbon tetrachloride, THF) and temperature can vary from 0° C. to 100° C. The halide can react with various phenols through $SN_2$ reaction under similar basic conditions as described above for the SNAr reaction.

Mitsunobu reaction. An alternative method to construct the ether bond is by reacting alcohol 5a with various phenols via Mitsunobu reaction ("The Mitsunobu reaction in the 21st century." Fletcher, S. *Org. Chem. Front.* 2015, 2, 739-752).

Finally, hydrolysis of ester R (R=Me, Et, or other suitable alkyl substituent) of compound 5b using a typical alkali hydroxide base can provide compounds of Formula I-B.

SCHEME 6

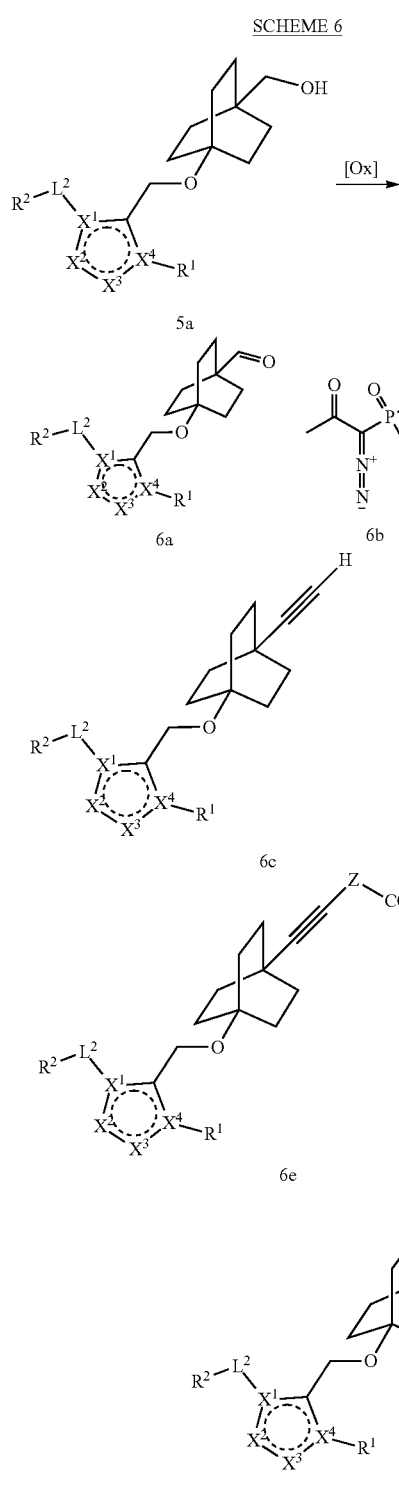

Scheme 6 describes the synthesis of compounds of Formula I-C (a subset of Formula I), wherein: Z=6- to 10-membered aryl, or 5- to 10-membered heteroaryl ring.

Compound 5a (Scheme 5) can be oxidized to aldehyde 6a, by one of ordinary skill in the art using typical oxidation conditions (e.g. Dess-Martin periodinane, Swern oxidation, PDC or PCC). Aldehyde 6a can be reacted with dimethyl 1-diazo-2-oxopropylphosphonate 6b under basic conditions (e.g. $K_2CO_3$, KOtBu) to yield alkyne 6c (See Seyferth, D., et al. *J. Org. Chem.* 1971, 36, 1379-1386; Seyferth-Gilbert homologation). Alkyne 6c can be coupled with aryl or heteroaryl halides 6d (X=Cl, Br, I) under typical Sonogashira conditions (Sonogashira, K. *J. Organomet. Chem.* 2002, 653, 46-49) to yield compound 6e. Hydrolysis of ester R (R=Me, Et, or other suitable alkyl substituent) using a typical alkali hydroxide base can yield compounds of Formula I-C.

SCHEME 7

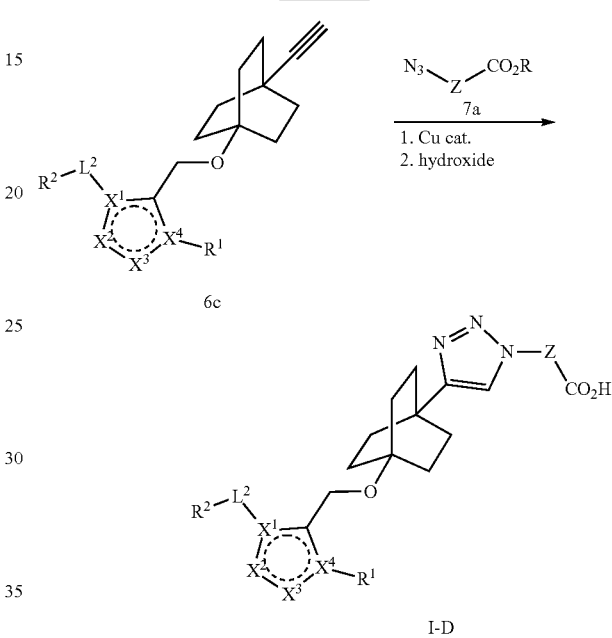

Scheme 9 describes the synthesis of compounds of Formula I-D (a subset of Formula I), wherein: Z=6-membered aryl or 5- to 10-membered heteroaryl ring.

Compound 6c (Scheme 6) can be reacted with various aryl or heteroaryl azides 7a via "click" chemistry in the presence of copper catalyst (e.g. copper (I) iodide, copper(II) sulfate pentahydrate) ("Click Chemistry: Diverse Chemical Function from a Few Good Reactions." Kolb, H. C.; Finn, M. G.; Sharpless, K. B. *Angew. Chem. Int. Ed.* 2001, 40, 2004-2021), to generate 1H-1,2,3 triazole. Hydrolysis of ester R (R=Me, Et, or other suitable alkyl substituent) using a typical alkali hydroxide base can provide compounds of Formula I-D.

SCHEME 8

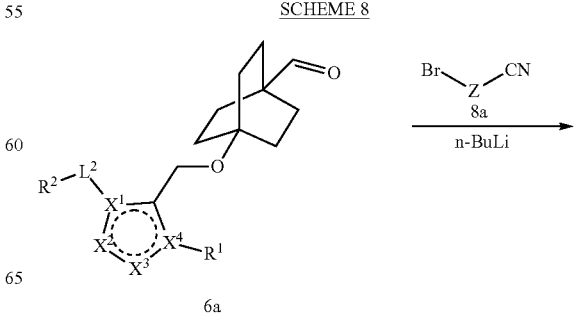

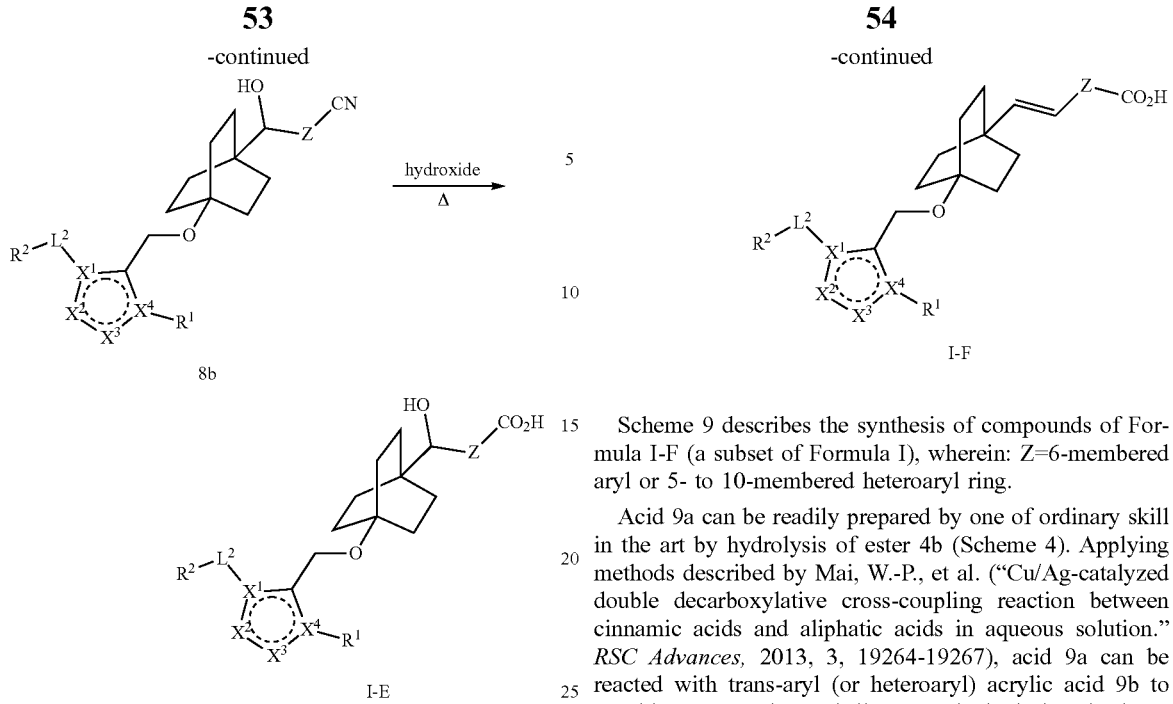

Scheme 8 describes the synthesis of compounds of Formula I-E (a subset of Formula I), wherein: Z=6-membered aryl or 5- to 10-membered heteroaryl ring.

Lithium-halogen exchange of compound 8a can be accomplished using an alkyllithium reagent (e.g. n-butyllithium, t-butyllithium) in an ethereal solvent (e.g. ether, THF, 1,4-dioxane), at low temperature (0° C. to −78° C.). The resultant aryllithium species can be reacted with aldehyde 6a to provide intermediate 8b. Nitrile 8b can be hydrolyzed using a typical alkali hydroxide base at elevated temperature (60° C. to 100° C.), to provide compounds of Formula I-E.

Scheme 9 describes the synthesis of compounds of Formula I-F (a subset of Formula I), wherein: Z=6-membered aryl or 5- to 10-membered heteroaryl ring.

Acid 9a can be readily prepared by one of ordinary skill in the art by hydrolysis of ester 4b (Scheme 4). Applying methods described by Mai, W.-P., et al. ("Cu/Ag-catalyzed double decarboxylative cross-coupling reaction between cinnamic acids and aliphatic acids in aqueous solution." *RSC Advances*, 2013, 3, 19264-19267), acid 9a can be reacted with trans-aryl (or heteroaryl) acrylic acid 9b to provide compound 9c. Nitrile 9c can be hydrolyzed using a typical alkali hydroxide base at elevated temperature (60° C. to 100° C.), to provide compounds of Formula I-F.

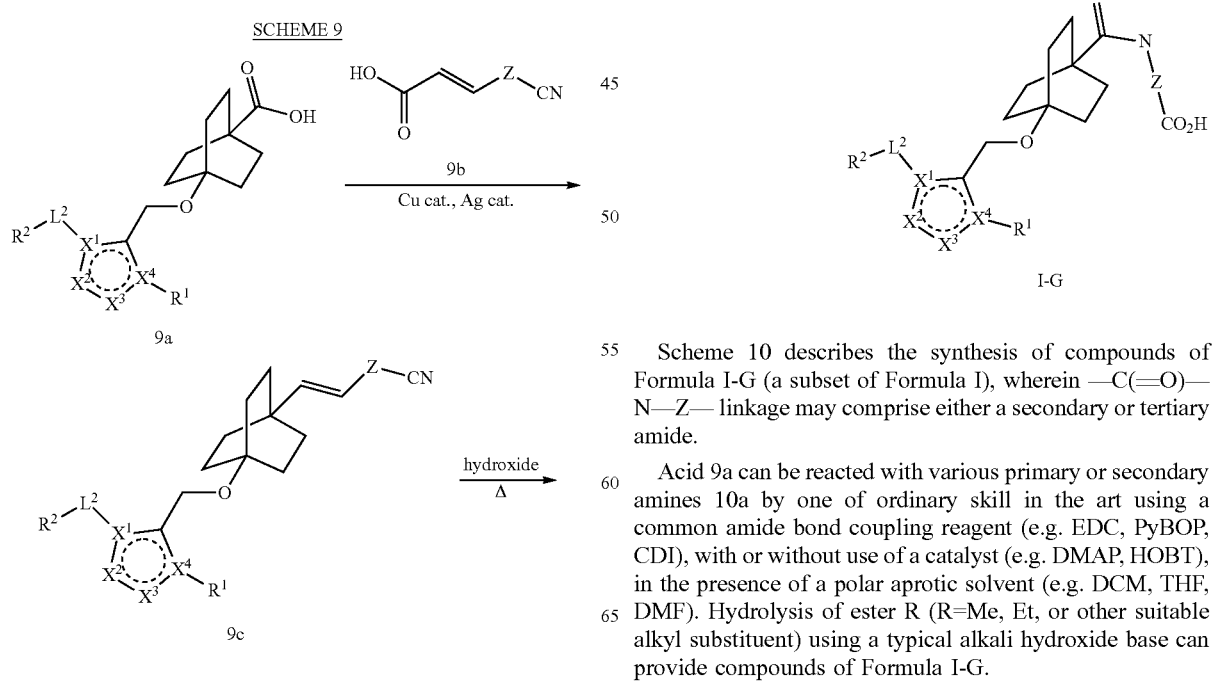

Scheme 10 describes the synthesis of compounds of Formula I-G (a subset of Formula I), wherein —C(=O)—N—Z— linkage may comprise either a secondary or tertiary amide.

Acid 9a can be reacted with various primary or secondary amines 10a by one of ordinary skill in the art using a common amide bond coupling reagent (e.g. EDC, PyBOP, CDI), with or without use of a catalyst (e.g. DMAP, HOBT), in the presence of a polar aprotic solvent (e.g. DCM, THF, DMF). Hydrolysis of ester R (R=Me, Et, or other suitable alkyl substituent) using a typical alkali hydroxide base can provide compounds of Formula I-G.

SCHEME 11

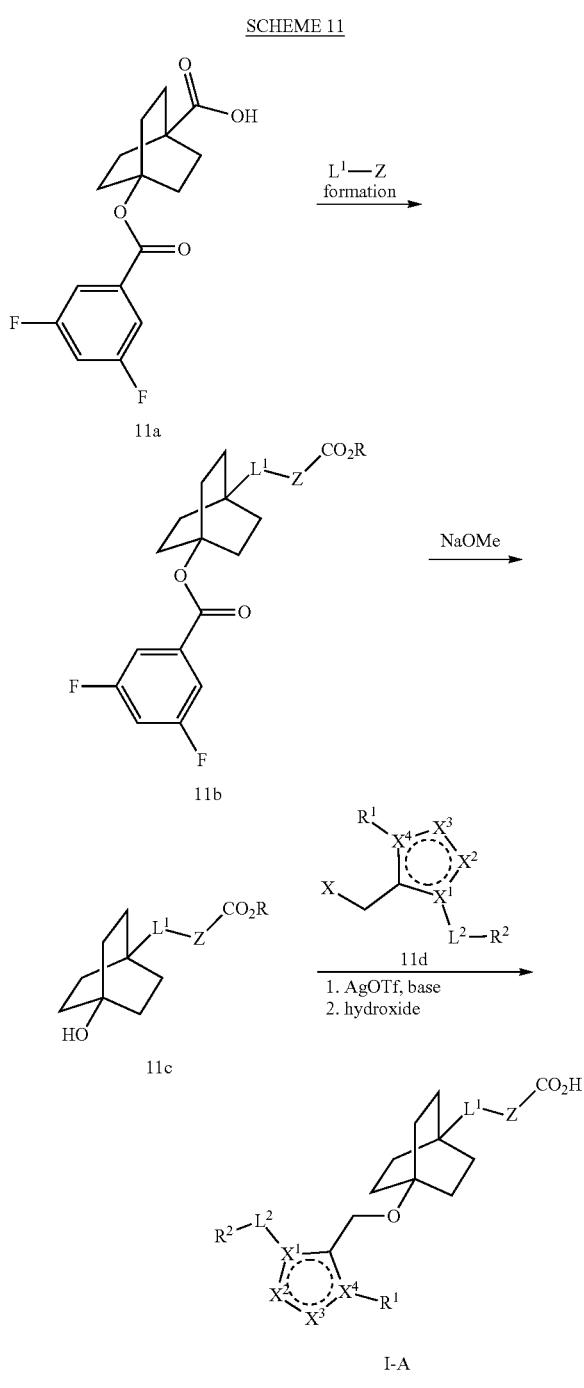

Scheme 11 describes an alternative synthetic approach to compounds of Formula I-A (a subset of Formula I).

Starting material 4-((3,5-difluorobenzoyl)oxy) bicyclo[2.2.2]octane-1-carboxylic acid 11a, can be prepared according to procedures described in WO 2014/159802 (Shi, Y. et al.). From acid 11a, $L^1$-Z formation can be accomplished according methods described in Schemes 1 through 10. Sodium methoxide can be used to selectively cleave 3,5-difluorobenzoate ester compound 11b in the presence of ester R (R=Me, Et, or other suitable alkyl substituent) to provide compound 11c. Heteroaryl methyl halides 11d (X=Cl, Br, I) can be readily prepared by one of ordinary skill in the art using numerous and well established procedures, with representative examples found in WO 2012/087519 (Tully, D. C., et al.), WO 2009/012125 (Genin, M. J., et al.), and WO 2008/051942 (Navas, F. et al.). Using general procedures described in WO 2014/159802 (Shi, Y. et al.), alcohol 11c can be alkylated with halides 11d in the presence of silver triflate and base (e.g. pyridine, 2,6-lutidene, 2,6-di-tert-butylpyridine). Hydrolysis of ester R (R=Me, Et, or other suitable alkyl substituent) using a typical alkali hydroxide base can provide compounds of Formula I-A.

SCHEME 12

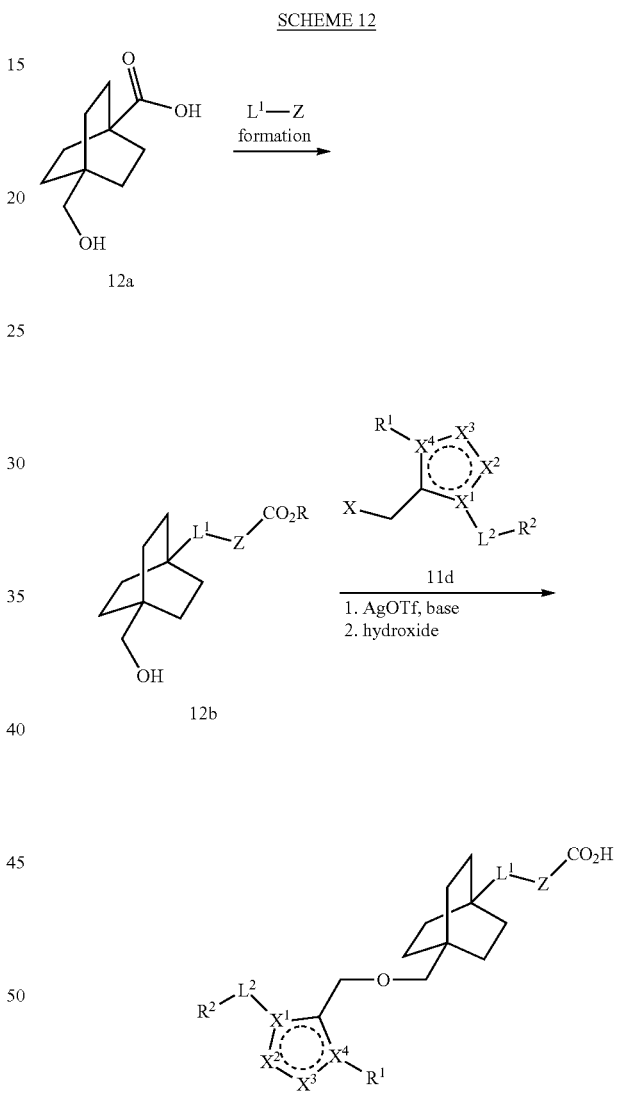

Scheme 6 describes the synthesis of compounds of Formula I-H, (a subset of Formula I).

Starting material 4-(hydroxymethyl)bicyclo[2.2.2]octane-1-carboxylic acid 12a can be prepared by one of ordinary skill in the art following procedures described in WO 2001/034610 (Kiesman W. F. et al.). From acid 12a, $L^1$-Z formation can be accomplished according methods described in Schemes 1 through 10. The resultant alcohol 12b can be reacted with halide 11d by methods described in Scheme 11 to furnish compounds of Formula I-H.

SCHEME 13

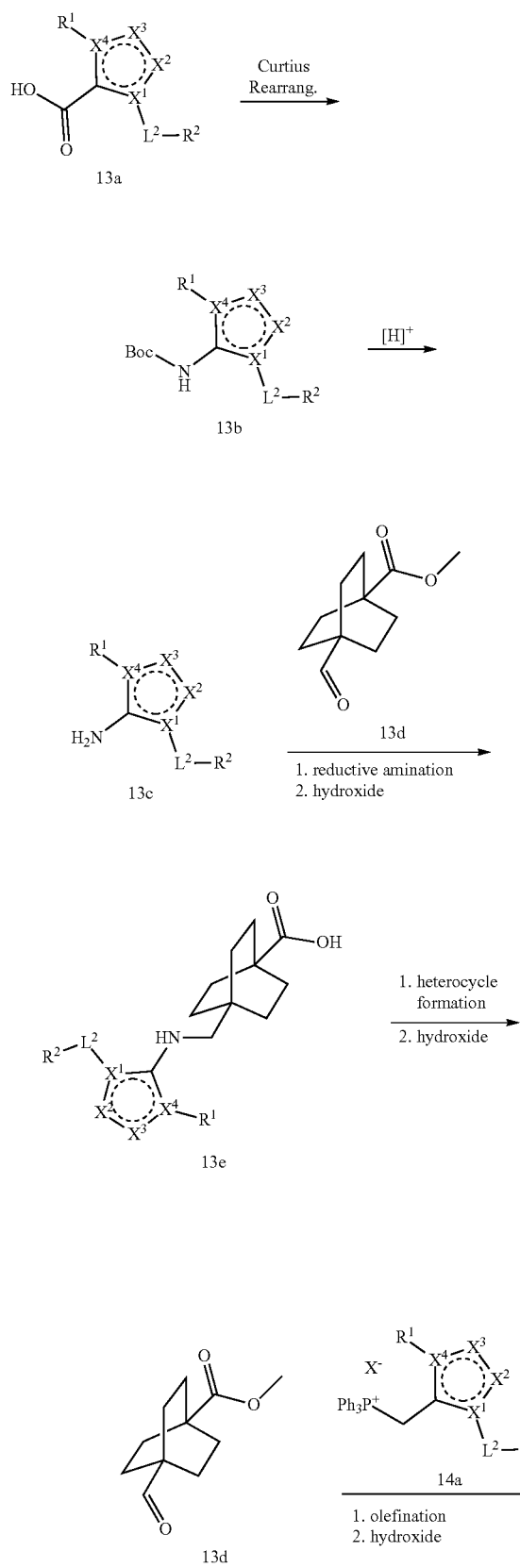

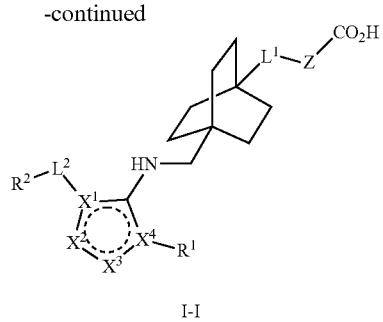

Scheme 13 describes the synthesis of compounds of Formula I-I (a subset of Formula I).

Heteroaryl carboxylate acid compounds 13a can be readily prepared by one of ordinary skill in the art using numerous and well established procedures, with representative examples found in WO 2012/087519 (Tully, D. C., et al.), WO 2009/012125 (Genin, M. J., et al.), and WO 2008/051942 (Navas, F. et al.). Aldehyde 13d can be prepared according to procedures described in US 2015/0133428 (Velaparthi, U. et al.).

Acid 13a can be reacted with diphenylphosphoryl azide (DPPA) ("New convenient reagent for a modified Curtius reaction and for peptide synthesis." Shioiri, T. et al. *J. Am. Chem. Soc.* 1972, 94, 6203-6205) in the presence of t-butanol at elevated temperatures (85° C.) to generate tert-butyl carbamate compound 13b. Deprotection under acidic conditions (e.g. TFA, HCl) can provide amine 13c. Amine 13c can undergo reductive amination with aldehyde 13d in the presence of a polar protic solvent (e.g. MeOH, EtOH) and a reducing agent (e.g. sodium cyanoborohydride, sodium triacetoxyborohydride), with temperature varying between 0° C. and 80° C. Subsequent hydrolysis of the methyl ester using a typical alkali hydroxide base can provide acid 13e. From acid 13e, $L^1$-Z formation can be accomplished according methods described in Schemes 1 through 10. Hydrolysis of ester R (R=Me, Et, or other suitable alkyl substituent) using a typical alkali hydroxide base can provide compounds of Formula I-I.

SCHEME 14

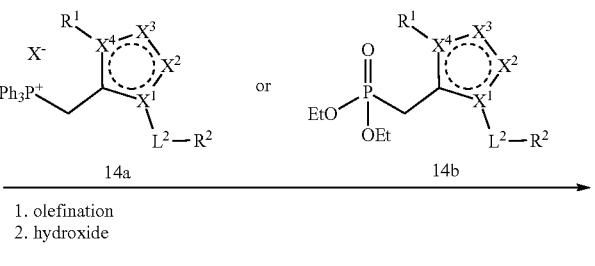

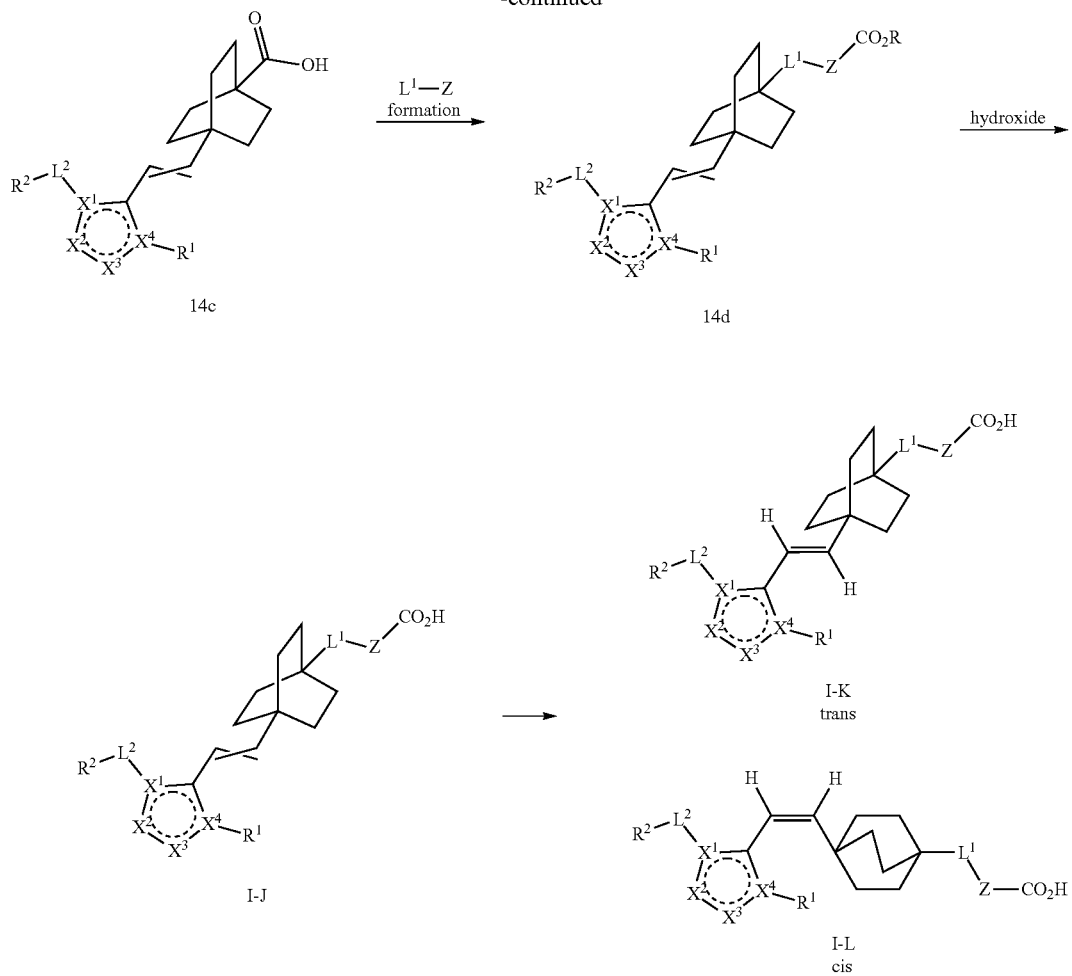

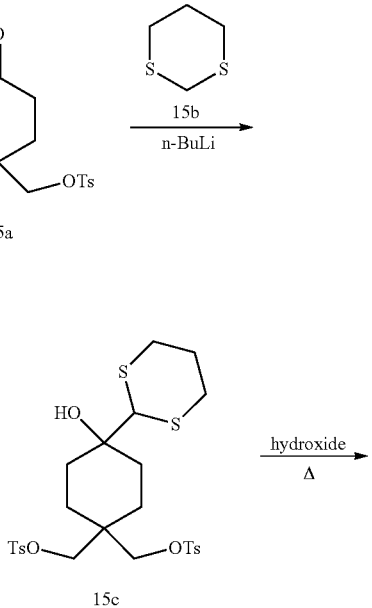

SCHEME 15

Scheme 14 describes the syntheses of compounds of Formula I-J, I-K and I-L (a subset of Formula I).

Phosphonium salt 14a can be prepared from heteroaryl methyl halides 11d (Scheme 11) by methods described in PCT Int. Appl., 2010/127975 (Jakob-Roetne, R. et al.). Phosphonate ester 14b can be readily prepared by one of ordinary skill in the art by reaction of 11d with triethylphosphite at elevated temperatures (100° C. to 160° C.). Aldehyde 13d can be olefinated using phosphonium salt 14a or phosphonate 14b in presence of base (e.g. lithium bis (trimethylsilyl)amide, KOtBu, sodium hydride), in an ethereal solvent (e.g. THF, 1,4-dioxane) at temperatures between −78° C. and 60° C. Hydrolysis of the methyl ester using hydroxide base can provide acid 14c. From acid 14c, $L^1$-Z formation can be accomplished according methods described in Schemes 1 through 10 to provide compound 14d. Hydrolysis of ester R (R=Me, Et, or other suitable alkyl substituent) using a typical alkali hydroxide base can provide compounds of Formula I-J. Compounds of Formula I-J can be separated into trans and cis isomers by one of ordinary skill in the art using common purification methods (e.g. flash column chromatography on silica gel, reverse phase preparative HPLC) to provide compounds of Formula I-K and I-L, respectively.

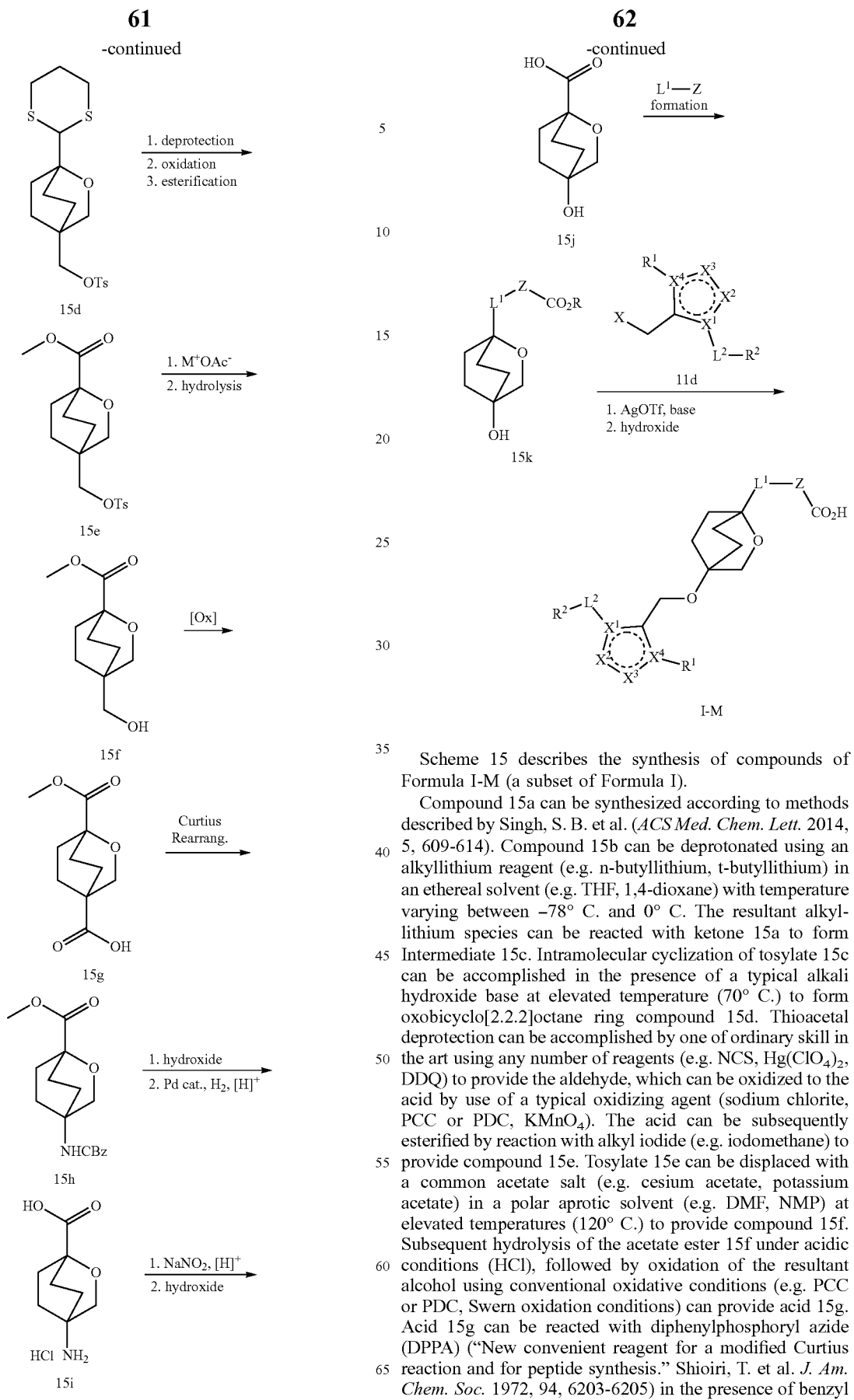

Scheme 15 describes the synthesis of compounds of Formula I-M (a subset of Formula I).

Compound 15a can be synthesized according to methods described by Singh, S. B. et al. (*ACS Med. Chem. Lett.* 2014, 5, 609-614). Compound 15b can be deprotonated using an alkyllithium reagent (e.g. n-butyllithium, t-butyllithium) in an ethereal solvent (e.g. THF, 1,4-dioxane) with temperature varying between −78° C. and 0° C. The resultant alkyllithium species can be reacted with ketone 15a to form Intermediate 15c. Intramolecular cyclization of tosylate 15c can be accomplished in the presence of a typical alkali hydroxide base at elevated temperature (70° C.) to form oxobicyclo[2.2.2]octane ring compound 15d. Thioacetal deprotection can be accomplished by one of ordinary skill in the art using any number of reagents (e.g. NCS, Hg(ClO$_4$)$_2$, DDQ) to provide the aldehyde, which can be oxidized to the acid by use of a typical oxidizing agent (sodium chlorite, PCC or PDC, KMnO$_4$). The acid can be subsequently esterified by reaction with alkyl iodide (e.g. iodomethane) to provide compound 15e. Tosylate 15e can be displaced with a common acetate salt (e.g. cesium acetate, potassium acetate) in a polar aprotic solvent (e.g. DMF, NMP) at elevated temperatures (120° C.) to provide compound 15f. Subsequent hydrolysis of the acetate ester 15f under acidic conditions (HCl), followed by oxidation of the resultant alcohol using conventional oxidative conditions (e.g. PCC or PDC, Swern oxidation conditions) can provide acid 15g. Acid 15g can be reacted with diphenylphosphoryl azide (DPPA) ("New convenient reagent for a modified Curtius reaction and for peptide synthesis." Shioiri, T. et al. *J. Am. Chem. Soc.* 1972, 94, 6203-6205) in the presence of benzyl alcohol with temperature varying between 10° C. and 120°

C. to generate benzylcarbamate compound 15h. Hydrolysis of the methyl ester using a common alkali hydroxide base, followed by hydrogenation of the benzylcarbamate in the presence of palladium catalyst (palladium on carbon), can provide amine 15i. Diazotization of the amine using sodium nitrite, followed by hydrolysis of the diazonium species with an alkali hydroxide base can provide compound 15j. From acid 15j, $L^1$-Z formation can be accomplished according methods described in Schemes 1 through 10 to provide compound 15k. The resultant alcohol 15k can be reacted with halide 11d by methods described in Scheme 11 to furnish compounds of Formula I-M.

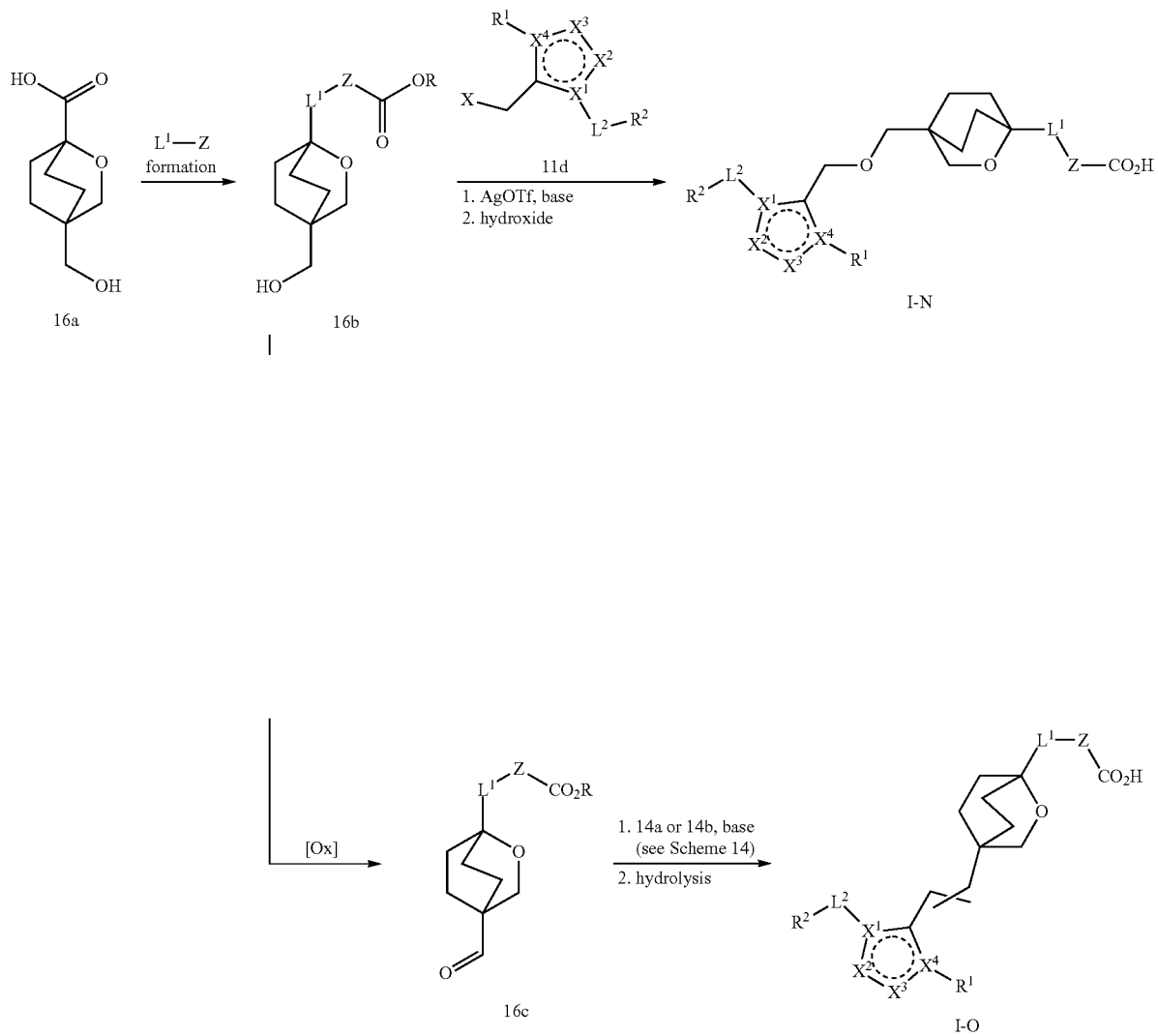

Scheme 16 describes the syntheses of compounds of Formula I-N and I-O (a subset of Formula I).

Compound 16a can be prepared by ester hydrolysis of compound 15f (Scheme 15) using a typical alkali hydroxide base. From acid 16a, $L^1$-Z formation can be accomplished according methods described in Schemes 1 through 10. Alcohol 16b can be reacted with halide 11d using methods described in Scheme 11 to furnish compounds of Formula I-N. Alternatively, compound 16b can be oxidized to aldehyde 16c using methods described in Scheme 6. Aldehyde 16b can be reacted with 14a or 14b using methods described in Scheme 14 to provide compounds of Formula I-O. Compounds of Formula I-O can be separated into trans and cis isomers by one of ordinary skill in the art using common purification methods (e.g. flash column chromatography on silica gel, reverse phase preparative HPLC).

SCHEME 17

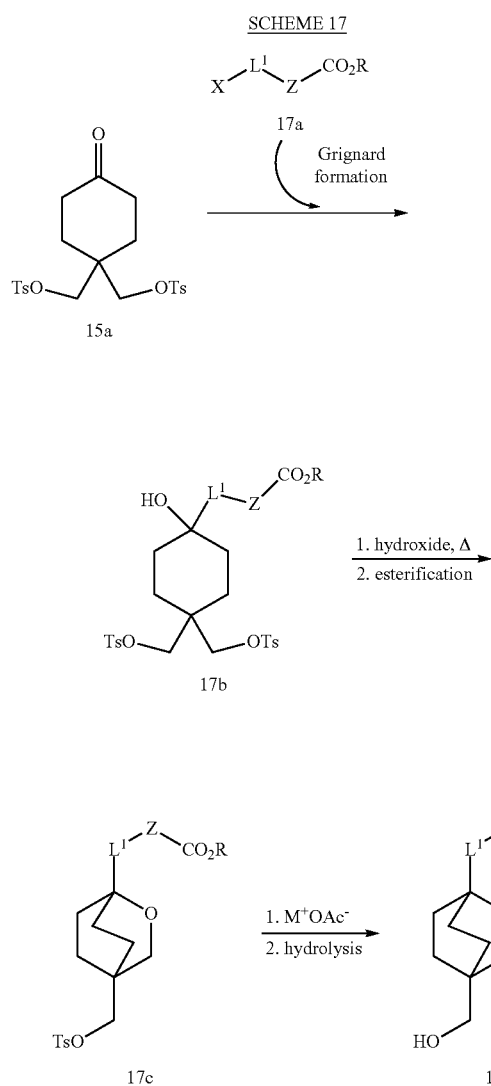

SCHEME 18

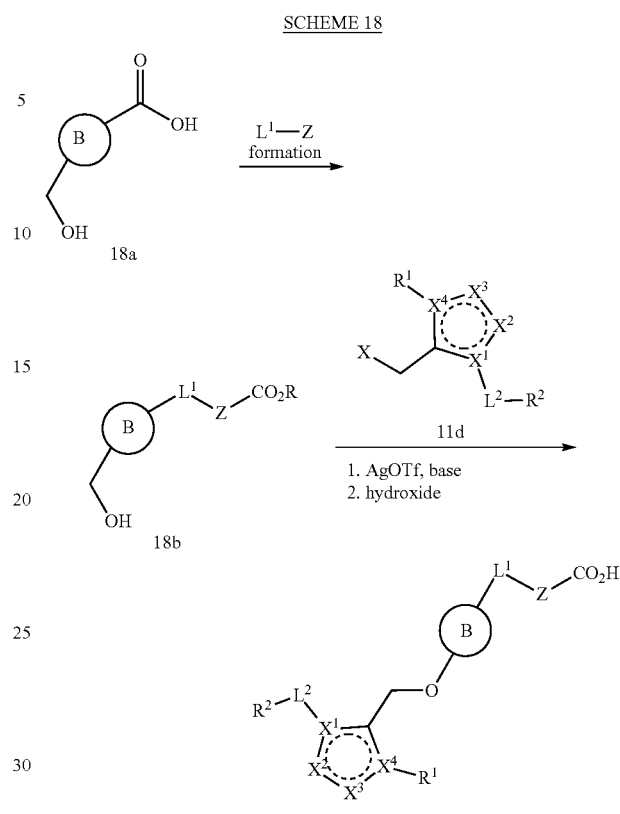

Scheme 17 describes an alternate synthesis of compound 16a, wherein: $L^1$=covalent bond. Z=6- to 10-membered aryl ring.

Aryl halide 17a (X=Cl, Br, I) can be converted to Grignard reagent by one of ordinary skill in the art using numerous known and well established methods ("The Grignard reagent: Preparation, structure, and some reactions." Orchin, M. *J. Chem. Educ.*, 1989, 66, 586). The resultant Grignard reagent can be reacted with ketone 15a in an ethereal solvent (e.g. ether, THF, 1,4-dioxane), with temperatures between −78° C. to 25° C., to provide 17b. Intermediate 17b can be cyclized in the presence of a typical alkali hydroxide base at elevated temperature (70° C.), and subsequently re-esterified with alkyl iodide (e.g. iodomethane, iodoethane) to form oxobicyclo[2.2.2]octane ring compound 17c. Tosylate 17c can be displaced with a common acetate salt (e.g. cesium acetate, potassium acetate) in a polar aprotic solvent (e.g. DMF, NMP) at elevated temperatures (120° C.). The resultant acetate can be hydrolyzed with sodium methoxide to provide alcohol 16a. Methods described in Scheme 16 can be used to convert 16a to compounds of Formula I-N and I-O.

Scheme 18 describes the synthesis of compounds of Formula I-P (a subset of Formula I), wherein: B=bicyclo [1.1.1]pentane or 1,4-substituted cubane.

Acid 18a can be prepared by hydrolysis of the methyl ester precursors. These methyl ester precursors are available commercially, or can be obtained by one of ordinary skill in the art using known methods: methyl 3-(hydroxymethyl) bicyclo[1.1.1]pentane-1-carboxylate (Goh, Y. L. et al. *ACS Med. Chem. Lett.* 2017, 8, 516-520); or methyl (1r,2R,3R, 4s,5s,6S,7S,8r)-4-(hydroxymethyl)cubane-1-carboxylate (Curry, K. et al. WO 99/54280). From acid 18a, $L^1$-Z formation can be accomplished according methods described in Schemes 1 through 10. The resultant alcohol 18b can be reacted with halide 11d by methods described in Scheme 11 to furnish compounds of Formula I-P.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

Example 1

3-(5-(4-((5-cyclopropyl-3-(2-(trifluoromethoxy)phenyl)isoxazol-4-yl)methoxy) bicyclo[2.2.2]octan-1-yl)-1,2,4-oxadiazol-3-yl)benzoic acid

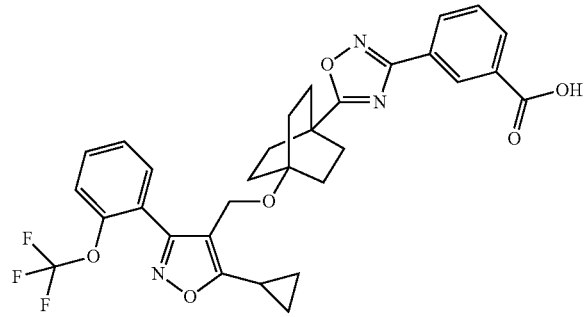

(1)

Step A. Intermediate 1A. Preparation of 4-(3-(3-(methoxycarbonyl)phenyl)-1,2,4-oxadiazol-5-yl) bicyclo[2.2.2]octan-1-yl 3,5-difluorobenzoate

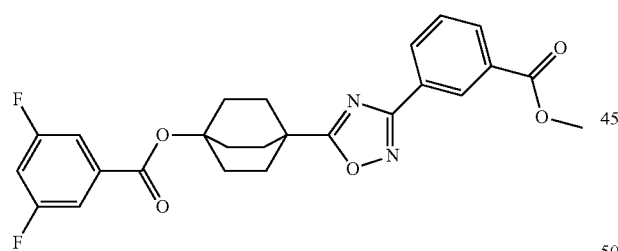

To a 25 mL pear shaped flask were added 4-((3,5-difluorobenzoyl)oxy) bicyclo[2.2.2]octane-1-carboxylic acid (0.20 g, 0.65 mmol) (Shi, Y. et al. WO 2014/159802) and DCM (2 mL). To this mixture was added CDI (0.16 g, 0.97 mmol) in one portion, upon which gas evolution was observed. The reaction was stirred for 1 h, then methyl (Z)-3-(N'-hydroxycarbamimidoyl)benzoate (0.23 g, 1.2 mmol) (Tung, R. D. WO 2016/073545) was added. After stirring 18 h under N$_2$, the solvent was concentrated, the residue was dissolved in toluene (5 mL) and the reaction was stirred at reflux. After 3 h, the mixture was cooled, the solvent was concentrated and the residue was dissolved in EtOAc (50 mL). The organic phase was washed with brine, dried over Na$_2$SO$_4$, filtered and concentrated. The crude product was purified by flash column chromatography (24 g silica gel cartridge; A=Hex, B=EtOAc; 15 min grad.; 0% B to 20% B; flow rate=24 mL/min). The pure fractions were combined, concentrated and dried in vacuo to afford the title compound (0.29 g, 0.62 mmol, 96% yield) as a pale yellow oil. $^1$H NMR (400 MHz, CHLOROFORM-d) δ 8.75 (t, J=1.5 Hz, 1H), 8.28 (d, J=7.7 Hz, 1H), 8.20 (d, J=8.1 Hz, 1H), 7.59 (t, J=7.8 Hz, 1H), 7.55-7.48 (m, 2H), 7.07-6.98 (m, 1H), 3.99 (s, 3H), 2.33 (s, 14H). MS (ESI) 469 (M+H).

Step B. Intermediate 1B. Preparation of methyl 3-(5-(4-hydroxybicyclo[2.2.2]octan-1-yl)-1,2,4-oxadiazol-3-yl)benzoate

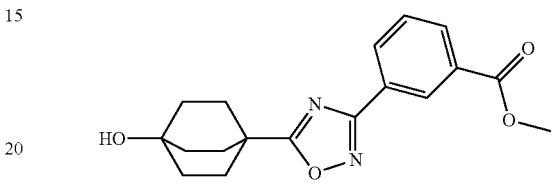

To a 250 mL round bottomed flask were added Intermediate 1A (0.29 g, 0.62 mmol), MeOH (6 mL), THF (12 mL) and sodium methoxide (0.25 mL, 1.2 mmol) (5 N in MeOH). After stirring 1 h under N$_2$, the reaction was quenched with 5% citric acid (aq.), further diluted with water (50 mL), and extracted with EtOAc (2×25 mL). The organic phase was combined, washed with brine, dried over Na$_2$SO$_4$, filtered and concentrated. The crude product was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (0.16 g, 0.47 mmol, 76% yield) as a colorless oil. $^1$H NMR (400 MHz, CHLOROFORM-d) δ 8.74 (t, J=1.4 Hz, 1H), 8.27 (d, J=7.9 Hz, 1H), 8.19 (d, J=7.9 Hz, 1H), 7.63-7.54 (m, 1H), 3.98 (s, 3H), 2.28-2.20 (m, 6H), 1.88-1.80 (m, 6H). MS (ESI) 329 (M+H).

Step C. Intermediate 1C. Preparation of methyl 3-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)benzoate

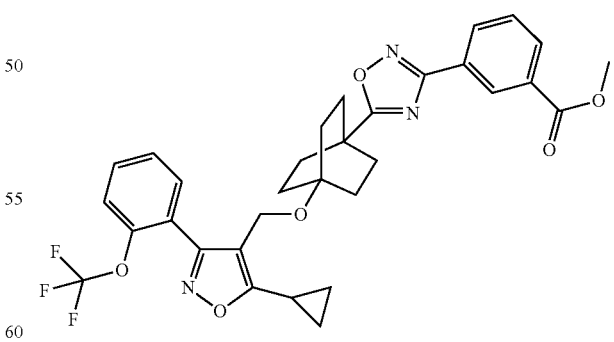

To a 50 mL round bottomed flask were added Intermediate 1B (0.050 g, 0.15 mmol), silver trifluoromethanesulfonate (0.24 g, 0.91 mmol), 2,6-di-tert-butylpyridine (0.20 mL, 0.91 mmol) and DCM (2 mL). The mixture was cooled to 0° C., and 4-(bromomethyl)-5-cyclopropyl-3-(2-(trifluoromethoxy)phenyl)isoxazole (0.083 g, 0.23 mmol) was added. After stirring 18 h under N₂, the mixture was filtered and the resultant filtrate was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (0.029 g, 0.048 mmol, 31% yield) as a colorless oil. $^1$H NMR (400 MHz, METHANOL-d₄) δ 8.66 (s, 1H), 8.27-8.23 (m, 1H), 8.19-8.14 (m, 1H), 7.63-7.56 (m, 3H), 7.50-7.42 (m, 2H), 4.30-4.28 (m, 2H), 3.96 (s, 3H), 3.35-3.31 (m, 1H), 2.19-2.12 (m, 6H), 1.78-1.71 (m, 6H), 1.22-1.12 (m, 4H). MS (ESI) 610 (M+H).

Step D. Example 1

To a 20 mL pear shaped flask were added Intermediate 1C (0.020 g, 0.033 mmol), MeOH (1 mL), and 1 M NaOH (aq.) (0.33 mL, 0.33 mmol). After stirring 18 h, the mixture was diluted with 1 M HCl (aq.) (20 mL) and extracted with EtOAc (2×10 mL). The organic phase was combined, washed with brine, dried over Na₂SO₄, filtered and concentrated. The crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 15 minutes, then a 5-minute hold at 100% B; Flow: 20 mL/min.). Fractions containing the desired product were combined, concentrated and dried in vacuo to afford the title compound (0.017 g, 0.029 mmol, 88% yield). $^1$H NMR (500 MHz, DMSO-d₆) δ 8.64-8.40 (m, 1H), 8.20-8.03 (m, 2H), 7.71-7.63 (m, 2H), 7.63-7.58 (m, 1H), 7.58-7.48 (m, 2H), 4.20 (s, 2H), 2.31-2.22 (m, 1H), 2.10-1.99 (m, 6H), 1.64 (br d, J=7.3 Hz, 6H), 1.20-1.09 (m, 4H). FXR EC₅₀ (nM)=110. MS (ESI) 596 (M+H).

Example 2

4-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)benzoic acid (2)

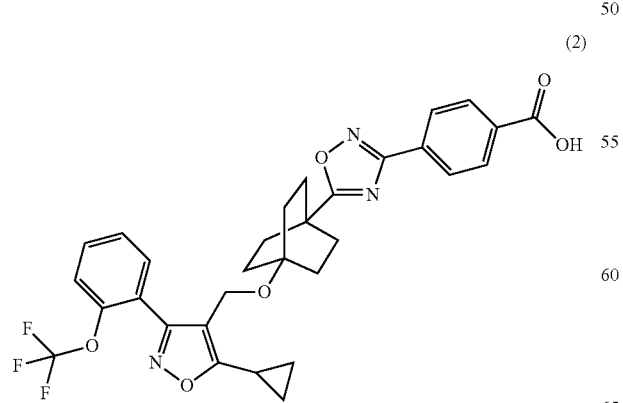

Step A. Intermediate 2A. Preparation of 4-(3-(4-(methoxycarbonyl)phenyl)-1,2,4-oxadiazol-5-yl)bicyclo[2.2.2]octan-1-yl 3,5-difluorobenzoate

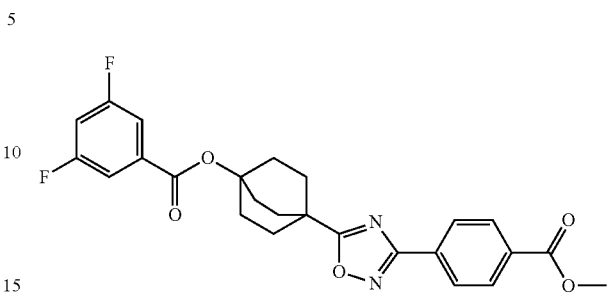

The title compound was prepared according to methods described for the synthesis of Intermediate 1A, substituting methyl (Z)-4-(N'-hydroxycarbamimidoyl) benzoate (Tale, R. H., et al. J. Chem. Pharm. Res., 2011, 3, 496-505) where appropriate: (0.33 g, 0.70 mmol, 87% yield, white solid). $^1$H NMR (400 MHz, CHLOROFORM-d) δ 8.20-8.13 (m, 4H), 7.56-7.47 (m, 2H), 7.07-6.97 (m, 1H), 3.98 (s, 3H), 2.32 (br d, J=1.3 Hz, 12H). MS (ESI) 469 (M+H).

Step B. Intermediate 2B. Preparation of methyl 4-(5-(4-hydroxybicyclo[2.2.2]octan-1-yl)-1,2,4-oxadiazol-3-yl)benzoate

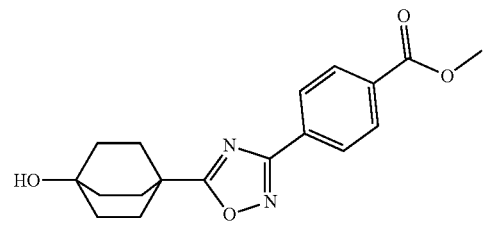 [SMILES: COC(=O)c1ccc(-c2noc(C34CCC(O)(CC3)CC4)n2)cc1]

The title compound was prepared according to methods described for the synthesis of Intermediate 1B, substituting Intermediate 2A where appropriate: (0.19 g, 0.58 mmol, 82% yield, off-white solid). $^1$H NMR (500 MHz, DICHLOROMETHANE-d₂) δ 8.17 (d, J=0.8 Hz, 4H), 3.97 (s, 3H), 2.29-2.18 (m, 6H), 1.89-1.78 (m, 6H). MS (ESI) 329 (M+H).

Step C. Intermediate 2C. Preparation of methyl 4-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)benzoate

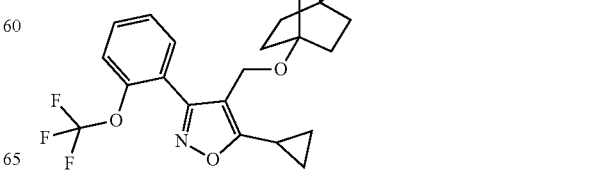

The title compound was prepared according to methods described for the synthesis of Intermediate 1C, substituting Intermediate 2B where appropriate: (0.027 g, 0.044 mmol, 31% yield, pale yellow oil). $^1$H NMR (500 MHz, DMSO-$d_6$) δ 8.17-8.07 (m, 4H), 7.71-7.65 (m, 1H), 7.65-7.61 (m, 1H), 7.60-7.54 (m, 2H), 4.21 (s, 2H), 3.89 (s, 3H), 2.33-2.24 (m, 1H), 2.05 (br s, 6H), 1.65 (br d, J=7.6 Hz, 6H), 1.17-1.11 (m, 2H), 1.10-1.03 (m, 2H). MS (ESI) 610 (M+H).

Step D. Example 2

The title compound was prepared according to methods described for the synthesis of Example 1 (Step D), substituting Intermediate 2C where appropriate: (17 mg, 0.028 mmol, 80% yield). $^1$H NMR (500 MHz, DMSO-$d_6$) δ 8.07 (br s, 4H), 7.71-7.66 (m, 1H), 7.65-7.61 (m, 1H), 7.60-7.52 (m, 2H), 4.21 (s, 2H), 2.32-2.24 (m, 1H), 2.06 (br s, 6H), 1.71-1.58 (m, 6H), 1.22-1.03 (m, 5H). FXR EC$_{50}$ (nM)=170. MS (ESI) 596 (M+H).

Example 3

4-(5-(4-((5-cyclopropyl-3-(2,6-dichlorophenyl)isoxazol-4-yl)methoxy) bicyclo[2.2.2]octan-1-yl)-1,2,4-oxadiazol-3-yl)-N-(methylsulfonyl)benzamide (3)

To a 20 mL scintillation vial were added Example 28 (0.017 g, 0.029 mmol), methanesulfonamide (5.6 mg, 0.059 mmol), DMAP (7.2 mg, 0.059 mmol) and DMF (1 mL). To this mixture was added EDC (0.011 g, 0.059 mmol) and the reaction was stirred. After 2 h, the reaction was filtered and the crude filtrate was purified by preparative HPLC (Column: waters Xbridge c-18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 45-90% B over 20 minutes, then a 5-minute hold at 100% B; Flow: 20 mL/min). Fractions containing the desired product were combined, concentrated and dried in vacuo to afford the title compound (0.0095 g, 0.014 mmol, 49% yield). $^1$H NMR (500 MHz, DMSO-$d_6$) δ 8.11-8.06 (m, 2H), 8.05-8.00 (m, 2H), 7.65-7.60 (m, 2H), 7.59-7.53 (m, 1H), 4.19 (s, 2H), 3.19 (s, 3H), 2.32-2.25 (m, 1H), 2.01 (br d, J=8.2 Hz, 6H), 1.59-1.48 (m, 6H), 1.19-1.12 (m, 2H), 1.11-1.05 (m, 2H). FXR EC$_{50}$ (nM)=890. MS (ESI) 596 (M+H).

Example 4

5-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)-2-methoxybenzoic acid (4)

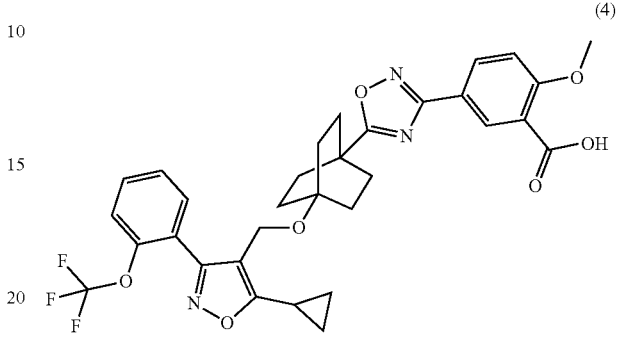

Step A. Intermediate 4A. Preparation of methyl 4-iodobicyclo[2.2.2]octane-1-carboxylate

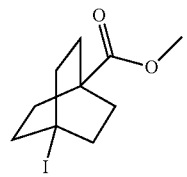

To a 500 mL pear shaped flask were added 4-(methoxycarbonyl) bicyclo[2.2.2]octane-1-carboxylic acid (1.0 g, 4.7 mmol), chlorobenzene (200 mL), lead tetraacetate (2.7 g, 6.1 mmol), followed by iodine (2.6 g, 10 mmol). The reaction was stirred at 80° C. under N$_2$, and irradiated with blue LED (Kessil). After 2.5 h, the reaction was cooled, filtered, and the filter cake was washed with DCM. The combined filtrates were concentrated, and the crude product was purified by flash column chromatography (120 g silica gel cartridge; A=Hex, B=EtOAc; 30 min grad.; 0% B to 10% B; flow rate=80 mL/min) (product is UV-active; TLC Rf=0.5; 4:1 Hex:EtOAc). The pure fractions were combined, concentrated and dried in vacuo to afford the title compound (1.3 g, 4.4 mmol, 92% yield) as a white solid. $^1$H NMR (400 MHz, CHLOROFORM-d) δ 3.65 (s, 3H), 2.61-2.31 (m, 6H), 2.04-1.84 (m, 6H).

Step B. Intermediate 4B. Preparation of 4-iodobicyclo[2.2.2]octane-1-carboxylic acid

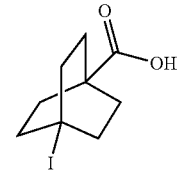 [SMILES: O=C(O)C12CCC(I)(CC1)CC2]

To a 100 mL pear shaped flask were added Intermediate 4A (1.3 g, 4.4 mmol), 1 M NaOH (aq.) (31 mL, 31 mmol), and THF (30 mL). After stirring 18 h, the reaction was diluted with 5% citric acid (aq.) (150 mL) and extracted with EtOAc (2×75 mL). The organic phase was combined, washed with brine, dried over Na$_2$SO$_4$, filtered and concentrated. The product was dried in vacuo to afford the title compound (1.2 g, 4.28 mmol, 98% yield) as a white solid. $^1$H NMR (500 MHz, METHANOL-d$_4$) δ 2.57-2.34 (m, 6H), 2.10-1.86 (m, 6H).

Step C. Intermediate 4C. Preparation of methyl (Z)-5-(N'-hydroxycarbamimidoyl)-2-methoxybenzoate

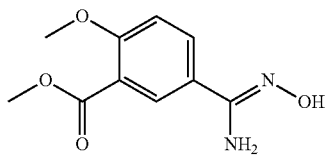 [SMILES: COC(=O)c1cc(/C(N)=N/O)ccc1OC]

To a 100 mL pear shaped flask were added methyl 5-cyano-2-methoxybenzoate (0.23 g, 1.2 mmol), hydroxylamine hydrochloride (0.42 g, 6.0 mmol), MeOH (12 mL), and TEA (0.84 mL, 6.0 mmol). After stirring 18 h, the solvent was concentrated and the residue was dissolved in EtOAc (150 mL). The organic phase was washed with brine, dried over Na$_2$SO$_4$, filtered and concentrated. The crude product was purified by flash column chromatography (80 g silica gel cartridge; A=Hex, B=EtOAc; 25 min grad.; 0% B to 100% B; flow rate=60 mL/min). The pure fractions were combined, concentrated and dried in vacuo to afford the title compound (0.252 g, 1.124 mmol, 93% yield) as a white solid. $^1$H NMR (400 MHz, DMSO-d$_6$) δ 9.55 (s, 1H), 7.98 (d, J=2.2 Hz, 1H), 7.87-7.78 (m, 1H), 7.16 (d, J=8.8 Hz, 1H), 5.82 (s, 2H), 3.85 (s, 3H), 3.80 (s, 3H). MS (ESI) 225 (M+H).

Step D. Intermediate 4D. Preparation of methyl 5-(5-(4-iodobicyclo[2.2.2]octan-1-yl)-1,2,4-oxadiazol-3-yl)-2-methoxybenzoate

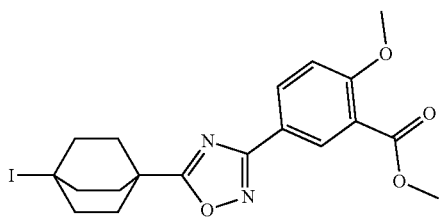 [SMILES: COC(=O)c1cc(-c2noc(C34CCC(I)(CC3)CC4)n2)ccc1OC]

Step 1: To a 100 mL pear shaped flask were added Intermediate 4B (0.21 g, 0.75 mmol) and DCM (3 mL). To this mixture was added CDI (0.18 g, 1.1 mmol) in one portion, upon which gas evolution was observed. After stirring 15 min, Intermediate 4C (0.25 g, 1.1 mmol) was added and the reaction was stirred under N$_2$ for 18 h.

Step 2: The solvent was concentrated and the residue was dissolved in toluene (5 mL) and stirred at reflux. After 5 h, the reaction was cooled and the solvent was concentrated. The residue was dissolved in EtOAc (50 mL), washed with brine, dried over Na$_2$SO$_4$, filtered and concentrated. The crude product was purified by flash column chromatography (24 g silica gel cartridge; A=Hex, B=EtOAc; 15 min grad.; 0% B to 20% B; flow rate=24 mL/min). The pure fractions were combined, concentrated and dried in vacuo to afford the title compound (0.30 g, 0.64 mmol, 85% yield) as a white solid. $^1$H NMR (500 MHz, CHLOROFORM-d) δ 8.64-8.47 (m, 1H), 8.35-8.14 (m, 1H), 7.44-7.23 (m, 1H), 7.21-7.01 (m, 1H), 3.99 (s, 3H), 3.94 (s, 3H), 2.79-2.57 (m, 6H), 2.36-2.16 (m, 6H). MS (ESI) 469 (M+H).

Step E. Example 4

Step 1. To a 20 mL scintillation vial equipped with a pressure release cap were added Intermediate 4D (0.05 g, 0.11 mmol), (5-cyclopropyl-3-(2-(trifluoromethoxy)phenyl)isoxazol-4-yl)methanol (0.096 g, 0.32 mmol), silver trifluoromethanesulfonate (0.22 g, 0.85 mmol), and 2,6-di-tert-butylpyridine (0.48 mL, 2.1 mmol). The vessel was flushed with nitrogen, capped and stirred at 80° C. for 18 h. The reaction was cooled, diluted with DCM:MeOH (1:1; 4 mL), the solids were filtered and the filtrate was concentrated. The residue was filtered through a plug of SiO$_2$, eluting with hexanes first, then EtOAc to collect crude product. The filtrate was concentrated and the residue was taken onto the next step.

Step 2: The product of Step 1 above was dissolved in 1 M NaOH (aq.) (10 mL) and THF (10 mL) and stirred at 45° C. After 1 h, the reaction was cooled, diluted with 5% citric acid (aq.) (50 mL) and extracted with EtOAc (2×25 mL). The organic phase was combined, washed with brine, dried over Na$_2$SO$_4$, filtered and concentrated. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 57-82% B over 20 minutes, then a 2-minute hold at 100% B; Flow: 20 mL/min.). Fractions containing the desired product were combined, concentrated and dried in vacuo to afford the title compound (13 mg, 0.021 mmol, 19% yield). $^1$H NMR (500 MHz, DMSO-d$_6$) δ 8.21 (s, 1H), 8.10-8.04 (m, 1H), 7.71-7.65 (m, 1H), 7.61 (s, 1H), 7.56 (br s, 2H), 7.29 (d, J=8.9 Hz, 1H), 4.21 (s, 2H), 3.89 (s, 3H), 2.31-2.23 (m, 1H), 2.07-2.00 (m, 6H), 1.68-1.59 (m, 6H), 1.17-1.10 (m, 2H), 1.10-1.03 (m, 2H). FXR EC$_{50}$ (nM)=110. MS (ESI) 626 (M+H).

Example 6

2-(4-((5-cyclopropyl-3-(2-(trifluoromethyl)phenyl)
isoxazol-4-yl)methoxy) bicyclo[2.2.2]octan-1-yl)
benzo[d]thiazole-6-carboxylic acid

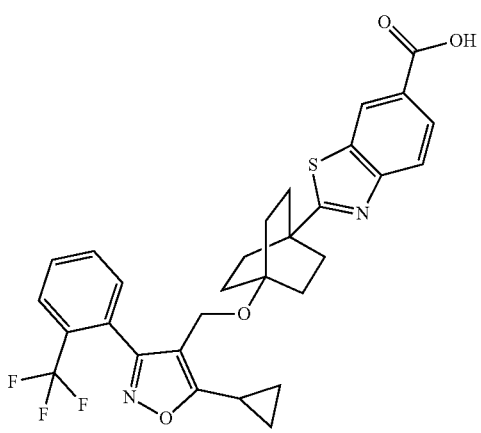

(6)

Step A. Intermediate 6A. Preparation of 4-(6-cyanobenzo[d]thiazol-2-yl) bicyclo[2.2.2]octan-1-yl 3,5-difluorobenzoate

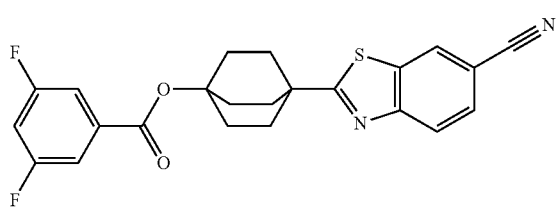 [SMILES: N#Cc1ccc2nc(C34CCC(OC(=O)c5cc(F)cc(F)c5)(CC3)CC4)sc2c1]

To a 20 mL scintillation vial equipped with a pressure release cap were added 4-((3,5-difluorobenzoyl)oxy)bicyclo[2.2.2]octane-1-carboxylic acid (0.3 g, 0.97 mmol), 4-amino-3-mercaptobenzonitrile (0.17 g, 1.2 mmol) (See generally Chedekel, M. R., et al. Synth. Commun. 1980, 10, 167-173; synthesis of various 2-aminobenzenethiols), pyridine (0.24 mL, 2.9 mmol) and DCE (4 mL). To this mixture was added T3P (1.4 mL, 2.4 mmol) (50% w/v solution in EtOAc) and the vial was capped and the homogenous solution was stirred at 80° C. After 18 h, a yellowish precipitate was observed. The reaction was cooled, the solvent concentrated and the crude product was purified by flash column chromatography (40 g silica gel cartridge; A=Hex, B=EtOAc; 20 min grad.; 0% B to 100% B; flow rate=24 mL/min). The pure fractions were combined, concentrated and dried in vacuo to afford the title compound (0.39 g, 0.92 mmol, 95% yield) as a pale yellow solid. $^1$H NMR (400 MHz, CHLOROFORM-d) δ 8.26-8.19 (m, 1H), 8.08-8.03 (m, 1H), 7.77-7.70 (m, 1H), 7.56-7.47 (m, 2H), 7.06-6.99 (m, 1H), 2.40-2.27 (m, 12H). MS (ESI) 425 (M+H).

Step B. Intermediate 6B. Preparation of 2-(4-hydroxybicyclo[2.2.2]octan-1-yl) benzo[d]thiazole-6-carbonitrile

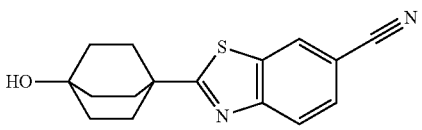 [SMILES: N#Cc1ccc2nc(C34CCC(O)(CC3)CC4)sc2c1]

To a 100 mL pear shaped flask were added Intermediate 6A (0.39 g, 0.92 mmol), THF (9 mL) and MeOH (9 mL). To this mixture was added sodium methoxide (0.37 mL, 1.8 mmol) (5 N solution in THF) and the reaction was stirred. After 1 h, the reaction was diluted with water (50 mL), acidified with 5% citric acid (aq.) and extracted with EtOAc (2×25 mL). The organic phase was combined, washed with brine, dried over Na$_2$SO$_4$, filtered and concentrated. The crude product was purified by flash column chromatography (40 g silica gel cartridge; A=Hex, B=EtOAc; 20 min grad.; 0% B to 60% B; flow rate=40 mL/min). The pure fractions were combined, concentrated and dried in vacuo to afford the title compound (0.35 g, 0.92 mmol, 75% yield) as a pale yellow solid. $^1$H NMR (500 MHz, METHANOL-d$_4$) δ 8.44 (d, J=1.1 Hz, 1H), 8.06 (d, J=8.3 Hz, 1H), 7.80 (dd, 1.5 Hz, 1H), 2.28-2.18 (m, 6H), 1.87-1.83 (m, 6H). MS (ESI) 285 (M+H).

Step C. Example 6

Step 1. To 50 mL vial were added Intermediate 6B (0.11 g, 0.30 mmol), silver trifluoromethanesulfonate (0.46 g, 1.8 mmol), 2,6-di-tert-butylpyridine (0.39 mL, 1.8 mmol) and THF (6 mL). The vessel was flushed with N$_2$ and cooled to 0° C. To this mixture was added 4-(bromomethyl)-5-cyclopropyl-3-(2-(trifluoromethyl)phenyl)isoxazole (0.16 g, 0.45 mmol), the vessel was flushed again with N$_2$ and the mixture was stirred at rt. After 48 h, the reaction was filtered and the filtrate was concentrated. The crude residue was purified by flash column chromatography (40 g silica gel cartridge; A=Hex, B=EtOAc; 25 min grad.; 0% B to 100% B; flow rate=40 mL/min). The pure fractions were combined, concentrated and dried in vacuo. The material was taken onto the next step without characterization.

Step 2: The product of Step 1 above was dissolved in MeOH (5 mL), THF (5 mL) and 1 M NaOH (aq.) (5 mL). After stirring at 90° C. for 18 h, the reaction was cooled, diluted with 5% citric acid (aq.) (50 mL) and extracted with EtOAc (2×25 mL). The organic phase was combined, washed with brine, dried over Na$_2$SO$_4$, filtered and concentrated. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 40-80% B over 24 minutes, then a 5-minute hold at 100% B; Flow: 20 mL/min). Fractions containing the desired product were combined, concentrated and dried in vacuo to afford the title compound (2.4 mg, 4.1 μmol, 1% yield). $^1$H NMR (500 MHz, DMSO-d$_6$) δ 8.65 (s, 1H), 8.00 (s, 1H), 7.98-7.94 (m, 1H), 7.92 (d, J=7.6 Hz, 1H), 7.82 (br d, J=7.3 Hz, 1H), 7.77 (br d, J=7.6 Hz, 1H), 7.57 (d, J=7.3 Hz, 1H), 4.14 (s, 2H), 2.31-2.24 (m, 1H), 2.07-1.96 (m, 6H), 1.59 (br s, 6H), 1.16-1.11 (m, 2H), 1.10-1.04 (m, 2H). FXR EC$_{50}$ (nM) =4200. MS (ESI) 569 (M+H).

Example 7

(E)-3-(2-(4-((5-cyclopropyl-3-(2,6-dichlorophenyl) isoxazol-4-yl)methoxy) bicyclo[2.2.2]octan-1-yl) vinyl)benzoic acid (7)

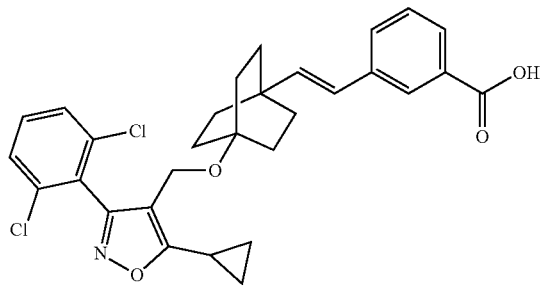

Step A. Intermediate 7A. Preparation of (E)-4-(3-cyanostyryl)bicyclo[2.2.2]octan-1-yl 3,5-difluorobenzoate

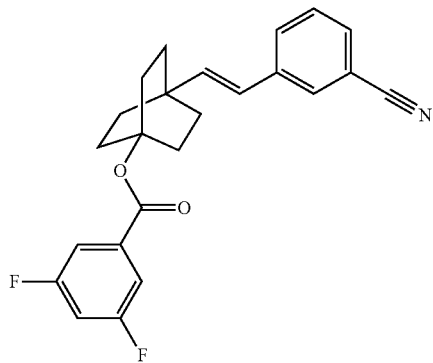 [SMILES: N#Cc1cccc(/C=C/C23CCC(OC(=O)c4cc(F)cc(F)c4)(CC2)CC3)c1]

To a 25 mL pear shaped flask were added 4-((3,5-difluorobenzoyl)oxy) bicyclo[2.2.2]octane-1-carboxylic acid (0.27 g, 0.87 mmol), (E)-3-(3-cyanophenyl)acrylic acid (0.10 g, 0.58 mmol), copper powder (1.8 mg, 0.029 mmol), silver nitrate (0.020 g, 0.12 mmol), potassium persulfate (0.16 g, 0.56 mmol), acetonitrile (2 mL) and water (2 mL). The reaction flask was equipped with a reflux condenser and the mixture was stirred at 90° C., uncapped and open to the air. After 18 h, the reaction was cooled, diluted with water (50 mL) and extracted with EtOAc (2×25 mL). The organic phase was combined, washed with brine, dried over Na$_2$SO$_4$, filtered and concentrated. The crude product was purified by flash column chromatography (40 g silica gel cartridge; A=Hex, B=EtOAc; 30 min grad.; 0% B to 50% B; flow rate=40 mL/min). The pure fractions were combined, concentrated and dried in vacuo to afford the title compound (98 mg, 0.25 mmol, 43% yield) as a pale yellow oil. $^1$H NMR (400 MHz, CHLOROFORM-d) δ 7.66-7.62 (m, 1H), 7.59-7.54 (m, 1H), 7.54-7.47 (m, 3H), 7.45-7.38 (m, 1H), 7.04-6.97 (m, 1H), 6.31-6.17 (m, 2H), 2.28-2.18 (m, 6H), 1.90-1.82 (m, 6H). MS (ESI) 394 (M+H).

Step B. Intermediate 7B. Preparation of (E)-3-(2-(4-hydroxybicyclo[2.2.2]octan-1-yl)vinyl)benzonitrile

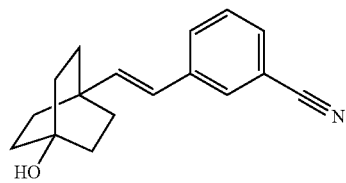 [SMILES: N#Cc1cccc(/C=C/C23CCC(O)(CC2)CC3)c1]

To a 250 mL round bottomed flask were added Intermediate 7A (0.36 g, 0.92 mmol), MeOH (10 mL), THF (10 mL) and sodium methoxide (0.37 mL, 1.8 mmol) (5 M in MeOH). The reaction was stirred under N$_2$. After 1 h, the reaction quenched with 5% citric acid (aq.), diluted with water (50 mL) and extracted with EtOAc (2×25 mL). The organic phase was combined, washed with brine, dried over Na$_2$SO$_4$, filtered and concentrated. The crude product was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (0.21 g, 0.83 mmol, 91% yield) as an off-white solid. $^1$H NMR (500 MHz, CHLOROFORM-d) δ 7.65-7.61 (m, 1H), 7.59-7.54 (m, 1H), 7.52-7.47 (m, 1H), 7.44-7.37 (m, 1H), 6.30-6.16 (m, 2H). MS (ESI) 254 (M+H).

Step C. Example 7

The title compound was prepared according methods described for the synthesis of Example 6 (Step C), by reaction of Intermediate 7B and 4-(bromomethyl)-5-cyclopropyl-3-(2,6-dichlorophenyl)isoxazole: (2.4 mg, 4.5 μmol, 2% yield). $^1$H NMR (500 MHz, DMSO-d$_6$) δ 8.02-7.94 (m, 1H), 7.87-7.81 (m, 1H), 7.69-7.65 (m, 1H), 7.64-7.59 (m, 1H), 7.58-7.53 (m, 1H), 7.50-7.43 (m, 1H), 7.38-7.29 (m, 1H), 6.26-6.18 (m, 2H), 4.14 (s, 2H), 2.27 (br s, 1H), 1.63-1.52 (m, 6H), 1.44-1.34 (m, 6H), 1.13 (br d, J=8.2 Hz, 2H), 1.06 (br d, J=2.7 Hz, 2H). FXR EC$_{50}$ (nM)=150. MS (ESI) 539 (M+H).

Example 8

(E)-4-(((4-(3-(1H-tetrazol-5-yl)styryl)bicyclo[2.2.2] octan-1-yl)oxy)methyl)-5-cyclopropyl-3-(2-(trifluoromethoxy)phenyl)isoxazole (8)

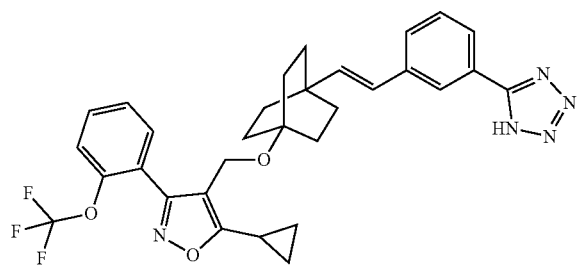

Step A. Intermediate 8A. Preparation of (E)-3-(2-(4-((5-cyclopropyl-3-(2-(trifluoromethoxy)phenyl)isoxazol-4-yl)methoxy)bicyclo[2.2.2]octan-1-yl)vinyl) benzonitrile

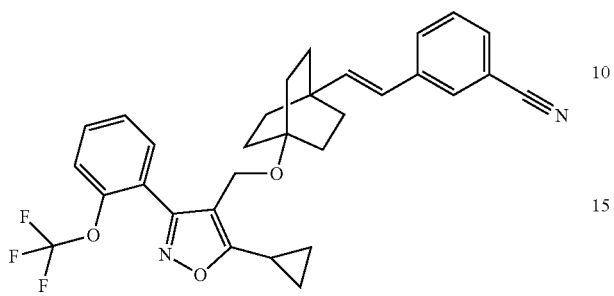

To a 100 mL round bottomed flask were added Intermediate 7B (0.15 g, 0.59 mmol), silver trifluoromethanesulfonate (0.91 g, 3.6 mmol), 2,6-di-tert-butylpyridine (0.78 mL, 3.6 mmol) and DCM (8 mL). The mixture was flushed with $N_2$ and cooled to 0° C. To this mixture was added 4-(bromomethyl)-5-cyclopropyl-3-(2-(trifluoromethoxy)phenyl)isoxazole (0.32 g, 0.89 mmol) and the vessel was flushed again with $N_2$ and stirred. After 18 h, the mixture was diluted with DCM:MeOH (4 mL; 1:1), filtered and the filtrate was concentrated. The crude product was purified by flash column chromatography (24 g silica gel cartridge; A=Hex, B=EtOAc; 15 min grad.; 0% B to 50% B; flow rate=24 mL/min). The pure fractions were combined, concentrated and dried in vacuo to afford the title compound (0.060 g, 0.11 mmol, 19% yield) as a colorless residue. $^1$H NMR (400 MHz, CHLOROFORM-d) δ 7.54-7.48 (m, 2H), 7.47-7.35 (m, 3H), 7.34-7.21 (m, 3H), 6.09 (d, J=3.7 Hz, 2H), 4.18 (s, 2H), 2.12-2.00 (m, 1H), 1.59 (br d, J=5.3 Hz, 12H), 1.17-1.11 (m, 2H), 1.04-0.97 (m, 2H). MS (ESI) 535 (M+H).

Step B. Example 8

To a 20 mL scintillation vial equipped with a pressure release cap were added Intermediate 8A (0.060 g, 0.11 mmol), toluene (5 mL), dibutyltin oxide (0.028 g, 0.11 mmol) and azidotrimethylsilane (0.13 g, 1.1 mmol). The vessel was capped and stirred at 100° C. After 18 h, the reaction was cooled, diluted with EtOAc (50 mL) and quenched slowly with ceric ammonium nitrate (0.68 g, 1.2 mmol) dissolved in water (50 mL). The mixture was stirred for 10 min, the layers were separated and the aqueous phase extracted with EtOAc (20 mL). The organic phase was combined, washed with brine, dried over $Na_2SO_4$, filtered and concentrated. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 60-85% B over 25 minutes, then a 2-minute hold at 85% B; Flow: 20 mL/min). Fractions containing the desired product were combined and dried in vacuo to afford the title compound (4.7 mg, 8.0 μmot, 7% yield). $^1$H NMR (500 MHz, DMSO-$d_6$) δ 8.07-7.97 (m, 1H), 7.87-7.79 (m, 1H), 7.70-7.64 (m, 1H), 7.64-7.58 (m, 1H), 7.58-7.48 (m, 4H), 6.38-6.21 (m, 2H), 2.30-2.20 (m, 1H), 1.63 (br d, J=8.8 Hz, 6H), 1.54 (br d, J=8.0 Hz, 5H), 1.18-1.10 (m, 2H), 1.09-1.02 (m, 2H). FXR $EC_{50}$ (nM)=380. MS (ESI) 578 (M+H).

Example 9

6-(5-(4-((5-cyclopropyl-3-(2,6-dichlorophenyl)isoxazol-4-yl)methoxy)bicyclo[2.2.2]octan-1-yl)-1,2,4-oxadiazol-3-yl)nicotinic acid

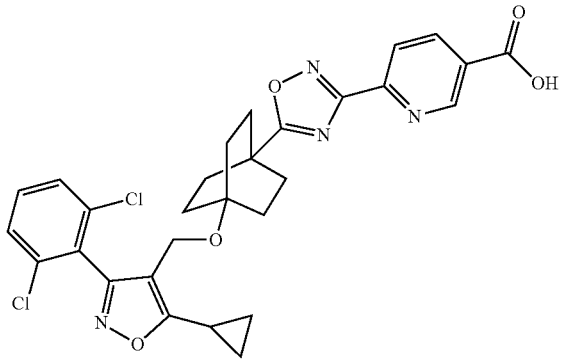

(9)

Step A. Intermediate 9A. Preparation of methyl 6-(5-(4-iodobicyclo[2.2.2]octan-1-yl)-1,2,4-oxadiazol-3-yl)nicotinate

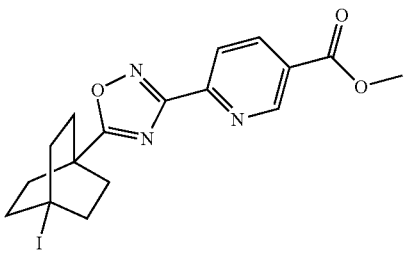 [SMILES: COC(=O)c1ccc(-c2noc(C34CCC(I)(CC3)CC4)n2)nc1]

The title compound was prepared according to methods described for the synthesis of Intermediate 4D, starting with Intermediate 4B and substituting methyl (Z)-6-(N'-hydroxycarbamimidoyl)nicotinate (Ho, J. Z. et al. WO 2001/079261) where appropriate: (0.085 g, 0.19 mmol, 19% yield, colorless oil). $^1$H NMR (500 MHz, CHLOROFORM-d) δ 9.38 (s, 1H), 8.47 (dd, J=8.3, 1.9 Hz, 1H), 8.22 (d, J=8.3 Hz, 1H), 4.02 (s, 3H), 2.69-2.55 (m, 6H), 2.28-2.20 (m, 6H). MS (ESI) 440 (M+H).

Step B. Example 9 The title compound was prepared according to methods described for the synthesis of Example 4 (Step E), by reaction of Intermediate 9A and (5-cyclopropyl-3-(2,6-dichlorophenyl)isoxazol-4-yl)methanol: (12 mg, 0.020 mmol, 22% yield). $^1$H NMR (500 MHz, DMSO-d$_6$) δ 9.27-9.05 (m, 1H), 8.50-8.32 (m, 1H), 8.18-7.98 (m, 1H), 7.67-7.60 (m, 2H), 7.60-7.54 (m, 1H), 4.21-4.14 (m, 2H), 2.34-2.26 (m, 1H), 2.05-1.96 (m, 6H), 1.54-1.45 (m, 6H), 1.19-1.12 (m, 2H), 1.11-1.04 (m, 2H). FXR EC$_{50}$ (nM)=950. MS (ESI) 582 (M+H)

Example 10

2-(5-(4-((5-cyclopropyl-3-(2,6-dichlorophenyl)isoxazol-4-yl)methoxy)bicyclo[2.2.2]octan-1-yl)-1,2,4-oxadiazol-3-yl)isonicotinic acid (10)

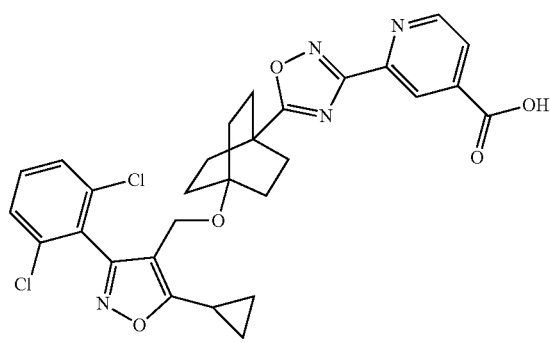

Step A. Intermediate 10A. Preparation of methyl (Z)-2-(N'-hydroxycarbamimidoyl)isonicotinate The title compound was prepared according to methods described for the synthesis of Intermediate 4C, using methyl 2-cyanoisonicotinate as starting material: (0.51 g, 2.6 mmol, 85% yield, white solid). $^1$H NMR (500 MHz, METHANOL-d$_4$) δ 11.06-11.06 (m, 1H), 8.75 (d, J=5.2 Hz, 1H), 8.50-8.35 (m, 1H), 7.95-7.80 (m, 1H), 3.98 (s, 3H). MS (ESI) 196 (M+H).

Step B. Intermediate 10B. Preparation of methyl 2-(5-(4-((3,5-difluorobenzoyl)oxy)bicyclo[2.2.2]octan-1-yl)-1,2,4-oxadiazol-3-yl)isonicotinate

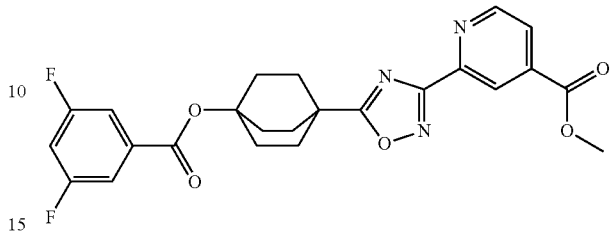

The title compound was prepared according to methods described for the synthesis of Intermediate 1A, substituting Intermediate 10A where appropriate: (0.14 g, 0.30 mmol, 31% yield, white solid). $^1$H NMR (500 MHz, THF) δ 7.07 (d, J=5.0 Hz, 1H), 6.71 (s, 1H), 6.14 (dd, J=5.0, 1.7 Hz, 1H), 5.75-5.65 (m, 2H), 5.49-5.37 (m, 1H), 2.14 (s, 3H), 0.57-0.46 (m, 12H). MS (ESI) 470 (M+H).

Step C. Intermediate 10C. Preparation of methyl 2-(5-(4-hydroxybicyclo[2.2.2]octan-1-yl)-1,2,4-oxadiazol-3-yl)isonicotinate

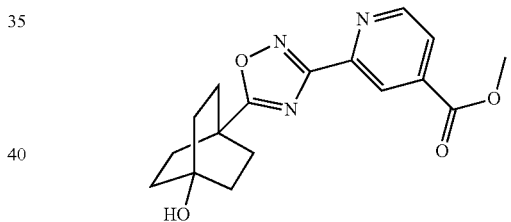

The title compound was prepared according to methods described for the synthesis Intermediate 1B: (0.097 g, 0.30 mmol, 99% yield, colorless oil). $^1$H NMR (500 MHz, METHANOL-d$_4$) δ 8.93-8.87 (m, 1H), 8.65-8.57 (m, 1H), 8.13-8.05 (m, 1H), 2.95 (s, 3H), 2.29-2.19 (m, 6H), 1.88-1.78 (m, 6H). MS (ESI) 330 (M+H).

Step D. Example 10

The title compound was prepared according to methods described for the synthesis of Example 1 (Step C and D), by reaction of Intermediate 10C and 4-(bromomethyl)-5-cyclopropyl-3-(2,6-dichlorophenyl)isoxazole: (0.026 g, 0.045 mmol, 15% yield). $^1$H NMR (500 MHz, DMSO-d$_6$) δ 8.85-8.77 (m, 1H), 8.40-8.32 (m, 1H), 7.97-7.88 (m, 1H), 7.66-7.60 (m, 2H), 7.60-7.52 (m, 1H), 4.22-4.12 (m, 2H), 2.35-2.23 (m, 1H), 2.04-1.95 (m, 6H), 1.56-1.42 (m, 6H), 1.15 (br s, 2H), 1.10-1.03 (m, 2H). FXR EC$_{50}$ (nM)=2700. MS (ESI) 582 (M+H).

Example 11

5-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)nicotinic acid

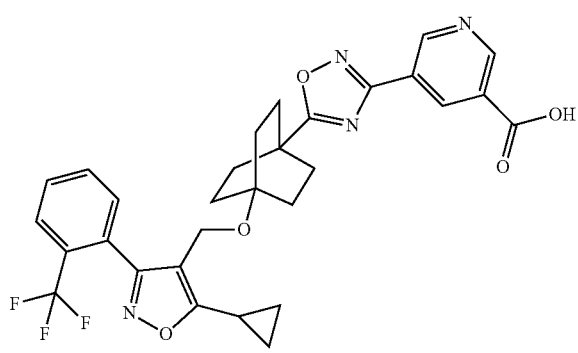

(11)

Step A. Intermediate 11A. Preparation of methyl (Z)-5-(N∝-hydroxycarbamimidoyl)nicotinate

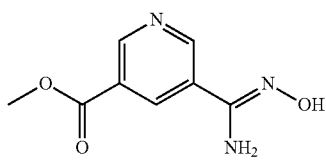

The title compound was prepared according to methods described for the synthesis of Intermediate 4C, using methyl 5-cyanonicotinate as starting material: (1.2 g, 6.1 mmol, 98% yield, white solid). $^1$H NMR (400 MHz, DMSO-d$_6$) δ 10.06-9.92 (m, 1H), 9.15-9.00 (m, 2H), 8.61-8.43 (m, 1H), 6.19-6.02 (m, 2H), 3.92 (s, 3H). MS (ESI) 196 (M+H).

Step B. Intermediate 11B. Preparation of methyl 5-(5-(4-iodobicyclo[2.2.2]octan-1-yl)-1,2,4-oxadiazol-3-yl)nicotinate

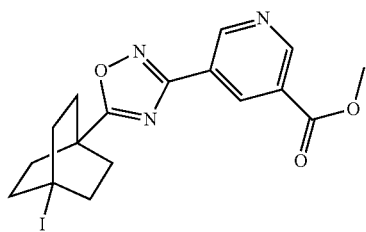 [SMILES: COC(=O)c1cncc(-c2noc(C34CCC(I)(CC3)CC4)n2)c1]

The title compound was prepared according to methods described for the synthesis of Intermediate 4D, starting with Intermediate 4B and substituting Intermediate 11A where appropriate: (0.59 g, 1.3 mmol, 94% yield, white solid). $^1$H NMR (500 MHz, DICHLOROMETHANE-d$_2$) δ 9.43 (d, J=1.9 Hz, 1H), 9.32 (d, J=1.9 Hz, 1H), 8.90 (t, J=2.1 Hz, 1H), 4.01 (s, 3H), 2.68-2.58 (m, 6H), 2.30-2.19 (m, 6H). MS (ESI) 330 (M+H).

Step C. Example 11

The title compound was prepared according to methods described for the synthesis of Example 4 (Step E), by reaction of Intermediate 11B and (5-cyclopropyl-3-(2-(trifluoromethyl)phenyl)isoxazol-4-yl)methanol: (49 mg, 0.083 mmol, 73% yield). $^1$H NMR (500 MHz, DMSO-d$_6$) δ 9.33-9.27 (m, 1H), 9.26-9.18 (m, 1H), 8.73-8.63 (m, 1H), 7.95-7.89 (m, 1H), 7.86-7.81 (m, 1H), 7.79-7.73 (m, 1H), 7.60-7.51 (m, 1H), 4.13 (s, 2H), 2.32-2.24 (m, 1H), 2.07-1.97 (m, 6H), 1.62-1.51 (m, 6H), 1.17-1.11 (m, 2H), 1.09-1.03 (m, 2H). FXR EC$_{50}$ (nM)=2900. MS (ESI) 581 (M+H).

Example 12

5-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)picolinic acid

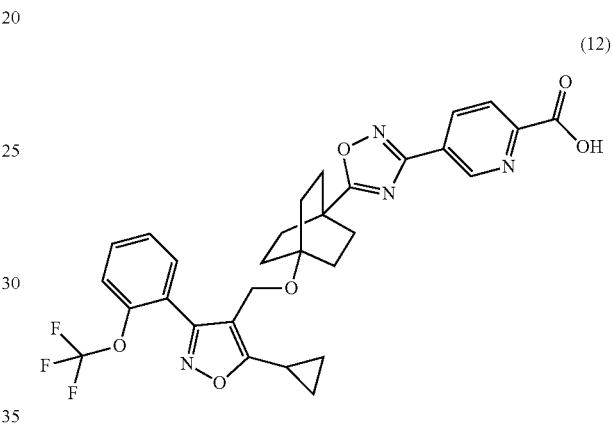

(12)

Step A. Intermediate 12A. Preparation of methyl 5-(5-(4-iodobicyclo[2.2.2]octan-1-yl)-1,2,4-oxadiazol-3-yl)picolinate

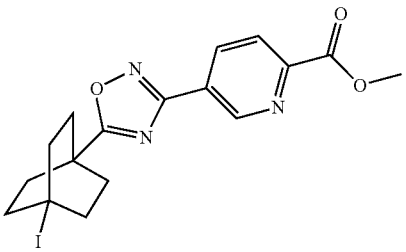 [SMILES: COC(=O)c1ccc(-c2noc(C34CCC(I)(CC3)CC4)n2)cn1]

The title compound was prepared according to methods described for the synthesis of Intermediate 4D, starting with Intermediate 4B and substituting methyl (Z)-5-(N'-hydroxycarbamimidoyl)picolinate (Quattropani, A. et al. WO 2010/100142) where appropriate: (0.43 g, 0.98 mmol, 69% yield, white solid). $^1$H NMR (500 MHz, DICHLOROMETHANE-d$_2$) δ 9.37 (d, J=1.4 Hz, 1H), 8.54-8.46 (m, 1H), 8.28-8.20 (m, 1H), 4.03 (s, 3H), 2.69-2.60 (m, 6H), 2.29-2.20 (m, 6H). MS (ESI) 330 (M+H).

Step B. Example 12

The title compound was prepared according to methods described for the synthesis of Example 4 (Step E), by reaction of Intermediate 12A and (5-cyclopropyl-3-(2-(trifluoromethoxy)phenyl)isoxazol-4-yl)methanol: (15 mg, 0.024 mmol, 21% yield). ¹H NMR (500 MHz, DMSO-d₆) δ 9.16 (br s, 1H), 8.42 (br d, J=7.6 Hz, 1H), 8.20-8.08 (m, 1H), 7.71-7.65 (m, 1H), 7.64-7.60 (m, 1H), 7.59-7.50 (m, 2H), 4.21 (s, 2H), 2.29-2.23 (m, 1H), 2.09-2.01 (m, 6H), 1.69-1.59 (m, 6H), 1.18-1.11 (m, 2H), 1.06 (br d, J=2.7 Hz, 2H). FXR EC₅₀ (nM)=1200. MS (ESI) 597 (M+H).

Example 13

6-(5-(4-((5-cyclopropyl-3-(2,6-dichlorophenyl)isoxazol-4-yl)methoxy)bicyclo[2.2.2]octan-1-yl)-1,2,4-oxadiazol-3-yl)picolinic acid

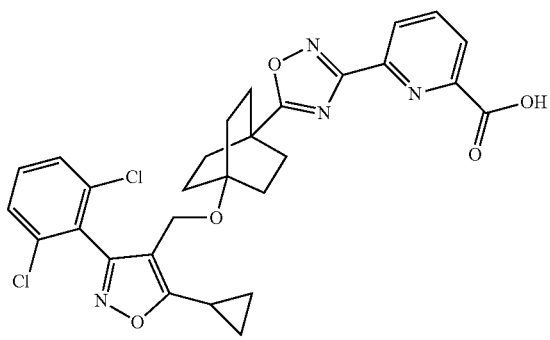

(13)

Step A. Intermediate 13A. Preparation of methyl (Z)-6-(N'-hydroxycarbamimidoyl) picolinate

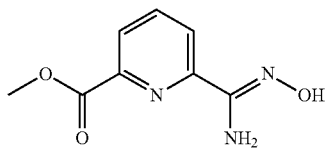

The title compound was prepared according to methods described for the synthesis of Intermediate 4C, using methyl 6-cyanopicolinate as starting material: (1.1 g, 5.5 mmol, 89% yield, white solid). ¹H NMR (500 MHz, DMSO-d₆) δ 10.16-10.09 (m, 1H), 8.12-8.06 (m, 2H), 8.05-7.97 (m, 1H), 5.93-5.78 (m, 2H), 3.92 (s, 3H). MS (ESI) 196 (M+H).

Step B. Intermediate 13B. Preparation of methyl 6-(5-(4-iodobicyclo[2.2.2]octan-1-yl)-1,2,4-oxadiazol-3-yl)picolinate

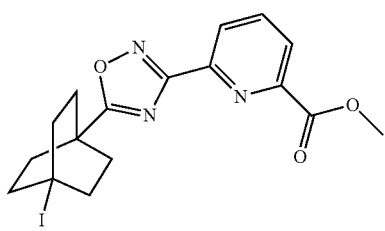 [SMILES: COC(=O)c1cccc(-c2noc(C34CCC(I)(CC3)CC4)n2)n1]

The title compound was prepared according to methods described for the synthesis of Intermediate 4D, starting with Intermediate 4B and substituting Intermediate 13A where appropriate: (0.23 g, 0.52 mmol, 54% yield, white solid). ¹H NMR (500 MHz, DICHLOROMETHANE-d₂) δ 8.32-8.23 (m, 2H), 8.07-8.01 (m, 1H), 4.05 (s, 3H), 2.70-2.60 (m, 6H), 2.32-2.24 (m, 6H). MS (ESI) 330 (M+H).

Step C. Example 13

The title compound was prepared according to methods described for the synthesis of Example 4 (Step E), by reaction of Intermediate 13B and (5-cyclopropyl-3-(2,6-dichlorophenyl)isoxazol-4-yl)methanol: (17 mg, 0.029 mmol, 32% yield). ¹H NMR (500 MHz, DMSO-d₆) δ 8.16-7.99 (m, 3H), 7.66-7.55 (m, 3H), 4.24-4.14 (m, 2H), 2.32-2.22 (m, 1H), 2.03 (br s, 6H), 1.52 (br s, 6H), 1.19-1.12 (m, 2H), 1.11-1.05 (m, 2H). FXR EC₅₀ (nM)=270. MS (ESI) 582 (M+H).

Example 14

4-(5-(4-((5-cyclopropyl-3-(2,6-dichlorophenyl)isoxazol-4-yl)methoxy)bicyclo[2.2.2]octan-1-yl)-1,2,4-oxadiazol-3-yl)picolinic acid

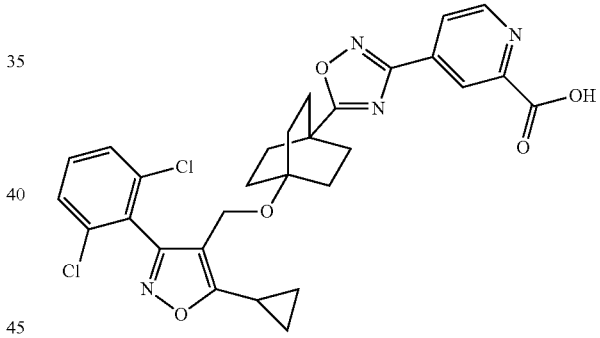

(14)

Step A. Intermediate 14A. Preparation of ethyl (Z)-4-(N'-hydroxycarbamimidoyl) picolinate

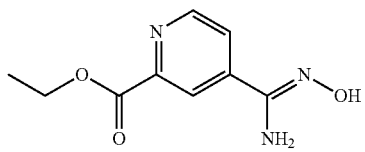

The title compound was prepared according to methods described for the synthesis of Intermediate 4C, using ethyl 4-cyanopicolinate as starting material: (0.30 g, 1.4 mmol, 100% yield, white solid). ¹H NMR (400 MHz, DMSO-d₆) δ 10.23-10.16 (m, 1H), 8.77-8.69 (m, 1H), 8.39-8.30 (m, 1H), 7.92-7.81 (m, 1H), 6.21-6.09 (m, 2H), 4.52-4.26 (m, 2H), 1.35 (t, J=7.2 Hz, 3H). MS (ESI) 210 (M+H).

Step B. Intermediate 14B. Preparation of ethyl 4-(5-(4-iodobicyclo[2.2.2]octan-1-yl)-1,2,4-oxadiazol-3-yl)picolinate

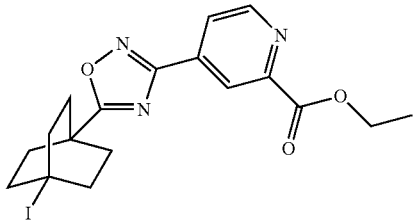 [SMILES: CCOC(=O)c1cc(-c2noc(C34CCC(I)(CC3)CC4)n2)ccn1]

The title compound was prepared according to methods described for the synthesis of Intermediate 4D, starting with Intermediate 4B and substituting Intermediate 14A where appropriate: (0.34 g, 0.75 mmol, 78% yield, white solid). $^1$H NMR (500 MHz, DICHLOROMETHANE-d$_2$) δ 8.92-8.86 (m, 1H), 8.72-8.67 (m, 1H), 8.15-8.08 (m, 1H), 4.50 (d, J=7.2 Hz, 2H), 2.71-2.55 (m, 6H), 2.29-2.20 (m, 6H), 1.48 (t, J=7.2 Hz, 3H). MS (ESI) 454 (M+H).

Step C. Example 14

The title compound was prepared according to methods described for the synthesis of Example 4 (Step E), by reaction of Intermediate 14B and (5-cyclopropyl-3-(2,6-dichlorophenyl)isoxazol-4-yl)methanol: (6.8 mg, 0.012 mmol, 13% yield). $^1$H NMR (500 MHz, DMSO-d$_6$) δ 8.91-8.80 (m, 1H), 8.50-8.41 (m, 1H), 8.08-7.98 (m, 1H), 7.69-7.61 (m, 2H), 7.61-7.51 (m, 1H), 4.18 (s, 2H), 2.35-2.26 (m, 1H), 2.06-1.98 (m, 6H), 1.56-1.47 (m, 6H), 1.18-1.12 (m, 2H), 1.11-1.06 (m, 2H). FXR EC$_{50}$ (nM)=130. MS (ESI) 582 (M+H).

Example 15

2-(4-((5-cyclopropyl-3-(2-(trifluoromethoxy)phenyl)isoxazol-4-yl)methoxy)bicyclo[2.2.2]octan-1-yl)-4-fluorobenzo[d]thiazole-6-carboxylic acid

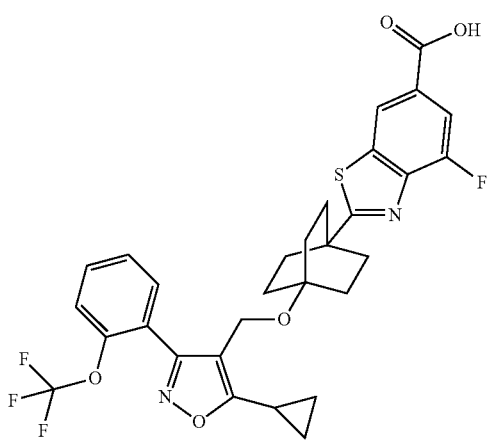

(15)

Step A. Intermediate 15A. Preparation of ethyl 2-amino-4-fluorobenzo[d]thiazole-6-carboxylate

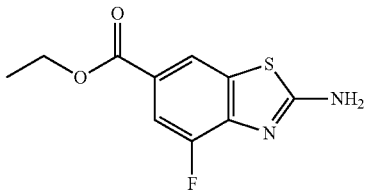 [SMILES: CCOC(=O)c1cc(F)c2nc(N)sc2c1]

To 200 mL pear shaped flask were added ethyl 4-amino-3-fluorobenzoate (3.7 g, 20 mmol), sodium thiocyanate (6.5 g, 80 mmol) and glacial AcOH (25 mL). The reaction was cooled to 0° C. To this mixture was added bromine (1 mL) dissolved in glacial AcOH (5 mL) over a period of 5 minutes. The mixture was stirred at 30° C. for 48 h. The reaction was cooled, the solids removed by vacuum filtration and the filter cake washed with DCM (2×10 mL). The filtrate was concentrated, the residue was diluted in water (50 mL) and conc. NH$_4$OH was added until pH ~9 (ca. 5 mL). The suspension was stirred 2 h and the solid product was collected by vacuum filtration and the filter cake washed with water (3×10 mL). The product was dried in vacuo to afford the title compound (3.0 g, 12 mmol, 62% yield) as a yellow solid. $^1$H NMR (400 MHz, DMSO-d$_6$) δ8.35-8.00 (m, 2H), 7.57 (dd, 1.5 Hz, 1H), 4.30 (q, J=7.1 Hz, 2H), 1.32 (t, J=7.0 Hz, 3H). MS (ESI) 241 (M+H).

Step B. Intermediate 15B. Preparation of ethyl 4-fluorobenzo[d]thiazole-6-carboxylate

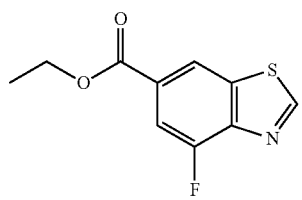

To a 250 mL round bottomed flask were added Intermediate 15A (1.5 g, 6.2 mmol), THF (20 mL), followed by isoamyl nitrite (2.5 mL, 19 mmol). The suspension was stirred at reflux under N$_2$ for 2 h, cooled to rt and stirred for 18 h. The solvent was concentrated and the crude product was purified by flash column chromatography (40 g silica gel cartridge; A=Hex, B=EtOAc; 20 min grad.; 0% B to 100% B; flow rate=40 mL/min). The pure fractions were combined, concentrated and dried in vacuo to afford the title compound (1.0 g, 4.6 mmol, 74% yield) as a pale yellow solid. $^1$H NMR (400 MHz, CHLOROFORM-d) δ 9.17 (d, J=0.7 Hz, 1H), 8.52 (d, J=1.1 Hz, 1H), 7.91 (dd, J=10.6, 1.3 Hz, 1H), 4.46 (d, J=7.0 Hz, 2H), 1.46 (t, J=7.2 Hz, 4H). MS (ESI) 226 (M+H).

Step C. Intermediate 15C. Preparation of 4-fluorobenzo[d]thiazole-6-carboxylic acid

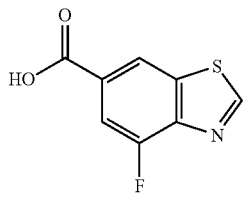 [SMILES: O=C(O)c1cc(F)c2ncsc2c1]

To a 250 mL round bottomed flask were added Intermediate 15B (1.0 g, 4.6 mmol), THF (23 mL), followed by 1 M NaOH (aq.) (23 mL, 23 mmol). The reaction was stirred for 18 h and diluted with 5% citric acid (aq.) (100 mL). The suspension was extracted with EtOAc (2×50 mL). The organic phase was combined, washed with brine, dried over $Na_2SO_4$, filtered and concentrated. The product was dried in vacuo to afford the title compound (0.90 g, 4.6 mmol, 99% yield) as a pale yellow solid. $^1$H NMR (500 MHz, DMSO-$d_6$) δ 13.62-12.50 (br s, 1H), 9.62 (s, 1H), 8.68 (d, J=1.4 Hz, 1H), 7.82 (dd, 1.4 Hz, 1H). MS (ESI) 198 (M+H).

Step D. Intermediate 15D. Preparation of tert-butyl 4-fluorobenzo[d]thiazole-6-carboxylate

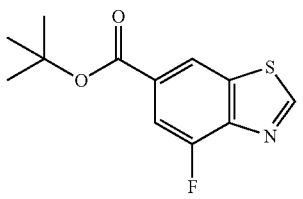 [SMILES: CC(C)(C)OC(=O)c1cc(F)c2ncsc2c1]

To a 250 mL round bottomed flask were added Intermediate 15C (0.90 g, 4.6 mmol) and t-butanol (11 mL). To the reaction was added tert-butyl (Z)—N,N'-diisopropylcarbamimidate (9.2 g, 46 mmol) (Mathias, L. J. *Synthesis* 1979, 1979, 561-576.) dissolved in THF (11 mL). After stirring 18 h, the reaction was filtered and the filtrate was concentrated. The crude product was purified by flash column chromatography (40 g silica gel cartridge; A=Hex, B=EtOAc; 20 min grad.; 0% B to 50% B; flow rate=40 mL/min). The pure fractions were combined, concentrated and dried in vacuo to afford the title compound (0.75 g, 3.0 mmol, 65% yield) as a tan solid. $^1$H NMR (400 MHz, CHLOROFORM-d) δ 9.17-9.12 (m, 1H), 8.47-8.41 (m, 1H), 7.89-7.81 (m, 1H), 1.66 (s, 11H). MS (ESI) 254 (M+H).

Step E. Intermediate 15E. Preparation of tert-butyl 4-amino-3-fluoro-5-mercaptobenzoate

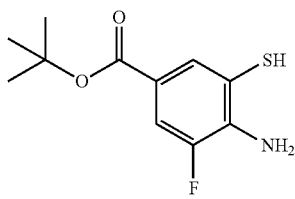 [SMILES: CC(C)(C)OC(=O)c1cc(F)c(N)c(S)c1]

To a 100 mL pear shaped flask were added Intermediate 15D (0.75 g, 3.0 mmol), 95% EtOH (aq.) (10 mL) and hydrazine hydrate (6.4 mL, 100 mmol). The reaction was stirred 2.5 h, the solvent concentrated and the crude product purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (0.38 g, 1.5 mmol, 52% yield) as a pale yellow oil. $^1$H NMR (500 MHz, CHLOROFORM-d) δ 7.88-7.83 (m, 1H), 7.61-7.55 (m, 1H), 4.67-4.53 (m, 2H), 3.14-2.95 (m, 1H), 1.59 (s, 9H). MS (ESI) 244 (M+H).

Step F. Intermediate 15F. Preparation of tert-butyl 4-fluoro-2-(4-iodobicyclo[2.2.2]octan-1-yl)benzo[d]thiazole-6-carboxylate

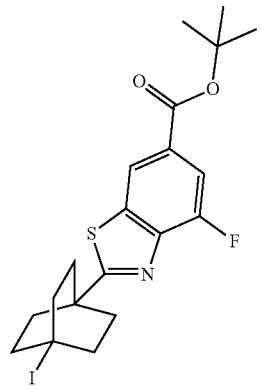 [SMILES: CC(C)(C)OC(=O)c1cc(F)c2nc(C34CCC(I)(CC3)CC4)sc2c1]

To a 100 mL pear shaped flask were added Intermediate 15E (0.35 g, 1.3 mmol), Intermediate 4B (0.46 g, 1.5 mmol), pyridine (0.30 mL, 3.8 mmol) and DCE (8 mL). To this mixture was added T3P (1.9 mL, 3.1 mmol) (50% w/v solution in EtOAc) and the reaction was stirred at 80° C. under $N_2$ for 5 h. The solvent was concentrated and the crude product was purified by flash column chromatography (40 g silica gel cartridge; A=Hex, B=EtOAc; 20 min grad.; 0% B to 100% B; flow rate=40 mL/min). The pure fractions were combined, concentrated and dried in vacuo to afford the title compound (0.17 g, 0.35 mmol, 28% yield) as a pale yellow solid. $^1$H NMR (500 MHz, DICHLOROMETHANE-$d_2$) δ 8.35 (d, J=1.4 Hz, 1H), 7.84-7.72 (m, 1H), 2.70-2.62 (m, 6H), 2.30-2.21 (m, 6H), 1.64 (s, 9H). MS (ESI) 488 (M+H).

Step G. Example 15

Step 1: To a 2 dram vial equipped with a pressure release cap were added Intermediate 15F (0.030 g, 0.062 mmol), (5-cyclopropyl-3-(2-(trifluoromethyl)phenyl) isoxazol-4-yl) methanol (0.055 g, 0.19 mmol), silver trifluoromethanesulfonate (0.13 g, 0.49 mmol), and 2,6-di-tert-butylpyridine (0.28 mL, 1.2 mmol). The vessel was flushed with $N_2$, capped and stirred at 80° C. After 18 h, the reaction was cooled, diluted with DCM/MeOH, filtered and the filtrate was concentrated. The residue was filtered through a plug of $SiO_2$, eluting with hexanes first, then EtOAc to collect crude product. The filtrate was concentrated and the crude residue was taken onto the next step.

Step 2: The product of Step 1 above was dissolved in KOH (5 mL) (2 M in MeOH) and THF (5 mL) and stirred. After 2 h, the reaction was diluted with 5% citric acid (aq.)

(50 mL) and extracted with EtOAc (2×25 mL). The organic phase was combined, washed with brine, dried over Na$_2$SO$_4$, filtered and concentrated. The crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 4-minute hold at 100% B; Flow: 20 mL/min). Fractions containing the desired product were combined, concentrated and dried in vacuo to afford the title compound (1.4 mg, 2.3 μmol, 4% yield). $^1$H NMR (500 MHz, DMSO-d$_6$) δ 8.44-8.31 (m, 1H), 7.77-7.61 (m, 3H), 7.57 (br t, J=6.7 Hz, 2H), 4.23 (s, 2H), 2.31-2.27 (m, 1H), 2.07 (br s, 6H), 1.68 (br d, J=7.3 Hz, 6H), 1.17-1.11 (m, 2H), 1.10-1.04 (m, 2H). FXR EC$_{50}$ (nM)=210. MS (ESI) 603 (M+H).

Example 16

2-(4-((5-cyclopropyl-3-(2,6-dichlorophenyl)isoxazol-4-yl)methoxy)bicyclo[2.2.2]octan-1-yl)-4-fluorobenzo[d]thiazole-6-carboxylic acid (16)

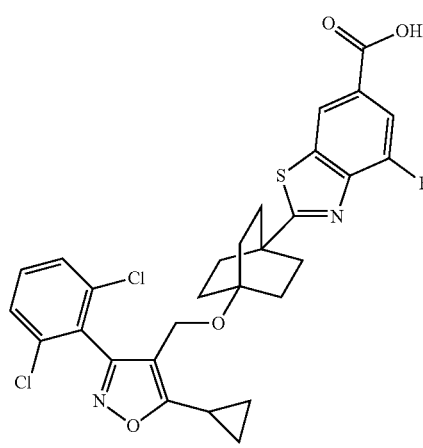

Step A. Intermediate 16A. Preparation of methyl 4-((5-cyclopropyl-3-(2,6-dichlorophenyl)isoxazol-4-yl)methoxy)bicyclo[2.2.2]octane-1-carboxylate

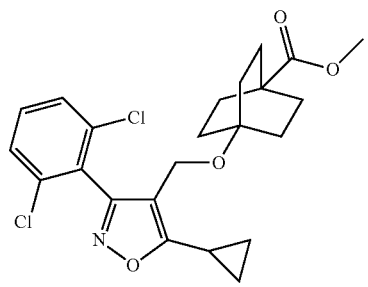 [SMILES: COC(=O)C12CCC(OCc3c(-c4c(Cl)cccc4Cl)noc3C3CC3)(CC1)CC2]

To a 25 mL round bottom flask were added Intermediate 4A (280 mg, 0.97 mmol), (5-cyclopropyl-3-(2,6-dichlorophenyl)isoxazol-4-yl)methanol, followed by 2,6-di-tert-butylpyridine (2.6 mL, 12 mmol), and silver trifluoromethanesulfonate (2.0 mg, 7.7 mmol). The reaction was stirred at 80° C. for 4 h, cooled to rt and diluted with DCM/MeOH (20 mL; 1:1). The resultant suspension was filtered, the filter cake was washed with DCM (10 mL), and the filtrate was concentrated. The crude product was purified by flash column chromatography (40 g silica gel cartridge; A=Hex, B=EtOAc; 20 min grad.; 0% B to 100% B; flow rate=40 mL/min). The pure fractions were combined, concentrated and dried in vacuo to afford the title compound (250 mg, 0.56 mmol, 58% yield) as a white solid. $^1$H NMR (500 MHz, CHLOROFORM-d) δ 7.46-7.39 (m, 2H), 7.38-7.32 (m, 1H), 4.18 (s, 2H), 3.63 (s, 3H), 2.18-2.08 (m, 1H), 1.91-1.78 (m, 6H), 1.55-1.42 (m, 6H), 1.30-1.22 (m, 2H), 1.15-1.07 (m, 2H). MS (ESI) 451 (M+H).

Step B. Intermediate 16B. Preparation of 4-((5-cyclopropyl-3-(2,6-dichlorophenyl)isoxazol-4-yl)methoxy)bicyclo[2.2.2]octane-1-carboxylic acid

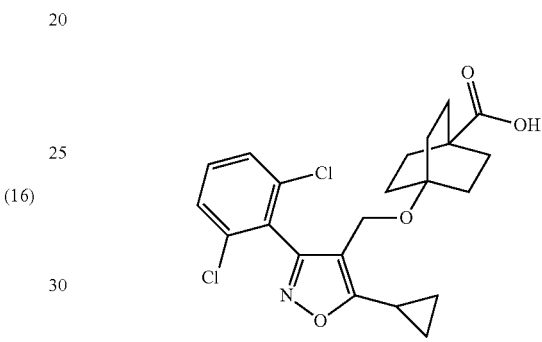

To a 100 mL pear shaped flask were added Intermediate 16A (150 mg, 0.22 mmol), 1 M NaOH (aq.) (2.2 mL, 2.2 mmol), and THF (2 mL). The reaction was stirred at 40° C. for 18 h, after which time the reaction was cooled, diluted with 5% citric acid (aq.) (50 mL) and extracted with EtOAc (2×25 mL). The organic phase was combined, washed with brine, dried over Na$_2$SO$_4$, filtered and concentrated. The product was dried in vacuo to afford the title compound (110 mg, 0.19 mmol, 87% yield) as a white solid. $^1$H NMR (400 MHz, METHANOL-d$_4$) δ 7.57-7.46 (m, 3H), 4.86 (s, 2H), 2.28-2.19 (m, 1H), 1.87-1.79 (m, 6H), 1.51-1.43 (m, 6H), 1.20-1.14 (m, 4H). MS (ESI) 437 (M+H).

Step C. Example 16

Step 1: To a 100 mL pear shaped flask were added Intermediate 16B (110 mg, 0.19 mmol), Intermediate 15E (100 mg, 0.42 mmol), pyridine (0.046 mL, 0.57 mmol) and DCE (2 mL). To this mixture was added T3P (0.28 mL, 0.47 mmol) (50% w/v solution in EtOAc) and the reaction was stirred at 80° C. under N$_2$. After 18 h, the reaction was cooled, the solvent was concentrated and the crude product was purified by flash column chromatography (12 g silica gel cartridge; A=DCM, B=EtOAc; 20 min grad.; 0% B to 10% B; flow rate=12 mL/min). The pure fractions were combined and concentrated. The residue was taken onto the next step without characterization.

The product of Step 1 above was dissolved in KOH (5 mL) (2 M in MeOH) and THF (5 mL) and stirred. After 1.5 h, the reaction was diluted with water (50 mL) and the MeOH was azeotropically removed by rotary evaporation. The resultant water layer was acidified with 5% citric acid (aq.) and the aqueous phase was extracted with EtOAc (2×25 mL). The organic phase was combined, washed with brine, dried over Na$_2$SO$_4$, filtered and concentrated. The crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-64% B over 22 minutes, then a 4-minute hold at 100% B; Flow: 20 mL/min). Fractions containing the desired product were combined, concentrated and dried in vacuo to afford the title compound (37 mg, 0.062 mmol, 33% yield). $^1$H NMR (500 MHz, DMSO-d$_6$) δ 8.55-8.50 (m, 1H), 7.78-7.73 (m, 1H), 7.67-7.62 (m, 2H), 7.62-7.56 (m, 1H), 4.20 (s, 2H), 2.35-2.28 (m, 1H), 2.07-1.98 (m, 6H), 1.57-1.49 (m, 6H), 1.19-1.13 (m, 2H), 1.12-1.06 (m, 2H). FXR EC$_{50}$ (nM)=36. MS (ESI) 588 (M+H).

Example 17

2-(4-((5-cyclopropyl-3-(2,6-dichlorophenyl)isoxazol-4-yl)methoxy)bicyclo[2.2.2]octan-1-yl)-1H-benzo[d]imidazole-5-carboxylic acid

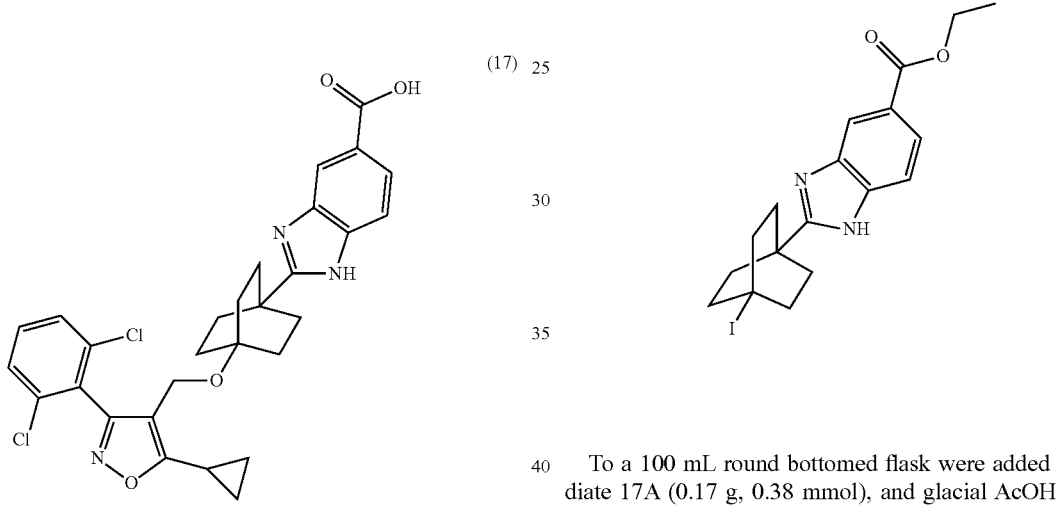

(17)

Step A. Intermediate 17A. Preparation of ethyl 3-amino-4-(4-iodobicyclo[2.2.2]octane-1-carboxamido)benzoate

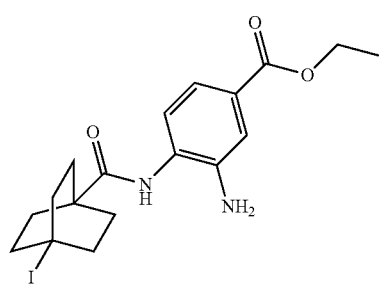 [SMILES: CCOC(=O)c1ccc(NC(=O)C23CCC(I)(CC2)CC3)c(N)c1]

To a 20 mL scintillation vial were added Intermediate 4B (0.30 g, 1.1 mmol), ethyl 3,4-diaminobenzoate (0.29 g, 1.6 mmol), DMAP (0.26 g, 2.1 mmol) followed by DMF (5 mL). To this mixture was added EDC (0.41 g, 2.1 mmol) and the vial was capped and stirred for 18 h. The reaction was diluted with water (50 mL) and extracted with EtOAc (2×25 mL). The organic phase was combined, washed with brine, dried over Na$_2$SO$_4$, filtered and concentrated. The crude product was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to afford the title compound (0.17 g, 0.38 mmol, 36% yield) as a pale yellow oil. $^1$H NMR (500 MHz, METHANOL-d$_4$) δ 7.73-7.68 (m, 1H), 7.68-7.63 (m, 1H), 6.87-6.77 (m, 1H), 4.37-4.25 (m, 2H), 2.60-2.51 (m, 6H), 2.13-2.05 (m, 6H), 1.42-1.32 (m, 3H). MS (ESI) 443 (M+H).

Step B. Intermediate 17B. Preparation of ethyl 2-(4-iodobicyclo[2.2.2]octan-1-yl)-1H-benzo[d]imidazole-5-carboxylate To a 100 mL round bottomed flask were added Intermediate 17A (0.17 g, 0.38 mmol), and glacial AcOH (8 mL). The reaction was stirred at 115° C. under N$_2$. After 18 h, the reaction was cooled, the solvent concentrated and the crude product purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to afford the title compound (0.16 g, 0.38 mmol, 98% yield) as a tan solid. $^1$H NMR (400 MHz, METHANOL-d$_4$) δ 8.34-8.11 (m, 1H), 7.94-7.87 (m, 1H), 7.66-7.43 (m, 1H), 4.42-4.36 (m, 2H), 2.68-2.58 (m, 6H), 2.19 (br d, J=8.1 Hz, 6H), 1.41 (t, J=7.2 Hz, 3H). MS (ESI) 425 (M+H).

Step C. Example 17

The title compound was prepared according to methods described for the synthesis of Example 4 (Step E), by reaction of Intermediate 17B and (5-cyclopropyl-3-(2,6-dichlorophenyl)isoxazol-4-yl)methanol: (24 mg, 0.043 mmol, 37% yield). $^1$H NMR (500 MHz, DMSO-d$_6$) δ 8.17-7.95 (m, 1H), 7.82-7.71 (m, 1H), 7.64 (s, 2H), 7.62-7.56 (m, 1H), 7.55-7.41 (m, 1H), 4.23-4.16 (m, 2H), 2.35-2.27 (m, 1H), 2.00-1.92 (m, 6H), 1.54-1.44 (m, 6H), 1.18-1.13 (m, 2H), 1.12-1.05 (m, 2H). FXR EC$_{50}$ (nM)=2700. MS (ESI) 553 (M+H).

Example 18

3-(5-(4-((5-cyclopropyl-3-(2-(trifluoromethoxy)phenyl)isoxazol-4-yl)methoxy)bicyclo[2.2.2]octan-1-yl)-1,3,4-oxadiazol-2-yl)benzoic acid

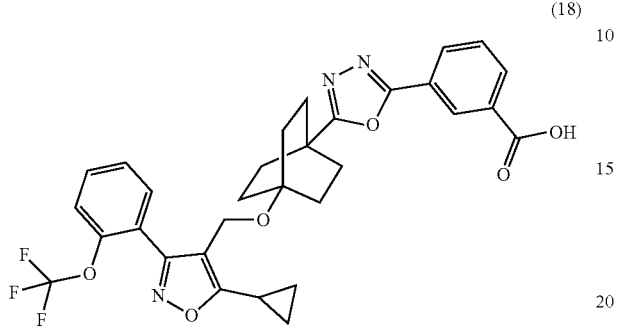

(18)

Step A. Intermediate 18A. Preparation of methyl 3-(5-(4-iodobicyclo[2.2.2]octan-1-yl)-1,3,4-oxadiazol-2-yl)benzoate

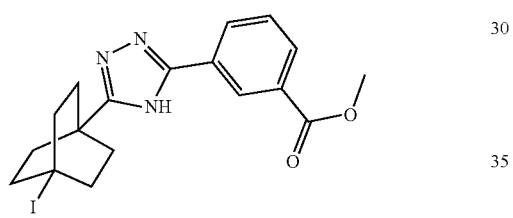

To a mixture of Intermediate 4B (0.24 g, 0.84 mmol), methyl 3-(hydrazinecarbonyl) benzoate (0.16 g, 0.84 mmol) (Bradner, J. E. et al. WO 2014/071247) and DIEA (0.44 mL, 2.5 mmol) in MeCN (10 mL) was added TBTU (0.30 g, 0.92 mmol). After stirring 2 h, DIEA (0.29 mL, 1.7 mmol), followed by p-toluenesulfonyl chloride (0.48 g, 2.5 mmol) were successively added and the resulting reaction mixture was stirred under $N_2$. After 18 h, the mixture was diluted with 1 M $K_2HPO_4$ (aq.) (50 mL) and extracted with EtOAc (2×25 mL). The organic phase was combined, washed with brine, dried over $Na_2SO_4$, filtered and concentrated. The crude product was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to afford the title compound (0.063 g, 0.14 mmol, 17% yield) as a white solid. $^1$H NMR (500 MHz, DICHLOROMETHANE-$d_2$) δ 8.69-8.60 (m, 1H), 8.31-8.19 (m, 2H), 7.69-7.60 (m, 1H), 3.99 (s, 3H), 2.70-2.61 (m, 6H), 2.24 (br d, J=8.3 Hz, 6H). MS (ESI) 439 (M+H).

Step B. Example 18

The title compound was prepared according to methods described for the synthesis of Example 4 (Step E), by reaction of Intermediate 18A and (5-cyclopropyl-3-(2-(trifluoromethoxy)phenyl)isoxazol-4-yl)methanol: (19 mg, 0.033 mmol, 47% yield). $^1$H NMR (500 MHz, DMSO-$d_6$) δ 8.48-8.42 (m, 1H), 8.19-8.11 (m, 2H), 7.73-7.66 (m, 2H), 7.66-7.61 (m, 1H), 7.60-7.52 (m, 2H), 4.22 (s, 2H), 2.32-2.24 (m, 1H), 2.08-1.99 (m, 6H), 1.69-1.59 (m, 6H), 1.17-1.11 (m, 2H), 1.10-1.03 (m, 2H). FXR $EC_{50}$ (nM)=1100. MS (ESI) 596 (M+H).

Example 19

3-(5-(4-((5-cyclopropyl-3-(2-(trifluoromethoxy)phenyl)isoxazol-4-yl)methoxy)bicyclo[2.2.2]octan-1-yl)-1,3,4-thiadiazol-2-yl)benzoic acid

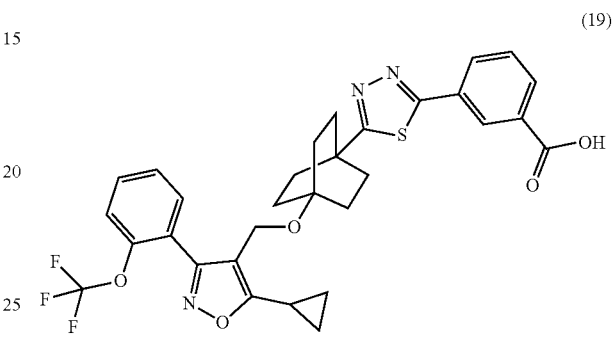

(19)

Step A. Intermediate 19A. Preparation of methyl 3-(5-(4-iodobicyclo[2.2.2]octan-1-yl)-1,3,4-thiadiazol-2-yl)benzoate

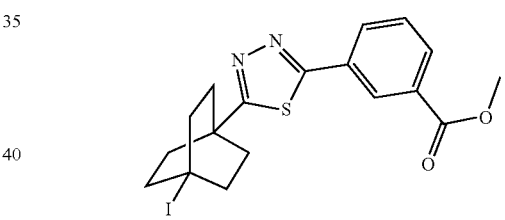

Step 1: To a mixture of Intermediate 4B (0.24 g, 0.84 mmol), methyl 3-(hydrazinecarbonyl)benzoate (0.16 g, 0.84 mmol) (Bradner, J. E. et al. WO 2014/071247), TEA (0.18 mL, 1.3 mmol) and HOBT (0.039 g, 0.25 mmol) in DMF (6 mL) was added EDC (0.24 g, 1.3 mmol) and the resulting mixture was stirred. After 2 h, the reaction was diluted with water (50 mL) and extracted with EtOAc (2×25 mL). The organic phase was combined, washed with brine, dried over $Na_2SO_4$, filtered and concentrated. The residue was dried in vacuo and taken onto the next step without characterization.

Step 2: The product of Step 1 was dissolved in THF (5 mL), phosphorus pentasulfide (0.48 g, 2.2 mmol) was added and the reaction was stirred at 50° C. After 18 h, the reaction was cooled, filtered and the filtrate was concentrated. The crude product was purified by flash column chromatography (40 g silica gel cartridge; A=Hex, B=EtOAc; 20 min grad.; 0% B to 60% B; flow rate=40 mL/min). The pure fractions were combined, concentrated and dried in vacuo to afford the title compound (60 mg, 0.13 mmol, 16% yield) as a white solid. $^1$H NMR (400 MHz, DICHLOROMETHANE-$d_2$) δ 8.41 (t, J=1.5 Hz, 1H), 8.05 (td, J=7.9, 1.4 Hz, 2H), 7.48 (t, J=7.8 Hz, 1H), 3.85 (s, 3H), 2.58-2.50 (m, 6H), 2.17-2.05 (m, 6H). MS (ESI) 455 (M+H).

Step B. Example 19

The title compound was prepared according to methods described for the synthesis of Example 4 (Step E), by reaction of Intermediate 19A and (5-cyclopropyl-3-(2-(trifluoromethoxy)phenyl)isoxazol-4-yl)methanol: (4.1 mg, 0.0067 mmol, 10% yield). $^1$H NMR (500 MHz, DMSO-$d_6$) δ 8.40 (br s, 1H), 8.08 (br t, J=9.0 Hz, 2H), 7.71-7.60 (m, 3H), 7.56 (br t, J=7.0 Hz, 2H), 4.21 (s, 2H), 2.31-2.24 (m, 1H), 2.08-1.99 (m, 6H), 1.71-1.59 (m, 6H), 1.18-1.10 (m, 2H), 1.09-1.03 (m, 2H). FXR EC$_{50}$ (nM)=1700. MS (ESI) 612 (M+H).

Example 20

3-(3-(4-((5-cyclopropyl-3-(2-(trifluoromethyl)phenyl)isoxazol-4-yl)methoxy) bicyclo[2.2.2]octan-1-yl)-1,2,4-oxadiazol-5-yl)benzoic acid

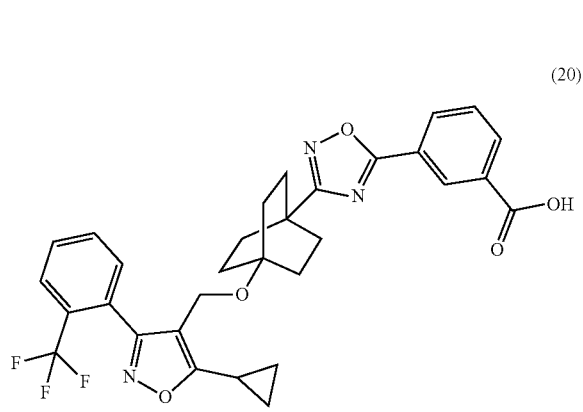 [SMILES: O=C(O)c1cccc(-c2nc(C34CCC(OCc5c(-c6ccccc6C(F)(F)F)noc5C5CC5)(CC3)CC4)no2)c1]

(20)

Step A. Intermediate 20A. Preparation of 4-iodobicyclo[2.2.2]octane-1-carbonitrile

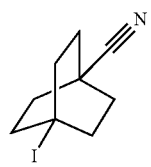 [SMILES: N#CC12CCC(I)(CC1)CC2]

Step 1: To a 250 mL round bottomed flask were added Intermediate 4B (0.56 g, 2.0 mmol), THF (20 mL) and TEA (0.42 mL, 3.0 mmol). The mixture was cooled to −30° C., then ethyl chloroformate (0.23 mL, 2.4 mmol) was added dropwise. The mixture was stirred for 1 h at −30° C. The reaction was filtered, both flask and filter cake were washed with an additional amount of ice cold THF (15 mL), and the reaction was cooled to −20° C.

Step 2: The mixture generated above was cooled to −20° C. and ammonia gas was dispersed through the mixture for 10 min. After stirring at this temperature for 40 min, the solvent was concentrated and the residue was taken onto the next step without purification or characterization.

Step 3: The residue from above was dissolved in THF (12 mL), pyridine (0.53 mL, 6.6 mmol) was added and the mixture was cooled to 0° C. To this mixture was added trifluoroacetic anhydride (0.57 mL, 4.0 mmol) and the reaction was stirred at this temperature for 2 h. To this mixture was added MeOH (5 mL) and 1 M K$_2$HPO$_4$ (aq.) (5 mL) and stirred for 30 min. The mixture was diluted with water (100 mL) and extracted with EtOAc (2×50 mL). The organic phase was combined, washed with 1 M HCl (aq.), brine, dried over Na$_2$SO$_4$, filtered and concentrated. The crude product was purified by flash column chromatography (40 g silica gel cartridge; A=Hex, B=EtOAc; 20 min grad.; 0% B to 50% B; flow rate=40 mL/min). The pure fractions were combined, concentrated and dried in vacuo to afford the title compound (0.37 g, 1.4 mmol, 71% yield) as a white solid. $^1$H NMR (500 MHz, CHLOROFORM-d) δ 2.56-2.46 (m, 6H), 2.14-2.04 (m, 6H).

Step B. Intermediate 20B. Preparation of (Z)—N'-hydroxy-4-iodobicyclo[2.2.2]octane-1-carboximidamide

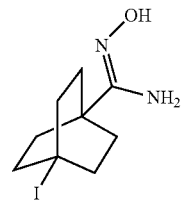 [SMILES: N/C(=N\O)C12CCC(I)(CC1)CC2]

To a 100 mL pear shaped flask were added Intermediate 20A (0.37 g, 1.4 mmol), hydroxylamine hydrochloride (0.49 g, 7.1 mmol), MeOH (14 mL), and TEA (0.99 mL, 7.1 mmol). The reaction was stirred at reflux for 18 h. The reaction was cooled, diluted with water (200 mL), and extracted with EtOAc (2×100 mL). The organic phase was combined, dried over Na$_2$SO$_4$, filtered and concentrated. The product was dried in vacuo to afford the title compound (0.40 g, 1.4 mmol, 96% yield) as a white solid. $^1$H NMR (500 MHz, CHLOROFORM-d) δ 7.26-7.14 (br s, 1H), 4.55-4.33 (br s, 2H), 2.51 (br d, J=8.3 Hz, 6H), 1.93-1.85 (m, 6H).

Step C. Intermediate 20C. Preparation of methyl 3-(3-(4-iodobicyclo[2.2.2]octan-1-yl)-1,2,4-oxadiazol-5-yl)benzoate

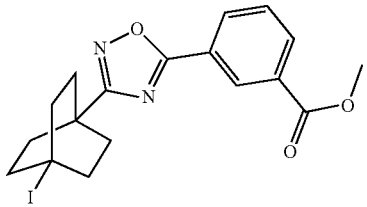 [SMILES: COC(=O)c1cccc(-c2nc(C34CCC(I)(CC3)CC4)no2)c1]

Step 1: To a 100 mL pear shaped flask were added 3-(methoxycarbonyl)benzoic acid (0.14 g, 0.75 mmol) and DCM (4 mL). To this mixture was added CDI (0.13 g, 0.82 mmol) in one portion, upon which gas evolution was observed. The reaction was stirred for 30 min, Intermediate 20B (0.20 g, 0.68 mmol) was added and the reaction was stirred under N$_2$.

Step 2: The solvent was concentrated and the residue was dissolved in toluene (5 mL) and stirred at reflux. After 2 h, the reaction was cooled, the solvent concentrated and the crude product was purified by flash column chromatography (40 g silica gel cartridge; A=Hex, B=EtOAc; 20 min grad.; 0% B to 50% B; flow rate=40 mL/min). The pure fractions were combined, concentrated and dried in vacuo to afford the title compound (0.25 g, 0.57 mmol, 84% yield) as a white solid. $^1$H NMR (500 MHz, CHLOROFORM-d) δ 8.80-8.75 (m, 1H), 8.33-8.24 (m, 2H), 7.67-7.60 (m, 1H), 4.00 (s, 3H), 2.67-2.58 (m, 6H), 2.23-2.13 (m, 6H). MS (ESI) 439 (M+H).

Step D. Example 20

The title compound was prepared according to methods described for the synthesis of Example 4 (Step E), by reaction of Intermediate 20C and (5-cyclopropyl-3-(2-(trifluoromethyl)phenyl)isoxazol-4-yl)methanol: (27 mg, 0.047, 41% yield). $^1$H NMR (500 MHz, DMSO-d$_6$) δ 8.59-8.54 (m, 1H), 8.29-8.25 (m, 1H), 8.24-8.20 (m, 1H), 7.93-7.88 (m, 1H), 7.85-7.80 (m, 1H), 7.79-7.72 (m, 2H), 7.59-7.53 (m, 1H), 4.21 (s, 2H), 2.33-2.21 (m, 1H), 2.04-1.91 (m, 6H), 1.64-1.51 (m, 6H), 1.15 (br d, J=2.3 Hz, 2H), 1.10-1.05 (m, 2H). FXR EC$_{50}$ (nM)=510. MS (ESI) 580 (M+H).

Example 21

4-(3-(4-((5-cyclopropyl-3-(2-(trifluoromethyl)phenyl)isoxazol-4-yl)methoxy) bicyclo[2.2.2]octan-1-yl)-1,2,4-oxadiazol-5-yl)benzoic acid (21)

Step A. Intermediate 21A. Preparation of methyl 4-(3-(4-iodobicyclo[2.2.2]octan-1-yl)-1,2,4-oxadiazol-5-yl)benzoate

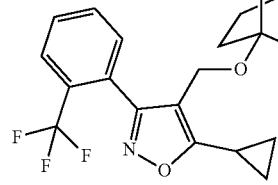

The title compound was prepared according to methods described for the synthesis of Intermediate 20C, by reaction of Intermediate 20B and 4-(methoxycarbonyl)benzoic acid: (240 mg, 0.55 mmol, 81% yield, white solid). $^1$H NMR (500 MHz, CHLOROFORM-d) δ 8.25-8.15 (m, 4H), 3.99 (s, 3H), 2.68-2.58 (m, 6H), 2.23-2.13 (m, 6H). MS (ESI) 439 (M+H).

Step B. Example 21

The title compound was prepared according to methods described for the synthesis of Example 4 (Step E), by reaction of Intermediate 21A and (5-cyclopropyl-3-(2-(trifluoromethyl)phenyl)isoxazol-4-yl)methanol: (41 mg, 0.070 mmol, 60% yield). $^1$H NMR (500 MHz, DMSO-d$_6$) δ 8.13 (s, 4H), 7.93-7.88 (m, 1H), 7.85-7.79 (m, 1H), 7.79-7.73 (m, 1H), 7.58-7.53 (m, 1H), 4.21 (s, 2H), 2.30-2.24 (m, 1H), 2.02-1.93 (m, 6H), 1.62-1.53 (m, 6H), 1.16-1.11 (m, 2H), 1.10-1.05 (m, 2H). FXR EC$_{50}$ (nM)=880. MS (ESI) 580 (M+H).

Example 22

4-(3-(4-((5-cyclopropyl-3-(2,6-dichlorophenyl)isoxazol-4-yl)methoxy)bicyclo[2.2.2]octan-1-yl)-1,2,4-oxadiazol-5-yl)picolinic acid (22)

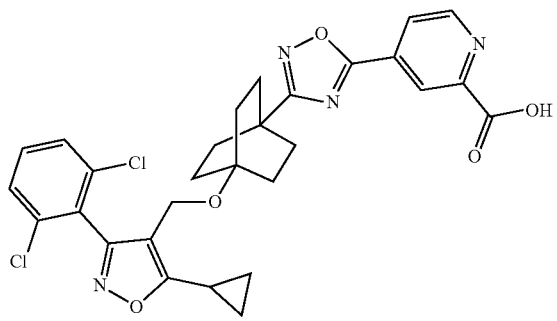

Step A. Intermediate 22A. Preparation of methyl 4-(3-(4-iodobicyclo[2.2.2]octan-1-yl)-1,2,4-oxadiazol-5-yl)picolinate

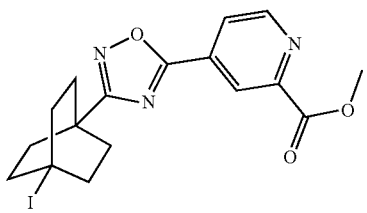 [SMILES: COC(=O)c1cc(-c2nc(C34CCC(I)(CC3)CC4)no2)ccn1]

The title compound was prepared according to methods described for the synthesis of Intermediate 20C, by reaction of Intermediate 20B and 2-(methoxycarbonyl)isonicotinic acid: (0.25 g, 0.57 mmol, 76% yield, white solid). $^1$H NMR (500 MHz, CHLOROFORM-d) δ 8.39-8.31 (m, 2H), 8.12-8.06 (m, 1H), 4.07 (s, 3H), 2.66-2.60 (m, 6H), 2.22-2.16 (m, 6H). MS (ESI) 440 (M+H).

Step B. Example 22

The title compound was prepared according to methods described for the synthesis of Example 4 (Step E), by reaction of Intermediate 22A and (5-cyclopropyl-3-(2,6-dichlorophenyl)isoxazol-4-yl)methanol: (2.4 mg, 0.0041, 4% yield). ¹H NMR (500 MHz, DMSO-d₆) δ 9.02-8.94 (m, 1H), 8.54-8.45 (m, 1H), 8.23-8.15 (m, 1H), 7.68-7.62 (m, 2H), 7.61-7.54 (m, 1H), 4.19 (s, 2H), 2.35-2.27 (m, 1H), 1.98-1.88 (m, 6H), 1.56-1.44 (m, 6H), 1.18-1.12 (m, 2H), 1.11-1.06 (m, 2H). FXR EC$_{50}$ (nM)=210. MS (ESI) 582 (M+H).

Example 23

6-(3-(4-((5-cyclopropyl-3-(2-(trifluoromethyl)phenyl)isoxazol-4-yl)methoxy)bicyclo[2.2.2]octan-1-yl)-1,2,4-oxadiazol-5-yl)picolinic acid reaction of Intermediate 22A and (5-cyclopropyl-3-(2-(trifluoromethyl)phenyl)isoxazol-4-yl)methanol: (12 mg, 0.020 mmol, 17% yield). ¹H NMR (500 MHz, DMSO-d₆) δ 8.37-8.31 (m, 1H), 8.29-8.19 (m, 2H), 7.94-7.90 (m, 1H), 7.86-7.80 (m, 1H), 7.80-7.74 (m, 1H), 7.59-7.54 (m, 1H), 4.14 (s, 2H), 2.31-2.24 (m, 1H), 2.02-1.90 (m, 6H), 1.61-1.51 (m, 6H), 1.17-1.12 (m, 2H), 1.08 (br d, J=2.7 Hz, 2H). FXR EC$_{50}$ (nM)=2800. MS (ESI) 581 (M+H).

Example 24

2-(4-((5-cyclopropyl-3-(2,6-dichlorophenyl)isoxazol-4-yl)methoxy)bicyclo[2.2.2]octan-1-yl)quinazoline-6-carboxylic acid

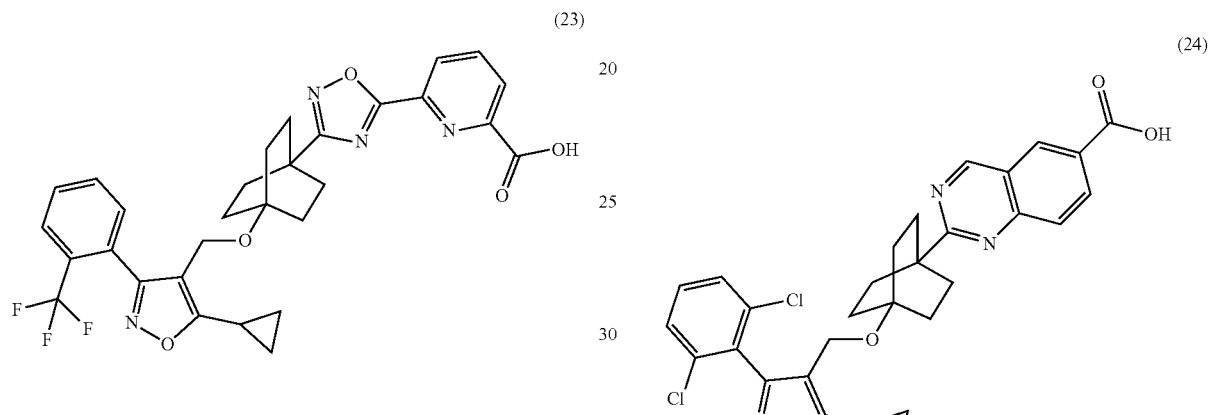

(23)

(24)

Step A. Intermediate 23A. Preparation of methyl 6-(3-(4-iodobicyclo[2.2.2]octan-1-yl)-1,2,4-oxadiazol-5-yl)picolinate

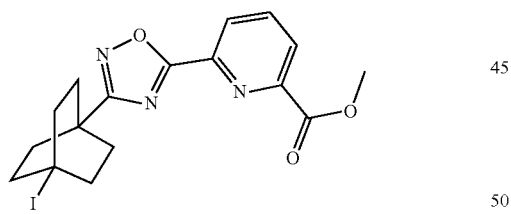

The title compound was prepared according to methods described for the synthesis of Intermediate 20C, by reaction of Intermediate 20B and 6-(methoxycarbonyl)picolinic acid: (0.24 g, 0.55 mmol, 73% yield, white solid). ¹H NMR (500 MHz, CHLOROFORM-d) δ 9.03-8.97 (m, 1H), 8.82-8.76 (m, 1H), 8.18-8.12 (m, 1H), 4.10 (s, 3H), 2.67-2.60 (m, 6H), 2.22-2.13 (m, 6H). MS (ESI) 440 (M+H).

Step B. Example 23

The title compound was prepared according to methods described for the synthesis of Example 4 (Step E), by Step A. Intermediate 24A. Preparation of methyl 4-amino-3-((4-iodobicyclo[2.2.2]octane-1-carboxamido)methyl)benzoate

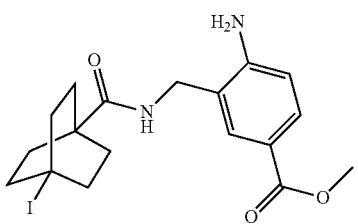 [SMILES: COC(=O)c1ccc(N)c(CNC(=O)C23CCC(I)(CC2)CC3)c1]

To a 50 mL round bottomed flask were added Intermediate 4B (0.19 g, 0.69 mmol), MeCN (7 mL) and HBTU (0.31 g, 0.83 mmol). After stirring for 30 min, a solution of methyl 4-amino-3-(aminomethyl)benzoate dihydrochloride (0.26 g, 0.69 mmol) (Pascal, R. et al. *Eur. J. Org. Chem.* 2000, 22, 3755-3761) and DIEA (0.48 mL, 2.8 mmol) dissolved in MeCN (3 mL) was added and the reaction was stirred under $N_2$. After 2 h, the solvent was concentrated and the crude product was purified by flash column chromatography (40 g silica gel cartridge; A=Hex, B=EtOAc; 20 min grad.; 0% B to 100% B; flow rate=40 mL/min). The pure fractions were combined, concentrated and dried in vacuo to afford the title compound (0.29 g, 0.66 mmol, 95% yield) as a pale yellow solid. $^1$H NMR (400 MHz, CHLOROFORM-d) δ 7.81-7.77 (m, 1H), 7.76-7.73 (m, 1H), 6.63-6.56 (m, 1H), 5.85-5.73 (m, 1H), 4.94-4.84 (m, 2H), 3.87 (s, 3H), 2.53-2.45 (m, 6H), 1.95-1.86 (m, 6H). MS (ESI) 443 (M+H).

Step B. Intermediate 24B. Preparation of methyl 2-(4-iodobicyclo[2.2.2]octan-1-yl)-3,4-dihydroquinazoline-6-carboxylate

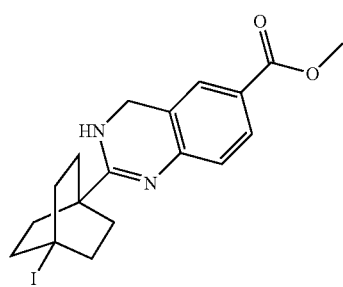 [SMILES: COC(=O)c1ccc2c(c1)CNC(C13CCC(I)(CC1)CC3)=N2]

To a 50 mL round bottomed flask were added Intermediate 24A (0.29 g, 0.66 mmol) and glacial AcOH (7 mL). The mixture was stirred at reflux. After 18 h, the reaction was cooled, concentrated, the residue was dissolved in MeOH (5 mL) and diluted with 1 M $K_2HPO_4$ (aq.) (50 mL). The resultant suspension was extracted with EtOAc (2×25 mL), the organic phase was combined, washed with brine, dried over $Na_2SO_4$, filtered and concentrated. The product was dried in vacuo to afford the title compound (0.24 g, 0.57 mmol, 86% yield) as a pale yellow solid. $^1$H NMR (500 MHz, METHANOL-$d_4$) δ 7.79 (d, J=8.3 Hz, 1H), 7.62 (s, 1H), 6.96 (d, J=8.3 Hz, 1H), 4.54 (s, 2H), 3.87 (s, 3H), 2.57-2.52 (m, 6H), 1.99 (br s, 6H). MS (ESI) 425 (M+H).

Step C. Intermediate 24C. Preparation of methyl 2-(4-iodobicyclo[2.2.2]octan-1-yl) quinazoline-6-carboxylate

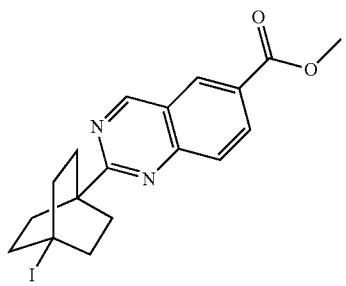 [SMILES: COC(=O)c1ccc2nc(C34CCC(I)(CC3)CC4)ncc2c1]

To a 25 mL round bottomed flask were added Intermediate 24B (0.24 g, 0.57 mmol), THF (6 mL), and DDQ (0.13 g, 0.57 mmol). The reaction was stirred under $N_2$ for 25 minutes, after which time the reaction was partitioned into 1 M $K_2HPO_4$ (aq.) (75 mL) and extracted with EtOAc (2×50 mL). The organic phase was combined, washed with brine, dried over $Na_2SO_4$, filtered and concentrated. The crude product was purified by flash column chromatography (24 g silica gel cartridge; A=Hex, B=EtOAc; 15 min grad.; 0% B to 70% B; flow rate=24 mL/min). The pure fractions were combined, concentrated and dried in vacuo to afford the title compound (0.17 g, 0.40 mmol, 71% yield) as a pale yellow oil. $^1$H NMR (500 MHz, CHLOROFORM-d) δ 9.44-9.42 (m, 1H), 8.69-8.63 (m, 1H), 8.51-8.43 (m, 1H), 8.05-7.98 (m, 1H), 4.03 (s, 3H), 2.72-2.64 (m, 6H), 2.34-2.24 (m, 6H). MS (ESI) 423 (M+H).

Step D. Example 24

The title compound was prepared according to methods described for the synthesis of Example 4 (Step E), by reaction of Intermediate 24C and (5-cyclopropyl-3-(2,6-dichlorophenyl)isoxazol-4-yl)methanol: (41 mg, 0.072 mmol, 60% yield). $^1$H NMR (500 MHz, DMSO-$d_6$) δ 9.64 (s, 1H), 8.71-8.65 (m, 1H), 8.44-8.34 (m, 1H), 7.96-7.91 (m, 1H), 7.64 (s, 2H), 7.61-7.57 (m, 1H), 4.20 (s, 2H), 2.35-2.27 (m, 1H), 2.07-1.99 (m, 6H), 1.56-1.45 (m, 6H), 1.19-1.13 (m, 2H), 1.10-1.05 (m, 2H). FXR $EC_{50}$ (nM)=250. MS (ESI) 565 (M+H).

The following Examples in Table 1 were prepared according to methods described elsewhere herein using appropriate starting materials, reagents and conditions.

TABLE 1

| Ex. No. | Structure & Name | ¹H NMR, FXR EC$_{50}$ & MS (ESI) | Method |
|---|---|---|---|
| 5 | 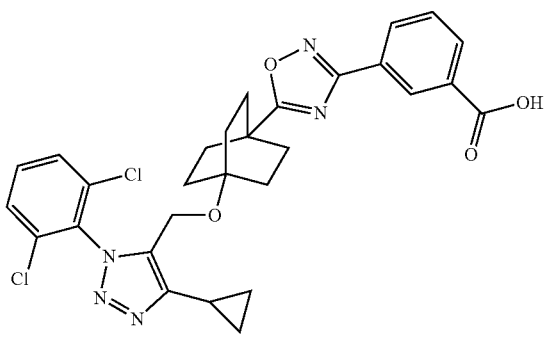<br>3-(5-(4-((4-cyclopropyl-1-(2,6-dichlorophenyl)-1H-1,2,3-triazol-5-yl)methoxy)bicyclo[2.2.2]octan-1-yl)-1,2,4-oxadiazol-3-yl)benzoic acid | ¹H NMR (500 MHz, DMSO-d$_6$) δ 8.53-8.49 (m, 1H), 8.22-8.16 (m, 1H), 8.16-8.10 (m, 1H), 7.82-7.76 (m, 2H), 7.74-7.65 (m, 2H), 4.43 (s, 2H), 2.09-2.05 (m, 1H), 2.04-1.98 (m, 6H), 1.55-1.46 (m, 6H), 1.02 (s, 2H), 0.97-0.92 (m, 2H). FXR EC$_{50}$ (nM) = 71. MS (ESI) 581 (M + H). | Ex. 4 |
| 25 | 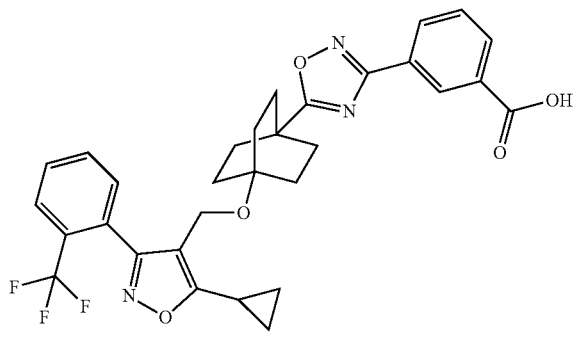<br>3-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)benzoic acid | ¹H NMR (500 MHz, DMSO-d$_6$) δ 8.52-8.48 (m, 1H), 8.16-8.08 (m, 2H), 7.95-7.89 (m, 1H), 7.85-7.80 (m, 1H), 7.79-7.73 (m, 1H), 7.69-7.62 (m, 1H), 7.59-7.53 (m, 1H), 4.12 (s, 2H), 2.32-2.23 (m, 1H), 2.01 (br d, J = 8.5 Hz, 6H), 1.56 (br d, J = 7.9 Hz, 6H), 1.18-1.05 (m, 4H). FXR EC$_{50}$ (nM) = 300. MS (ESI) 580 (M + H). | Ex. 1 |
| 26 | 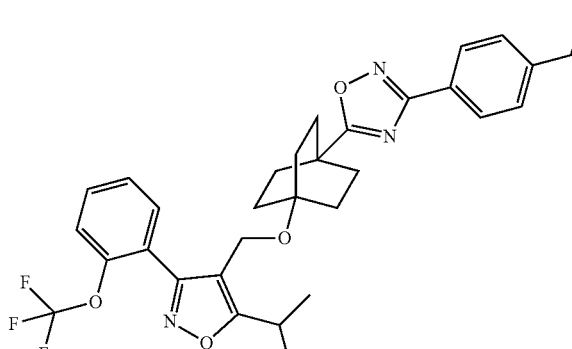<br>4-(5-(4-((5-isopropyl-3-(2-(trifluoromethoxy)phenyl)isoxazol-4-yl)methoxy)bicyclo[2.2.2]octan-1-yl)-1,2,4-oxadiazol-3-yl)benzoic acid | ¹H NMR (500 MHz, DMSO-d$_6$) δ 8.11-7.99 (m, 4H), 7.73-7.63 (m, 2H), 7.62-7.51 (m, 2H), 4.16 (s, 2H), 3.39-3.25 (m, 1H), 2.12-1.99 (m, 6H), 1.72-1.59 (m, 6H), 1.32 (br d, J = 6.9 Hz, 6H). FXR EC$_{50}$ (nM) = 980. MS (ESI) 598 (M + H). | Ex. 1 |

TABLE 1-continued

| Ex. No. | Structure & Name | $^1$H NMR, FXR EC$_{50}$ & MS (ESI) | Method |
|---|---|---|---|
| 27 | 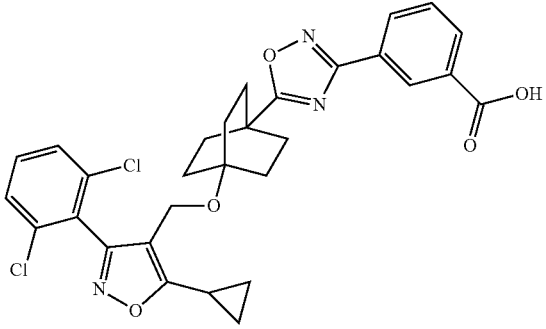<br>3-(5-(4-((5-cyclopropyl-3-(2,6-dichlorophenyl)isoxazol-4-yl)methoxy)bicyclo[2.2.2]octan-1-yl)-1,2,4-oxadiazol-3-yl)benzoic acid | $^1$H NMR (500 MHz, DMSO-d$_6$) δ 8.46-7.94 (m, 3H), 7.64-7.59 (m, 2H), 7.59-7.53 (m, 1H), 4.20-4.12 (m, 2H), 2.33-2.21 (m, 1H), 2.00 (br d, J = 7.0 Hz, 6H), 1.55-1.40 (m, 6H), 1.06 (br s, 4H). FXR EC$_{50}$ (nM) = 26. MS (ESI) 581 (M + H). | Ex. 1 |
| 28 | 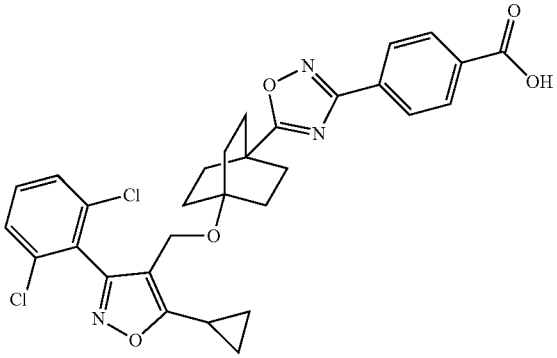<br>4-(5-(4-((5-cyclopropyl-3-(2,6-dichlorophenyl)isoxazol-4-yl)methoxy)bicyclo[2.2.2]octan-1-yl)-1,2,4-oxadiazol-3-yl)benzoic acid | $^1$H NMR (400 MHz, METHANOL-d$_4$) δ 8.18-8.09 (m, 4H), 7.59-7.48 (m, 3H), 4.30-4.25 (m, 2H), 2.32-2.22 (m, 1H), 2.16-2.08 (m, 6H), 1.68-1.59 (m, 6H), 1.21-1.15 (m, 4H). FXR EC$_{50}$ (nM) = 40. MS (ESI) 581 (M + H). | Ex. 1 |
| 29 | 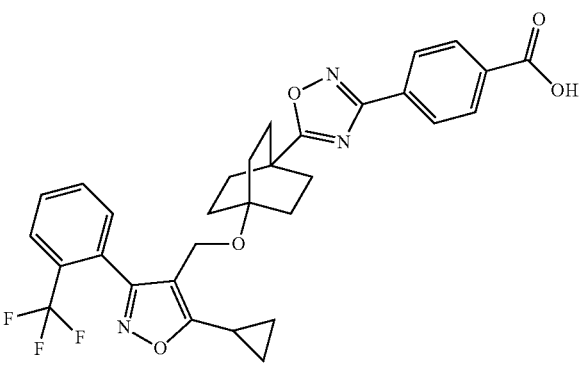<br>4-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)benzoic acid | $^1$H NMR (500 MHz, DMSO-d$_6$) δ 8.40-8.04 (m, 3H), 7.95-7.90 (m, 1H), 7.86-7.81 (m, 1H), 7.80-7.74 (m, 1H), 7.60-7.53 (m, 1H), 4.15 (s, 2H), 2.33-2.24 (m, 1H), 2.06 (br s, 6H), 1.59 (br s, 6H). FXR EC$_{50}$ (nM) = 330. MS (ESI) 580 (M + H). | Ex. 1 |

TABLE 1-continued

| Ex. No. | Structure & Name | $^1$H NMR, FXR $EC_{50}$ & MS (ESI) | Method |
|---|---|---|---|
| 30 | 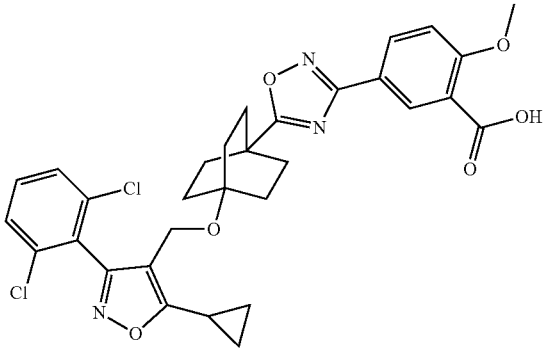<br>5-(5-(4-((5-cyclopropyl-3-(2,6-dichlorophenyl)isoxazol-4-yl)methoxy)bicyclo[2.2.2]octan-1-yl)-1,2,4-oxadiazol-3-yl)-2-methoxybenzoic acid | $^1$H NMR (500 MHz, DMSO-d$_6$) δ 8.23 (d, J = 1.8 Hz, 1H), 8.08 (dd, J = 8.7, 2.0 Hz, 1H), 7.67-7.62 (m, 2H), 7.60 (s, 1H), 7.31 (d, J = 8.9 Hz, 1H), 4.19 (s, 2H), 3.90 (s, 3H), 2.35-2.27 (m, 1H), 2.04-1.94 (m, 6H), 1.50 (br s, 6H), 1.19-1.12 (m, 2H), 1.11-1.04 (m, 2H). FXR $EC_{50}$ (nM) = 37. MS (ESI) 611 (M + H). | Ex. 4 |
| 31 | 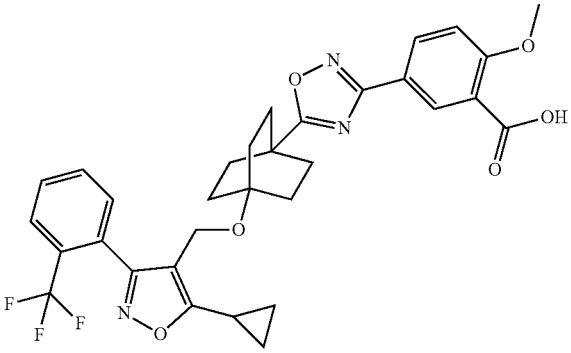<br>5-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)-2-methoxybenzoic acid | $^1$H NMR (500 MHz, DMSO-d$_6$) δ 8.24-8.19 (m, 1H), 8.10-8.04 (m, 1H), 7.95-7.88 (m, 1H), 7.85-7.79 (m, 1H), 7.79-7.73 (m, 1H), 7.59-7.52 (m, 1H), 7.33-7.27 (m, 1H), 4.12 (s, 2H), 3.89 (s, 3H), 2.31-2.22 (m, 1H), 2.05-1.95 (m, 6H), 1.60-1.50 (m, 6H), 1.13 (br d, J = 8.2 Hz, 2H), 1.09-1.02 (m, 2H). FXR $EC_{50}$ (nM) = 370. MS (ESI) 610 (M + H). | Ex. 4 |
| 32 | 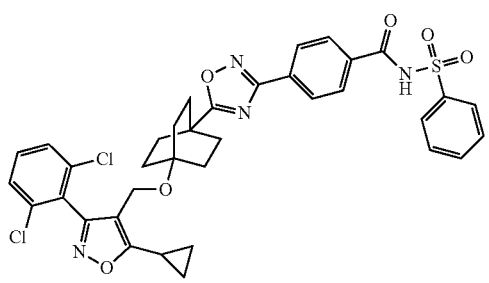<br>4-(5-(4-((5-cyclopropyl-3-(2,6-dichlorophenyl)isoxazol-4-yl)methoxy)bicyclo[2.2.2]octan-1-yl)-1,2,4-oxadiazol-3-yl)-N-(phenylsulfonyl)benzamide | $^1$H NMR (500 MHz, DMSO-d$_6$) δ 8.04-8.00 (m, 2H), 7.93-7.88 (m, 2H), 7.86-7.82 (m, 2H), 7.65-7.60 (m, 2H), 7.59-7.54 (m, 1H), 7.45-7.38 (m, 3H), 4.21-4.13 (m, 2H), 2.33-2.25 (m, 1H), 2.02-1.94 (m, 6H), 1.53-1.43 (m, 6H), 1.17-1.11 (m, 2H), 1.09-1.04 (m, 2H). FXR $EC_{50}$ (nM) = 300. MS (ESI) 720 (M + H). | Ex. 3 |

| Ex. No. | Structure & Name | $^1$H NMR, FXR EC$_{50}$ & MS (ESI) | Method |
|---|---|---|---|
| 33 | 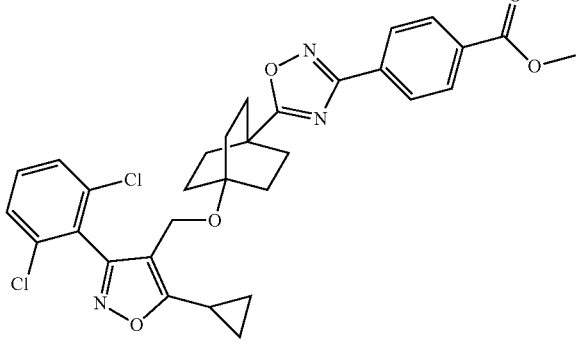<br>methyl 4-(5-(4-(((5-cyclopropyl-3-(2,6-dichlorophenyl)isoxazol-4-yl)methoxy)bicyclo[2.2.2]octan-1-yl)-1,2,4-oxadiazol-3-yl)benzoate | $^1$H NMR (500 MHz, DMSO-d$_6$) δ 8.17-8.06 (m, 4H), 7.65-7.60 (m, 2H), 7.60-7.53 (m, 1H), 4.20-4.13 (m, 2H), 3.88 (s, 3H), 2.33-2.24 (m, 1H), 1.98 (br d, J = 8.5 Hz, 6H), 1.56-1.41 (m, 6H), 1.18-1.11 (m, 2H), 1.10-1.03 (m, 2H). FXR EC$_{50}$ (nM) = 170. MS (ESI) 595 (M + H). | Ex. 1 |
| 34 | 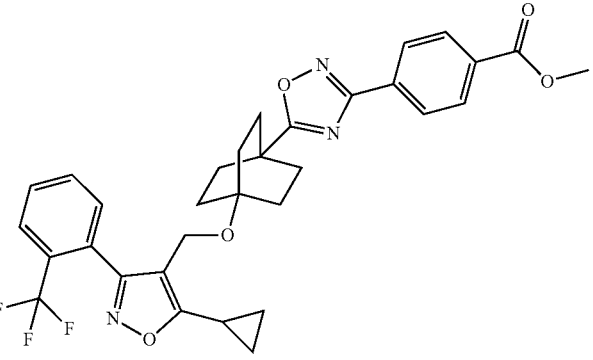<br>methyl 4-(5-(4-(((5-cyclopropyl-3-(2-(trifluoromethyl)phenyl)isoxazol-4-yl)methoxy)bicyclo[2.2.2]octan-1-yl)-1,2,4-oxadiazol-3-yl)benzoate | $^1$H NMR (500 MHz, DMSO-d$_6$) δ 8.11 (s, 4H), 7.95-7.89 (m, 1H), 7.85-7.79 (m, 1H), 7.78-7.72 (m, 1H), 7.60-7.50 (m, 1H), 4.16-4.08 (m, 2H), 3.88 (s, 3H), 2.30-2.21 (m, 1H), 2.05-1.96 (m, 6H), 1.62-1.50 (m, 6H), 1.18-1.10 (m, 2H), 1.09-1.03 (m, 2H). FXR EC$_{50}$ (nM) = 5100. MS (ESI) 594 (M + H). | Ex. 1 |
| 35 | 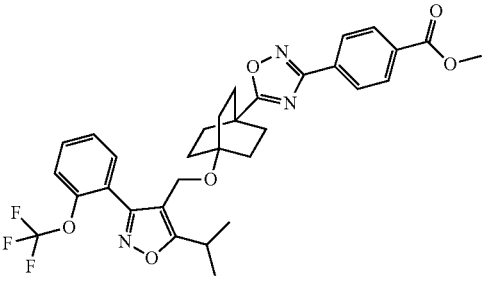<br>methyl 4-(5-(4-(((5-isopropyl-3-(2-(trifluoromethoxy)phenyl)isoxazol-4-yl)methoxy)bicyclo[2.2.2]octan-1-yl)-1,2,4-oxadiazol-3-yl)benzoate | $^1$H NMR (500 MHz, DMSO-d$_6$) δ 8.11 (s, 4H), 7.71-7.66 (m, 1H), 7.65-7.61 (m, 1H), 7.60-7.52 (m, 2H), 4.15 (s, 2H), 3.88 (s, 3H), 3.37-3.28 (m, 1H), 2.11-2.00 (m, 6H), 1.70-1.60 (m, 6H), 1.31 (d, J = 7.0 Hz, 6H). FXR EC$_{50}$ (nM) = 2400. MS (ESI) 612 (M + H). | Ex. 1 |

| Ex. No. | Structure & Name | ¹H NMR, FXR EC$_{50}$ & MS (ESI) | Method |
|---|---|---|---|
| 36 | 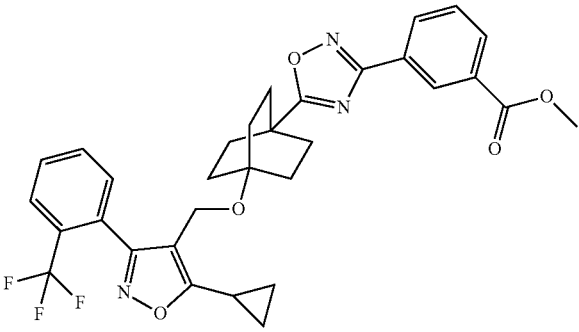<br>methyl 3-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)benzoate | ¹H NMR (500 MHz, DMSO-d$_6$) δ 8.54-8.48 (m, 1H), 8.26-8.21 (m, 1H), 8.18-8.12 (m, 1H), 7.94-7.89 (m, 1H), 7.85-7.80 (m, 1H), 7.73 (s, 2H), 7.57 (s, 1H), 4.13 (s, 2H), 3.91 (s, 3H), 2.31-2.24 (m, 1H), 2.07-1.99 (m, 6H), 1.63-1.51 (m, 6H), 1.18-1.11 (m, 2H), 1.10-1.04 (m, 2H). FXR EC$_{50}$ (nM) = 3500. MS (ESI) 594 (M + H). | Ex. 1 |
| 37 | 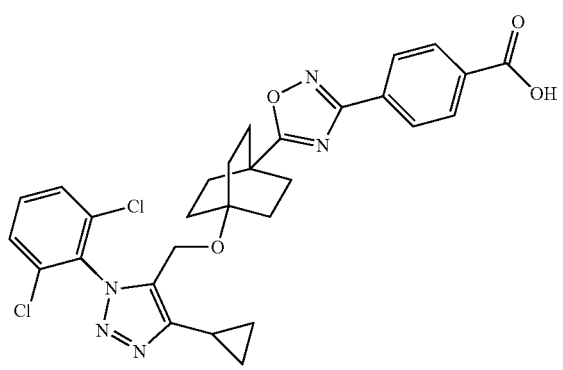<br>4-(5-(4-((4-cyclopropyl-1-(2,6-dichlorophenyl)-1H-1,2,3-triazol-5-yl)methoxy)bicyclo[2.2.2]octan-1-yl)-1,2,4-oxadiazol-3-yl)benzoic acid | ¹H NMR (500 MHz, DMSO-d$_6$) δ 8.76-7.92 (m, 4H), 7.82-7.75 (m, 2H), 7.74-7.66 (m, 1H), 4.41 (s, 2H), 2.09-2.02 (m, 1H), 1.97 (br s, 6H), 1.47 (br s, 6H), 1.01 (d, J = 6.1 Hz, 2H), 0.93 (br d, J = 2.7 Hz, 2H). FXR EC$_{50}$ (nM) = 190. MS (ESI) 581 (M + H). | Ex. 4 |
| 38 | 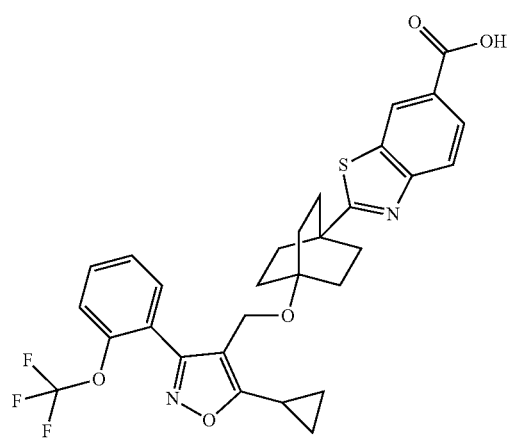<br>2-(4-((5-cyclopropyl-3-(2-(trifluoromethoxy)phenyl)isoxazol-4-yl)methoxy)bicyclo[2.2.2]octan-1-yl)benzo[d]thiazole-6-carboxylic acid | ¹H NMR (500 MHz, DMSO-d$_6$) δ 8.74-8.61 (m, 1H), 8.00 (br s, 2H), 7.72-7.61 (m, 2H), 7.57 (br s, 2H), 4.22 (s, 2H), 2.32-2.25 (m, 1H), 2.06 (br s, 6H), 1.68 (br d, J = 7.6 Hz, 6H), 1.17-1.11 (m, 2H), 1.10-1.04 (m, 2H). FXR EC$_{50}$ (nM) = 360. MS (ESI) 585 (M + H). | Ex. 6 |

TABLE 1-continued

| Ex. No. | Structure & Name | $^1$H NMR, FXR $EC_{50}$ & MS (ESI) | Method |
|---|---|---|---|
| 39 | 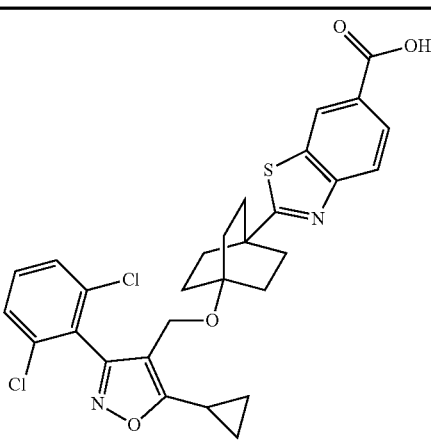<br>2-(4-((5-cyclopropyl-3-(2,6-dichlorophenyl)isoxazol-4-yl)methoxy)bicyclo[2.2.2]octan-1-yl)benzo[d]thiazole-6-carboxylic acid | $^1$H NMR (500 MHz, DMSO-d$_6$) δ 8.66 (s, 1H), 7.99 (br d, J = 11.3 Hz, 2H), 7.69-7.62 (m, 2H), 7.59 (br d, J = 7.3 Hz, 1H), 4.19 (s, 2H), 2.35-2.28 (m, 1H), 2.07-1.95 (m, 6H), 1.53 (br d, J = 7.6 Hz, 6H), 1.18-1.12 (m, 2H), 1.11-1.05 (m, 2H). FXR EC$_{50}$ (nM) = 140. MS (ESI) 570 (M + H). | Ex. 6 |
| 40 | 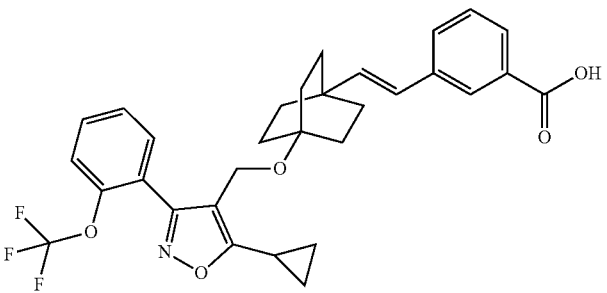<br>(E)-3-(2-(4-((5-cyclopropyl-3-(2-(trifluoromethoxy)phenyl)isoxazol-4-yl)methoxy)bicyclo[2.2.2]octan-1-yl)vinyl)benzoic acid | $^1$H NMR (500 MHz, DMSO-d$_6$) δ 8.23-7.83 (m, 3H), 7.72-7.66 (m, 1H), 7.64-7.60 (m, 1H), 7.58-7.53 (m, 2H), 7.50-7.31 (m, 1H), 6.43-6.21 (m, 2H), 4.19 (s, 2H), 2.29-2.20 (m, 1H), 1.74-1.62 (m, 6H), 1.61-1.52 (m, 6H), 1.15-1.10 (m, 2H), 1.09-1.04 (m, 2H). FXR EC$_{50}$ (nM) = 100. MS (ESI) 554 (M + H). | Ex. 7 |
| 41 | 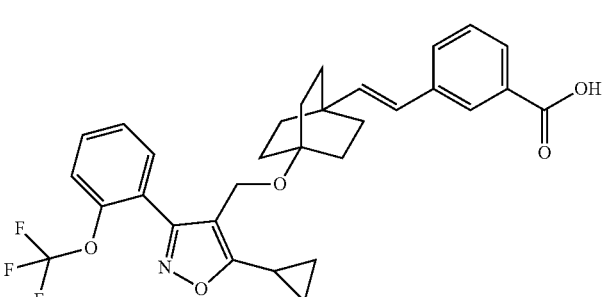<br>(E)-3-(2-(4-((5-cyclopropyl-3-(2-(trifluoromethyl)phenyl)isoxazol-4-yl)methoxy)bicyclo[2.2.2]octan-1-yl)vinyl)benzoic acid | $^1$H NMR (500 MHz, DMSO-d$_6$) δ 8.57-8.23 (m, 2H), 7.98-7.89 (m, 2H), 7.85-7.80 (m, 1H), 7.78-7.73 (m, 1H), 7.58-7.53 (m, 1H), 7.47-7.28 (m, 1H), 6.39-6.16 (m, 2H), 4.10 (s, 2H), 2.30-2.20 (m, 1H), 1.71-1.54 (m, 6H), 1.52-1.41 (m, 6H), 1.16-1.11 (m, 2H), 1.09-1.04 (m, 2H). FXR EC$_{50}$ (nM) = 470. MS (ESI) 538 (M + H). | Ex. 7 |

TABLE 1-continued

| Ex. No. | Structure & Name | $^1$H NMR, FXR EC$_{50}$ & MS (ESI) | Method |
|---|---|---|---|
| 42 | 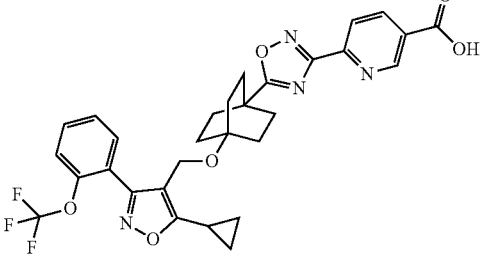<br>6-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)nicotinic acid | $^1$H NMR (500 MHz, DMSO-d$_6$) δ 9.20-9.13 (m, 1H), 8.45-8.38 (m, 1H), 8.15-8.07 (m, 1H), 7.71-7.65 (m, 1H), 7.65-7.60 (m, 1H), 7.59-7.52 (m, 2H), 4.21 (s, 2H), 2.27 (br d, J = 4.9 Hz, 1H), 2.12-1.99 (m, 6H), 1.70-1.57 (m, 6H), 1.18-1.10 (m, 2H), 1.06 (br d, J = 2.7 Hz, 2H). FXR EC$_{50}$ (nM) = 1500. MS (ESI) 597 (M + H). | Ex. 4 |
| 43 | 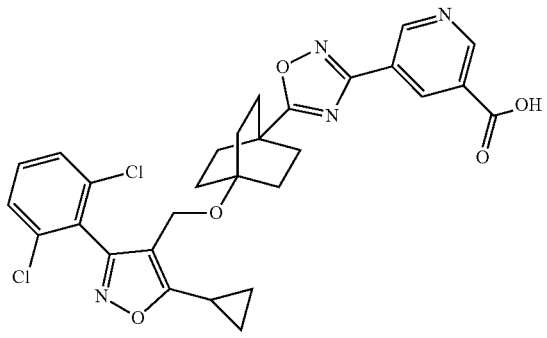<br>5-(5-(4-((5-cyclopropyl-3-(2,6-dichlorophenyl)isoxazol-4-yl)methoxy)bicyclo[2.2.2]octan-1-yl)-1,2,4-oxadiazol-3-yl)nicotinic acid | $^1$H NMR (500 MHz, DMSO-d$_6$) δ 9.33-9.27 (m, 1H), 9.25-9.19 (m, 1H), 8.71-8.64 (m, 1H), 7.63 (s, 2H), 7.61-7.54 (m, 1H), 4.19 (s, 2H), 2.34-2.27 (m, 1H), 2.06-1.97 (m, 6H), 1.55-1.47 (m, 6H), 1.17-1.12 (m, 2H), 1.11-1.05 (m, 2H). FXR EC$_{50}$ (nM) = 230. MS (ESI) 582 (M + H). | Ex. 4 |
| 44 | 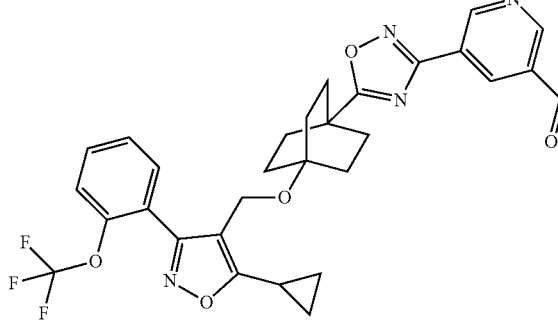<br>5-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)nicotinic acid | $^1$H NMR (500 MHz, DMSO-d$_6$) δ 9.31 (d, J = 1.2 Hz, 1H), 9.23 (s, 1H), 8.70 (s, 1H), 7.77-7.61 (m, 2H), 7.61-7.52 (m, 2H), 4.23 (s, 2H), 2.35-2.24 (m, 1H), 2.14-2.02 (m, 6H), 1.72-1.61 (m, 6H), 1.17-1.12 (m, 2H), 1.11-1.05 (m, 2H). FXR EC$_{50}$ (nM) = 870. MS (ESI) 597 (M + H). | Ex. 4 |

TABLE 1-continued

| Ex. No. | Structure & Name | ¹H NMR, FXR EC$_{50}$ & MS (ESI) | Method |
|---|---|---|---|
| 45 | 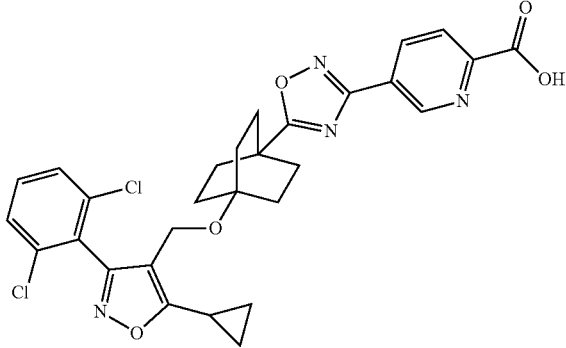<br>5-(5-(4-((5-cyclopropyl-3-(2,6-dichlorophenyl)isoxazol-4-yl)methoxy)bicyclo[2.2.2]octan-1-yl)-1,2,4-oxadiazol-3-yl)picolinic acid | ¹H NMR (500 MHz, DMSO-d$_6$) δ 9.19-9.10 (m, 1H), 8.45-8.36 (m, 1H), 8.17-8.07 (m, 1H), 7.67-7.62 (m, 2H), 7.61-7.54 (m, 1H), 4.18 (s, 2H), 2.33-2.27 (m, 1H), 2.05-1.97 (m, 6H), 1.51 (br d, J = 7.3 Hz, 6H), 1.17-1.12 (m, 2H), 1.11-1.04 (m, 2H). FXR EC$_{50}$ (nM) = 490. MS (ESI) 582 (M + H). | Ex. 4 |
| 46 | 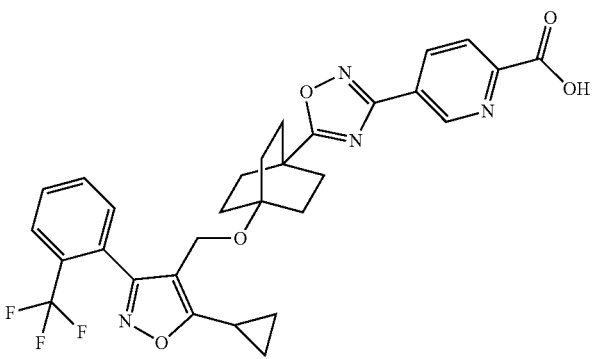<br>5-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)picolinic acid | ¹H NMR (500 MHz, DMSO-d$_6$) δ 8.80-8.70 (m, 1H), 8.68-8.50 (m, 1H), 8.42-8.25 (m, 1H), 8.00-7.88 (m, 1H), 7.86-7.68 (m, 2H), 7.64-7.47 (m, 1H), 4.24-4.01 (m, 2H), 2.27 (br s, 1H), 2.02 (br s, 6H), 1.56 (br s, 6H), 1.21-1.00 (m, 4H). FXR EC$_{50}$ (nM) = 2700. MS (ESI) 581 (M + H). | Ex. 4 |
| 47 | 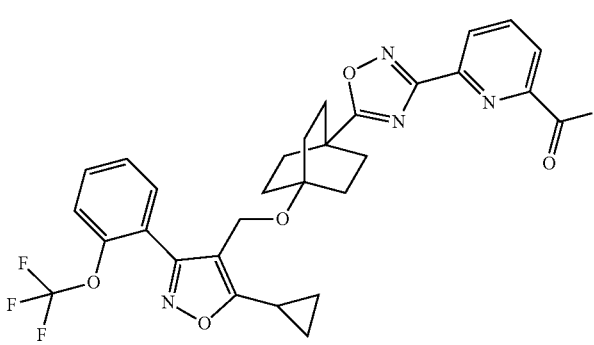<br>6-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)picolinic acid | ¹H NMR (500 MHz, DMSO-d$_6$) δ 8.15-8.04 (m, 3H), 7.72-7.66 (m, 1H), 7.66-7.61 (m, 1H), 7.61-7.51 (m, 2H), 4.22 (s, 2H), 2.33-2.24 (m, 1H), 2.12-2.02 (m, 6H), 1.69-1.60 (m, 6H), 1.15 (br s, 2H), 1.08 (br d, J = 3.1 Hz, 2H). FXR EC$_{50}$ (nM) = 550 MS (ESI) 597 (M + H). | Ex. 4 |

TABLE 1-continued

| Ex. No. | Structure & Name | $^1$H NMR, FXR EC$_{50}$ & MS (ESI) | Method |
|---|---|---|---|
| 48 | 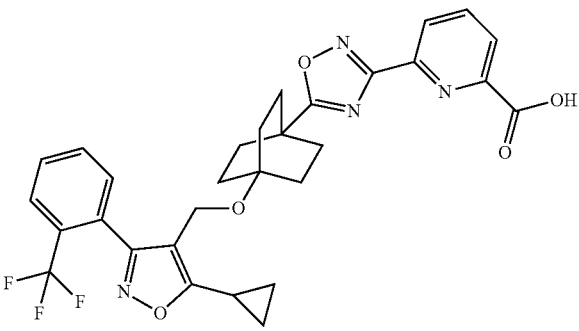<br>6-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)picolinic acid | $^1$H NMR (500 MHz, DMSO-d$_6$) δ 8.16-8.07 (m, 3H), 7.94-7.89 (m, 1H), 7.85-7.80 (m, 1H), 7.79-7.72 (m, 1H), 7.59-7.53 (m, 1H), 4.12 (s, 2H), 2.31-2.23 (m, 1H), 2.07-1.99 (m, 6H), 1.61-1.49 (m, 6H), 1.17-1.11 (m, 2H), 1.07 (br d, J = 2.7 Hz, 2H). FXR EC$_{50}$ (nM) = 2100. MS (ESI) 581 (M + H). | Ex. 4 |
| 49 | 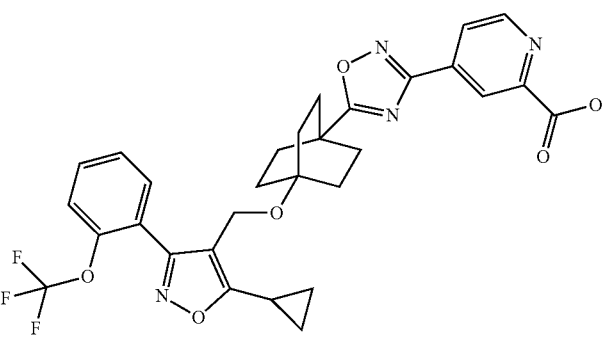<br>4-(5-(4-((5-cyclopropyl-3-(2-(trifluoromethoxy)phenyl)isoxazol-4-yl)methoxy)bicyclo[2.2.2]octan-1-yl)-1,2,4-oxadiazol-3-yl)picolinic acid | $^1$H NMR (500 MHz, DMSO-d$_6$) δ 8.83-8.74 (m, 1H), 8.48-8.38 (m, 1H), 7.98-7.90 (m, 1H), 7.72-7.66 (m, 1H), 7.66-7.61 (m, 1H), 7.61-7.52 (m, 2H), 4.22 (s, 2H), 2.32-2.25 (m, 1H), 2.12-2.02 (m, 6H), 1.71-1.60 (m, 6H), 1.17-1.11 (m, 2H), 1.08 (br d, J = 2.7 Hz, 2H). FXR EC$_{50}$ (nM) = 1200. MS (ESI) 597 (M + H). | Ex. 4 |
| 50 | 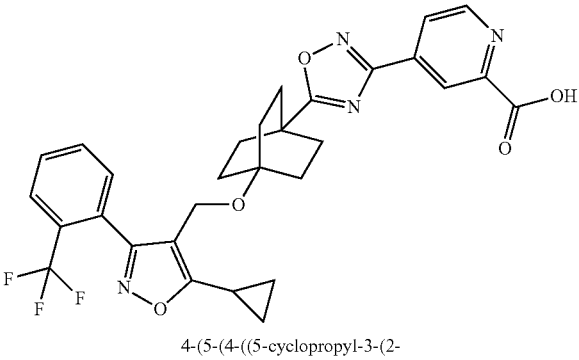<br>4-(5-(4-((5-cyclopropyl-3-(2-(trifluoromethyl)phenyl)isoxazol-4-yl)methoxy)bicyclo[2.2.2]octan-1-yl)-1,2,4-oxadiazol-3-yl)picolinic acid | $^1$H NMR (500 MHz, DMSO-d$_6$) δ 8.94-8.75 (m, 1H), 8.50-8.41 (m, 1H), 8.03-7.95 (m, 1H), 7.95-7.89 (m, 1H), 7.87-7.80 (m, 1H), 7.80-7.74 (m, 1H), 7.62-7.52 (m, 1H), 4.13 (s, 2H), 2.32-2.23 (m, 1H), 2.09-1.96 (m, 6H), 1.64-1.49 (m, 6H), 1.14 (br d, J = 7.9 Hz, 2H), 1.08 (br d, J = 2.7 Hz, 2H). FXR EC$_{50}$ (nM) = 2100. MS (ESI) 581 (M + H). | Ex. 4 |

TABLE 1-continued

| Ex. No. | Structure & Name | ¹H NMR, FXR EC$_{50}$ & MS (ESI) | Method |
|---|---|---|---|
| 51 | 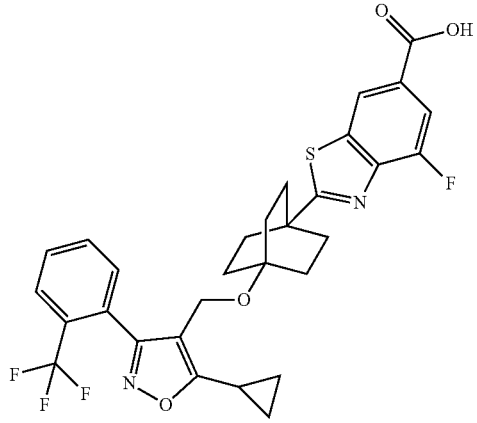  2-(4-((5-cyclopropyl-3-(2-(trifluoromethyl)phenyl)isoxazol-4-yl)methoxy)bicyclo[2.2.2]octan-1-yl)-4-fluorobenzo[d]thiazole-6-carboxylic acid | ¹H NMR (500 MHz, DMSO-d$_6$) δ 8.48 (s, 1H), 7.92 (br d, J = 7.6 Hz, 1H), 7.86-7.80 (m, 1H), 7.80-7.70 (m, 2H), 7.57 (br d, J = 7.3 Hz, 1H), 4.14 (s, 2H), 2.31-2.24 (m, 1H), 2.07-1.97 (m, 6H), 1.63-1.53 (m, 6H), 1.18-1.11 (m, 2H), 1.08 (br d, J = 2.7 Hz, 2H). FXR EC$_{50}$ (nM) = 500. MS (ESI) 587 (M + H). | Ex. 15 |
| 52 | 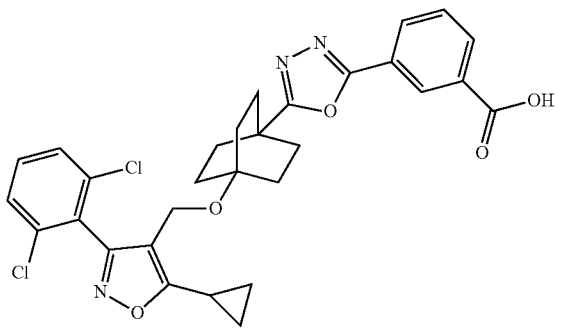  3-(5-(4-((5-cyclopropyl-3-(2,6-dichlorophenyl)isoxazol-4-yl)methoxy)bicyclo[2.2.2]octan-1-yl)-1,3,4-oxadiazol-2-yl)benzoic acid | ¹H NMR (500 MHz, DMSO-d$_6$) δ 8.47-8.40 (m, 1H), 8.17-8.08 (m, 2H), 7.63 (s, 3H), 7.61-7.55 (m, 1H), 4.18 (s, 2H), 2.35-2.27 (m, 1H), 2.03-1.94 (m, 6H), 1.55-1.44 (m, 6H), 1.19-1.12 (m, 2H), 1.12-1.05 (m, 2H). FXR EC$_{50}$ (nM) = 170. MS (ESI) 581 (M + H). | Ex. 18 |
| 53 | 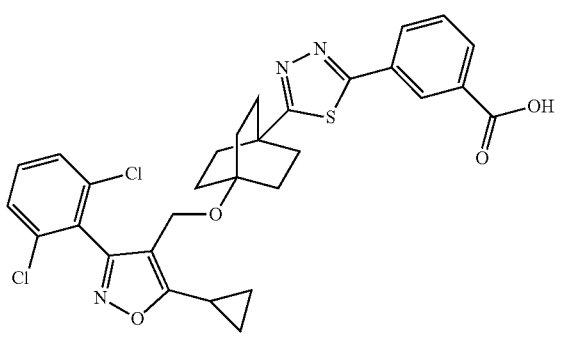  3-(5-(4-((5-cyclopropyl-3-(2,6-dichlorophenyl)isoxazol-4-yl)methoxy)bicyclo[2.2.2]octan-1-yl)-1,3,4-thiadiazol-2-yl)benzoic acid | ¹H NMR (500 MHz, DMSO-d$_6$) δ 8.43-8.37 (m, 1H), 8.09-8.00 (m, 2H), 7.69-7.62 (m, 2H), 7.60 (br d, J = 8.5 Hz, 2H), 4.20 (s, 2H), 2.35-2.28 (m, 1H), 2.06-1.94 (m, 6H), 1.60-1.46 (m, 6H), 1.19-1.12 (m, 2H), 1.12-1.06 (m, 2H). FXR EC$_{50}$ (nM) = 100. MS (ESI) 597 (M + H). | Ex. 19 |

TABLE 1-continued

| Ex. No. | Structure & Name | $^1$H NMR, FXR EC$_{50}$ & MS (ESI) | Method |
|---|---|---|---|
| 54 | 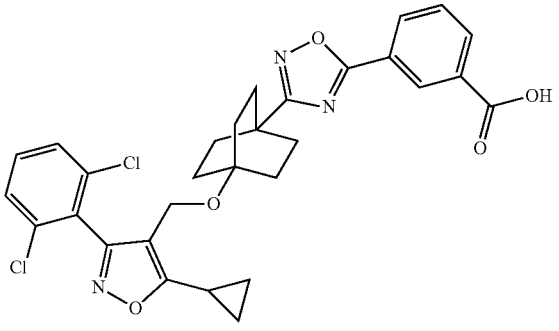<br>3-(3-(4-((5-cyclopropyl-3-(2,6-dichlorophenyl)isoxazol-4-yl)methoxy)bicyclo[2.2.2]octan-1-yl)-1,2,4-oxadiazol-5-yl)benzoic acid | $^1$H NMR (500 MHz, DMSO-d$_6$) δ 8.56 (s, 1H), 8.26 (br d, J = 7.6 Hz, 1H), 8.22 (br d, J = 7.6 Hz, 1H), 7.75 (t, J = 7.8 Hz, 1H), 7.68-7.63 (m, 2H), 7.62-7.56 (m, 1H), 4.19 (s, 2H), 2.35-2.27 (m, 1H), 1.97-1.88 (m, 6H), 1.55-1.45 (m, 6H), 1.15 (br d, J = 7.9 Hz, 2H), 1.09 (br d, J = 3.1 Hz, 2H). FXR EC$_{50}$ (nM) = 24. MS (ESI) 597 (M + H). | Ex. 20 |
| 55 | 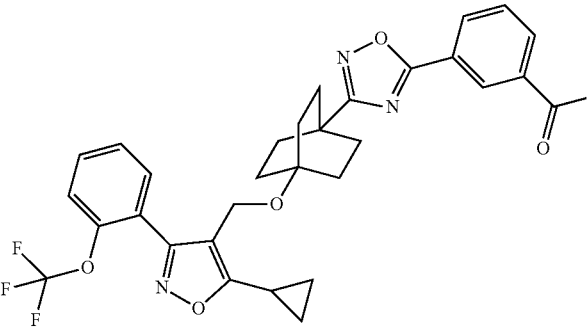<br>3-(3-(4-((5-cyclopropyl-3-(2-(trifluoromethoxy)phenyl)isoxazol-4-yl)methoxy)bicyclo[2.2.2]octan-1-yl)-1,2,4-oxadiazol-5-yl)benzoic acid | $^1$H NMR (500 MHz, DMSO-d$_6$) δ 8.57 (s, 1H), 8.24 (br dd, J = 20.0, 7.8 Hz, 2H), 7.78-7.63 (m, 3H), 7.58 (br t, J = 7.2 Hz, 2H), 4.23 (s, 2H), 2.34-2.24 (m, 1H), 2.03-1.95 (m, 5H), 1.71-1.59 (m, 6H), 1.18-1.12 (m, 2H), 1.09 (br d, J = 2.7 Hz, 2H). FXR EC$_{50}$ (nM) = 250. MS (ESI) 596 (M + H). | Ex. 20 |
| 56 | 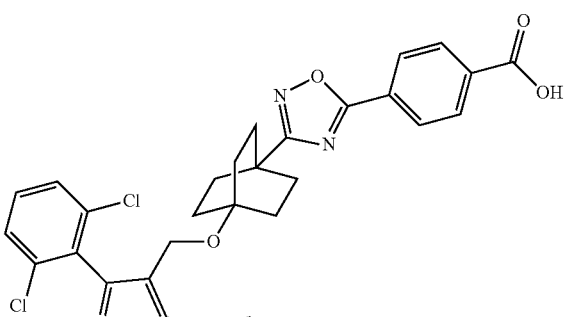<br>4-(3-(4-((5-cyclopropyl-3-(2,6-dichlorophenyl)isoxazol-4-yl)methoxy)bicyclo[2.2.2]octan-1-yl)-1,2,4-oxadiazol-5-yl)benzoic acid | $^1$H NMR (500 MHz, DMSO-d$_6$) δ 8.16 (q, J = 8.2 Hz, 4H), 7.68-7.62 (m, 2H), 7.61-7.56 (m, 1H), 4.19 (s, 2H), 2.35-2.28 (m, 1H), 1.98-1.89 (m, 6H), 1.56-1.45 (m, 6H), 1.18-1.13 (m, 2H), 1.09 (br d, J = 3.1 Hz, 2H). FXR EC$_{50}$ (nM) = 75. MS (ESI) 581 (M + H). | Ex. 20 |

TABLE 1-continued

| Ex. No. | Structure & Name | $^1$H NMR, FXR EC$_{50}$ & MS (ESI) | Method |
|---|---|---|---|
| 57 | 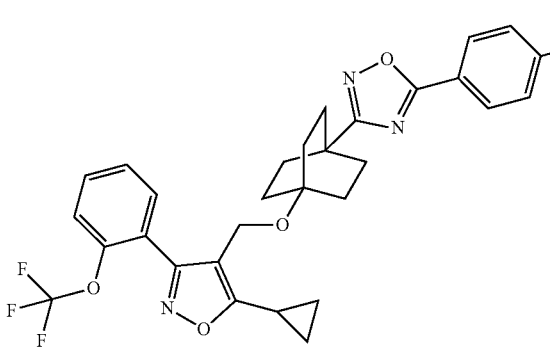<br>4-(3-(4-((5-cyclopropyl-3-(2-(trifluoromethoxy)phenyl)isoxazol-4-yl)methoxy)bicyclo[2.2.2]octan-1-yl)-1,2,4-oxadiazol-5-yl)benzoic acid | $^1$H NMR (500 MHz, DMSO-d$_6$) δ 8.19-8.08 (m, 4H), 7.72-7.67 (m, 1H), 7.67-7.63 (m, 1H), 7.61-7.54 (m, 2H), 4.23 (s, 2H), 2.32-2.25 (m, 1H), 2.03-1.94 (m, 6H), 1.71-1.59 (m, 6H), 1.17-1.12 (m, 2H), 1.11-1.04 (m, 2H). FXR EC$_{50}$ (nM) = 650. MS (ESI) 596 (M + H). | Ex. 20 |
| 58 | 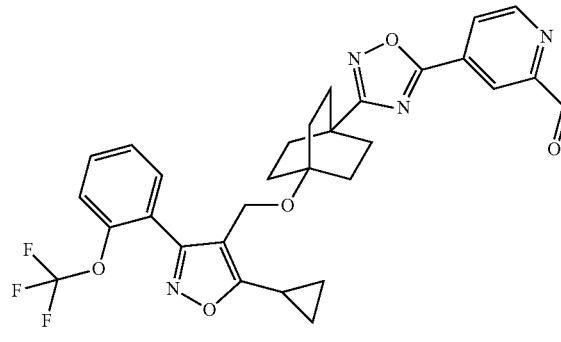<br>4-(3-(4-((5-cyclopropyl-3-(2-(trifluoromethoxy)phenyl)isoxazol-4-yl)methoxy)bicyclo[2.2.2]octan-1-yl)-1,2,4-oxadiazol-5-yl)picolinic acid | $^1$H NMR (500 MHz, DMSO-d$_6$) δ 8.70-8.45 (m, 1H), 8.26-8.09 (m, 1H), 7.99-7.93 (m, 1H), 7.72-7.60 (m, 2H), 7.60-7.52 (m, 2H), 4.26-4.20 (m, 2H), 2.33-2.25 (m, 1H), 2.08-1.94 (m, 6H), 1.74-1.56 (m, 6H), 1.19-1.11 (m, 2H), 1.11-1.05 (m, 2H). FXR EC$_{50}$ (nM) = 4000. MS (ESI) 597 (M + H). | Ex. 20 |
| 59 | 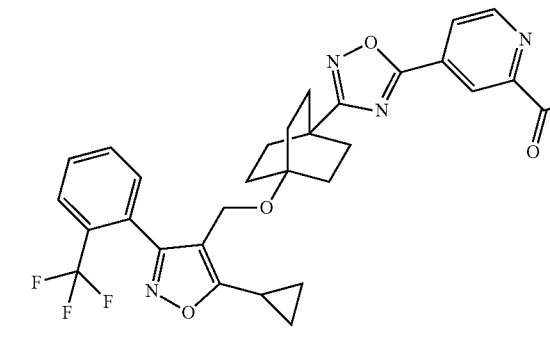<br>4-(3-(4-((5-cyclopropyl-3-(2-(trifluoromethyl)phenyl)isoxazol-4-yl)methoxy)bicyclo[2.2.2]octan-1-yl)-1,2,4-oxadiazol-5-yl)picolinic acid | $^1$H NMR (500 MHz, DMSO-d$_6$) δ 9.01-8.94 (m, 1H), 8.52-8.47 (m, 1H), 8.23-8.17 (m, 1H), 7.99-7.95 (m, 1H) 7.95-7.89 (m, 1H), 7.86-7.82 (m, 1H), 7.80-7.73 (m, 1H), 7.62-7.54 (m, 1H), 4.15 (s, 2H), 2.33-2.25 (m, 1H), 1.97 (br s, 6H), 1.58 (br d, J = 7.6 Hz, 6H), 1.19-1.13 (m, 2H), 1.09 (br d, J = 2.7 Hz, 2H). FXR EC$_{50}$ (nM) = 3800. MS (ESI) 581 (M + H). | Ex. 20 |

TABLE 1-continued

| Ex. No. | Structure & Name | $^1$H NMR, FXR EC$_{50}$ & MS (ESI) | Method |
|---|---|---|---|
| 60 | 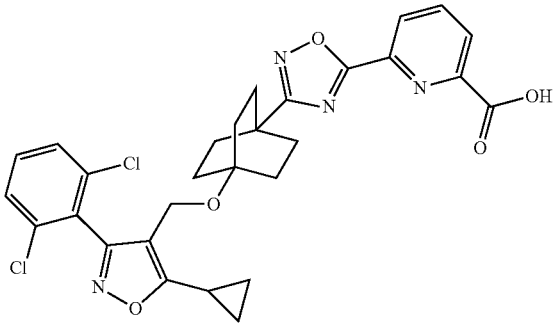<br>6-(3-(4-((5-cyclopropyl-3-(2,6-dichlorophenyl)isoxazol-4-yl)methoxy)bicyclo[2.2.2]octan-1-yl)-1,2,4-oxadiazol-5-yl)picolinic acid | $^1$H NMR (500 MHz, DMSO-d$_6$) δ 8.40-8.17 (m, 3H), 7.69-7.50 (m, 3H), 4.22-4.12 (m, 2H), 2.33-2.23 (m, 1H), 1.97-1.83 (m, 6H), 1.52-1.41 (m, 6H), 1.19-1.12 (m, 2H), 1.10-1.03 (m, 2H). FXR EC$_{50}$ (nM) = 220. MS (ESI) 582 (M + H). | Ex. 20 |
| 61 | 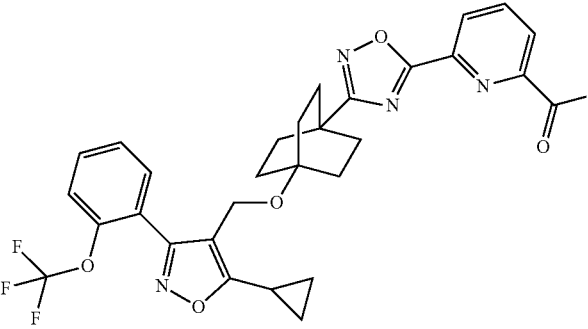<br>6-(3-(4-((5-cyclopropyl-3-(2-(trifluoromethoxy)phenyl)isoxazol-4-yl)methoxy)bicyclo[2.2.2]octan-1-yl)-1,2,4-oxadiazol-5-yl)picolinic acid | $^1$H NMR (500 MHz, DMSO-d$_6$) δ 8.18 (br s, 2H), 8.12-8.06 (m, 1H), 7.72-7.67 (m, 1H), 7.67-7.62 (m, 1H), 7.62-7.55 (m, 2H), 4.22 (s, 2H), 2.33-2.25 (m, 1H), 2.03-1.94 (m, 6H), 1.64 (br d, J = 7.6 Hz, 6H), 1.18-1.12 (m, 2H), 1.11-1.05 (m, 2H). FXR EC$_{50}$ (nM) = 840. MS (ESI) 597 (M + H). | Ex. 20 |
| 62 | 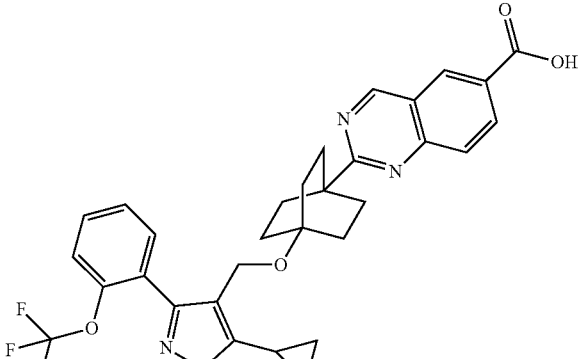<br>2-(4-((5-cyclopropyl-3-(2-(trifluoromethoxy)phenyl)isoxazol-4-yl)methoxy)bicyclo[2.2.2]octan-1-yl)quinazoline-6-carboxylic acid | $^1$H NMR (500 MHz, DMSO-d$_6$) δ 9.68 (s, 1H), 8.74 (s, 1H), 8.42-8.36 (m, 1H), 8.00-7.96 (m, 1H), 7.72-7.62 (m, 2H), 7.61-7.54 (m, 2H), 4.24 (s, 2H), 2.32-2.25 (m, 1H), 2.14-2.04 (m, 6H), 1.71-1.61 (m, 6H), 1.17-1.12 (m, 2H), 1.11-1.05 (m, 2H). FXR EC$_{50}$ (nM) = 1300. MS (ESI) 580 (M + H). | Ex. 24 |

Example 64

5-(5-(4-((5-Cyclopropyl-3-(2,6-dichlorophenyl)isoxazol-4-yl)methoxy)bicyclo[2.2.2]octan-1-yl)-1,2,4-oxadiazol-3-yl)-2-fluorobenzoic acid

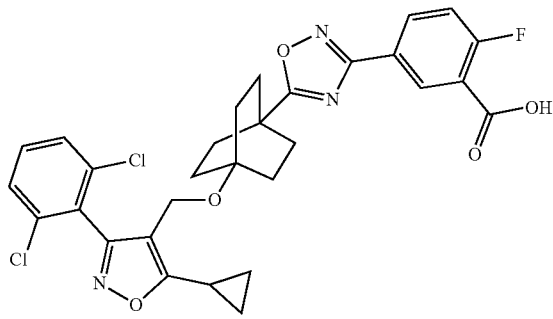 [SMILES: O=C(O)c1cc(-c2noc(C34CCC(OCc5c(-c6c(Cl)cccc6Cl)noc5C5CC5)(CC3)CC4)n2)ccc1F]

Step A. Intermediate 64A. Preparation of ethyl 5-cyano-2-fluorobenzoate

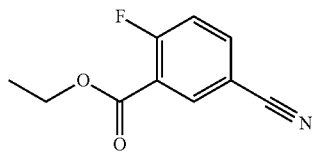

To a solution of 5-cyano-2-fluorobenzoic acid (0.50 g, 3.0 mmol) in EtOH (20 mL) was added thionyl chloride (0.51 mL, 7.0 mmol). The mixture was stirred at 65° C. After 18 h, the reaction was cooled, the solvent concentrated and the crude product was purified by flash column chromatography (40 g silica gel cartridge, A=Hex, B=EtOAc; 25 min grad.; 0% B to 25% B flow rate=40 mL/min). The pure fractions were combined, concentrated and dried in vacuo to afford the title compound (0.50 g, 2.6 mmol, 85% yield) as a white solid. $^1$H NMR (500 MHz, CHLOROFORM-d) δ 8.29 (dd, J=6.6, 2.2 Hz, 1H), 7.82 (ddd, J=8.6, 4.3, 2.2 Hz, 1H), 7.36-7.21 (m, 1H), 4.44 (q, J=7.2 Hz, 2H), 1.42 (t, J=7.2 Hz, 3H). MS (ESI) 194 (M+H).

Step B. Intermediate 64B. Preparation of ethyl (Z)-2-fluoro-5-(N'-hydroxycarbamimidoyl) benzoate

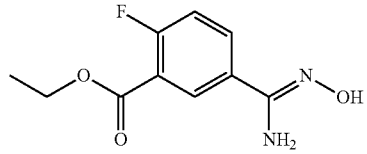 [SMILES: CCOC(=O)c1cc(/C(N)=N/O)ccc1F]

The title compound was prepared according to methods described for the synthesis of Intermediate 4C, using Intermediate 64A as starting material: (0.51 g, 2.3 mmol, 88% yield, light yellow solid). $^1$H NMR (500 MHz, DMSO-d$_6$) δ 9.77 (s, 1H), 8.19 (dd, J=7.2, 2.5 Hz, 1H), 7.92 (ddd, J=8.7, 4.5, 2.5 Hz, 1H), 7.36 (dd, J=10.6, 8.7 Hz, 1H), 5.95 (s, 2H), 4.33 (q, J=7.1 Hz, 2H), 1.32 (t, J=7.2 Hz, 3H). MS (ESI) 227 (M+H).

Step C. Example 64

Step 1: To a solution of Intermediate 16B (33 mg, 0.076 mmol), Intermediate 64B (17 mg, 0.076 mmol) and BOP (37 mg, 0.083 mmol) in DMF (0.10 mL) was added TEA (32 μL, 0.23 mmol) and the reaction was stirred at 80° C. under N$_2$. After 18 h, the reaction was cooled, diluted with EtOAc, washed with 10% lithium chloride (aq.), water and brine. The organic phase was dried over anhydrous Na$_2$SO$_4$, filtered and concentrated. The crude residue was taken onto the next step without further purification or characterization.

Step 2: The product of Step 1 above was dissolved in 1 M NaOH (aq.) (1.5 mL) and THF (1.5 mL) and stirred at room temperature. After 7 h, the reaction was acidified with 5% citric acid (aq.) and the aqueous phase was extracted with EtOAc (2×). The organic phase was combined, washed with brine, dried over Na$_2$SO$_4$, filtered and concentrated. The crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 4-minute hold at 100% B; Flow: 20 mL/min.). Fractions containing the desired product were combined, concentrated and dried in vacuo to afford the title compound (15 mg, 0.023 mmol, 30% yield). $^1$H NMR (500 MHz, DMSO-d$_6$) δ 8.48-8.20 (m, 1H), 8.03 (br d, J=7.9 Hz, 1H), 7.66-7.59 (m, 2H), 7.59-7.53 (m, 1H), 7.46 (br s, 1H), 4.16 (s, 2H), 2.35-2.21 (m, 1H), 2.04-1.93 (m, 6H), 1.59-1.40 (m, 6H), 1.13 (br d, J=8.2 Hz, 2H), 1.06 (br d, J=3.1 Hz, 2H). FXR EC$_{50}$ (nM)=140. MS (ESI) 598 (M+H).

Example 66

4-(((4-(6-(1H-tetrazol-5-yl)benzo[d]thiazol-2-yl)bicyclo[2.2.2]octan-1-yl)oxy)methyl)-5-cyclopropyl-3-(2,6-dichlorophenyl)isoxazole

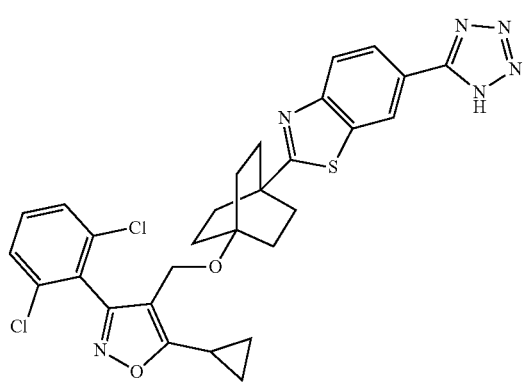

(66)

Step A. Intermediate 66A. Preparation of 2-(4-((5-cyclopropyl-3-(2,6-dichlorophenyl)isoxazol-4-yl)methoxy)bicyclo[2.2.2]octan-1-yl)benzo[d]thiazole-6-carbonitrile

Example 68

3-(5-(4-((5-Cyclopropyl-3-(2,6-dichlorophenyl)isoxazol-4-yl)methoxy)bicyclo[2.2.2]octan-1-yl)-1,2,4-oxadiazol-3-yl)-2,6-difluorobenzoic acid

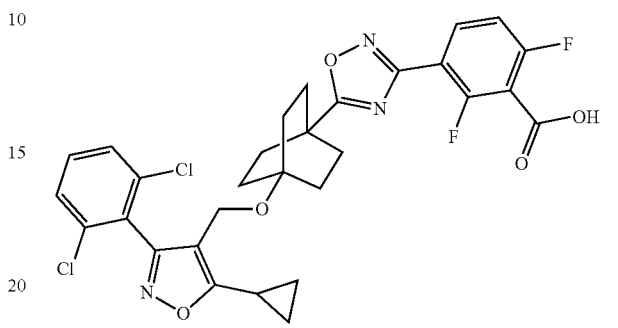

(68)

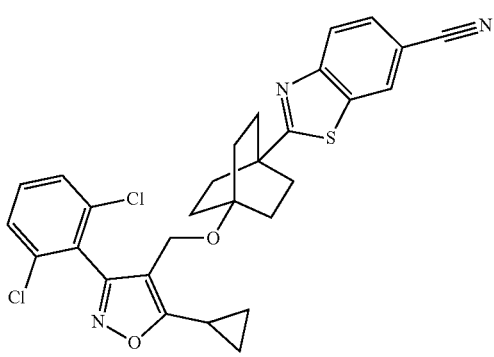 [SMILES: N#Cc1ccc2nc(C34CCC(OCc5c(-c6c(Cl)cccc6Cl)noc5C5CC5)(CC3)CC4)sc2c1]

The title compound was prepared according to methods described for the synthesis of Example 16 (Step C), by reaction of Intermediate 16B and 4-amino-3-mercaptobenzonitrile (See generally Chedekel, M. R., et al. Synth. Commun. 1980, 10, 167-173): (17 mg, 0.031 mmol, 30% yield, white solid). $^1$H NMR (500 MHz, CHLOROFORM-d) δ 8.21-8.12 (m, 1H), 8.00 (d, J=8.5 Hz, 1H), 7.69 (dd, J=8.4, 1.5 Hz, 1H), 7.46-7.41 (m, 2H), 7.37-7.31 (m, 1H), 4.23 (s, 2H), 2.32-1.95 (m, 7H), 1.69-1.61 (m, 6H), 1.29-1.20 (m, 2H), 1.16-1.04 (m, 2H). MS (ESI) 550 (M+H).

Step B. Example 66

A solution of Intermediate 66A (17 mg, 0.031 mmol), sodium azide (12 mg, 0.18 mmol) and ammonium chloride (9.8 mg, 0.18 mmol) in NMP (0.21 mL) was stirred at 120° C. After 18 h, the reaction was cooled, diluted with EtOAc and washed with brine. The organic phase was separated, dried over anhydrous Na$_2$SO$_4$, filtered and concentrated. The crude product was purified by Preparative HPLC (Column: Phenomenex Luna AXIA 5u C18 21.2×100 mm; Mobile Phase B: 90:10 MeOH:H$_2$O with 0.1% TFA; Mobile Phase A=10:90 MeOH:H$_2$O with 0.1% TFA; Gradient: 10 to 100% B over 10 min then a 5 min hold at 100% B; Flow: 20 mL/min. Fractions containing the desired product were combined, concentrated and dried in vacuo to afford the title compound (11 mg, 0.019 mmol, 61% yield) as a white solid. $^1$H NMR (500 MHz, DMSO-d$_6$) δ 8.75 (s, 1H), 8.14-8.03 (m, 2H), 7.65 (d, J=1.1 Hz, 1H), 7.63 (s, 1H), 7.60-7.55 (m, 1H), 4.19 (s, 2H), 2.33-2.26 (m, 1H), 2.05-1.98 (m, 6H), 1.56-1.49 (m, 6H), 1.14 (dt, J=8.3, 3.0 Hz, 2H), 1.10-1.04 (m, 2H). FXR EC$_{50}$ (nM)=390. MS (ESI) 593 (M+H).

Step A. Intermediate 68A. Preparation of ethyl 3-cyano-2,6-difluorobenzoate

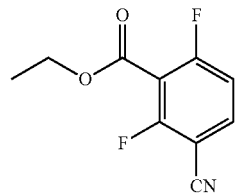

The title compound was prepared according to methods described for the synthesis of Intermediate 64A, using 3-cyano-2,6-difluorobenzoic acid as starting material: (0.46 g, 2.2 mmol, 79% yield, white solid). $^1$H NMR (500 MHz, CHLOROFORM-d) δ 7.89-7.64 (m, 1H), 7.11 (td, J=8.6, 1.2 Hz, 1H), 4.47 (q, J=7.2 Hz, 2H), 1.42 (t, J=7.2 Hz, 3H). MS (ESI) 212 (M+H).

Step B. Intermediate 68B. Preparation of ethyl (Z)-2,6-difluoro-3-(N'-hydroxycarbamimidoyl)benzoate

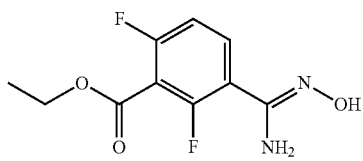 [SMILES: CCOC(=O)c1c(F)ccc(/C(N)=N/O)c1F]

The title compound was prepared according to methods described for the synthesis of Intermediate 4C, using Intermediate 68A as starting material: (0.2 g, 0.81 mmol, 38% yield, light yellow solid). $^1$H NMR (500 MHz, DMSO-d$_6$) δ 9.71 (s, 1H), 7.68 (td, J=8.4, 6.6 Hz, 1H), 7.31-7.14 (m, 1H), 5.92 (s, 2H), 4.38 (q, J=7.2 Hz, 2H), 1.31 (t, J=7.2 Hz, 3H). MS (ESI) 245 (M+H).

Step C. Example 68

The title compound was prepared according to methods described for the synthesis of Example 64 (Step C), by reaction of Intermediate 68B and Intermediate 16B: (24 mg, 0.037 mmol, 40% yield, off-white solid). $^1$H NMR (500 MHz, DMSO-$d_6$) δ 14.42-14.05 (br.s, 1H), 8.11 (td, J=8.4, 6.3 Hz, 1H), 7.65-7.61 (m, 2H), 7.59-7.52 (m, 1H), 7.41 (t, J=8.8 Hz, 1H), 4.18 (s, 2H), 2.30 (tt, J=8.3, 5.2 Hz, 1H), 2.07-1.92 (m, 6H), 1.59-1.43 (m, 6H), 1.14 (dt, J=8.3, 2.9 Hz, 2H), 1.11-1.01 (m, 2H). FXR $EC_{50}$ (nM)=250. MS (ESI) 616 (M+H).

Example 69

5-(5-(4-((5-Cyclopropyl-3-(3,5-dichloropyridin-4-yl)isoxazol-4-yl)methoxy)bicyclo[2.2.2]octan-1-yl)-1,2,4-oxadiazol-3-yl)-2-methoxybenzoic acid (69)

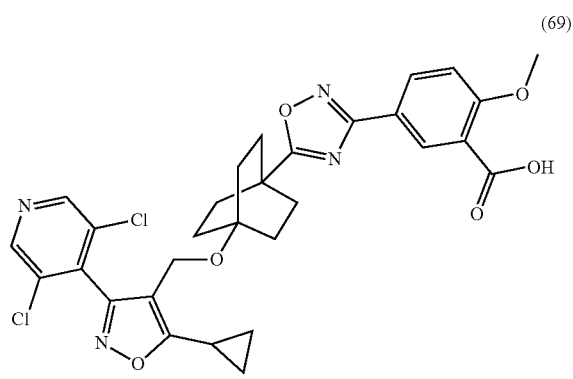 [SMILES: COc1ccc(-c2noc(C34CCC(OCc5c(-c6c(Cl)cncc6Cl)noc5C5CC5)(CC3)CC4)n2)cc1C(=O)O]

Step A. Intermediate 69A. Preparation of methyl 4-((5-cyclopropyl-3-(3,5-dichloropyridin-4-yl)isoxazol-4-yl)methoxy)bicyclo[2.2.2]octane-1-carboxylate

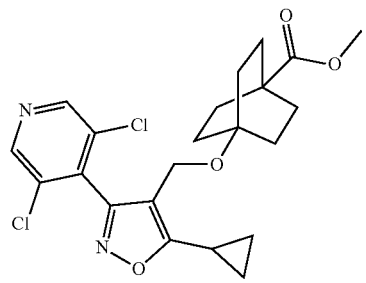 [SMILES: COC(=O)C12CCC(OCc3c(-c4c(Cl)cncc4Cl)noc3C3CC3)(CC1)CC2]

To a 20 mL scintillation vial equipped with pressure release cap were added Intermediate 4A (0.47 g, 1.6 mmol), (5-cyclopropyl-3-(3,5-dichloropyridin-4-yl)isoxazol-4-yl)methanol (0.45 g, 1.6 mmol), silver trifluoromethanesulfonate (0.49 g, 1.9 mmol), 2,6-di-tert-butylpyridine (0.70 mL, 3.2 mmol) and DCE (2 mL). The vessel was flushed with $N_2$, capped and stirred at 100° C. for 1 h. The reaction was cooled, filtered and the filtrate was concentrated. The crude product was purified by flash column chromatography (40 g silica gel cartridge; A=Hex, B=EtOAc; 19 min grad.; 0% B to 70% B; flow rate=40 mL/min). The pure fractions were combined, concentrated and dried in vacuo to afford the title compound (0.24 g, 0.52 mmol, 33% yield) as a white solid. $^1$H NMR (500 MHz, CHLOROFORM-d) δ 8.61 (s, 2H), 4.20 (s, 2H), 3.62 (s, 3H), 2.08 (tt, J=8.5, 5.0 Hz, 1H), 1.88-1.77 (m, 6H), 1.48-1.40 (m, 6H), 1.27-1.21 (m, 2H), 1.16-1.08 (m, 2H). MS (ESI) 451 (M+H).

Step B. Intermediate 69B. Preparation of 4-((5-cyclopropyl-3-(3,5-dichloropyridin-4-yl)isoxazol-4-yl)methoxy)bicyclo[2.2.2]octane-1-carboxylic acid

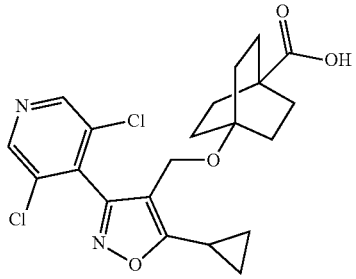 [SMILES: O=C(O)C12CCC(OCc3c(-c4c(Cl)cncc4Cl)noc3C3CC3)(CC1)CC2]

A solution of Intermediate 69A (240 mg, 0.52 mmol), 1 M NaOH (aq.) (5.2 mL, 5.2 mmol) in MeOH (4 mL) and THF (1 mL) was stirred at 40° C. for 1 h. The reaction was cooled, the solvent was concentrated and the residue was treated with water (7.5 mL) and acidified with 1 M HCl (aq.). The precipitate was filtered, washed well with water and dried in vacuo to afford the title compound (180 mg, 0.41 mmol, 78% yield) as a white solid. $^1$H NMR (500 MHz, DMSO-$d_6$) δ 12.01 (s, 1H), 8.81 (s, 2H), 4.19 (s, 2H), 2.29 (tt, J=8.4, 5.1 Hz, 1H), 1.75-1.62 (m, 6H), 1.37-1.28 (m, 6H), 1.14 (dt, J=8.3, 3.0 Hz, 2H), 1.09-1.02 (m, 2H). MS (ESI) 437 (M+H).

Step C. Intermediate 69C. Preparation of methyl (Z)-5-(N'-hydroxycarbamimidoyl)-2-methoxybenzoate

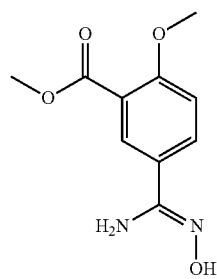

The title compound was prepared according to methods described for the synthesis of Intermediate 4C, using methyl 5-cyano-2-methoxybenzoate as starting material: (0.18 g, 0.78 mmol, 30% yield, off-white solid). $^1$H NMR (500 MHz, DMSO-$d_6$) δ 9.58-9.52 (m, 1H), 7.99 (d, J=2.5 Hz, 1H), 7.83 (dd, J=8.8, 2.5 Hz, 1H), 7.17 (d, J=8.8 Hz, 1H), 5.82 (s, 2H), 3.85 (s, 3H), 3.80 (s, 3H). MS (ESI) 225 (M+H).

Step D. Example 69

The title compound was prepared according to methods described for the synthesis of Example 64 (Step C), by reaction of Intermediate 69B and Intermediate 69C: (40 mg, 0.061 mmol, 67% yield): $^1$H NMR (500 MHz, DMSO-$d_6$) δ 8.82 (s, 2H), 8.13 (d, J=1.5 Hz, 1H), 8.01 (dd, J=8.7, 2.0 Hz, 1H), 7.25 (d, J=8.9 Hz, 1H), 4.24 (s, 2H), 3.86 (s, 3H), 2.37-2.25 (m, 1H), 2.02-1.96 (m, 6H), 1.51-1.40 (m, 6H), 1.26-1.13 (m, 2H), 1.13-1.03 (m, 2H). FXR EC$_{50}$ (nM)=56. MS (ESI) 611 (M+H).

Example 70

3-(3-(4-((5-Cyclopropyl-3-(2,6-dichlorophenyl)isoxazol-4-yl)methoxy)bicyclo[2.2.2]octan-1-yl)-1,2,4-oxadiazol-5-yl)-1-methyl-1H-pyrazole-5-carboxylic acid (70)

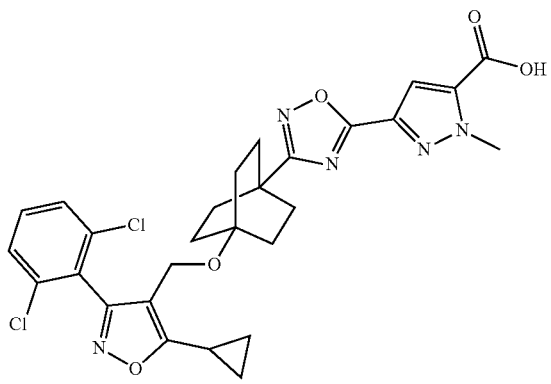

Step A. Intermediate 70A. Preparation of 4-((5-Cyclopropyl-3-(2,6-dichlorophenyl) isoxazol-4-yl)methoxy)bicyclo[2.2.2]octane-1-carbonitrile

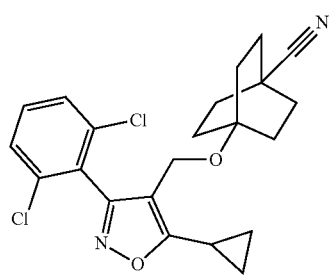 [SMILES: N#CC12CCC(OCc3c(-c4c(Cl)cccc4Cl)noc3C3CC3)(CC1)CC2]

The title compound was prepared according to methods described for the synthesis of Intermediate 20A, using Intermediate 16B as starting material: (57 mg, 0.14 mmol, 83% yield, white solid). $^1$H NMR (500 MHz, DMSO-d$_6$) δ 7.63-7.59 (m, 2H), 7.58-7.51 (m, 1H), 4.10 (s, 2H), 2.32-2.20 (m, 1H), 1.91-1.82 (m, 6H), 1.41-1.32 (m, 6H), 1.17-1.09 (m, 2H), 1.08-1.00 (m, 2H). FXR EC$_{50}$ (nM)=470. MS (ESI) 417 (M+H).

Step B. Intermediate 70B. Preparation of (Z)-4-((5-cyclopropyl-3-(2,6-dichlorophenyl)isoxazol-4-yl)methoxy)-N'-hydroxybicyclo[2.2.2]octane-1-carboximidamide

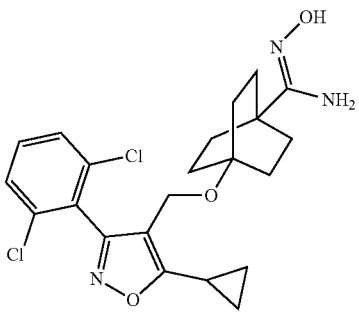 [SMILES: N/C(=N\O)C12CCC(OCc3c(-c4c(Cl)cccc4Cl)noc3C3CC3)(CC1)CC2]

The title compound was prepared according to methods described for the synthesis of Intermediate 4C, using Intermediate 70A as starting material: (32 mg, 0.071 mmol, 92% yield, clear oil). $^1$H NMR (500 MHz, CHLOROFORM-d) δ 7.45-7.38 (m, 2H), 7.37-7.29 (m, 1H), 4.46 (br s, 2H), 4.17 (s, 2H), 2.16-2.07 (m, 1H), 1.83-1.69 (m, 6H), 1.54-1.41 (m, 6H), 1.26-1.21 (m, 2H), 1.13-1.05 (m, 2H). MS (ESI) 450 (M+H).

Step C. Example 70

The title compound was prepared according to methods described for the synthesis of Example 64, by reaction of Intermediate 70B and 5-(methoxycarbonyl)-1-methyl-1H-pyrazole-3-carboxylic acid: (5.1 mg, 0.088 mmol, 25% yield). $^1$H NMR (500 MHz, DMSO-d$_6$) δ 7.63-7.58 (m, 2H), 7.57-7.52 (m, 1H), 7.31 (s, 1H), 4.21-4.15 (m, 5H), 2.31-2.22 (m, 1H), 1.93-1.86 (m, 6H), 1.53-1.44 (m, 6H), 1.16-1.10 (m, 2H), 1.08-1.01 (m, 2H). FXR EC$_{50}$ (nM)=430. MS (ESI) 584 (M+H).

Example 71

3-(5-(4-((5-Cyclopropyl-3-(3,5-dichloropyridin-4-yl)isoxazol-4-yl)methoxy)bicyclo[2.2.2]octan-1-yl)-1,2,4-oxadiazol-3-yl)-2-fluorobenzoic acid (71)

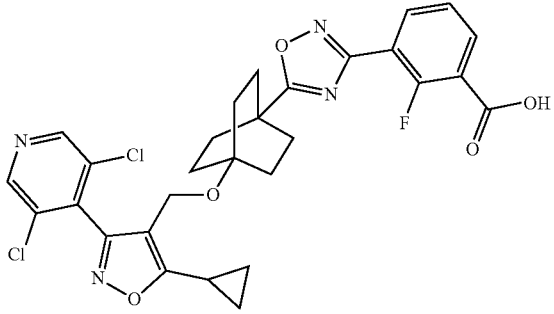

139

Step A. Intermediate 71A. Preparation of ethyl 3-cyano-2-fluorobenzoate

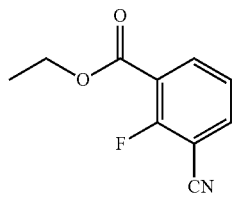

The title compound was prepared according to methods described for the synthesis of Intermediate 64A, using 3-cyano-2-fluorobenzoic acid as starting material: (0.55 g, 2.8 mmol, 93% yield, white solid). $^1$H NMR (400 MHz, DMSO-$d_6$) δ 8.24-8.08 (m, 2H), 7.54 (t, J=7.8 Hz, 1H), 4.36 (q, J=7.0 Hz, 2H), 1.32 (t, J=7.2 Hz, 3H). MS (ESI) 194 (M+H).

Step B. Intermediate 71B. Preparation of ethyl (Z)-2-fluoro-3-(N'-hydroxycarbamimidoyl) benzoate

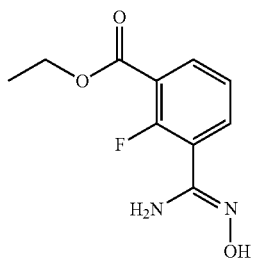 [SMILES: CCOC(=O)c1cccc(/C(N)=N/O)c1F]

The title compound was prepared according to methods described for the synthesis of Intermediate 4C, using Intermediate 71A as starting material: (0.35 g, 1.6 mmol, 55% yield, white solid). $^1$H NMR (500 MHz, DMSO-$d_6$) δ 9.67 (s, 1H), 7.92-7.84 (m, 1H), 7.73-7.65 (m, 1H), 7.32 (t, J=7.7 Hz, 1H), 5.90 (s, 2H), 4.33 (q, J=7.2 Hz, 2H), 1.32 (t, J=7.2 Hz, 3H). MS (ESI) 227 (M+H).

Step C. Example 71

The title compound was prepared according to methods described for the synthesis of Example 64 (Step C), by reaction of Intermediate 69B and Intermediate 71B: (16 mg, 0.027 mmol, 59% yield): $^1$H NMR (500 MHz, DMSO-$d_6$) δ 8.84 (s, 2H), 8.15 (br t, J=6.4 Hz, 1H), 8.05 (br t, J=6.6 Hz, 1H), 7.48 (t, J=7.6 Hz, 1H), 4.26 (s, 2H), 2.38-2.28 (m, 1H), 2.06-1.97 (m, 6H), 1.56-1.41 (m, 6H), 1.22-1.13 (m, 2H), 1.11-1.00 (m, 2H). FXR EC$_{50}$ (nM)=69. MS (ESI) 599 (M+H).

140

Example 72

2-(5-(4-((5-cyclopropyl-3-(2,6-dichlorophenyl)isoxazol-4-yl)methoxy)bicyclo[2.2.2]octan-1-yl)-1,2,4-oxadiazol-3-yl)acetic acid

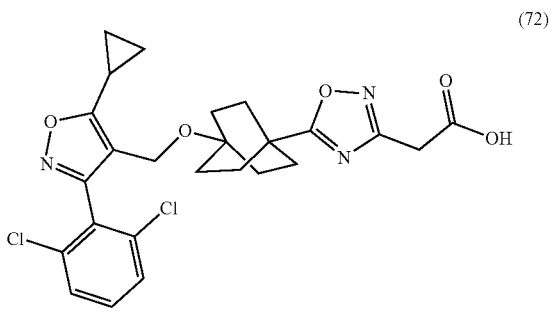 [SMILES: O=C(O)Cc1noc(C23CCC(OCc4c(-c5c(Cl)cccc5Cl)noc4C4CC4)(CC2)CC3)n1]

(72)

Step 1: To a solution of Intermediate 16B (20 mg, 0.046 mmol), tert-butyl (E)-3-amino-3-(hydroxyimino)propanoate (8.0 mg, 0.046 mmol) and BOP (22 mg, 0.050 mmol) in DMF (0.1 mL) was added and Et$_3$N (0.019 mL, 0.14 mmol). The reaction was stirred for 2 h at room temperature and at 80° C. for 12 h. The mixture was cooled, diluted with water and extracted with EtOAc (2×). The combined organic layers were washed with 10% lithium chloride (aq.), brine, dried over anhydrous Na$_2$SO$_4$, filtered, and concentrated to give a crude product (26 mg, 0.045 mmol, 99% yield) as a tan solid, which was used for next step without further purification. MS (ESI) 574 (M+H).

Step 2: To the product (26 mg, 0.045 mmol) of Step 1 above was added HCl (0.23 mL, 0.91 mmol) (4 M in 1,4-dioxane). The reaction mixture was stirred 18 h at room temperature and concentrated. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 20 minutes, then a 4-minute hold at 100% B; Flow: 20 mL/min.). Fractions containing the desired product were combined, concentrated and dried in vacuo to afford the title compound (0.90 mg, 1.7 μma 4% yield). $^1$H NMR (500 MHz, DMSO-$d_6$) δ 7.64 (br d, J=7.6 Hz, 2H), 7.61-7.55 (m, 1H), 4.17 (s, 2H), 3.63 (br s, 2H), 2.31 (br s, 1H), 1.98-1.84 (m, 6H), 1.48 (br s, 6H), 1.19-1.11 (m, 2H), 1.08 (br s, 2H). FXR EC$_{50}$ (nM)=3100. MS (ESI) 518 (M+H).

Example 76

1-((4-((5-cyclopropyl-3-(2,6-dichlorophenyl)isoxazol-4-yl)methoxy)bicyclo[2.2.2]octan-1-yl)methyl)-1H-pyrazole-4-carboxylic acid

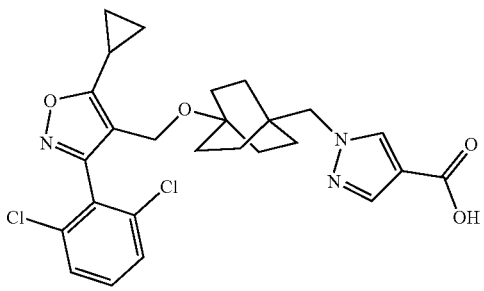
(76)

Step A. Intermediate 76A. Preparation of ethyl 1-((4-((5-cyclopropyl-3-(2,6-dichlorophenyl)isoxazol-4-yl)methoxy)bicyclo[2.2.2]octan-1-yl)methyl)-1H-pyrazole-4-carboxylate

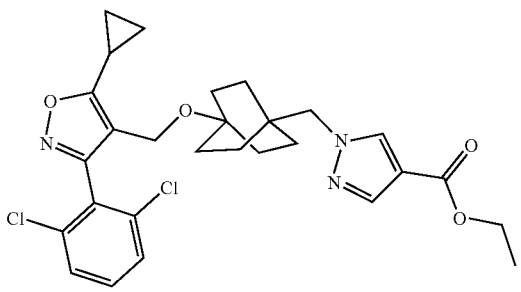 [SMILES: CCOC(=O)c1cnn(CC23CCC(OCc4c(-c5c(Cl)cccc5Cl)noc4C4CC4)(CC2)CC3)c1]

To a solution of Intermediate 104A (20 mg, 0.047 mmol), and ethyl 1H-pyrazole-4-carboxylate (8.6 mg, 0.062 mmol) in toluene (0.2 mL) was added cyanomethylenetributylphosphorane (18 mg, 0.076 mmol) at rt. The reaction was heated to 100° C. and stirred. After 6 h, the reaction was cooled, and the crude reaction mixture was purified by flash column chromatography (4 g silica gel cartridge; A=Hex, B=EtOAc; 20 min grad.; 0% B to 100% B; flow rate=4 mL/min). The pure fractions were combined, concentrated and dried in vacuo to afford the title compound (25 mg, 0.046 mmol, 97% yield) as a light brown oil. MS (ESI) 544 (M+H).

Step B. Example 76

To a solution of Intermediate 76A (25 mg, 0.046 mmol) in MeOH (0.5 mL) was added 1 M NaOH (aq.) (0.23 mL, 0.23 mmol). The reaction mixture was stirred at 60° C. After 1 h, the reaction was cooled and the crude reaction mixture was purified by preparative HPLC (Phenomenex Luna AXIA 5u C18 21.2×100 mm, 10 min gradient, 15 min run, 0% to 100% Solvent B=90% MeOH-10% $H_2O$-0.1% TFA, Solvent A=10% MeOH-90% $H_2O$-0.1% TFA). The desired fraction was concentrated and dried in vacuo to afford the title compound (6.3 mg, 0.012 mmol, 26% yield) as a white solid. $^1$H NMR (500 MHz, DMSO-$d_6$) δ 8.01-7.93 (m, 1H), 7.67 (s, 1H), 7.62-7.53 (m, 3H), 4.11 (s, 2H), 3.79 (s, 2H), 2.30-2.23 (m, 1H), 1.38-1.32 (m, 6H), 1.32-1.24 (m, 6H), 1.12 (dt, J=8.5, 2.9 Hz, 2H), 1.08-1.02 (m, 2H). FXR $EC_{50}$ (nM)=290. MS (ESI) 516 (M+H).

Example 80 cis-3-((4-((5-cyclopropyl-3-(2-trifluoromethoxy)phenyl)isoxazol-4-yl)methoxy) bicyclo[2.2.2]octan-1-yl)methoxy)cyclohexanecarboxylic acid

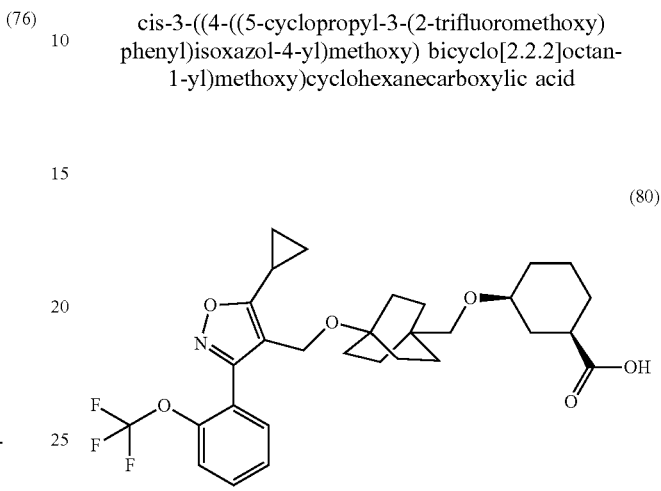
(80)

Step A. Intermediate 80A. Preparation of methyl 4-((5-cyclopropyl-3-(2-(trifluoromethoxy)phenyl)isoxazol-4-yl)methoxy)bicyclo[2.2.2]octane-1-carboxylate

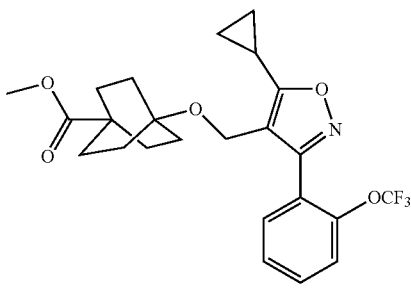 [SMILES: COC(=O)C12CCC(OCc3c(-c4ccccc4OC(F)(F)F)noc3C3CC3)(CC1)CC2]

The title compound was prepared according to methods described for the synthesis of Intermediate 16A, substituting (5-cyclopropyl-3-(2-(trifluoromethoxy)phenyl)isoxazol-4-yl)methanol where appropriate: (0.21 g, 0.45 mmol, 44% yield, colorless oil). $^1$H NMR (500 MHz, CHLOROFORM-d) δ 7.63-7.56 (m, 1H), 7.55-7.50 (m, 1H), 7.40 (s, 2H), 4.23 (s, 2H), 3.65 (s, 3H), 2.16-2.10 (m, 1H), 1.93-1.86 (m, 6H), 1.67-1.59 (m, 6H), 1.27-1.20 (m, 2H), 1.13-1.07 (m, 2H).

Step B. Intermediate 80B. Preparation of (4-((5-cyclopropyl-3-(2-(trifluoromethoxy)phenyl)isoxazol-4-yl)methoxy)bicyclo[2.2.2]octan-1-yl)methanol

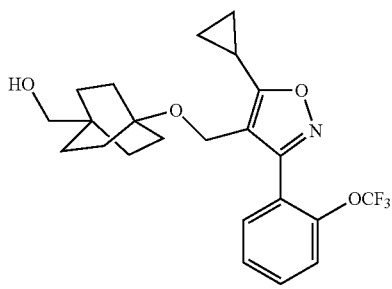 [SMILES: FC(F)(F)Oc1ccccc1-c1noc(C2CC2)c1COC12CCC(CBr)(CC1)CC2]

The title compound was prepared according to methods described for the synthesis of Intermediate 104A, using Intermediate 80A as starting material: (0.15 g, 0.35 mmol, 80% yield, colorless oil). $^1$H NMR (500 MHz, CHLOROFORM-d) δ 7.62-7.58 (m, 1H), 7.55-7.49 (m, 1H), 7.44-7.36 (m, 2H), 4.24 (s, 2H), 3.27 (s, 2H), 2.18-2.11 (m, 1H), 1.59 (m, 6H), 1.54 (m, 6H), 1.25-1.21 (m, 2H), 1.12-1.08 (m, 2H).

Step C. Intermediate 80C. Preparation of 4-((4-bromomethyl)bicyclo[2.2.2]octan-1-yloxy)methyl)-5-cyclopropyl-3-(2-(trifluoromethoxy)phenyl)isoxazole

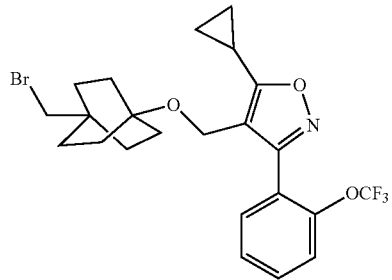

To a solution of Intermediate 80B (450 mg, 1.0 mmol) in CH$_2$Cl$_2$ (3 mL) was added Ph$_3$P (410 mg, 1.5 mmol). The reaction was cooled in an ice bath and CBr$_4$ (510 mg, 1.5 mmol) was added in portions. After stirring 2 d, the solvent was concentrated and the crude product was purified by flash column chromatography (40 g silica gel cartridge; A=Hex, B=EtOAc; 25 min grad.; 0% B to 30% B; flow rate=40 mL/min). The pure fractions were combined, concentrated and dried in vacuo to afford the title compound (310 mg, 0.62 mmol, 60% yield) as a white solid. $^1$H NMR (500 MHz, CHLOROFORM-d)) δ 7.61-7.54 (m, 1H), 7.53-7.47 (m, 1H), 7.42-7.33 (m, 2H), 4.22 (s, 2H), 3.17 (s, 2H), 2.17-2.06 (m, 1H), 1.59 (s, 12H), 1.24-1.17 (m, 2H), 1.11-1.04 (m, 2H). MS (ESI) 500.0 (M+H).

Step D. Example 80

A solution of methyl (1S,3R)-3-hydroxycyclohexane-1-carboxylate (63 mg, 0.40 mmol) in anhydrous NMP (0.5 mL) at room temperature was added KOtBu (27 mg, 0.24 mmol). After 5 minutes, Intermediate 80C (40 mg, 0.080 mmol) was added. The reaction was stirred at 120° C. for 2 h. After cooling to room temperature, the reaction was acidified by the dropwise addition of 1 M HCl (aq.) to pH ~3. The resulting reaction mixture was diluted with DMF and purified via preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-64% B over 20 minutes, then a 4-minute hold at 100% B; Flow: 20 mL/min). Fractions containing the desired product were combined and dried via centrifugal evaporation. The material was further purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 31-71% B over 20 minutes, then a 4-minute hold at 100% B; Flow: 20 mL/min). Fractions containing the desired product were combined, concentrated and dried in vacuo to afford the title compound (8.2 mg, 17% yield). $^1$H NMR (500 MHz, DMSO-d$_6$) δ 7.70-7.63 (m, 1H), 7.59 (br d, J=6.5 Hz, 1H), 7.53 (t, J=7.7 Hz, 2H), 4.17 (s, 2H), 3.65 (s, 2H), 3.46-3.35 (m, 1H), 2.31 (tt, J=12.2, 3.4 Hz, 1H), 2.26-2.19 (m, 1H), 2.05-1.99 (m, 1H), 1.85-1.66 (m, 3H), 1.53-1.42 (m, 12H), 1.29-1.20 (m, 1H), 1.20-1.15 (m, 1H), 1.15-1.09 (m, 3H), 1.07-1.00 (m, 3H). FXR EC$_{50}$ (nM)=5100. MS (ESI) 564 (M+H).

Example 85

3-((4-((5-cyclopropyl-3-(2-trifluoromethoxy)phenyl)isoxazol-4-yl)methoxy)bicyclo[2.2.2]octan-1-yl)methylamino)benzoic acid (85)

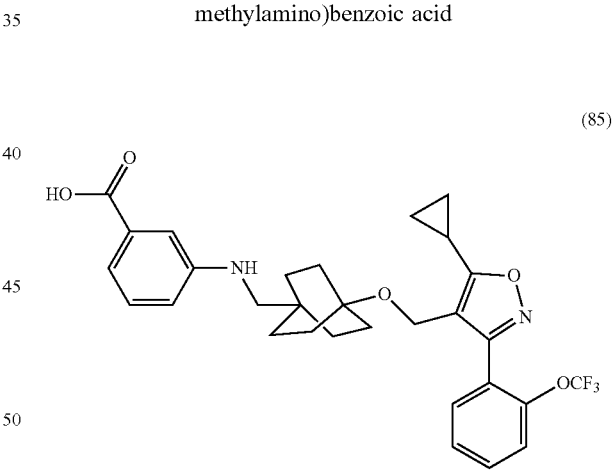

To a solution of Intermediate 80C (35 mg, 0.070 mmol) and ethyl 3-aminobenzoate (14 mg, 0.084 mmol) in DMF (1 mL) was added KOtBu (7.9 mg, 0.070 mmol). The reaction was stirred at room temperature for 4 h, and 100° C. for 1 h. After cooling to room temperature, the reaction mixture was diluted with H$_2$O, and extracted with EtOAc (3×). The combined organic extracts were concentrated and the crude material was purified via preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-64% B over 20 minutes, then a 4-minute hold at 100% B; Flow: 20 mL/min). Fractions containing the desired product were combined and dried via centrifugal evaporation. The material was further purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 31-71% B over 20 minutes, then a 4-minute hold at 100% B; Flow: 20 mL/min). Fractions containing the desired product were combined, concentrated and dried in vacuo to provide the title compound (8.1 mg, 21% yield). $^1$H NMR (500 MHz, DMSO-$d_6$) δ 7.69-7.63 (m, 1H), 7.62-7.57 (m, 1H), 7.57-7.50 (m, 2H), 7.18 (s, 1H), 7.16-7.11 (m, 1H), 7.11-7.07 (m, 1H), 6.80 (br d, J=7.3 Hz, 1H), 4.16 (s, 2H), 3.83 (s, 2H), 2.29-2.19 (m, 1H), 1.57-1.43 (m, 12H), 1.15-1.08 (m, 2H), 1.07-1.01 (m, 2H). FXR $EC_{50}$ (nM)=610. MS (ESI) 557 (M+H).

Example 89

4-((4-((3-(2H-tetrazol-5-yl)phenoxy)methyl)bicyclo[2.2.2]octan-1-yloxy)methyl)-5-cyclopropyl-3-(2,6-dichlorophenyl)isoxazole

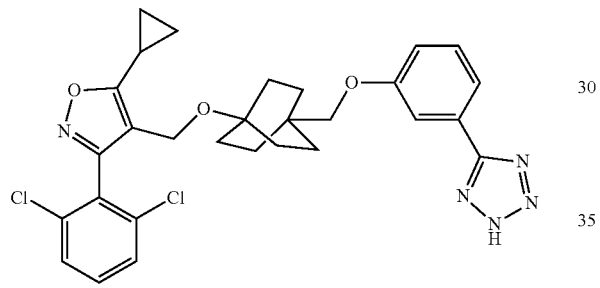

(89)

A mixture of Example 88 (19 mg, 0.036 mmol), dibutylstannanone (18 mg, 0.073 mmol) and azidotrimethylsilane (42 mg, 0.36 mmol) in toluene (0.5 mL) was stirred at 100° C. for 4 h. After cooling to room temperature, the reaction was diluted with $H_2O$ and extracted with EtOAc (3×). The combined organic extracts were concentrated and the crude material was purified via preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-64% B over 20 minutes, then a 4-minute hold at 100% B; Flow: 20 mL/min). Fractions containing the desired product were combined and dried via centrifugal evaporation. The material was further purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 31-71% B over 20 minutes, then a 4-minute hold at 100% B; Flow: 20 mL/min). Fractions containing the desired product were combined, concentrated and dried in vacuo to provide the title compound (4.1 mg, 0.0070 mmol, 19% yield). $^1$H NMR (500 MHz, DMSO-$d_6$) δ 7.69-7.61 (m, 2H), 7.59-7.51 (m, 2H), 7.48 (br s, 1H), 7.29 (br t, J=7.9 Hz, 1H), 6.89-6.81 (m, 1H), 4.15 (s, 2H), 3.57 (s, 2H), 2.35-2.24 (m, 1H), 1.65-1.47 (m, 6H), 1.44-1.30 (m, 6H), 1.18-1.10 (m, 2H), 1.09-1.03 (m, 2H). FXR $EC_{50}$ (nM)=120. MS (ESI) 566 (M+H).

Example 104

2-(2-((4-((5-cyclopropyl-3-(2,6-dichlorophenyl)isoxazol-4-yl)methoxy)bicyclo[2.2.2]octan-1-yl)methoxy)pyridin-4-yl)acetic acid

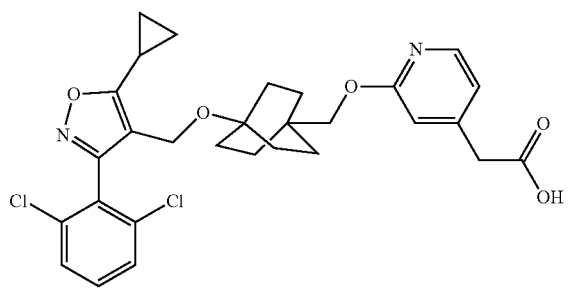

(104)

Step A. Intermediate 104A. Preparation of (4-((5-cyclopropyl-3-(2,6-dichlorophenyl)isoxazol-4-yl)methoxy)bicyclo[2.2.2]octan-1-yl)methanol

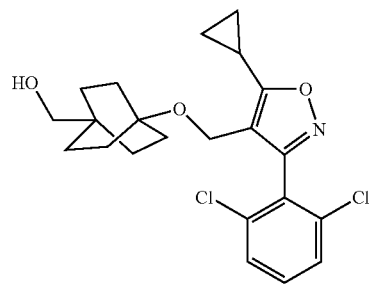 [SMILES: OCC12CCC(OCc3c(-c4c(Cl)cccc4Cl)noc3C3CC3)(CC1)CC2]

To a stirred solution of Intermediate 16A (0.35 g, 0.78 mmol) in THF (5 mL) at −78° C. was added lithium aluminum hydride (0.39 mL, 0.78 mmol) (2 M solution in THF) dropwise. The reaction was slowly warmed to rt over a period of 30 min. The reaction was cooled to 0° C. and EtOAc and 1 M HCl (aq.) were added and the reaction was stirred for 30 min. The reaction mixture was concentrated and diluted with EtOAc. The organic layer was washed with $H_2O$, dried over $MgSO_4$, filtered and concentrated. The crude product was purified by flash column chromatography (24 g silica gel cartridge; A=Hex, B=EtOAc; 15 min grad.; 10% B to 100% B; flow rate=24 mL/min). The pure fractions were combined, concentrated and dried in vacuo to afford the title compound (0.32 g, 0.76 mmol, 97% yield) as a white foam. $^1$H NMR (500 MHz, CHLOROFORM-d) δ 7.45-7.40 (m, 2H), 7.39-7.32 (m, 1H), 4.20 (s, 2H), 3.23 (s, 2H), 2.18-2.10 (m, 1H), 1.47 (s, 12H), 1.28-1.22 (m, 2H), 1.17-1.07 (m, 2H). MS (ESI) 422.0 (M+H).

Step B. Intermediate 104B. Preparation of ethyl 2-(2-((4-((5-cyclopropyl-3-(2,6-dichlorophenyl)isoxazol-4-yl)methoxy)bicyclo[2.2.2]octan-1-yl)methoxy)pyridin-4-yl) acetate

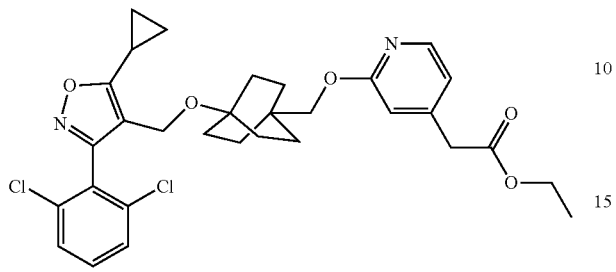

To a stirred solution of Intermediate 104A (15 mg, 0.036 mmol) in THF (1 mL) was added KOtBu (8.0 mg, 0.071 mmol). After 5 min, ethyl 2-(2-fluoropyridin-4-yl)acetate (9.8 mg, 0.053 mmol) was added and the reaction was stirred at 100° C. for 2 h. The reaction mixture was cooled to rt, concentrated and diluted with EtOAc. The organic layer was washed with sat. NaHCO$_3$ (aq.), dried over MgSO$_4$, filtered and concentrated. The crude product was purified by flash column chromatography (12 g silica gel cartridge; A=Hex, B=EtOAc; 15 min grad.; 0% B to 60% B; flow rate=12 mL/min). The pure fractions were combined, concentrated and dried in vacuo to afford the title compound (10 mg, 0.017 mmol, 48% yield) as a clear liquid. $^1$H NMR (500 MHz, CHLOROFORM-d) δ 8.11 (d, J=5.2 Hz, 1H), 7.49-7.41 (m, 2H), 7.38-7.35 (m, 1H), 6.85-6.76 (m, 1H), 6.65 (d, J=7.2 Hz, 1H), 4.38 (q, J=7.2 Hz, 1H), 4.18 (s, 2H), 3.78-3.69 (m, 2H), 3.56 (d, J=2.8 Hz, 2H), 2.22-2.07 (m, 2H), 1.71-1.55 (m, 6H), 1.53-1.46 (m, 6H), 1.43-1.38 (m, 3H), 1.30-1.23 (m, 2H), 1.16-1.08 (m, 2H). MS (ESI) 585.2 (M+H).

Step C. Example 104

To a stirred solution of Intermediate 104B (10 mg, 0.017 mmol) in THF (1 mL) was added lithium hydroxide monohydrate (1.4 mg, 0.034 mmol) in water (1 mL). The reaction was stirred at rt for 3 h. The reaction was concentrated and the crude material was purified via preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-64% B over 20 minutes, then a 4-minute hold at 100% B; Flow: 20 mL/min). Fractions containing the desired product were combined and dried via centrifugal evaporation. The material was further purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 31-71% B over 20 minutes, then a 4-minute hold at 100% B; Flow: 20 mL/min). Fractions containing the desired product were combined, concentrated and dried in vacuo to afford the title compound (2.3 mg, 0.0041 mmol, 24%). $^1$H NMR (500 MHz, DMSO-d$_6$) δ 8.02 (d, J=5.2 Hz, 1H), 7.68-7.60 (m, 2H), 7.60-7.50 (m, 1H), 6.85 (d, J=4.9 Hz, 1H), 6.67 (s, 1H), 4.16 (s, 2H), 3.82 (s, 2H), 3.58 (s, 2H), 2.28 (td, J=8.4, 4.6 Hz, 1H), 1.58-1.42 (m, 6H), 1.36 (br d, J=8.5 Hz, 6H), 1.14 (br d, J=8.2 Hz, 2H), 1.07 (br d, J=2.7 Hz, 2H). FXR EC$_{50}$ (nM)=210 nM. MS (ESI) 557.3 (M+H).

Example 105

6-((4-((5-cyclopropyl-3-(2,6-dichlorophenyl)isoxazol-4-yl)methoxy)bicyclo[2.2.2]octan-1-yl)methoxy)quinoline-2-carboxylic acid (105)

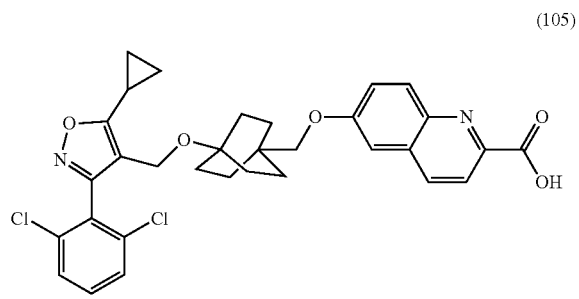 [SMILES: O=C(O)c1ccc2cc(OCC34CCC(OCc5c(-c6c(Cl)cccc6Cl)noc5C5CC5)(CC3)CC4)ccc2n1]

Step A. Intermediate 105A. Preparation of methyl 6-((4-((5-cyclopropyl-3-(2,6-dichlorophenyl)isoxazol-4-yl)methoxy)bicyclo[2.2.2]octan-1-yl)methoxy)quinoline-2-carboxylate

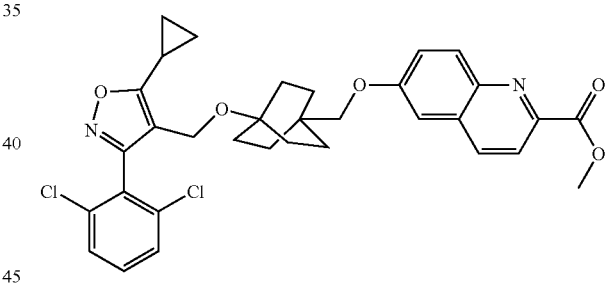

To a stirred solution of Intermediate 104A (17 mg, 0.039 mmol) and methyl 6-hydroxyquinoline-2-carboxylate (12 mg, 0.059 mmol) in 1,4-dioxane (1 mL) were added 1,1'-(azodicarbonyl)dipiperidine (20 mg, 0.078 mmol) and tri-n-butylphosphine (16 mg, 0.078 mmol). The reaction was stirred at 80° C. for 16 h. The reaction mixture was concentrated and diluted with EtOAc. The organic layer was washed with H$_2$O, dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to afford the title compound (20 mg, 0.033 mmol, 84% yield) as a clear liquid. $^1$H NMR (500 MHz, CHLOROFORM-d) δ 8.23-8.12 (m, 2H), 7.48-7.39 (m, 3H), 7.36 (dd, J=8.9, 7.3 Hz, 1H), 7.29 (s, 1H), 7.05 (d, J=2.8 Hz, 1H), 4.23 (s, 2H), 4.09 (s, 3H), 3.68 (s, 2H), 2.18-2.10 (m, 1H), 1.72-1.62 (m, 6H), 1.60-1.50 (m, 6H), 1.34-1.21 (m, 2H), 1.11 (td, J=8.0, 2.8 Hz, 2H). MS (ESI) 607.0 (M+H).

Step B. Example 105

The title compound was prepared according to methods described for the synthesis of Example 104 (Step C), using Intermediate 105A as starting material: (7.4 mg, 0.012 mmol, 38% yield, white solid). $^1$H NMR (500 MHz, DMSO-$d_6$) δ 8.31 (br d, J=8.5 Hz, 1H), 8.02 (br t, J=8.4 Hz, 2H), 7.71-7.62 (m, 2H), 7.62-7.54 (m, 1H), 7.43 (br d, J=9.2 Hz, 1H), 7.37 (br s, 1H), 4.18 (s, 2H), 3.71 (s, 2H), 2.36-2.25 (m, 1H), 1.57 (br d, J=7.9 Hz, 6H), 1.48-1.34 (m, 6H), 1.20-1.11 (m, 2H), 1.08 (br d, J=2.7 Hz, 2H). FXR EC$_{50}$ (nM)=76 nM. MS (ESI) 593.2 (M+H).

The following Examples in Table 2 were prepared according to methods described elsewhere herein using appropriate starting materials, reagents and conditions.

TABLE 2

| Ex. No. | Structure & Name | $^1$H NMR, FXR EC$_{50}$ & MS (ESI) | Method |
|---|---|---|---|
| 73 | 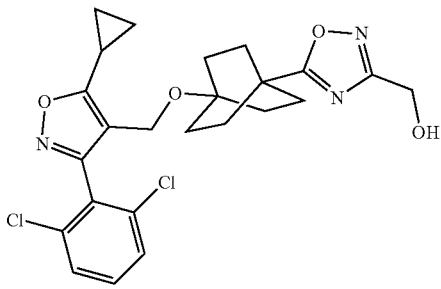 [SMILES: OCc1noc(C23CCC(OCc4c(-c5c(Cl)cccc5Cl)noc4C4CC4)(CC2)CC3)n1]<br>(5-(4-((5-cyclopropyl-3-(2,6-dichlorophenyl)isoxazol-4-yl)methoxy)bicyclo[2.2.2]octan-1-yl)-1,2,4-oxadiazol-3-yl)methanol | $^1$H NMR (500 MHz, DMSO-$d_6$) δ 7.63 (s, 2H), 7.60-7.54 (m, 1H), 5.65 (s, 1H), 4.48 (d, J = 6.4 Hz, 2H), 4.17 (s, 2H), 2.34-2.26 (m, 1H), 1.96-1.87 (m, 6H), 1.53-1.42 (m, 6H), 1.17-1.11 (m, 2H), 1.08 (br d, J = 3.1 Hz, 2H). FXR EC$_{50}$ (nM) = 600. MS (ESI) 490 (M + H). | Ex. 72 |
| 74 | 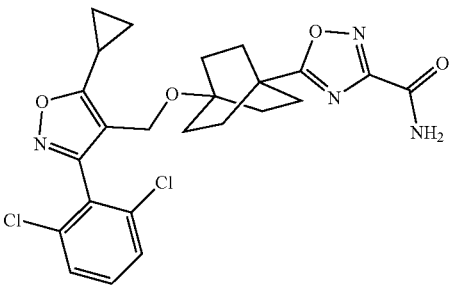 [SMILES: NC(=O)c1noc(C23CCC(OCc4c(-c5c(Cl)cccc5Cl)noc4C4CC4)(CC2)CC3)n1]<br>5-(4-((5-cyclopropyl-3-(2,6-dichlorophenyl)isoxazol-4-yl)methoxy)bicyclo[2.2.2]octan-1-yl)-1,2,4-oxadiazole-3-carboxamide | $^1$H NMR (500 MHz, DMSO-$d_6$) δ 7.63 (s, 2H), 7.60-7.54 (m, 1H), 5.65 (s, 1H), 4.48 (d, J = 6.4 Hz, 2H), 4.17 (s, 2H), 2.34-2.26 (m, 1H), 1.96-1.87 (m, 6H), 1.53-1.42 (m, 6H), 1.17-1.11 (m, 2H), 1.08 (br d, J = 3.1 Hz, 2H). FXR EC$_{50}$ (nM) = 520. MS (ESI) 503 (M + H). | Ex. 72 |
| 77 | 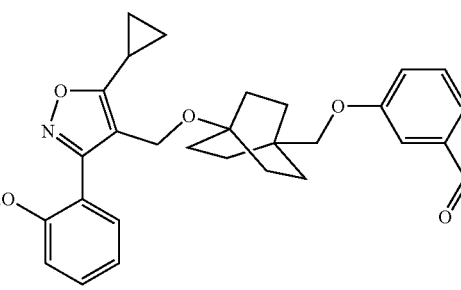<br>3-((4-((5-cyclopropyl-3-(2-trifluoromethoxy)phenyl)isoxazol-4-yl)methoxy)bicyclo[2.2.2]octan-1-yl)methoxy)benzoic acid | $^1$H NMR (500 MHz, DMSO-$d_6$) δ 7.69-7.63 (m, 1H), 7.63-7.58 (m, 1H), 7.57-7.51 (m, 2H), 7.49 (br d, J = 7.6 Hz, 1H), 7.40-7.32 (m, 2H), 7.15-7.08 (m, 1H), 4.17 (s, 2H), 3.58 (s, 2H), 2.29-2.21 (m, 1H), 1.61-1.46 (m, 12H), 1.15-1.08 (m, 2H), 1.08-1.02 (m, 2H). FXR EC$_{50}$ (nM) = 180. MS (ESI) 558 (M + H). | Ex. 105 |

TABLE 2-continued

| Ex. No. | Structure & Name | ¹H NMR, FXR EC$_{50}$ & MS (ESI) | Method |
|---|---|---|---|
| 78 | 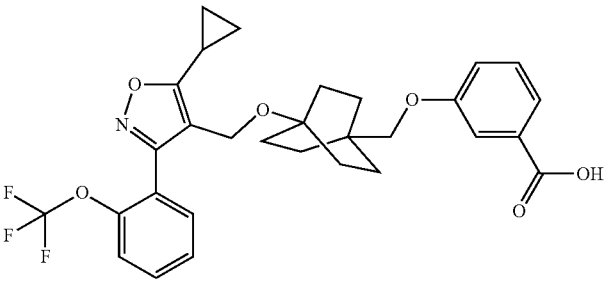 [SMILES: O=C(O)c1cccc(OCC23CCC(OCc4c(-c5ccccc5OC(F)(F)F)noc4C4CC4)(CC2)CC3)c1]<br>3-((4-((5-cyclopropyl-3-(2-trifluoromethoxy)phenyl)isoxazol-4-yl)methoxy)bicyclo[2.2.2]octan-1-yl)methoxy)nicotinic acid | ¹H NMR (500 MHz, DMSO-d$_6$) δ 8.62-8.57 (m, 1H), 8.33 (br s, 1H), 7.65 (br s, 2H), 7.62-7.58 (m, 1H), 7.53 (br t, J = 6.7 Hz, 2H), 4.17 (s, 2H), 3.66 (s, 2H), 2.28-2.20 (m, 1H), 1.60-1.45 (m, 12H), 1.15-1.08 (m, 2H), 1.07-1.01 (m, 2H). FXR EC$_{50}$ (nM) = 1400. MS (ESI) 559 (M + H). | Ex. 105 |
| 79 | 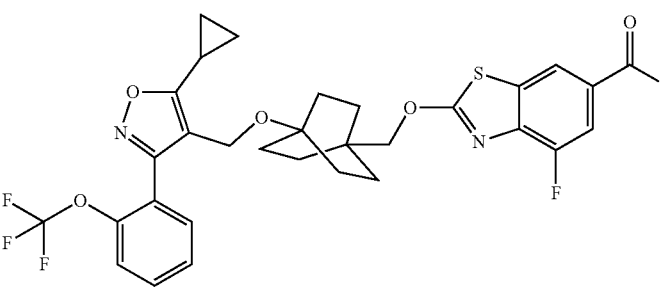<br>2-((4-((5-cyclopropyl-3-(2-trifluoromethoxy)phenyl)isoxazol-4-yl)methoxy)bicyclo[2.2.2]octan-1-yl)methoxy)-4-fluorobenzo[d]thiazole-6-carboxylic acid | ¹H NMR (500 MHz, DMSO-d$_6$) δ 8.33-8.29 (m, 1H), 7.71-7.62 (m, 2H), 7.58 (br d, J = 6.3 Hz, 1H), 7.52 (br t, J = 7.8 Hz, 2H), 4.25 (s, 2H), 4.17 (s, 2H), 2.26-2.20 (m, 1H), 1.63-1.47 (m, 12H), 1.14-1.08 (m, 2H), 1.07-1.02 (m, 2H). FXR EC$_{50}$ (nM) = 130. MS (ESI) 633 (M + H). | Ex. 104 |
| 81 | 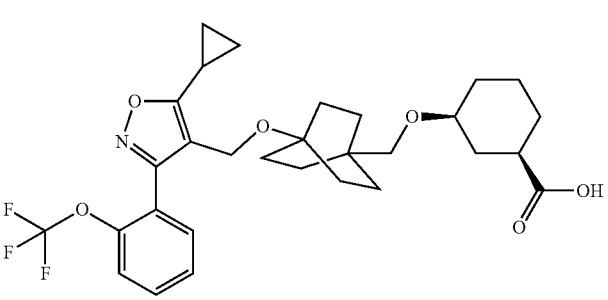 [SMILES: O=C(O)[C@@H]1CCC[C@H](OCC23CCC(OCc4c(-c5ccccc5OC(F)(F)F)noc4C4CC4)(CC2)CC3)C1]<br>trans-3-((4-((5-cyclopropyl-3-(2-trifluoromethoxy)phenyl)isoxazol-4-yl)methoxy)bicyclo[2.2.2]octan-1-yl)methoxy)cyclohexanecarboxylic acid | ¹H NMR (500 MHz, DMSO-d$_6$) δ 7.69-7.63 (m, 1H), 7.62-7.57 (m, 1H), 7.56-7.50 (m, 2H), 4.15 (s, 2H), 3.63 (s, 2H), 3.45-3.35 (m, 1H), 2.35-2.19 (m, 2H), 2.05-1.96 (m, 1H), 1.84-1.63 (m, 3H), 1.52-1.36 (m, 12H), 1.30-1.19 (m, 1H), 1.17-1.01 (m, 7H). FXR EC$_{50}$ (nM) = 4700. MS (ESI) 564 (M + H). | Ex. 80 |
| 82 | 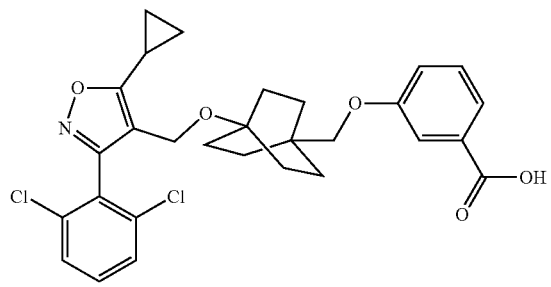 [SMILES: O=C(O)c1cccc(OCC23CCC(OCc4c(-c5c(Cl)cccc5Cl)noc4C4CC4)(CC2)CC3)c1]<br>3-((4-((5-cyclopropyl-3-(2,6-dichlorophenyl)isoxazol-4-yl)methoxy)bicyclo[2.2.2]octan-1-yl)methoxy) benzoic acid | ¹H NMR (500 MHz, DMSO-d$_6$) δ 7.65-7.59 (m, 2H), 7.58-7.53 (m, 1H), 7.49 (br d, J = 7.9 Hz, 1H), 7.40-7.33 (m, 2H), 7.14-7.08 (m, 1H), 4.14 (s, 2H), 3.56 (s, 2H), 2.32-2.23 (m, 1H), 1.55-1.46 (m, 6H), 1.41-1.30 (m, 6H), 1.17-1.10 (m, 2H), 1.09-1.03 (m, 2H). FXR EC$_{50}$ (nM) = 22. MS (ESI) 542 (M + H). | Ex. 105 |

TABLE 2-continued

| Ex. No. | Structure & Name | ¹H NMR, FXR EC$_{50}$ & MS (ESI) | Method |
|---|---|---|---|
| 83 | 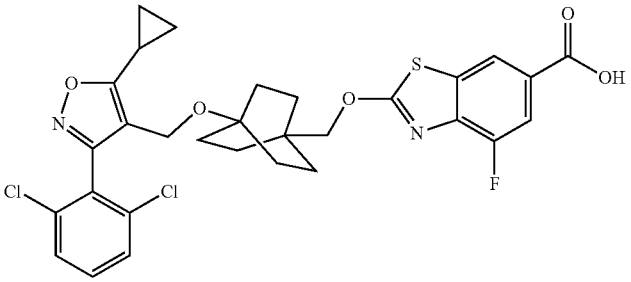 [SMILES: O=C(O)c1cc(F)c2nc(OCC34CCC(OCc5c(-c6c(Cl)cccc6Cl)noc5C5CC5)(CC3)CC4)sc2c1]<br>2-((4-((5-cyclopropyl-3-(2,6-dichlorophenyl)isoxazol-4-yl)methoxy)bicyclo[2.2.2]octan-1-yl)methoxy)-4-fluorobenzo[d]thiazole-6-carboxylic acid | ¹H NMR (500 MHz, DMSO-d$_6$) δ 8.38-8.33 (m, 1H), 7.69 (br d, J = 10.7 Hz, 1H), 7.65-7.59 (m, 2H), 7.56 (br d, J = 7.0 Hz, 1H), 4.21 (s, 2H), 3.89 (s, 2H), 2.32-2.22 (m, 1H), 1.55-1.43 (m, 6H), 1.40-1.30 (m, 6H), 1.17-1.02 (m, 4H). FXR EC$_{50}$ (nM) = 18. MS (ESI) 617 (M + H). | Ex. 104 |
| 84 | 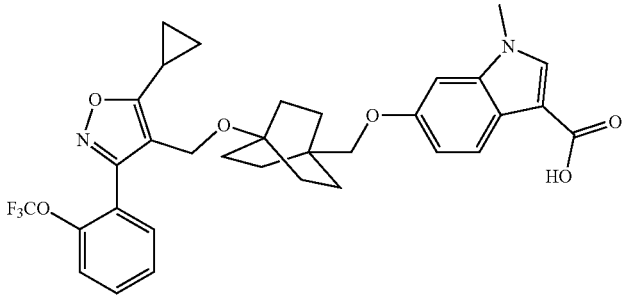 [SMILES: Cn1cc(C(=O)O)c2ccc(OCC34CCC(OCc5c(-c6ccccc6OC(F)(F)F)noc5C5CC5)(CC3)CC4)cc21]<br>6-((4-((5-cyclopropyl-3-(2-trifluoromethoxy)phenyl)isoxazol-4-yl)methoxy)bicyclo[2.2.2]octan-1-yl)methoxy)-methyl-1H-indole-3-carboxylic acid | ¹H NMR (500 MHz, DMSO-d$_6$) δ 7.93-7.84 (m, 1H), 7.72 (br s, 1H), 7.69-7.64 (m, 1H), 7.61 (br d, J = 6.2 Hz, 1H), 7.54 (t, J = 7.7 Hz, 2H), 6.94 (s, 1H), 6.76 (br d, J = 7.5 Hz, 1H), 4.20 (s, 2H), 3.74 (s, 3H), 2.30-2.19 (m, 1H), 1.68-1.58 (m, 6H), 1.55-1.45 (m, 6H), 1.16-1.09 (m, 2H), 1.09-1.03 (m, 2H). FXR EC$_{50}$ (nM) = 320. MS (ESI) 611 (M + H). | Ex. 105 |
| 88 | 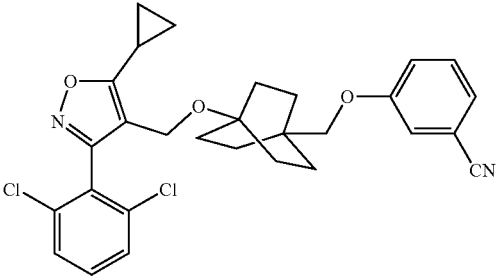 [SMILES: N#Cc1cccc(OCC23CCC(OCc4c(-c5c(Cl)cccc5Cl)noc4C4CC4)(CC2)CC3)c1]<br>3-((4-((5-cyclopropyl-3-(2,6-dichlorophenyl)isoxazol-4-yl)methoxy)bicyclo[2.2.2]octan-1-yl)methoxy)benzonitrile | ¹H NMR (500 MHz, DMSO-d$_6$) δ 7.64-7.59 (m, 2H), 7.59-7.53 (m, 1H), 7.48-7.41 (m, 1H). 7.38-7.32 (m, 2H), 7.23 (br d, J = 8.5 Hz, 1H), 4.15 (s, 2H), 3.59 (s, 2H), 2.32-2.23 (m, 1H), 1.53-1.45 (m, 6H), 1.41-1.32 (m, 6H), 1.17-1.10 (m, 2H), 1.09-1.03 (m, 2H). FXR EC$_{50}$ (nM) = 960. MS (ESI) 523 (M + H). | Ex. 105 |

TABLE 2-continued

| Ex. No. | Structure & Name | $^1$H NMR, FXR EC$_{50}$ & MS (ESI) | Method |
|---|---|---|---|
| 90 | 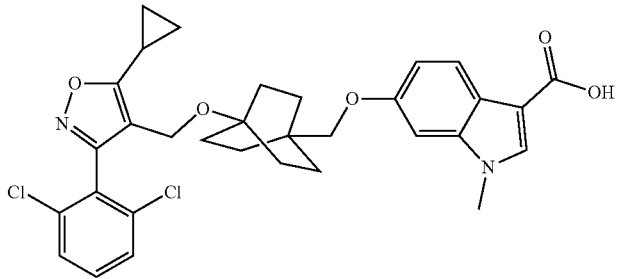 [SMILES: Cn1cc(C(=O)O)c2ccc(OCC34CCC(OCc5c(-c6c(Cl)cccc6Cl)noc5C5CC5)(CC3)CC4)cc21]<br>6-((4-((5-cyclopropyl-3-(2,6-dichlorophenyl)isoxazol-4-yl)methoxy)bicyclo[2.2.2]octan-1-yl)methoxy)-1-methyl-1H-indole-3-carboxylic acid | 1H NMR (500 MHz, DMSO-d$_6$) δ 7.85 (s, 1H), 7.81 (d, J = 8.8 Hz, 1H), 7.66-7.59 (m, 2H), 7.59-7.53 (m, 1H), 6.96 (s, 1H), 6.77 (br d, J = 8.7 Hz, 1H), 4.15 (s, 2H), 3.75 (s, 2H), 2.32-2.23 (m, 1H), 1.61-1.49 (m, 6H), 1.43-1.29 (m, 6H), 1.21-1.13 (m, 2H), 1.09-1.02 (m, 2H). FXR EC$_{50}$ (nM) = 11. MS (ESI) 595 (M + H). | Ex. 104 |
| 91 | 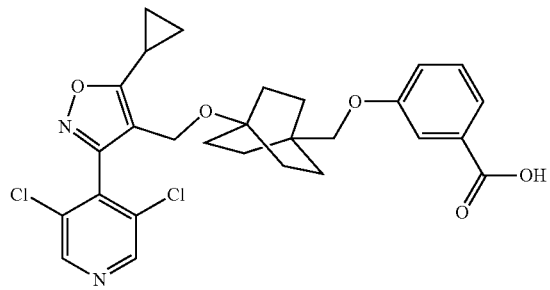 [SMILES: O=C(O)c1cccc(OCC23CCC(OCc4c(-c5c(Cl)cncc5Cl)noc4C4CC4)(CC2)CC3)c1]<br>3-((4-((5-cyclopropyl-3-(3,5-dichloropyridin-4-yl)isoxazol-4-yl)methoxy)bicyclo[2.2.2]octan-1-yl)methoxy) benzoic acid | $^1$H NMR (500 MHz, DMSO-d$_6$) δ 8.84 (s, 2H), 7.48 (br d, J = 7.6 Hz, 1H), 7.38 (br s, 1H), 7.32 (t, J = 7.9 Hz, 1H), 7.06 (br d, J = 7.9 Hz, 1H), 4.24 (s, 2H), 3.57 (s, 2H), 2.39-2.25 (m, 1H), 1.61-1.49 (m, 6H), 1.43-1.29 (m, 6H), 1.21-1.13 (m, 2H), 1.09-1.02 (m, 2H). FXR EC$_{50}$ (nM) = 33. MS (ESI) 543 (M + H). | Ex. 105 |
| 92 | 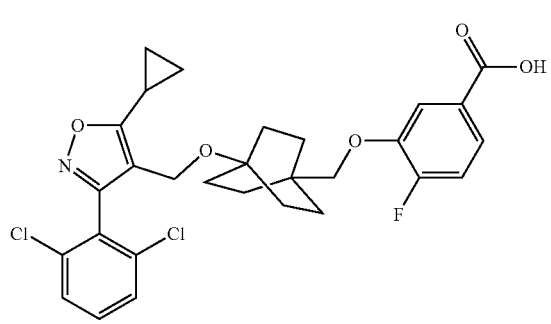 [SMILES: O=C(O)c1ccc(F)c(OCC23CCC(OCc4c(-c5c(Cl)cccc5Cl)noc4C4CC4)(CC2)CC3)c1]<br>3-((4-((5-cyclopropyl-3-(2,6-dichlorophenyl)isoxazol-4-yl)methoxy)bicyclo[2.2.2]octan-1-yl)methoxy)-4-fluorobenzoic acid | $^1$H NMR (500 MHz, DMSO-d$_6$) δ 7.66-7.59 (m, 2H), 7.59-7.48 (m, 3H), 7.30-7.22 (m, 1H), 4.15 (s, 2H), 3.64 (s, 2H), 2.32-2.24 (m, 1H), 1.55-1.47 (m, 6H), 1.40-1.32 (m, 6H), 1.16-1.09 (m, 2H), 1.08-1.02 (m, 2H). FXR EC$_{50}$ (nM) = 23. MS (ESI) 560 (M + H). | Ex. 105 |

TABLE 2-continued

| Ex. No. | Structure & Name | ¹H NMR, FXR EC$_{50}$ & MS (ESI) | Method |
|---|---|---|---|
| 93 | 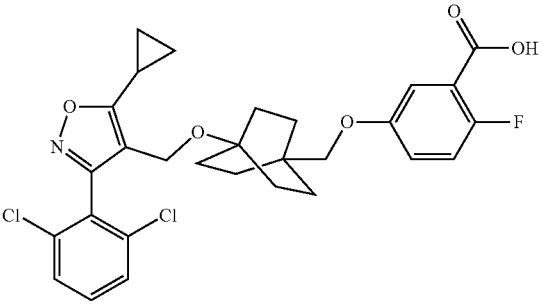 [SMILES: O=C(O)c1cc(OCC23CCC(OCc4c(-c5c(Cl)cccc5Cl)noc4C4CC4)(CC2)CC3)ccc1F]<br>5-((4-((5-cyclopropyl-3-(2,6-dichlorophenyl)isoxazol-4-yl)methoxy)bicyclo[2.2.2]octan-1-yl)methoxy)-2-fluorobenzoic acid | ¹H NMR (500 MHz, DMSO-d$_6$) δ 7.65-7.59 (m, 2H), 7.58-7.52 (m, 1H), 7.21-7.16 (m, 1H), 7.15-7.08 (m, 1H), 7.03 (br d, J = 8.9 Hz, 1H), 4.14 (s, 2H), 3.51 (s, 2H), 2.32-2.23 (m, 1H), 1.53-1.45 (m, 6H), 1.40-1.31 (m, 6H), 1.16-1.09 (m, 2H), 1.08-1.02 (m, 2H). FXR EC$_{50}$ (nM) = 32. MS (ESI) 560 (M + H). | Ex. 105 |
| 94 | 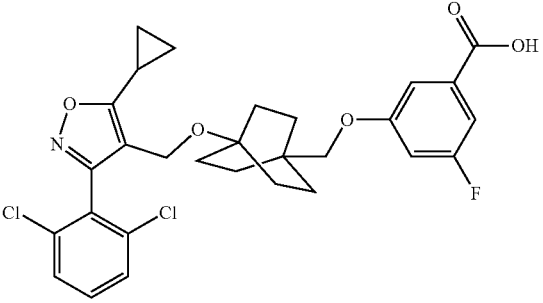 [SMILES: O=C(O)c1cc(F)cc(OCC23CCC(OCc4c(-c5c(Cl)cccc5Cl)noc4C4CC4)(CC2)CC3)c1]<br>3-((4-((5-cyclopropyl-3-(2,6-dichlorophenyl)isoxazol-4-yl)methoxy)bicyclo[2.2.2]octan-1-yl)methoxy)-5-fluorobenzoic acid | ¹H NMR (500 MHz, DMSO-d$_6$) δ 7.67-7.59 (m, 2H), 7.58-7.51 (m, 1H), 7.36-7.07 (m, 2H), 6.96 (br s, 1H), 4.14 (s, 2H), 3.56 (br s, 2H), 2.33-2.22 (m, 1H), 1.53-1.45 (m, 6H), 1.40-1.31 (m, 6H), 1.16-1.09 (m, 2H), 1.08-1.02 (m, 2H). FXR EC$_{50}$ (nM) = 18. MS (ESI) 560 (M + H). | Ex. 105 |
| 95 | 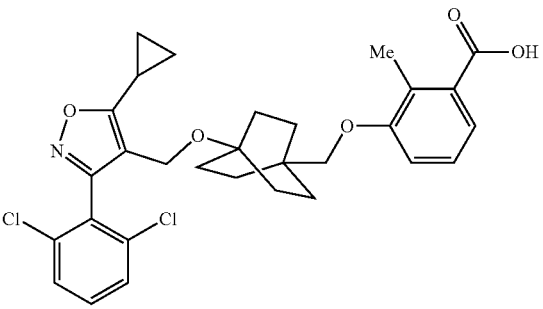 [SMILES: Cc1c(OCC23CCC(OCc4c(-c5c(Cl)cccc5Cl)noc4C4CC4)(CC2)CC3)cccc1C(=O)O]<br>3-((4-((5-cyclopropyl-3-(2,6-dichlorophenyl)isoxazol-4-yl)methoxy)bicyclo[2.2.2]octan-1-yl)methoxy)-2-methylbenzoic acid | ¹H NMR (500 MHz, DMSO-d$_6$) δ 7.66-7.59 (m, 2H), 7.58-7.52 (m, 1H), 7.35-7.10 (m, 2H), 7.05-6.79 (m, 1H), 4.14 (s, 2H), 3.50 (s, 2H), 2.42-2.21 (m, 4H), 1.55-1.45 (m, 6H), 1.41-1.32 (m, 6H), 1.16-1.09 (m, 2H), 1.08-1.02 (m, 2H). FXR EC$_{50}$ (nM) = 400. MS (ESI) 556 (M + H). | Ex. 105 |

TABLE 2-continued

| Ex. No. | Structure & Name | ¹H NMR, FXR EC$_{50}$ & MS (ESI) | Method |
|---|---|---|---|
| 96 | 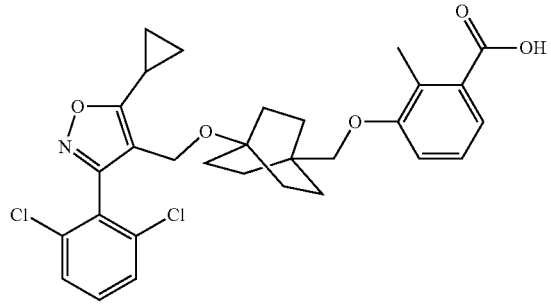<br>3-((4-((5-cyclopropyl-3-(2,6-dichlorophenyl)isoxazol-4-yl)methoxy)bicyclo[2.2.2]octan-1-yl)methoxy)-2-methylbenzoic acid | ¹H NMR (500 MHz, DMSO-d$_6$) δ 7.65-7.59 (m, 2H), 7.58-7.51 (m, 1H), 7.33-7.21 (m, 2H), 7.15-7.08 (m, 1H), 4.14 (s, 2H), 3.60 (s, 2H), 2.32-2.22 (m, 1H), 1.55-1.45 (m, 6H), 1.41-1.32 (m, 6H), 1.16-1.09 (m, 2H), 1.08-1.02 (m, 2H). FXR EC$_{50}$ (nM) = 120. MS (ESI) 560 (M + H). | Ex. 105 |
| 97 | 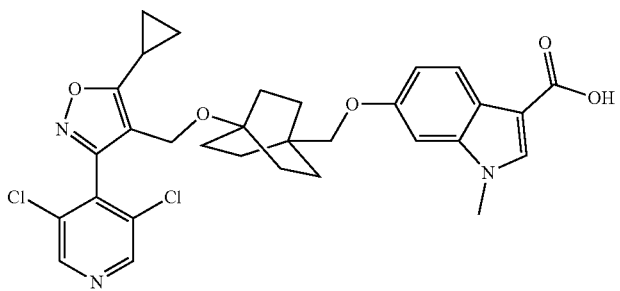 [SMILES: Cn1cc(C(=O)O)c2ccc(OCC34CCC(OCc5c(-c6c(Cl)cncc6Cl)noc5C5CC5)(CC3)CC4)cc21]<br>6-((4-((5-cyclopropyl-3-(3,5-dichloropyridin-4-yl)isoxazol-4-yl)methoxy)bicyclo[2.2.2]octan-1-yl)methoxy)-1-methyl-1H-indole-3-carboxylic acid | ¹H NMR (500 MHz, DMSO-d$_6$) δ 8.80 (s, 2H), 7.84 (s, 1H), 7.80 (d, J = 8.5 Hz, 1H), 6.96 (s, 1H), 6.78 (dd, J = 8.7, 1.7 Hz, 1H), 4.21 (s, 2H), 3.75 (s, 2H), 2.33-2.24 (m, 1H), 1.58-1.47 (m, 6H), 1.39-1.30 (m, 6H), 1.18-1.12 (m, 2H), 1.10-1.03 (m, 2H). FXR EC$_{50}$ (nM) = 28. MS (ESI) 596 (M + H). | Ex. 105 |
| 98 | 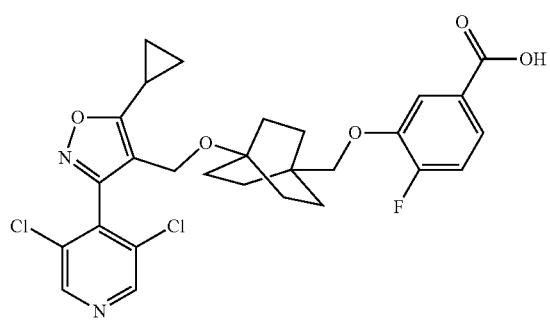 [SMILES: O=C(O)c1ccc(F)c(OCC23CCC(OCc4c(-c5c(Cl)cncc5Cl)noc4C4CC4)(CC2)CC3)c1]<br>3-((4-((5-cyclopropyl-3-(3,5-dichloropyridin-4-yl)isoxazol-4-yl)methoxy)bicyclo[2.2.2]octan-1-yl)methoxy)-4-fluorobenzoic acid | ¹H NMR (500 MHz, DMSO-d$_6$) δ 8.81 (s, 2H), 7.61-7.47 (m, 2H), 7.29 (dd, J = 10.7, 8.5 Hz, 1H), 4.22 (s, 2H), 3.66 (s, 2H), 2.35-2.24 (m, 1H), 1.59-1.47 (m, 6H), 1.41-1.30 (m, 6H), 1.22-1.11 (m, 2H), 1.10-1.03 (m, 2H). FXR EC$_{50}$ (nM) = 22. MS (ESI) 561 (M + H). | Ex. 105 |

TABLE 2-continued

| Ex. No. | Structure & Name | ¹H NMR, FXR EC$_{50}$ & MS (ESI) | Method |
|---|---|---|---|
| 99 | 4-((4-((5-cyclopropyl-3-(2,6-dichlorophenyl)isoxazol-4-yl)methoxy)bicyclo[2.2.2]octan-1-yl)methoxy) benzoic acid | ¹H NMR (500 MHz, DMSO-d$_6$) δ 7.84 (d, J = 8.5 Hz, 2H), 7.64-7.59 (m, 2H), 7.58-7.52 (m, 1H), 6.94 (d, J = 8.9 Hz, 2H), 4.14 (s, 2H), 3.59 (s, 2H), 2.32-2.23 (m, 1H), 1.54-1.46 (m, 6H), 1.40-1.31 (m, 6H), 1.17-1.10 (m, 2H), 1.08-1.02 (m, 2H). FXR EC$_{50}$ (nM) = 140. MS (ESI) 542 (M + H). | Ex. 105 |
| 100 | 6-((4-((5-cyclopropyl-3-(2,6-dichlorophenyl)isoxazol-4-yl) methoxy)bicyclo[2.2.2]octan-1-yl) methoxy)-4-(trifluoromethyl) quinoline-2-carboxylic acid | ¹H NMR (500 MHz, DMSO-d$_6$) δ 8.34-8.27 (m, 1H), 8.21 (br s, 1H), 7.70-7.50 (m, 4H), 7.28 (br s, 1H), 4.15 (s, 2H), 3.76 (s, 2H), 2.31-2.18 (m, 1H), 1.64-1.52 (m, 6H), 1.49-1.35 (m, 6H), 1.19-1.09 (m, 2H), 1.08-1.01 (m, 2H). FXR EC$_{50}$ (nM) = 7. MS (ESI) 661 (M + H). | Ex. 105 |
| 101 | 6-((4-((5-cyclopropyl-3-(3,5-dichloropyridin-4-yl)isoxazol-4-yl) methoxy)bicyclo[2.2.2]octan-1-yl) methoxy)-4-(trifluoromethyl)quinoline-2-carboxylic acid | ¹H NMR (500 MHz, DMSO-d$_6$) δ 13.82-13.55 (s, 1H), 8.83 (s, 2H), 8.30 (s, 1H), 8.22 (d, J = 9.4 Hz, 1H), 7.66 (dd, J = 9.2, 2.3 Hz, 1H), 7.25 (br s, 1H), 4.23 (s, 2H), 3.76 (s, 2H), 2.39-2.24 (m, 1H), 1.65-1.50 (m, 6H), 1.45-1.31 (m, 6H), 1.21-1.13 (m, 2H), 1.12-1.04 (m, 2H). FXR EC$_{50}$ (nM) = 8. MS (ESI) 662 (M + H). | Ex. 105 |

TABLE 2-continued

| Ex. No. | Structure & Name | $^1$H NMR, FXR EC$_{50}$ & MS (ESI) | Method |
|---|---|---|---|
| 102 | 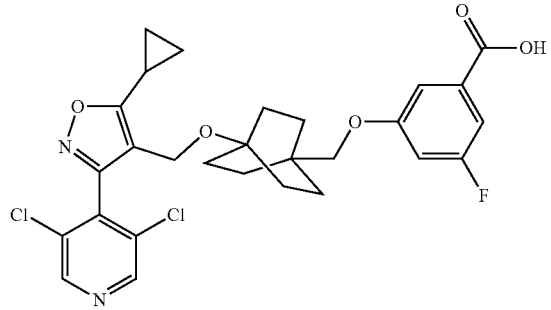 [SMILES: O=C(O)c1cc(F)cc(OCC23CCC(OCc4c(-c5c(Cl)cncc5Cl)noc4C4CC4)(CC2)CC3)c1]<br>3-((4-((5-cyclopropyl-3-(3,5-dichloropyridin-4-yl)isoxazol-4-yl)methoxy)bicyclo[2.2.2]octan-1-yl)methoxy)-5-fluorobenzoic acid | $^1$H NMR (500 MHz, DMSO-d$_6$) δ 8.78 (s, 2H), 7.23 (s, 1H), 7.19 (br d, J = 8.7 Hz, 1H), 6.97 (br d, J = 10.4 Hz, 1H), 4.21 (s, 2H), 3.60 (s, 2H), 2.32-2.21 (m, 1H), 1.58-1.47 (m, 6H), 1.43-1.32 (m, 6H), 1.18-1.10 (m, 2H), 1.09-1.02 (m, 2H). FXR EC$_{50}$ (nM) = 18. MS (ESI) 560 (M + H). | Ex. 105 |
| 103 | 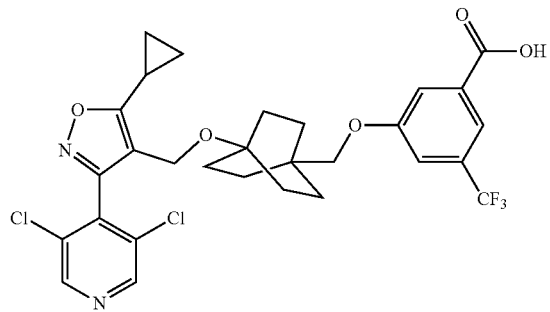 [SMILES: O=C(O)c1cc(OCC23CCC(OCc4c(-c5c(Cl)cncc5Cl)noc4C4CC4)(CC2)CC3)cc(C(F)(F)F)c1]<br>3-((4-((5-cyclopropyl-3-(3,5-dichloropyridin-4-yl)isoxazol-4-yl)methoxy)bicyclo[2.2.2]octan-1-yl)methoxy)-5-(trifluoromethyl)benzoic acid | $^1$H NMR (500 MHz, DMSO-d$_6$) δ 8.79 (s, 2H), 7.72 (s, 1H), 7.64 (s, 1H), 7.41 (s, 1H), 4.23 (s, 2H), 3.69 (s, 2H), 2.33-2.23 (m, 1H), 1.60-1.50 (m, 6H), 1.43-1.33 (m, 6H), 1.20-1.12 (m, 2H), 1.11-1.03 (m, 2H). FXR EC$_{50}$ (nM) = 4. MS (ESI) 611 (M + H). | Ex. 105 |
| 106 | 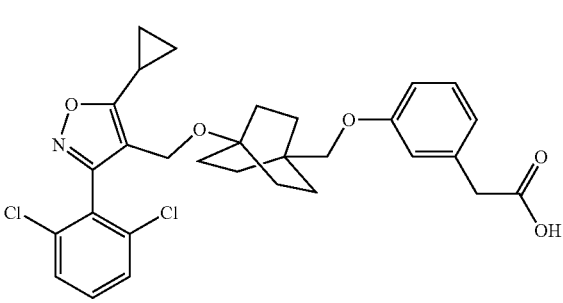 [SMILES: O=C(O)Cc1cccc(OCC23CCC(OCc4c(-c5c(Cl)cccc5Cl)noc4C4CC4)(CC2)CC3)c1]<br>2-(3-((4-((5-cyclopropyl-3-(2,6-dichlorophenyl)isoxazol-4-yl)methoxy)bicyclo[2.2.2]octan-1-yl)methoxy)phenyl)acetic acid | $^1$H NMR (500 MHz, DMSO-d$_6$) δ 7.68-7.61 (m, 2H), 7.60-7.51 (m, 1H), 7.16 (t, J = 7.8 Hz, 1H), 6.84-6.69 (m, 3H), 4.16 (s, 2H), 3.91 (s, 2H), 3.18 (s, 2H), 2.37-2.22 (m, 1H), 1.58-1.44 (m, 6H), 1.40-1.30 (m, 6H), 1.14 (br d, J = 8.2 Hz, 2H), 1.07 (br d, J = 2.7 Hz, 2H). FXR EC$_{50}$ (nM) = 160. MS (ESI) 556 (M + H). | Ex. 105 |

TABLE 2-continued

| Ex. No. | Structure & Name | ¹H NMR, FXR EC$_{50}$ & MS (ESI) | Method |
|---|---|---|---|
| 107 | 6-((4-((5-cyclopropyl-3-(2,6-dichlorophenyl)isoxazol-4-yl)methoxy)bicyclo[2.2.2]octan-1-yl)methoxy)nicotinic acid | ¹H NMR (500 MHz, DMSO-d$_6$) δ 8.57-8.11 (m, 1H), 8.13-7.76 (m, 1H), 7.24-6.91 (m, 3H), 6.84-6.55 (m, 1H), 4.71-4.32 (m, 2H), 4.29-3.95 (m, 2H), 2.36-2.03 (m, 1H), 1.95-1.16 (m, 12H), 1.05-0.63 (m, 4H). FXR EC$_{50}$ (nM) = 77. MS (ESI) 543 (M + H). | Ex. 104 |
| 108 | 2-((4-((5-cyclopropyl-3-(2,6-dichlorophenyl)isoxazol-4-yl)methoxy)bicyclo[2.2.2]octan-1-yl)methoxy)pyrimidine-4-carboxylic acid | ¹H NMR (500 MHz, DMSO-d$_6$) δ 8.49 (br d, J = 4.3 Hz, 1H), 7.62 (s, 2H), 7.61-7.54 (m, 1H), 7.25 (br s, 1H), 4.16 (s, 2H), 3.90-3.86 (m, 2H), 2.36-2.23 (m, 1H), 1.54-1.46 (m, 6H), 1.36 (br d, J = 14.3 Hz, 6H), 1.19-1.11 (m, 2H), 1.07 (br d, J = 2.1 Hz, 2H). FXR EC$_{50}$ (nM) = 540. MS (ESI) 544 (M+H). | Ex. 104 |
| 109 | 5-((4-((5-cyclopropyl-3-(2,6-dichlorophenyl)isoxazol-4-yl)methoxy)bicyclo[2.2.2]octan-1-yl)methoxy)nicotinic acid | ¹H NMR (500 MHz, DMSO-d$_6$) δ 8.63 (br s, 1H), 8.51-8.30 (m, 1H), 7.73-7.61 (m, 2H), 7.61-7.53 (m, 1H), 4.17 (s, 2H), 3.75-3.62 (m, 2H), 2.37-2.24 (m, 2H), 1.53 (br d, J = 15.3 Hz, 6H), 1.37 (br d, J = 15.0 Hz, 6H), 1.22-1.12 (m, 2H), 1.08 (br d, J = 2.7 Hz, 2H). FXR EC$_{50}$ (nM) = 150. MS (ESI) 543 (M + H). | Ex. 105 |

TABLE 2-continued

| Ex. No. | Structure & Name | $^1$H NMR, FXR EC$_{50}$ & MS (ESI) | Method |
|---|---|---|---|
| 110 | 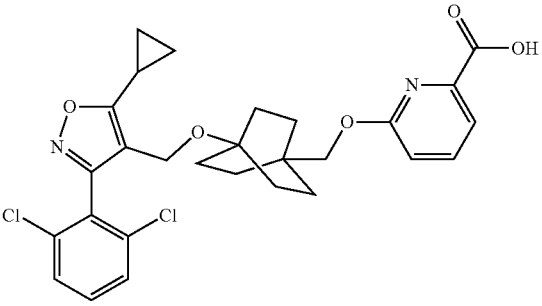 [SMILES: O=C(O)c1cccc(OCC23CCC(OCc4c(-c5c(Cl)cccc5Cl)noc4C4CC4)(CC2)CC3)n1]<br>6-((4-((5-cyclopropyl-3-(2,6-dichlorophenyl)isoxazol-4-yl)methoxy)bicyclo[2.2.2]octan-1-yl)methoxy)picolinic acid | $^1$H NMR (500 MHz, DMSO-d$_6$) δ 7.87-7.74 (m, 1H), 7.67-7.61 (m, 2H), 7.61-7.53 (m, 2H), 6.95 (br s, 1H), 4.16 (s, 2H), 3.90 (s, 2H), 2.35-2.24 (m, 1H), 1.50 (br d, J = 7.9 Hz, 6H), 1.37 (br d, J = 5.8 Hz, 6H), 1.21-1.11 (m, 2H), 1.10-1.03 (m, 2H). FXR EC$_{50}$ (nM) = 52. MS (ESI) 543 (M + H). | Ex. 104 |
| 111 | 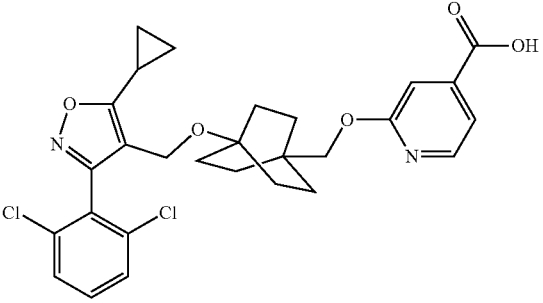 [SMILES: O=C(O)c1ccnc(OCC23CCC(OCc4c(-c5c(Cl)cccc5Cl)noc4C4CC4)(CC2)CC3)c1]<br>2-((4-((5-cyclopropyl-3-(2,6-dichlorophenyl)isoxazol-4-yl)methoxy)bicyclo[2.2.2]octan-1-yl)methoxy)isonicotinic acid | $^1$H NMR (500 MHz, DMSO-d$_6$) δ 8.12 (br d, J = 4.9 Hz, 1H), 7.68-7.61 (m, 2H), 7.60-7.51 (m, 1H), 7.30 (br d, J = 4.9 Hz, 1H), 7.08 (s, 1H), 4.16 (s, 2H), 3.85 (s, 2H), 2.36-2.23 (m, 1H), 1.59-1.45 (m, 6H), 1.41-1.32 (m, 6H), 1.19-1.11 (m, 2H), 1.08 (br d, J = 2.7 Hz, 2H). FXR EC$_{50}$ (nM) = 110. MS (ESI) 543 (M + H). | Ex. 104 |
| 112 | 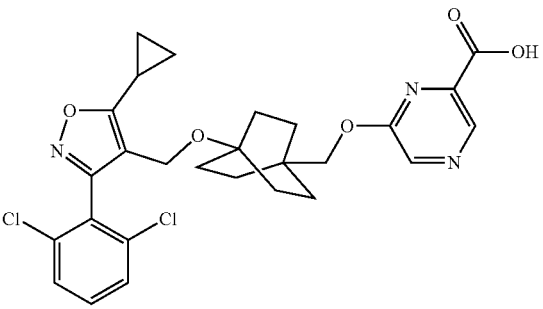 [SMILES: O=C(O)c1cncc(OCC23CCC(OCc4c(-c5c(Cl)cccc5Cl)noc4C4CC4)(CC2)CC3)n1]<br>6-((4-((5-cyclopropyl-3-(2,6-dichlorophenyl)isoxazol-4-yl)methoxy)bicyclo[2.2.2]octan-1-yl)methoxy)pyrazine-2-carboxylic acid | $^1$H NMR (500 MHz, DMSO-d$_6$) δ 8.59 (s, 1H), 8.24 (br s, 1H), 7.68-7.61 (m, 2H), 7.61-7.55 (m, 1H), 4.16 (s, 2H), 3.90 (s, 2H), 2.37-2.24 (m, 1H), 1.51 (br d, J = 7.7 Hz, 6H), 1.36 (br s, 6H), 1.14 (br d, J = 7.9 Hz, 2H), 1.07 (br s, 2H). FXR EC$_{50}$ (nM) = 690. MS (ESI) 544 (M + H) | Ex. 104 |

TABLE 2-continued

| Ex. No. | Structure & Name | $^1$H NMR, FXR EC$_{50}$ & MS (ESI) | Method |
|---|---|---|---|
| 113 | 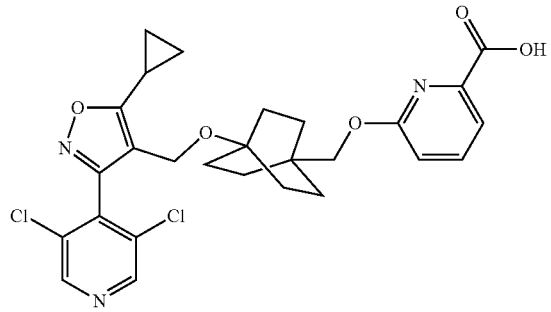 [SMILES: O=C(O)c1cccc(OCC23CCC(OCc4c(-c5c(Cl)cncc5Cl)noc4C4CC4)(CC2)CC3)n1]<br>6-((4-((5-cyclopropyl-3-(3,5-dichloropyridin-4-yl)isoxazol-4-yl)methoxy)bicyclo[2.2.2]octan-1-yl)methoxy)picolinic acid | $^1$H NMR (500 MHz, DMSO-d$_6$) δ 8.83 (s, 2H), 7.80 (br t, J = 7.6 Hz, 1H), 7.59 (br d, J = 7.0 Hz, 1H), 6.95 (br d, J = 8.2 Hz, 1H), 4.23 (s, 2H), 3.90 (d, J = 4.6 Hz, 2H), 2.38-2.24 (m, 1H), 1.51 (br d, J = 7.9 Hz, 6H), 1.35 (br d, J = 7.3 Hz, 6H), 1.23-1.13 (m, 2H), 1.09 (br d, J = 2.7 Hz, 2H). FXR EC$_{50}$ (nM) = 92. MS (ESI) 544 (M + H). | Ex. 104 |
| 114 | 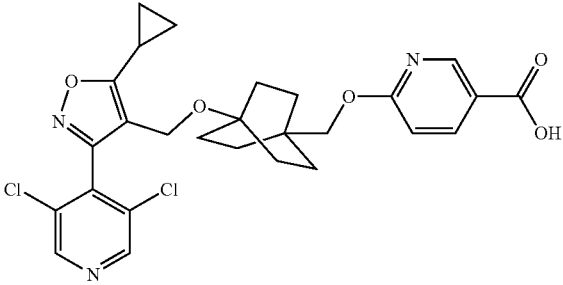 [SMILES: O=C(O)c1ccc(OCC23CCC(OCc4c(-c5c(Cl)cncc5Cl)noc4C4CC4)(CC2)CC3)nc1]<br>6-((4-((5-cyclopropyl-3-(3,5-dichloropyridin-4-yl)isoxazol-4-yl)methoxy)bicyclo[2.2.2]octan-1-yl)methoxy)nicotinic acid | $^1$H NMR (500 MHz, DMSO-d$_6$) δ 8.84 (s, 2H), 8.26 (d, J = 5.2 Hz, 1H), 7.36 (br d, J = 5.2 Hz, 1H), 7.15 (s, 1H), 4.24 (s, 2H), 3.90 (s, 2H), 2.46-2.19 (m, 1H), 1.52 (br d, J = 7.9 Hz, 6H), 1.42-1.26 (m, 6H), 1.17 (br d, J = 8.2 Hz, 2H), 1.10 (br d, J = 2.7 Hz, 2H). FXR EC$_{50}$ (nM) = 140. MS (ESI) 544 (M + H). | Ex. 104 |
| 115 | 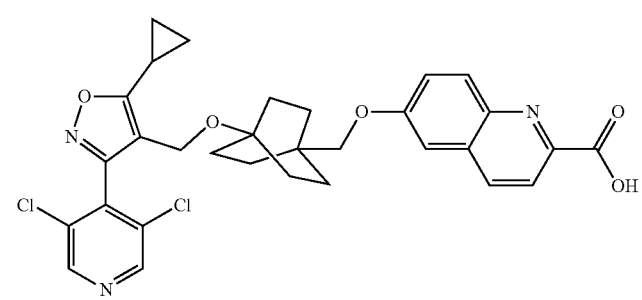 [SMILES: O=C(O)c1ccc2cc(OCC34CCC(OCc5c(-c6c(Cl)cncc6Cl)noc5C5CC5)(CC3)CC4)ccc2n1]<br>6-((4-((5-cyclopropyl-3-(3,5-dichloropyridin-4-yl)isoxazol-4-yl)methoxy)bicyclo[2.2.2]octan-1-yl)methoxy)quinoline-2-carboxylic acid | $^1$H NMR (500 MHz, DMSO-d$_6$) δ 8.83 (s, 2H), 8.35 (br d, J = 8.5 Hz, 1H), 8.04 (br t, J = 9.8 Hz, 2H), 7.45 (br d, J = 9.2 Hz, 1H), 7.40 (br s, 1H), 4.24 (s, 2H), 3.72 (s, 2H), 2.38-2.26 (m, 1H), 1.70-1.50 (m, 6H), 1.45-1.30 (m, 6H), 1.24-1.13 (m, 2H), 1.09 (br d, J = 2.7 Hz, 2H). FXR EC$_{50}$ (nM) = 52. MS (ESI) 594 (M + H). | Ex. 105 |

TABLE 2-continued

| Ex. No. | Structure & Name | ¹H NMR, FXR EC₅₀ & MS (ESI) | Method |
|---|---|---|---|
| 116 | 2-(2-((4-((5-cyclopropyl-3-(2,6-dichlorophenyl)isoxazol-4-yl)methoxy)bicyclo[2.2.2]octan-1-yl)methoxy)phenyl)acetic acid | $^1$H NMR (500 MHz, DMSO-$d_6$) δ 7.68-7.61 (m, 2H), 7.60-7.53 (m, 1H), 7.27-7.10 (m, 2H), 6.93-6.80 (m, 2H), 4.15 (s, 2H), 3.49 (s, 2H), 3.47 (s, 2H), 2.36-2.23 (m, 1H), 1.60-1.45 (m, 6H), 1.42-1.31 (m, 6H), 1.22-1.11 (m, 2H), 1.08 (br d, J = 3.1 Hz, 2H). FXR EC₅₀ (nM) = 900. MS (ESI) 556 (M + H). | Ex. 105 |
| 117 | 6-((4-((5-cyclopropyl-3-(2,6-dichlorophenyl)isoxazol-4-yl)methoxy)bicyclo[2.2.2]octan-1-yl)methoxy)picolinamide | $^1$H NMR (500 MHz, DMSO-$d_6$) δ 7.95 (br s, 1H), 7.82 (t, J = 7.8 Hz, 1H), 7.68-7.61 (m, 2H), 7.61-7.53 (m, 3H), 6.95 (d, J = 8.2 Hz, 1H), 4.16 (s, 2H), 4.00 (s, 2H), 2.34-2.25 (m, 1H), 1.58-1.47 (m, 6H), 1.42-1.31 (m, 6H), 1.19-1.11 (m, 2H), 1.08 (br d, J = 2.7 Hz, 2H).). FXR EC₅₀ (nM) = 310. MS (ESI) 542 (M + H) | Ex. 104 |
| 118 | 6-((4-((5-cyclopropyl-3-(3,5-dichloropyridin-4-yl)isoxazol-4-yl)methoxy)bicyclo[2.2.2]octan-1-yl)methoxy)-5-fluoronicotinic acid | $^1$H NMR (500 MHz, DMSO-$d_6$) δ 8.80 (s, 2H), 8.41 (s, 1H), 7.90 (br d, J = 10.4 Hz, 1H), 4.21 (s, 2H), 3.99 (s, 2H), 2.36-2.21 (m, 1H), 1.60-1.42 (m, 6H), 1.39-1.25 (m, 6H), 1.20-1.12 (m, 2H), 1.10-0.99 (m, 2H). FXR EC₅₀ (nM) = 33. MS (ESI) 562 (M + H). | Ex. 104 |

TABLE 2-continued

| Ex. No. | Structure & Name | $^1$H NMR, FXR EC$_{50}$ & MS (ESI) | Method |
|---|---|---|---|
| 119 | 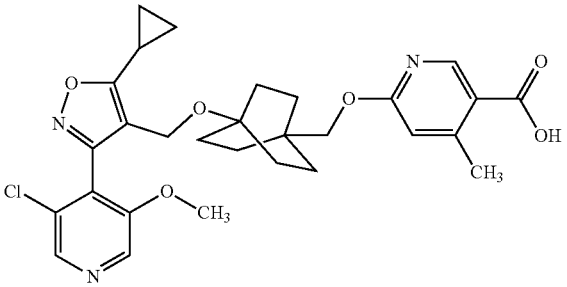 [SMILES: COc1cncc(Cl)c1-c1noc(C2CC2)c1COC12CCC(COc3cc(C)c(C(=O)O)cn3)(CC1)CC2]<br>6-((4-((3-(3-chloro-5-methoxypyridin-4-yl)-5-cyclopropylisoxazol-4-yl)methoxy)bicyclo[2.2.2]octan-1-yl)methoxy)-4-methylnicotinic acid | $^1$H NMR (500 MHz, DMSO-d$_6$) δ 8.61-8.32 (m, 3H), 6.62 (br s, 1H), 4.14 (s, 2H), 3.94-3.32 (m, 5H), 2.55 (s, 3H), 2.38-2.18 (m, 1H), 1.61-1.44 (m, 6H), 1.43-1.28 (m, 6H), 1.19-1.09 (m, 2H), 1.09-1.02 (m, 2H). FXR EC$_{50}$ (nM) = 120. MS (ESI) 554 (M + H). | Ex. 104 |
| 120 | 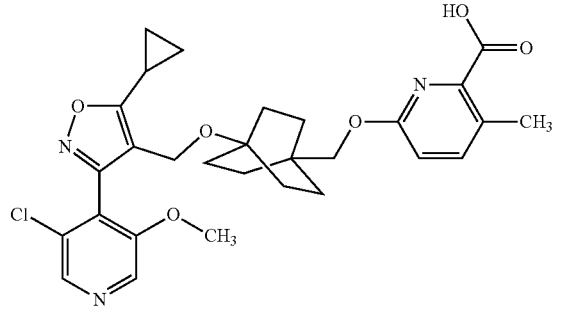 [SMILES: COc1cncc(Cl)c1-c1noc(C2CC2)c1COC12CCC(COc3ccc(C)c(C(=O)O)n3)(CC1)CC2]<br>6-((4-((3-(3-chloro-5-methoxypyridin-4-yl)-5-cyclopropylisoxazol-4-yl)methoxy)bicyclo[2.2.2]octan-1-yl)methoxy)-3-methylpicolinic acid | $^1$H NMR (500 MHz, DMSO-d$_6$) δ 8.56 (br s, 2H), 7.77-7.49 (m, 1H), 7.06-6.71 (m, 1H), 4.12 (br s, 2H), 3.89 (br s, 3H), 3.83 (br d, J = 4.3 Hz, 1H), 2.56 (s, 3H), 2.42-2.29 (m, 2H), 1.48 (br s, 6H), 1.33 (br s, 6H), 1.13 (br d, J = 7.3 Hz, 2H), 1.05 (br s, 2H). FXR EC$_{50}$ (nM) = 2300. MS (ESI) 554 (M + H). | Ex. 104 |

Example 121

3-((4-((5-cyclopropyl-3-(2,6-dichlorophenyl)isoxazol-4-yl)methoxy)bicyclo[2.2.2]octan-1-yl)(hydroxy)methyl)-4-fluorobenzoic acid

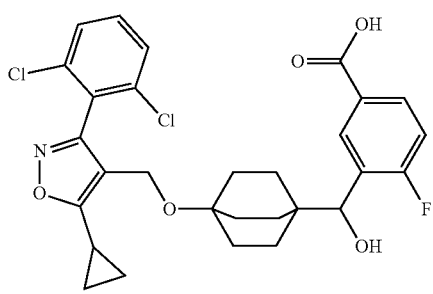

(121)

Step A. Intermediate 121A. Preparation of 4-((5-cyclopropyl-3-(2,6-dichlorophenyl)isoxazol-4-yl)methoxy)bicyclo[2.2.2]octane-1-carbaldehyde

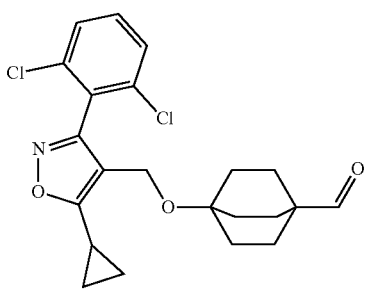 [SMILES: O=CC12CCC(OCc3c(-c4c(Cl)cccc4Cl)noc3C3CC3)(CC1)CC2]

A solution of oxalyl chloride (0.15 mL, 1.7 mmol) in CH$_2$Cl$_2$ (9 mL) was cooled to −78° C. and a solution of DMSO (0.28 mL, 3.9 mmol) in CH$_2$Cl$_2$ (4 mL) was added dropwise. The reaction mixture was stirred for 10 min. A solution of Intermediate 104A (0.55 g, 1.3 mmol) in CH$_2$Cl$_2$ was added slowly and the reaction mixture was stirred for 30 min. Triethylamine (0.91 mL, 6.5 mmol) was added and the reaction mixture was warmed to rt and stirred for 30 min. The reaction mixture was diluted with CH$_2$Cl$_2$, washed with 1 M HCl (aq.), 1 M K$_2$HPO$_4$ (aq.), brine, dried (MgSO$_4$), filtered, and concentrated. The product was dried in vacuo to afford the title compound (0.54 g, 1.3 mmol, 99% yield) as an off-white solid. ¹H NMR (400 MHz, CHLOROFORM-d) δ 9.41 (s, 1H), 7.42 (d, J=1.5 Hz, 1H), 7.40 (s, 1H), 7.37-7.31 (m, 1H), 4.19 (s, 2H), 2.11 (tt, J=8.4, 5.1 Hz, 1H), 1.71-1.62 (m, 6H), 1.54-1.46 (m, 6H), 1.27-1.22 (m, 2H), 1.14-1.07 (m, 2H). MS (ESI) 420 (M+H).

Step B. Intermediate 121B. Preparation of 3-((4-((5-cyclopropyl-3-(2,6-dichlorophenyl)isoxazol-4-yl)methoxy)bicyclo[2.2.2]octan-1-yl)(hydroxy)methyl)-4-fluorobenzonitrile

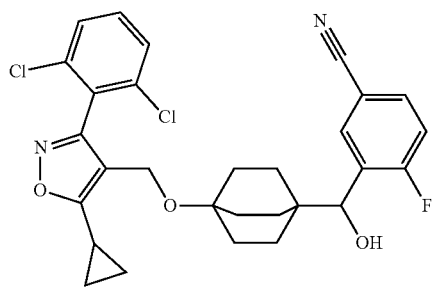 [SMILES: N#Cc1ccc(F)c(C(O)C23CCC(OCc4c(-c5c(Cl)cccc5Cl)noc4C4CC4)(CC2)CC3)c1]

To a solution of 3-bromo-4-fluorobenzonitrile (0.027 g, 0.13 mmol) in anhydrous THF (0.56 mL) at −78° C. was added n-butyllithium (0.084 mL, 0.13 mmol) (1.6 M solution in THF). The reaction mixture was stirred at −78° C. for 1 h. A solution of Intermediate 121A (0.028 g, 0.067 mmol) in THF (0.11 mL) was added dropwise via cannula. The reaction mixture was stirred at −78° C. for 1 h. The reaction was quenched with water and warmed to rt. The reaction mixture was diluted with EtOAc and washed with brine. The organic layer was dried (MgSO₄) and concentrated. The crude product was purified by flash column chromatography (12 g silica gel cartridge; A=Hex, B=EtOAc; 15 min grad.; 10% B to 100% B; flow rate=12 mL/min). The pure fractions were combined, concentrated and dried in vacuo to afford the title compound (0.022 g, 0.040 mmol, 59% yield) as a colorless glass. ¹H NMR (400 MHz, CHLOROFORM-d) δ 7.74 (dd, J=6.5, 2.1 Hz, 1H), 7.55 (ddd, J=8.6, 4.6, 2.2 Hz, 1H), 7.41-7.39 (m, 1H), 7.38 (d, J=0.7 Hz, 1H), 7.35-7.29 (m, 1H), 7.09 (dd, J=9.4, 8.7 Hz, 1H), 4.70 (d, J=3.3 Hz, 1H), 4.13 (s, 2H), 4.12-4.09 (m, 1H), 2.13-2.07 (m, 1H), 1.62-1.48 (m, 4H), 1.40 (br d, J=3.5 Hz, 8H), 1.24-1.19 (m, 2H), 1.12-1.03 (m, 2H). MS (ESI) 541 (M+H).

Step C. Example 121

To a solution of Intermediate 121B (0.022 g, 0.040 mmol) in EtOH (0.40 mL) was added 6 M (aq.) NaOH (0.13 mL, 0.79 mmol). The reaction mixture was stirred at 110° C. in a pressure vial for 18 h. The reaction mixture was cooled, acidified with 1 M HCl (aq.) and extracted with EtOAc (3×). The combined organic layers were dried (MgSO₄) and concentrated. The crude material was purified by preparative HPLC Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 38-78% B over 20 minutes, then a 4-minute hold at 100% B; Flow: 20 mL/min). Fractions containing the desired product were combined, concentrated and dried in vacuo to provide the title compound (0.018 g, 0.033 mmol, 82% yield). ¹H NMR (500 MHz, DMSO-d₆) δ 7.95 (br d, J=5.1 Hz, 1H), 7.84 (td, J=5.4, 2.3 Hz, 1H), 7.60-7.55 (m, 2H), 7.55-7.49 (m, 1H), 7.20 (t, J=9.2 Hz, 1H), 4.47 (br d, J=3.8 Hz, 1H), 4.07 (s, 2H), 2.28-2.18 (m, 1H), 1.45 (br d, J=4.9 Hz, 3H), 1.36-1.17 (m, 9H), 1.14-1.08 (m, 2H), 1.05-1.01 (m, 2H). FXR EC₅₀ (nM)=1500. MS (ESI) 560 (M+H).

Example 122

2-((4-((5-cyclopropyl-3-(2,6-dichlorophenyl)isoxazol-4-yl)methoxy)bicyclo[2.2.2]octan-1-yl)(hydroxy)methyl)-4-fluorobenzo[d]thiazole-6-carboxylic acid

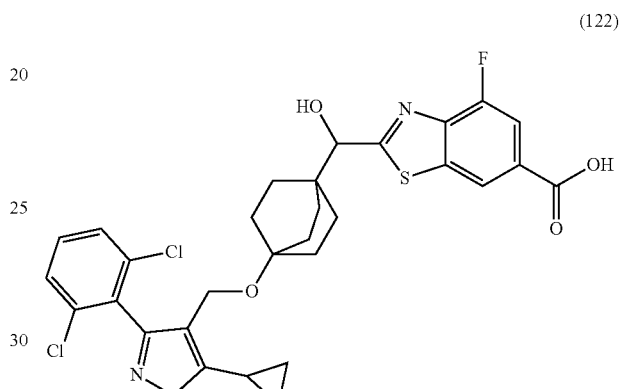

(122)

Step A. Intermediate 122A. Preparation of (6-bromo-4-fluorobenzo[d]thiazol-2-yl)(4-((5-cyclopropyl-3-(2,6-dichlorophenyl)isoxazol-4-yl)methoxy)bicyclo[2.2.2]octan-1-yl)methanol

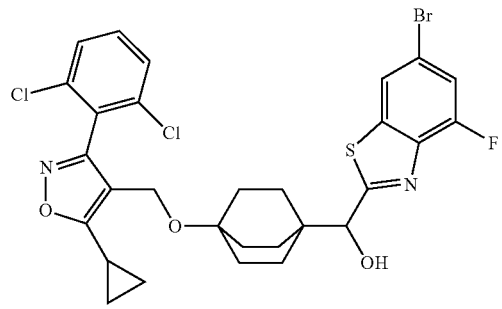 [SMILES: OC(c1nc2c(F)cc(Br)cc2s1)C12CCC(OCc3c(-c4c(Cl)cccc4Cl)noc3C3CC3)(CC1)CC2]

The title compound was prepared according to methods described for the synthesis of Example 121 (Step B), by reaction of Intermediate 121A with 2,6-dibromo-4-fluorobenzo[d]thiazole: (0.030 g, 0.046 mmol, 69% yield). ¹H NMR (500 MHz, CHLOROFORM-d) δ 7.80 (d, J=0.8 Hz, 1H), 7.39 (s, 1H), 7.37 (s, 1H), 7.35 (dd, 1.7 Hz, 1H), 7.33-7.29 (m, 1H), 4.67 (d, J=4.4 Hz, 1H), 4.15 (s, 2H), 4.14-4.10 (m, 1H), 2.13-2.07 (m, 1H), 1.71-1.60 (m, 6H), 1.44 (br t, J=7.7 Hz, 6H), 1.24-1.20 (m, 2H), 1.11-1.04 (m, 2H). MS (ESI) 653 (M+H).

Step B. Intermediate 122B. Preparation of 2-((4-((5-cyclopropyl-3-(2,6-dichlorophenyl)isoxazol-4-yl)methoxy)bicyclo[2.2.2]octan-1-yl)(hydroxy)methyl)-4-fluorobenzo[d]thiazole-6-carbonitrile

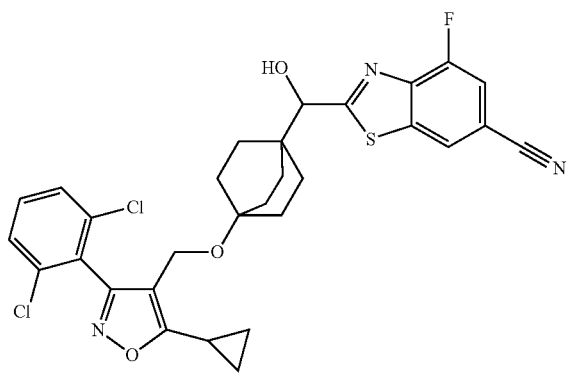 [SMILES: N#Cc1cc(F)c2nc(C(O)C34CCC(OCc5c(-c6c(Cl)cccc6Cl)noc5C5CC5)(CC3)CC4)sc2c1]

A microwave vial containing (6-bromo-4-fluorobenzo[d]thiazol-2-yl)(4-((5-cyclopropyl-3-(2,6-dichlorophenyl)isoxazol-4-yl)methoxy)bicyclo[2.2.2]octan-1-yl)methanol (0.030 g, 0.046 mmol), Xantphos (5.3 mg, 9.2 μmol), Pd$_2$(dba)$_3$ (8.5 mg, 9.3 μmol), and zinc cyanide (11 mg, 0.092 mmol) was purged with nitrogen (3×) and anhydrous DMF (0.5 mL) was added. The reaction mixture was irradiated at 110° C. (microwave) for 1.5 h. The reaction mixture was diluted with EtOAc and washed with water (3×). The organic layer was washed with brine, dried (MgSO$_4$) and concentrated. The crude product was purified by flash column chromatography (12 g silica gel cartridge; A=Hex, B=EtOAc; 15 min grad.; 10% B to 100% B; flow rate=12 mL/min). The pure fractions were combined, concentrated and dried in vacuo to afford the title compound (0.021 g, 0.034 mmol, 75% yield) as a colorless foam. $^1$H NMR (400 MHz, CHLOROFORM-d) δ 8.02 (d, J=0.9 Hz, 1H), 7.45 (dd, J=9.6, 1.4 Hz, 1H), 7.39 (d, J=1.5 Hz, 1H), 7.37 (s, 1H), 7.34-7.28 (m, 1H), 4.74 (d, J=5.1 Hz, 1H), 4.15 (s, 2H), 4.14-4.10 (m, 1H), 2.13-2.06 (m, 1H), 1.74-1.58 (m, 6H), 1.50-1.42 (m, 6H), 1.25-1.18 (m, 2H), 1.11-1.03 (m, 2H). MS (ESI) 598 (M+H).

Step C. Example 122

The title compound was prepared according to methods described for the synthesis of Example 121 (Step C), using Intermediate 122B as starting material: (0.0049 g, 0.0079 mmol, 23% yield). $^1$H NMR (500 MHz, DMSO-d$_6$) δ 8.25 (dd, J=4.8, 1.7 Hz, 1H), 8.17 (dd, J=7.4, 1.7 Hz, 1H), 7.53 (br d, J=19.7 Hz, 2H), 7.43 (br d, J=3.9 Hz, 1H), 7.10 (dd, J=7.4, 4.9 Hz, 1H), 6.31 (s, 1H), 6.02 (br d, J=7.7 Hz, 1H), 5.21 (quin, J=7.0 Hz, 1H), 3.98 (sxt, J=7.8 Hz, 1H), 2.60 (d, J=4.7 Hz, 4H), 2.48-2.41 (m, 1H), 2.41-2.33 (m, 1H), 2.31-2.23 (m, 1H), 2.23-2.10 (m, 2H), 1.93 (br t, J=9.5 Hz, 2H), 1.29-1.17 (m, 2H), 1.01 (d, J=6.3 Hz, 1H), 0.86-0.73 (m, 2H). FXR EC$_{50}$ (nM)=1000. MS (ESI) 617 (M+H).

Example 127

3-(2-(4-((5-cyclopropyl-3-(2,6-dichlorophenyl)isoxazol-4-yl)methoxy)bicyclo[2.2.2]octan-1-yl)-2-hydroxyethyl)benzoic acid

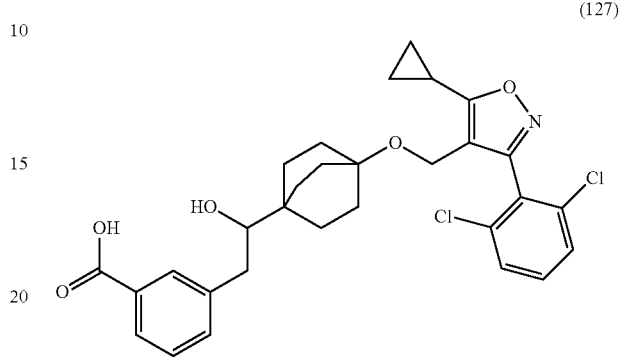

(127)

Step A. Intermediate 127A. Preparation of 2-(3-bromophenyl)-1-(4-((5-cyclopropyl-3-(2,6-dichlorophenyl)isoxazol-4-yl)methoxy)bicyclo[2.2.2]octan-1-yl)ethan-1-ol

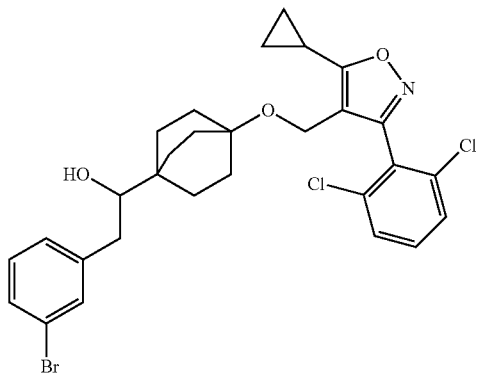 [SMILES: OC(Cc1cccc(Br)c1)C12CCC(OCc3c(-c4c(Cl)cccc4Cl)noc3C3CC3)(CC1)CC2]

The title compound was prepared according to methods described for the synthesis of Example 121 (Step B), by reaction of Intermediate 121A with (3-bromobenzyl)magnesium bromide: (0.024 g, 0.040 mmol, 50% yield). $^1$H NMR (500 MHz, CHLOROFORM-d) δ 7.46-7.41 (m, 2H), 7.40-7.31 (m, 3H), 7.21-7.15 (m, 1H), 7.14-7.10 (m, 1H), 4.21 (s, 2H), 4.18-4.12 (m, 1H), 3.33 (br d, J=10.7 Hz, 1H), 2.77 (br d, J=13.8 Hz, 1H), 2.19-2.11 (m, 1H), 1.52-1.45 (m, 6H), 1.34-1.21 (m, 6H), 1.16-1.06 (m, 3H), 0.94-0.81 (m, 2H). MS (ESI) 592 (M+H).

Step B. Example 127

To a solution of Intermediate 127A (0.024 g, 0.040 mmol) in THF (0.40 mL) at −78° C. was added n-butyllithium (0.028 mL, 0.044 mmol) (1.6 M solution in THF). After 5 min, a spatula tip full of freshly crushed dry ice was added and the reaction mixture was warmed to rt. The reaction mixture was acidified with 1 M HCl (aq.) and extracted with EtOAc (3×). The combined organic layers were dried (MgSO$_4$) and concentrated. The crude material was purified by preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 19-59% B over 20 minutes, then a 4-minute hold at 100% B; Flow: 20 mL/min). Fractions containing the desired product were combined, concentrated and dried in vacuo to provide the title compound to afford the title compound (0.013 g, 0.023 mmol, 57% yield). $^1$H NMR (500 MHz, DMSO-d$_6$) δ 7.77 (s, 1H), 7.74 (br d, J=7.6 Hz, 1H), 7.64 (s, 1H), 7.63 (s, 1H), 7.60-7.54 (m, 1H), 7.43-7.38 (m, 1H), 7.38-7.32 (m, 1H), 4.14 (s, 2H), 3.10 (br d, J=8.5 Hz, 1H), 2.72 (br d, J=14.0 Hz, 1H), 2.36-2.23 (m, 2H), 1.54-1.37 (m, 6H), 1.36-1.26 (m, 6H), 1.19-1.11 (m, 2H), 1.10-1.03 (m, 2H). FXR EC$_{50}$ (nM)=280. MS (ESI) 556 (M+H).

Example 130

3-((4-((5-cyclopropyl-3-(2,6-dichlorophenyl)isoxazol-4-yl)methoxy)bicyclo[2.2.2]octan-1-yl)ethynyl) benzoic acid

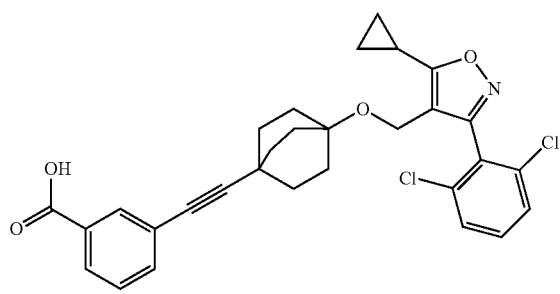 [SMILES: O=C(O)c1cccc(C#CC23CCC(OCc4c(-c5c(Cl)cccc5Cl)noc4C4CC4)(CC2)CC3)c1]

Step A. Intermediate 130A. Preparation of 5-cyclopropyl-3-(2,6-dichlorophenyl)-4-(((4-ethynylbicyclo[2.2.2]octan-1-yl)oxy)methyl)isoxazole

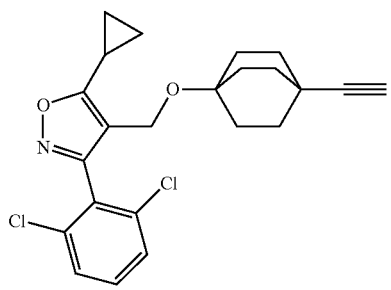 [SMILES: C#CC12CCC(OCc3c(-c4c(Cl)cccc4Cl)noc3C3CC3)(CC1)CC2]

To a solution of Intermediate 121A (0.056 g, 0.13 mmol) and K$_2$CO$_3$ (0.037 g, 0.27 mmol) was added anhydrous MeOH (0.5 mL) and the mixture was stirred at rt for 30 min. Dimethyl (1-diazo-2-oxopropyl)phosphonate (0.030 g, 0.16 mmol) was added via syringe and the reaction mixture was stirred for 1 h. The reaction mixture was diluted with ether, washed with 1 M K$_2$HPO$_4$ (aq.), dried (MgSO$_4$), filtered and concentrated to provide the title compound (0.054 g, 0.13 mmol, 99% yield) as an off-white foam, which was used without further purification. $^1$H NMR (500 MHz, CHLOROFORM-d) δ 7.43 (d, J=0.8 Hz, 1H), 7.42 (s, 1H), 7.38-7.33 (m, 1H), 4.16 (s, 2H), 2.15-2.09 (m, 1H), 2.07 (s, 1H), 1.89-1.76 (m, 6H), 1.53-1.41 (m, 6H), 1.28-1.22 (m, 2H), 1.15-1.06 (m, 2H). MS (ESI) 416 (M+H).

Step B. Intermediate 130B. Preparation of methyl 3-((4-((5-cyclopropyl-3-(2,6-dichlorophenyl)isoxazol-4-yl)methoxy)bicyclo[2.2.2]octan-1-yl)ethynyl) benzoate

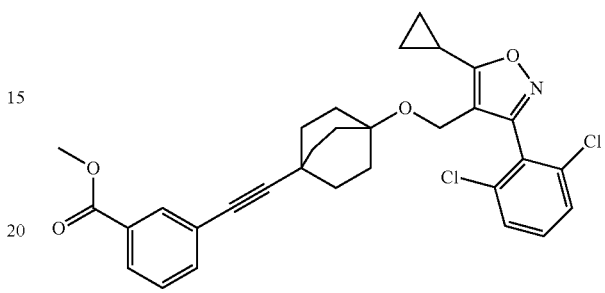

A flask with copper(I) iodide (0.18 mg, 0.94 µmol) and Pd(dppf)Cl$_2$.CH$_2$Cl$_2$ adduct (0.77 mg, 0.94 µmol) was purged with nitrogen. Methyl 3-iodobenzoate (0.015 g, 0.056 mmol) and Intermediate 130A (0.020 g, 0.047 mmol) were added along with THF (0.37 mL) and TEA (0.099 mL). The reaction mixture was stirred at 70° C. for 18 h. The reaction mixture was diluted with EtOAc, filtered, and concentrated. The crude material was purified by flash column chromatography (12 g silica gel cartridge; A=Hex, B=EtOAc; 15 min grad.; 10% B to 100% B; flow rate=12 mL/min). The pure fractions were combined, concentrated and dried in vacuo to afford the title compound (0.016 g, 0.029 mmol, 62% yield). $^1$H NMR (500 MHz, CHLOROFORM-d) δ 8.04-7.99 (m, 1H), 7.94-7.89 (m, 1H), 7.52-7.48 (m, 1H), 7.43 (d, J=0.8 Hz, 1H), 7.41 (s, 1H), 7.37-7.31 (m, 2H), 4.17 (s, 2H), 3.91 (s, 3H), 2.12 (tt, J=8.5, 5.0 Hz, 1H), 1.94-1.83 (m, 6H), 1.54-1.45 (m, 6H), 1.27-1.22 (m, 2H), 1.14-1.06 (m, 2H). MS (ESI) 550 (M+H).

Step C. Example 130

To a solution of Intermediate 130B (0.016 g, 0.029 mmol) in THF (0.29 mL) was added 1 M NaOH (aq.) (0.18 mL, 0.18 mmol) and several drops of MeOH. The reaction mixture was stirred at 70° C. for 2 h. The reaction mixture was acidified with 1 M HCl (aq.) and extracted with EtOAc (3×). The combined organic layers were dried (MgSO$_4$) and concentrated. The crude material was purified by preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 26-66% B over 20 minutes, then a 4-minute hold at 100% B; Flow: 20 mL/min). Fractions containing the desired product were combined, concentrated and dried in vacuo to afford the title compound (15 mg, 0.029 mmol, 98% yield). $^1$H NMR (500 MHz, DMSO-d$_6$) δ 7.87 (br d, J=7.8 Hz, 1H), 7.81 (s, 1H), 7.65 (s, 1H), 7.63 (s, 1H), 7.60-7.55 (m, 1H), 7.54 (br d, J=7.7 Hz, 1H), 7.50-7.42 (m, 1H), 4.13 (s, 2H), 2.34-2.24 (m, 1H), 1.88-1.75 (m, 6H), 1.47-1.34 (m, 6H), 1.19-1.11 (m, 2H), 1.10-1.03 (m, 2H). FXR EC$_{50}$ (nM)=68. MS (ESI) 536 (M+H).

Example 131

3-(4-(4-((5-cyclopropyl-3-(2,6-dichlorophenyl)isoxazol-4-yl)methoxy)bicyclo[2.2.2]octan-1-yl)-1H-1,2,3-triazol-1-yl)benzoic acid

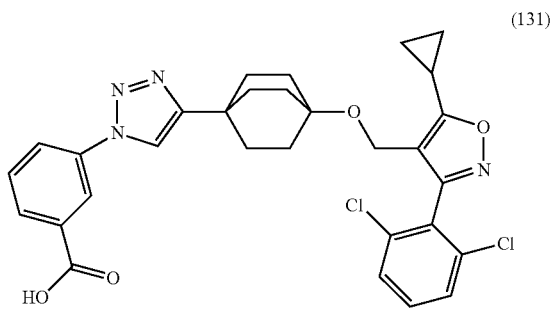 [SMILES: O=C(O)c1cccc(-n2cc(C34CCC(OCc5c(-c6c(Cl)cccc6Cl)noc5C5CC5)(CC3)CC4)nn2)c1]
(131)

Step A. Intermediate 131A. Preparation of ethyl 3-(4-(4-((5-cyclopropyl-3-(2,6-dichlorophenyl)isoxazol-4-yl)methoxy)bicyclo[2.2.2]octan-1-yl)-1H-1,2,3-triazol-1-yl)benzoate

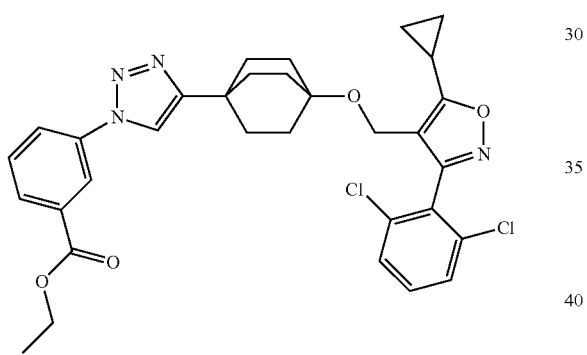

To a pressure vial was added Intermediate 130A (0.020 g, 0.048 mmol), ethyl 3-azidobenzoate (0.018 g, 0.096 mmol), and copper(I) iodide (0.91 mg, 4.8 μmol). The flask was purged with nitrogen (3×), then THF (0.48 mL) and TEA (0.013 mL, 0.096 mmol) were added. The reaction mixture was stirred at 50° C. for 3 h and 18 h at rt. The reaction mixture was concentrated and the crude product was purified by flash column chromatography (12 g silica gel cartridge; A=Hex, B=EtOAc; 15 min grad.; 10% B to 100% B; flow rate=12 mL/min). The pure fractions were combined, concentrated and dried in vacuo to afford the title compound (0.023 g, 0.038 mmol, 79% yield) as a colorless glass. $^1$H NMR (500 MHz, CHLOROFORM-d) δ 8.27 (s, 1H), 8.09 (d, J=7.7 Hz, 1H), 7.99 (dd, J=8.1, 1.2 Hz, 1H), 7.68 (s, 1H), 7.59 (t, J=7.8 Hz, 1H), 7.46-7.40 (m, 2H), 7.39-7.31 (m, 1H), 4.43 (q, J=7.1 Hz, 2H), 4.23 (s, 2H), 2.18-2.10 (m, 1H), 2.04-1.94 (m, 6H), 1.67-1.56 (m, 6H), 1.43 (t, J=7.2 Hz, 3H), 1.28-1.23 (m, 2H), 1.15-1.06 (m, 2H). MS (ESI) 607 (M+H).

Step B. Example 131

The title compound was prepared according to methods described for the synthesis of Example 130 (Step C): (20 mg, 0.034 mmol, 91% yield). $^1$H NMR (500 MHz, DMSO-d$_6$) δ 8.61 (s, 1H), 8.35 (s, 1H), 8.07 (br d, J=7.9 Hz, 1H), 7.99 (br d, J=7.6 Hz, 1H), 7.68 (t, J=7.9 Hz, 1H), 7.65 (s, 1H), 7.64 (s, 1H), 7.61-7.55 (m, 1H), 4.19 (s, 2H), 2.35-2.25 (m, 1H), 1.92-1.82 (m, 6H), 1.55-1.40 (m, 6H), 1.15 (br d, J=8.2 Hz, 2H), 1.11-1.04 (m, 2H). FXR EC$_{50}$ (nM)=460. MS (ESI) 579 (M+H).

Example 134

2-(4-((5-cyclopropyl-3-(2,6-dichlorophenyl)isoxazol-4-yl)methoxy)bicyclo[2.2.2]octan-1-yl)quinoline-6-carboxylic acid

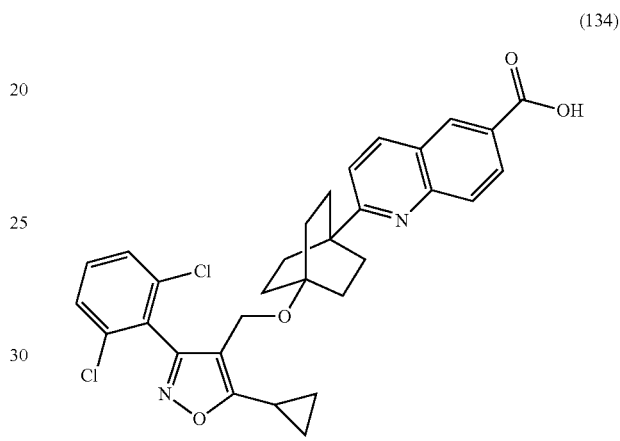
(134)

Step A. Intermediate 134A. Preparation of 4-iodobicyclo[2.2.2]octan-1-yl 3,5-difluorobenzoate

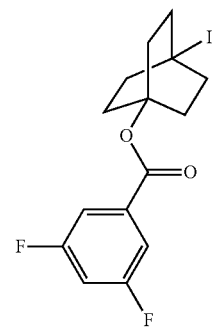 [SMILES: O=C(OC12CCC(I)(CC1)CC2)c1cc(F)cc(F)c1]

To a 100 mL pear shaped flask was added 4-((3,5-difluorobenzoyl)oxy) bicyclo[2.2.2]octane-1-carboxylic acid (200 mg, 0.65 mmol) (Shi, Y. et al. WO 2014/159802), chlorobenzene (26 mL), lead tetraacetate (370 mg, 0.84 mmol), followed by iodine (360 mg, 1.4 mmol). The reaction was stirred at 80° C. under N$_2$, and irradiated with blue LED (Kessil) for 2.5 h. The reaction was filtered and the combined filtrates were concentrated. The product was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (220 mg, 0.55 mmol, 85% yield) as a colorless oil. $^1$H NMR (400 MHz, CHLOROFORM-d) δ 7.54-7.40 (m, 2H), 7.08-6.88 (m, 1H), 2.69-2.50 (m, 6H), 2.34-2.19 (m, 6H).

Step B. Intermediate 134B. Preparation of methyl 2-(4-((3,5-difluorobenzoyl)oxy) bicyclo[2.2.2]octan-1-yl)quinoline-6-carboxylate

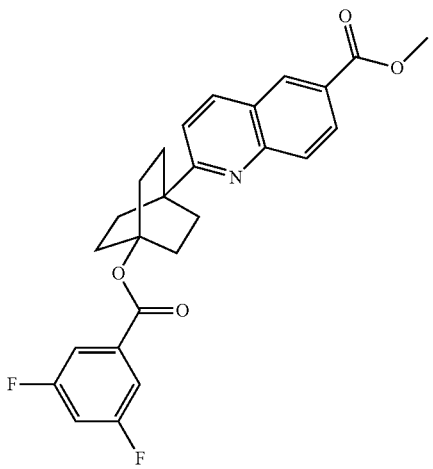 [SMILES: COC(=O)c1ccc2nc(C34CCC(OC(=O)c5cc(F)cc(F)c5)(CC3)CC4)ccc2c1]

To a sealed reaction vessel containing methyl quinoline-6-carboxylate (17 mg, 0.89 mmol) in ethanol (1.2 mL) was added TFA (69 µL, 0.89 mmol) at 0° C. The ice bath was removed, Intermediate 134A (140 mg, 0.36 mmol) and tris(trimethylsilyl)silane (240 µL, 0.79 mmol) were added. The reaction was stirred at 90° C. until the mixture became homogenous, after which time AIBN (70 mg, 0.43 mmol) was added. The reaction vessel was sealed and stirred at 90° C. for 16 h. The reaction was cooled, poured into 1 M K$_2$HPO$_4$ (aq.) solution and extracted with EtOAc. The organic phase was washed with brine, dried over sodium sulfate and concentrated. The product was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (65 mg, 0.14 mmol, 40% yield) as a white solid. $^1$H NMR (400 MHz, CHLOROFORM-d) δ 8.60-8.49 (m, 1H), 8.26 (dd, J=8.8, 2.0 Hz, 1H), 8.20-8.13 (m, 1H), 8.06 (d, J=8.8 Hz, 1H), 7.56-7.42 (m, 3H), 7.06-6.89 (m, 1H), 4.02-3.96 (m, 3H), 2.40-2.18 (m, 12H). MS (ESI) 452 (M+H).

Step C. Intermediate 134C. Preparation of methyl 2-(4-hydroxybicyclo[2.2.2]octan-1-yl)quinoline-6-carboxylate

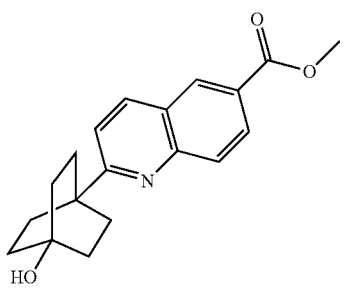 [SMILES: COC(=O)c1ccc2nc(C34CCC(O)(CC3)CC4)ccc2c1]

To a vial containing Intermediate 134B (80 mg, 0.18 mmol), THF (2 mL), and MeOH (2 mL) was added sodium methoxide (66 µL, 0.35 mmol) (5.4 M in MeOH). The reaction was stirred at room temperature for 1 h, diluted with 5% citric acid (aq.) (10 mL), and extracted with EtOAc (2×25 mL). The organic layers were combined, washed with brine, dried over sodium sulfate, filtered and concentrated. The product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to afford the title compound (19 mg, 0.061 mmol, 34% yield) as a white solid. $^1$H NMR (400 MHz, CHLOROFORM-d) δ 8.53 (d, J=2.0 Hz, 1H), 8.25 (dd, 2.0 Hz, 1H), 8.15 (d, J=8.6 Hz, 1H), 8.05 (d, J=8.8 Hz, 1H), 7.65-7.47 (m, 1H), 4.03-3.80 (m, 3H), 2.30-2.09 (m, 6H), 1.87-1.79 (m, 6H). MS (ESI) 312 (M+H).

Step D. Intermediate 134D. Preparation of methyl 2-(4-((5-cyclopropyl-3-(2,6-dichlorophenyl)isoxazol-4-yl)methoxy)bicyclo[2.2.2]octan-1-yl)quinoline-6-carboxylate

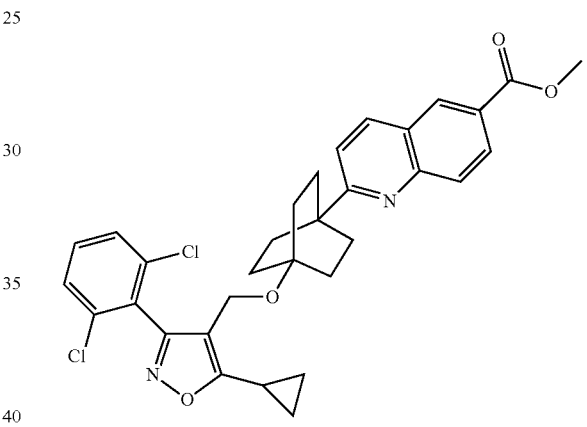

To a flask were added Intermediate 134C (19 mg, 0.061 mmol), silver trifluoromethanesulfonate (94 mg, 0.37 mmol), and 2,6-di-tert-butylpyridine (81 µL, 0.37 mmol) and DCM (1.2 mL). The mixture was cooled to 0° C., 4-(bromomethyl)-5-cyclopropyl-3-(2,6-dichlorophenyl)isoxazole (32 mg, 0.092 mmol) was added and the reaction was allowed to slowly reach room temperature and stirred for 7 h. The mixture was filtered and concentrated. The product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to afford the title compound (11 mg, 0.019 mmol, 31% yield) as a colorless oil. $^1$H NMR (400 MHz, CHLOROFORM-d) δ 8.54-8.46 (m, 1H), 8.24 (dd, J=8.9, 1.9 Hz, 1H), 8.13 (d, J=8.8 Hz, 1H), 8.02 (d, J=8.8 Hz, 1H), 7.47-7.39 (m, 2H), 7.38-7.28 (m, 2H), 4.29-4.19 (m, 2H), 3.98 (s, 3H), 2.21-2.12 (m, 1H), 2.10-1.98 (m, 6H), 1.68-1.58 (m, 6H), 1.30-1.22 (m, 2H), 1.15-1.05 (m, 2H). MS (ESI) 577 (M+H).

Step E. Example 134

The title compound was prepared according to methods described for the synthesis of Example 1 (Step D), starting from Intermediate 134D: (3.3 mg, 0.0060 mmol, 30% yield). $^1$H NMR (500 MHz, DMSO-d$_6$) δ 8.54 (s, 1H), 8.39 (d, J=8.9 Hz, 1H), 8.16 (br d, J=8.9 Hz, 1H), 7.94 (d, J=8.9 Hz, 1H), 7.67-7.56 (m, 4H), 4.20 (s, 2H), 2.31 (br t, J=4.9 Hz, 1H), 2.07-1.91 (m, 6H), 1.56-1.43 (m, 6H), 1.23-1.12 (m, 2H), 1.08 (br d, J=2.7 Hz, 2H). FXR EC$_{50}$ (nM)=83. MS (ESI) 563 (M+H).

Example 135

6-(4-((5-cyclopropyl-3-(2,6-dichlorophenyl)isox-azol-4-yl)methoxy)bicyclo[2.2.2]octan-1-yl)-1-methyl-1H-pyrrolo[2,3-b]pyridine-3-carboxylic acid (135)

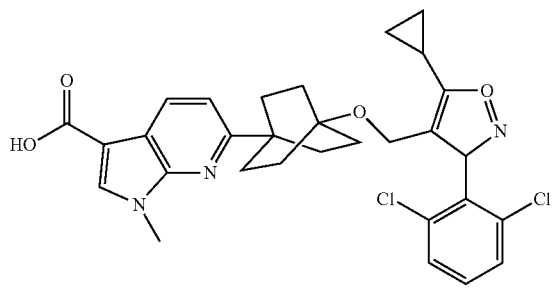

Step A. Intermediate 135A. Preparation of 5-cyclopropyl-3-(2,6-dichlorophenyl)-4-(((4-iodobicyclo[2.2.2]octan-1-yl)oxy)methyl)isoxazole

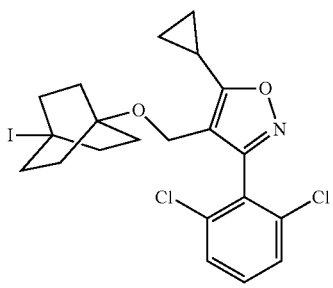 [SMILES: Clc1cccc(Cl)c1-c1noc(C2CC2)c1COC12CCC(I)(CC1)CC2]

To a vial was added Intermediate 16B (0.11 g, 0.25 mmol), chlorobenzene (3 mL), lead tetraacetate (0.15 g, 0.33 mmol), followed by iodine (0.14 g, 0.56 mmol). The reaction was stirred at 80° C. under nitrogen, and irradiated with blue LED (Kessil) for 2 h. The reaction was cooled, filtered, and the filter cake was washed with DCM. The organic layer was washed with sodium thiosulfate, brine, dried over sodium sulfate and concentrated. The product was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (100 mg, 0.20 mmol, 77% yield) as a white solid. $^1$H NMR (400 MHz, CHLOROFORM-d) δ 7.54-7.13 (m, 3H), 2.55-2.34 (m, 6H), 2.13-1.90 (m, 1H), 1.66-1.44 (m, 6H), 1.28-1.17 (m, 2H), 1.11-0.98 (m, 2H). MS (ESI) 518 (M+H).

Step B. Intermediate 135B. Preparation of methyl 6-(4-((5-cyclopropyl-3-(2,6-dichlorophenyl)isox-azol-4-yl)methoxy)bicyclo[2.2.2]octan-1-yl)-1-methyl-1H-pyrrolo[2,3-b]pyridine-3-carboxylate

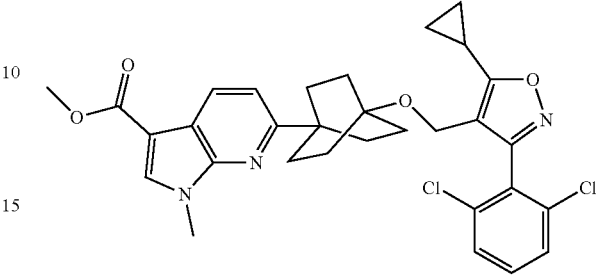

To a sealed reaction vessel containing methyl 1-methyl-1H-pyrrolo[2,3-b]pyridine-3-carboxylate (37 mg, 0.19 mmol) in ethanol (0.4 mL) was added TFA (15 μL, 0.19 mmol) at 0° C. The ice bath was removed, and Intermediate 135A (40 mg, 0.077 mmol) and tris(trimethylsilyl)silane (52 μL, 0.17 mmol) were added. The mixture was stirred at 90° C. until homogenous, after which time AIBN (15 mg, 0.093 mmol) was added. The reaction was stirred at 90° C. for 15 h. The reaction was cooled, poured into 1 M K$_2$HPO$_4$ (aq.), extracted with EtOAc, and the organic phase was washed with brine, dried over sodium sulfate and concentrated. The product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to afford the title compound (4.0 mg, 6.9 μma 9% yield). MS (ESI) 580 (M+H).

Step C. Example 135

The title compound was prepared according to methods described for the synthesis of Example 1 (Step D), starting from Intermediate 135B: (1.7 mg, 0.0030 mmol, 42% yield). $^1$H NMR (500 MHz, DMSO-d$_6$) δ 8.34-8.12 (m, 1H), 7.76-7.62 (m, 1H), 7.39-7.16 (m, 2H), 7.13 (br s, 1H), 7.03 (br s, 1H), 4.20 (s, 2H), 3.81 (s, 3H), 2.32 (br s, 1H), 2.01-1.79 (m, 6H), 1.59-1.37 (m, 6H), 1.21-1.12 (m, 2H), 1.09 (br d, J=2.9 Hz, 2H). FXR EC$_{50}$ (nM)=9. MS (ESI) 566 (M+H).

Example 139

2-(4-((5-cyclopropyl-3-(2,6-dichlorophenyl)isox-azol-4-yl)methoxy)bicyclo[2.2.2]octane-1-carbonyl)-1,2,3,4-tetrahydroisoquinoline-5-carboxylic acid

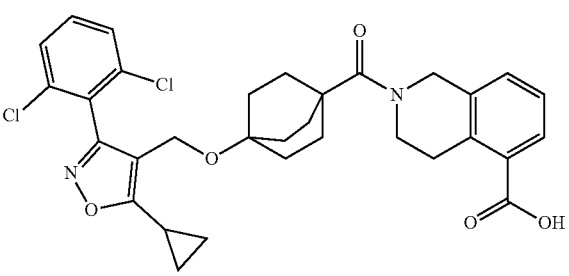 [SMILES: O=C(O)c1cccc2c1CCN(C(=O)C13CCC(OCc4c(-c5c(Cl)cccc5Cl)noc4C4CC4)(CC1)CC3)C2]

Step A. Intermediate 139A. Preparation of ethyl 2-(4-((5-cyclopropyl-3-(2,6-dichlorophenyl)isoxazol-4-yl)methoxy)bicyclo[2.2.2]octane-1-carbonyl)-1,2,3,4-tetrahydroisoquinoline-5-carboxylate

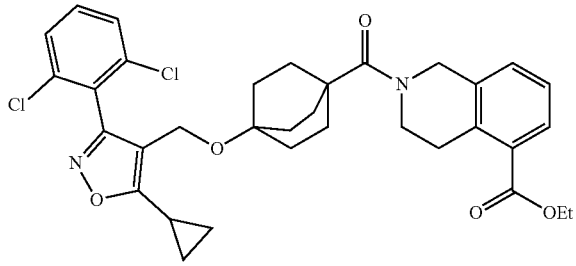 [SMILES: CCOC(=O)c1cccc2c1CCN(C(=O)C13CCC(OCc4c(-c5c(Cl)cccc5Cl)noc4C4CC4)(CC1)CC3)C2]

To a solution of Intermediate 16B (0.020 g, 0.050 mmol) in DMF (0.23 mL) was added HATU (0.020 g, 0.060 mmol). After stirring 5 min, ethyl 1,2,3,4-tetrahydroisoquinoline-5-carboxylate (0.010 g, 0.060 mmol) and Hunig's Base (0.02 mL, 0.12 mmol) were added and the reaction mixture was stirred at rt. After 18 h, the mixture was diluted with EtOAc, and the organic phase was washed with water and brine, dried (MgSO$_4$) and concentrated. The crude product was purified by flash column chromatography (4 g silica cartridge; A=Hex, B=EtOAc; 15 min grad.; 0% B to 100% B; flow rate=18 mL/min). The pure fractions were combined, concentrated and dried in vacuo to afford the title compound (22 mg, 0.040 mmol, 77% yield). MS (ESI) 624 (M+H). $^1$H NMR (500 MHz, CHLOROFORM-d) δ 7.84 (br d, J=6.1 Hz, 1H), 7.44 (br d, J=7.7 Hz, 2H), 7.40-7.33 (m, 1H), 7.32-7.25 (m, 2H), 4.74 (br s, 2H), 4.37 (q, J=6.9 Hz, 2H), 4.20 (s, 2H), 3.81 (br s, 2H), 3.25 (br s, 2H), 2.14 (br d, J=4.4 Hz, 1H), 1.97 (br s, 6H), 1.90-1.82 (m, 1H), 1.41 (br t, J=6.9 Hz, 4H), 1.34-1.21 (m, 5H), 1.12 (br d, J=6.1 Hz, 3H).

Step D. Example 139

To a solution of Intermediate 139A (0.020 g, 0.040 mmol) in THF (0.39 mL), MeOH (0.20 mL) and water (0.20 mL) was added lithium hydroxide monohydrate (0.012 g, 0.28 mmol). The reaction was stirred at room temperature for 18 h, after which time the solvent was concentrated. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 40-80% B over 20 minutes, then a 3-minute hold at 100% B; Flow: 20 mL/min.). Fractions containing the desired product were combined, concentrated and dried in vacuo to afford the title compound (0.017 g, 0.029 mmol, 88% yield). $^1$H NMR (500 MHz, DMSO-d$_6$) δ 7.68-7.63 (m, 1H), 7.60-7.55 (m, 2H), 7.54-7.49 (m, 1H), 7.35 (br d, J=7.3 Hz, 1H), 7.23 (t, J=7.6 Hz, 1H), 4.61 (br s, 2H), 4.07 (s, 2H), 3.68 (br s, 1H), 3.01 (br s, 2H), 2.28-2.19 (m, 1H), 1.81-1.72 (m, 6H), 1.39-1.30 (m, 6H), 1.14-1.06 (m, 2H), 1.02 (br d, J=2.7 Hz, 2H), 0.95 (d, J=6.1 Hz, 1H). FXR EC$_{50}$ (nM)=1400. MS (ESI) 596 (M+H).

The following Examples in Table 3 were prepared according to methods described elsewhere herein using appropriate starting materials, reagents and conditions.

TABLE 3

| Ex. No. | Structure & Name | $^1$H NMR, FXR EC$_{50}$ & MS (ESI) | Method |
|---|---|---|---|
| 123 | 2-((4-((5-cyclopropyl-3-(2,6-dichlorophenyl)isoxazol-4-yl)methoxy)bicyclo[2.2.2]octan-1-yl)(hydroxy)methyl)-4-fluorobenzo[d]thiazole-6-carboxamide | FXR EC$_{50}$ (nM) = 280. MS (ESI) 616 (M + H). | Ex. 122 |

TABLE 3-continued

| Ex. No. | Structure & Name | ¹H NMR, FXR EC$_{50}$ & MS (ESI) | Method |
|---|---|---|---|
| 124 | 2-((4-((5-cyclopropyl-3-(2,6-dichlorophenyl)isoxazol-4-yl)methoxy)bicyclo[2.2.2]octan-1-yl)(hydroxy)methyl)benzo[d]thiazole-6-carboxylic acid | ¹H NMR (500 MHz, DMSO-d$_6$) δ 8.68 (s, 1H), 8.06-7.98 (m, 2H), 7.63-7.58 (m, 2H), 7.57-7.51 (m, 1H), 4.50 (s, 1H), 4.11 (s, 2H), 2.31-2.22 (m, 1H), 1.65-1.45 (m, 6H), 1.30 (br t, J = 7.8 Hz, 6H), 1.16-1.09 (m, 2H), 1.06 (br d, J = 2.7 Hz, 2H). FXR EC$_{50}$ (nM) = 490. MS (ESI) 590 (M + H). | Ex. 121 |
| 125 | 4-((4-((5-cyclopropyl-3-(2,6-dichlorophenyl)isoxazol-4-yl)methoxy)bicyclo[2.2.2]octan-1-yl)(hydroxy)methyl)-3-fluorobenzoic acid | ¹H NMR (500 MHz, DMSO-d$_6$) δ 7.74 (d, J = 7.9 Hz, 1H), 7.60 (s, 1H), 7.59 (s, 1H), 7.58-7.52 (m, 2H), 7.49 (t, J = 7.5 Hz, 1H), 4.51 (s, 1H), 4.10 (s, 2H), 2.30-2.21 (m, 1H), 1.48 (br s, 3H), 1.39-1.18 (m, 9H), 1.15-1.09 (m, 2H), 1.05 (br d, J = 3.1 Hz, 2H). FXR EC$_{50}$ (nM) = 1600. MS (ESI) 560 (M + H). | Ex. 121 |
| 126 | 6-((4-((5-cyclopropyl-3-(2,6-dichlorophenyl)isoxazol-4-yl)methoxy)bicyclo[2.2.2]octan-1-yl)(hydroxy)methyl)-2-naphthoic acid | 1H NMR (500 MHz, DMSO-d$_6$) δ 8.54 (s, 1H), 8.02-7.91 (m, 3H), 7.74 (s, 1H), 7.61-7.55 (m, 2H), 7.55-7.48 (m, 1H), 7.45 (br d, J = 8.5 Hz, 1H), 4.32 (s, 1H), 4.08 (s, 2H), 2.29-2.19 (m, 1H), 1.92 (s, 1H), 1.59-1.45 (m, 3H), 1.35 (br d, J = 6.7 Hz, 3H), 1.28-1.18 (m, 6H), 1.15-1.08 (m, 2H), 1.06-0.98 (m, 2H). FXR EC$_{50}$ (nM) = 600. MS (ESI) 592 (M + H) | Ex. 121 |

TABLE 3-continued

| Ex. No. | Structure & Name | $^1$H NMR, FXR EC$_{50}$ & MS (ESI) | Method |
|---|---|---|---|
| 128 | 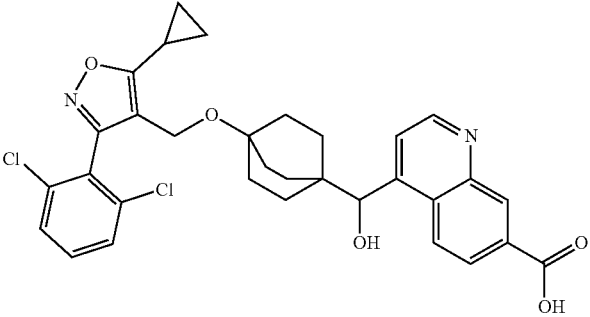 [SMILES: O=C(O)c1ccc2c(C(O)C34CCC(OCc5c(-c6c(Cl)cccc6Cl)noc5C5CC5)(CC3)CC4)ccnc2c1]<br>4-((4-((5-cyclopropyl-3-(2,6-dichlorophenyl)isoxazol-4-yl)methoxy)bicyclo[2.2.2]octan-1-yl)(hydroxy)methyl)quinoline-7-carboxylic acid | $^1$H NMR (500 MHz, DMSO-d$_6$) δ 9.03 (d, J = 4.6 Hz, 1H), 8.31 (d, J = 8.2 Hz, 1H), 8.28 (d, J = 7.0 Hz, 1H), 7.93 (t, J = 7.8 Hz, 1H), 7.64-7.59 (m, 1H), 7.57 (s, 1H), 7.56 (d, J = 4.3 Hz, 1H), 7.54-7.50 (m, 1H), 4.13 (s, 1H), 4.07 (s, 2H), 3.91 (s, 1H), 2.26-2.20 (m, 1H), 1.65-1.40 (m, 6H), 1.24 (br d, J = 7.3 Hz, 6H), 1.10 (dt, J = 8.2, 2.9 Hz, 2H), 1.04 (br d, J = 2.7 Hz, 2H). FXR EC$_{50}$ (nM) = 700. MS (ESI) 593 (M + H). | Ex. 121 |
| 129 | 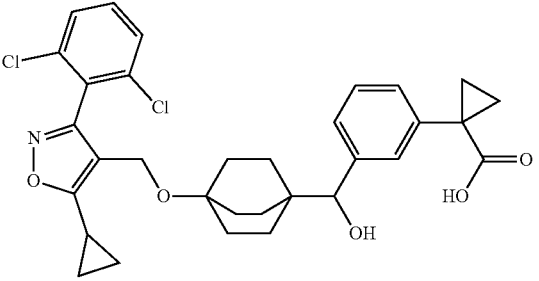 [SMILES: O=C(O)C1(c2cccc(C(O)C34CCC(OCc5c(-c6c(Cl)cccc6Cl)noc5C5CC5)(CC3)CC4)c2)CC1]<br>1-(3-((4-((5-cyclopropyl-3-(2,6-dichlorophenyl)isoxazol-4-yl)methoxy)bicyclo[2.2.2]octan-1-yl)(hydroxy)methyl)phenyl)cyclopropane-1-carboxylic acid | $^1$H NMR (500 MHz, DMSO-d$_6$) δ 7.62-7.58 (m, 2H), 7.57-7.50 (m, 1H), 7.22-7.12 (m, 2H), 7.10 (br s, 1H), 7.02 (br d, J = 6.4 Hz, 1H), 4.09 (s, 3H), 2.31-2.20 (m, 1H), 1.43 (br s, 5H), 1.29 (br d, J = 6.1 Hz, 3H), 1.23 (br d, J = 7.3 Hz, 6H), 1.15-1.09 (m, 2H), 1.09-1.00 (m, 4H). FXR EC$_{50}$ (nM) = 3000. MS (ESI) 582 (M + H). | Ex. 121 |
| 132 | 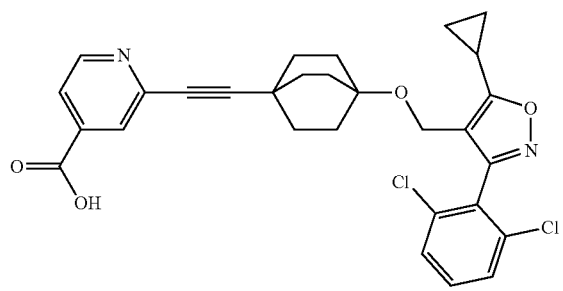 [SMILES: O=C(O)c1ccnc(C#CC23CCC(OCc4c(-c5c(Cl)cccc5Cl)noc4C4CC4)(CC2)CC3)c1]<br>2-((4-((5-cyclopropyl-3-(2,6-dichlorophenyl)isoxazol-4-yl)methoxy)bicyclo[2.2.2]octan-1-yl)ethynyl)isonicotinic acid | $^1$H NMR (500 MHz, DMSO-d$_6$) δ 8.67 (d, J = 5.0 Hz, 1H), 7.72 (d, J = 5.0 Hz, 1H), 7.70 (s, 1H), 7.64 (s, 1H), 7.63 (s, 1H), 7.60-7.54 (m, 1H), 4.13 (s, 2H), 2.33-2.25 (m, 1H), 1.90-1.76 (m, 6H), 1.48-1.36 (m, 6H), 1.14 (dt, J = 8.2, 2.9 Hz, 2H), 1.10-1.03 (m, 2H). FXR EC$_{50}$ (nM) = 3500. MS (ESI) 537 (M + H). | Ex. 130 |

TABLE 3-continued

| Ex. No. | Structure & Name | $^1$H NMR, FXR EC$_{50}$ & MS (ESI) | Method |
|---|---|---|---|
| 133 | 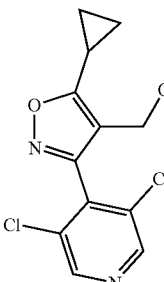<br>2-((4-((5-cyclopropyl-3-(3,5-dichloropyridin-4-yl)isoxazol-4-yl)methoxy)bicyclo[2.2.2]octan-1-yl)ethynyl)-4-fluorobenzo[d]thiazole-6-carboxylic acid | $^1$H NMR (500 MHz, DMSO-d$_6$) δ 8.79 (s, 2H), 8.53 (s, 1H), 7.79 (d, J = 11.1 Hz, 1H), 4.21 (s, 2H), 2.33-2.24 (m, 1H), 1.98-1.85 (m, 6H), 1.52-1.39 (m, 6H), 1.20-1.12 (m, 2H), 1.10-1.02 (m, 2H). FXR EC$_{50}$ (nM) = 180. MS (ESI) 537 (M + H) | Ex. 130 |
| 136 | 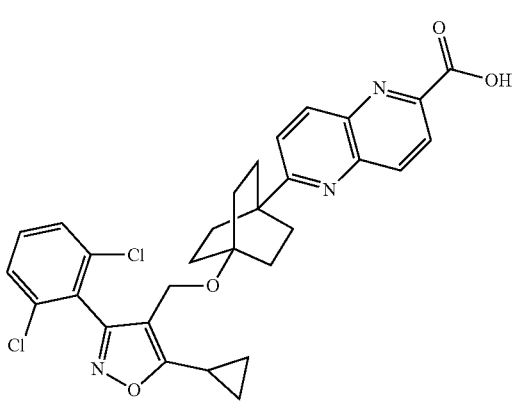 [SMILES: O=C(O)c1ccc2nc(C34CCC(OCc5c(-c6c(Cl)cccc6Cl)noc5C5CC5)(CC3)CC4)ccc2n1]<br>6-(4-((5-cyclopropyl-3-(2,6-dichlorophenyl)isoxazol-4-yl)methoxy)bicyclo[2.2.2]octan-1-yl)-1,5-naphthyridine-2-carboxylic acid | $^1$H NMR (600 MHz, DMSO-d$_6$) δ 8.39 (d, J = 8.9 Hz, 1H), 8.33 (d, J = 8.7 Hz, 1H), 8.22 (d, J = 8.7 Hz, 1H), 7.84 (d, J = 9.1 Hz, 1H), 7.65 (d, J = 1.1 Hz, 1H), 7.64 (s, 1H), 7.61-7.55 (m, 1H), 4.20 (s, 2H), 2.32 (tt, J = 8.4, 5.1 Hz, 1H), 2.02-1.96 (m, 6H), 1.54-1.46 (m, 6H), 1.14 (dt, J = 8.3, 3.1 Hz, 2H), 1.10-1.07 (m, 2H). FXR EC$_{50}$ (nM) = 36. MS (ESI) 564 (M + H). | Ex. 135 |
| 137 | 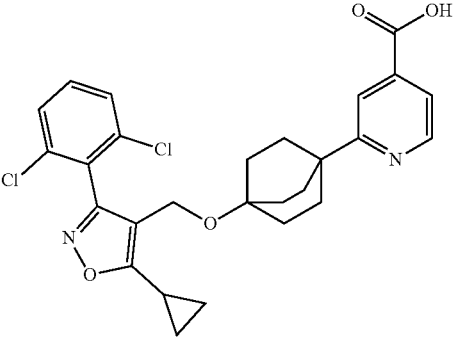 [SMILES: O=C(O)c1ccnc(C23CCC(OCc4c(-c5c(Cl)cccc5Cl)noc4C4CC4)(CC2)CC3)c1]<br>2-(4-((5-cyclopropyl-3-(2,6-dichlorophenyl)isoxazol-4-yl)methoxy)bicyclo[2.2.2]octan-1-yl)isonicotinic acid | $^1$H NMR (500 MHz, DMSO-d$_6$) δ 8.57 (br s, 1H), 7.68-7.61 (m, 3H), 7.61-7.50 (m, 2H), 4.18 (s, 2H), 2.44-2.27 (m, 1H), 1.91-1.83 (m, 6H), 1.53-1.41 (m, 6H), 1.15 (br d, J = 8.2 Hz, 2H), 1.09 (br d, J = 2.7 Hz, 2H) FXR EC$_{50}$ (nM) = 420. MS (ESI) 513 (M + H). | Ex. 135 |

TABLE 3-continued

| Ex. No. | Structure & Name | ¹H NMR, FXR EC$_{50}$ & MS (ESI) | Method |
|---|---|---|---|
| 138 | 6-(4-((5-cyclopropyl-3-(2,6-dichlorophenyl)isoxazol-4-yl)methoxy)bicyclo[2.2.2]octan-1-yl)nicotinic acid | ¹H NMR (500 MHz, DMSO-d$_6$) δ 8.94 (s, 1H), 8.14 (br d, J = 8.2 Hz, 1H), 7.70-7.53 (m, 3H), 7.42 (d, J = 8.2 Hz, 1H), 4.18 (s, 2H), 2.37-2.22 (m, 1H), 1.93-1.81 (m, 6H), 1.52-1.41 (m, 6H), 1.15 (br d, J = 8.2 Hz, 2H), 1.08 (br d, J = 2.7 Hz, 2H) FXR EC$_{50}$ (nM) = 440. MS (ESI) 513 (M + H). | Ex. 135 |
| 140 | 2-(4-((5-cyclopropyl-3-(2,6-dichlorophenyl)isoxazol-4-yl)methoxy)bicyclo[2.2.2]octane-1-carbonyl)-1,2,3,4-tetrahydroisoquinoline-6-carboxylic acid | ¹H NMR (500 MHz, DMSO-d$_6$) δ 7.67 (br d, J = 3.4 Hz, 2H), 7.60-7.54 (m, 2H), 7.54-7.49 (m, 1H), 7.27 (br d, J = 8.2 Hz, 1H), 4.64 (br s, 2H), 4.07 (s, 2H), 3.71 (br s, 2H), 2.77 (br s, 2H), 2.28-2.17 (m, 1H), 1.75 (br d, J = 7.0 Hz, 6H), 1.39-1.28 (m, 6H), 1.08 (br d, J = 8.2 Hz, 2H), 1.02 (br d, J = 3.1 Hz, 1H), 0.95 (d, J = 6.1 Hz, 1H) FXR EC$_{50}$ (nM) = 1700. MS (ESI) 596 (M + H). | Ex. 139 |
| 141 | 4-((4-((5-cyclopropyl-3-(2,6-dichlorophenyl)isoxazol-4-yl)methoxy)bicyclo[2.2.2]octane-1-carboxamido)methyl)benzoic acid | ¹H NMR (500 MHz, DMSO-d$_6$) δ 8.00 (br s, 1H), 7.85 (br d, J = 6.7 Hz, 2H), 7.65-7.59 (m, 2H), 7.58-7.51 (m, 1H), 7.26 (br d, J = 6.4 Hz, 2H), 4.25 (br s, 2H), 4.13 (s, 2H), 2.32-2.23 (m, 1H), 1.70 (br s, 6H), 1.35 (br d, J = 7.3 Hz, 6H), 1.15-1.09 (m, 2H), 1.06 (br d, J = 2.4 Hz, 2H). FXR EC$_{50}$ (nM) = 2800. MS (ESI) 570 (M + H). | Ex. 139 |
| 142 | 2-((4-((5-cyclopropyl-3-(2,6-dichlorophenyl)isoxazol-4-yl)methoxy)bicyclo[2.2.2]octane-1-carboxamido)methyl)benzoic acid | ¹H NMR (500 MHz, DMSO-d$_6$) δ 7.90 (br s, 1H), 7.78-7.73 (m, 1H), 7.59-7.54 (m, 2H), 7.53-7.48 (m, 1H), 7.43-7.37 (m, 1H), 7.25 (br t, J = 7.5 Hz, 1H), 7.14 (br d, J = 7.6 Hz, 1H), 4.44 (br d, J = 5.5 Hz, 2H), 4.08 (s, 2H), 2.26-2.19 (m, 1H), 1.71-1.60 (m, 6H), 1.34-1.24 (m, 6H), 1.12-1.04 (m, 2H), 1.04-0.98 (m, 2H). FXR EC$_{50}$ (nM) = 1300. MS (ESI) 570 (M + H). | Ex. 139 |

TABLE 3-continued

| Ex. No. | Structure & Name | $^1$H NMR, FXR EC$_{50}$ & MS (ESI) | Method |
|---|---|---|---|
| 143 | 3-((4-((5-cyclopropyl-3-(2,6-dichlorophenyl)isoxazol-4-yl)methoxy)bicyclo[2.2.2]octane-1-carboxamido)methyl)benzoic acid | $^1$H NMR (500 MHz, DMSO-d$_6$) δ 8.01-7.95 (m, 1H), 7.75-7.67 (m, 2H), 7.58-7.53 (m, 2H), 7.53-7.47 (m, 1H), 7.39-7.32 (m, 2H), 4.19 (br d, J = 5.8 Hz, 2H), 4.07 (s, 2H), 2.26-2.17 (m, 1H), 1.69-1.59 (m, 6H), 1.33-1.24 (m, 6H), 1.12-1.04 (m, 2H), 1.03-0.97 (m, 2H). FXR EC$_{50}$ (nM) = 1300. MS (ESI) 570 (M + H). | Ex. 139 |
| 144 | 2-((4-((5-cyclopropyl-3-(2,6-dichlorophenyl)isoxazol-4-yl)methoxy)-N-methylbicyclo[2.2.2]octane-1-carboxamido)methyl)benzoic acid | $^1$H NMR (500 MHz, DMSO-d$_6$) δ 7.83 (br d, J = 7.6 Hz, 1H), 7.59-7.54 (m, 2H), 7.53-7.45 (m, 2H), 7.30 (br t, J = 7.5 Hz, 1H), 6.93 (br d, J = 7.6 Hz, 1H), 4.79 (br s, 2H), 4.07 (s, 2H), 2.95-2.83 (m, 3H), 2.22 (br s, 1H), 1.79 (br s, 6H), 1.32 (br s, 6H), 1.11-1.05 (m, 2H), 1.01 (br d, J = 3.1 Hz, 2H). FXR EC$_{50}$ (nM) = 160. MS (ESI) 584 (M + H). | Ex. 139 |
| 145 | 2-(1-(4-((5-cyclopropyl-3-(2,6-dichlorophenyl)isoxazol-4-yl)methoxy)bicyclo[2.2.2]octane-1-carbonyl)piperidin-4-yl)acetic acid | $^1$H NMR (500 MHz, DMSO-d$_6$) δ 7.60-7.54 (m, 2H), 7.54-7.49 (m, 1H), 4.15 (br d, J = 13.1 Hz, 2H), 4.06 (s, 2H), 2.72-2.58 (m, 2H), 2.29-2.18 (m, 1H), 2.08 (br d, J = 6.9 Hz, 2H), 1.88-1.76 (m, 1H), 1.75-1.64 (m, 6H), 1.59 (br d, J = 11.7 Hz, 2H), 1.37-1.24 (m, 6H), 1.08 (br d, J = 8.2 Hz, 2H), 1.01 (br d, J = 2.7 Hz, 2H), 0.96-0.83 (m, 2H). FXR EC$_{50}$ (nM) = 3800. MS (ESI) 562 (M + H). | Ex. 139 |
| 146 | 2-(4-((5-cyclopropyl-3-(2,6-dichlorophenyl)isoxazol-4-yl)methoxy)bicyclo[2.2.2]octane-1-carbonyl)-1,2,3,4-tetrahydroisoquinoline-8-carboxylic acid | $^1$H NMR (500 MHz, DMSO-d$_6$) δ 7.77 (s, 1H), 7.67 (br d, J = 8.5 Hz, 1H), 7.60-7.55 (m, 2H), 7.54-7.48 (m, 1H), 7.21 (br d, J = 7.9 Hz, 1H), 4.66 (br s, 2H), 4.07 (s, 2H), 3.74-3.62 (m, 2H), 2.76 (br s, 2H), 2.30-2.17 (m, 1H), 1.82-1.70 (m, 6H), 1.41-1.30 (m, 6H), 1.13-1.05 (m, 2H), 1.05-0.99 (m, 2H). FXR EC$_{50}$ (nM) = 3100. MS (ESI) 596 (M + H). | Ex. 139 |

Example 151

3-(5-(4-(((5-cyclopropyl-3-(2,6-dichlorophenyl)isoxazol-4-yl)methoxy)methyl)bicyclo[2.2.2]octan-1-yl)-1,2,4-oxadiazol-3-yl)benzoic acid

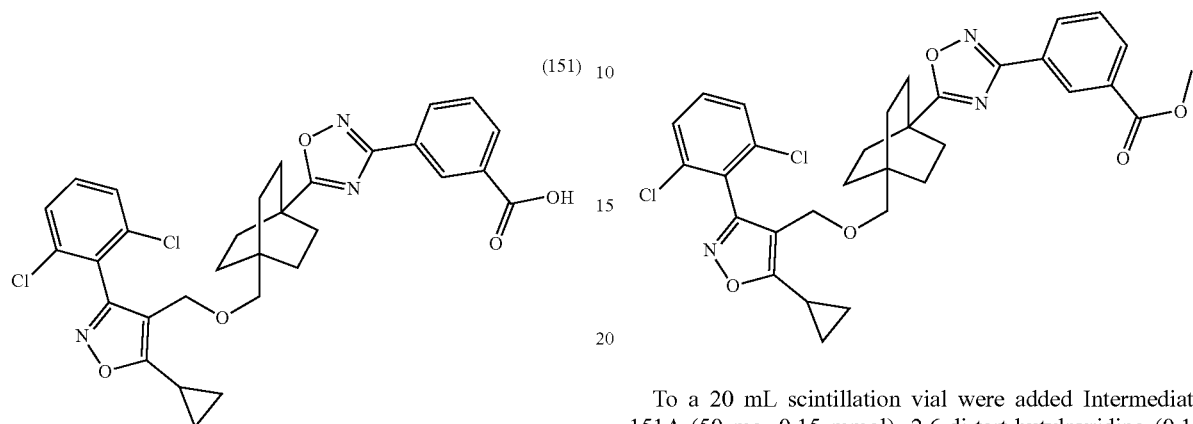

Step A. Intermediate 151A. Preparation of methyl 4-(5-(4-hydroxymethyl)bicyclo[2.2.2] octan-1-yl)-1,2,4-oxadiazol-3-yl)benzoate

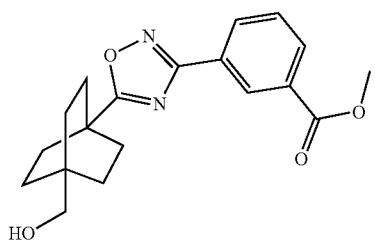 [SMILES: COC(=O)c1cccc(-c2noc(C34CCC(CO)(CC3)CC4)n2)c1]

To a 25 mL pear shaped flask were added 4-(hydroxymethyl)bicyclo[2.2.2]octane-1-carboxylic acid (160 mg, 0.85 mmol) (Kiesman W. F. et. al. WO 2001/034610) and BOP (38 mg, 0.85 mmol) in DMF (1 mL) followed by methyl (Z)-3-(N'-hydroxycarbamimidoyl)benzoate (Tung, R. D. WO 2016/073545) (150 mg, 0.77 mmol). To this mixture was added Et₃N (0.32 mL, 2.3 mmol) at 0° C. The reaction mixture was stirred for 2 h at rt, and 4 h at 100° C. The reaction was cooled, the solvent was concentrated and the residue was dissolved in EtOAc (50 mL). The organic phase was washed with brine, dried over Na₂SO₄, filtered and concentrated. The crude product was purified by flash column chromatography (24 g silica gel column; A=Hex, B=EtOAc; 15 min grad.; 0-30% B; flow rate=24 mL/min). The pure fractions were combined, concentrated and dried in vacuo to afford the title compound (120 mg, 45% yield) as a pale yellow solid. $^1$H NMR (400 MHz, DMSO-d₆) δ=8.54 (t, J=1.5 Hz, 1H), 8.26 (dt, J=7.8, 1.5 Hz, 1H), 8.16 (dt, J=7.9, 1.6 Hz, 1H), 7.74 (t, J=7.7 Hz, 1H), 5.76 (s, 1H), 4.46 (t, J=5.5 Hz, 1H), 3.99-3.85 (m, 3H), 3.11 (d, J=5.4 Hz, 2H), 1.99 (d, J=7.8 Hz, 6H), 1.55-1.39 (m, 6H). MS (ESI) 343 (M+H).

Step B. Intermediate 151B. Preparation of methyl 3-(5-(4-(((5-cyclopropyl-3-(2,6-dichloro phenyl)isoxazol-4-yl)methoxy)methyl)bicyclo[2.2.2]octan-1-yl)-1,2,4-oxadiazol-3-yl) benzoate

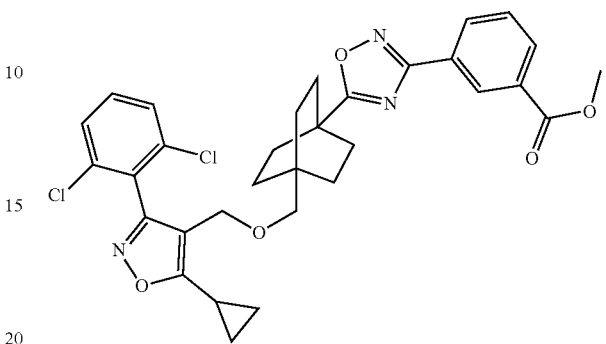

To a 20 mL scintillation vial were added Intermediate 151A (50 mg, 0.15 mmol), 2,6-di-tert-butylpyridine (0.12 mL, 0.51 mmol), dry DCM (1 mL) followed by silver trifluoromethanesulfonate (110 mg, 0.44 mmol). A solution of 4-(bromomethyl)-5-cyclopropyl-3-(2,6-dichlorophenyl) isoxazole (150 mg, 0.44 mmol) in DCM (1 mL) was added dropwise at 0° C. The reaction was stirred at rt for 12 h, and diluted with DCM:MeOH (1:1; 4 mL). The solids were filtered and the filtrate was concentrated. The residue was filtered through a plug of SiO₂, eluting with hexanes first, and then EtOAc to collect crude product. The filtrate was concentrated and the crude material was purified by preparative HPLC (Waters XBridge C18, 19×150 mm, 5-μm particles; Mobile Phase A: 10-mM ammonium acetate; Mobile Phase B: acetonitrile; Gradient: 45-95% B over 25 minutes, then a 5-minute hold at 100% B; Flow: 15 mL/min). Fractions containing the desired product were combined, concentrated and dried in vacuo afford the title compound (13 mg, 14% yield). $^1$H NMR (400 MHz, DMSO-d₆) δ 8.59-8.46 (m, 1H), 8.24 (dd, 1.3 Hz, 1H), 8.19-8.10 (m, 1H), 7.80-7.69 (m, 1H), 7.69-7.62 (m, 2H), 7.61-7.50 (m, 1H), 4.25 (s, 2H), 3.91 (s, 3H), 2.96 (s, 2H), 2.38-2.22 (m, 1H), 2.00-1.74 (m, 6H), 1.42-1.21 (m, 6H), 1.19-1.01 (m, 4H). MS (ESI) 608 (M+H).

Step C. Example 151

To a stirred solution of Intermediate 151B (23 mg, 0.038 mmol) in MeOH (1 mL), was added a solution of NaOH (7.6 mg, 0.19 mmol) in H₂O (0.5 mL) at 0° C. The reaction mixture was warmed to rt and stirred. After 18 h, the mixture was diluted with 5% citric acid (aq.) (20 mL) and extracted with EtOAc (2×25 mL). The organic phase was combined, washed with brine, dried over Na₂SO₄, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-55% B over 25 minutes, then a 5-minute hold at 100% B; Flow: 15 mL/min). Fractions containing the desired product were combined, concentrated and dried in vacuo to provide the title compound (0.0096 g, 42% yield). $^1$H NMR (400 MHz, DMSO-d₆) δ 8.58-8.48 (m, 1H), 8.19 (dt, J=7.7, 1.4 Hz, 1H), 8.12 (dt, J=7.8, 1.3 Hz, 1H), 7.76-7.62 (m, 3H), 7.62-7.50 (m, 1H), 4.26 (s, 2H), 2.97 (s, 2H), 2.34-2.26 (m, 1H), 1.97-1.79 (m, 6H), 1.42-1.25 (m, 6H), 1.20-1.02 (m, 4H). FXR EC$_{50}$ (nM)=150. MS (ESI) 594 (M+H).

Example 159

(E)-3-(5-(4-(2-(5-cyclopropyl-3-(2,6-dichlorophenyl)isoxazol-4-yl)vinyl) bicycle[2.2.2]octan-1-yl)-1,2,4-oxadiazol-3-yl)benzoic acid (159)

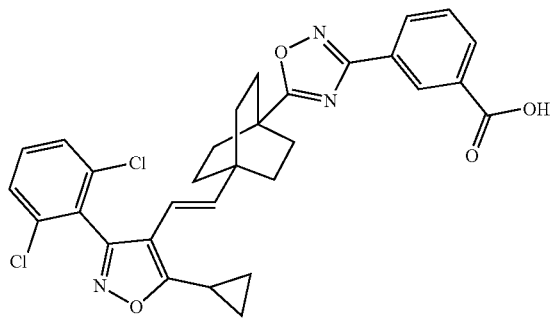

Step A. Intermediate 159A. Preparation of methyl 4-(hydroxymethyl)bicycle[2.2.2]octane-1-carboxylate

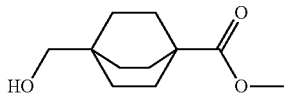

To a stirred solution of 4-(methoxycarbonyl)bicyclo[2.2.2]octane-1-carboxylic acid (1.5 g, 7.1 mmol) in THF (17 mL), was added borane dimethyl sulfide complex (2.0 mL, 21 mmol) at 0° C. The reaction was warmed to rt and stirred. After 4 h, the reaction mixture was quenched with MeOH (dropwise addition over 15 mins with cooling) and stirred at rt for 2 h. The solvent was concentrated and the crude product was purified by flash column chromatography (80 g silica gel cartridge; A=PE, B=EtOAc; 25 min grad.; 0% to 50% B; flow rate=60 mL/min; TLC visualized with KMnO$_4$). The pure fractions were combined, concentrated and dried in vacuo to afford the title compound (1.3 g, 6.6 mmol, 93% yield) as a white solid. $^1$H NMR (400 MHz, DMSO-d$_6$) δ 3.56 (s, 3H), 3.36 (s, 2H), 3.05 (s, 1H), 1.78-1.64 (m, 6H), 1.37-1.27 (m, 6H).

Step B. Intermediate 159B. Preparation of methyl 4-formylbicyclo[2.2.2]octane-1-carboxylate

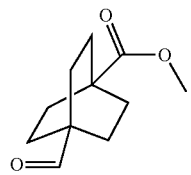

To a solution of Intermediate 159A (0.10 g, 0.50 mmol) in DCM (5 mL) was added DMP (0.28 g, 0.66 mmol) and the reaction was stirred at rt. After 3 h, the reaction was cooled to 0° C. and carefully quenched with a solution of sat. NaHCO$_3$ (aq.) (30 mL). The layers were separated, and the aqueous layer was extracted with CH$_2$Cl$_2$ (2×15 mL). The organic layers were combined, washed with brine, dried over Na$_2$SO$_4$, filtered and concentrated. The crude product was purified by flash column chromatography (12 g silica gel cartridge, A=PE, B=EtOAc; 15 min grad.; 20% to 100% B; flow rate=12 mL/min; TLC visualized with KMnO$_4$). The pure fractions were combined, concentrated and dried in vacuo to afford the title compound (0.070 g, 0.34 mmol, 67% yield) as colorless oil. $^1$H NMR (400 MHz, CHLOROFORM-d) δ 9.4 (s, 1H), 3.66 (s, 3H), 1.86-1.82 (m, 7H), 1.69-1.66 (m, 5H).

Step C. Intermediate 159C. Preparation of 5-cyclopropyl-3-(2,6-dichlorophenyl)isoxazol-4-yl)methyl)triphenylphosphonium bromide

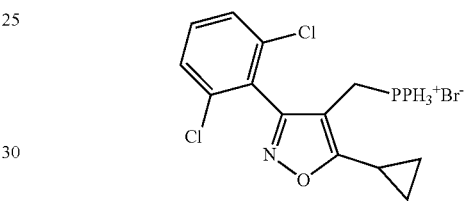

To a solution of 4-(bromomethyl)-5-cyclopropyl-3-(2,6-dichlorophenyl)isoxazole (1.5 g, 4.3 mmol) in toluene (20 mL) was added triphenylphosphine (2.3 g, 8.6 mmol) and the resulting mixture was stirred at 120° C. After 24 h, the reaction was cooled, the mixture was filtered and solid product was washed with toluene to afford the title compound (2.2 g, 3.5 mmol, 80% yield) as a white solid. $^1$H NMR (400 MHz, DMSO-d$_6$) δ 7.88-7.80 (m, 3H), 7.65-7.41 (m, 15H), 4.93 (d, J=14H, 2H), 1.76-1.66 (m, 1H), 0.73-0.56 (m, 4H). MS (ESI) 528 (M+H).

Step D. Intermediate 159D. Preparation of methyl 4-(2-(5-cyclopropyl-3-(2,6-dichlorophenyl)isoxazol-4-yl)vinyl)bicyclo[2.2.2]octane-1-carboxylate

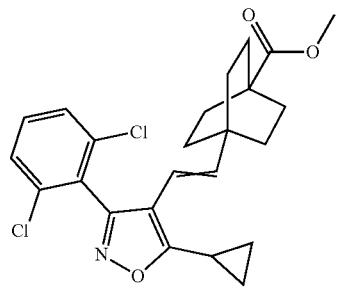 [SMILES: COC(=O)C12CCC(C=Cc3c(-c4c(Cl)cccc4Cl)noc3C3CC3)(CC1)CC2]

To a suspension of Intermediate 159C (0.26 g, 0.43 mmol) (fresh azeotrope with toluene) in THF (5 mL) at −78° C. was added lithium bis(trimethylsilyl)amide (0.57 mL, 0.57 mmol) (1 M solution in THF). The color of the reaction mixture turned yellow upon addition of base. The resulting mixture was stirred at −78° C. for 15 min, and at rt for 30 min, upon which the color changed to dark brown. To the above mixture was added dropwise Intermediate 159B (0.070 g, 0.36 mmol) in THF (2 mL) upon which the color changed back to yellow. The reaction mixture was stirred at 60° C. After 6 h, the reaction was cooled, quenched with sat. NH$_4$C$_1$ (aq.) (40 mL) and extracted with EtOAc (2×20 mL). The organic phase was combined, washed with brine, dried over Na$_2$SO$_4$, filtered and concentrated. The crude residue was purified by flash column chromatography (12 g silica gel cartridge, A=PE, B=EtOAc; 15 min grad.; 0% to 40% B; flow rate=12 mL/min). The pure fractions were combined, concentrated and dried in vacuo to afford the title compound (0.045 g, 0.072 mmol, 20% yield) as a colorless residue. $^1$H NMR (400 MHz, CHLOROFORM-d) δ 7.42-7.34 (m, 3H), 5.82 (d, J=16.2 Hz, 1H), 5.33 (d, J=16.2 Hz, 1H), 3.65 (s, 3H), 1.78-1.66 (m, 7H), 1.42-1.31 (m, 6H), 1.22-1.12 (m, 4H). MS (ESI) 447 (M+H). The product was obtained as a 3:1 mixture of trans/cis isomers which could not be separated by flash column chromatography. The ratio was determined by $^1$H NMR based on integration of characteristic protons.

Step E. Intermediate 159E. Preparation of 4-(2-(5-cyclopropyl-3-(2,6-dichlorophenyl) isoxazol-4-yl) vinyl)bicyclo[2.2.2]octane-1-carboxylic acid

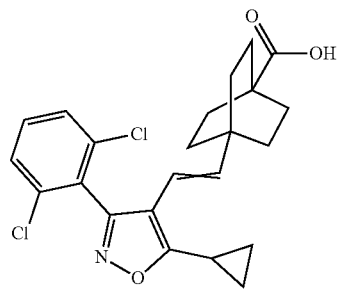 [SMILES: O=C(O)C12CCC(C=Cc3c(-c4c(Cl)cccc4Cl)noc3C3CC3)(CC1)CC2]

Intermediate 159D (40 mg, 0.090 mmol) was dissolved in MeOH (1 mL). To this solution was added sodium hydroxide (9.0 mg, 0.22 mmol) dissolved in water (0.2 mL). The reaction was stirred at 75° C. After 6 h, the reaction was cooled, diluted with water (10 mL), and acidified with 1.5 M HCl to pH ~3. The aqueous phase was extracted with EtOAc (2×10 mL), the organic phase was combined, dried over Na$_2$SO$_4$, filtered and concentrated. The product was dried in vacuo to afford the title compound (35 mg, 0.063 mmol, 70% yield) which was used in subsequent steps without further purification or characterization. MS (ESI) 432 (M+H).

Step F. Intermediate 159F. Preparation of methyl 3-(5-(4-(2-(5-cyclopropyl-3-(2,6-dichlorophenyl) isoxazol-4-yl)vinyl)bicyclo[2.2.2]octan-1-yl)-1,2,4-oxadiazol-3-yl)benzoate

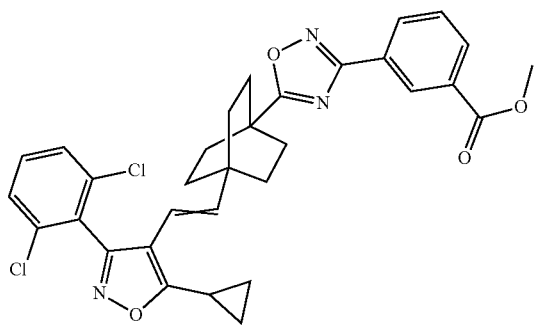 [SMILES: COC(=O)c1cccc(-c2noc(C34CCC(C=Cc5c(-c6c(Cl)cccc6Cl)noc5C5CC5)(CC3)CC4)n2)c1]

To a stirred solution of Intermediate 159E (20 mg, 0.046 mmol) in DMF (1 mL) were added methyl (Z)-3-(N'-hydroxycarbamimidoyl)benzoate (Tung, R. D. WO 2016/073545) (9.0 mg, 0.046 mmol), BOP (23 mg, 0.051 mmol) and triethylamine (0.019 mL, 0.14 mmol). The reaction was stirred at rt for 2 h, and 4 h at 100° C. The reaction was cooled, the solvent was concentrated. The residue was dissolved in EtOAc (50 mL), washed with brine, dried over Na$_2$SO$_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-90% B over 25 minutes, then a 5-minute hold at 100% B; Flow: 15 mL/min). Fractions containing the desired product were combined, concentrated and dried in vacuo to afford the title compound (8.0 mg, 29% yield): $^1$H NMR (400 MHz, DMSO-d$_6$) δ 8.51 (s, 1H), 8.24 (d, J=7.1 Hz, 1H), 8.15 (d, J=7.8 Hz, 1H), 7.78-7.49 (m, 4H), 6.06 (d, J=16.4 Hz, 1H), 5.25 (d, J=16.4 Hz, 1H), 3.90 (s, 3H), 2.43-2.34 (m, 1H), 2.04-1.81 (m, 6H), 1.51-1.36 (m, 6H), 1.20-0.97 (m, 4H). FXR EC$_{50}$ (nM)=4600. MS (ESI) 590 (M+H). The product was obtained as a mixture of trans/cis isomers in ca. 1:1 ratio. The ratio was determined by $^1$H NMR based on integration of characteristic protons.

Step G. Example 159

The title compound was prepared according to methods described for the synthesis of Example 151 (Step C), substituting Intermediate 159F where appropriate. The cis/trans isomers were separated by preparative HPLC (Column: Waters XBridge C18, 19×150 mm, 5-μm particles; Mobile Phase A: 10-mM ammonium acetate; Mobile Phase B: acetonitrile; Gradient: 15-75% B over 25 minutes, then a 5-minute hold at 100% B; Flow: 15 mL/min) to provide the title compound (4.8 mg, 15% yield) as an off white solid. $^1$H NMR (400 MHz, DMSO-d$_6$) δ 8.51 (s, 1H), 8.20 (d, J=7.6 Hz, 1H), 8.12 (d, J=7.6 Hz, 1H), 7.76-7.64 (m, 3H), 7.64-7.54 (m, 1H), 6.05 (d, J=16.6 Hz, 1H), 5.25 (d, J=16.6 Hz, 1H), 2.41-2.35 (m, 1H), 2.03-1.86 (m, 6H), 1.55-1.36 (m, 6H), 1.21-0.98 (m, 4H). FXR EC$_{50}$ (nM)=14. MS (ESI) 576 (M+H). The product thus obtained was predominantly the trans isomer as determined by $^1$H NMR based on integration of characteristic protons. The cis isomer is designated below as Example 163.

Example 162

2-(4-(((5-cyclopropyl-3-(2,6-dichlorophenyl)isoxazol-4-yl)methoxy)methyl) bicyclo[2.2.2] octan-1-yl)thiazole-4-carboxylic acid

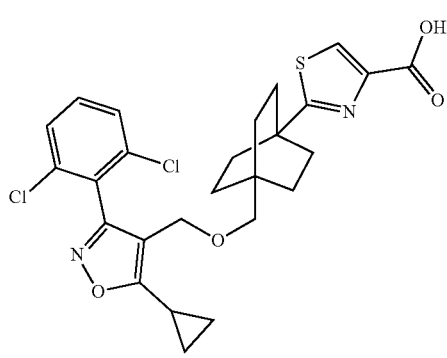

(162)

Step A. Intermediate 162A. Preparation of methyl 4-(((5-cyclopropyl-3-(2,6-dichlorophenyl)isoxazol-4-yl)methoxy)methyl)bicyclo[2.2.2]octane-1-carboxylate

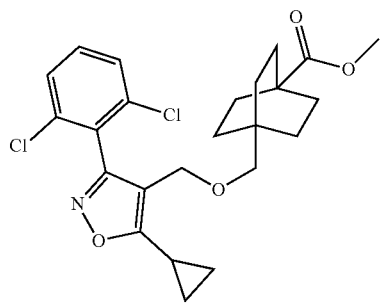 [SMILES: COC(=O)C12CCC(COCc3c(-c4c(Cl)cccc4Cl)noc3C3CC3)(CC1)CC2]

To a 20 mL scintillation vial were added methyl 4-(hydroxymethyl) bicyclo[2.2.2]octane-1-carboxylate (200 mg, 1.0 mmol) (Al Hussainy, R. et al. *Nucl. Med. Biol.* 2012, 39, 1068-1076), 2,6-di-tert-butylpyridine (0.91 mL, 4.0 mmol), dry DCM (2 mL) followed by silver trifluoromethanesulfonate (780 mg, 3.0 mmol) at 0° C. A solution of 4-(bromomethyl)-5-yclopropyl-3-(2,6-dichlorophenyl)isoxazole (1.1 g, 3.0 mmol) in DCM (2 mL) was added dropwise at 0° C. The reaction was stirred at rt for 12 h and diluted with DCM:MeOH (1:1; 10 mL). The solids were filtered and the filtrate was concentrated. The crude product was purified by flash column chromatography (24 g silica gel cartridge; A=Hex, B=EtOAc; 15 min grad.; 0% B to 25% B; flow rate=24 mL/min). The pure fractions were combined, concentrated and dried in vacuo to afford the title compound (0.18 g, 35% yield) as a pale yellow solid. MS (ESI) 464 (M+H).

Step B. Intermediate 162B. Preparation of 4-(((5-cyclopropyl-3-(2,6-dichlorophenyl)isoxazol-4-yl)methoxy)methyl)bicyclo[2.2.2]octane-1-carboxylic acid

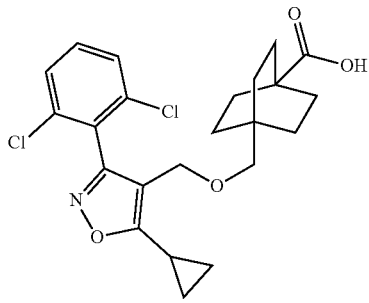 [SMILES: O=C(O)C12CCC(COCc3c(-c4c(Cl)cccc4Cl)noc3C3CC3)(CC1)CC2]

To a stirred solution of the product Intermediate 162A (180 mg, 0.39 mmol) in MeOH (4 mL), was added a solution of sodium hydroxide (39 mg, 0.97 mmol) in H$_2$O (1 mL). The reaction was stirred for 4 h at 70° C., cooled, diluted with 5% citric acid (aq.) (50 mL) and extracted with EtOAc (2×25 mL). The organic phase was combined, washed with brine, dried over Na$_2$SO$_4$, filtered, concentrated. The product was dried in vacuo to afford the title compound (0.12 g, 67% yield) as an off-white solid. $^1$H NMR (400 MHz, DMSO-d$_6$) δ=11.94 (s, 1H), 7.71-7.46 (m, 3H), 4.22 (s, 2H), 2.88 (s, 2H), 2.37-2.23 (m, 1H), 1.64-1.45 (m, 6H), 1.24-1.00 (m, 10H).

Step C. Intermediate 162C. Preparation of 4-(((5-cyclopropyl-3-(2,6-dichlorophenyl)isoxazol-4-yl)methoxy)methyl)bicyclo[2.2.2]octane-1-carboxamide

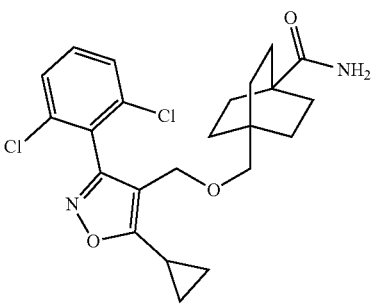 [SMILES: NC(=O)C12CCC(COCc3c(-c4c(Cl)cccc4Cl)noc3C3CC3)(CC1)CC2]

To a 25 mL pear shaped flask were added Intermediate 162B (45 mg, 0.10 mmol), BOP (49 mg, 0.11 mmol) and DMF (2 mL). To this mixture were added Et$_3$N (0.070 mL, 0.50 mmol) and ammonium chloride (53 mg, 1.0 mmol). After stirring 18 h, the solvent was concentrated and the residue was dissolved in EtOAc (50 mL). The organic phase was washed with brine, dried over Na$_2$SO$_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-55% B over 20 minutes, then a 5-minute hold at 100% B; Flow: 15 mL/min). Fractions containing the desired product were combined, concentrated and dried in vacuo to afford the title compound (10 mg, 22% yield). $^1$H NMR (400 MHz, DMSO-d$_6$) δ 7.70-7.61 (m, 2H), 7.60-7.47 (m, 1H), 6.82 (br s, 1H), 6.62 (br s, 1H), 4.21 (s, 2H), 2.88 (s, 2H), 2.32-2.21 (m, 1H), 1.60-1.37 (m, 6H), 1.21-0.94 (m, 10H). FXR EC$_{50}$ (nM)=180. MS (ESI) 449 (M+H).

Step D. Intermediate 162D. Preparation of 4-(((5-cyclopropyl-3-(2,6-dichlorophenyl)isoxazol-4-yl)methoxy)methyl)bicyclo[2.2.2]octane-1-carbothioamide

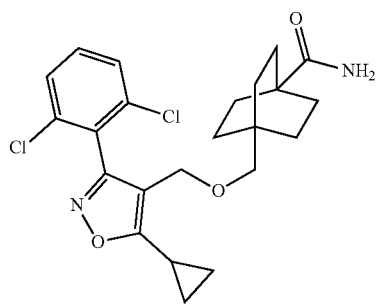 [SMILES: NC(=O)C12CCC(COCc3c(-c4c(Cl)cccc4Cl)noc3C3CC3)(CC1)CC2]

To a stirred solution of Intermediate 162C (55 mg, 0.12 mmol) in THF (2 mL), was added Lawesson's reagent (50 mg, 0.12 mmol) and the reaction mixture was stirred at reflux. After 2 h, the reaction was cooled, diluted with water (20 mL) and extracted with EtOAc (2×25 mL). The organic phase was combined, washed with brine, dried over Na$_2$SO$_4$, filtered and concentrated. The product was dried in vacuo to afford the title compound (0.045 g, 18% yield) as a pale yellow solid which was used in subsequent steps without further purification or characterization. MS (ESI) 465 (M+H).

Step E. Example 162

To a stirred solution of Intermediate 162D (40 mg, 0.086 mmol) in 1,4-dioxane was added 3-bromo-2-oxopropanoic acid (14 mg, 0.086 mmol). The reaction was stirred at 90° C. After 4 h, the reaction was cooled, diluted with 5% citric acid (aq.) (50 mL) and extracted with EtOAc (2×25 mL). The organic phase was combined, washed with brine, dried over Na$_2$SO$_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-50% B over 25 minutes, then a 5-minute hold at 100% B; Flow: 15 mL/min.). Fractions containing the desired product were combined, concentrated and dried in vacuo to afford the title compound (0.013 g, 27% yield) as an off-white solid. $^1$H NMR (400 MHz, DMSO-d$_6$) δ 8.28 (s, 1H), 7.71-7.60 (m, 2H), 7.60-7.51 (m, 1H), 4.25 (s, 2H), 2.95 (s, 2H), 2.33-2.25 (m, 1H), 1.84-1.69 (m, 6H), 1.37-1.20 (m, 6H), 1.17-1.07 (m, 4H). FXR EC$_{50}$ (nM)=1300. MS (ESI) 533 (M+H).

Example 163

(Z)-3-(5-(4-(2-(5-cyclopropyl-3-(2,6-dichlorophenyl)isoxazol-4-yl)vinyl)bicyclo[2.2.2]octan-1-yl)-1,2,4-oxadiazol-3-yl)benzoic acid (163)

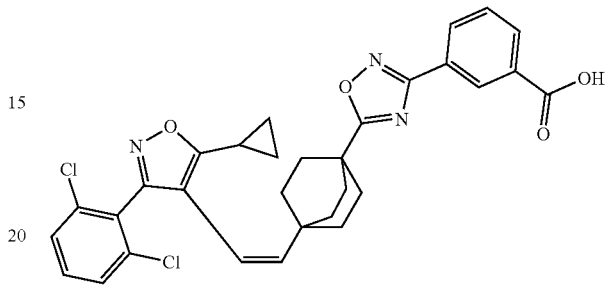

The title compound was obtained by separating the trans/cis isomers in Step G for the preparation of Example 159: (3.6 mg, 12% yield, off-white solid). $^1$H NMR (400 MHz, DMSO-d$_6$) δ 13.34 (s, 1H), 8.51 (br s, 1H), 8.19 (d, J=8.1 Hz, 1H), 8.11 (br s, 1H), 7.76-7.59 (m, 3H), 7.59-7.51 (m, 1H), 5.82 (d, J=12.2 Hz, 1H), 5.63 (d, J=12.2 Hz, 1H), 2.13-2.07 (m, 1H), 1.97-1.85 (m, 6H), 1.62-1.51 (m, 6H), 1.19-1.08 (m, 4H). FXR EC$_{50}$ (nM)=211. MS (ESI) 576 (M+H). The product thus obtained was predominantly the cis isomer as determined by $^1$H NMR based on integration of characteristic protons. The trans isomer is designated above as Example 159.

Example 166

3-(5-(4-(((5-cyclopropyl-3-(2,6-dichlorophenyl)isoxazol-4-yl)amino)methyl)bicyclo[2.2.2]octan-1-yl)-1,2,4-oxadiazol-3-yl)benzoic acid (166)

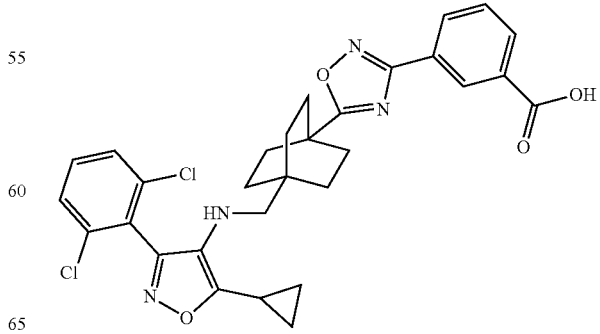

Step A. Intermediate 166A. Preparation of 5-cyclopropyl-3-(2,6-dichlorophenyl)isoxazole-4-carboxylic acid

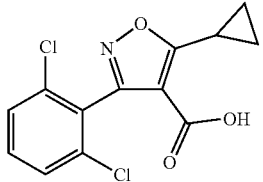 [SMILES: O=C(O)c1c(-c2c(Cl)cccc2Cl)noc1C1CC1]

To a 25 mL pear shaped flask were added methyl 5-cyclopropyl-3-(2,6-dichlorophenyl)isoxazole-4-carboxylate (2.0 g, 6.1 mmol) (Genin, M. J., et al. WO 2009/012125) and EtOH (10 mL). The mixture was cooled to 0° C., then 1 M NaOH (aq.) (12 mL, 12 mmol) was added. After stirring 2 h at 80° C., the reaction was cooled and the solvent was concentrated. The residue was dissolved in EtOAc (50 mL), washed with brine, dried over $Na_2SO_4$, filtered and concentrated. The product was dried in vacuo to afford the title compound (1.8 g, 85% yield) as a white solid. $^1$H NMR (400 MHz, DMSO-$d_6$) δ=7.78-7.30 (m, 3H), 2.96-2.81 (m, 1H), 1.43-1.08 (m, 4H). MS (ESI)=298 (M+H).

Step B. Intermediate 166B. Preparation of tert-butyl (5-cyclopropyl-3-(2,6-dichlorophenyl) isoxazol-4-yl)carbamate

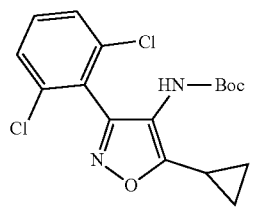 [SMILES: CC(C)(C)OC(=O)Nc1c(-c2c(Cl)cccc2Cl)noc1C1CC1]

To a 25 mL pear shaped flask were added Intermediate 166A (1.8 g, 5.9 mmol), $Et_3N$ (0.82 mL, 5.9 mmol) and t-butanol (20 mL). To this mixture was added DPPA (1.3 mL, 5.9 mmol) dropwise over a period of 5 min. The reaction was stirred at 85° C. After 12 h, the reaction was cooled and the solvent was concentrated. The residue was dissolved in EtOAc (50 mL), washed with brine, dried over $Na_2SO_4$, filtered and concentrated. The crude product was purified by flash column chromatography (40 g silica gel cartridge; A=Hex, B=EtOAc; 25 min grad.; 0% B to 30% B; flow rate=24 mL/min). The pure fractions were combined, concentrated and dried in vacuo to afford the title compound (1.3 g, 50% yield) as a pale yellow solid. $^1$H NMR (400 MHz, DMSO-$d_6$) δ=8.62 (br. s., 1H), 7.73-7.39 (m, 3H), 2.23-1.99 (m, 1H), 1.40-1.19 (m, 9H), 1.14-0.79 (m, 4H). MS (ESI) 369 (M+H).

Step C. Intermediate 166C. Preparation of 5-cyclopropyl-3-(2,6-dichlorophenyl)isoxazol-4-amine

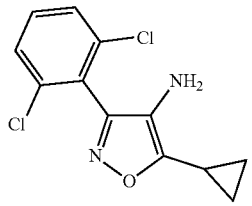 [SMILES: Nc1c(-c2c(Cl)cccc2Cl)noc1C1CC1]

To a 25 mL pear shaped flask was added Intermediate 166B (500 mg, 1.4 mmol) in DCM (5 mL). To this mixture was added TFA (1.0 mL, 14 mmol) at 0° C. The mixture was warmed to rt stirred. After 18 h, the solvent was concentrated and the residue was diluted with sat. $NaHCO_3$ (aq.) (250 mL) and extracted with EtOAc (250 mL). The organic phase was washed with brine, dried over $Na_2SO_4$, filtered and concentrated. The product was dried in vacuo to afford the title compound (230 mg, 50% yield) as a pale yellow solid. $^1$H NMR (400 MHz, DMSO-$d_6$) δ=7.68-7.49 (m, 3H), 3.86 (s, 2H), 2.18 (s, 1H), 1.09-0.86 (m, 4H). MS (ESI)=269 (M+H).

Step D. Intermediate 166D. Preparation of methyl 4-(((5-cyclopropyl-3-(2,6-dichlorophenyl) isoxazol-4-yl)amino)methyl)bicyclo[2.2.2]octane-1-carboxylate

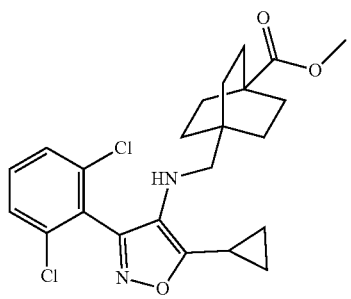 [SMILES: COC(=O)C12CCC(CNc3c(-c4c(Cl)cccc4Cl)noc3C3CC3)(CC1)CC2]

To a 25 mL pear shaped flask were added Intermediate 166C (200 mg, 0.74 mmol), Intermediate 159B (150 mg, 0.74 mmol) and MeOH (5 mL). The mixture was cooled to 0° C., then glacial AcOH (4.3 µl, 0.074 mmol) was added. After stirring at 80° C. for 2 h, the reaction was cooled to rt, then sodium cyanoborohydride (47 mg, 0.74 mmol) was added. After stirring 30 min, the solvent was concentrated and the residue was diluted with sat. $NaHCO_3$ (aq.) (25 mL) and extracted with EtOAc (25 mL). The organic phase was washed with brine, dried over $Na_2SO_4$, filtered and concentrated. The product was dried in vacuo to afford the title compound (300 mg, 75% yield) as a pale yellow solid. MS (ESI)=449 (M+H).

Step E. Intermediate 166E. Preparation of 4-(((5-cyclopropyl-3-(2,6-dichlorophenyl)isoxazol-4-yl)amino)methyl)bicyclo[2.2.2]octane-1-carboxylic acid

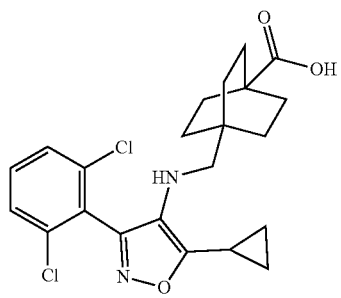 [SMILES: O=C(O)C12CCC(CNc3c(-c4c(Cl)cccc4Cl)noc3C3CC3)(CC1)CC2]

To a 25 mL pear shaped flask were added Intermediate 166D (150 mg, 0.33 mmol), MeOH (2 mL) and water (1 mL). To this mixture was added sodium hydroxide (33 mg, 0.83 mmol). After stirring 4 h at 70° C., the reaction was cooled to rt, acidified with 1 M HCl (aq.) (50 mL), and extracted with EtOAc (2×25 mL). The organic phase was combined, washed with brine, dried over $Na_2SO_4$, filtered and concentrated. The product was dried in vacuo to afford the title compound (90 mg, 43% yield) as a pale yellow solid. $^1$H NMR (400 MHz, DMSO-$d_6$) δ=11.92 (s, 1H), 7.71-7.47 (m, 3H), 4.10 (q, J=5.1 Hz, 1H), 3.51 (t, J=7.3 Hz, 1H), 3.17 (s, 2H), 2.30-2.16 (m, 1H), 1.63-1.50 (m, 6H), 1.25-1.12 (m, 6H), 1.10-0.90 (m, 4H). MS (ESI)=435 (M+H).

Step F. Intermediate 166F. Preparation of methyl 3-(5-(4-(((5-cyclopropyl-3-(2,6-dichlorophenyl)isoxazol-4-yl)amino)methyl)bicyclo[2.2.2]octan-1-yl)-1,2,4-oxadiazol-3-yl) benzoate

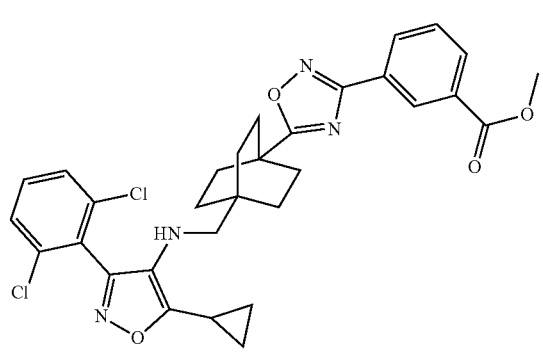 [SMILES: COC(=O)c1cccc(-c2noc(C34CCC(CNc5c(-c6c(Cl)cccc6Cl)noc5C5CC5)(CC3)CC4)n2)c1]

To a solution of Intermediate 166E (20 mg, 0.046 mmol) and methyl (E)-3-(N'-hydroxycarbamimidoyl)benzoate (8.9 mg, 0.046 mmol) dissolved in DMF (1 mL) were added BOP (22 mg, 0.051 mmol) and triethylamine (0.019 mL, 0.14 mmol). The reaction was stirred at rt for 2 h, and at 100° C. for 4 h. The reaction was cooled, and diluted with EtOAc (40 mL) and water (10 mL). The layers were separated, the aqueous layer was extracted with EtOAc (2×20 mL) and the combined organic layers were washed with brine, dried over $MgSO_4$, filtered and concentrated. The crude material was purified by preparative HPLC (Column: Waters XBridge C18, 19×150 mm, 5-µm particles; Mobile Phase A: 10-mM ammonium acetate; Mobile Phase B: acetonitrile; Gradient: 15-45% B over 25 minutes, then a 5-minute hold at 100% B; Flow: 15 mL/min). Fractions containing the desired product were combined, concentrated and dried in vacuo to afford the title compound (14 mg, 50% yield) as a pale yellow solid. $^1$H NMR (400 MHz, DMSO-$d_6$) 8.51 (t, J=1.5 Hz, 1H), 8.24 (d, J=7.8 Hz, 1H), 8.15 (d, J=8.1 Hz, 1H), 7.72 (t, J=7.8 Hz, 1H), 7.68-7.61 (m, 2H), 7.60-7.53 (m, 1H), 3.91 (s, 3H), 3.60 (t, J=7.9 Hz, 1H), 2.31-2.24 (m, 1H), 2.00-1.78 (m, 6H), 1.43-1.27 (m, 6H), 1.12-1.04 (m, 2H), 1.02-0.91 (m, 2H). MS (ESI) 593 (M+H).

Step G. Example 166

The title compound was prepared according to methods described for the synthesis of Example 151 (Step C), substituting Intermediate 166F where appropriate: (0.012 g, 40% yield, off-white solid). $^1$H NMR (400 MHz, DMSO-$d_6$) δ 8.51 (s, 1H), 8.16 (d, J=8.1 Hz, 1H), 8.11 (d, J=7.1 Hz, 1H), 7.76-7.60 (m, 3H), 7.60-7.50 (m, 1H), 3.60 (br s, 1H), 3.3 (s, 2H), 2.32-2.23 (m, 1H), 1.99-1.78 (m, 6H), 1.45-1.26 (m, 6H), 1.12-1.03 (m, 2H), 1.02-0.92 (m, 2H). FXR $EC_{50}$ (nM)=580. MS (ESI) 579 (M+H).

Example 168

2-(4-(((5-cyclopropyl-3-(2,6-dichlorophenyl)isoxazol-4-yl)methoxy)methyl)bicyclo[2.2.2] octan-1-yl)benzo[d]thiazole-6-carboxylic acid (168)

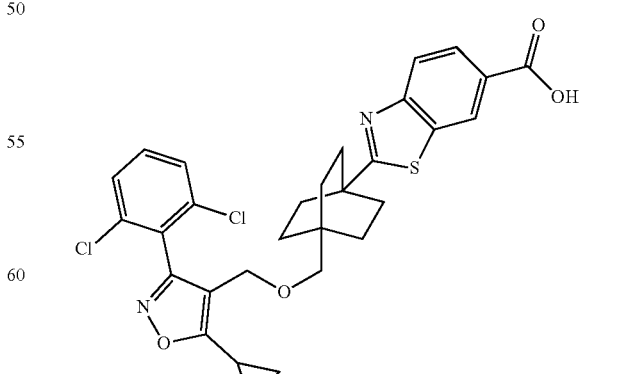

Step A. Intermediate 168A. Preparation of methyl 3-chloro-4-(4-(((5-cyclopropyl-3-(2,6-dichlorophenyl)isoxazol-4-yl)methoxy)methyl)bicyclo[2.2.2]octane-1-carbothioamido)benzoate

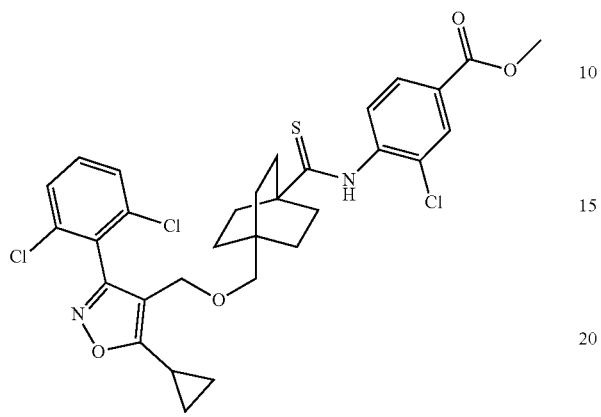

To a stirred solution of Intermediate 170A (75 mg, 0.12 mmol) in dry toluene (1 mL) was added Lawesson's reagent (25 mg, 0.061 mmol) at rt. After stirring 18 h at 120° C., the reaction was cooled, diluted with water (20 mL) and extracted with EtOAc (2×25 mL). The organic phase was combined, washed with brine, dried over $Na_2SO_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-55% B over 20 minutes, then a 5-minute hold at 100% B; Flow: 15 mL/min). Fractions containing the desired product were combined, concentrated and dried in vacuo to afford the title compound (0.0034 g, 5% yield) as an off-white solid. $^1$H NMR (400 MHz, DMSO-$d_6$) δ 10.65 (s, 1H), 8.01 (d, J=1.7 Hz, 1H), 7.93 (dd, J=8.2, 1.6 Hz, 1H), 7.64 (d, J=7.6 Hz, 2H), 7.60-7.52 (m, 1H), 7.45 (d, J=8.3 Hz, 1H), 4.24 (s, 2H), 3.87 (s, 3H), 2.94 (s, 2H), 2.33-2.24 (m, 1H), 1.92-1.72 (m, 6H), 1.34-1.18 (m, 6H), 1.18-0.97 (m, 4H). FXR $EC_{50}$ (nM)=4385. MS (ESI) 619 (M+H).

Step B. Example 168

To a stirred solution of sodium hydride (2.8 mg, 0.071 mmol) (60% dispersion in mineral oil) in NMP (1 mL) was added Intermediate 168A (30 mg, 0.047 mmol). After stirring at 130° C. for 3 h, the mixture was cooled and the residue was dissolved in diethyl ether (50 mL). The organic phase was washed with $H_2O$, brine, dried over $Na_2SO_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 15-45% B over 25 minutes, then a 5-minute hold at 100% B; Flow: 15 mL/min). Fractions containing the desired product were combined, concentrated and dried in vacuo to afford the title compound (0.0030 g, 10% yield) as an off-white solid. $^1$H NMR (400 MHz, DMSO-$d_6$) δ 8.65 (s, 1H), 8.10-7.91 (m, 2H), 7.75-7.62 (m, 2H), 7.61-7.52 (m, 1H), 4.26 (s, 2H), 2.97 (s, 2H), 2.33-2.25 (m, 1H), 1.94-1.74 (m, 6H), 1.39-1.26 (m, 6H), 1.18-1.06 (m, 4H). FXR $EC_{50}$ (nM)=1200. MS (ESI) 583 (M+H).

Example 170

3-chloro-4-(4-(((5-cyclopropyl-3-(2,6-dichlorophenyl)isoxazol-4-yl)methoxy)methyl)bicyclo[2.2.2]octane-1-carboxamido)benzoic acid

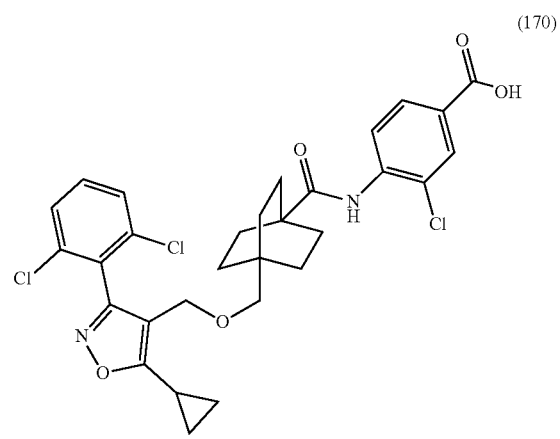 [SMILES: O=C(O)c1ccc(NC(=O)C23CCC(COCc4c(-c5c(Cl)cccc5Cl)noc4C4CC4)(CC2)CC3)c(Cl)c1]

(170)

Step A. Intermediate 170A. Preparation of methyl 3-chloro-4-(4-(((5-cyclopropyl-3-(2,6-dichlorophenyl)isoxazol-4-yl)methoxy)methyl)bicyclo[2.2.2]octane-1-carboxamido)benzoate

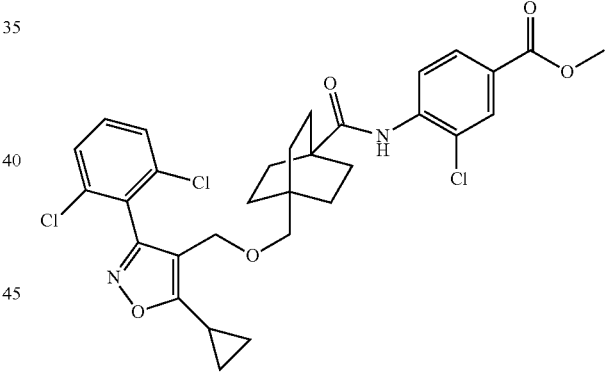

To a stirring solution of Intermediate 162B (25 mg, 0.056 mmol) in dry DCM (1 mL) was added oxalyl chloride (4.9 μl, 0.056 mmol). After stirring 1 h, the mixture was concentrated and the residue was dissolved in DCM (1 mL). The mixture was cooled to 0° C., and DIEA (9.7 μl, 0.056 mmol) was added followed by the dropwise addition of methyl 4-amino-3-chlorobenzoate (10 mg, 0.056 mmol) dissolved in DCM (1 mL). The reaction was warmed to rt and stirred. After 18 h, the solvent was concentrated and the residue was dissolved in EtOAc (50 mL), washed with brine, dried over $Na_2SO_4$, filtered and concentrated. The crude material was purified via preparative HPLC (Column: Waters XBridge C18, 19×150 mm, 5-μm particles; Mobile Phase A: 10-mM ammonium acetate; Mobile Phase B: acetonitrile; Gradient: 15-55% B over 20 minutes, then a 5-minute hold at 100% B; Flow: 15 mL/min). Fractions containing the desired product were combined, concentrated and dried in vacuo to afford the title compound (0.0020 g, 6% yield) as an off-white solid. $^1$H NMR (400 MHz, DMSO-$d_6$) δ 8.86 (s, 1H), 7.98 (d, J=2.0 Hz, 1H), 7.89 (dd, J=8.6, 2.0 Hz, 1H), 7.83 (d, J=8.3 Hz, 1H), 7.69-7.61 (m, 2H), 7.60-7.53 (m, 1H), 4.24 (s, 2H), 3.85 (s, 3H), 2.93 (s, 2H), 2.32-2.27 (m, 1H), 1.76-1.65 (m, 6H), 1.26-1.16 (m, 6H), 1.16-1.07 (m, 4H). FXR EC$_{50}$ (nM)=2400. MS (ESI) 619 (M+H).

Step B. Example 170

The title compound was prepared according to methods described for the synthesis of Example 151 (Step C), substituting Intermediate 170A where appropriate: (0.014 g, 55% yield, off white solid). $^1$H NMR (400 MHz, DMSO-$d_6$) δ 8.83 (s, 1H), 7.95 (d, J=2.0 Hz, 1H), 7.86 (dd, J=8.3, 2.0 Hz, 1H), 7.78 (d, J=8.3 Hz, 1H), 7.69-7.61 (m, 2H), 7.60-7.52 (m, 1H), 4.28-4.21 (m, 2H), 2.93 (s, 2H), 2.34-2.28 (m, 1H), 1.79-1.63 (m, 6H), 1.26-1.17 (m, 6H), 1.16-1.08 (m, 4H). FXR EC$_{50}$ (nM)=636. MS (ESI) 603 (M+H).

Example 171

3-chloro-4-(4-(((5-cyclopropyl-3-(2,6-dichlorophenyl)isoxazol-4-yl)methoxy)methyl) bicyclo[2.2.2]octane-1-carbothioamido)benzoic acid (171)

Example 172

2-(4-(((5-cyclopropyl-3-(2,6-dichlorophenyl)isoxazol-4-yl)methoxy)methyl) bicyclo[2.2.2]octan-1-yl)benzo[d]thiazole-7-carboxylic acid (172)

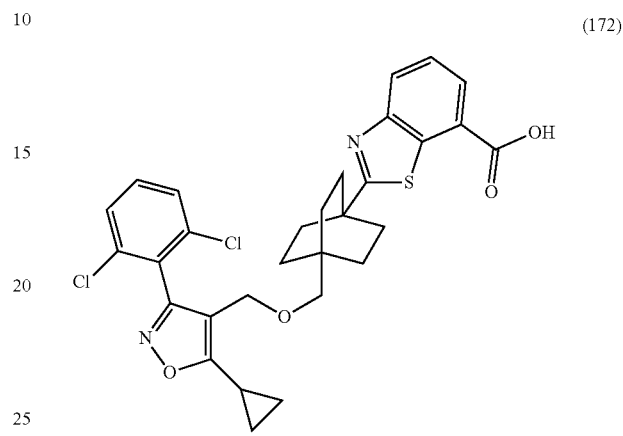

Step A. Intermediate 172A. Preparation of methyl 2-chloro-3-(4-(((5-cyclopropyl-3-(2,6-dichlorophenyl)isoxazol-4-yl)methoxy)methyl)bicyclo[2.2.2]octane-1-carboxamido) benzoate

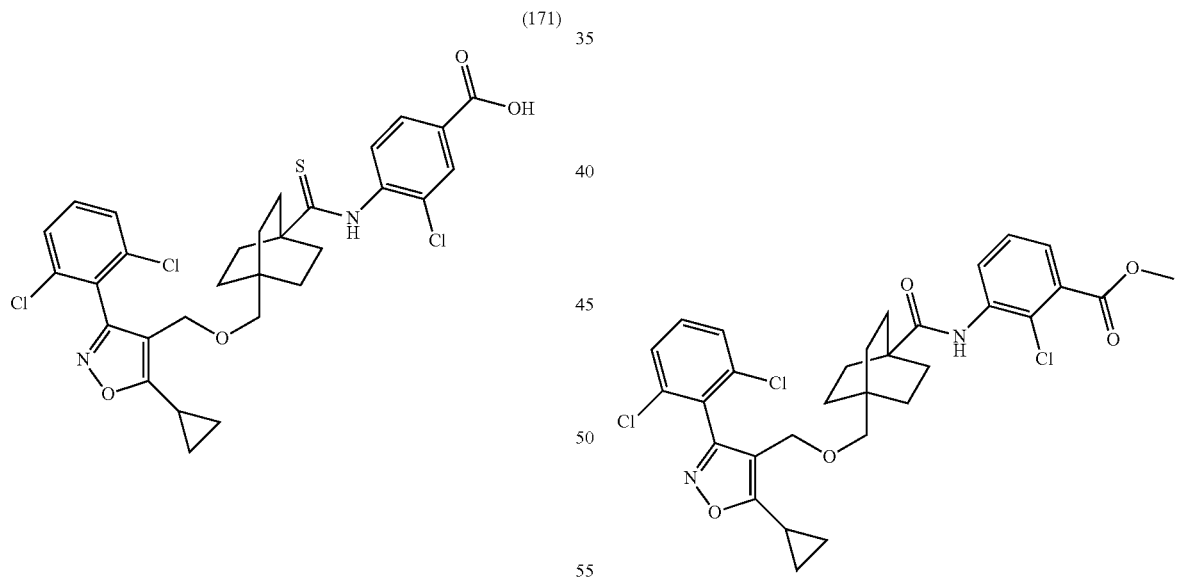

The title compound was prepared according to methods described for the synthesis of Example 151 (Step C), substituting Intermediate 168A where appropriate: (0.0020 g, 10% yield, off white solid). $^1$H NMR (400 MHz, DMSO-$d_6$) δ 10.59 (br s, 1H), 7.95 (s, 1H), 7.86 (d, J=8.8 Hz, 1H), 7.65 (d, J=7.6 Hz, 2H), 7.60-7.53 (m, 1H), 7.33 (d, J=8.6 Hz, 1H), 4.24 (s, 2H), 2.94 (s, 2H), 2.32-2.30 (m, 1H), 1.89-1.79 (m, 6H), 1.25-1.22 (m, 6H), 1.16-1.08 (m, 4H). FXR EC$_{50}$ (nM)=4700. MS (ESI) 620 (M+H).

The title compound was prepared according to methods described for the synthesis of Intermediate 170A, substituting methyl 3-amino-2-chlorobenzoate where appropriate:

(85 mg, 0.056 mmol, 25%). MS (ESI) 619 (M+H).

Step B. Intermediate 172B. Preparation of methyl 2-(4-(((5-cyclopropyl-3-(2,6-dichlorophenyl)isoxazol-4-yl)methoxy)methyl)bicyclo[2.2.2]octan-1-yl)benzo[d]thiazole-7-carboxylate

Example 174

4-(4-(((5-cyclopropyl-3-(2,6-dichlorophenyl)isoxazol-4-yl)methoxy)methyl) bicyclo[2.2.2]octan-1-yl) benzoic acid

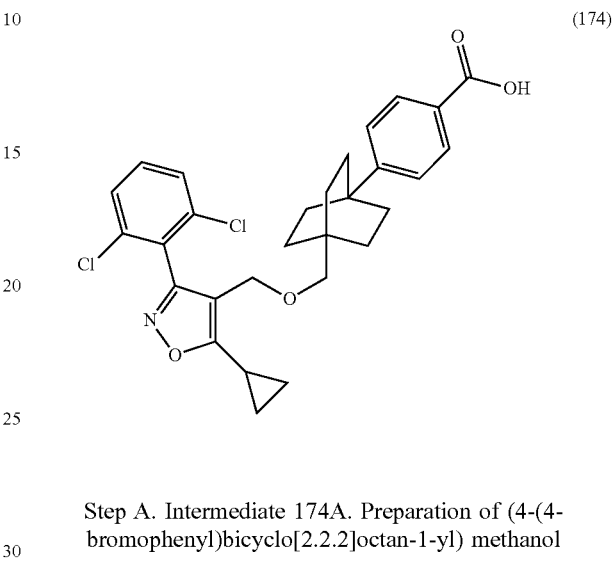

(174)

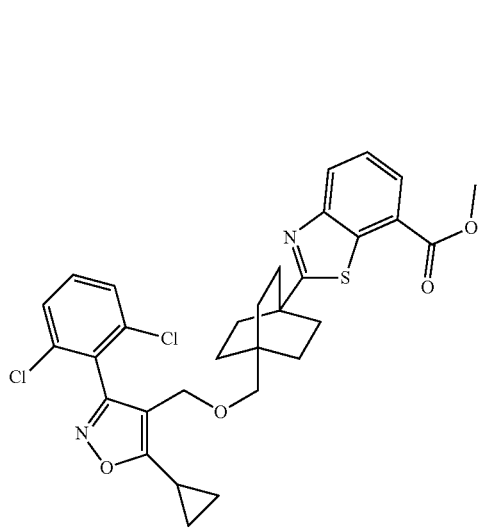 [SMILES: COC(=O)c1cccc2nc(C34CCC(COCc5c(-c6c(Cl)cccc6Cl)noc5C5CC5)(CC3)CC4)sc12]

Step A. Intermediate 174A. Preparation of (4-(4-bromophenyl)bicyclo[2.2.2]octan-1-yl) methanol

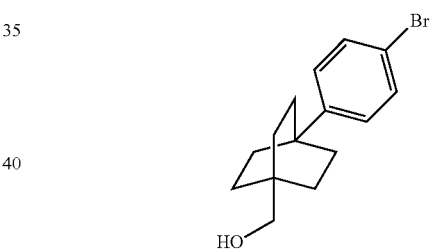

To a solution of Intermediate 172A (60 mg, 0.097 mmol) in toluene (1 mL), was added Lawesson's reagent (59 mg, 0.15 mmol). After stirring 18 h at 120° C., the reaction was cooled, diluted with water (20 mL), and extracted with EtOAc (2×15 mL). The combined organic phase was washed with brine, dried over Na$_2$SO$_4$, filtered and concentrated to afford the title compound (40 mg, 0.067 mmol, 69%) which was used in subsequent steps without further purification or characterization. MS (ESI) 597 (M+H).

Step C. Example 172

The title compound was prepared according to methods described for the synthesis of Example 151 (Step C), substituting intermediate 172B where appropriate: (0.013 g, 34% yield, off white solid). $^1$H NMR (400 MHz, DMSO-d$_6$) δ 8.14 (d, J=8.1 Hz, 1H), 8.01 (d, J=6.8 Hz, 1H), 7.70-7.63 (m, 2H), 7.62-7.51 (m, 2H), 4.26 (s, 2H), 2.97 (s, 2H), 2.34-2.30 (m, 1H), 1.95-1.82 (m, 6H), 1.38-1.28 (m, 6H), 1.18-1.08 (m, 4H). FXR EC$_{50}$ (nM)=89. MS (ESI) 583 (M+H).

To a 25 mL round bottomed flask was added methyl 4-(4-bromophenyl) bicyclo[2.2.2]octane-1-carboxylate (0.65 g, 2.0 mmol) (Velaparthi U. et al. US 2015/0133428) dissolved in DCM (5 mL). The solution was cooled to −78° C. and DIBAL-H (4.0 mL, 4.0 mmol) (1 M solution in DCM) was added. The reaction mixture was stirred for 30 min at the same temperature and for 2 h at rt. The mixture was quenched with 1.5 M HCl (aq.) (20 mL) at 0° C., the layers were separated and the aqueous phase extracted with EtOAc (20 mL). The organic phase was combined, washed with brine, dried over Na$_2$SO$_4$, filtered and concentrated. The crude product was purified by flash column chromatography (24 g silica gel cartridge; A=Hex, B=EtOAc; 15 min grad.; 0% B to 15% B; flow rate=24 mL/min). The pure fractions were combined, concentrated and dried in vacuo to afford the title compound (0.59 g, 99% yield) as a yellow solid. $^1$H NMR (300 MHz, DMSO-d$_6$) δ=7.55-7.38 (m, 2H), 7.33-7.17 (m, 2H), 4.35 (t, J=5.3 Hz, 1H), 3.08 (d, J=5.3 Hz, 2H), 1.84-1.63 (m, 5H), 1.56-1.24 (m, 6H).

Step B. Intermediate 174B. Preparation of 4-(((4-(4-bromophenyl)bicyclo[2.2.2]octan-1-yl) methoxy)methyl)-5-cyclopropyl-3-(2,6-dichlorophenyl)isoxazole

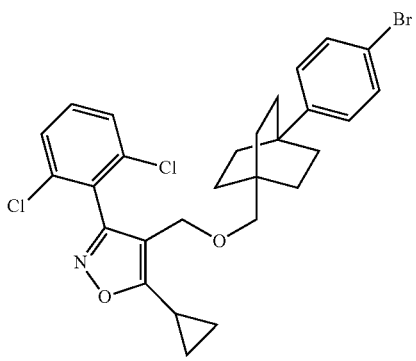 [SMILES: Clc1cccc(Cl)c1-c1noc(C2CC2)c1COCC12CCC(c3ccc(Br)cc3)(CC1)CC2]

To a 20 mL round bottomed flask was added Intermediate 174A (200 mg, 0.68 mmol) and 2,6-di-tert-butylpyridine (0.61 mL, 2.7 mmol) in dry DCM (1 mL). The mixture was cooled to 0° C., and silver trifluoromethanesulfonate (520 mg, 2.0 mmol) was added followed by the dropwise addition of 4-(bromomethyl)-5-cyclopropyl-3-(2,6-dichlorophenyl)isoxazole (710 mg, 2.0 mmol) in DCM (2 mL). The reaction was flushed with $N_2$ and allowed to slowly reach room temperature. After stirring 18 h, the mixture was diluted with DCM:MeOH (1:1; 4 mL), filtered and the filtrate was concentrated. The crude product was purified by flash column chromatography (24 g silica gel cartridge; A=Hex, B=EtOAc; 15 min grad.; 0% B to 25% B; flow rate=24 mL/min). The pure fractions were combined, concentrated and dried in vacuo to afford the title compound (0.13 g, 0.23 mmol, 34% yield) as a colorless residue. $^1$H NMR (400 MHz, CHLOROFORM-d) δ=7.31 (s, 5H), 7.09 (d, J=8.0 Hz, 2H), 4.32-4.23 (m, 2H), 2.98 (s, 2H), 1.76-1.66 (m, 7H), 1.43-1.31 (m, 6H), 1.30-1.22 (m, 2H), 1.18-1.05 (m, 2H). MS (ESI) 561 (M+H).

Step C. Example 174

Step 1: To a 2 dram vial equipped with a pressure release cap were added Intermediate 174B (20 mg, 0.036 mmol), copper(I) cyanide (9.6 mg, 0.11 mmol), and dry DMF (1 mL). After stirring at 150° C. for 18 h, the reaction was cooled and poured into ice water. The resultant precipitate was collected by vacuum filtration and the product was dried in vacuo to afford the title compound (0.015 g, 30% yield). MS (ESI) 507 (M+H).

Step 2: The product of Step 1 above was dissolved in EtOH:$H_2$O (2 mL, 1:1), and 5.9 M KOH (aq.) (0.066 mL, 0.39 mmol) was added. After stirring 8 h at 100° C., the reaction was cooled, diluted with 5% citric acid (aq.) (50 mL) and extracted with EtOAc (2×25 mL). The organic phase was combined, washed with brine, dried over $Na_2SO_4$, filtered and concentrated. The crude material was purified by preparative HPLC (Column: Waters XBridge C18, 19×150 mm, 5-μm particles; Mobile Phase A: 10-mM ammonium acetate; Mobile Phase B: acetonitrile; Gradient: 25-85% B over 20 minutes, then a 5-minute hold at 100% B; Flow: 15 mL/min). Fractions containing the desired product were combined, concentrated and dried in vacuo to afford the title compound (0.0029 mg, 14% yield). $^1$H NMR (400 MHz, DMSO-$d_6$) δ 7.95-7.73 (m, J=8.1 Hz, 2H), 7.69-7.49 (m, 3H), 7.47-7.28 (m, J=8.3 Hz, 2H), 4.24 (s, 2H), 2.94 (s, 2H), 2.32-2.20 (m, 1H), 1.78-1.50 (m, 6H), 1.37-1.19 (m, 6H), 1.17-1.00 (m, 4H). FXR $EC_{50}$ (nM)=210. MS (ESI) 526 (M+H).

Example 176

2-((4-(((5-cyclopropyl-3-(2,6-dichlorophenyl)isoxazol-4-yl)methoxy)methyl)bicyclo[2.2.2]octan-1-yl)methoxy)thiazole-4-carboxylic acid (176)

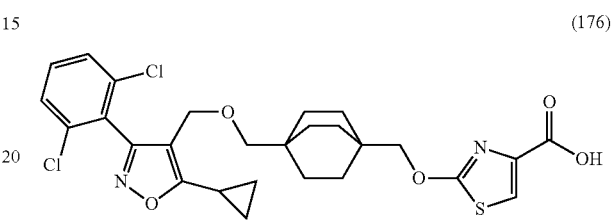

Step A. Intermediate 176A. Preparation of (4-(((5-cyclopropyl-3-(2,6dichlorophenyl)isoxazol-4-yl)methoxy)methyl)bicyclo[2.2.2]octan-1-yl)methanol

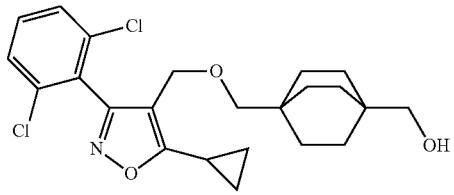 [SMILES: OCC12CCC(COCc3c(-c4c(Cl)cccc4Cl)noc3C3CC3)(CC1)CC2]

To a stirred solution of Intermediate 162A (200 mg, 0.43 mmol) in THF (4 mL) was added DIBAL-H (1.1 mL, 1.1 mmol) (1 M solution in heptane) at −78° C. The reaction was warmed to rt and stirred. After 2 h, the mixture was cooled to 0° C. and quenched with 1.5 M HCl (aq.) (50 mL). The aqueous phase was extracted with EtOAc (2×25 mL), and the organic phase was dried over $Na_2SO_4$, filtered and concentrated. The crude product was purified by flash column chromatography (12 g silica gel cartridge; A=Hex, B=EtOAc; 15 min grad.; 0% B to 60% B; flow rate=12 mL/min). The pure fractions were combined, concentrated and dried in vacuo to afford the title compound (160 mg, 0.37 mmol, 85% yield) as a white solid. $^1$H NMR (400 MHz, DMSO-$d_6$) δ 7.63-7.57 (m, 3H), 4.21 (s, 1H), 4.20 (s, 2H), 2.97 (d, J=5.60 Hz, 2H), 2.86 (s, 2H), 2.32-2.33 (m, 1H), 1.20-1.09 (m, 16H). MS (ESI) 436 (M+H).

Step B. Example 176

To a stirred solution of Intermediate 176A (30 mg, 0.069 mmol) in DMF (0.5 mL) was added sodium hydride (4.1 mg, 0.10 mmol) (60% dispersion in mineral oil) at 0° C. After stirring 10 min, methyl 2-bromothiazole-4-carboxylate (23 mg, 0.10 mmol) dissolved in DMF (0.35 mL) was added. The reaction mixture was warmed to rt and stirred. After 18 h, the reaction was concentrated, the residue was diluted with water (10 mL), acidified with 1.5 M HCl (aq.) (pH ~3) and extracted with EtOAc (3×20 mL). The combined organic phase was dried over Na₂SO₄, filtered and concentrated. The crude material was purified by preparative HPLC (Column: Waters XBridge C18, 19×150 mm, 5-μm particles; Mobile Phase A: 10 mM ammonium acetate; Mobile Phase B: acetonitrile; Gradient: 10-35% B over 25 minutes, then a 5-minute hold at 100% B; Flow: 15 mL/min). Fractions containing the desired product were combined, concentrated and dried in vacuo to afford title compound (1.4 mg, 2.4 μma 4% yield). ¹H NMR (400 MHz, DMSO-d₆) δ 7.74 (s, 1H), 7.68-7.59 (m, 2H), 7.59-7.47 (m, 1H), 4.22 (s, 2H), 4.01 (s, 2H), 2.90 (s, 2H), 2.32-2.22 (m, 1H), 1.45-1.26 (m, 6H), 1.22-1.02 (m, 10H). FXR EC₅₀ (nM)=740. MS (ESI) 563 (M+H).

Example 177

2-(4-(((5-cyclopropyl-3-(2,6-dichlorophenyl)isoxazol-4-yl)methoxy)methyl) bicyclo[2.2.2]octan-1-yl)oxazole-4-carboxylic acid (177)

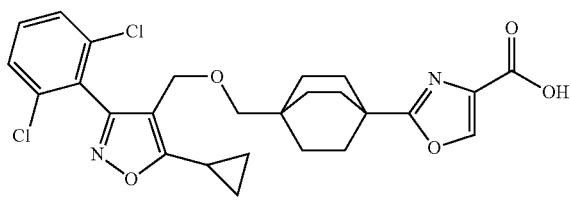

Step A. Intermediate 177A. Preparation of ethyl 2-(4-(((5-cyclopropyl-3-(2,6-dichlorophenyl)isoxazol-4-yl)methoxy)methyl)bicyclo[2.2.2]octan-1-yl)oxazole-4-carboxylate

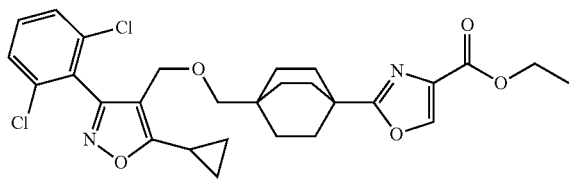 [SMILES: CCOC(=O)c1coc(C23CCC(COCc4c(-c5c(Cl)cccc5Cl)noc4C4CC4)(CC2)CC3)n1]

To a stirred solution of Intermediate 162C (35 mg, 0.078 mmol) in THF (2 mL) was added NaHCO₃ (33 mg, 0.39 mmol) followed by ethyl bromopyruvate (0.024 mL, 0.20 mmol). After stirring at 80° C. for 16 h, the reaction mixture was cooled and filtered. To the filtrate was added and trifluoroacetic anhydride (0.13 mL, 0.94 mmol). After stirring 2 h, the mixture was diluted with sat. NaHCO₃ (aq.) (20 mL) and extracted with EtOAc (2×20 mL). The organic phase was combined, dried over Na₂SO₄, filtered and concentrated to afford title compound (40 mg, 0.073 mmol, 94% yield) as a dark oil. MS (ESI) 545 (M+H).

Step B. Example 177

The title compound was prepared according to methods described for the synthesis of Example 151 (Step C), substituting intermediate 177A where appropriate: (2.7 mg, 5.1 μmol, 7% yield). ¹H NMR (400 MHz, DMSO-d₆) δ 8.22 (s, 1H), 7.70-7.61 (m, 2H), 7.60-7.51 (m, 1H), 4.25 (s, 2H), 2.94 (s, 2H), 2.29 (d, J=8.2 Hz, 1H), 1.80-1.63 (m, 6H), 1.29-1.18 (m, 7H), 1.16-1.04 (m, 4H). FXR EC₅₀ (nM)= 1800. MS (ESI) 517 (M+H).

Example 178

2-(4-(((5-cyclopropyl-3-(2,6-dichlorophenyl)isoxazol-4-yl)methoxy)methyl) bicyclo[2.2.2]octan-1-yl)benzo[d]oxazole-6-carboxylic acid (178)

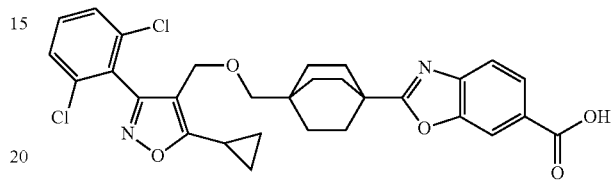

Step A. Intermediate 178A. Preparation of methyl 4-(4-(((5-cyclopropyl-3-(2,6-dichlorophenyl)isoxazol-4-yl)methoxy)methyl)bicyclo[2.2.2]octane-1-carboxamido)-3-hydroxybenzoate

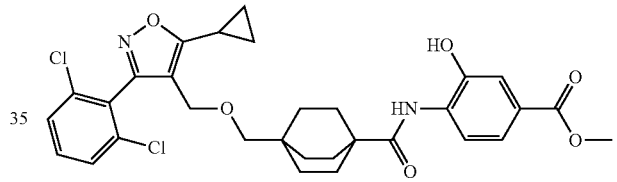

To a solution of Intermediate 162B (60 mg, 0.13 mmol) in DMF were added methyl 4-amino-3-hydroxybenzoate (25 mg, 0.15 mmol), TEA (55 μL, 0.40 mmol) followed by BOP (65 mg, 0.15 mmol). After stirring 4 h, the mixture was diluted with water (40 mL) and extracted with EtOAc (2×25 mL). The organic phase was combined, dried over Na₂SO₄, filtered and concentrated to afford title compound (50 mg, 0.083 mmol, 63% yield) as a pale yellow oil. ¹H-NMR (400 MHz, DMSO-d₆) δ 9.36 (s, 1H), 7.66-7.50 (m, 4H), 7.25-7.23 (m, 2H), 4.24 (s, 2H), 3.75 (s, 2H), 3.72 (s, 3H), 2.33-2.32 (m, 1H), 1.82-1.78 (m, 6H), 1.24-1.09 (m, 10H). MS (ESI) 599 (M+H).

Step B. Intermediate 178B. Preparation of methyl 2-(4-(((5-cyclopropyl-3-(2,6-dichlorophenyl)isoxazol-4-yl)methoxy)methyl)bicyclo[2.2.2]octan-1-yl)benzo[d]oxazole-6-carboxylate

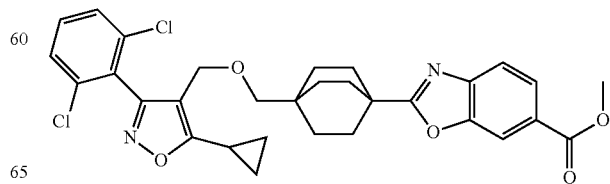

To a solution of Intermediate 178A (50 mg, 0.083 mmol) in toluene (2 mL) was added p-toluenesulfonic acid monohydrate (16 mg, 0.083 mmol). After stirring at 125° C. for 18 h, the reaction was cooled, concentrated, and diluted with EtOAc (20 mL). The organic phase was washed with sat. NaHCO₃ (aq.) (2×10 mL), brine (10 mL), dried over Na₂SO₄, filtered and concentrated. The product was dried in vacuo to afford title compound (40 mg, 0.069 mmol, 82% yield) as an orange oil which was used in subsequent steps without further purification or characterization. MS (ESI) 581 (M+H).

Step C. Example 178

The title compound was prepared according to methods described for the synthesis of Example 151 (Step C), substituting Intermediate 178B where appropriate: (2.8 mg, 4.8 μmol, 8% yield). ¹H NMR (400 MHz, DMSO-d₆) δ 13.06 (s, 1H), 8.13 (s, 1H), 7.94 (dd, J=8.3, 1.5 Hz, 1H), 7.74 (d, J=8.3 Hz, 1H), 7.68-7.61 (m, 2H), 7.61-7.53 (m, 1H), 4.26 (s, 2H), 2.97 (s, 2H), 2.32-2.25 (m, 1H), 1.92-1.82 (m, 6H), 1.34-1.20 (m, 6H), 1.17-1.07 (m, 4H). FXR EC$_{50}$ (nM)=910. MS (ESI) 568 (M+H).

Example 179

2-(4-(((5-cyclopropyl-3-(2,6-dichlorophenyl)isoxazol-4-yl)methoxy)methyl) bicyclo[2.2.2]octan-1-yl)-4-methylthiazole-5-carboxylic acid

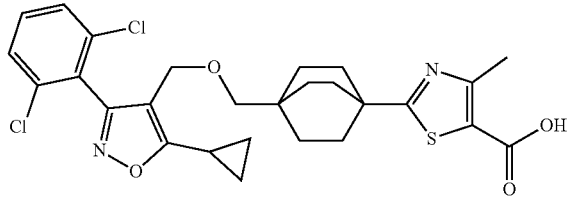

(179)

Step A. Intermediate 179A. Preparation of ethyl 2-(4-(((5-cyclopropyl-3-(2,6-dichlorophenyl)isoxazol-4-yl)methoxy)methyl)bicyclo[2.2.2]octan-1-yl)-4-methylthiazole-5-carboxylate

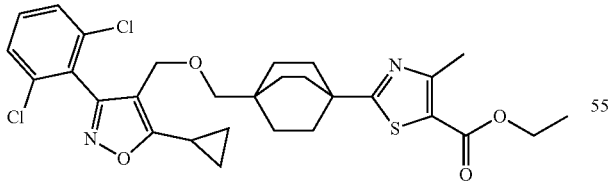

To a stirred solution of Intermediate 162A (40 mg, 0.086 mmol) in ethanol (1.5 mL) was added ethyl 2-chloroacetoacetate (16 mg, 0.095 mmol). After stirring at 100° C. for 18 h, the reaction mixture cooled, diluted with water (20 mL), and extracted with EtOAc (2×20 mL). The combined organic phase was dried over Na₂SO₄, filtered and concentrated. The crude product was purified by flash column chromatography (4 g silica gel cartridge; A=Hex, B=EtOAc; 10 min grad.; 0% B to 60% B; flow rate=4 mL/min). The pure fractions were combined, concentrated and dried in vacuo to afford the title compound (15 mg, 0.026 mmol, 30% yield) as yellow liquid which was used in subsequent steps without further purification or characterization. MS (ESI) 575 (M+H).

Step B. Example 179

The title compound was prepared according to methods described for the synthesis of Example 151 (Step C), substituting Intermediate 178B where appropriate: (0.8 mg, 1.5 μma 7% yield). ¹H NMR (400 MHz, DMSO-d₆) δ 7.72-7.60 (m, 2H), 7.59-7.48 (m, 1H), 4.24 (s, 2H), 2.93 (s, 2H), 2.54 (s, 3H), 2.32-2.25 (m, 1H), 1.80-1.63 (m, 6H), 1.33-1.19 (m, 6H), 1.18-1.00 (m, 4H). FXR EC$_{50}$ (nM)=560. MS (ESI) 548 (M+H).

Example 180

(E)-2-(4-(2-(5-cyclopropyl-3-(2,6-dichlorophenyl)isoxazol-4-yl)vinyl) bicyclo[2.2.2]octan-1-yl)benzo[d]thiazole-6-carboxylic acid

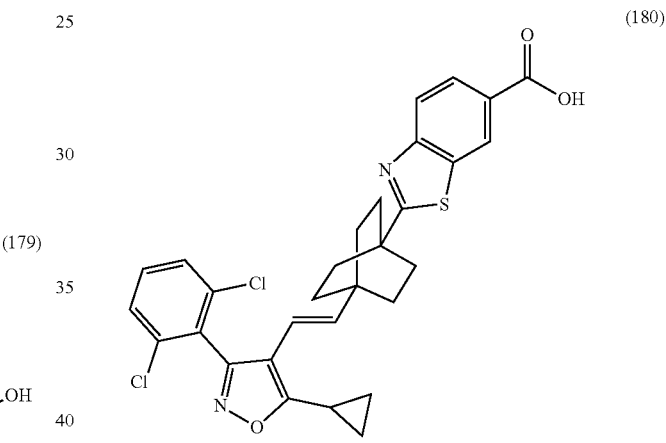

(180)

Step A. Intermediate 180A. Preparation of methyl 3-chloro-4-(4-(2-(5-cyclopropyl-3-(2,6-dichlorophenyl)isoxazol-4-yl)vinyl)bicyclo[2.2.2]octane-1-carboxamido)benzoate

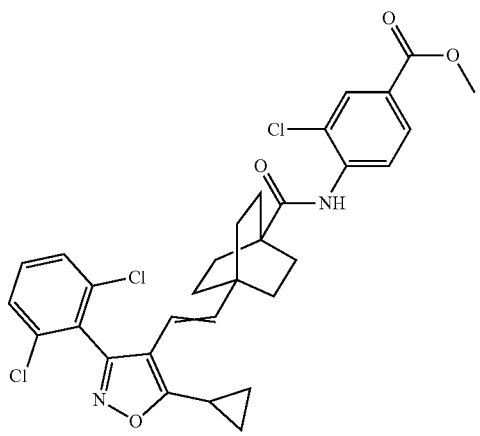 [SMILES: COC(=O)c1ccc(NC(=O)C23CCC(C=Cc4c(-c5c(Cl)cccc5Cl)noc4C4CC4)(CC2)CC3)c(Cl)c1]

To a solution of methyl 4-amino-3-chlorobenzoate (25 mg, 0.14 mmol) and Intermediate 159E (50 mg, 0.10 mmol) in DCM (2 mL) was added pyridine (0.059 mL, 0.34 mmol). The mixture was cooled to 0° C., and phosphorus oxychloride (39 mg, 0.26 mmol) was added and the reaction was stirred at rt. After 18 h, the mixture was diluted with DCM (20 mL) and washed with water (2×10 mL). The organic phase was combined, dried over $Na_2SO_4$, filtered and concentrated. The crude product was purified by flash column chromatography (24 g silica gel cartridge; A=Hex, B=EtOAc; 15 min grad.; 0% B to 50% B; flow rate=40 mL/min). The pure fractions were combined, concentrated and dried in vacuo to afford the title compound (0.045 g, 0.057 mmol, 55% yield) as a colorless residue. $^1$H NMR (400 MHz, DMSO-$d_6$) δ 8.89 (s, 1H), 7.97 (s, 1H), 7.87-7.80 (m, 2H), 7.68-7.62 (m, 3H), 6.01 (d, J=16.4 Hz, 1H), 5.23 (d, J=16.4 Hz, 1H), 3.85 (s, 3H), 1.81-1.77 (m, 7H), 1.49-1.35 (m, 6H), 1.26-1.08 (m, 4H). MS (ESI) 601 (M+H).

Step B. Intermediate 180B. Preparation of methyl 3-chloro-4-(4-(2-(5-cyclopropyl-3-(2,6-dichlorophenyl)isoxazol-4-yl)vinyl)bicyclo[2.2.2]octane-1-carbothiamido)benzoate

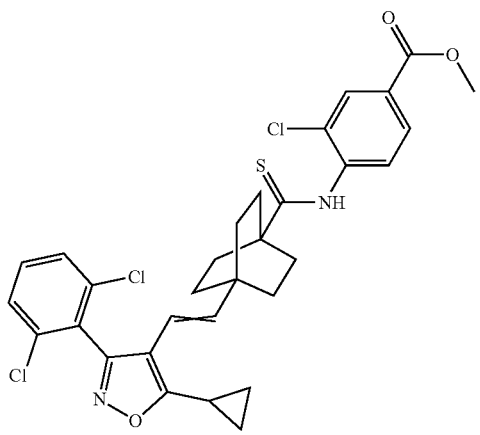 [SMILES: COC(=O)c1ccc(NC(=S)C23CCC(C=Cc4c(-c5c(Cl)cccc5Cl)noc4C4CC4)(CC2)CC3)c(Cl)c1]

The title compound was prepared according to methods described for the synthesis of Intermediate 168A, substituting Intermediate 180A where appropriate: (30 mg, 0.049 mmol, 97% yield). MS (ESI) 617.0 (M+H).

Step C. Example 180

The title compound was prepared according to methods described for the synthesis of Example 168 (Step B), substituting Intermediate 180B where appropriate. The cis/trans isomers were separated by preparative HPLC (Column: Waters XBridge C18, 19×150 mm, 5-μm particles; Mobile Phase A: 10-mM ammonium acetate; Mobile Phase B: acetonitrile; Gradient: 15-75% B over 25 minutes, then a 5-minute hold at 100% B; Flow: 15 mL/min) to provide the title compound (6.7 mg, 0.011 mmol, 19% yield). $^1$H NMR (400 MHz, DMSO-$d_6$) 13.07 (s, 1H), 8.66 (d, J=1.0 Hz, 1H), 8.07-7.91 (m, 2H), 7.73-7.65 (m, 2H), 7.64-7.56 (m, 1H), 6.05 (d, J=16.4 Hz, 1H), 5.27 (d, J=16.6 Hz, 1H), 2.40-2.34 (m, 1H), 2.03-1.89 (m, 6H), 1.59-1.42 (m, 7H), 1.21-1.13 (m, 2H), 1.12-1.02 (m, 2H). FXR $EC_{50}$ (nM)=43. MS (ESI) 567.2 (M+H). The product thus obtained was predominantly the trans isomer as determined by $^1$H NMR based on integration of characteristic protons. The cis isomer is designated below as Example 181.

Example 181

(Z)-2-(4-(2-(5-cyclopropyl-3-(2,6-dichlorophenyl)isoxazol-4-yl)vinyl)bicyclo[2.2.2]octan-1-yl)benzo[d]thiazole-6-carboxylic acid

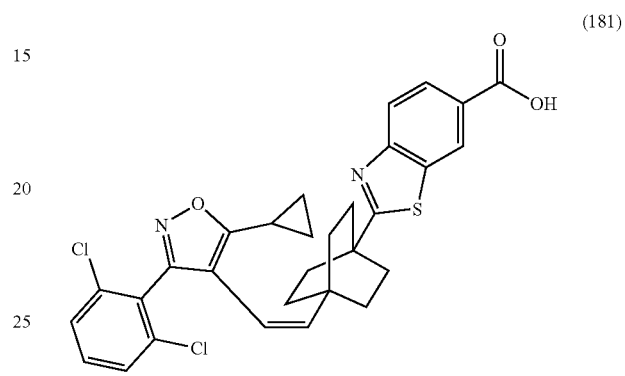

The title compound was obtained by separating the trans/cis isomers in Step C for the preparation of Example 180: (2.1 mg, 3.6 μmol 6% yield). $^1$H NMR (400 MHz, DMSO-$d_6$) δ 8.65 (s, 1H), 8.07-7.91 (m, 2H), 7.74-7.62 (m, 2H), 7.61-7.52 (m, 1H), 5.81 (d, J=12.2 Hz, 1H), 5.63 (d, J=12.5 Hz, 1H), 2.13-2.04 (m, 1H), 1.97-1.85 (m, 6H), 1.65-1.50 (m, 6H), 1.22-1.01 (m, 4H). FXR $EC_{50}$ (nM)=780. MS (ESI) 567.2 (M+H). The product thus obtained was predominantly the cis isomer as determined by $^1$H NMR based on integration of characteristic protons. The trans isomer is designated above as Example 180.

Example 182

(E)-2-(4-(2-(5-cyclopropyl-3-(2-(trifluoromethoxy)phenyl)isoxazol-4-yl)vinyl) bicyclo[2.2.2]octan-1-yl)benzo[d]thiazole-6-carboxylic acid

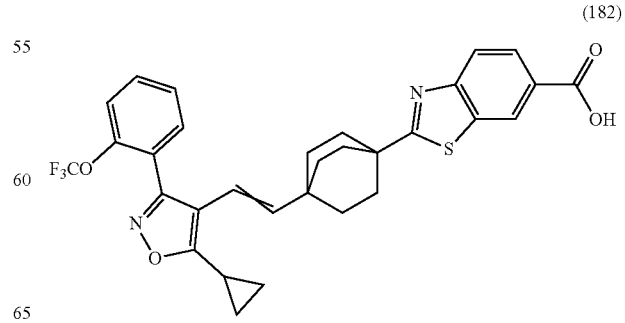

Step A. Intermediate 182A. Preparation of 5-cyclopropyl-3-(2-trifluoromethoxyphenyl)isoxazol-4-yl)methyl)triphenylphosphonium bromide

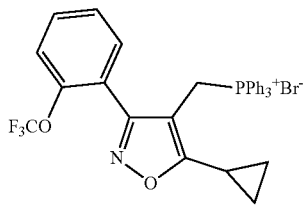

The title compound was prepared according to methods described for the synthesis of Intermediate 159C, substituting 4-(bromomethyl)-5-cyclopropyl-3-(2-(trifluoromethoxy)phenyl)isoxazole where appropriate: (1.2 g, 1.7 mmol, 87% yield, white solid). $^1$H NMR (400 MHz, DMSO-d$_6$) δ 7.84-7.80 (m, 3H), 7.62-7.40 (m, 13H), 7.39-7.28 (m, 3H), 4.93 (d, J=13.6H, 2H), 1.76-1.66 (m, 1H), 0.73-0.56 (m, 4H). MS (ESI) 544. (M+H).

Step B. Intermediate 182B. Preparation of methyl 4-(2-(5-cyclopropyl-3-(2-trifluoromethoxyphenyl)isoxazol-4-yl)vinyl)bicyclo[2.2.2]octane-1-carboxylate

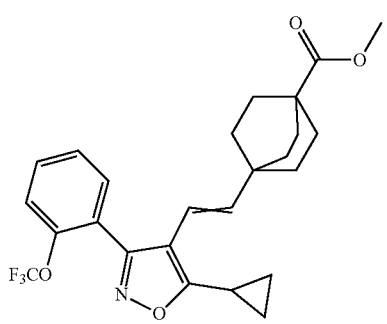 [SMILES: COC(=O)C12CCC(C=Cc3c(-c4ccccc4OC(F)(F)F)noc3C3CC3)(CC1)CC2]

The title compound was prepared according to methods described for the synthesis of Intermediate 159D, substituting Intermediate 182A where appropriate: (0.22 g, 0.42 mmol, 55% yield). The product was obtained as a mixture of trans/cis isomers. $^1$H NMR (400 MHz, DMSO-d$_6$) δ 7.58-7.52 (m, 4H), 5.92-5.86 (m, 1H), 5.54-5.51 (m, 1H), 3.55 (s, 3H), 1.76-1.11 (m, 17H). MS (ESI) 462 (M+H).

Step C. Intermediate 182C. Preparation of 4-(2-(5-cyclopropyl-3-(2-trifluoromethoxy phenyl)isoxazol-4-yl)vinyl)bicyclo[2.2.2]octane-1-carboxylic acid

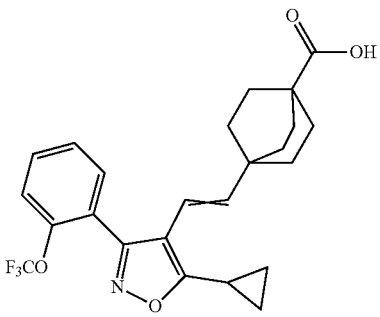

The title compound was prepared according to methods described for the synthesis of Intermediate 159E, substituting Intermediate 182B where appropriate: (0.17 g, 0.38 mmol, 88% yield). MS (ESI) 448.5 (M+H).

Step D. Intermediate 182D. Preparation of methyl 3-chloro-4-(4-(2-(5-cyclopropyl-3-(2-trifluoromethoxyphenyl)isoxazol-4-yl)vinyl)bicyclo[2.2.2]octane-1-carboxamido)benzoate The title compound was prepared according to methods described for the synthesis of Intermediate 170A, substituting Intermediate 182C where appropriate: (25 mg, 0.018 mmol, 9% yield, white solid). $^1$H NMR (400 MHz, DMSO-d$_6$) δ 8.92-8.86 (m, 1H), 7.97-7.92 (m, 1H), 7.89-7.74 (m, 2H), 7.56-7.52 (m, 3H), 5.92-5.86 (m, 1H), 5.58-5.54 (m, 1H), 3.85 (s, 3H), 1.85-1.11 (m, 17H). MS (ESI) 617 (M+H).

Step E. Intermediate 182E. Preparation of methyl 3-chloro-4-(4-(2-(5-cyclopropyl-3-(2-trifluoromethoxyphenyl)isoxazol-4-yl)vinyl)bicyclo[2.2.2]octane-1-carbothiamido) benzoate

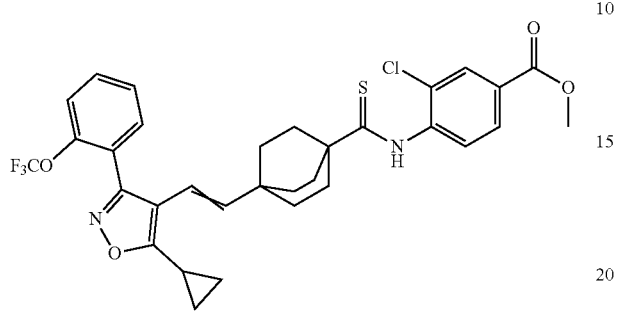

The title compound was prepared according to methods described for the synthesis of Intermediate 168A, substituting Intermediate 182D where appropriate: (0.020 g, 0.032 mmol, 78% yield). MS (ESI) 631 (M+H).

Step F. Example 182

The title compound was prepared according to methods described for the synthesis of Example 168 (Step B), substituting Intermediate 182E where appropriate: (2.0 mg, 3.3 μmol, 11% yield). $^1$H NMR (400 MHz, DMSO-d$_6$) δ 8.65 (d, J=1.0 Hz, 1H), 7.99-7.96 (m, 2H), 7.71-7.68 (m, 1H), 7.57-7.55 (m, 3H), 5.97 (d, J=16.4 Hz, 1H), 5.55 (d, J=16.4 Hz, 1H), 2.32-2.02 (m, 1H), 2.00-1.96 (m, 6H), 1.57-1.53 (m, 6H), 1.17-1.13 (m, 4H). FXR EC$_{50}$ (nM)=100. MS (ESI) 581 (M+H).

Example 193

3-(5-(4-((5-cyclopropyl-3-(2,6-dichlorophenyl)isoxazol-4-yl)methoxy)-2-oxabicyclo[2.2.2]octan-1-yl)-1,2,4-oxadiazol-3-yl)benzoic acid

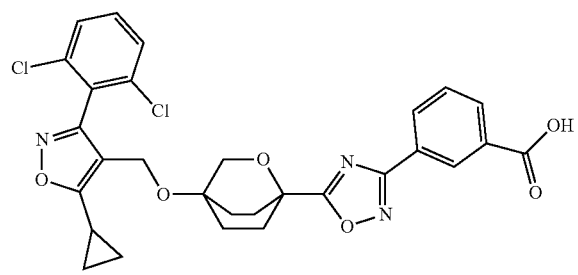

(193)

Step A. Intermediate 193A. Preparation of (4-(1,3-dithian-2-yl)-4-hydroxycyclohexane-1,1-diyl)bis(methylene) bis(4-methylbenzenesulfonate)

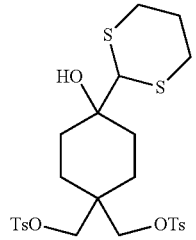 [SMILES: Cc1ccc(S(=O)(=O)OCC2(COS(=O)(=O)c3ccc(C)cc3)CCC(O)(C3SCCCS3)CC2)cc1]

To a stirring solution of 1,3-dithiane (4.6 g, 39 mmol) in THF (90 mL) was added dropwise n-butyllithium (17 mL, 42 mmol) (2.5 M solution in hexanes) at −78° C. The reaction was allowed to slowly warm to 0° C. and stirred at this temperature for 1 h. The reaction mixture was cooled −78° C., and a solution of (4-oxocyclohexane-1,1-diyl)bis(methylene) bis(4-methylbenzenesulfonate) (15 g, 32 mmol) (*ACS Med Chem. Lett.* 2014, 5, 609-614) dissolved in THF (60 mL) was added. The reaction was warmed to rt and stirred. After 1 h, the mixture was quenched with sat. NH$_4$Cl (aq.) (400 mL) and extracted with EtOAc (2×200 mL). The organic phase was combined, washed with brine, dried over Na$_2$SO$_4$, filtered and concentrated. The crude product was purified by flash column chromatography (80 g silica gel cartridge; A=CH$_3$Cl, B=MeOH; 25 min grad.; 0% B to 7% B; flow rate=40 mL/min). The pure fractions were combined, concentrated and dried in vacuo to afford the title compound (14 g, 20 mmol, 61% yield) as a white solid. $^1$H NMR (400 MHz, DMSO-d$_6$) δ 7.73 (dd, J=2.80, 8.20 Hz, 4H), 7.48 (d, J=7.20 Hz, 4H), 4.54 (s, 1H), 4.05 (s, 1H), 3.84 (s, 2H), 3.67 (s, 2H), 2.78-2.84 (m, 4H), 2.42 (s, 6H), 1.80-2.00 (m, 1H), 1.50-1.70 (m, 1H), 1.19-1.39 (m, 8H). MS (ESI) 587 (M+H).

Step B. Intermediate 193B. Preparation of (1-(1,3-dithian-2-yl)-2-oxabicyclo[2.2.2]octan-4-yl)methyl 4-methylbenzenesulfonate

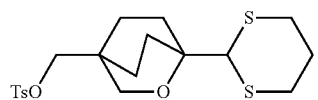 [SMILES: Cc1ccc(S(=O)(=O)OCC23CCC(C4SCCCS4)(CC2)OC3)cc1]

To a stirred solution of Intermediate 193A (3.2 g, 5.5 mmol) in THF (100 mL) was added powdered NaOH (0.65 g, 16 mmol). The reaction mixture was stirred at reflux. After 18 h, the reaction was cooled and the solvent was concentrated. The residue was diluted with water (50 mL) and extracted with EtOAc (2×50 mL). The combined organic layer was washed with brine, dried over Na$_2$SO$_4$, filtered and concentrated. The product was dried in vacuo to afford the title compound (2.6 g, 4.5 mmol, 83% yield) as an off-white solid. $^1$H NMR (400 MHz, DMSO-d$_6$) δ 7.78 (d, J=8.40 Hz, 2H), 7.49 (d, J=8.00 Hz, 2H), 4.17 (s, 1H), 3.74 (s, 2H), 3.48 (s, 2H), 2.81-2.84 (m, 4H), 2.34 (s, 3H), 1.90-2.00 (m, 1H), 1.85-1.87 (m, 2H), 1.63-1.65 (m, 3H), 1.42-1.51 (m, 4H). MS (ESI) 587 (M+H).

Step C. Intermediate 193C. Preparation of (1-formyl-2-oxabicyclo[2.2.2]octan-4-yl) methyl 4-methylbenzenesulfonate

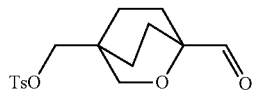

To a stirred solution of Intermediate 193B (2.4 g, 5.8 mmol) in DCM (100 mL) and water (12 mL) was added NCS (2.7 g, 20 mmol). After stirring 1 h, the reaction mixture was washed with water (150 mL) and brine. The organic phase was dried over $Na_2SO_4$, filtered and concentrated. The product was used in subsequent steps without purification. $^1$H NMR (400 MHz, DMSO-$d_6$) δ 11.05 (s, 1H), 7.78 (d, J=8.00 Hz, 2H), 7.49 (d, J=8.00 Hz, 2H), 3.78 (s, 2H), 3.45 (s, 2H), 2.45 (s, 3H), 1.85-1.75 (m, 4H), 1.49-1.42 (m, 4H).

Step D. Intermediate 193D. Preparation of 4-((tosyloxy)methyl)-2-oxabicyclo[2.2.2]octane-1-carboxylic acid

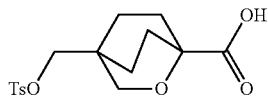

To a solution of Intermediate 193C (2.4 g, 7.4 mmol) in t-butanol (72 mL) was added 2-methyl-2-butene (2.4 mL, 22 mmol). To this mixture was added sodium chlorite (3.4 g, 37 mmol) and sodium dihydrogen phosphate monohydrate (8.9 g, 74 mmol) dissolved in water (24 mL). After stirring 1 h, the reaction mixture was concentrated, diluted with water (50 mL) and acidified with 1.5 M HCl (aq.) solution. The aqueous phase was extracted with EtOAc (2×50 mL), the organic phase was combined, dried over $Na_2SO_4$, filtered and concentrated. The product was used in subsequent steps without purification. MS (ESI) 341 (M+H).

Step E. Intermediate 193E. Preparation of methyl 4-((tosyloxy)methyl)-2-oxabicyclo[2.2.2]octane-1-carboxylate

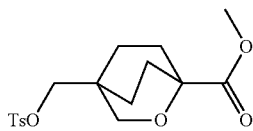 [SMILES: COC(=O)C12CCC(COS(=O)(=O)c3ccc(C)cc3)(CC1)CO2]

To a stirred solution of Intermediate 193D (2.8 g, 8.2 mmol) in DMF (40 mL) was added $K_2CO_3$ (2.3 g, 17 mmol). After stirring 5 min, iodomethane (1.0 mL, 17 mmol) was added. After 30 min, the solvent was concentrated and the crude product was purified by flash column chromatography (24 g silica gel cartridge; A=Hex, B=EtOAc; 15 min grad.; 0% B to 50% B; flow rate=24 mL/min). The pure fractions were combined, concentrated and dried in vacuo to afford the title compound (1.4 g, 3.9 mmol, 48% yield) as brown solid. $^1$H NMR (400 MHz, DMSO-$d_6$) δ 7.78 (d, J=8.40 Hz, 2H), 7.49 (d, J=8.00 Hz, 2H), 3.76 (s, 2H), 3.60 (s, 3H), 3.55 (s, 2H), 2.43 (s, 3H), 1.82-1.89 (m, 4H), 1.52-1.54 (m, 4H). MS (ESI) 355 (M+H).

Step F. Intermediate 193F. Preparation of methyl 4-(acetoxymethyl)-2-oxabicyclo[2.2.2]octane-1-carboxylate

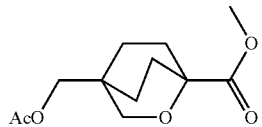

To a stirred solution of Intermediate 193E (1.4 g, 4.0 mmol) in DMF (20 mL) was added cesium acetate (1.9 g, 9.9 mmol). After stirring 4 h at 120° C., the reaction was cooled and the solvent was concentrated. The residue was diluted with water (50 mL) and extracted with EtOAc (2×80 mL). The combined organic layer was washed with brine, dried over $Na_2SO_4$, filtered and concentrated. The product was dried in vacuo to afford the title compound (0.85 g, 3.5 mmol, 89% yield). $^1$H NMR (400 MHz, DMSO-$d_6$) δ 3.76 (s, 3H), 3.62 (s, 4H), 2.02 (s, 3H), 1.85-1.96 (m, 4H), 1.50-1.70 (m, 4H).

Step G. Intermediate 193G. Preparation of methyl 4-(hydroxymethyl)-2-oxabicyclo[2.2.2]octane-1-carboxylate

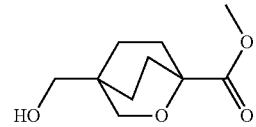

To Intermediate 193F (0.85 g, 3.5 mmol) was added HCl (8.0 mL, 24 mmol) (3 M in MeOH) and stirred at rt. After 2 h, the reaction mixture was concentrated and co-distilled with toluene (2×20 mL) to afford the title compound (0.68 g, 3.4 mmol, 97% yield) as a brown semisolid. $^1$H NMR (400 MHz, DMSO-$d_6$) δ 3.63 (s, 2H), 3.63 (s, 3H), 3.10 (s, 2H), 1.80-1.94 (m, 4H), 1.53-1.61 (m, 2H), 1.42-1.49 (m, 2H).

Step H. Intermediate 193H. Preparation of 1-(methoxycarbonyl)-2-oxabicyclo[2.2.2]octane-4-carboxylic acid

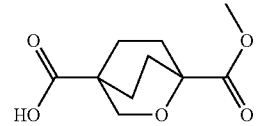

To a stirred solution of Intermediate 193G (680 mg, 3.4 mmol) in DMF (10 mL) was added pyridinium dichromate (450 mg, 12 mmol) at 0° C. The mixture was warmed to rt, and stirred at 40° C. After 3 h, the reaction mixture was diluted with water (50 mL) and extracted with EtOAc (5×30 mL). The combined organic layer was washed with brine, dried over Na$_2$SO$_4$, filtered and concentrated. The product was dried in vacuo to afford the title compound (580 mg, 2.7 mmol, 80% yield) as brown solid. $^1$H NMR (400 MHz, DMSO-d$_6$) δ 12.50 (s, 1H), 3.85 (s, 2H), 3.62 (s, 3H), 1.97-1.85 (m, 8H).

Step I. Intermediate 193I. Preparation of methyl 4-(((benzyloxy)carbonyl)amino)-2-oxabicyclo[2.2.2]octane-1-carboxylate

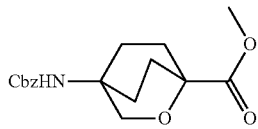 [SMILES: COC(=O)C12CCC(NC(=O)OCc3ccccc3)(CC1)CO2]

To a stirred solution of Intermediate 193H (580 mg, 2.7 mmol) in toluene (12 mL) was added DIEA (0.95 mL, 5.4 mmol) followed by the dropwise addition of DPPA (0.70 mL, 3.3 mmol) at 10° C. After stirring 2 h at reflux, the mixture was cooled to 60° C. and benzyl alcohol (0.56 mL, 5.4 mmol) was added. Stirring was continued at reflux. After 18 h, the mixture was cooled and diluted with EtOAc (30 mL). The organic layer was washed with water (20 mL), brine, dried over Na$_2$SO$_4$, filtered and concentrated. The crude product was purified by flash column chromatography (24 g silica gel cartridge; A=Hex, B=EtOAc; 15 min grad.; 0% B to 70% B; flow rate=24 mL/min). The pure fractions were combined, concentrated and dried in vacuo to afford the title compound (400 mg, 1.3 mmol, 46% yield) as brown semisolid. $^1$H NMR (400 MHz, DMSO-d$_6$) δ 7.31-7.38 (m, 5H), 7.23 (s, 1H), 5.75 (s, 2H), 3.85 (s, 2H), 3.61 (s, 3H), 1.84-2.00 (m, 8H). MS (ESI) 320 (M+H).

Step J. Intermediate 193J. Preparation of 4-(((benzyloxy)carbonyl)amino)-2-oxabicyclo[2.2.2]octane-1-carboxylic acid

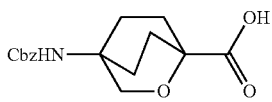

To a stirred solution of Intermediate 193I (400 mg, 1.3 mmol) in MeOH (8 mL) was added NaOH (130 mg, 3.1 mmol) in water (1 mL). After stirring at 75° C. for 1 h, the reaction mixture was cooled and concentrated. The residue was diluted with water (10 mL) and washed with EtOAc (10 mL). The aqueous layer was acidified (pH ~2) with 1.5 M HCl (aq.) solution and extracted with EtOAc (2×25 mL). The combined organic layer was washed with brine, dried over Na$_2$SO$_4$, filtered and concentrated. The product was dried in vacuo to afford the title compound (340 mg, 1.1 mmol, 89% yield) as a brown semisolid. $^1$H NMR (400 MHz, DMSO-d$_6$) δ 7.29-7.38 (m, 5H), 7.19 (s, 1H), 4.96 (s, 2H), 3.82 (s, 2H), 1.81-1.99 (m, 8H). MS (ESI) 306 (M+H).

Step K. Intermediate 193K. Preparation of 4-amino-2-oxabicyclo[2.2.2]octane-1-carboxylic acid hydrochloride

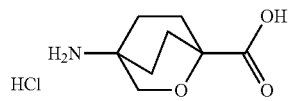

To a stirred solution of Intermediate 193J (340 mg, 1.1 mmol) in MeOH (5 mL) was added 1.25 M HCl (aq.) (1.4 mL, 1.1 mmol). The reaction vessel was purged and flushed with N$_2$, then palladium on carbon (120 mg, 0.11 mmol) (10% wt. loading, matrix activated carbon support) was added and the vessel was purged and flushed again. The reaction was stirred under hydrogen (1 atm, balloon). After 4 h, the reaction mixture was filtered and filtrate was concentrated and co-distilled with toluene (2×10 mL) to afford the title compound (230 mg, 1.1 mmol, 99% yield) as a white solid. $^1$H NMR (400 MHz, DMSO-d$_6$) δ 8.43 (s, 2H), 3.80 (s, 2H), 1.85-2.03 (m, 8H). MS (ESI) 172 (M+H).

Step L. Intermediate 193L. Preparation of 4-hydroxy-2-oxabicyclo[2.2.2]octane-1-carboxylic acid

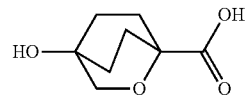

To a stirred solution of Intermediate 193K (250 mg, 1.5 mmol) in AcOH (2 mL, 10% v/v) was added dropwise sodium nitrite (300 mg, 4.4 mmol) dissolved in water (1 mL) at 0° C. After completion of addition, the reaction mixture was stirred at 65° C. After 18 h, the reaction mixture was cooled to 5° C. and a solution of KOH (740 mg, 13 mmol) dissolved in MeOH (0.8 mL) was added dropwise. After stirring at 65° C. for 4 h, the reaction mixture was cooled and concentrated. The residue was diluted with water (10 mL), acidified with conc. HCl (pH ~2) and extracted with EtOAc (2×25 mL). The combined organic layer was washed with brine, dried over Na$_2$SO$_4$, filtered and concentrated. The product was dried in vacuo to afford the title compound (100 mg, 0.58 mmol, 39% yield) as a brown semisolid. $^1$H NMR (400 MHz, DMSO-d$_6$) δ 3.52 (s, 2H), 1.91-1.97 (m, 4H), 1.60-1.71 (m, 4H). MS (ESI) 171.0 (M–H).

Step M. Intermediate 193M. Preparation of methyl 3-(5-(4-hydroxy-2-oxabicyclo[2.2.2]octan-1-yl)-1,2,4-oxadiazol-3-yl)benzoate

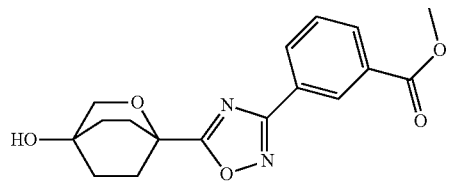 [SMILES: COC(=O)c1cccc(-c2noc(C34CCC(O)(CC3)CO4)n2)c1]

To a stirred solution of Intermediate 193L (50 mg, 0.29 mmol) in DMF (1 mL) were added TEA (0.12 mL, 0.87 mmol), methyl 3-(N'-hydroxycarbamimidoyl)benzoate (110 mg, 0.58 mmol) followed by BOP (140 mg, 0.32 mmol). After stirring 30 min at rt, the reaction mixture was heated and stirred at 100° C. After 2 h, the reaction mixture was cooled, concentrated and the residue was diluted with water (10 mL) and extracted with EtOAc (2×10 mL). The combined organic phase was washed with water (20 mL), brine, dried over $Na_2SO_4$, filtered and concentrated. The crude product was purified by flash column chromatography (12 g silica gel cartridge; A=Hex, B=EtOAc; 15 min grad.; 0% B to 70% B; flow rate=12 mL/min). The pure fractions were combined, concentrated and dried in vacuo to afford the title compound (120 mg, 0.16 mmol, 53% yield) as a brown semisolid. MS (ESI) 331 (M+H).

Step N. Intermediate 193N. Preparation of methyl 3-(5-(4-((5-cyclopropyl-3-(2,6-dichlorophenyl)isoxazol-4-yl)methoxy)-2-oxabicyclo[2.2.2]octan-1-yl)-1,2,4-oxadiazol-3-yl)benzoate

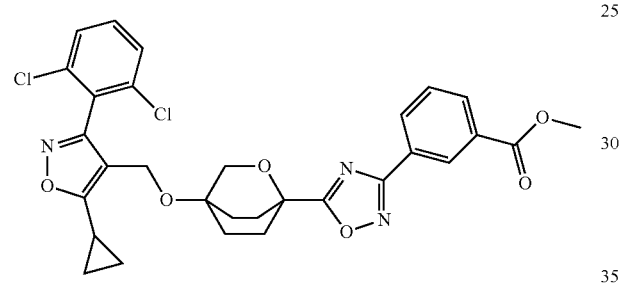

To a stirred solution of Intermediate 193M (50 mg, 0.15 mmol) in DCM (1 mL) was added silver trifluoromethanesulfonate (120 mg, 0.45 mmol) followed by 2,6-di-tert-butylpyridine (120 mg, 0.61 mmol). To this mixture was added 4-(bromomethyl)-5-cyclopropyl-3-(2,6-dichlorophenyl)isoxazole (160 mg, 0.45 mmol) in DCM (0.5 mL) and the resulting mixture was stirred at rt. After 18 h, the reaction mixture was diluted with DCM (15 mL) and filtered through Celite. The organic phase was washed with water (10 mL), brine, dried over $Na_2SO_4$, filtered and concentrated. The crude product was purified by flash column chromatography (12 g silica gel cartridge; A=Hex, B=EtOAc; 15 min grad.; 0% B to 50% B; flow rate=12 mL/min). The pure fractions were combined, concentrated and dried in vacuo to afford the title compound (50 mg, 0.041 mmol, 27% yield). MS (ESI) 596 (M+H).

Step O. Example 193

The title compound was prepared according to methods described for the synthesis of Example 151 (Step C), substituting Intermediate 193N where appropriate: (8.0 mg, 0.014 mmol, 16% yield). $^1$H NMR (400 MHz, METHANOL-$d_4$) δ 8.66 (s, 1H), 8.13-8.08 (m, 2H), 7.60-7.51 (m, 4H), 4.34 (s, 2H), 3.65 (s, 2H), 2.40-2.36 (m, 2H), 2.30-2.23 (m, 3H), 1.99-1.93 (m, 2H), 1.71-1.67 (m, 2H), 1.21-1.17 (m, 4H). FXR $EC_{50}$ (nM)=26. MS (ESI) 582 (M+H).

Example 194

(E)-4-(4-(2-(5-cyclopropyl-3-(2,6-dichlorophenyl)isoxazol-4-yl)vinyl)-2-oxabicyclo[2.2.2]octan-1-yl)benzoic acid

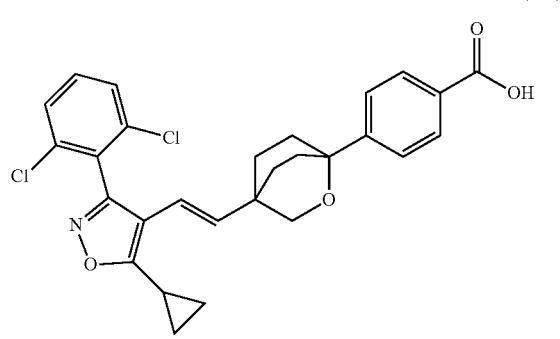

(194)

Step A. Intermediate 194A. Preparation of methyl 4-(1-hydroxy-4,4-bis((tosyloxy)methyl)cyclohexyl)benzoate

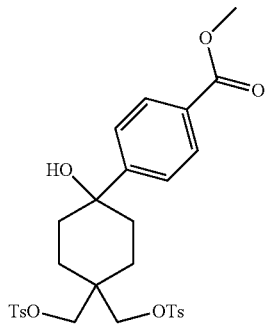 [SMILES: COC(=O)c1ccc(C2(O)CCC(COS(=O)(=O)c3ccc(C)cc3)(COS(=O)(=O)c3ccc(C)cc3)CC2)cc1]

To a stirred solution of methyl 4-iodobenzoate (1.8 g, 6.7 mmol) in THF (10 mL) was added isopropyl magnesium chloride (5.4 mL, 7.0 mmol) at 0° C. The mixture was warmed to 5° C. and stirred for 10 min. The reaction mixture was cooled to 0° C. and a solution of (4-oxocyclohexane-1,1-diyl)bis(methylene)bis(4-methyl benzenesulfonate) (2.5 g, 5.4 mmol) (*ACS Med Chem. Lett.* 2014, 5, 609-614) in THF (5 mL) was added dropwise. The mixture was warmed to 5° C. and stirred. After 1 h, the reaction was quenched with sat. $NH_4Cl$ (aq.) (10 mL) and extracted with EtOAc (2×25 mL). The combined organic phase was washed with water (10 mL), brine, dried over $Na_2SO_4$, filtered and concentrated. The crude product was purified by flash column chromatography (24 g silica gel cartridge; A=Hex, B=EtOAc; 15 min grad.; 25% B to 50% B; flow rate=24 mL/min). The pure fractions were combined, concentrated and dried in vacuo to afford the title compound (2.7 g, 2.8 mmol, 52% yield) as yellow solid. MS (ESI) 620 (M+H+17).

Step B. Intermediate 194B. Preparation of 4-(4-((tosyloxy)methyl)-2-oxabicyclo[2.2.2]octan-1-yl)benzoic acid

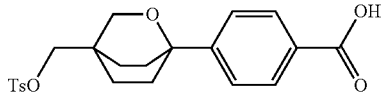

To a stirred solution of Intermediate 194A (2.7 g, 4.5 mmol) in THF (75 mL) was added powdered NaOH (0.18 g, 4.5 mmol). The mixture was stirred at reflux for 18 h, cooled to rt and concentrated. The residue was diluted with water (50 mL) and acidified (pH ~2) with 1.5 M HCl (aq.), and extracted with EtOAc (2×100 mL). The combined organic phase was washed with brine, dried over $Na_2SO_4$, filtered and concentrated. The product was dried in vacuo to afford the title compound (1.8 g, 4.3 mmol, 96% yield) which was used in subsequent steps without further purification or characterization. MS (ESI) 434 (M+H+17).

Step C. Intermediate 194C. Preparation of methyl 4-(4-((tosyloxy)methyl)-2-oxabicyclo[2.2.2]octan-1-yl)benzoate

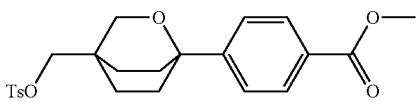

To a stirred solution of Intermediate 194B (1.8 g, 4.3 mmol) in DMF (20 mL) was added $K_2CO_3$ (1.2 g, 8.6 mmol). After stirring 10 min, iodomethane (0.54 mL, 8.6 mmol) was added. After stirring 1 h, the mixture was concentrated, and the crude material was purified by flash column chromatography (24 g silica gel cartridge; A=Hex, B=EtOAc; 15 min grad.; 25% B to 100% B; flow rate=24 mL/min). The pure fractions were combined, concentrated and dried in vacuo to afford the title compound (1.0 g, 2.0 mmol, 47% yield) as a white solid. MS (ESI) 448 (M+H+17).

Step D. Intermediate 194D. Preparation of methyl 4-(4-(acetoxymethyl)-2-oxabicyclo[2.2.2]octan-1-yl)benzoate

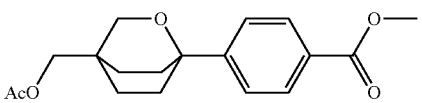 [SMILES: COC(=O)c1ccc(C23CCC(COC(C)=O)(CC2)CO3)cc1]

To a stirred solution of Intermediate 194C (0.90 g, 2.1 mmol) in DMF (10 mL) was added cesium acetate (1.0 g, 5.2 mmol). After stirring at 120° C. for 4 h, the reaction mixture was cooled to rt and concentrated. The residue was diluted with water (50 mL) and extracted with EtOAc (2×80 mL). The combined organic phase was washed with brine, dried over $Na_2SO_4$, filtered and concentrated. The product was dried in vacuo to afford the title compound (660 mg, 1.6 mmol, 78% yield) as a brown semisolid. $^1$H NMR (400 MHz, DMSO-$d_6$) δ 7.90 (dd, J=1.60, 6.80 Hz, 2H), 7.53 (dd, J=1.60, 6.80 Hz, 2H), 3.84 (s, 3H), 3.82 (s, 2H), 2.84 (s, 2H), 2.14-2.08 (m, 2H), 2.04 (s, 3H), 1.85-1.68 (m, 6H). MS (ESI) 319 (M+H).

Step E. Intermediate 194E. Preparation of methyl 4-(4-(hydroxymethyl)-2-oxabicyclo[2.2.2]octan-1-yl)benzoate

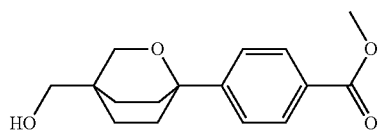

To a stirred solution of Intermediate 194D (660 mg, 2.1 mmol) in MeOH (7 mL) was added sodium methoxide (45 mg, 0.21 mmol) (25% w/v in MeOH). After stirring 1 h, the reaction mixture was diluted with DCM (20 mL) and washed with water (10 mL), brine, dried over $Na_2SO_4$, filtered and concentrated. The product was dried in vacuo to afford the title compound (550 mg, 1.8 mmol, 88% yield) as a white solid. $^1$H NMR (400 MHz, DMSO-$d_6$) δ 7.88 (dd, J=2.00, 5.20 Hz, 2H), 7.53 (dd, J=4.80, 5.20 Hz, 2H), 4.55-4.52 (m, 1H), 3.83 (s, 3H), 3.80 (s, 2H), 3.17 (s, 1H), 3.15 (s, 1H), 2.11-2.05 (m, 2H), 1.82-1.54 (m, 6H). MS (ESI) 277 (M+H).

Step F. Intermediate 194F. Preparation of methyl 4-(4-formyl-2-oxabicyclo[2.2.2]octan-1-yl)benzoate

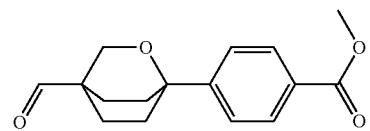 [SMILES: COC(=O)c1ccc(C23CCC(C=O)(CC2)CO3)cc1]

To a stirred solution of Intermediate 194E (200 mg, 0.72 mmol) in DCM (4 mL) was added DMP (460 mg, 1.1 mmol) at rt. After stirring 1 h, the reaction mixture was diluted with DCM (15 mL) and washed with 10% $NaHCO_3$ solution (aq.) (2×25 mL), brine, dried over $Na_2SO_4$, filtered and concentrated. The crude material was purified by flash column chromatography (24 g silica gel cartridge; A=Hex, B=EtOAc; 15 min grad.; 0% B to 100% B; flow rate=24 mL/min). The pure fractions were combined, concentrated and dried in vacuo to afford the title compound (170 mg, 0.47 mmol, 65% yield) as a white solid. $^1$H NMR (400 MHz, DMSO-$d_6$) δ 9.52 (s, 1H), 7.92 (d, J=8.40 Hz, 2H), 7.55 (d, J=8.00 Hz, 2H), 4.02 (s, 2H), 3.85 (s, 3H), 2.18-2.15 (m, 2H), 1.92-1.90 (m, 6H). MS (ESI) 275 (M+H).

Step G. Intermediate 194G. Preparation of diethyl ((5-cyclopropyl-3-(2,6-dichlorophenyl)isoxazol-4-yl)methyl)phosphonate

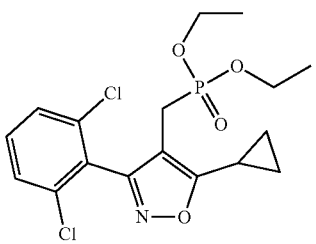 [SMILES: CCOP(=O)(Cc1c(-c2c(Cl)cccc2Cl)noc1C1CC1)OCC]

A solution of 4-(bromomethyl)-5-cyclopropyl-3-(2,6-dichlorophenyl)isoxazole (2.0 g, 5.8 mmol) in triethylphosphite (8 mL, 46 mmol) was stirred for 2.5 h at 160° C. The reaction mixture was cooled to rt, diluted with water (50 mL), and extracted with EtOAc (2×50 mL). The combined organic phase was washed with brine, dried over $Na_2SO_4$, filtered and concentrated. To the crude residue was added hexanes (50 mL) and stirred for 5 min. The resultant precipitate was collected by vacuum filtration, the filter cake was washed with hexanes (5 mL), and the solid product was dried in vacuo to afford the title compound (1.9 g, 4.7 mmol, 82% yield) as a white solid. $^1$H NMR (400 MHz, DMSO-$d_6$) δ 7.65-7.63 (m, 1H), 7.59-7.55 (m, 2H), 3.88-3.78 (m, 4H), 2.89 (d, J=20.40 Hz, 2H), 2.36-2.32 (m, 1H), 1.15-1.11 (m, 10H). MS (ESI) 404 (M+H).

Step H. Intermediate 194H. Preparation of methyl (E)-4-(4-(2-(5-cyclopropyl-3-(2,6-dichlorophenyl)isoxazol-4-yl)vinyl)-2-oxabicyclo[2.2.2]octan-1-yl)benzoate

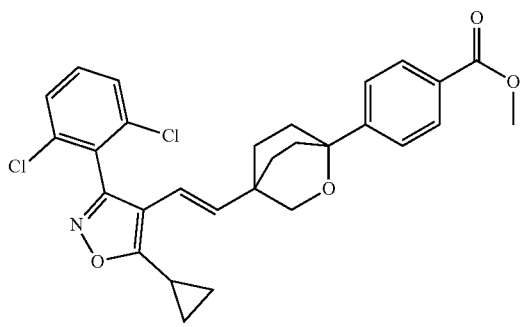 [SMILES: COC(=O)c1ccc(C23CCC(/C=C/c4c(-c5c(Cl)cccc5Cl)noc4C4CC4)(CC2)CO3)cc1]

To a stirred solution of Intermediate 194G (88 mg, 0.22 mmol) in THF (1 mL) was added lithium bis(trimethylsilyl)amide (0.23 mL, 0.23 mmol) (1 M solution in THF) at −78° C. The mixture was slowly warmed to 0° C. and stirred. After 30 min, the reaction was re-cooled to −78° C. To this mixture was added a solution of Intermediate 194F (40 mg, 0.15 mmol) dissolved in THF (0.5 mL). The reaction was slowly warmed to rt and stirred. After 18 h, the reaction mixture was quenched with sat. $NH_4Cl$ (aq.) (10 mL) and extracted with EtOAc (2×20 mL). The combined organic phase was washed with brine, dried over $Na_2SO_4$, filtered and concentrated. The crude product was purified by flash column chromatography (12 g silica gel cartridge; A=Hex, B=EtOAc; 15 min grad.; 0% B to 70% B; flow rate=12 mL/min). The pure fractions were combined, concentrated and dried in vacuo to afford the title compound (27 mg, 0.048 mmol, 33% yield) as a brown semisolid. $^1$H NMR (400 MHz, DMSO-$d_6$) δ 7.88 (d, J=8.8 Hz, 2H), 7.70-7.62 (m, 3H), 7.49 (d, J=8.4 Hz, 2H), 6.14 (d, J=16.8 Hz, 1H), 5.16 (d, J=16.4 Hz, 1H), 3.83 (s, 3H), 3.64 (s, 2H), 2.09-2.04 (m, 3H), 1.81-1.79 (m, 2H), 1.63-1.61 (m, 4H), 1.18-1.10 (m, 4H). MS (ESI) 524 (M+H).

Step I. Example 194

The title compound was prepared according to methods described for the synthesis of Example 151 (Step C), substituting Intermediate 194H where appropriate: (11 mg, 0.022 mmol, 45% yield). $^1$H NMR (400 MHz, DMSO-$d_6$) δ12.80 (br. s., 1H), 7.86 (d, J=8.3 Hz, 2H), 7.69-7.67 (m, 2H), 7.64-7.59 (m, 1H), 7.46 (d, J=8.3 Hz, 2H), 6.13 (d, J=16.4 Hz, 1H), 5.17 (d, J=16.4 Hz, 1H), 3.64 (s, 2H), 2.44-2.35 (m, 1H), 2.16-1.99 (m, 2H), 1.88-1.73 (m, 2H), 1.69-1.52 (m, 4H), 1.22-1.00 (m, 4H). FXR $EC_{50}$ (nM)=34. MS (ESI) 510 (M+H).

Example 195

3-(4-(((5-cyclopropyl-3-(2,6-dichlorophenyl)isoxazol-4-yl)methoxy)methyl)-2-oxabicyclo[2.2.2]octan-1-yl)benzoic acid (195)

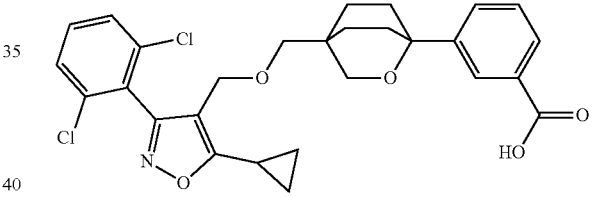

Step A. Intermediate 195A. Preparation of (ethyl 3-(1-hydroxy-4,4-bis((tosyloxy)methyl) cyclohexyl) benzoate

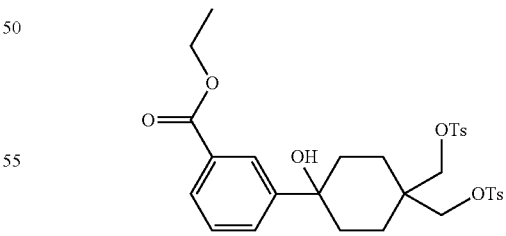

The title compound was prepared according to methods described for the synthesis of Intermediate 194A, substituting ethyl 3-iodobenzoate where appropriate: (1.4 g, 2.1 mmol, 48% yield, white solid). $^1$H NMR (400 MHz, DMSO-$d_6$): δ 8.00 (s, 1H), 7.76-7.83 (m, 5H), 7.44-7.51 (m, 6H), 4.95 (s, 1H), 4.33 (q, J=7.2 Hz, 2H), 4.04 (s, 2H), 3.74 (s, 2H), 2.44 (s, 3H), 2.33 (s, 3H), 1.58-1.61 (m, 2H), 1.26-1.36 (m, 9H). MS (ESI) 634 (M+18).

Step B. Intermediate 195B. Preparation of 3-(4-((tosyloxy)methyl)-2-oxabicyclo [2.2.2]octan-1-yl)benzoic acid

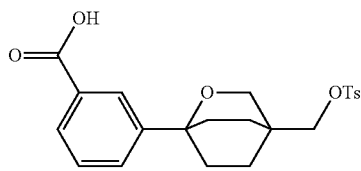 [SMILES: Cc1ccc(S(=O)(=O)OCC23CCC(c4cccc(C(=O)O)c4)(CC2)OC3)cc1]

The title compound was prepared according to methods described for the synthesis of Intermediate 194B, substituting Intermediate 195A where appropriate: (0.7 g, 1.7 mmol, 87% yield, brown oil) $^1$H NMR 400 MHz, DMSO-d$_6$: δ 12.89 (br s, 1H), 7.96 (s, 1H), 7.77-7.95 (m, 3H), 7.57-7.59 (m, 1H), 7.49-7.51 (m, 2H), 7.39-7.43 (m, 1H), 3.83 (s, 2H), 3.73 (s, 2H), 2.44 (s, 3H), 1.99-2.11 (m, 2H), 1.79-1.91 (m, 2H), 1.50-1.70 (m, 4H). MS (ESI) 434 (M+18).

Step C. Intermediate 195C. Preparation of methyl 3-(4-((tosyloxy)methyl)-2-oxabicyclo[2.2.2]octan-1-yl)benzoate

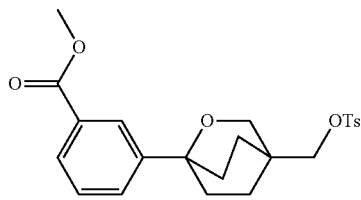 [SMILES: COC(=O)c1cccc(C23CCC(COS(=O)(=O)c4ccc(C)cc4)(CC2)CO3)c1]

The title compound was prepared according to methods described for the synthesis of Intermediate 194C, substituting intermediate 195B where appropriate: (820 mg, 1.9 mmol, 92% yield, pale yellow oil). $^1$H NMR 400 MHz, DMSO-d$_6$: δ7.97-7.98 (m, 1H), 7.81-7.83 (m, 3H), 7.61-7.63 (m, 1H), 7.44-7.52 (m, 3H), 3.80-3.84 (m, 5H), 3.74 (s, 2H), 2.44 (s, 3H), 2.08-2.09 (m, 2H), 1.79-1.80 (m, 2H), 1.59-1.62 (m, 4H). MS (ESI) 448 (M+18).

Step D. Intermediate 195D. Preparation of methyl 3-(4-(acetoxymethyl)-2-oxabicyclo[2.2.2]octan-1-yl)benzoate

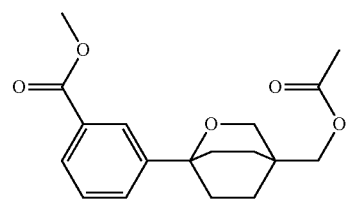 [SMILES: COC(=O)c1cccc(C23CCC(COC(C)=O)(CC2)CO3)c1]

The title compound was prepared according to methods described for the synthesis of Intermediate 194D, substituting intermediate 195C where appropriate: (450 mg, 1.4 mmol, 87% yield). $^1$H NMR 400 MHz, DMSO-d$_6$: δ8.00-8.01 (m, 1H), 7.80-7.83 (m, 1H), 7.63-7.66 (m, 1H), 7.44-7.48 (m, 1H), 3.82-3.94 (m, 7H), 2.09-2.13 (m, 2H), 2.04 (s, 3H), 1.83-1.86 (m, 2H), 1.64-1.71 (m, 4H). MS (ESI) 336 (M+18).

Step E. Intermediate 195E. Preparation of methyl 3-(4-(hydroxymethyl)-2-oxabicyclo[2.2.2] octan-1-yl)benzoate

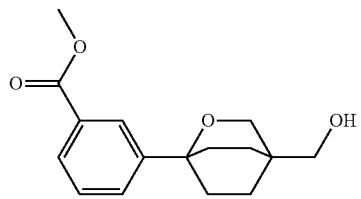 [SMILES: COC(=O)c1cccc(C23CCC(CO)(CC2)CO3)c1]

The title compound was prepared according to methods described for the synthesis Intermediate 194E (Step D & E), substituting Intermediate 195D where appropriate: (160 mg, 0.58 mmol, 61% yield, yellow wax). $^1$H NMR (400 MHz, DMSO-d$_6$) δ 8.00-8.01 (m, 1H), 7.80-7.82 (m, 1H), 7.63-7.65 (m, 1H), 7.43-7.47 (m, 1H), 4.53 (t, J=5.60 Hz, 1H), 3.81-3.86 (m, 5H), 3.16 (d, J=5.60 Hz, 2H), 2.05-2.09 (m, 2H), 1.78-1.82 (m, 2H), 1.50-1.70 (m, 4H). MS (ESI) 294 (M+18).

Step F. Example 195

To a stirred solution of Intermediate 195E (45 mg, 0.16 mmol) in DMF (0.5 mL) was added sodium hydride (9.8 mg, 0.24 mmol) (60% dispersion in mineral oil) at 0 to 5° C. After stirring at this temperature for 10 min, 4-(bromomethyl)-5-cyclopropyl-3-(2,6-dichlorophenyl) isoxazole (68 mg, 0.20 mmol) was added. The reaction was warmed to rt and stirred. After 18 h, the mixture was concentrated, diluted with water (5 mL), acidified with 1.5 M HCl (aq.) (0.5 mL), and extracted with EtOAc (2×5 mL). The combined organic phase was washed with brine, dried over Na$_2$SO$_4$, filtered and concentrated. The crude residue was purified by preparative HPLC (Column: Waters XBridge C18, 19×150 mm, 5-μm particles; Mobile Phase A: 10-mM ammonium acetate; Mobile Phase B: acetonitrile; Gradient: 10-45% B over 25 minutes, then a 5-minute hold at 100% B; Flow: 15 mL/min). The pure fractions were combined, concentrated and dried in vacuo to afford the title compound: (2.0 mg, 3.8 μmol, 2% yield). $^1$H NMR (400 MHz, DMSO-d$_6$) δ 7.94 (s, 1H), 7.77 (d, J=7.6 Hz, 1H), 7.72-7.63 (m, 2H), 7.62-7.47 (m, 2H), 7.45-7.30 (m, 1H), 4.25 (s, 2H), 3.61 (s, 2H), 3.02 (s, 2H), 2.35-2.31 (m, 1H), 2.06-1.92 (m, 2H), 1.80-1.66 (m, 2H), 1.55-1.31 (m, 4H), 1.22-1.01 (m, 4H). FXR EC$_{50}$ (nM)=47. MS (ESI) 530 (M+2).

Example 197

(E)-3-(2-(4-(((5-cyclopropyl-3-(2-(trifluoromethoxy)phenyl)isoxazol-4-yl) methoxy)methyl)-2-oxabicyclo[2.2.2]octan-1-yl)vinyl)benzoic acid

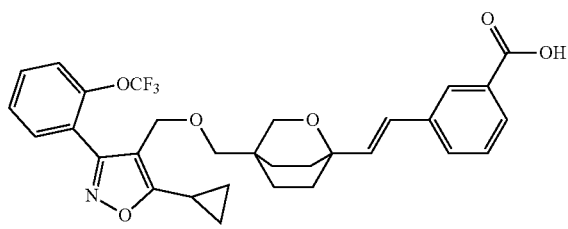

(197)

Step A. Intermediate 197A. Preparation of (E)-ethyl 3-(2-(4-(acetoxymethyl)-2-oxabicyclo[2.2.2]octan-1-yl)vinyl)benzoate To a stirred solution of (1-vinyl-2-oxabicyclo[2.2.2]octan-4-yl)methyl 4-methylbenzenesulfonate (60 mg, 0.19 mmol) (*ACS Med Chem. Lett.*, 2014, 5, 609-614) in DMF (2 mL) were added ethyl 3-bromobenzoate (47 mg, 0.21 mmol), potassium acetate (46 mg, 0.47 mmol) and tetrabutylammonium bromide (60 mg, 0.19 mmol). The reaction mixture was purged with nitrogen for 10 min, after which time tetrakis(triphenylphosphine) palladium(0) (22 mg, 0.019 mmol) was added. The vial was sealed and the mixture was stirred at 110° C. After 18 h, the reaction mixture was cooled to rt and concentrated. The crude product was purified by flash column chromatography (24 g silica gel cartridge; A=Hex, B=EtOAc; 15 min grad.; 0% B to 40% B; flow rate=24 mL/min). The pure fractions were combined, concentrated and dried in vacuo to afford the title compound (50 mg, 0.13 mmol, 71% yield, colorless semisolid). $^1$H NMR (300 MHz, CHLOROFORM-d) δ 8.05 (s, 1H), 7.89 (d, J=7.80 Hz, 1H), 7.53 (d, J=8.10 Hz, 1H), 7.39-7.34 (m, 1H), 6.57 (d, J=16.20 Hz, 1H), 6.26 (d, J=16.20 Hz, 1H), 3.86 (s, 3H), 3.82 (s, 2H), 2.07 (s, 3H), 2.07-1.61 (m, 6H), 1.40-1.26 (m, 4H). MS (ESI) 359 (M+H).

Step B. Intermediate 197B. Preparation of (E)-methyl 3-(2-(4-(hydroxymethyl)-2-oxabicyclo[2.2.2]octan-1-yl)vinyl)benzoate

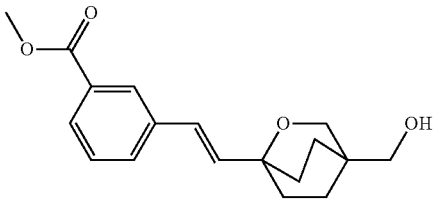 [SMILES: COC(=O)c1cccc(/C=C/C23CCC(CO)(CC2)CO3)c1]

The title compound was prepared according to methods described for the synthesis Intermediate 194E (Step D & E), substituting Intermediate 197A where appropriate: (30 mg, 0.063 mmol, 57% yield) as a colorless semisolid. $^1$H NMR (400 MHz, DMSO-d$_6$) δ 7.95 (s, 1H), 7.81-7.79 (m, 1H), 7.70-7.68 (m, 1H), 7.48-7.44 (m, 1H), 6.55 (d, J=16.00 Hz, 1H), 6.34 (d, J=16.00 Hz, 1H), 4.50 (s, 1H), 3.85 (s, 3H), 3.69 (s, 2H), 3.12 (s, 2H), 1.82-1.78 (m, 4H), 1.64-1.46 (m, 4H). MS (ESI) 303 (M+H).

Step C. Intermediate 197C. Preparation of (E)-methyl 3-(2-(4-(((5-cyclopropyl-3-(2-(trifluoromethoxy)phenyl)isoxazol-4-yl)methoxy)methyl)-2-oxabicyclo[2.2.2]octan-1-yl) vinyl)benzoate

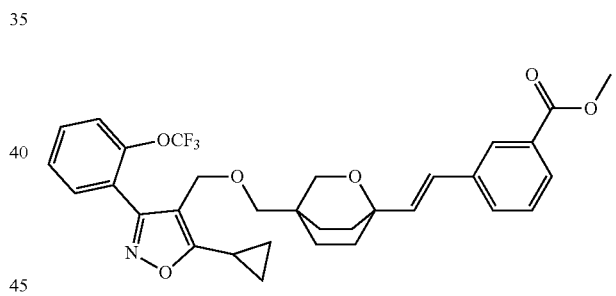

The title compound was prepared according to methods described for the synthesis of Intermediate 193N by starting with Intermediate 197B and substituting 4-(bromomethyl)-5-cyclopropyl-3-(2trifluoromethoxyphenyl)isoxazole where appropriate: (40 mg, 0.050 mmol, 30% yield) as a colorless semisolid. MS (ESI) 584 (M+H).

Step D. Example 197

The title compound was prepared according to methods described for the synthesis of Example 151 (Step C), substituting Intermediate 197C where appropriate: (7.2 mg, 0.013 mmol, 21% yield). $^1$H NMR (400 MHz, DMSO-d$_6$) δ7.92 (s, 1H), 7.77 (d, J=8.00 Hz, 1H), 7.68-7.66 (m, 1H), 7.63-7.61 (m, 2H), 7.57-7.55 (m, 2H), 7.42 (t, J=7.60 Hz, 1H), 6.50 (d, J=16.00 Hz, 1H), 6.27 (d, J=16.40 Hz, 1H), 4.29 (s, 2H), 3.49 (s, 2H), 3.00 (s, 2H), 2.32-2.30 (m, 1H), 1.73-1.70 (m, 4H), 1.44-1.34 (m, 4H), 1.14-1.09 (m, 4H). FXR EC$_{50}$ (nM)=90. MS (ESI) 570 (M+H).

Example 203

4-(4-(((5-cyclopropyl-3-(2,6-dichlorophenyl)isoxazol-4-yl)amino)methyl)-2-oxabicyclo[2.2.2]octan-1-yl)benzoic acid

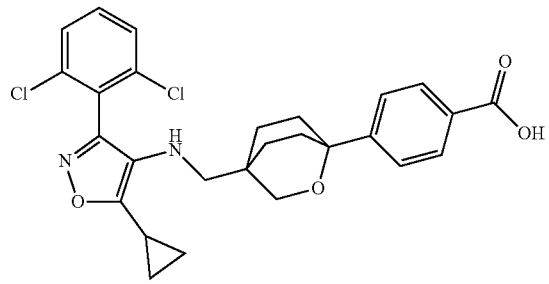

(203)

Step A. Intermediate 203A. Preparation of methyl 4-(4-(((5-cyclopropyl-3-(2,6-dichlorophenyl) isoxazol-4-yl)amino)methyl)-2-oxabicyclo[2.2.2]octan-1-yl)benzoate

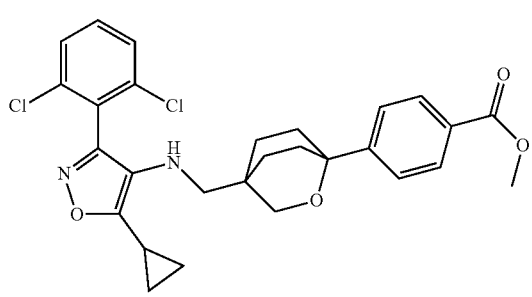 [SMILES: COC(=O)c1ccc(C23CCC(CNc4c(-c5c(Cl)cccc5Cl)noc4C4CC4)(CC2)CO3)cc1]

To a stirred solution of Intermediate 166C (0.098 g, 0.37 mmol) and Intermediate 194F (0.1 g, 0.37 mmol) in MeOH (3 mL) was added AcOH (0.042 mL, 0.73 mmol) followed by 4 Å molecular sieves (10 mg). After stirring at 60° C. for 18 h, the mixture was cooled to 0° C., and sodium cyanoborohydride (0.046 g, 0.73 mmol) was added. The reaction was warmed to rt and stirred. After 2 h, the mixture was quenched with water (20 mL) and extracted with EtOAc (2×25 mL). The combined organic phase was washed with brine, dried over $Na_2SO_4$, filtered and concentrated. The crude residue was purified by preparative HPLC (Column: Waters XBridge C18, 19×150 mm, 5-μm particles; Mobile Phase A: 10-mM ammonium acetate; Mobile Phase B: acetonitrile; Gradient: 25-90% B over 20 minutes, then a 5-minute hold at 100% B; Flow: 15 mL/min.). Fractions containing the desired product were combined, concentrated and dried in vacuo to afford the title compound (110 mg, 0.21 mol, 59% yield). $^1$H NMR (400 MHz, DMSO-$d_6$) δ 7.88-7.86 (m, 2H), 7.67-7.64 (m, 2H), 7.61-7.55 (m, 1H), 7.48-7.46 (m, 2H), 3.82 (s, 3H), 3.77 (t, J=7.5 Hz, 1H), 3.57 (s, 2H), 2.51-2.53 (m, 2H), 2.33-2.24 (m, 1H), 2.08-1.94 (m, 2H), 1.82-1.59 (m, 2H), 1.56-1.30 (m, 4H), 1.12-1.03 (m, 2H), 1.02-0.89 (m, 2H). FXR $EC_{50}$ (nM)=2800. MS (ESI) 527 (M+H).

Step B. Example 203

The title compound was prepared according to methods described for the synthesis of Example 151 (Step C), substituting Intermediate 203A where appropriate: (100 mg, 0.2 mmol, 95% yield). $^1$H NMR (400 MHz, DMSO-$d_6$) δ12.78 (br. s., 1H), 7.84 (d, J=8.3 Hz, 2H), 7.74-7.62 (m, 2H), 7.62-7.53 (m, 1H), 7.44 (d, J=8.6 Hz, 2H), 3.83-3.70 (m, 1H), 3.57 (s, 2H), 2.53 (m, 2H), 2.32-2.22 (m, 1H), 2.07-1.90 (m, 2H), 1.71 (m, 2H), 1.55-1.33 (m, 4H), 1.14-1.03 (m, 2H), 1.03-0.90 (m, 2H). FXR $EC_{50}$ (nM)=420. MS (ESI) 513 (M+H).

Example 208

4-(4-(((5-cyclopropyl-3-(2,6-dichlorophenyl)isoxazol-4-yl)amino)methyl)-2-oxabicyclo[2.2.2]octan-1-yl)benzamide

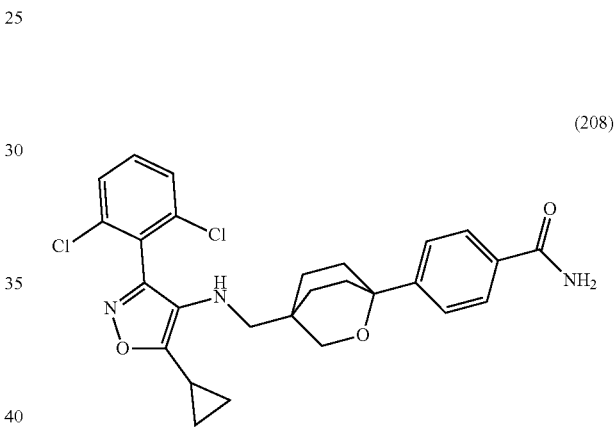

(208)

To a stirred solution of Example 203 (30 mg, 0.058 mmol) in DMF (2 mL) was added $NH_4Cl$ (9.4 mg, 0.18 mmol) and TEA (0.024 mL, 0.18 mmol). To this mixture was added BOP (28 mg, 0.064 mmol) and the reaction was stirred at rt. After 1 h, the reaction was filtered and the filtrate was concentrated. The crude material was purified via preparative HPLC (Column: Waters XBridge C18, 19×150 mm, 5-μm particles; Mobile Phase A: 10-mM ammonium acetate; Mobile Phase B: acetonitrile; Gradient: 15-55% B over 25 minutes, then a 5-minute hold at 100% B; Flow: 15 mL/min.). Fractions containing the desired product were combined, concentrated and dried in vacuo to afford the title compound (2.7 mg, 5.3 μma 9% yield). $^1$H NMR (400 MHz, DMSO-$d_6$) δ 7.87 (br. s., 1H), 7.81-7.71 (m, 2H), 7.70-7.62 (m, 2H), 7.61-7.49 (m, 1H), 7.43-7.31 (m, 2H), 7.25 (br. s., 1H), 3.76 (t, J=7.5 Hz, 1H), 3.57 (s, 2H), 2.32-2.25 (m, 1H), 2.06-1.90 (m, 2H), 1.71 (d, J=5.6 Hz, 2H), 1.55-1.33 (m, 4H), 1.14-1.05 (m, 2H), 1.04-0.89 (m, 2H). 2H buried under solvent peak. FXR $EC_{50}$ (nM)=710. MS (ESI) 512 (M+H).

Example 209

4-(5-(4-(((5-cyclopropyl-3-(2-(trifluoromethoxy)phenyl)isoxazol-4-yl)methoxy)methyl)-2-oxabicyclo[2.2.2]octan-1-yl)-1,2,4-oxadiazol-3-yl)benzoic acid

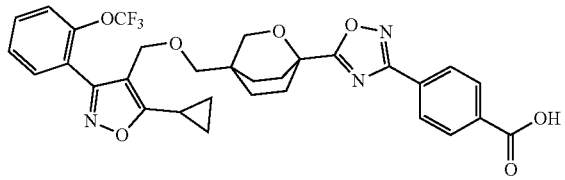
(209)

Step A. Intermediate 209A. Preparation of methyl 4-(((5-cyclopropyl-3-(2-(trifluoromethoxy)phenyl)isoxazol-4-yl)methoxy)methyl)-2-oxabicyclo[2.2.2]octane-1-carboxylate

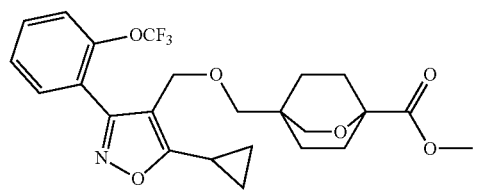 [SMILES: COC(=O)C12CCC(COCc3c(-c4ccccc4OC(F)(F)F)noc3C3CC3)(CC1)CO2]

The title compound was prepared according to methods described for the synthesis Intermediate 193N, substituting Intermediate 193G and 4-(bromomethyl)-5-cyclopropyl-3-(2-(trifluoromethoxy)phenyl)isoxazole where appropriate (70 mg, 0.13 mmol, 26% yield). $^1$H NMR (400 MHz, DMSO-d$_6$) δ 7.70-7.52 (m, 4H), 4.30 (s, 1H), 4.28 (s, 1H), 3.59 (s, 3H), 3.42 (s, 2H), 2.98 (s, 2H), 2.31-2.27 (m, 1H), 1.80-1.76 (m, 4H), 1.42-1.26 (m, 4H), 1.20-1.02 (m, 4H). MS (ESI) 482 (M+H).

Step B. Intermediate 209B. Preparation of 4-(((5-cyclopropyl-3-(2-(trifluoromethoxy) phenyl)isoxazol-4-yl)methoxy)methyl)-2-oxabicyclo[2.2.2]octane-1-carboxylic acid

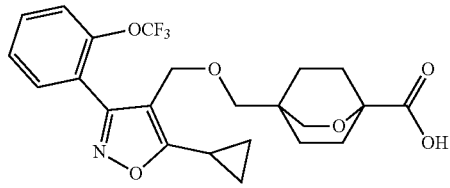 [SMILES: O=C(O)C12CCC(COCc3c(-c4ccccc4OC(F)(F)F)noc3C3CC3)(CC1)CO2]

The title compound was prepared according to methods described for the synthesis of Example 151 (Step C), substituting Intermediate 209A where appropriate: (60 mg, 0.11 mmol, 73% yield). $^1$H NMR (400 MHz, DMSO-d$_6$) δ 12.30 (s, 1H), 7.67-7.54 (m, 4H), 4.28 (s, 2H), 3.42 (s, 2H), 2.98 (s, 2H), 2.30-2.29 (m, 1H), 1.79-1.75 (m, 4H), 1.39-1.24 (m, 4H), 1.14-1.06 (m, 4H). MS (ESI) 468 (M+H).

Step C. Intermediate 209C. Preparation of methyl 4-(5-(4-(((5-cyclopropyl-3-(2-(trifluoromethoxy)phenyl)isoxazol-4-yl)methoxy)methyl)-2-oxabicyclo[2.2.2]octan-1-yl)-1,2,4-oxadiazol-3-yl)benzoate

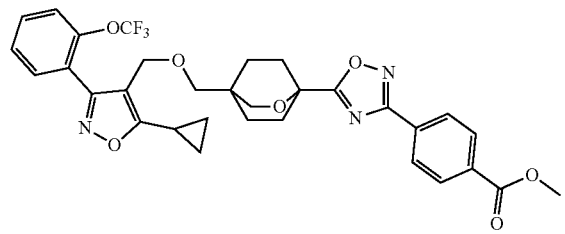 [SMILES: COC(=O)c1ccc(-c2noc(C34CCC(COCc5c(-c6ccccc6OC(F)(F)F)noc5C5CC5)(CC3)CO4)n2)cc1]

The title compound was prepared according to methods described for the synthesis of Example 193 (Step M), starting with Intermediate 209B and substituting methyl 4-(N'-hydroxycarbamimidoyl)benzoate where appropriate. MS (ESI) 626 (M+H).

Step D. Example 209

The title compound was prepared according to methods described for the synthesis of Example 151 (Step C), substituting Intermediate 209C where appropriate: (3.6 mg, 5.6 μmol, 14% yield). $^1$H NMR (400 MHz, DMSO-d$_6$) δ 8.10 (s, 4H), 7.74-7.66 (m, 1H), 7.65-7.60 (m, 1H), 7.60-7.49 (m, 2H), 4.32 (s, 2H), 3.58 (s, 2H), 3.06 (s, 2H), 2.35-2.27 (m, 1H), 2.18-2.20 (m, 2H), 2.12-1.98 (m, 2H), 1.65-1.38 (m, 4H), 1.20-1.02 (m, 4H). FXR EC$_{50}$ (nM)=470. MS (ESI) 612 (M+H).

Example 210

3-(5-(4-(((5-cyclopropyl-3-(2,6-dichlorophenyl)isoxazol-4-yl)methoxy)methyl)-2-oxabicyclo[2.2.2]octan-1-yl)-1,2,4-oxadiazol-3-yl)benzoic acid

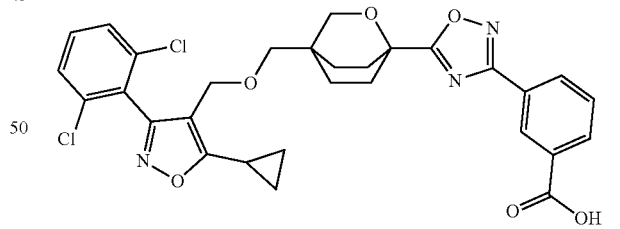
(210)

Step A. Intermediate 210A. Preparation of 4-((tosyloxy)methyl)-2-oxabicyclo[2.2.2]octane-1-carboxylic acid

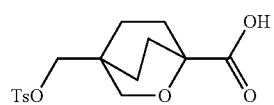

To a stirred solution of (1-vinyl-2-oxabicyclo[2.2.2]octan-4-yl)methyl 4-methyl benzenesulfonate (0.46 g, 1.4 mmol) (Singh, S. B. et al. *ACS Med. Chem. Lett.,* 2014, 5, 609-614) in carbon tetrachloride (10 mL) and MeCN (10 mL) were added sodium periodate (1.2 g, 5.7 mmol) in water (15 mL) followed by ruthenium(III) chloride hydrate (0.016 g, 0.071 mmol). After stirring 2 h, the reaction mixture was filtered through Celite and the filter cake was washed with DCM (30 mL). The filtrate was washed with brine, dried over sodium sulfate and concentrated to afford the title compound (0.42 g, 1.2 mmol, 80% yield) as a brown semisolid. $^1$H NMR (400 MHz, DMSO-$d_6$) δ 12.44 (s, 1H), 7.79 (d, J=8.40 Hz, 2H), 7.50 (d, J=8.00 Hz, 2H), 3.78 (s, 2H), 3.55 (s, 2H), 2.43 (s, 3H), 2.00-1.78 (m, 4H), 1.51-1.47 (m, 4H). MS (ESI) 358 (M+H+17).

Step B. Intermediate 210B. Preparation of methyl 3-(5-(4-((tosyloxy)methyl)-2-oxabicyclo[2.2.2]octan-1-yl)-1,2,4-oxadiazol-3-yl)benzoate

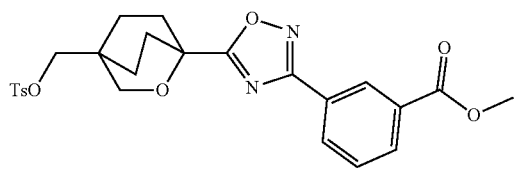 [SMILES: COC(=O)c1cccc(-c2noc(C34CCC(COS(=O)(=O)c5ccc(C)cc5)(CC3)CO4)n2)c1]

The title compound was prepared according to methods described for the synthesis Intermediate 1A, substituting Intermediate 210A where appropriate: (50 mg, 0.085 mmol, 7% yield, brown semisolid). $^1$H NMR (400 MHz, DMSO-$d_6$) δ 8.53 (s, 1H), 8.30-8.15 (m, 2H), 7.81 (d, J=8.40 Hz, 2H), 7.76-7.72 (m, 1H), 7.51 (d, J=8.00 Hz, 2H), 3.91 (s, 3H), 3.85 (s, 2H), 3.73 (s, 2H), 2.49 (s, 3H), 2.32-2.13 (m, 4H), 1.70-1.62 (m, 4H). MS (ESI) 499 (M+H).

Step C. Intermediate 210C. Preparation of methyl 3-(5-(4-(acetoxymethyl)-2-oxabicyclo[2.2.2]octan-1-yl)-1,2,4-oxadiazol-3-yl)benzoate

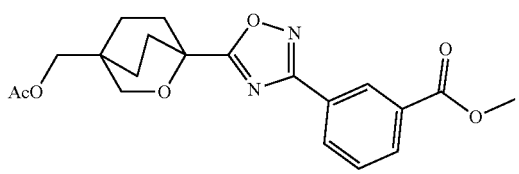 [SMILES: COC(=O)c1cccc(-c2noc(C34CCC(COC(C)=O)(CC3)CO4)n2)c1]

The title compound was prepared according to methods described for the synthesis of Intermediate 194D, substituting Intermediate 210B where appropriate: (25 mg, 0.060 mmol, 60% yield, brown semisolid). $^1$H NMR (400 MHz, DMSO-$d_6$) δ 8.55-8.54 (m, 1H), 8.28-8.16 (m, 2H), 7.77-7.73 (m, 1H), 3.91 (s, 3H), 3.84 (s, 2H), 3.83 (s, 2H), 2.33-2.18 (m, 4H), 2.05 (s, 3H), 1.77-1.71 (m, 4H). MS (ESI) 387 (M+H).

Step D. Intermediate 210D. Preparation of methyl 3-(5-(4-(hydroxymethyl)-2-oxabicyclo[2.2.2]octan-1-yl)-1,2,4-oxadiazol-3-yl)benzoate

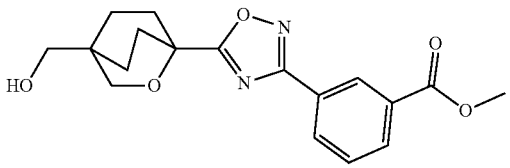 [SMILES: COC(=O)c1cccc(-c2noc(C34CCC(CO)(CC3)CO4)n2)c1]

The title compound was prepared according to methods described for the synthesis Intermediate 194E, by using Intermediate 210C where appropriate (20 mg, 0.048 mmol, 93% yield). $^1$H NMR (400 MHz, DMSO-$d_6$) δ 8.55-8.54 (m, 1H), 8.26-8.16 (m, 2H), 7.74-7.70 (m, 1H), 4.60 (s, 1H), 3.91 (s, 3H), 3.80 (s, 2H), 3.18 (s, 2H), 2.33-2.11 (m, 4H), 1.76-1.57 (m, 4H). MS (ESI) 345 (M+H).

Step E. Example 210

The title compound was prepared according to methods described for the synthesis of Example 193 (Step N and O), substituting Intermediate 210D where appropriate: (6.1 mg, 10.0 μmol, 41% yield). $^1$H NMR (400 MHz, DMSO-$d_6$) δ 8.53-8.52 (m, 1H), 8.17-8.11 (m, 2H), 7.69-7.57 (m, 4H), 4.27 (s, 2H), 3.60 (s, 2H), 3.05 (s, 2H), 2.34-2.32 (m, 1H), 2.21-2.19 (m, 2H), 2.09-2.06 (m, 2H), 1.54-1.44 (m, 4H), 1.18-1.10 (m, 4H). FXR EC$_{50}$ (nM)=960. MS (ESI) 596 (M+H).

Example 219

3-(5-(4-((5-cyclopropyl-3-(2,6-dichlorophenyl)isoxazol-4-yl)methoxy)-2-oxabicyclo[2.2.2]octan-1-yl)-1,2,4-oxadiazol-3-yl)-5-fluorobenzoic acid (219)

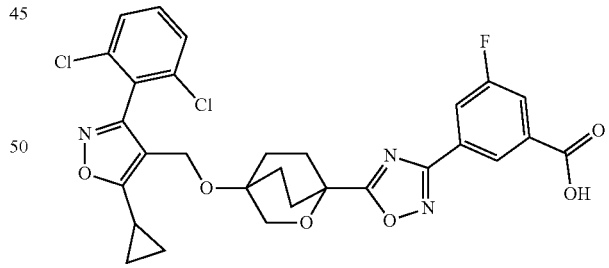

Step A. Intermediate 219A. Preparation of methyl 4-hydroxy-2-oxabicyclo[2.2.2]octane-1-carboxylate

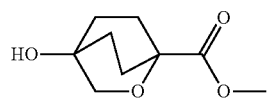

To a stirred solution of Intermediate 193L (60 mg, 0.348 mmol) in DMF (2 mL) was added K$_2$CO$_3$ (72.2 mg, 0.523 mmol) followed by iodomethane (0.033 mL, 0.523 mmol). After stirring 2 h, the reaction mixture was concentrated, the residue was diluted with water (10 mL) and extracted with ethyl acetate (2×10 mL). The combined organic layer was dried over sodium sulfate and concentrated to afford the title compound (65 mg, 0.25 mmol, 72% yield) as a brown semisolid. $^1$H NMR (400 MHz, DMSO-d$_6$) δ 4.82 (s, 1H), 3.60 (s, 3H), 3.36 (s, 2H), 2.00-1.90 (m, 4H), 1.70-1.50 (m, 4H). MS (ESI) 187 (M+H).

Step B. Intermediate 219B. Preparation of methyl 4-((5-cyclopropyl-3-(2,6-dichlorophenyl)isoxazol-4-yl)methoxy)-2-oxabicyclo[2.2.2]octane-1-carboxylate

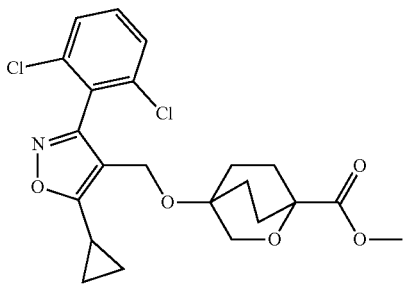 [SMILES: COC(=O)C12CCC(OCc3c(-c4c(Cl)cccc4Cl)noc3C3CC3)(CC1)CO2]

The title compound was prepared according to methods described for the synthesis Intermediate 193N, substituting Intermediate 219A where appropriate: (55 mg, 0.12 mmol, 26% yield). $^1$H NMR (400 MHz, DMSO-d$_6$) δ 7.65-7.57 (m, 3H), 4.20 (s, 2H), 3.65 (s, 3H), 3.31 (s, 2H), 2.33-2.29 (m, 1H), 1.91-1.88 (m, 4H), 1.70-1.60 (m, 2H), 1.45-1.30 (m, 2H), 1.15-1.05 (m, 4H). MS (ESI) 452 (M+H).

Step C. Intermediate 219C. Preparation of 4-((5-cyclopropyl-3-(2,6-dichlorophenyl)isoxazol-4-yl)methoxy)-2-oxabicyclo[2.2.2]octane-1-carboxylic acid

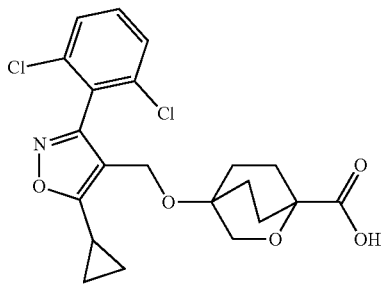 [SMILES: O=C(O)C12CCC(OCc3c(-c4c(Cl)cccc4Cl)noc3C3CC3)(CC1)CO2]

The title compound was prepared according to methods described for the synthesis of Example 151 (Step C), substituting Intermediate 219B where appropriate: (45 mg, 0.10 mmol, 92% yield). MS (ESI) 438 (M+H).

Step D. Example 219

The title compound was prepared according to methods described for the synthesis of Example 64 (Step C), by reaction of Intermediate 219C and methyl (Z)-3-fluoro-5-(N'-hydroxycarbamimidoyl)benzoate: (1.0 mg, 1.7 μmol, 7% yield). $^1$H NMR (400 MHz, DMSO-d$_6$) δ 8.33 (s, 1H), 7.83 (br. s., 2H), 7.71-7.53 (m, 2H), 7.29 (d, J=16.4 Hz, 1H), 4.26 (s, 2H), 3.51 (s, 2H), 2.32-2.27 (m, 3H), 2.19-2.15 (m, 2H), 1.82 (br. s., 2H), 1.54 (br. s., 2H), 1.31-1.20 (m, 2H), 1.15-1.08 (m, 2H). FXR EC$_{50}$ (nM)=300. MS (ESI) 600 (M+H).

Example 220

4-(((1-(3-(1H-tetrazol-5-yl)phenyl)-2-oxabicyclo [2.2.2]octan-4-yl)methoxy)methyl)-5-cyclopropyl-3-(2,6-dichlorophenyl)isoxazole

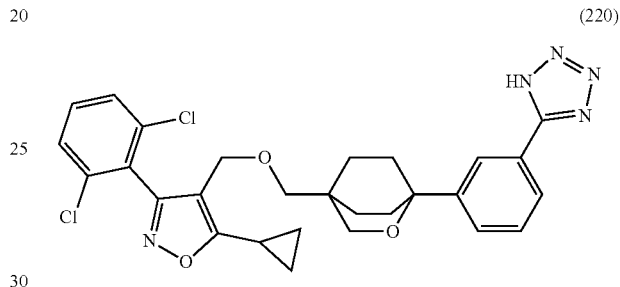

(220)

Step A. Intermediate 220A. Preparation of 3-(4-(((5-cyclopropyl-3-(2,6-dichlorophenyl)isoxazol-4-yl)methoxy)methyl)-2-oxabicyclo[2.2.2]octan-1-yl)benzonitrile

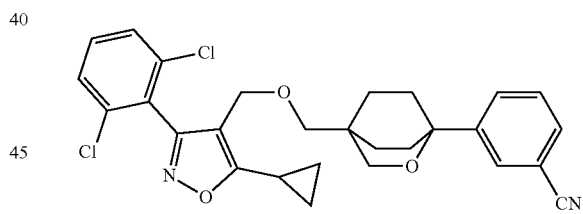

The title compound was prepared according to methods described for the synthesis of Intermediate 20A, substituting Example 195 where appropriate: (25 mg, 0.049 mmol, 65% yield). MS (ESI) 509 (M+H).

Step B. Example 220

The title compound was prepared according to methods described for the synthesis of Example 8 (Step B), substituting Intermediate 220A where appropriate: (2.8 mg, 5.0 μmol, 10% yield). $^1$H NMR (400 MHz, DMSO-d$_6$) δ 8.05 (s, 1H), 7.86 (d, J=5.6 Hz, 1H), 7.72-7.61 (m, 2H), 7.60-7.53 (m, 1H), 7.53-7.39 (m, 2H), 4.26 (s, 2H), 3.64 (s, 2H), 3.03 (s, 2H), 2.37-2.26 (m, 1H), 2.09-1.95 (m, 2H), 1.85-1.67 (m, 2H), 1.54-1.35 (m, 4H), 1.21-1.04 (m, 4H). FXR EC$_{50}$ (nM)=870. MS (ESI) 552 (M+H).

Example 221

3-(5-((1r,4r)-4-((5-cyclopropyl-3-(2,6-dichlorophenyl)isoxazol-4-yl)methoxy)bicyclo[2.2.1]heptan-1-yl)-1,2,4-oxadiazol-3-yl)benzoic acid

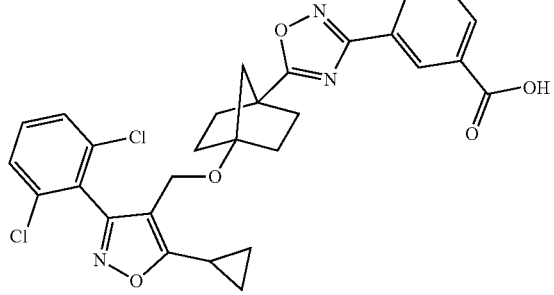
(221)

Step A. Intermediate 221A. Preparation of methyl 3-(5-((1r,4r)-4-hydroxybicyclo[2.2.1] heptan-1-yl)-1,2,4-oxadiazol-3-yl)benzoate The title compound was prepared according to methods described for the synthesis of Intermediate 151A, substituting 4-hydroxybicyclo[2.2.1]heptane-1-carboxylic acid (Brydon, B. et al. WO2012/145569) where appropriate: (0.030 g, 34% yield, white solid). $^1$H NMR (400 MHz, DMSO-$d_6$) δ=8.53 (s, 1H), 8.38-8.30 (m, 1H), 8.28-8.22 (m, 1H), 7.73 (t, J=8 Hz, 1H), 5.2 (s, 1H), 3.91 (s, 3H), 2.27-2.21 (m, 2H), 1.98-1.62 (m, 8H). MS (ESI) 314 (M+H).

Step B. Intermediate 221B. Preparation of methyl 3-(5-(4-((5-cyclopropyl-3-(2,6-dichlorophenyl)isoxazol-4-yl)methoxy)bicyclo[2.2.2]octan-1-yl)-1,2,4-oxadiazol-3-yl) benzoate

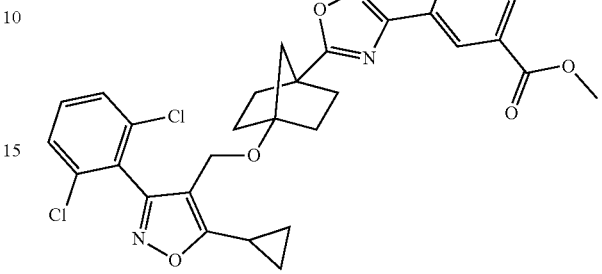

The title compound was prepared according to methods described for the synthesis of Intermediate 151B, substituting intermediate 221A where appropriate: (0.020 g, 36% yield, pale yellow solid). MS (ESI) 580 (M+H).

Step C. Example 221

The title compound was prepared according to methods described for the synthesis of Example 151 (Step C), substituting Intermediate 221B where appropriate: (7.7 mg, 25% yield). $^1$H NMR (400 MHz, DMSO-$d_6$) δ 8.51 (s, 1H), 8.21 (d, J=7.3 Hz, 1H), 8.13 (d, J=7.6 Hz, 1H), 7.70 (t, J=7.6 Hz, 1H), 7.66-7.61 (m, 2H), 7.60-7.54 (m, 1H), 4.31 (s, 2H), 2.35-2.32 (s, 1H), 2.11-2.07 (m, 2H), 1.94-1.90 (m, 2H), 1.76-1.72 (m, 2H), 1.66-1.62 (m, 2H), 1.50-1.46 (m, 2H), 1.17-1.12 (m, 2H), 1.11-1.07 (m, 2H). FXR EC$_{50}$ (nM)=300. MS (ESI) 566 (M+H).

Example 226

4-(5-(4-(2-(5-cyclopropyl-3-(2,6-dichlorophenyl)isoxazol-4-yl)vinyl)bicyclo[2.2.1]heptan-1-yl)-1,2,4-oxadiazol-3-yl)benzoic acid

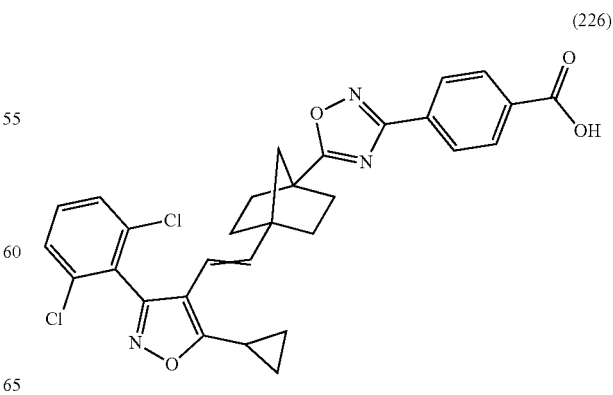
(226)

Step A. Intermediate 226A. Preparation of methyl 4-(2-(5-cyclopropyl-3-(2,6-dichlorophenyl)isoxazol-4-yl)vinyl)bicyclo[2.2.1]heptane-1-carboxylate

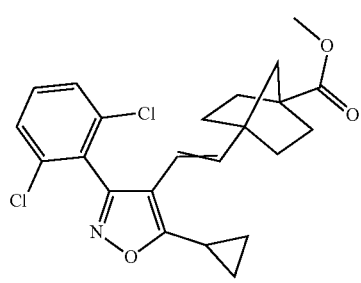 [SMILES: COC(=O)C12CCC(C=Cc3c(-c4c(Cl)cccc4Cl)noc3C3CC3)(CC1)C2]

The title compound was prepared according to methods described for the synthesis of Intermediate 159D, substituting methyl 4-formylbicyclo[2.2.1]heptane-1-carboxylate (Velaparthi U. et al. US 2015/0133428) where appropriate: (0.18 g, 0.42 mmol, 54% yield). $^1$H NMR (400 MHz, DMSO-$d_6$) δ 7.67-7.61 (m, 3H), 6.12 (d, J=16.4 Hz, 1H), 5.56 (d, J=16.4 Hz, 1H), 3.60 (s, 3H), 2.45-2.35 (m, 1H), 1.91-1.78 (m, 2H), 1.61-1.09 (m, 12H). MS (ESI) 432 (M+H).

Step B. Intermediate 226B. Preparation of (1r,4r)-4-(2-(5-cyclopropyl-3-(2,6-dichlorophenyl)isoxazol-4-yl)vinyl)bicyclo[2.2.1]heptane-1-carboxylic acid

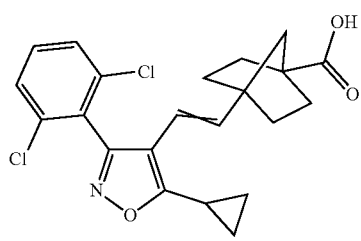 [SMILES: O=C(O)C12CCC(C=Cc3c(-c4c(Cl)cccc4Cl)noc3C3CC3)(CC1)C2]

The title compound was prepared according to methods described for the synthesis of Intermediate 159E, substituting Intermediate 226A where appropriate: (0.090 g, 0.22 mmol, 58% yield). $^1$H NMR (400 MHz, DMSO-$d_6$) δ 12.1 (br s, 1H), 7.78-7.51 (m, 3H), 6.12 (d, J=16.4 Hz, 1H), 5.55 (d, J=16.4 Hz, 1H), 2.42-2.36 (m, 1H), 1.91-1.78 (m, 2H), 1.61-1.09 (m, 12H). MS (ESI) 418 (M+H). The product was obtained as a mixture of trans/cis isomers in 7:3 ratio. The ratio was determined by $^1$H NMR based on integration of characteristic protons.

Step C. Intermediate 226C. Preparation of methyl 4-(5-(4-(2-(5-cyclopropyl-3-(2,6-dichlorophenyl)isoxazol-4-yl)vinyl)bicyclo[2.2.1]heptan-1-yl)-1,2,4-oxadiazol-3-yl)benzoate The title compound was prepared according to methods described for the synthesis of Intermediate 159F, substituting Intermediate 226B where appropriate: (3.0 mg, 5.2 μmol, 22% yield). $^1$H NMR (400 MHz, DMSO-$d_6$) δ 8.12 (s, 4H), 7.70-7.53 (m, 3H), 6.20 (d, J=16.4 Hz, 1H), 5.61 (d, J=16.4 Hz, 1H), 3.89 (s, 3H), 2.44-2.35 (m, 1H), 2.20-2.00 (m, 2H), 1.97-1.78 (m, 2H), 1.73 (s, 2H), 1.71-1.54 (m, 2H), 1.49 (d, J=8.3 Hz, 2H), 1.21-1.03 (m, 4H). FXR EC$_{50}$ (nM)=2500. MS (ESI) 576 (M+H). The product was obtained as a mixture of trans/cis isomers in 5:1 ratio. The ratio was determined by $^1$H NMR based on integration of characteristic protons.

Step D. Example 226

The title compound was prepared according to methods described for the synthesis of Example 151 (Step C), substituting intermediate 226C where appropriate: (1.8 mg, 3.1 μmol, 5% yield). $^1$H NMR (400 MHz, DMSO-$d_6$) δ 8.15-7.96 (m, 4H), 7.75-7.49 (m, 3H), 6.21 (d, J=16.4 Hz, 1H), 5.62 (d, J=16.4 Hz, 1H), 2.45-2.35 (m, 1H), 2.21-2.00 (m, 2H), 1.96-1.80 (m, 2H), 1.79-1.55 (m, 4H), 1.50 (d, J=8.3 Hz, 2H), 1.22-1.01 (m, 4H). FXR EC$_{50}$ (nM)=420. MS (ESI) 562 (M+H). The product was obtained as a mixture of trans/cis isomers in 4:1 ratio. The ratio was determined by $^1$H NMR based on integration of characteristic protons.

The following Examples in Table 4 were prepared according to methods described elsewhere herein using appropriate starting materials, reagents and conditions.

TABLE 4

| Ex. No. | Structure & Name | $^1$H NMR, FXR EC$_{50}$ & MS (ESI) | Method |
|---|---|---|---|
| 152 | 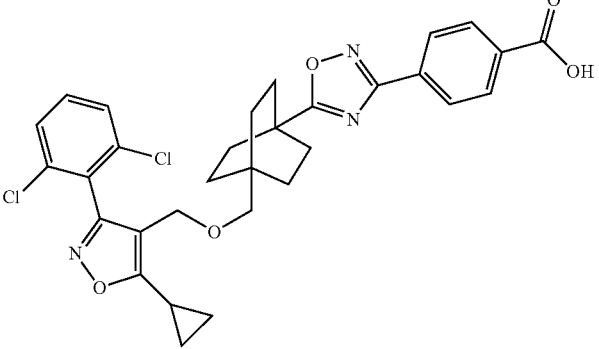<br>4-(5-(4-(((5-cyclopropyl-3-(2,6-dichlorophenyl)isoxazol-4-yl)methoxy)methyl)bicyclo[2.2.2]octan-1-yl)-1,2,4-oxadiazol-3-yl)benzoic acid | $^1$H NMR (500 MHz, DMSO-d$_6$) δ 8.09 (s, 4H), 7.70-7.63 (m, 2H), 7.61-7.52 (m, 1H), 4.26 (s, 2H), 2.97 (s, 2H), 2.33-2.26 (m, 1H), 1.96-1.76 (m, 6H), 1.39-1.24 (m, 6H), 1.19-1.05 (m, 4H). FXR EC$_{50}$ (nM) = 140. MS (ESI) 594 (M + H). | Ex. 151 |
| 153 | 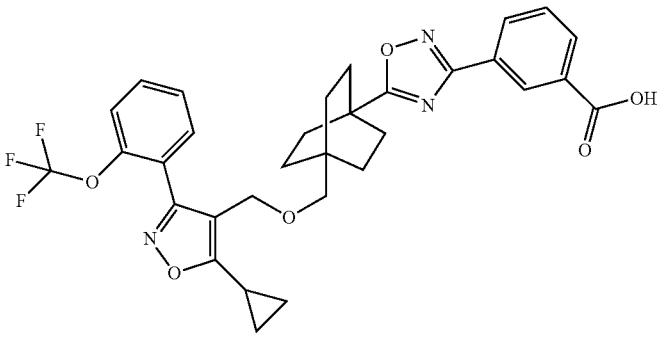<br>3-(5-(4-(((5-cyclopropyl-3-(2-(trifluoromethoxy)phenyl)isoxazol-4-yl)methoxy)methyl)bicyclo[2.2.2]octan-1-yl)-1,2,4-oxadiazol-3-yl)benzoic acid | $^1$H NMR (400 MHz, DMSO-d$_6$) δ 8.57-8.48 (m, 1H), 8.18 (dd, J = 7.8, 1.5 Hz, 1H), 8.11 (dt, J = 7.7, 1.2 Hz, 1H), 7.75-7.64 (m, 2H), 7.64-7.60 (m, 1H), 7.59-7.49 (m, 2H), 4.31 (s, 2H), 2.99 (s, 2H), 2.33-2.29 (m, 1H), 1.97-1.80 (m, 6H), 1.41-1.27 (m, 6H), 1.19-0.99 (m, 4H). FXR EC$_{50}$ (nM) = 320. MS (ES) 610 (M + H). | Ex. 151 |
| 154 | 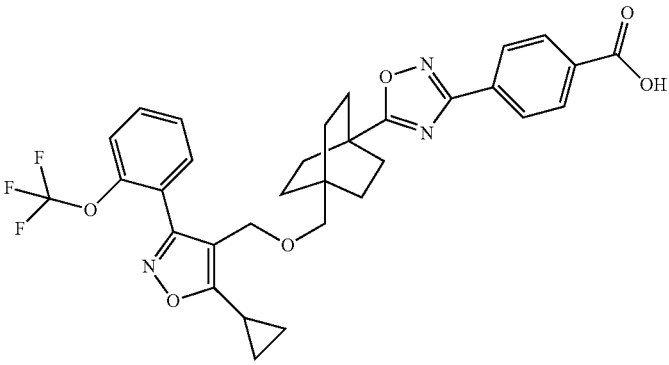<br>4-(5-(4-(((5-cyclopropyl-3-(2-(trifluoromethoxy)phenyl)isoxazol-4-yl)methoxy)methyl)bicyclo[2.2.2]octan-1-yl)-1,2,4-oxadiazol-3-yl)benzoic acid | $^1$H NMR (400 MHz, DMSO-d$_6$) δ 8.08 (br s, 4H), 7.76-7.48 (m, 4H), 4.30 (s, 2H), 2.99 (s, 2H), 2.34-2.26 (m, 1H), 1.99-1.71 (m, 6H), 1.45-1.23 (m, 6H), 1.19-0.98 (m, 4H). FXR EC$_{50}$ (nM) = 960. MS (ESI) 610 (M + H) | Ex 151 |

TABLE 4-continued

| Ex. No. | Structure & Name | ¹H NMR, FXR EC$_{50}$ & MS (ESI) | Method |
|---|---|---|---|
| 155 | 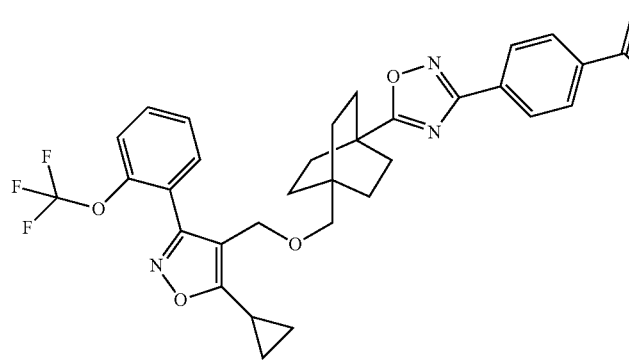<br>Methyl 4-(5-(4-(((5-cyclopropyl-3-(2-(trifluoromethoxy)phenyl)isoxazol-4-yl)methoxy)methyl)bicyclo[2.2.2]octan-1-yl)-1,2,4-oxadiazol-3-yl)benzoate | ¹H NMR (400 MHz, DMSO-d$_6$) δ 8.12 (s, 4H), 7.73-7.64 (m, 1H), 7.64-7.60 (m, 1H), 7.59-7.48 (m, 2H), 4.31 (s, 2H), 3.89 (s, 3H), 2.99 (s, 2H), 2.34-2.27 (m, 1H), 1.97-1.81 (m, 6H), 1.45-1.28 (m, 6H), 1.19-1.02 (m, 4H). FXR EC$_{50}$ (nM) = 2500. MS (ESI) 624 (M + H). | Ex. 151 |
| 156 | 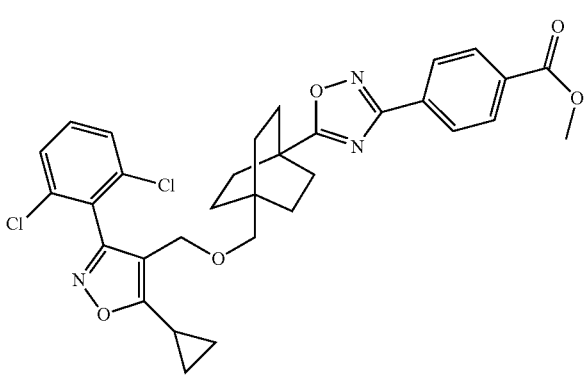<br>methyl 4-(5-(4-(((5-cyclopropyl-3-(2,6-dichlorophenyl)isoxazol-4-yl)methoxy)methyl)bicyclo[2.2.2]octan-1-yl)-1,2,4-oxadiazol-3-yl)benzoate | ¹H NMR (500 MHz, DMSO-d$_6$) δ 8.25-8.01 (m, 4H), 7.74-7.61 (m, 2H), 7.61-7.49 (m, 1H), 4.25 (s, 2H), 3.89 (s, 3H), 2.96 (s, 2H), 2.37-2.24 (m, 1H), 1.96-1.76 (m, 6H), 1.39-1.22 (m, 6H), 1.18-0.98 (m, 4H). FXR EC$_{50}$ (nM) = 1700. MS (ESI). 608 (M + H). | Ex. 151 |
| 158 | 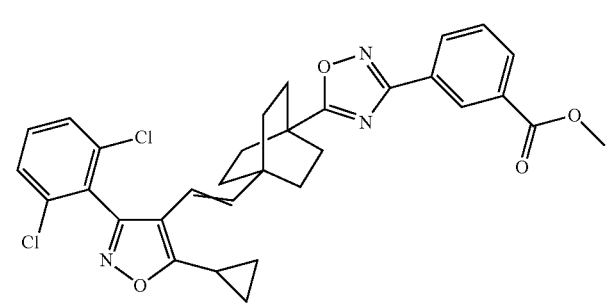<br>Methyl 3-(5-(4-(2-(5-cyclopropyl-3-(2,6-dichlorophenyl)isoxazol-4-yl)vinyl)bicyclo[2.2.2]octan-1-yl)-1,2,4-oxadiazol-3-yl)benzoate | ¹H NMR (400 MHz, DMSO-d$_6$) δ 8.51 (s, 1H), 8.24 (d, J = 7.1 Hz, 1H), 8.15 (d, J = 7.8 Hz, 1H), 7.78-7.49 (m, 4H), 6.06 (d, J = 16.4 Hz, 1H), 5.25 (d, J = 16.4 Hz, 1H), 3.90 (s, 3H), 2.43-2.34 (m, 1H), 2.04-1.81 (m, 6H), 1.51-1.36 (m, 6H), 1.20-0.97 (m, 4H). FXR EC$_{50}$ (nM) = 4600. MS (ESI) 590 (M + H). | Ex. 159 |

| Ex. No. | Structure & Name | $^1$H NMR, FXR EC$_{50}$ & MS (ESI) | Method |
|---|---|---|---|
| 160 | 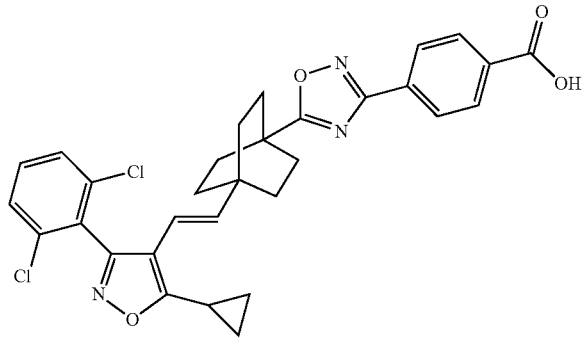<br>(E)-4-(5-(4-(2-(5-cyclopropyl-3-(2,6-dichlorophenyl)isoxazol-4-yl)vinyl)bicyclo[2.2.2]octan-1-yl)-1,2,4-oxadiazol-3-yl)benzoic acid | $^1$H NMR (400 MHz, DMSO-d$_6$) δ 13.3 (br s, 1H), 8.09 (s, 4H), 7.76-7.66 (m, 2H), 7.64-7.56 (m, 1H), 6.05 (d, J = 16.6 Hz, 1H), 5.25 (d, J = 16.4 Hz, 1H), 2.44-2.34 (m, 1H), 2.04-1.87 (m, 6H), 1.55-1.38 (m, 6H), 1.14-1.06 (m, 4H). FXR EC$_{50}$ (nM) = 51. MS (ESI) 576 (M + H). Predominantly trans isomer (See Ex. 164) | Ex. 159 |
| 161 | 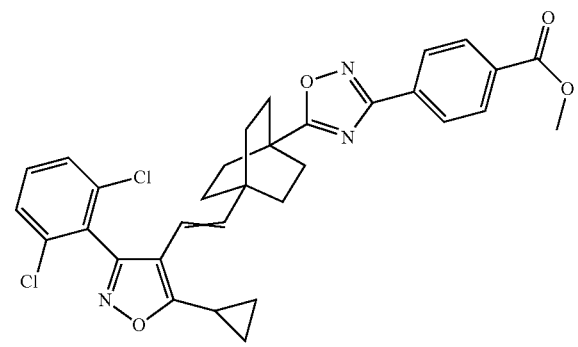<br>Methyl 4-(5-(4-(2-(5-cyclopropyl-3-(2,6-dichloro phenyl)isoxazol-4-yl)vinyl)bicyclo[2.2.2]octan-1-l)-1,2,4-oxadiazol-3-yl)benzoate | $^1$H NMR (400 MHz, DMSO-d$_6$) δ 8.11 (s, 4H), 7.76-7.49 (m, 3H), 6.05 (d, J = 16.4 Hz, 1H), 5.24 (d, J = 16.6 Hz, 1H), 3.88 (s, 3H), 2.42-2.33 (m, 1H), 2.03-1.80 (m, 6H), 1.62-1.36 (m, 6H), 1.24-1.01 (m, 4H). FXR EC$_{50}$ (nM) = 950. MS (ES) 590 (M + H). | Ex. 159 |
| 164 | 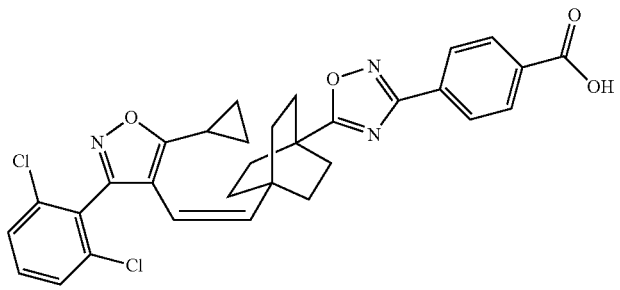<br>(Z)-4-(5-(4-(2-(5-cyclopropyl-3-(2,6-dichlorophenyl)isoxazol-4-yl)vinyl)bicyclo[2.2.2]octan-1-yl)-1,2,4-oxadiazol-3-yl)benzoic acid | $^1$H NMR (400 MHz, DMSO-d$_6$) δ 8.08 (s, 4H), 7.75-7.61 (m, 2H), 7.61-7.47 (m, 1H), 5.82 (d, J = 12.5 Hz, 1H), 5.62 (d, J = 12.5 Hz, 1H), 2.13-2.05 (m, 1H), 1.99-1.84 (m, 6H), 1.65-1.44 (m, 6H), 1.22-1.09 (m, 4H). FXR EC$_{50}$ (nM) = 1600. MS (ESI) 576 (M + H). Predominantly cis isomer (See Ex. 160) | Ex. 159 |

TABLE 4-continued

| Ex. No. | Structure & Name | ¹H NMR, FXR EC₅₀ & MS (ESI) | Method |
|---|---|---|---|
| 165 | Methyl 3-chloro-4-(4-(((5-cyclopropyl-3-(2,6-dichlorophenyl)isoxazol-4-yl)methoxy)methyl)bicyclo[2.2.2]octane-1-carboxamido)benzoate | $^1$H NMR (400 MHz, DMSO-d$_6$) δ 8.86 (s, 1H), 7.98 (d, J = 2.0 Hz, 1H), 7.89 (dd, J = 8.6, 2.0 Hz, 1H), 7.83 (d, J = 8.3 Hz, 1H), 7.69-7.61 (m, 2H), 7.60-7.53 (m, 1H), 4.24 (s, 2H), 3.85 (s, 3H), 2.93 (s, 2H), 2.32-2.27 (m, 1H), 1.76-1.65 (m, 6H), 1.26-1.16 (m, 6H), 1.16-1.07 (m, 4H). FXR EC$_{50}$ (nM) = 2400. MS (ESI) 619 (M + H). | Ex. 170 |
| 167 | 4-(5-(4-(((5-cyclopropyl-3-(2,6-dichlorophenyl)isoxazol-4-yl)amino)methyl)bicyclo[2.2.2]octan-1-yl)-1,2,4-oxadiazol-3-yl)benzoic acid | $^1$H NMR (400 MHz, DMSO-d$_6$) δ 8.19-7.97 (m, 4H), 7.72-7.61 (m, 2H), 7.60-7.51 (m, 1H), 3.60 (br s, 1H), 2.32-2.20 (m, 1H), 2.00-1.78 (m, 6H), 1.45-1.25 (m, 6H), 1.13-1.04 (m, 2H), 1.03-0.91 (m, 2H). FXR EC$_{50}$ (nM) = 530. MS (ESI) 579 (M + H). | Ex. 166 |
| 169 | methyl 3-chloro-4-(4-(((5-cyclopropyl-3-(2,6-dichlorophenyl)isoxazol-4-yl)methoxy)methyl)bicyclo[2.2.2]octane-1-carbothioamido)benzoate | $^1$H NMR (400 MHz, DMSO-d$_6$) δ 10.65 (s, 1H), 8.01 (d, J = 1.7 Hz, 1H), 7.93 (dd, J = 8.2, 1.6 Hz, 1H), 7.64 (d, J = 7.6 Hz, 2H), 7.60-7.52 (m, 1H), 7.45 (d, J = 8.3 Hz, 1H), 4.24 (s, 2H), 3.87 (s, 3H), 2.94 (s, 2H), 2.33-2.24 (m, 1H), 1.92-1.72 (m, 6H), 1.34-1.18 (m, 6H), 1.18-0.97 (m, 4H). FXR EC$_{50}$ (nM) = 4400. MS (ESI) 619 (M + H). | Ex. 168 |

TABLE 4-continued

| Ex. No. | Structure & Name | ¹H NMR, FXR EC$_{50}$ & MS (ESI) | Method |
|---|---|---|---|
| 173 | 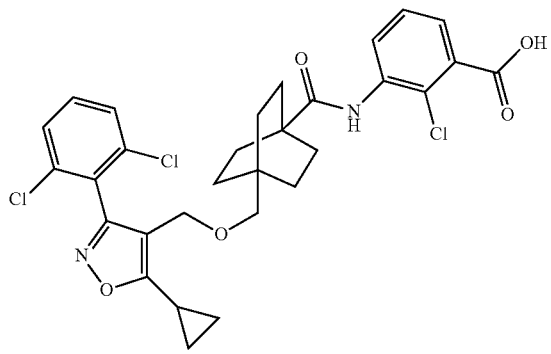<br>2-chloro-3-(4-(((5-cyclopropyl-3-(2,6-dichlorophenyl)isoxazol-4-ylmethoxy)methyl)bicyclo[2.2.2]octane-1-carboxamido)benzoic acid | ¹H NMR (400 MHz, DMSO-d$_6$) δ 8.54 (s, 1H), 7.70-7.62 (m, 2H), 7.61-7.52 (m, 1H), 7.39 (d, J = 7.6 Hz, 1H), 7.11 (t, J = 7.6 Hz, 1H), 7.05 (dd, J = 7.6, 1.7 Hz, 1H), 4.24 (s, 2H), 2.92 (s, 2H), 2.32-2.26 (m, 1H), 1.75-1.61 (m, 6H), 1.25-1.17 (m, 6H), 1.16-1.05 (m, 4H). FXR EC$_{50}$ (nM) = 1400. MS (ESI) 603 (M + H). | Ex. 170 |
| 183 | 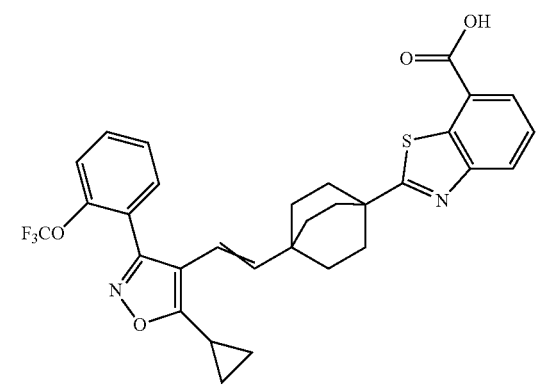<br>2-(4-(2-(5-cyclopropyl-3-(2-(trifluoromethoxy)phenyl)isoxazol-4-yl)vinyl)bicyclo[2.2.2]octan-1-yl)benzo[d]thiazole-7-carboxylic acid | ¹H NMR (400 MHz, DMSO-d$_6$) δ 8.15 (d, J = 8.6 Hz, 1H), 8.01 (d, J = 7.8 Hz, 1H), 7.71-7.53 (m, 5H), 5.97 (d, J = 16.4 Hz, 1H), 5.55 (d, J = 16.4 Hz, 1H), 2.32-2.31 (m, 1H), 2.08-1.97 (m, 6H), 1.57-1.53 (m, 6H), 1.17-1.04 (m, 4H). FXR EC$_{50}$ (nM) = 13. MS (ESI) 581 (M + H).<br>trans/cis 3:1 ratio | Ex. 182 |
| 184 | 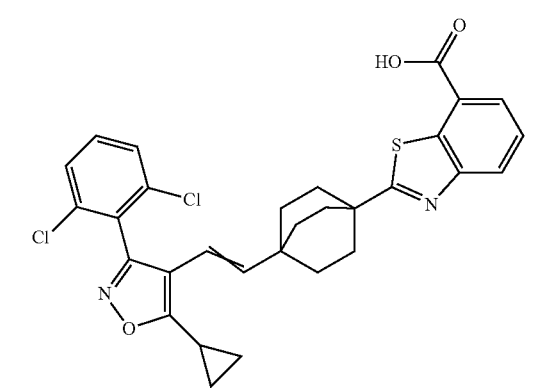<br>2-(4-(2-(5-cyclopropyl-3-(2,6-dichlorophenyl)isoxazol-4-yl)vinyl)bicyclo[2.2.2]octan-1-yl)benzo[d]thiazole-7-carboxylic acid | ¹H NMR (400 MHz, METHANOL-d$_4$) δ 8.02-7.82 (m, 2H), 7.76-7.55 (m, 3H), 7.46 (t, J = 7.6 Hz, 1H), 6.04 (d, J = 16.4 Hz, 1H), 5.28 (d, J = 16.4 Hz, 1H), 2.39-2.34 (m, 1H), 2.05-1.82 (m, 6H), 1.56-1.41 (m, 6H), 1.22-1.13 (m, 2H), 1.13-1.00 (m, 2H). FXR EC$_{50}$ (nM) = 20. MS (ESI) 565 (M + H). | Ex. 182 |

TABLE 4-continued

| Ex. No. | Structure & Name | $^1$H NMR, FXR EC$_{50}$ & MS (ESI) | Method |
|---|---|---|---|
| 185 | 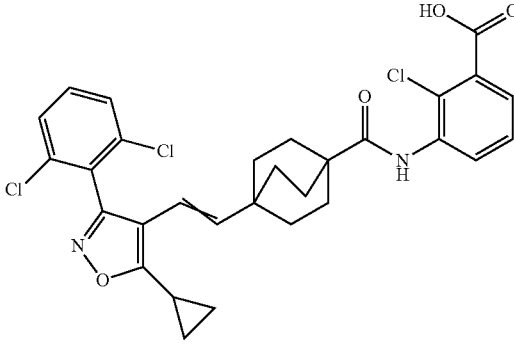<br>2-chloro-3-(4-(2-(5-cyclopropyl-3-(2,6-dichlorophenyl)isoxazol-4-yl)vinyl)bicyclo[2.2.2]octane-1-carboxamido)benzoic acid | $^1$H NMR (500 MHz, DMSO-d$_6$) δ 8.57 (s, 1H), 7.75-7.51 (m, 3H), 7.36 (d, J = 7.8 Hz, 1H), 7.14-6.97 (m, 2H), 6.00 (d, J = 16.4 Hz, 1H), 5.23 (d, J = 16.4 Hz, 1H), 2.38-2.33 (m, 1H), 1.84-1.70 (m, 6H), 1.44-1.23 (m, 6H), 1.21-1.01 (m, 4H). FXR EC$_{50}$ (nM) = 1400. MS (ESI) 585 (M + H). | Ex. 170 |
| 186 | 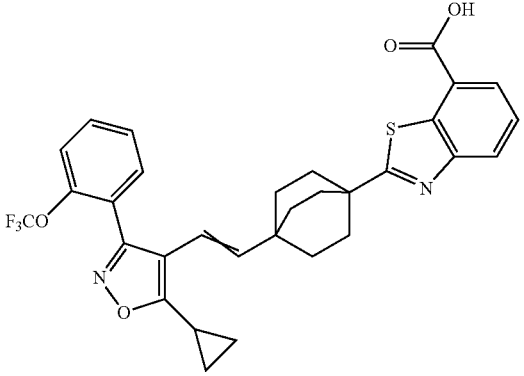<br>2-(4-(2-(5-cyclopropyl-3-(2-(trifluoromethoxy)phenyl)isoxazol-4-yl)vinyl)bicyclo[2.2.2]octan-1-yl)benzo[d]thiazole-7-carboxylic acid | $^1$H NMR (400 MHz, DMSO-d$_6$) δ 8.10 (d, J = 8.6 Hz, 1H), 8.01 (d, J = 7.8 Hz, 1H), 7.69-7.53 (m, 5H), 5.93 (d, J = 12.4 Hz, 1H), 5.61 (d, J = 12.4 Hz, 1H), 2.12-2.10 (m, 1H), 1.86-1.82 (m, 6H), 1.41-1.37 (m, 6H), 1.16-1.06 (m, 4H). FXR EC$_{50}$ (nM) = 67. MS (ESI) 581 (M + H). trans/cis 1:6 ratio | Ex. 182 |
| 187 | 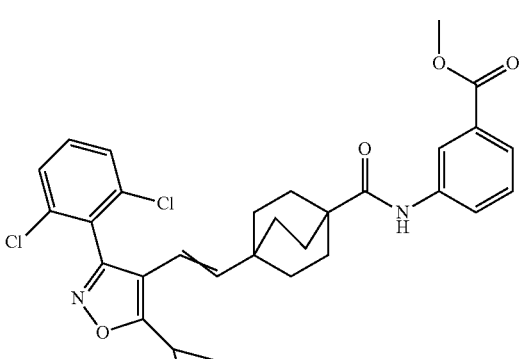<br>methyl 3-(4-(2-(5-cyclopropyl-3-(2,6-dichlorophenyl)isoxazol-4-yl)vinyl)bicyclo[2.2.2]octane-1-carboxamido)benzoate | $^1$H NMR (400 MHz, DMSO-d$_6$) δ 9.34 (s, 1H), 8.27 (s, 1H), 7.92 (d, J = 8.3 Hz, 1H), 7.74-7.52 (m, 3H), 7.41 (t, J = 7.9 Hz, 1H), 6.01 (d, J = 16.4 Hz, 1H), 5.23 (d, J = 16.4 Hz, 1H), 3.84 (s, 3H), 2.5-2.4 (m, 1H), 1.82-1.67 (m, 6H), 1.41-1.31 (m, 6H), 1.17-1.07 (m, 4H). FXR EC$_{50}$ (nM) = 3000. MS ESI) 565 (M + H). trans/cis 6:1 ratio | Ex. 170 |

TABLE 4-continued

| Ex. No. | Structure & Name | $^1$H NMR, FXR EC$_{50}$ & MS (ESI) | Method |
|---|---|---|---|
| 188 | 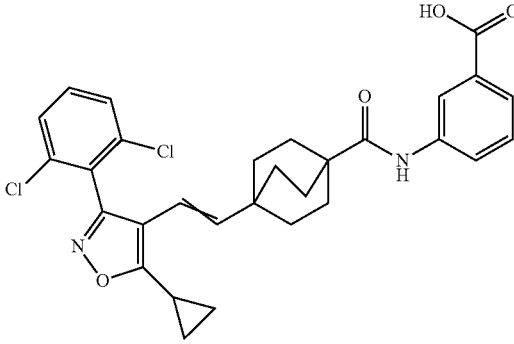<br>3-(4-(2-(5-cyclopropyl-3-(2,6-dichlorophenyl)isoxazol-4-yl)vinyl)bicyclo[2.2.2]octane-1-carboxamido)benzoic acid | $^1$H NMR (400 MHz, DMSO-d$_6$) δ 9.26 (s, 1H), 8.16 (s, 1H), 7.81 (d, J = 8.6 Hz, 1H), 7.68-7.56 (m, 4H), 7.33 (t, J = 7.8 Hz, 1H), 5.77 (d, J = 16.4 Hz, 1H), 5.61 (d, J = 16.4 Hz, 1H), 2.12-2.03 (m, 1H), 1.79-1.66 (m, 6H), 1.52-1.39 (m, 6H), 1.19-1.06 (m, 4H). FXR EC$_{50}$ (nM) = 120. MS (ESI) 551 (M + H). trans/cis 6:1 ratio | Ex 170 |
| 189 | 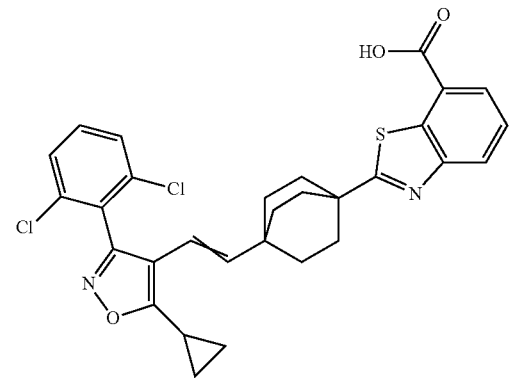<br>2-(4-(2-(5-cyclopropyl-3-(2,6-dichlorophenyl)isoxazol-4-yl)vinyl)bicyclo[2.2.2]octan-1-yl)benzo[d]thiazole-7-carboxylic acid | $^1$H NMR (400 MHz, DMSO-d$_6$) δ 7.90 (d, J = 7.6 Hz, 2H), 7.70-7.60 (m, 2H), 7.59-7.52 (m, 1H), 7.46 (br. s., 1H), 5.81 (d, J = 12.5 Hz, 1H), 5.63 (d, J = 12.5 Hz, 1H), 2.16-2.05 (m, 1H), 2.02-1.77 (m, 6H), 1.66-1.40 (m, 6H), 1.21-1.08 (m, 4H). FXR EC$_{50}$ (nM) = 63. MS (ESI) 565 (M + H). trans/cis 1:2 ratio | Ex. 182 |
| 190 | 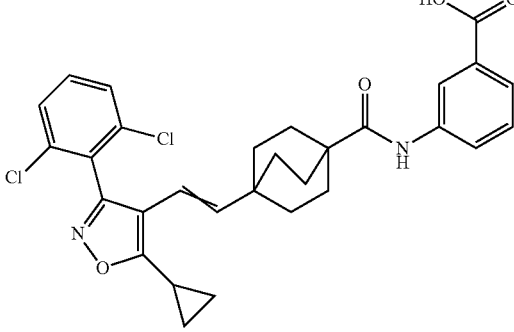<br>3-(4-(2-(5-cyclopropyl-3-(2,6-dichlorophenyl)isoxazol-4-yl)vinyl)bicyclo[2.2.2]octane-1-carboxamido)benzoic acid | $^1$H NMR (400 MHz, DMSO-d$_6$) δ 9.24 (s, 1H), 8.16 (s, 1H), 7.81 (d, J = 7.6 Hz, 2H), 7.70-7.51 (m, 3H), 7.35-7.31 (m, 1H), 5.77 (d, J = 12.5 Hz, 1H), 5.61 (d, J = 12.5 Hz, 1H), 2.09-2.05 (m, 1H), 1.77-1.70 (m, 6H), 1.49-1.43 (m, 6H), 1.14-1.08 (m, 4H). FXR EC$_{50}$ (nM) = 3500. MS (ESI) 553 (M + H). trans/cis 1:9 ratio | Ex. 170 |

TABLE 4-continued

| Ex. No. | Structure & Name | $^1$H NMR, FXR EC$_{50}$ & MS (ESI) | Method |
|---|---|---|---|
| 191 | 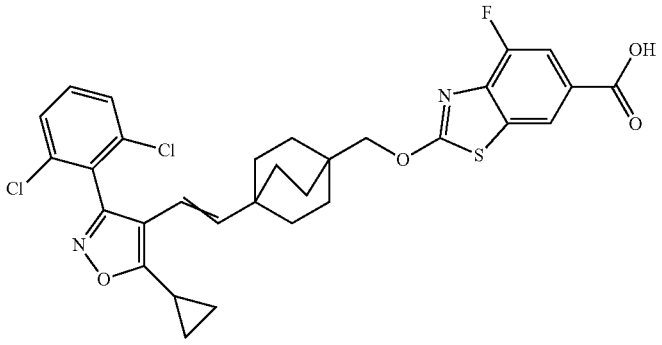<br>2-((4-(2-(5-cyclopropyl-3-(2,6-dichlorophenyl)isoxazol-4-yl)vinyl)bicyclo[2.2.2]octan-1-yl)methoxy)-4-fluorobenzo[d]thiazole-6-carboxylic acid | $^1$H NMR (400 MHz, DMSO-d$_6$) δ 8.31 (s, 1H), 7.73-7.63 (m, 3H), 7.63-7.52 (m, 1H), 5.98 (d, J = 16.6 Hz, 1H), 5.22 (d, J = 16.6 Hz, 1H), 4.25 (s, 2H), 2.34-2.33 (m, 1H), 1.54-1.45 (m, 6H), 1.39-1.28 (m, 6H), 1.15-1.12 (m, 2H), 1.10-1.02 (m, 2H). FXR EC$_{50}$ (nM) = 58. MS (ESI) 613 (M + H). trans/cis 4:1 ratio | Ex. 176 |
| 192 | 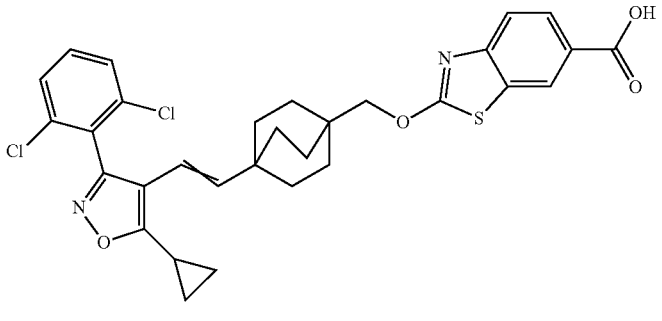<br>2-((4-(2-(5-cyclopropyl-3-(2,6-dichlorophenyl)isoxazol-4-yl)vinyl)bicyclo[2.2.2]octan-1-yl)methoxy)benzo[d]thiazole-6-carboxylic acid | $^1$H NMR (500 MHz, DMSO-d$_6$) δ 8.49 (s, 1H), 7.94 (d, J = 8.8 Hz, 1H), 7.76-7.53 (m, 4H), 5.98 (d, J = 16.6 Hz, 1H), 5.22 (d, J = 16.6 Hz, 1H), 4.23 (s, 2H), 2.34-2.32 (m, 1H), 1.49-1.46 (m, 6H), 1.35-1.32 (m, 6H), 1.15-1.07 (m, 4H). FXR EC$_{50}$ (nM) = 7.2. MS (ESI) 595 (M + H). | Ex. 176 |
| 196 | 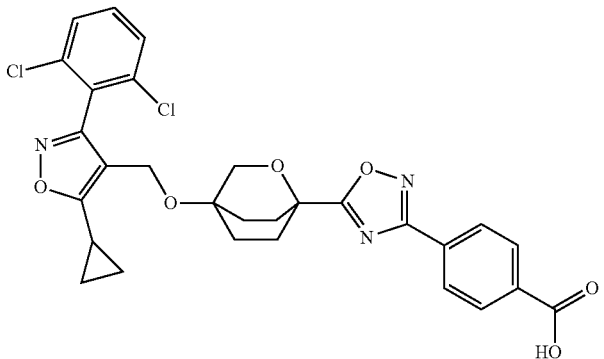<br>4-(5-(4-((5-cyclopropyl-3-(2,6-dichlorophenyl)isoxazol-4-yl)methoxy)-2-oxabicyclo[2.2.2]octan-1-yl)-1,2,4-oxadiazol-3-yl)benzoic acid | $^1$H NMR (400 MHz, DMSO-d$_6$) δ 13.28 (br. s., 1H), 8.10 (s, 4H), 7.72-7.63 (m, 2H), 7.62-7.53 (m, 1H), 4.26 (s, 2H), 3.51 (s, 2H), 2.37-2.23 (m, 3H), 2.22-2.08 (m, 2H), 1.92-1.72 (m, 2H), 1.55 (td, J = 10.0, 3.8 Hz, 2H), 1.22-0.98 (m, 4H). FXR EC$_{50}$ (nM) = 83. MS (ESI) 582 (M + H). | Ex. 193 |

TABLE 4-continued

| Ex. No. | Structure & Name | ¹H NMR, FXR EC$_{50}$ & MS (ESI) | Method |
|---|---|---|---|
| 198 | 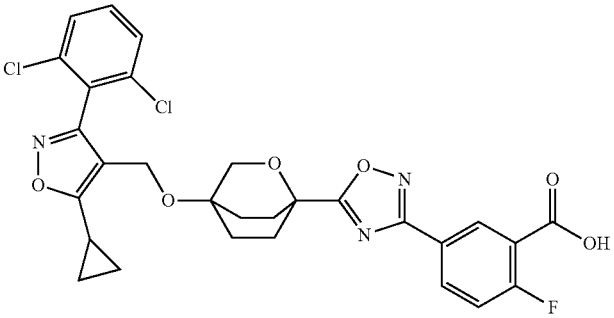<br>5-(5-(4-((5-cyclopropyl-3-(2,6-dichlorophenyl)isoxazol-4-yl)methoxy)-2-oxabicyclo[2.2.2]octan-1-yl)-1,2,4-oxadiazol-3-yl)-2-fluorobenzoic acid | ¹H NMR (400 MHz, DMSO-d$_6$) δ 8.44 (dd, J = 7.1, 2.2 Hz, 1H), 8.22-8.84 (m, 1H), 7.67-7.64 (m, 2H), 7.62-7.55 (m, 1H), 7.55-7.49 (m, 1H), 4.26 (s, 2H), 3.51 (s, 2H), 2.38-2.22 (m, 3H), 2.22-2.12 (m, 2H), 1.85-1.74 (m, 2H), 1.57-1.53 (m, 2H), 1.21-1.03 (m, 4H). FXR EC$_{50}$ (nM) = 98. MS (ESI) 600 (M + H). | Ex. 193 |
| 199 | 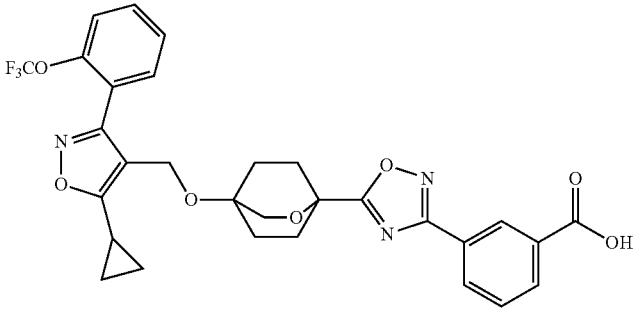<br>3-(5-(4-((5-cyclopropyl-3-(2-(trifluoromethoxy)phenyl)isoxazol-4-yl)methoxy)-2-oxabicyclo[2.2.2]octan-1-yl)-1,2,4-oxadiazol-3-yl)benzoic acid | ¹H NMR (400 MHz, DMSO-d$_6$) δ 8.52 (s, 1H), 8.17 (d, J = 8.1 Hz, 1H), 8.12 (d, J= 7.6 Hz, 1H), 7.74-7.64 (m, 2H), 7.64-7.50 (m, 3H), 4.30 (s, 2H), 3.65 (s, 2H), 2.35-2.28 (m, 3H), 2.27-2.17 (m, 2H), 2.00-1.87 (m, 2H), 1.79-1.71 (m, 2H), 1.20-1.11 (m, 2H), 1.10-0.99 (m, 2H). FXR EC$_{50}$ (nM) = 220. MS (ESI) 598 (M + H). | Ex. 193 |
| 200 | 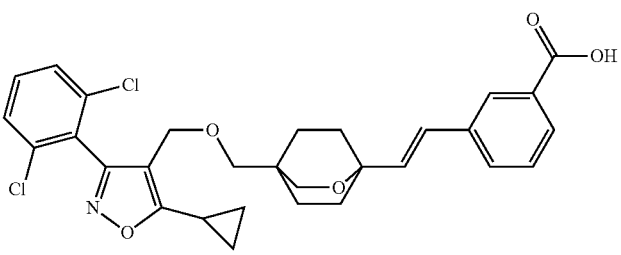<br>(E)-3-(2-(4-(((5-cyclopropyl-3-(2,6-dichlorophenyl)isoxazol-4-yl)methoxy)methyl)-2-oxabicyclo[2.2.2]octan-1-yl)vinyl)benzoic acid | ¹H NMR (400 MHz, DMSO-d$_6$) δ 7.92 (s, 1H), 7.77 (d, J = 7.20 Hz, 1H), 7.67-7.56 (m, 2H), 7.41 (t, J = 7.20 Hz, 3H), 6.50 (d, J = 16.00 Hz, 1H), 6.27 (d, J = 16.00 Hz, 1H), 4.24 (s, 2H), 3.49 (s, 2H), 2.98 (s, 2H), 2.31-2.28 (m, 1H), 1.72-1.70 (m, 4H), 1.40-1.30 (m, 4H), 1.16-1.09 (m, 4H). FXR EC$_{50}$ (nM) = 220. MS (ESI) 554 (M + H). | Ex. 197 |

TABLE 4-continued

| Ex. No. | Structure & Name | ¹H NMR, FXR EC₅₀ & MS (ESI) | Method |
|---|---|---|---|
| 201 | 4-(4-(((5-cyclopropyl-3-(2,6-dichlorophenyl)isoxazol-4-yl)methoxy)methyl)-2-oxabicyclo[2.2.2]octan-1-yl)benzoic acid | $^1$H NMR (400 MHz, DMSO-$d_6$) δ 12.79 (br. s., 1H), 7.85 (d, J = 8.1 Hz, 2H), 7.73-7.62 (m, 2H), 7.62-7.54 (m, 1H), 7.45 (d, J = 8.1 Hz, 2H), 4.25 (s, 2H), 3.60 (s, 2H), 3.02 (s, 2H), 2.34-2.25 (m, 1H), 2.08-1.88 (m, 2H), 1.82-1.64 (m, 2H), 1.55-1.32 (m, 4H), 1.22-1.02 (m, 4H). FXR EC$_{50}$ (nM) = 270. MS (ESI) 528 (M + H). | Ex. 195 |
| 202 | 5-(4-(((5-cyclopropyl-3-(2,6-dichlorophenyl)isoxazol-4-yl)methoxy)methyl)-2-oxabicyclo[2.2.2]octan-1-yl)-2-fluorobenzoic acid | $^1$H NMR (400 MHz, DMSO-$d_6$) δ 13.18 (br. s., 1H), 7.83 (d, J = 6.8 Hz, 1H), 7.67-7.64 (m, 2H), 7.59-7.55 (m, 2H), 7.23-7.18 (m, 1H), 4.25 (s, 2H), 3.60 (s, 2H), 3.01 (s, 2H), 2.37-2.27 (m, 1H), 2.06-1.90 (m, 2H), 1.71-1.67 (m, 2H), 1.51-1.32 (m, 4H), 1.21-1.0 (m, 4H). FXR EC$_{50}$ (nM) = 390. MS (ESI) 546 (M + H). | Ex. 195 |
| 204 | 3-(4-(((5-cyclopropyl-3-(2-trifluoromethoxyphenyl)isoxazol-4-yl)methoxy)methyl)-2-oxabicyclo[2.2.2]octan-1-yl)benzoic acid | $^1$H NMR (400 MHz, DMSO-$d_6$) δ 7.93 (s, 1H), 7.76 (d, J = 7.1 Hz, 1H), 7.73-7.65 (m, 1H), 7.62 (d, J = 6.4 Hz, 1H), 7.53 (d, J = 6.4 Hz, 1H), 7.57 (d, J = 7.6 Hz, 2H), 7.43-7.34 (m, 1H), 4.31 (s, 2H), 3.62 (s, 2H), 3.04 (s, 2H), 2.32-2.26 (m, 1H), 2.06-1.94 (m, 2H), 1.73 (d, J = 5.4 Hz, 2H), 1.56-1.36 (m, 4H), 1.17-1.06 (m, 4H). FXR EC$_{50}$ (nM) = 440. MS (ESI) 544 (M + H). | Ex. 195 |
| 205 | 4-(4-(((5-cyclopropyl-3-(2-(trifluoromethoxy)phenyl)isoxazol-4-yl)methoxy)methyl)-2-oxabicyclo[2.2.2]octan-1-yl)benzoic acid | $^1$H NMR (400 MHz, DMSO-$d_6$) δ 12.79 (br. s., 1H), 7.94-7.76 (m, 2H), 7.73-7.64 (m, 1H), 7.64-7.59 (m, 1H), 7.59-7.51 (m, 2H), 7.45 (d, J = 7.8 Hz, 2H), 4.31 (s, 2H), 3.61 (s, 2H), 3.04 (s, 2H), 2.33-2.23 (m, 1H), 2.09-1.92 (m, 2H), 1.81-1.64 (m, 2H), 1.57-1.34 (m, 4H), 1.20-1.01 (m, 4H). FXR EC$_{50}$ (nM) = 450. MS (ESI) 544 (M + H). | Ex. 195 |

TABLE 4-continued

| Ex. No. | Structure & Name | $^{1}$H NMR, FXR EC$_{50}$ & MS (ESI) | Method |
|---|---|---|---|
| 206 | 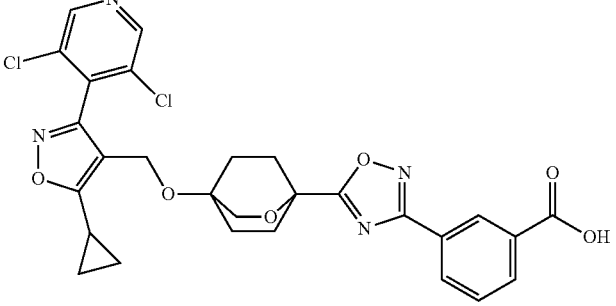<br>3-(5-(4-(((5-cyclopropyl-3-(3,5-dichloropyridin-4-yl)isoxazol-4-yl)methoxy)-2-oxabicyclo[2.2.2]octan-1-yl)-1,2,4-oxadiazol-3-yl)benzoic acid | $^{1}$H NMR (400 MHz, DMSO-d$_6$) δ 8.85 (s, 2H), 8.50 (s, 1H), 8.06 (d, J = 7.6 Hz, 1H), 8.00 (d, J = 7.8 Hz, 1H), 7.53 (t, J = 7.6 Hz, 1H), 4.33 (s, 2H), 3.53 (s, 2H), 2.39-2.25 (m, 3H), 2.24-2.14 (m, 2H), 1.87-1.70 (m, 2H), 1.64-1.45 (m, 2H), 1.17 (d, J = 8.3 Hz, 2H), 1.13-1.02 (m, 2H). FXR EC$_{50}$ (nM) = 490. MS (ESI) 583 (M + H). | Ex. 193 |
| 207 | 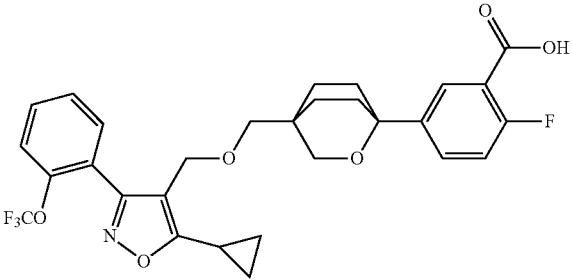<br>5-(4-(((5-cyclopropyl-3-(2-(trifluoromethoxy)phenyl)isoxazol-4-yl)methoxy)methyl)-2-oxabicyclo[2.2.2]octan-1-yl)-2-fluorobenzoic acid | $^{1}$H NMR (400 MHz, DMSO-d$_6$) δ 13.18 (br. s., 1H), 7.82 (d, J = 4.4 Hz, 1H), 7.72-7.66 (m, 1H), 7.64-7.59 (m, 1H), 7.59-7.47 (m, 3H), 7.26-7.11 (m, 1H), 4.31 (s, 2H), 3.61 (s, 2H), 3.04 (s, 2H), 2.33-2.24 (m, 1H), 2.07-1.89 (m, 2H), 1.71 (br. s., 2H), 1.57-1.34 (m, 4H), 1.20-1.01 (m, 4H).). FXR EC$_{50}$ (nM) = 570. MS (ESI) 562 (M + H). | Ex. 195 |
| 211 | 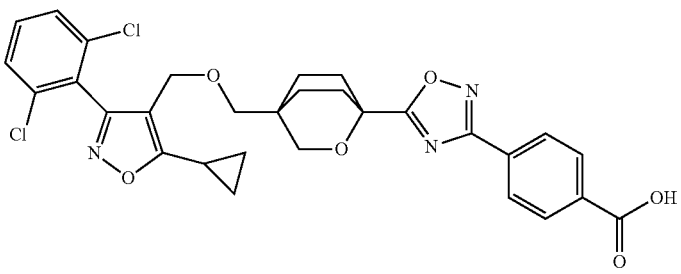<br>(4-(5-(4-(((5-cyclopropyl-3-(2,6-dichlorophenyl)isoxazol-4-yl)methoxy)methyl)-2-oxabicyclo[2.2.2]octan-1-yl)-1,2,4-oxadiazol-3-yl)benzoic acid | $^{1}$H NMR (400 MHz, DMSO-d$_6$) δ 8.09-7.93 (m, 4H), 7.71-7.64 (m, 2H), 7.61-7.52 (m, 1H), 4.26 (s, 2H), 3.59 (s, 2H), 3.04 (s, 2H), 2.28-2.3 (m, 1H), 2.17 (m, 2H), 2.10-1.98 (m, 2H), 1.53-1.45 (m, 4H), 1.20-1.03 (m, 4H). FXR EC$_{50}$ (nM) = 980. MS (ESI) 596 (M + H). | Ex. 209 |

TABLE 4-continued

| Ex. No. | Structure & Name | $^1$H NMR, FXR EC$_{50}$ & MS (ESI) | Method |
|---|---|---|---|
| 212 | 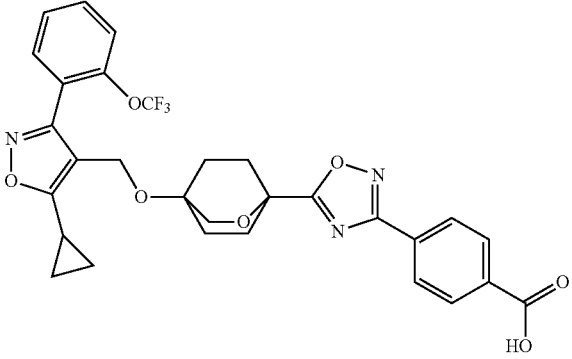<br>4-(5-(4-(((5-cyclopropyl-3-(2-(trifluoromethoxy)phenyl)isoxazol-4-yl)methoxy)-2-oxabicyclo[2.2.2]octan-1-yl)-1,2,4-oxadiazol-3-yl)benzoic acid | $^1$H NMR (400 MHz, DMSO-d$_6$) δ 8.10 (s, 4H), 7.75-7.66 (m, 1H), 7.64-7.48 (m, 3H), 4.30 (s, 2H), 3.65 (s, 2H), 2.39-2.27 (m, 3H), 2.22 (td, J = 12.5, 4.2 Hz, 2H), 2.03-1.83 (m, 2H), 1.79-1.61 (m, 2H), 1.23-0.98 (m, 4H). FXR EC$_{50}$ (nM) = 1000. MS (ESI) 598 (M + H). | Ex. 193 |
| 213 | 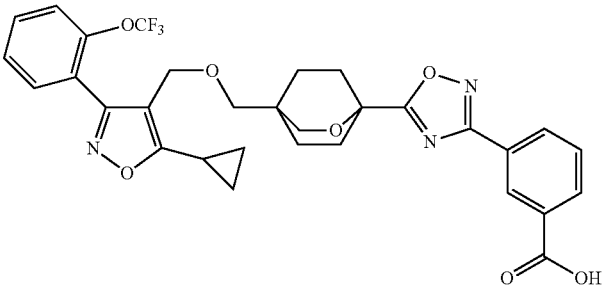<br>3-(5-(4-(((5-cyclopropyl-3-(2-(trifluoromethoxy)phenyl)isoxazol-4-yl)methoxy)methyl)-2-oxabicyclo[2.2.2]octan-1-yl)-1,2,4-oxadiazol-3-yl)benzoic acid | $^1$H NMR (400 MHz, DMSO-d$_6$) δ 8.51 (s, 1H), 8.16 (d, J = 6.8 Hz, 1H), 8.12 (d, J = 8.1 Hz, 1H), 7.74-7.60 (m, 3H), 7.60-7.51 (m, 2H), 4.32 (s, 2H), 3.58 (s, 2H), 3.06 (s, 2H), 2.31-2.29 (m, 1H), 2.19-2.17 (m, 2H), 2.11-1.97 (m, 2H), 1.56-1.48 (m, 4H), 1.18-1.01 (m, 4H). FXR EC$_{50}$ (nM) = 1200. MS (ESI) 612 (M + H). | Ex. 209 |
| 214 | 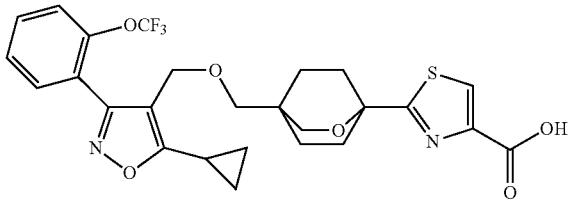<br>2-(4-(((5-cyclopropyl-3-(2-(trifluoromethoxy)phenyl)ixoazol-4-yl)methoxy)methyl)-2-oxabicyclo[2.2.2]octan-1-yl)thiazole-4-carboxylic acid | $^1$H NMR (400 MHz, DMSO-d$_6$) δ 8.33 (s, 1H), 7.69-7.66 (m, 1H), 7.62-7.61 (m, 1H), 7.58-7.53 (m, 2H), 4.30 (s, 2H), 3.63 (s, 2H), 3.04 (s, 2H), 2.33-2.28 (m, 1H), 2.13-2.03 (m, 2H), 1.87-1.82 (m, 2H), 1.50-1.45 (m, 4H), 1.27-1.15 (m, 4H). FXR EC$_{50}$ (nM) = 1400. MS (ESI) 551 (M + H). | Ex. 162 |

TABLE 4-continued

| Ex. No. | Structure & Name | $^1$H NMR, FXR EC$_{50}$ & MS (ESI) | Method |
|---|---|---|---|
| 215 | 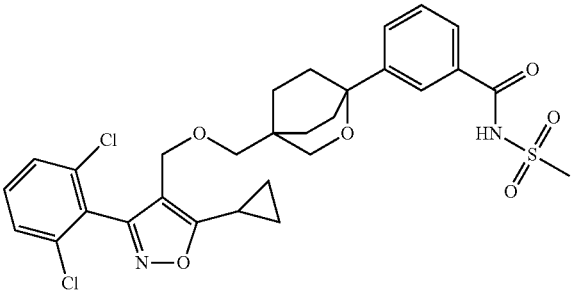<br>3-(4-(((5-cyclopropyl-3-(2,6-dichlorophenyl)isoxazol-4-yl)methoxy)methyl)-2-oxabicyclo[2.2.2]octan-1-yl)-N-(methylsulfonyl)benzamide | $^1$H NMR (400 MHz, DMSO-d$_6$) δ 7.94 (s, 1H), 7.75 (d, J = 7.6 Hz, 1H), 7.70-7.62 (m, 2H), 7.62-7.51 (m, 1H), 7.46 (d, J = 7.1 Hz, 1H), 7.37-7.29 (m, 1H), 4.26 (s, 2H), 3.62 (s, 2H), 3.08 (s, 3H), 3.02 (s, 2H), 2.33-2.25 (m, 1H), 2.05-1.93 (m, 2H), 1.74 (d, J = 10.0 Hz, 2H), 1.53-1.29 (m, 4H), 1.22-1.00 (m, 4H). FXR EC$_{50}$ (nM) = 1600. MS (ESI) 605 (M + H). | Ex. 3 |
| 216 | 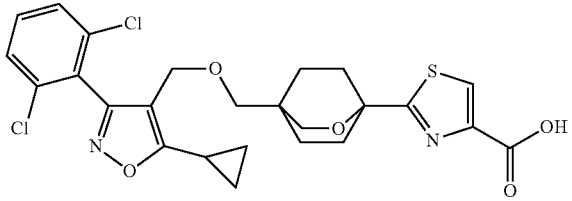<br>2-(4-(((5-cyclopropyl-3-(2,6-dichlorophenyl)isoxazol-4-yl)methoxy)methyl)-2-oxabicyclo[2.2.2]octan-1-yl)thiazole-4-carboxylic acid | $^1$H NMR (400 MHz, DMSO-d$_6$) δ 12.90 (s, 1H), 8.34 (s, 1H), 7.66 (d, J = 8.00 Hz, 2H), 7.56-7.60 (m, 1H), 4.25 (s, 2H), 3.63 (s, 2H), 3.03 (s, 2H), 2.34-2.32 (m, 1H), 2.06-2.03 (m, 2H), 1.86-1.84 (m, 2H), 1.45-1.42 (m, 4H), 1.24-1.16 (m, 4H). FXR EC$_{50}$ (nM) = 2000. MS (ESI) 535 (M + H). | Ex. 162 |
| 217 | 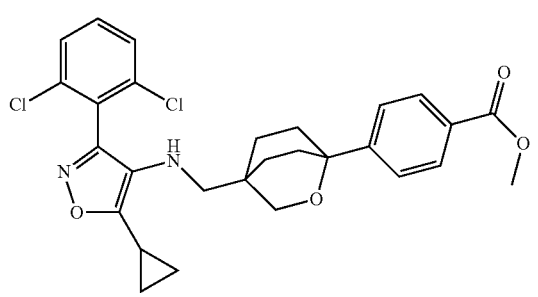<br>methyl 4-(4-(((5-cyclopropyl-3-(2,6-dichlorophenyl)isoxazol-4-yl)amino)methyl)-2-oxabicyclo[2.2.2]octan-1-yl)benzoate | $^1$H NMR (400 MHz, DMSO-d$_6$) δ 7.88-7.86 (m, 2H), 7.67-7.64 (m, 2H), 7.61-7.55 (m, 1H), 7.48-7.46 (m, 2H), 3.82 (s, 3H), 3.77 (t, J = 7.5 Hz, 1H), 3.57 (s, 2H), 2.51-2.53 (m, 2H), 2.33-2.24 (m, 1H), 2.08-1.94 (m, 2H), 1.82-1.59 (m, 2H), 1.56-1.30 (m, 4H), 1.12-1.03 (m, 2H), 1.02-0.89 (m, 2H). FXR EC$_{50}$ (nM) = 2800. MS (ESI) 527 (M + H). | Ex. 203 |

TABLE 4-continued

| Ex. No. | Structure & Name | $^1$H NMR, FXR EC$_{50}$ & MS (ESI) | Method |
|---|---|---|---|
| 218 | 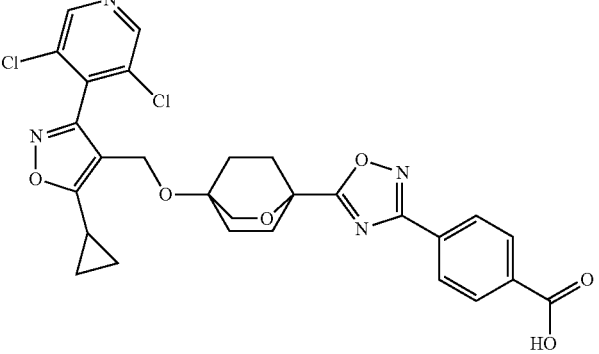<br>4-(5-(4-((5-cyclopropyl-3-(3,5-dichloropyridin-4-yl)isoxazol-4-yl)methoxy)-2-oxabicyclo[2.2.2]octan-1-yl)-1,2,4-oxadiazol-3-yl)benzoic acid | $^1$H NMR (400 MHz, DMSO-d$_6$) δ 13.28 (br. s., 1H), 8.86 (s, 2H), 8.10 (s, 4H), 4.33 (s, 2H), 3.53 (s, 2H), 2.40-2.24 (m, 3H), 2.24-2.12 (m, 2H), 1.82 (br. s., 2H), 1.57 (br. s., 2H), 1.23-1.06 (m, 4H). FXR EC$_{50}$ (nM) = 160. MS (ESI) 583 (M + H). | Ex. 193 |
| 222 | 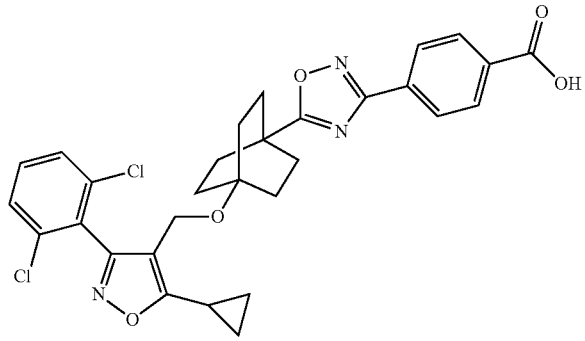<br>4-(5-((1r,4r)-4-((5-cyclopropyl-3-(2,6-dichlorophenyl)isoxazol-4-yl)methoxy)bicyclo[2.2.1]heptan-1-yl)-1,2,4-oxadiazol-3-yl)benzoic acid | $^1$H NMR (400 MHz, DMSO-d$_6$) δ 8.11-8.05 (m, 4H), 7.67-7.63 (m, 2H), 7.60-7.55 (m, 1H), 4.32 (s, 2H), 2.38-2.30 (m, 1H), 2.12-2.08 (m, 2H), 1.91-1.87 (m, 2H), 1.77-1.73 (s, 2H), 1.67-1.63 (m, 2H), 1.52-1.48 (m, 2H), 1.19-1.07 (m, 4H). FXR EC$_{50}$ (nM) = 710. MS (ESI) 566 (M + H). | Ex. 221 |
| 223 | 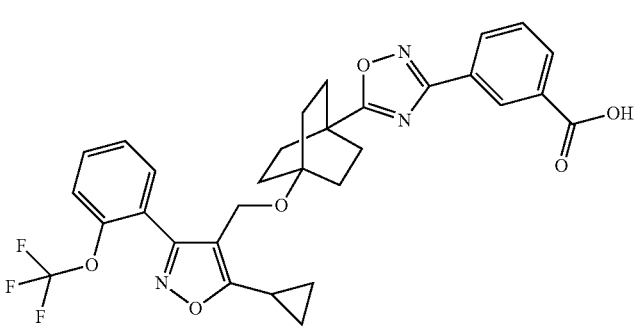<br>3-(5-((1r,4r)-4-((5-cyclopropyl-3-(2-(trifluoromethoxy)phenyl)isoxazol-4-yl)methoxy)bicyclo[2.2.1]heptan-1-yl)-1,2,4-oxadiazol-3-yl)benzoic acid | $^1$H NMR (400 MHz, DMSO-d$_6$) δ 8.51 (s, 1H), 8.04 (dd, J = 13.7, 7.8 Hz, 2H), 7.71-7.63 (m, 2H), 7.60-7.52 (m, 3H), 4.36 (s, 2H), 2.36-2.30 (m, 1H), 2.22-2.13 (m, 2H), 1.99-1.89 (m, 4H), 1.79-1.75 (m, 2H), 1.61 (d, J = 9.3 Hz, 2H), 1.18-1.06 (m, 4H). FXR EC$_{50}$ (nM) = 4700. MS (ESI) 581 (M + H). | Ex. 221 |

TABLE 4-continued

| Ex. No. | Structure & Name | $^1$H NMR, FXR EC$_{50}$ & MS (ESI) | Method |
|---|---|---|---|
| 224 | 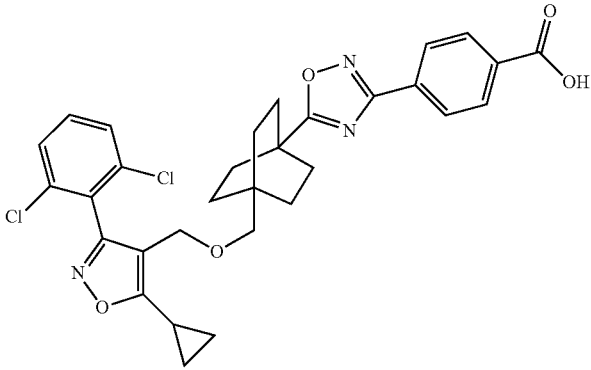<br>4-(5-((1r,4r)-4-(((5-cyclopropyl-3-(2,6-dichlorophenyl)isoxazol-4-yl)methoxy)methyl)bicyclo[2.2.1]heptan-1-yl)-1,2,4-oxadiazol-3-yl)benzoic acid | $^1$H NMR (400 MHz, DMSO-d$_6$) δ 8.12 (s, 4H), 7.70-7.57 (m, 2H), 7.56-7.47 (m, 1H), 4.32 (s, 2H), 3.39 (s, 2H), 2.35-2.30 (m, 1H), 2.09-1.95 (m, 2H), 1.81 (d, J = 7.3 Hz, 2H), 1.54 (s, 4H), 1.33-1.21 (m, 2H), 1.19-1.04 (m, 4H). FXR EC$_{50}$ (nM) = 2000. MS (ESI) 580 (M + H). | Ex. 151 |
| 225 | 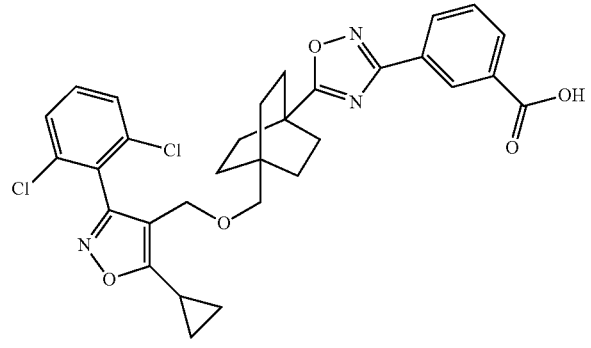<br>3-(5-((1r,4r)-4-(((5-cyclopropyl-3-(2,6-dichlorophenyl)isoxazol-4-yl)methoxy)methyl)bicyclo[2.2.1]heptan-1-yl)-1,2,4-oxadiazol-3-yl)benzoic acid | $^1$H NMR (400 MHz, DMSO-d$_6$) δ 8.55 (s, 1H), 8.23 (d, J = 7.8 Hz, 1H), 8.13 (d, J = 7.8 Hz, 1H), 7.70 (t, J = 7.8 Hz, 1H), 7.67-7.60 (m, 2H), 7.57-7.46 (m, 1H), 4.32 (s, 2H), 2.89 (s, 1H), 2.37-2.30 (m, 1H), 2.12-1.94 (m, 2H), 1.84 (d, J = 8.1 Hz, 2H), 1.54 (s, 4H), 1.28 (d, J = 6.8 Hz, 2H), 1.20-1.04 (m, 4H). FXR EC$_{50}$ (nM) = 310. MS (ESI) 580 (M + H). | Ex. 151 |
| 227 | 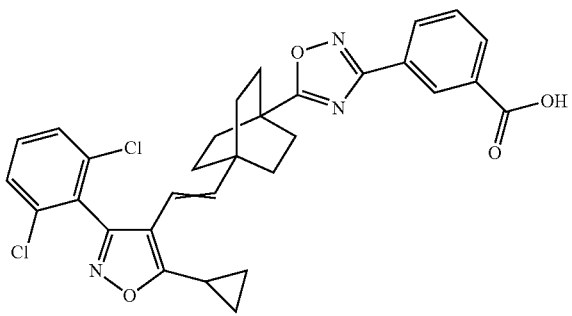<br>4-(5-(4-(2-(5-cyclopropyl-3-(2,6-dichlorophenyl)isoxazol-4-yl)vinyl)bicyclo[2.2.1]heptan-1-yl)-1,2,4-oxadiazol-3-yl)benzoic acid | $^1$H NMR (500 MHz, DMSO-d$_6$) δ 8.52 (s, 1H), 8.18 (d, J = 8.8 Hz, 1H), 8.12 (d, J = 7.6 Hz, 1H), 7.72-7.64 (m, 4H), 6.22 (d, J = 16.4 Hz, 1H), 5.61 (d, J = 16.4 Hz, 1H), 2.42 (d, J = 8.6 Hz, 1H), 2.15-1.5 (m, 11H) 1.21-1.09 (m, 4H). FXR EC$_{50}$ (nM) = 5100. MS (ESI) 562 (M + H). | Ex. 226 |

TABLE 4-continued

| Ex. No. | Structure & Name | ¹H NMR, FXR EC$_{50}$ & MS (ESI) | Method |
|---|---|---|---|
| 228 | methyl 4-(5-(4-(2-(5-cyclopropyl-3-(2,6-dichlorophenyl)isoxazol-4-yl)vinyl)bicyclo[2.2.1]heptan-1-yl)-1,2,4-oxadiazol-3-yl)benzoate | ¹H NMR (500 MHz, DMSO-d$_6$) δ 8.12 (s, 4H), 7.70-7.53 (m, 3H), 6.20 (d, J = 16.4 Hz, 1H), 5.61 (d, J = 16.4 Hz, 1H), 3.89 (s, 3H), 2.44-2.35 (m, 1H), 2.20-2.00 (m, 2H), 1.97-1.78 (m, 2H), 1.73 (s, 2H), 1.71-1.54 (m, 2H), 1.49 (d, J = 8.3 Hz, 2H), 1.21-1.03 (m, 4H). FXR EC$_{50}$ (nM) = 2500. MS (ESI) 576 (M + H). | Ex. 226 |
| 229 | methyl 3-(4-(2-(5-cyclopropyl-3-(2,6-dichlorophenyl)isoxazol-4-yl)vinyl)bicyclo[2.2.1]heptane-1-carboxamido)benzoate | ¹H NMR (500 MHz, DMSO-d$_6$) δ 9.46 (s, 1H), 8.27 (d, J = 2.0 Hz, 1H), 8.01-7.82 (m, 1H), 7.76-7.50 (m, 4H), 7.42 (t, J = 7.9 Hz, 1H), 6.15 (d, J = 16.4 Hz, 1H), 5.59 (d, J = 16.4 Hz, 1H), 3.84 (s, 3H), 2.40-2.32 (m, 1H), 2.00-1.76 (m, 2H), 1.75-1.62 (m, 2H), 1.61-1.44 (m, 4H), 1.43-1.30 (m, 2H), 1.20-0.96 (m, 4H). FXR EC$_{50}$ (nM) = 3600. MS (ESI) 551 (M + H). trans/cis 4:1 ratio | Ex. 170 |
| 230 | 3-(4-(2-(5-cyclopropyl-3-(2,6-dichlorophenyl)isoxazol-4-yl)vinyl)bicyclo[2.2.1]heptane-1-carboxamido)benzoic acid | ¹H NMR (500 MHz, DMSO-d$_6$) δ 9.42 (s, 1H), 8.23 (t, J = 1.8 Hz, 1H), 7.90 (dd, J = 7.9, 1.1 Hz, 1H), 7.75-7.51 (m, 4H), 7.39 (t, J = 7.9 Hz, 1H), 6.15 (d, J = 16.4 Hz, 1H), 5.59 (d, J = 16.4 Hz, 1H), 2.39-2.32 (m, 1H), 2.00-1.77 (m, 2H), 1.74-1.62 (m, 2H), 1.61-1.43 (m, 4H), 1.43-1.28 (m, 2H), 1.23-1.00 (m, 4H). FXR EC$_{50}$ (nM) = 890. MS (ESI) 537 (M + H). trans/cis 5:1 ratio | Ex. 170 |

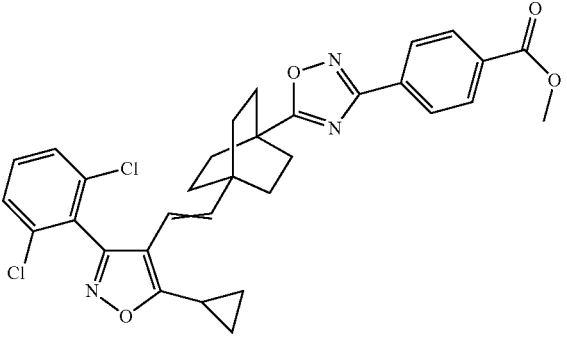

Example 234

5-(3-(4-((5-cyclopropyl-3-(3,5-dichloropyridin-4-yl)isoxazol-4-yl)methoxy) bicyclo[2.2.2]octan-1-yl)-1,2,4-oxadiazol-5-yl)-2-methoxybenzoic acid

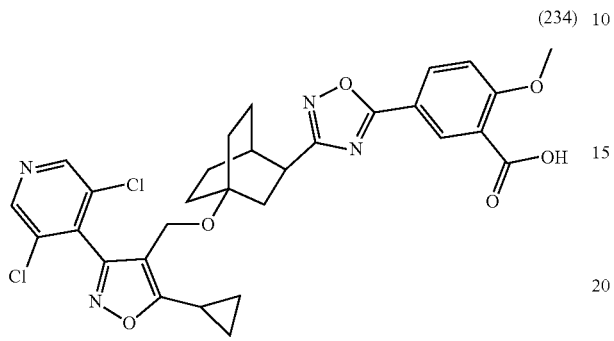

(234)

Step A. Intermediate 234A. Preparation of (Z)-4-((5-cyclopropyl-3-(3,5-dichloropyridin-4-yl)isoxazol-4-yl)methoxy)-N'-hydroxybicyclo[2.2.2]octane-1-carboximidamide

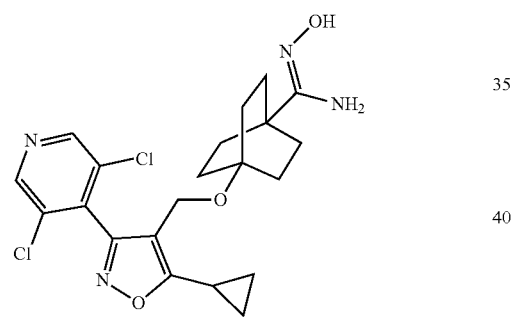

The title compound was prepared according to methods described for the synthesis of Intermediate 70A, using Intermediate 69B as starting material: (23 mg, 0.051 mmol, 71% yield, clear oil). $^1$H NMR (400 MHz, CHLOROFORM-d) δ 8.63-8.58 (m, 2H), 4.45 (br s, 2H), 4.22-4.18 (m, 2H), 2.13-2.06 (m, 1H), 1.80-1.73 (m, 6H), 1.52-1.42 (m, 6H), 1.26-1.22 (m, 2H), 1.16-1.09 (m, 2H). MS (ESI) 451 (M+H).

Step B. Example 234

The title compound was prepared according to methods described for the synthesis of Example 64 (Step C), by reaction of Intermediate 234A and 4-methoxy-3-(methoxycarbonyl)benzoic acid: $^1$H NMR (500 MHz, DMSO-d$_6$) δ 8.82 (s, 2H), 8.26 (d, J=1.8 Hz, 1H), 8.15 (dd, J=8.9, 1.8 Hz, 1H), 7.33 (d, J=8.9 Hz, 1H), 4.24 (s, 2H), 3.91 (s, 3H), 2.36-2.25 (m, 1H), 1.97-1.82 (m, 6H), 1.50-1.40 (m, 6H), 1.17-1.12 (m, 2H), 1.10-1.05 (m, 2H). FXR EC$_{50}$ (nM)=190. MS (ESI) 611 (M+H).

Example 235

3-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-5-(trifluoromethyl)benzoic acid

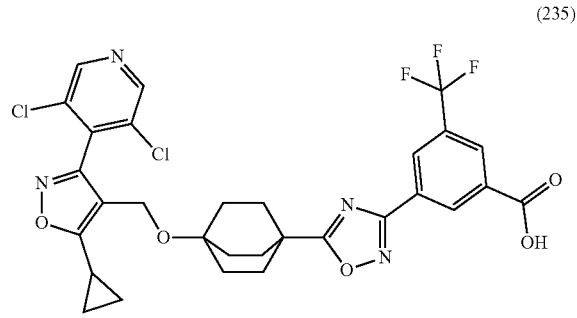 [SMILES: O=C(O)c1cc(-c2noc(C34CCC(OCc5c(-c6c(Cl)cncc6Cl)noc5C5CC5)(CC3)CC4)n2)cc(C(F)(F)F)c1]

(235)

Step A. Intermediate 235A. Preparation of methyl (Z)-3-(N'-hydroxycarbamimidoyl)-5-(trifluoromethyl)benzoate

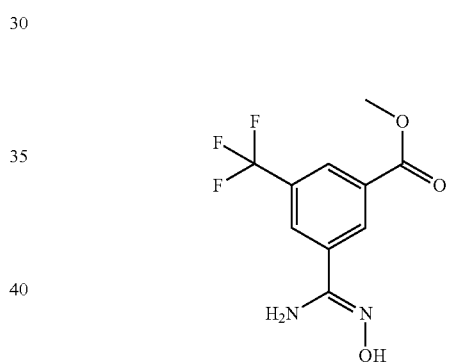

The title compound was prepared according to methods described for the synthesis of Intermediate 4C, using methyl 3-cyano-5-(trifluoromethyl)benzoate as starting material: (60 mg, 0.23 mmol, 97% yield, white solid). $^1$HNMR (500 MHz, DMSO-d$_6$) δ 10.02 (s, 1H), 8.57 (s, 1H), 8.27 (s, 1H), 8.17 (s, 1H), 6.16 (s, 2H), 3.92 (s, 3H). MS (ESI) 263 (M+H).

Step B. Example 235

The title compound was prepared according to methods described for the synthesis of Example 64 (Step C), by reaction of Intermediate 69B and Intermediate 235A: $^1$H NMR (500 MHz, DMSO-d$_6$) δ 8.75 (s, 2H), 8.67 (br s, 1H), 8.34 (s, 1H), 8.30 (br s, 1H), 4.22 (s, 2H), 2.29-2.20 (m, 1H), 2.05-1.93 (m, 6H), 1.52-1.43 (m, 6H), 1.17-1.11 (m, 2H), 1.05 (br d, J=3.4 Hz, 2H). FXR EC$_{50}$ (nM)=25. MS (ESI) 649 (M+H).

Example 238

5-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-3-fluoro-2-methoxybenzoic acid

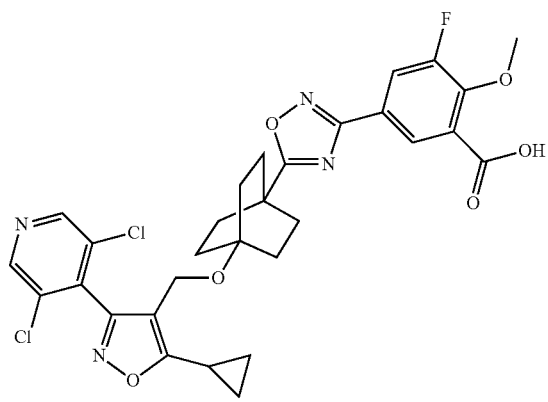

(238)

Step A. Intermediate 238A. Preparation of methyl 5-bromo-3-fluoro-2-methoxybenzoate

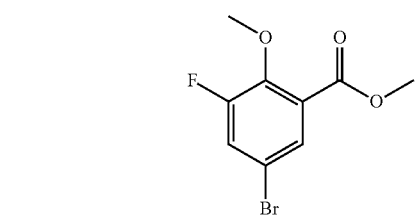

To a 0° C. solution of 5-bromo-3-fluoro-2-hydroxybenzoic acid (0.50 g, 2.1 mmol) and $K_2CO_3$ (1.5 g, 11 mmol) in DMF (12 mL) was added iodomethane (0.40 mL, 6.4 mmol). After stirring at 0° C. for 1 h, the reaction was warmed to room temperature and stirred for an additional for 5 h. The reaction mixture was diluted with water and extracted with DCM (3×). The combined organic layers were washed with water, brine, dried over anhydrous $Na_2SO_4$ and concentrated. The crude product was purified by flash column chromatography (40 g silica gel cartridge, A=Hex, B=EtOAc; 12 min grad.; 0% B to 25% B; flow rate=40 mL/min). The pure fractions were concentrated and dried in vacuo to afford the title compound (0.48 g, 1.8 mmol, 86% yield) as a clear oil. $^1$H NMR (500 MHz, CHLOROFORM-d) δ 7.69 (t, J=2.1 Hz, 1H), 7.41 (dd, J=10.2, 2.5 Hz, 1H), 3.98 (d, J=1.4 Hz, 3H), 3.93 (s, 3H). MS (ESI) 263 (M+H).

Step B. Intermediate 238B. Preparation of methyl 5-cyano-3-fluoro-2-methoxybenzoate

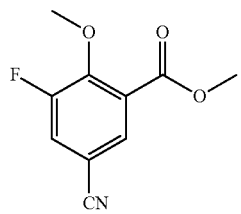

A mixture of Intermediate 238A (50 mg, 0.19 mmol) and copper(I) cyanide (21 mg, 0.23 mmol) in DMF (1 mL) was stirred at 120° C. in a sealed reaction vial. After 18 h, the reaction mixture was cooled, diluted with water and extracted with EtOAc (3×). The combined organic layers were washed with brine, dried over anhydrous $Na_2SO_4$, and concentrated. The crude product was purified by flash column chromatography (12 g silica gel cartridge, A=Hex, B=EtOAc; 10 min grad.; 0% B to 15% B; flow rate=30 mL/min). The pure fractions were concentrated and dried in vacuo to afford the title compound (10 mg, 0.049 mmol, 26% yield) as a tan solid. $^1$H NMR (400 MHz, CHLOROFORM-d) δ 7.88-7.83 (m, 1H), 7.53 (dd, J=10.8, 2.2 Hz, 1H), 4.10 (d, J=2.9 Hz, 3H), 3.95 (s, 3H). MS (ESI) 210 (M+H).

Step C. Intermediate 238C. Preparation of methyl (Z)-3-fluoro-5-(N'-hydroxycarbamimidoyl)-2-methoxybenzoate

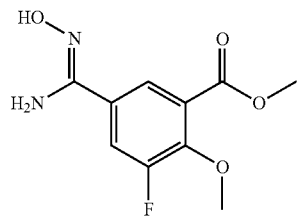 [SMILES: COC(=O)c1cc(/C(N)=N/O)cc(F)c1OC]

The title compound was prepared according to methods described for the synthesis of Intermediate 4C, using Intermediate 238B as starting material: (11.9 mg, 0.049 mmol, 100% yield) as an off-white solid. MS (ESI) 243 (M+H).

Step D. Example 238

The title compound was prepared according to methods described for the synthesis of Example 64 (Step C), by reaction of Intermediate 69B and Intermediate 238C: $^1$H NMR (500 MHz, DMSO-$d_6$) δ 13.67-13.29 (br s, 1H), 8.83 (s, 2H), 8.06 (d, J=1.9 Hz, 1H), 7.94 (dd, J=11.6, 2.2 Hz, 1H), 4.25 (s, 2H), 3.94 (d, J=1.1 Hz, 3H), 2.38-2.28 (m, 1H), 2.02-1.96 (m, 6H), 1.52-1.43 (m, 6H), 1.15 (dt, J=8.5, 2.9 Hz, 2H), 1.11-1.05 (m, 2H). FXR $EC_{50}$ (nM)=21. MS (ESI) 629 (M+H).

Example 239

3-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-5-methoxybenzoic acid

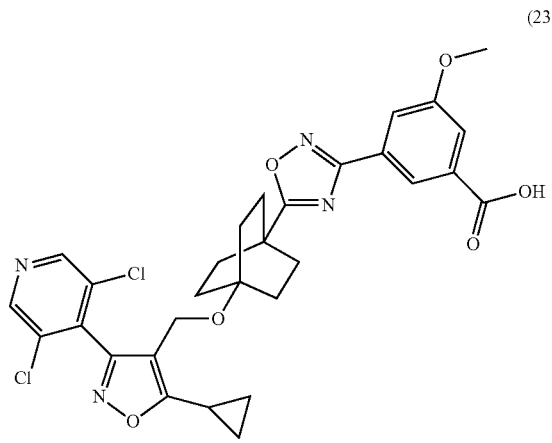

(239)

Step A. Intermediate 239A. Preparation of methyl (Z)-3-(N'-hydroxycarbamimidoyl)-5-methoxybenzoate

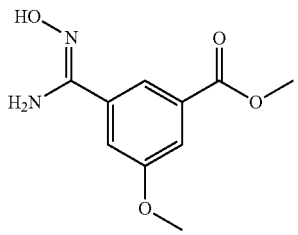 [SMILES: COC(=O)c1cc(OC)cc(/C(N)=N/O)c1]

The title compound was prepared according to methods described for the synthesis of Intermediate 4C, using methyl 3-cyano-5-methoxybenzoate (Wensbo, D. et. al. WO 2004/014902) as starting material: (0.23 g, 1.0 mmol, 79% yield, white solid). $^1$HNMR (400 MHz, DMSO-$d_6$) δ 9.76 (s, 1H), 7.91 (t, J=1.5 Hz, 1H), 7.49 (dd, J=2.4, 1.5 Hz, 1H), 7.43 (dd, J=2.5, 1.4 Hz, 1H), 5.93 (s, 2H), 3.86 (s, 3H), 3.84 (s, 3H). MS (ESI) 225 (M+H).

Step B. Example 239

The title compound was prepared according to methods described for the synthesis of Example 64 (Step C), by reaction of Intermediate 69B and Intermediate 239A: $^1$H NMR (500 MHz, DMSO-$d_6$) δ 8.82 (s, 2H), 8.09 (s, 1H), 7.62 (br d, J=17.7 Hz, 2H), 4.24 (s, 2H), 3.87 (s, 3H), 2.38-2.27 (m, 1H), 2.05-1.93 (m, 6H), 1.53-1.42 (m, 6H), 1.18-1.14 (m, 2H), 1.09 (br d, J=2.7 Hz, 2H). FXR $EC_{50}$ (nM)=79. MS (ESI) 611 (M+H).

Example 240

5-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-methoxybenzamide

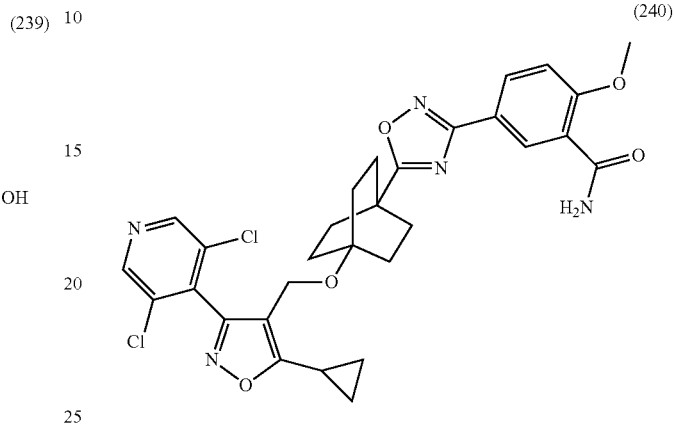

(240)

The title compound was prepared according to methods described for the synthesis of Intermediate 20A (Step 1 and 2), using Example 69 as starting material: (5.2 mg, 8.5 mol, 21% yield, white solid). $^1$HNMR (500 MHz, CHLOROFORM-d) δ 8.89 (d, J=2.2 Hz, 1H), 8.64 (s, 2H), 8.20 (dd, J=8.8, 2.2 Hz, 1H), 7.90 (br s, 1H), 7.11 (d, J=8.8 Hz, 1H), 6.97 (br s, 1H), 4.26 (s, 2H), 4.07 (s, 3H), 2.14-2.03 (m, 7H), 1.63-1.54 (m, 6H), 1.29-1.23 (m, 2H), 1.18-1.08 (m, 2H). FXR $EC_{50}$ (nM)=170. MS (ESI) 610 (M+H).

Example 241

5-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-fluoro-3-methoxybenzoic acid

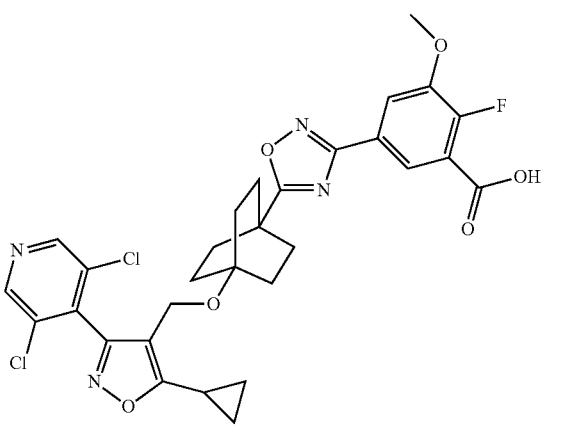

(241)

Step A. Intermediate 241A. Preparation of methyl 5-cyano-2-fluoro-3-methoxybenzoate

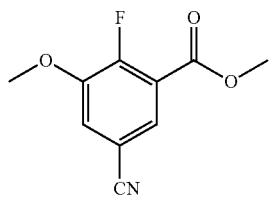

The title compound was prepared according to methods described for the synthesis of Intermediate 238B, using methyl 5-bromo-2-fluoro-3-methoxybenzoate as starting material: (25 mg, 0.12 mmol, 32% yield, white solid). $^1$H NMR (500 MHz, CHLOROFORM-d) δ 7.86-7.80 (m, 1H), 7.34 (dd, J=6.9, 1.9 Hz, 1H), 3.97 (s, 3H), 3.96 (s, 3H). MS (ESI) 210 (M+H).

Step B. Intermediate 241B. Preparation of methyl (Z)-2-fluoro-5-(N'-hydroxycarbamimidoyl)-3-methoxybenzoate

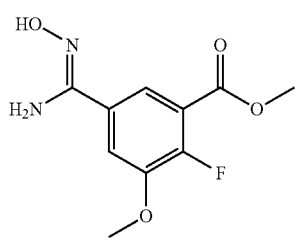 [SMILES: COC(=O)c1cc(/C(N)=N/O)cc(OC)c1F]

The title compound was prepared according to methods described for the synthesis of Intermediate 4C, using Intermediate 241A as starting material: (29 mg, 0.12 mmol, 98% yield, off-white solid). $^1$H NMR (400 MHz, DMSO-d$_6$) δ 9.75 (s, 1H), 7.74 (dd, J=5.9, 2.0 Hz, 1H), 7.65 (dd, J=7.7, 2.2 Hz, 1H), 5.97 (br s, 2H), 3.90 (s, 3H), 3.86 (s, 3H). MS (ESI) 243 (M+H).

Step C. Example 241

The title compound was prepared according to methods described for the synthesis of Example 64 (Step C), by reaction of Intermediate 69B and Intermediate 241B: $^1$H NMR (500 MHz, DMSO-d$_6$) δ 8.79 (s, 2H), 7.92 (br d, J=4.3 Hz, 1H), 7.74 (br d, J=6.1 Hz, 1H), 4.21 (s, 2H), 3.91 (s, 3H), 2.32-2.22 (m, 1H), 2.00-1.92 (m, 6H), 1.48-1.39 (m, 6H), 1.14-1.08 (m, 2H), 1.07-1.01 (m, 2H). FXR EC$_{50}$ (nM)=130. MS (ESI) 629 (M+H).

Example 242

4-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-(1H-tetrazol-5-yl)phenol

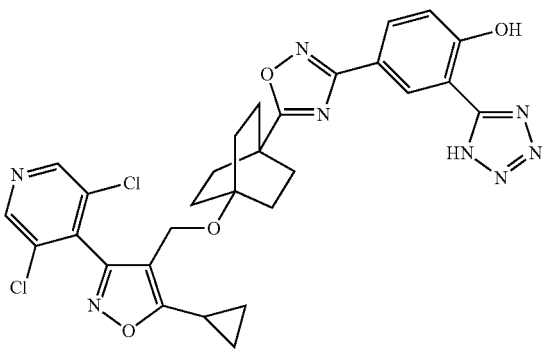

(242)

Step A. Intermediate 242A. Preparation of 5-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-methoxybenzonitrile

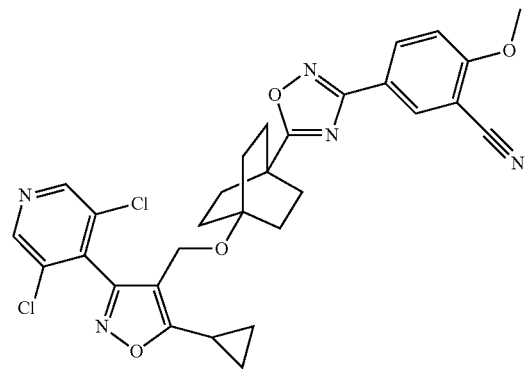 [SMILES: COc1ccc(-c2noc(C34CCC(OCc5c(-c6c(Cl)cncc6Cl)noc5C5CC5)(CC3)CC4)n2)cc1C#N]

The title compound was prepared according to methods described for the synthesis of Intermediate 20A, using Example 69 as starting material: (9.1 mg, 0.015 mmol, 38% yield, white solid). $^1$H NMR (400 MHz, CHLOROFORM-d) δ 8.63 (s, 2H), 8.27 (d, J=2.0 Hz, 1H), 8.23 (dd, J=8.9, 2.1 Hz, 1H), 7.06 (d, J=9.0 Hz, 1H), 4.26 (s, 2H), 4.01 (s, 3H), 2.09 (dt, J=8.6, 3.7 Hz, 7H), 1.63-1.53 (m, 6H), 1.34-1.23 (m, 2H), 1.19-1.08 (m, 2H). MS (ESI) 592 (M+H).

Step B. Example 242

A solution of Intermediate 242A (9.1 mg, 0.015 mmol), sodium azide (6.0 mg, 0.092 mmol) and NH$_4$Cl (4.9 mg, 0.092 mmol) in NMP (0.15 mL) was stirred at 120° C. in a sealed reaction vial. After 18 h, additional sodium azide (5.99 mg, 0.092 mmol) and NH$_4$Cl (4.9 mg, 0.092 mmol) were added and stirring was continued at 120° C. After 18 h, the reaction was cooled, diluted with EtOAc and washed with brine. The organic layer was dried over anhydrous Na$_2$SO$_4$, filtered and concentrated. The crude product was purified by preparative HPLC (Column: Phenomenex Luna AXIA 5u C18 21.2×100 mm; Solvent B=90%/10% MeOH: H₂O with 0.1% TFA, Solvent A=10%/90% MeOH:H₂O with 0.1% TFA; Gradient 15% to 100% Solvent B over 10 minutes then a 5-minute hold at 100% B; Flow: 20 mL/min). The pure fraction was concentrated and dried in vacuo to afford the title compound (3.4 mg, 5.4 µma 35% yield) as a white solid. ¹H NMR (400 MHz, DMSO-d₆) δ 8.84 (s, 2H), 8.61 (d, J=2.2 Hz, 1H), 7.98 (dd, J=8.6, 2.2 Hz, 1H), 7.21 (d, J=8.8 Hz, 1H), 4.25 (s, 2H), 2.39-2.24 (m, 1H), 2.06-1.96 (m, 6H), 1.53-1.43 (m, 6H), 1.17-1.13 (m, 2H), 1.11-1.05 (m, 2H). FXR EC$_{50}$ (nM)=1400. MS (ESI) 621 (M+H).

Example 243

5-(5-(4-((5-cyclopropyl-3-(3,5-dichloropyridin-4-yl) isoxazol-4-yl)methoxy)bicyclo[2.2.2]octan-1-yl)-1,2,4-oxadiazol-3-yl)-2,3-dimethoxybenzoic acid

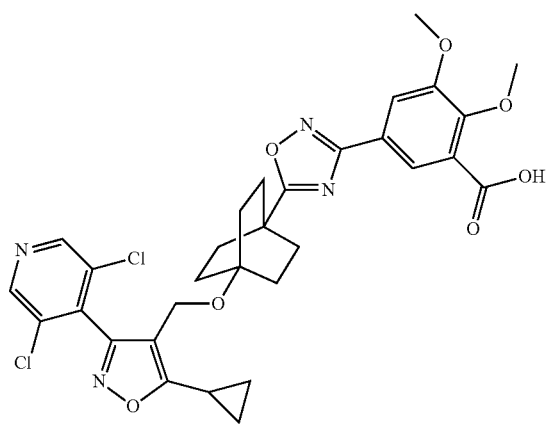

(243)

Step A. Intermediate 243A. Preparation of ethyl 5-bromo-2,3-dimethoxybenzoate

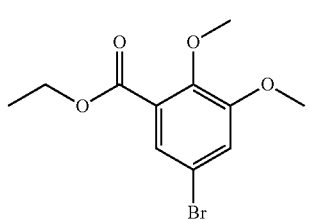 [SMILES: CCOC(=O)c1cc(Br)cc(OC)c1OC]

The title compound was prepared according to methods described for the synthesis of Intermediate 64A, using 5-bromo-2,3-dimethoxybenzoic acid as starting material: (0.53 g, 1.9 mmol, 96% yield, yellow oil). ¹H NMR (500 MHz, CHLOROFORM-d) δ 7.45 (d, J=2.5 Hz, 1H), 7.15 (d, J=2.2 Hz, 1H), 4.37 (q, J=7.2 Hz, 2H), 3.89 (d, J=2.8 Hz, 6H), 1.40 (t, J=7.2 Hz, 3H). MS (ESI) 291 (M+H).

Step B. Intermediate 243B. Preparation of ethyl 5-cyano-2,3-dimethoxybenzoate

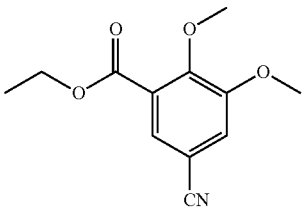 [SMILES: CCOC(=O)c1cc(C#N)cc(OC)c1OC]

The title compound was prepared according to methods described for the synthesis of Intermediate 238B, using Intermediate 243A as starting material: (57 mg, 0.24 mmol, 71% yield, off-white solid). ¹H NMR (500 MHz, CHLOROFORM-d) δ 7.66 (d, J=1.9 Hz, 1H), 7.25-7.22 (m, 1H), 4.40 (q, J=7.2 Hz, 2H), 3.97 (s, 3H), 3.93 (s, 3H), 1.41 (t, J=7.2 Hz, 3H). MS (ESI) 236 (M+H).

Step C. Intermediate 243C. Preparation of ethyl (Z)-5-(N'-hydroxycarbamimidoyl)-2,3-dimethoxybenzoate

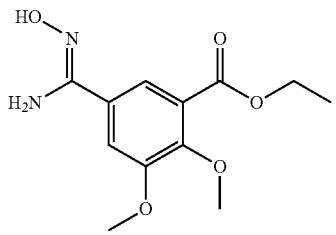 [SMILES: CCOC(=O)c1cc(/C(N)=N/O)cc(OC)c1OC]

The title compound was prepared according to methods described for the synthesis of Intermediate 4C, using Intermediate 243B as starting material: (64 mg, 0.24 mmol, 99% yield, off-white solid). ¹H NMR (500 MHz, DMSO-d₆) δ 9.66 (s, 1H), 7.50 (dd, J=10.7, 1.9 Hz, 2H), 5.88 (s, 2H), 4.29 (q, J=7.2 Hz, 2H), 3.86 (s, 3H), 3.77 (s, 3H), 1.31 (t, J=7.2 Hz, 3H). MS (ESI) 269 (M+H).

Step D. Example 243

The title compound was prepared according to methods described for the synthesis of Example 64 (Step C), by reaction of Intermediate 69B and Intermediate 243C: ¹H NMR (500 MHz, DMSO-d₆) δ 8.77 (s, 2H), 7.76 (d, J=1.5 Hz, 1H), 7.63 (d, J=1.6 Hz, 1H), 4.23 (s, 2H), 3.89 (s, 3H), 3.81 (s, 3H), 2.33-2.22 (m, 1H), 2.02-1.93 (m, 6H), 1.54-1.42 (m, 6H), 1.18-1.12 (m, 2H), 1.10-1.00 (m, 2H). FXR EC$_{50}$ (nM)=120. MS (ESI) 641 (M+H).

Example 244

3-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-fluoro-5-methoxybenzoic acid

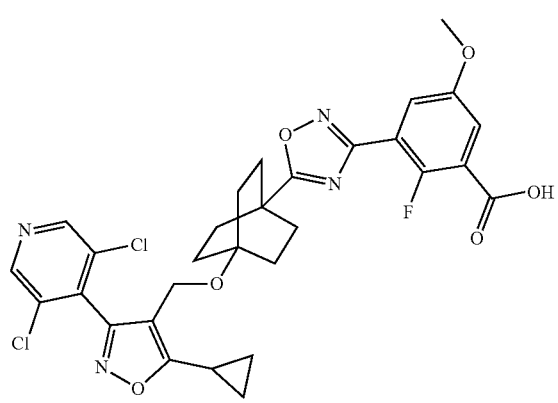

(244)

Step A. Intermediate 244A. Preparation of methyl 3-cyano-2-fluoro-5-methoxybenzoate

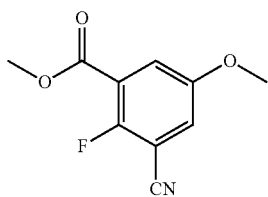

The title compound was prepared according to methods described for the synthesis of Intermediate 238B, using methyl 3-bromo-2-fluoro-5-methoxybenzoate (Lu, L. et. al. WO 2016/134320) as starting material: (74 mg, 0.35 mmol, 70% yield, white solid). $^1$H NMR (500 MHz, DMSO-$d_6$) δ 7.86-7.80 (m, 1H), 7.65 (dd, J=5.8, 3.3 Hz, 1H), 3.89 (s, 3H), 3.85 (s, 3H). MS (ESI) 210 (M+H).

Step B. Intermediate 244B. Preparation of methyl (Z)-2-fluoro-3-(N'-hydroxycarbamimidoyl)-5-methoxybenzoate

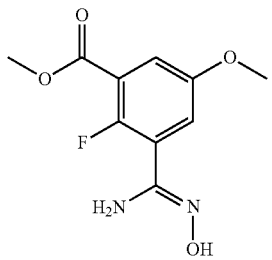

The title compound was prepared according to methods described for the synthesis of Intermediate 4C, using Intermediate 244A as starting material: (67 mg, 0.28 mmol, 81% yield, white solid). $^1$H NMR (500 MHz, DMSO-$d_6$) δ 9.70 (s, 1H), 7.34 (dd, J=5.0, 3.3 Hz, 1H), 7.23 (dd, J=5.1, 3.4 Hz, 1H), 5.89 (s, 2H), 3.86 (s, 3H), 3.80 (s, 3H). MS (ESI) 243 (M+H).

Step C. Example 244

The title compound was prepared according to methods described for the synthesis of Example 64 (Step C), by reaction of Intermediate 69B and Intermediate 244B: $^1$H NMR (500 MHz, DMSO-$d_6$) δ 8.83 (s, 2H), 7.30 (t, J=3.8 Hz, 1H), 7.25 (br d, J=4.5 Hz, 1H), 4.25 (s, 2H), 3.78 (s, 3H), 2.37-2.25 (m, 1H), 2.04-1.94 (m, 6H), 1.53-1.43 (m, 6H), 1.15 (dt, J=8.1, 3.0 Hz, 2H), 1.12-1.04 (m, 2H). FXR EC$_{50}$ (nM)=230. MS (ESI) 629 (M+H).

Example 245

3-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-5-fluoro-2-methoxybenzoic acid

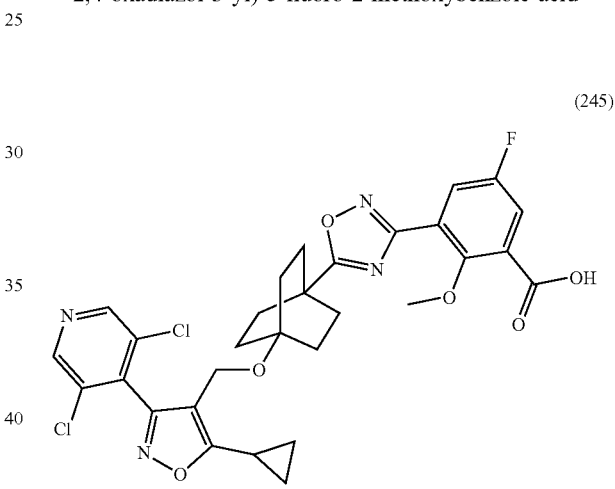

(245)

Step A. Intermediate 245A. Preparation of methyl 3-bromo-5-fluoro-2-methoxybenzoate

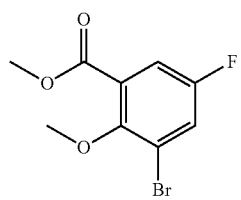

The title compound was prepared according to methods described for the synthesis of Intermediate 238A, using 3-bromo-5-fluoro-2-hydroxybenzoic acid (Xu, R., et. al. *J. Med Chem.* 2010, 53, 7035) as starting material: (0.16 g, 0.60 mmol, 56% yield, yellow oil). $^1$H NMR (500 MHz, METHANOL-$d_4$) δ 7.64 (dd, J=7.6, 3.2 Hz, 1H), 7.51 (dd, J=8.4, 3.2 Hz, 1H), 3.92 (s, 3H), 3.87 (s, 3H). MS (ESI) 263 (M+H).

Step B. Intermediate 245B. Preparation of methyl 3-cyano-5-fluoro-2-methoxybenzoate

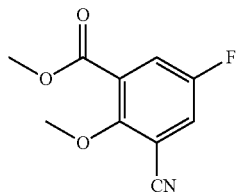

The title compound was prepared according to methods described for the synthesis of Intermediate 238B, using Intermediate 245A as starting material: (84 mg, 0.12 mmol, 68% yield, white solid). $^1$H NMR (500 MHz, DMSO-$d_6$) δ 8.11 (dd, J=7.8, 3.2 Hz, 1H), 7.91 (dd, J=8.5, 3.3 Hz, 1H), 3.93 (s, 3H), 3.88 (s, 3H). MS (ESI) 210 (M+H).

Step C. Intermediate 245C. Preparation of methyl (Z)-5-fluoro-3-(N'-hydroxycarbamimidoyl)-2-methoxybenzoate

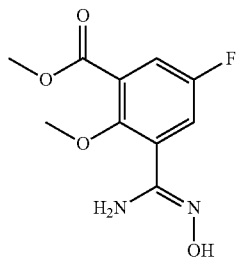 [SMILES: COC(=O)c1cc(F)cc(/C(N)=N/O)c1OC]

The title compound was prepared according to methods described for the synthesis of Intermediate 4C, using Intermediate 245B as starting material: (88 mg, 0.36 mmol, 92% yield, light yellow oil). $^1$H NMR (500 MHz, DMSO-$d_6$) δ 9.71-9.61 (m, 1H), 7.52 (dd, J=8.5, 3.3 Hz, 1H), 7.39 (dd, J=8.8, 3.3 Hz, 1H), 5.84 (br s, 2H), 3.85 (s, 3H), 3.73 (s, 3H). MS (ESI) 243 (M+H).

Step D. Example 245

The title compound was prepared according to methods described for the synthesis of Example 64 (Step C), by reaction of Intermediate 69B and Intermediate 245C: $^1$H NMR (500 MHz, DMSO-$d_6$) δ 8.81 (s, 2H), 7.75 (dd, J=8.4, 3.2 Hz, 1H), 7.65 (dd, J=8.2, 3.1 Hz, 1H), 4.23 (s, 2H), 3.64 (br s, 3H), 2.36-2.25 (m, 1H), 2.03-1.90 (m, 6H), 1.53-1.37 (m, 6H), 1.20-1.12 (m, 2H), 1.07 (br d, J=2.4 Hz, 2H). FXR EC$_{50}$ (nM)=46. MS (ESI) 629 (M+H).

Example 246

3-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-2,5-dimethoxybenzoic acid

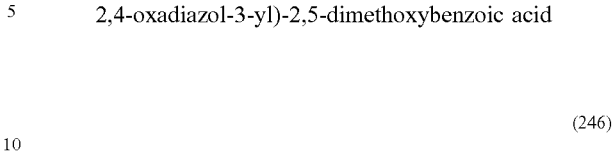

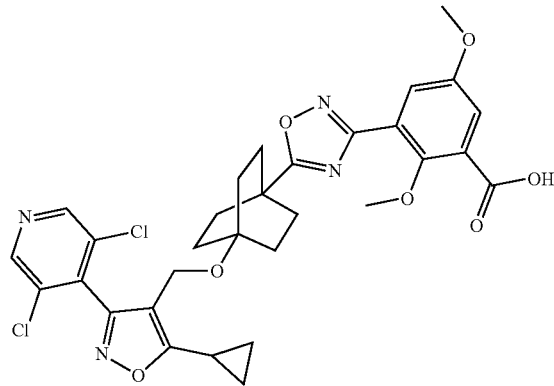

(246)

Step A. Intermediate 246A. Preparation of methyl 3-cyano-2,5-dimethoxybenzoate

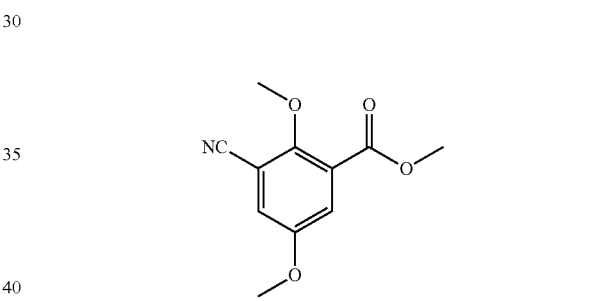

The title compound was prepared according to methods described for the synthesis of Intermediate 238B, using methyl 3-bromo-2,5-dimethoxybenzoate (Miller, C. P. et. al. US 2006/0004087) as starting material: (38 mg, 0.17 mmol, 77% yield, white solid). $^1$H NMR (500 MHz, DMSO-$d_6$) δ 7.66 (d, J=3.3 Hz, 1H), 7.53 (d, J=3.3 Hz, 1H), 3.88 (s, 3H), 3.87 (s, 3H), 3.82 (s, 3H). MS (ESI) 222 (M+H).

Step B. Intermediate 246B. Preparation of methyl (Z)-3-(N'-hydroxycarbamimidoyl)-2,5-dimethoxybenzoate

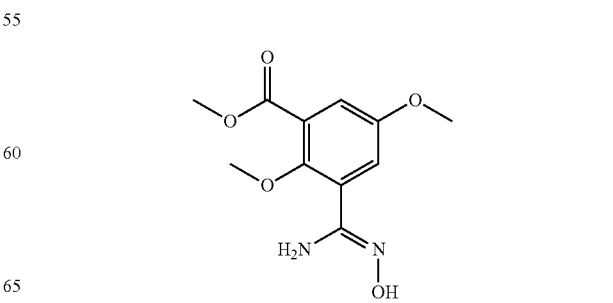

The title compound was prepared according to methods described for the synthesis of Intermediate 4C, using Intermediate 246A as starting material: (40 mg, 0.16 mmol, 94% yield, white solid). $^1$H NMR (500 MHz, DMSO-d$_6$) δ 9.56 (s, 1H), 7.19 (d, J=3.3 Hz, 1H), 7.10 (d, J=3.3 Hz, 1H), 5.76 (s, 2H), 3.84 (s, 3H), 3.76 (s, 3H), 3.69 (s, 3H). MS (ESI) 255 (M+H).

Step C. Example 246

The title compound was prepared according to methods described for the synthesis of Example 64 (Step C), by reaction of Intermediate 69B and Intermediate 246B: $^1$H NMR (500 MHz, DMSO-d$_6$) δ 8.84 (s, 2H), 7.42 (d, J=3.1 Hz, 1H), 7.32 (br d, J=2.7 Hz, 1H), 4.26 (s, 2H), 3.80 (s, 3H), 3.72 (s, 3H), 2.36-2.30 (m, 1H), 2.03-1.97 (m, 6H), 1.52-1.45 (m, 6H), 1.16 (dt, J=8.2, 2.9 Hz, 2H), 1.10 (br d, J=2.4 Hz, 2H). FXR EC$_{50}$ (nM)=90. MS (ESI) 641 (M+H).

Example 249

4-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)picolinic acid (249)

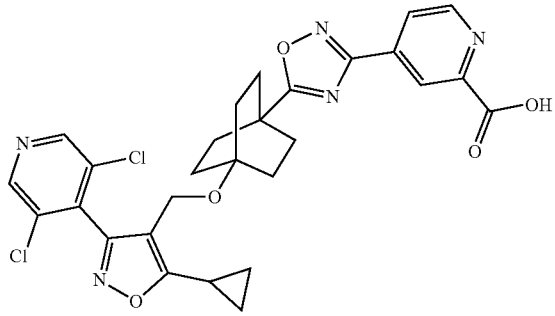

Step A. Intermediate 249A. Preparation of methyl (Z)-4-(N'-hydroxycarbamimidoyl) picolinate

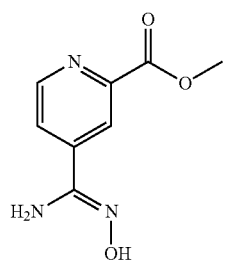

The title compound was prepared according to methods described for the synthesis of Intermediate 4C, using methyl 4-cyanopicolinate as starting material: (7.1 mg, 0.036 mmol, 100% yield) as a yellow solid. MS (ESI) 196 (M+H).

Step B. Example 249

The title compound was prepared according to methods described for the synthesis of Example 64 (Step C), by reaction of Intermediate 69B and Intermediate 249A: $^1$H NMR (500 MHz, DMSO-d$_6$) δ 8.88 (br s, 1H), 8.82 (s, 2H), 8.46 (br s, 1H), 8.07 (br s, 1H), 4.25 (s, 2H), 2.36-2.27 (m, 1H), 2.04-1.98 (m, 6H), 1.53-1.43 (m, 6H), 1.17 (br d, J=7.9 Hz, 2H), 1.09 (br d, J=2.4 Hz, 2H). FXR EC$_{50}$ (nM)=240. MS (ESI) 582 (M+H).

Example 250

3-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-fluoro-6-methoxybenzoic acid (250)

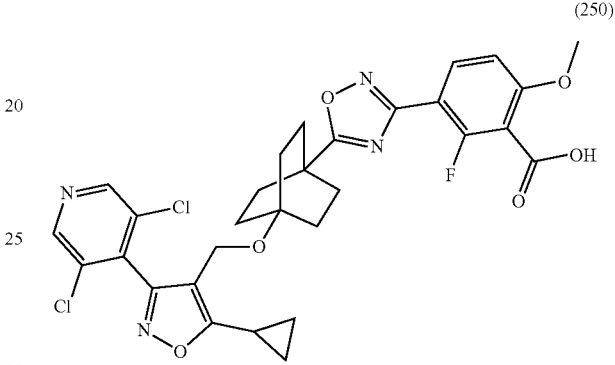

Step A. Intermediate 250A. Preparation of methyl 3-cyano-2-fluoro-6-methoxybenzoate

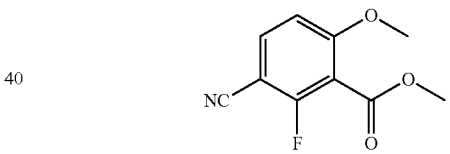

The title compound was prepared according to methods described for the synthesis of Intermediate 238B, using methyl 3-bromo-2-fluoro-6-methoxybenzoate as starting material: (56 mg, 0.27 mmol, 57% yield, white solid). $^1$H NMR (400 MHz, DMSO-d$_6$) δ 8.07 (dd, J=8.9, 7.8 Hz, 1H), 7.22 (dd, J=9.0, 0.7 Hz, 1H), 3.94 (s, 3H), 3.87 (s, 3H). MS (ESI) 210 (M+H).

Step B. Intermediate 250B. Preparation of methyl (Z)-2-fluoro-3-(N'-hydroxycarbamimidoyl)-6-methoxybenzoate

The title compound was prepared according to methods described for the synthesis of Intermediate 4C, using Intermediate 250A as starting material: (63 mg, 0.26 mmol, 100% yield, yellow solid). $^1$H NMR (500 MHz, DMSO-d$_6$) δ 9.58 (s, 1H), 7.56 (t, J=8.7 Hz, 1H), 6.99 (d, J=8.8 Hz, 1H), 5.79 (s, 2H), 3.84 (d, J=0.8 Hz, 6H). MS (ESI) 243 (M+H).

Step C. Example 250

The title compound was prepared according to methods described for the synthesis of Example 64 (Step C), by reaction of Intermediate 69B and Intermediate 250B: $^1$H NMR (500 MHz, DMSO-d$_6$) δ 8.81 (br s, 2H), 7.89 (br t, J=8.7 Hz, 1H), 7.07 (br d, J=8.5 Hz, 1H), 4.23 (s, 2H), 3.88 (s, 3H), 2.37-2.21 (m, 1H), 2.00-1.88 (m, 6H), 1.53-1.39 (m, 6H), 1.15 (br d, J=7.9 Hz, 2H), 1.07 (br d, J=2.1 Hz, 2H). FXR EC$_{50}$ (nM)=730. MS (ESI) 629 (M+H).

Example 251

3-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-5-isopropoxybenzoic acid (m, 1H), 7.41-7.37 (m, 1H), 5.91 (s, 2H), 4.70 (dt, J=12.0, 5.9 Hz, 1H), 3.85 (s, 3H), 1.29 (s, 3H), 1.28 (s, 3H). MS (ESI) 253 (M+H).

Step B. Example 251

The title compound was prepared according to methods described for the synthesis of Example 64 (Step C), by reaction of Intermediate 69B and Intermediate 251A: $^1$H NMR (500 MHz, DMSO-d$_6$) δ 8.74 (s, 2H), 8.03 (s, 1H), 7.60 (s, 1H), 7.55 (s, 1H), 4.74-4.61 (m, 1H), 4.21 (s, 2H), 2.30-2.17 (m, 1H), 2.01-1.92 (m, 6H), 1.51-1.42 (m, 6H), 1.28 (d, J=6.0 Hz, 6H), 1.17-1.11 (m, 2H), 1.05 (br d, J=2.6 Hz, 2H). FXR EC$_{50}$ (nM)=16. MS (ESI) 639 (M+H).

Example 252

5-(4-(4-((5-cyclopropyl-3-(3,5-dichloropyridin-4-yl)isoxazol-4-yl)methoxy) bicyclo[2.2.2]octan-1-yl) oxazol-2-yl)-2-methoxybenzoic acid

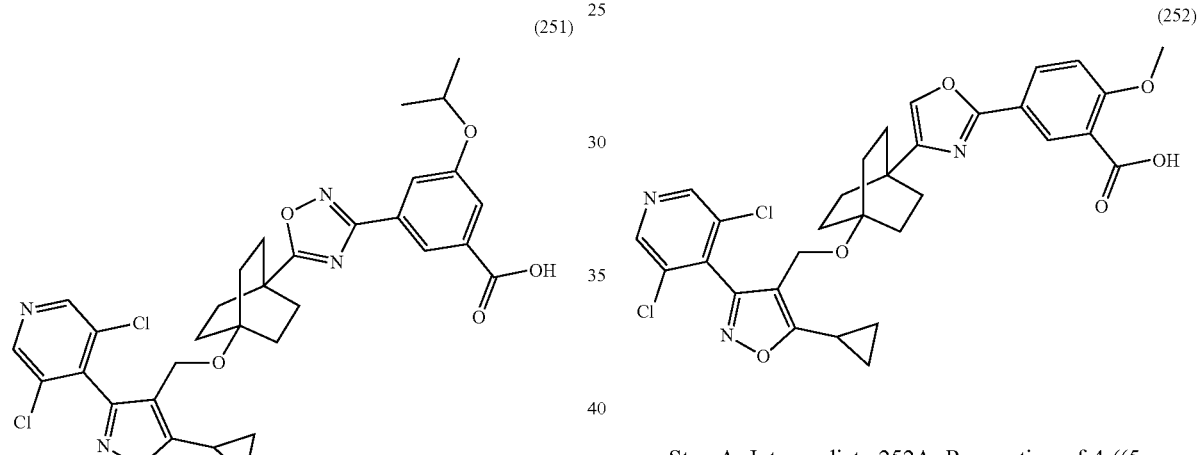

(251)

(252)

Step A. Intermediate 251A. Preparation of methyl (Z)-3-(N'-hydroxycarbamimidoyl)-5-isopropoxybenzoate

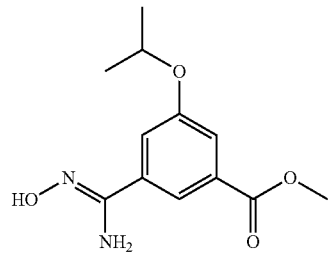 [SMILES: COC(=O)c1cc(OC(C)C)cc(/C(N)=N/O)c1]

The title compound was prepared according to methods described for the synthesis of Intermediate 4C, using methyl 3-cyano-5-isopropoxybenzoate as starting material: (68 mg, 0.27 mmol, 100% yield, clear oil). $^1$H NMR (500 MHz, DMSO-d$_6$) δ 9.75 (s, 1H), 7.88 (t, J=1.4 Hz, 1H), 7.47-7.44

Step A. Intermediate 252A. Preparation of 4-((5-cyclopropyl-3-(3,5-dichloropyridin-4-yl)isoxazol-4-yl)methoxy)bicyclo[2.2.2]octane-1-carbonyl chloride

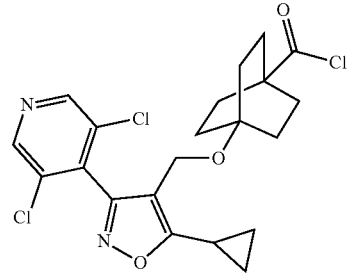 [SMILES: O=C(Cl)C12CCC(OCc3c(-c4c(Cl)cncc4Cl)noc3C3CC3)(CC1)CC2]

To a solution of Intermediate 69B (100 mg, 0.23 mmol) in DCM (0.50 mL) was added oxalyl chloride (0.030 mL, 0.34 mmol) followed by DMF (1.7 μL). After stirring at room temperature for 18 h, the solvent was concentrated to afford the title compound (100 mg, 0.23 mmol, 100% yield) as a crude yellow oil which was used in the next step without purification. MS (ESI) 451 (M−Cl+OMe+H).

Step B. Intermediate 252B. Preparation of 1-(4-((5-cyclopropyl-3-(3,5-dichloropyridin-4-yl)isoxazol-4-yl)methoxy)bicyclo[2.2.2]octan-1-yl)-2-diazoethan-1-one

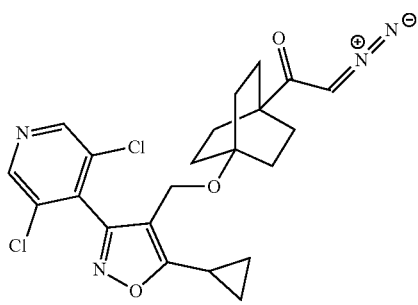 [SMILES: [N-]=[N+]=CC(=O)C12CCC(OCc3c(-c4c(Cl)cncc4Cl)noc3C3CC3)(CC1)CC2]

To a 0° C. solution of calcium oxide (28 mg, 0.50 mmol) in THF (1 mL) and MeCN (1 mL) was added (trimethylsilyl) diazomethane (0.23 mL, 0.46 mmol) (2.0 M in hexanes). After stirring 20 min at 0° C., a solution of Intermediate 252A (100 mg, 0.23 mmol) in THF (0.10 mL) and MeCN (0.10 mL) was added. The reaction mixture was slowly warmed to rt and stirred 18 h. The reaction was filtered through pad of Celite and the filtrate was concentrated. The crude product was purified by flash column chromatography (4 g silica gel cartridge, A=Hex, B=EtOAc; 11 min grad.; 0% B to 100% B; flow rate=18 mL/min). The pure fractions were combined, concentrated and dried in vacuo to afford the title compound (79 mg, 0.17 mmol, 75% yield) as a light yellow solid. $^1$H NMR (500 MHz, CHLOROFORM-d) δ 8.61 (s, 2H), 5.28 (s, 1H), 4.20 (s, 2H), 2.11-2.05 (m, 1H), 1.78-1.71 (m, 6H), 1.48-1.43 (m, 6H), 1.27-1.22 (m, 2H), 1.17-1.09 (m, 2H). MS (ESI) 461 (M+H).

Step C. Intermediate 252C. Preparation of 2-chloro-1-(4-((5-cyclopropyl-3-(3,5-dichloropyridin-4-yl)isoxazol-4-yl)methoxy)bicyclo[2.2.2]octan-1-yl)ethan-1-one

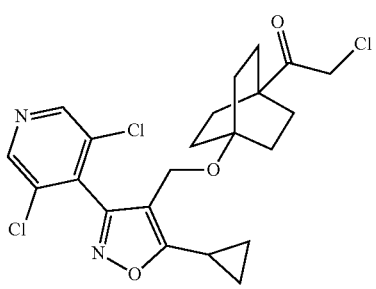 [SMILES: O=C(CCl)C12CCC(OCc3c(-c4c(Cl)cncc4Cl)noc3C3CC3)(CC1)CC2]

To a 0° C. solution of Intermediate 252B (79 mg, 0.17 mmol) in DCM (2 mL) was added HCl (0.13 mL, 0.51 mmol) (4 M in 1,4-dioxane) dropwise. After stirring at 0° C. for 30 min, the solvent was concentrated. The crude product was purified by flash column chromatography (4 g silica gel cartridge, A=Hex, B=EtOAc; 11 min grad.; 0% B to 75% B; flow rate=18 mL/min). The pure fractions were combined, concentrated and dried in vacuo to afford the title compound (66 mg, 0.14 mmol, 82% yield) as a white solid. $^1$H NMR (400 MHz, CHLOROFORM-d) δ 8.61 (s, 2H), 4.24 (s, 2H), 4.22-4.19 (m, 1H), 4.21 (s, 1H), 2.13-2.00 (m, 1H), 1.86-1.77 (m, 6H), 1.52-1.45 (m, 6H), 1.29-1.22 (m, 2H), 1.17-1.08 (m, 2H). MS (ESI) 471 (M+H).

Step D. Intermediate 252D. Preparation of methyl 5-carbamoyl-2-methoxybenzoate

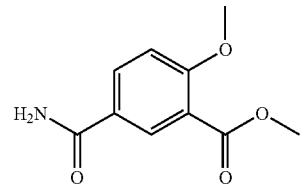

The title compound was prepared according to methods described for the synthesis of Intermediate 20A (Step 1 and Step 2), using 4-methoxy-3-(methoxycarbonyl)benzoic acid (Casagrande, C. et. al. EP 1270558) as starting material: (40 mg, 0.19 mmol, 62% yield, white solid). $^1$H NMR (500 MHz, DMSO-d$_6$) δ 8.19 (d, J=2.2 Hz, 1H), 8.06 (dd, J=8.8, 2.5 Hz, 1H), 7.97 (br s, 1H), 7.29 (br s, 1H), 7.21 (d, J=8.8 Hz, 1H), 3.88 (s, 3H), 3.81 (s, 3H). MS (ESI) 210 (M+H).

Step E. Intermediate 252E. Preparation of methyl 5-(4-(4-((5-cyclopropyl-3-(3,5-dichloropyridin-4-yl)isoxazol-4-yl)methoxy)bicyclo[2.2.2]octan-1-yl)oxazol-2-yl)-2-methoxybenzoate

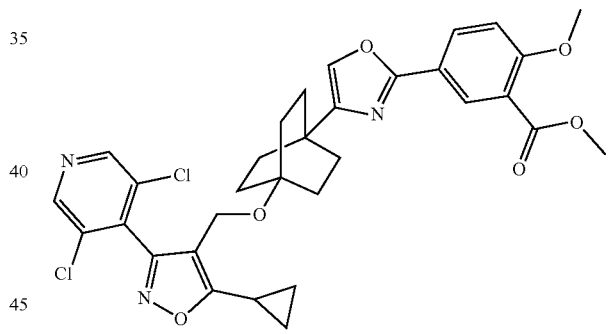

To a solution of Intermediate 252C (10 mg, 0.021 mmol) in 1,4-dioxane (0.20 mL) was added Intermediate 252D (6.7 mg, 0.032 mmol). After stirring at 175° C. in a sealed reaction vial for 4 h, the reaction was cooled to room temperature and concentrated. The crude product was purified by preparative HPLC (Column: Phenomenex Luna AXIA 5u C18 21.2×100 mm, Mobile Phase A: 10:90 methanol: water with 10-0.1% TFA; Mobile Phase B: 90:10 methanol: water with 0.1% TFA; Gradient: 15-100% B over 10 minutes, then a 5-minute hold at 100% B; Flow: 20 mL/min). Fractions containing the desired product were combined, concentrated and dried in vacuo to afford the title compound (8.3 mg, 0.013 mmol, 62% yield) as a brown solid. MS (ESI) 624 (M+H).

Step F. Example 252

Intermediate 252E (8.4 mg, 0.013 mmol) was dissolved in THF (0.50 mL) and 1 M NaOH (aq.) (0.50 mL) and stirred at 50° C. After 6.5 h, the reaction was cooled to room temperature, diluted with 5% citric acid (aq.) and extracted with EtOAc (2×). The combined organic layers were washed with brine, dried over Na₂SO₄ and concentrated. The crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 20 minutes, then a 4-minute hold at 100% B; Flow: 20 mL/min). Fractions containing the desired product were combined, concentrated and dried in vacuo to afford the title compound (2.9 mg, 4.7 μmol, 35% yield). ¹H NMR (500 MHz, DMSO-d₆) δ 8.74 (s, 2H), 7.99 (s, 1H), 7.87 (br d, J=8.6 Hz, 1H), 7.62 (s, 1H), 7.12 (d, J=8.8 Hz, 1H), 4.21 (s, 2H), 3.81 (s, 3H), 2.29-2.17 (m, 1H), 1.81-1.69 (m, 6H), 1.47-1.35 (m, 6H), 1.16-1.11 (m, 2H), 1.09-1.00 (m, 2H). FXR EC₅₀ (nM)=86. MS (ESI) 610 (M+H).

Example 253

6-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-3-methoxypicolinic acid

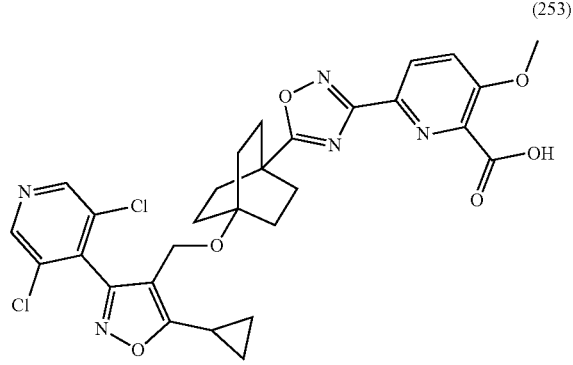 [SMILES: COc1ccc(-c2noc(C34CCC(OCc5c(-c6c(Cl)cncc6Cl)noc5C5CC5)(CC3)CC4)n2)nc1C(=O)O]

(253)

Step A. Intermediate 253A. Preparation of methyl 6-cyano-3-methoxypicolinate

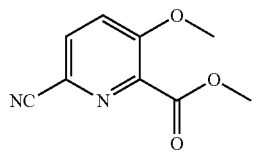

To a purged solution of methyl 6-bromo-3-methoxypicolinate (50 mg, 0.20 mmol) in NMP (1 mL) were added zinc cyanide (48 mg, 0.41 mmol) and Pd(PPh₃)₄ (12 mg, 10 μmol). After stirring at 65° C. for 22 h, the reaction was cooled to room temperature, diluted with EtOAc and washed with water. The organic layer was dried over anhydrous Na₂SO₄, filtered and concentrated. The crude product was purified by flash column chromatography (12 g silica gel cartridge, A=Hex, B=EtOAc; 11 min grad.; 0% B to 100% B; flow rate=30 mL/min). The pure fractions were concentrated and dried in vacuo to afford the title compound (33 mg, 0.17 mmol, 86% yield) as a white solid. ¹H NMR (400 MHz, DMSO-d₆) δ 8.22 (d, J=8.8 Hz, 1H), 7.86 (d, J=8.8 Hz, 1H), 3.96 (s, 3H), 3.87 (s, 3H). MS (ESI) 193 (M+H).

Step B. Intermediate 253B. Preparation of methyl (Z)-6-(N'-hydroxycarbamimidoyl)-3-methoxypicolinate

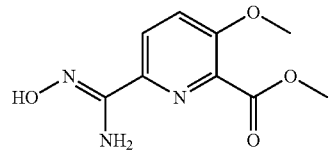 [SMILES: COC(=O)c1nc(/C(N)=N/O)ccc1OC]

The title compound was prepared according to methods described for the synthesis of Intermediate 4C, using Intermediate 253A as starting material: (23 mg, 0.10 mmol, 61% yield, yellow solid). ¹H NMR (500 MHz, DMSO-d₆) δ 9.84 (s, 1H), 7.96 (d, J=9.1 Hz, 1H), 7.69 (d, J=9.1 Hz, 1H), 5.69 (s, 2H), 3.88 (s, 3H), 3.86 (s, 3H). MS (ESI) 226 (M+H).

Step C. Example 253

The title compound was prepared according to methods described for the synthesis of Example 64 (Step C), by reaction of Intermediate 69B and Intermediate 253B: ¹H NMR (500 MHz, DMSO-d₆) δ 8.83 (s, 2H), 7.92 (br s, 1H), 7.57 (br d, J=8.2 Hz, 1H), 4.25 (s, 2H), 3.90-3.77 (m, 3H), 2.32 (br dd, J=8.2, 4.9 Hz, 1H), 2.00 (br s, 6H), 1.48 (br s, 6H), 1.17 (br d, J=8.2 Hz, 2H), 1.09 (br d, J=2.7 Hz, 2H). FXR EC₅₀ (nM)=740. MS (ESI) 612 (M+H).

Example 254

5-(5-(4-((5-cyclopropyl-3-(3,5-dichloropyridin-4-yl) isoxazol-4-yl)methoxy) bicyclo[2.2.2]octan-1-yl)-1, 2,4-oxadiazol-3-yl)-2-(trifluoromethyl)benzoic acid

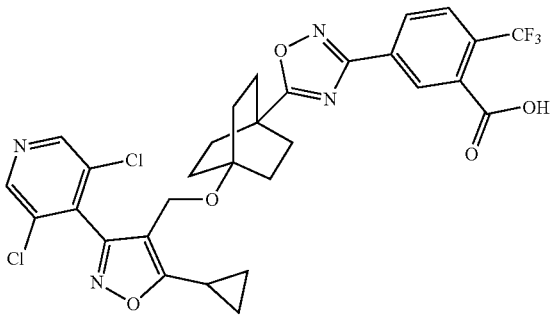

(254)

Step A. Intermediate 254A. Preparation of methyl (Z)-5-(N'-hydroxycarbamimidoyl)-2-(trifluoromethyl)benzoate

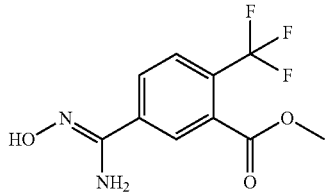 [SMILES: COC(=O)c1cc(/C(N)=N/O)ccc1C(F)(F)F]

The title compound was prepared according to methods described for the synthesis of Intermediate 4C, using methyl 5-cyano-2-(trifluoromethyl)benzoate as starting material: (69 mg, 0.26 mmol, 100% yield, clear oil). $^1$H NMR (500 MHz, DMSO-d$_6$) δ 10.04 (s, 1H), 8.13 (s, 1H), 8.03 (d, J=8.3 Hz, 1H), 7.89 (d, J=8.3 Hz, 1H), 6.07 (s, 2H), 3.89 (s, 3H). MS (ESI) 263 (M+H).

Step B. Example 254

The title compound was prepared according to methods described for the synthesis of Example 64 (Step C), by reaction of Intermediate 69B and Intermediate 254A: $^1$H NMR (500 MHz, DMSO-d$_6$) δ 8.80 (s, 2H), 8.03 (s, 1H), 7.98 (br d, J=8.2 Hz, 1H), 7.79 (br d, J=8.2 Hz, 1H), 4.23 (s, 2H), 2.34-2.25 (m, 1H), 2.03-1.95 (m, 6H), 1.51-1.41 (m, 6H), 1.17-1.13 (m, 2H), 1.07 (br d, J=2.7 Hz, 2H). FXR EC$_{50}$ (nM)=2000. MS (ESI) 649 (M+H).

Example 255

5-(4-(4-((5-cyclopropyl-3-(3,5-dichloropyridin-4-yl)isoxazol-4-yl)methoxy) bicyclo[2.2.2]octan-1-yl)thiazol-2-yl)-2-methoxybenzoic acid

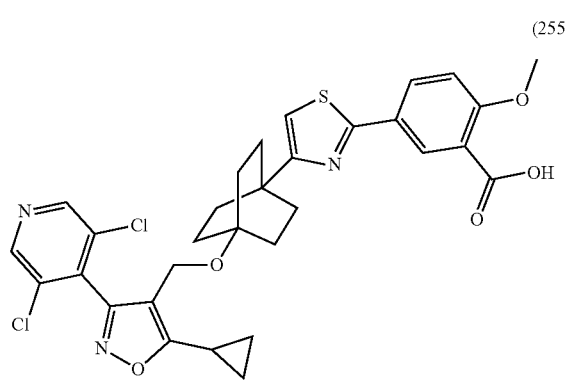

(255)

Step A. Intermediate 255A. Preparation of methyl 5-carbamothioyl-2-methoxybenzoate

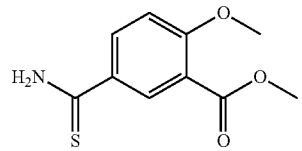

Diethylphosphorodithioate (0.21 mL, 1.3 mmol) was added to solution of methyl 5-cyano-2-methoxybenzoate (0.20 g, 1.1 mmol) in THF (3 mL) and water (1 mL). The reaction was stirred at 80° C. After 17 h, the mixture was cooled to room temperature and the solvent was concentrated to afford a yellow oil. The residue was diluted with EtOAc (25 mL), and the resultant precipitate was collected by vacuum filtration and dried in vacuo to afford the title compound (0.12 g, 0.55 mmol, 53% yield) as a crude light yellow solid which was used in the next step without further purification. $^1$H NMR (500 MHz, DMSO-d$_6$) δ 9.77 (br s, 1H), 9.47 (br s, 1H), 8.33 (d, J=2.5 Hz, 1H), 8.12 (dd, J=8.8, 2.5 Hz, 1H), 7.19 (d, J=8.8 Hz, 1H), 3.88 (s, 3H), 3.81 (s, 3H). MS (ESI) 226 (M+H).

Step B. Example 255

The title compound was prepared according to methods described for the synthesis of Example 252, substituting Intermediate 255A where appropriate: $^1$H NMR (500 MHz, DMSO-d$_6$) δ 8.77 (s, 2H), 8.03 (br s, 1H), 7.99-7.80 (m, 1H), 7.16 (br d, J=8.9 Hz, 1H), 7.09 (s, 1H), 4.21 (s, 2H), 3.79 (s, 3H), 2.26 (br s, 1H), 1.85-1.77 (m, 6H), 1.44-1.33 (m, 6H), 1.16-1.11 (m, 2H), 1.04 (br d, J=2.4 Hz, 2H). FXR EC$_{50}$ (nM)=18. MS (ESI) 626 (M+H).

Example 256

5-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-2-isopropoxybenzoic acid

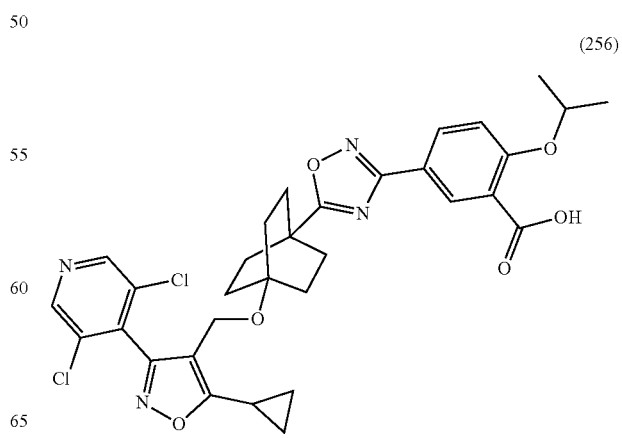

(256)

Step A. Intermediate 256A. Preparation of methyl 5-cyano-2-isopropoxybenzoate

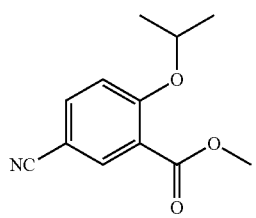 [SMILES: COC(=O)c1cc(C#N)ccc1OC(C)C]

The title compound was prepared according to methods described for the synthesis of Intermediate 238B, using methyl 5-bromo-2-isopropoxybenzoate as starting material: (65 mg, 0.30 mmol, 54% yield, clear oil). $^1$H NMR (500 MHz, DMSO-$d_6$) δ 8.03 (d, J=2.2 Hz, 1H), 7.95 (dd, J=8.8, 2.2 Hz, 1H), 7.36 (d, J=8.8 Hz, 1H), 4.83 (dt, J=12.1, 6.1 Hz, 1H), 3.80 (s, 3H), 1.30 (s, 3H), 1.28 (s, 3H). MS (ESI) 220 (M+H).

Step B. Intermediate 256B. Preparation methyl (Z)-5-(N'-hydroxycarbamimidoyl)-2-isopropoxybenzoate

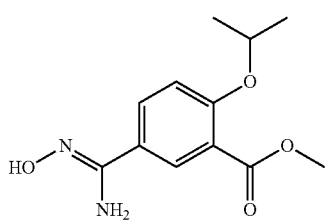 [SMILES: COC(=O)c1cc(/C(N)=N/O)ccc1OC(C)C]

The title compound was prepared according to methods described for the synthesis of Intermediate 4C, using Intermediate 256A as starting material: (67 mg, 0.27 mmol, 94% yield, white solid). $^1$H NMR (500 MHz, DMSO-$d_6$) δ 9.53 (s, 1H), 7.93 (d, J=2.5 Hz, 1H), 7.77 (dd, J=8.7, 2.3 Hz, 1H), 7.16 (d, J=9.1 Hz, 1H), 5.79 (s, 2H), 4.68 (dt, J=12.0, 5.9 Hz, 1H), 3.79 (s, 3H), 1.28 (s, 3H), 1.26 (s, 3H). MS (ESI) 253 (M+H).

Step C. Example 256

The title compound was prepared according to methods described for the synthesis of Example 64 (Step C), by reaction of Intermediate 69B and Intermediate 256B: $^1$H NMR (500 MHz, DMSO-$d_6$) δ 8.77 (s, 2H), 8.13 (s, 1H), 7.99 (br d, J=8.8 Hz, 1H), 7.26 (br d, J=8.8 Hz, 1H), 4.73 (dt, J=11.9, 6.0 Hz, 1H), 4.23 (s, 2H), 2.27 (br s, 1H), 2.03-1.93 (m, 6H), 1.53-1.42 (m, 6H), 1.30 (s, 3H), 1.29 (s, 3H), 1.18-1.10 (m, 2H), 1.10-1.02 (m, 2H). FXR $EC_{50}$ (nM)=260. MS (ESI) 639 (M+H).

Example 257

4-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-6-methoxypicolinic acid

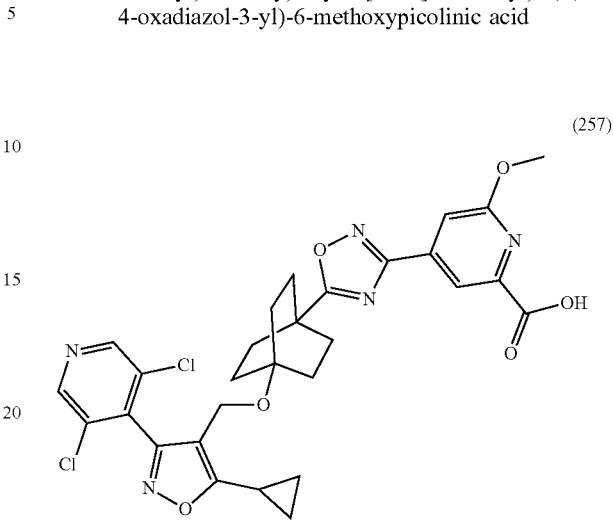

(257)

Step A. Intermediate 257A. Preparation of methyl 4-cyano-6-methoxypicolinate

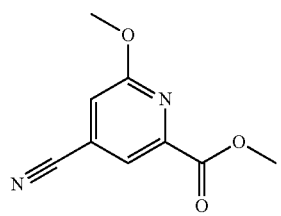

The title compound was prepared according to methods described for the synthesis of Intermediate 20A, using 2-methoxy-6-(methoxycarbonyl)isonicotinic acid (Bilcer, G. M. et al. WO 2012/054510) as starting material: (90 mg, 0.47 mmol, 76% yield, white solid). $^1$H NMR (400 MHz, DMSO-$d_6$) δ 7.99 (d, J=1.1 Hz, 1H), 7.72 (d, J=1.1 Hz, 1H), 3.96 (s, 3H), 3.90 (s, 3H). MS (ESI) 193 (M+H).

Step B. Intermediate 257B. Preparation of methyl (Z)-4-(N'-hydroxycarbamimidoyl)-6-methoxypicolinate

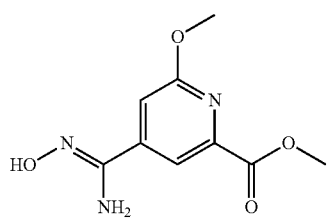

The title compound was prepared according to methods described for the synthesis of Intermediate 4C, using Intermediate 257A as starting material: (81 mg, 0.36 mmol, 79% yield, white solid). $^1$H NMR (500 MHz, DMSO-$d_6$) δ 10.16 (s, 1H), 8.01 (d, J=1.1 Hz, 1H), 7.33 (d, J=1.4 Hz, 1H), 6.09 (s, 2H), 3.92 (s, 3H), 3.87 (s, 3H). MS (ESI) 226 (M+H).

Step C. Example 257

The title compound was prepared according to methods described for the synthesis of Example 64 (Step C), by reaction of Intermediate 69B and Intermediate 257B: $^1$H NMR (500 MHz, DMSO-$d_6$) δ 8.81 (s, 2H), 8.02 (s, 1H), 7.30 (s, 1H), 4.24 (s, 2H), 3.93 (s, 3H), 2.35-2.25 (m, 1H), 2.03-1.94 (m, 6H), 1.52-1.41 (m, 6H), 1.15 (br d, J=7.9 Hz, 2H), 1.08 (br d, J=2.7 Hz, 2H). FXR EC$_{50}$ (nM)=79. MS (ESI) 612 (M+H).

Example 258

4-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-6-isopropoxypicolinic acid (258)

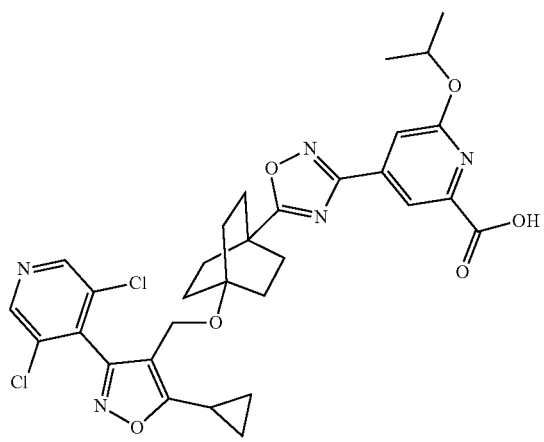

Step A. Intermediate 258A. Preparation of tert-butyl 2-chloro-6-isopropoxyisonicotinate

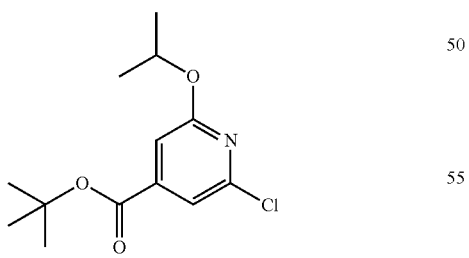

To a solution of 2-chloro-6-isopropoxyisonicotinic acid (1.1 g, 5.0 mmol) (Bolli, M. et. al. WO 2008/029371) and di-tert-butyl dicarbonate (2.7 mL, 11 mmol) in NMP (5 mL) was added DMAP (0.61 g, 5.0 mmol). After stirring at room temperature for 2 h, the reaction was diluted water and extracted with EtOAc (3×). The combined organic layers were washed with brine, dried over anhydrous Na$_2$SO$_4$ and concentrated. The crude product was purified by flash column chromatography (80 g silica gel cartridge, A=Hex, B=EtOAc; 20 min grad.; 0% B to 5% B; flow rate=60 mL/min). The pure fractions were combined, concentrated and dried in vacuo to afford the title compound (0.46 g, 1.7 mmol, 34% yield) as a clear oil. $^1$H NMR (400 MHz, CHLOROFORM-d) δ 7.33 (d, J=1.1 Hz, 1H), 7.11 (d, J=0.9 Hz, 1H), 5.36-5.26 (m, 1H), 1.58 (s, 9H), 1.36 (s, 3H), 1.35 (s, 3H). MS (ESI) 272 (M+H).

Step B. Intermediate 258B. Preparation of 4-(tert-butyl) 2-methyl 6-isopropoxypyridine-2,4-dicarboxylate

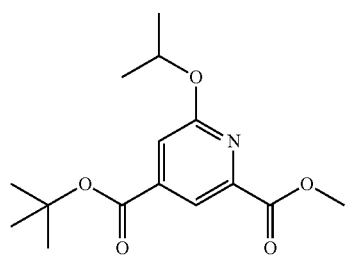 [SMILES: COC(=O)c1cc(C(=O)OC(C)(C)C)cc(OC(C)C)n1]

To a solution of Intermediate 258A (0.33 g, 1.2 mmol) and TEA (0.56 mL, 4.0 mmol) in DMSO (3 mL) and MeOH (3 mL) was added palladium(II) acetate (0.030 g, 0.13 mmol) followed by dppf (0.075 g, 0.13 mmol). The reaction was stirred under an atmosphere of carbon monoxide (1 atm, balloon) at 80° C. for 9 h. After cooling to room temperature, the reaction was filtered through a pad of Celite and the filtrate was concentrated to remove MeOH. The DMSO containing residue was diluted with water and extracted with EtOAc (3×). The combined organic layers were washed with water, brine, dried over anhydrous Na$_2$SO$_4$ and concentrated. The crude product was purified by flash column chromatography (24 g silica gel cartridge, A=Hex, B=EtOAc; 10 min grad.; 0% B to 15% B; flow rate=35 mL/min). The pure fractions were concentrated and dried in vacuo to afford the title compound (0.30 g, 1.0 mmol, 83% yield) as a white solid. $^1$H NMR (400 MHz, DMSO-$d_6$) δ 7.91 (d, J=1.3 Hz, 1H), 7.32 (d, J=1.3 Hz, 1H), 5.39-5.30 (m, 1H), 3.89 (s, 3H), 1.56 (s, 9H), 1.33 (s, 3H), 1.31 (s, 3H). MS (ESI) 296 (M+H).

Step C. Intermediate 258C. Preparation of 2-isopropoxy-6-(methoxycarbonyl)isonicotinic acid TFA (2.8 mL, 36 mmol) was added to Intermediate 258B (0.30 g, 1.0 mmol) and the reaction was stirred at room temperature for 3 h. The TFA was concentrated and the residue was dried in vacuo to afford the title compound (0.23 g, 0.96 mmol, 96% yield) as a crude off-white solid which was used in the next step without purification. ¹H NMR (500 MHz, DMSO-d₆) δ 13.88 (br s, 1H), 7.97 (d, J=1.1 Hz, 1H), 7.33 (s, 1H), 5.34 (dt, J=12.4, 6.2 Hz, 1H), 3.89 (s, 3H), 1.33 (s, 3H), 1.32 (s, 3H). MS (ESI) 240 (M+H).

Step D. Intermediate 258D. Preparation of methyl 4-cyano-6-isopropoxypicolinate

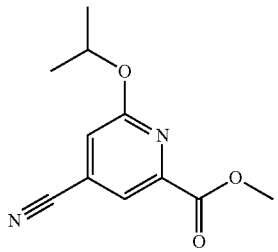 [SMILES: COC(=O)c1cc(C#N)cc(OC(C)C)n1]

The title compound was prepared according to methods described for the synthesis of Intermediate 20A, using Intermediate 258C as starting material: (0.18 g, 0.83 mmol, 88% yield, white solid). ¹H NMR (500 MHz, DMSO-d₆) δ 7.93 (d, J=0.8 Hz, 1H), 7.61 (d, J=0.8 Hz, 1H), 5.33 (dt, J=12.4, 6.2 Hz, 1H), 3.89 (s, 3H), 1.33 (s, 3H), 1.32 (s, 3H). MS (ESI) 221 (M+H).

Step E. Intermediate 258E. Preparation of methyl (Z)-4-(N'-hydroxycarbamimidoyl)-6-isopropoxypicolinate

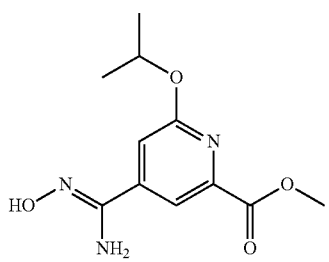

The title compound was prepared according to methods described for the synthesis of Intermediate 4C, using Intermediate 258D as starting material: (74 mg, 0.29 mmol, 35% yield, white solid). ¹H NMR (500 MHz, DMSO-d₆) δ 10.14 (s, 1H), 7.96 (d, J=1.4 Hz, 1H), 7.29-7.19 (m, 1H), 6.05 (s, 2H), 5.40-5.19 (m, 1H), 3.86 (s, 3H), 1.32 (s, 3H), 1.31 (s, 3H). MS (ESI) 254 (M+H).

Step F. Example 258

The title compound was prepared according to methods described for the synthesis of Example 64 (Step C), by reaction of Intermediate 69B and Intermediate 257B: ¹H NMR (500 MHz, DMSO-d₆) δ 13.54-13.26 (br s, 1H), 8.83 (s, 2H), 8.06-8.01 (m, 1H), 7.37 (d, J=1.1 Hz, 1H), 5.40 (quin, J=6.1 Hz, 1H), 4.25 (s, 2H), 2.38-2.28 (m, 1H), 2.03-1.95 (m, 6H), 1.56-1.43 (m, 6H), 1.34 (s, 3H), 1.32 (s, 3H), 1.15 (dt, J=8.3, 3.0 Hz, 2H), 1.11-1.05 (m, 2H). FXR EC₅₀ (nM)=8. MS (ESI) 640 (M+H).

Example 259

5-(4-(4-((5-cyclopropyl-3-(3,5-dichloropyridin-4-yl) isoxazol-4-yl)methoxy) bicyclo[2.2.2]octan-1-yl)-1H-imidazol-2-yl)-2-methoxybenzoic acid

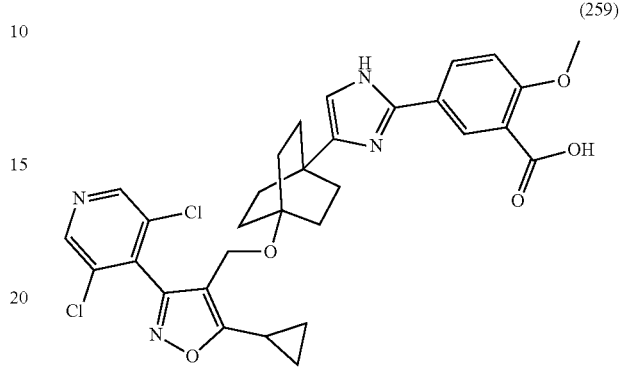

(259)

Step A. Intermediate 259A. Preparation of methyl 5-carbamimidoyl-2-methoxybenzoate, HCl

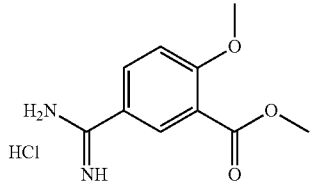

Step 1: To a 0° C. solution of methyl 5-cyano-2-methoxybenzoate (250 mg, 1.3 mmol) in MeOH (0.14 mL), water (0.029 mL) and diethyl ether (0.16 mL) was added thionyl chloride (0.095 mL, 1.3 mmol). The reaction mixture was slowly warmed to rt and stirred. After 18 h, the resultant precipitate was collected by vacuum filtration, the filter cake was washed with diethyl ether and the product was dried under vacuum at 50° C. for 1 h to yield a crude white solid which was taken onto the next step.

Step 2: The product of Step 1 above was suspended in MeOH (1 mL), then ammonia (0.24 mL, 1.7 mmol) (7 M in MeOH) was added in one portion. After stirring at room temperature for 24 h, the solvent was concentrated and the residue was dried in vacuo to afford the title compound (0.26 g, 1.1 mmol, 80% yield) as a crude white solid which was used in the next step without further purification. ¹H NMR (500 MHz, DMSO-d₆) δ 9.40-8.94 (m, 4H), 8.15 (d, J=2.5 Hz, 1H), 8.04 (dd, J=8.9, 2.3 Hz, 1H), 7.40 (d, J=9.1 Hz, 1H), 3.94 (s, 3H), 3.84 (s, 3H). MS (ESI) 209 (M+H).

Step B. Example 259

Step 1: To a solution of Intermediate 259A (5.2 mg, 0.021 mmol) and potassium bicarbonate (4.3 mg, 0.043 mmol) in THF (0.10 mL) and water (0.10 mL) was added Intermediate 252C (10 mg, 0.021 mmol). After stirring at 65° C. in a sealed reaction vial for 20 h, the reaction mixture was cooled to room temperature, diluted with EtOAc and filtered.

The filtrate was concentrated and the crude residue was taken onto the next step.

Step 2: The product of Step 1 above was dissolved in THF (0.50 mL) and 1 M NaOH (aq.) (0.50 mL). After stirring at 65° C. for 3 h, the reaction was cooled to room temperature, diluted with 5% citric acid (aq.) and extracted with EtOAc. The organic layer was washed with water, brine, dried over anhydrous $Na_2SO_4$ and concentrated. The crude product was purified by preparative HPLC (Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 18% B, 18-58% B over 20 minutes, then a 4-minute hold at 100% B; Flow Rate: 20 mL/min). Fractions containing the desired product were combined, concentrated and dried in vacuo to afford the title compound (4.3 mg, 7.1 μmol, 33% yield). $^1$H NMR (500 MHz, DMSO-$d_6$) δ 8.78 (s, 2H), 8.15 (d, J=1.9 Hz, 1H), 7.97 (dd, J=8.7, 1.9 Hz, 1H), 7.15 (d, J=8.8 Hz, 1H), 6.65 (s, 1H), 4.23 (s, 2H), 3.84 (s, 3H), 2.32-2.20 (m, 1H), 1.87-1.71 (m, 6H), 1.48-1.35 (m, 6H), 1.18-1.12 (m, 2H), 1.10-0.97 (m, 2H). FXR $EC_{50}$ (nM)=5500. MS (ESI) 609 (M+H).

Example 260

6-cyclopropoxy-4-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)picolinic acid

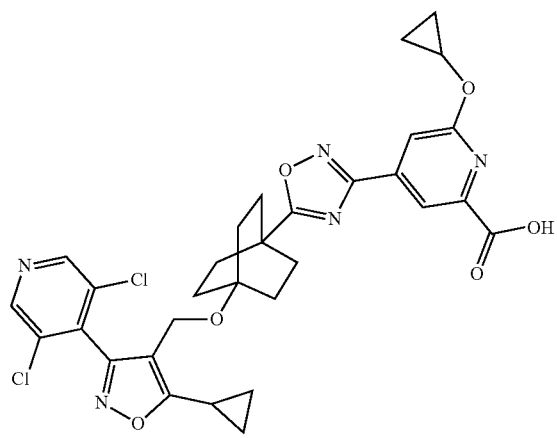

(260)

Step A. Intermediate 260A. Preparation of 2-chloro-6-cyclopropoxyisonicotinonitrile

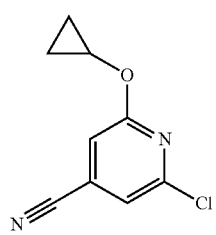 [SMILES: N#Cc1cc(Cl)nc(OC2CC2)c1]

Sodium hydride (0.17 g, 4.3 mmol) (60% dispersion in mineral oil) was slowly added to a room temperature solution of cyclopropanol (0.18 mL, 2.9 mmol) in 1,4-dioxane (4 mL). After stirring for 10 min, 2,6-dichloroisonicotinonitrile (0.50 g, 2.9 mmol) was added and the reaction mixture was stirred at 60° C. for 2.5 h. Upon cooling to room temperature, the reaction was diluted with EtOAc, washed with 1 M HCl (aq.) and brine. The organic layer was dried over anhydrous $Na_2SO_4$ and concentrated. The crude product was purified by flash column chromatography (40 g silica gel cartridge, A=Hex, B=EtOAc; 13 min grad.; 0% B to 25% B; flow rate=40 mL/min). The pure fractions were concentrated and dried in vacuo to afford the title compound (0.35 g, 1.8 mmol, 62% yield) as a light yellow solid. $^1$H NMR (400 MHz, DMSO-$d_6$) δ 7.71 (d, J=1.1 Hz, 1H), 7.49 (d, J=1.1 Hz, 1H), 4.24 (tt, J=6.2, 3.1 Hz, 1H), 0.87-0.78 (m, 2H), 0.78-0.68 (m, 2H). MS (ESI) 195 (M+H).

Step B. Intermediate 260B. Preparation of methyl 4-cyano-6-cyclopropoxypicolinate

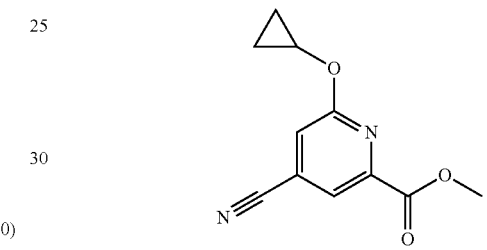

The title compound was prepared according to methods described for the synthesis of Intermediate 258B, using Intermediate 260A as starting material: (0.21 g, 0.96 mmol, 53% yield, white solid). $^1$H NMR (500 MHz, DMSO-$d_6$) δ 8.06-7.98 (m, 1H), 7.74 (d, J=0.8 Hz, 1H), 4.34 (tt, J=6.2, 3.1 Hz, 1H), 3.90 (s, 3H), 0.88-0.81 (m, 2H), 0.76-0.69 (m, 2H). MS (ESI) 219 (M+H)

Step C. Intermediate 260C. Preparation of methyl (Z)-6-cyclopropoxy-4-(N'-hydroxycarbamimidoyl)picolinate

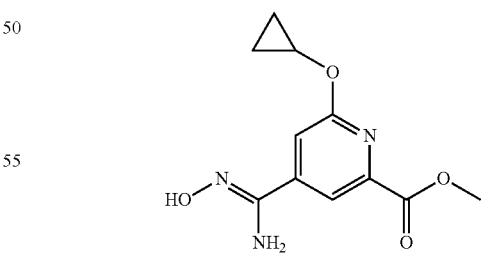

The title compound was prepared according to methods described for the synthesis of Intermediate 4C, using Intermediate 260B as starting material: (0.22 mg, 0.86 mmol, 91% yield, white solid). $^1$H NMR (500 MHz, DMSO-$d_6$) δ 10.17 (s, 1H), 8.03 (d, J=1.1 Hz, 1H), 7.38 (d, J=1.1 Hz, 1H), 6.09 (s, 2H), 4.35-4.26 (m, 1H), 3.87 (s, 3H), 0.85-0.76 (m, 2H), 0.72-0.65 (m, 2H). MS (ESI) 252 (M+H).

Step D. Example 260

The title compound was prepared according to methods described for the synthesis of Example 64 (Step C), by reaction of Intermediate 69B and Intermediate 260C: $^1$H NMR (500 MHz, DMSO-d$_6$) δ 8.81 (s, 2H), 8.08 (s, 1H), 7.46 (s, 1H), 4.38 (br s, 1H), 4.24 (s, 2H), 2.38-2.25 (m, 1H), 2.05-1.93 (m, 6H), 1.53-1.40 (m, 6H), 1.19-1.14 (m, 2H), 1.08 (br d, J=2.7 Hz, 2H), 0.81 (br d, J=6.1 Hz, 2H), 0.72 (br s, 2H). FXR EC$_{50}$ (nM)=39. MS (ESI) 638 (M+H).

Example 261

6-cyclobutoxy-4-(5-(4-(((5-cyclopropyl-3-(3,5-dichloropyridin-4-yl)isoxazol-4-yl) methoxy)bicyclo[2.2.2]octan-1-yl)-1,2,4-oxadiazol-3-yl)picolinic acid (261)

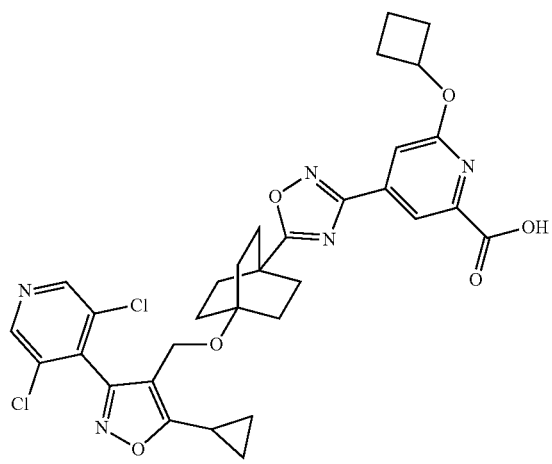

Step A. Intermediate 261A. Preparation of tert-butyl 2-chloro-6-cyclobutoxyisonicotinate

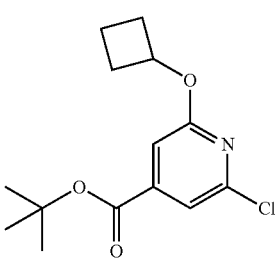 [SMILES: CC(C)(C)OC(=O)c1cc(Cl)nc(OC2CCC2)c1]

The title compound was prepared according to methods described for the synthesis of Intermediate 258A, using 2-chloro-6-cyclobutoxyisonicotinic acid (Bolli, M. H., et. al. *Eur. J. Med. Chem.* 2016, 115, 326) as starting material: (0.33 mg, 1.2 mmol, 82% yield, clear oil). $^1$H NMR (400 MHz, DMSO-d$_6$) δ 7.35 (d, J=1.1 Hz, 1H), 7.10 (d, J=0.9 Hz, 1H), 5.10 (dd, J=7.8, 6.9 Hz, 1H), 2.44-2.35 (m, 2H), 2.13-2.01 (m, 2H), 1.84-1.73 (m, 1H), 1.72-1.60 (m, 1H), 1.54 (s, 9H). MS (ESI) 284 (M+H).

Step B. Intermediate 261B. Preparation of 4-(tert-butyl) 2-methyl 6-cyclobutoxypyridine-2,4-dicarboxylate

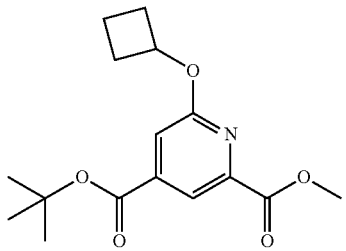 [SMILES: COC(=O)c1cc(C(=O)OC(C)(C)C)cc(OC2CCC2)n1]

The title compound was prepared according to methods described for the synthesis of Intermediate 258B, using Intermediate 261A as starting material: (0.28 mg, 0.91 mmol, 78% yield, white solid). $^1$H NMR (500 MHz, DMSO-d$_6$) δ 7.93 (d, J=1.1 Hz, 1H), 7.36 (d, J=1.1 Hz, 1H), 5.20 (t, J=7.6 Hz, 1H), 3.89 (s, 3H), 2.47-2.37 (m, 2H), 2.08 (ddd, J=9.8, 7.8, 2.5 Hz, 2H), 1.80 (br d, J=9.9 Hz, 1H), 1.73-1.62 (m, 1H), 1.56 (s, 9H). MS (ESI) 308 (M+H).

Step C. Intermediate 261C. Preparation of 2-cyclobutoxy-6-(methoxycarbonyl) isonicotinic acid

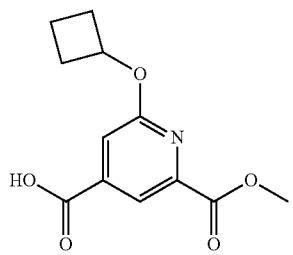 [SMILES: COC(=O)c1cc(C(=O)O)cc(OC2CCC2)n1]

The title compound was prepared according to methods described for the synthesis of Intermediate 258C, using Intermediate 261B as starting material: (0.27 mg, 1.1 mmol, 119% yield, crude off-white solid containing TFA). $^1$H NMR (500 MHz, DMSO-d$_6$) δ 14.26-13.31 (m, 1H), 7.99 (d, J=1.1 Hz, 1H), 7.37 (d, J=1.1 Hz, 1H), 5.19 (quin, J=7.4 Hz, 1H), 3.89 (s, 3H), 2.46-2.39 (m, 2H), 2.19-2.02 (m, 2H), 1.85-1.74 (m, 1H), 1.71-1.63 (m, 1H). MS (ESI) 252 (M+H).

Step D. Intermediate 261D. Preparation of methyl 4-cyano-6-cyclobutoxypicolinate

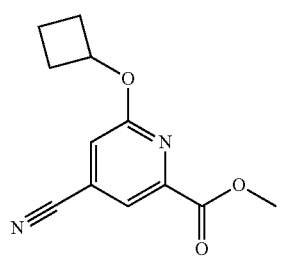 [SMILES: COC(=O)c1cc(C#N)cc(OC2CCC2)n1]

The title compound was prepared according to methods described for the synthesis of Intermediate 20A, using Intermediate 261C as starting material: (0.11 g, 0.48 mmol, 51% yield, white solid). $^1$H NMR (500 MHz, DMSO-d$_6$) δ 7.96 (s, 1H), 7.65 (s, 1H), 5.17 (quin, J=7.4 Hz, 1H), 3.89 (s, 3H), 2.47-2.39 (m, 2H), 2.14-2.03 (m, 2H), 1.80 (q, J=10.3 Hz, 1H), 1.73-1.61 (m, 1H). MS (ESI) 233 (M+H).

Step E. Intermediate 261E. Preparation of methyl (Z)-6-cyclobutoxy-4-(N'-hydroxycarbamimidoyl)picolinate

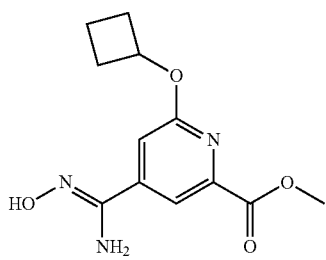 [SMILES: COC(=O)c1cc(/C(N)=N/O)cc(OC2CCC2)n1]

The title compound was prepared according to methods described for the synthesis of Intermediate 4C, using Intermediate 261D as starting material: (0.12 g, 0.46 mmol, 96% yield, white solid). $^1$H NMR (500 MHz, DMSO-d$_6$) δ 10.15 (s, 1H), 7.98 (d, J=1.1 Hz, 1H), 7.28 (d, J=1.1 Hz, 1H), 6.07 (s, 2H), 5.17 (quin, J=7.4 Hz, 1H), 3.86 (s, 3H), 2.46-2.36 (m, 2H), 2.15-1.99 (m, 2H), 1.83-1.75 (m, 1H), 1.72-1.60 (m, 1H). MS (ESI) 266 (M+H).

Step F. Example 261

The title compound was prepared according to methods described for the synthesis of Example 64 (Step C), by reaction of Intermediate 69B and Intermediate 261E: $^1$H NMR (500 MHz, DMSO-d$_6$) δ 8.78 (s, 2H), 8.03 (s, 1H), 7.35 (s, 1H), 5.26 (quin, J=7.3 Hz, 1H), 4.24 (s, 2H), 2.44 (br d, J=7.2 Hz, 2H), 2.33-2.23 (m, 1H), 2.14-2.05 (m, 2H), 2.04-1.95 (m, 6H), 1.80 (br d, J=9.8 Hz, 1H), 1.70-1.60 (m, 1H), 1.54-1.43 (m, 6H), 1.21-1.12 (m, 2H), 1.07 (br d, J=2.5 Hz, 2H). FXR EC$_{50}$ (nM)=36. MS (ESI) 652 (M+H).

Example 262

4-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-6-(dimethylamino)picolinic acid (262)

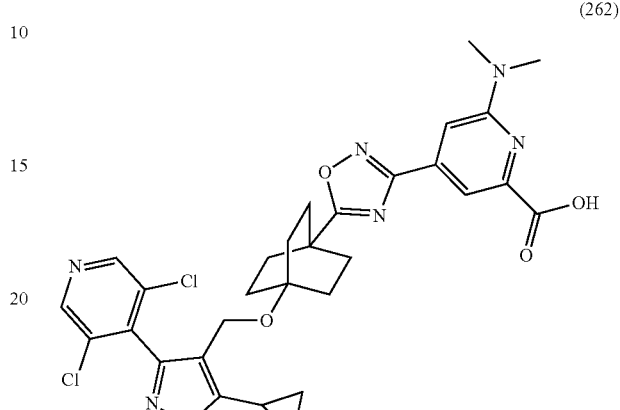

Step A. Intermediate 262A. Preparation of methyl 4-cyano-6-(dimethylamino)picolinate

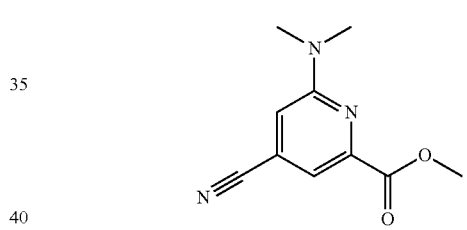

The title compound was prepared according to methods described for the synthesis of Intermediate 258B, using 2-chloro-6-(dimethylamino)isonicotinonitrile (Fruttardo, F. et. al. WO 2014/135617) as starting material: (28 mg, 0.14 mmol, 66% yield, yellow solid). $^1$H NMR (500 MHz, DMSO-d$_6$) δ 7.48-7.40 (m, 1H), 7.37 (d, J=0.8 Hz, 1H), 3.85 (s, 3H), 3.10 (s, 6H). MS (ESI) 206 (M+H).

Step B. Intermediate 262B. Preparation of methyl (Z)-6-(dimethylamino)-4-(N'-hydroxycarbamimidoyl)picolinate

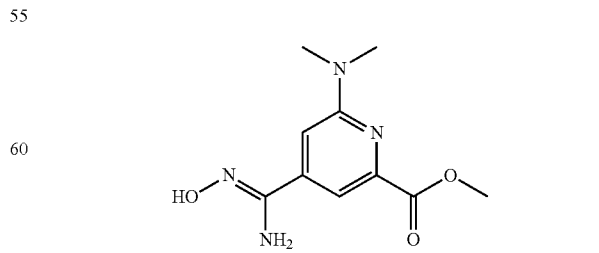

The title compound was prepared according to methods described for the synthesis of Intermediate 4C, using Intermediate 262A as starting material: (30 mg, 0.12 mmol, 91% yield, yellow solid). $^1$H NMR (500 MHz, DMSO-$d_6$) δ 9.96 (s, 1H), 7.57 (s, 1H), 7.10 (s, 1H), 6.02 (s, 2H), 3.83 (s, 3H), 3.09 (s, 6H). MS (ESI) 239 (M+H).

Step C. Example 262

The title compound was prepared according to methods described for the synthesis of Example 64 (Step C), by reaction of Intermediate 69B and Intermediate 262B: $^1$H NMR (500 MHz, DMSO-$d_6$) δ 8.82 (s, 2H), 7.65 (s, 1H), 7.20 (s, 1H), 4.24 (s, 2H), 3.12 (s, 6H), 2.37-2.24 (m, 1H), 2.03-1.96 (m, 6H), 1.50-1.40 (m, 6H), 1.15 (br d, J=8.2 Hz, 2H), 1.08 (br d, J=2.4 Hz, 2H). FXR EC$_{50}$ (nM)=53. MS (ESI) 625 (M+H).

Example 263

4-(5-(4-((5-cyclopropyl-3-(3,5-dichloropyridin-4-yl) isoxazol-4-yl)methoxy) bicyclo[2.2.2]octan-1-yl)-1,2,4-oxadiazol-3-yl)-6-(2,2,2-trifluoroethoxy)picolinic acid (263)

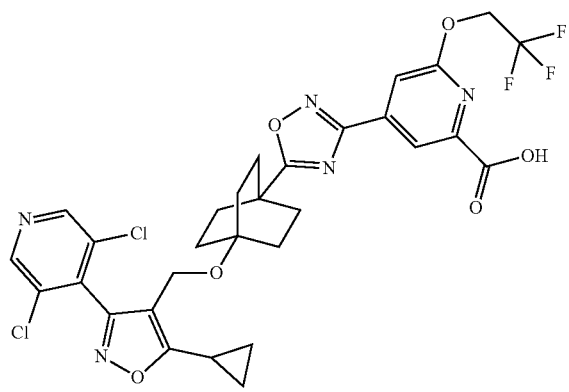

Step A. Intermediate 263A. Preparation of methyl 4-cyano-6-(2,2,2-trifluoroethoxy)picolinate

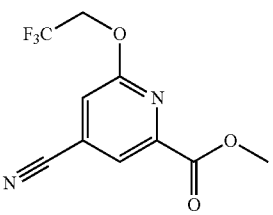 [SMILES: COC(=O)c1cc(C#N)cc(OCC(F)(F)F)n1]

The title compound was prepared according to methods described for the synthesis of Intermediate 258B, using 2-chloro-6-(2,2,2-trifluoroethoxy)isonicotinonitrile (Arvela, R. et. al. WO 2012/152983) as starting material: (0.19 g, 0.74 mmol, 64% yield, white solid). $^1$H NMR (500 MHz, CHLOROFORM-d) δ 7.99 (d, J=0.8 Hz, 1H), 7.33 (d, J=0.8 Hz, 1H), 4.90 (q, J=8.3 Hz, 2H), 4.01 (s, 3H). MS (ESI) 261 (M+H).

Step B. Intermediate 263B. Preparation of methyl (Z)-4-(N'-hydroxycarbamimidoyl)-6-(2,2,2-trifluoroethoxy)picolinate

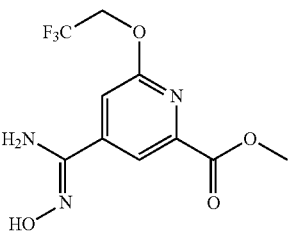 [SMILES: COC(=O)c1cc(/C(N)=N/O)cc(OCC(F)(F)F)n1]

The title compound was prepared according to methods described for the synthesis of Intermediate 4C, using Intermediate 263A as starting material: (69 mg, 0.24 mmol, 32% yield, white solid). $^1$H NMR (500 MHz, DMSO-$d_6$) δ 10.26 (s, 1H), 8.13 (d, J=1.1 Hz, 1H), 7.51 (d, J=0.8 Hz, 1H), 6.14 (s, 2H), 5.06 (q, J=9.1 Hz, 2H), 3.89 (s, 3H). MS (ESI) 294 (M+H).

Step C. Example 263

The title compound was prepared according to methods described for the synthesis of Example 64 (Step C), by reaction of Intermediate 69B and Intermediate 263B: $^1$H NMR (500 MHz, DMSO-$d_6$) δ 8.81 (s, 2H), 8.15 (s, 1H), 7.54 (s, 1H), 5.13 (q, J=8.9 Hz, 2H), 4.24 (s, 2H), 2.35-2.25 (m, 1H), 2.03-1.95 (m, 6H), 1.51-1.41 (m, 6H), 1.19-1.12 (m, 2H), 1.10-1.03 (m, 2H). FXR EC$_{50}$ (nM)=95. MS (ESI) 680 (M+H).

Example 264

4-(5-(4-((5-cyclopropyl-3-(3,5-dichloropyridin-4-yl) isoxazol-4-yl)methoxy) bicyclo[2.2.2]octan-1-yl)-1,2,4-oxadiazol-3-yl)-6-(trifluoromethyl)picolinic acid (264)

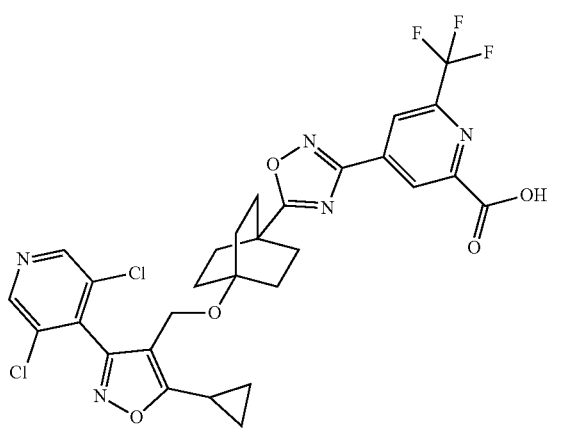

Step A. Intermediate 264A. Preparation of methyl 4-cyano-6-(trifluoromethyl) picolinate

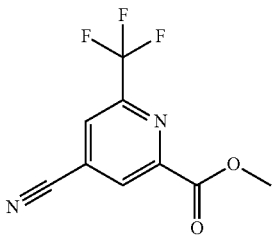 [SMILES: COC(=O)c1cc(C#N)cc(C(F)(F)F)n1]

The title compound was prepared according to methods described for the synthesis of Intermediate 258B, using 2-chloro-6-(trifluoromethyl)isonicotinonitrile (Rodgers, J. D. et. al. WO 2012/068450) as starting material: (10 mg, 0.045 mmol, 42% yield, white solid). $^1$H NMR (500 MHz, CHLOROFORM-d) δ 8.53 (s, 1H), 8.09 (s, 1H), 4.08 (s, 3H). MS (ESI) 231 (M+H).

Step B. Intermediate 264B. Preparation of methyl (Z)-4-(N'-hydroxycarbamimidoyl)-6-(trifluoromethyl)picolinate

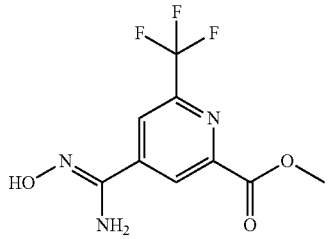 [SMILES: COC(=O)c1cc(/C(N)=N/O)cc(C(F)(F)F)n1]

The title compound was prepared according to methods described for the synthesis of Intermediate 4C, using Intermediate 264A as starting material: (6.0 mg, 0.023 mmol, 51% yield, white solid). MS (ESI) 264 (M+H).

Step C. Example 264

The title compound was prepared according to methods described for the synthesis of Example 64 (Step C), by reaction of Intermediate 69B and Intermediate 264B: $^1$H NMR (500 MHz, DMSO-d$_6$) δ 8.80 (s, 2H), 8.58 (br s, 1H), 8.27-8.13 (m, 1H), 4.23 (s, 2H), 2.33-2.23 (m, 1H), 2.04-1.96 (m, 6H), 1.49-1.41 (m, 6H), 1.19-1.12 (m, 2H), 1.09-1.03 (m, 2H). FXR EC$_{50}$ (nM)=180. MS (ESI) 650 (M+H).

Example 265

5-(5-(4-((5-cyclopropyl-3-(3,5-dichloropyridin-4-yl)isoxazol-4-yl)methoxy) bicyclo[2.2.2]octan-1-yl)-1,2,4-oxadiazol-3-yl)-3-methoxypicolinic acid

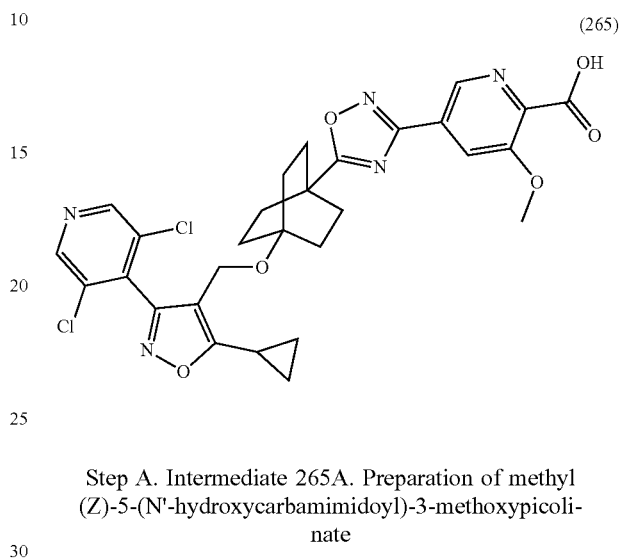

(265)

Step A. Intermediate 265A. Preparation of methyl (Z)-5-(N'-hydroxycarbamimidoyl)-3-methoxypicolinate

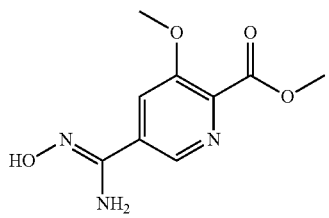 [SMILES: COC(=O)c1ncc(/C(N)=N/O)cc1OC]

The title compound was prepared according to methods described for the synthesis of Intermediate 4C, using methyl 5-cyano-3-methoxypicolinate as starting material: (15 mg, 0.065 mmol, 100% yield, white solid). $^1$H NMR (500 MHz, CHLOROFORM-d) δ 8.59 (d, J=2.2 Hz, 1H), 8.41-8.39 (m, 1H), 4.84 (br d, J=1.1 Hz, 2H), 4.09 (s, 3H), 3.92 (s, 3H). MS (ESI) 226 (M+H).

Step B. Example 265

The title compound was prepared according to methods described for the synthesis of Example 64 (Step C), by reaction of Intermediate 69B and Intermediate 265A: $^1$H NMR (500 MHz, DMSO-d$_6$) δ 8.81 (s, 2H), 8.79 (br d, J=2.1 Hz, 1H), 8.43 (br s, 1H), 4.23 (s, 2H), 3.96 (s, 3H), 2.34-2.25 (m, 1H), 2.02-1.94 (m, 6H), 1.50-1.40 (m, 6H), 1.19-1.13 (m, 2H), 1.10-1.01 (m, 2H). FXR EC$_{50}$ (nM)=1500. MS (ESI) 612 (M+H).

Example 266

2-(5-(4-((5-cyclopropyl-3-(2,6-dichlorophenyl)isoxazol-4-yl)methoxy) bicyclo[2.2.2]octan-1-yl)-1,2,4-oxadiazol-3-yl)cyclopropane-1-carboxylic acid

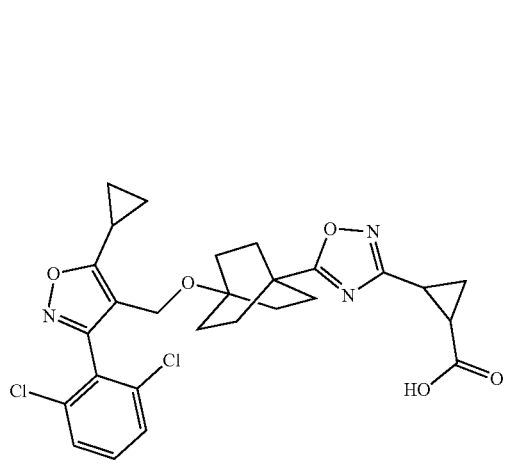

(266)

Step A. Intermediate 266A. Preparation of ethyl (Z)-2-(N'-hydroxycarbamimidoyl)cyclopropane-1-carboxylate

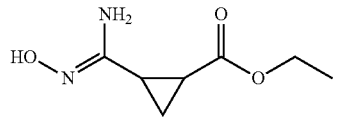

The title compound was prepared according to methods described for the synthesis of Intermediate 4C, using ethyl 2-cyanocyclopropane-1-carboxylate as starting material: (230 mg, 1.4 mmol, 95% yield, clear oil). $^1$HNMR (500 MHz, DMSO-$d_6$) δ 8.94 (s, 1H), 5.43 (br s, 2H), 4.16-3.99 (m, 2H), 1.93-1.78 (m, 2H), 1.30-1.23 (m, 1H), 1.23-1.16 (m, 3H), 1.15-1.09 (m, 1H). MS (ESI) m/z 173 (M+H).

Step B. Example 266

The title compound was prepared according to methods described for the synthesis of Example 64 (Step C), by reaction of Intermediate 69B and Intermediate 266A: $^1$H NMR (500 MHz, DMSO-$d_6$) δ 7.64-7.60 (m, 2H), 7.59-7.53 (m, 1H), 4.15 (s, 2H), 2.40-2.34 (m, 1H), 2.33-2.24 (m, 1H), 1.91-1.85 (m, 7H), 1.49-1.39 (m, 7H), 1.33-1.26 (m, 1H), 1.16-1.09 (m, 2H), 1.09-1.04 (m, 2H). FXR EC$_{50}$ (nM)=720. MS (ESI) 544 (M+H).

Example 267

5-(4-((5-cyclopropyl-3-(2,6-dichlorophenyl)isoxazol-4-yl)methoxy)bicyclo[2.2.2]octan-1-yl)-3-(2H-tetrazol-5-yl)-1,2,4-oxadiazole

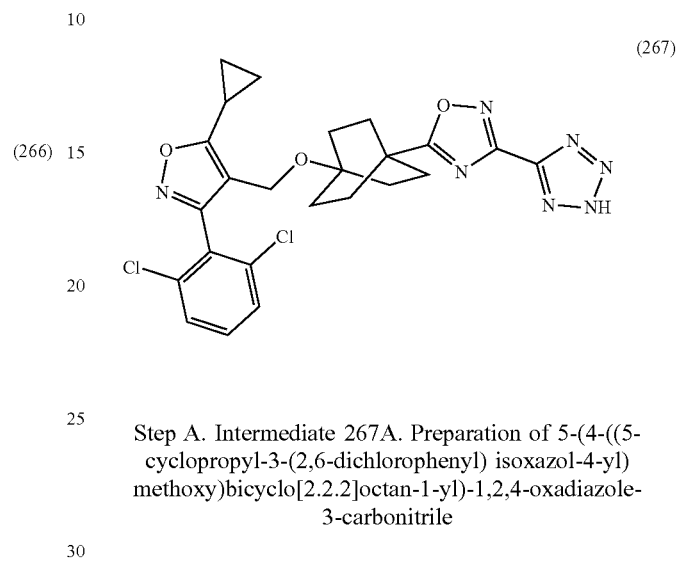

(267)

Step A. Intermediate 267A. Preparation of 5-(4-((5-cyclopropyl-3-(2,6-dichlorophenyl) isoxazol-4-yl)methoxy)bicyclo[2.2.2]octan-1-yl)-1,2,4-oxadiazole-3-carbonitrile

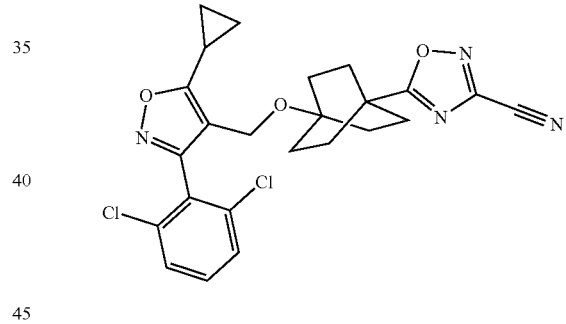

The title compound was prepared according to methods described for the synthesis of Intermediate 20A (Step 3), substituting Example 74 where appropriate: (9.6 mg, 0.020 mmol, 59% yield, white solid). $^1$H NMR (500 MHz, DMSO-$d_6$) δ 7.64-7.61 (m, 2H), 7.59-7.54 (m, 1H), 4.16 (s, 2H), 2.33-2.24 (m, 1H), 1.99-1.91 (m, 6H), 1.51-1.45 (m, 6H), 1.16-1.10 (m, 2H), 1.09-1.05 (m, 2H). MS (ESI) 485 (M+H).

Step B. Example 267

The title compound was prepared according to methods described for the synthesis of Example 66 (Step B), substituting Intermediate 267A where appropriate: (4.3 mg, 8.1 μmol, 56% yield, white solid). $^1$H NMR (500 MHz, DMSO-$d_6$) δ 7.71-7.62 (m, 2H), 7.61-7.55 (m, 1H), 4.19 (s, 2H), 2.32 (ddd, J=13.2, 8.3, 5.2 Hz, 1H), 2.04-1.95 (m, 6H), 1.57-1.43 (m, 6H), 1.20-1.12 (m, 2H), 1.12-1.03 (m, 2H). FXR EC$_{50}$ (nM)=4400. MS (ESI) 528 (M+H).

Example 272

2-(5-((4-((5-cyclopropyl-3-(3,5-dichloropyridin-4-yl)isoxazol-4-yl)methoxy) bicyclo[2.2.2]octan-1-yl)methyl)-1,2,4-oxadiazol-3-yl)cyclopropane-1-carboxylic acid

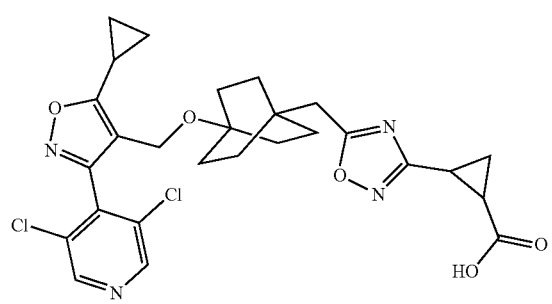

(272)

Step A. Intermediate 272A. Preparation of 2-(4-((5-cyclopropyl-3-(3,5-dichloropyridin-4-yl)isoxazol-4-yl)methoxy)bicyclo[2.2.2]octan-1-yl)acetic acid

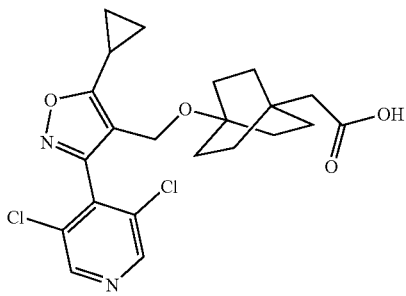 [SMILES: O=C(O)CC12CCC(OCc3c(-c4c(Cl)cncc4Cl)noc3C3CC3)(CC1)CC2]

A mixture of Intermediate 69B (30 mg, 0.069 mmol) in thionyl chloride (5.0 µl, 0.069 mmol) was stirred at 60° C. for 2 h and concentrated. The residue was dissolved in acetonitrile (0.6 mL) and trimethylsilyldiazomethane (0.041 mL, 0.082 mmol) (0.5 M in hexanes) was added. The mixture was stirred at rt for 2 h. To this mixture were added silver trifluoroacetate (23 mg, 0.10 mmol), TEA (0.019 mL, 0.14 mmol) and H$_2$O (0.06 mL). The mixture was stirred at rt for 20 h and filtered. The filtrate was concentrated to afford the title compound (31 mg, 0.069 mmol, 100% yield) as a yellow oil, which was used in the next step without further purification. MS (ESI) 451 (M+H).

Step B. Example 272

The title compound was prepared according to methods described for the synthesis of Example 64 (Step C), by reaction of Intermediate 266A and Intermediate 272A: $^1$H NMR (500 MHz, METHANOL-d$_4$) δ 8.67 (s, 2H), 4.26-4.19 (m, 2H), 2.65-2.55 (m, 2H), 2.51-2.41 (m, 1H), 2.25-2.15 (m, 1H), 2.06-1.99 (m, 1H), 1.56-1.47 (m, 6H), 1.47-1.39 (m, 6H), 1.38-1.31 (m, 2H), 1.19-1.11 (m, 4H). EC$_{50}$ (nM)=400. MS (ESI) 559 (M+H).

Example 273

5-(5-(4-((3-(4-chloro-1-methyl-1H-pyrazol-5-yl)-5-cyclopropylisoxazol-4-yl)methoxy) bicyclo[2.2.2]octan-1-yl)-1,2,4-oxadiazol-3-yl)-2-methoxybenzoic acid

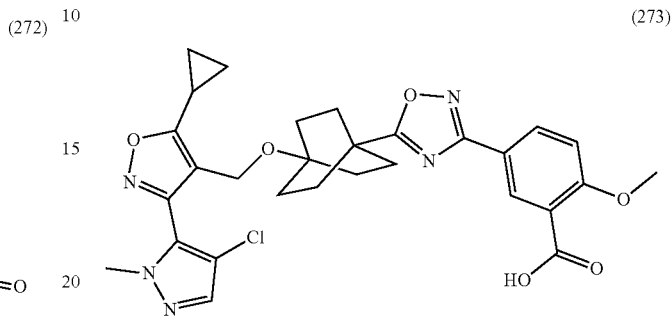

(273)

Step A. Intermediate 273A. Preparation of (E)-4-chloro-1-methyl-1H-pyrazole-5-carbaldehyde oxime

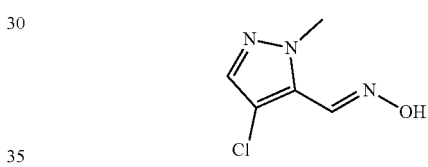

3 M NaOH (aq.) (1.3 mL, 3.8 mmol) was added dropwise to a stirred suspension of hydroxylamine hydrochloride (260 mg, 3.8 mmol) in water (0.2 mL) at 0° C. To this mixture was added dropwise a solution of 4-chloro-1-methyl-1H-pyrazole-5-carbaldehyde (500 mg, 3.5 mmol) in EtOH (4 mL). The reaction was stirred at reflux for 16 h. The mixture was cooled, the EtOH was concentrated and the remaining aqueous layer was diluted with water and extracted with EtOAc (2×). The organic phases were combined, washed with brine, dried over Na$_2$SO$_4$, filtered and concentrated to afford the title compound (550 mg, 3.5 mmol, 100% yield) as an off-white solid, which was used in the next step without further purification. MS (ESI) 160 (M+H).

Step B. Intermediate 273B. Preparation of (Z)-4-chloro-N'-hydroxy-1-methyl-1H-pyrazole-5-carbimidoyl chloride

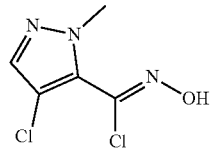

Intermediate 273A (530 mg, 3.3 mmol) was dissolved in DMF (2.5 mL) and heated to 40° C. NCS (532 mg, 4.0 mmol) dissolved in DMF (2 mL) was added in portions over a period of 10 min. The reaction was stirred at 40° C. for 48 h, then at rt for 16 h. The mixture was poured into ice water and extracted with EtOAc. The organics were washed with brine and the combined aqueous layers were back-extracted with EtOAc. The combined organic layers were dried over Na$_2$SO$_4$, filtered and concentrated. The crude product was purified by flash column chromatography (40 g silica gel cartridge, A=Hex, B=EtOAc; 15 min grad.; 0% B to 40% B; flow rate=40 mL/min). The pure fractions were concentrated and dried in vacuo to afford the title compound (430 mg, 2.2 mmol, 67% yield) as a white solid. MS (ESI) 192 (M+H).

Step C. Intermediate 273C. Preparation of methyl 3-(4-chloro-1-methyl-1H-pyrazol-5-yl)-5-cyclopropylisoxazole-4-carboxylate

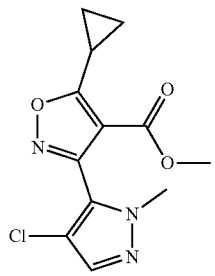 [SMILES: COC(=O)c1c(-c2c(Cl)cnn2C)noc1C1CC1]

To methyl 3-cyclopropyl-3-oxopropanoate (0.27 mL, 2.2 mmol) was added TEA (0.62 mL, 4.4 mmol) and the resulting clear solution was stirred at room temperature for 15 min. The reaction mixture was cooled to 5° C. To this solution was added Intermediate 273B (430 mg, 2.2 mmol) dissolved in EtOH (1 mL) over 10 min (the clear solution became a yellow/white suspension during addition). The resultant suspension was stirred at room temperature for 2 h. The reaction mixture was concentrated, the resulting residue was diluted with H$_2$O and extracted with EtOAc (2×). The combined organic phases were washed with brine, dried over anhydrous Na$_2$SO$_4$, filtered and concentrated. The crude product was purified by flash column chromatography (40 g silica gel cartridge, A=Hex, B=EtOAc; 15 min grad.; 0% B to 40% B; flow rate=40 mL/min). The pure fractions were combined, concentrated and dried in vacuo to give the title compound (320 mg, 1.1 mmol, 51% yield) as a white solid. $^1$H NMR (500 MHz, CHLOROFORM-d) δ 7.52 (s, 1H), 3.83 (s, 3H), 3.79-3.76 (m, 3H), 2.91 (s, 1H), 1.43-1.38 (m, 2H), 1.34-1.27 (m, 2H). (ESI) 282 (M+H).

Step D. Intermediate 273D. Preparation of (3-(4-chloro-1-methyl-1H-pyrazol-5-yl)-5-cyclopropylisoxazol-4-yl)methanol

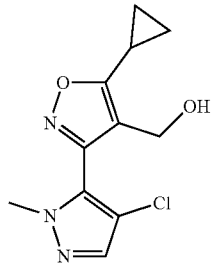 [SMILES: Cn1ncc(Cl)c1-c1noc(C2CC2)c1CO]

Intermediate 273C (220 mg, 0.78 mmol) was dissolved in DCM (5 mL) and cooled to −10° C. DIBAL-H (2.0 mL, 2.0 mmol) (1 M solution in DCM) was added dropwise while maintaining internal reaction temperature below −5° C. (ca. 15 minute period of addition). After stirring an additional 15 min, the reaction was quenched with EtOAc (0.5 mL). The mixture was diluted with EtOAc (2 mL) and sat. Rochelle's salt solution (aq.) (2 mL). The solution was extracted with EtOAc (2×), the organic layers were combined, dried over Na$_2$SO$_4$, filtered and concentrated. The crude product was purified by flash column chromatography (40 g silica gel cartridge, A=DCM, B=MeOH; 10 min grad.; 0% B to 10% B; flow rate=40 mL/min). The pure fractions were combined, concentrated and dried in vacuo to give the title compound (190 mg, 0.73 mmol, 93% yield) as a white solid. $^1$H NMR (500 MHz, CHLOROFORM-d) δ 7.49 (s, 1H), 4.54 (s, 2H), 3.81 (s, 3H), 2.28-2.15 (m, 1H), 1.28-1.21 (m, 2H), 1.18-1.12 (m, 2H). MS (ESI) 254 (M+H).

Step E. Intermediate 273E. Preparation of methyl 4-((3-(4-chloro-1-methyl-1H-pyrazol-5-yl)-5-cyclopropylisoxazol-4-yl)methoxy)bicyclo[2.2.2]octane-1-carboxylate

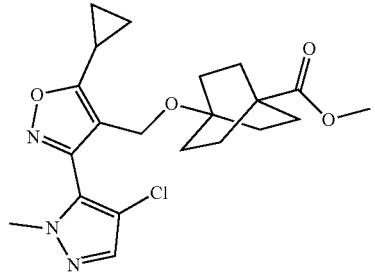

To a solution of Intermediate 273D (180 mg, 0.71 mmol), and Intermediate 4A (210 mg, 0.71 mmol) in DCE (0.70 mL) was added silver trifluoromethanesulfonate (220 mg, 0.85 mmol) and 2,6-di-tert-butylpyridine (0.23 mL, 1.1 mmol). The reaction was stirred at 100° C. for 1 h. The reaction mixture was cooled, filtered and concentrated. The crude product was purified by flash column chromatography (40 g silica gel cartridge, A=Hex, B=EtOAc; 15 min grad.; 0% B to 100% B; flow rate=40 mL/min). The pure fractions were combined, concentrated and dried in vacuo to give the title compound (180 mg, 0.43 mmol, 60% yield) as a clear oil. $^1$H NMR (500 MHz, CHLOROFORM-d) δ 7.44-7.40 (m, 1H), 4.16 (s, 2H), 3.72 (s, 3H), 3.54 (s, 3H), 2.06 (tt, J=8.5, 5.0 Hz, 1H), 1.83-1.77 (m, 6H), 1.55-1.48 (m, 6H), 1.16-1.11 (m, 2H), 1.07-0.94 (m, 2H). MS (ESI) 420 (M+H).

Step E. Intermediate 273F. Preparation of 4-((3-(4-chloro-1-methyl-1H-pyrazol-5-yl)-5-cyclopropylisoxazol-4-yl)methoxy)bicyclo[2.2.2]octane-1-carboxylic acid

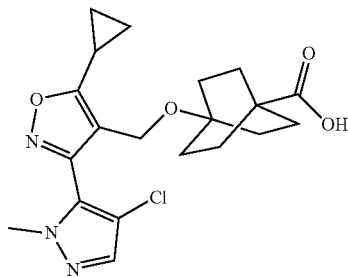 [SMILES: Cn1ncc(Cl)c1-c1noc(C2CC2)c1COC12CCC(C(=O)O)(CC1)CC2]

A mixture of Intermediate 273E (180 mg, 0.43 mmol) and 1 M NaOH (aq.) (4.3 mL, 4.3 mmol) in MeOH (3 mL) and THF (1 mL) was stirred at rt for 2 h. The organic solvents were concentrated and the remaining aqueous phase was acidified with 1 M HCl (aq.) (5 mL). The precipitate was collected by vacuum filtration and dried in vacuo to provide the title compound (170 mg, 0.42 mmol, 98% yield) as a white solid, which was used in the next step without further purification. MS (ESI) 406 (M+H).

Step F. Example 273

The title compound was prepared according to methods described for the synthesis of Example 64 (Step C), by reaction of Intermediate 69B and Intermediate 273F: $^1$H NMR (500 MHz, DMSO-$d_6$) δ 7.96-7.90 (m, 1H), 7.86-7.80 (m, 1H), 7.79-7.74 (m, 1H), 7.16-7.01 (m, 1H), 4.25 (s, 2H), 3.80 (s, 3H), 3.72 (s, 3H), 2.38-2.29 (m, 2H), 2.12-2.00 (m, 6H), 1.68-1.55 (m, 6H), 1.20-1.13 (m, 2H), 1.13-1.07 (m, 2H). EC$_{50}$ (nM)=3300. MS (ESI) 580 (M+H).

The following Examples in Table 5 were prepared according to methods described elsewhere herein using appropriate starting materials, reagents and conditions.

TABLE 5

| Ex. No. | Structure & Name | $^1$H NMR, FXR EC$_{50}$ & MS (ESI) | Method |
|---|---|---|---|
| 231 | 2-(4-((5-cyclopropyl-3-(3,5-dichloropyridin-4-yl)isoxazol-4-yl)methoxy)bicyclo[2.2.2]octan-1-yl)-4-fluorobenzo[d]thiazole-6-carboxylic acid | $^1$H NMR (500 MHz, DMSO-$d_6$) δ 8.79 (s, 2H), 8.48 (s, 1H), 7.70 (d, J = 11.3 Hz, 1H), 4.22 (s, 2H), 2.34-2.25 (m, 1H), 2.01-1.93 (m, 6H), 1.51-1.43 (m, 6H), 1.15-1.09 (m, 2H), 1.08-1.03 (m, 2H). FXR EC$_{50}$ (nM) = 53. MS (ESI) 588 (M + H). | Ex. 16 |
| 232 | 3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)benzoic acid | $^1$H NMR (500 MHz, DMSO-$d_6$) δ 8.83 (br s, 2H), 8.49 (br d, J = 8.2 Hz, 1H), 8.20-8.04 (m, 2H), 7.70 (br s, 1H), 4.24 (s, 2H), 2.37-2.25 (m, 1H), 2.04-1.94 (m, 6H), 1.55-1.40 (m, 6H), 1.19-1.12 (m, 2H), 1.09 (br d, J = 2.7 Hz, 2H). FXR EC$_{50}$ (nM) = 100. MS (ESI) 581 (M + H). | Ex. 64 |

TABLE 5-continued

| Ex. No. | Structure & Name | $^1$H NMR, FXR EC$_{50}$ & MS (ESI) | Method |
|---|---|---|---|
| 233 | 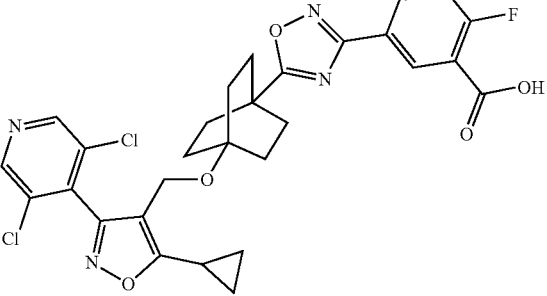<br>5-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-fluorobenzoic acid | $^1$H NMR (500 MHz, DMSO-d$_6$) δ 8.81 (s, 2H), 8.39 (dd, J = 6.9, 2.0 Hz, 1H), 8.13 (br dd, J = 5.4, 3.0 Hz, 1H), 7.44 (t, J = 9.5 Hz, 1H), 4.25 (s, 2H), 2.34-2.26 (m, 1H), 2.09-1.93 (m, 6H), 1.63-1.43 (m, 6H), 1.22-1.13 (m, 2H), 1.10-0.98 (m, 2H). FXR EC$_{50}$ (nM) = 92. MS (ESI) 599 (M + H). | Ex. 64 |
| 236 | 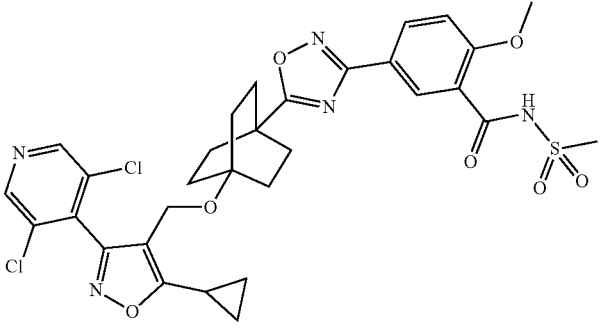 [SMILES: COc1ccc(-c2noc(C34CCC(OCc5c(-c6c(Cl)cncc6Cl)noc5C5CC5)(CC3)CC4)n2)cc1C(=O)NS(C)(=O)=O]<br>5-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-methoxy-N-(methylsulfonyl)benzamide | $^1$H NMR (500 MHz, DMSO-d$_6$) δ 11.75 (s, 1H), 8.83 (s, 2H), 8.18-7.96 (m, 2H), 7.33 (d, J = 8.8 Hz, 1H), 4.25 (s, 2H), 3.93 (s, 3H), 3.37 (s, 3H), 2.38-2.28 (m, 1H), 2.03-1.94 (m, 6H), 1.54-1.42 (m, 6H), 1.22-1.13 (m, 2H), 1.10-1.03 (m, 2H). FXR EC$_{50}$ (nM) = 26. MS (ESI) 688 (M + H). | Ex. 3 |
| 237 | 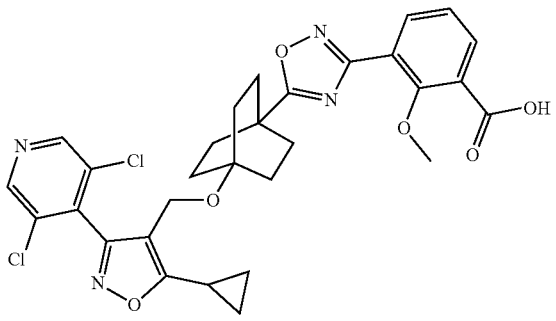 [SMILES: COc1c(C(=O)O)cccc1-c1noc(C23CCC(OCc4c(-c5c(Cl)cncc5Cl)noc4C4CC4)(CC2)CC3)n1]<br>3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-methoxybenzoic acid | $^1$H NMR (400 MHz, DMSO-d$_6$) δ 13.34-12.97 (br s, 1H), 8.84 (s, 2H), 7.98 (dd, J = 7.8, 1.9 Hz, 1H), 7.87 (dd, J = 7.7, 1.8 Hz, 1H), 7.36 (t, J = 7.8 Hz, 1H), 4.25 (s, 2H), 3.78 (s, 3H), 2.38-2.28 (m, 1H), 2.05-1.95 (m, 6H), 1.55-1.41 (m, 6H), 1.16 (dt, J = 8.4, 2.9 Hz, 2H), 1.11-1.01 (m, 2H). FXR EC$_{50}$ (nM) = 27. MS (ESI) 611 (M + H). | Ex. 64 |

TABLE 5-continued

| Ex. No. | Structure & Name | $^1$H NMR, FXR EC$_{50}$ & MS (ESI) | Method |
|---|---|---|---|
| 247 | 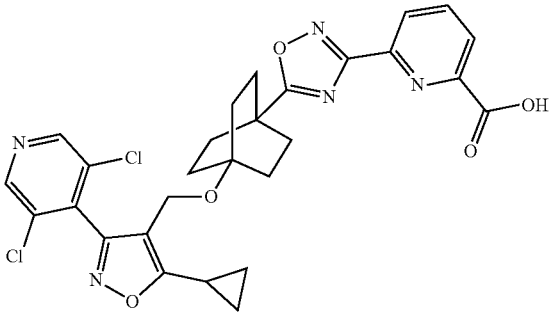 [SMILES: O=C(O)c1cccc(-c2noc(C34CCC(OCc5c(-c6c(Cl)cncc6Cl)noc5C5CC5)(CC3)CC4)n2)n1]<br>6-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)picolinic acid | $^1$H NMR (500 MHz, DMSO-d$_6$) δ 8.82 (s, 2H), 8.23-8.09 (m, 3H), 4.25 (s, 2H), 2.34-2.23 (m, 1H), 2.05-1.95 (m, 6H), 1.52-1.43 (m, 6H), 1.18-1.11 (m, 2H), 1.08 (br d, J = 2.7 Hz, 2H). FXR EC$_{50}$ (nM) = 580. MS (ESI) 582 (M + H). | Ex. 64 |
| 248 | 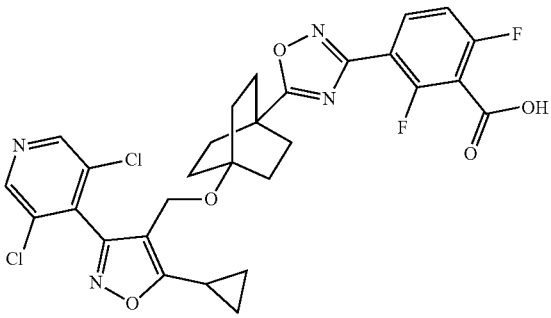 [SMILES: O=C(O)c1c(F)ccc(-c2noc(C34CCC(OCc5c(-c6c(Cl)cncc6Cl)noc5C5CC5)(CC3)CC4)n2)c1F]<br>3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2,6-difluorobenzoic acid | $^1$H NMR (500 MHz, DMSO-d$_6$) δ 8.77 (br s, 2H), 7.85-7.70 (m, 1H), 7.15 (br t, J = 8.2 Hz, 1H), 4.21 (s, 2H), 2.31-2.22 (m, 1H), 2.01-1.91 (m, 6H), 1.48-1.38 (m, 6H), 1.17-1.11 (m, 2H), 1.07-1.02 (m, 2H). FXR EC$_{50}$ (nM) = 1100. MS (ESI) 617 (M + H). | Ex. 64 |
| 268 | 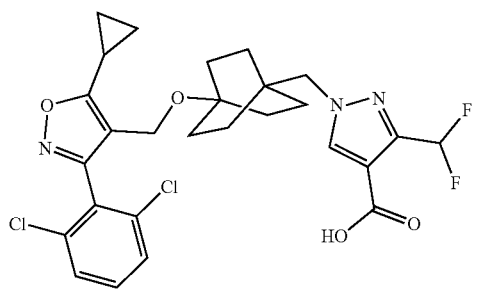 [SMILES: O=C(O)c1cn(CC23CCC(OCc4c(-c5c(Cl)cccc5Cl)noc4C4CC4)(CC2)CC3)nc1C(F)F]<br>1-((4-((5-cyclopropyl-3-(2,6-dichlorophenyl)isoxazol-4-yl)methoxy)bicyclo[2.2.2]octan-1-yl)methyl)-3-(difluoromethyl)-1H-pyrazole-4-carboxylic acid | $^1$H NMR (500 MHz, DMSO-d$_6$) δ 8.18 (s, 1H), 7.65-7.57 (m, 2H), 7.57-7.50 (m, 1H), 7.36-7.00 (m, 1H), 4.10 (s, 2H), 3.86 (s, 2H), 2.32-2.19 (m, 1H), 1.35 (br d, J = 7.7 Hz, 6H), 1.31-1.26 (m, 6H), 1.13-1.08 (m, 2H), 1.07-1.02 (m, 2H). EC$_{50}$ (nM) = 460. MS (ESI) 566 (M + H). | Ex. 76 |

TABLE 5-continued

| Ex. No. | Structure & Name | ¹H NMR, FXR EC₅₀ & MS (ESI) | Method |
|---|---|---|---|
| 269 | 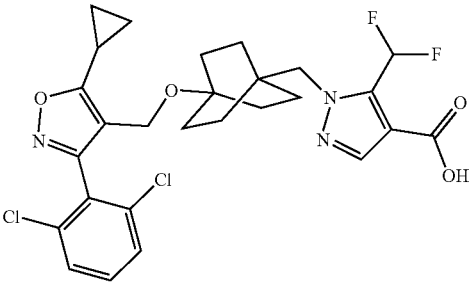 [SMILES: O=C(O)c1cnn(CC23CCC(OCc4c(-c5c(Cl)cccc5Cl)noc4C4CC4)(CC2)CC3)c1C(F)F]<br>1-((4-((5-cyclopropyl-3-(2,6-dichlorophenyl)isoxazol-4-yl)methoxy)bicyclo[2.2.2]octan-1-yl)methyl)-5-(difluoromethyl)-1H-pyrazole-4-carboxylic acid | $^1$H NMR (500 MHz, CHLOROFORM-d) δ 7.90 (s, 1H), 7.67-7.40 (m, 1H), 7.42-7.36 (m, 2H), 7.35-7.29 (m, 1H), 4.15 (s, 2H), 2.15-2.05 (m, 1H), 1.81-1.68 (m, 2H), 1.61-1.51 (m, 6H), 1.44 (br d, J = 7.4 Hz, 6H), 1.27-1.20 (m, 2H), 1.12-1.05 (m, 2H). EC₅₀ (nM) = 700. MS (ESI) 566 (M + H). | Ex. 76 |
| 270 | 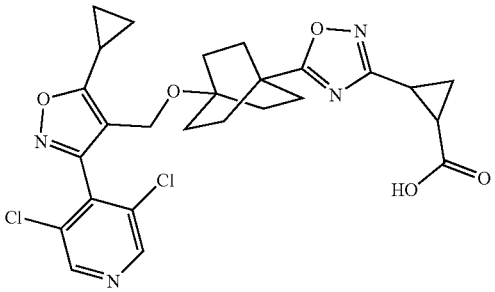 [SMILES: O=C(O)C1CC1c1noc(C23CCC(OCc4c(-c5c(Cl)cncc5Cl)noc4C4CC4)(CC2)CC3)n1]<br>2-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)cyclopropane-1-carboxylic acid | $^1$H NMR (500 MHz, DMSO-d₆) δ 8.79 (s, 2H), 4.21 (s, 2H), 2.45-2.37 (m, 1H), 2.33-2.25 (m, 1H), 1.96-1.91 (m, 1H), 1.89-1.81 (m, 6H), 1.49-1.45 (m, 1H), 1.41 (br s, 6H), 1.37-1.31 (m, 1H), 1.18-1.11 (m, 2H), 1.09-1.02 (m, 2H). EC₅₀ (nM) = 1500. MS (ESI) 545 (M + H). | Ex. 64 |
| 271 | 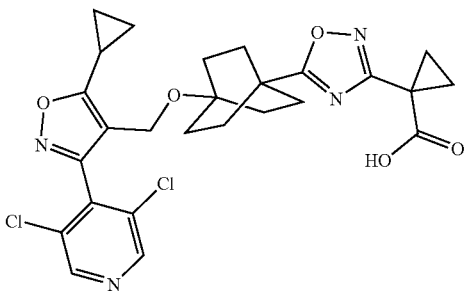 [SMILES: O=C(O)C1(c2noc(C34CCC(OCc5c(-c6c(Cl)cncc6Cl)noc5C5CC5)(CC3)CC4)n2)CC1]<br>1-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)cyclopropane-1-carboxylic acid | $^1$H NMR (500 MHz, DMSO-d₆) δ 8.81 (s, 2H), 4.22 (s, 2H), 2.36-2.25 (m, 1H), 1.93-1.85 (m, 6H), 1.51-1.47 (m, 2H), 1.46-1.40 (m, 6H), 1.29 (br d, J = 3.1 Hz, 2H), 1.18-1.12 (m, 2H), 1.10-1.04 (m, 2H). EC₅₀ (nM) = 1100. MS (ESI) 545 (M + H). | Ex. 64 |

TABLE 5-continued

| Ex. No. | Structure & Name | $^1$H NMR, FXR EC$_{50}$ & MS (ESI) | Method |
|---|---|---|---|
| 274 | 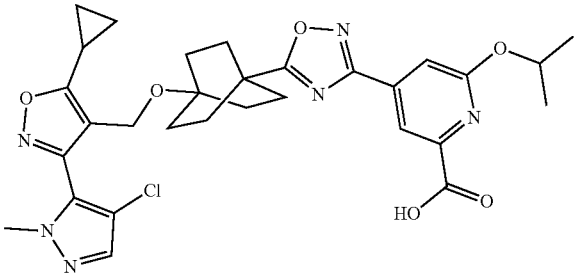 [SMILES: CC(C)Oc1cc(-c2noc(C34CCC(OCc5c(-c6c(Cl)cnn6C)noc5C5CC5)(CC3)CC4)n2)cc(C(=O)O)n1]<br>4-(5-(4-((3-(4-chloro-1-methyl-1H-pyrazol-5-yl)-5-cyclopropylisoxazol-4-yl)methoxy)bicyclo[2.2.2]octan-1-yl)-1,2,4-oxadiazol-3-yl)-6-isopropoxypicolinic acid | $^1$H NMR (500 MHz, DMSO-d$_6$) δ 7.95 (s, 1H), 7.72 (s, 1H), 7.22 (s, 1H), 5.42-5.37 (m, 1H), 4.21 (s, 2H), 2.87 (s, 1H), 2.71 (s, 1H), 2.31-2.25 (m, 1H), 2.06-1.99 (m, 6H), 1.62-1.55 (m, 6H), 1.28 (d, J = 6.1 Hz, 6H), 1.20-1.11 (m, 2H), 1.11-1.03 (m, 2H), 0.89-0.89 (m, 1H). EC$_{50}$ (nM) = 890. MS (ESI) 609 (M + H). | Ex. 64 |
| 275 | 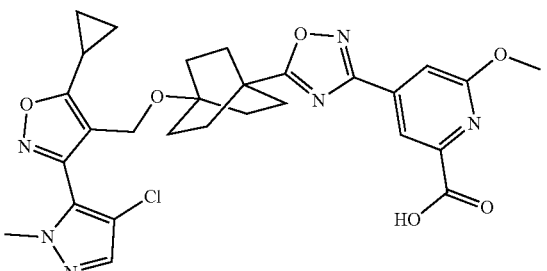<br>4-(5-(4-((3-(4-chloro-1-methyl-1H-pyrazol-5-yl)-5-cyclopropylisoxazol-4-yl)methoxy)bicyclo[2.2.2]octan-1-yl)-1,2,4-oxadiazol-3-yl)-6-methoxypicolinic acid | $^1$H NMR (500 MHz, DMSO-d$_6$) δ 8.08 (s, 1H), 7.71 (s, 1H), 7.45 (s, 1H), 4.24 (s, 2H), 3.98 (s, 3H), 3.70 (s, 3H), 2.30 (br d, J = 4.9 Hz, 1H), 2.13-2.01 (m, 6H), 1.70-1.59 (m, 6H), 1.19-1.13 (m, 2H), 1.12-1.05 (m, 2H). EC$_{50}$ (nM) = 2500. MS (ESI) 581 (M + H). | Ex. 64 |

Example 276

4-((4-((5-cyclopropyl-3-(3,5-dichloropyridin-4-yl)isoxazol-4-yl)methoxy) bicyclo[2.2.2]octan-1-yl)methoxy)-3-fluorobenzoic acid (276)

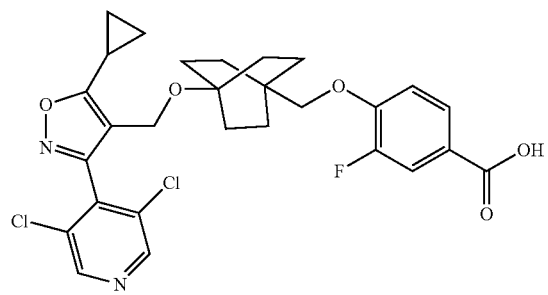

Step A. Intermediate 276A. Preparation of (4-((5-cyclopropyl-3-(3,5-dichloropyridin-4-yl)isoxazol-4-yl)methoxy)bicyclo[2.2.2]octan-1-yl)methanol

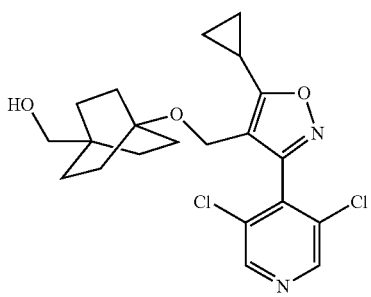 [SMILES: OCC12CCC(OCc3c(-c4c(Cl)cncc4Cl)noc3C3CC3)(CC1)CC2]

The title compound was prepared according combined methods described for the syntheses of Intermediate 16A and Intermediate 104A, substituting (5-cyclopropyl-3-(3,5-dichloropyridin-4-yl)isoxazol-4-yl)methanol where appropriate: $^1$H NMR (500 MHz, CHLOROFORM-d) δ 8.62 (s, 2H), 4.23 (s, 2H), 3.24 (d, J=5.5 Hz, 2H), 2.18-2.08 (m, 1H), 1.53-1.40 (m, 12H), 1.34-1.23 (m, 2H), 1.20-1.09 (m, 2H). MS (ESI) 423.0 (M+H).

Step B. Intermediate 276B. Preparation of methyl 4-((4-((5-cyclopropyl-3-(3,5-dichloropyridin-4-yl)isoxazol-4-yl)methoxy)bicyclo[2.2.2]octan-1-yl)methoxy)-3-fluorobenzoate

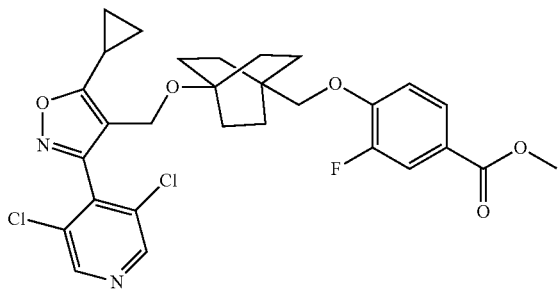 [SMILES: COC(=O)c1ccc(OCC23CCC(OCc4c(-c5c(Cl)cncc5Cl)noc4C4CC4)(CC2)CC3)c(F)c1]

Intermediate 276A (34 mg, 0.080 mmol), methyl 3-fluoro-4-hydroxybenzoate (11 mg, 0.067 mmol), Ph₃P (17 mg, 0.064 mmol) and diisopropyl (E)-diazene-1,2-dicarboxylate (0.013 mL, 0.064 mmol) were dissolved in THF (0.5 mL) and stirred at 100° C. in a sealed vial. After 1 h, the mixture was cooled to rt and the solvent was concentrated. The crude product was purified by flash column chromatography (12 g silica gel cartridge, A=Hex, B=EtOAc; 15 min grad.; 0% B to 60% B; flow rate=40 mL/min). The pure fractions were combined, concentrated and dried in vacuo to afford the title compound (24 mg, 0.042 mmol, 62% yield) as a clear liquid. MS (ESI) 575.0 (M+H).

Step C. Example 276

The title compound was prepared according to methods described for the synthesis of Example 104 (Step C), using Intermediate 276B as starting material: $^1$H NMR (500 MHz, DMSO-$d_6$) δ 8.82 (s, 2H), 7.96-7.48 (m, 2H), 7.20 (br s, 1H), 4.21 (s, 2H), 3.67 (s, 2H), 2.36-2.25 (m, 1H), 1.50 (br d, J=7.9 Hz, 6H), 1.40-1.30 (m, 6H), 1.17-1.12 (m, 2H), 1.10-1.05 (m, 2H). FXR EC$_{50}$ (nM)=170. MS (ESI) 561 (M+H).

Example 278

6-((4-((5-cyclopropyl-3-(3,5-dichloropyridin-4-yl)isoxazol-4-yl)methoxy) bicyclo[2.2.2]octan-1-yl)methoxy)-5-(trifluoromethyl)nicotinamide (278)

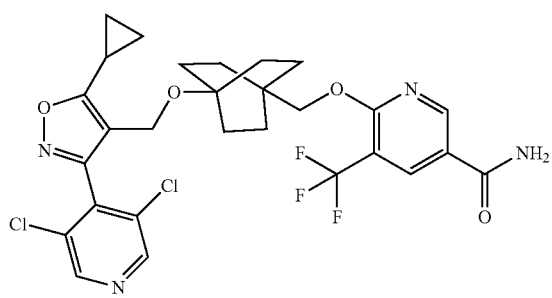

Step A. Intermediate 278A. Preparation of 4-(((4-((5-bromo-3-(trifluoromethyl) pyridin-2-yl)oxy)methyl) bicyclo[2.2.2]octan-1-yl)oxy)methyl)-5-cyclopropyl-3-(3,5-dichloropyridin-4-yl)isoxazole

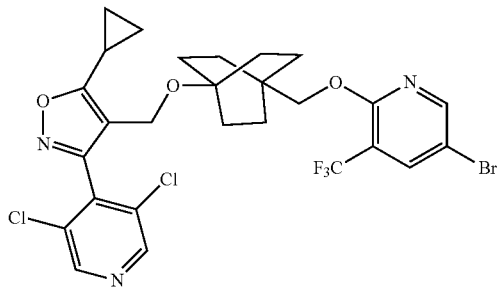 [SMILES: FC(F)(F)c1cc(Br)cnc1OCC12CCC(OCc3c(-c4c(Cl)cncc4Cl)noc3C3CC3)(CC1)CC2]

The title compound was prepared according to methods described for the synthesis of Example 276 (Step B and C), by reaction of Intermediate 276A and 5-bromo-3-(trifluoromethyl)pyridin-2-ol: $^1$H NMR (500 MHz, CHLOROFORM-d) δ 8.61 (s, 2H), 8.30 (d, J=2.4 Hz, 1H), 7.93 (d, J=2.4 Hz, 1H), 4.22 (s, 2H), 3.94 (s, 2H), 2.18-2.00 (m, 1H), 1.67-1.54 (m, 6H), 1.53-1.40 (m, 6H), 1.33-1.21 (m, 2H), 1.18-1.07 (m, 2H). MS (ESI) 645.9 (M+H).

Step B. Intermediate 278B. Preparation of 6-((4-((5-cyclopropyl-3-(3,5-dichloropyridin-4-yl)isoxazol-4-yl)methoxy)bicyclo[2.2.2]octan-1-yl)methoxy)-5-(trifluoromethyl)nicotinonitrile

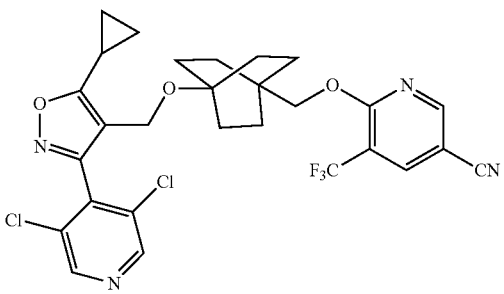 [SMILES: N#Cc1cnc(OCC23CCC(OCc4c(-c5c(Cl)cncc5Cl)noc4C4CC4)(CC2)CC3)c(C(F)(F)F)c1]

A pressure reaction vial containing Intermediate 278A (42 mg, 0.065 mmol), Xantphos (7.5 mg, 0.013 mmol), Pd₂(dba)₃ (12 mg, 0.013 mmol) and zinc cyanide (7.6 mg, 0.065 mmol) was purged with nitrogen (3×). Anhydrous DMF (0.5 mL) was added and the vial was capped and the mixture was stirred at 70° C. After 3 h, the reaction was cooled to room temperature, diluted with water, and extracted with EtOAc (2×). The combined organic extracts were washed with brine, dried (Na₂SO₄), filtered and concentrated. The crude product was purified by flash column chromatography (12 g silica gel cartridge, A=Hex, B=EtOAc; 15 min grad.; 0% B to 30% B; flow rate=12 mL/min). The pure fractions were combined, concentrated and dried in vacuo to afford the title compound (20 mg, 0.034 mmol, 52% yield) as an off-white foam. MS (ESI) 593.1 (M+H).

Step C. Example 278

Intermediate 278B (20 mg, 0.034 mmol) was dissolved in EtOH (1 mL), and 5 M NaOH (aq.) (0.1 mL, 0.5 mmol) was added. The reaction was stirred at 100° C. for 3 h. The reaction mixture was cooled, concentrated and acidified with 1 M HCl (aq.). The aqueous layer was extracted with EtOAc (3×). The combined organic layers were concentrated. The crude material was purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 53-76% B over 25 minutes, then a 2-minute hold at 100% B; Flow: 20 mL/min). Fractions containing the desired product were combined, concentrated and dried in vacuo to afford the title compound (8.0 mg, 39% yield): $^1$H NMR (500 MHz, DMSO-$d_6$) δ 8.91-8.85 (m, 1H), 8.81 (s, 2H), 8.34 (s, 1H), 4.21 (s, 2H), 4.05 (s, 2H), 2.35-2.23 (m, 1H), 1.58-1.44 (m, 6H), 1.40-1.29 (m, 6H), 1.19-1.11 (m, 2H), 1.10-1.03 (m, 2H). FXR $EC_{50}$ (nM)=620. MS (ESI) 611 (M+H).

Example 279

6-((4-((5-cyclopropyl-3-(3,5-dichloropyridin-4-yl) isoxazol-4-yl)methoxy) bicyclo[2.2.2]octan-1-yl) methoxy)-5-(trifluoromethyl)nicotinic acid

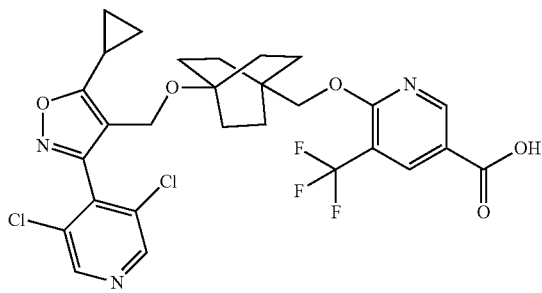

(279)

The title compound was isolated during the purification of Example 278 (Step C): (7.6 mg, 36% yield). $^1$H NMR (500 MHz, DMSO-$d_6$) δ 8.85 (s, 1H), 8.82 (s, 2H), 8.46 (s, 1H), 4.21 (s, 2H), 4.03 (s, 2H), 2.34-2.26 (m, 1H), 1.55-1.46 (m, 6H), 1.38-1.3 (m, 6H), 1.18-1.12 (m, 2H), 1.10-1.03 (m, 2H). FXR $EC_{50}$ (nM)=190. MS (ESI) 612 (M+H).

Example 280

6-((4-((5-cyclopropyl-3-(3,5-dichloropyridin-4-yl) isoxazol-4-yl)methoxy) bicyclo[2.2.2]octan-1-yl) methoxy)-4-(trifluoromethyl)picolinic acid

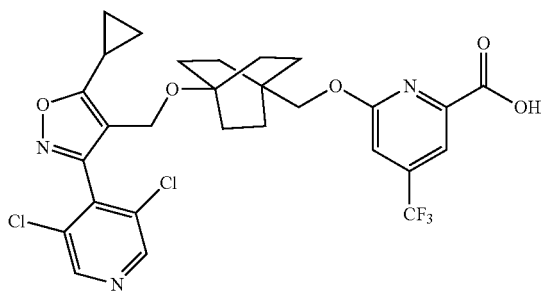

(280)

Step A. Intermediate 280A. Preparation of 2-(methoxycarbonyl)-4-(trifluoromethyl)pyridine 1-oxide

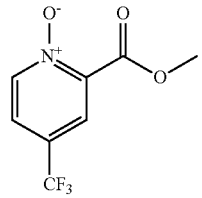

A solution of ethyl 4-(trifluoromethyl)picolinate (300 mg, 1.4 mmol), urea hydrogen peroxide (260 mg, 2.7 mmol) and trifluoroacetic anhydride (0.39 mL, 2.7 mmol) in DCM (6 mL) was stirred at rt for 16 h. The solids were filtered and the filtrate was concentrated. The crude product was purified by flash column chromatography (24 g silica gel cartridge, A=Hex, B=EtOAc; 15 min grad.; 0% B to 100% B; flow rate=24 mL/min). The pure fractions were combined, concentrated and dried in vacuo to afford the title compound (300 mg, 1.3 mmol, 93% yield) as a white foam. MS (ESI) 235.9 (M+H).

Step B. Intermediate 280B. Preparation of methyl 6-chloro-4-(trifluoromethyl)picolinate

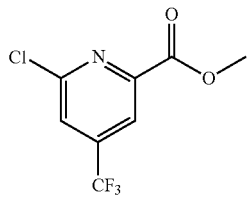

A suspension of Intermediate 280A (300 mg, 1.3 mmol) in phosphorus oxychloride (3 mL, 32 mmol) was stirred at reflux for 30 min. After cooling to rt, the reaction mixture was poured into ice, basified with conc. ammonium hydroxide and extracted with DCM (3×). The combined organic extracts were washed with brine, dried ($MgSO_4$), filtered and concentrated. The crude product was purified by flash column chromatography (24 g silica gel cartridge, A=Hex, B=EtOAc; 15 min grad.; 0% B to 30% B; flow rate=24 mL/min). The pure fractions were combined, concentrated and dried in vacuo to afford the title compound (180 mg, 0.70 mmol, 55% yield) as a colorless oil. $^1$H NMR (500 MHz, CHLOROFORM-d) δ 8.25 (s, 1H), 7.75 (s, 1H), 4.52 (q, J=7.1 Hz, 2H), 1.46 (t, J=7.0 Hz, 3H). MS (ESI) 254 (M+H).

Step C. Example 280

The title compound was prepared according to methods described for the synthesis of Example 104, by reaction of Intermediate 276A and Intermediate 280B: $^1$H NMR (500 MHz, DMSO-$d_6$) δ 8.77 (s, 2H), 7.71 (s, 1H), 7.24 (s, 1H), 4.21 (s, 2H), 3.99 (s, 2H), 2.31-2.21 (m, 1H), 1.60-1.45 (m, 6H), 1.43-1.30 (m, 6H), 1.19-1.11 (m, 3H), 1.09-1.01 (m, 2H). FXR $EC_{50}$ (nM)=23. MS (ESI) 612 (M+H).

Example 282

6-((4-((5-cyclopropyl-3-(3,5-dichloropyridin-4-yl)isoxazol-4-yl)methoxy)bicyclo[2.2.2]octan-1-yl)methoxy)-4-methoxyquinoline-2-carboxylic acid

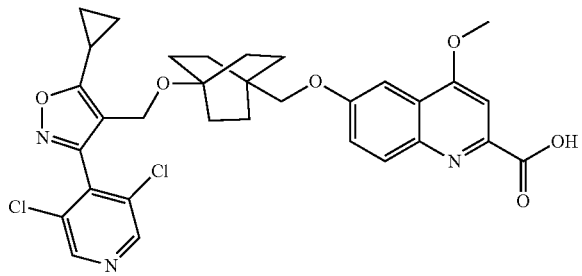

(282)

Step A. Intermediate 282A. Preparation of methyl 6-bromo-4-methoxyquinoline-2-carboxylate

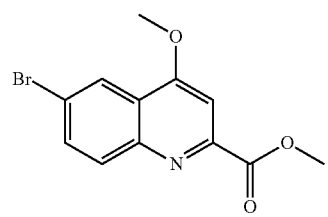 [SMILES: COC(=O)c1cc(OC)c2cc(Br)ccc2n1]

To a stirred solution of methyl 6-bromo-4-hydroxyquinoline-2-carboxylate (0.6 g, 2.1 mmol) in acetonitrile (5 mL) was added iodomethane (0.20 mL, 3.2 mmol) and $K_2CO_3$ (0.44 g, 3.2 mmol). The reaction was stirred 3 h at 60° C. The reaction mixture was concentrated and diluted with EtOAc. The organic layer was washed with brine, dried over $Na_2SO_4$, filtered and concentrated. The crude product was purified by flash column chromatography (24 g silica gel cartridge, A=Hex, B=EtOAc; 15 min grad.; 0% B to 70% B; flow rate=24 mL/min). The pure fractions were combined, concentrated and dried in vacuo to afford the title compound (530 mg, 1.8 mmol, 84% yield) as an off-white solid.

Step B. Intermediate 282B. Preparation of methyl 4-methoxy-6-(4,4,5,5-tetramethyl-1,3,2-dioxaborolan-2-yl)quinoline-2-carboxylate

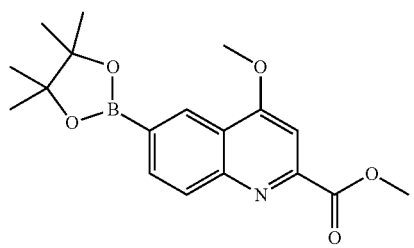

A stirring mixture of Intermediate 282A (530 mg, 1.8 mmol), 4,4,4',4',5,5,5',5'-octamethyl-2,2'-bi(1,3,2-dioxaborolane) (590 mg, 2.3 mmol) and potassium acetate (530 mg, 5.4 mmol) in 1,4-dioxane (8 mL) was flushed with nitrogen for 2 min. To this mixture was added Pd(dppf)Cl$_2$.CH$_2$Cl$_2$ adduct (290 mg, 0.36 mmol) and the reaction was stirred at 90° C. for 3 h. After cooling to rt, the reaction mixture was diluted with water and extracted with ethyl acetate (2×). The organic layers were combined, washed with brine, dried over $Na_2SO_4$, filtered and concentrated. The crude product was purified by flash column chromatography (24 g silica gel cartridge, A=Hex, B=EtOAc; 15 min grad.; 0% B to 70% B; flow rate=24 mL/min). The pure fractions were combined, concentrated and dried in vacuo to afford the title compound (270 mg, 0.77 mmol, 43% yield) as a white foam.

Step C. Intermediate 282C. Preparation of methyl 6-hydroxy-4-methoxyquinoline-2-carboxylate

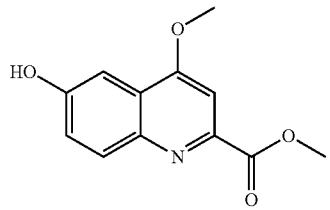 [SMILES: COC(=O)c1cc(OC)c2cc(O)ccc2n1]

1 M NaOH (aq.) (1.5 mL, 1.5 mmol), followed by 30% $H_2O_2$ (aq.) (0.24 mL, 2.4 mmol) were added to a stirring 0° C. solution of Intermediate 282B (270 mg, 0.77 mmol) in THF (4 mL). The reaction was stirred at 0° C. for 10 min. The reaction was diluted with EtOAc and quenched with 10% $Na_2SO_3$ (aq.) and washed with water and brine. The combined aqueous layers were back extracted with EtOAc. The organic layers were combined, washed with brine, dried over $Na_2SO_4$, filtered and concentrated. The crude product was purified by flash column chromatography (24 g silica gel cartridge, A=Hex, B=EtOAc; 15 min grad.; 0% B to 60% B; flow rate=24 mL/min). The pure fractions were combined, concentrated and dried in vacuo to afford the title compound (150 mg, 0.65 mmol, 84% yield) as a white solid.

Step D. Example 282

The title compound was prepared according to methods described for the synthesis of Example 276 (Step B and C), by reaction of Intermediate 276A and Intermediate 282C: $^1$H NMR (500 MHz, DMSO-d$_6$) δ 8.80 (s, 2H), 7.99 (s, 1H), 7.52 (s, 1H), 7.43 (dd, 2.4 Hz, 1H), 7.35 (d, J=2.1 Hz, 1H), 4.22 (s, 2H), 4.09 (s, 3H), 3.68 (s, 2H), 2.35-2.23 (m, 1H), 1.60-1.49 (m, 6H), 1.40-1.28 (m, 6H), 1.19-1.11 (m, 2H), 1.09-1.03 (m, 2H). FXR EC$_{50}$ (nM)=60. MS (ESI) 624 (M+H).

Example 284

6-((4-((5-cyclopropyl-3-(3,5-dichloropyridin-4-yl)isoxazol-4-yl)methoxy) bicyclo[2.2.2]octan-1-yl)methoxy)-4-(difluoromethoxy)quinoline-2-carboxylic acid

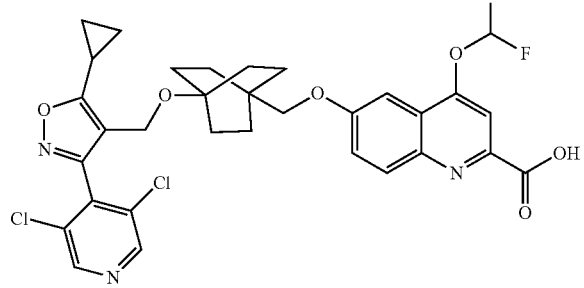

(284)

Step A. Intermediate 284A. Preparation of methyl 6-bromo-4-(difluoromethoxy)quinoline-2-carboxylate

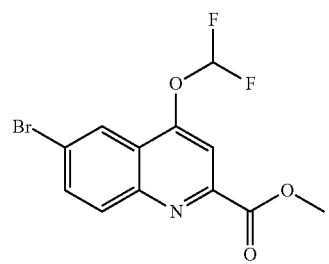 [SMILES: COC(=O)c1cc(OC(F)F)c2cc(Br)ccc2n1]

To a stirred solution of Cs$_2$CO$_3$ (980 mg, 3.0 mmol) in DMF (5 mL) at 0° C. was added methyl 6-bromo-4-hydroxyquinoline-2-carboxylate (280 mg, 1.0 mmol) and sodium chlorodifluoroacetate (460 mg, 3.0 mmol). The reaction stirred at 80° C. for 30 min. After cooling the reaction mixture to room temperature, water (25 mL) was added. The resulting suspension was stirred for 1 h. The solid was collected by vacuum filtration and the filter cake was washed with water (2×5 mL). The solid product was collected and dried in vacuo to afford the title compound (280 mg, 0.81 mmol, 81% yield) as a white solid. $^1$H NMR (400 MHz, CHLOROFORM-d) δ 8.38 (d, J=2.20 Hz, 1H), 8.16 (d, J=9.02 Hz, 1H), 7.91 (dd, J=2.20, 9.24 Hz, 1H), 7.85 (t, J=1.10 Hz, 1H), 6.61-7.17 (m, 1H), 4.09 (s, 3H). MS (ESI) 333.9 (M+H).

Step B. Intermediate 284B. Preparation of methyl 6-hydroxy-4-(difluoromethoxy)quinoline-2-carboxylate

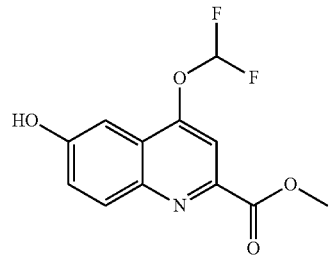 [SMILES: COC(=O)c1cc(OC(F)F)c2cc(O)ccc2n1]

The title compound was prepared according to methods described for the synthesis of Intermediate 282C (Step B & C), using Intermediate 284A as starting material: $^1$H NMR (500 MHz, CHLOROFORM-d) δ 8.70 (s, 1H), 8.15 (d, J=9.00 Hz, 1H), 7.73 (d, J=2.20 Hz, 1H), 7.46 (t, J=1.10 Hz, 1H), 7.34 (dd, J=2.20, 9.20 Hz, 1H), 6.61-7.17 (m, 1H), 4.09 (s, 3H). MS (ESI) 269.9 (M+H).

Step C. Example 284

The title compound was prepared according to methods described for the synthesis of Example 276 (Step B and C), by reaction of Intermediate 276A and Intermediate 284B: $^1$H NMR (500 MHz, DMSO-d$_6$) δ 8.81 (s, 2H), 8.07 (br d, J=9.2 Hz, 1H), 7.76 (s, 1H), 7.73 (t, J=70 Hz, 1H), 7.56-7.47 (m, 1H), 7.29 (br s, 1H), 4.22 (s, 2H), 3.73 (s, 2H), 2.35-2.23 (m, 1H), 1.64-1.49 (m, 6H), 1.43-1.30 (m, 6H), 1.22-1.11 (m, 2H), 1.10-1.03 (m, 2H). FXR EC$_{50}$ (nM)=8. MS (ESI) 660 (M+H).

Example 285

5-((4-((5-cyclopropyl-3-(3,5-dichloropyridin-4-yl)isoxazol-4-yl)methoxy)bicyclo[2.2.2]octan-1-yl)methoxy)-3-(trifluoromethyl)picolinic acid

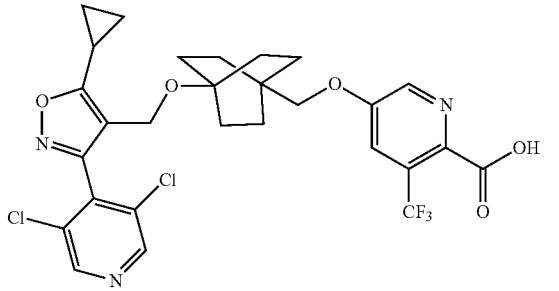

(285)

Step A. Intermediate 285A. Preparation of methyl 5-hydroxy-3-(trifluoromethyl) picolinate

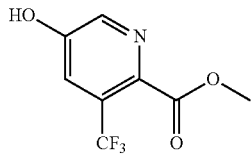

The title compound was prepared according to methods described for the synthesis of Intermediate 282C (Step B & C), using methyl 5-bromo-3-(trifluoromethyl)picolinate as starting material: $^1$H NMR (500 MHz, CHLOROFORM-d) δ 8.41 (d, J=2.5 Hz, 1H), 7.59 (d, J=2.5 Hz, 1H), 3.99 (s, 3H). MS (ESI) 221.9 (M+H).

Step B. Example 285

The title compound was prepared according to methods described for the synthesis of Example 276 (Step B and C), by reaction of Intermediate 276A and Intermediate 285A: $^1$H NMR (500 MHz, DMSO-$d_6$) δ 8.84-8.77 (m, 2H), 8.44 (br s, 1H), 7.65 (d, J=2.1 Hz, 1H), 4.21 (s, 2H), 3.75 (s, 2H), 2.34-2.24 (m, 1H), 1.59-1.47 (m, 6H), 1.41-1.28 (m, 6H), 1.20-1.11 (m, 2H), 1.11-1.02 (m, 2H). FXR EC$_{50}$ (nM)=130. MS (ESI) 612 (M+H).

Example 291

6-((4-((5-cyclopropyl-3-(3,5-dichloropyridin-4-yl)isoxazol-4-yl)methoxy) bicyclo[2.2.2]octan-1-yl)methoxy)-4-(trifluoromethyl)quinoline-2-carboxamide

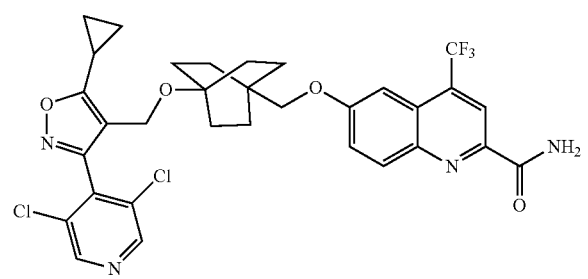
(291)

To a solution of Example 105 (40 mg, 0.060 mmol) in DCM (1 mL) were added 2,4,6-tripropyl-1,3,5,2,4,6 trioxatriphosphorinane-2,4,6-trioxide (0.071 mL, 0.24 mmol) and Hunig's base (0.042 mL, 0.24 mmol). The mixture was stirred for 15 min, then ammonium chloride (13 mg, 0.24 mmol) was added. After stirring 16 h, the reaction was diluted with DCM and washed with H$_2$O. The organic layer was concentrated. The crude material was purified via preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 50-75% B over 25 minutes, then a 2-minute hold at 100% B; Flow: 20 mL/min). Fractions containing the desired product were combined, concentrated and dried in vacuo to provide the title compound: (29 mg, 0.043 mmol, 72% yield). $^1$H NMR (500 MHz, DMSO-$d_6$) δ 8.82 (s, 2H), 8.34 (s, 2H), 8.18 (d, J=9.2 Hz, 1H), 7.88 (br s, 1H), 7.65 (dd, J=9.2, 2.1 Hz, 1H), 7.25 (br s, 1H), 4.22 (s, 2H), 3.74 (s, 2H), 2.36-2.26 (m, 1H), 1.64-1.52 (m, 6H), 1.43-1.30 (m, 6H), 1.18-1.12 (m, 2H), 1.10-1.01 (m, 2H). FXR EC$_{50}$ (nM)=230. MS (ESI) 661 (M+H).

Example 292

4-((4-((5-cyclopropyl-3-(3,5-dichloropyridin-4-yl)isoxazol-4-yl)methoxy) bicyclo[2.2.2]octan-1-yl)methoxy)isoquinoline-1-carboxylic acid

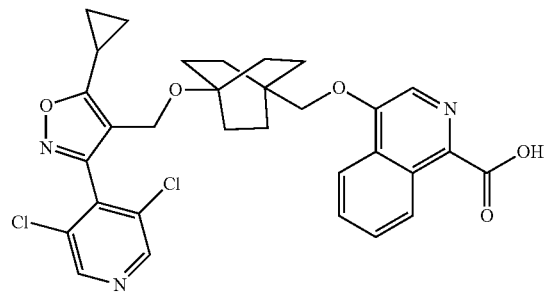
(292)

Step A. Intermediate 292A. Preparation of methyl 4-hydroxyisoquinoline-1-carboxylate

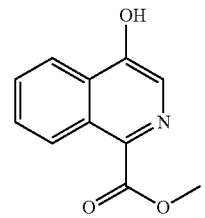

The title compound was prepared according to methods described for the synthesis of Intermediate 282C (Step B & C), using methyl bromoisoquinoline-1-carboxylate as starting material: $^1$H NMR (500 MHz, DMSO-$d_6$) δ 11.51-11.23 (m, 1H), 8.78-8.61 (m, 1H), 8.32-8.19 (m, 1H), 8.15 (s, 1H), 7.84-7.62 (m, 2H), 3.92 (s, 3H). MS (ESI) 204.0 (M+H).

Step B. Example 292

The title compound was prepared according to methods described for the synthesis of Example 276 (Step B and C), by reaction of Intermediate 276A and Intermediate 292A: $^1$H NMR (500 MHz, DMSO-$d_6$) δ 8.80-8.73 (m, 2H), 8.20 (br d, J=7.9 Hz, 1H), 8.11 (br s, 1H), 8.05-8.05 (m, 1H), 7.86-7.79 (m, 1H), 7.79-7.72 (m, 1H), 4.20 (s, 1H), 3.77 (br s, 2H), 2.31-2.20 (m, 1H), 1.64-1.52 (m, 6H), 1.43-1.30 (m, 6H), 1.18-1.12 (m, 2H), 1.10-1.01 (m, 2H). FXR EC$_{50}$ (nM)=9. MS (ESI) 594 (M+H).

Example 293

5-((4-((5-cyclopropyl-3-(3,5-dichloropyridin-4-yl)isoxazol-4-yl)methoxy) bicyclo[2.2.2]octan-1-yl)methoxy)-3-(methoxymethyl)picolinic acid

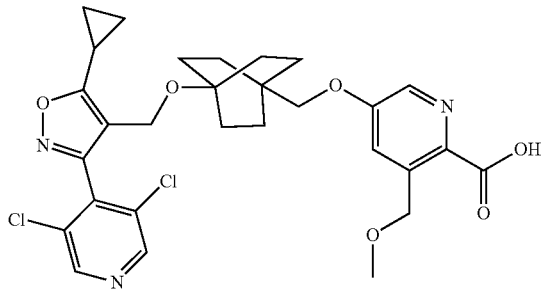

(293)

Step A. Intermediate 293A. Preparation of methyl 5-bromo-3-(bromomethyl)picolinate

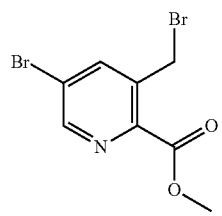

A mixture of methyl 5-bromo-3-methylpicolinate (450 mg, 2.0 mmol), NBS (350 mg, 2.0 mmol) and AIBN (32 mg, 0.20 mmol) in carbon tetrachloride (10 mL) was stirred at 90° C. After 18 h, the reaction was cooled to rt, filtered, and the solid was washed with carbon tetrachloride. The combined organic layers were washed with sat. NaHCO$_3$ (aq.), brine, dried over Na$_2$SO$_4$, filtered and concentrated. The crude product was purified by flash column chromatography (40 g silica gel cartridge, A=Hex, B=EtOAc; 15 min grad.; 0% B to 60% B; flow rate=40 mL/min). The pure fractions were combined, concentrated and dried in vacuo to afford the title compound (400 mg, 1.3 mmol, 66% yield) as an off-white foam. MS (ESI) 307.8 (M+H).

Step B. Intermediate 293B. Preparation of methyl 5-bromo-3-(methoxymethyl) picolinate

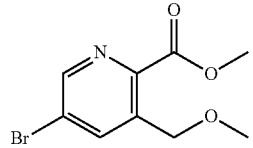

To a stirred solution of Intermediate 293A (380 mg, 1.2 mmol) in MeOH (3 mL) was added sodium methoxide (2.7 mL, 1.4 mmol) (0.5 M in MeOH). The reaction was stirred 20 min. The reaction was concentrated and the residue was dissolved in DCM. The organic layer was washed with water, dried over Na$_2$SO$_4$, filtered and concentrated. The crude product was purified by flash column chromatography (24 g silica gel cartridge, A=Hex, B=EtOAc; 15 min grad.; 0% B to 80% B; flow rate=24 mL/min). The pure fractions were combined, concentrated and dried in vacuo to afford the title compound (140 mg, 0.52 mmol, 42% yield) as a white foam. $^1$H NMR (500 MHz, CHLOROFORM-d) δ 8.67 (d, J=2.2 Hz, 1H), 8.30-8.28 (m, 1H), 4.86 (s, 2H), 3.99 (s, 3H), 3.52 (s, 3H). MS (ESI) 259.9 (M+H).

Step C. Intermediate 293C. Preparation of methyl 5-hydroxy-3-(methoxymethyl) picolinate

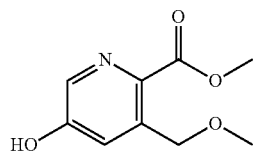

The title compound was prepared according to methods described for the synthesis of Intermediate 282C (Step B & C), using Intermediate 293B as starting material: $^1$H NMR (500 MHz, CHLOROFORM-d) δ 9.50 (s, 1H), 8.17 (d, J=2.2 Hz, 1H), 7.81-7.78 (m, 1H), 4.90 (s, 2H), 3.99 (s, 3H), 3.52 (s, 3H). MS (ESI) 197.9 (M+H).

Step D. Example 293

The title compound was prepared according to methods described for the synthesis of Example 276 (Step B and C), by reaction of Intermediate 276A and Intermediate 293C: $^1$H NMR (500 MHz, DMSO-d$_6$) δ 8.76 (s, 2H), 8.20-8.12 (m, 1H), 7.41 (br s, 1H), 4.70 (br s, 2H), 4.19 (s, 2H), 3.83-3.61 (m, 2H), 3.34 (s, 3H), 2.31-2.20 (m, 1H), 1.56-1.45 (m, 6H), 1.36-1.27 (m, 6H), 1.16-1.09 (m, 2H), 1.08-0.99 (m, 2H). FXR EC$_{50}$ (nM)=16. MS (ESI) 588 (M+H).

Example 294

5-((4-((5-cyclopropyl-3-(3,5-dichloropyridin-4-yl)isoxazol-4-yl)methoxy) bicyclo[2.2.2]octan-1-yl)methoxy)-3-ethoxypicolinic acid

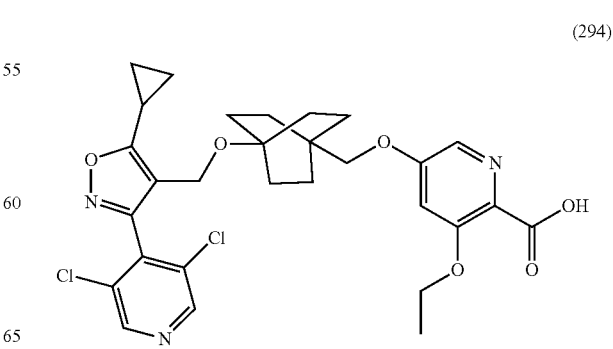

(294)

Step A. Intermediate 294A. Preparation of 5-bromo-3-ethoxypicolinonitrile

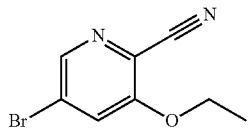

To a suspension of 5-bromo-3-nitropicolinonitrile (1.0 g, 4.4 mmol) in EtOH (12 mL) at was added sodium ethoxide (1.6 mL, 4.4 mmol) (21% w/v in EtOH). The reaction was stirred for 2 min. The reaction mixture was concentrated and diluted with EtOAc. The organic layer was washed with $H_2O$, dried over $MgSO_4$, filtered and concentrated. The crude product was purified by flash column chromatography (40 g silica gel cartridge, A=Hex, B=EtOAc; 15 min grad.; 0% B to 50% B; flow rate=40 mL/min). The pure fractions were combined, concentrated and dried in vacuo to afford the title compound (670 mg, 3.0 mmol, 67% yield) as a beige solid. $^1$H NMR (500 MHz, CHLOROFORM-d) δ 8.33 (d, J=1.9 Hz, 1H), 7.50 (d, J=1.7 Hz, 1H), 4.20 (q, J=7.1 Hz, 2H), 1.53 (t, J=7.0 Hz, 3H). MS (ESI) 227.0 (M+H).

Step B. Intermediate 294B. Preparation of 5-hydroxy-3-ethoxypicolinonitrile

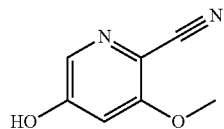

The title compound was prepared according to methods described for the synthesis of Intermediate 282C (Step B & C), using Intermediate 294A as starting material: $^1$H NMR (500 MHz, DMSO-$d_6$) δ 11.44-11.00 (m, 1H), 7.84 (d, J=2.2 Hz, 1H), 6.99 (d, J=2.2 Hz, 1H), 4.17 (q, J=7.0 Hz, 2H), 1.36 (t, J=7.0 Hz, 3H). MS (ESI) 165.0 (M+H).

Step C. Example 294

The title compound was prepared according to combined methods described for the syntheses of Intermediate 276B and Example 278 (Step C), by reaction of Intermediate 276A and Intermediate 294B: $^1$H NMR (500 MHz, DMSO-$d_6$) δ 8.81 (s, 2H), 7.81 (br s, 1H), 7.05 (br s, 1H), 4.21 (s, 2H), 4.10 (br d, J=7.0 Hz, 2H), 3.68 (br s, 1H), 2.34-2.25 (m, 1H), 1.56-1.45 (m, 6H), 1.42-1.26 (m, 9H), 1.23-1.11 (m, 2H), 1.10-1.05 (m, 2H). FXR $EC_{50}$ (nM)=32. MS (ESI) 588 (M+H).

Example 298

6-((4-((5-cyclopropyl-3-(3,5-dichloropyridin-4-yl)isoxazol-4-yl)methoxy) bicyclo[2.2.2]octan-1-yl)methoxy)-1,5-naphthyridine-2-carboxylic acid

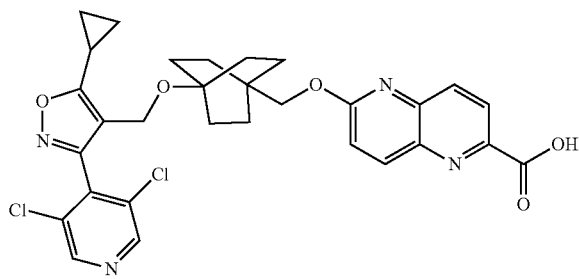

(298)

Step A. Intermediate 298A. Preparation of 2-chloro-6-((4-methoxybenzyl)oxy)-1,5-naphthyridine

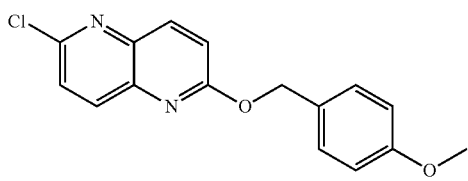 [SMILES: COc1ccc(COc2ccc3nc(Cl)ccc3n2)cc1]

To a solution of (4-methoxyphenyl)methanol (140 mg, 1.0 mmol) in NMP (8 mL) was added sodium hydride (40 mg, 1.0 mmol) (60% dispersion in mineral oil) in portions. After stirring 15 min, 2,6-dichloro-1,5-naphthyridine (200 mg, 1.0 mmol) was added. After stirring 30 min, the reaction was quenched with sat. $NH_4Cl$ (aq.) and extracted with EtOAc (3×). The combined organic extracts were washed with brine, dried over $Na_2SO_4$, filtered and concentrated. The crude product was purified by flash column chromatography (24 g silica gel cartridge, A=Hex, B=EtOAc; 15 min grad.; 0% B to 100% B; flow rate=24 mL/min). The pure fractions were combined, concentrated and dried in vacuo to afford the title compound (230 mg, 0.75 mmol, 75% yield) as a white foam. $^1$H NMR (500 MHz, CHLOROFORM-d) δ 8.16-8.06 (m, 2H), 7.54 (d, J=8.5 Hz, 1H), 7.45 (d, J=8.5 Hz, 2H), 7.17 (d, J=8.8 Hz, 1H), 6.94 (d, J=8.5 Hz, 2H), 5.47 (s, 2H), 3.83 (s, 3H). MS (ESI) 301.0 (M+H).

Step B. Intermediate 298B. Preparation of methyl 6-((4-methoxybenzyl)oxy)-1,5-naphthyridine-2-carboxylate

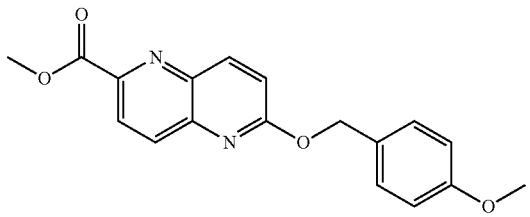

To a suspension of Intermediate 298A (230 mg, 0.75 mmol) in MeOH (12 mL) was added Pd(dppf)Cl$_2$.CH$_2$Cl$_2$ adduct (55 mg, 0.075 mmol), followed by Et$_3$N (0.21 mL, 1.50 mmol). The reaction was stirred under carbon monoxide atmosphere (40-50 psi) at 85° C. After 16 h, the reaction mixture was cooled to rt, filtered through Celite and the filtrate was concentrated. The crude product was purified by flash column chromatography (24 g silica gel cartridge, A=Hex, B=EtOAc; 15 min grad.; 0% B to 100% B; flow rate=24 mL/min). The pure fractions were combined, concentrated and dried in vacuo to afford the title compound (180 mg, 0.55 mmol, 74% yield) as a white foam. $^1$H NMR (500 MHz, CHLOROFORM-d) δ 8.42-8.34 (m, 2H), 8.27 (d, J=8.8 Hz, 1H), 7.47 (d, J=8.8 Hz, 2H), 7.21 (d, J=9.1 Hz, 1H), 6.94 (d, J=8.5 Hz, 2H), 5.51 (s, 2H), 4.09 (s, 3H), 3.83 (s, 3H). MS (ESI) 325.0 (M+H).

Step C. Intermediate 298C. Preparation of methyl 6-hydroxy-1,5-naphthyridine-2-carboxylate

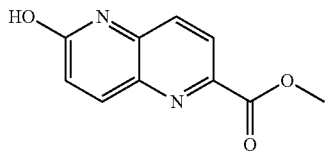

A stirred solution of Intermediate 298B (120 mg, 0.37 mmol) in EtOAc (2 mL) and EtOH (7 mL) was purged and flushed with nitrogen. To this mixture was added palladium on carbon (90 mg, 0.085 mmol) (10% wt. loading, matrix activated carbon support) and the mixture was again purged and flushed with nitrogen. The reaction was stirred under hydrogen (1 atm, balloon). After 1.5 h, the reaction mixture was filtered and filtrate concentrated. The crude product was purified by flash column chromatography (12 g silica gel cartridge, A=Hex, B=EtOAc; 15 min grad.; 0% B to 100% B; flow rate=12 mL/min). The pure fractions were combined and dried in vacuo to afford the title compound (53 mg, 0.26 mmol, 70% yield) as a white solid. $^1$H NMR (500 MHz, METHANOL-d$_4$) δ 8.25 (d, J=8.5 Hz, 1H), 8.11 (d, J=9.9 Hz, 1H), 7.84 (d, J=8.5 Hz, 1H), 6.93 (d, J=9.6 Hz, 1H), 4.01 (s, 3H). MS (ESI) 204.9 (M+H).

Step D. Example 298

The title compound was prepared according to methods described for the synthesis of Example 276 (Step B and C), by reaction of Intermediate 276A and Intermediate 298C: $^1$H NMR (500 MHz, DMSO-d$_6$) δ 8.81 (s, 2H), 8.34 (br d, J=8.9 Hz, 1H), 8.21 (s, 2H), 7.29 (br d, J=9.2 Hz, 1H), 4.22 (s, 2H), 4.04 (s, 2H), 2.34-2.21 (m, 1H), 1.62-1.48 (m, 6H), 1.43-1.30 (m, 6H), 1.19-1.11 (m, 2H), 1.10-1.05 (m, 2H). FXR EC$_{50}$ (nM)=63. MS (ESI) 595 (M+H).

Example 300

5-((4-((5-cyclopropyl-3-(3,5-dichloropyridin-4-yl) isoxazol-4-yl)methoxy) bicyclo[2.2.2]octan-1-yl) methoxy)-3-(2,2,2-trifluoroethoxy)picolinic acid (300)

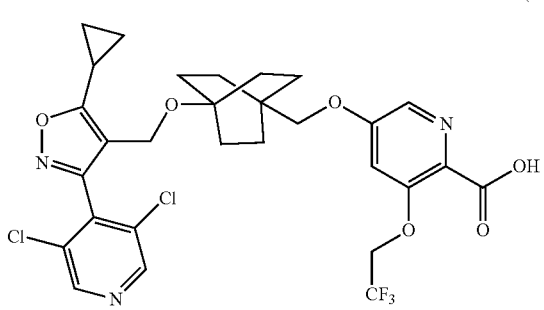

Step A. Intermediate 300A. Preparation of 5-bromo-3-(2,2,2-trifluoroethoxy)picolinonitrile

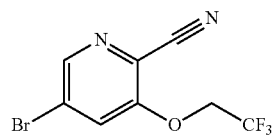 [SMILES: N#Cc1ncc(Br)cc1OCC(F)(F)F]

To a stirred solution of 5-bromo-3-nitropicolinonitrile (0.34 g, 1.5 mmol) and 2,2,2-trifluoroethan-1-ol (1.5 g, 15 mmol) was added 5 M NaOH (aq.) (1.5 mL, 7.5 mmol). The reaction mixture was stirred at 60° C. After 10 min, the mixture was cooled, concentrated and diluted with EtOAc. The organic layer was washed with 1 M HCl (aq.), dried over MgSO$_4$, filtered and concentrated. The crude product was purified by flash column chromatography (24 g silica gel cartridge, A=Hex, B=EtOAc; 15 min grad.; 0% B to 70% B; flow rate=24 mL/min). The pure fractions were combined, concentrated and dried in vacuo to afford the title compound (170 mg, 0.59 mmol, 39% yield) as a light yellow solid. $^1$H NMR (500 MHz, CHLOROFORM-d) δ 8.33 (d, J=1.9 Hz, 1H), 7.50 (d, J=1.7 Hz, 1H), 4.48 (q, J=7.9 Hz, 2H). MS (ESI) 280.9 (M+H).

Step B. Intermediate 300B. Preparation of 5-hydroxy-3-(2,2,2-trifluoroethoxy) picolinonitrile

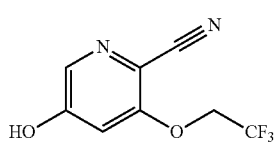

The title compound was prepared according to methods described for the synthesis of Intermediate 335B, using Intermediate 300A as starting material (115 mg, 0.527 mmol, 90% yield): $^1$H NMR (500 MHz, CHLOROFORM-d) δ 8.05 (d, J=2.2 Hz, 1H), 7.27 (s, 1H), 6.87 (d, J=1.9 Hz, 1H), 4.50 (q, J=7.9 Hz, 2H). MS (ESI) 218.9 (M+H).

Step C. Example 300

The title compound was prepared according to combined methods described for the syntheses of Intermediate 276B and Example 278 (Step C), by reaction of Intermediate 276A and Intermediate 300B: $^1$H NMR (500 MHz, DMSO-$d_6$) δ 8.77 (s, 2H), 7.93 (d, J=1.5 Hz, 1H), 7.20 (s, 1H), 4.80 (q, J=8.5 Hz, 2H), 4.20 (s, 2H), 3.70 (br s, 2H), 2.31-2.20 (m, 1H), 1.57-1.44 (m, 6H), 1.39-1.28 (m, 6H), 1.20-1.10 (m, 2H), 1.08-1.00 (m, 2H). FXR $EC_{50}$ (nM)=57. MS (ESI) 642 (M+H).

Example 301

6-((4-((5-cyclopropyl-3-(3,5-dichloropyridin-4-yl)isoxazol-4-yl)methoxy) bicyclo[2.2.2]octan-1-yl)methoxy)-4-methoxynicotinic acid (301)

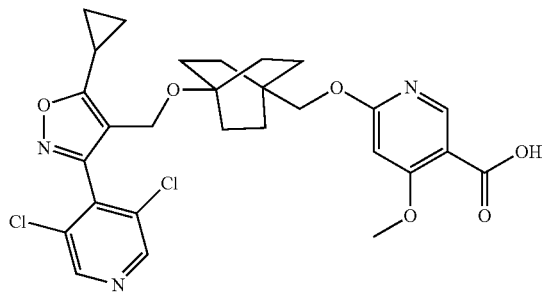

Step A. Intermediate 301A. Preparation of tert-butyl-6-chloro-4-methoxynicotinate

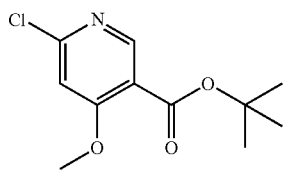 [SMILES: COc1cc(Cl)ncc1C(=O)OC(C)(C)C]

The title compound was prepared according to methods described for the synthesis of Intermediate 321A, using 6-chloro-4-methoxynicotinic acid as starting material: (160 mg, 36% yield). $^1$H NMR (500 MHz, CHLOROFORM-d) δ 8.68 (s, 1H), 6.90 (s, 1H), 3.96 (s, 3H), 1.58 (s, 9H). MS (ESI) 243.9 (M+H).

Step B. Example 301

Step 1: A solution of Intermediate 276A (80 mg, 0.19 mmol) in anhydrous THF (1 mL) was added KOtBu (32 mg, 0.28 mmol). After stirring 5 min, Intermediate 301A (55 mg, 0.23 mmol) was added. After stirring 5 min, the reaction was quenched with sat. $NH_4Cl$ (aq.), diluted with water and extracted with EtOAc (3×). The combined organic layers were washed with brine, dried ($Na_2SO_4$) and concentrated. The crude product was purified by flash column chromatography (12 g silica gel cartridge, A=Hex, B=EtOAc; 15 min grad.; 0% B to 60% B; flow rate=12 mL/min). The pure fractions were combined, concentrated and dried in vacuo to afford t-butyl ester intermediate (30 mg, 0.048 mmol, 25% yield) as a clear liquid.

Step 2: The product of Step 1 (30 mg, 0.048 mmol) was dissolved in 1,4-dioxane (1 mL) and 1 M HCl (aq.) (0.48 mL, 0.48 mmol). The reaction was stirred at 100° C. After 30 min, the reaction mixture was cooled and concentrated. The crude material was purified via preparative HPLC (Column: XBridge C18, 30×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 26-66% B over 20 minutes, then a 2-minute hold at 100% B; Flow: 45 mL/min). Fractions containing the desired product were combined, concentrated and dried in vacuo to afford the title compound: (2.7 mg, 10% yield). $^1$H NMR (500 MHz, DMSO-$d_6$) δ 8.83 (s, 2H), 8.13 (s, 1H), 6.26 (s, 1H), 4.23 (s, 2H), 3.84 (s, 2H), 3.77 (s, 3H), 2.35-2.28 (m, 1H), 1.57-1.44 (m, 6H), 1.39-1.28 (m, 6H), 1.20-1.10 (m, 2H), 1.08-1.00 (m, 2H). FXR $EC_{50}$ (nM)=42. MS (ESI) 574 (M+H).

Example 303

6-((4-((5-cyclopropyl-3-(3,5-dichloropyridin-4-yl)isoxazol-4-yl)methoxy) bicyclo[2.2.2]octan-1-yl)methoxy)-8-fluoro-4-methoxyquinoline-2-carboxylic acid (303)

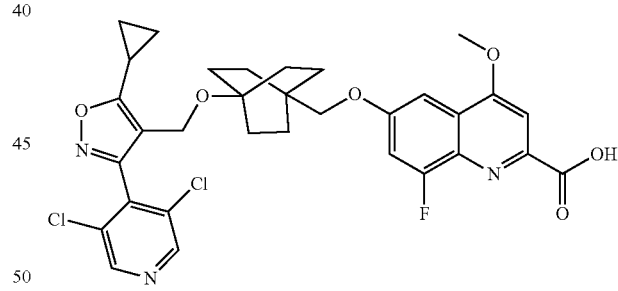

Step A. Intermediate 303A. Preparation of dimethyl 2-((4-(benzyloxy)-2-fluorophenyl)amino)maleate

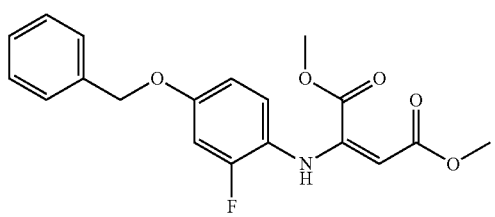 [SMILES: COC(=O)/C=C(/Nc1ccc(OCc2ccccc2)cc1F)C(=O)OC]

To a solution of 4-(benzyloxy)-2-fluoroaniline (1.5 g, 6.9 mmol) in MeOH (20 mL) was added dimethyl but-2-ynedioate (1.3 g, 9.0 mmol). After stirring 5 min, the reaction was concentrated. The crude product was purified by flash column chromatography (120 g silica gel cartridge, A=Hex, B=EtOAc; 30 min grad.; 0% B to 50% B; flow rate=80 mL/min). The pure fractions were combined, concentrated and dried in vacuo to afford the title compound (1.5 g, 4.0 mmol, 58% yield) as a yellow liquid. $^1$H NMR (500 MHz, CHLOROFORM-d) δ 9.44 (s, 1H), 7.45-7.31 (m, 5H), 6.90 (t, J=8.9 Hz, 1H), 6.74 (dd, J=12.2, 2.6 Hz, 1H), 6.69 (dd, J=8.8, 1.7 Hz, 1H), 5.46 (s, 1H), 5.02 (s, 2H), 3.86 (s, 1H), 3.75 (s, 3H), 3.71 (s, 3H). MS (ESI) 360.0 (M+H).

Step B. Intermediate 303B. Preparation of methyl 6-(benzyloxy)-8-fluoro-4-oxo-1,4-dihydroquinoline-2-carboxylate

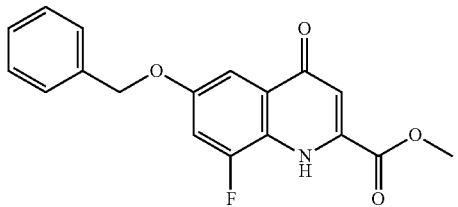 [SMILES: COC(=O)c1cc(=O)c2cc(OCc3ccccc3)cc(F)c2[nH]1]

A reaction mixture of Intermediate 303A (1.4 g, 4.0 mmol) and diphenyl ether (9 mL) was stirred at reflux. After 30 min, the reaction was cooled to rt and diluted with hexanes (120 mL), upon which a gummy solid formed. The mother liquor was decanted. The crude product was purified by flash column chromatography (120 g silica gel cartridge, A=Hex, B=EtOAc; 30 min grad.; 0% B to 100% B; flow rate=80 mL/min). The pure fractions were combined, concentrated and dried in vacuo to afford the title compound (0.85 g, 2.6 mmol, 65% yield) as a beige solid. $^1$H NMR (500 MHz, CHLOROFORM-d) δ 9.20-9.04 (m, 1H), 7.62 (d, J=2.2 Hz, 1H), 7.49-7.45 (m, 2H), 7.42 (t, J=7.3 Hz, 2H), 7.39-7.34 (m, 1H), 7.18 (dd, J=11.7, 2.6 Hz, 1H), 6.96 (d, J=1.9 Hz, 1H), 5.17 (s, 2H), 4.06 (s, 3H). MS (ESI) 328.1 (M+H).

Step C. Intermediate 303C. Preparation of methyl 6-(benzyloxy)-8-fluoro-4-methoxyquinoline-2-carboxylate

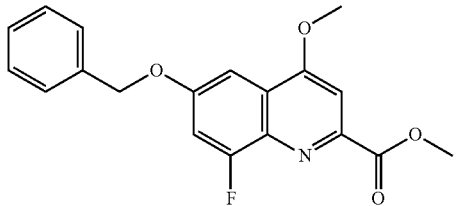 [SMILES: COC(=O)c1cc(OC)c2cc(OCc3ccccc3)cc(F)c2n1]

To a stirred solution of Intermediate 303B (90 mg, 0.28 mmol) in acetonitrile (3 mL) were added iodomethane (0.051 mL, 0.83 mmol) and $K_2CO_3$ (110 mg, 0.83 mmol). The reaction was stirred at 60° C. After 1 h, the reaction mixture was cooled, concentrated and diluted with EtOAc.

The organic layer was washed with sat. $NaHCO_3$ (aq.), dried over $MgSO_4$, filtered and concentrated. The crude product was purified by flash column chromatography (12 g silica gel cartridge, A=Hex, B=EtOAc; 15 min grad.; 0% B to 100% B; flow rate=12 mL/min). The pure fractions were combined, concentrated and dried in vacuo to afford the title compound (86 mg, 0.25 mmol, 92% yield) as a light yellow solid. $^1$H NMR (500 MHz, CHLOROFORM-d) δ 7.64-7.61 (m, 1H), 7.51-7.47 (m, 2H), 7.46-7.41 (m, 2H), 7.40-7.35 (m, 2H), 7.25-7.18 (m, 1H), 5.23-5.18 (m, 2H), 4.13 (s, 3H), 4.06 (s, 3H). MS (ESI) 342.0 (M+H).

Step D. Intermediate 303D. Preparation of methyl 8-fluoro-6-hydroxy-4-methoxyquinoline-2-carboxylate

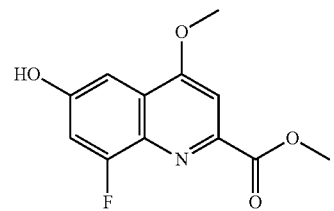 [SMILES: COC(=O)c1cc(OC)c2cc(O)cc(F)c2n1]

The title compound was prepared according to methods described for the synthesis of Intermediate 324C, using Intermediate 303C as starting material: $^1$H NMR (500 MHz, METHANOL-$d_4$) δ 7.57-7.51 (m, 1H), 7.23 (br s, 1H), 7.09 (br d, J=11.8 Hz, 1H), 4.11 (s, 3H), 4.01 (s, 3H). MS (ESI) 252.0 (M+H).

Step E. Example 303

The title compound was prepared according to methods described for the synthesis of Example 276 (Step B and C), by reaction of Intermediate 276A and Intermediate 303D: $^1$H NMR (500 MHz, DMSO-$d_6$) δ 8.78 (s, 2H), 7.55 (s, 1H), 7.31 (br d, J=11.9 Hz, 1H), 7.20 (br s, 1H), 4.22 (s, 2H), 4.09 (s, 3H), 3.71 (s, 2H), 2.36-2.22 (m, 1H), 1.61-1.52 (m, 6H), 1.42-1.32 (m, 6H), 1.19-1.12 (m, 2H), 1.10-1.04 (m, 2H). FXR $EC_{50}$ (nM)=24. MS (ESI) 642 (M+H).

Example 304

6-((4-((5-cyclopropyl-3-(3,5-dichloropyridin-4-yl) isoxazol-4-yl)methoxy) bicyclo[2.2.2]octan-1-yl) methoxy)-8-fluoro-4-isopropoxyquinoline-2-carboxylic acid (304)

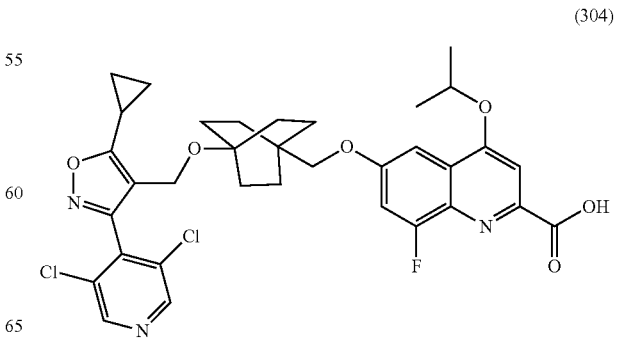

365

Step A. Intermediate 304A. Preparation of methyl 8-fluoro-6-hydroxy-4-isopropoxyquinoline-2-carboxylate

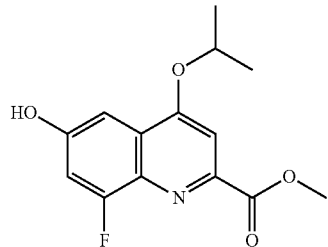 [SMILES: COC(=O)c1cc(OC(C)C)c2cc(O)cc(F)c2n1]

The title compound was prepared according to methods described for the synthesis of Intermediate 303D (Step C and D), using Intermediate 303B and 2-iodopropane as starting material: $^1$H NMR (500 MHz, DMSO-$d_6$) δ 11.58-10.15 (m, 1H), 7.49 (s, 1H), 7.30-6.93 (m, 2H), 5.58-4.83 (m, 1H), 3.92 (s, 3H), 1.42 (d, J=6.1 Hz, 6H). MS (ESI) 280.0 (M+H).

Step B. Example 304

The title compound was prepared according to methods described for the synthesis of Example 276 (Step B and C), by reaction of Intermediate 276A and Intermediate 304A: $^1$H NMR (500 MHz, DMSO-$d_6$) δ 8.81 (s, 2H), 7.52 (s, 1H), 7.42-7.30 (m, 1H), 7.16 (br s, 1H), 5.00 (dt, J=11.8, 5.8 Hz, 1H), 4.21 (s, 2H), 3.68 (s, 2H), 2.35-2.22 (m, 1H), 1.58-1.49 (m, 6H), 1.41 (d, J=6.1 Hz, 6H), 1.37-1.28 (m, 6H), 1.19-1.12 (m, 2H), 1.09-1.02 (m, 2H). FXR $EC_{50}$ (nM)=11. MS (ESI) 670 (M+H).

366

Step A. Intermediate 306A. Preparation of methyl 8-fluoro-6-hydroxy-4-ethoxyquinoline-2-carboxylate

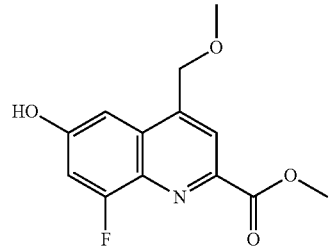 [SMILES: COCc1cc(C(=O)OC)nc2c(F)cc(O)cc12]

The title compound was prepared according to methods described for the synthesis of Intermediate 303D (Step C and D), using Intermediate 303B and iodoethane as starting material: $^1$H NMR (400 MHz, DMSO-$d_6$) δ 10.75 (brs, 1H), 7.48 (s, 1H), 7.33-7.11 (m, 2H), 4.36 (q, J=6.8 Hz, 2H), 3.92 (s, 3H), 1.48 (t, J=6.9 Hz, 3H). MS (ESI) 266.0 (M+H).

Step B. Example 306

The title compound was prepared according to methods described for the synthesis of Example 276 (Step B and C), by reaction of Intermediate 276A and Intermediate 306A: $^1$H NMR (500 MHz, DMSO-$d_6$) δ 8.78 (s, 2H), 7.52 (d, J=4.2 Hz, 1H), 7.33 (br s, 1H), 7.20 (br s, 1H), 4.38 (q, J=6.5 Hz, 2H), 4.22 (s, 2H), 3.70 (br s, 2H), 2.33-2.22 (m, 1H), 1.63-1.52 (m, 6H), 1.48 (br t, J=6.5 Hz, 3H), 1.43-1.33 (m, 6H), 1.19-1.11 (m, 2H), 1.10-1.03 (m, 2H). FXR $EC_{50}$ (nM)=11. MS (ESI) 656 (M+H).

Example 306

6-((4-((5-cyclopropyl-3-(3,5-dichloropyridin-4-yl)isoxazol-4-yl)methoxy) bicyclo[2.2.2]octan-1-yl)methoxy)-4-ethoxy-8-fluoroquinoline-2-carboxylic acid Example 307

6-((4-((5-cyclopropyl-3-(3,5-dichloropyridin-4-yl)isoxazol-4-yl)methoxy) bicyclo[2.2.2]octan-1-yl)methoxy)-8-fluoro-4-methylquinoline-2-carboxylic acid

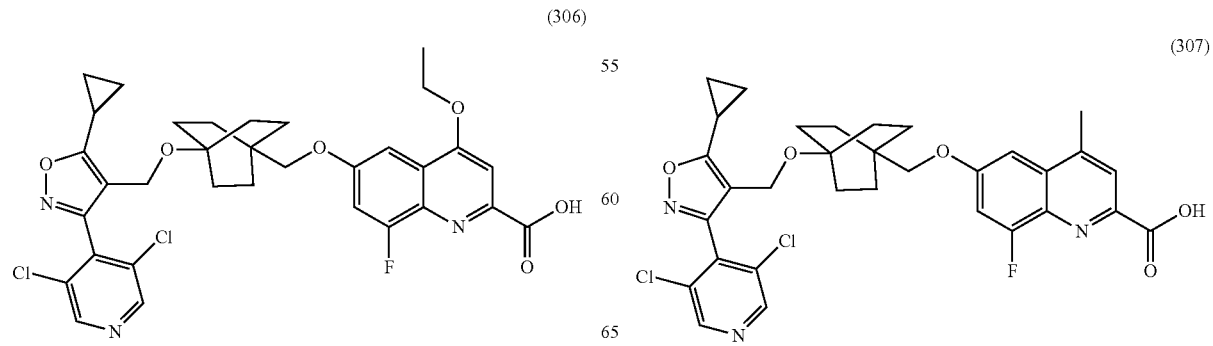

Step A. Intermediate 307A. Preparation of methyl 6-(benzyloxy)-4-chloro-8-fluoroquinoline-2-carboxylate

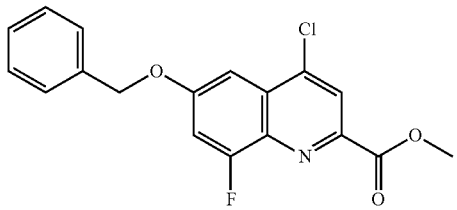 [SMILES: COC(=O)c1cc(Cl)c2cc(OCc3ccccc3)cc(F)c2n1]

To a stirred solution of Intermediate 303B (320 mg, 0.96 mmol) in DCM (8 mL) was added oxalyl chloride (0.33 mL, 3.9 mmol) and DMF (1 drop). The reaction was stirred at 55° C. After 1 h, the mixture was cooled, concentrated and diluted with EtOAc. The organic layer was washed with sat. NaHCO$_3$ (aq.), dried over MgSO$_4$, filtered and concentrated. The crude product was purified by flash column chromatography (12 g silica gel cartridge, A=Hex, B=EtOAc; 15 min grad.; 0% B to 70% B; flow rate=12 mL/min). The pure fractions were combined, concentrated and dried in vacuo to afford the title compound (290 mg, 0.84 mmol, 87% yield) as a light yellow solid. MS (ESI) 346.0 (M+H)

Step B. Intermediate 307B. Preparation of methyl 8-fluoro-6-hydroxy-4 methylquinoline-2-carboxylate

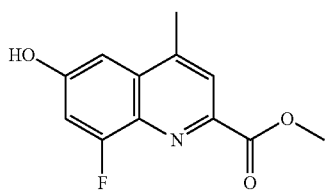 [SMILES: COC(=O)c1cc(C)c2cc(O)cc(F)c2n1]

The title compound was prepared according to methods described for the synthesis of Intermediate 324C (Step B and C), using Intermediate 307A and methyl boronic acid as starting material: $^1$H NMR (400 MHz, DMSO-d$_6$) δ 10.81 (brs, 1H), 7.96 (s, 1H), 7.24 (dd, J=12.1, 2.4 Hz, 1H), 7.11 (d, J=1.8 Hz, 1H), 3.92 (s, 3H), 2.63 (s, 3H). MS (ESI) 236.0 (M+H).

Step C. Example 307

The title compound was prepared according to methods described for the synthesis of Example 276 (Step B and C), by reaction of Intermediate 276A and Intermediate 307B: $^1$H NMR (500 MHz, DMSO-d$_6$) δ 8.77 (s, 2H), 7.93 (br s, 1H), 7.29 (br s, 1H), 7.14 (br s, 1H), 4.22 (s, 2H), 3.75 (br s, 2H), 2.65 (s, 3H), 2.30-2.22 (m, 1H), 1.63-1.52 (m, 6H), 1.43-1.33 (m, 6H), 1.19-1.11 (m, 2H), 1.10-1.03 (m, 2H). FXR EC$_{50}$ (nM)=20. MS (ESI) 626 (M+H).

Example 308

4-cyclobutoxy-6-((4-((5-cyclopropyl-3-(3,5-dichloropyridin-4-yl)isoxazol-4-yl)methoxy) bicyclo[2.2.2]octan-1-yl)methoxy)-8-fluoroquinoline-2-carboxylic acid

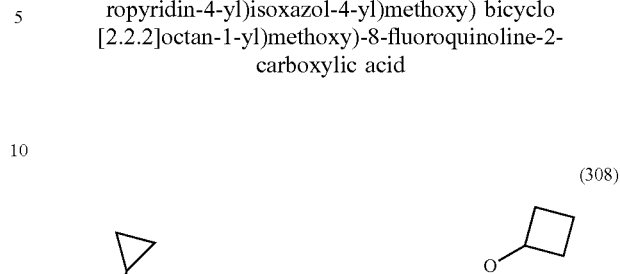

(308)

Step A. Intermediate 308A. Preparation of methyl 4-cyclobutoxy-8-fluoro-6-hydroxyquinoline-2-carboxylate

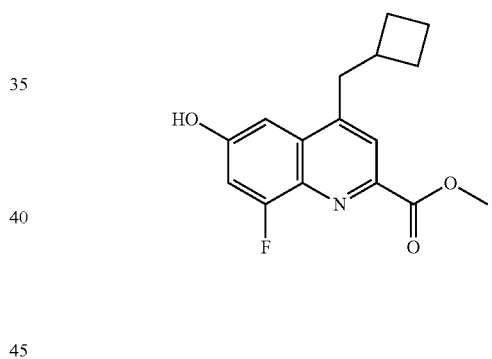

The title compound was prepared according to methods described for the synthesis of Intermediate 303D (Step C and D), using Intermediate 303B and bromocyclobutane as starting material: $^1$H NMR (400 MHz, DMSO-d$_6$) δ 7.32 (s, 1H), 7.25-7.19 (m, 2H), 5.12-5.03 (m, 1H), 3.92 (s, 3H), 2.62-2.52 (m, 2H), 2.27-2.13 (m, 2H), 1.96-1.67 (m, 2H). MS (ESI) 292.1 (M+H).

Step B. Example 308

The title compound was prepared according to methods described for the synthesis of Example 276 (Step B and C), by reaction of Intermediate 276A and Intermediate 308A: $^1$H NMR (500 MHz, DMSO-d$_6$) δ 8.77 (s, 2H), 7.35 (s, 1H), 7.30 (br d, J=11.3 Hz, 1H), 7.20 (br s, 1H), 5.05 (br t, J=6.8 Hz, 1H), 4.22 (s, 2H), 3.71 (s, 2H), 2.60-2.52 (m, 2H), 2.32-2.17 (m, 3H), 1.88 (q, J=9.9 Hz, 1H), 1.81-1.71 (m, 1H), 1.60-1.52 (m, 6H), 1.42-1.34 (m, 6H), 1.19-1.11 (m, 2H), 1.09-1.03 (m, 2H). FXR EC$_{50}$ (nM)=12. MS (ESI) 682 (M+H).

369

Example 309

6-((4-((5-cyclopropyl-3-(3,5-dichloropyridin-4-yl)isoxazol-4-yl)methoxy) bicyclo[2.2.2]octan-1-yl)methoxy)-8-fluoro-4-propylquinoline-2-carboxylic acid

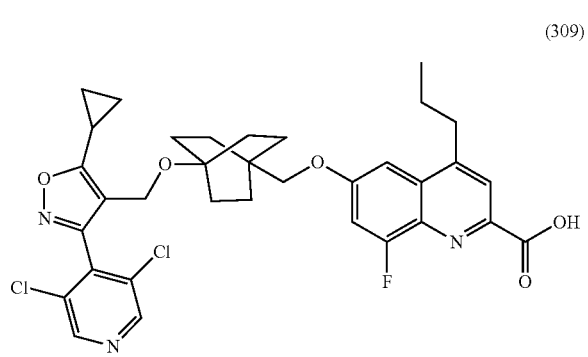 [SMILES: CCCc1cc(C(=O)O)nc2c(F)cc(OCC34CCC(OCc5c(-c6c(Cl)cncc6Cl)noc5C5CC5)(CC3)CC4)cc12]

(309)

Step A. Intermediate 309A. Preparation of methyl 8-fluoro-6-hydroxy-4-propylquinoline-2-carboxylate

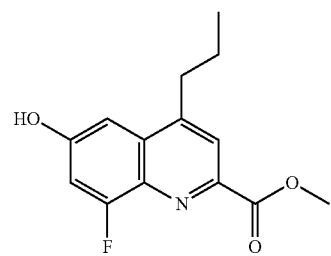 [SMILES: CCCc1cc(C(=O)OC)nc2c(F)cc(O)cc12]

The title compound was prepared according to methods described for the synthesis of Intermediate 324C (Step B and C), using Intermediate 307A and propyl boronic acid as starting material: $^1$H NMR (500 MHz, CHLOROFORM-d) δ 8.15-7.95 (m, 1H), 7.22-7.09 (m, 2H), 4.05 (s, 3H), 3.07-2.95 (m, 2H), 1.86-1.75 (m, 2H), 1.06 (t, J=7.3 Hz, 3H). MS (ESI) 264.0 (M+H).

Step B. Example 309

The title compound was prepared according to methods described for the synthesis of Example 276 (Step B and C), by reaction of Intermediate 276A and Intermediate 309A: $^1$H NMR (500 MHz, DMSO-d$_6$) δ 8.77 (s, 2H), 7.92 (s, 1H), 7.31 (br d, J=10.9 Hz, 1H), 7.18 (br s, 1H), 4.21 (s, 2H), 3.75 (s, 2H), 3.03 (br t, J=7.3 Hz, 2H), 2.31-2.18 (m, 1H), 1.80-1.67 (m, 2H), 1.64-1.52 (m, 6H), 1.44-1.33 (m, 6H), 1.19-1.11 (m, 2H), 1.10-1.01 (m, 2H), 0.95 (t, J=7.3 Hz, 3H). FXR EC$_{50}$ (nM)=13. MS (ESI) 654 (M+H).

370

Example 311

4-cyclopropyl-6-((4-((5-cyclopropyl-3-(3,5-dichloropyridin-4-yl)isoxazol-4-yl)methoxy) bicyclo[2.2.2]octan-1-yl)methoxy)-8-fluoroquinoline-2-carboxylic acid

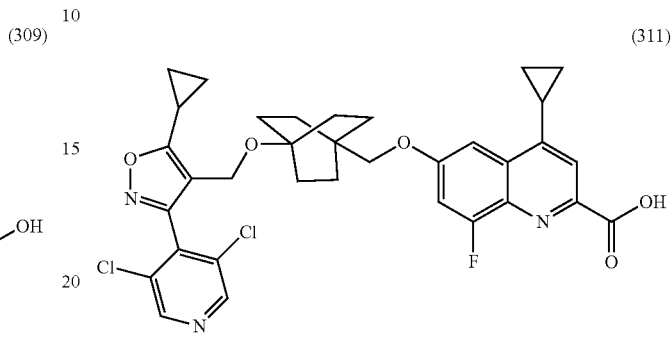

(311)

Step A. Intermediate 311A. Preparation of methyl 4-cyclopropyl-8-fluoro-6-hydroxyquinoline-2-carboxylate

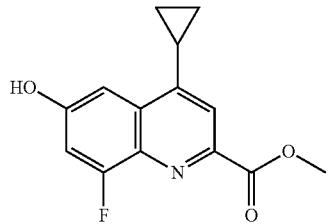 [SMILES: COC(=O)c1cc(C2CC2)c2cc(O)cc(F)c2n1]

The title compound was prepared according to methods described for the synthesis of Intermediate 324C (Step B and C), using Intermediate 307A and cyclopropylboronic acid as starting material: $^1$H NMR (400 MHz, DMSO-d$_6$) δ 7.92 (s, 1H), 7.66 (s, 1H), 7.44 (d, J=2.0 Hz, 1H), 7.25 (ddd, J=12.0, 6.3, 2.4 Hz, 2H), 7.17 (d, J=2.2 Hz, 1H), 3.92 (d, J=4.8 Hz, 6H), 3.07-2.91 (m, 2H), 1.71 (d, J=7.7 Hz, 2H), 1.16 (dd, J=8.4, 2.0 Hz, 2H), 0.98 (t, J=7.4 Hz, 2H), 0.86 (dd, J=5.3, 1.8 Hz, 2H). MS (ESI) 262.1 (M+H).

Step B. Example 311

The title compound was prepared according to methods described for the synthesis of Example 276 (Step B and C), by reaction of Intermediate 276A and Intermediate 311A: $^1$H NMR (500 MHz, DMSO-d$_6$) δ 8.81 (s, 2H), 7.63 (s, 1H), 7.45 (s, 1H), 7.34 (br d, J=11.6 Hz, 1H), 4.22 (s, 2H), 3.76 (s, 2H), 2.59-2.50 (m, 1H), 2.37-2.22 (m, 1H), 1.63-1.50 (m, 6H), 1.44-1.31 (m, 6H), 1.22-1.11 (m, 4H), 1.10-1.03 (m, 2H), 0.89-0.81 (m, 2H). FXR EC$_{50}$ (nM)=9. MS (ESI) 653 (M+H).

Example 312

6-((4-((5-cyclopropyl-3-(3,5-dichloropyridin-4-yl)isoxazol-4-yl)methoxy) bicyclo[2.2.2]octan-1-yl)methoxy)-8-fluoro-4-(oxetan-3-yloxy)quinoline-2-carboxylic acid

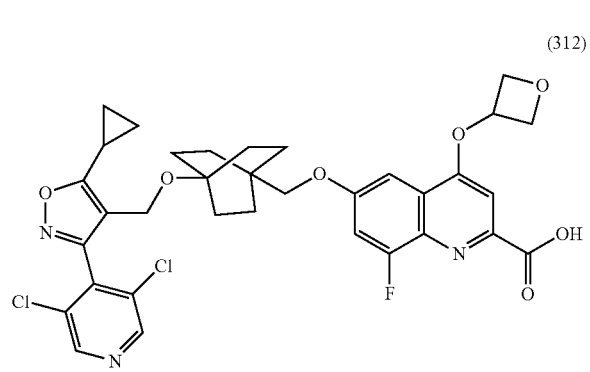 [SMILES: O=C(O)c1cc(OC2COC2)c2cc(OCC34CCC(OCc5c(-c6c(Cl)cncc6Cl)noc5C5CC5)(CC3)CC4)cc(F)c2n1]

(312)

Step A. Intermediate 312A. Preparation of methyl 8-fluoro-6-hydroxy-4-(oxetan-3-yloxy)quinoline-2-carboxylate

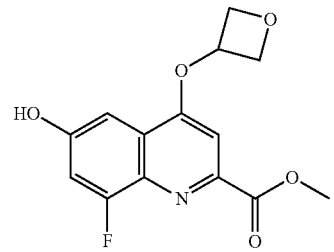 [SMILES: COC(=O)c1cc(OC2COC2)c2cc(O)cc(F)c2n1]

The title compound was prepared according methods described for the synthesis of Intermediate 303D (Step C and D), using Intermediate 303B and 3-iodooxetane as starting material: $^1$H NMR (500 MHz, DMSO-d$_6$) δ 11.25-10.33 (m, 1H), 7.31 (d, J=1.9 Hz, 1H), 7.26 (dd, J=12.1, 2.5 Hz, 1H), 7.12 (s, 1H), 5.68 (t, J=5.1 Hz, 1H), 5.06 (t, J=6.7 Hz, 2H), 4.68 (dd, J=7.7, 4.7 Hz, 2H), 3.92 (s, 3H). MS (ESI) 294.1 (M+H).

Step B. Example 312

The title compound was prepared according to methods described for the synthesis of Example 276 (Step B and C), by reaction of Intermediate 276A and Intermediate 312A: $^1$H NMR (500 MHz, DMSO-d$_6$) δ 8.82 (s, 2H), 7.37 (br d, J=11.9 Hz, 1H), 7.30 (br s, 1H), 7.13 (s, 1H), 5.68-5.60 (m, 1H), 5.04 (br t, J=6.6 Hz, 2H), 4.82-4.68 (m, 2H), 4.23 (s, 2H), 3.74 (s, 2H), 2.59-2.50 (m, 1H), 2.37-2.22 (m, 1H), 1.63-1.50 (m, 6H), 1.44-1.31 (m, 6H), 1.22-1.11 (m, 4H), 1.10-1.03 (m, 2H). FXR EC$_{50}$ (nM)=47. MS (ESI) 685 (M+H).

Example 313

6-((4-((5-cyclopropyl-3-(3,5-dichloropyridin-4-yl)isoxazol-4-yl)methoxy) bicyclo[2.2.2]octan-1-yl)methoxy)-4-ethoxy-7-fluoroquinoline-2-carboxylic acid

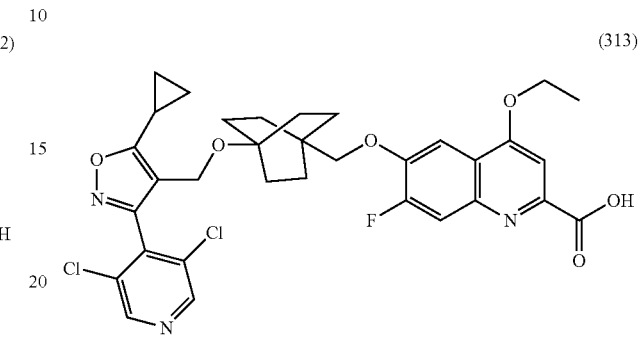

(313)

Step A. Intermediate 313A. Preparation of methyl 4-ethoxy-7-fluoro-6-hydroxy-quinoline-2-carboxylate

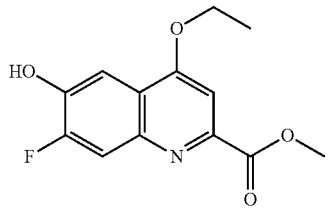 [SMILES: CCOc1cc(C(=O)OC)nc2cc(F)c(O)cc12]

The title compound was prepared according to methods described for the synthesis of Intermediate 303D (Step C and D), using 4-amino-2-fluorophenol and iodoethane as starting material: $^1$H NMR (500 MHz, CHLOROFORM-d) δ 7.98-7.88 (m, 1H), 7.75 (d, J=9.6 Hz, 1H), 7.51 (s, 1H), 4.54 (q, J=7.0 Hz, 2H), 4.35 (q, J=7.0 Hz, 2H), 1.64-1.55 (m, 3H), 1.48 (t, J=7.0 Hz, 3H). MS (ESI) 280.1 (M+H).

Step B. Example 313

The title compound was prepared according to methods described for the synthesis of Example 276 (Step B and C), by reaction of Intermediate 276A and Intermediate 313A: $^1$H NMR (500 MHz, DMSO-d$_6$) δ 8.80 (s, 2H), 7.80 (br d, J=12.2 Hz, 1H), 7.52-7.37 (m, 2H), 4.34 (q, J=6.7 Hz, 2H), 4.21 (s, 2H), 3.75 (s, 2H), 2.34-2.24 (m, 1H), 1.60-1.51 (m, 6H), 1.46 (br t, J=6.9 Hz, 3H), 1.39-1.31 (m, 6H), 1.20-1.11 (m, 2H), 1.09-1.02 (m, 2H). FXR EC$_{50}$ (nM)=48. MS (ESI) 657 (M+H).

Example 314

6-((4-((5-cyclopropyl-3-(3,5-dichloropyridin-4-yl) isoxazol-4-yl)methoxy) bicyclo[2.2.2]octan-1-yl) methoxy)-4-(cyclopropylmethoxy)-7-fluoroquinoline-2-carboxylic acid

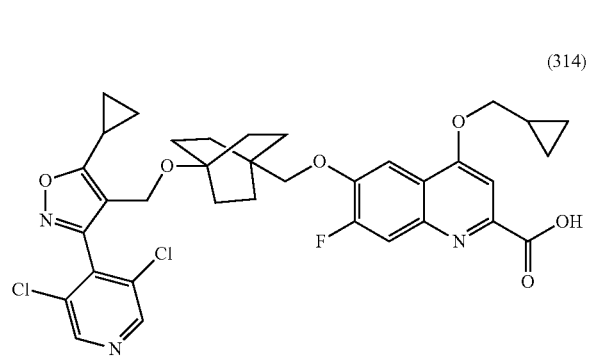 [SMILES: O=C(O)c1cc(OCC2CC2)c2cc(OCC34CCC(OCc5c(-c6c(Cl)cncc6Cl)noc5C5CC5)(CC3)CC4)c(F)cc2n1]

(314)

Step A. Intermediate 314A. Preparation of methyl 4-(cyclopropylmethoxy)-7-fluoro-6-hydroxy-quinoline-2-carboxylate

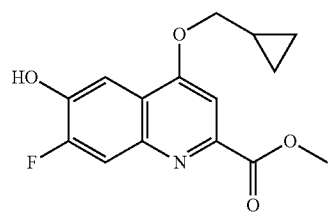 [SMILES: COC(=O)c1cc(OCC2CC2)c2cc(O)c(F)cc2n1]

The title compound was prepared according to methods described for the synthesis of Intermediate 303D (Step C and D), using 4-amino-2-fluorophenol and (bromomethyl) cyclopropane as starting material: $^1$H NMR (500 MHz, CHLOROFORM-d) δ 7.98-7.87 (m, 1H), 7.80 (d, J=9.4 Hz, 1H), 7.48 (s, 1H), 4.53 (q, J=7.0 Hz, 2H), 4.12 (d, J=6.9 Hz, 2H), 1.47 (t, J=7.0 Hz, 3H), 1.44-1.35 (m, 1H), 0.78-0.68 (m, 2H), 0.52-0.42 (m, 2H). MS (ESI) 306.1 (M+H).

Step B. Example 314

The title compound was prepared according to methods described for the synthesis of Example 276 (Step B and C), by reaction of Intermediate 276A and Intermediate 314A: $^1$H NMR (500 MHz, DMSO-d$_6$) δ 8.81 (s, 2H), 7.85 (d, J=11.9 Hz, 1H), 7.53-7.47 (m, 2H), 4.22 (s, 2H), 4.19 (br d, J=7.0 Hz, 2H), 3.79 (s, 2H), 2.34-2.25 (m, 1H), 1.62-1.52 (m, 6H), 1.41-1.32 (m, 7H), 1.19-1.12 (m, 2H), 1.10-1.04 (m, 2H), 0.67-0.60 (m, 2H), 0.46-0.40 (m, 2H). FXR EC$_{50}$ (nM)=67. MS (ESI) 683 (M+H).

Example 321

3-((4-((5-cyclopropyl-3-(3,5-dichloropyridin-4-yl) isoxazol-4-yl)methoxy) bicyclo[2.2.2]octan-1-yl) methoxy)-5-methoxybenzoic acid

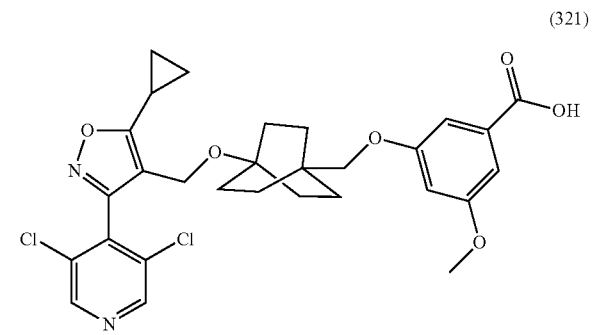 [SMILES: COc1cc(OCC23CCC(OCc4c(-c5c(Cl)cncc5Cl)noc4C4CC4)(CC2)CC3)cc(C(=O)O)c1]

(321)

Step A. Intermediate 321A. Preparation of tert-butyl 3-hydroxy-5-methoxybenzoate

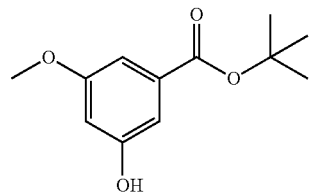 [SMILES: COc1cc(O)cc(C(=O)OC(C)(C)C)c1]

To a solution of 3-hydroxy-5-methoxybenzoic acid (80 mg, 0.48 mmol) in THF (3 mL) and t-butanol (0.30 mL, 3.1 mmol) was added tert-butyl (E)-N,N'-diisopropylcarbamimidate (190 mg, 0.95 mmol) dropwise. The reaction was stirred at ambient temperature for 3 h. The reaction mixture was concentrated and diluted with EtOAc. The organic layer was washed with H$_2$O, dried over MgSO$_4$, filtered and concentrated. The crude product was purified by flash column chromatography (12 g silica gel cartridge; A=Hex, B=EtOAc; 15 min grad.; 0% B to 80% B; flow rate=12 mL/min). Fractions containing the desired product were combined, concentrated and dried in vacuo to afford the title compound (40 mg, 0.18 mmol, 38% yield) as a clear liquid. $^1$H NMR (400 MHz, CHLOROFORM-d) δ 7.20 (dd, J=2.3, 1.4 Hz, 1H), 7.10 (dd, J=2.4, 1.3 Hz, 1H), 6.62 (t, J=2.3 Hz, 1H), 6.36 (s, 1H), 3.80 (s, 3H), 1.58 (s, 9H). MS (ESI) 225.0 (M+H).

Step B. Example 321

Step 1: Intermediate 276A (18 mg, 0.043 mmol), Intermediate 321A (11 mg, 0.047 mmol), Ph$_3$P (17 mg, 0.064 mmol) and diisopropyl (E)-diazene-1,2-dicarboxylate (0.013 mL, 0.064 mmol) were dissolved in THF (0.5 mL). The mixture was stirred at 100° C. in a sealed vial. After 1 h, the reaction was cooled to rt, diluted with DCM and purified by flash column chromatography (12 g silica gel cartridge; A=Hex, B=EtOAc; 15 min grad.; 0% B to 100% B; flow rate=12 mL/min) to give t-butyl ester (15 mg, 0.024 mmol, 56% yield) as a clear liquid.

Step 2: The t-butyl ester from Step 1 above (15 mg, 0.024 mmol) was dissolved in 1,4-dioxane (1 mL) and 1 M HCl (aq.) (0.24 mL, 0.24 mmol). The reaction was stirred at 100° C. After 1 h, the reaction mixture was cooled and concentrated. The crude material was purified via preparative HPLC (Column: XBridge C18, 30×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 26-66% B over 20 minutes, then a 2-minute hold at 100% B; Flow: 45 mL/min). Fractions containing the desired product were combined, concentrated and dried in vacuo to afford the title compound (2.5 mg, 20% yield). $^1$H NMR (500 MHz, DMSO-$d_6$) δ 8.82 (s, 2H), 7.00 (br d, J=17.1 Hz, 2H), 6.56 (s, 1H), 4.22 (s, 2H), 3.74 (s, 2H), 3.53 (br d, J=11.3 Hz, 3H), 2.41-2.20 (m, 1H), 1.60-1.44 (m, 6H), 1.40-1.28 (m, 6H), 1.21-1.13 (m, 2H), 1.11-1.01 (m, 2H). FXR $EC_{50}$ (nM)=7. MS (ESI) 573.2 (M+H).

Example 324

4-cyclopropyl-6-((4-((5-cyclopropyl-3-(3,5-dichloro-pyridin-4-yl)isoxazol-4-yl)methoxy) bicyclo[2.2.2]octan-1-yl)methoxy)quinoline-2-carboxylic acid

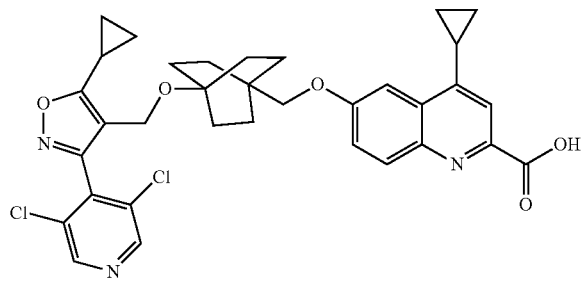

(324)

Step A. Intermediate 324A. Preparation of ethyl 6-(benzyloxy)-4-chloroquinoline-2-carboxylate

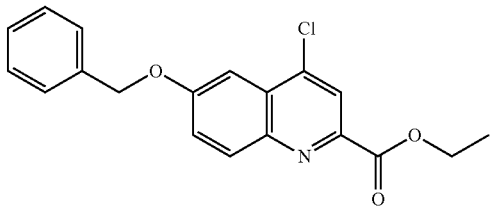

To a stirred solution of ethyl 6-(benzyloxy)-4-oxo-1,4-dihydroquinoline-2-carboxylate (100 mg, 0.31 mmol) in DCM (5 mL) was added oxalyl chloride (0.62 mL, 1.2 mmol) and DMF (1 drop). The reaction was stirred at 55° C. for 1 hr. The reaction mixture was concentrated and diluted with EtOAc. The organic layer was washed with sat. NaHCO$_3$ (aq.), dried over MgSO$_4$, filtered and concentrated. The crude product was purified by flash column chromatography (12 g silica gel cartridge; A=Hex, B=EtOAc; 15 min grad.; 0% B to 70% B; flow rate=12 mL/min). Fractions containing the desired product were combined, concentrated and dried in vacuo to afford the title compound (93 mg, 0.27 mmol, 88% yield) as a light yellow solid. $^1$H NMR (500 MHz, CHLOROFORM-d) δ 8.29-8.20 (m, 2H), 7.61-7.49 (m, 4H), 7.48-7.41 (m, 2H), 7.41-7.35 (m, 1H), 5.25 (s, 2H), 4.56 (q, J=7.2 Hz, 2H), 1.50 (t, J=7.2 Hz, 3H). MS (ESI) 342.0 (M+H).

Step B. Intermediate 324B. Preparation of ethyl 6-(benzyloxy)-4-cyclopropylquinoline-2-carboxylate

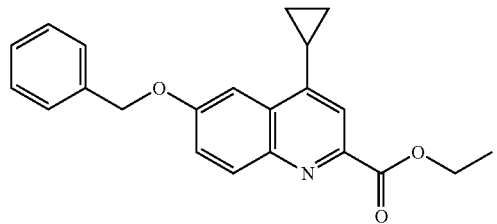 [SMILES: CCOC(=O)c1cc(C2CC2)c2cc(OCc3ccccc3)ccc2n1]

To a stirred solution of Intermediate 324A (45 mg, 0.13 mmol) in 1,4-dioxane (1 mL) was added cyclopropylboronic acid (28 mg, 0.33 mmol) and K$_2$CO$_3$ (64 mg, 0.46 mmol). The mixture was degassed with N$_2$ for 5 min, Pd(dppf)Cl$_2$.CH$_2$Cl$_2$ adduct (9.6 mg, 0.013 mmol) was added and the reaction was stirred at 100° C. After 3 h, the reaction mixture was cooled, concentrated and diluted with EtOAc. The organic layer was washed with H$_2$O, dried over MgSO$_4$, filtered and concentrated. The crude product was purified by flash column chromatography (24 g silica gel cartridge; A=Hex, B=EtOAc; 15 min grad.; 0% B to 50% B; flow rate=24 mL/min). Fractions containing the desired product were combined, concentrated and dried in vacuo to afford the title compound (20 mg, 0.058 mmol, 44% yield) as a clear liquid. $^1$H NMR (500 MHz, CHLOROFORM-d) δ 8.25 (d, J=9.4 Hz, 1H), 7.85 (s, 1H), 7.68 (d, J=2.8 Hz, 1H), 7.57-7.50 (m, 3H), 7.45 (t, J=7.4 Hz, 2H), 7.42-7.35 (m, 1H), 5.28 (s, 2H), 4.56 (q, J=7.2 Hz, 2H), 2.39-2.27 (m, 1H), 1.50 (t, J=7.2 Hz, 3H), 1.25-1.14 (m, 2H), 0.96-0.86 (m, 2H). MS (ESI) 348.0 (M+H).

Step C. Intermediate 324C. Preparation of ethyl 4-cyclopropyl-6-hydroxyquinoline-2-carboxylate

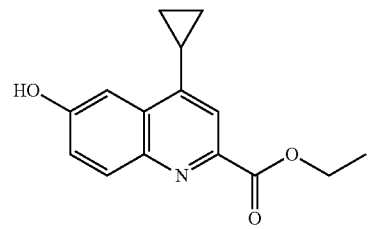 [SMILES: CCOC(=O)c1cc(C2CC2)c2cc(O)ccc2n1]

A stirred solution of Intermediate 324B (63 mg, 0.18 mmol) in EtOAc (3 mL) was degassed with N$_2$. To this mixture was added palladium on carbon (29 mg, 0.0027 mmol) (10% wt. loading, matrix activated carbon support). The reaction was stirred under H$_2$ (1 atm, balloon) for 4 h. A mixture of cyclopropyl and n-propyl products were observed. The reaction mixture was filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (25 mg, 0.097 mmol, 54% yield) as a white solid. $^1$H NMR (500 MHz, CHLOROFORM-d) δ 8.88-8.42 (m, 1H), 8.11 (d, J=9.1 Hz, 1H), 7.82 (s, 1H), 7.70 (d, J=2.5 Hz, 1H), 7.38 (dd, J=9.2, 2.6 Hz, 1H), 4.50 (q, J=7.0 Hz, 2H), 2.46-2.21 (m, 1H), 1.41 (t, J=7.2 Hz, 3H), 1.20-1.09 (m, 2H), 0.97-0.82 (m, 2H). MS (ESI) 258.2 (M+H).

Step D. Example 324

The title compound was prepared according to methods described for the synthesis of Example 276 (Step B and C), by reaction of Intermediate 276A and Intermediate 324C: $^1$H NMR (500 MHz, DMSO-d$_6$) δ 8.79 (s, 2H), 8.05 (br d, J=7.4 Hz, 1H), 7.62 (br d, J=10.3 Hz, 2H), 7.47 (br d, J=8.7 Hz, 1H), 4.23 (s, 2H), 3.78 (s, 2H), 2.36-2.20 (m, 1H), 1.59 (br d, J=7.7 Hz, 6H), 1.39 (br s, 6H), 1.29-1.12 (m, 5H), 1.08 (br s, 2H), 0.85 (br d, J=3.6 Hz, 2H). FXR EC$_{50}$ (nM)=22. MS (ESI) 634.2 (M+H).

Example 327

6-((4-((5-cyclopropyl-3-(3,5-dichloropyridin-4-yl)isoxazol-4-yl)methoxy) bicyclo[2.2.2]octan-1-yl)methoxy)-4-hydroxyquinoline-2-carboxylic acid

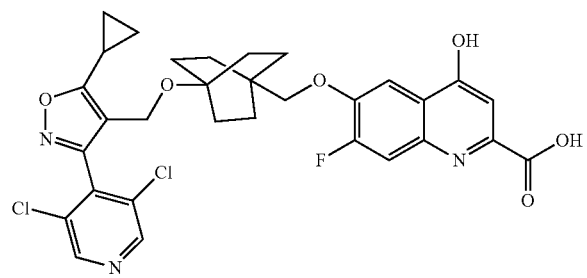

(327)

Step A. Intermediate 327A. Preparation of ethyl 4-acetoxy-6-(benzyloxy)quinoline-2-carboxylate

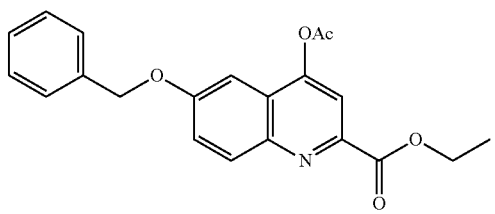 [SMILES: CCOC(=O)c1cc(OC(C)=O)c2cc(OCc3ccccc3)ccc2n1]

To a stirred solution of ethyl 6-(benzyloxy)-4-oxo-1,4-dihydroquinoline-2-carboxylate (80 mg, 0.25 mmol) in acetonitrile (3 mL) was added Hunig's base (0.086 mL, 0.50 mmol) and acetyl chloride (0.021 mL, 0.30 mmol). The reaction was stirred for 3 h at rt. The reaction mixture was concentrated and diluted with EtOAc. The organic layer was washed with sat. NaHCO$_3$ (aq.), dried over MgSO$_4$, filtered and concentrated. The crude product was purified by flash column chromatography (12 g silica gel cartridge; A=Hex, B=EtOAc; 15 min grad.; 0% B to 70% B; flow rate=12 mL/min). Fractions containing the desired product were combined, concentrated and dried in vacuo to afford the title compound (90 mg, 0.27 mmol, 100% yield) as a light yellow solid. $^1$H NMR (400 MHz, CHLOROFORM-d) δ 8.24 (d, J=9.2 Hz, 1H), 8.02 (s, 1H), 7.59-7.34 (m, 6H), 7.22 (d, J=2.9 Hz, 1H), 5.21 (s, 2H), 4.54 (q, J=7.1 Hz, 2H), 2.47 (s, 3H), 1.47 (t, J=7.0 Hz, 3H). MS (ESI) 366.1 (M+H).

Step B. Intermediate 327B. Preparation of ethyl 4-acetoxy-6-hydroxyquinoline-2-carboxylate

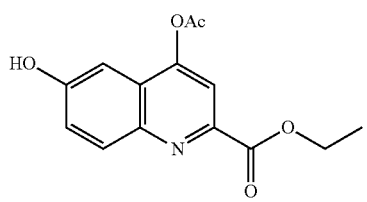 [SMILES: CCOC(=O)c1cc(OC(C)=O)c2cc(O)ccc2n1]

The title compound was prepared according to methods described for the synthesis of Intermediate 324C, using Intermediate 327A as starting material: (54 mg, 0.196 mmol, 90% yield). $^1$H NMR (400 MHz, CHLOROFORM-d) δ 9.69 (br d, J=2.4 Hz, 1H), 8.04 (d, J=9.2 Hz, 1H), 8.00 (s, 1H), 7.42 (dd, J=9.2, 2.6 Hz, 1H), 7.28 (d, J=2.6 Hz, 1H), 4.46 (q, J=7.1 Hz, 2H), 2.38 (s, 3H), 1.35 (t, J=7.2 Hz, 3H). MS (ESI) 276.1 (M+H).

Step C. Example 327

The title compound was prepared according to methods described for the synthesis of Example 276 (Step B and C), by reaction of Intermediate 276A and Intermediate 327B: $^1$H NMR (500 MHz, DMSO-d$_6$) δ 8.82 (s, 2H), 7.96 (br d, J=9.0 Hz, 1H), 7.49-7.33 (m, 3H), 4.26 (s, 2H), 3.24 (br s, 2H), 2.34-2.26 (m, 1H), 1.77-1.58 (m, 6H), 1.53-1.39 (m, 6H), 1.21-1.13 (m, 2H), 1.10 (br d, J=2.4 Hz, 2H). FXR EC$_{50}$ (nM)=170. MS (ESI) 610.3 (M+H).

Example 328

6-((4-((5-cyclopropyl-3-(3,5-dichloropyridin-4-yl)isoxazol-4-yl)methoxy) bicyclo[2.2.2]octan-1-yl)methoxy)-4-isopropoxyquinoline-2-carboxylic acid (328)

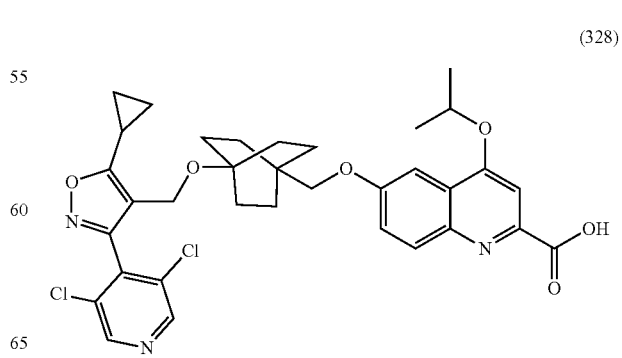

Step A. Intermediate 328A. Preparation of ethyl 6-(benzyloxy)-4-isopropoxyquinoline-2-carboxylate

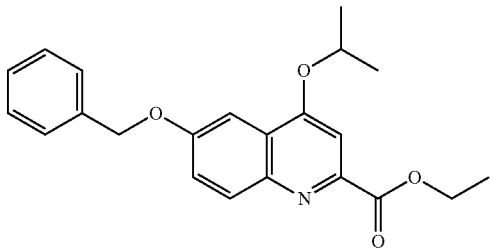 [SMILES: CCOC(=O)c1cc(OC(C)C)c2cc(OCc3ccccc3)ccc2n1]

To a stirred solution of ethyl 6-(benzyloxy)-4-oxo-1,4-dihydroquinoline-2-carboxylate (80 mg, 0.25 mmol) in acetonitrile (3 mL) was added 2-iodopropane (126 mg, 0.74 mmol) and $K_2CO_3$ (103 mg, 0.74 mmol). The reaction was stirred for 3 h at 60° C. The reaction mixture was concentrated and diluted with EtOAc. The organic layer was washed with sat. $NaHCO_3$ (aq.), dried over $MgSO_4$, filtered and concentrated. The crude product was purified by flash column chromatography (12 g silica gel cartridge; A=Hex, B=EtOAc; 15 min grad.; 0% B to 70% B; flow rate=12 mL/min). Fractions containing the desired product were combined, concentrated and dried in vacuo to afford the title compound (56 mg, 0.15 mmol, 62% yield) as a light yellow solid. $^1$H NMR (400 MHz, CHLOROFORM-d) δ 8.13 (d, J=9.2 Hz, 1H), 7.56 (d, J=2.9 Hz, 1H), 7.54 (s, 1H), 7.52-7.48 (m, 2H), 7.47-7.39 (m, 3H), 7.38-7.32 (m, 1H), 5.21 (s, 2H), 4.94 (spt, J=6.1 Hz, 1H), 4.54 (q, J=7.0 Hz, 2H), 1.56-1.45 (m, 9H). MS (ESI) 366.2 (M+H).

Step B. Intermediate 328B. Preparation of ethyl 6-hydroxy-4-isopropoxyquinoline-2-carboxylate

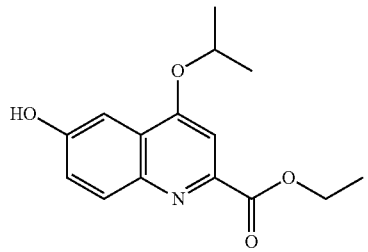 [SMILES: CCOC(=O)c1cc(OC(C)C)c2cc(O)ccc2n1]

The title compound was prepared according to methods described for the synthesis of Intermediate 324C, using Intermediate 328A as starting material: $^1$H NMR (400 MHz, CHLOROFORM-d) δ 8.68-8.19 (m, 1H), 7.99 (d, J=9.2 Hz, 1H), 7.54 (d, J=2.9 Hz, 1H), 7.50 (s, 1H), 7.31 (dd, J=9.2, 2.9 Hz, 1H), 4.91 (spt, J=6.0 Hz, 1H), 4.47 (q, J=7.2 Hz, 2H), 1.46 (d, J=6.2 Hz, 6H), 1.38 (t, J=7.2 Hz, 3H). MS (ESI) 276.2 (M+H).

Step C. Example 328

The title compound was prepared according to methods described for the synthesis of Example 276 (Step B and C), by reaction of Intermediate 276A and Intermediate 328B: NMR (500 MHz, DMSO-d$_6$) δ 8.81 (s, 2H), 8.00 (d, J=9.3 Hz, 1H), 7.50 (s, 1H), 7.46 (dd, J=9.2, 2.7 Hz, 1H), 7.38 (d, J=2.5 Hz, 1H), 5.14-4.98 (m, 1H), 4.24 (s, 2H), 3.72 (s, 2H), 2.37-2.22 (m, 1H), 1.69-1.54 (m, 6H), 1.45 (d, J=6.0 Hz, 6H), 1.44-1.36 (m, 6H), 1.22-1.13 (m, 2H), 1.13-1.03 (m, 2H). FXR EC$_{50}$ (nM)=15. MS (ESI) 652.3 (M+H).

Example 329

6-((4-((5-cyclopropyl-3-(3,5-dichloropyridin-4-yl)isoxazol-4-yl)methoxy) bicyclo[2.2.2]octan-1-yl)methoxy)-4-(3-methoxyazetidin-1-yl)quinoline-2-carboxylic acid (329)

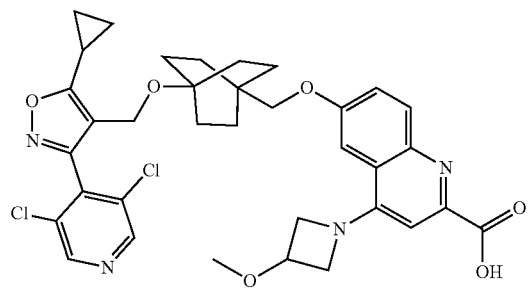

Step A. Intermediate 329A. Preparation of ethyl 6-(benzyloxy)-4-(3-methoxyazetidin-1-yl)quinoline-2-carboxylate

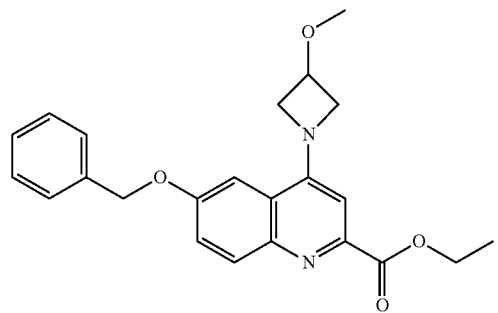 [SMILES: CCOC(=O)c1cc(N2CC(OC)C2)c2cc(OCc3ccccc3)ccc2n1]

To a stirred solution of Intermediate 324A (40 mg, 0.12 mmol) in DMF (1 mL) was added 3-methoxyazetidine (100 mg, 1.2 mmol) and Hunig's base (0.31 mL, 1.8 mmol). The reaction was stirred at 100° C. for 30 h. The reaction mixture was cooled, concentrated, and diluted with EtOAc. The organic layer was washed with sat. $NaHCO_3$ (aq.), dried over $MgSO_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (27 mg, 0.069 mmol, 59% yield) as a clear liquid. $^1$H NMR (500 MHz, CHLOROFORM-d) δ 8.13 (d, J=9.1 Hz, 1H), 7.52-7.46 (m, 2H), 7.46-7.40 (m, 3H), 7.40-7.33 (m, 1H), 7.21 (d, J=2.5 Hz, 1H), 7.05 (s, 1H), 5.21 (s, 2H), 4.53 (q, J=7.2 Hz, 2H), 4.48-4.42 (m, 2H), 4.41-4.31 (m, 1H), 4.14 (dd, J=8.8, 3.9 Hz, 2H), 3.38 (s, 3H), 1.49 (t, J=7.2 Hz, 3H). MS (ESI) 393.1 (M+H).

Step B. Intermediate 329B. Preparation of ethyl 6-hydroxy-4-(3-methoxyazetidin-1-yl) quinoline-2-carboxylate

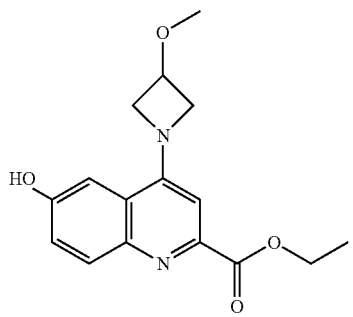 [SMILES: CCOC(=O)c1cc(N2CC(OC)C2)c2cc(O)ccc2n1]

The title compound was prepared according to methods described for the synthesis of Intermediate 324C, using Intermediate 329A as starting material (16 mg, 0.053 mmol, 77% yield): $^1$H NMR (400 MHz, CHLOROFORM-d) δ 7.87 (d, J=9.0 Hz, 1H), 7.29 (d, J=2.6 Hz, 1H), 7.23 (dd, J=9.2, 2.6 Hz, 1H), 6.85 (s, 1H), 4.44 (dd, J=8.8, 6.6 Hz, 2H), 4.38 (q, J=7.1 Hz, 2H), 4.31-4.22 (m, 1H), 4.18-4.05 (m, 2H), 3.29 (s, 3H), 1.29 (t, J=7.2 Hz, 3H). MS (ESI) 303.1 (M+H).

Step C. Example 329

The title compound was prepared according to methods described for the synthesis of Example 276 (Step B and C), by reaction of Intermediate 276A and Intermediate 329B: $^1$H NMR (500 MHz, DMSO-$d_6$) δ 8.82 (d, J=1.5 Hz, 2H), 8.16 (br d, J=9.3 Hz, 1H), 7.59 (br d, J=9.0 Hz, 1H), 7.32 (br s, 1H), 6.80 (s, 1H), 4.46 (br s, 1H), 4.23 (s, 2H), 3.83-3.50 (m, 7H), 3.41-3.28 (m, 2H), 2.35-2.24 (m, 1H), 1.54 (br d, J=8.1 Hz, 6H), 1.35 (br s, 6H), 1.20-1.12 (m, 2H), 1.08 (br s, 2H). FXR EC$_{50}$ (nM)=1400. MS (ESI) 679.3 (M+H).

Example 331

4-cyclopropoxy-6-((4-((5-cyclopropyl-3-(3,5-dichloropyridin-4-yl)isoxazol-4-yl)methoxy)bicyclo[2.2.2]octan-1-yl)methoxy)quinoline-2-carboxylic acid (331)

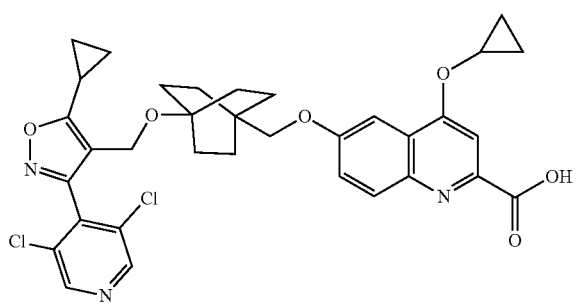

Step A. Intermediate 331A. Preparation of ethyl 6-(benzyloxy)-4-cyclopropoxyquinoline-2-carboxylate

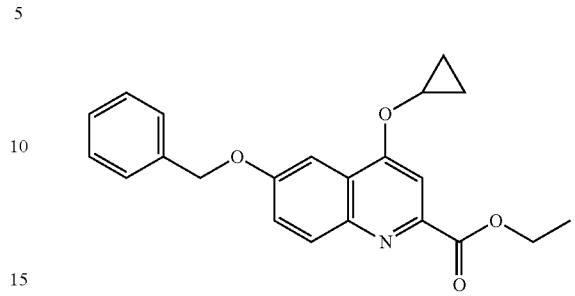

A mixture of Pd$_2$dba$_3$ (6.7 mg, 7.3 μmol), Cs$_2$CO$_3$ (48 mg, 0.15 mmol) and 2,2'-bis(diphenylphosphino)-1,1'-binaphthyl (14 mg, 0.022 mmol) in toluene (1 mL) was degassed with N$_2$ for 5 min. Intermediate 324A (25 mg, 0.073 mmol) and cyclopropanol (8.5 mg, 0.15 mmol) were added and the reaction was stirred at 100° C. for 16 h. The reaction mixture was cooled, filtered and concentrated. The crude material was purified by preparative HPLC (Phenomenex Luna AXIA 5m C18 30×100 mm column; detection at 220 nm; flow rate=40 mL/min; continuous gradient from 0% B to 100% B over 12 min+3 min hold time at 100% B, where A=90:10:0.1 H$_2$O:MeOH:TFA and B=90:10:0.1 MeOH:H$_2$O:TFA) to afford the title compound (12 mg, 0.033 mmol, 45% yield) as a white solid. $^1$H NMR (500 MHz, CHLOROFORM-d) δ 8.41 (br d, J=9.1 Hz, 1H), 8.02 (s, 1H), 7.65 (br dd, J=8.9, 2.1 Hz, 1H), 7.53 (d, J=2.5 Hz, 1H), 7.52-7.48 (m, 2H), 7.45 (t, J=7.3 Hz, 2H), 7.43-7.38 (m, 1H), 5.24 (s, 2H), 4.59 (q, J=7.0 Hz, 2H), 4.22 (tt, J=5.9, 2.9 Hz, 1H), 1.51 (t, J=7.0 Hz, 3H), 1.18-1.00 (m, 4H). MS (ESI) 364.1 (M+H).

Step B. Intermediate 331B. Preparation of ethyl 4-cyclopropoxy-6-hydroxyquinoline-2-carboxylate

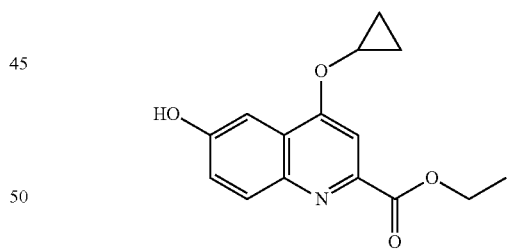

The title compound was prepared according to methods described for the synthesis of Intermediate 324C, using Intermediate 331A as starting material: $^1$H NMR (500 MHz, CHLOROFORM-d) δ 8.06 (d, J=9.1 Hz, 1H), 7.89 (s, 1H), 7.46 (d, J=2.8 Hz, 1H), 7.35 (dd, J=9.1, 2.8 Hz, 1H), 4.52 (q, J=7.2 Hz, 2H), 4.06 (tt, J=5.9, 3.0 Hz, 1H), 1.43 (t, J=7.0 Hz, 3H), 1.05-0.85 (m, 4H). MS (ESI) 274.1 (M+H).

Step C. Example 331

The title compound was prepared according to methods described for the synthesis of Example 276 (Step B and C), by reaction of Intermediate 276A and Intermediate 331B: $^1$H NMR (500 MHz, DMSO-$d_6$) δ 8.75 (s, 2H), 8.05 (br d, J=8.2

Hz, 1H), 7.82 (s, 1H), 7.45 (br d, J=7.2 Hz, 1H), 7.28 (br s, 1H), 4.21 (s, 2H), 3.83-3.72 (m, 1H), 3.60 (s, 2H), 2.25 (br s, 1H), 1.54 (br d, J=7.7 Hz, 6H), 1.36 (br d, J=6.9 Hz, 6H), 1.15 (br d, J=5.7 Hz, 2H), 1.05 (br s, 2H), 0.96 (br d, J=5.6 Hz, 2H), 0.86 (br s, 2H). FXR $EC_{50}$ (nM)=23. MS (ESI) 650.2 (M+H).

Example 332

6-((4-((5-cyclopropyl-3-(3,5-dichloropyridin-4-yl) isoxazol-4-yl)methoxy) bicyclo[2.2.2]octan-1-yl) methoxy)-4-(methylsulfonyl)quinoline-2-carboxylic acid (332)

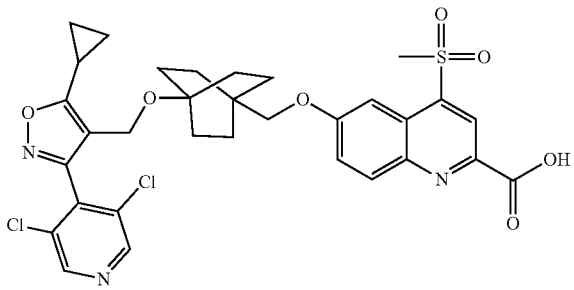

Step A. Intermediate 332A. Preparation of methyl 6-(benzyloxy)-4-(methylthio)quinoline-2-carboxylate

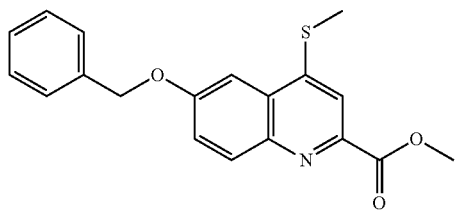 [SMILES: COC(=O)c1cc(SC)c2cc(OCc3ccccc3)ccc2n1]

Step 1: To a stirred solution of Intermediate 324A (35 mg, 0.10 mmol) in MeOH (1 mL) was added sodium thiomethoxide (14 mg, 0.21 mmol). The reaction was stirred at 60° C. for 16 h. An additional amount of sodium thiomethoxide (70 mg, 1.1 mmol) was added and the reaction was stirred at 60° C. for 2 days. The reaction mixture was cooled, concentrated and diluted with EtOAc. The organic layer was washed with 1 M HCl (aq.), dried over $MgSO_4$, filtered and concentrated to afford the acid as a yellow solid. MS (ESI) 326.1 (M+H).

Step 2: To the product of Step 1 above dissolved in DMF (1 mL) was added $K_2CO_3$ (38 mg, 0.28 mmol) and methyl iodide (0.14 mL, 0.28 mmol). The mixture was stirred at rt for 14 h. The reaction mixture was partitioned between brine and EtOAc. The organic layer was separated, washed with brine, dried over anhydrous $MgSO_4$, filtered and concentrated to afford the title compound (44 mg, 0.13 mmol, 100% yield) as a yellow solid. $^1$H NMR (500 MHz, CHLOROFORM-d) δ 8.19 (d, J=9.4 Hz, 1H), 7.94 (s, 1H), 7.55-7.48 (m, 3H), 7.47-7.42 (m, 3H), 7.41-7.35 (m, 1H), 5.24 (s, 2H), 4.09 (s, 3H), 2.71 (s, 3H). MS (ESI) 340.1 (M+H).

Step B. Intermediate 332B. Preparation of methyl 6-(benzyloxy)-4-(methylsulfonyl)quinoline-2-carboxylate

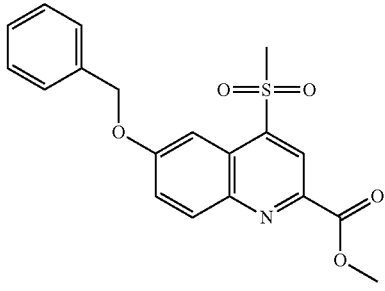 [SMILES: COC(=O)c1cc(S(C)(=O)=O)c2cc(OCc3ccccc3)ccc2n1]

To a stirred solution of Intermediate 332A (42 mg, 0.12 mmol) in DCM (5 mL) was added mCPBA (140 mg, 0.62 mmol). The reaction was stirred at rt for 4 h. The reaction mixture was concentrated and diluted with EtOAc. The organic layer was washed with sat. $NaHCO_3$ (aq.), dried over $MgSO_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (35 mg, 0.094 mmol, 76% yield) as a white solid. $^1$H NMR (400 MHz, CHLOROFORM-d) δ 8.76 (s, 1H), 8.35 (d, J=9.5 Hz, 1H), 8.03 (d, J=2.9 Hz, 1H), 7.64 (dd, J=9.4, 2.8 Hz, 1H), 7.55-7.47 (m, 2H), 7.46-7.38 (m, 2H), 7.38-7.31 (m, 1H), 5.34 (s, 2H), 4.09 (s, 3H), 2.97 (s, 3H). MS (ESI) 372.1 (M+H).

Step C. Intermediate 332C. Preparation of methyl 6-hydroxy-4-(methylsulfonyl)quinoline-2-carboxylate

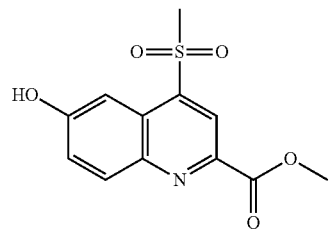 [SMILES: COC(=O)c1cc(S(C)(=O)=O)c2cc(O)ccc2n1]

The title compound was prepared according to methods described for the synthesis of Intermediate 324C, using Intermediate 332A as starting material: (12 mg, 0.043 mmol, 45% yield). $^1$H NMR (400 MHz, CHLOROFORM-d) δ 8.75 (s, 1H), 8.32 (d, J=9.2 Hz, 1H), 7.90 (d, J=2.4 Hz, 1H), 7.60-7.49 (m, 1H), 7.28 (d, J=0.9 Hz, 1H), 4.09 (s, 3H), 3.24 (s, 3H). MS (ESI) 282.0 (M+H).

Step D. Example 332

The title compound was prepared according to methods described for the synthesis of Example 276 (Step B and C), by reaction of Intermediate 276A and Intermediate 332C: $^1$H NMR (500 MHz, DMSO-$d_6$) δ 8.83 (s, 2H), 8.53 (s, 1H), 8.23 (br d, J=8.5 Hz, 1H), 7.79 (br s, 1H), 7.60 (br d, J=7.6 Hz, 1H), 4.24 (s, 2H), 3.77 (s, 2H), 3.42 (s, 3H), 2.39-2.22

(m, 1H), 1.58 (br d, J=8.2 Hz, 6H), 1.37 (br s, 6H), 1.21-1.13 (m, 2H), 1.09 (br d, J=2.7 Hz, 2H). FXR EC$_{50}$ (nM)=830. MS (ESI) 672.1 (M+H).

Example 334

5-((4-((5-cyclopropyl-3-(3,5-dichloropyridin-4-yl) isoxazol-4-yl)methoxy) bicyclo[2.2.2]octan-1-yl) methoxy)-3-isopropoxypicolinic acid

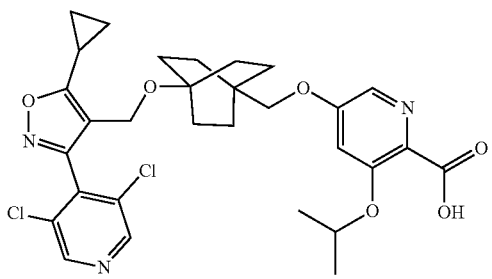

(334)

Step A. Intermediate 334A. Preparation of 5-fluoro-3-isopropoxypicolinonitrile

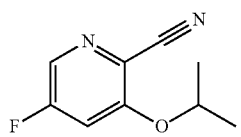

To a stirred solution of sodium isopropoxide (82 mg, 1.0 mmol) in 2-propanol (2 mL) was added 3,5-difluoropicolinonitrile (140 mg, 1.0 mmol) in 2-propanol (2 mL). The reaction was stirred at rt for 1 h. An additional amount of sodium isopropoxide (30 mg) was added and reaction was completed after 20 min. The reaction mixture was concentrated and diluted with EtOAc. The organic layer was washed with H$_2$O, dried over MgSO$_4$, filtered and concentrated. The crude product was purified by flash column chromatography (40 g silica gel cartridge; A=Hex, B=EtOAc; 20 min grad.; 0% B to 100% B; flow rate=40 mL/min). Fractions containing the desired product were combined, concentrated and dried in vacuo to afford the title compound (60 mg, 0.33 mmol, 33% yield) as a clear liquid. $^1$H NMR (500 MHz, CHLOROFORM-d) δ 8.15 (d, J=2.2 Hz, 1H), 7.09 (dd, J=9.6, 2.2 Hz, 1H), 4.65 (dt, J=12.1, 6.1 Hz, 1H), 1.47 (d, J=6.1 Hz, 6H). MS (ESI) 180.3 (M+H).

Step B. Intermediate 334B. Preparation of 5-(tert-butoxy)-3-isopropoxypicolinonitrile

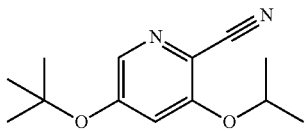 [SMILES: CC(C)Oc1cc(OC(C)(C)C)cnc1C#N]

To a stirred solution of Intermediate 334A (62 mg, 0.34 mmol) in THF (1 mL) at 0° C. was added sodium tert-butoxide (0.38 mL, 0.38 mmol) (1 M in THF). The mixture was warmed to rt and stirred for 2 h. The reaction mixture was concentrated and diluted with EtOAc. The organic layer was washed with H$_2$O, dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (70 mg, 0.30 mmol, 87% yield) as a clear liquid. $^1$H NMR (400 MHz, CHLOROFORM-d) δ 7.98 (d, J=2.2 Hz, 1H), 6.87 (d, J=1.8 Hz, 1H), 4.65-4.52 (m, 1H), 1.45 (s, 9H), 1.42 (d, J=6.2 Hz, 6H). MS (ESI) 235.2 (M+H).

Step C. Intermediate 334C. Preparation of 5-hydroxy-3-isopropoxypicolinonitrile

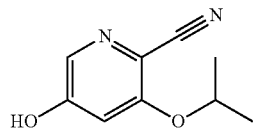

To a stirred solution of Intermediate 334B (70 mg, 0.30 mmol) in DCM (6 mL) was added TFA (0.23 mL, 3.0 mmol). The reaction was stirred for 2 h. The reaction mixture was concentrated and diluted with EtOAc. The organic layer was washed with H$_2$O, dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (40 mg, 0.22 mmol, 75% yield) as a clear liquid. $^1$H NMR (500 MHz, CHLOROFORM-d) δ 7.93 (d, J=1.7 Hz, 1H), 6.96 (d, J=1.9 Hz, 1H), 4.68 (spt, J=6.1 Hz, 1H), 1.44 (d, J=6.1 Hz, 6H). MS (ESI) 179.2 (M+H).

Step D. Example 334

The title compound was prepared according to combined methods described for the syntheses of Intermediate 276B and Example 278 (Step C), by reaction of Intermediate 276A and Intermediate 334C: $^1$H NMR (500 MHz, DMSO-d$_6$) δ 8.80 (s, 2H), 7.83 (br s, 1H), 7.07 (br s, 1H), 4.81-4.61 (m, 1H), 4.23 (s, 2H), 3.69 (br s, 2H), 2.35-2.23 (m, 1H), 1.53 (br d, J=8.1 Hz, 6H), 1.43-1.34 (m, 6H), 1.27 (br d, J=6.0 Hz, 6H), 1.19-1.12 (m, 2H), 1.08 (br d, J=2.9 Hz, 2H). FXR EC$_{50}$ (nM)=21. MS (ESI) 602.2 (M+H).

Example 335

5-((4-((5-cyclopropyl-3-(3,5-dichloropyridin-4-yl)isoxazol-4-yl)methoxy) bicyclo[2.2.2]octan-1-yl)methoxy)-3-methoxypicolinic acid (335)

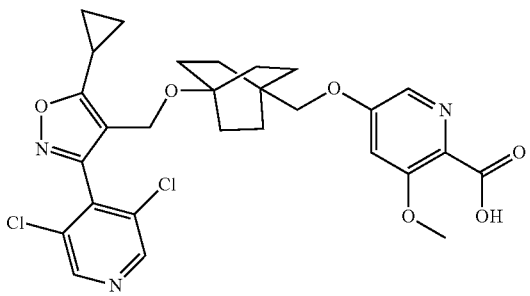

Step A. Intermediate 335A. Preparation of 5-bromo-3-methoxypicolinonitrile

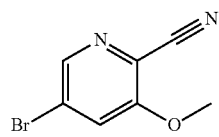

To a stirred solution of 5-bromo-3-nitropicolinonitrile (530 mg, 2.3 mmol) in MeOH (5 mL) at 0° C. was added sodium methoxide (0.58 mL, 2.5 mmol). The reaction was warmed to rt and stirred for 1 hr. The reaction mixture was concentrated and diluted with EtOAc. The organic layer was washed with $H_2O$, dried over $MgSO_4$, filtered and concentrated. The crude product was purified by flash column chromatography (24 g silica gel cartridge; A=Hex, B=EtOAc; 15 min grad.; 0% B to 70% B; flow rate=24 mL/min). Fractions containing the desired product were combined, concentrated and dried in vacuo to afford the title compound (300 mg, 1.4 mmol, 61% yield) as a light yellow solid. $^1$H NMR (500 MHz, CHLOROFORM-d) δ 8.38 (d, J=1.7 Hz, 1H), 7.55 (d, J=1.7 Hz, 1H), 4.01 (s, 3H). MS (ESI) 215.0 (M+H).

Step B. Intermediate 335B. Preparation of 5-hydroxy-3-methoxypicolinonitrile

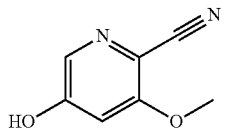

To a stirred solution of Intermediate 335A (54 mg, 0.25 mmol) in DMSO (0.5 mL) was added acetohydroxamic acid (57 mg, 0.76 mmol) and $K_2CO_3$ (180 mg, 1.3 mmol). The reaction was stirred at 80° C. for 2 h. The reaction mixture was cooled, concentrated and diluted with EtOAc. The organic layer was washed with $H_2O$, dried over $MgSO_4$, filtered and concentrated. The crude product was purified by flash column chromatography (24 g silica gel cartridge; A=Hex, B=EtOAc; 15 min grad.; 0% B to 70% B; flow rate=24 mL/min). Fractions containing the desired product were combined, concentrated and dried in vacuo to afford the title compound (40 mg, 0.27 mmol, 100% yield) as a white solid. $^1$H NMR (400 MHz, CHLOROFORM-d) δ 7.85 (d, J=2.2 Hz, 1H), 6.79 (d, J=2.2 Hz, 1H), 3.92 (s, 3H). MS (ESI) 151.2 (M+H).

Step C. Example 335

The title compound was prepared according to combined methods described for the syntheses of Intermediate 276B and Example 278 (Step C), by reaction of Intermediate 276A and Intermediate 335B: $^1$H NMR (500 MHz, DMSO-$d_6$) δ 8.79 (s, 2H), 7.75 (br s, 1H), 7.56 (br s, 1H), 4.22 (br s, 2H), 3.78 (br s, 3H), 3.42 (br s, 2H), 2.28 (br s, 1H), 1.51 (br s, 6H), 1.37 (br s, 6H), 1.15 (br d, J=8.0 Hz, 2H), 1.07 (br s, 2H). FXR $EC_{50}$ (nM)=170. MS (ESI) 574.2 (M+H).

Example 338

6-((4-((5-cyclopropyl-3-(3,5-dichloropyridin-4-yl)isoxazol-4-yl)methoxy) bicyclo[2.2.2]octan-1-yl)methoxy)-4-propylquinoline-2-carboxylic acid (338)

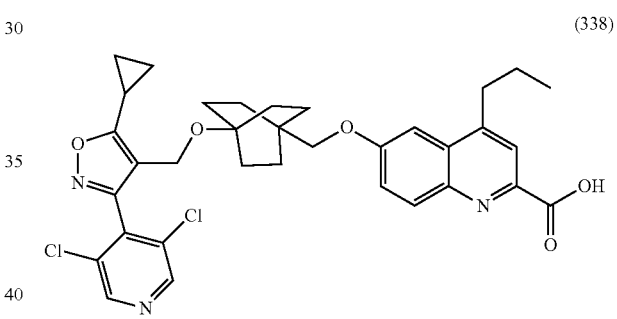

Step A. Intermediate 338A. Preparation of ethyl 6-hydroxy-4-propylquinoline-2-carboxylate

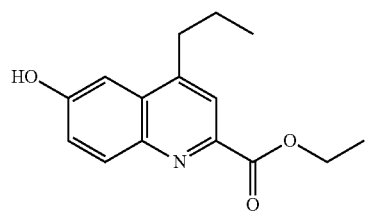 [SMILES: CCCc1cc(C(=O)OCC)nc2ccc(O)cc12]

To a stirred solution of Intermediate 324B (85 mg, 0.25 mmol) in ethanol (5 mL) and water (1 mL) was added palladium on carbon (26 mg, 0.024 mmol) (10% wt. loading, matrix activated carbon support) and ammonium formate (150 mg, 2.5 mmol). The reaction was stirred at 55° C. for 1 hr. The mixture was cooled, filtered through Celite and the filtrate was concentrated. The crude product was purified by flash column chromatography (12 g silica gel cartridge; A=Hex, B=EtOAc; 15 min grad.; 10% B to 100% B; flow rate=12 mL/min). Fractions containing the desired product were combined, concentrated and dried in vacuo to afford the title compound (55 mg, 0.21 mmol, 87% yield) as a white solid. $^1$H NMR (500 MHz, CHLOROFORM-d) δ 8.05 (d, J=9.4 Hz, 1H), 7.99 (s, 1H), 7.44 (d, J=2.8 Hz, 1H), 7.39 (dd, J=9.2, 2.6 Hz, 1H), 4.46 (q, J=7.2 Hz, 2H), 3.03-2.88 (m, 2H), 1.74 (sxt, J=7.5 Hz, 2H), 1.36 (t, J=7.2 Hz, 3H), 0.97 (t, J=7.3 Hz, 3H). MS (ESI) 260.1 (M+H).

Step B. Example 338

The title compound was prepared according to methods described for the synthesis of Example 276 (Step B and C), by reaction of Intermediate 276A and Intermediate 338A: $^1$H NMR (500 MHz, DMSO-d$_6$) δ 8.83 (s, 2H), 8.04 (br d, J=9.5 Hz, 1H), 7.91 (s, 1H), 7.46 (br d, J=8.2 Hz, 1H), 7.36 (br s, 1H), 4.24 (s, 2H), 3.76 (br s, 2H), 3.07 (br t, J=7.2 Hz, 2H), 2.32 (br s, 1H), 1.86-1.69 (m, 2H), 1.58 (br d, J=6.1 Hz, 6H), 1.38 (br s, 6H), 1.17 (br d, J=7.6 Hz, 2H), 1.09 (br s, 2H), 0.98 (br t, J=7.2 Hz, 3H). FXR EC$_{50}$ (nM)=17. MS (ESI) 636.3 (M+H).

Example 348

5-((4-((5-cyclopropyl-3-(3,5-dichloropyridin-4-yl)isoxazol-4-yl)methoxy) bicyclo[2.2.2]octan-1-yl)methoxy)-3-methylpicolinic acid

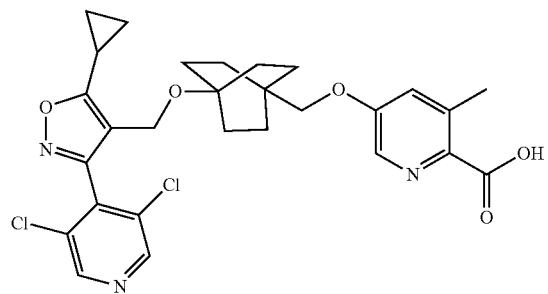

(348)

Step A. Intermediate 348A. Preparation of methyl 5-hydroxy-3-methylpicolinate

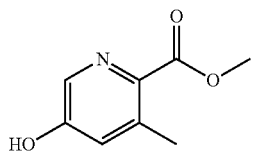

To a stirred solution of methyl 5-bromo-3-methylpicolinate (70 mg, 0.30 mmol) in DMSO (600 µl) was added acetohydroxamic acid (69 mg, 0.91 mmol) and K$_2$CO$_3$ (210 mg, 1.5 mmol). The mixture was stirred at 80° C. for 5 h. The reaction mixture was cooled, concentrated and diluted with EtOAc. The organic layer was washed with H$_2$O, dried over MgSO$_4$, filtered and concentrated. The crude product was purified by flash column chromatography (12 g silica gel cartridge; A=Hex, B=EtOAc; 15 min grad.; 0% B to 70% B; flow rate=12 mL/min). Fractions containing the desired product were combined, concentrated and dried in vacuo to afford the title compound (17 mg, 0.10 mmol, 33% yield) as a white solid. $^1$H NMR (500 MHz, Acetone) δ 9.46 (br s, 1H), 8.10 (d, J=2.5 Hz, 1H), 7.15 (d, J=2.5 Hz, 1H), 3.84 (s, 3H), 2.50 (s, 3H). MS (ESI) 168.2 (M+H).

Step B. Example 348

The title compound was prepared according to methods described for the synthesis of Example 276 (Step B and C), by reaction of Intermediate 276A and Intermediate 348A: $^1$H NMR (500 MHz, DMSO-d$_6$) δ 8.79 (s, 2H), 8.09 (br s, 1H), 7.28 (br s, 1H), 4.21 (s, 2H), 3.72 (br s, 2H), 2.48 (s, 3H), 2.33-2.22 (m, 1H), 1.49 (br d, J=7.9 Hz, 6H), 1.33 (br d, J=7.0 Hz, 6H), 1.20-1.12 (m, 2H), 1.06 (br d, J=2.7 Hz, 2H). FXR EC$_{50}$ (nM)=59. MS (ESI) 558.1 (M+H).

Example 349

8-cyclobutoxy-2-((4-((5-cyclopropyl-3-(3,5-dichloropyridin-4-yl)isoxazol-4-yl)methoxy) bicyclo[2.2.2]octan-1-yl)methoxy)quinoline-5-carboxylic acid

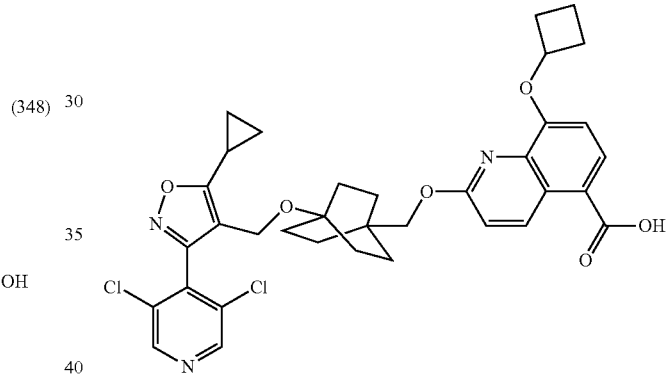

(349)

Step A. Intermediate 349A. Preparation of methyl 8-hydroxyquinoline-5-carboxylate

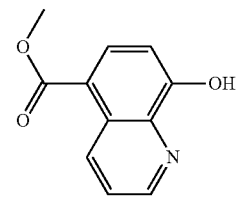

Step 1: To a stirred suspension of 3-amino-4-hydroxybenzoic acid (2.0 g, 13 mmol) in 6 M HCl (aq.) (10 mL) was added acrylaldehyde (1.1 g, 20 mmol) dropwise. The reaction was stirred at 100° C. for 2 h. The reaction was cooled to rt, conc. NH$_4$OH was added until pH ~9, and the reaction mixture was filtered to remove the solid. The filtrate was acidified with glacial AcOH to pH 4-5, and the solid was collected by vacuum filtration. The solid was suspended in 1:1 acetone/water (30 mL), and the product was collected by vacuum filtration to provide the desired acid (1.5 g) as a light brown solid.

Step 2: The crude acid was dissolved in MeOH (15 mL) and 1 mL concentrated $H_2SO_4$. The mixture was stirred at 80° C. for 24 h. The reaction mixture was cooled, concentrated and diluted with EtOAc. The organic layer was washed with 1 M NaOH (aq.), dried over $MgSO_4$, filtered and concentrated. The crude product was purified by flash column chromatography (40 g silica gel cartridge; A=Hex, B=EtOAc; 15 min grad.; 0% B to 100% B; flow rate=40 mL/min). Fractions containing the desired product were combined, concentrated and dried in vacuo to afford the title compound (290 mg, 1.4 mmol, 11% yield) as a white solid. $^1$H NMR (500 MHz, CHLOROFORM-d) δ 9.53 (dd, 1.5 Hz, 1H), 8.84 (dd, J=4.1, 1.7 Hz, 1H), 8.39 (d, J=8.3 Hz, 1H), 7.62 (dd, J=8.7, 4.3 Hz, 1H), 7.19 (d, J=8.3 Hz, 1H), 4.00 (s, 3H). MS (ESI) 204.2 (M+H).

Step B. Intermediate 349B. Preparation of cyclobutyl 8-cyclobutoxyquinoline-5-carboxylate

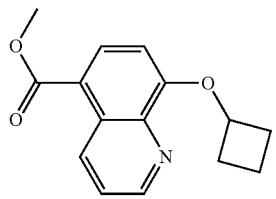 [SMILES: COC(=O)c1ccc(OC2CCC2)c2ncccc12]

Intermediate 349A (84 mg, 0.41 mmol), bromocyclobutane (84 mg, 0.62 mmol) and $Cs_2CO_3$ (400 mg, 1.2 mmol) were dissolved in dry DMF (1 mL) and stirred at 95° C. in a sealed vial. After 16 h, the reaction mixture was cooled, concentrated and diluted with EtOAc. The organic layer was washed with 1 M HCl (aq.), dried over $MgSO_4$, filtered and concentrated. The crude product was purified by flash column chromatography (12 g silica gel cartridge; A=Hex, B=EtOAc; 15 min grad.; 0% B to 50% B; flow rate=12 mL/min). Fractions containing the desired product were combined, concentrated and dried in vacuo to afford the title compound (103 mg, 0.40 mmol, 97% yield) as a clear liquid. $^1$H NMR (400 MHz, CHLOROFORM-d) δ 9.45 (dd, J=8.8, 1.8 Hz, 1H), 8.97 (dd, J=4.2, 1.8 Hz, 1H), 8.27 (d, J=8.4 Hz, 1H), 7.54 (dd, J=8.7, 4.1 Hz, 1H), 6.88 (d, J=8.4 Hz, 1H), 4.93 (quin, J=7.2 Hz, 1H), 3.95 (s, 3H), 2.67-2.55 (m, 2H), 2.53-2.41 (m, 2H), 2.01-1.86 (m, 1H), 1.83-1.68 (m, 1H). MS (ESI) 258.2 (M+H).

Step C. Intermediate 349. Preparation of methyl 2-chloro-8-cyclobutoxyquinoline-5-carboxylate

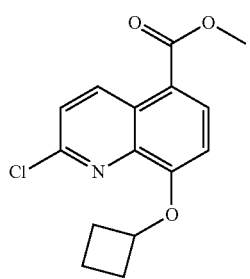 [SMILES: COC(=O)c1ccc(OC2CCC2)c2nc(Cl)ccc12]

Step 1: To a stirred suspension of Intermediate 349B (103 mg, 0.40 mmol) in DCM (3 mL) was added mCPBA (150 mg, 0.52 mmol). The reaction was stirred at rt for 20 h. The mixture was diluted with DCM. The organic layer was washed with sodium metabisulfite solution (aq.), sat. $NaHCO_3$ (aq.), dried over $MgSO_4$, filtered and concentrated to give crude N-oxide (130 mg, 0.48 mmol, 119% yield) as a yellow solid (contains some mCPBA). MS (ESI) 274.2 (M+H).

Step 2: To solution of the product of Step 1 above (130 mg, 0.48 mmol) in DCM (5 mL) were added phosphorus oxychloride (0.053 mL, 0.57 mmol) and DMF (0.018 mL, 0.24 mmol) at 0° C. After stirring 5 min, the reaction was brought to rt and stirred at 70° C. for 3 h. The reaction mixture was cooled, concentrated and diluted with EtOAc. The organic layer was washed with 1 M NaOH (aq.), dried over $MgSO_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (50 mg, 0.17 mmol, 36% yield) as a clear liquid. $^1$H NMR (400 MHz, CHLOROFORM-d) δ 9.45 (d, J=9.0 Hz, 1H), 8.28 (d, J=8.6 Hz, 1H), 7.53 (d, J=9.0 Hz, 1H), 6.92 (d, J=8.6 Hz, 1H), 4.93 (quin, J=7.2 Hz, 1H), 3.97 (s, 3H), 2.70-2.56 (m, 2H), 2.54-2.41 (m, 2H), 2.04-1.89 (m, 1H), 1.86-1.71 (m, 1H). MS (ESI) 292.1 (M+H).

Step D. Example 349

The title compound was prepared according to methods described for the synthesis of Example 104, by reaction of Intermediate 276A and Intermediate 349C: $^1$H NMR (500 MHz, DMSO-$d_6$) δ 9.60 (br d, J=9.3 Hz, 1H), 8.80 (s, 2H), 7.74 (br d, J=7.9 Hz, 1H), 6.89 (d, J=8.2 Hz, 1H), 6.86 (d, J=9.3 Hz, 1H), 4.90-4.81 (m, 1H), 4.24 (s, 2H), 4.06 (s, 2H), 2.49-2.41 (m, 2H), 2.34-2.26 (m, 1H), 2.20-2.08 (m, 2H), 1.90-1.77 (m, 1H), 1.67 (br d, J=10.4 Hz, 1H), 1.61-1.53 (m, 6H), 1.45-1.33 (m, 6H), 1.20-1.13 (m, 2H), 1.09 (br d, J=2.8 Hz, 2H). FXR $EC_{50}$ (nM)=130. MS (ESI) 664.1 (M+H).

Example 350

2-((4-((3-(3-chloro-5-methoxypyridin-4-yl)-5-cyclopropylisoxazol-4-yl)methoxy) bicyclo[2.2.2]octan-1-yl)methoxy)-4-methoxyquinoline-6-carboxylic acid

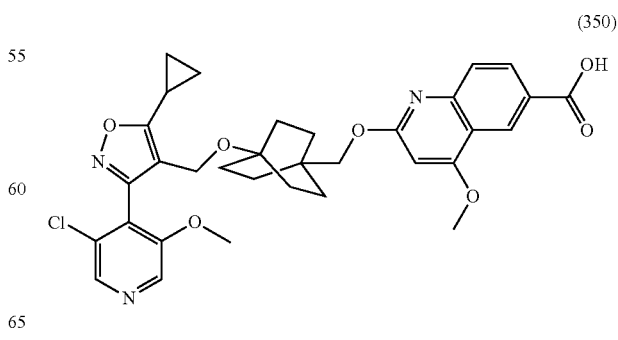

(350)

Step A. Intermediate 350A. Preparation of methyl 4-methoxyquinoline-6-carboxylate

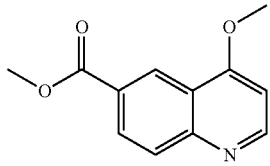

To a stirred suspension of methyl 4-bromoquinoline-6-carboxylate (130 mg, 0.47 mmol) in MeOH (3 mL) was added sodium methoxide (0.22 mL, 0.94 mmol). The reaction was stirred at 80° C. for 16 h. The reaction mixture was cooled, concentrated and dissolved with MeOH (3 mL). To this solution was added concentrated $H_2SO_4$ (0.5 mL) and the mixture was stirred at 80° C. for 15 h. The reaction mixture was cooled, concentrated and diluted with EtOAc. The organic layer was washed with 1 M NaOH (aq.), dried over $MgSO_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (74 mg, 0.34 mmol, 73% yield) as a white solid. $^1$H NMR (500 MHz, CHLOROFORM-d) δ 8.97 (d, J=1.7 Hz, 1H), 8.84 (d, J=5.2 Hz, 1H), 8.29 (dd, J=8.8, 1.9 Hz, 1H), 8.07 (d, J=8.8 Hz, 1H), 6.80 (d, J=5.2 Hz, 1H), 4.10 (s, 3H), 4.00 (s, 3H). MS (ESI) 218.2 (M+H).

Step B. Intermediate 350B. Preparation of methyl 2-chloro-4-methoxyquinoline-6-carboxylate

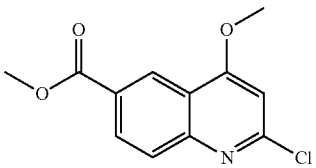 [SMILES: COC(=O)c1ccc2nc(Cl)cc(OC)c2c1]

The title compound was prepared according to methods described for the synthesis of Intermediate 349C, substituting Intermediate 350A where appropriate: (47 mg, 0.19 mmol, 24% yield, white solid). $^1$H NMR (400 MHz, CHLOROFORM-d) δ 8.89 (d, J=2.0 Hz, 1H), 8.31 (dd, J=8.8, 2.0 Hz, 1H), 7.98 (d, J=8.8 Hz, 1H), 6.81 (s, 1H), 4.12 (s, 3H), 4.01 (s, 3H). MS (ESI) 252.1 (M+H).

Step C. Example 350

The title compound was prepared according to methods described for the synthesis of Example 104, by reaction of Intermediate 276A and Intermediate 350B: $^1$H NMR (500 MHz, DMSO-$d_6$) δ 8.56 (s, 1H), 8.51 (s, 1H), 8.43 (s, 1H), 8.12 (br d, J=8.4 Hz, 1H), 7.54 (br d, J=8.5 Hz, 1H), 6.37 (s, 1H), 4.15 (s, 2H), 4.02 (s, 3H), 3.91 (s, 2H), 3.40 (s, 3H), 2.26 (ddd, J=13.2, 8.4, 4.8 Hz, 1H), 1.67-1.49 (m, 6H), 1.47-1.33 (m, 6H), 1.20-1.10 (m, 2H), 1.07 (br d, J=3.3 Hz, 2H). FXR $EC_{50}$ (nM)=890. MS (ESI) 620.4 (M+H).

Example 351

2-((4-((3-(3-chloro-5-methoxypyridin-4-yl)-5-cyclopropylisoxazol-4-yl)methoxy) bicyclo[2.2.2]octan-1-yl)methoxy)-8-cyclopropylquinoline-6-carboxylic acid

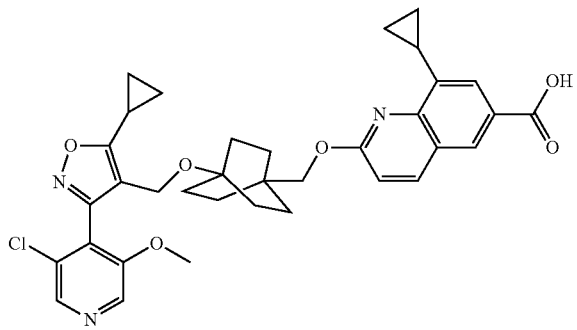

(351)

Step A. Intermediate 351A. Preparation of methyl 8-bromoquinoline-6-carboxylate

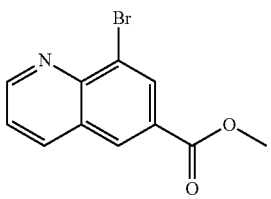

To a stirred suspension of quinoline-6-carboxylic acid (350 mg, 2.0 mmol) in TFA (1 mL) and 0.3 mL concentrated $H_2SO_4$ was added NBS (530 mg, 3.0 mmol). The reaction was stirred at 80° C. for 16 h. The reaction mixture was cooled and diluted with EtOAc. The organic layer was washed with 1 M NaOH (aq.), dried over $MgSO_4$, filtered and concentrated. The residue was dissolved in MeOH (5 mL) and 0.5 mL concentrated $H_2SO_4$. The mixture was stirred at 80° C. for 3 h. The reaction mixture was cooled, concentrated and diluted with EtOAc. The organic layer was washed with 1 M NaOH (aq.), dried over $MgSO_4$, filtered and concentrated. The crude product was purified by flash column chromatography (24 g silica gel cartridge; A=Hex, B=EtOAc; 15 min grad.; 0% B to 100% B; flow rate=24 mL/min). Fractions containing the desired product were combined, concentrated and dried in vacuo to afford the title compound (170 mg, 0.64 mmol, 32% yield) as a white solid. $^1$H NMR (400 MHz, CHLOROFORM-d) δ 8.98 (dd, J=4.3, 1.7 Hz, 1H), 8.48 (d, J=2.0 Hz, 1H), 8.39 (d, J=1.8 Hz, 1H), 8.12 (dd, J=8.3, 1.7 Hz, 1H), 7.39 (dd, J=8.1, 4.2 Hz, 1H), 3.86 (s, 3H). MS (ESI) 268.0 (M+H).

Step B. Intermediate 351B. Preparation of methyl 8-cyclopropylquinoline-6-carboxylate

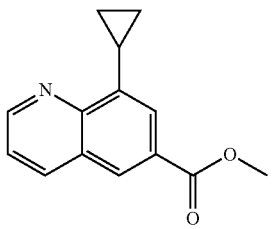 [SMILES: COC(=O)c1cc(C2CC2)c2ncccc2c1]

The title compound was prepared according to methods described for the synthesis of Intermediate 324B, substituting Intermediate 351A where appropriate: (45 mg, 0.35 mmol, 80% yield, clear liquid). $^1$H NMR (400 MHz, CHLOROFORM-d) δ 9.07 (dd, J=4.2, 1.8 Hz, 1H), 8.39 (d, J=1.8 Hz, 1H), 8.25 (dd, J=8.4, 1.8 Hz, 1H), 7.78 (d, J=2.0 Hz, 1H), 7.49 (dd, J=8.4, 4.2 Hz, 1H), 3.99 (s, 3H), 3.21 (tt, J=8.6, 5.3 Hz, 1H), 1.29-1.18 (m, 2H), 1.01-0.90 (m, 2H). MS (ESI) 228.2 (M+H).

Step C. Intermediate 351C. Preparation of methyl 2-chloro-8-cyclopropylquinoline-6-carboxylate

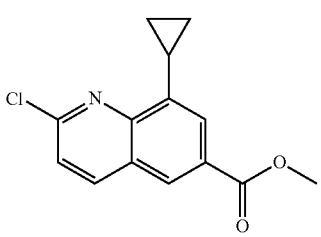 [SMILES: COC(=O)c1cc(C2CC2)c2nc(Cl)ccc2c1]

The title compound was prepared according to methods described for the synthesis of Intermediate 349C, substituting Intermediate 351B where appropriate: (13 mg, 0.050 mmol, 30% yield, clear liquid). $^1$H NMR (400 MHz, CHLOROFORM-d) δ 8.35 (d, J=1.8 Hz, 1H), 8.18 (d, J=8.6 Hz, 1H), 7.75 (d, J=2.0 Hz, 1H), 7.46 (d, J=8.6 Hz, 1H), 3.99 (s, 3H), 3.19 (tt, J=8.6, 5.3 Hz, 1H), 1.30-1.17 (m, 2H), 1.00-0.88 (m, 2H). MS (ESI) 262.1 (M+H).

Step D. Example 351

The title compound was prepared according to methods described for the synthesis of Example 104, by reaction of Intermediate 276A and Intermediate 351C: $^1$H NMR (500 MHz, DMSO-d$_6$) δ 8.52 (s, 1H), 8.45 (s, 1H), 8.31 (br d, J=8.9 Hz, 1H), 8.25 (s, 1H), 7.61 (s, 1H), 7.03 (br d, J=8.9 Hz, 1H), 4.14 (br s, 2H), 4.12 (br s, 2H), 3.90 (s, 3H), 2.97 (br s, 1H), 2.28 (br s, 1H), 1.56 (br d, J=6.4 Hz, 6H), 1.38 (br s, 6H), 1.20-1.00 (m, 6H), 0.82 (br d, J=3.4 Hz, 2H). FXR EC$_{50}$ (nM)=23. MS (ESI) 630.3 (M+H).

Example 352

3-((4-((5-cyclopropyl-3-(3,5-dichloropyridin-4-yl)isoxazol-4-yl)methoxy) bicyclo[2.2.2]octan-1-yl)methoxy)quinoline-8-carboxylic acid

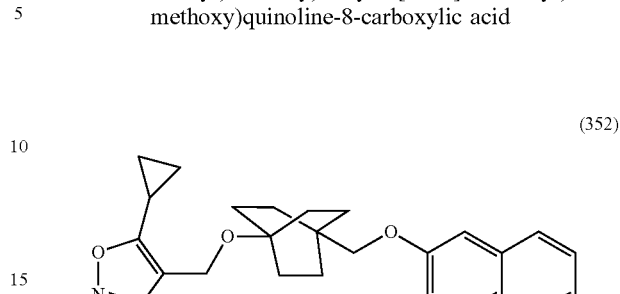

(352)

Step A. Intermediate 352A. Preparation of methyl quinoline-8-carboxylate

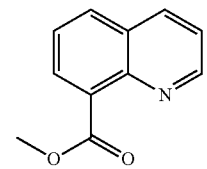

To a stirred solution of quinoline-8-carboxylic acid (140 mg, 0.78 mmol) in MeOH (4 mL) was added concentrated H$_2$SO$_4$ (0.1 mL). The reaction was stirred at 70° C. for 16 h. The reaction mixture was cooled, concentrated and diluted with EtOAc. The organic layer was washed with 1 M HCl (aq.), dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (110 mg, 0.60 mmol, 77% yield) as a light yellow liquid. $^1$H NMR (500 MHz, CHLOROFORM-d) δ 9.07 (dd, J=4.3, 1.8 Hz, 1H), 8.19 (dd, J=8.3, 1.7 Hz, 1H), 8.05 (dd, J=7.2, 1.4 Hz, 1H), 7.95 (dd, J=8.1, 1.2 Hz, 1H), 7.65-7.53 (m, 1H), 7.47 (dd, J=8.3, 4.1 Hz, 1H), 4.07 (s, 3H). MS (ESI) 188.2 (M+H).

Step B. Intermediate 352B. Preparation of methyl 3-hydroxyquinoline-8-carboxylate

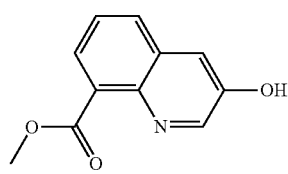

To a stirred solution of Intermediate 352A (110 mg, 0.60 mmol) in glacial acetic acid (1 mL) was added 30% H$_2$O$_2$ (0.12 mL, 1.2 mmol). The reaction was stirred at 70° C. for 2 h. The reaction mixture was cooled, concentrated and diluted with EtOAc. The organic layer was washed with sat. NaHCO$_3$ (aq.), dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (30 mg, 0.15 mmol, 24% yield) as a yellow solid. $^1$H NMR (500 MHz, CHLOROFORM-d) δ 8.73 (d, J=2.5 Hz, 1H), 7.93 (dd, J=7.2, 0.8 Hz, 1H), 7.79-7.73 (m, 1H), 7.55 (d, J=2.5 Hz, 1H), 7.48 (t, J=7.7 Hz, 1H), 4.01 (s, 3H). MS (ESI) 204.2 (M+H).

Step C. Example 352

The title compound was prepared according to methods described for the synthesis of Example 276 (Step B and C), by reaction of Intermediate 276A and Intermediate 352B: $^1$H NMR (500 MHz, DMSO-d$_6$) δ 8.84 (s, 3H), 8.28 (br d, J=5.8 Hz, 1H), 8.18 (br d, J=8.5 Hz, 1H), 8.09 (br s, 1H), 7.76 (t, J=7.6 Hz, 1H), 4.25 (s, 2H), 3.80 (s, 2H), 2.36-2.26 (m, 1H), 1.69-1.53 (m, 6H), 1.46-1.32 (m, 6H), 1.22-1.13 (m, 2H), 1.12-1.04 (m, 2H). FXR
EC$_{50}$ (nM)=55. MS (ESI) 594.3 (M+H).

Example 354

4-((1-chloro-3-hydroxypropan-2-yl)oxy)-6-((4-((5-cyclopropyl-3-(3,5-dichloropyridin-4-yl)isoxazol-4-yl)methoxy)bicyclo[2.2.2]octan-1-yl)methoxy)quinoline-2-carboxylic acid (354)

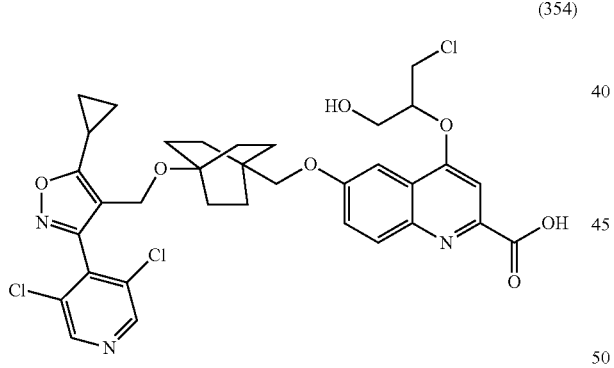

To a stirred solution of Example 361 (20 mg, 0.029 mmol) in 1,4-dioxane (1 mL) was added 1 M HCl (aq.) (0.10 mL, 0.10 mmol). After stirring 1 h, the reaction was concentrated. The crude material was purified by preparative HPLC (Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 27% B, 27-67% B over 20 minutes, then a 4-minute hold at 100% B; Flow Rate: 20 mL/min; Column Temperature: 25° C. Fraction collection was triggered by UV signals). Fractions containing the desired product were combined, concentrated and dried in vacuo to provide the title compound: (12 mg, 57% yield). $^1$H NMR (500 MHz, DMSO-d$_6$) δ 8.82 (s, 2H), 8.02 (br d, J=9.2 Hz, 1H), 7.52 (s, 1H), 7.49-7.39 (m, 2H), 4.42-4.34 (m, 1H), 4.33-4.27 (m, 1H), 4.27-4.23 (m, 1H), 4.23 (s, 2H), 3.90-3.81 (m, 1H), 3.81-3.75 (m, 1H), 3.72 (br s, 2H), 2.35-2.25 (m, 1H), 1.56 (br d, J=7.3 Hz, 6H), 1.36 (br d, J=7.3 Hz, 6H), 1.22-1.13 (m, 2H), 1.11-1.04 (m, 2H). FXR EC$_{50}$ (nM)=200. MS (ESI) 702.1 (M+H).

Example 357

7-((4-((5-cyclopropyl-3-(3,5-dichloropyridin-4-yl)isoxazol-4-yl)methoxy) bicyclo[2.2.2]octan-1-yl) methoxy)-1-isopropoxyisoquinoline-3-carboxylic acid (357)

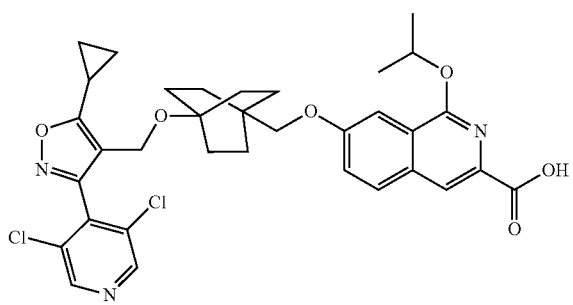

Step A. Intermediate 357A. Preparation of 2-(tert-butyl) 3-methyl (R)-7-hydroxy-3,4-dihydroisoquinoline-2,3(1H)-dicarboxylate

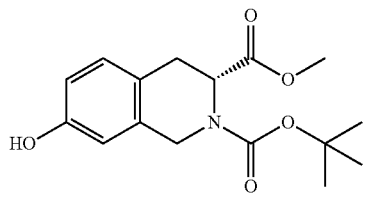 [SMILES: COC(=O)[C@H]1Cc2ccc(O)cc2CN1C(=O)OC(C)(C)C]

To a stirred solution of (R)-2-(tert-butoxycarbonyl)-7-hydroxy-1,2,3,4-tetrahydroisoquinoline-3-carboxylic acid (1.0 g, 3.4 mmol) in DCM (10 mL) was added Hunig's base (1.2 mL, 6.8 mmol) and iodomethane (3.4 mL, 6.8 mmol). The reaction was stirred at 65° C. for 48 h. The reaction mixture was cooled, washed with sat. NH$_4$Cl (aq.), dried over MgSO$_4$, filtered and concentrated to afford the title compound (1.5 g, 4.9 mmol, 143% yield) as a dark brown liquid. $^1$H NMR (400 MHz, CHLOROFORM-d) δ 6.98-6.86 (m, 1H), 6.69-6.49 (m, 2H), 5.04 (br dd, J=5.9, 2.9 Hz, 1H), 4.63-4.50 (m, 1H), 4.37 (br t, J=16.4 Hz, 1H), 3.57 (s, 3H), 3.18 (qd, J=7.4, 3.3 Hz, 1H), 3.01 (br d, J=4.8 Hz, 1H), 1.39 (s, 9H). MS (ESI) 308.2 (M+H).

Step B. Intermediate 357B. Preparation of 2-(tert-butyl) 3-methyl (R)-7-(benzyloxy)-3,4-dihydroisoquinoline-2,3(1H)-dicarboxylate

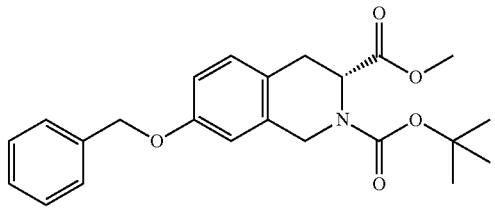 [SMILES: COC(=O)[C@H]1Cc2ccc(OCc3ccccc3)cc2CN1C(=O)OC(C)(C)C]

To a stirred solution of Intermediate 357A (1.5 g, 4.9 mmol) in DMF (15 mL) was added K₂CO₃ (1.0 g, 7.3 mmol) and benzyl bromide (0.76 mL, 6.3 mmol). The reaction was stirred at 70° C. for 24 h. The reaction mixture was diluted with EtOAc and washed with H₂O, dried over MgSO₄, filtered and concentrated. The crude product was purified by flash column chromatography (80 g silica gel cartridge; A=Hex, B=EtOAc; 25 min grad.; 0% B to 100% B; flow rate=60 mL/min). Fractions containing the desired product were combined, concentrated and dried in vacuo to afford the title compound (0.88 g, 2.2 mmol, 45% yield) as a light yellow liquid. $^1$H NMR (500 MHz, CHLOROFORM-d) δ 7.49-7.38 (m, 4H), 7.38-7.32 (m, 1H), 7.08 (d, J=8.3 Hz, 1H), 6.88-6.73 (m, 2H), 5.21-5.11 (m, 1H), 5.06 (s, 2H), 4.76-4.63 (m, 1H), 4.57-4.43 (m, 1H), 3.67 (s, 3H), 3.29-3.18 (m, 1H), 3.16-3.07 (m, 1H), 1.58 (s, 9H). MS (ESI) 398.2 (M+H).

Step C. Intermediate 357C. Preparation of methyl 7-(benzyloxy)isoquinoline-3-carboxylate

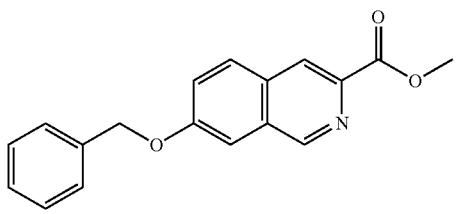 [SMILES: COC(=O)c1cc2ccc(OCc3ccccc3)cc2cn1]

A stirred solution of Intermediate 357B (880 mg, 2.2 mmol) in 0.4 M HCl (aq.) (5.5 mL, 22 mmol) was stirred at rt for 1 h. The reaction was concentrated and dissolved in toluene (5 mL). To this mixture was added DDQ (1.0 g, 4.4 mmol) and the reaction was stirred at reflux for 30 min. The reaction mixture was cooled, diluted with EtOAc and washed with H₂O. The organic layer was dried over MgSO₄, filtered and concentrated. The crude product was purified by flash column chromatography (80 g silica gel cartridge; A=Hex, B=EtOAc; 25 min grad.; 0% B to 100% B; flow rate=60 mL/min). Fractions containing the desired product were combined, concentrated and dried in vacuo to afford the title compound (230 mg, 0.78 mmol, 35% yield) as a light yellow solid. $^1$H NMR (400 MHz, CHLOROFORM-d) δ 9.23 (s, 1H), 8.55 (s, 1H), 7.92 (d, J=9.0 Hz, 1H), 7.58-7.49 (m, 3H), 7.47-7.37 (m, 4H), 5.26 (s, 2H), 4.06 (s, 3H). MS (ESI) 294.1 (M+H).

Step D. Intermediate 357D. Preparation of methyl 7-(benzyloxy)-1-chloroisoquinoline-3-carboxylate

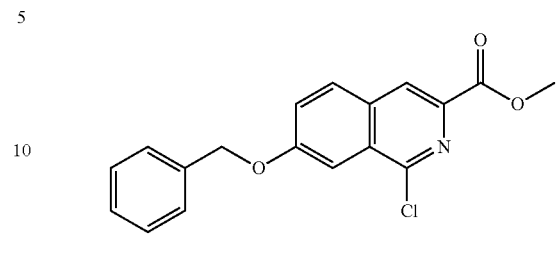

The title compound was prepared according to methods described for the synthesis of Intermediate 349C, substituting Intermediate 357C where appropriate: (74 mg, 0.23 mmol, 58% yield, white solid). $^1$H NMR (400 MHz, CHLOROFORM-d) δ 8.48 (s, 1H), 7.93 (d, J=9.0 Hz, 1H), 7.75 (d, J=2.4 Hz, 1H), 7.61-7.50 (m, 3H), 7.49-7.36 (m, 3H), 5.29 (s, 2H), 4.05 (s, 3H). MS (ESI) 328.1 (M+H).

Step E. Intermediate 357E. Preparation of methyl 7-(benzyloxy)-1-isopropoxyisoquinoline-3-carboxylate

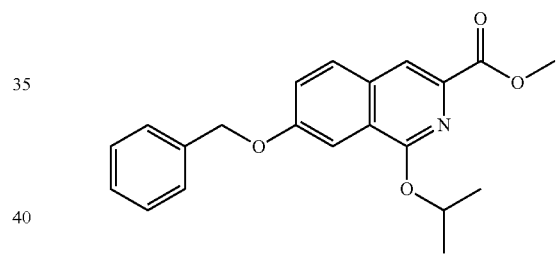

Step 1: To a stirred solution of Intermediate 357D (62 mg, 0.19 mmol) in 2-propanol (1.9 mL) was added sodium isopropoxide (62 mg, 0.76 mmol). The reaction was stirred at 90° C. for 3 days. The reaction mixture was cooled, concentrated and diluted with EtOAc. The organic layer was washed with 1 M HCl (aq.), dried over MgSO₄, filtered and concentrated to give the acid (110 mg). MS (ESI) 338.2 (M+H).

Step 2: To a solution of the product of Step 1 above dissolved in acetone (5 mL), were added K₂CO₃ (53 mg, 0.38 mmol) and iodomethane (40 mg, 0.285 mmol). The mixture was stirred at 60° C. After 5 h, the reaction was cooled, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (20 mg, 0.057 mmol, 30% yield) as a light yellow liquid. $^1$H NMR (500 MHz, CHLOROFORM-d) δ 8.10 (s, 1H), 7.80 (d, J=9.1 Hz, 1H), 7.71 (d, J=2.5 Hz, 1H), 7.53 (d, J=7.4 Hz, 2H), 7.49-7.42 (m, 3H), 7.42-7.35 (m, 1H), 5.75 (spt, J=6.2 Hz, 1H), 5.25 (s, 2H), 4.00 (s, 3H), 1.50 (d, J=6.3 Hz, 6H). MS (ESI) 352.2 (M+H).

Step F. Intermediate 357F. Preparation of methyl 7-hydroxy-1-isopropoxyisoquinoline-3-carboxylate

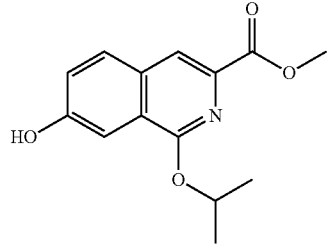 [SMILES: COC(=O)c1cc2ccc(O)cc2c(OC(C)C)n1]

The title compound was prepared according to methods described for the synthesis of Intermediate 324C, substituting Intermediate 357E where appropriate: (12 mg, 0.046 mmol, 81% yield, white solid). $^1$H NMR (500 MHz, ACETONE-$d_6$) δ 8.20 (s, 1H), 7.99 (d, J=8.8 Hz, 1H), 7.90 (br s, 1H), 7.67 (d, J=1.9 Hz, 1H), 7.48 (dd, J=8.8, 2.5 Hz, 1H), 5.72 (spt, J=6.2 Hz, 1H), 4.03 (s, 3H), 1.57 (d, J=6.3 Hz, 6H). MS (ESI) 262.2 (M+H).

Step G. Example 357

The title compound was prepared according to methods described for the synthesis of Example 276 (Step B and C), by reaction of Intermediate 276A and Intermediate 352B: $^1$H NMR (500 MHz, DMSO-$d_6$) δ 8.82 (s, 2H), 8.08 (s, 1H), 7.98 (d, J=8.9 Hz, 1H), 7.43 (br d, J=8.9 Hz, 1H), 7.40 (s, 1H), 5.63 (quin, J=6.1 Hz, 1H), 4.23 (s, 2H), 3.90 (s, 2H), 2.35-2.26 (m, 1H), 1.63-1.51 (m, 6H), 1.40 (d, J=6.1 Hz, 6H), 1.38-1.32 (m, 6H), 1.20-1.12 (m, 2H), 1.11-1.04 (m, 2H). FXR $EC_{50}$ (nM)=13. MS (ESI) 652.3 (M+H).

Example 362

2-((4-((5-cyclopropyl-3-(2,6-dichlorophenyl)isoxazol-4-yl)methoxy)bicyclo[2.2.2]octan-1-yl)methyl)-1,2,3,4-tetrahydroisoquinoline-7-carboxylic acid (362)

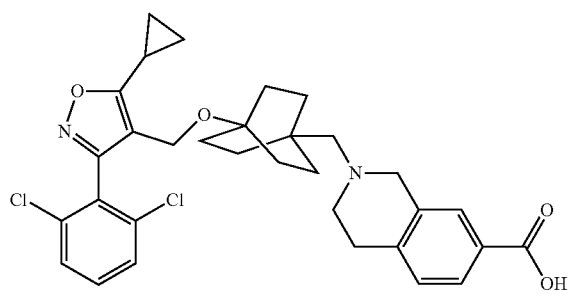

Step A. Intermediate 362A. Preparation of methyl 2-((4-((5-cyclopropyl-3-(2,6-dichlorophenyl)isoxazol-4-yl)methoxy)bicyclo[2.2.2]octan-1-yl)methyl)-1,2,3,4-tetrahydroisoquinoline-7-carboxylate

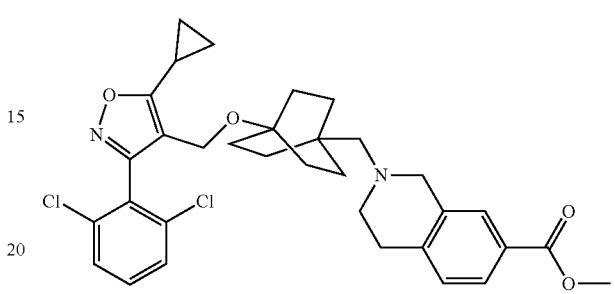

To a solution of Intermediate 121A (15 mg, 0.036 mmol) in DCE (1 mL) were added methyl 1,2,3,4-tetrahydroisoquinoline-7-carboxylate, HCl (24 mg, 0.11 mmol), glacial AcOH (2 drops) and 3 Å molecular sieves (100 mg), followed by sodium triacetoxyborohydride (45 mg, 0.21 mmol). The reaction was stirred at 85° C. for 12 h. The reaction mixture was cooled, filtered, concentrated and diluted with EtOAc. The organic layer was washed with sat. NH$_4$Cl (aq.), dried over MgSO$_4$, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (15 mg, 0.025 mmol, 71% yield) as a white solid. $^1$H NMR (400 MHz, CHLOROFORM-d) δ 7.77 (dd, J=7.9, 1.5 Hz, 1H), 7.65 (d, J=1.1 Hz, 1H), 7.39 (d, J=1.5 Hz, 1H), 7.37 (s, 1H), 7.34-7.28 (m, 1H), 7.14 (d, J=7.9 Hz, 1H), 4.15 (s, 2H), 3.89 (s, 3H), 3.65 (s, 2H), 2.94-2.83 (m, 2H), 2.78-2.66 (m, 2H), 2.34 (t, J=7.6 Hz, 1H), 2.13-2.06 (m, 2H), 1.54-1.36 (m, 12H), 1.25-1.16 (m, 2H), 1.13-1.03 (m, 2H). MS (ESI) 595.3 (M+H).

Step B. Example 362

The title compound was prepared according to methods described for the synthesis of Example 104 (Step C), using Intermediate 362A as starting material: $^1$H NMR (500 MHz, DMSO-$d_6$) δ 7.66 (br d, J=7.6 Hz, 1H), 7.62-7.48 (m, 4H), 7.18 (d, J=7.9 Hz, 1H), 4.11 (s, 2H), 3.55 (s, 2H), 2.79 (br d, J=4.9 Hz, 2H), 2.70-2.60 (m, 2H), 2.33-2.18 (m, 1H), 2.09 (s, 2H), 1.38 (br d, J=8.5 Hz, 6H), 1.32-1.21 (m, 6H), 1.17-1.09 (m, 2H), 1.07-0.98 (m, 2H). FXR $EC_{50}$ (nM)=170. MS (ESI) 581.3 (M+H).

The following Examples (in Table 6) were prepared according to methods described elsewhere herein using appropriate starting materials, reagents and conditions.

TABLE 6

| Ex. No. | Structure & Name | $^1$H NMR, FXR EC$_{50}$ & MS (ESI) | Method |
|---|---|---|---|
| 277 | 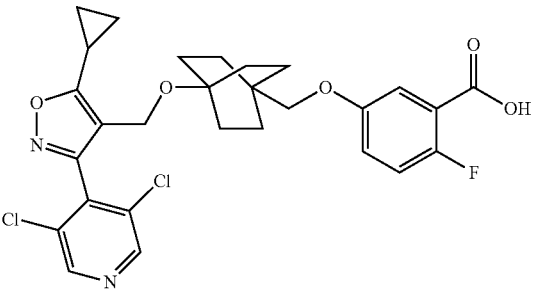<br>5-((4-((5-cyclopropyl-3-(3,5-dichloropyridin-4-yl)isoxazol-4-yl)methoxy)bicyclo[2.2.2]octan-1-yl)methoxy)-2-fluorobenzoic acid | $^1$H NMR (500 MHz, DMSO-d$_6$) δ 8.78 (s, 2H), 7.20 (dd, J = 5.5, 3.2 Hz, 1H), 7.16-7.08 (m, 1H), 7.08-7.00 (m, 1H), 4.21 (s, 2H), 3.53 (s, 2H), 2.33-2.22 (m, 1H), 1.60-1.47 (m, 6H), 1.44-1.31 (m, 6H), 1.19-1.11 (m, 2H), 1.10-1.03 (m, 2H). FXR EC$_{50}$ (nM) = 47. MS (ESI) 561 (M + H). | Ex. 276 |
| 283 | 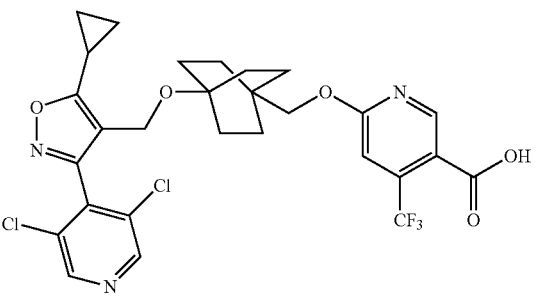<br>6-((4-((5-cyclopropyl-3-(3,5-dichloropyridin-4-yl)isoxazol-4-yl)methoxy)bicyclo[2.2.2]octan-1-yl)methoxy)-4-(trifluoromethyl)nicotinic acid | $^1$H NMR (500 MHz, DMSO-d$_6$) δ 8.78 (s, 2H), 8.62 (s, 1H), 7.11 (s, 1H), 4.21 (s, 2H), 3.98 (s, 2H), 2.32-2.22 (m, 1H), 1.58-1.46 (m, 6H), 1.42-1.32 (m, 6H), 1.20-1.11 (m, 2H), 1.11-1.02 (m, 2H). FXR EC$_{50}$ (nM) = 15. MS (ESI) 612 (M + H). | Ex. 104 |
| 286 | 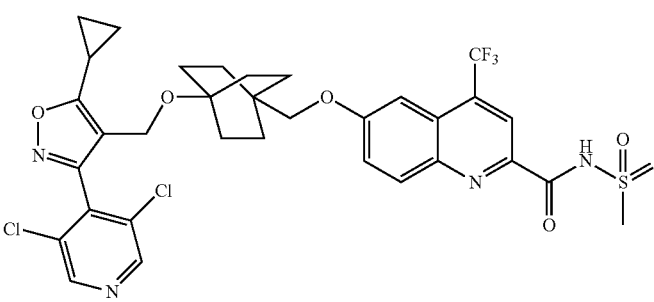<br>6-((4-((5-cyclopropyl-3-(3,5-dichloropyridin-4-yl)isoxazol-4-yl)methoxy)bicyclo[2.2.2]octan-1-yl)methoxy)-N-(methylsulfonyl)-4-(trifluoromethyl)quinoline-2-carboxamide | $^1$H NMR (500 MHz, DMSO-d$_6$) δ 8.80 (s, 2H), 8.34 (s, 1H), 8.20 (br d, J = 9.5 Hz, 1H), 7.60 (br d, J = 7.6 Hz, 1H), 7.22 (br s, 1H), 4.21 (s, 2H), 3.72 (s, 2H), 3.07 (s, 3H), 2.33-2.23 (m, 1H), 1.62-1.51 (m, 6H), 1.39-1.29 (m, 6H), 1.21-1.11 (m, 2H), 1.08-1.03 (m, 2H). FXR EC$_{50}$ (nM) = 19. MS (ESI) 739 (M + H). | Ex. 3 |
| 287 | 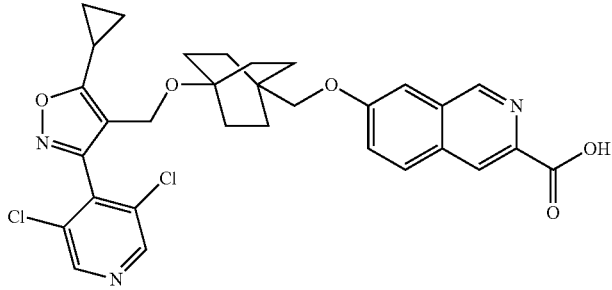<br>7-((4-((5-cyclopropyl-3-(3,5-dichloropyridin-4-yl)isoxazol-4-yl)methoxy)bicyclo[2.2.2]octan-1-yl)methoxy)isoquinoline-3-carboxylic acid | $^1$H NMR (500 MHz, DMSO-d$_6$) δ 9.19 (s, 1H), 8.82 (s, 2H), 8.48 (s, 1H), 8.03 (d, J = 8.9 Hz, 1H), 7.54 (br s, 1H), 7.44 (br d, J = 8.9 Hz, 1H), 4.23 (s, 2H), 3.73 (s, 2H), 2.37-2.25 (m, 1H), 1.65-1.50 (m, 6H), 1.45-1.33 (m, 6H), 1.21-1.12 (m, 2H), 1.11-1.02 (m, 2H). FXR EC$_{50}$ (nM) = 96. MS (ESI) 594 (M + H). | Ex. 276 |

TABLE 6-continued

| Ex. No. | Structure & Name | ¹H NMR, FXR EC$_{50}$ & MS (ESI) | Method |
|---|---|---|---|
| 288 | 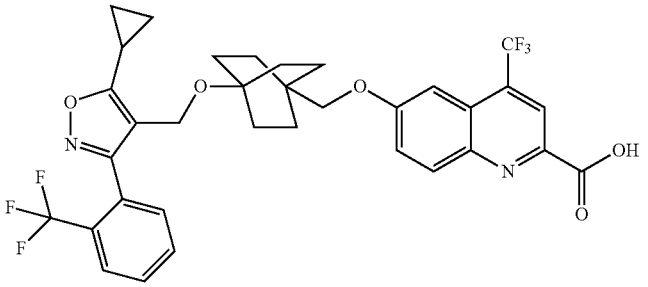  6-((4-((5-cyclopropyl-3-(2-(trifluoromethyl)phenyl)isoxazol-4-yl)methoxy)bicyclo[2.2.2]octan-1-yl)methoxy)-4-(trifluoromethyl)quinoline-2-carboxylic acid | ¹H NMR (500 MHz, DMSO-d$_6$) δ 8.39-8.07 (m, 2H), 7.88 (d, J = 7.9 Hz, 1H), 7.82-7.76 (m, 1H), 7.75-7.69 (m, 1H), 7.62-7.47 (m, 2H), 7.21 (br s, 1H), 4.07 (s, 2H), 3.92-3.64 (m, 2H), 2.30-2.16 (m, 1H), 1.62-1.50 (m, 6H), 1.47-1.33 (m, 6H), 1.18-1.08 (m, 2H), 1.06-0.99 (m, 2H). FXR EC$_{50}$ (nM) = 250. MS (ESI) 661 (M + H). | Ex. 276 |
| 289 | 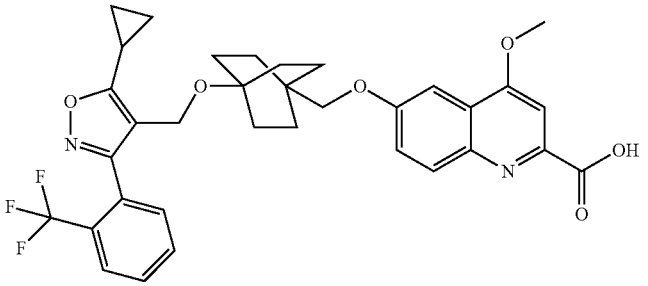  6-((4-((5-cyclopropyl-3-(2-(trifluoromethyl)phenyl)isoxazol-4-yl)methoxy)bicyclo[2.2.2]octan-1-yl)methoxy)-4-methoxyquinoline-2-carboxylic acid | ¹H NMR (500 MHz, DMSO-d$_6$) δ 8.02-7.95 (m, 1H), 7.90 (d, J = 7.6 Hz, 1H), 7.80 (s, 1H), 7.77-7.70 (m, 1H), 7.54 (br d, J = 7.6 Hz, 1H), 7.51 (s, 1H), 7.40 (dd, J = 9.2, 2.1 Hz, 1H), 7.34 (br d, J = 1.8 Hz, 1H), 4.10 (s, 2H), 4.07 (s, 3H), 3.68 (s, 2H), 2.30-2.19 (m, 1H), 1.61-1.51 (m, 6H), 1.49-1.38 (m, 6H), 1.16-1.09 (m, 2H), 1.08-1.01 (m, 2H). FXR EC$_{50}$ (nM) = 150. MS (ESI) 623 (M + H) | Ex. 276 |
| 290 | 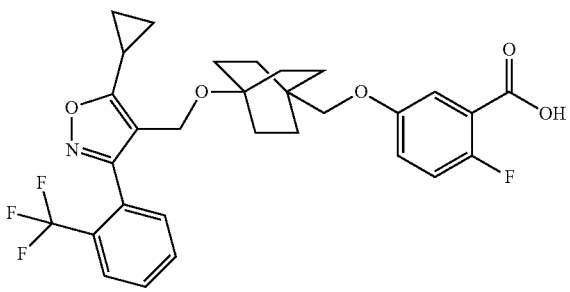  5-((4-((5-cyclopropyl-3-(2-(trifluoromethyl)phenyl)isoxazol-4-yl)methoxy)bicyclo[2.2.2]octan-1-yl)methoxy)-2-fluorobenzoic acid | ¹H NMR (500 MHz, DMSO-d$_6$) δ 7.90-7.84 (m, 1H), 7.76 (br d, J = 7.3 Hz, 1H), 7.74-7.68 (m, 1H), 7.50 (br d, J = 7.6 Hz, 1H), 7.19-7.08 (m, 2H), 7.05-6.97 (m, 1H), 4.06 (s, 2H), 3.49 (s, 2H), 2.26-2.14 (m, 1H), 1.62-1.50 (m, 6H), 1.47-1.33 (m, 6H), 1.16-1.08 (m, 2H), 1.05-0.97 (m, 2H). FXR EC$_{50}$ (nM) = 260. MS (ESI) 560 (M + H). | Ex. 276 |
| 295 | 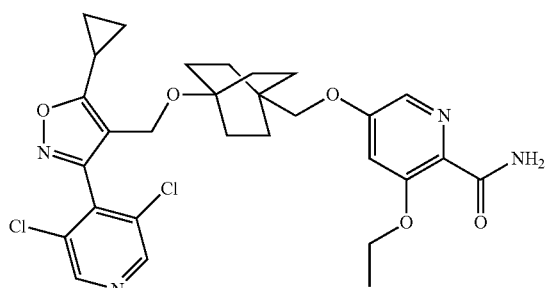  5-((4-((5-cyclopropyl-3-(3,5-dichloropyridin-4-yl)isoxazol-4-yl)methoxy)bicyclo[2.2.2]octan-1-yl)methoxy)-3-ethoxypicolinamide | ¹H NMR (500 MHz, DMSO-d$_6$) δ 8.80 (s, 2H), 7.02 (br s, 2H), 4.21 (s, 2H), 4.16-4.06 (m, 2H), 3.67 (s, 2H), 2.30-2.22 (m, 1H), 1.56-1.45 (m, 6H), 1.42-1.26 (m, 9H), 1.23-1.11 (m, 2H), 1.10-1.05 (m, 2H). FXR EC$_{50}$ (nM) = 230. MS (ESI) 587 (M + H). | Ex. 278 & 279 |

TABLE 6-continued

| Ex. No. | Structure & Name | $^1$H NMR, FXR EC$_{50}$ & MS (ESI) | Method |
|---|---|---|---|
| 296 | 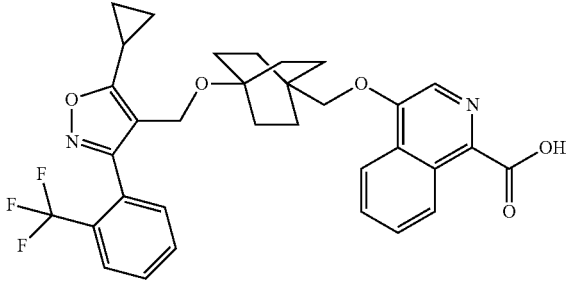4-((4-((5-cyclopropyl-3-(2-(trifluoromethyl)phenyl)isoxazol-4-yl)methoxy)bicyclo[2.2.2]octan-1-yl)methoxy)isoquinoline-1-carboxylic acid | $^1$H NMR (500 MHz, DMSO-d$_6$) δ 8.21-8.14 (m, 1H), 8.04 (br s, 1H), 7.87 (br d, J = 8.6 Hz, 2H), 7.78 (br d, J = 7.4 Hz, 2H), 7.75-7.67 (m, 2H), 7.50 (br d, J = 7.5 Hz, 1H), 4.09 (s, 2H), 3.61 (br s, 2H), 2.30-2.22 (m, 1H), 1.56-1.45 (m, 6H), 1.42-1.26 (m, 6H), 1.23-1.11 (m, 2H), 1.10-1.05 (m, 2H). FXR EC$_{50}$ (nM) = 62. MS (ESI) 593 (M + H). | Ex. 276 |
| 297 | 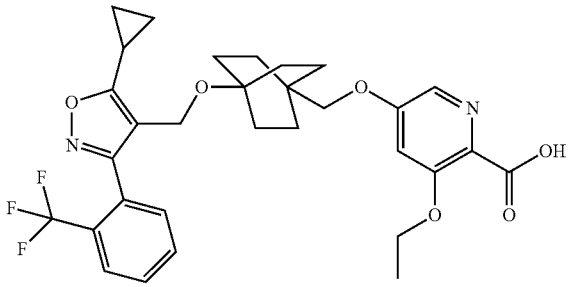5-((4-((5-cyclopropyl-3-(2-(trifluoromethyl)phenyl)isoxazol-4-yl)methoxy)bicyclo[2.2.2]octan-1-yl)methoxy)-3-ethoxypicolinic acid | $^1$H NMR (500 MHz, DMSO-d$_6$) δ 7.89 (br d, J = 7.3 Hz, 1H), 7.84-7.77 (m, 2H), 7.75 (br d, J = 7.3 Hz, 1H), 7.54 (br d, J = 7.3 Hz, 1H), 7.07 (s, 1H), 4.17-4.05 (m, 5H), 3.69 (br s, 2H), 2.29-2.19 (m, 1H), 1.58-1.48 (m, 6H), 1.425-1.36 (m, 6H), 1.30 (br t, J = 6.4 Hz, 3H), 1.16-1.08 (m, 2H), 1.08-1.01 (m, 2H). FXR EC$_{50}$ (nM) = 543. MS (ESI) 587 (M + H). | Ex. 278 & 279 |
| 299 | 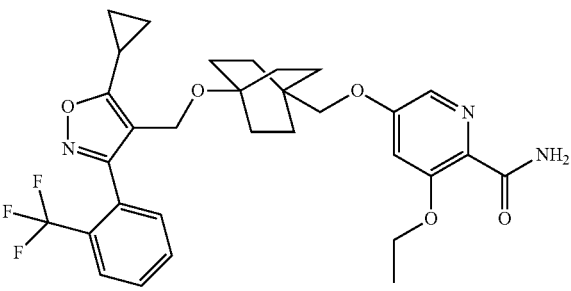5-((4-((5-cyclopropyl-3-(2-(trifluoromethyl)phenyl)isoxazol-4-yl)methoxy)bicyclo[2.2.2]octan-1-yl)methoxy)-3-ethoxypicolinamide | $^1$H NMR (500 MHz, DMSO-d$_6$) δ 7.89 (br d, J = 7.9 Hz, 1H), 7.84-7.71 (m, 3H), 7.53 (br d, J = 7.6 Hz, 1H), 7.05 (s, 1H), 4.09 (br s, 4H), 3.67 (br s, 2H), 2.28-2.18 (m, 1H), 1.56-1.48 (m, 6H), 1.44-1.37 (m, 6H), 1.31 (br t, J = 6.7 Hz, 3H), 1.14-0.90 (m, 2H), 1.06-1.01 (m, 2H). FXR EC$_{50}$ (nM) = 2300. MS (ESI) 586 (M + H). | Ex. 278 & 279 |
| 302 | 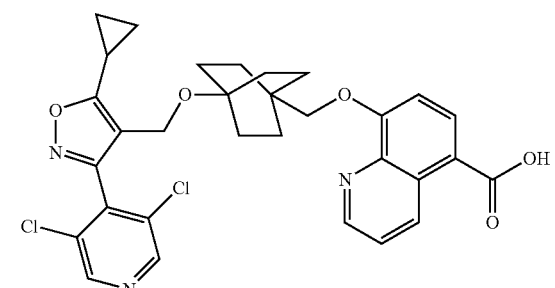8-((4-((5-cyclopropyl-3-(3,5-dichloropyridin-4-yl)isoxazol-4-yl)methoxy)bicyclo[2.2.2]octan-1-yl)methoxy)quinoline-5-carboxylic acid | $^1$H NMR (500 MHz, DMSO-d$_6$) δ 9.45-9.34 (m, 1H), 8.93 (br d, J = 2.7 Hz, 1H), 8.83 (s, 2H), 8.24 (d, J = 8.5 Hz, 1H), 7.65 (dd, J = 8.5, 4.0 Hz, 1H), 7.17 (br d, J = 8.2 Hz, 1H), 4.24 (s, 2H), 3.79 (s, 2H), 2.37-2.24 (m, 1H), 1.67-1.55 (m, 6H), 1.44-1.30 (m, 6H), 1.19-1.12 (m, 2H), 1.12-1.05 (m, 2H). FXR EC$_{50}$ (nM) = 54. MS (ESI) 594 (M + H). | Ex. 276 |

TABLE 6-continued

| Ex. No. | Structure & Name | $^1$H NMR, FXR EC$_{50}$ & MS (ESI) | Method |
|---|---|---|---|
| 305 | 8-((4-((5-cyclopropyl-3-(2-(trifluoromethyl)phenyl)isoxazol-4-yl)methoxy)bicyclo[2.2.2]octan-1-yl)methoxy)quinoline-5-carboxylic acid | $^1$H NMR (500 MHz, DMSO-d$_6$) δ 9.38 (br d, J = 8.8 Hz, 1H), 8.89 (br d, J = 3.5 Hz, 1H), 8.21 (d, J = 8.3 Hz, 1H), 7.88 (d, J = 7.8 Hz, 1H), 7.83-7.76 (m, 1H), 7.76-7.70 (m, 1H), 7.62 (dd, J = 8.8, 4.0 Hz, 1H), 7.52 (br d, J = 7.5 Hz, 1H), 7.15 (d, J = 8.4 Hz, 1H), 4.10 (s, 2H), 3.80 (s, 2H), 2.27-2.18 (m, 1H), 1.71-1.61 (m, 6H), 1.53-1.41 (m, 6H), 1.17-1.09 (m, 2H), 1.07-1.01 (m, 2H). FXR EC$_{50}$ (nM) = 104. MS (ESI) 593 (M + H). | Ex. 276 |
| 310 | 2-((4-((5-cyclopropyl-3-(3,5-dichloropyridin-4-yl)isoxazol-4-yl)methoxy)bicyclo[2.2.2]octan-1-yl)methoxy)-8-methoxyquinoline-6-carboxylic acid | $^1$H NMR (500 MHz, DMSO-d$_6$) δ 8.81 (s, 2H), 8.31 (d, J = 8.9 Hz, 1H), 8.10 (s, 1H), 7.54 (s, 1H), 7.04 (d, J = 8.9 Hz, 1H), 4.21 (s, 2H), 4.01 (s, 2H), 3.95 (s, 3H), 2.34-2.21 (m, 1H), 1.61-1.50 (m, 6H), 1.41-1.29 (m, 6H), 1.18-1.11 (m, 2H), 1.10-1.03 (m, 2H). FXR EC$_{50}$ (nM) = 62. MS (ESI) 625 (M + H). | Ex. 276 |
| 315 | 3-((4-((5-cyclopropyl-3-(3,5-dichloropyridin-4-yl)isoxazol-4-yl)methoxy)bicyclo[2.2.2]octan-1-yl)methoxy)-1-methyl-1H-pyrazole-5-carboxylic acid | $^1$H NMR (500 MHz, DMSO-d$_6$) δ 8.80 (s, 2H), 6.10 (s, 1H), 4.20 (s, 2H), 3.87 (s, 3H), 3.60 (s, 2H), 2.35-2.22 (m, 1H), 1.53-1.42 (m, 6H), 1.38-1.25 (m, 6H), 1.20-1.10 (m, 2H), 1.09-1.01 (m, 2H). FXR EC$_{50}$ (nM) = 340. MS (ESI) 547 (M + H). | Ex. 276 |
| 316 | 3-((4-((5-cyclopropyl-3-(3,5-dichloropyridin-4-yl)isoxazol-4-yl)methoxy)bicyclo[2.2.2]octan-1-yl)methoxy)-1-ethyl-1H-pyrazole-5-carboxylic acid | $^1$H NMR (500 MHz, DMSO-d$_6$) δ 8.80 (s, 2H), 6.12 (s, 1H), 4.30 (q, J = 7.0 Hz, 2H), 4.20 (s, 2H), 3.60 (s, 2H), 2.33-2.24 (m, 1H), 1.51-1.40 (m, 6H), 1.37-1.28 (m, 6H), 1.23 (t, J = 7.0 Hz, 3H), 1.17-1.11 (m, 2H), 1.09-1.02 (m, 2H). FXR EC$_{50}$ (nM) = 64. MS (ESI) 561 (M + H). | Ex. 276 |

TABLE 6-continued

| Ex. No. | Structure & Name | $^1$H NMR, FXR EC$_{50}$ & MS (ESI) | Method |
|---|---|---|---|
| 317 | 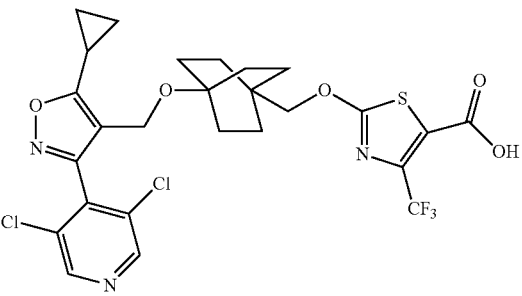<br>2-((4-((5-cyclopropyl-3-(3,5-dichloropyridin-4-yl)isoxazol-4-yl)methoxy)bicyclo[2.2.2]octan-1-yl)methoxy)-4-(trifluoromethyl)thiazole-5-carboxylic acid | $^1$H NMR (500 MHz, DMSO-d$_6$) δ 8.80 (s, 2H), 4.20 (s, 2H), 4.03 (s, 2H), 2.33-2.25 (m, 1H), 1.55-1.42 (m, 6H), 1.38-1.26 (m, 6H), 1.17-1.11 (m, 2H), 1.10-1.03 (m, 2H). FXR EC$_{50}$ (nM) = 210. MS (ESI) 618 (M + H) | Ex. 104 |
| 318 | 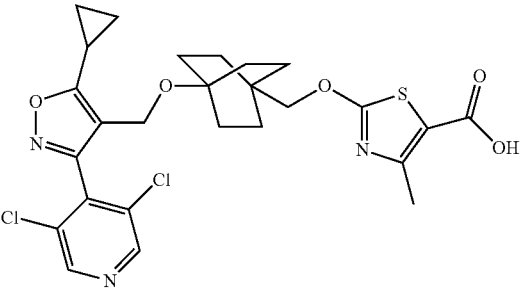<br>2-((4-((5-cyclopropyl-3-(3,5-dichloropyridin-4-yl)isoxazol-4-yl)methoxy)bicyclo[2.2.2]octan-1-yl)methoxy)-4-methylthiazole-5-carboxylic acid | $^1$H NMR (500 MHz, DMSO-d$_6$) δ 8.79 (s, 2H), 4.19 (s, 2H), 3.85 (s, 2H), 2.35 (s, 3H), 2.32-2.23 (m, 1H), 1.50-1.39 (m, 6H), 1.36-1.25 (m, 6H), 1.18-1.10 (m, 2H), 1.08-1.02 (m, 2H). FXR EC$_{50}$ (nM) = 180. MS (ESI) 564 (M + H). | Ex. 104 |
| 319 | 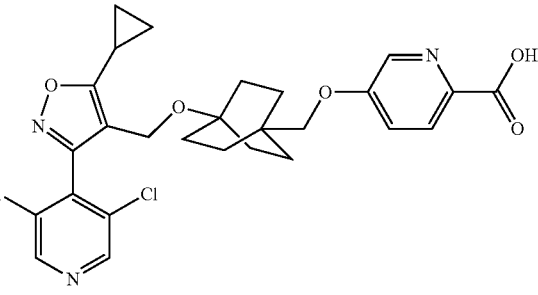<br>5-((4-((5-cyclopropyl-3-(3,5-dichloropyridin-4-yl)isoxazol-4-yl)methoxy)bicyclo[2.2.2]octan-1-yl)methoxy)picolinic acid | $^1$H NMR (500 MHz, DMSO-d$_6$) δ 8.80 (s, 2H), 8.30 (br s, 1H), 7.97 (br d, J = 8.7 Hz, 1H), 7.42 (dd, J = 8.7, 2.4 Hz, 1H), 4.24 (s, 2H), 3.71 (s, 2H), 2.36-2.24 (m, 1H), 1.67-1.48 (m, 6H), 1.46-1.27 (m, 6H), 1.22-1.12 (m, 2H), 1.12-1.03 (m, 2H). FXR EC$_{50}$ (nM) = 270. MS (ESI) 543.9 (M + H). | Ex. 276 |
| 320 | 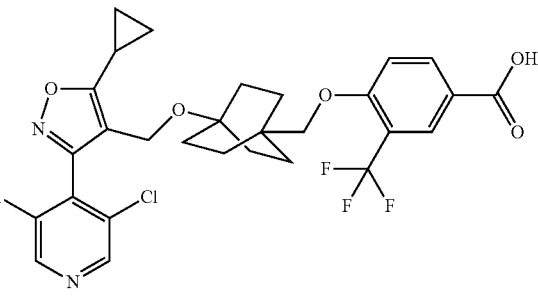<br>4-((4-((5-cyclopropyl-3-(3,5-dichloropyridin-4-yl)isoxazol-4-yl)methoxy)bicyclo[2.2.2]octan-1-yl)methoxy)-3-(trifluoromethyl)benzoic acid | $^1$H NMR (500 MHz, DMSO-d$_6$) δ 8.80 (s, 2H), 8.13 (br d, J = 8.8 Hz, 1H), 8.09 (s, 1H), 7.27 (br d, J = 8.7 Hz, 1H), 4.23 (s, 2H), 3.76 (s, 2H), 2.33-2.25 (m, 1H), 1.61-1.50 (m, 6H), 1.44-1.33 (m, 6H), 1.21-1.12 (m, 2H), 1.09 (br d, J = 2.8 Hz, 2H). FXR EC$_{50}$ (nM) = 410. MS (ESI) 611.0 (M + H). | Ex. 276 |

TABLE 6-continued

| Ex. No. | Structure & Name | $^1$H NMR, FXR EC$_{50}$ & MS (ESI) | Method |
|---|---|---|---|
| 322 | 3-((4-((5-cyclopropyl-3-(3,5-dichloropyridin-4-yl)isoxazol-4-yl)methoxy)bicyclo[2.2.2]octan-1-yl)methoxy)-5-methylbenzoic acid | $^1$H NMR (500 MHz, DMSO-d$_6$) δ 8.81 (br s, 2H), 7.29 (s, 1H), 7.17 (br s, 1H), 6.92 (br s, 1H), 3.89 (s, 2H), 3.65 (br s, 2H), 3.17 (br s, 3H), 2.40-2.18 (m, 1H), 1.49 (br s, 6H), 1.33 (br d, J = 7.0 Hz, 6H), 1.20-1.11 (m, 2H), 1.07 (br d, J = 2.4 Hz, 2H). FXR EC$_{50}$ (nM) = 7. MS (ESI) 557.2 (M + H). | Ex. 321 |
| 323 | 6-((4-((5-cyclopropyl-3-(3,5-dichloropyridin-4-yl)isoxazol-4-yl)methoxy)bicyclo[2.2.2]octan-1-yl)methoxy)-4-methoxypicolinic acid | $^1$H NMR (500 MHz, DMSO-d$_6$) δ 8.80 (s, 2H), 7.15 (s, 1H), 6.54-6.43 (m, 1H), 4.22 (s, 2H), 3.83 (s, 2H), 3.71-3.56 (m, 3H), 2.39-2.20 (m, 1H), 1.49 (br d, J = 7.9 Hz, 6H), 1.32 (br s, 6H), 1.20-1.12 (m, 2H), 1.07 (br d, J = 2.7 Hz, 2H). FXR EC$_{50}$ (nM) = 74. MS (ESI) 574.2 (M + H). | Ex. 104 |
| 325 | 6-((4-((5-cyclopropyl-3-(3,5-dichloropyridin-4-yl)isoxazol-4-yl)methoxy)bicyclo[2.2.2]octan-1-yl)methoxy)-4-methylquinoline-2-carboxylic acid | $^1$H NMR (500 MHz, DMSO-d$_6$) δ 8.77 (s, 2H), 8.03 (br d, J = 6.6 Hz, 1H), 7.89 (br s, 1H), 7.43 (br d, J = 7.8 Hz, 1H), 7.29 (br s, 1H), 4.22 (s, 2H), 3.75 (s, 2H), 2.66 (br s, 3H), 2.34-2.18 (m, 1H), 1.57 (br d, J = 7.7 Hz, 6H), 1.38 (br d, J = 6.6 Hz, 6H), 1.15 (br d, J = 7.6 Hz, 2H), 1.06 (br s, 2H). FXR EC$_{50}$ (nM) = 52. MS (ESI) 608.4 (M + H). | Ex. 276 |
| 326 | 3-((4-((5-cyclopropyl-3-(3,5-dichloropyridin-4-yl)isoxazol-4-yl)methoxy)bicyclo[2.2.2]octan-1-yl)methoxy)-5-isopropoxybenzoic acid | $^1$H NMR (500 MHz, DMSO-d$_6$) δ 8.78 (s, 2H), 6.99 (s, 1H), 6.97 (s, 1H), 6.61 (s, 1H), 4.60 (dt, J = 12.0, 6.0 Hz, 1H), 4.22 (s, 2H), 3.55 (s, 2H), 2.35-2.20 (m, 1H), 1.60-1.45 (m, 6H), 1.42-1.31 (m, 6H), 1.21-1.12 (m, 2H), 1.11-1.01 (m, 2H). FXR EC$_{50}$ (nM) = 17. MS (ESI) 601.2 (M + H). | Ex. 276 |

TABLE 6-continued

| Ex. No. | Structure & Name | $^1$H NMR, FXR $EC_{50}$ & MS (ESI) | Method |
|---|---|---|---|
| 330 | 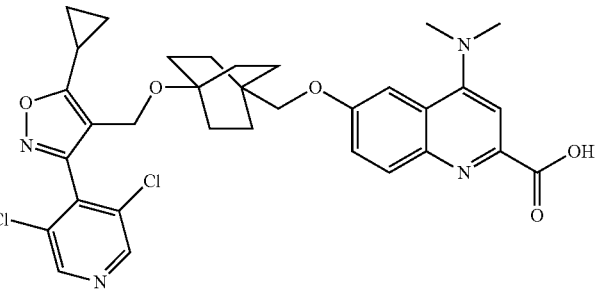<br>6-((4-((5-cyclopropyl-3-(3,5-dichloropyridin-4-yl)isoxazol-4-yl)methoxy)bicyclo[2.2.2]octan-1-yl)methoxy)-4-(dimethylamino)quinoline-2-carboxylic acid | $^1$H NMR (500 MHz, DMSO-$d_6$) δ 8.83 (s, 2H), 8.14 (br d, J = 7.0 Hz, 1H), 7.48 (br d, J = 9.5 Hz, 1H), 7.37 (br s, 2H), 4.24 (s, 2H), 3.71 (br s, 2H), 3.21 (br s, 6H), 2.37-2.22 (m, 1H), 1.57 (br s, 6H), 1.37 (br s, 6H), 1.16 (br dd, J = 7.5, 2.9 Hz, 2H), 1.09 (br d, J = 2.1 Hz, 2H). FXR $EC_{50}$ (nM) = 1500. MS (ESI) 637.1 (M + H). | Ex. 276 |
| 333 | 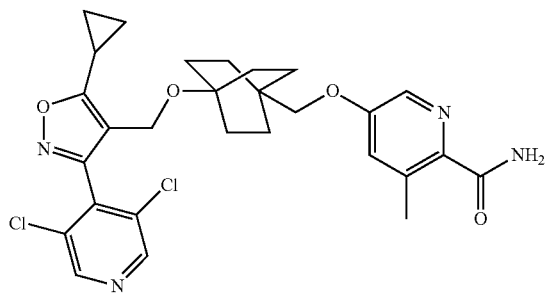<br>5-((4-((5-cyclopropyl-3-(3,5-dichloropyridin-4-yl)isoxazol-4-yl)methoxy)bicyclo[2.2.2]octan-1-yl)methoxy)-3-methylpicolinamide | $^1$H NMR (500 MHz, DMSO-$d_6$) δ 8.77 (s, 2H), 8.04 (s, 1H), 7.72 (br s, 1H), 7.21 (br s, 1H), 7.02 (br s, 1H), 4.21 (s, 2H), 3.66 (s, 2H), 2.53 (br s, 3H), 2.33-2.18 (m, 1H), 1.51 (br d, J = 8.2 Hz, 6H), 1.42-1.30 (m, 6H), 1.15 (br d, J = 5.9 Hz, 2H), 1.06 (br s, 2H). FXR $EC_{50}$ (nM) = 540. MS (ESI) 558.0 (M + H). | Ex. 278 & 279 |
| 336 | 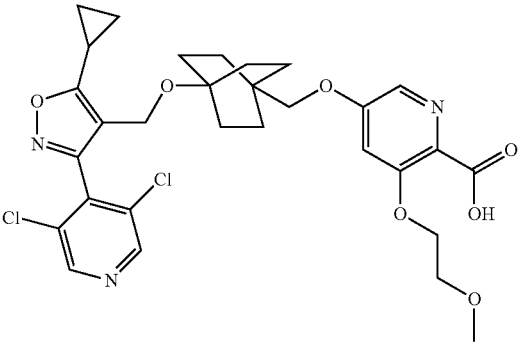<br>5-((4-((5-cyclopropyl-3-(3,5-dichloropyridin-4-yl)isoxazol-4-yl)methoxy)bicyclo[2.2.2]octan-1-yl)methoxy)-3-(2-methoxyethoxy)picolinic acid | $^1$H NMR (500 MHz, DMSO-$d_6$) δ 8.78 (s, 2H), 7.82 (br s, 1H), 7.08 (br s, 1H), 4.22 (s, 2H), 4.18 (br s, 2H), 3.77-3.62 (m, 5H), 3.32 (s, 2H), 2.34-2.22 (m, 1H), 1.52 (br d, J = 7.9 Hz, 6H), 1.42-1.32 (m, 6H), 1.20-1.11 (m, 2H), 1.07 (br d, J = 2.8 Hz, 2H). FXR $EC_{50}$ = 160. MS (ESI) 617.9 (M + H). | Ex. 278 & 279 |
| 337 | 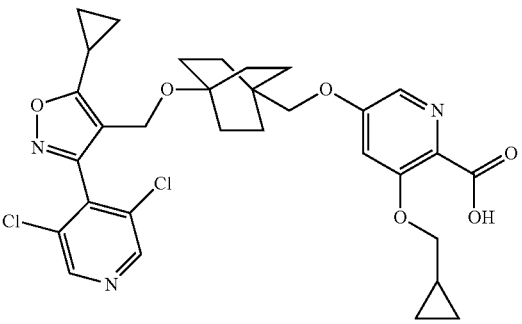<br>5-((4-((5-cyclopropyl-3-(3,5-dichloropyridin-4-yl)isoxazol-4-yl)methoxy)bicyclo[2.2.2]octan-1-yl)methoxy)-3-(cyclopropylmethoxy)picolinic acid | $^1$H NMR (500 MHz, DMSO-$d_6$) δ 8.50 (s, 2H), 7.52 (br s, 1H), 6.75 (br s, 1H), 3.95 (s, 2H), 3.66 (br d, J = 6.5 Hz, 2H), 3.41 (br s, 2H), 2.05-1.93 (m, 1H), 1.24 (br d, J = 7.2 Hz, 6H), 1.08 (br s, 6H), 0.99-0.85 (m, 3H), 0.79 (br s, 2H), 0.28 (br d, J = 7.4 Hz, 2H), 0.07 (br d, J = 4.0 Hz, 2H). FXR $EC_{50}$ (nM) = 27. MS (ESI) 614.1 (M + H). | Ex. 278 & 279 |

TABLE 6-continued

| Ex. No. | Structure & Name | $^1$H NMR, FXR EC$_{50}$ & MS (ESI) | Method |
|---|---|---|---|
| 339 | 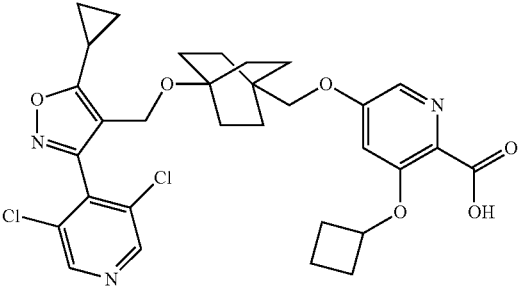<br>3-cyclobutoxy-5-((4-((5-cyclopropyl-3-(3,5-dichloropyridin-4-yl)isoxazol-4-yl)methoxy)bicyclo[2.2.2]octan-1-yl)methoxy)picolinic acid | $^1$H NMR (500 MHz, DMSO-d$_6$) δ 8.82 (s, 2H), 7.80 (br s, 1H), 6.81 (br s, 1H), 4.79 (quin, J = 6.9 Hz, 1H), 4.23 (s, 2H), 3.67 (s, 2H), 2.41 (br d, J = 6.4 Hz, 2H), 2.36-2.23 (m, 1H), 2.13-1.96 (m, 2H), 1.86-1.72 (m, 1H), 1.70-1.58 (m, 1H), 1.52 (br d, J = 7.9 Hz, 6H), 1.35 (br d, J = 1.9 Hz, 6H), 1.16 (br d, J = 7.9 Hz, 2H), 1.08 (br d, J = 2.7 Hz, 2H). FXR EC$_{50}$ (nM) = 28. MS (ESI) 614.1 (M + H). | Ex. 278 & 279 |
| 340 | 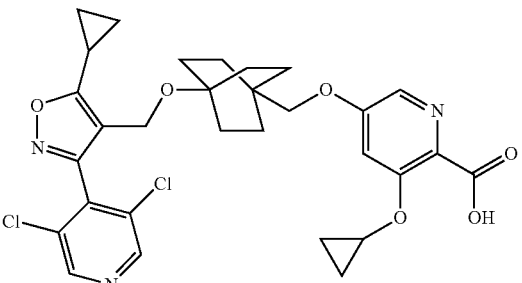<br>3-cyclopropoxy-5-((4-((5-cyclopropyl-3-(3,5-dichloropyridin-4-yl)isoxazol-4-yl)methoxy)bicyclo[2.2.2]octan-1-yl)methoxy)picolinic acid | $^1$H NMR (500 MHz, DMSO-d$_6$) δ 8.80 (s, 2H), 7.85 (br s, 1H), 7.27 (s, 1H), 4.23 (s, 2H), 3.98 (dt, J = 5.7, 3.0 Hz, 1H), 3.71 (s, 2H), 2.36-2.23 (m, 1H), 1.67-1.48 (m, 6H), 1.46-1.32 (m, 6H), 1.20-1.12 (m, 2H), 1.11-1.03 (m, 2H), 0.86-0.74 (m, 2H), 0.68 (br s, 2H). FXR EC$_{50}$ (nM) = 46. MS (ESI) 600.2 (M + H). | Ex. 278 & 279 |
| 341 | 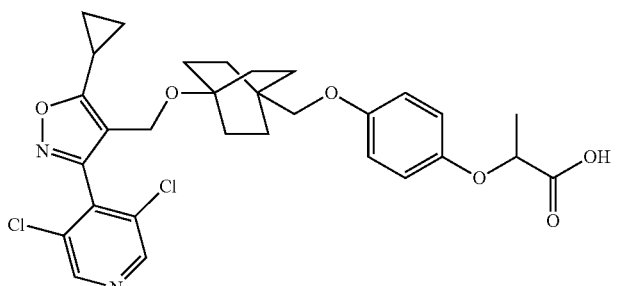<br>2-(4-((4-((5-cyclopropyl-3-(3,5-dichloropyridin-4-yl)isoxazol-4-yl)methoxy)bicyclo[2.2.2]octan-1-yl)methoxy)phenoxy)propanoic acid | $^1$H NMR (500 MHz, DMSO-d$_6$) δ 8.82 (s, 2H), 6.75 (s, 4H), 4.54 (br d, J = 6.7 Hz, 1H), 4.22 (s, 2H), 3.44 (s, 2H), 2.36-2.24 (m, 1H), 1.48 (br d, J = 7.9 Hz, 6H), 1.42 (br d, J = 6.4 Hz, 3H), 1.34 (br d, J = 7.3 Hz, 6H), 1.16 (br d, J = 7.9 Hz, 2H), 1.08 (br s, 2H). FXR EC$_{50}$ (nM) = 1500. MS (ESI) 587.2 (M + H). | Ex. 276 |
| 342 | 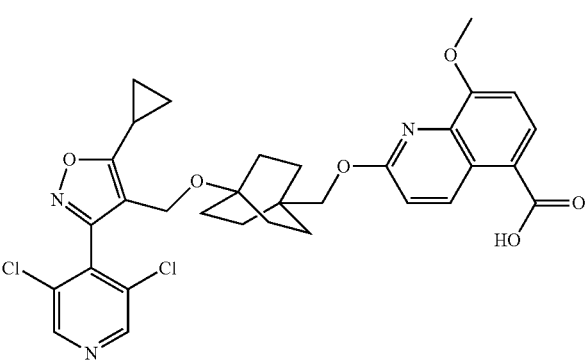<br>2-((4-((5-cyclopropyl-3-(3,5-dichloropyridin-4-yl)isoxazol-4-yl)methoxy)bicyclo[2.2.2]octan-1-yl)methoxy)-8-methoxyquinoline-5-carboxylic acid | $^1$H NMR (500 MHz, DMSO-d$_6$) δ 9.32 (br d, J = 9.1 Hz, 1H), 8.77 (s, 2H), 7.91 (d, J = 8.2 Hz, 1H), 7.11 (d, J = 8.2 Hz, 1H), 6.98 (d, J = 9.1 Hz, 1H), 4.21 (s, 2H), 3.94 (s, 3H), 3.52 (br s, 2H), 2.32-2.21 (m, 1H), 1.61-1.49 (m, 6H), 1.44-1.31 (m, 6H), 1.19-1.12 (m, 2H), 1.09-1.01 (m, 2H). FXR EC$_{50}$ (nM) = 33. MS (ESI) 624.2 (M + H). | Ex. 104 |

TABLE 6-continued

| Ex. No. | Structure & Name | $^1$H NMR, FXR EC$_{50}$ & MS (ESI) | Method |
|---|---|---|---|
| 343 | 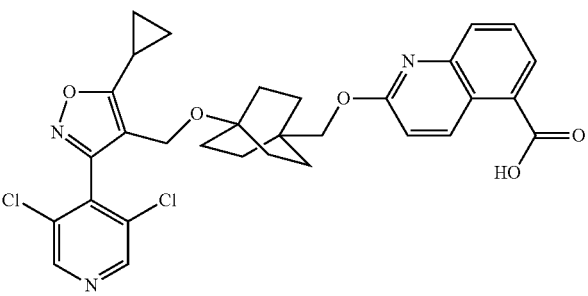<br>2-((4-((5-cyclopropyl-3-(3,5-dichloropyridin-4-yl)isoxazol-4-yl)methoxy)bicyclo[2.2.2]octan-1-yl)methoxy)-quinoline-5-carboxylic acid | $^1$H NMR (500 MHz, DMSO-d$_6$) δ 9.14 (br d, J = 9.5 Hz, 1H), 8.83 (s, 2H), 8.02 (br d, J = 7.0 Hz, 1H), 7.93 (br d, J = 8.2 Hz, 1H), 7.71 (br t, J = 7.8 Hz, 1H), 7.11 (br d, J = 9.2 Hz, 1H), 4.24 (s, 2H), 3.91 (s, 2H), 2.36-2.26 (m, 1H), 1.56 (br d, J = 7.9 Hz, 6H), 1.43-1.31 (m, 6H), 1.21-1.13 (m, 2H), 1.09 (br d, J = 2.7 Hz, 2H). FXR EC$_{50}$ (nM) = 75. MS (ESI) 594.0 (M + H). | Ex. 104 |
| 344 | 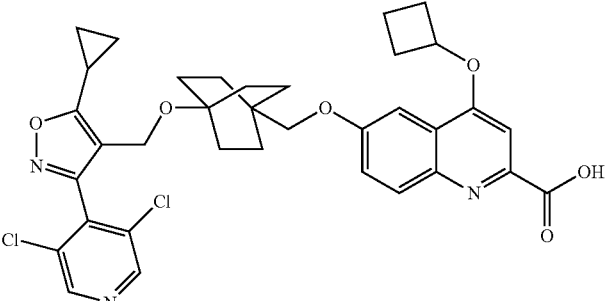<br>4-cyclobutoxy-6-((4-((5-cyclopropyl-3-(3,5-dichloropyridin-4-yl)isoxazol-4-yl)methoxy)bicyclo[2.2.2]octan-1-yl)methoxy)quinoline-2-carboxylic acid | $^1$H NMR (500 MHz, DMSO-d$_6$) δ 8.79 (s, 2H), 8.03 (d, J = 9.3 Hz, 1H), 7.48 (dd, J = 9.2, 2.4 Hz, 1H), 7.40 (d, J = 2.2 Hz, 1H), 7.35 (s, 1H), 5.10 (quin, J = 7.0 Hz, 1H), 4.23 (s, 2H), 3.73 (s, 2H), 2.66-2.55 (m, 2H), 2.36-2.18 (m, 3H), 2.00-1.85 (m, 1H), 1.84-1.72 (m, 1H), 1.65-1.52 (m, 6H), 1.48-1.32 (m, 6H), 1.21-1.13 (m, 2H), 1.08 (br d, J = 2.9 Hz, 2H). FXR EC$_{50}$ (nM) = 17. MS (ESI) 664.3 (M + H). | Ex. 276 |
| 345 | 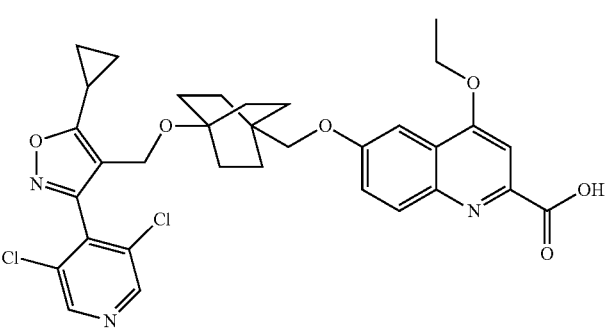<br>6-((4-((5-cyclopropyl-3-(3,5-dichloropyridin-4-yl)isoxazol-4-yl)methoxy)bicyclo[2.2.2]octan-1-yl)methoxy)-4-ethoxyquinoline-2-carboxylic acid | $^1$H NMR (500 MHz, DMSO-d$_6$) δ 8.80 (s, 2H), 8.02 (d, J = 9.3 Hz, 1H), 7.51 (s, 1H), 7.47 (dd, J = 9.2, 2.4 Hz, 1H), 7.39 (d, J = 2.2 Hz, 1H), 4.41 (q, J = 6.9 Hz, 2H), 4.24 (s, 2H), 3.72 (s, 2H), 2.35-2.24 (m, 1H), 1.66-1.54 (m, 6H), 1.50 (t, J = 6.9 Hz, 3H), 1.44-1.33 (m, 6H), 1.21-1.12 (m, 2H), 1.08 (br d, J = 2.8 Hz, 2H). FXR EC$_{50}$ (nM) = 14. MS (ESI) 638.2 (M + H). | Ex. 276 |

TABLE 6-continued

| Ex. No. | Structure & Name | ¹H NMR, FXR EC$_{50}$ & MS (ESI) | Method |
|---|---|---|---|
| 346 | 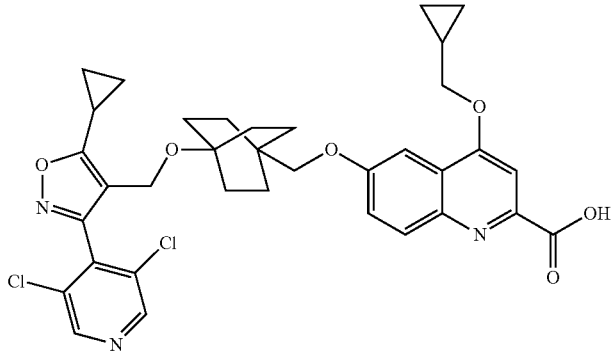<br>6-((4-((5-cyclopropyl-3-(3,5-dichloropyridin-4-yl)isoxazol-4-yl)methoxy)bicyclo[2.2.2]octan-1-yl)methoxy)-4-(cyclopropyl-methoxy)quinoline-2-carboxylic acid | ¹H NMR (500 MHz, DMSO-d$_6$) δ 8.85 (s, 2H), 8.07 (br d, J = 9.2 Hz, 1H), 7.61-7.47 (m, 2H), 7.42 (br d, J = 1.8 Hz, 1H), 4.27 (s, 2H), 4.24 (br d, J = 7.0 Hz, 2H), 3.74 (s, 2H), 2.41-2.25 (m, 1H), 1.60 (br d, J = 7.6 Hz, 6H), 1.40 (br d, J = 7.0 Hz, 6H), 1.32-1.26 (m, 1H), 1.20 (br d, J = 7.9 Hz, 2H), 1.12 (br d, J = 2.7 Hz, 2H), 0.69 (br d, J = 7.3 Hz, 2H), 0.48 (br d, J = 4.3 Hz, 2H). FXR EC$_{50}$ (nM) = 18. MS (ESI) 664.4 (M + H). | Ex. 276 |
| 347 | 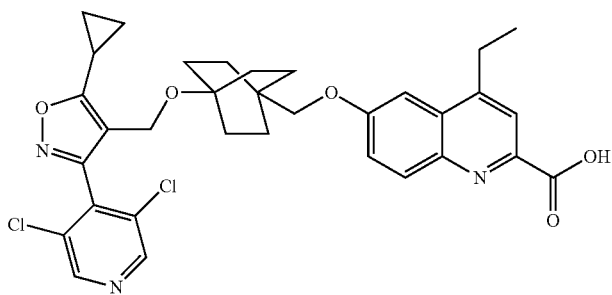<br>6-((4-((5-cyclopropyl-3-(3,5-dichloropyridin-4-yl)isoxazol-4-yl)methoxy)bicyclo[2.2.2]octan-1-yl)methoxy)-4-ethylquinoline-2-carboxylic acid | ¹H NMR (500 MHz, DMSO-d$_6$) δ 8.81 (s, 2H), 8.15-8.00 (m, 1H), 7.92 (br s, 1H), 7.45 (br d, J = 8.9 Hz, 1H), 7.34 (br s, 1H), 4.24 (s, 2H), 3.62 (br s, 2H), 3.10 (br d, J = 7.3 Hz, 2H), 2.38-2.23 (m, 1H), 1.57 (br d, J = 7.6 Hz, 6H), 1.43-1.27 (m, 9H), 1.16 (br d, J = 7.9 Hz, 2H), 1.11-1.03 (m, 2H). FXR EC$_{50}$ (nM) = 24. MS (ESI) 622.3 (M + H). | Ex. 276 |
| 353 | 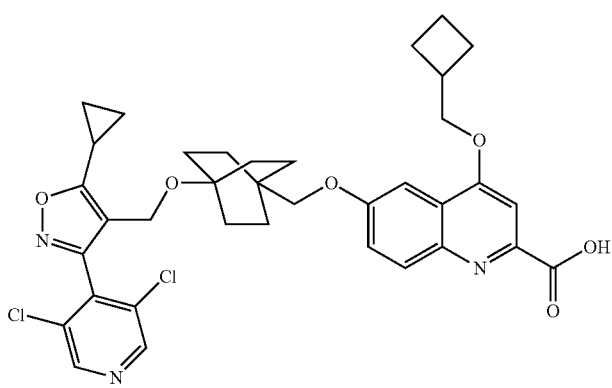<br>4-(cyclobutylmethoxy)-6-((4-((5-cyclopropyl-3-(3,5-dichloropyridin-4-yl)isoxazol-4-yl)methoxy)bicyclo[2.2.2]octan-1-yl)methoxy) quinoline-2-carboxylic acid | ¹H NMR (500 MHz, DMSO-d$_6$) δ 8.80 (s, 2H), 8.02 (br s, 1H), 7.58-7.40 (m, 2H), 7.34 (br s, 1H), 4.30 (br d, J = 4.9 Hz, 2H), 4.21 (s, 2H), 3.62 (s, 2H), 2.98-2.78 (m, 1H), 2.36-2.23 (m, 1H), 2.14 (br d, J = 6.4 Hz, 2H), 1.92 (br s, 4H), 1.54 (br s, 6H), 1.33 (br s, 6H), 1.22-1.12 (m, 2H), 1.09-1.00 (m, 2H). FXR EC$_{50}$ (nM) = 11. MS (ESI) 678.4 (M + H). | Ex. 276 |

TABLE 6-continued

| Ex. No. | Structure & Name | $^1$H NMR, FXR EC$_{50}$ & MS (ESI) | Method |
|---|---|---|---|
| 355 | 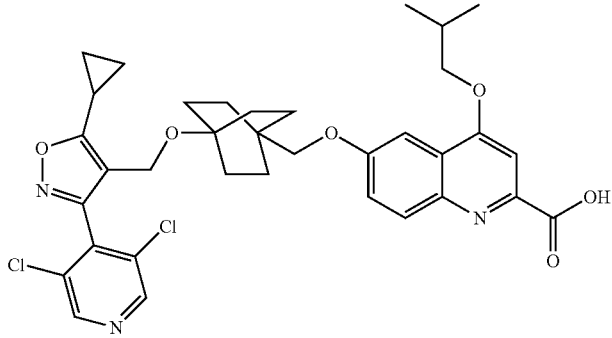<br>4-(cyclobutylmethoxy)-6-((4-((5-cyclopropyl-3-(3,5-dichloropyridin-4-yl)isoxazol-4-yl)methoxy)bicyclo[2.2.2]octan-1-yl)methoxy)-4-isobutoxyquinoline-2-carboxylic acid | $^1$H NMR (500 MHz, DMSO-d$_6$) δ 8.80 (s, 2H), 8.07 (d, J = 9.2 Hz, 1H), 7.59-7.47 (m, 2H), 7.36 (d, J = 2.1 Hz, 1H), 4.21 (s, 2H), 4.12 (br d, J = 6.4 Hz, 2H), 3.17 (s, 2H), 2.34-2.25 (m, 1H), 2.20 (dt, J = 13.2, 6.7 Hz, 1H), 1.54 (br d, J = 7.9 Hz, 6H), 1.34 (br d, J = 7.3 Hz, 6H), 1.22-1.11 (m, 2H), 1.10-1.04 (m, 2H), 1.06 (br d, J = 6.7 Hz, 6H). FXR EC$_{50}$ (nM) = 18. MS (ESI) 666.1 (M + H). | Ex. 276 |
| 356 | 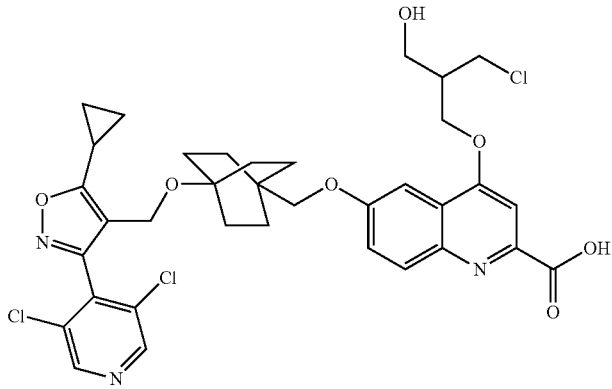<br>4-(3-chloro-2-(hydroxymethyl)propoxy)-6-((4-((5-cyclopropyl-3-(3,5-dichloropyridin-4-yl)isoxazol-4-yl)methoxy)bicyclo[2.2.2]octan-1-yl)methoxy)quinoline-2-carboxylic acid | $^1$H NMR (500 MHz, DMSO-d$_6$) δ 8.81 (s, 2H), 8.02 (br d, J = 9.2 Hz, 1H), 7.54 (s, 1H), 7.47 (br d, J = 9.2 Hz, 1H), 7.39 (br d, J = 1.8 Hz, 1H), 4.50-4.30 (m, 2H), 4.22 (s, 2H), 4.00-3.84 (m, 2H), 3.71 (s, 2H), 3.69-3.62 (m, 2H), 2.49-2.43 (m, 1H), 2.35-2.23 (m, 1H), 1.55 (br d, J = 7.9 Hz, 6H), 1.42-1.28 (m, 6H), 1.22-1.12 (m, 2H), 1.11-1.00 (m, 2H). FXR EC$_{50}$ (nM) = 110. MS (ESI) 716.2 (M + H). | Ex. 354 |
| 358 | 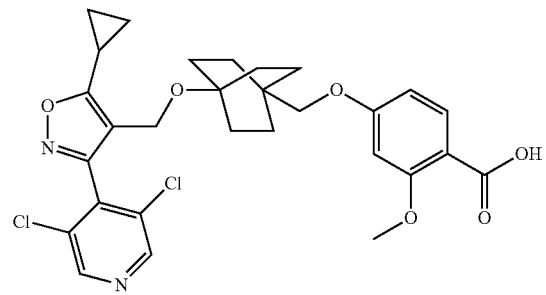<br>4-((4-((5-cyclopropyl-3-(3,5-dichloropyridin-4-yl)isoxazol-4-yl)methoxy)bicyclo[2.2.2]octan-1-yl)methoxy)-2-methoxybenzoic acid | $^1$H NMR (500 MHz, DMSO-d$_6$) δ 8.81 (s, 2H), 7.66 (d, J = 8.5 Hz, 1H), 6.53 (s, 1H), 6.50 (br d, J = 8.5 Hz, 1H), 4.22 (s, 2H), 3.78 (s, 2H), 3.60 (s, 3H), 2.34-2.25 (m, 1H), 1.58-1.44 (m, 6H), 1.39-1.28 (m, 6H), 1.19-1.12 (m, 2H), 1.11-1.03 (m, 2H). FXR EC$_{50}$ (nM) = 52. MS (ESI) 573.1 (M + H). | Ex. 276 |

TABLE 6-continued

| Ex. No. | Structure & Name | ¹H NMR, FXR EC$_{50}$ & MS (ESI) | Method |
|---|---|---|---|
| 360 | 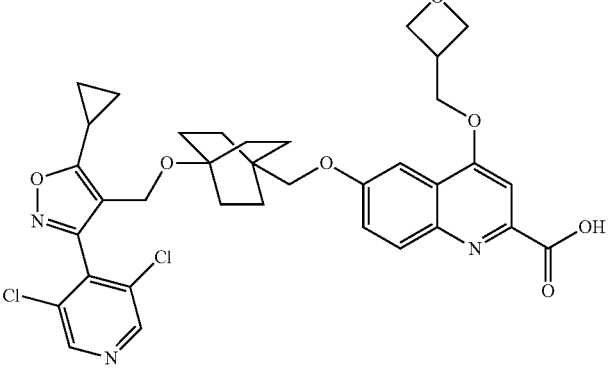<br>6-((4-((5-cyclopropyl-3-(3,5-dichloropyridin-4-yl)isoxazol-4-yl)methoxy)bicyclo[2.2.2]octan-1-yl)methoxy)-4-(oxetan-3-ylmethoxy)quinoline-2-carboxylic acid | ¹H NMR (500 MHz, DMSO-d$_6$) δ 8.80 (br s, 2H), 8.04 (br d, J = 9.2 Hz, 1H), 7.57 (s, 1H), 7.49 (br d, J = 9.4 Hz, 1H), 7.40 (br s, 1H), 4.63-4.51 (m, 2H), 4.38 (br d, J = 5.8 Hz, 2H), 4.24 (s, 2H), 4.23-4.15 (m, 2H), 3.73 (s, 2H), 2.35-2.24 (m, 1H), 2.20 (dt, J = 11.6, 5.9 Hz, 1H), 1.58 (br d, J = 3.4 Hz, 6H), 1.40 (br s, 6H), 1.16 (br d, J = 8.0 Hz, 2H), 1.09 (br d, J = 2.7 Hz, 2H). FXR EC$_{50}$ (nM) = 140. MS (ESI) 680.1 (M + H). | Ex. 276 |
| 361 | 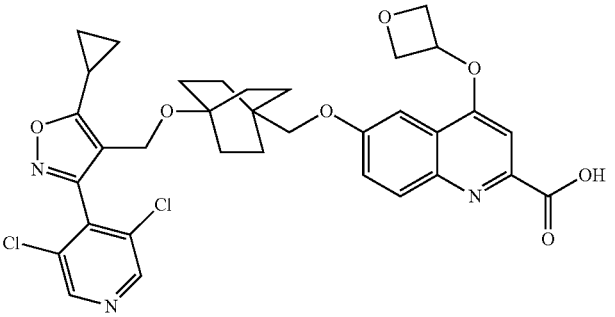<br>6-((4-((5-cyclopropyl-3-(3,5-dichloropyridin-4-yl)isoxazol-4-yl)methoxy)bicyclo[2.2.2]octan-1-yl)methoxy)-4-(oxetan-3-yloxy)quinoline-2-carboxylic acid | ¹H NMR (500 MHz, DMSO-d$_6$) δ 8.82 (s, 2H), 8.00 (br d, J = 8.9 Hz, 1H), 7.56-7.38 (m, 2H), 7.09 (s, 1H), 5.63 (quin, J = 5.1 Hz, 1H), 5.06 (t, J = 6.7 Hz, 2H), 4.73 (dd, J = 7.3, 4.6 Hz, 2H), 4.23 (s, 2H), 3.73 (s, 2H), 2.37-2.22 (m, 1H), 1.56 (br d, J = 8.2 Hz, 6H), 1.45-1.30 (m, 6H), 1.23-1.12 (m, 2H), 1.12-1.00 (m, 2H). FXR EC$_{50}$ (nM) = 71. MS (ESI) 666.3 (M + H). | Ex. 276 |

Example 384

8-cyano-2-(4-((5-cyclopropyl-3-(3,5-dichloropyridin-4-yl)isoxazol-4-yl)methoxy) bicyclo[2.2.2]octan-1-yl)quinoline-5-carboxylic acid

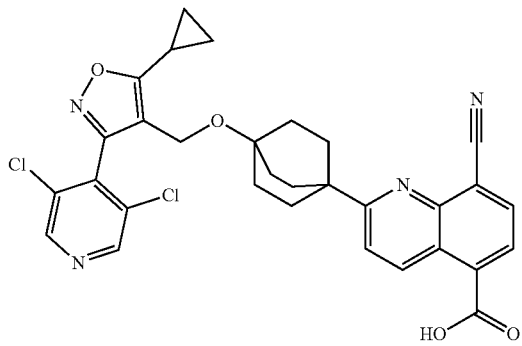

(384)

Step A. Intermediate 384A. Preparation of methyl 8-bromoquinoline-5-carboxylate

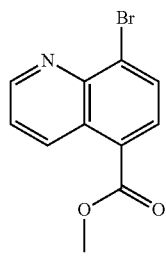

A solution of 3-amino-4-bromobenzoic acid (3.6 g, 17 mmol), glycerol (2.4 mL, 33 mmol), and 3-nitrobenzenesulfonic acid sodium salt (11 g, 50 mmol) in 75% H$_2$SO$_4$ (aq.) (40 mL) was stirred at 100° C. for 2 h and 140° C. for 1 h. The reaction mixture was cooled to rt and MeOH (40 mL) was added. The reaction was stirred at 60° C. After 18 h, the mixture was cooled to rt, poured into ice water and made basic with 12 M NH$_4$OH (aq.). EtOAc was added and the solution was filtered. The layers were separated and the aqueous layer was extracted with EtOAc (2×). The combined organic layers were washed with brine, dried (MgSO$_4$), filtered and concentrated. The crude product was purified by flash column chromatography (120 g silica gel cartridge; A=Hex, B=EtOAc; 30 min grad.; 0% B to 70% B; flow rate=80 mL/min). The pure fractions were combined, concentrated and dried in vacuo to provide the title compound (3.8 g, 14 mmol, 85% yield) as a white solid. $^1$H NMR (500 MHz, CHLOROFORM-d) δ 9.48-9.35 (m, 1H), 9.10 (dd, J=3.9, 1.7 Hz, 1H), 8.17-8.05 (m, 2H), 7.60 (dd, J=8.8, 4.1 Hz, 1H), 4.02 (s, 3H). MS (ESI) 265.8, 267.8 (M+H).

Step B. Intermediate 384B. Preparation of methyl 8-bromo-2-(4-(methoxycarbonyl)bicyclo[2.2.2]octan-1-yl)quinoline-5-carboxylate, TFA

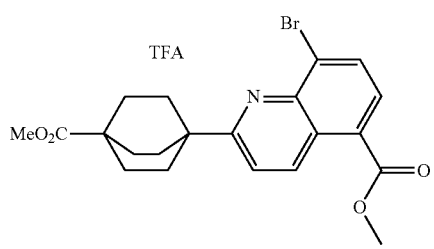 [SMILES: COC(=O)c1ccc(Br)c2nc(C34CCC(C(=O)OC)(CC3)CC4)ccc12]

To a solution of Intermediate 384A (1.8 g, 6.6 mmol), silver nitrate (0.84 g, 4.9 mmol), and 4-(methoxycarbonyl)bicyclo[2.2.2]octane-1-carboxylic acid (2.1 g, 9.9 mmol) in 10% H$_2$SO$_4$ (aq.) (27 mL) at 75° C. was dropwise added a solution of ammonium persulfate (2.3 g, 9.9 mmol) in water (30 mL). The reaction mixture was stirred at 75° C. for 10 min. The reaction mixture was poured onto crushed ice and made basic with 12 M NH$_4$OH (aq.). The solution was extracted with EtOAc (3×) and the combined organic layers were washed with brine, dried (MgSO$_4$), filtered and concentrated. The crude product was purified by preparative HPLC (Column: Phenomenex Luna AXIA 5u C18 21.2×100 mm; Mobile Phase B: 90:10 MeOH:H$_2$O with 0.1% TFA; Mobile Phase A=10:90 MeOH:H$_2$O with 0.1% TFA; Gradient: 40 to 100% B over 10 min then a 5 min hold at 100% B; Flow: 20 mL/min) to provide the title compound (1.7 g, 3.9 mmol, 59% yield) as a beige solid. MS (ESI) 432.0, 434.0 (M+H).

Step C. Intermediate 384C. Preparation of 8-bromo-2-(4-carboxybicyclo[2.2.2]octan-1-yl)quinoline-5-carboxylic acid

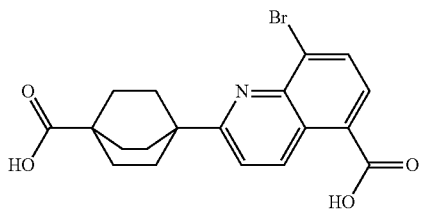 [SMILES: O=C(O)c1ccc(Br)c2nc(C34CCC(C(=O)O)(CC3)CC4)ccc12]

To a solution of Intermediate 384B (0.78 g, 1.4 mmol) in THF (14 mL) and MeOH (14 mL) was added 1 M NaOH (aq.) (8.5 mL, 8.5 mmol). The reaction was stirred at 70° C. for 3 h. The mixture was cooled, concentrated and acidified with 1 M HCl (aq.). The precipitate was filtered and dried in vacuo to provide the title compound (0.34 g, 0.83 mmol, 59% yield) as an off-white solid. $^1$H NMR (500 MHz, THF) δ 7.59 (d, J=9.1 Hz, 1H), 6.30-6.25 (m, 1H), 6.24-6.20 (m, 1H), 5.82 (d, J=9.1 Hz, 1H), 0.30-0.21 (m, 6H), 0.16-0.06 (m, 6H). MS (ESI) 403.9, 405.9 (M+H).

Step D. Intermediate 384D. Preparation of methyl 8-bromo-2-(4-iodobicyclo[2.2.2]octan-1-yl)quinoline-5-carboxylate

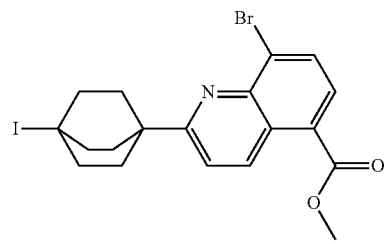 [SMILES: COC(=O)c1ccc(Br)c2nc(C34CCC(I)(CC3)CC4)ccc12]

A solution of Intermediate 384C (0.34 g, 0.83 mmol), iodobenzene diacetate (0.35 g, 1.1 mmol), and iodine (0.53 g, 2.1 mmol) in chlorobenzene (42 ml) was stirred at 85° C. and irradiated with blue LED. After 2 h, the reaction mixture was cooled and concentrated. The crude material was dissolved in DMF (9 mL), then K$_2$CO$_3$ (0.35 g, 2.5 mmol) and iodomethane (0.10 mL, 1.7 mmol) were added. After stirring 18 h, the reaction mixture was diluted with EtOAc, the organic layer was washed with water (5×), brine, dried (MgSO$_4$), filtered and concentrated. The crude product was purified by flash column chromatography (40 g silica gel cartridge; A=Hex, B=EtOAc; 20 min grad.; 0% B to 70% B; flow rate=80 mL/min). The pure fractions were combined, concentrated and dried in vacuo to provide the title compound (0.24 g, 0.48 mmol, 58% yield) as a white powder. MS (ESI) 499.9, 501.9 (M+H).

Step E. Intermediate 384E. Preparation of methyl 8-bromo-2-(4-((5-cyclopropyl-3-(3,5-dichloropyridin-4-yl)isoxazol-4-yl)methoxy)bicyclo[2.2.2]octan-1-yl)quinoline-5-carboxylate

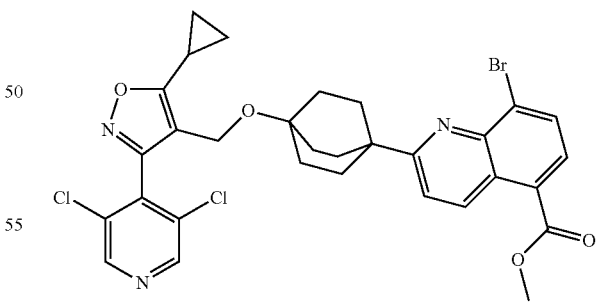

To a solution of (5-cyclopropyl-3-(3,5-dichloropyridin-4-yl)isoxazol-4-yl)methanol (0.10 g, 0.36 mmol) and Intermediate 384D (0.12 g, 0.24 mmol) in DCE (0.47 mL) was added silver trifluoromethanesulfonate (0.12 g, 0.47 mmol) followed by 2,6-di-tert-butylpyridine (0.21 mL, 0.95 mmol). The reaction mixture was heated in a pressure vial to 100° C. for 3 h and cooled to rt. The crude product was purified by reverse phase flash column chromatography (24 g C-18

429 reverse phase silica gel cartridge; A=Water with 0.1% TFA, B=MeOH with 0.1% TFA; 15 min grad.; 20% B to 100% B; flow rate=24 mL/min). The pure fractions were combined, concentrated and dried in vacuo to provide the title compound (0.061 g, 0.092 mmol, 39% yield) as a colorless glass. $^1$H NMR (500 MHz, CHLOROFORM-d) δ 9.23 (d, J=9.1 Hz, 1H), 8.64 (br s, 2H), 8.04 (s, 2H), 7.53 (d, J=9.1 Hz, 1H), 4.29 (s, 2H), 3.99 (s, 3H), 2.21-2.01 (m, 7H), 1.68-1.52 (m, 6H), 1.30-1.24 (m, 2H), 1.19-1.09 (m, 2H). MS (ESI) 656.0, 658.0 (M+H).

Step F. Intermediate 384F. Preparation of methyl 8-cyano-2-(4-((5-cyclopropyl-3-(3,5-dichloropyridin-4-yl)isoxazol-4-yl)methoxy)bicyclo[2.2.2]octan-1-yl)quinoline-5-carboxylate

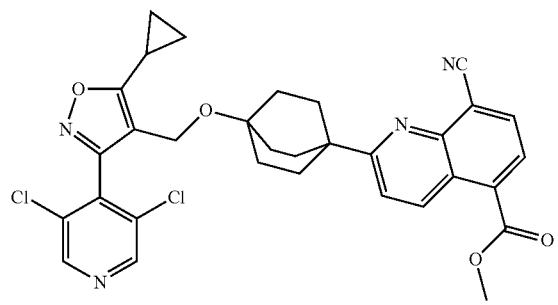 [SMILES: COC(=O)c1ccc(C#N)c2nc(C34CCC(OCc5c(-c6c(Cl)cncc6Cl)noc5C5CC5)(CC3)CC4)ccc12]

A pressure vial containing methyl Intermediate 384E (0.015 g, 0.023 mmol), Xantphos (2.6 mg, 4.6 μmop, Pd$_2$(dba)$_3$ (4.2 mg, 4.6 μmop, and zinc cyanide (5.4 mg, 0.046 mmol) was purged with nitrogen (3×) and anhydrous DMF (0.23 mL) was added. The reaction vial was capped and the mixture was stirred at 90° C. After 18 h, the reaction was cooled to rt, diluted with EtOAc, and washed with water (3×). The organic layer was washed with brine, dried (MgSO$_4$), filtered and concentrated. The crude product was taken on without further purification.

Step G. Example 384

The title compound was prepared according to methods described for the synthesis of Example 130 (Step C), substituting Intermediate 384F where appropriate: $^1$H NMR (500 MHz, DMSO-d$_6$) δ 9.15 (br d, J=9.2 Hz, 1H), 8.84 (s, 2H), 8.35 (d, J=7.6 Hz, 1H), 8.17 (br d, J=7.3 Hz, 1H), 7.81 (br d, J=8.9 Hz, 1H), 4.28 (s, 2H), 2.37-2.27 (m, 1H), 2.05-1.93 (m, 6H), 1.55-1.42 (m, 6H), 1.19-1.13 (m, 2H), 1.13-1.06 (m, 2H). FXR EC$_{50}$ (nM)=820. MS (ESI) 589.1 (M+H).

430

Example 385

8-cyclopropyl-2-(4-((5-cyclopropyl-3-(3,5-dichloropyridin-4-yl)isoxazol-4-yl)methoxy) bicyclo[2.2.2]octan-1-yl)quinoline-5-carboxylic acid (385)

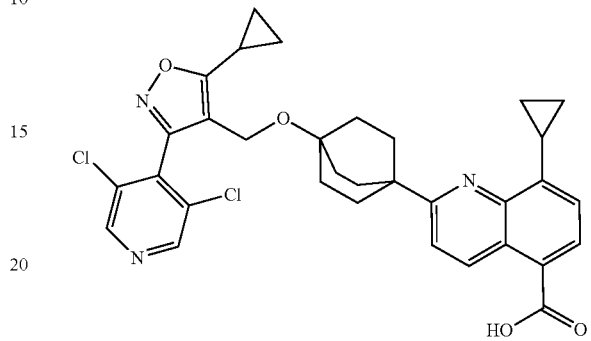

Step A. Intermediate 385A. Preparation of methyl 8-cyclopropyl-2-(4-((5-cyclopropyl-3-(3,5-dichloropyridin-4-yl)isoxazol-4-yl)methoxy)bicyclo[2.2.2]octan-1-yl)quinoline-5-carboxylate

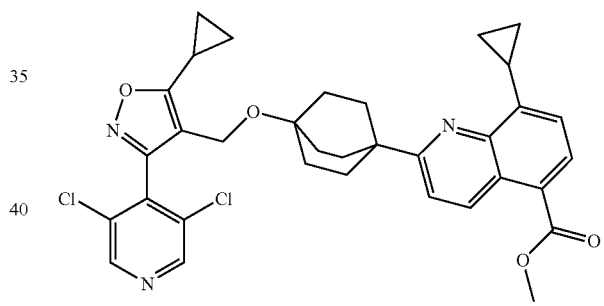

To a pressure vial was added cyclopropylboronic acid (2.9 mg, 0.034 mmol), Intermediate 384E (0.015 g, 0.023 mmol), K$_3$PO$_4$ (0.015 g, 0.068 mmol), and Pd(Ph$_3$P)$_4$ (1.3 mg, 1.1 μmol). The vial was purged with nitrogen (3×), then toluene (0.28 mL) and degassed water (0.028 mL) were added. The reaction vial was capped and the mixture was stirred at 90° C. After 18 h, the reaction mixture was diluted with EtOAc and washed with brine. The layers were separated and the organic layer was dried (MgSO$_4$) and concentrated. The crude product was taken on without further purification.

Step B. Example 385

The title compound was prepared according to methods described for the synthesis of Example 130 (Step C), substituting Intermediate 385A where appropriate: $^1$H NMR (500 MHz, DMSO-d$_6$) δ 9.54-9.04 (m, 1H), 8.86 (br s, 2H), 8.25-7.86 (m, 1H), 7.63 (br s, 1H), 7.28 (br s, 1H), 4.27 (s, 2H), 3.48 (br s, 1H), 2.33 (br s, 1H), 1.99 (br s, 6H), 1.48 (br s, 6H), 1.17 (br d, J=4.6 Hz, 4H), 1.10 (br d, J=2.7 Hz, 2H), 0.91 (br s, 2H). FXR EC$_{50}$ (nM)=13. MS (ESI) 604.3 (M+H).

Example 391

2-(4-((5-cyclopropyl-3-(3,5-dichloropyridin-4-yl)isoxazol-4-yl)methoxy)bicyclo[2.2.2]octan-1-yl)-8-isopropoxyquinoline-5-carboxylic acid

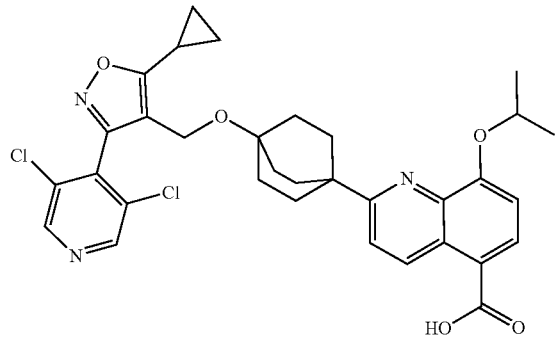
(391)

Step A. Intermediate 391A. Preparation of methyl 2-(4-((5-cyclopropyl-3-(3,5-dichloropyridin-4-yl)isoxazol-4-yl)methoxy)bicyclo[2.2.2]octan-1-yl)-8-hydroxyquinoline-5-carboxylate

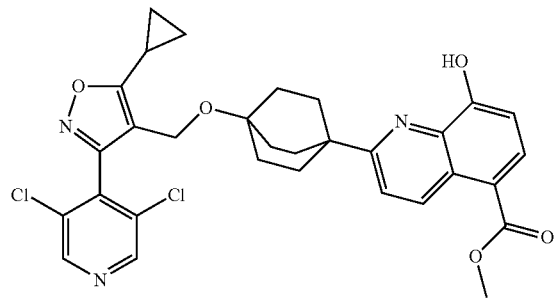

Step 1: To a pressure vial was added Intermediate 384E (0.056 g, 0.085 mmol), bis(pinacolato)diboron (0.043 g, 0.17 mmol), potassium acetate (0.033 g, 0.34 mmol), and Pd(dppf)Cl$_2$.CH$_2$Cl$_2$ adduct (3.5 mg, 4.3 µmol). The vial was purged with nitrogen (3×). DMF (0.6 mL) was added and the vial was capped and the reaction was stirred at 95° C. After 4 h, the reaction mixture was diluted with EtOAc, washed with water, brine, dried (MgSO$_4$), filtered and concentrated. The crude boronate ester product was taken forward without further purification.

Step 2: To a solution of the product of Step 1 above (0.060 g, 0.085 mmol) in EtOAc (2 mL) was added dropwise 30% hydrogen peroxide (aq.) (0.087 mL, 0.85 mmol) at 0° C. The reaction mixture was slowly warmed to rt and stirred. After 18 h, the reaction mixture was cooled to 0° C. and quenched with sat. sodium sulfite solution (aq.). The product was extracted with EtOAc (3×). The organic layer was combined, washed with brine, dried (MgSO$_4$), filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (0.032 g, 0.053 mmol, 63% yield) as a colorless glass. $^1$H NMR (500 MHz, CHLOROFORM-d) δ 9.37 (d, J=9.1 Hz, 1H), 8.64 (s, 2H), 8.28 (d, J=8.0 Hz, 1H), 7.55 (d, J=9.1 Hz, 1H), 7.13 (d, J=8.3 Hz, 1H), 4.29 (s, 2H), 3.95 (s, 3H), 2.17-2.11 (m, 1H), 2.11-2.05 (m, 6H), 1.69-1.56 (m, 6H), 1.29-1.25 (m, 2H), 1.18-1.10 (m, 2H). MS (ESI) 594.1 (M+H).

Step B. Intermediate 391B. Preparation of methyl 2-(4-((5-cyclopropyl-3-(3,5-dichloropyridin-4-yl)isoxazol-4-yl)methoxy)bicyclo[2.2.2]octan-1-yl)-8-isopropoxyquinoline-5-carboxylate

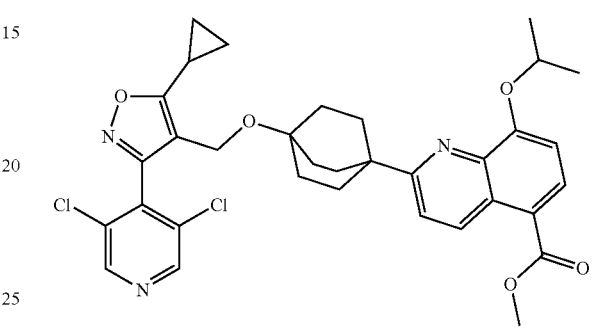

To a solution of Intermediate 391A (0.016 g, 0.027 mmol) in acetonitrile (0.27 mL) was added K$_2$CO$_3$ (0.011 g, 0.081 mmol) and 2-iodopropane (8.1 µL, 0.081 mmol). The reaction mixture was stirred at 70° C. After 18 h, the reaction mixture was filtered and concentrated and taken on without further purification. MS (ESI) 636.2 (M+H).

Step C. Example 391

The title compound was prepared according to methods described for the synthesis of Example 130 (Step C), substituting Intermediate 391B where appropriate: $^1$H NMR (500 MHz, DMSO-d$_6$) δ 9.26 (br d, J=9.2 Hz, 1H), 8.84 (s, 2H), 8.16 (br d, J=8.2 Hz, 1H), 7.65 (d, J=9.2 Hz, 1H), 7.21 (br d, J=8.2 Hz, 1H), 4.93 (dt, J=11.9, 6.0 Hz, 1H), 4.27 (s, 2H), 2.36-2.28 (m, 1H), 2.03-1.89 (m, 6H), 1.54-1.42 (m, 6H), 1.38 (d, J=6.1 Hz, 6H), 1.21-1.14 (m, 2H), 1.12-1.06 (m, 2H). FXR EC$_{50}$ (nM)=14. MS (ESI) 622.2 (M+H).

Example 410

2-(4-((5-cyclopropyl-3-(3,5-dichloropyridin-4-yl)isoxazol-4-yl)methoxy)bicyclo[2.2.2]octan-1-yl)-8-morpholinoquinoline-5-carboxylic acid

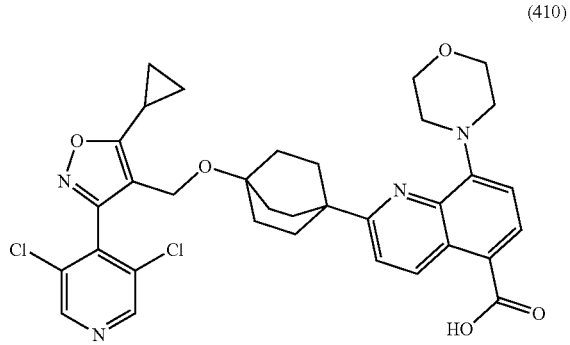 [SMILES: O=C(O)c1ccc(N2CCOCC2)c2nc(C34CCC(OCc5c(-c6c(Cl)cncc6Cl)noc5C5CC5)(CC3)CC4)ccc12]
(410)

433

Step A. Intermediate 410A. Preparation of ethyl 2-(4-((5-cyclopropyl-3-(3,5-dichloropyridin-4-yl)isoxazol-4-yl)methoxy)bicyclo[2.2.2]octan-1-yl)-8-morpholinoquinoline-5-carboxylate

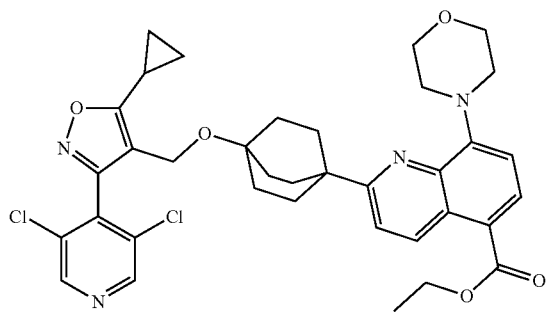 [SMILES: CCOC(=O)c1ccc(N2CCOCC2)c2nc(C34CCC(OCc5c(-c6c(Cl)cncc6Cl)noc5C5CC5)(CC3)CC4)ccc12]

To a pressure vial was added Intermediate 384E (0.020 g, 0.030 mmol), cesium carbonate (0.019 g, 0.060 mmol), and 2nd generation RuPhos precatalyst (1.2 mg, 1.5 μmol). The vial was purged with nitrogen (3×) and 1,4-dioxane (0.30 mL) and morpholine (0.013 mL, 0.15 mmol) were added. The reaction mixture was stirred at 90° C. After 18 h, the reaction mixture was cooled to rt, diluted with EtOAc, washed with water and brine, dried (MgSO$_4$), filtered and concentrated. The crude material was taken on without further purification. MS (ESI) 677.4 (M+H).

Step B. Example 410

The title compound was prepared according to methods described for the synthesis of Example 130 (Step C), substituting Intermediate 410A where appropriate: $^1$H NMR (500 MHz, DMSO-d$_6$) δ 9.30 (br d, J=9.2 Hz, 1H), 8.83 (s, 2H), 8.11 (br d, J=8.2 Hz, 1H), 7.62 (br d, J=9.2 Hz, 1H), 7.07 (br d, J=7.9 Hz, 1H), 4.27 (s, 2H), 3.86 (br s, 4H), 3.63-3.40 (m, 2H), 2.56 (s, 2H), 2.37-2.24 (m, 1H), 2.02-1.87 (m, 6H), 1.55-1.39 (m, 6H), 1.21-1.14 (m, 2H), 1.12-1.05 (m, 2H). FXR EC$_{50}$ (nM)=36. MS (ESI) 649.1 (M+H).

Example 418

2-(4-((5-cyclopropyl-3-(3,5-dichloropyridin-4-yl)isoxazol-4-yl)methoxy) bicyclo[2.2.2]octan-1-yl)-8-(2-hydroxy-2-methylpropoxy)quinoline-5-carboxylic acid (418)

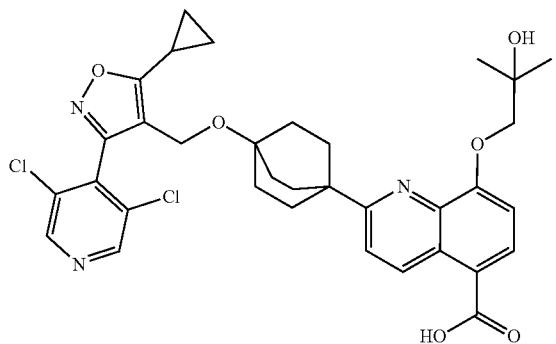

434

Step A. Intermediate 418A. Preparation of ethyl 2-(4-((5-cyclopropyl-3-(3,5-dichloropyridin-4-yl)isoxazol-4-yl)methoxy)bicyclo[2.2.2]octan-1-yl)-8-(2-hydroxy-2-methylpropoxy)quinoline-5-carboxylate To a solution of ethyl 2-(4-((5-cyclopropyl-3-(3,5-dichloropyridin-4-yl)isoxazol-4-yl)methoxy)bicyclo[2.2.2]octan-1-yl)-8-hydroxyquinoline-5-carboxylate (21 mg, 0.035 mmol) and K$_2$CO$_3$ (19 mg, 0.14 mmol) in acetonitrile (0.5 mL) and water (0.033 mL) was added 2,2-dimethyloxirane (9.2 μL, 0.10 mmol). The reaction mixture was irradiated at 120° C. (microwave) for 35 min. The reaction mixture was transferred into a pressure vial and DMF (0.35 mL) was added followed by additional 2,2-dimethyloxirane (9.2 μL, 0.10 mmol). The reaction mixture was stirred at 80° C. (conventional heating) for 18 h. Additional 2,2-dimethyloxirane (62 μL, 0.70 mmol) was added and the reaction was stirred at 80° C. After 18 h, the reaction mixture was diluted with EtOAc, washed with water, brine, dried (MgSO$_4$), filtered and concentrated. The crude product was taken forward without further purification. MS (ESI) 680.4 (M+H).

Step B. Example 418

The title compound was prepared according to methods described for the synthesis of Example 130 (Step C), substituting Intermediate 418A where appropriate: $^1$H NMR (500 MHz, DMSO-d$_6$) δ 9.24 (br d, J=9.0 Hz, 1H), 8.80 (br s, 2H), 8.18 (d, J=8.3 Hz, 1H), 7.65 (d, J=9.1 Hz, 1H), 7.18 (d, J=8.3 Hz, 1H), 4.27 (s, 2H), 3.98 (s, 2H), 2.34-2.23 (m, 1H), 2.08-1.95 (m, 6H), 1.59-1.42 (m, 6H), 1.33 (s, 6H), 1.21-1.14 (m, 2H), 1.13-1.04 (m, 2H). FXR EC$_{50}$ (nM)=120. MS (ESI) 652.3 (M+H).

Example 423

2-(4-((5-cyclopropyl-3-(dicyclopropylmethyl)isoxazol-4-yl)methoxy)bicyclo[2.2.2]octan-1-yl)-7-(trifluoromethyl)quinoline-5-carboxylic acid

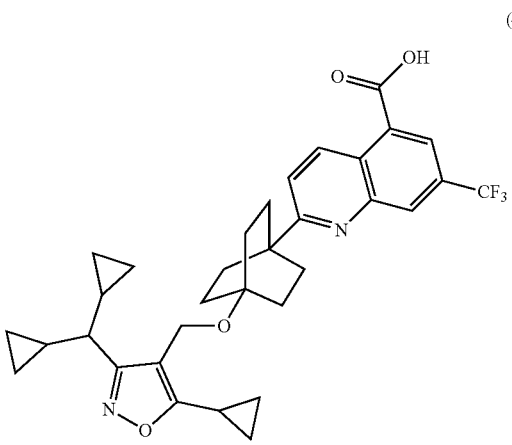
(423)

Step A. Intermediate 423A. Preparation of (E)-2,2-dicyclopropylacetaldehyde oxime

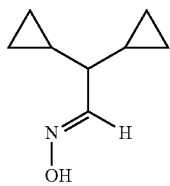

Hydroxylamine hydrochloride (1.7 g, 24 mmol) was added to a solution of 2,2-dicyclopropylacetaldehyde (2.0 g, 16 mmol) in pyridine (8 mL). After stirring 1 h, the reaction mixture was diluted with water and extracted with EtOAc. The organic layer was washed with water, brine, dried over Na$_2$SO$_4$, filtered and concentrated. The product was dried in vacuo to provide the title compound (1.7 g, 12 mmol, 76% yield) as a colorless oil. $^1$H NMR (400 MHz, CHLOROFORM-d) δ 7.43 (dd, J=1.7, 0.8 Hz, 1H), 1.75 (br s, 1H), 1.01-0.93 (m, 2H), 0.32-0.11 (m, 4H), 0.09-0.13 (m, 4H)

Step B. Intermediate 423B. Preparation of (Z)-2,2-dicyclopropyl-N'-hydroxyacetimidoyl chloride

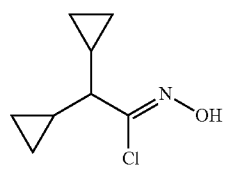 [SMILES: O/N=C(\Cl)C(C1CC1)C1CC1]

To a solution of Intermediate 423A (1.7 g, 12 mmol) in DMF (16 mL) was added NCS (2.0 g, 15 mmol) in portions. The reaction was stirred at 40° C. After 1.5 h, the mixture was poured into water and extracted with EtOAc (2×). The organic phase was combined, washed with brine, dried over Na$_2$SO$_4$, filtered and concentrated. The crude product was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to provide the title compound (1.5 g, 8.9 mmol, 73% yield) as a colorless oil. $^1$H NMR (400 MHz, CHLOROFORM-d) δ 7.46 (s, 1H), 0.93-0.80 (m, 2H), 0.76-0.60 (m, 1H), 0.43 (dddd, J=9.1, 8.0, 5.8, 4.5 Hz, 2H), 0.33-0.22 (m, 2H), 0.12 (dt, J=5.6, 4.7 Hz, 2H), 0.05-0.06 (m, 2H).

Step C. Intermediate 423C. Preparation of methyl 5-cyclopropyl-3-(dicyclopropylmethyl)isoxazole-4-carboxylate

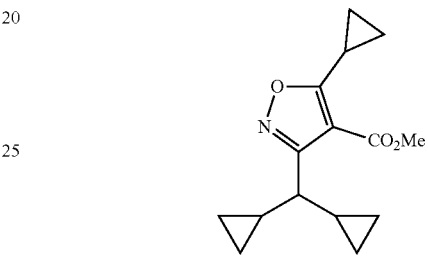

To a 25 mL flask containing methyl 3-cyclopropyl-3-oxopropanoate (0.75 g, 5.3 mmol) was added Et$_3$N (1.4 mL, 10 mmol). The mixture was stirred at rt for 30 min, then cooled to 0° C. To this mixture was added a solution of Intermediate 423B in EtOH (3 mL) over a period of 5 min. The reaction was warmed to rt and stirred. After 3 h, the mixture was poured into water and extracted with EtOAc (2×). The organic phase was combined, washed with brine, dried over Na$_2$SO$_4$, filtered and concentrated. The crude product was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to provide the title compound (0.68 g, 2.6 mmol, 52% yield) as a colorless oil. $^1$H NMR (400 MHz, CHLOROFORM-d) δ 3.69 (s, 3H), 2.66-2.57 (m, 1H), 1.54 (dd, J=2.6, 2.0 Hz, 1H), 1.15-1.11 (m, 2H), 1.01-0.97 (m, 4H), 0.44-0.34 (m, 2H), 0.21 (br dd, J=8.4, 4.4 Hz, 2H), 0.12 (dd, J=9.5, 4.6 Hz, 2H), −0.01 (dd, J=9.6, 4.3 Hz, 2H). MS (ESI) 262.1 (M+H).

Step D. Intermediate 423D. Preparation of (5-cyclopropyl-3-(dicyclopropylmethyl)isoxazol-4-yl)methanol

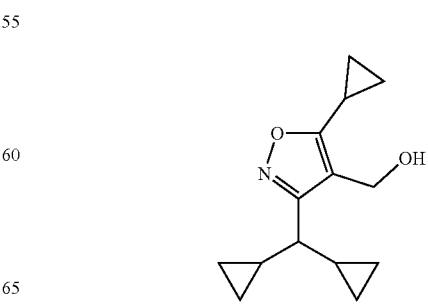

To a solution of Intermediate 423C (1.2 g, 4.6 mmol) in DCM (50 mL) was added DIBAL-H (13 mL, 13 mmol) (1 M solution in DCM) at −78° C. The reaction was stirred at this temperature for 1 h. To this mixture was added a solution of Rochelle's salt (aq.) (ca. 100 mL), and the mixture was warmed to rt and stirred. After 4 h, the organic layer was separated, washed with brine, dried over $Na_2SO_4$, filtered and concentrated. The crude product was purified by flash column chromatography (40 g silica gel cartridge; A=Hex, B=EtOAc; 15 min grad.; 0% B to 100% B; flow rate=20 mL/min). The pure fractions were combined, concentrated and dried in vacuo to provide the title compound (0.82 g, 3.5 mmol, 76% yield.) as a white solid. $^1$H NMR (500 MHz, CHLOROFORM-d) δ 4.62 (d, J=5.5 Hz, 2H), 2.11-2.06 (m, 1H), 1.65 (t, J=9.2 Hz, 1H), 1.43 (t, J=5.4 Hz, 1H), 1.31-1.22 (m, 2H), 1.18 (dd, J=4.8, 2.1 Hz, 2H), 1.08 (dd, J=8.3, 2.5 Hz, 2H), 0.68-0.61 (m, 2H), 0.48-0.42 (m, 2H), 0.34 (dd, J=9.5, 4.8 Hz, 2H), 0.20 (dd, J=9.5, 4.8 Hz, 2H). MS (ESI) 234.0 (M+H).

Step E. Example 423

The title compound was prepared according to methods described for the synthesis of Example 384, substituting Intermediate 423D and methyl 7-(trifluoromethyl)quinoline-5-carboxylate where appropriate: $^1$H NMR (500 MHz, DMSO-$d_6$) δ 9.18 (br d, J=9.1 Hz, 1H), 8.39 (s, 1H), 8.23 (s, 1H), 7.85 (br d, J=9.1 Hz, 1H), 4.22 (s, 2H), 2.13-2.08 (m, 1H), 2.04 (br d, J=7.3 Hz, 6H), 1.76 (br s, 6H), 1.48-1.39 (m, 1H), 1.13 (br dd, J=8.2, 4.4 Hz, 2H), 1.02-0.96 (m, 2H), 0.90 (br d, J=2.6 Hz, 2H), 0.53-0.41 (m, 2H), 0.28-0.20 (m, 4H), 0.02 (br d, J=5.5 Hz, 2H). FXR $EC_{50}$ (nM)=67. MS (ESI) 581.4 (M+H)

Example 425

2-(4-((5-cyclopropyl-3-(2,2-difluoro-1-methylcyclopropyl)isoxazol-4-yl)methoxy) bicyclo[2.2.2]octan-1-yl)quinoline-5-carboxylic acid

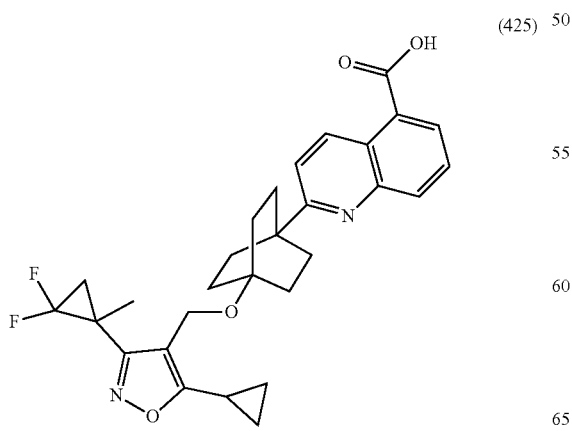
(425)

Step A. Intermediate 425A. Preparation of (2,2-difluoro-1-methylcyclopropyl) methanol

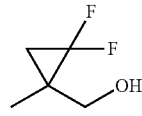

To a suspension of LAH (0.17 g, 4.5 mmol) in THF (8 mL) was dropwise added a solution of 2,2-difluoro-1-methylcyclopropane-1-carboxylic acid (0.61 g, 4.5 mmol) in THF (8 mL) at 0° C. The reaction was warmed to rt and stirred. After 4 h, the reaction was carefully quenched with water (0.17 mL), followed by 15% NaOH (aq.) (0.17 mL). After stirring 15 min, solid $MgSO_4$ was added. After stirring an additional 15 min, the reaction was filtered and concentrated to afford the title compound (0.53 g, 4.3 mmol, 97% yield) as a colorless oil. $^1$H NMR (400 MHz, CHLOROFORM-d) δ 3.72-3.68 (m, 1H), 3.62-3.57 (m, 1H), 1.91-1.82 (m, 1H), 1.31 (dd, J=2.9, 1.5 Hz, 3H), 1.24 (ddd, J=13.8, 7.6, 4.1 Hz, 1H), 1.07 (ddd, J=12.1, 7.8, 4.1 Hz, 1H).

Step B. Intermediate 425B. Preparation of 2,2-difluoro-1-methylcyclopropane-1-carbaldehyde

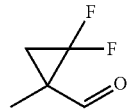

PCC (0.64 g, 3.0 mmol) was added to a solution of Intermediate 425A (0.33 g, 2.7 mmol) in DCM (10 mL). After stirring 2 h, the mixture was filtered through Celite, the filter cake was washed with DCM (10 mL), and the resultant filtrate was taken onto subsequent steps without additional workup or characterization.

Step C. Intermediate 425C. Preparation of (E)-2,2-difluoro-1-methylcyclopropane-1-carbaldehyde oxime

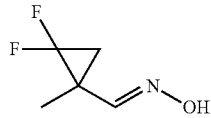

Pyridine (2.6 mL, 32 mmol) was added to a solution of Intermediate 425B (0.32 g, 2.7 mmol) in DCM (20 mL). To this mixture was added hydroxylamine hydrochloride (0.28 g, 4.1 mmol). After stirring for 3.5 h, the reaction was diluted with water and extracted with DCM. The organic layers were washed with brine, dried over $MgSO_4$, filtered and concentrated to afford the title compound (0.29 g, 2.1 mmol, 79% yield) as a greenish semisolid. MS (ESI) 136.0 (M+H).

Step C. Intermediate 425C. Preparation of (Z)-2,2-difluoro-N-hydroxy-1-methylcyclopropane-1-carbimidoyl chloride

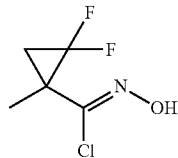

To a solution of Intermediate 425B (0.29 g, 2.2 mmol) in DMF (3 mL) was added NCS (0.32 g, 2.4 mmol) in portions. The reaction was stirred at 40° C. After 2.5 h, the mixture was poured into water and extracted with EtOAc (2×). The organic phase was combined, washed with brine, dried over $Na_2SO_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (150 mg, 0.885 mmol, 41% yield) as a colorless oil. MS (ESI) 169.9 (M+H).

Step D. Intermediate 425D. Preparation of methyl 5-cyclopropyl-3-(2,2-difluoro-1-methylcyclopropyl)isoxazole-4-carboxylate

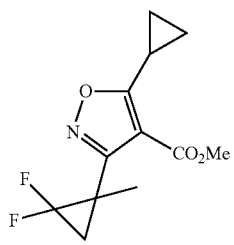 [SMILES: COC(=O)c1c(C2(C)CC2(F)F)noc1C1CC1]

To a vial containing methyl 3-cyclopropyl-3-oxopropanoate (140 mg, 0.97 mmol) was added $Et_3N$ (250 µL, 1.8 mmol). The mixture was stirred at rt. After 20 min, a solution of Intermediate 425C (150 mg, 0.89 mmol) in EtOH (0.5 mL) was added upon which the clear solution became a suspension. After stirring 1 h, the mixture was diluted with EtOAc. The organic layer was washed with water, brine, dried over $Na_2SO_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (150 mg, 0.58 mmol, 66% yield) as a colorless oil. $^1$H NMR (400 MHz, CHLOROFORM-d) δ 3.97-3.85 (m, 3H), 2.91-2.73 (m, 1H), 1.96 (ddd, J=13.0, 8.2, 4.3 Hz, 1H), 1.53 (d, J=1.5 Hz, 3H), 1.50-1.42 (m, 1H), 1.25-1.17 (m, 4H). MS (ESI) 258.1 (M+H).

Step E. Intermediate 425E. Preparation of (5-cyclopropyl-3-(2,2-difluoro-1-methylcyclopropyl)isoxazol-4-yl)methanol

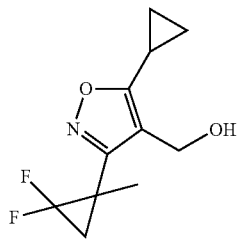 [SMILES: CC1(c2noc(C3CC3)c2CO)CC1(F)F]

To a solution of Intermediate 425D (150 mg, 0.58 mmol) in DCM (6 mL) was added DIBAL-H (1.6 mL, 1.6 mmol) (1 M solution in DCM) at −78° C. The reaction was stirred at this temperature for 1 h. To this mixture was added a solution of Rochelle's salt (aq.) (ca. 5 mL), and the mixture was warmed to rt and stirred. After 2 h, the organic layer was separated, washed with brine, dried over $Na_2SO_4$, filtered and concentrated. The crude product was purified by flash column chromatography (4 g silica gel cartridge; A=Hex, B=EtOAc; 15 min grad.; 0% B to 100% B; flow rate=4 mL/min). The pure fractions were combined, concentrated and dried in vacuo to provide the title compound (90 mg, 0.39 mmol, 67% yield) as a white solid. $^1$H NMR (400 MHz, CHLOROFORM-d) δ 4.60 (d, J=3.7 Hz, 2H), 2.15-1.99 (m, 3H), 1.56 (dd, J=3.0, 1.9 Hz, 3H), 1.47 (ddd, J=12.0, 8.0, 5.3 Hz, 1H), 1.14 (td, J=3.1, 1.3 Hz, 2H), 1.10-1.03 (m, 2H). MS (ESI) 230.1 (M+H).

Step F. Example 425

The title compound was prepared according to methods described for the synthesis of Example 384, substituting Intermediate 425E and methyl quinoline-5-carboxylate where appropriate: (3.7 mg, 0.0070 mmol, 13% yield). $^1$H NMR (500 MHz, DMSO-$d_6$) δ 9.20 (br d, J=8.9 Hz, 1H), 8.11 (br t, J=7.5 Hz, 2H), 7.80-7.58 (m, 2H), 4.45-4.24 (m, 2H), 2.23-2.05 (m, 7H), 2.04-1.95 (m, 1H), 1.88 (br d, J=8.9 Hz, 6H), 1.79-1.69 (m, 1H), 1.52 (br s, 3H), 1.09 (br d, J=8.2 Hz, 2H), 0.99 (br d, J=7.0 Hz, 2H). FXR $EC_{50}$ (nM)=3400. MS (ESI) 509.3 (M+H).

Example 426

8-chloro-2-(4-((5-cyclopropyl-3-(3,5-dichloropyridin-4-yl)isoxazol-4-yl)methoxy) bicyclo[2.2.2]octan-1-yl)-6-methoxyquinoline-5-carboxy c acid

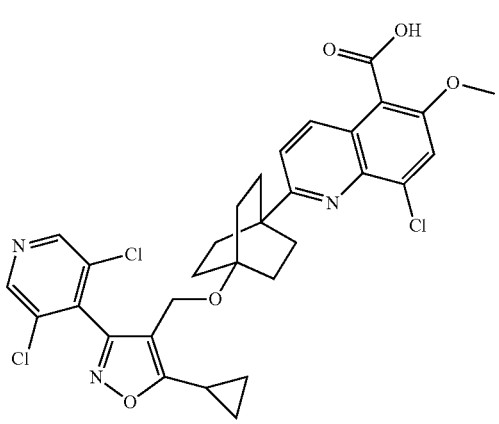
(426)

Step A. Intermediate 426A. Preparation of methyl 6-bromo-8-chloroquinoline-5-carboxylate

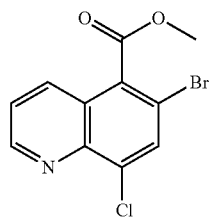 [SMILES: COC(=O)c1c(Br)cc(Cl)c2ncccc12]

To a solution of 6-bromo-8-chloroquinoline-5-carboxylic acid (2.6 g, 9.0 mmol) in DMF (18 mL) were added K$_2$CO$_3$ (3.7 g, 27 mmol) and iodomethane (6.7 mL, 14 mmol) (2 M solution in t-butyl methyl ether). After stirring 3 h, the mixture was diluted with water and the aqueous phase was extracted with EtOAc. The organic phase was washed with brine, dried over Na$_2$SO$_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (2.3 g, 7.5 mmol, 84% yield) as a brown solid. $^1$H NMR (400 MHz, CHLOROFORM-d) δ 9.08 (dd, J=4.2, 1.5 Hz, 1H), 8.16 (dd, J=8.6, 1.8 Hz, 1H), 8.04 (s, 1H), 7.56 (dd, J=8.6, 4.2 Hz, 1H), 4.08 (s, 3H). MS (ESI) 301.9 (M+H).

Step B. Intermediate 426B. Preparation of methyl 6-bromo-8-chloro-2-(4-(methoxycarbonyl)bicyclo[2.2.2]octan-1-yl)quinoline-5-carboxylate

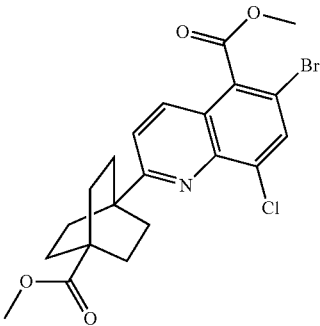 [SMILES: COC(=O)c1c(Br)cc(Cl)c2nc(C34CCC(C(=O)OC)(CC3)CC4)ccc12]

The title compound was prepared according to methods described for the synthesis of Intermediate 384B, substituting Intermediate 426A where appropriate: (0.79 g, 1.7 mmol, 39% yield). $^1$H NMR (400 MHz, CHLOROFORM-d) δ 8.06-7.99 (m, 1H), 7.96 (s, 1H), 7.55 (d, J=8.8 Hz, 1H), 4.05 (s, 3H), 3.69 (s, 3H), 2.11-2.04 (m, 6H), 2.01-1.93 (m, 6H). MS (ESI) 468.1 (M+H).

Step C. Intermediate 426C. Preparation of methyl 8-chloro-2-(4-(methoxycarbonyl) bicyclo[2.2.2]octan-1-yl)-6-(4,4,5,5-tetramethyl-1,3,2-dioxaborolan-2-yl)quinoline-5-carboxylate

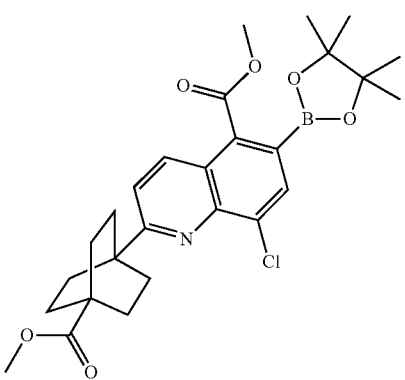

To a round bottomed flask were added Intermediate 426B (0.79 g, 1.7 mmol), bis(pinacolato)diboron (0.65 g, 2.5 mmol), potassium acetate (0.50 g, 5.1 mmol), and Pd(dppf)Cl$_2$·CH$_2$Cl$_2$ adduct (0.062 g, 0.085 mmol). The vessel was purged and flushed with nitrogen. To this mixture was added 1,4-dioxane (11 mL) and the reaction mixture was stirred at 80° C. After 16 h, the mixture was cooled and diluted with EtOAc. The organic layer was washed with water, brine, dried over Na$_2$SO$_4$, filtered and concentrated. The product was dried in vacuo to afford the title compound (ca. 1.2 g, crude) as a brown foam. MS (ESI) 514.3 (M+H).

Step D. Intermediate 426D. Preparation of methyl 8-chloro-6-hydroxy-2-(4-(methoxycarbonyl)bicyclo[2.2.2]octan-1-yl)quinoline-5-carboxylate

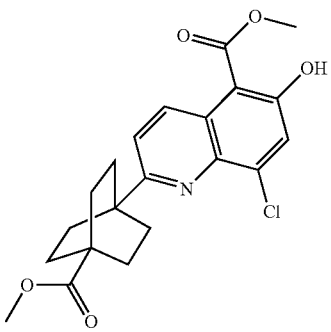 [SMILES: COC(=O)c1c(O)cc(Cl)c2nc(C34CCC(C(=O)OC)(CC3)CC4)ccc12]

To a solution of Intermediate 426C (0.87 g, 1.7 mmol) dissolved in EtOAc (34 mL) was added dropwise 30% hydrogen peroxide (aq.) (1.7 mL, 17 mmol) at 0° C. The reaction was warmed to rt and stirred. After 2 h, the mixture was cooled to 0° C. and quenched with sat. sodium disulfite (aq.). The aqueous phase was extracted with EtOAc (3×). The organic phase was combined, washed with brine, dried over $Na_2SO_4$, filtered and concentrated. The crude product was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to provide the title compound (0.68 g, 1.7 mmol, 100% yield) as a brown oil. $^1$H NMR (400 MHz, CHLOROFORM-d) δ 9.03-8.91 (m, 1H), 7.57-7.41 (m, 2H), 4.09 (s, 3H), 3.74-3.62 (m, 4H), 2.08-2.03 (m, 6H), 2.00-1.95 (m, 6H). MS (ESI) 404.1 (M+H).

Step E. Intermediate 426E. Preparation of methyl 8-chloro-6-methoxy-2-(4-(methoxycarbonyl)bicyclo[2.2.2]octan-1-yl)quinoline-5-carboxylate

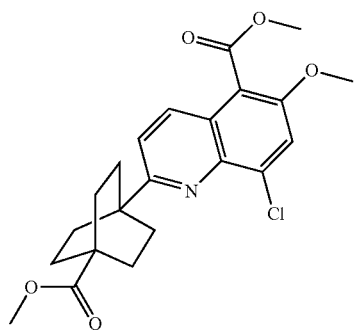

To a solution of Intermediate 426D (250 mg, 0.62 mmol) and $K_2CO_3$ (260 mg, 1.9 mmol) in DMF (4 mL) was added iodomethane (460 μL, 0.93 mmol) (2 M solution in t-butyl methyl ether). After stirring 18 h, the reaction mixture was diluted with EtOAc. The organic layer was washed with water, brine, dried over $Na_2SO_4$, filtered and concentrated. The crude product was purified by flash column chromatography (24 g silica gel cartridge; A=DCM, B=MeOH; 15 min grad.; 100% A; flow rate=24 mL/min). The pure frac- tions were combined, concentrated and dried in vacuo to provide the title compound (200 mg, 0.48 mmol, 77% yield) as a white solid. $^1$H NMR (400 MHz, CHLOROFORM-d) δ 8.09 (d, J=9.0 Hz, 1H), 7.60 (s, 1H), 7.51-7.44 (m, 1H), 4.01 (d, J=1.3 Hz, 3H), 3.98-3.95 (m, 3H), 3.69 (d, J=1.3 Hz, 3H), 2.10-2.02 (m, 6H), 2.00-1.91 (m, 6H). MS (ESI) 418.2 (M+H).

Step F. Intermediate 426F. Preparation of 4-(8-chloro-6-methoxy-5-(methoxycarbonyl) quinolin-2-yl)bicyclo[2.2.2]octane-1-carboxylic acid

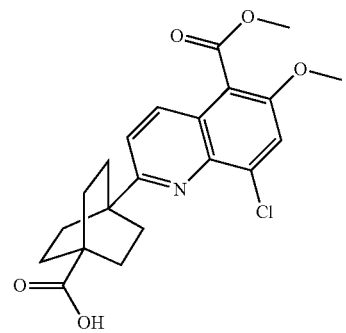 [SMILES: COC(=O)c1c(OC)cc(Cl)c2nc(C34CCC(C(=O)O)(CC3)CC4)ccc12]

To a solution of Intermediate 426E (200 mg, 0.48 mmol) dissolved in THF (4 mL) and MeOH (1 mL) was added 2 M NaOH (aq.) (2.4 mL, 4.8 mmol). After stirring 18 h, the volatile solvents were concentrated. The resultant aqueous phase was acidified with 1 M HCl (aq.) (pH ~3) and extracted with EtOAc. The organic phase was washed with brine, dried over $Na_2SO_4$, filtered and concentrated. The product was dried in vacuo to provide the title compound (190 mg, 0.47 mmol, 98% yield) as a white solid. $^1$H NMR (400 MHz, CHLOROFORM-d) δ 8.09 (d, J=9.0 Hz, 1H), 7.61 (s, 1H), 7.49 (d, J=9.0 Hz, 1H), 4.01 (s, 3H), 3.98 (s, 3H), 2.10-2.05 (m, 6H), 2.04-1.97 (m, 7H). MS (ESI) 418.2 (M+H). MS (ESI) 404.2 (M+H).

Step G. Intermediate 426G. Preparation of methyl 8-chloro-2-(4-iodobicyclo[2.2.2]octan-1-yl)-6-methoxyquinoline-5-carboxylate

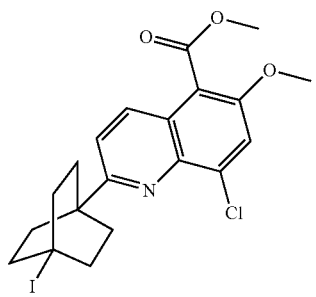 [SMILES: COC(=O)c1c(OC)cc(Cl)c2nc(C34CCC(I)(CC3)CC4)ccc12]

To a solution of Intermediate 426F (190 mg, 0.47 mmol) in chlorobenzene (23 mL) were added iodobenzene diacetate (170 mg, 0.52 mmol) and iodine (360 mg, 1.4 mmol). The reaction was stirred at 85° C. and irradiated under blue LED. After 3 h, the mixture was cooled and concentrated. The crude product was purified by flash column chromatography (12 g silica gel cartridge; A=Hex, B=EtOAc; 15 min grad.;

0% B to 100% B; flow rate=12 mL/min). The pure fractions were combined, concentrated and dried in vacuo to provide the title compound (130 mg, 0.26 mmol, 55% yield) as a white solid. ¹H NMR (400 MHz, CHLOROFORM-d) δ 8.08 (d, J=9.0 Hz, 1H), 7.60 (s, 1H), 7.42 (d, J=9.0 Hz, 1H), 4.00 (s, 3H), 3.97 (s, 3H), 2.66-2.60 (m, 6H), 2.21-2.15 (m, 6H). MS (ESI) 485.7 (M+H).

Step H. Example 426

The title compound was prepared according to methods described for the synthesis of Example 4 (Step E), by reaction of Intermediate 426G and (5-cyclopropyl-3-(3,5-dichloropyridin-4-yl)isoxazol-4-yl)methanol: (3.7 mg, 0.0070 mmol, 13% yield). ¹H NMR (500 MHz, DMSO-$d_6$) δ 8.80 (s, 2H), 8.06 (br d, J=8.8 Hz, 1H), 7.77 (s, 1H), 7.57 (d, J=8.8 Hz, 1H), 4.27 (s, 2H), 3.91 (s, 3H), 2.34-2.26 (m, 1H), 1.97 (br d, J=7.6 Hz, 6H), 1.49 (br d, J=6.9 Hz, 6H), 1.20-1.13 (m, 2H), 1.08 (br s, 2H). FXR $EC_{50}$ (nM)=12. MS (ESI) 628.3 (M+H).

Example 430

6-(2-(4-((5-cyclopropyl-3-(3,5-dichloropyridin-4-yl)isoxazol-4-yl)methoxy) bicyclo[2.2.2]octan-1-yl)ethyl)-4-(trifluoromethyl)quinoline-2-carboxylic acid

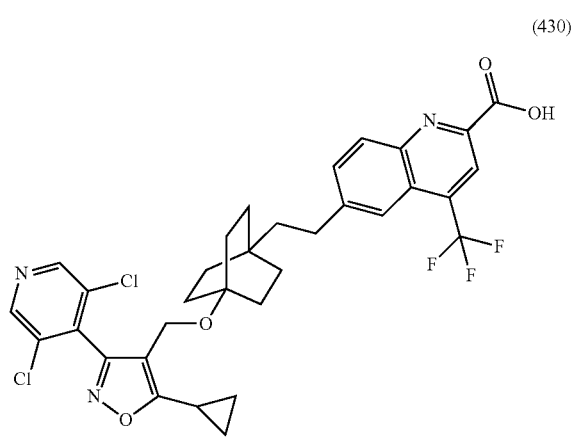 [SMILES: O=C(O)c1cc(C(F)(F)F)c2cc(CCC34CCC(OCc5c(-c6c(Cl)cncc6Cl)noc5C5CC5)(CC3)CC4)ccc2n1]

(430)

Step A. Intermediate 430A. Preparation of methyl 4-ethynylbicyclo[2.2.2]octane-1-carboxylate

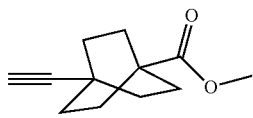

To an oven dried flask were added Intermediate 159B (120 mg, 0.61 mmol) and $K_2CO_3$ (170 mg, 1.2 mmol). Anhydrous MeOH (2.4 mL) was added and the reaction was stirred under $N_2$. After 30 min, dimethyl (1-diazo-2-oxopropyl)phosphonate (140 mg, 0.73 mmol) was added. After stirring 1 h, the mixture was diluted with ether, washed with water, brine, dried over $MgSO_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (75 mg, 0.39 mmol, 64% yield) as a white solid. ¹H NMR (400 MHz, CHLOROFORM-d) δ 3.64 (s, 3H), 2.09 (s, 1H), 1.80 (s, 12H).

Step B. Intermediate 430B. Preparation of methyl 4-ethynylbicyclo[2.2.2]octane-1-carboxylate

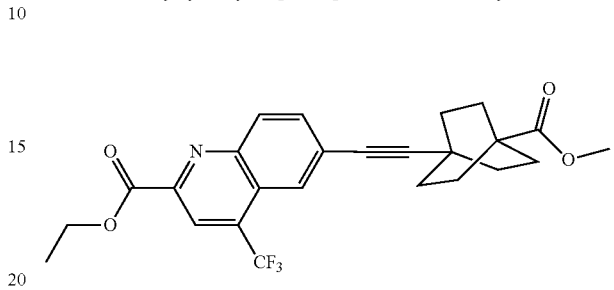

The title compound was prepared according to methods described for the synthesis of Intermediate 130B, substituting Intermediate 430A where appropriate: (100 mg, 0.22 mmol, 91% yield, white solid). ¹H NMR (400 MHz, CHLOROFORM-d) δ 8.45 (s, 1H), 8.30 (d, J=8.8 Hz, 1H), 8.14 (s, 1H), 7.81 (dd, J=8.9, 1.7 Hz, 1H), 4.58 (q, J=7.1 Hz, 2H), 3.67 (s, 3H), 1.98-1.84 (m, 12H), 1.50 (t, J=7.2 Hz, 3H). MS (ESI) 460.6 (M+H).

Step C. Intermediate 430C. Preparation of ethyl 6-(2-(4-(methoxycarbonyl) bicyclo[2.2.2]octan-1-yl)ethyl)-4-(trifluoromethyl)quinoline-2-carboxylate

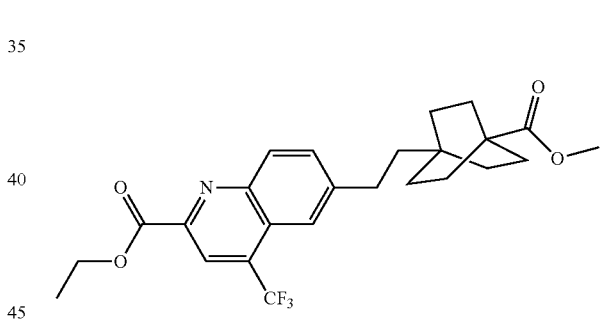

A solution of Intermediate 430B (100 mg, 0.22 mmol) in MeOH (7 mL) was purged and flushed with $N_2$. To this mixture was added palladium on carbon (23 mg, 0.022 mmol) (10% wt. loading, matrix activated carbon support), and the vessel was purged and flushed again with $N_2$. The reaction was stirred under hydrogen (1 atm, balloon). After 18 h, the mixture was diluted with 1,4-dioxane (2 mL) and DDQ (150 mg, 0.65 mmol) was added. After stirring 10 min, the reaction was diluted with EtOAc. The organic layer was washed with 2 N NaOH (aq.), brine, dried over $Na_2SO_4$, filtered and concentrated. The crude product was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (30 mg, 0.065 mmol, 30% yield) as a brown oil. ¹H NMR (500 MHz, CHLOROFORM-d) δ 8.48-8.46 (m, 1H), 8.37-8.29 (m, 1H), 7.92 (br s, 1H), 7.74 (dd, J=8.8, 1.4 Hz, 1H), 4.61 (d, J=7.2 Hz, 2H), 3.68 (s, 3H), 2.83-2.75 (m, 2H), 1.94-1.89 (m, 2H), 1.88-1.82 (m, 6H), 1.58-1.52 (m, 9H). MS (ESI) 464.4 (M+H).

Step D. Intermediate 430D. Preparation of methyl 6-(2-(4-iodobicyclo[2.2.2]octan-1-yl)ethyl)-4-(trifluoromethyl)quinoline-2-carboxylate

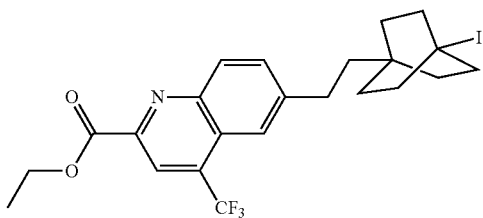 [SMILES: CCOC(=O)c1cc(C(F)(F)F)c2cc(CCC34CCC(I)(CC3)CC4)ccc2n1]

The title compound was prepared according to methods described for the synthesis of Intermediate 426G (Step F and G), substituting Intermediate 430C where appropriate: (19 mg, 0.037 mmol, 53% yield) (with impurity). MS (ESI) 518.2 (M+H).

Step F. Example 430

The title compound was prepared according to methods described for the synthesis of Example 4 (Step E), by reaction of Intermediate 430D and (5-cyclopropyl-3-(3,5-dichloropyridin-4-yl)isoxazol-4-yl)methanol: (2.4 mg, 0.0040 mmol, 29% yield). $^1$H NMR (500 MHz, DMSO-d$_6$) δ 8.87-8.68 (m, 2H), 8.40-8.07 (m, 2H), 7.85-7.63 (m, 2H), 4.33-4.09 (m, 2H), 2.77-2.64 (m, 2H), 2.34-2.21 (m, 1H), 1.47-1.39 (m, 6H), 1.37 (br d, J=8.5 Hz, 2H), 1.31 (br d, J=7.0 Hz, 6H), 1.18-1.12 (m, 2H), 1.07 (br d, J=2.7 Hz, 2H). FXR EC$_{50}$ (nM)=24. MS (ESI) 660.3 (M+H).

The following Examples (in Table 7) were prepared according to methods described elsewhere herein using appropriate starting materials, reagents and conditions.

TABLE 7

| Ex. No. | Structure & Name | $^1$H NMR, FXR EC$_{50}$ & MS (ESI) | Method |
|---|---|---|---|
| 363 | 6-((4-((5-cyclopropyl-3-(3,5-dichloropyridin-4-yl)isoxazol-4-yl)methoxy)bicyclo[2.2.2]octan-1-yl)ethynyl)-1-methyl-1H-pyrrolo[2,3-b]pyridine-3-carboxylic acid | $^1$H NMR (500 MHz, DMSO-d$_6$) δ 8.85 (br s, 2H), 8.25 (br s, 2H), 7.26 (br s, 1H), 4.22 (s, 2H), 3.81 (br s, 3H), 2.36-2.26 (m, 1H), 1.94-1.74 (m, 6H), 1.49-1.31 (m, 6H), 1.16 (br s, 2H), 1.13-1.05 (m, 2H). FXR EC$_{50}$ (nM) = 260. MS (ESI) 591.2 (M + H). | Ex. 130 |
| 364 | 6-((4-((5-cyclopropyl-3-(3,5-dichloropyridin-4-yl)isoxazol-4-yl)methoxy)bicyclo[2.2.2]octan-1-yl)ethynyl)-4-(trifluoromethyl)quinoline-2-carboxylic acid | $^1$H NMR (500 MHz, DMSO-d$_6$) δ 8.81 (s, 2H), 8.36 (br s, 1H), 8.28 (br d, J = 8.4 Hz, 1H), 7.98 (br d, J = 8.7 Hz, 1H), 7.88 (br d, J = 6.1 Hz, 1H), 4.23 (s, 2H), 2.35-2.25 (m, 1H), 2.02-1.81 (m, 6H), 1.56-1.36 (m, 6H), 1.20-1.13 (m, 2H), 1.13-1.04 (m, 2H). FXR EC$_{50}$ (nM) = 42. MS (ESI) 656 (M + H). | Ex. 130 |

TABLE 7-continued

| Ex. No. | Structure & Name | $^1$H NMR, FXR $EC_{50}$ & MS (ESI) | Method |
|---|---|---|---|
| 365 | 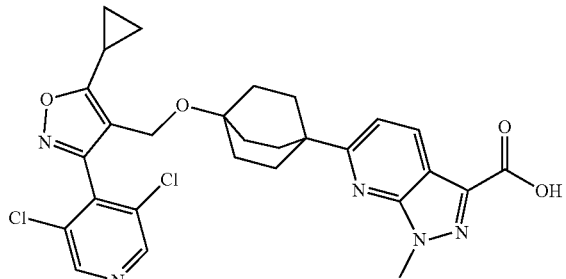<br>6-(4-((5-cyclopropyl-3-(3,5-dichloropyridin-4-yl)isoxazol-4-yl)methoxy)bicyclo[2.2.2]octan-1-yl)-1-methyl-1H-pyrazolo[3,4-b]pyridine-3-carboxylic acid | $^1$H NMR (500 MHz, DMSO-$d_6$) δ 8.82 (s, 2H), 8.33 (d, J = 8.4 Hz, 1H), 7.34 (d, J = 8.5 Hz, 1H), 4.28 (s, 2H), 4.07 (s, 3H), 2.36-2.26 (m, 1H), 2.09-1.90 (m, 6H), 1.63-1.42 (m, 6H), 1.22-1.13 (m, 2H), 1.10 (br d, J = 3.0 Hz, 2H). FXR $EC_{50}$ (nM) = 49. MS (ESI) 568.3 (M + H). | Ex. 384 |
| 366 | 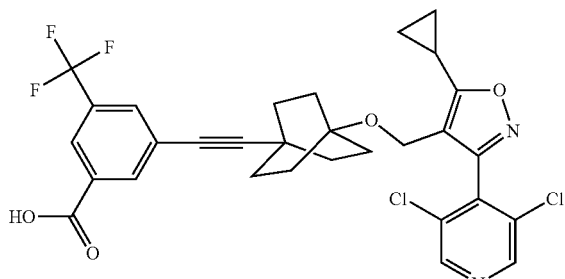<br>3-((4-((5-cyclopropyl-3-(3,5-dichloropyridin-4-yl)isoxazol-4-yl)methoxy)bicyclo[2.2.2]octan-1-yl)ethynyl)-5-(trifluoromethyl)benzoic acid | $^1$H NMR (500 MHz, DMSO-$d_6$) δ 8.81 (s, 2H), 8.07 (s, 1H), 8.04 (s, 1H), 7.77 (s, 1H), 3.53-3.27 (m, 2H), 2.35-2.25 (m, 1H), 1.98-1.78 (m, 6H), 1.56-1.35 (m, 6H), 1.15 (dt, J = 8.2, 2.9 Hz, 2H), 1.11-1.05 (m, 2H). FXR $EC_{50}$ (nM) = 27. MS (ESI) 605.1 (M + H). | Ex. 130 |
| 367 | 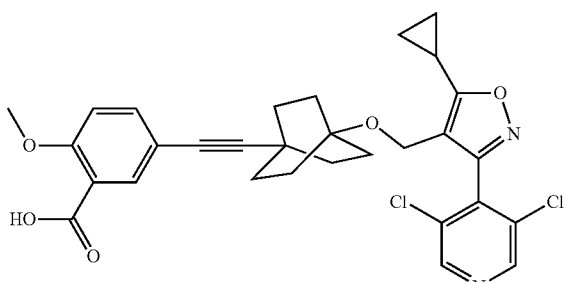<br>5-((4-((5-cyclopropyl-3-(3,5-dichloropyridin-4-yl)isoxazol-4-yl)methoxy)bicyclo[2.2.2]octan-1-yl)ethynyl)-2-methoxybenzoic acid | $^1$H NMR (500 MHz, DMSO-$d_6$) δ 8.80 (s, 2H), 7.52 (d, J = 1.8 Hz, 1H), 7.42 (br d, J = 8.7 Hz, 1H), 7.07 (d, J = 8.8 Hz, 1H), 4.21 (s, 2H), 3.82 (s, 3H), 2.34-2.23 (m, 1H), 1.89-1.71 (m, 6H), 1.49-1.33 (m, 6H), 1.20-1.13 (m, 2H), 1.11-1.02 (m, 2H). FXR $EC_{50}$ (nM) = 91. MS (ESI) 567.1 (M + H). | Ex. 130 |
| 368 | 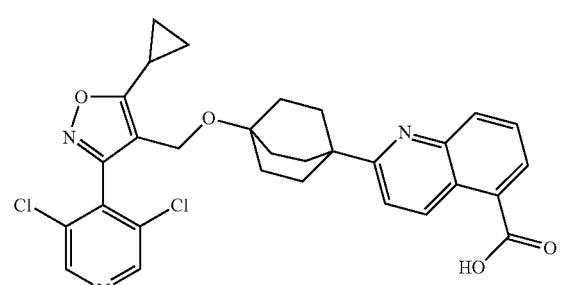<br>2-(4-((5-cyclopropyl-3-(3,5-dichloropyridin-4-yl)isoxazol-4-yl)methoxy)bicyclo[2.2.2]octan-1-yl)quinoline-5-carboxylic acid | $^1$H NMR (500 MHz, DMSO-$d_6$) δ 9.16 (br d, J = 4.2 Hz, 1H), 8.83 (s, 2H), 8.15 (br s, 1H), 8.11 (br d, J = 7.5 Hz, 1H), 7.79 (br s, 1H), 7.66 (br s, 1H), 4.29 (s, 2H), 2.36-2.27 (m, 1H), 2.08-1.92 (m, 6H), 1.61-1.45 (m, 6H), 1.22-1.14 (m, 2H), 1.13-1.07 (m, 2H). FXR $EC_{50}$ (nM) = 36. MS (ESI) 564.1 (M + H). | Ex. 384 |

TABLE 7-continued

| Ex. No. | Structure & Name | $^1$H NMR, FXR EC$_{50}$ & MS (ESI) | Method |
|---|---|---|---|
| 369 | 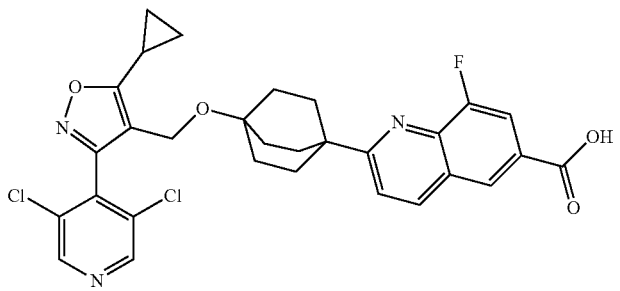

2-(4-((5-cyclopropyl-3-(3,5-dichloropyridin-4-yl)isoxazol-4-yl)methoxy)bicyclo[2.2.2]octan-1-yl)-8-fluoroquinoline-6-carboxylic acid | $^1$H NMR (500 MHz, DMSO-d$_6$) δ 8.85 (s, 2H), 8.41 (br d, J = 8.9 Hz, 1H), 8.29 (s, 1H), 7.87 (br d, J = 11.6 Hz, 1H), 7.66 (d, J = 8.9 Hz, 1H), 4.28 (s, 2H), 2.39-2.29 (m, 1H), 2.05-1.94 (m, 6H), 1.56-1.43 (m, 6H), 1.21-1.14 (m, 2H), 1.13-1.06 (m, 2H). FXR EC$_{50}$ (nM) = 41. MS (ESI) 582.2 (M + H). | Ex. 384 |
| 370 | 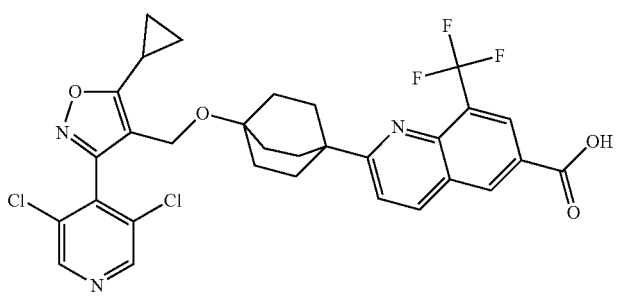

2-(4-((5-cyclopropyl-3-(3,5-dichloropyridin-4-yl)isoxazol-4-yl)methoxy)bicyclo[2.2.2]octan-1-yl)-8-(trifluoromethyl)quinoline-6-carboxylic acid | $^1$H NMR (500 MHz, DMSO-d$_6$) δ 8.87 (s, 1H), 8.85 (s, 2H), 8.59 (d, J = 8.9 Hz, 1H), 8.46 (s, 1H), 7.80 (d, J = 8.9 Hz, 1H), 4.28 (s, 2H), 2.39-2.28 (m, 1H), 2.05-1.91 (m, 6H), 1.57-1.42 (m, 6H), 1.23-1.15 (m, 2H), 1.14-1.05 (m, 2H). FXR EC$_{50}$ (nM) = 56. MS (ESI) 632.2 (M + H). | Ex. 384 |
| 371 | 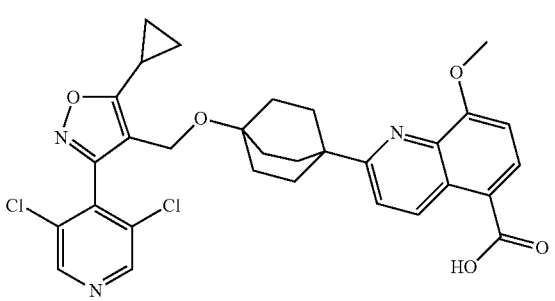

2-(4-((5-cyclopropyl-3-(3,5-dichloropyridin-4-yl)isoxazol-4-yl)methoxy)bicyclo[2.2.2]octan-1-yl)-8-methoxyquinoline-5-carboxylic acid | $^1$H NMR (500 MHz, DMSO-d$_6$) δ 9.27 (d, J = 9.2 Hz, 1H), 8.84 (s, 2H), 8.21 (d, J = 8.2 Hz, 1H), 7.66 (d, J = 9.2 Hz, 1H), 7.21 (d, J = 8.5 Hz, 1H), 4.27 (s, 2H), 4.02 (s, 3H), 2.37-2.28 (m, 1H), 2.03-1.89 (m, 6H), 1.53-1.40 (m, 6H), 1.23-1.15 (m, 2H), 1.10 (br d, J = 2.7 Hz, 2H). FXR EC$_{50}$ (nM) = 18. MS (ESI) 594.1 (M + H). | Ex. 384 |
| 372 | 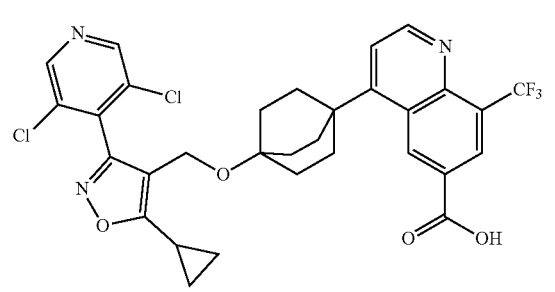

4-(4-((5-cyclopropyl-3-(3,5-dichloropyridin-4-yl)isoxazol-4-yl)methoxy)bicyclo[2.2.2]octan-1-yl)-8-(trifluoromethyl)quinoline-6-carboxylic acid | $^1$H NMR (500 MHz, DMSO-d$_6$) δ 9.28 (s, 1H), 8.97 (br d, J = 4.5 Hz, 1H), 8.82 (s, 2H), 8.54 (s, 1H), 7.51 (br d, J = 4.5 Hz, 1H), 4.32 (s, 2H), 2.38-2.28 (m, 1H), 2.16 (br s, 6H), 1.63 (br s, 6H), 1.22-1.15 (m, 2H), 1.11 (br d, J = 2.7 Hz, 2H). FXR EC$_{50}$ (nM) = 570. MS (ESI) 632.1 (M + H). | Ex. 384 |

TABLE 7-continued

| Ex. No. | Structure & Name | $^1$H NMR, FXR EC$_{50}$ & MS (ESI) | Method |
|---|---|---|---|
| 373 | 6-((4-((5-cyclopropyl-3-(3,5-dichloropyridin-4-yl)isoxazol-4-yl)methoxy)bicyclo[2.2.2]octan-1-yl)ethynyl)-4-(trifluoromethyl)picolinic acid | $^1$H NMR (500 MHz, DMSO-d$_6$) δ 8.83 (s, 2H), 8.22-7.90 (m, 1H), 7.87-7.54 (m, 1H), 4.21 (s, 2H), 2.37-2.26 (m, 1H), 1.99-1.75 (m, 6H), 1.40 (br s, 6H), 1.20-1.13 (m, 2H), 1.09 (br d, J = 3.1 Hz, 2H). FXR EC$_{50}$ (nM) = 460. MS (ESI) 606.2 (M + H). | Ex. 130 |
| 374 | 6-((4-((5-cyclopropyl-3-(3,5-dichloropyridin-4-yl)isoxazol-4-yl)methoxy)bicyclo[2.2.2]octan-1-yl)ethynyl)-4-(trifluoromethyl)nicotinic acid | $^1$H NMR (500 MHz, DMSO-d$_6$) δ 8.83 (s, 2H), 8.80 (s, 1H), 7.65 (s, 1H), 4.21 (s, 2H), 2.35-2.26 (m, 1H), 1.91-1.79 (m, 6H), 1.47-1.34 (m, 6H), 1.20-1.12 (m, 2H), 1.11-1.05 (m, 2H). FXR EC$_{50}$ (nM) = 130. MS (ESI) 606.1 (M + H). | Ex. 130 |
| 375 | 6-((4-((5-cyclopropyl-3-(3,5-dichloropyridin-4-yl)isoxazol-4-yl)methoxy)bicyclo[2.2.2]octan-1-yl)ethynyl)-4-methoxyquinoline-2-carboxylic acid | $^1$H NMR (500 MHz, DMSO-d$_6$) δ 8.84 (s, 2H), 8.07 (s, 1H), 8.02 (br d, J = 8.2 Hz, 1H), 7.69 (br d, J = 8.9 Hz, 1H), 7.56 (s, 1H), 4.21 (s, 3H), 4.12 (s, 2H), 2.36-2.24 (m, 1H), 1.86 (br d, J = 7.9 Hz, 6H), 1.46-1.36 (m, 6H), 1.21-1.13 (m, 2H), 1.12-1.05 (m, 2H). FXR EC$_{50}$ (nM) = 57. MS (ESI) 618.1 (M + H). | Ex. 130 |
| 376 | 6-((4-((5-cyclopropyl-3-(3,5-dichloropyridin-4-yl)isoxazol-4-yl)methoxy)bicyclo[2.2.2]octan-1-yl)ethynyl)-4-(difluoromethoxy)quinoline-2-carboxylic acid | $^1$H NMR (500 MHz, DMSO-d$_6$) δ 8.84 (s, 2H), 8.13 (s, 1H), 8.04 (s, 1H), 7.87-7.73 (m, 2H), 7.69-7.49 (m, 1H), 4.23 (s, 2H), 2.37-2.25 (m, 1H), 2.05-1.79 (m, 6H), 1.58-1.34 (m, 6H), 1.27-1.15 (m, 2H), 1.14-0.98 (m, 2H). FXR EC$_{50}$ (nM) = 27. MS (ESI) 654 (M + H). | Ex. 130 |

TABLE 7-continued

| Ex. No. | Structure & Name | ¹H NMR, FXR EC₅₀ & MS (ESI) | Method |
|---|---|---|---|
| 377 | 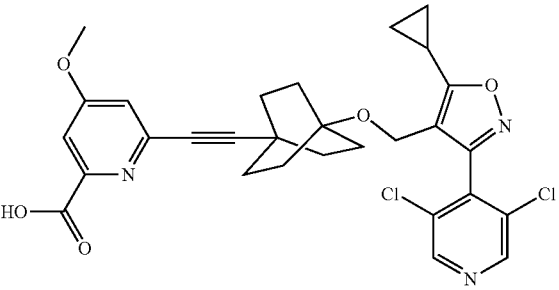<br>6-((4-((5-cyclopropyl-3-(3,5-dichloropyridin-4-yl)isoxazol-4-yl)methoxy)bicyclo[2.2.2]octan-1-yl)ethynyl)-4-methoxypicolinic acid | $^1$H NMR (500 MHz, DMSO-d$_6$) δ 8.83 (s, 2H), 7.45 (d, J = 2.1 Hz, 1H), 7.14 (d, J = 2.1 Hz, 1H), 4.21 (s, 2H), 3.88 (s, 3H), 2.36-2.25 (m, 1H), 1.94-1.79 (m, 6H), 1.44-1.35 (m, 6H), 1.20-1.13 (m, 2H), 1.11-1.02 (m, 2H). FXR EC$_{50}$ (nM) = 390. MS (ESI) 568.3 (M + H). | Ex. 130 |
| 378 | 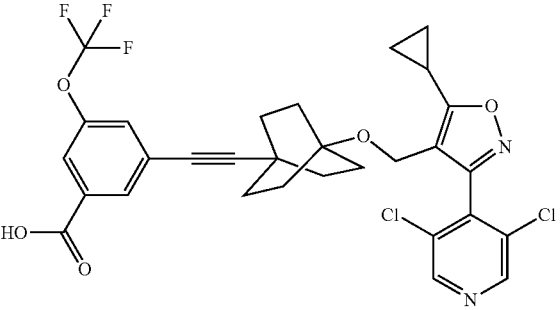<br>3-((4-((5-cyclopropyl-3-(3,5-dichloropyridin-4-yl)isoxazol-4-yl)methoxy)bicyclo[2.2.2]octan-1-yl)ethynyl)-5-(trifluoromethoxy)benzoic acid | $^1$H NMR (500 MHz, DMSO-d$_6$) δ 8.82 (s, 2H), 7.80 (br s, 1H), 7.72 (br s, 1H), 7.51 (s, 1H), 4.20 (s, 2H), 2.34-2.23 (m, 1H), 1.87-1.75 (m, 6H), 1.43-1.33 (m, 6H), 1.20-1.13 (m, 2H), 1.11-1.02 (m, 2H). FXR EC$_{50}$ (nM) = 130. MS (ESI) 621.1 (M + H). | Ex. 130 |
| 379 | 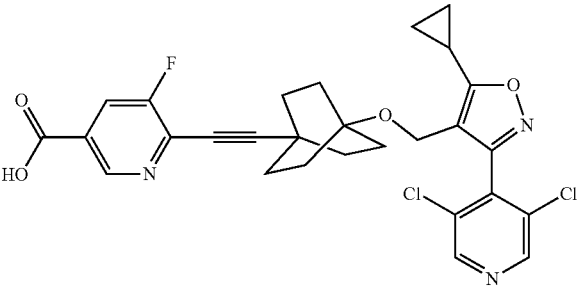<br>6-((4-((5-cyclopropyl-3-(3,5-dichloropyridin-4-yl)isoxazol-4-yl)methoxy)bicyclo[2.2.2]octan-1-yl)ethynyl)-5-fluoronicotinic acid | $^1$H NMR (500 MHz, DMSO-d$_6$) δ 8.80 (s, 2H), 8.78 (br s, 1H), 8.01 (br d, J = 5.8 Hz, 1H), 4.21 (s, 2H), 2.35-2.24 (m, 1H), 1.92-1.81 (m, 6H), 1.50-1.38 (m, 6H), 1.21-1.13 (m, 2H), 1.11-1.04 (m, 2H). FXR EC$_{50}$ (nM) = 240. MS (ESI) 556.2 (M + H). | Ex. 130 |
| 380 | 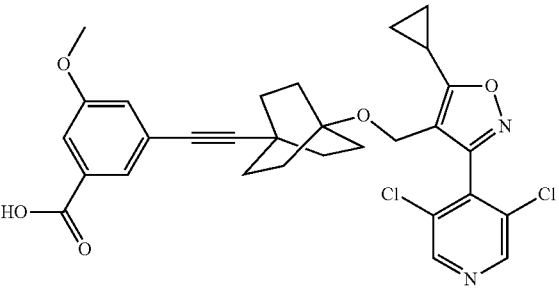<br>3-((4-((5-cyclopropyl-3-(3,5-dichloropyridin-4-yl)isoxazol-4-yl)methoxy)bicyclo[2.2.2]octan-1-yl)ethynyl)-5-methoxybenzoic acid | $^1$H NMR (500 MHz, DMSO-d$_6$) δ 8.80 (s, 2H), 7.39 (s, 1H), 7.35 (s, 1H), 7.03 (s, 1H), 4.19 (s, 2H), 3.78 (s, 3H), 2.33-2.22 (m, 1H), 1.88-1.74 (m, 6H), 1.44-1.31 (m, 6H), 1.20-1.12 (m, 2H), 1.09-1.01 (m, 2H). FXR EC$_{50}$ (nM) = 24. MS (ESI) 567 (M + H). | Ex. 130 |

TABLE 7-continued

| Ex. No. | Structure & Name | $^1$H NMR, FXR EC$_{50}$ & MS (ESI) | Method |
|---|---|---|---|
| 381 | 3-((4-((5-cyclopropyl-3-(3,5-dichloropyridin-4-yl)isoxazol-4-yl)methoxy)bicyclo[2.2.2]octan-1-yl)ethynyl)-2-methoxybenzoic acid | $^1$H NMR (500 MHz, DMSO-d$_6$) δ 8.80 (s, 2H), 7.54 (br d, J = 7.6 Hz, 1H), 7.41 (br d, J = 7.0 Hz, 1H), 7.11 (t, J = 7.6 Hz, 1H), 4.19 (s, 2H), 3.81 (s, 3H), 2.33-2.22 (m, 1H), 1.88-1.76 (m, 6H), 1.43-1.31 (m, 6H), 1.20-1.12 (m, 2H), 1.10-1.03 (m, 2H). FXR EC$_{50}$ (nM) = 220. MS (ESI) 567.1 (M + H). | Ex. 130 |
| 382 | 6-((4-((5-cyclopropyl-3-(3,5-dichloropyridin-4-yl)isoxazol-4-yl)methoxy)bicyclo[2.2.2]octan-1-yl)ethynyl)quinoline-2-carboxylic acid | $^1$H NMR (500 MHz, DMSO-d$_6$) δ 8.83 (s, 2H), 8.46 (br d, J = 7.0 Hz, 1H), 8.06 (br s, 3H), 7.69 (br d, J = 8.2 Hz, 1H), 4.21 (s, 2H), 2.35-2.26 (m, 1H), 1.94-1.78 (m, 6H), 1.49-1.34 (m, 6H), 1.21-1.13 (m, 2H), 1.14-1.04 (m, 2H). FXR EC$_{50}$ (nM) = 62. MS (ESI) 588.2 (M + H). | Ex. 130 |
| 383 | 3-((4-((5-cyclopropyl-3-(3,5-dichloropyridin-4-yl)isoxazol-4-yl)methoxy)bicyclo[2.2.2]octan-1-yl)ethynyl)-2-methoxybenzoic acid | $^1$H NMR (500 MHz, DMSO-d$_6$) δ 8.77 (s, 2H), 4.15 (s, 2H), 3.71-3.68 (m, 3H), 3.66 (s, 3H), 2.31-2.19 (m, 1H), 1.57-1.42 (m, 6H), 1.36-1.23 (m, 6H), 1.18-1.10 (m, 2H), 1.08-0.99 (m, 2H). FXR EC$_{50}$ (nM) = 820. MS (ESI) 567.1 (M + H). | Ex. 130 |
| 386 | 3-((4-((5-cyclopropyl-3-(3,5-dichloropyridin-4-yl)isoxazol-4-yl)methoxy)bicyclo[2.2.2]octan-1-yl)ethynyl)-5-(methoxymethyl)benzoic acid | $^1$H NMR (500 MHz, DMSO-d$_6$) δ 8.80 (s, 2H), 7.80 (s, 1H), 7.71 (s, 1H), 7.45 (s, 1H), 4.42 (s, 1H), 4.19 (s, 1H), 3.66 (s, 2H), 3.28 (s, 3H), 2.32-2.21 (m, 1H), 1.87-1.73 (m, 6H), 1.44-1.29 (m, 6H), 1.21-1.11 (m, 2H), 1.09-1.01 (m, 2H). FXR EC$_{50}$ (nM) = 31. MS (ESI) 581.4 (M + H). | Ex. 130 |

TABLE 7-continued

| Ex. No. | Structure & Name | $^{1}$H NMR, FXR $EC_{50}$ & MS (ESI) | Method |
|---|---|---|---|
| 387 | 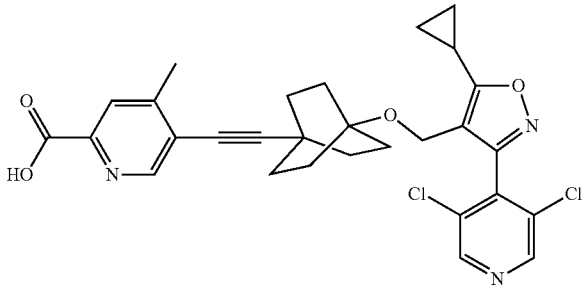<br>5-((4-((5-cyclopropyl-3-(3,5-dichloropyridin-4-yl)isoxazol-4-yl)methoxy)bicyclo[2.2.2]octan-1-yl)ethynyl)-4-methylpicolinic acid | $^{1}$H NMR (500 MHz, DMSO-$d_6$) δ 8.83 (s, 2H), 8.47 (br s, 1H), 7.89 (br s, 1H), 4.21 (s, 2H), 2.35 (br s, 3H), 2.33-2.28 (m, 1H), 1.91-1.77 (m, 6H), 1.46-1.31 (m, 6H), 1.21-1.12 (m, 2H), 1.11-1.05 (m, 2H). FXR $EC_{50}$ (nM) = 57. MS (ESI) 552 (M + H). | Ex. 130 |
| 388 | 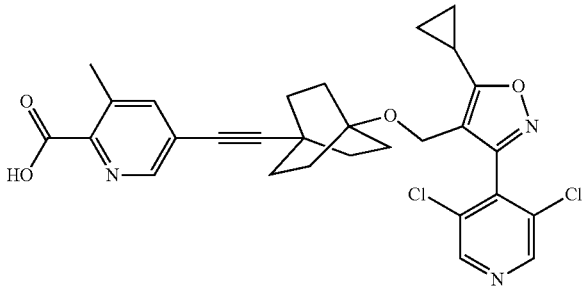<br>5-((4-((5-cyclopropyl-3-(3,5-dichloropyridin-4-yl)isoxazol-4-yl)methoxy)bicyclo[2.2.2]octan-1-yl)ethynyl)-3-methylpicolinic acid | $^{1}$H NMR (500 MHz, DMSO-$d_6$) δ 8.76 (br s, 2H), 7.40-7.06 (m, 2H), 4.13 (br s, 2H), 2.55 (s, 3H), 2.24 (br s, 1H), 1.64-1.19 (m, 12H), 1.13 (br s, 2H), 1.03 (br s, 2H). FXR $EC_{50}$ (nM) = 55. MS (ESI) 552.2 (M + H). | Ex. 130 |
| 389 | 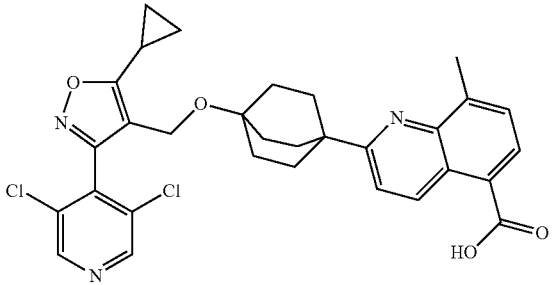<br>2-(4-((5-cyclopropyl-3-(3,5-dichloropyridin-4-yl)isoxazol-4-yl)methoxy)bicyclo[2.2.2]octan-1-yl)-8-methylquinoline-5-carboxylic acid | $^{1}$H NMR (500 MHz, DMSO-$d_6$) δ 9.21 (br d, J = 9.2 Hz, 1H), 8.85 (s, 2H), 8.09 (br d, J = 7.3 Hz, 1H), 7.71-7.60 (m, 2H), 4.28 (s, 2H), 2.74 (s, 3H), 2.40-2.28 (m, 1H), 2.08-1.89 (m, 6H), 1.56-1.43 (m, 6H), 1.20-1.14 (m, 2H), 1.14-1.04 (m, 2H). FXR $EC_{50}$ (nM) = 6. MS (ESI) 578.1 (M + H). | Ex. 385 |
| 390 | 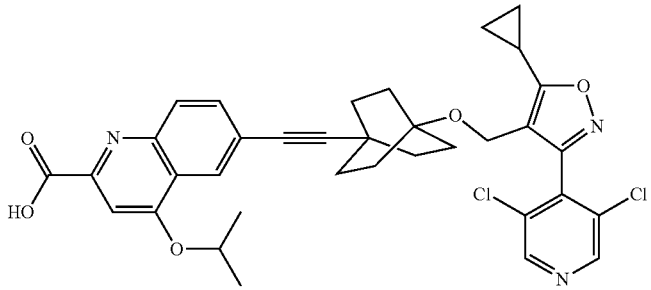<br>6-((4-((5-cyclopropyl-3-(3,5-dichloropyridin-4-yl)isoxazol-4-yl)methoxy)bicyclo[2.2.2]octan-1-yl)ethynyl)-4-isopropoxyquinoline-2-carboxylic acid | $^{1}$H NMR (500 MHz, DMSO-$d_6$) δ 8.82 (s, 2H), 8.04 (s, 1H), 8.01 (br d, J = 8.9 Hz, 1H), 7.68 (br d, J = 8.2 Hz, 1H), 7.52 (s, 1H), 5.11-5.00 (m, 1H), 4.20 (s, 2H), 2.35-2.26 (m, 1H), 1.85 (br d, J = 7.6 Hz, 6H), 1.43 (br d, J = 5.8 Hz, 6H), 1.40 (br d, J = 7.3 Hz, 6H), 1.21-1.13 (m, 2H), 1.11-1.02 (m, 2H). FXR $EC_{50}$ (nM) = 20. MS (ESI) 646.3 (M + H). | Ex. 130 |

TABLE 7-continued

| Ex. No. | Structure & Name | ¹H NMR, FXR EC$_{50}$ & MS (ESI) | Method |
|---|---|---|---|
| 392 | 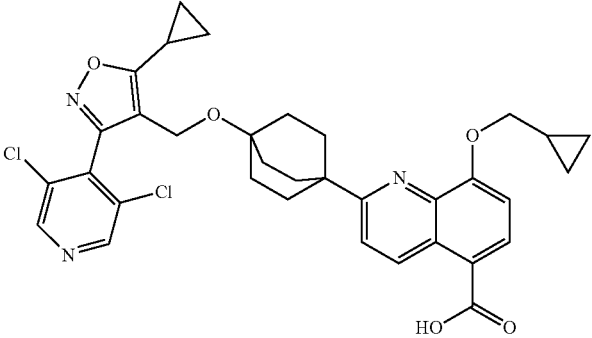<br>2-(4-((5-cyclopropyl-3-(3,5-dichloropyridin-4-yl)isoxazol-4-yl)methoxy)bicyclo[2.2.2]octan-1-yl)-8-(cyclopropyl-methoxy)quinoline-5-carboxylic acid | ¹H NMR (500 MHz, DMSO-d$_6$) δ 9.29 (br d, J = 9.0 Hz, 1H), 8.81 (s, 2H), 8.11 (br d, J = 8.2 Hz, 1H), 7.59 (br d, J = 8.8 Hz, 1H), 7.16 (br d, J = 8.2 Hz, 1H), 4.28 (s, 2H), 4.15 (d, J = 6.4 Hz, 2H), 2.30 (td, J = 8.5, 4.7 Hz, 1H), 2.05-1.94 (m, 6H), 1.56-1.45 (m, 6H), 1.39-1.29 (m, 1H), 1.21-1.14 (m, 2H), 1.13-1.04 (m, 2H), 0.67-0.56 (m, 2H), 0.52-0.39 (m, 2H). FXR EC$_{50}$ (nM) = 24. MS (ESI) 634.1 (M + H). | Ex. 391 |
| 393 | 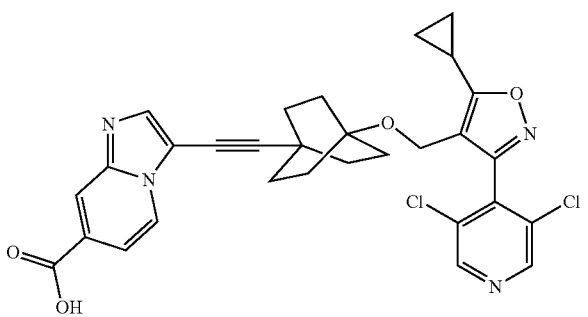<br>3-((4-((5-cyclopropyl-3-(3,5-dichloropyridin-4-yl)isoxazol-4-yl)methoxy)bicyclo[2.2.2]octan-1-yl)ethynyl)imidazo[1,2-a]pyridine-7-carboxylic acid | ¹H NMR (500 MHz, DMSO-d$_6$) δ 8.81 (s, 2H), 8.29 (br d, J = 7.0 Hz, 1H), 8.05 (s, 1H), 7.83 (s, 1H), 7.49 (br d, J = 7.0 Hz, 1H), 4.21 (s, 2H), 2.34-2.25 (m, 1H), 1.91-1.81 (m, 6H), 1.46-1.33 (m, 6H), 1.20-1.13 (m, 2H), 1.11-1.02 (m, 2H). FXR EC$_{50}$ (nM) = 270. MS (ESI) 577 (M + H). | Ex. 130 |
| 394 | 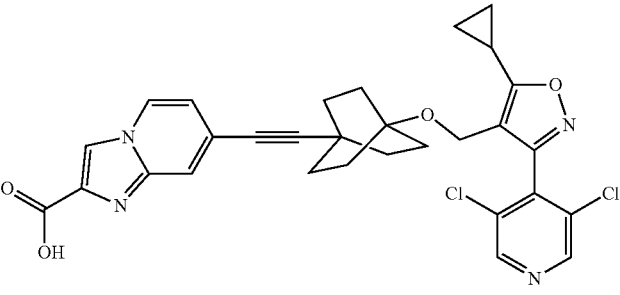<br>7-((4-((5-cyclopropyl-3-(3,5-dichloropyridin-4-yl)isoxazol-4-yl)methoxy)bicyclo[2.2.2]octan-1-yl)ethynyl)imidazo[1,2-a]pyridine-2-carboxylic acid | ¹H NMR (500 MHz, DMSO-d$_6$) δ 8.77 (s, 2H), 8.58-8.26 (m, 2H), 7.63-7.38 (m, 1H), 6.83 (br s, 1H), 4.19 (s, 2H), 2.31-2.19 (m, 1H), 1.89-1.75 (m, 6H), 1.46-1.35 (m, 6H), 1.18-1.11 (m, 2H), 1.09-1.02 (m, 2H). FXR EC$_{50}$ (nM) = 180. MS (ESI) 577.3 (M + H). | Ex. 130 |
| 395 | 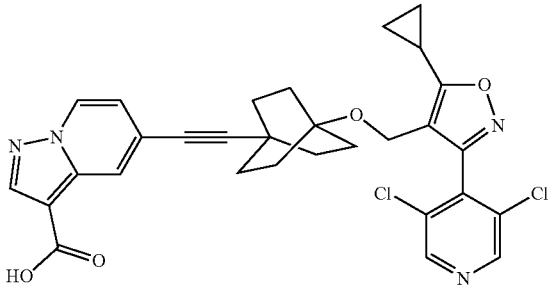<br>5-((4-((5-cyclopropyl-3-(3,5-dichloropyridin-4-yl)isoxazol-4-yl)methoxy)bicyclo[2.2.2]octan-1-yl)ethynyl)pyrazolo[1,5-a]pyridine-3-carboxylic acid | ¹H NMR (500 MHz, DMSO-d$_6$) δ 8.83 (s, 2H), 8.76 (br d, J = 7.0 Hz, 1H), 8.40 (br s, 1H), 7.94 (br s, 1H), 6.96 (br d, J = 7.0 Hz, 1H), 4.21 (s, 2H), 2.30 (br s, 1H), 1.95-1.75 (m, 6H), 1.39 (br s, 6H), 1.20-1.12 (m, 2H), 1.11-1.05 (m, 2H). FXR EC$_{50}$ (nM) = 120. MS (ESI) 577.2 (M + H). | Ex. 130 |

TABLE 7-continued

| Ex. No. | Structure & Name | $^1$H NMR, FXR EC$_{50}$ & MS (ESI) | Method |
|---|---|---|---|
| 396 | 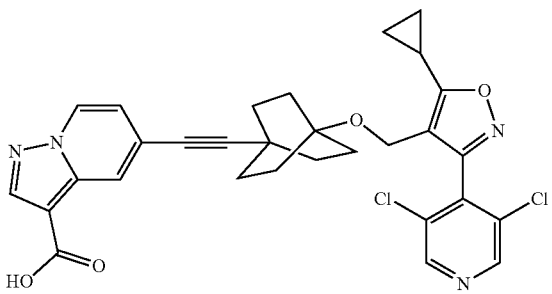<br>5-((4-((5-cyclopropyl-3-(3,5-dichloropyridin-4-yl)isoxazol-4-yl)methoxy)bicyclo[2.2.2]octan-1-yl)ethynyl)pyrazolo[1,5-a]pyridine-3-carboxylic acid | $^1$H NMR (500 MHz, DMSO-d$_6$) δ 8.76 (s, 2H), 8.55 (br s, 1H), 8.21 (br s, 1H), 7.38 (br s, 1H), 4.19 (s, 2H), 2.30 (br s, 3H), 2.26-2.19 (m, 1H), 1.88-1.77 (m, 6H), 1.46-1.35 (m, 6H), 1.18-1.12 (m, 2H), 1.10-1.03 (m, 2H). FXR EC$_{50}$ (nM) = 1100. MS (ESI) 591.3 (M + H). | Ex. 130 |
| 397 | 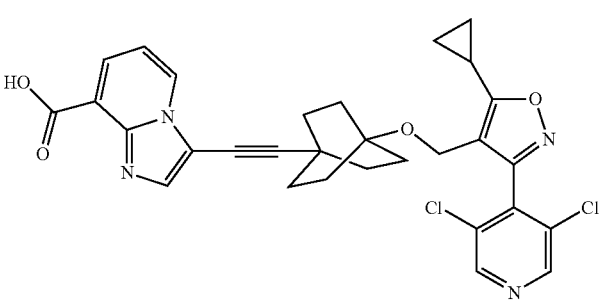<br>3-((4-((5-cyclopropyl-3-(3,5-dichloropyridin-4-yl)isoxazol-4-yl)methoxy)bicyclo[2.2.2]octan-1-yl)ethynyl)imidazo[1,2-a]pyridine-8-carboxylic acid | $^1$H NMR (500 MHz, DMSO-d$_6$) δ 8.83 (s, 2H), 8.57 (d, J = 6.4 Hz, 1H), 8.02 (d, J = 7.0 Hz, 1H), 7.91 (s, 1H), 7.24 (t, J = 7.0 Hz, 1H), 4.22 (s, 2H), 2.37-2.25 (m, 1H), 2.01-1.84 (m, 6H), 1.50-1.35 (m, 6H), 1.20-1.13 (m, 2H), 1.12-1.04 (m, 2H). FXR EC$_{50}$ (nM) = 48. MS (ESI) 577 (M + H). | Ex. 130 |
| 398 | 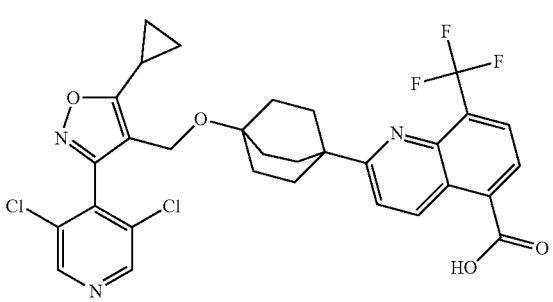<br>2-(4-((5-cyclopropyl-3-(3,5-dichloropyridin-4-yl)isoxazol-4-yl)methoxy)bicyclo[2.2.2]octan-1-yl)-8-(trifluoromethyl)quinoline-5-carboxylic acid | $^1$H NMR (500 MHz, DMSO-d$_6$) δ 9.13 (br d, J = 9.2 Hz, 1H), 8.84 (s, 2H), 8.12 (br d, J = 7.6 Hz, 1H), 8.05 (br d, J = 7.6 Hz, 1H), 7.72 (br d, J = 9.2 Hz, 1H), 4.27 (s, 2H), 2.38-2.25 (m, 1H), 2.02-1.92 (m, 6H), 1.54-1.41 (m, 6H), 1.21-1.14 (m, 2H), 1.13-1.05 (m, 2H). FXR EC$_{50}$ (nM) = 30. MS (ESI) 632.1 (M + H). | Ex. 384 |
| 399 | 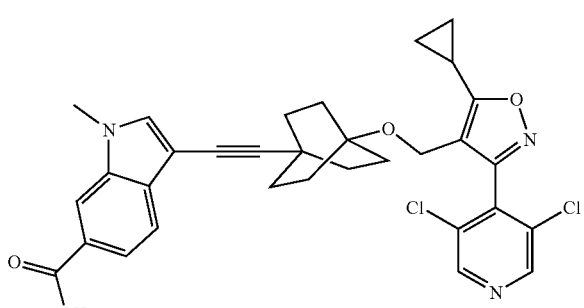<br>3-((4-((5-cyclopropyl-3-(3,5-dichloropyridin-4-yl)isoxazol-4-yl)methoxy)bicyclo[2.2.2]octan-1-yl)ethynyl)-1-methyl-1H-indole-6-carboxylic acid | $^1$H NMR (500 MHz, DMSO-d$_6$) δ 8.80 (d, J = 2.0 Hz, 2H), 8.04 (s, 1H), 7.71 (br d, J = 8.2 Hz, 1H), 7.60 (s, 1H), 7.47 (d, J = 8.2 Hz, 1H), 4.21 (s, 2H), 3.81 (s, 3H), 2.29 (br s, 1H), 1.86 (br d, J = 7.5 Hz, 6H), 1.42 (br s, 6H), 1.21-1.13 (m, 2H), 1.12-1.03 (m, 2H). FXR EC$_{50}$ (nM) = 83. MS (ESI) 590.1 (M + H). | Ex. 130 |

TABLE 7-continued

| Ex. No. | Structure & Name | ¹H NMR, FXR EC₅₀ & MS (ESI) | Method |
|---|---|---|---|
| 400 | 3-((4-((5-cyclopropyl-3-(3,5-dichloropyridin-4-yl)isoxazol-4-yl)methoxy)bicyclo[2.2.2]octan-1-yl)ethynyl)-5-isopropoxybenzoic acid | $^1$H NMR (500 MHz, DMSO-d$_6$) δ 8.78 (br s, 2H), 7.41-7.27 (m, 2H), 7.01 (br s, 1H), 4.69-4.57 (m, 1H), 4.19 (br s, 2H), 2.26 (br s, 1H), 1.81 (br s, 6H), 1.39 (br s, 6H), 1.25 (br d, J = 5.6 Hz, 6H), 1.19-1.12 (m, 2H), 1.10-1.02 (m, 2H). FXR EC$_{50}$ (nM) = 29. MS (ESI) 595.3 (M + H). | Ex. 130 |
| 401 | 5-((4-((5-cyclopropyl-3-(3,5-dichloropyridin-4-yl)isoxazol-4-yl)methoxy)bicyclo[2.2.2]octan-1-yl)ethynyl)-1H-indazole-7-carboxylic acid | $^1$H NMR (500 MHz, DMSO-d$_6$) 8.81 (s, 2H), 8.18 (s, 1H), 8.03 (s, 1H), 7.81 (s, 1H), 4.20 (s, 2H), 3.60 (br s, 1H), 2.28 (br d, J = 4.0 Hz, 1H), 1.91-1.72 (m, 6H), 1.46-1.33 (m, 6H), 1.20-1.12 (m, J = 7.3 Hz, 2H), 1.11-1.02 (m, 2H). FXR EC$_{50}$ (nM) = 74. MS (ESI) 577.2 (M + H). | Ex. 130 |
| 402 | 4-cyclobutoxy-6-((4-((5-cyclopropyl-3-(3,5-dichloropyridin-4-yl)isoxazol-4-yl)methoxy)bicyclo[2.2.2]octan-1-yl)ethynyl)quinoline-2-carboxylic acid | $^1$H NMR (500 MHz, DMSO-d$_6$) δ 8.80 (s, 2H), 8.09 (s, 1H), 8.01 (br d, J = 8.6 Hz, 1H), 7.68 (br d, J = 8.4 Hz, 1H), 7.36 (s, 1H), 5.17-5.03 (m, 1H), 4.21 (s, 2H), 2.61-2.56 (m, 2H), 2.32-2.17 (m, 3H), 1.95-1.83 (m, 7H), 1.82-1.69 (m, 1H), 1.50-1.36 (m, 6H), 1.21-1.12 (m, 2H), 1.11-1.03 (m, 2H). FXR EC$_{50}$ (nM) = 52. MS (ESI) 658.1 (M + H). | Ex. 130 |
| 403 | 6-(4-((5-cyclopropyl-3-(3,5-dichloropyridin-4-yl)isoxazol-4-yl)methoxy)bicyclo[2.2.2]octan-1-yl)-1-ethyl-1H-pyrazolo[3,4-b]pyridine-3-carboxylic acid | $^1$H NMR (500 MHz, DMSO-d$_6$) δ 8.83 (s, 2H), 8.32 (br d, J = 8.2 Hz, 1H), 7.36 (br d, J = 8.5 Hz, 1H), 4.58-4.41 (m, 2H), 4.27 (s, 2H), 2.37-2.25 (m, 1H), 2.00-1.87 (m, 6H), 1.54-1.38 (m, 9H), 1.21-1.14 (m, 2H), 1.13-1.04 (m, 2H). FXR EC$_{50}$ (nM) = 4. MS (ESI) 582.3 (M + H). | Ex. 384 |

TABLE 7-continued

| Ex. No. | Structure & Name | ¹H NMR, FXR EC$_{50}$ & MS (ESI) | Method |
|---|---|---|---|
| 404 | 6-((4-((5-cyclopropyl-3-(3,5-dichloropyridin-4-yl)isoxazol-4-yl)methoxy)bicyclo[2.2.2]octan-1-yl)ethynyl)imidazo[1,2-a]pyridine-8-carboxylic acid | ¹H NMR (500 MHz, DMSO-d$_6$) δ 8.85 (s, 1H), 8.80 (s, 2H), 8.00 (s, 1H), 7.71 (s, 1H), 7.67 (s, 1H), 4.21 (s, 2H), 2.34-2.23 (m, 1H), 1.90-1.79 (m, 6H), 1.48-1.37 (m, 6H), 1.21-1.12 (m, 2H), 1.11-1.02 (m, 2H). FXR EC$_{50}$ (nM) = 140. MS (ESI) 577 (M + H). | Ex. 130 |
| 405 | 8-cyclobutoxy-2-(4-((5-cyclopropyl-3-(3,5-dichloropyridin-4-yl)isoxazol-4-yl)methoxy)bicyclo[2.2.2]octan-1-yl)quinoline-5-carboxylic acid | ¹H NMR (500 MHz, DMSO-d$_6$) δ 9.25 (br d, J = 8.9 Hz, 1H), 8.82 (s, 2H), 8.15 (br d, J = 8.2 Hz, 1H), 7.64 (br d, J = 9.1 Hz, 1H), 7.03 (br d, J = 8.2 Hz, 1H), 5.05-4.88 (m, 1H), 4.28 (s, 2H), 2.62-2.54 (m, 2H), 2.36-2.28 (m, 1H), 2.25-2.13 (m, 2H), 2.05-1.95 (m, 6H), 1.93-1.82 (m, 1H), 1.81-1.69 (m, 1H), 1.58-1.46 (m, 6H), 1.21-1.14 (m, 2H), 1.13-1.06 (m, 2H). FXR EC$_{50}$ (nM) = 28. MS (ESI) 634.3 (M + H). | Ex. 391 |
| 406 | 2-(4-((5-cyclopropyl-3-(3,5-dichloropyridin-4-yl)isoxazol-4-yl)methoxy)bicyclo[2.2.2]octan-1-yl)-8-(oxetan-3-yloxy)quinoline-5-carboxylic acid | ¹H NMR (500 MHz, DMSO-d$_6$) δ 9.26 (br d, J = 8.9 Hz, 1H), 8.84 (s, 2H), 8.13 (br d, J = 8.2 Hz, 1H), 7.71 (br d, J = 9.2 Hz, 1H), 6.85 (br d, J = 7.9 Hz, 1H), 5.59-5.45 (m, 1H), 5.05 (br t, J = 6.6 Hz, 2H), 4.73-4.60 (m, 2H), 4.28 (s, 2H), 2.40-2.29 (m, 1H), 2.27-2.11 (m, 1H), 2.05-1.91 (m, 5H), 1.66-1.56 (m, 1H), 1.54-1.42 (m, 5H), 1.22-1.15 (m, 2H), 1.14-1.03 (m, 2H). FXR EC$_{50}$ (nM) = 54. MS (ESI) 636.2 (M + H). | Ex. 391 |
| 407 | 2-(4-((5-cyclopropyl-3-(3,5-dichloropyridin-4-yl)isoxazol-4-yl)methoxy)bicyclo[2.2.2]octan-1-yl)-8-hydroxy-quinoline-5-carboxylic acid | ¹H NMR (500 MHz, DMSO-d$_6$) δ 9.34 (br d, J = 9.2 Hz, 1H), 8.85 (s, 2H), 8.17 (br d, J = 8.2 Hz, 1H), 7.67 (br d, J = 9.2 Hz, 1H), 7.11 (d, J = 7.9 Hz, 1H), 4.29 (s, 2H), 2.40-2.31 (m, 1H), 2.10-1.93 (m, 6H), 1.57-1.41 (m, 6H), 1.21-1.16 (m, 2H), 1.16-1.06 (m, 2H). FXR EC$_{50}$ (nM) = 19. MS (ESI) 580.3 (M + H). | Ex. 391 |

TABLE 7-continued

| Ex. No. | Structure & Name | ¹H NMR, FXR EC$_{50}$ & MS (ESI) | Method |
|---|---|---|---|
| 408 | 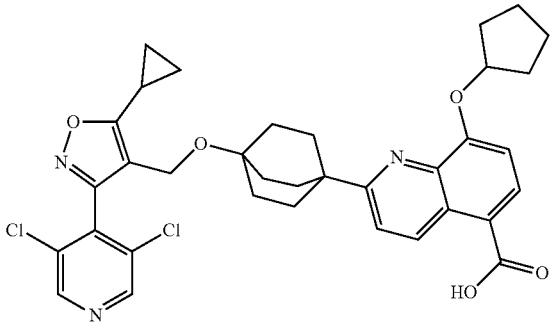<br>8-(cyclopentyloxy)-2-(4-((5-cyclopropyl-3-(3,5-dichloropyridin-4-yl)isoxazol-4-yl)methoxy)bicyclo[2.2.2]octan-1-yl)quinoline-5-carboxylic acid | ¹H NMR (500 MHz, DMSO-d$_6$) δ 9.25 (br d, J = 10.4 Hz, 1H), 8.83 (s, 2H), 8.17 (br d, J = 7.9 Hz, 1H), 7.65 (br d, J = 8.9 Hz, 1H), 7.18 (br d, J = 8.2 Hz, 1H), 5.11 (br s, 1H), 4.27 (s, 2H), 2.35-2.29 (m, 1H), 2.03-1.91 (m, 8H), 1.90-1.71 (m, 4H), 1.70-1.59 (m, 2H), 1.54-1.41 (m, 6H), 1.21-1.14 (m, 2H), 1.12-1.03 (m, 2H). FXR EC$_{50}$ (nM) = 10. MS (ESI) 648.3 (M + H). | Ex. 391 |
| 409 | 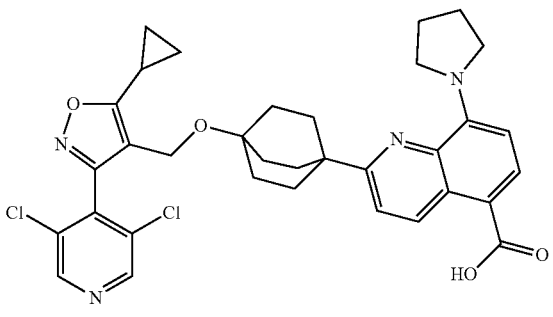<br>2-(4-((5-cyclopropyl-3-(3,5-dichloropyridin-4-yl)isoxazol-4-yl)methoxy)bicyclo[2.2.2]octan-1-yl)-8-(pyrrolidin-1-yl)quinoline-5-carboxylic acid | ¹H NMR (500 MHz, DMSO-d$_6$) δ 9.37 (d, J = 9.2 Hz, 1H), 8.84 (s, 2H), 8.06 (d, J = 8.5 Hz, 1H), 7.54 (d, J = 9.2 Hz, 1H), 6.63 (d, J = 8.9 Hz, 1H), 4.26 (s, 2H), 3.83 (br s, 2H), 2.52-2.50 (m, 4H), 2.38-2.28 (m, 1H), 2.01-1.86 (m, 8H), 1.54-1.38 (m, 6H), 1.21-1.14 (m, 2H), 1.13-1.05 (m, 2H). FXR EC$_{50}$ (nM) = 81. MS (ESI) 633.1 (M + H). | Ex. 410 |
| 411 | 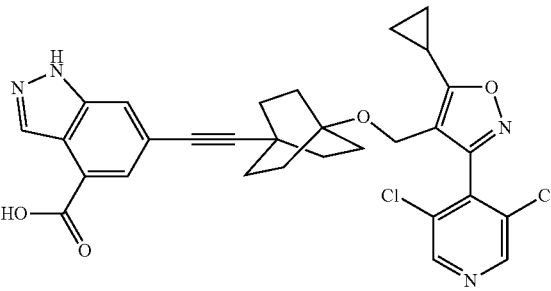<br>6-((4-((5-cyclopropyl-3-(3,5-dichloropyridin-4-yl)isoxazol-4-yl)methoxy)bicyclo[2.2.2]octan-1-yl)ethynyl)-1H-indazole-4-carboxylic acid | ¹H NMR (500 MHz, DMSO-d$_6$) δ 8.83 (s, 2H), 8.37 (br s, 1H), 7.73 (s, 1H), 7.62 (s, 1H), 4.21 (s, 2H), 2.37-2.23 (m, 1H), 1.94-1.77 (m, 6H), 1.47-1.32 (m, 6H), 1.21-1.12 (m, 2H), 1.11-1.02 (m, 2H). FXR EC$_{50}$ (nM) = 89. MS (ESI) 577 (M + H). | Ex. 130 |
| 412 | 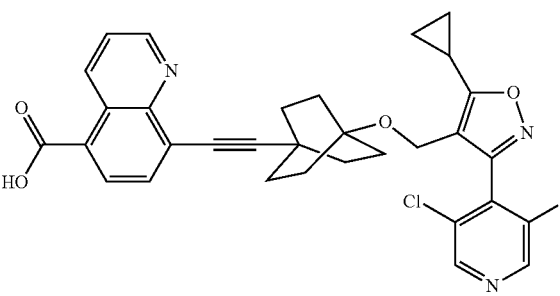<br>8-((4-((5-cyclopropyl-3-(3,5-dichloropyridin-4-yl)isoxazol-4-yl)methoxy)bicyclo[2.2.2]octan-1-yl)ethynyl)quinoline-5-carboxylic acid | ¹H NMR (500 MHz, DMSO-d$_6$) δ 9.28 (dd, J = 8.7, 1.1 Hz, 1H), 8.99 (br d, J = 2.4 Hz, 1H), 8.81 (s, 2H), 8.16 (d, J = 7.6 Hz, 1H), 7.84 (d, J = 7.6 Hz, 1H), 7.67 (dd, J = 8.7, 4.1 Hz, 1H), 4.20 (s, 2H), 2.35-2.23 (m, 1H), 2.00-1.83 (m, 6H), 1.50-1.34 (m, 6H), 1.20-1.12 (m, 2H), 1.12-1.02 (m, 2H). FXR EC$_{50}$ (nM) = 10. MS (ESI) 588.3 (M + H). | Ex. 130 |

TABLE 7-continued

| Ex. No. | Structure & Name | $^1$H NMR, FXR EC$_{50}$ & MS (ESI) | Method |
|---|---|---|---|
| 413 | 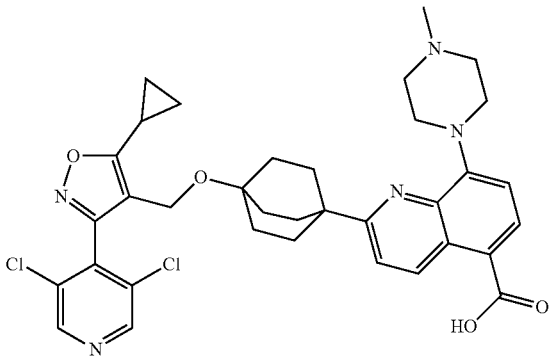<br>2-(4-((5-cyclopropyl-3-(3,5-dichloropyridin-4-yl)isoxazol-4-yl)methoxy)bicyclo[2.2.2]octan-1-yl)-8-(4-methyl-piperazin-1-yl)quinoline-5-carboxylic acid | $^1$H NMR (500 MHz, DMSO-d$_6$) δ 9.54 (br d, J = 8.2 Hz, 1H), 8.85 (s, 2H), 7.85 (br d, J = 5.5 Hz, 1H), 7.42 (br d, J = 8.2 Hz, 1H), 6.95 (br d, J = 6.7 Hz, 1H), 4.28 (s, 2H), 2.64-2.53 (m, 6H), 2.41-2.32 (m, 1H), 2.28 (s, 3H), 1.97 (br s, 6H), 1.83 (br s, 2H), 1.57-1.44 (m, 6H), 1.22-1.15 (m, 2H), 1.14-1.04 (m, 2H). FXR EC$_{50}$ (nM) = 1500. MS (ESI) 662.1 (M + H). | Ex. 410 |
| 414 | 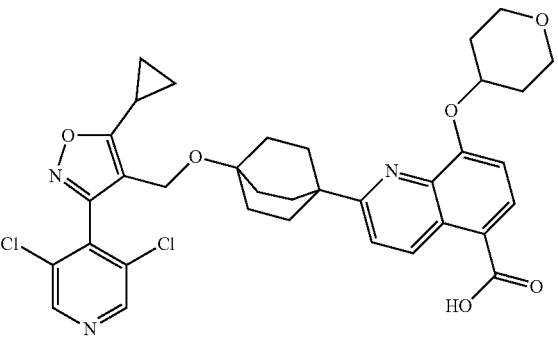<br>2-(4-((5-cyclopropyl-3-(3,5-dichloropyridin-4-yl)isoxazol-4-yl)methoxy)bicyclo[2.2.2]octan-1-yl)-8-((tetrahydro-2H-pyran-4-yl)oxy)quinoline-5-carboxylic acid | $^1$H NMR (500 MHz, DMSO-d$_6$) δ 9.27 (br d, J = 9.2 Hz, 1H), 8.84 (s, 2H), 8.13 (br d, J = 8.2 Hz, 1H), 7.64 (br d, J = 8.9 Hz, 1H), 7.28 (br d, J = 8.2 Hz, 1H), 4.99 (br s, 1H), 4.27 (s, 2H), 4.00-3.85 (m, 2H), 2.33 (br s, 1H), 2.10-1.87 (m, 10H), 1.75 (br d, J = 7.6 Hz, 2H), 1.49 (br d, J = 7.0 Hz, 6H), 1.22-1.14 (m, 2H), 1.12-1.01 (m, 2H). FXR EC$_{50}$ (nM) = 29. MS (ESI) 664.3 (M + H). | Ex. 391 |
| 415 | 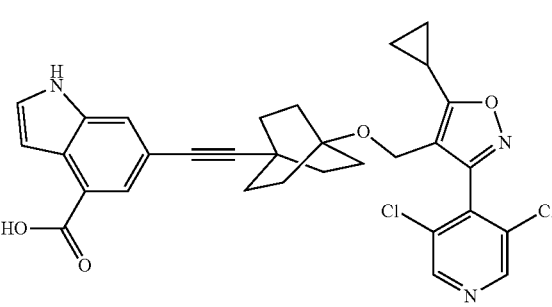<br>6-((4-((5-cyclopropyl-3-(3,5-dichloropyridin-4-yl)isoxazol-4-yl)methoxy)bicyclo[2.2.2]octan-1-yl)ethynyl)-1H-indole-4-carboxylic acid | $^1$H NMR (500 MHz, DMSO-d$_6$) δ 11.44 (br s, 1H), 8.81 (s, 2H), 7.61-7.57 (m, 1H), 7.57-7.55 (m, 1H), 7.53 (br s, 1H), 6.92 (br s, 1H), 4.19 (s, 2H), 2.33-2.24 (m, 1H), 1.88-1.74 (m, 6H), 1.44-1.29 (m, 6H), 1.21-1.12 (m, 2H), 1.11-1.02 (m, 2H). FXR EC$_{50}$ (nM) = 63. MS (ESI) 576.4 (M + H). | Ex. 130 |

TABLE 7-continued

| Ex. No. | Structure & Name | ¹H NMR, FXR EC$_{50}$ & MS (ESI) | Method |
|---|---|---|---|
| 416 | 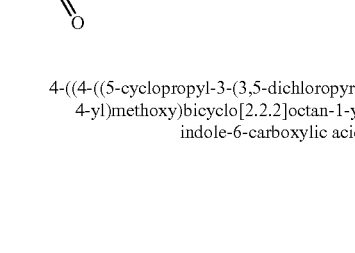<br>4-((4-((5-cyclopropyl-3-(3,5-dichloropyridin-4-yl)isoxazol-4-yl)methoxy)bicyclo[2.2.2]octan-1-yl)ethynyl)-1H-indole-6-carboxylic acid | ¹H NMR (500 MHz, DMSO-d$_6$) δ 11.61 (br s, 1H), 8.84 (s, 2H), 7.99 (s, 1H), 7.61 (br s, 1H), 7.54 (s, 1H), 6.46 (br s, 1H), 4.22 (s, 2H), 2.36-2.26 (m, 1H), 1.97-1.82 (m, 6H), 1.49-1.35 (m, 6H), 1.21-1.12 (m, 2H), 1.12-1.04 (m, 2H). FXR EC$_{50}$ (nM) = 40. MS (ESI) 576.2 (M + H). | Ex. 130 |
| 417 | 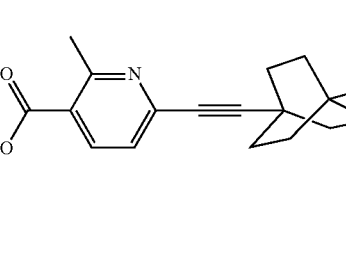<br>6-((4-((5-cyclopropyl-3-(3,5-dichloropyridin-4-yl)isoxazol-4-yl)methoxy)bicyclo[2.2.2]octan-1-yl)ethynyl)-2-methylnicotinic acid | ¹H NMR (500 MHz, DMSO-d$_6$) δ 8.78 (d, J = 2.3 Hz, 2H), 8.08 (d, J = 8.1 Hz, 1H), 7.29 (d, J = 8.0 Hz, 1H), 4.20 (s, 2H), 2.65 (s, 3H), 2.31-2.19 (m, 1H), 1.84 (br d, J = 6.6 Hz, 6H), 1.41 (br s, 6H), 1.21-1.12 (m, 2H), 1.10-1.01 (m, 2H). FXR EC$_{50}$ (nM) = 300. MS (ESI) 552.2 (M + H). | Ex. 130 |
| 419 | 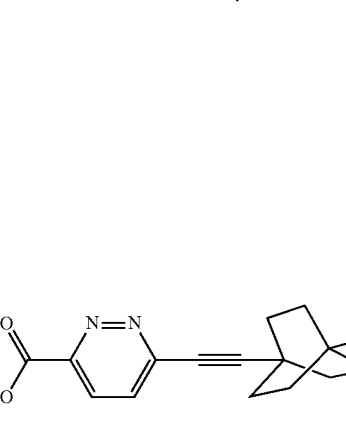<br>6-((4-((5-cyclopropyl-3-(3,5-dichloropyridin-4-yl)isoxazol-4-yl)methoxy)bicyclo[2.2.2]octan-1-yl)ethynyl)pyridazine-3-carboxylic acid | ¹H NMR (500 MHz, DMSO-d$_6$) δ 8.81 (s, 2H), 8.16-7.96 (m, 1H), 7.74 (br d, J = 7.6 Hz, 1H), 4.20 (s, 2H), 2.35-2.22 (m, 1H), 1.92-1.77 (m, 6H), 1.50-1.34 (m, 6H), 1.21-1.12 (m, 2H), 1.11-1.00 (m, 2H). FXR EC$_{50}$ (nM) = 2000. MS (ESI) 539.2 (M + H). | Ex. 130 |

TABLE 7-continued

| Ex. No. | Structure & Name | $^1$H NMR, FXR EC$_{50}$ & MS (ESI) | Method |
|---|---|---|---|
| 420 | 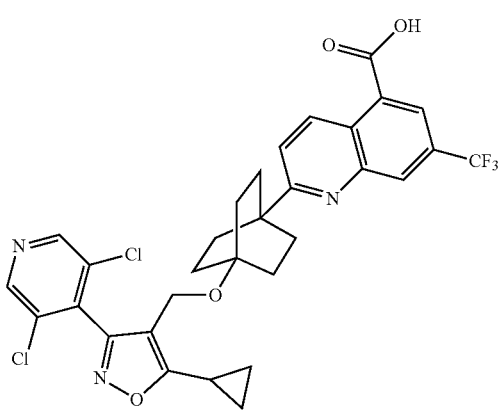<br>2-(4-((5-cyclopropyl-3-(3,5-dichloropyridin-4-yl)isoxazol-4-yl)methoxy)bicyclo[2.2.2]octan-1-yl)-7-(trifluoromethyl)quinoline-5-carboxylic acid | $^1$H NMR (500 MHz, DMSO-d$_6$) δ 9.22 (br d, J = 9.1 Hz, 1H), 8.81 (s, 2H), 8.38 (s, 1H), 8.25 (s, 1H), 7.80 (br d, J = 9.2 Hz, 1H), 4.28 (s, 2H), 2.35-2.24 (m, 1H), 2.04-1.95 (m, 6H), 1.57-1.47 (m, 6H), 1.17 (br dd, J = 8.2, 2.4 Hz, 2H), 1.10-1.04 (m, 2H). FXR EC$_{50}$ (nM) = 3. MS (ESI) 632.1 (M + H) | Ex. 384 |
| 421 | 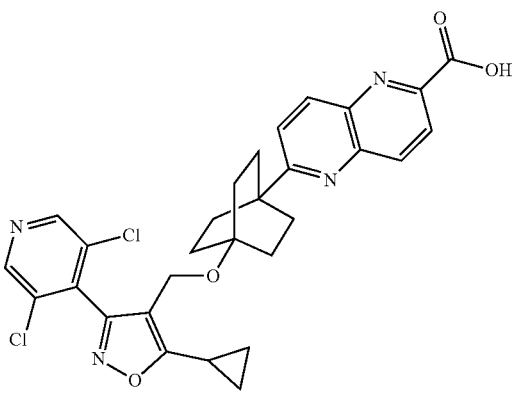<br>6-(4-((5-cyclopropyl-3-(3,5-dichloropyridin-4-yl)isoxazol-4-yl)methoxy)bicyclo[2.2.2]octan-1-yl)-1,5-naphthyridine-2-carboxylic acid | $^1$H NMR (500 MHz, DMSO-d$_6$) δ 8.85 (s, 2H), 8.42 (br dd, J = 15.6, 8.9 Hz, 2H), 8.28 (br d, J = 8.9 Hz, 1H), 7.89 (br d, J = 8.9 Hz, 1H), 4.28 (s, 2H), 2.34 (br t, J = 4.7 Hz, 1H), 2.06-1.92 (m, 6H), 1.57-1.44 (m, 6H), 1.21-1.14 (m, 2H), 1.11 (br d, J = 3.1 Hz, 2H). FXR EC$_{50}$ (nM) = 53. MS (ESI) 565.2 (M + H) | Ex. 384 |
| 422 | 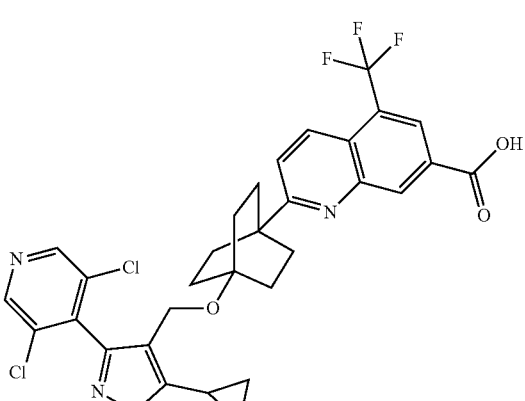<br>2-(4-((5-cyclopropyl-3-(3,5-dichloropyridin-4-yl)isoxazol-4-yl)methoxy)bicyclo[2.2.2]octan-1-yl)-5-(trifluoromethyl)quinoline-7-carboxylic acid | $^1$H NMR (500 MHz, DMSO-d$_6$) δ 8.82 (s, 2H), 8.70 (s, 1H), 8.43 (br d, J = 8.3 Hz, 1H), 8.35 (s, 1H), 7.87 (br d, J = 9.1 Hz, 1H), 4.29 (s, 2H), 2.32 (br t, J = 5.0 Hz, 1H), 2.07-1.97 (m, 6H), 1.57-1.50 (m, 6H), 1.21-1.16 (m, 2H), 1.13-1.07 (m, 2H). FXR EC$_{50}$ (nM) = 360. MS (ESI) 632.1 (M + H) | Ex. 384 |

TABLE 7-continued

| Ex. No. | Structure & Name | $^1$H NMR, FXR EC$_{50}$ & MS (ESI) | Method |
|---|---|---|---|
| 424 | 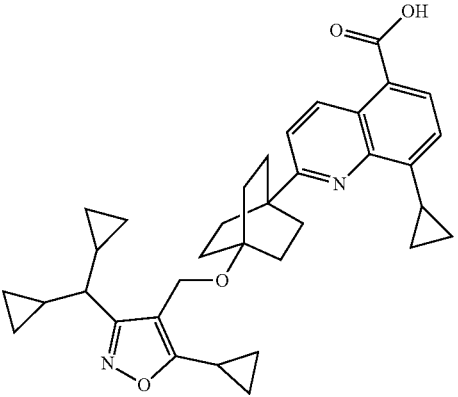

8-cyclopropyl-2-(4-((5-cyclopropyl-3-(dicyclopropyl-methyl)isoxazol-4-yl)methoxy)bicyclo[2.2.2]octan-1-yl)quinoline-5-carboxylic acid | $^1$H NMR (500 MHz, DMSO-d$_6$) δ 9.26-8.95 (m, 1H), 8.01 (d, J = 7.9 Hz, 1H), 7.65 (d, J = 9.2 Hz, 1H), 7.13 (d, J = 7.9 Hz, 1H), 4.21 (s, 2H), 3.27 (br s, 1H), 2.12-1.98 (m, 7H), 1.81-1.69 (m, 6H), 1.43 (t, J = 9.2 Hz, 1H), 1.15-1.07 (m, 4H), 0.98 (br dd, J = 8.1, 2.6 Hz, 2H), 0.88 (br s, 4H), 0.52-0.40 (m, 2H), 0.28-0.13 (m, 4H), 0.01 (br d, J = 5.2 Hz, 2H). FXR EC$_{50}$ (nM) = 500. MS (ESI) 553.2 (M + H) | Ex. 384 |
| 427 | 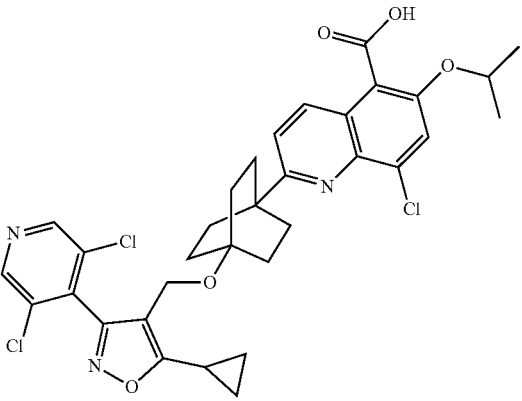

8-chloro-2-(4-((5-cyclopropyl-3-(3,5-dichloropyridin-4-yl)isoxazol-4-yl)methoxy)bicyclo[2.2.2]octan-1-yl)-6-isopropoxyquinoline-5-carboxylic acid | $^1$H NMR (500 MHz, DMSO-d$_6$) δ 8.81 (s, 2H), 8.06 (br d, J = 8.9 Hz, 1H), 7.80 (s, 1H), 7.60 (d, J = 8.9 Hz, 1H), 4.84-4.72 (m, 1H), 4.28 (s, 2H), 2.37-2.26 (m, 1H), 2.04-1.93 (m, 6H), 1.56-1.45 (m, 6H), 1.28 (d, J = 6.0 Hz, 6H), 1.20-1.15 (m, 2H), 1.10 (br d, J = 2.8 Hz, 2H). FXR EC$_{50}$ (nM) = 5. MS (ESI) 656.1 (M + H) | Ex. 426 |
| 428 | 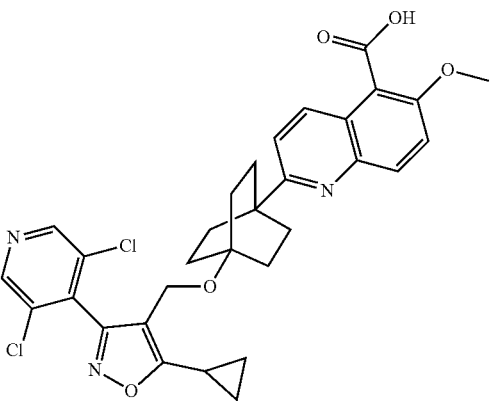

2-(4-((5-cyclopropyl-3-(3,5-dichloropyridin-4-yl)isoxazol-4-yl)methoxy)bicyclo[2.2.2]octan-1-yl)-6-methoxyquinoline-5-carboxylic acid | $^1$H NMR (500 MHz, DMSO-d$_6$) δ 8.81 (s, 2H), 8.00 (br dd, J = 11.9, 9.5 Hz, 2H), 7.65 (d, J = 9.2 Hz, 1H), 7.55 (br d, J = 9.2 Hz, 1H), 4.25 (s, 2H), 3.71-3.68 (m, 3H), 2.34-2.26 (m, 1H), 1.96-1.90 (m, 6H), 1.48-1.42 (m, 6H), 1.18-1.15 (m, 2H), 1.09-1.06 (m, 2H). FXR EC$_{50}$ (nM) = 120. MS (ESI) 594.1 (M + H) | Ex. 426 |

| Ex. No. | Structure & Name | $^1$H NMR, FXR EC$_{50}$ & MS (ESI) | Method |
|---|---|---|---|
| 429 | 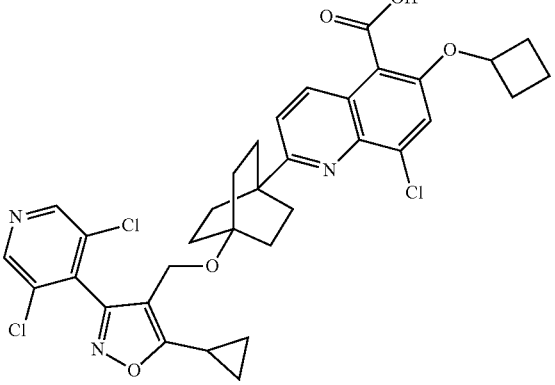<br>8-chloro-6-cyclobutoxy-2-(4-(((5-cyclopropyl-3-(3,5-dichloro-pyridin-4-yl)isoxazol-4-yl)methoxy)bicyclo[2.2.2]octan-1-yl)quinoline-5-carboxylic acid | $^1$H NMR (500 MHz, DMSO-d$_6$) δ 8.80 (br s, 2H), 8.08 (br d, J = 8.6 Hz, 1H), 7.61 (br d, J = 5.6 Hz, 2H), 4.91 (br s, 1H), 4.27 (s, 2H), 2.42 (br d, J = 6.9 Hz, 2H), 2.30 (br s, 1H), 2.11-2.03 (m, 2H), 1.98 (br s, 6H), 1.80 (br d, J = 9.3 Hz, 1H), 1.64 (br d, J = 10.0 Hz, 1H), 1.50 (br s, 6H), 1.17 (br d, J = 4.3 Hz, 2H), 1.08 (br s, 2H). FXR EC$_{50}$ (nM) = 4. MS (ESI) 668.3 (M + H) | Ex. 426 |

Example 435

2-(4-((5-cyclopropyl-3-(3,5-dichloropyridin-4-yl)isoxazol-4-yl)methoxy) bicyclo[2.2.2]octan-1-yl)-5-(trifluoromethyl)benzo[d]thiazole-7-carboxamide

Example 436

(E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-5-(trifluoromethyl)benzoic acid

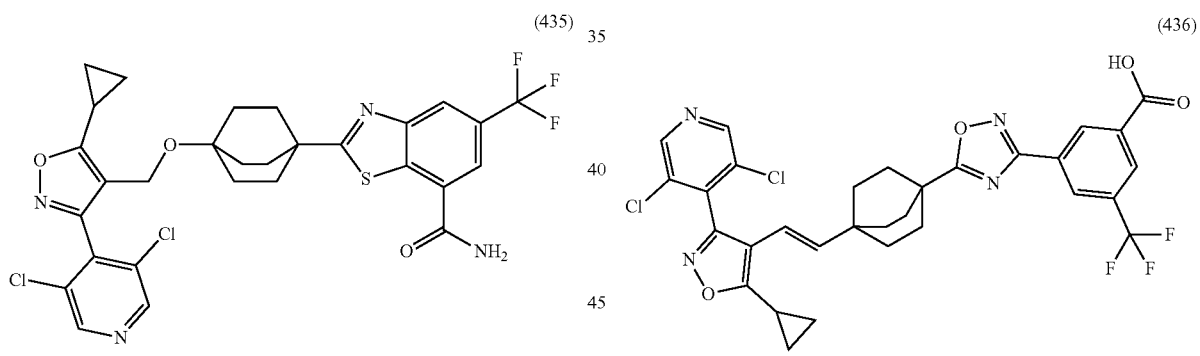

(435)

(436)

To a stirred solution of Example 434 (20 mg, 0.031 mmol) and DMF (1 mL) were added BOP (17 mg, 0.038 mmol), ammonium chloride (17 mg, 0.31 mmol) and Et$_3$N (0.022 mL, 0.16 mmol) at 0° C. The reaction was warmed to rt and stirred. After 12 h, the solvent was concentrated and the crude product was purified via preparative HPLC (Column: Waters XBridge C18, 19×150 mm, 5-nm particles; Mobile Phase A: 10-mM ammonium acetate; Mobile Phase B: acetonitrile; Gradient: 10-40% B over 20 minutes, then a 5-minute hold at 100% B; Flow: 15 mL/min). Fractions containing the desired product were combined, concentrated and dried in vacuo to provide the title compound (4.2 mg, 6.6 µmol, 21% yield). $^1$H NMR (400 MHz, DMSO-d$_6$) δ 8.85 (s, 2H), 8.59 (br. s., 1H), 8.43 (d, J=5.1 Hz, 2H), 7.92 (br. s., 1H), 4.27 (s, 2H), 2.37-2.32 (m, 1H), 2.11-1.98 (m, 6H), 1.63-1.46 (m, 6H), 1.21-1.08 (m, 4H). FXR EC$_{50}$ (nM)=460. MS (ESI) 637 (M+H).

Step A. Intermediate 436A. Preparation of diethyl ((5-cyclopropyl-3-(3,5-dichloropyridin-4-yl)isoxazol-4-yl)methyl)phosphonate

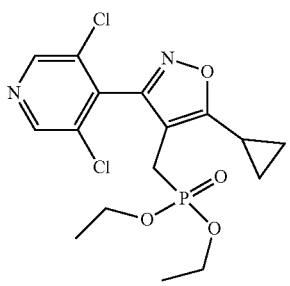 [SMILES: CCOP(=O)(Cc1c(-c2c(Cl)cncc2Cl)noc1C1CC1)OCC]

The title compound was prepared according to methods described for the synthesis of Intermediate 194G, substituting 4-(bromomethyl)-5-cyclopropyl-3-(3,5-dichloropyridin-4-yl)isoxazole where appropriate: (800 mg, 2.0 mmol, 52% yield, white solid). $^1$H NMR (400 MHz, DMSO-d$_6$) δ 8.83 (s, 2H), 3.88-3.83 (m, 4H), 2.97 (d, J=20.00 Hz, 2H), 2.49 (m, 1H), 1.16-1.12 (m, 2H), 1.12-1.08 (m, 8H). MS (ESI) 405 (M+H).

Step B. Intermediate 436B. Preparation of (E)-methyl 4-(2-(5-cyclopropyl-3-(3,5-dichloropyridin-4-yl)isoxazol-4-yl)vinyl)bicyclo[2.2.2]octane-1-carboxylate

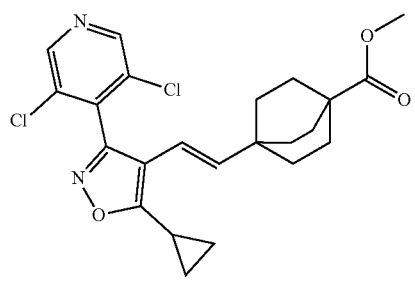 [SMILES: COC(=O)C12CCC(/C=C/c3c(-c4c(Cl)cncc4Cl)noc3C3CC3)(CC1)CC2]

The title compound was prepared according to methods described for the synthesis of Intermediate 194H, by reaction of Intermediate 436A and Intermediate 159B: (0.085 g, 0.19 mmol, 73% yield, white solid). $^1$H NMR (400 MHz, DMSO-d$_6$) δ 8.86 (s, 2H), 5.99 (d, J=16.8 Hz, 1H), 5.24 (d, J=16.8 Hz, 1H), 3.54 (s, 3H), 2.36-2.33 (m, 1H), 1.68-1.64 (m, 6H), 1.36-1.32 (m, 6H), 1.26-1.14 (m, 4H). MS (ESI) 447 (M+H).

Step C. Intermediate 436C. Preparation of (E)-4-(2-(5-cyclopropyl-3-(3,5-dichloropyridin-4-yl)isoxazol-4-yl)vinyl)bicyclo[2.2.2]octane-1-carboxylic acid

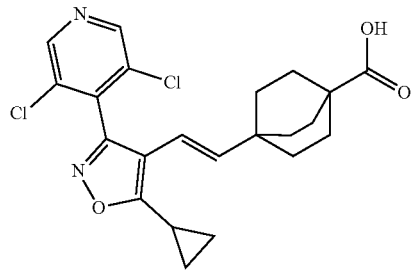 [SMILES: O=C(O)C12CCC(/C=C/c3c(-c4c(Cl)cncc4Cl)noc3C3CC3)(CC1)CC2]

The title compound was prepared according to methods described for the synthesis of Intermediate 159E, substituting Intermediate 436B where appropriate: (0.06 g, 0.138 mmol, 88% yield, white solid). MS (ESI) 433 (M+H).

Step D. Example 436

The title compound was prepared according to methods described for the synthesis of Example 64 (Step C), by reaction of Intermediate 436C and Intermediate 264B: (10 mg, 0.016 μmol, 53% yield). $^1$H NMR (400 MHz, DMSO-d$_6$) δ 8.89 (s, 2H), 8.74 (s, 1H), 8.32 (d, J=8.1 Hz, 2H), 6.08 (d, J=16.6 Hz, 1H), 5.32 (d, J=16.6 Hz, 1H), 2.45-2.37 (m, 1H), 2.07-1.93 (m, 6H), 1.59-1.42 (m, 6H), 1.23-1.16 (m, 2H), 1.15-1.06 (m, 2H). FXR EC$_{50}$ (nM)=18. MS (ESI) 645 (M+H).

Example 443

(E)-methyl 3-(5-(4-(2-(5-cyclopropyl-3-(3,5-dichloropyridin-4-yl)isoxazol-4-yl)vinyl) bicyclo[2.2.2]octan-1-yl)-1,2,4-oxadiazol-3-yl)-5-(difluoromethoxy)benzoate (443)

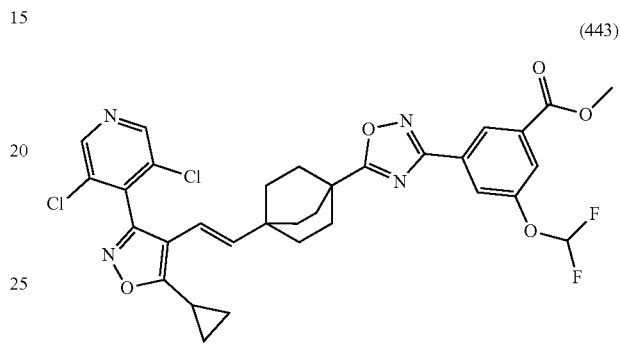

Step A. Intermediate 443A. Preparation of methyl 3-bromo-5-(difluoromethoxy) benzoate

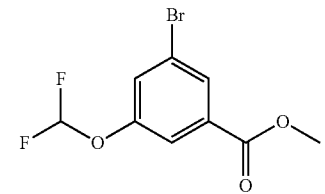

To a stirred solution of methyl 3-bromo-5-hydroxybenzoate (900 mg, 3.9 mmol) (Park, K. et al. WO 2014/112798) in DMF (18 mL) was added potassium carbonate (540 mg, 3.9 mmol) followed by methyl chlorodifluoroacetate (560 mg, 3.9 mmol). The mixture was stirred at 80° C. After 18 h, the reaction was cooled, concentrated, diluted with water and extracted with ethyl acetate (2×30 mL). The organic layer was combined, washed with brine, dried over MgSO$_4$, and concentrated. The crude product was purified by flash column chromatography (40 g silica gel cartridge; A=PE, B=EtOAc; 20 min grad.; 0% B to 50% B; flow rate=40 mL/min). The pure fractions were combined, concentrated and dried in vacuo to provide the title compound (350 mg, 1.2 mmol, 30% yield) as a viscous oil. MS (ESI) 281 (M+H).

Step B. Intermediate 443B. Preparation of methyl 3-cyano-5-(difluoromethoxy) benzoate

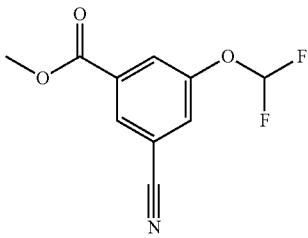 [SMILES: COC(=O)c1cc(C#N)cc(OC(F)F)c1]

To a solution of Intermediate 443A (350 mg, 1.3 mmol) in DMF (5 mL) was added copper(I) cyanide (170 mg, 1.9 mmol). The mixture was stirred at 150° C. After 12 h, the reaction was cooled to rt, diluted with EtOAc and filtered through Celite. The filtrate was washed with brine, dried over MgSO$_4$, filtered and concentrated. The crude product was purified by flash column chromatography (40 g silica gel cartridge; A=PE, B=EtOAc; 20 min grad.; 0% B to 50% B; flow rate=40 mL/min). The pure fractions were combined, concentrated and dried in vacuo to provide the title compound (140 mg, 0.62 mmol, 50% yield). $^1$H NMR (400 MHz, DMSO-d$_6$) δ 8.22 (t, J=1.5 Hz, 1H), 8.09 (dd, J=2.5, 1.5 Hz, 1H), 7.99-7.97 (m, 1H), 7.64-7.26 (m, 1H), 3.90 (s, 3H).

Step C. Intermediate 443C. Preparation of methyl (Z)-3-(difluoromethoxy)-5-(N'-hydroxycarbamimidoyl)benzoate

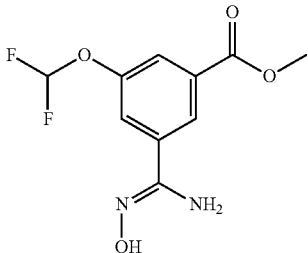 [SMILES: COC(=O)c1cc(OC(F)F)cc(/C(N)=N/O)c1]

The title compound was prepared according to methods described for the synthesis of Intermediate 4C, using Intermediate 443B as starting material: (60 mg, 0.21 mmol, 41% yield, white solid). MS (ESI) 261 (M+H).

Step D. Example 443

The title compound was prepared according to methods described for the synthesis of Example 64 (Step C), by reaction of Intermediate 436C and Intermediate 443C: (20 mg, 0.031 mmol, 41% yield). $^1$H NMR (400 MHz, DMSO-d$_6$) δ 8.90 (s, 2H), 8.37 (t, J=1.3 Hz, 1H), 7.92 (s, 1H), 7.86 (s, 1H), 7.45 (t, J=73.2 Hz, 1H), 6.08 (d, J=16.4 Hz, 1H), 5.31 (d, J=16.6 Hz, 1H), 2.47-2.37 (m, 1H), 2.08-1.87 (m, 6H), 1.61-1.41 (m, 6H), 1.23-1.15 (m, 2H), 1.15-1.03 (m, 2H). FXR EC$_{50}$ (nM)=49. MS (ESI) 643 (M+H).

Example 444

(E)-3-((4-(2-(5-cyclopropyl-3-(3,5-dichloropyridin-4-yl)isoxazol-4-yl)vinyl) bicyclo[2.2.2]octan-1-yl)methoxy)-5-(difluoromethoxy)benzoic acid (444)

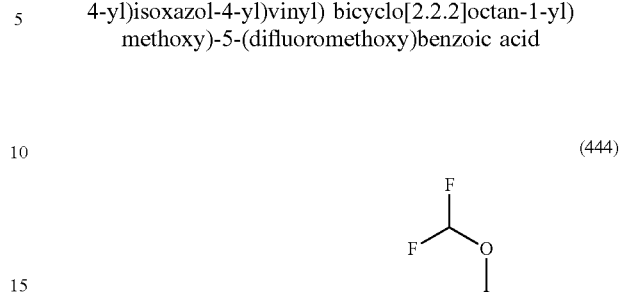

Step A. Intermediate 444A. Preparation of (E)-(4-(2-(5-cyclopropyl-3-(3,5-dichloropyridin-4-yl)isoxazol-4-yl)vinyl)bicyclo[2.2.2]octan-1-yl)methanol

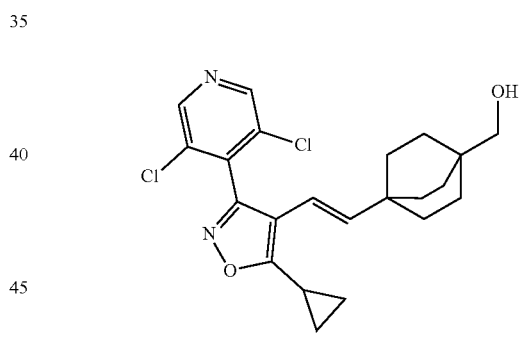

A solution of intermediate 436B (65 mg, 0.15 mmol) in DCM (8 mL) was cooled to −78° C. under Ar. To this mixture was added dropwise DIBAL-H (0.36 mL, 0.36 mmol) (1 M solution in heptane). After stirring 0.5 h at the same temperature, the reaction mixture was quenched with sat. NH$_4$Cl (aq.) (20 mL) and the aqueous layer was extracted with DCM (2×20 mL). The combined organic layer was washed with brine, dried over Na$_2$SO$_4$, filtered and concentrated. The crude product was purified by flash column chromatography (12 g silica gel cartridge; A=PE, B=EtOAc; 15 min grad.; 0% B to 50% B; flow rate=12 mL/min). The pure fractions were combined, concentrated and dried in vacuo to provide the title compound (42 mg, 0.098 mmol, 68% yield). $^1$H NMR (400 MHz, CHLOROFORM-d) δ 8.6 (s, 2H), 5.83 (d, J=16.8 Hz, 1H), 5.38 (d, J=16.8 Hz, 1H), 4.12 (d, J=7.2 Hz, 2H), 3.25 (m, 1H), 2.36-2.33 (m, 1H), 1.68-1.64 (m, 6H), 1.36-1.32 (m, 6H), 1.26-1.14 (m, 4H). MS (ESI) 419 (M+H).

Step B. Intermediate 444B. Preparation of (E)-methyl 3-((4-(2-(5-cyclopropyl-3-(3,5-dichloropyridin-4-yl)isoxazol-4-yl)vinyl)bicyclo[2.2.2]octan-1-yl)methoxy)-5-(difluoromethoxy) benzoate

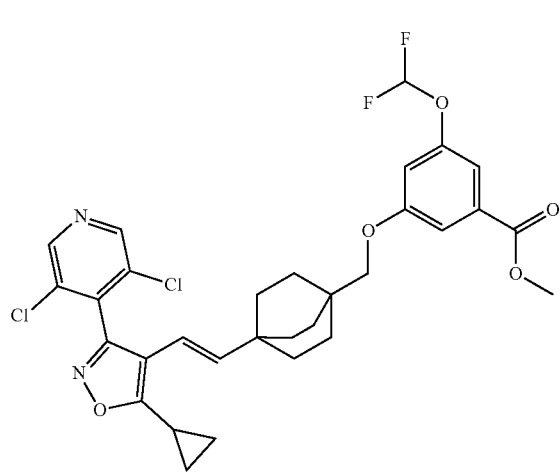 [SMILES: COC(=O)c1cc(OCC23CCC(/C=C/c4c(-c5c(Cl)cncc5Cl)noc4C4CC4)(CC2)CC3)cc(OC(F)F)c1]

To a stirred solution of Intermediate 444A in toluene (1 mL), were added methyl 3-(difluoromethoxy)-5-hydroxybenzoate (13 mg, 0.057 mmol) and cyanomethylenetributylphosphorane (23 mg, 0.095 mmol). The reaction mixture was heated to 100° C. and stirred. After 2 h, the reaction mixture was cooled, poured into ice water and the aqueous layer was extracted with EtOAc (2×50 mL). The combined organic layers were dried over MgSO$_4$, filtered and concentrated. The crude product was purified by flash column chromatography (12 g silica gel cartridge; A=PE, B=EtOAc; 15 min grad.; 0% B to 50% B; flow rate=12 mL/min). The pure fractions were combined, concentrated and dried in vacuo to provide the title compound (27 mg, 0.031 mmol, 64% yield). MS (ESI) 619 (M+H).

Step C. Example 444

The title compound was prepared according methods described for the synthesis of Example 151 (Step C), substituting Intermediate 444B where appropriate: (14 mg, 0.023 mmol, 72% yield). $^1$H NMR (400 MHz, DMSO-d$_6$) δ 8.88 (s, 2H), 7.39-7.24 (m, 2H), 7.22 (s, 1H), 6.89 (s, 1H), 6.01 (d, J=16.6 Hz, 1H), 5.28 (d, J=16.4 Hz, 1H), 3.64 (s, 2H), 2.41-2.34 (m, 1H), 1.59-1.45 (m, 6H), 1.42-1.32 (m, 6H), 1.22-1.04 (m, 4H). FXR EC$_{50}$ (nM)=16. MS (ESI) 605 (M+H).

Example 446

(E)-5-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-2-(difluoromethoxy)benzoic acid

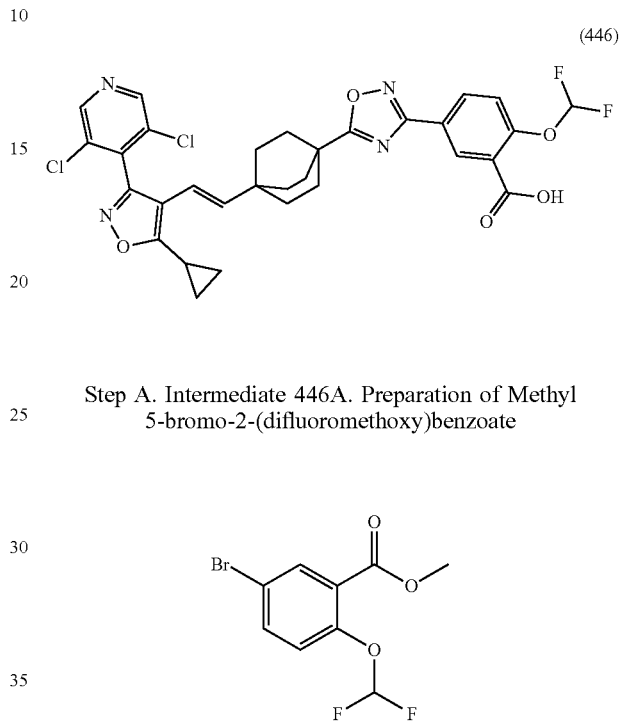

(446)

Step A. Intermediate 446A. Preparation of Methyl 5-bromo-2-(difluoromethoxy)benzoate

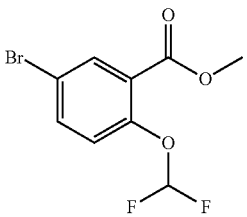

The title compound was prepared according methods described for the synthesis of intermediate 443A, substituting methyl 5-bromo-2-hydroxybenzoate where appropriate: (1.0 g, 3.6 mmol, 55% yield). $^1$H NMR (400 MHz, CHLOROFORM-d) δ 8.02 (d, J=2.5 Hz, 1H), 7.66-7.61 (m, 1H), 7.15 (d, J=8.5 Hz, 1H), 6.74-6.36 (m, 1H), 3.93 (s, 3H).

Step B. Intermediate 446B. Preparation of methyl 5-cyano-2-(difluoromethoxy)benzoate

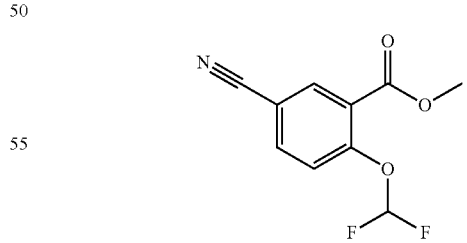

The title compound was prepared according methods described for the synthesis of intermediate 443B, substituting intermediate 446A where appropriate: (350 mg, 1.5 mmol, 67% yield). $^1$H NMR (400 MHz, DMSO-d$_6$) δ 8.30 (d, J=2.0 Hz, 1H), 8.17 (dd, J=8.5, 2.0 Hz, 1H), 7.54 (d, J=8.5 Hz, 1H), 7.4 (t, J=73 Hz, 1H), 3.87 (s, 3H). MS (ESI) 228 (M+H).

487

Step C. Intermediate 446C. Preparation of methyl (Z)-2-(difluoromethoxy)-5-(N'-hydroxycarbamimidoyl)benzoate

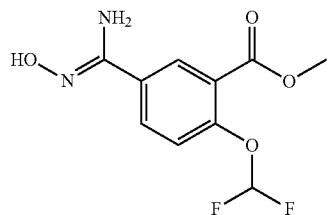 [SMILES: COC(=O)c1cc(/C(N)=N/O)ccc1OC(F)F]

The title compound was prepared according methods described for the synthesis of Intermediate 4C, substituting intermediate 446B where appropriate: (120 mg, 0.44 mmol, 40% yield). $^1$H NMR (400 MHz, DMSO-d$_6$) δ 9.78 (d, J=1.0 Hz, 1H), 8.16-8.15 (m, 1H), 7.94-7.90 (m, 1H), 7.40-7.02 (m, 2H), 5.94 (s, 2H), 3.85 (s, 3H). MS (ESI) 261 (M+H).

Step D. Example 446

The title compound was prepared according to methods described for the synthesis of Example 64 (Step C), by reaction of Intermediate 436C and Intermediate 446C: (15 mg, 0.023 mmol, 30% yield). $^1$H NMR (400 MHz, DMSO-d$_6$) δ 13.52 (s, 1H), 8.89 (s, 2H), 8.39 (d, J=2.2 Hz, 1H), 8.19 (dd, J=8.7, 2.3 Hz, 1H), 7.49-7.46 (m, 1H), 7.31 (t, J=73.6 Hz, 1H), 6.07 (d, J=16.6 Hz, 1H), 5.32 (d, J=16.4 Hz, 1H), 2.46-2.37 (m, 1H), 2.07-1.86 (m, 6H), 1.62-1.42 (m, 6H), 1.22-1.05 (m, 4H). FXR EC$_{50}$ (nM)=350. MS (ESI) 643 (M+H).

Example 452

(E)-6-((4-(2-(5-cyclopropyl-3-(3,5-dichloropyridin-4-yl)isoxazol-4-yl)vinyl) bicyclo[2.2.2]octan-1-yl)methoxy)-4-(trifluoromethyl)quinoline-2-carboxylic acid (452)

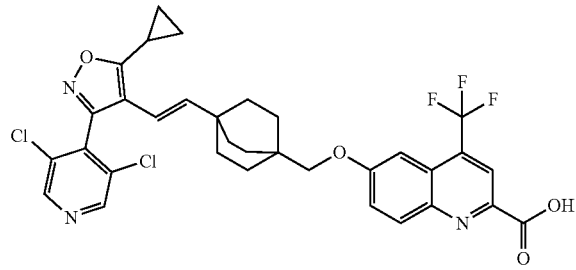

488

Step A. Intermediate 452A. Preparation of ethyl 6-(5,5-dimethyl-1,3,2-dioxaborinan-2-yl)-4-(trifluoromethyl)quinoline-2-carboxylate

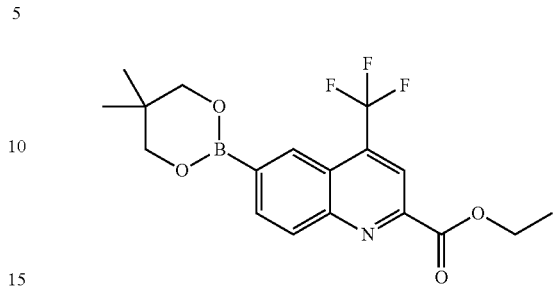

To a stirred solution of ethyl 6-chloro-4-(trifluoromethyl)quinoline-2-carboxylate (350 mg, 1.2 mmol) in 1,4-dioxane (14 mL) were added potassium acetate (510 mg, 5.2 mmol) and 5,5,5',5'-tetramethyl-2,2'-bi(1,3,2-dioxaborinane) (520 mg, 2.3 mmol). The reaction mixture was purged with Ar for 5 min. To this mixture was added Pd(dppf)Cl$_2$ (42 mg, 0.058 mmol) and the reaction was stirred at 110° C. After 4 h, the reaction mixture was concentrated, diluted with water and extracted with ethyl acetate (2×20 mL). The combined organic layer was dried over sodium sulfate, filtered and concentrated. The crude product was purified by flash column chromatography (80 g silica gel cartridge; A=PE, B=EtOAc; 20 min grad.; 0% B to 70% B; flow rate=60 mL/min). The pure fractions were combined, concentrated and dried in vacuo to provide the title compound (230 mg, 0.57 mmol, 50% yield, yellow viscous oil). MS (ESI) 382 (M+H).

Step B. Intermediate 452B. Preparation of ethyl 6-hydroxy-4-(trifluoromethyl)quinoline-2-carboxylate

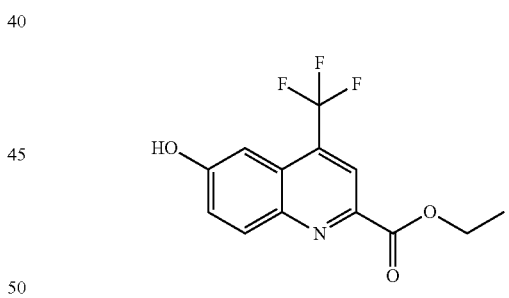

To a stirred solution of Intermediate 452A (230 mg, 0.60 mmol) in H$_2$O (2 mL) and THF (2 mL) was added sodium perborate tetrahydrate (370 mg, 2.4 mmol). The reaction was stirred at 45° C. After 30 min, the reaction mixture was concentrated, diluted with water (20 mL) and extracted with ethyl acetate (2×20 mL). The combined organic layer was dried over sodium sulfate, filtered and concentrated. The crude product was purified by flash column chromatography (24 g silica gel cartridge; A=PE, B=EtOAc; 15 min grad.; 0% B to 60% B; flow rate=24 mL/min). The pure fractions were combined, concentrated and dried in vacuo to provide the title compound (130 mg, 0.43 mmol, 72% yield) as a yellow solid. $^1$H NMR (400 MHz, DMSO-d$_6$) δ 8.24 (s, 1H), 8.22 (d, J=9.5 Hz, 1H), 7.57 (dd, J=9.5, 2.5 Hz, 1H), 7.36 (br s, 1H), 4.44 (q, J=7.0 Hz, 2H), 1.45 (t, J=7.0 Hz, 3H). MS (ESI) 286 (M+H).

Step C. Example 452

The title compound was prepared according to methods described for the synthesis of Example 444 (Step B and C), substituting Intermediate 452B where appropriate: (4.0 mg, 6.0 μmol, 16% yield). $^1$H NMR (400 MHz, DMSO-$d_6$) δ 8.89 (s, 2H), 8.31 (s, 1H), 8.21 (d, J=9.3 Hz, 1H), 7.64 (dd, J=9.4, 2.6 Hz, 1H), 7.27 (br. s., 1H), 6.02 (d, J=16.4 Hz, 1H), 5.29 (d, J=16.4 Hz, 1H), 3.80 (s, 2H), 2.42-2.34 (m, 1H), 1.63-1.50 (m, 6H), 1.47-1.32 (m, 6H), 1.19 (dt, J=8.3, 3.1 Hz, 2H), 1.14-1.03 (m, 2H). FXR EC$_{50}$ (nM)=14. MS (ESI) 658 (M+H).

Example 456

2-(4-(2-(5-cyclopropyl-3-(2-(trifluoromethoxy)phenyl)isoxazol-4-yl)ethyl) bicyclo[2.2.2]octan-1-yl) benzo[d]thiazole-7-carboxylic acid

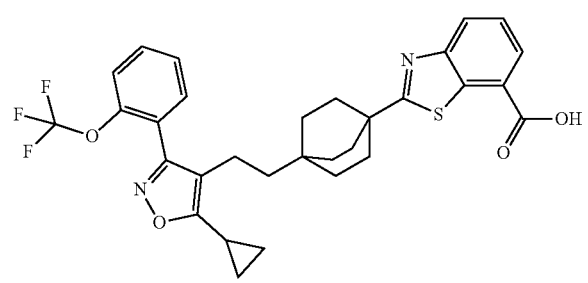

(456)

Step A. Intermediate 456A. Preparation of methyl 4-(2-(5-cyclopropyl-3-(2-(trifluoromethoxy)phenyl)isoxazol-4-yl)ethyl)bicyclo[2.2.2]octane-1-carboxylate

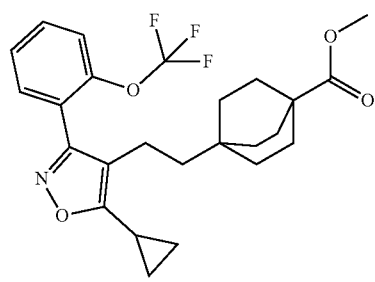 [SMILES: COC(=O)C12CCC(CCc3c(-c4ccccc4OC(F)(F)F)noc3C3CC3)(CC1)CC2]

A stirred solution of Intermediate 182B (140 mg, 0.30 mmol) in ethanol (2 mL) was degassed with nitrogen. To this mixture was added palladium on carbon (52 mg, 0.049 mmol) (10% wt. loading, matrix activated carbon support). The reaction was stirred under H$_2$ (1 atm, balloon). After 2 h, the mixture was diluted with methanol (10 mL) and filtered. The filtrate was concentrated and dried in vacuo to afford the title compound (140 mg, 0.29 mmol, 96% yield). MS (ESI) 464 (M+H).

Step B. Intermediate 456B. Preparation of 4-(2-(5-cyclopropyl-3-(2-(trifluoromethoxy) phenyl)isoxazol-4-yl)ethyl)bicyclo[2.2.2]octane-1-carboxylic acid

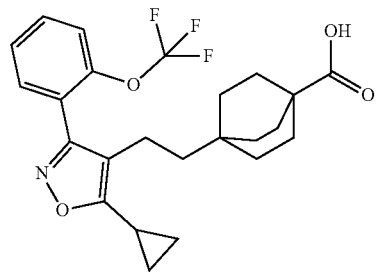 [SMILES: O=C(O)C12CCC(CCc3c(-c4ccccc4OC(F)(F)F)noc3C3CC3)(CC1)CC2]

The title compound was prepared according to methods described for the synthesis of Intermediate 159E, substituting Intermediate 456A where appropriate: (110 mg, 0.25 mmol, 76% yield). $^1$H NMR (400 MHz, DMSO-$d_6$) δ 12.00 (br. s, 1H), 7.66-7.70 (m, 1H), 7.54-7.58 (m, 3H), 2.20-2.30 (m, 2H), 2.10-2.20 (m, 1H), 1.70-1.81 (m, 6H), 1.17-1.25 (m, 6H), 1.06-1.10 (m, 4H), 0.97-1.04 (m, 2H). MS (ESI) 450 (M+H).

Step C. Example 456

The title compound was prepared according to methods described for the synthesis of Example 182 (Step D, E and F), substituting Intermediate 456B where appropriate: (8.5 mg, 0.015 mmol, 9% yield). $^1$H NMR (400 MHz, DMSO-$d_6$) δ 13.61 (s, 1H), 8.16 (d, J=7.8 Hz, 1H), 8.02 (d, J=7.3 Hz, 1H), 7.75-7.64 (m, 1H), 7.63-7.48 (m, 4H), 2.35-2.27 (m, 2H), 2.21-2.12 (m, 1H), 2.01-1.82 (m, 6H), 1.48-1.31 (m, 6H), 1.19-1.06 (m, 4H), 1.04-0.94 (m, 2H). FXR EC$_{50}$ (nM)=22. MS (ESI) 583 (M+H).

Example 464

3-((4-(((5-cyclopropyl-3-(3,5-dichloropyridin-4-yl) isoxazol-4-yl)methoxy)methyl) bicyclo[2.2.2]octan-1-yl)methoxy)-5-(trifluoromethyl)benzoic acid

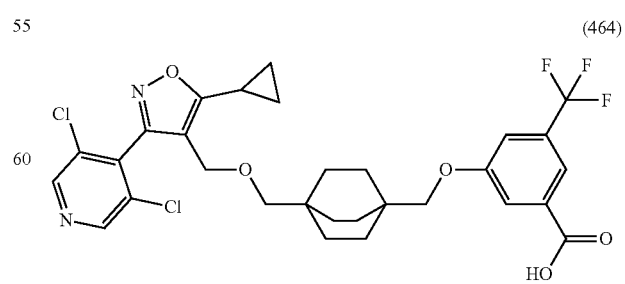

(464)

Step A. Intermediate 464A. Preparation of methyl 4-(((5-cyclopropyl-3-(3,5-dichloropyridin-4-yl)isoxazol-4-yl)methoxy)methyl)bicyclo[2.2.2]octane-1-carboxylate

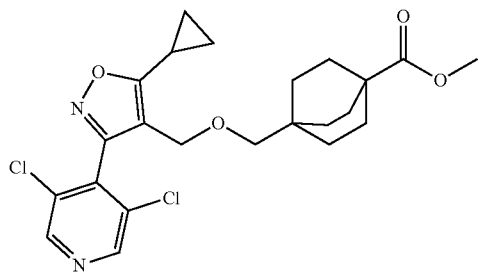 [SMILES: COC(=O)C12CCC(COCc3c(-c4c(Cl)cncc4Cl)noc3C3CC3)(CC1)CC2]

The title compound was prepared according to methods described for the synthesis of Intermediate 162A, substituting 4-(bromomethyl)-5-cyclopropyl-3-(3,5-dichloropyridin-4-yl)isoxazole where appropriate: (400 mg, 0.84 mmol, 56% yield) as a white solid. $^1$H NMR (400 MHz, DMSO-$d_6$) δ8.83 (s, 2H), 4.28 (s, 2H), 3.55 (s, 3H), 2.90 (s, 2H), 2.32 (s, 1H), 1.70-1.64 (m, 4H), 1.59-1.52 (m, 4H), 1.37-1.31 (m, 4H), 1.12-1.05 (m, 4H). MS (ESI) 465 (M+H).

Step B. Intermediate 464B. Preparation of (4-(((5-cyclopropyl-3-(3,5-dichloropyridin-4-yl)isoxazol-4-yl)methoxy)methyl)bicyclo[2.2.2]octan-1-yl)methanol

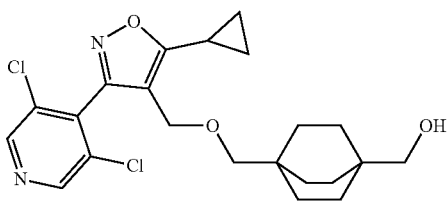 [SMILES: OCC12CCC(COCc3c(-c4c(Cl)cncc4Cl)noc3C3CC3)(CC1)CC2]

The title compound was prepared according to methods described for the synthesis of Intermediate 444A, substituting Intermediate 464A where appropriate: (100 mg, 0.21 mmol, 52% yield). $^1$H NMR (400 MHz, DMSO-$d_6$) δ8.82 (s, 2H), 4.28 (s, 2H), 4.24-4.21 (m, 1H), 2.96 (d, J=5.5 Hz, 2H), 2.87 (s, 2H), 1.54-1.51 (m, 1H), 1.37-1.35 (m, 2H), 1.17-1.2 (m, 10H), 1.06-1.01 (m, 4H). MS (ESI) 437 (M+H).

Step C. Example 464

The title compound was prepared according to methods described for the synthesis of Example 444 (Step B and C), by reaction of Intermediate 464B and methyl 3-hydroxy-5-(trifluoromethyl)benzoate: (3.9 mg, 6.2 μmol, 13% yield). $^1$H NMR (400 MHz, DMSO-$d_6$) δ 8.84 (s, 2H), 7.72 (s, 1H), 7.64 (s, 1H), 7.34 (s, 1H), 4.30 (s, 2H), 3.68 (s, 2H), 2.96 (s, 2H), 2.35-2.28 (m, 1H), 1.48-1.27 (m, 6H), 1.26-0.98 (m, 10H). FXR EC$_{50}$ (nM)=300. MS (ESI) 625 (M+H).

Example 467

(E)-3-(5-(4-(2-(5-cyclopropyl-3-(3,5-dichloropyridin-4-yl)isoxazol-4-yl)vinyl)-2-oxabicyclo[2.2.2]octan-1-yl)-1,2,4-oxadiazol-3-yl)benzoic acid

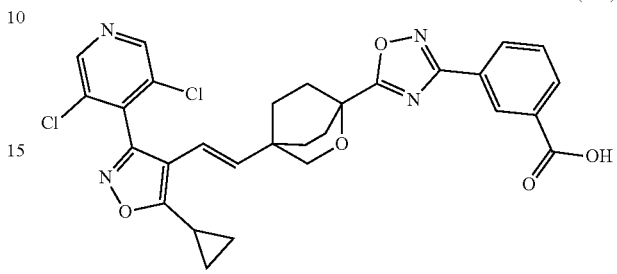

(467)

Step A. Intermediate 467A. Preparation of methyl 3-(5-(4-formyl-2-oxabicyclo[2.2.2]octan-1-yl)-1,2,4-oxadiazol-3-yl)benzoate

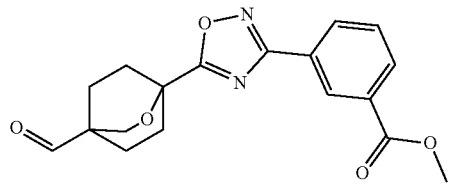 [SMILES: COC(=O)c1cccc(-c2noc(C34CCC(C=O)(CC3)CO4)n2)c1]

To a stirred solution of Intermediate 210D (110 mg, 0.32 mmol) in DCM (3 mL) was added DMP (200 mg, 0.48 mmol). After stirring 30 min, the reaction mixture was diluted with DCM (15 mL) and washed with 10% NaHCO$_3$ (aq.) (2×20 mL), brine, dried over Na$_2$SO$_4$, filtered and concentrated. The crude product was purified by flash column chromatography (12 g silica gel cartridge; A=PE, B=EtOAc; 15 min grad.; 0% B to 50% B; flow rate=12 mL/min). The pure fractions were combined, concentrated and dried in vacuo to provide the title compound (90 mg, 0.26 mmol, 82% yield) as a colorless solid. MS (ESI) 343 (M+H).

Step B. Intermediate 467B. Preparation of methyl (E)-3-(5-(4-(2-(5-cyclopropyl-3-(3,5-dichloropyridin-4-yl)isoxazol-4-yl)vinyl)-2-oxabicyclo[2.2.2]octan-1-yl)-1,2,4-oxadiazol-3-yl)benzoate

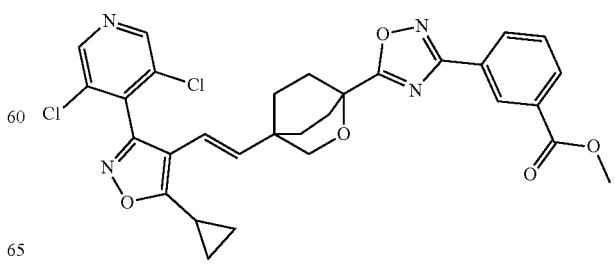

The title compound was prepared according to methods described for the synthesis of Intermediate 194H, by reaction of Intermediate 436A and Intermediate 467A: (25 mg, 0.042 mmol, 48% yield, brown solid). $^1$H NMR (400 MHz, DMSO-d$_6$) δ 9.51 (s, 1H), 8.53 (t, J=1.5 Hz, 1H), 8.28-8.26 (m, 1H), 8.18-8.16 (m, 1H), 7.76-7.73 (m, 1H), 4.02 (s, 2H), 3.91 (s, 3H), 2.38-2.32 (m, 2H), 2.25-2.18 (m, 2H), 2.00-1.93 (m, 4H). MS (ESI) 593 (M+H).

Step C. Example 467

The title compound was prepared according to methods described for the synthesis of Example 151 (Step C), substituting Intermediate 467B where appropriate: (5.0 mg, 8.6 μmol, 20% yield). $^1$H NMR (400 MHz, DMSO-d$_6$) δ 8.90 (s, 2H), 8.52 (s, 1H), 8.10 (d, J=7.6 Hz, 2H), 7.61 (t, J=7.7 Hz, 1H), 6.18 (d, J=16.6 Hz, 1H), 5.29 (d, J=16.6 Hz, 1H), 3.71 (s, 2H), 2.48-2.41 (m, 1H), 2.32-2.24 (m, 2H), 2.20-2.04 (m, 2H), 1.82-1.59 (m, 4H), 1.29-1.10 (m, 4H). FXR EC$_{50}$ (nM)=260. MS (ESI) 579 (M+H).

Example 468

(E)-3-((4-(2-(5-cyclopropyl-3-(3,5-dichloropyridin-4-yl)isoxazol-4-yl)vinyl)-2-oxabicyclo[2.2.2]octan-1-yl)methoxy)-5-(trifluoromethyl)benzoic acid

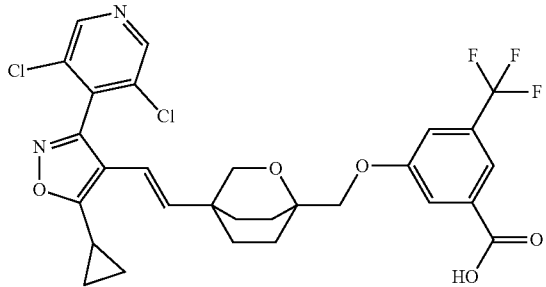

(468)

Step A. Intermediate 468A. Preparation of (1-(hydroxymethyl)-2-oxabicyclo[2.2.2]octan-4-yl)methyl 4-methylbenzenesulfonate

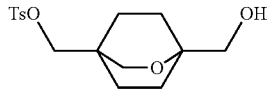

To a stirred solution of Intermediate 193D (6.0 g, 18 mmol) in THF (15 mL), was added borane dimethyl sulfide complex (5.0 mL, 53 mmol) at 0° C. The reaction mixture was slowly warmed to rt and stirred. After 2 h, the reaction was cooled to 0° C., quenched with MeOH and stirred at rt. After 2 h, the solvent was concentrated. The crude product was purified by flash column chromatography (12 g silica gel cartridge; A=PE, B=EtOAc; 15 min grad.; 0% B to 100% B; flow rate=12 mL/min). The pure fractions were combined, concentrated and dried in vacuo to provide the title compound (3.7 g, 11 mmol, 60% yield) as a white solid. $^1$H NMR (400 MHz, DMSO-d$_6$) δ 7.79 (d, J=8.0 Hz, 2H), 7.50 (d, J=8.0 Hz, 2H), 4.49 (t, J=6.0 Hz, 1H), 3.74 (s, 2H), 3.48 (s, 2H), 3.13 (d, J=6.00 Hz, 2H), 2.44 (s, 3H), 1.40-1.63 (m, 8H). MS (ESI) 344 (M+NH$_3$).

Step B. Intermediate 468B. Preparation of methyl 3-((4-((tosyloxy)methyl)-2-oxabicyclo[2.2.2]octan-1-yl)methoxy)-5-(trifluoromethyl)benzoate

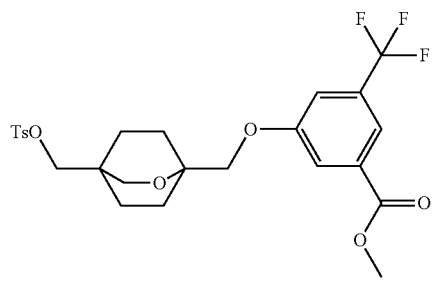 [SMILES: COC(=O)c1cc(OCC23CCC(COS(=O)(=O)c4ccc(C)cc4)(CC2)CO3)cc(C(F)(F)F)c1]

To a stirred solution of Intermediate 468A (200 mg, 0.61 mmol) in THF (6 mL) were added methyl 3-hydroxy-5-(trifluoromethyl)benzoate (160 mg, 0.74 mmol), triphenylphosphine (400 mg, 1.5 mmol) followed by diisopropyl azodicarboxylate (0.30 mL, 1.5 mmol). After stirring at reflux 1.5 h, the reaction was cooled and diluted with ethyl acetate (20 mL). The organic phase was washed with water (20 mL), brine, dried over Na$_2$SO$_4$, filtered and concentrated. The crude product was purified by flash column chromatography (40 g silica gel cartridge; A=PE, B=EtOAc; 15 min grad.; 0% B to 70% B; flow rate=40 mL/min). The pure fractions were combined, concentrated and dried in vacuo to provide the title compound (400 mg, 0.55 mmol, 90% yield) as a pink semisolid. MS (ESI) 546 (M+NH$_3$).

Step C. Intermediate 468C. Preparation of methyl 3-((4-(hydroxymethyl)-2-oxabicyclo[2.2.2]octan-1-yl)methoxy)-5-(trifluoromethyl)benzoate

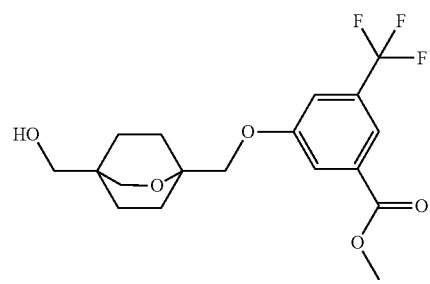 [SMILES: COC(=O)c1cc(OCC23CCC(CO)(CC2)CO3)cc(C(F)(F)F)c1]

The title compound was prepared according to methods described for the synthesis Intermediate 194E (Step D & E), substituting Intermediate 468B where appropriate: (70 mg, 0.19 mmol, 97% yield, white solid). $^1$H NMR (400 MHz, DMSO-d$_6$) δ 7.76 (s, 1H), 7.72 (s, 1H), 7.58 (s, 1H), 4.49 (s, 1H), 3.95 (s, 2H), 3.90 (s, 3H), 3.63 (s, 2H), 3.12 (d, J=4.80 Hz, 2H), 1.86-1.89 (m, 2H), 1.58-1.69 (m, 6H). MS (ESI) 392 (M+NH$_3$).

Step D. Intermediate 468D. Preparation of methyl 3-((4-formyl-2-oxabicyclo[2.2.2]octan-1-yl)methoxy)-5-(trifluoromethyl)benzoate

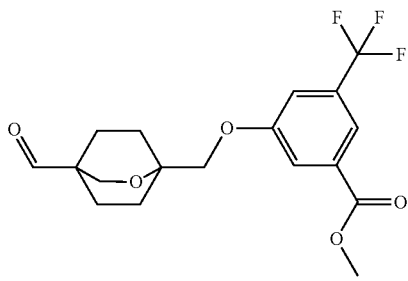 [SMILES: COC(=O)c1cc(OCC23CCC(C=O)(CC2)CO3)cc(C(F)(F)F)c1]

The title compound was prepared according to methods described for the synthesis Intermediate 194F, substituting Intermediate 468C where appropriate: (60 mg, 0.16 mmol, 80% yield, brown solid). $^1$H NMR (400 MHz, DMSO-$d_6$) δ 9.47 (s, 1H), 7.76 (s, 1H), 7.73 (s, 1H), 7.59 (s, 1H), 4.00 (s, 2H), 3.90 (s, 3H), 3.84 (s, 2H), 1.80-1.99 (m, 8H).

Step E. Example 468

The title compound was prepared according to methods described for the synthesis of Example 194 (Step H and I), by reaction of Intermediate 468D and Intermediate 436A: $^1$H NMR (400 MHz, METHANOL-$d_4$) δ 8.75 (s, 2H), 7.84 (s, 1H), 7.75 (s, 1H), 7.27 (s, 1H), 6.10 (d, J=16.6 Hz, 1H), 5.33 (d, J=16.6 Hz, 1H), 3.89 (s, 2H), 3.65 (s, 2H), 2.34-2.26 (m, 1H), 2.10-2.00 (m, 2H), 1.84-1.75 (m, 2H), 1.70 (d, J=9.0 Hz, 4H), 1.25-1.21 (m, 2H), 1.20-1.14 (m, 2H). FXR EC$_{50}$ (nM)=70. MS (ESI) 609 (M+H).

Example 471

6-((4-((5-cyclopropyl-3-(3,5-dichloropyridin-4-yl)isoxazol-4-yl)methoxy)-2-oxabicyclo[2.2.2]octan-1-yl)methoxy)-4-(difluoromethoxy)quinoline-2-carboxylic acid (471)

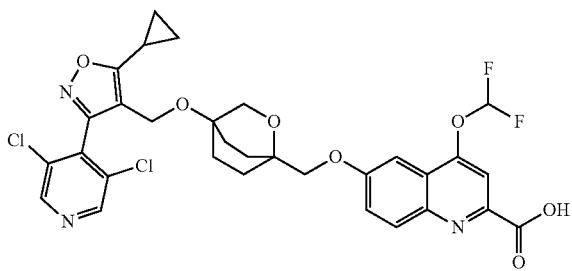

Step A. Intermediate 471A. Preparation of 4-((5-cyclopropyl-3-(3,5-dichloropyridin-4-yl)isoxazol-4-yl)methoxy)-2-oxabicyclo[2.2.2]octane-1-carboxylic acid

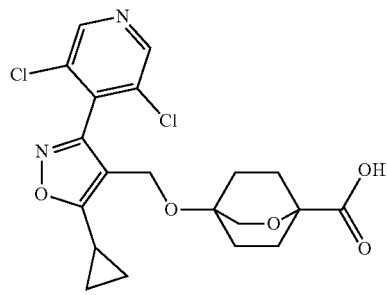 [SMILES: O=C(O)C12CCC(OCc3c(-c4c(Cl)cncc4Cl)noc3C3CC3)(CC1)CO2]

The title compound was prepared according to methods described for the synthesis of Intermediate 219C, substituting 4-(bromomethyl)-5-cyclopropyl-3-(3,5-dichloropyridin-4-yl)isoxazole where appropriate: (100 mg, 0.18 mmol, 56% yield) as colorless solid. MS (ESI) 439 (M+H).

Step B. Intermediate 471B. Preparation of (4-((5-cyclopropyl-3-(3,5-dichloropyridin-4-yl)isoxazol-4-yl)methoxy)-2-oxabicyclo[2.2.2]octan-1-yl)methanol

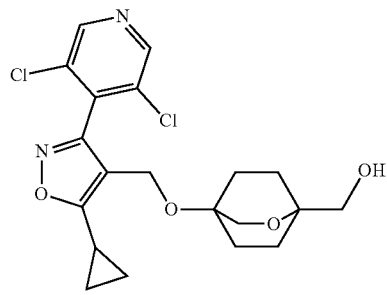 [SMILES: OCC12CCC(OCc3c(-c4c(Cl)cncc4Cl)noc3C3CC3)(CC1)CO2]

The title compound was prepared according to the method described for the synthesis of Intermediate 468A, substituting Intermediate 471A where appropriate: (50 mg, 0.099 mmol, 44% yield, colorless oil). MS (ESI) 425 (M+H).

Step C. Example 471

The title compound was prepared according to methods described for the synthesis of Example 444 (Step B and C), by reaction of Intermediate 471B and Intermediate 284B: (1.6 mg, 2.4 μmol, 4% yield). $^1$H NMR (400 MHz, DMSO-$d_6$) δ 8.86 (s, 2H), 8.08 (d, J=9.60 Hz, 1H), 7.77-7.97 (m, 2H), 7.57 (d, J=11.60 Hz, 1H), 7.35 (s, 1H), 4.31 (s, 2H), 3.95 (s, 2H), 2.34-2.35 (m, 1H), 1.91-1.94 (m, 2H), 1.69-1.77 (m, 4H), 1.42-1.46 (m, 2H), 1.09-1.18 (m, 4H). FXR EC$_{50}$ (nM)=200. MS (ESI) 662 (M+H).

Example 472

(E)-6-((1-(2-(5-cyclopropyl-3-(3,5-dichloropyridin-4-yl)isoxazol-4-yl)vinyl)-2-oxabicyclo[2.2.2]octan-4-yl)methoxy)-4-(difluoromethoxy)quinoline-2-carboxylic acid (472)

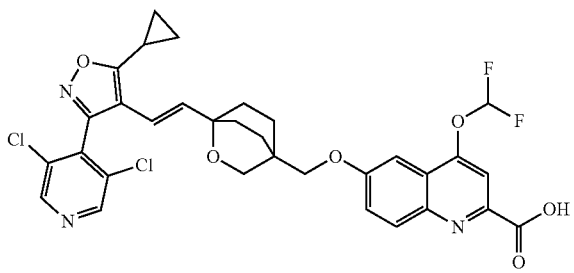

Step A. Intermediate 472A. Preparation of (1-formyl-2-oxabicyclo[2.2.2]octan-4-yl)methyl 4-methylbenzenesulfonate

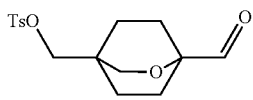

To a stirred solution of oxalyl chloride (0.67 mL, 7.7 mmol) in DCM (10 mL) was added DMSO (0.54 mL, 7.7 mmol) in DCM (5 mL) at −78° C. After stirring at this temperature for 15 min, Intermediate 468A (1.0 g, 3.1 mmol) in DCM (10 mL) was added and the reaction was stirred at −78° C. After 3 h at this temperature, TEA (3.0 mL, 22 mmol) was added and the reaction was warmed to rt and stirred. After 2 h, the mixture was diluted with DCM (35 mL) and washed with 10% NaHCO$_3$ solution (aq.) (2×35 mL), brine, dried over Na$_2$SO$_4$, filtered and concentrated. The crude product was purified by flash column chromatography (80 g silica gel cartridge; A=PE, B=EtOAc; 15 min grad.; 0% B to 70% B; flow rate=60 mL/min). The pure fractions were combined, concentrated and dried in vacuo to provide the title compound (800 mg, 2.5 mmol, 80% yield) as a white solid. $^1$H NMR (400 MHz, DMSO-d$_6$) δ 9.48 (s, 1H), 7.79 (d, J=6.80 Hz, 2H), 7.50 (d, J=8.40 Hz, 2H), 3.78 (s, 2H), 3.62 (s, 2H), 2.44 (s, 3H), 1.67-1.79 (m, 4H), 1.51-1.57 (m, 4H).

Step B. Intermediate 472B. Preparation of (E)-(1-(2-(5-cyclopropyl-3-(3,5-dichloropyridin-4-yl)isoxazol-4-yl)vinyl)-2-oxabicyclo[2.2.2]octan-4-yl)methyl 4-methylbenzenesulfonate

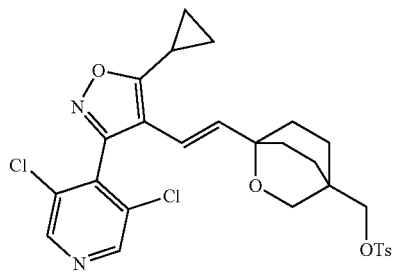 [SMILES: Cc1ccc(S(=O)(=O)OCC23CCC(/C=C/c4c(-c5c(Cl)cncc5Cl)noc4C4CC4)(CC2)OC3)cc1]

The title compound was prepared according to methods described for the synthesis of Intermediate 194H, by reaction of Intermediate 436A and Intermediate 472A: (600 mg, 1.0 mmol, 48% yield) as a brown semisolid. $^1$H NMR (400 MHz, DMSO-d$_6$) δ 8.87 (s, 2H), 7.85-7.70 (m, J=8.3 Hz, 2H), 7.55-7.38 (m, J=8.1 Hz, 2H), 6.18 (d, J=16.4 Hz, 1H), 5.32 (d, J=16.4 Hz, 1H), 3.72 (s, 2H), 3.51 (s, 2H), 2.43 (s, 3H), 2.39-2.26 (m, 1H), 1.65-1.35 (m, 8H), 1.24-1.15 (m, 2H), 1.14-1.01 (m, 2H). MS (ESI) 575 (M+H).

Step C. Intermediate 472C. Preparation of (E)-(1-(2-(5-cyclopropyl-3-(3,5-dichloropyridin-4-yl)isoxazol-4-yl)vinyl)-2-oxabicyclo[2.2.2]octan-4-yl)methanol

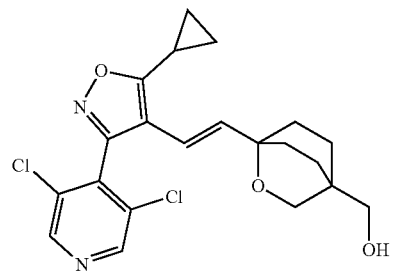 [SMILES: OCC12CCC(/C=C/c3c(-c4c(Cl)cncc4Cl)noc3C3CC3)(CC1)OC2]

The title compound was prepared according to methods described for the synthesis Intermediate 194E (Step D & E), substituting Intermediate 472D where appropriate: (330 mg, 0.78 mmol, 72% yield, white solid). MS (ESI) 421 (M+H).

Step D. Example 472

The title compound was prepared according to methods described for the synthesis of Example 444 (Step B and C), by reaction of Intermediate 472C and Intermediate 284B: $^1$H NMR (400 MHz, DMSO-d$_6$) δ 8.90 (s, 2H), 8.00 (d, J=9.3 Hz, 1H), 7.85-7.45 (m, 2H), 77.43 (dd, J=9.5, 2.9 Hz, 1H), 7.27 (d, J=2.9 Hz, 1H), 6.25 (d, J=16.4 Hz, 1H), 5.40 (d, J=16.4 Hz, 1H), 3.82 (s, 2H), 3.79 (s, 2H), 2.41-2.37 (m, 1H), 1.76 (d, J=5.4 Hz, 2H), 1.67 (br s, 6H), 1.33-1.17 (m, 2H), 1.14-1.10 (m, 2H). FXR EC$_{50}$ (nM)=290. MS (ESI) 658 (M+H).

Example 478

(E)-3-(5-(4-(2-(5-cyclopropyl-3-(3,5-dichloropyridin-4-yl)isoxazol-4-yl)vinyl)-2-oxabicyclo[2.2.2]octan-1-yl)-1,2,4-oxadiazol-3-yl)-5-(trifluoromethyl)benzoic acid

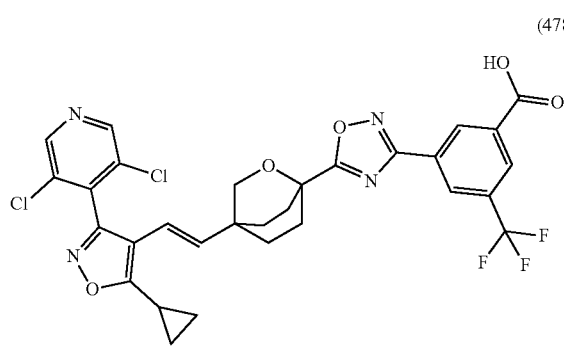

Step A. Intermediate 478A. Preparation of (1-(hydroxymethyl)-2-oxabicyclo[2.2.2]octan-4-yl)methyl acetate

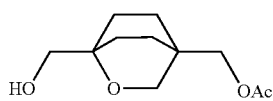

The title compound was prepared according to methods described for the synthesis of Intermediate 194D, substituting Intermediate 468A where appropriate: (1.3 g, 6.1 mmol, 99% yield, brown semisolid). $^1$H NMR (400 MHz, DMSO-$d_6$) δ4.48 (t, J=6.0 Hz, 1H), 3.73 (s, 2H), 3.58 (s, 2H), 3.15 (d, J=6.0 Hz, 2H), 2.01 (s, 3H), 1.66-1.46 (m, 8H).

Step B. Intermediate 478B. Preparation of (1-((tosyloxy)methyl)-2-oxabicyclo[2.2.2]octan-4-yl)methyl acetate

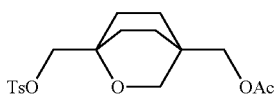 [SMILES: CC(=O)OCC12CCC(COS(=O)(=O)c3ccc(C)cc3)(CC1)OC2]

To a stirred solution of Intermediate 478A (1.3 g, 6.1 mmol) in pyridine (15 mL) was added p-toluenesulfonyl chloride (1.4 g, 7.3 mmol) at 0° C. The reaction was warmed to rt and stirred. After 18 h, the reaction mixture was diluted with water (100 mL) and extracted with ethyl acetate (2×50 mL). The organic layer was combined, washed with 1.5 N HCl (aq.) (3×50 mL), brine, dried over Na$_2$SO$_4$, filtered and concentrated. The crude product was purified by flash column chromatography (80 g silica gel cartridge; A=PE, B=EtOAc; 15 min grad.; 0% B to 70% B; flow rate=60 mL/min). The pure fractions were combined, concentrated and dried in vacuo to provide the title compound (1.5 g, 3.5 mmol, 58% yield) as a brown solid. $^1$H NMR (400 MHz, DMSO-$d_6$) δ7.76 (d, J=8.5 Hz, 2H), 7.47 (d, J=8.0 Hz, 2H), 3.78 (s, 2H), 3.71 (s, 2H), 3.54 (s, 2H), 2.42 (s, 3H), 1.99 (s, 3H), 1.68-1.43 (m, 8H). MS (ESI) 369 (M+H).

Step C. Intermediate 478C. Preparation of (4-(hydroxymethyl)-2-oxabicyclo[2.2.2]octan-1-yl)methyl 4-methylbenzenesulfonate

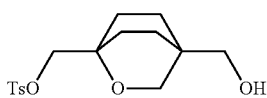 [SMILES: Cc1ccc(S(=O)(=O)OCC23CCC(CO)(CC2)CO3)cc1]

The title compound was prepared according to methods described for the synthesis of Intermediate 194E, substituting Intermediate 478B where appropriate: (1.2 g, 3.6 mmol, 67% yield, white solid). $^1$H NMR (400 MHz, DMSO-$d_6$) δ7.80-7.75 (m, 2H), 7.49 (d, J=8.0 Hz, 2H), 4.47 (t, J=5.3 Hz, 1H), 3.77 (s, 2H), 3.53 (s, 2H), 3.07 (d, J=5.0 Hz, 2H), 2.43 (s, 3H), 1.68-1.59 (m, 2H), 1.52-1.34 (m, 6H). MS (ESI) 327 (M+H).

Step D. Intermediate 478D. Preparation of (4-formyl-2-oxabicyclo[2.2.2]octan-1-yl)methyl 4-methylbenzenesulfonate

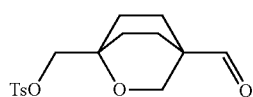

The title compound was prepared according to the method described for the synthesis of Intermediate 472A, substituting Intermediate 478C where appropriate: (60 mg, 0.19 mmol, 86% yield, white solid). $^1$H NMR (400 MHz, DMSO-$d_6$) δ9.41 (s, 1H), 7.80-7.77 (m, 2H), 7.49 (d, J=8.0 Hz, 2H), 3.82 (s, 2H), 3.74 (s, 2H), 2.43 (s, 3H), 1.78-1.70 (m, 5H), 1.59-1.51 (m, 3H). MS (ESI) 325 (M+H).

Step E. Intermediate 478E. Preparation of (E)-(4-(2-(5-cyclopropyl-3-(3,5-dichloropyridin-4-yl)isoxazol-4-yl)vinyl)-2-oxabicyclo[2.2.2]octan-1-yl)methyl 4-methylbenzenesulfonate

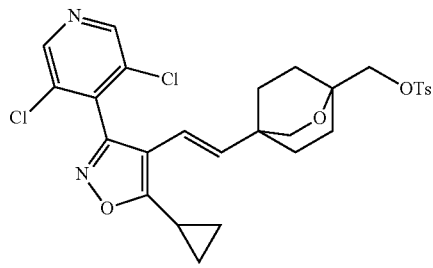 [SMILES: Cc1ccc(S(=O)(=O)OCC23CCC(/C=C/c4c(-c5c(Cl)cncc5Cl)noc4C4CC4)(CC2)CO3)cc1]

The title compound was prepared according to methods described for the synthesis of Intermediate 194H, by reaction of Intermediate 478D and Intermediate 436A: (70 mg, 0.12 mmol, 56% yield). MS (ESI) 575 (M+H).

Step F. Intermediate 478F. Preparation of (E)-(4-(2-(5-cyclopropyl-3-(3,5-dichloropyridin-4-yl)isoxazol-4-yl)vinyl)-2-oxabicyclo[2.2.2]octan-1-yl)methanol

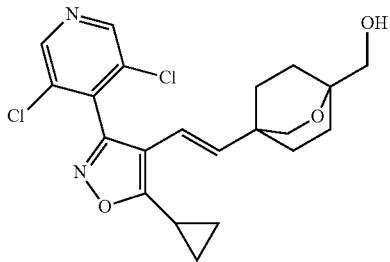 [SMILES: OCC12CCC(/C=C/c3c(-c4c(Cl)cncc4Cl)noc3C3CC3)(CC1)CO2]

The title compound was prepared according to methods described for the synthesis Intermediate 194E (Step D & E), substituting Intermediate 478E where appropriate: (340 mg, 0.80 mmol, 67% yield). $^1$H NMR (400 MHz, DMSO-$d_6$) δ 8.87 (s, 2H), 6.05 (d, J=16.6 Hz, 1H), 5.17 (d, J=16.6 Hz, 1H), 4.46 (t, J=6.0 Hz, 1H), 3.44 (s, 2H), 3.12 (d, J=6.0 Hz, 2H), 2.33-2.31 (m, 1H), 1.63-1.58 (m, 2H), 1.53-1.43 (m, 6H), 1.19-1.14 (m, 2H), 1.11-1.06 (m, 2H). MS (ESI) 421 (M+H).

Step G. Intermediate 478G. Preparation of (E)-4-(2-(5-cyclopropyl-3-(3,5-dichloropyridin-4-yl)isoxazol-4-yl)vinyl)-2-oxabicyclo[2.2.2]octane-1-carboxylic acid

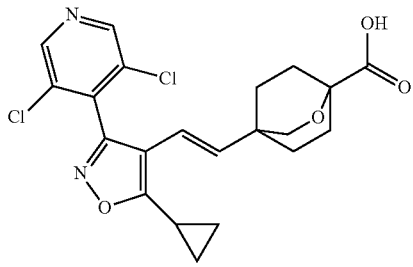 [SMILES: O=C(O)C12CCC(/C=C/c3c(-c4c(Cl)cncc4Cl)noc3C3CC3)(CC1)CO2]

To a stirred solution of Intermediate 478F (150 mg, 0.36 mmol) in DMF (3 mL) was added PDC (400 mg, 1.1 mmol) at 0° C. The reaction was warmed to 40° C. and stirred. After 3 h, the mixture was diluted with water (50 mL) and extracted with ethyl acetate (5×30 mL). The organic layer was combined, dried over $Na_2SO_4$, filtered and concentrated. The crude product was purified by flash column chromatography (24 g silica gel cartridge; A=PE, B=EtOAc; 15 min grad.; 0% B to 100% B; flow rate=24 mL/min). The pure fractions were combined, concentrated and dried in vacuo to provide the title compound (60 mg, 0.087 mmol, 24% yield) as a brown solid. $^1$H NMR (400 MHz, DMSO-$d_6$) δ12.42 (bs, 1H), 8.88 (s, 2H), 6.08 (d, J=16.6 Hz, 1H), 5.18 (d, J=16.6 Hz, 1H), 3.52 (s, 2H), 2.43-2.38 (m, 1H), 1.93-1.79 (m, 2H), 1.56-1.52 (m, 6H), 1.22-1.08 (m, 4H). MS (ESI) 435 (M+H).

Step H. Example 478

The title compound was prepared according to methods described for the synthesis of Example 64 (Step C), by reaction of Intermediate 478G and Intermediate 235A: (5.2 mg, 7.9 μmol, 21% yield). $^1$H NMR (400 MHz, DMSO-$d_6$) δ 8.90 (s, 2H), 8.75 (s, 1H), 8.44 (s, 1H), 8.37 (s, 1H), 6.19 (d, J=16.6 Hz, 1H), 5.28 (d, J=16.6 Hz, 1H), 3.72 (s, 2H), 2.48-2.43 (m, 1H), 2.29 (br s, 2H), 2.18 (d, J=11.5 Hz, 2H), 1.80-1.64 (m, 4H), 1.30-1.18 (m, 2H), 1.16-1.10 (m, 2H). FXR $EC_{50}$ (nM)=120. MS (ESI) 647 (M+H).

The following Examples in Table 8 were prepared according to methods described elsewhere herein using appropriate starting materials, reagents and conditions.

TABLE 8

| Ex. No. | Structure & Name | $^1$H NMR, FXR $EC_{50}$ & MS (ESI) | Method |
|---|---|---|---|
| 432 | 2-(4-((5-cyclopropyl-3-(3,5-dichloropyridin-4-yl)isoxazol-4-yl)methoxy)bicyclo[2.2.2]octan-1-yl)benzo[d]thiazole-7-carboxylic acid | $^1$H NMR (400 MHz, CHLOROFORM-d) δ 8.64 (s, 2H), 8.17 (dd, J = 15.6, 7.5 Hz, 2H), 7.56 (t, J = 7.8 Hz, 1H), 4.27 (s, 2H), 2.14 (d, J = 8.0 Hz, 7H), 1.70-1.55 (m, 6H), 1.31-1.12 (m, 2H), 1.33-1.07 (m, 2H). FXR $EC_{50}$ (nM) = 23. MS (ESI) 570 (M + H). | Ex. 168 |

TABLE 8-continued

| Ex. No. | Structure & Name | ¹H NMR, FXR EC$_{50}$ & MS (ESI) | Method |
|---|---|---|---|
| 433 | 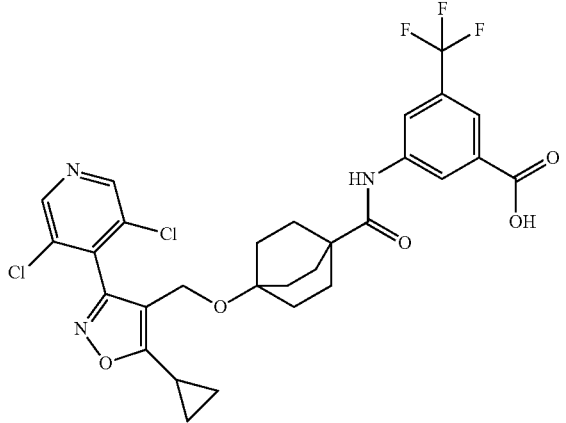 [SMILES: O=C(O)c1cc(NC(=O)C23CCC(OCc4c(-c5c(Cl)cncc5Cl)noc4C4CC4)(CC2)CC3)cc(C(F)(F)F)c1]<br>3-(4-((5-cyclopropyl-3-(3,5-dichloropyridin-4-yl)isoxazol-4-yl)methoxy)bicyclo[2.2.2]octane-1-carboxamido)-5-(trifluoromethyl)benzoic acid | ¹H NMR (400 MHz, DMSO-d$_6$) δ 9.51 (s, 1H), 8.85 (s, 2H), 8.28 (s, 1H), 8.19 (s, 1H), 7.78 (s, 1H), 4.24 (s, 2H), 2.34-2.29 (m, 1H), 1.89-1.76 (m, 6H), 1.44-1.31 (m, 6H), 1.18-1.08 (m, 4H). FXR EC$_{50}$ (nM) = 1300. MS (ESI) 624 (M + H). | Ex. 170 |
| 434 | 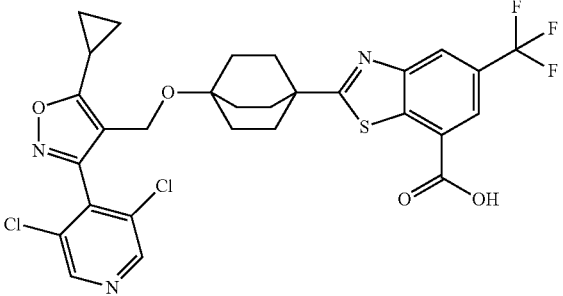 [SMILES: O=C(O)c1cc(C(F)(F)F)cc2nc(C34CCC(OCc5c(-c6c(Cl)cncc6Cl)noc5C5CC5)(CC3)CC4)sc12]<br>2-(4-((5-cyclopropyl-3-(3,5-dichloropyridin-4-yl)isoxazol-4-yl)methoxy)bicyclo[2.2.2]octan-1-yl)-5-(trifluoromethyl)benzo[d]thiazole-7-carboxylic acid | ¹H NMR (400 MHz, DMSO-d$_6$) δ 8.85 (s, 2H), 8.53 (s, 1H), 8.18 (s, 1H), 4.28 (s, 2H), 2.35-2.32 (m, 1H), 2.06 (d, J = 7.1 Hz, 6H), 1.54 (br. s., 6H), 1.21-1.06 (m, 4H). FXR EC$_{50}$ (nM) = 18. MS (ESI) 638 (M + H). | Ex. 168 |
| 437 | 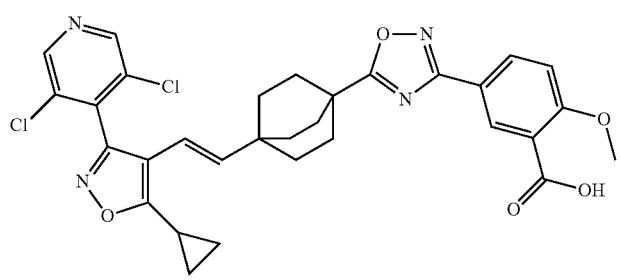<br>(E)-5-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-2-methoxybenzoic acid | ¹H NMR (400 MHz, DMSO-d$_6$) δ 8.89 (s, 2H), 8.07 (d, J = 2.4 Hz, 1H), 7.95 (dd, J = 8.7, 2.1 Hz, 1H), 7.18 (d, J = 9.0 Hz, 1H), 6.07 (d, J = 16.6 Hz, 1H), 5.32 (d, J = 16.4 Hz, 1H), 3.85 (s, 3H), 2.47-2.36 (m, 1H), 2.05-1.86 (m, 6H), 1.59-1.39 (m, 6H), 1.23-1.05 (m, 4H). FXR EC$_{50}$ (nM) = 23. MS (ESI) 607 (M + H). | Ex. 436 |

TABLE 8-continued

| Ex. No. | Structure & Name | $^1$H NMR, FXR EC$_{50}$ & MS (ESI) | Method |
|---|---|---|---|
| 438 | 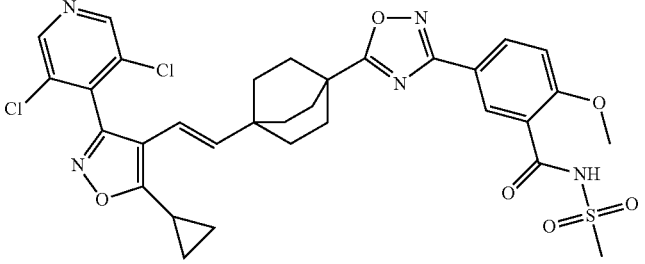 [SMILES: COc1ccc(-c2noc(C34CCC(/C=C/c5c(-c6c(Cl)cncc6Cl)noc5C5CC5)(CC3)CC4)n2)cc1C(=O)NS(C)(=O)=O]<br>(E)-5-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-2-methoxy-N-(methylsulfonyl)benzamide | $^1$H NMR (400 MHz, DMSO-d$_6$) δ 11.76 (br. s., 1H), 8.89 (s, 2H), 8.21-7.99 (m, 2H), 7.33 (d, J = 9.0 Hz, 1H), 6.07 (d, J = 16.4 Hz, 1H), 5.32 (d, J = 16.4 Hz, 1H), 3.94 (s, 3H), 3.37 (s, 3H), 2.46-2.36 (m, 1H), 2.08-1.83 (m, 6H), 1.63-1.39 (m, 6H), 1.25-1.05 (m, 4H). FXR EC$_{50}$ (nM) = 33. MS (ESI) 684 (M + H). | Ex. 3 |
| 439 | 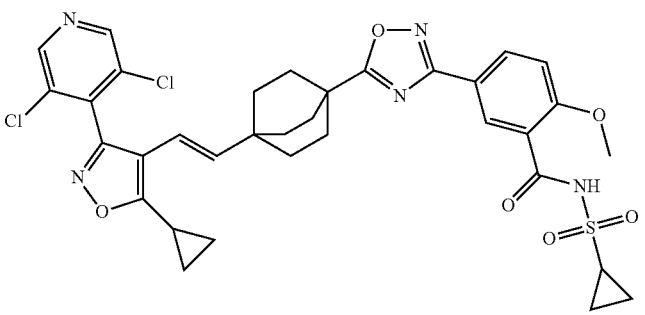 [SMILES: COc1ccc(-c2noc(C34CCC(/C=C/c5c(-c6c(Cl)cncc6Cl)noc5C5CC5)(CC3)CC4)n2)cc1C(=O)NS(=O)(=O)C1CC1]<br>(E)-5-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-N-(cyclopropylsulfonyl)-2-methoxybenzamide | $^1$H NMR (400 MHz, DMSO-d$_6$) δ 11.71 (br. s., 1H), 8.89 (s, 2H), 8.11 (d, J = 8.6 Hz, 1H), 8.06 (d, J = 1.7 Hz, 1H), 7.33 (d, J = 9.0 Hz, 1H), 6.07 (d, J = 16.6 Hz, 1H), 5.32 (d, J = 16.4 Hz, 1H), 3.94 (s, 3H), 3.10 (br. s., 1H), 2.42-2.39 (m, 1H), 2.04-1.87 (m, 6H), 1.62-1.39 (m, 6H), 1.37-1.07 (m, 8H). FXR EC$_{50}$ (nM) = 280. MS (ESI) 710 (M + H) | Ex. 3 |
| 440 | 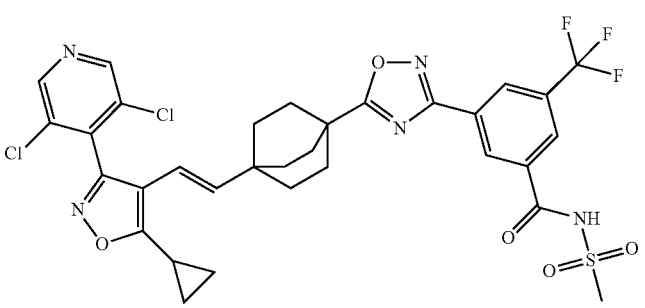 [SMILES: CS(=O)(=O)NC(=O)c1cc(-c2noc(C34CCC(/C=C/c5c(-c6c(Cl)cncc6Cl)noc5C5CC5)(CC3)CC4)n2)cc(C(F)(F)F)c1]<br>(E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-N-(methylsulfonyl)-5-(trifluoromethyl)benzamide | $^1$H NMR (400 MHz, DMSO-d$_6$) δ 8.89 (s, 2H), 8.79 (s, 1H), 8.43 (s, 1H), 8.31 (s, 1H), 6.07 (d, J = 16.4 Hz, 1H), 5.32 (d, J = 16.4 Hz, 1H), 3.11 (s, 3H), 2.43-2.37 (m, 1H), 2.06-1.92 (m, 6H), 1.59-1.41 (m, 6H), 1.35-1.06 (m, 4H). FXR EC$_{50}$ (nM) = 400. MS (ESI) 722 (M + H). | Ex. 3 |
| 441 | 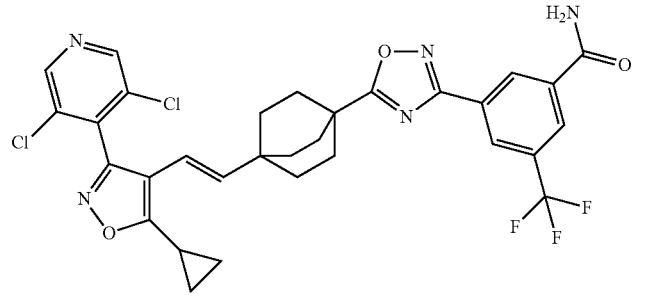 [SMILES: NC(=O)c1cc(-c2noc(C34CCC(/C=C/c5c(-c6c(Cl)cncc6Cl)noc5C5CC5)(CC3)CC4)n2)cc(C(F)(F)F)c1] | $^1$H NMR (400 MHz, DMSO-d$_6$) δ 8.90 (s, 2H), 8.75 (s, 1H), 8.44 (br. s., 2H), 8.34 (s, 1H), 7.78 (s, 1H), 6.08 (d, J = 16.6 Hz, 1H), 5.32 (d, J = 16.6 Hz, 1H), 2.43-2.39 (m, 1H), 2.09-1.88 (m, 6H), 1.60-1.40 (m, 6H), 1.23-1.07 (m, 4H). FXR EC$_{50}$ (nM) = 150. MS (ESI) 644 (M + H). | Ex. 435 |

TABLE 8-continued

| Ex. No. | Structure & Name | ¹H NMR, FXR EC$_{50}$ & MS (ESI) | Method |
|---|---|---|---|
| | (E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-5-(trifluoromethyl)benzamide | | |
| 442 | (E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-5-fluorobenzoic acid | ¹H NMR (400 MHz, DMSO-d$_6$) δ 8.90 (s, 2H), 8.35 (s, 1H), 7.86 (s, 2H), 6.08 (d, J = 16.4 Hz, 1H), 5.31 (d, J = 16.6 Hz, 1H), 2.08 (s, 1H), 2.04-1.94 (m, 6H), 1.51-1.44 (m, 6H), 1.21-1.18 (m, 2H), 1.13-1.09 (m, 2H). FXR EC$_{50}$ (nM) = 79. MS (ESI) 595 (M + H). | Ex. 436 |
| 445 | (E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-N-(methylsulfonyl)-5-(trifluoromethyl)benzamide | ¹H NMR (400 MHz, DMSO-d$_6$) δ 8.90 (s, 2H), 8.41 (s, 1H), 7.91 (s, 1H), 7.88 (s, 1H), 7.39 (t, J = 73.2 Hz, 1H), 6.08 (d, J = 16.9 Hz, 1H), 5.32 (d, J = 16.6 Hz, 1H), 3.26 (s, 3H), 2.44-2.37 (m, 1H), 2.08-1.89 (m, 6H), 1.61-1.43 (m, 6H), 1.25 (br s, 2H), 1.12 (d, J = 2.4 Hz, 2H). FXR EC$_{50}$ (nM) = 220. MS (ESI) 720 (M + H) | Ex. 3 |
| 447 | (E)-4-((4-(2-(5-cyclopropyl-3-(3,5-dichloropyridin-4-yl)isoxazol-4-yl)vinyl)bicyclo[2.2.2]octan-1-yl)methoxy)-8-fluoro-2-methylquinoline-6-carboxylic acid | ¹H NMR (400 MHz, DMSO-d$_6$) δ 13.38 (br. s., 1H), 8.88 (s, 2H), 8.50 (d, J = 1.2 Hz, 1H), 7.87 (dd, J = 11.4, 1.8 Hz, 1H), 7.12 (s, 1H), 6.04 (d, J = 16.6 Hz, 1H), 5.32 (d, J = 16.4 Hz, 1H), 3.92 (s, 2H), 2.64 (s, 3H), 2.42-2.35 (m, 1H), 1.70-1.52 (m, 6H), 1.51-1.33 (m, 6H), 1.22-1.05 (m, 4H). FXR EC$_{50}$ (nM) = 2400. MS (ESI) 622 (M + H). | Ex. 444 |

TABLE 8-continued

| Ex. No. | Structure & Name | $^1$H NMR, FXR EC$_{50}$ & MS (ESI) | Method |
|---|---|---|---|
| 448 | 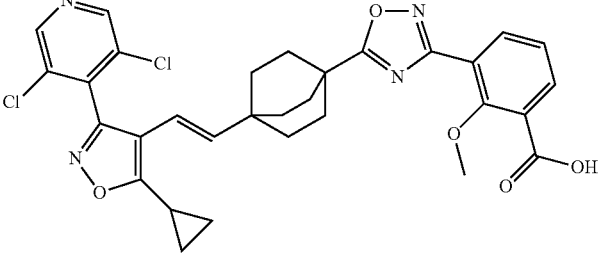<br>(E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-2-methoxybenzoic acid | $^1$H NMR (400 MHz, DMSO-d$_6$) δ 8.89 (s, 2H), 7.72 (d, J = 7.6 Hz, 1H), 7.56 (d, J = 7.6 Hz, 1H), 7.17 (t, J = 7.7 Hz, 1H), 6.07 (d, J = 16.6 Hz, 1H), 5.32 (d, J = 16.6 Hz, 1H), 3.79 (s, 3H), 2.45-2.39 (m, 1H), 2.02-1.91 (m, 6H), 1.62-1.40 (m, 6H), 1.23-1.02 (m, 4H). FXR EC$_{50}$ (nM) = 10. MS (ESI) 607 (M + H). | Ex. 436 |
| 449 | 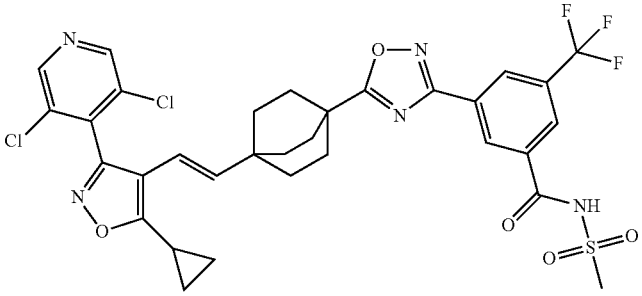<br>(E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)-N-(methylsulfonyl)-5-(trifluoromethyl)benzamide | $^1$H NMR (400 MHz, DMSO-d$_6$) δ 12.24 (br s, 1H), 8.94-8.84 (m, 2H), 7.97 (d, J = 6.6 Hz, 1H), 7.68 (d, J = 6.1 Hz, 1H), 7.36 (t, J = 7.7 Hz, 1H), 6.07 (d, J = 16.6 Hz, 1H), 5.32 (d, J = 16.6 Hz, 1H), 3.77 (s, 3H), 3.34 (s, 3H), 2.44-2.38 (m, 1H), 2.04-1.93 (m, 6H), 1.55-1.41 (m, 6H), 1.28-1.15 (m, 2H), 1.14-1.07 (m, 2H). FXR EC$_{50}$ (nM) = 16. MS (ESI) 684 (M + H). | Ex. 3 |
| 450 | 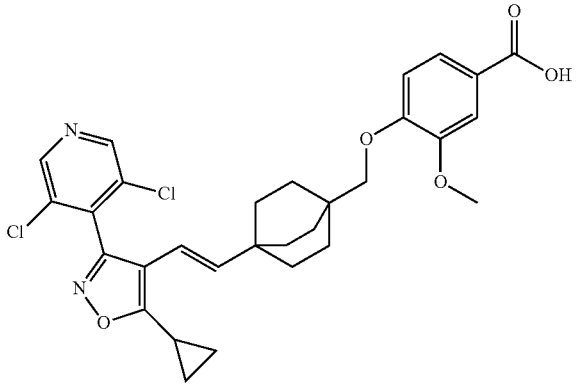 [SMILES: COc1cc(C(=O)O)ccc1OCC12CCC(/C=C/c3c(-c4c(Cl)cncc4Cl)noc3C3CC3)(CC1)CC2]<br>(E)-4-((4-(2-(5-cyclopropyl-3-(3,5-dichloropyridin-4-yl)isoxazol-4-yl)vinyl)bicyclo[2.2.2]octan-1-yl)methoxy)-3-methoxybenzoic acid | $^1$H NMR (400 MHz, DMSO-d$_6$) δ 12.61 (br. s., 1H), 8.88 (s, 2H), 7.54 (dd, J = 8.4, 2.1 Hz, 1H), 7.39 (d, J = 2.0 Hz, 1H), 7.03 (d, J = 8.6 Hz, 1H), 6.01 (d, J = 16.4 Hz, 1H), 5.28 (d, J = 16.4 Hz, 1H), 3.83 (s, 3H), 3.60 (s, 2H), 2.41-2.33 (m, 1H), 1.58-1.44 (m, 6H), 1.42-1.30 (m, 6H), 1.22-1.14 (m, 2H), 1.14-1.03 (m, 2H). FXR EC$_{50}$ (nM) = 18. MS (ESI) 569 (M + H). | Ex. 444 |

| Ex. No. | Structure & Name | ¹H NMR, FXR EC$_{50}$ & MS (ESI) | Method |
|---|---|---|---|
| 451 | 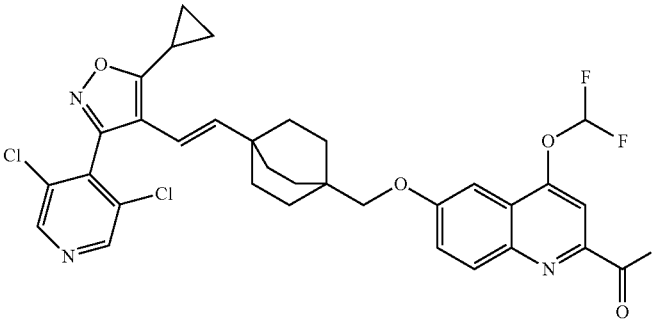<br>(E)-6-((4-(2-(5-cyclopropyl-3-(3,5-dichloropyridin-4-yl)isoxazol-4-yl)vinyl)bicyclo[2.2.2]octan-1-yl)methoxy)-4-(difluoromethoxy)quinoline-2-carboxylic acid | ¹H NMR (400 MHz, DMSO-d$_6$) δ 8.89 (s, 2H), 8.09 (d, J = 9.0 Hz, 1H), 7.88-7.69 (m, 1H), 7.76 (t, J = 72.0 Hz, 1H), 7.56 (dd, J = 9.2, 2.8 Hz, 1H), 7.35 (d, J = 2.9 Hz, 1H), 6.02 (d, J = 16.6 Hz, 1H), 5.29 (d, J = 16.6 Hz, 1H), 3.80 (s, 2H), 2.42-2.35 (m, 1H), 1.66-1.51 (m, 6H), 1.47-1.34 (m, 6H), 1.27-1.15 (m, 2H), 1.14-1.05 (m, 2H). FXR EC$_{50}$ (nM) = 35. MS (ESI) 656 (M + H). | Ex. 444 |
| 454 | 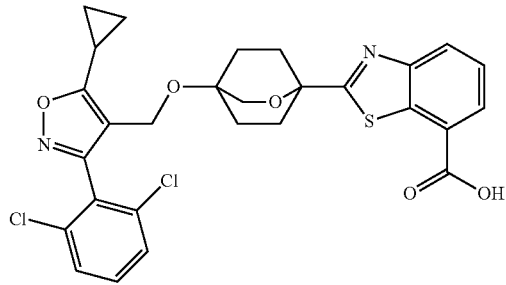 [SMILES: O=C(O)c1cccc2nc(C34CCC(OCc5c(-c6c(Cl)cccc6Cl)noc5C5CC5)(CC3)CO4)sc12]<br>2-(4-((5-cyclopropyl-3-(2,6-dichlorophenyl)isoxazol-4-yl)methoxy)-2-oxabicyclo[2.2.2]octan-1-yl)benzo[d]thiazole-7-carboxylic acid | ¹H NMR (400 MHz, DMSO-d$_6$) δ 7.88 (t, J = 6.7 Hz, 2H), 7.76-7.55 (m, 3H), 7.44 (t, J = 7.8 Hz, 1H), 4.27 (s, 2H), 3.56 (s, 2H), 2.33-2.31 (m, 1H), 2.27-2.13 (m, 2H), 2.05 (d, J = 15.7 Hz, 2H), 1.88-1.78 (m, 2H), 1.64-1.37 (m, 2H), 1.15 (d, J = 8.1 Hz, 2H), 1.09 (d, J = 2.9 Hz, 2H). FXR EC$_{50}$ (nM) = 680. MS (ESI) 571 (M + H). | Ex. 168 |
| 455 | 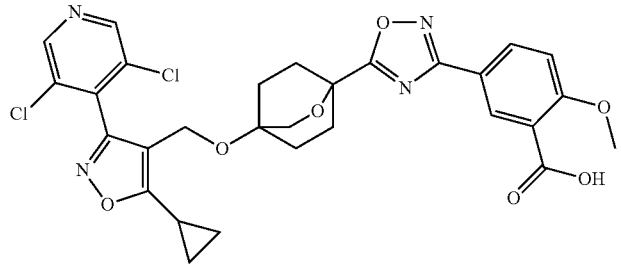 [SMILES: COc1ccc(-c2noc(C34CCC(OCc5c(-c6c(Cl)cncc6Cl)noc5C5CC5)(CC3)CO4)n2)cc1C(=O)O]<br>5-(5-(4-((5-cyclopropyl-3-(3,5-dichloropyridin-4-yl)isoxazol-4-yl)methoxy)-2-oxabicyclo[2.2.2]octan-1-yl)-1,2,4-oxadiazol-3-yl)-2-methoxybenzoic acid | ¹H NMR (400 MHz, DMSO-d$_6$) δ 8.85 (s, 2H), 8.12 (s, 1H), 8.00 (d, J = 9.3 Hz, 1H), 7.23 (d, J = 8.6 Hz, 1H), 4.32 (s, 2H), 3.86 (s, 3H), 3.51 (s, 2H), 2.38-2.30 (m, 1H), 2.26 (d, J = 7.1 Hz, 2H), 2.22-2.10 (m, 2H), 1.88-1.74 (m, 2H), 1.62-1.47 (m, 2H), 1.16 (d, J = 8.3 Hz, 2H), 1.10 (d, J = 3.4 Hz, 2H). FXR EC$_{50}$ (nM) = 290. MS (ESI) 613 (M + H). | Ex. 193 |
| 457 | 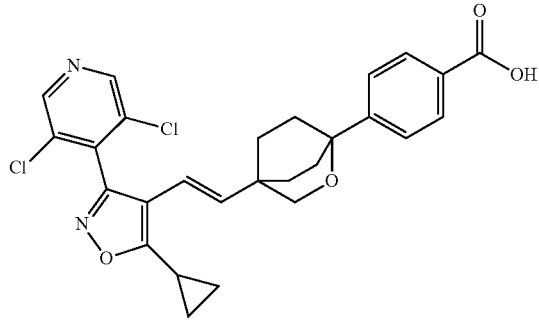 [SMILES: O=C(O)c1ccc(C23CCC(/C=C/c4c(-c5c(Cl)cncc5Cl)noc4C4CC4)(CC2)CO3)cc1] | ¹H NMR (400 MHz, DMSO-d$_6$) δ 8.88 (s, 2H), 7.83 (d, J = 8.3 Hz, 2H), 7.41 (d, J = 8.3 Hz, 2H), 6.14 (d, J = 16.40 Hz, 1H), 5.26 (d, J = 16.80 Hz, 1H), 3.67 (s, 2H), 2.43-2.38 (m, 1H), 2.08-2.03 (m, 2H), 1.85-1.81 (m, 2H), 1.68-1.64 (m, 4H), 1.24-1.22 (m, 2H), 1.12-1.10 (m, 2H). FXR EC$_{50}$ (nM) = 87. MS (ESI) 511 (M + H). | Ex. 194 |

TABLE 8-continued

| Ex. No. | Structure & Name | ¹H NMR, FXR EC₅₀ & MS (ESI) | Method |
|---|---|---|---|
| | (E)-4-(4-(2-(5-cyclopropyl-3-(3,5-dichloropyridin-4-yl)isoxazol-4-yl)vinyl)-2-oxabicyclo[2.2.2]octan-1-yl)benzoic acid | | |
| 458 | 3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-5-fluorobenzoic acid | $^1$H NMR (400 MHz, DMSO-$d_6$) δ 8.83 (s, 2H), 8.32 (s, 1H), 7.96-7.78 (m, 2H), 4.25 (s, 2H), 2.36-2.27 (m, 1H), 2.05-1.90 (m, 6H), 1.57-1.42 (m, 6H), 1.20-1.02 (m, 4H). FXR EC$_{50}$ (nM) = 85. MS (ESI) 599 (M + H). | Ex. 64 |
| 459 | 3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-4-methoxybenzoic acid | $^1$H NMR (400 MHz, DMSO-$d_6$) δ 8.81 (s, 2H), 8.39 (s, 1H), 8.08 (d, J = 8.8 Hz, 1H), 7.29 (d, J = 7.6 Hz, 1H), 4.24 (s, 2H), 3.91 (s, 3H), 2.36-2.27 (m, 1H), 1.98-1.95 (m, 6H), 1.51-1.42 (m, 6H), 1.15-1.08 (m, 4H). FXR EC$_{50}$ (nM) = 630. MS (ESI) 611 (M + H). | Ex. 64 |
| 460 | 3-(5-(4-((5-cyclopropyl-3-(3-fluoropyridin-4-yl)isoxazol-4-yl)methoxy)bicyclo[2.2.2]octan-1-yl)-1,2,4-oxadiazol-3-yl)benzoic acid | $^1$H NMR (400 MHz, DMSO-$d_6$) δ 8.78 (s, 1H), 8.61 (d, J = 4.6 Hz, 1H), 8.51 (s, 1H), 8.19 (d, J = 7.6 Hz, 1H), 8.12 (d, J = 7.6 Hz, 1H), 7.76-7.60 (m, 2H), 4.32 (s, 2H), 2.32-2.25 (m, 1H), 2.16-2.00 (m, 6H), 1.76-1.50 (m, 6H), 1.21-0.97 (m, 4H). FXR EC$_{50}$ (nM) = 4500. MS (ESI) 530 (M + H). | Ex. 1 |
| 461 | | $^1$H NMR (400 MHz, DMSO-$d_6$) δ 13.41 (br. s., 1H), 8.84 (s, 2H), 8.54 (dd, J = 6.8, 2.2 Hz, 1H), 8.16 (ddd, J = 8.6, 4.7, 2.3 Hz, 1H), 7.56 (dd, J = 10.1, 8.9 Hz, 1H), 4.25 (s, 2H), 2.38-2.33 (m, 1H), 2.07-1.90 (m, 6H), 1.55-1.39 (m, 6H), 1.20-1.05 (m, 4H). FXR EC$_{50}$ (nM) = 190. MS (ESI) 599 (M + H) | Ex. 64 |

TABLE 8-continued

| Ex. No. | Structure & Name | ¹H NMR, FXR EC$_{50}$ & MS (ESI) | Method |
|---|---|---|---|
| | 3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-4-fluorobenzoic acid | | |
| 462 | 6-((4-((5-cyclopropyl-3-(3,5-dichloropyridin-4-yl)isoxazol-4-yl)methoxy)bicyclo[2.2.2]octan-1-yl)methoxy)imidazo[1,2-b]pyridazine-3-carbonitrile | ¹H NMR (400 MHz, DMSO-d$_6$) δ 8.83 (s, 2H), 8.39 (s, 1H), 8.21 (d, J = 9.8 Hz, 1H), 7.18 (d, J = 9.8 Hz, 1H), 4.23 (s, 2H), 3.94 (s, 2H), 2.35-2.28 (m, 1H), 1.64-1.45 (m, 6H), 1.42 -1.23 (m, 6H), 1.20-1.00 (m, 4H). FXR EC$_{50}$ (nM) = 220. MS (ESI) 565 (M + H). | Ex. 104 |
| 463 | 2-((4-((5-cyclopropyl-3-(3,5-dichloropyridin-4-yl)isoxazol-4-yl)methoxy)bicyclo[2.2.2]octan-1-yl)methoxy)-5-fluorobenzo[d]thiazole-7-carboxylic acid | ¹H NMR (400 MHz, DMSO-d$_6$) δ 8.81 (s, 2H), 7.76 (dd, J = 9.3, 2.4 Hz, 1H), 7.64 (dd, J = 9.4, 2.6 Hz, 1H), 4.22 (s, 2H), 4.18 (s, 2H), 2.34-2.27 (m, 1H), 1.62-1.43 (m, 6H), 1.42-1.24 (m, 6H), 1.19-1.04 (m, 4H). FXR EC$_{50}$ (nM) = 41. MS (ESI) 618 (M + H). | Ex. 176 |
| 465 | 2-((4-((5-cyclopropyl-3-(3,5-dichloropyridin-4-yl)isoxazol-4-yl)methoxy)bicyclo[2.2.2]octan-1-yl)methoxy)thiazole-4-carboxylic acid | ¹H NMR (400 MHz, DMSO-d$_6$) δ 8.83 (s, 2H), 7.44 (br. s., 1H), 4.22 (s, 2H), 3.98 (s, 2H), 2.33-2.28 (m, 1H), 1.57-1.42 (m, 6H), 1.41-1.27 (m, 6H), 1.19-1.05 (m, 4H). FXR EC$_{50}$ (nM) = 180. MS (ESI) 550 (M + H). | Ex. 176 |

TABLE 8-continued

| Ex. No. | Structure & Name | $^1$H NMR, FXR EC$_{50}$ & MS (ESI) | Method |
|---|---|---|---|
| 466 | 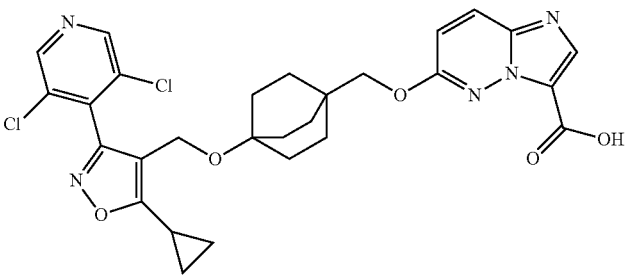 [SMILES: O=C(O)c1cnc2ccc(OCC34CCC(OCc5c(-c6c(Cl)cncc6Cl)noc5C5CC5)(CC3)CC4)nn12]<br>6-((4-((5-cyclopropyl-3-(3,5-dichloropyridin-4-yl)isoxazol-4-yl)methoxy)bicyclo[2.2.2]octan-1-yl)methoxy)imidazo[1,2-b]pyridazine-3-carboxylic acid | $^1$H NMR (400 MHz, DMSO-d$_6$) δ 12.9 (s, 1H), 8.83 (s, 2H), 8.20-7.97 (m, 2H), 7.05 (d, J = 9.3 Hz, 1H), 4.24 (s, 2H), 3.95 (s, 2H), 2.32-2.23 (m, 1H), 1.63-1.45 (m, 6H), 1.44-1.33 (m, 6H), 1.19-1.06 (m, 4H). FXR EC$_{50}$ (nM) = 390. MS (ESI) 584 (M + H). | Ex. 104 |
| 469 | 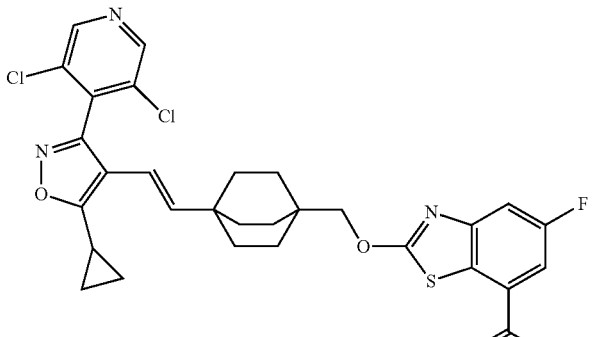<br>(E)-2-((4-(2-(5-cyclopropyl-3-(3,5-dichloropyridin-4-yl)isoxazol-4-yl)vinyl)bicyclo[2.2.2]octan-1-yl)methoxy)-5-fluorobenzo[d]thiazole-7-carboxylic acid | $^1$H NMR (400 MHz, DMSO-d$_6$) δ 8.88 (s, 2H), 7.73 (d, J = 9.0 Hz, 1H), 7.62 (d, J = 9.8 Hz, 1H), 6.01 (d, J = 16.4 Hz, 1H), 5.27 (d, J = 16.4 Hz, 1H), 4.22 (s, 2H), 2.37 (br s, 1H), 1.49 (d, J = 9.0 Hz, 6H), 1.38 (d, J = 8.6 Hz, 6H), 1.26-1.15 (m, 2H), 1.13-0.96 (m, 2H). FXR EC$_{50}$ (nM) = 190. MS (ESI) 614 (M + H). | Ex. 176 |
| 470 | 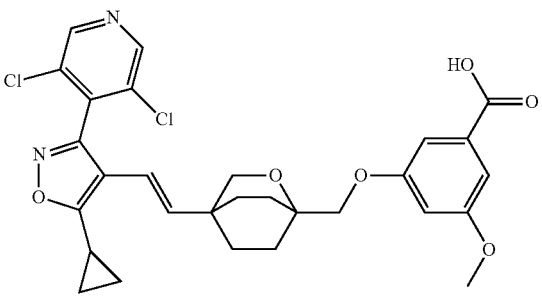 [SMILES: COc1cc(OCC23CCC(/C=C/c4c(-c5c(Cl)cncc5Cl)noc4C4CC4)(CC2)CO3)cc(C(=O)O)c1]<br>(E)-3-((4-(2-(5-cyclopropyl-3-(3,5-dichloropyridin-4-yl)isoxazol-4-yl)vinyl)-2-oxabicyclo[2.2.2]octan-1-yl)methoxy)-5-methoxybenzoic acid | $^1$H NMR (400 MHz, DMSO-d$_6$) δ 8.88 (s, 2H), 7.01 (d, J = 8.6 Hz, 2H), 6.57 (s, 1H), 6.10 (d, J = 16.6 Hz, 1H), 5.22 (d, J = 16.6 Hz, 1H), 3.75 (s, 5H), 3.51 (br s, 2H), 2.43-2.39 (m, 1H), 1.90-1.79 (m, 2H), 1.72-1.44 (m, 6H), 1.32-1.07 (m, 2H), 1.05 (d, J = 6.1 Hz, 2H). FXR EC$_{50}$ (nM) = 110. MS (ESI) 571 (M + H). | Ex. 444 |

TABLE 8-continued

| Ex. No. | Structure & Name | ¹H NMR, FXR EC$_{50}$ & MS (ESI) | Method |
|---|---|---|---|
| 473 | 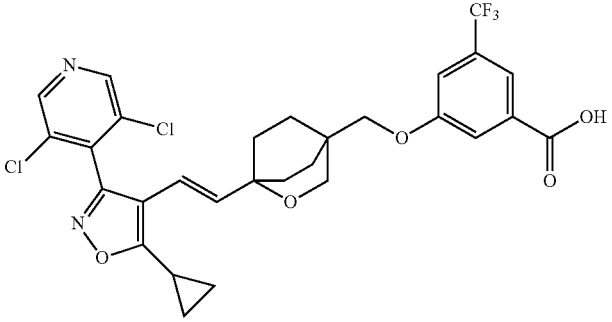 [SMILES: O=C(O)c1cc(OCC23CCC(/C=C/c4c(-c5c(Cl)cncc5Cl)noc4C4CC4)(CC2)OC3)cc(C(F)(F)F)c1]<br>(E)-3-((1-(2-(5-cyclopropyl-3-(3,5-dichloropyridin-4-yl)isoxazol-4-yl)vinyl)-2-oxabicyclo[2.2.2]octan-4-yl)methoxy)-5-(trifluoromethyl)benzoic acid | ¹H NMR (400 MHz, DMSO-d$_6$) δ 8.90 (s, 2H), 7.74 (s, 1H), 7.66 (s, 1H), 7.43 (s, 1H), 6.23 (d, J = 16.6 Hz, 1H), 5.39 (d, J = 16.4 Hz, 1H), 3.81 (s, 2H), 3.76 (s, 2H), 2.43-2.36 (m, 1H), 1.79-1.49 (m, 8H), 1.25-1.09 (m, 4H). FXR EC$_{50}$ (nM) = 320. MS (ESI) 609 (M + H) | Ex. 444 |
| 474 | 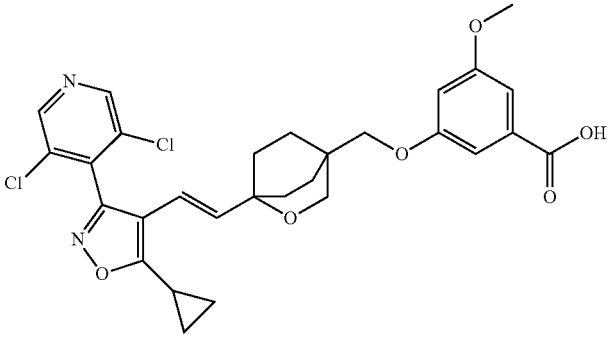 [SMILES: COc1cc(OCC23CCC(/C=C/c4c(-c5c(Cl)cncc5Cl)noc4C4CC4)(CC2)OC3)cc(C(=O)O)c1]<br>(E)-3-((1-(2-(5-cyclopropyl-3-(3,5-dichloropyridin-4-yl)isoxazol-4-yl)vinyl)-2-oxabicyclo[2.2.2]octan-4-yl)methoxy)-5-methoxybenzoic acid | ¹H NMR (400 MHz, DMSO-d$_6$) δ 13.03 (br s, 1H) 8.90 (s, 2H), 7.04 (s, 1H), 7.02 (s, 1H), 6.70 (s, 1H), 6.23 (d, J = 16.4 Hz, 1H), 5.38 (d, J = 16.4 Hz, 1H), 3.78 (s, 3H), 3.75 (s, 2H), 3.69 (s, 2H), 2.44-2.35 (m, 1H), 1.80-1.52 (m, 8H), 1.24-1.15 (m, 2H), 1.12 (d, J = 4.4 Hz, 2H). FXR EC$_{50}$ (nM) = 490. MS (ESI) 571 (M + H) | Ex. 444 |
| 475 | 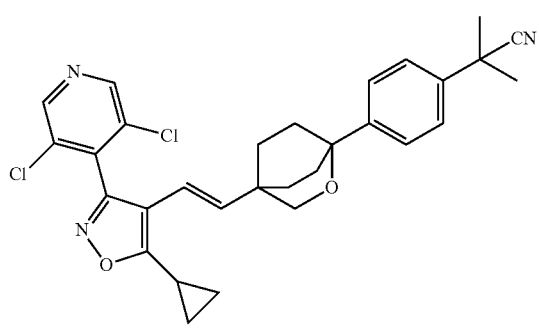 [SMILES: CC(C)(C#N)c1ccc(C23CCC(/C=C/c4c(-c5c(Cl)cncc5Cl)noc4C4CC4)(CC2)CO3)cc1]<br>(E)-2-(4-(4-(2-(5-cyclopropyl-3-(3,5-dichloropyridin-4-yl)isoxazol-4-yl)vinyl)-2-oxabicyclo[2.2.2]octan-1-yl)phenyl)-2-methylpropanenitrile | ¹H NMR (400 MHz, DMSO-d$_6$) δ 8.89 (s, 2H), 7.45-7.39 (m, 4H), 6.15 (d, J = 16.80 Hz, 1H), 5.27 (d, J = 16.80 Hz, 1H), 3.67 (s, 2H), 2.41-2.39 (m, 1H), 2.09-2.03 (m, 2H), 1.85-1.82 (m, 2H), 1.66-1.61 (m, 10H), 1.22-1.1 (m, 4H). FXR EC$_{50}$ (nM) = 1500. MS (ESI) 534 (M + H). | Ex. 194 |

TABLE 8-continued

| Ex. No. | Structure & Name | $^1$H NMR, FXR EC$_{50}$ & MS (ESI) | Method |
|---|---|---|---|
| 476 | 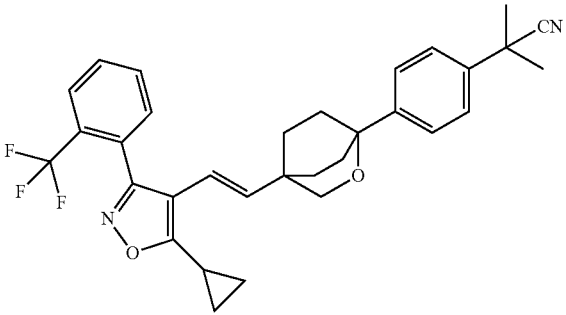 [SMILES: CC(C)(C#N)c1ccc(C23CCC(/C=C/c4c(-c5ccccc5C(F)(F)F)noc4C4CC4)(CC2)CO3)cc1]<br>(E)-2-(4-(4-(2-(5-cyclopropyl-3-(2-(trifluoromethyl)phenyl)isoxazol-4-yl)vinyl)-2-oxabicyclo[2.2.2]octan-1-yl)phenyl)-2-methylpropanenitrile | $^1$H NMR (400 MHz, DMSO-d$_6$): δ 7.94-7.96 (m, 1H), 7.77-7.85 (m, 2H), 7.51 (d, J = 8.00 Hz, 1H), 7.37-7.44 (m, 4H), 6.03 (d, J = 16.40 Hz, 1H), 5.21 (d, J = 16.40 Hz, 1H), 3.62 (s, 2H), 2.34-2.38 (m, 1H), 2.01-2.05 (m, 2H), 1.77-1.81 (m, 2H), 1.66 (s, 6H), 1.56-1.61 (m, 4H), 1.15-1.18 (m, 2H), 1.07-1.10 (m, 2H). FXR EC$_{50}$ (nM) = 690. MS (ESI) 532 (M + H). | Ex. 194 |
| 477 | 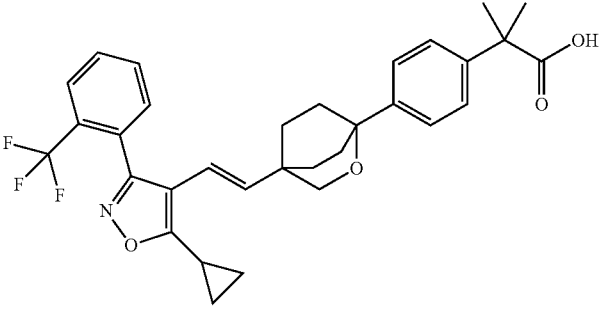 [SMILES: CC(C)(C(=O)O)c1ccc(C23CCC(/C=C/c4c(-c5ccccc5C(F)(F)F)noc4C4CC4)(CC2)CO3)cc1]<br>(E)-2-(4-(4-(2-(5-cyclopropyl-3-(2-(trifluoromethyl)phenyl)isoxazol-4-yl)vinyl)-2-oxabicyclo[2.2.2]octan-1-yl)phenyl)-2-methylpropanoic acid | $^1$H NMR (400 MHz, DMSO-d$_6$) δ 7.96 (d, J = 7.3 Hz, 1H), 7.86-7.73 (m, 2H), 7.52 (d, J = 7.1 Hz, 1H), 7.33-7.20 (m, 4H), 6.04 (d, J = 16.6 Hz, 1H), 5.20 (d, J = 16.6 Hz, 1H), 3.60 (s, 2H), 2.38-2.32 (m, 1H), 2.06-1.95 (m, 2H), 1.83-1.75 (m, 2H), 1.62-1.54 (m, 4H), 1.44 (s, 6H), 1.20-1.14 (m, 2H), 1.12-1.05 (m, 2H). FXR EC$_{50}$ (nM) = 1500. MS (ESI) 552 (M + H). | Ex. 194 |
| 479 | 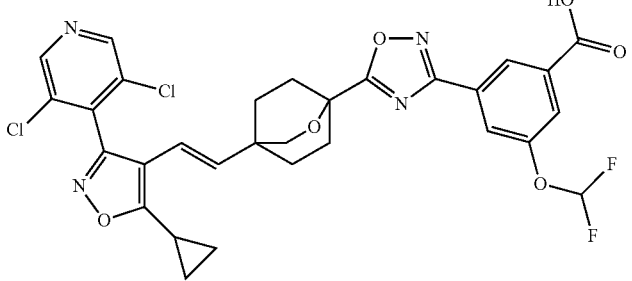<br>(E)-3-(5-(4-(2-(5-cyclopropyl-3-(3,5-dichloropyridin-4-yl)isoxazol-4-yl)vinyl)-2-oxabicyclo[2.2.2]octan-1-yl)-1,2,4-oxadiazol-3-yl)-5-(difluoromethoxy)benzoic acid | $^1$H NMR (400 MHz, DMSO-d$_6$) δ 13.71 (br s, 1H), 8.90 (s, 2H), 8.38 (s, 1H), 7.95 (s, 1H), 7.87 (s, 1H), 7.47 (t, J = 73.20 Hz, 1H), 6.19 (d, J = 16.9 Hz, 1H), 5.28 (d, J = 16.6 Hz, 1H), 3.71 (s, 2H), 2.48-2.42 (m, 1H), 2.29 (d, J = 6.1 Hz, 2H), 2.21-2.11 (m, 2H), 1.81-1.64 (m, 4H), 1.33-1.17 (m, 2H), 1.17-1.06 (m, 2H). FXR EC$_{50}$ (nM) = 360. MS (ESI) 645 (M + H). | Ex. 478 |

TABLE 8-continued

| Ex. No. | Structure & Name | ¹H NMR, FXR EC$_{50}$ & MS (ESI) | Method |
|---|---|---|---|
| 480 | 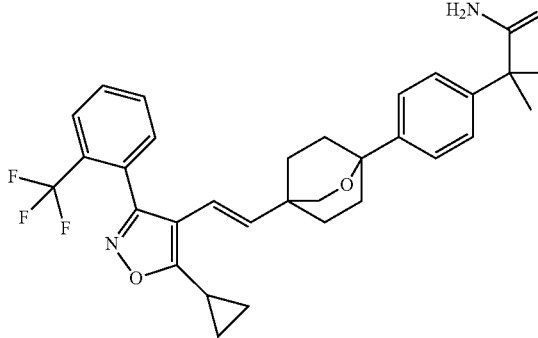<br>(E)-2-(4-(4-(2-(5-cyclopropyl-3-(2-(trifluoromethyl)phenyl)isoxazol-4-yl)vinyl)-2-oxabicyclo[2.2.2]octan-1-yl)phenyl)-2-methylpropanamide | ¹H NMR (400 MHz, DMSO-d$_6$) δ 7.96 (d, J = 6.4 Hz, 1H), 7.86-7.74 (m, 2H), 7.52 (d, J = 6.8 Hz, 1H), 7.34-7.18 (m, 4H), 6.85 (d, J = 6.8 Hz, 2H), 6.03 (d, J = 16.6 Hz, 1H), 5.20 (d, J = 16.6 Hz, 1H), 3.60 (s, 2H), 2.38-2.33 (m, 1H), 2.06-1.96 (m, 2H), 1.84-1.73 (m, 2H), 1.63-1.53 (m, 4H), 1.40 (s, 6H), 1.20-1.13 (m, 2H), 1.12-1.02 (m, 2H). FXR EC$_{50}$ (nM) = 1000. MS (ESI) 551 (M + H). | Ex. 194 |
| 481 | 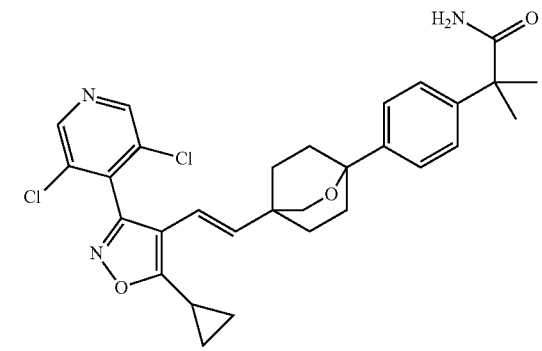 [SMILES: CC(C)(C(N)=O)c1ccc(C23CCC(/C=C/c4c(-c5c(Cl)cncc5Cl)noc4C4CC4)(CC2)CO3)cc1]<br>(E)-2-(4-(4-(2-(5-cyclopropyl-3-(3,5-dichloropyridin-4-yl)isoxazol-4-yl)vinyl)-2-oxabicyclo[2.2.2]octan-1-yl)phenyl)-2-methylpropanamide | ¹H NMR (400 MHz, DMSO-d$_6$) δ 8.89 (s, 2H), 7.27 (q, J = 8.7 Hz, 4H), 6.86 (d, J = 7.1 Hz, 2H), 6.15 (d, J = 16.6 Hz, 1H), 5.25 (d, J = 16.4 Hz, 1H), 3.65 (s, 2H), 2.45-2.38 (m, 1H), 2.11-1.96 (m, 2H), 1.88-1.75 (m, 2H), 1.71-1.53 (m, 4H), 1.40 (s, 6H), 1.26-1.16 (m, 2H), 1.15-1.05 (m, 2H). FXR EC$_{50}$ (nM) = 510. MS (ESI) 552 (M + H). | Ex. 194 |
| 482 | 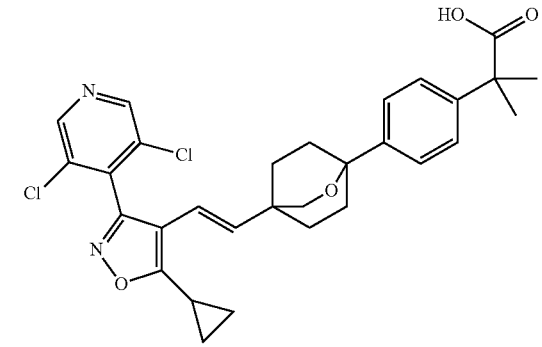 [SMILES: CC(C)(C(=O)O)c1ccc(C23CCC(/C=C/c4c(-c5c(Cl)cncc5Cl)noc4C4CC4)(CC2)CO3)cc1]<br>(E)-2-(4-(4-(2-(5-cyclopropyl-3-(3,5-dichloropyridin-4-yl)isoxazol-4-yl)vinyl)-2-oxabicyclo[2.2.2]octan-1-yl)phenyl)-2-methylpropanoic acid | ¹H NMR (400 MHz, DMSO-d$_6$) δ 8.89 (s, 2H), 7.33-7.22 (m, 4H), 6.15 (d, J = 16.6 Hz, 1H), 5.26 (d, J = 16.6 Hz, 1H), 3.65 (s, 2H), 2.46-2.40 (m, 1H), 2.02 (dd, J = 13.1, 5.3 Hz, 2H), 1.87-1.74 (m, 2H), 1.70-1.53 (m, 4H), 1.43 (s, 6H), 1.28-1.16 (m, 2H), 1.15-1.08 (m, 2H). FXR EC$_{50}$ (nM) = 950. MS (ESI) 553 (M + H). | Ex. 194 |

TABLE 8-continued

| Ex. No. | Structure & Name | ¹H NMR, FXR EC$_{50}$ & MS (ESI) | Method |
|---|---|---|---|
| 483 | 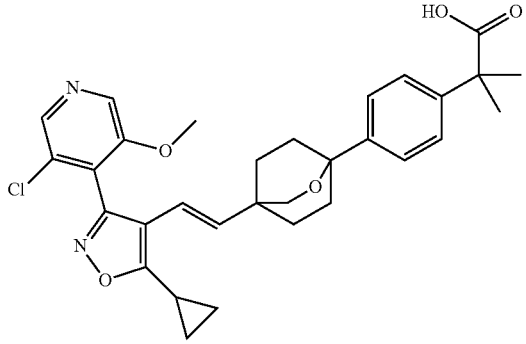 [SMILES: COc1cncc(Cl)c1-c1noc(C2CC2)c1/C=C/C12CCC(c3ccc(C(C)(C)C(=O)O)cc3)(CC1)OC2]<br>(E)-2-(4-(4-(2-(3-(3-chloro-5-methoxypyridin-4-yl)-5-cyclopropylisoxazol-4-yl)vinyl)-2-oxabicyclo[2.2.2]octan-1-yl)phenyl)-2-methylpropanoic acid | ¹H NMR (400 MHz, DMSO-d$_6$) δ 8.58 (s, 1H), 8.50 (s, 1H), 7.27 (q, J = 8.8 Hz, 4H), 6.07 (d, J = 16.4 Hz, 1H), 5.29 (d, J = 16.6 Hz, 1H), 3.92 (s, 3H), 3.64 (s, 2H), 2.40-2.33 (m, 1H), 2.09-1.97 (m, 2H), 1.83-1.78 (m, 2H), 1.63 (d, J = 7.6 Hz, 4H), 1.43 (s, 6H), 1.17 (dt, J = 8.4, 3.0 Hz, 2H), 1.12-1.05 (m, 2H). FXR EC$_{50}$ (nM) = 4500. MS (ESI) 549 (M + H). | Ex. 194 |
| 484 | 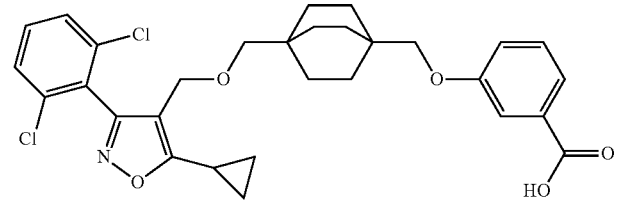 [SMILES: O=C(O)c1cccc(OCC23CCC(COCc4c(-c5c(Cl)cccc5Cl)noc4C4CC4)(CC2)CC3)c1]<br>3-((4-(((5-cyclopropyl-3-(2,6-dichlorophenyl)isoxazol-4-yl)methoxy)methyl)bicyclo[2.2.2]octan-1-yl)methoxy)benzoic acid | ¹H NMR (400 MHz, DMSO-d$_6$) δ 7.68-7.60 (m, 2H), 7.59-7.52 (m, 1H), 7.48 (d, J = 7.8 Hz, 1H), 7.41-7.26 (m, 2H), 7.10 (d, J = 8.6 Hz, 1H), 4.22 (s, 2H), 3.57 (s, 4H), 2.30 (s, 1H), 1.50-1.29 (m, 6H), 1.21-0.98 (m, 10H). FXR EC$_{50}$ (nM) = 200. MS (ESI) 556 (M + H). | Ex. 464 |
| 485 | 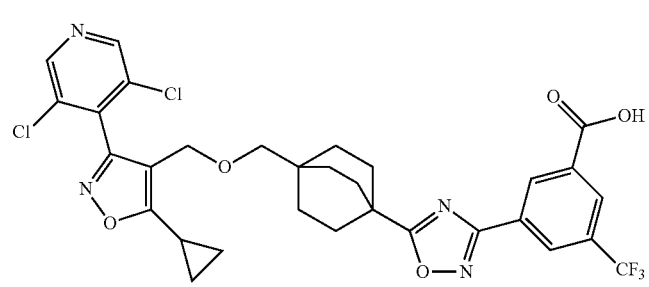 [SMILES: O=C(O)c1cc(-c2noc(C34CCC(COCc5c(-c6c(Cl)cncc6Cl)noc5C5CC5)(CC3)CC4)n2)cc(C(F)(F)F)c1]<br>3-(5-(4-(((5-cyclopropyl-3-(3,5-dichloropyridin-4-yl)isoxazol-4-yl)methoxy)methyl)bicyclo[2.2.2]octan-1-yl)-1,2,4-oxadiazol-3-yl)-5-(trifluoromethyl)benzoic acid | ¹H NMR (400 MHz, DMSO-d$_6$) δ 8.87 (s, 2H), 8.74 (s, 1H), 8.42 (s, 1H), 8.36 (s, 1H), 4.33 (s, 2H), 2.99 (s, 2H), 2.35-2.30 (m, 1H), 1.98-1.77 (m, 6H), 1.33-1.21 (m, 6H), 1.21-1.05 (m, 4H). FXR EC$_{50}$ (nM) = 380. MS (ESI) 663 (M + H). | Ex. 151 |
| 486 | 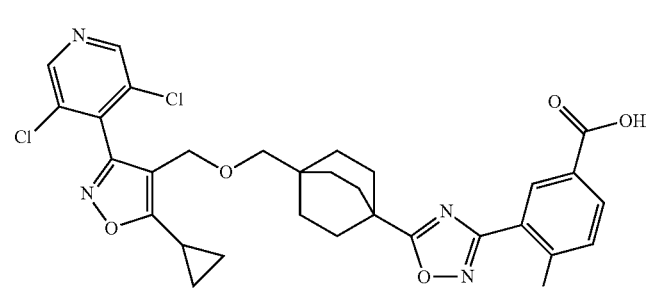 | ¹H NMR (400 MHz, DMSO-d$_6$) δ 8.88 (s, 2H), 8.54 (dd, J = 7.1, 2.0 Hz, 1H), 8.21-8.02 (m, 1H), 7.51-7.36 (m, 1H), 4.33 (s, 2H), 2.99 (s, 2H), 2.35-2.31 (m, 1H), 1.91-1.78 (m, 6H), 1.32-1.21 (m, 6H), 1.20-1.07 (m, 4H). FXR EC$_{50}$ (nM) = 2700. MS (ESI) 613 (M + H). | Ex. 151 |

TABLE 8-continued

| Ex. No. | Structure & Name | ¹H NMR, FXR EC$_{50}$ & MS (ESI) | Method |
|---|---|---|---|
| | 3-(5-(4-(((5-cyclopropyl-3-(3,5-dichloropyridin-4-yl)isoxazol-4-yl)methoxy)methyl)bicyclo[2.2.2]octan-1-yl)-1,2,4-oxadiazol-3-yl)-4-fluorobenzoic acid | | |
| 487 | 3-(5-(4-(((5-cyclopropyl-3-(3,5-dichloropyridin-4-yl)isoxazol-4-yl)methoxy)methyl)bicyclo[2.2.2]octan-1-yl)-1,2,4-oxadiazol-3-yl)-4-methoxybenzoic acid | ¹H NMR (400 MHz, DMSO-d$_6$) δ 12.94 (br s, 1H), 8.88 (s, 2H), 8.44 (d, J = 2.2 Hz, 1H), 8.11 (dd, J = 8.8, 2.2 Hz, 1H), 7.33 (d, J = 8.8 Hz, 1H), 4.33 (s, 2H), 3.96 (s, 3H), 2.99 (s, 2H), 2.37-2.34 (m, 1H), 1.94-1.77 (m, 6H), 1.35-1.21 (m, 6H), 1.20-1.11 (m, 4H). FXR EC$_{50}$ (nM) = 5400. MS (ESI) 625 (M + H). | Ex. 151 |
| 488 | 3-(4-(((5-cyclopropyl-3-(3,5-dichloropyridin-4-yl)isoxazol-4-yl)methoxy)methyl)-2-oxabicyclo[2.2.2]octan-1-yl)-5-(trifluoromethyl)benzonitrile | ¹H NMR (400 MHz, DMSO-d$_6$) δ 8.87 (s, 2H), 8.21 (s, 1H), 8.11 (s, 1H), 7.99 (s, 1H), 4.32 (s, 2H), 3.61 (s, 2H), 3.05 (s, 2H), 2.37-2.32 (m, 1H), 2.22-2.02 (m, 2H), 1.82-1.62 (m, 2H),1.48-1.32 (m, 4H), 1.22-1.07 (m, 4H). FXR EC$_{50}$ (nM) = 2400. MS (ESI) 578 (M + H). | Ex. 195 |
| 489 | 3-(4-(((5-cyclopropyl-3-(3,5-dichloropyridin-4-yl)isoxazol-4-yl)methoxy)methyl)-2-oxabicyclo[2.2.2]octan-1-yl)-5-(trifluoromethyl)benzamide | ¹H NMR (400 MHz, DMSO-d$_6$) δ 8.97-8.85 (m, 2H), 8.22 (s, 1H), 8.13 (s, 1H), 8.07 (s, 1H), 7.81 (s, 1H), 7.57 (s, 1H), 4.33 (s, 2H), 3.62 (s, 2H), 3.06 (s, 2H), 2.37-2.33 (m, 1H), 2.13-2.02 (m, 2H), 1.81-1.65 (m, 2H), 1.50-1.32 (m, 4H), 1.23-1.05 (m, 4H). FXR EC$_{50}$ (nM) = 1400. MS (ESI) 596 (M + H). | Ex. 195 |

TABLE 8-continued

| Ex. No. | Structure & Name | $^1$H NMR, FXR EC$_{50}$ & MS (ESI) | Method |
|---|---|---|---|
| 490 | 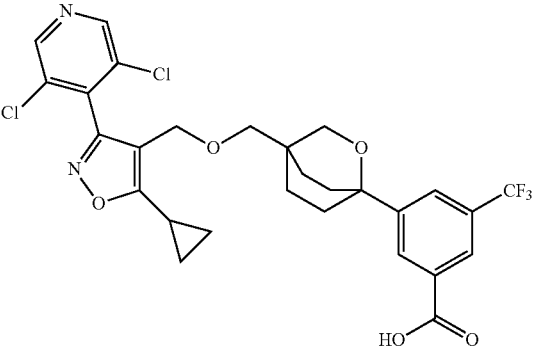 [SMILES: O=C(O)c1cc(C(F)(F)F)cc(C23CCC(COCc4c(-c5c(Cl)cncc5Cl)noc4C4CC4)(CC2)CO3)c1]<br>3-(4-(((5-cyclopropyl-3-(3,5-dichloropyridin-4-yl)isoxazol-4-yl)methoxy)methyl)-2-oxabicyclo[2.2.2]octan-1-yl)-5-(trifluoromethyl)benzoic acid | $^1$H NMR (400 MHz, DMSO-d$_6$) δ 8.87 (s, 2H), 8.18 (s, 1H), 8.03 (s, 1H), 7.87 (s, 1H), 4.33 (s, 2H), 3.62 (s, 2H), 3.05 (s, 2H), 2.37-2.32 (m, 1H), 2.15-2.03 (m, 2H), 1.73 (d, J = 11.2 Hz, 2H), 1.48-1.33 (m, 4H), 1.23-1.04 (m, 4H). FXR EC$_{50}$ (nM) = 96. MS (ESI) 597 (M + H). | Ex. 195 |
| 491 | 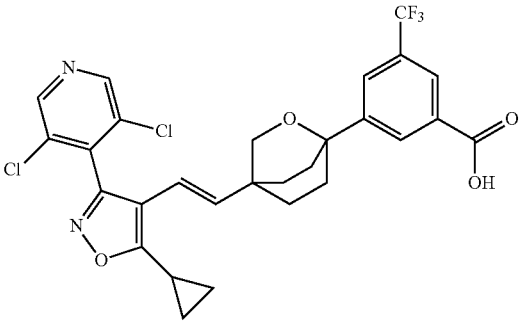 [SMILES: O=C(O)c1cc(C(F)(F)F)cc(C23CCC(/C=C/c4c(-c5c(Cl)cncc5Cl)noc4C4CC4)(CC2)CO3)c1]<br>(E)-3-(4-(2-(5-cyclopropyl-3-(3,5-dichloropyridin-4-yl)isoxazol-4-yl)vinyl)-2-oxabicyclo[2.2.2]octan-1-yl)-5-(trifluoromethyl)benzoic acid | $^1$H NMR (400 MHz, DMSO-d$_6$) δ 8.86 (s, 2H), 8.20 (s, 1H), 8.04 (s, 1H), 7.91 (s, 1H) 6.16 (d, J = 16.6 Hz, 1H), 5.28 (d, J = 16.6 Hz, 1H), 3.70 (s, 2H), 2.46-2.36 (m, 1H), 2.25-2.09 (m, 2H), 1.88-1.74 (m, 2H), 1.68 (d, J = 7.5 Hz, 4H), 1.30-1.07 (m, 4H). FXR EC$_{50}$ (nM) = 26. MS (ESI) 579 (M + H). | Ex. 194 |
| 492 | 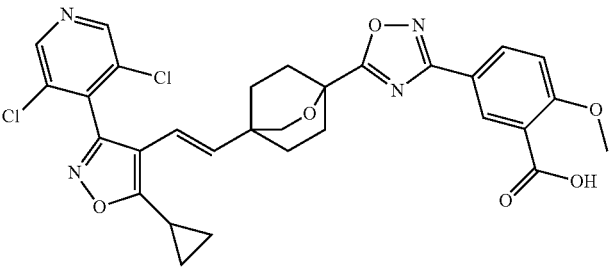<br>(E)-5-(5-(4-(2-(5-cyclopropyl-3-(3,5-dichloropyridin-4-yl)isoxazol-4-yl)vinyl)-2-oxabicyclo[2.2.2]octan-1-yl)-1,2,4-oxadiazol-3-yl)-2-methoxybenzoic acid | $^1$H NMR (400 MHz, DMSO-d$_6$) δ 8.90 (s, 2H), 8.18 (d, J = 2.2 Hz, 1H), 8.05 (dd, J = 8.7, 2.3 Hz,1H), 7.27 (d, J = 8.8 Hz, 1H), 6.30 (d, J = 16.4 Hz, 1H), 5.42 (d, J = 16.4 Hz, 1H), 3.31 (s, 2H), 3.89 (s, 3H), 2.46-2.37 (m, 1H), 2.23-2.05 (m, 4H), 1.88-1.70 (m, 4H), 1.28-1.07 (m, 4H). FXR EC$_{50}$ (nM) = 250. MS (ESI) 609 (M + H). | Ex. 478 |

TABLE 8-continued

| Ex. No. | Structure & Name | $^1$H NMR, FXR EC$_{50}$ & MS (ESI) | Method |
|---|---|---|---|
| 493 | 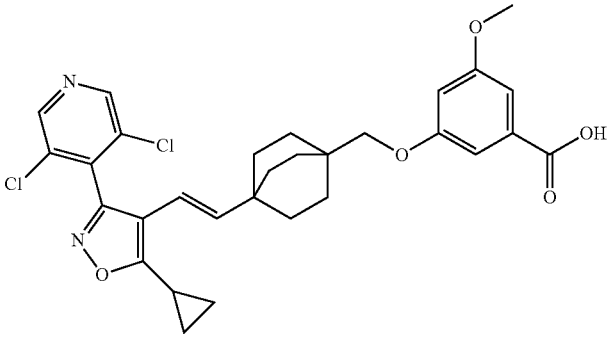 [SMILES: COc1cc(OCC23CCC(/C=C/c4c(-c5c(Cl)cncc5Cl)noc4C4CC4)(CC2)CC3)cc(C(=O)O)c1]<br>(E)-3-((4-(2-(5-cyclopropyl-3-(3,5-dichloropyridin-4-yl)isoxazol-4-yl)vinyl)bicyclo[2.2.2]octan-1-yl)methoxy)-5-methoxybenzoic acid | $^1$H NMR (400 MHz, DMSO-d$_6$) δ 8.90 (s, 2H), 7.02 (d, J = 2.2 Hz, 2H), 6.66 (dd, J = 8.7, 2.3 Hz, 1H), 6.00 (d, J = 16.4 Hz, 1H), 5.30 (d, J = 16.4 Hz, 1H), 3.60 (s, 2H), 3.77 (s, 3H), 2.46-2.37 (m, 1H), 2.23-2.05 (m, 4H), 1.88-1.70 (m, 6H), 1.28-1.07 (m, 6H). FXR EC$_{50}$ (nM) = 18. MS (ESI) 569 (M + H). | Ex. 444 |
| 494 | 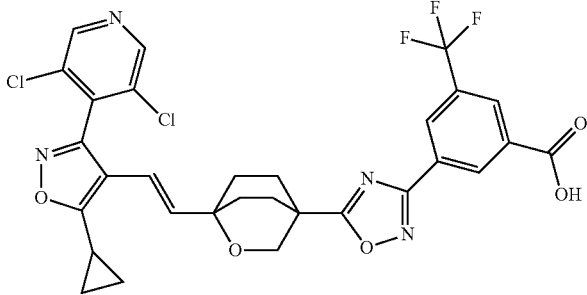 [SMILES: O=C(O)c1cc(-c2noc(C34CCC(/C=C/c5c(-c6c(Cl)cncc6Cl)noc5C5CC5)(CC3)OC4)n2)cc(C(F)(F)F)c1]<br>(E)-3-(5-(1-(2-(5-cyclopropyl-3-(3,5-dichloropyridin-4-yl)isoxazol-4-yl)vinyl)-2-oxabicyclo[2.2.2]octan-4-yl)-1,2,4-oxadiazol-3-yl)-5-(trifluoromethyl)benzoic acid | $^1$H NMR (400 MHz, DMSO-d$_6$) δ 8.90 (s, 2H), 8.73 (s, 1H), 8.36 (d, J = 8.1 Hz, 2H), 6.30 (d, J = 16.6 Hz, 1H), 5.43 (d, J = 16.4 Hz, 1H), 4.12 (s, 2H), 2.44-2.38 (m, 1H), 2.23-2.07 (m, 4H), 1.89-1.71 (m, 4H), 1.29-1.09 (m, 4H). FXR EC$_{50}$ (nM) = 130. MS (ESI) 647 (M + H). | Ex. 478 |
| 495 | 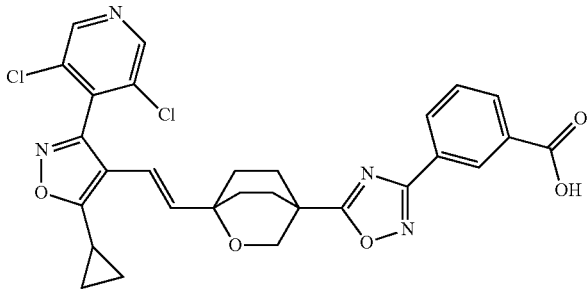 [SMILES: O=C(O)c1cccc(-c2noc(C34CCC(/C=C/c5c(-c6c(Cl)cncc6Cl)noc5C5CC5)(CC3)OC4)n2)c1]<br>(E)-3-(5-(1-(2-(5-cyclopropyl-3-(3,5-dichloropyridin-4-yl)isoxazol-4-yl)vinyl)-2-oxabicyclo[2.2.2]octan-4-yl)-1,2,4-oxadiazol-3-yl)benzoic acid | $^1$H NMR (400 MHz, DMSO-d$_6$) δ 8.91 (s, 2H), 8.52 (t, J = 1.6 Hz, 1H), 8.20 (d, J = 7.8 Hz, 1H), 8.17-8.08 (m, 1H), 7.69 (t, J = 7.7 Hz, 1H), 6.30 (d, J = 16.4 Hz, 1H), 5.42 (d, J = 16.4 Hz, 1H), 4.11 (s, 2H), 2.45-2.40 (m, 1H), 2.25-2.04 (m, 4H), 1.91-1.67 (m, 4H), 1.31-1.01 (m, 4H). FXR EC$_{50}$ (nM) = 1700. MS (ESI) 579 (M + H). | Ex. 478 |

TABLE 8-continued

| Ex. No. | Structure & Name | $^1$H NMR, FXR EC$_{50}$ & MS (ESI) | Method |
|---|---|---|---|
| 496 | 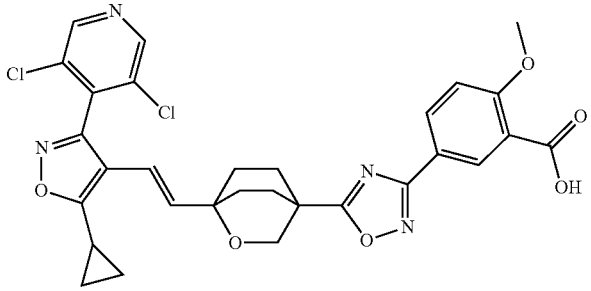 [SMILES: COc1ccc(-c2noc(C34CCC(/C=C/c5c(-c6c(Cl)cncc6Cl)noc5C5CC5)(CC3)OC4)n2)cc1C(=O)O]<br>(E)-5-(5-(1-(2-(5-cyclopropyl-3-(3,5-dichloropyridin-4-yl)isoxazol-4-yl)vinyl)-2-oxabicyclo[2.2.2]octan-4-yl)-1,2,4-oxadiazol-3-yl)-2-methoxybenzoic acid | $^1$H NMR (400 MHz, DMSO-d$_6$) δ 8.90 (s, 2H), 8.18 (d, J = 2.2 Hz, 1H), 8.05 (dd, J = 8.7, 2.3 Hz, 1H), 7.27 (d, J = 8.8 Hz, 1H), 6.30 (d, J = 16.4 Hz, 1H), 5.42 (d, J = 16.4 Hz, 1H), 4.09 (s, 2H), 3.89 (s, 3H), 2.46-2.37 (m, 1H), 2.23-2.05 (m, 4H), 1.88-1.70 (m, 4H), 1.28-1.07 (m, 4H). FXR EC$_{50}$ (nM) = 1000. MS (ESI) 609 (M + H). | Ex. 478 |
| 497 | 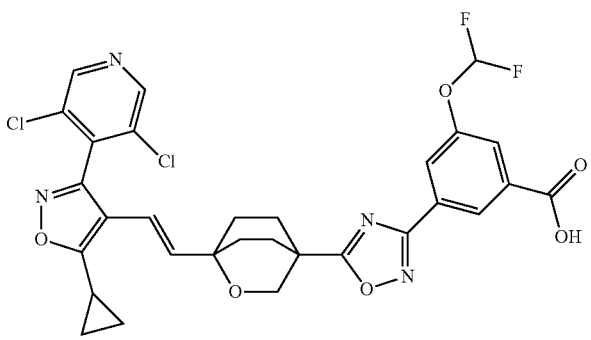 [SMILES: O=C(O)c1cc(OC(F)F)cc(-c2noc(C34CCC(/C=C/c5c(-c6c(Cl)cncc6Cl)noc5C5CC5)(CC3)OC4)n2)c1]<br>(E)-3-(5-(1-(2-(5-cyclopropyl-3-(3,5-dichloropyridin-4-yl)isoxazol-4-yl)vinyl)-2-oxabicyclo[2.2.2]octan-4-yl)-1,2,4-oxadiazol-3-yl)-5-(difluoromethoxy)benzoic acid | $^1$H NMR (400 MHz, DMSO-d$_6$) δ 8.91 (s, 2H), 8.37 (s, 1H), 7.92 (s, 1H), 7.86 (s, 1H), 7.46 (t, J = 73.1 Hz, 1H), 6.30 (d, J = 16.4 Hz, 1H), 5.42 (d, J = 16.4 Hz, 1H), 4.11 (s, 2H), 2.45-2.40 (m, 1H), 2.23-2.06 (m, 4H), 1.88-1.67 (m, 4H), 1.27-1.16 (m, 4H). FXR EC$_{50}$ (nM) = 460. MS (ESI) 645 (M + H). | Ex. 478 |
| 498 | 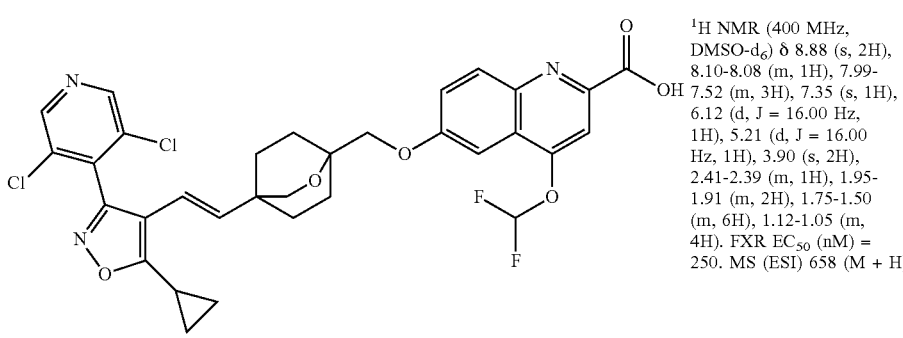<br>(E)-6-((4-(2-(5-cyclopropyl-3-(3,5-dichloropyridin-4-yl)isoxazol-4-yl)vinyl)-2-oxabicyclo[2.2.2]octan-1-yl)methoxy)-4-(difluoromethoxy)quinoline-2-carboxylic acid | $^1$H NMR (400 MHz, DMSO-d$_6$) δ 8.88 (s, 2H), 8.10-8.08 (m, 1H), 7.99-7.52 (m, 3H), 7.35 (s, 1H), 6.12 (d, J = 16.00 Hz, 1H), 5.21 (d, J = 16.00 Hz, 1H), 3.90 (s, 2H), 2.41-2.39 (m, 1H), 1.95-1.91 (m, 2H), 1.75-1.50 (m, 6H), 1.12-1.05 (m, 4H). FXR EC$_{50}$ (nM) = 250. MS (ESI) 658 (M + H) | Ex. 444 |

TABLE 8-continued

| Ex. No. | Structure & Name | $^1$H NMR, FXR EC$_{50}$ & MS (ESI) | Method |
|---|---|---|---|
| 499 | 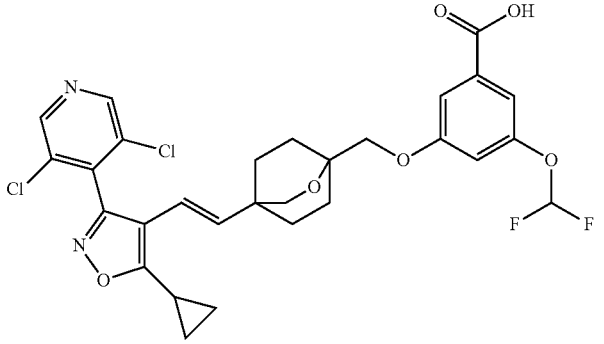 [SMILES: O=C(O)c1cc(OCC23CCC(/C=C/c4c(-c5c(Cl)cncc5Cl)noc4C4CC4)(CC2)CO3)cc(OC(F)F)c1]<br>(E)-3-((4-(2-(5-cyclopropyl-3-(3,5-dichloropyridin-4-yl)isoxazol-4-yl)vinyl)-2-oxabicyclo[2.2.2]octan-1-yl)methoxy)-5-(difluoromethoxy)benzoic acid | $^1$H NMR (400 MHz, DMSO-d$_6$) δ 8.88 (s, 2H), 7.52-6.99 (m, 4H), 6.11 (d, J = 16.8 Hz, 1H), 5.22 (d, J = 16.8 Hz, 1H), 3.83 (s, 2H), 3.50 (s, 2H), 2.41-2.38 (m, 1H), 1.91-1.85 (m, 2H), 1.69-1.54 (m, 6H), 1.20-1.01 (m, 4H). FXR EC$_{50}$ (nM) = 160. MS (ESI) 607 (M + H). | Ex. 444 |
| 500 | 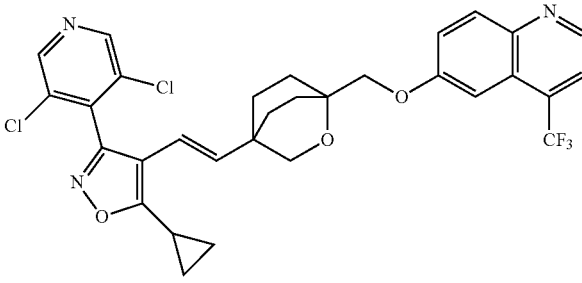<br>(E)-6-((4-(2-(5-cyclopropyl-3-(3,5-dichloropyridin-4-yl)isoxazol-4-yl)vinyl)-2-oxabicyclo[2.2.2]octan-1-yl)methoxy)-4-(trifluoromethyl)quinoline-2-carboxylic acid | $^1$H NMR (400 MHz, DMSO-d$_6$) δ 8.88 (s, 2H), 8.31 (s, 1H), 8.19 (d, J = 5.60 Hz, 1H), 7.64 (d, J = 8.00 Hz, 1H), 7.32 (s, 1H), 6.11 (d, J = 16.8 Hz, 1H), 5.22 (d, J = 16.8 Hz, 1H), 3.97 (s, 2H), 3.50 (s, 2H), 2.41-2.38 (m, 1H), 1.92-1.88 (m, 2H), 1.74-1.54 (m, 6H), 1.28-1.08 (m, 4H). FXR EC$_{50}$ (nM) = 160. MS (ESI) 660 (M + H). | Ex. 444 |
| 501 | 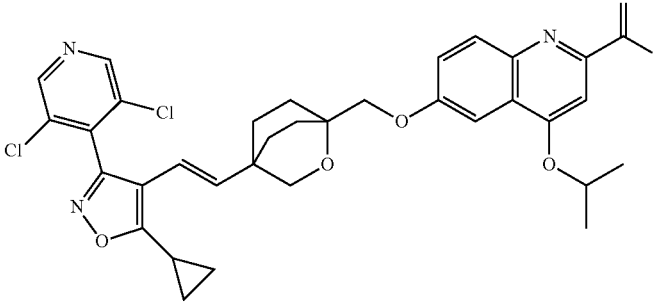<br>(E)-6-((4-(2-(5-cyclopropyl-3-(3,5-dichloropyridin-4-yl)isoxazol-4-yl)vinyl)-2-oxabicyclo[2.2.2]octan-1-yl)methoxy)-4-isopropoxyquinoline-2-carboxylic acid | $^1$H NMR (400 MHz, DMSO-d$_6$) δ 8.85 (s, 2H), 8.06 (d, J = 8.80 Hz, 1H), 7.52-7.5 (m, 2H), 7.41 (s, 1H), 6.10 (d, J = 20.0 Hz, 1H), 5.20 (d, J = 18.6 Hz, 1H), 5.18-5.2 (m, 1H), 2.45-2.40 (s, 1H), 1.86-1.78 (m, 2H), 1.72-1.57 (m, 6H), 1.42-1.40 (m, 6H), 1.16-1.07 (m, 4H). FXR EC$_{50}$ (nM) = 54. MS (ESI) 650 (M + H). | Ex. 444 |

US 10,730,863 B2

537                                                                                     538

TABLE 8-continued

| Ex. No. | Structure & Name | ¹H NMR, FXR EC₅₀ & MS (ESI) | Method |
|---|---|---|---|
| 502 | 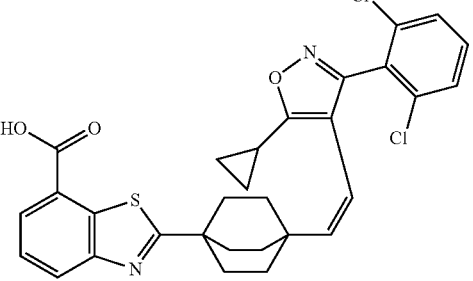<br>(Z)-2-(4-(2-(5-cyclopropyl-3-(2,6-dichlorophenyl)isoxazol-4-yl)vinyl)bicyclo[2.2.2]octan-1-yl)benzo[d]thiazole-7-carboxylic acid | ¹H NMR (400 MHz, DMSO-d₆) δ 9.58 (br s, 1H), 7.82 (d, J = 7.8 Hz, 2H), 7.66 (d, J = 8.1 Hz, 2H), 7.60-7.52 (m, 1H), 7.38 (t, J = 7.6 Hz, 1H), 5.80 (d, J = 12.2 Hz, 1H), 5.63 (d, J = 12.2 Hz, 1H), 2.51-2.49 (m, 1H), 1.94-1.84 (m, 6H), 1.60-1.51 (m, 6H), 1.23-1.10 (m, 4H). FXR EC₅₀ (nM) = 1500. MS (ESI) 565 (M + H). | Ex. 182 |
| 503 | 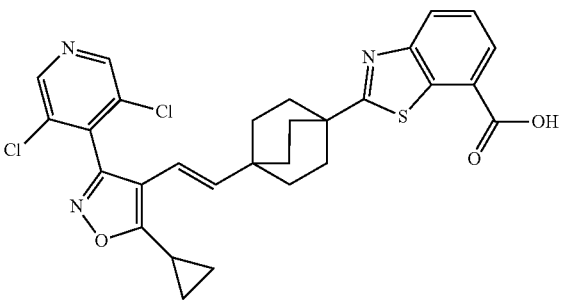 [SMILES: O=C(O)c1cccc2nc(C34CCC(/C=C/c5c(-c6c(Cl)cncc6Cl)noc5C5CC5)(CC3)CC4)sc12]<br>(E)-2-(4-(2-(5-cyclopropyl-3-(3,5-dichloropyridin-4-yl)isoxazol-4-yl)vinyl)bicyclo[2.2.2]octan-1-yl)benzo[d]thiazole-7-carboxylic acid | ¹H NMR (400 MHz, DMSO-d₆) δ 8.90 (s, 2H), 8.18 (dd, J = 8.1, 1.0 Hz, 1H), 8.03 (dd, J = 7.5, 1.1 Hz, 1H), 7.61 (t, J = 7.8 Hz, 1H), 6.08 (d, J = 16.6 Hz, 1H), 5.34 (d, J = 16.6 Hz, 1H), 2.44-2.38 (m, 1H), 2.07-1.88 (m, 6H), 1.63-1.44 (m, 6H), 1.23-1.06 (m, 4H). FXR EC₅₀ (nM) = 31. MS (ESI) 566 (M + H). | Ex. 182 |
| 504 | 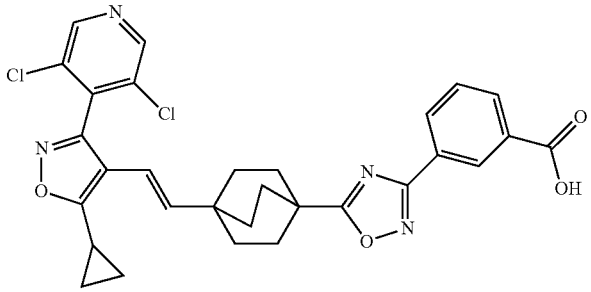 [SMILES: O=C(O)c1cccc(-c2noc(C34CCC(/C=C/c5c(-c6c(Cl)cncc6Cl)noc5C5CC5)(CC3)CC4)n2)c1]<br>(E)-3-(5-(4-(2-(5-cyclopropyl-3-(3,5-dichloropyridin-4-yl)isoxazol-4-yl)vinyl)bicyclo[2.2.2]octan-1-yl)-1,2,4-oxadiazol-3-yl)benzoic acid | ¹H NMR (400 MHz, DMSO-d₆) δ 13.31 (br s, 1H), 8.89 (s, 2H), 8.52 (s, 1H), 8.21 (d, J = 7.8 Hz, 1H), 8.13 (d, J = 7.8 Hz, 1H), 7.70 (t, J = 7.8 Hz, 1H), 6.08 (d, J = 16.6 Hz, 1H), 5.32 (d, J = 16.6 Hz, 1H), 2.44-2.36 (m, 1H), 2.05-1.90 (m, 6H), 1.60-1.42 (m, 6H), 1.23-1.07 (m, 4H). FXR EC₅₀ (nM) = 33. MS (ESI) 577 (M + H). | Ex. 478 |
| 505 | 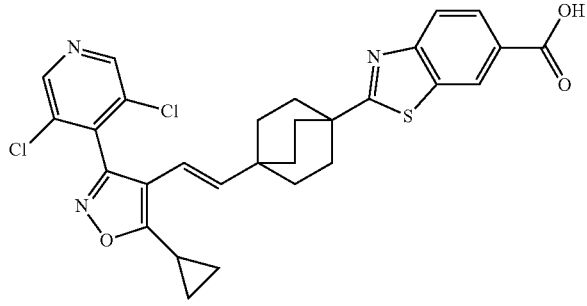 [SMILES: O=C(O)c1ccc2nc(C34CCC(/C=C/c5c(-c6c(Cl)cncc6Cl)noc5C5CC5)(CC3)CC4)sc2c1]<br>(E)-2-(4-(2-(5-cyclopropyl-3-(3,5-dichloropyridin-4-yl)isoxazol-4-yl) | ¹H NMR (400 MHz, DMSO-d₆) δ 13.06 (br s, 1H), 8.90 (s, 2H), 8.68 (d, J = 1.2 Hz, 1H), 8.08-7.92 (m, 2H), 6.08 (d, J = 16.6 Hz, 1H), 5.33 (d, J = 16.4 Hz, 1H), 2.46-2.36 (m, 1H), 2.07-1.86 (m, 6H), 1.60-1.43 (m, 6H), 1.24-1.06 (m, 4H). FXR EC₅₀ (nM) = 88. MS (ESI) 566 (M + H). | Ex. 478 |

TABLE 8-continued

| Ex. No. | Structure & Name | $^1$H NMR, FXR EC$_{50}$ & MS (ESI) | Method |
|---|---|---|---|
| | vinyl)bicyclo[2.2.2]octan-1-yl) benzo[d]thiazole-6-carboxylic acid | | |
| 506 | (E)-3-((4-(2-(5-cyclopropyl-3-(3,5-dichloropyridin-4-yl)isoxazol-4-yl) vinyl)bicyclo[2.2.2]octan-1-yl)methoxy)-5-(trifluoromethyl)benzoic acid | $^1$H NMR (400 MHz, DMSO-d$_6$) δ 8.88 (s, 2H), 7.73 (s, 1H), 7.66 (s, 1H), 7.47 (s, 1H), 6.01 (d, J = 16.6 Hz, 1H), 5.28 (d, J = 16.6 Hz, 1H), 3.74 (s, 2H), 2.40-2.35 (m, 1H), 1.59-1.47 (m, 6H), 1.43-1.31 (m, 6H), 1.21-1.09 (m, 4H). FXR EC$_{50}$ (nM) = 6. MS (ESI) 607 (M + H). | Ex. 444 |
| 507 | (E)-2-(4-(2-(5-cyclopropyl-3-(3,5-dichloropyridin-4-yl)isoxazol-4-yl) vinyl)bicyclo[2.2.2]octan-1-yl)-5-(trifluoromethyl)benzo[d]thiazole-7-carboxylic acid | $^1$H NMR (400 MHz, DMSO-d$_6$) δ 8.90 (s, 2H), 8.57 (s, 1H), 8.21 (d, J = 1.5 Hz, 1H), 6.08 (d, J = 16.6 Hz, 1H), 5.34 (d, J = 16.6 Hz, 1H), 2.45-2.40 (m, 1H), 2.09-1.92 (m, 6H), 1.60-1.47 (m, 6H), 1.23-1.08 (m, 4H). FXR EC$_{50}$ (nM) = 20. MS (ESI) 634 (M + H). | Ex. 182 |
| 508 | (E)-6-((4-(2-(5-cyclopropyl-3-(3,5-dichloropyridin-4-yl)isoxazol-4-yl)vinyl) bicyclo[2.2.2]octan-1-yl)methoxy)-4-methoxyquinoline-2-carboxylic acid | $^1$H NMR (400 MHz, DMSO-d$_6$) δ 8.89 (s, 2H), 8.00 (d, J = 9.0 Hz, 1H), 7.54 (s, 1H), 7.46 (dd, J = 9.2, 2.8 Hz, 1H), 7.40 (d, J = 2.9 Hz, 1H), 6.02 (d, J = 16.4 Hz, 1H), 5.29 (d, J = 16.6 Hz, 1H), 4.12 (s, 3H), 3.75 (s, 2H), 2.39-2.34 (m, 1H), 1.63-1.46 (m, 6H), 1.45-1.31 (m, 6H), 1.23-1.17 (m, 2H), 1.14-1.01 (m, 2H). FXR EC$_{50}$ (nM) = 100. MS (ESI) 620 (M + H). | Ex. 444 |

TABLE 8-continued

| Ex. No. | Structure & Name | ¹H NMR, FXR EC$_{50}$ & MS (ESI) | Method |
|---|---|---|---|
| 509 | 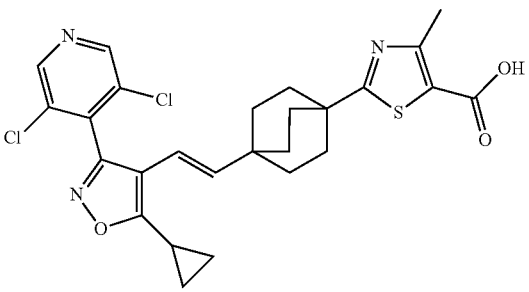 [SMILES: Cc1nc(C23CCC(/C=C/c4c(-c5c(Cl)cncc5Cl)noc4C4CC4)(CC2)CC3)sc1C(=O)O]<br>(E)-2-(4-(2-(5-cyclopropyl-3-(3,5-dichloropyridin-4-yl)isoxazol-4-yl)vinyl)bicyclo[2.2.2]octan-1-yl)-4-methylthiazole-5-carboxylic acid | ¹H NMR (400 MHz, DMSO-d$_6$) δ 8.89 (s, 2H), 6.04 (d, J = 16.6 Hz, 1H), 5.35 (d, J = 16.6 Hz, 1H), 2.55 (s, 3H), 2.43-2.35 (m, 1H), 1.55-1.40 (m, 6H), 1.36-1.21 (m, 6H), 1.20-1.16 (m, 2H), 1.14-1.06 (m, 2H). FXR EC$_{50}$ (nM) = 40. MS (ESI) 530 (M + H). | Ex. 162 |
| 510 | 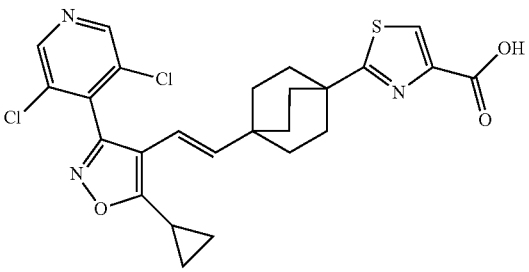 [SMILES: O=C(O)c1csc(C23CCC(/C=C/c4c(-c5c(Cl)cncc5Cl)noc4C4CC4)(CC2)CC3)n1]<br>(E)-2-(4-(2-(5-cyclopropyl-3-(3,5-dichloropyridin-4-yl)isoxazol-4-yl)vinyl)bicyclo[2.2.2]octan-1-yl)thiazole-4-carboxylic acid | ¹H NMR (400 MHz, DMSO-d$_6$) δ 8.89 (s, 2H), 7.94 (s, 1H), 6.05 (d, J = 16.6 Hz, 1H), 5.31 (d, J = 16.6 Hz, 1H), 2.42-2.36 (m, 1H), 1.92-1.79 (m, 6H), 1.54-1.41 (m, 6H), 1.22-1.14 (m, 2H), 1.13-1.06 (m, 2H). FXR EC$_{50}$ (nM) = 410. MS (ESI) 516 (M + H). | Ex. 162 |
| 511 | 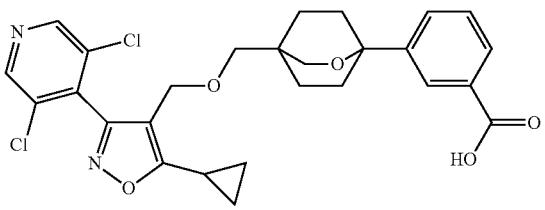 [SMILES: O=C(O)c1cccc(C23CCC(COCc4c(-c5c(Cl)cncc5Cl)noc4C4CC4)(CC2)CO3)c1]<br>3-(4-(((5-cyclopropyl-3-(3,5-dichloropyridin-4-yl)isoxazol-4-yl)methoxy)methyl)-2-oxabicyclo[2.2.2]octan-1-yl)benzoic acid | ¹H NMR (400 MHz, DMSO-d$_6$) δ 8.87 (s, 2H), 7.94 (s, 1H), 7.78 (d, J = 7.3 Hz, 1H), 7.56 (d, J = 6.8 Hz, 1H), 7.40 (t, J = 7.5 Hz, 1H), 4.32 (s, 2H), 3.57 (s, 2H), 3.03 (s, 2H), 2.36 (d, J = 3.4 Hz, 1H), 2.06-1.93 (m, 2H), 1.70 (m, 2H), 1.39 (d, J = 6.1 Hz, 4H), 1.21-0.97 (m, 4H). FXR EC$_{50}$ (nM) = 2900. MS (ESI) 529 (M + H). | Ex. 195 |

TABLE 8-continued

| Ex. No. | Structure & Name | $^1$H NMR, FXR EC$_{50}$ & MS (ESI) | Method |
|---|---|---|---|
| 512 | 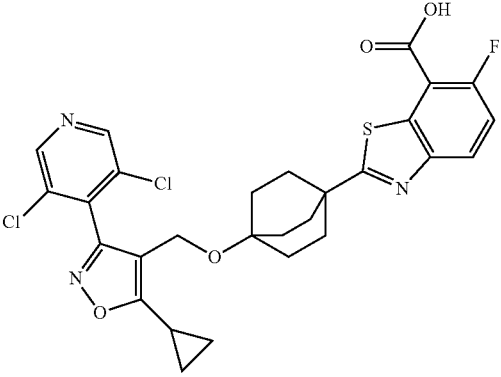 [SMILES: O=C(O)c1c(F)ccc2nc(C34CCC(OCc5c(-c6c(Cl)cncc6Cl)noc5C5CC5)(CC3)CC4)sc12]<br>2-(4-((5-cyclopropyl-3-(3,5-dichloropyridin-4-yl)isoxazol-4-yl)methoxy)bicyclo[2.2.2]octan-1-yl)-6-fluorobenzo[d]thiazole-7-carboxylic acid | $^1$H NMR (400 MHz, DMSO-d$_6$) δ 8.84 (s, 2H), 8.16 (dd, J = 8.8, 4.2 Hz, 1H), 7.46 (dd, J = 11.1, 8.9 Hz, 1H), 4.27 (s, 2H), 2.38-2.32 (m, 1H), 2.09-1.93 (m, 6H), 1.62-1.41 (m, 6H), 1.21-1.06 (m, 4H). FXR EC$_{50}$ (nM) = 43. MS (ESI) 588 (M + H). | Ex. 16 |
| 513 | 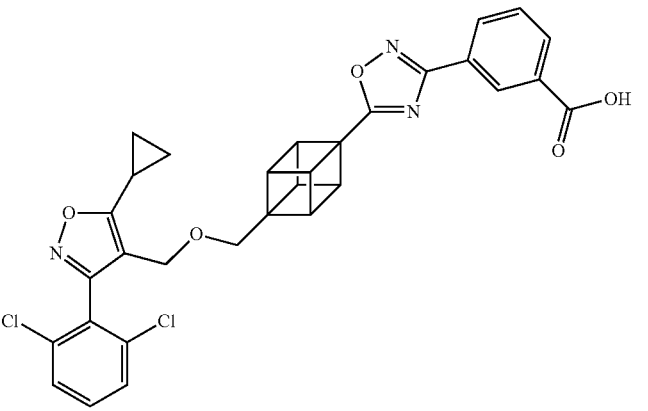 [SMILES: O=C(O)c1cccc(-c2noc(C34C5C6C3C3C4C5C63COCc3c(-c4c(Cl)cccc4Cl)noc3C3CC3)n2)c1]<br>3-(5-(4-(((5-cyclopropyl-3-(2,6-dichlorophenyl)isoxazol-4-yl)methoxy)methyl)cuban-1-yl)-1,2,4-oxadiazol-3-yl)benzoic acid | $^1$H NMR (500 MHz, DMSO-d$_6$) δ 8.58 (s, 1H), 8.26 (br d, J = 7.9 Hz, 1H), 8.16 (br d, J = 7.9 Hz, 1H), 7.73 (br t, J = 7.8 Hz, 1H), 7.67-7.61 (m, 2H), 7.59-7.49 (m, 1H), 4.41 (s, 2H), 3.75 (s, 2H), 3.46-3.42 (m, 3H), 3.16 (br s, 1H), 2.37 (br d, J = 15.0 Hz, 2H), 2.31-2.20 (m, 1H), 1.22-1.01 (m, 5H). FXR EC$_{50}$ (nM) = 960. MS (ESI) 588 (M + H) | Ex. 151 |
| 514 | 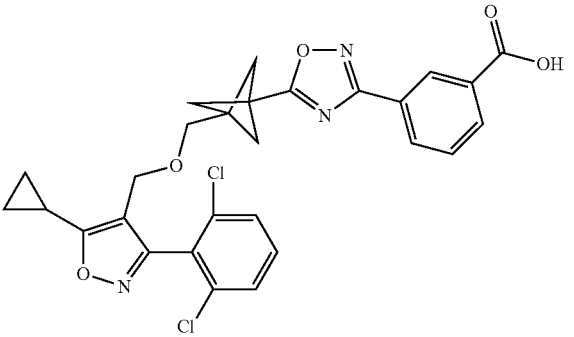 [SMILES: O=C(O)c1cccc(-c2noc(C34CC(COCc5c(-c6c(Cl)cccc6Cl)noc5C5CC5)(C3)C4)n2)c1]<br>3-(5-(3-(((5-cyclopropyl-3-(2,6-dichlorophenyl)isoxazol-4-yl)methoxy)methyl)bicyclo[1.1.1]pentan-1-yl)-1,2,4-oxadiazol-3-yl)benzoic acid | $^1$H NMR (500 MHz, DMSO) δ 8.50 (s, 1H), 8.19 (br d, J = 7.6 Hz, 1H), 8.12 (br d, J = 7.9 Hz, 1H), 7.72-7.62 (m, 3H), 7.60-7.54 (m, 1H), 4.29 (s, 2H), 2.38-2.29 (m, 1H), 2.07 (s, 6H), 1.19-1.13 (m, 2H), 1.12-1.05 (m, 2H). 2 protons missing due to water suppression. FXR EC$_{50}$ (nM) = 1700. MS (ESI) 552 (M + H) | Ex. 151 |

Example 515

6-(2-(4-(((5-cyclopropyl-3-(3,5-dichloropyridin-4-yl)isoxazol-4-yl)methoxy) bicyclo[2.2.2]octan-1-yl)ethyl)quinoline-2-carboxylicacid

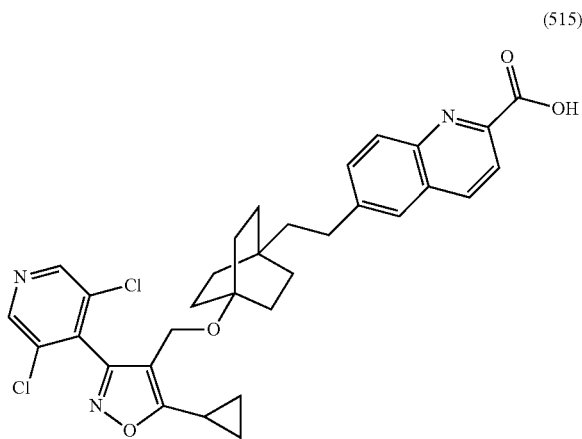 [SMILES: O=C(O)c1ccc2cc(CCC34CCC(OCc5c(-c6c(Cl)cncc6Cl)noc5C5CC5)(CC3)CC4)ccc2n1]

(515)

Step A. Intermediate 515A. Preparation of 5-cyclopropyl-3-(3,5-dichloropyridin-4-yl)-4-(((4-vinylbicyclo[2.2.2]octan-1-yl)oxy)methyl)isoxazole

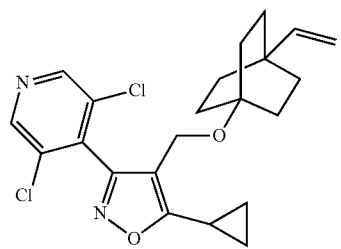 [SMILES: C=CC12CCC(OCc3c(-c4c(Cl)cncc4Cl)noc3C3CC3)(CC1)CC2]

To a suspension of methyltriphenylphosphonium bromide (2.4 g, 6.7 mmol) in toluene (56 mL) at 0° C. was added a solution of KHMDS (0.5 N in THF) (13 mL, 6.7 mmol). After stirring for 15 min, a solution of Intermediate 519D (1.2 g, 2.8 mmol) in toluene (6 mL) was added. The reaction mixture was stirred for 1 h at 0° C. The reaction was quenched with sat. aq. NH$_4$Cl and extracted with EtOAc. The organic layer was washed with brine, dried over anhydrous sodium sulfate, filtered and concentrated. The crude product was purified by flash column chromatography (80 g silica gel cartridge; A=Hex, B=EtOAc; 30 min grad.; 0% B to 100% B; flow rate=60 mL/min) to give the title compound as a colorless oil (0.84 g, 2.0 mmol, 72% yield). $^1$H NMR (400 MHz, CHLOROFORM-d) δ 8.77-8.29 (m, 2H), 5.66 (dd, J=17.4, 11.0 Hz, 1H), 4.85-4.75 (m, 2H), 4.20 (s, 2H), 2.12-2.06 (m, 1H), 1.55-1.50 (m, 6H), 1.45-1.41 (m, 6H), 1.24 (dd, J=5.0, 2.3 Hz, 2H), 1.11 (dd, J=8.3, 2.8 Hz, 2H). MS (ESI) 419 (M+H).

Step B. Example 515

To a solution of Intermediate 515A (66 mg, 0.16 mmol) in THF (530 μL) at 0° C. was added a solution of 9-BBN (0.5 N in THF) (76 μL, 0.38 mmol). After the addition, the reaction mixture was stirred for 1.5 h and then cooled to 0° C. Water (0.2 mL) was added. After stirring for 1 h at rt, half of the reaction mixture was added into a solution of methyl 6-bromoquinoline-2-carboxylate (HCl salt) (24 mg, 0.079 mmol), potassium phosphate tribasic (117 mg, 0.55 mmol), lithium chloride (20 mg, 0.47 mmol), and Pd(Ph$_3$P)$_4$ (20 mg, 0.017 mmol) in EtOH (1.0 mL). The reaction mixture was purged with N$_2$ and heated to 80° C. overnight. The reaction was quenched with sat. aq. NH$_4$Cl and extracted with EtOAc. The organic layer was washed with water and brine, dried over anhydrous sodium sulfate, and concentrated via vacuum. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 57-82% B over 20 minutes, then a 2-minute hold at 100% B; Flow: 20 mL/min.). Fractions containing the desired product were combined, concentrated and dried in vacuo to afford the title compound (3.2 mg, 0.005 mmol, 6.5% yield). $^1$H NMR (500 MHz, DMSO-d$_6$) δ 8.86-8.70 (m, 2H), 8.36 (br d, J=8.4 Hz, 1H), 8.03 (br d, J=8.5 Hz, 2H), 7.76 (s, 1H), 7.64 (br d, J=8.8 Hz, 1H), 4.21 (s, 2H), 2.74-2.61 (m, 2H), 2.35-2.19 (m, 1H), 1.53-1.41 (m, 8H), 1.39-1.30 (m, 6H), 1.15 (br d, J=8.2 Hz, 2H), 1.08 (br d, J=3.3 Hz, 2H). FXR EC$_{50}$ (nM)=87. MS (ESI) 592 (M+H).

Example 516

(E)-2-(4-(2-(4-((5-cyclopropyl-3-(3,5-dichloropyridin-4-yl)isoxazol-4-yl)methoxy) bicyclo[2.2.2]octan-1-yl)vinyl)phenyl)acetic acid

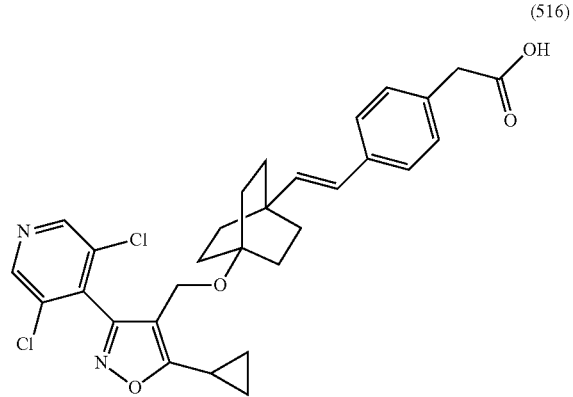 [SMILES: O=C(O)Cc1ccc(/C=C/C23CCC(OCc4c(-c5c(Cl)cncc5Cl)noc4C4CC4)(CC2)CC3)cc1]

(516)

To a solution of Intermediate 515A (43 mg, 0.10 mmol), ethyl 2-(4-bromophenyl)acetate (62 mg, 0.26 mmol), and K$_2$CO$_3$ (85 mg, 0.62 mmol) in DMF (2.0 mL) purged with N$_2$ was added PdCl$_2$(dppf) (6.6 mg, 9.2 μmop. The reaction mixture was stirred at 110° C. overnight. The reaction mixture was diluted with EtOAc. The organic layer was washed with water and brine, dried over anhydrous sodium sulfate, and concentrated via vacuum to give a dark brown oil. To the dark brown oil was added THF (1.0 mL), MeOH (0.5 mL) and 2 N NaOH (0.5 mL, 1.0 mmol). The reaction mixture was stirred for 1 h. The reaction mixture was concentrated, redissolved in DMF, acidified with acetic acid (0.05 mL), and filtered. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 57-82% B over 20 minutes, then a 2-minute hold at 100% B; Flow: 20 mL/min.). Fractions containing the desired product were combined, concentrated and dried in vacuo to afford the title compound (4.1 mg, 0.007 mmol, 6.8% yield). $^1$H NMR (500 MHz, DMSO-$d_6$) δ 8.94-8.45 (m, 2H), 7.26 (br d, J=7.9 Hz, 2H), 7.20-7.08 (m, 2H), 6.17 (d, J=17.0 Hz, 1H), 6.09 (d, J=17.0 Hz, 1H), 4.28-4.14 (m, 2H), 3.64-3.42 (m, 2H), 2.32-2.18 (m, 1H), 1.65-1.46 (m, 6H), 1.43-1.33 (m, 6H), 1.19-1.11 (m, 2H), 1.09-1.00 (m, 2H). FXR $EC_{50}$ (nM)=173. MS (ESI) 553 (M+H).

Example 517

(E)-7-(2-(4-((5-cyclopropyl-3-(3,5-dichloropyridin-4-yl)isoxazol-4-yl)methoxy) bicyclo[2.2.2]octan-1-yl)vinyl)-1-methoxyisoquinoline-3-carboxylic acid

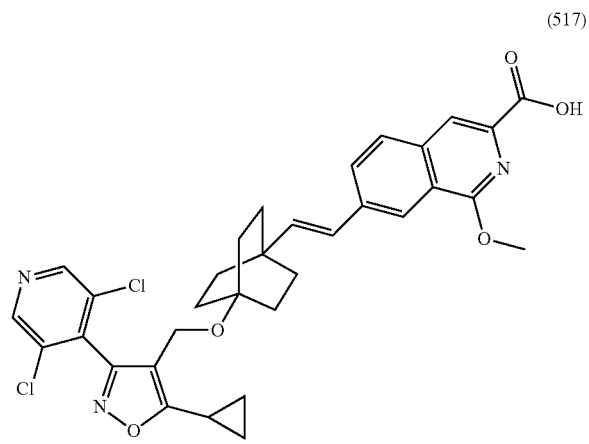 [SMILES: COc1nc(C(=O)O)cc2ccc(/C=C/C34CCC(OCc5c(-c6c(Cl)cncc6Cl)noc5C5CC5)(CC3)CC4)cc12]

(517)

Step A. Intermediate 517A. Preparation of methyl (E)-1-chloro-7-(2-(4-((5-cyclopropyl-3-(3,5-dichloropyridin-4-yl)isoxazol-4-yl)methoxy)bicyclo[2.2.2]octan-1-yl)vinyl) isoquinoline-3-carboxylate

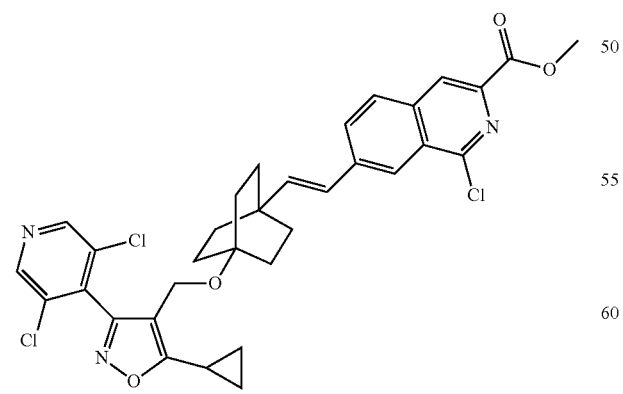

To a solution of Intermediate 515A (170 mg, 0.40 mmol), methyl 7-bromo-1-chloroisoquinoline-3-carboxylate (130 mg, 0.42 mmol), and $K_2CO_3$ (220 mg, 1.6 mmol) in DMF (4.0 mL) purged with $N_2$ was added $PdCl_2(dppf)$ (18 mg, 0.024 mmol). The reaction mixture was stirred at 100° C. overnight. The reaction mixture was diluted with EtOAc. The organic layer was washed with water and brine, dried over anhydrous sodium sulfate, and concentrated. The crude product was purified by flash column chromatography (24 g silica gel cartridge; A=Hex, B=EtOAc; 15 min grad.; 0% B to 100% B; flow rate=35 mL/min) to give the title compound (120 mg, 0.188 mmol, 46.9% yield). $^1$H NMR (400 MHz, CHLOROFORM-d) δ 8.69-8.57 (m, 2H), 8.46 (d, J=0.7 Hz, 1H), 8.17 (s, 1H), 7.96-7.75 (m, 2H), 6.42 (d, J=16.2 Hz, 1H), 6.34 (d, J=16.2 Hz, 1H), 4.24 (s, 2H), 4.03 (s, 3H), 2.11-2.09 (m, 1H), 1.73-1.68 (m, 6H), 1.54-1.49 (m, 6H), 1.27-1.24 (m, 2H), 1.15-1.10 (m, 2H). MS (ESI) 638 (M+H).

Step B. Example 517

To a solution of Intermediate 517A (17 mg, 0.027 mmol) in MeOH (0.30 mL) and THF (0.30 mL) was added a solution of 25% sodium methoxide in MeOH (0.030 mL, 0.13 mmol). The reaction mixture was stirred at rt overnight. Water (0.10 mL) was added and the reaction mixture was stirred for 0.5 h. The reaction mixture was concentrated, redissolved in DMF, acidified with acetic acid (0.05 mL), and filtered. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 57-82% B over 20 minutes, then a 2-minute hold at 100% B; Flow: 20 mL/min.). Fractions containing the desired product were combined, concentrated and dried in vacuo to afford the title compound (5.1 mg, 0.008 mmol, 30% yield). $^1$H NMR (500 MHz, DMSO-$d_6$) δ 8.82 (s, 2H), 8.14 (s, 1H), 8.06 (s, 1H), 8.00 (br d, J=8.5 Hz, 1H), 7.91 (br d, J=8.2 Hz, 1H), 6.44 (d, J=16.0 Hz, 1H), 6.38 (d, J=16.0 Hz, 1H), 4.22 (s, 2H), 4.11 (s, 3H), 2.34-2.26 (m, 1H), 1.65-1.56 (m, 6H), 1.42-1.34 (m, 6H), 1.19-1.12 (m, 2H), 1.08 (br d, J=2.4 Hz, 2H). FXR $EC_{50}$ (nM)=42. MS (ESI) 620 (M+H).

Example 518

(E)-7-(2-(4-((5-cyclopropyl-3-(3,5-dichloropyridin-4-yl)isoxazol-4-yl)methoxy) bicyclo[2.2.2]octan-1-yl)vinyl)-1-isopropoxyisoquinoline-3-carboxylic acid (518)

To a vial containing i-PrOH (291 μL) was added 60% NaH (7.3 mg, 0.18 mmol). After 10 min, Intermediate 517A (13 mg, 0.020 mmol) was added. After stirring at rt overnight, additional 60% NaH (7.3 mg, 0.18 mmol) and THF (0.2 mL) were added. The reaction mixture was heated to 70° C. for 1 h. The reaction was quenched with sat. aq. NH$_4$Cl and extracted with EtOAc. The organic layer was washed with water and brine, dried over anhydrous sodium sulfate, and concentrated via vacuum. The crude product was purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 57-82% B over 20 minutes, then a 2-minute hold at 100% B; Flow: 20 mL/min.). Fractions containing the desired product were combined, concentrated and dried in vacuo to afford the title compound (3.4 mg, 0.005 mmol, 24% yield). $^1$H NMR (400 MHz, DMSO-d$_6$) δ 8.84 (s, 2H), 8.10 (d, J=0.7 Hz, 1H), 8.05-7.86 (m, 3H), 6.55-6.27 (m, 2H), 5.64 (quin, J=6.2 Hz, 1H), 4.24 (s, 2H), 2.36-2.23 (m, 1H), 1.69-1.53 (m, 6H), 1.47-1.31 (m, 12H), 1.16 (dt, J=8.4, 2.9 Hz, 2H), 1.11-1.07 (m, 2H). FXR EC$_{50}$ (nM)=62. MS (ESI) 648 (M+H).

Example 519

7-((4-((5-cyclopropyl-3-(3,5-dichloropyridin-4-yl)isoxazol-4-yl)methoxy) bicyclo[2.2.2]octan-1-yl)ethynyl)-1-(4-methylpiperazin-1-yl)isoquinoline-3-carboxylic acid (519)

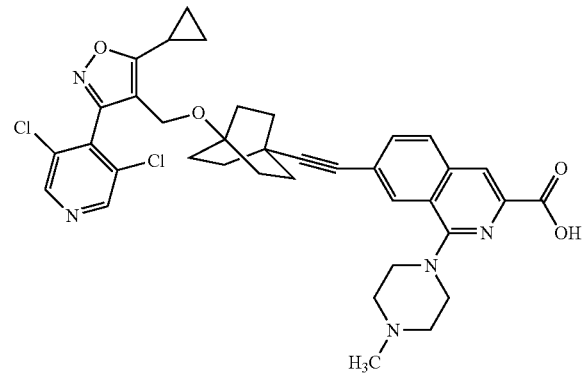

Step A. Intermediate 519A. Preparation of 3,5-dichloroisonicotinaldehyde oxime

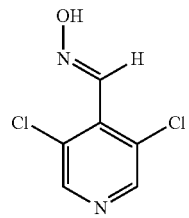 [SMILES: O/N=C/c1c(Cl)cncc1Cl]

Hydroxylamine hydrochloride (0.592 g, 8.52 mmol) was added to a solution of 3,5-dichloroisonicotinaldehyde (1.00 g, 5.68 mmol) in pyridine (2.8 mL) at rt, giving a mild exotherm. After 10 min, the excess pyridine was removed in vacuo. The residue was basified with 1 M aq. K$_2$HPO$_4$ and extracted with EtOAc. A white solid formed, which was collected by filtration. The organic layer was washed with brine, dried over Na$_2$SO$_4$, filtered and concentrated. The filtered solid and concentrated material were combined to provide the title compound (1.07 g, 5.60 mmol, 99% yield) as a white solid as a 2.5:1 E:Z ratio, which was used without further purification. Major isomer: $^1$H NMR (400 MHz, DMSO-d$_6$) δ 12.33 (s, 1H), 8.71 (s, 2H), 8.28 (s, 1H). Minor isomer: $^1$H NMR (400 MHz, DMSO-d$_6$) δ 11.88 (s, 1H), 8.69 (s, 2H), 7.70 (s, 1H). MS (ESI) 190.9 (M+H).

Step B. Intermediate 519B. Preparation of ethyl 5-cyclopropyl-3-(3,5-dichloropyridin-4-yl)isoxazole-4-carboxylate

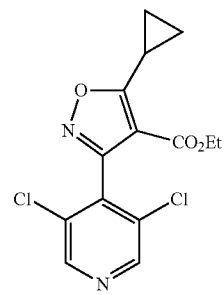 [SMILES: CCOC(=O)c1c(-c2c(Cl)cncc2Cl)noc1C1CC1]

To a 500 mL 3 neck round bottom flask containing ethyl 3-cyclopropyl-3-oxopropanoate (161 g, 1030 mmol) was added TEA (470 mL). The reaction mixture was stirred at rt for 15 min and then cooled to 5° C. A solution of Intermediate 519A (233 g, 1030 mmol) in EtOH (470 mL) was added over 10 min and the reaction mixture was warmed to rt and stirred for 15 h. The reaction mixture was concentrated and purified by silica gel chromatography. The isolated solid was suspended in n-pentane, stirred for 10 min, filtered, and washed with n-pentane to obtain the title compound (300 g, 917 mmol, 89% yield) as white solid. $^1$H NMR (400 MHz, CHLOROFORM-d) δ 8.61 (s, 2H), 4.15 (q, J=7.1 Hz, 2H), 2.94 (tt, J=8.4, 5.1 Hz, 1H), 1.47-1.38 (m, 2H), 1.34-1.26 (m, 2H), 1.06 (t, J=7.1 Hz, 3H). MS (ESI) 327.1 (M+H).

Step C. Intermediate 519C. Preparation of (5-cyclopropyl-3-(3,5-dichloropyridin-4-yl) isoxazol-4-yl)methanol

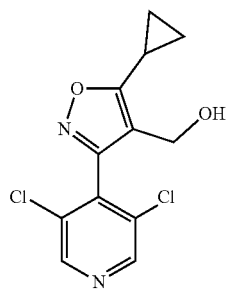 [SMILES: OCc1c(-c2c(Cl)cncc2Cl)noc1C1CC1]

To a solution of 519B (50.0 g, 153 mmol) in anhydrous CH₂Cl₂ (2000 mL) at −78° C. was added a 1 M solution of DIBAL-H in CH₂Cl₂ (428 mL, 428 mmol) over 8 min. After 5 min, the reaction was slowly quenched with an aqueous solution of Rochelle's salt (450 g in 1 L water). The reaction mixture was vigorously stirred at rt overnight. The layers were separated and the aqueous layer was extracted with CH₂Cl₂ (2000 L). The combined organic layers were washed with brine (1000 L), dried (Na₂SO₄), and concentrated. The crude material was dissolved in CH₂Cl₂ (100 mL) and while stirring, n-pentane (400 mL) was added. The mixture was stirred for 30 min and then the solution was decanted. The solid was washed with n-pentane (200 mL), which was decanted. The material was dried under vacuum to provide the title compound (41.0 g, 138 mmol, 90% yield) as white solid. ¹H NMR (500 MHz, CHLOROFORM-d) δ 8.64 (s, 2H), 4.46 (s, 2H), 2.19 (tt, J=8.4, 5.1 Hz, 1H), 1.33-1.26 (m, 2H), 1.22-1.14 (m, 2H). MS (ESI) 285.2 (M+H).

Step D. Intermediate 69A. Preparation of methyl 4-((5-cyclopropyl-3-(3,5-dichloropyridin-4-yl)isoxazol-4-yl)methoxy)bicyclo[2.2.2]octane-1-carboxylate

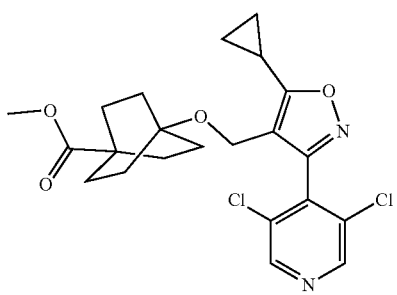 [SMILES: COC(=O)C12CCC(OCc3c(-c4c(Cl)cncc4Cl)noc3C3CC3)(CC1)CC2]

To a pressure vial was added Intermediate 519C (2.57 g, 9.00 mmol), Intermediate 4A (3.97 g, 13.5 mmol), and trifluoromethyltoluene (18 mL). The reaction mixture was stirred to ensure the materials were well mixed. Silver trifluoromethanesulfonate (3.47 g, 13.5 mmol) was added. While stirring 2,6-di-tert-butylpyridine (3.96 mL, 18.0 mmol) was added. The reaction mixture was capped and heated to 100° C. overnight. Additional Intermediate 4A (2.0 g) was added and the reaction mixture was heated to 100° C. for 2 h. The reaction mixture was diluted with EtOAc and washed with 1 M aq. HCl. The aqueous layer was extracted with EtOAc (2×). The combined organic layers were washed with 1 M aq. HCl (2×) and brine, dried (MgSO₄), and filtered through Celite. The crude material was purified by silica gel chromatography to provide the title compound (1.87 g, 4.15 mmol, 46% yield) as a colorless glass. ¹H NMR (500 MHz, CHLOROFORM-d) δ 8.61 (s, 2H), 4.20 (s, 2H), 3.62 (s, 3H), 2.08 (tt, J=8.5, 5.0 Hz, 1H), 1.88-1.77 (m, 6H), 1.48-1.40 (m, 6H), 1.27-1.21 (m, 2H), 1.16-1.08 (m, 2H). MS (ESI) 451.4 (M+H).

Step E. Intermediate 276A. Preparation of (4-((5-cyclopropyl-3-(3,5-dichloropyridin-4-yl)isoxazol-4-yl)methoxy)bicyclo[2.2.2]octan-1-yl)methanol

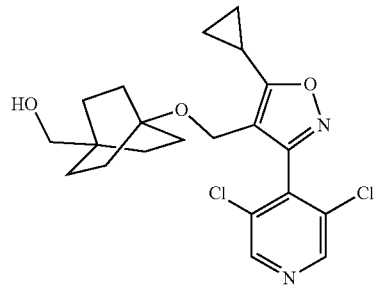 [SMILES: OCC12CCC(OCc3c(-c4c(Cl)cncc4Cl)noc3C3CC3)(CC1)CC2]

To a stirred solution of Intermediate 69A (1.10 g, 2.44 mmol) in THF (24 mL) at −78° C. was added a 2 M solution of LAH in THF (1.03 mL 2.07 mmol) dropwise. The reaction mixture was slowly warmed to 0° C. for 30 min. The reaction was quenched dropwise sequentially with water (0.08 mL), 15% aq. NaOH (0.08 mL), and water (0.24 mL). The reaction mixture was stirred vigorously for 1 h. MgSO₄ was added and the mixture was filtered and concentrated. The crude product was purified by silica gel chromatography to provide the title compound (1.01 g, 2.39 mmol, 98% yield) as a white foam. ¹H NMR (500 MHz, CHLOROFORM-d) δ 8.62 (s, 2H), 4.23 (s, 2H), 3.24 (d, J=5.5 Hz, 2H), 2.18-2.08 (m, 1H), 1.53-1.40 (m, 12H), 1.34-1.23 (m, 2H), 1.20-1.09 (m, 2H). MS (ESI) 423.0 (M+H).

Step F. Intermediate 519D. Preparation of 4-((5-cyclopropyl-3-(3,5-dichloropyridin-4-yl)isoxazol-4-yl)methoxy)bicyclo[2.2.2]octane-1-carbaldehyde

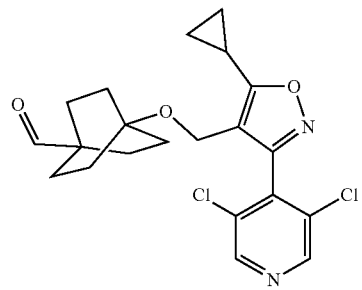 [SMILES: O=CC12CCC(OCc3c(-c4c(Cl)cncc4Cl)noc3C3CC3)(CC1)CC2]

To a solution of oxalyl chloride (0.019 mL, 0.21 mmol) in CH₂Cl₂ (1.1 mL) at −78° C. was added a solution of DMSO (0.035 mL, 0.49 mmol) in CH₂Cl₂ (0.55 mL) dropwise and the reaction mixture was stirred for 10 min. Then, a solution of Intermediate 276A (0.069 g, 0.16 mmol) in CH₂Cl₂ (1 mL) was added slowly, the flask was rinsed with CH₂Cl₂ (0.5), and the reaction mixture was stirred for 30 min. TEA (0.11 mL, 0.82 mmol) was added and the reaction mixture was warmed to rt and stirred for 30 min. The reaction mixture was diluted with CH₂Cl₂ and washed with water, sat. aq. NaHCO₃, and brine, dried (MgSO₄), and concentrated to provide the title compound (0.070 g, 0.16 mmol, 100% yield) as a foam, which solidified to an off-white solid. ¹H NMR (500 MHz, CHLOROFORM-d) δ 9.40 (s, 1H), 8.60 (s, 2H), 4.21 (s, 2H), 2.07 (tt, J=8.5, 5.0 Hz, 1H), 1.73-1.63 (m, 6H), 1.51-1.43 (m, 6H), 1.27-1.22 (m, 2H), 1.15-1.09 (m, 2H). MS (ESI) 421.0 (M+H).

Step G. Intermediate 519E. Preparation of 5-cyclopropyl-3-(3,5-dichloropyridin-4-yl)-4-(((4-ethynylbicyclo[2.2.2]octan-1-yl)oxy)methyl)isoxazole

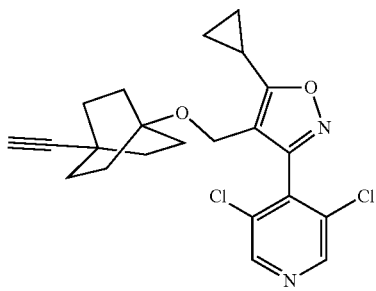 [SMILES: C#CC12CCC(OCc3c(-c4c(Cl)cncc4Cl)noc3C3CC3)(CC1)CC2]

To a mixture of Intermediate 519D (1.80 g, 4.26 mmol) and K$_2$CO$_3$ (1.18 g, 8.52 mmol) was added anhydrous MeOH (17 mL) and the mixture was stirred at rt for 30 min. Dimethyl (1-diazo-2-oxopropyl)phosphonate (0.98 g, 5.1 mmol) was added and the reaction mixture was stirred at rt overnight. The reaction mixture was diluted with Et$_2$O, washed with 1 M aq. K$_2$HPO$_4$, dried (MgSO$_4$), and concentrated. The crude product was purified by silica gel chromatography to afford the title compound (1.40 g, 3.36 mmol, 79% yield) as a colorless glass, which solidified to a white solid. $^1$H NMR (500 MHz, CHLOROFORM-d) δ 8.60 (s, 2H), 4.18 (s, 2H), 2.10-2.03 (m, 2H), 1.87-1.76 (m, 6H), 1.48-1.38 (m, 6H), 1.27-1.21 (m, 2H), 1.15-1.09 (m, 2H). MS (ESI) 417.4 (M+H).

Step H. Intermediate 519F. Preparation of methyl 5-bromo-2-(dibromomethyl) benzoate

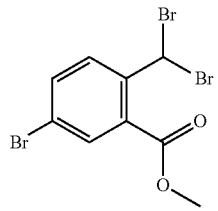

A solution of methyl 5-bromo-2-methylbenzoate (5.00 g, 21.8 mmol), NBS (3.88 g, 21.8 mmol), and AIBN (0.179 g, 1.09 mmol) was heated to reflux for 6 h and then stirred at rt overnight. Additional AIBN (0.179 g, 1.091 mmol) and NBS (3.88 g, 21.8 mmol) were added and the reaction mixture was refluxed for 2 days. Additional AIBN (0.179 g, 1.09 mmol) and NBS (3.88 g, 21.8 mmol) were added and the reaction mixture was refluxed overnight. The reaction mixture was filtered and diluted with CH$_2$Cl$_2$. The organic layer was washed with 1 M NaOH, aq. Na$_2$S$_2$O$_3$, and brine, dried (MgSO$_4$), and filtered through a plug of silica gel to provide the title compound (7.59 g, 19.6 mmol, 90% yield) as an off-white solid. $^1$H NMR (500 MHz, CHLOROFORM-d) δ 8.05 (d, J=7.7 Hz, 1H), 8.04 (d, J=1.1 Hz, 1H), 7.98 (s, 1H), 7.75 (dd, J=8.5, 2.2 Hz, 1H), 3.97 (s, 3H).

Step I. Intermediate 519G. Preparation of methyl 5-bromo-2-formylbenzoate

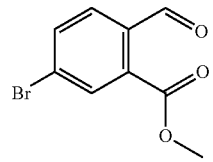

To a suspension of Intermediate 519F (7.31 g, 18.9 mmol) in i-PrOH (132 mL) in a flask protected from light was added a solution of silver nitrate (6.58 g, 38.7 mmol) in water (13 mL) dropwise over 20 min. The reaction mixture was heated to reflux for 1 h. The reaction mixture was filtered and concentrated to remove the i-PrOH. The product was extracted with EtOAc (3×) and the combined organic layers were washed with water and brine, dried (MgSO$_4$), and concentrated. The title compound (3.28 g, 13.5 mmol, 71% yield) was isolated and used without further purification. $^1$H NMR (500 MHz, CHLOROFORM-d) δ 10.59 (s, 1H), 8.14 (d, J=1.7 Hz, 1H), 7.85-7.82 (m, 1H), 7.82-7.78 (m, 1H), 4.00 (s, 3H).

Step J. Intermediate 519H. Preparation of methyl 7-bromo-1-oxo-1,2-dihydroisoquinoline-3-carboxylate

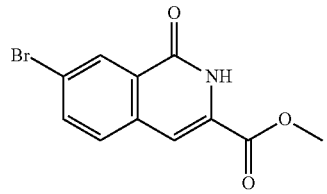 [SMILES: COC(=O)c1cc2ccc(Br)cc2c(=O)[nH]1]

Step. 1. A solution of Intermediate 519G (1.65 g, 6.79 mmol), benzoylglycine (1.34 g, 7.47 mmol), sodium acetate (0.613 g, 7.47 mmol), and acetic anhydride (3.2 mL, 34 mmol) was heated to 100° C. for 4 h. The reaction mixture was cooled to rt. Water was added to precipitate the product, which was filtered and washed with water. The material was dried under vacuum to provide crude methyl 5-bromo-2-((5-oxo-2-phenyloxazol-4(5H)-ylidene)methyl)benzoate as a dark yellow solid, which was taken forward without further purification.

Step 2. To a solution of the material from the previous step (2.62 g, 6.79 mmol) in MeOH (41 mL) was added KOH (0.762 g, 13.6 mmol). The reaction mixture was refluxed for 1 h. The reaction mixture was concentrated and partitioned between water/EtOAc. The layers were separated and the aqueous layer was extracted with EtOAc (2×). The combined organic layers were washed with water and brine, dried (MgSO$_4$), and concentrated. To the crude material was added 1:1 CH$_3$CN/water with 0.1% TFA (200 mL). The mixture was heated to 75° C. for 1 h. The reaction mixture was cooled to rt and then 0° C. The precipitated product was filtered, washed with water, and dried under vacuum to provide the title compound (1.83 g, 6.50 mmol, 53% yield) as a beige solid. $^1$H NMR (500 MHz, DMSO-d$_6$) δ 11.42 (br s, 1H), 8.32 (d, J=2.2 Hz, 1H), 7.98 (dd, J=8.5, 2.2 Hz, 1H), 7.89 (d, J=8.5 Hz, 1H), 7.46 (s, 1H), 3.89 (s, 3H). MS (ESI) 282.0, 284.0 (M+H).

Step K. Intermediate 519J. Preparation of methyl 7-bromo-1-chloroisoquinoline-3-carboxylate

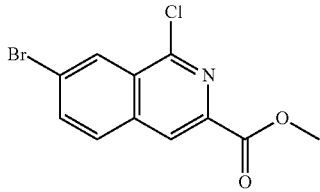 [SMILES: COC(=O)c1cc2ccc(Br)cc2c(Cl)n1]

To a solution of Intermediate 519H (0.7140 g, 2.53 mmol) in anhydrous toluene (7.7 mL) was added DIPEA (0.044 mL, 0.25 mmol) and POCl$_3$ (0.28 mL, 3.0 mmol). The reaction mixture was heated to reflux for 3.5 h. The reaction mixture was concentrated. The crude material was redissolved in CH$_2$Cl$_2$ and filtered through a plug of silica gel, washing with CH$_2$Cl$_2$, and concentrated to provide the title compound (0.750 g, 2.50 mmol, 99% yield) as a white solid. $^1$H NMR (500 MHz, CHLOROFORM-d) δ 8.62-8.58 (m, 1H), 8.51 (s, 1H), 7.97-7.92 (m, 1H), 7.91-7.86 (m, 1H), 4.06 (s, 3H). MS (ESI) 300.1, 302.1 (M+H).

Step L. Intermediate 519K. Preparation of methyl 7-bromo-1-(4-methylpiperazin-1-yl) isoquinoline-3-carboxylate

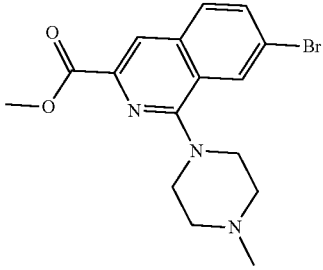 [SMILES: COC(=O)c1cc2ccc(Br)cc2c(N2CCN(C)CC2)n1]

To a solution of Intermediate 519J (0.750 g, 2.50 mmol) in DMF (8.9 mL) was added 1-methylpiperazine (0.83 mL, 7.5 mmol) followed by DIPEA (1.3 mL, 7.5 mmol). The reaction mixture was microwaved at 120° C. for 20 min. The reaction mixture was diluted with EtOAc and washed with water (5×) and brine, dried (MgSO$_4$), and concentrated to afford the title compound (0.865 g, 2.38 mmol, 95% yield) as a beige solid, which was used without further purification. $^1$H NMR (500 MHz, CHLOROFORM-d) δ 8.25 (d, J=1.1 Hz, 1H), 8.09 (d, J=0.8 Hz, 1H), 7.78-7.73 (m, 2H), 4.00 (s, 3H), 3.61-3.49 (m, 4H), 2.72 (br t, J=4.7 Hz, 4H), 2.43 (s, 3H). MS (ESI) 364.2, 366.2 (M+H).

Step M. Example 519

Step 1. A pressure with CuI (0.18 mg, 0.94 µmot) and PdCl$_2$(dppf) (0.68 mg, 0.94 µmol, Intermediate 519K (0.015 g, 0.061 mmol) and Intermediate 519E (0.020 g, 0.047 mmol)) was purged with nitrogen and vacuum (3×). Anhydrous THF (0.37 mL) and TEA (0.10 mL) were added and the reaction mixture was stirred at 70° C. for 1.5 h. The reaction mixture was filtered and concentrated.

Step 2. The crude material was dissolved in THF (0.39 mL) and 1 M aq. NaOH (0.28 mL, 0.28 mmol) was added. The reaction mixture was stirred at 70° C. for 2 h. The reaction mixture was concentrated, acidified with 1 M aq. HCl, and the product was extracted with EtOAc (3×). The combined organic layers were dried (MgSO$_4$) and concentrated. The crude material was purified by RP-Prep. HPLC to provide the title compound (11 mg, 0.020 mmol, 43% yield). $^1$H NMR (500 MHz, DMSO-d$_6$) δ 8.80 (s, 2H), 8.09 (s, 1H), 7.99 (br d, J=8.5 Hz, 1H), 7.91 (s, 1H), 7.60 (br d, J=8.2 Hz, 1H), 4.19 (s, 2H), 3.62-3.43 (m, 2H), 3.36 (br s, 2H), 2.65 (br s, 4H), 2.32 (s, 3H), 2.30-2.23 (m, 1H), 1.88-1.79 (m, 6H), 1.42-1.31 (m, 6H), 1.18-1.11 (m, 2H), 1.10-1.03 (m, 2H). FXR EC$_{50}$ (nM)=28. Mouse in vivo (3 mg/kg, @ 6 h): Cypa7a1=−92%, Ffg15=+1.4×. MS (ESI) 686.3 (M+H).

Example 520

3-((4-((5-cyclopropyl-3-(3,5-dichloropyridin-4-yl) isoxazol-4-yl)methoxy) bicyclo[2.2.2]octan-1-yl) ethynyl)-6-fluoroimidazo[1,2-a]pyridine-8-carboxylic acid

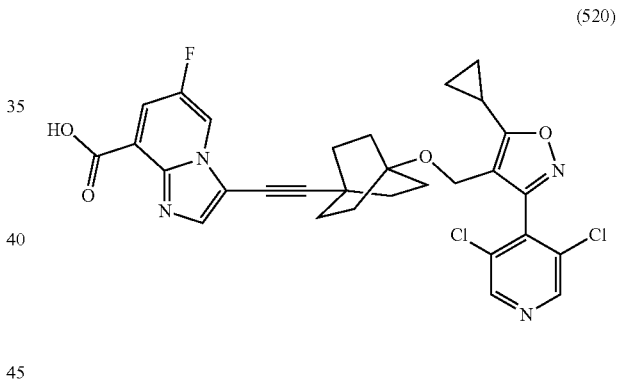

(520)

Step A. Intermediate 520A. Preparation of 8-bromo-6-fluoroimidazo[1,2-a]pyridine, HCl

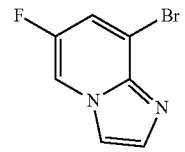

A pressure vial containing 3-bromo-5-fluoropyridin-2-amine (0.500 g, 2.62 mmol) and 50% aq. chloroacetaldehyde (0.67 mL, 5.2 mmol) was heated to 80° C. The reaction mixture was concentrated. The crude solid was suspended in CH$_2$Cl$_2$ and the yellow solution was decanted (3×). The title compound (0.674 g, 2.62 mmol, 100% yield) was isolated as a pale brown solid. $^1$H NMR (500 MHz, DMSO-d$_6$) δ 9.15 (dd, J=3.7, 2.1 Hz, 1H), 8.40-8.31 (m, 2H), 8.09 (s, 1H). MS (ESI) 215.1 (M+H).

Step B. Intermediate 520B. Preparation of 6-fluoro-imidazo[1,2-a]pyridine-8-carbonitrile

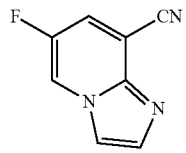 [SMILES: N#Cc1cc(F)cn2ccnc12]

A microwave vial containing Intermediate 520A (0.300 g, 1.40 mmol), Xantphos (0.040 g, 0.070 mmol), Pd$_2$(dba)$_3$ (0.032 g, 0.035 mmol), and zinc cyanide (0.328 g, 2.79 mmol) was purged with nitrogen (3×) and then anhydrous DMF (5 mL) was added. The reaction mixture was microwaved at 120° C. for 1 h. The solution was decanted from the solids in the bottom of the tube, which were rinsed with a small amount of DMF (2×). To the combined solutions was added water (20 mL) dropwise. A brown precipitate formed. The precipitate was filtered and washed with water. The aqueous filtrate was extracted with EtOAc (3×) and then the combined organic layers were washed with water (3×) and brine, dried (MgSO$_4$), and concentrated. The title compound (0.158 g, 0.983 mmol, 71% yield) was isolated as a beige solid, which was used without further purification. $^1$H NMR (500 MHz, CHLOROFORM-d) δ 8.34 (dd, J=3.4, 2.3 Hz, 1H), 7.87 (d, J=1.1 Hz, 1H), 7.77 (d, J=1.4 Hz, 1H), 7.59 (dd, J=7.7, 2.2 Hz, 1H). MS (ESI) 162.2 (M+H).

Step C. Intermediate 520C. Preparation of 6-fluoro-3-iodoimidazo[1,2-a]pyridine-8-carbonitrile

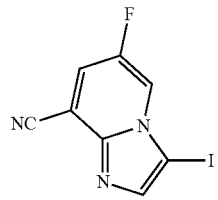 [SMILES: N#Cc1cc(F)cn2c(I)cnc12]

To a solution of Intermediate 520B (0.144 g, 0.892 mmol) in CH$_3$CN (3.6 mL) at 0° C. was added NIS in one portion. The reaction mixture was slowly warmed to rt and stirred at rt overnight. An addition 0.2 equiv of NIS were added at rt. After 10 min, the reaction mixture was concentrated. The material was suspended in CH$_2$Cl$_2$ and washed with 1 M NaOH (2×), aq. Na$_2$S$_2$O$_3$, and brine, dried (MgSO$_4$), and concentrated to provide the title compound (0.236 g, 0.822 mmol, 92% yield), which was used without further purification. $^1$H NMR (500 MHz, CHLOROFORM-d) δ 8.36 (dd, J=3.6, 2.2 Hz, 1H), 7.92 (s, 1H), 7.64 (dd, J=7.4, 2.2 Hz, 1H). MS (ESI) 288.1 (M+H).

Step D. Intermediate 520D. Preparation of methyl 6-fluoro-3-iodoimidazo[1,2-a]pyridine-8-carboxylate

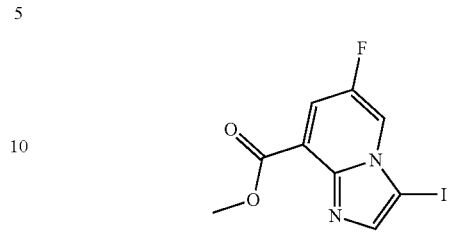

To a solution of Intermediate 520C (0.100 g, 0.348 mmol) in MeOH (3.5 mL) was added conc. H$_2$SO$_4$ (0.50 mL, 9.4 mmol). The reaction mixture was refluxed for 2 days. The reaction mixture was concentrated. The solution was partitioned between EtOAc and 1 M NaOH. The layers were separated and the aqueous layer was extracted with EtOAc (2×). The combined organic layers were washed with brine, dried (MgSO$_4$) and concentrated. The crude product was purified by silica gel chromatography to provide the title compound (0.0635 g, 0.198 mmol, 57% yield) as a tan solid. $^1$H NMR (500 MHz, CHLOROFORM-d) δ 8.30 (dd, J=3.6, 2.5 Hz, 1H), 7.94 (dd, J=8.4, 2.3 Hz, 1H), 7.87 (s, 1H), 4.06 (s, 3H). MS (ESI) 321.0 (M+H).

Step E. Example 520

The title compound was prepared from Intermediate 520D and Intermediate 519E according to methods described for the synthesis of Example 130 (Steps B and C): (9.7 mg, 0.016 mmol, 28% yield). $^1$H NMR (500 MHz, DMSO-d$_6$) δ 8.78 (s, 2H), 8.67 (br s, 1H), 7.99 (br d, J=8.1 Hz, 1H), 7.95 (s, 1H), 4.21 (s, 2H), 2.33-2.19 (m, 1H), 2.00-1.82 (m, 6H), 1.51-1.32 (m, 6H), 1.19-1.11 (m, 2H), 1.07 (br d, J=2.3 Hz, 2H). FXR EC$_{50}$ (nM)=4. MS (ESI) 595.0 (M+H).

Example 521

7-((4-((5-cyclopropyl-3-(3,5-dichloropyridin-4-yl)isoxazol-4-yl)methoxy)bicyclo[2.2.2]octan-1-yl)ethynyl)-1-methoxyisoquinoline-3-carboxylic acid

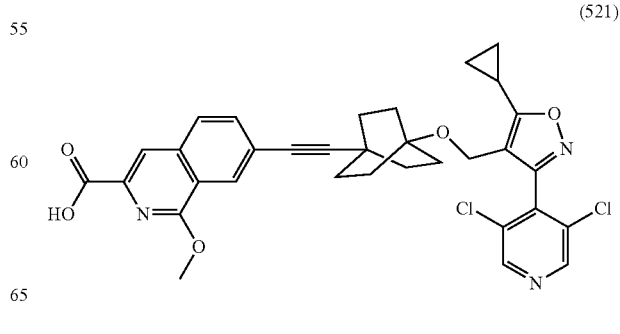

(521)

Step A. Intermediate 521A. Preparation of methyl 7-bromo-1-methoxyisoquinoline-3-carboxylate

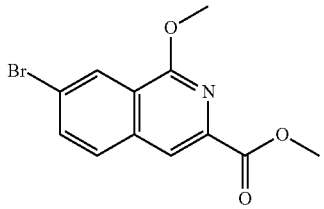 [SMILES: COC(=O)c1cc2ccc(Br)cc2c(OC)n1]

To a pressure vial containing Intermediate 519J (0.100 g, 0.333 mmol) was added 25% sodium methoxide (0.38 mL, 1.7 mmol) in MeOH. The reaction mixture was heated to 70° C. for 2 h.

The reaction mixture was cooled to rt and diluted with water. The precipitate was filtered, washed with water, and dried under vacuum to afford the title compound (0.0758 g, 0.256 mmol, 77% yield) as a white solid. $^1$H NMR (500 MHz, CHLOROFORM-d) δ 8.50-8.44 (m, 1H), 8.13 (s, 1H), 7.85-7.79 (m, 1H), 7.78-7.72 (m, 1H), 4.23 (s, 3H), 4.01 (s, 3H). MS (ESI) 296.0, 298.0 (M+H).

Step B. Example 521

The title compound was prepared from Intermediate 521A and Intermediate 519E according to methods described for the synthesis of Example 130 (Steps B and C): (11.8 mg, 0.019 mmol, 58% yield). $^1$H NMR (500 MHz, DMSO-$d_6$) δ 8.79 (d, J=1.4 Hz, 2H), 8.12 (s, 1H), 8.09 (s, 1H), 8.00 (d, J=8.3 Hz, 1H), 7.66 (br d, J=8.4 Hz, 1H), 4.20 (s, 2H), 4.12 (s, 3H), 2.32-2.21 (m, 1H), 1.95-1.78 (m, 6H), 1.49-1.36 (m, 6H), 1.18-1.11 (m, 2H), 1.08 (br s, 2H). FXR EC$_{50}$ (nM)=40. MS (ESI) 618.2 (M+H).

Example 522

6-((4-((5-cyclopropyl-3-(3,5-dichloropyridin-4-yl)isoxazol-4-yl)methoxy) bicyclo[2.2.2]octan-1-yl)ethynyl)-4-methoxy-N,N-dimethylquinoline-2-carboxamide (522)

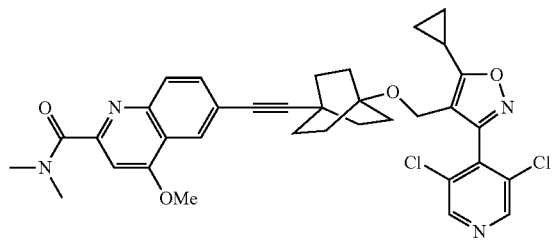

To a solution of Example 375 (0.012 g, 0.019 mmol) and HATU (8.1 mg, 0.021 mmol) in DMF (0.19 ml) was added a solution of 2 M dimethylamine in MeOH (0.015 ml, 0.029 mmol) followed by TEA (8.1 μL, 0.058 mmol). The reaction mixture was stirred at rt overnight. The reaction mixture was filtered, diluted with DMF, and purified by RP-Prep. HPLC to provide the title compound (10 mg, 0.016 mmol, 83% yield). $^1$H NMR (500 MHz, DMSO-$d_6$) δ 8.80 (s, 2H), 8.03 (s, 1H), 7.87 (d, J=8.5 Hz, 1H), 7.63 (br d, J=8.9 Hz, 1H), 7.09 (s, 1H), 4.19 (s, 2H), 4.04 (s, 3H), 3.03 (s, 3H), 2.94 (s, 3H), 2.33-2.22 (m, 1H), 1.88-1.77 (m, 6H), 1.45-1.31 (m, 6H), 1.20-1.10 (m, 2H), 1.06 (br d, J=2.1 Hz, 2H). FXR EC$_{50}$ (nM)=52. MS (ESI) 645.2 (M+H).

Example 523

5-((4-((5-cyclopropyl-3-(3,5-dichloropyridin-4-yl)isoxazol-4-yl)methoxy) bicyclo[2.2.2]octan-1-yl)ethynyl)-6-(3-fluoroazetidin-1-yl)nicotinic acid (523)

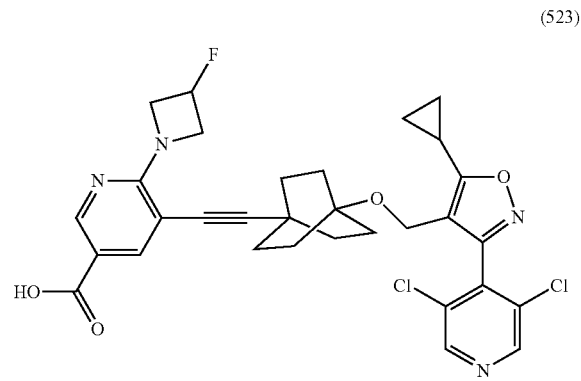 [SMILES: O=C(O)c1cnc(N2CC(F)C2)c(C#CC23CCC(OCc4c(-c5c(Cl)cncc5Cl)noc4C4CC4)(CC2)CC3)c1]

Step A. Intermediate 523A. Preparation of methyl 5-bromo-6-(3-fluoroazetidin-1-yl) nicotinate

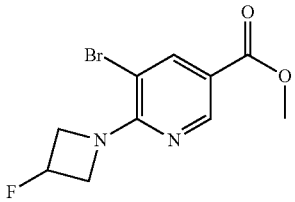 [SMILES: COC(=O)c1cnc(N2CC(F)C2)c(Br)c1]

To a solution of methyl 5-bromo-6-chloronicotinate (0.130 g, 0.519 mmol) in DMF (1.6 mL) was added 3-fluoroazetidine, HCl (0.174 g, 1.56 mmol) followed by Hunig's Base (0.54 mL, 3.1 mmol). The reaction mixture was microwaved at 120° C. for 20 min. The reaction mixture was diluted with water and a dark brown precipitate formed, which was filtered and washed with water. The solid was dissolved in EtOAc/CH$_2$Cl$_2$ and filtered through a plug of silica gel to obtain the title compound (0.135 g, 0.468 mmol, 90% yield) as a pale brown solid. $^1$H NMR (500 MHz, CHLOROFORM-d) δ 8.70 (d, J=1.9 Hz, 1H), 8.21 (d, J=1.9 Hz, 1H), 5.46-5.25 (m, 1H), 4.69 (ddd, J=11.1, 6.0, 1.7 Hz, 1H), 4.65 (ddd, J=11.1, 5.9, 1.7 Hz, 1H), 4.52-4.47 (m, 1H), 4.47-4.42 (m, 1H), 3.89 (s, 3H). MS (ESI) 289.0, 291.0 (M+H).

Step B. Example 523

The title compound was prepared from Intermediate 523A and Intermediate 519E according to methods described for the synthesis of Example 130 (Steps B and C): (18.8 mg, 0.031 mmol, 64% yield). $^1$H NMR (500 MHz, DMSO-$d_6$) δ

8.81 (s, 2H), 8.50 (s, 1H), 7.76 (d, J=1.5 Hz, 1H), 5.55-5.28 (m, 1H), 4.57 (br dd, J=16.6, 5.3 Hz, 2H), 4.31-4.20 (m, 2H), 4.19 (s, 2H), 2.35-2.21 (m, 1H), 1.87-1.73 (m, 6H), 1.44-1.29 (m, 6H), 1.14 (br d, J=7.9 Hz, 2H), 1.08 (br d, J=2.7 Hz, 2H). FXR EC$_{50}$ (nM)=24. MS (ESI) 611.3 (M+H).

INTERMEDIATES

Preparation of Intermediate for Example 524. tert-Butyl 2-(5-ethyl-3-hydroxy-1H-pyrazol-1-yl)acetate

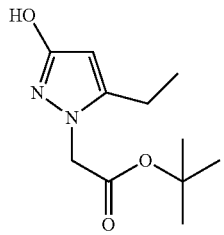 [SMILES: CCc1cc(O)nn1CC(=O)OC(C)(C)C]

5-ethyl-1H-pyrazol-3-ol (200 mg, 1.784 mmol) was combined with tert-butyl 2-bromoacetate (0.237 mL, 1.605 mmol) and K$_2$CO$_3$ (247 mg, 1.784 mmol) in acetone/DMF (8 mL/2 mL, 4:1). The reaction mixture was stirred at 25° C. for 16 hrs. Two isomers were formed in the reaction mixture. The reaction was concentrated, then diluted with EtOAc, washed with brine, dried over Na$_2$SO$_4$, filtered and concentrated. The residue was purified by column chromatography (24 g silica gel cartridge, eluting with 0-100% EtOAc/Hex) to give the title compound as a mixture, which was further purified via preparative HPLC (Column: Phenomenex Luna Axia 5u 30×100 (10 min grad); Mobile Phase A: 5:95 acetonitrile: water with 0.1% trifluoroacetic acid; Mobile Phase B: 95:5 acetonitrile: water with 0.1% trifluoroacetic acid; Gradient: 20-100% B over 10 minutes, then a 2-minute hold at 100% B; Flow: 40 mL/min). Fractions containing the desired product were combined, concentrated and dried in vacuo to afford the title compound (78 mg, 0.345 mmol, 19.33% yield) as a colorless oil. $^1$H NMR (500 MHz, CHLOROFORM-d) δ=5.48 (s, 1H), 4.49 (s, 2H), 2.47 (q, J=7.4 Hz, 2H), 1.46 (s, 9H), 1.25 (t, J=7.4 Hz, 3H). MS (ESI) 227.2 (M+H)$^+$.

Preparation of Intermediate for Example 527. Methyl 6-(bromomethyl)-4-(trifluoromethyl)picolinate

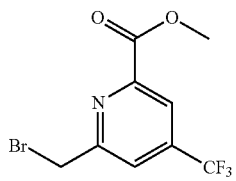 [SMILES: COC(=O)c1cc(C(F)(F)F)cc(CBr)n1]

A mixture of methyl 6-methyl-4-(trifluoromethyl)picolinate (300 mg, 1.369 mmol), NBS (244 mg, 1.369 mmol), and AIBN (22.48 mg, 0.137 mmol) in CCl$_4$ (7 ml) was stirred at 90° C. overnight. After cooling to RT, solid was filtered, and washed with CCl$_4$. Combined organic layers were washed with saturated aqueous NaHCO$_3$ and brine, dried over Na$_2$SO$_4$, and concentrated under reduced pressure. The residue was purified by column chromatography (24 g silica gel cartridge, eluting with 0-70% EtOAc/hexanes) to afford title compound (16 mg, 0.054 mmol, 3.92% yield) as an off-white foam. $^1$H NMR (500 MHz, CHLOROFORM-d) δ=8.27 (s, 1H), 7.91 (s, 1H), 4.70 (s, 2H), 4.06 (s, 3H). MS (ESI) 298.0 (M+H)$^+$.

Preparation of Intermediate for Example 528. Methyl 1-(cyclopropylmethyl)-3-hydroxy-1H-pyrazole-5-carboxylate

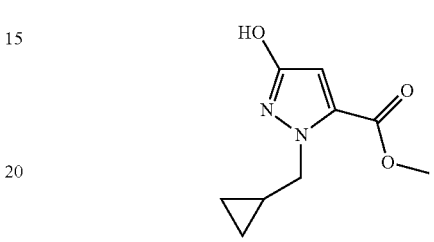

Step A. Intermediate 528A. Preparation of methyl 3-((tert-butyldimethylsilyl)oxy)-1H-pyrazole-5-carboxylate

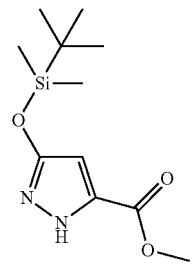 [SMILES: COC(=O)c1cc(O[Si](C)(C)C(C)(C)C)n[nH]1]

TBDMS-Cl (986 mg, 6.54 mmol) and imidazole (475 mg, 6.98 mmol) were added to a stirred suspension of methyl 3-hydroxy-1H-pyrazole-5-carboxylate (620 mg, 4.36 mmol) in acetonitrile (14 mL). The reaction mixture was stirred at RT for 20 min, and then concentrated. The residue was diluted with H$_2$O, extracted with EtOAc (2×). The combined organic layers were washed with brine, dried (Na$_2$SO$_4$), and concentrated under reduced pressure. The residue was purified by column chromatography (24 g silica gel cartridge, eluting with 0-30% EtOAc/hexanes) to give methyl 3-((tert-butyldimethylsilyl)oxy)-1H-pyrazole-5-carboxylate (980 mg, 3.82 mmol, 88% yield) as a white solid. $^1$H NMR (500 MHz, CHLOROFORM-d) 6.18 (s, 1H), 3.92 (s, 3H), 1.00 (s, 9H), 0.29 (s, 6H). MS (ESI) 257.1 (M+H)$^+$.

Step B. Intermediate 528B. Preparation of methyl 3-((tert-butyldimethylsilyl)oxy)-1-(cyclopropylmethyl)-1H-pyrazole-5-carboxylate

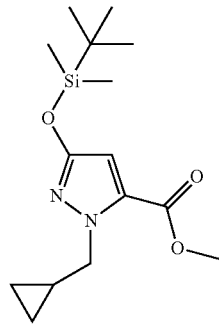 [SMILES: COC(=O)c1cc(O[Si](C)(C)C(C)(C)C)nn1CC1CC1]

Methyl 3-((tert-butyldimethylsilyl)oxy)-1H-pyrazole-5-carboxylate (200 mg, 0.780 mmol), cyclopropylmethanol (113 mg, 1.560 mmol), Ph₃P (368 mg, 1.404 mmol) and diisopropyl (E)-diazene-1,2-dicarboxylate (276 µl, 1.404 mmol) were dissolved in dry THF (3901 µl) and heated at 100° C. in a sealed vial for 16 hrs. After cooling to RT, the reaction mixture was directly purified by column chromatography (24 g, eluting with 0-60% EtOAc/Hexanes) to give methyl 3-((tert-butyldimethylsilyl)oxy)-1-(cyclopropylmethyl)-1H-pyrazole-5-carboxylate (160 mg, 0.515 mmol, 66.1% yield) as a colorless oil. $^1$H NMR (500 MHz, CHLOROFORM-d) δ 6.14 (s, 1H), 4.27 (d, J=7.2 Hz, 2H), 3.85 (s, 3H), 1.36-1.25 (m, 1H), 0.98 (s, 9H), 0.53-0.45 (m, 2H), 0.42-0.36 (m, 2H), 0.26 (s, 6H). MS (ESI) 311.2 (M+H)$^+$.

Step C. Intermediate 528. Methyl 1-(cyclopropylmethyl)-3-hydroxy-1H-pyrazole-5-carboxylate To a solution of methyl 3-((tert-butyldimethylsilyl)oxy)-1-(cyclopropylmethyl)-1H-pyrazole-5-carboxylate (160 mg, 0.515 mmol) in THF (2 mL) was added TBAF (0.773 mL, 0.773 mmol). The reaction was stirred at RT for 16 hrs. The reaction was diluted with water and extracted with ethyl acetate (2×). The combined organic layers were washed with brine and dried over sodium sulfate. The drying agent was removed by filtration and the filtrate concentrated under reduced pressure. The resulting residue was purified by column chromatography (24 g silica gel cartridge, eluting with 0-70% EtOAc/hexanes) to afford the title compound (69 mg, 0.352 mmol, 68.2% yield) as a white powder. $^1$H NMR (500 MHz, CHLOROFORM-d) δ 11.46 (br s, 1H), 6.16 (br s, 1H), 4.53-3.61 (m, 5H), 1.49-1.16 (m, 1H), 0.78-0.23 (m, 4H). MS (ESI) 197.1 (M+H)$^+$.

Preparation of Intermediate for Example 529. Methyl 1-ethyl-7-hydroxyisoquinoline-3-carboxylate

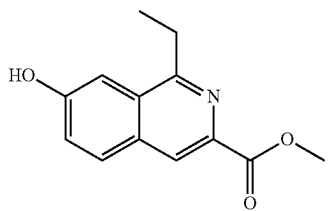 [SMILES: CCc1nc(C(=O)OC)cc2ccc(O)cc12]

Step A. Intermediate 529A. Preparation of methyl 1-ethyl-7-(4,4,5,5-tetramethyl-1,3,2-dioxaborolan-2-yl)isoquinoline-3-carboxylate

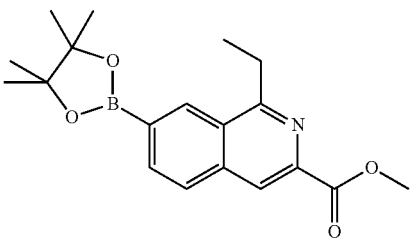

A mixture of methyl 7-chloro-1-ethylisoquinoline-3-carboxylate (160 mg, 0.641 mmol), 4,4,4',4',5,5,5',5'-octamethyl-2,2'-bi(1,3,2-dioxaborolane) (212 mg, 0.833 mmol) and potassium acetate (189 mg, 1.922 mmol) in Dioxane (3.2 mL) was sparged with nitrogen while stirring for 2 min. PdCl₂(dppf) (94 mg, 0.128 mmol) was then added and the reaction stirred at 100° C. for 2 hrs. After cooling to room temperature, the reaction was diluted with water and extracted with ethyl acetate (2×). Combined organic layers were washed with brine and dried over sodium sulfate. The drying agent was removed by filtration and the filtrate was concentrated under reduced pressure. The resulting residue was purified by column chromatography (12 g silica gel cartridge, eluting with 0-100% EtOAc/hexanes) to afford methyl 1-ethyl-7-(4,4,5,5-tetramethyl-1,3,2-dioxaborolan-2-yl)isoquinoline-3-carboxylate (219 mg, 0.645 mmol, 100% yield) as an oil. MS (ESI) 342.2 (M+H)$^+$.

Step B. Intermediate 529. Preparation of methyl 1-ethyl-7-hydroxyisoquinoline-3-carboxylate NaOH (1.290 mL, 1.290 mmol), followed by H₂O₂ (0.198 mL, 1.934 mmol) were added to a 0° C. solution of methyl 1-ethyl-7-(4,4,5,5-tetramethyl-1,3,2-dioxaborolan-2-yl)isoquinoline-3-carboxylate (219 mg, 0.645 mmol) in THF (3 mL). The reaction was maintained at 0° C. and after 5 minutes, the reaction was diluted with EtOAc and quenched with aq. Na₂SO₃ and washed with water and brine. Combined aqueous layers were back extracted with EtOAc and the combined organics were dried over Na₂SO₄, filtered and concentrated to dryness. The residue was purified by column chromatography (24 g silica gel cartridge, eluting with 0-60% EtOAc/Hexanes) to give methyl 1-ethyl-7-hydroxyisoquinoline-3-carboxylate (72 mg, 0.311 mmol, 48.3% yield) as a white solid. $^1$H NMR (500 MHz, CHLOROFORM-d) δ 8.41 (br s, 1H), 7.87 (br s, 1H), 7.66-7.40 (m, 2H), 4.00 (br s, 3H), 3.21 (br s, 2H), 1.28 (br s, 3H). MS (ESI) 232.1 (M+H)$^+$.

Preparation of Intermediate for Example 530. Ethyl 1-ethyl-3-hydroxy-4-methyl-1H-pyrazole-5-carboxylate

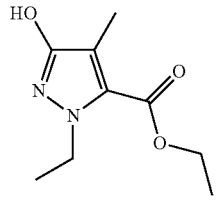

Step A. Intermediate 530A. Preparation of Ethyl 4-methyl-5-oxo-2,5-dihydro-1H-pyrazole-3-carboxylate

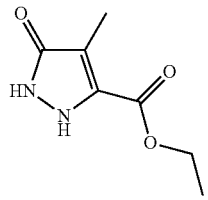

The title compound was prepared according to methods described in Organic Letters, 16(23), 6120-6123; 2014.

Step B. Intermediate 530B. Preparation of ethyl 1-ethyl-3-hydroxy-4-methyl-1H-pyrazole-5-carboxylate The title compound was prepared according to methods described for the synthesis of Intermediate 528, starting from Intermediate 530A and ethanol. $^1$H NMR (500 MHz, CHLOROFORM-d) δ 11.00 (s, 1H), 4.40-4.00 (m, 4H), 2.14 (br s, 3H), 1.64-0.90 (m, 6H). MS (ESI) 199.1 (M+H)$^+$.

Preparation of Intermediate for Example 531. Ethyl 3-hydroxy-1-isopropyl-4-methyl-1H-pyrazole-5-carboxylate

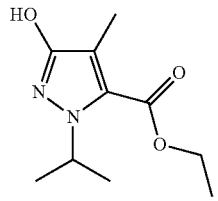

The title compound was prepared according to methods described for the synthesis of Intermediate 528, starting from Intermediate 530A and isopropanol. $^1$H NMR (500 MHz, DMSO-d$_6$) δ 9.88 (br s, 1H), 5.28-5.10 (m, 1H), 4.27 (q, J=6.3 Hz, 2H), 1.99 (br s, 3H), 1.45-1.1 (m, 9H). MS (ESI) 213.1 (M+H)$^+$.

Preparation of Intermediate for Example 532. Ethyl 1-(cyclopropylmethyl)-3-hydroxy-4-methyl-1H-pyrazole-5-carboxylate

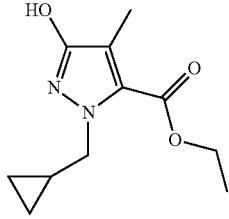 [SMILES: CCOC(=O)c1c(C)c(O)nn1CC1CC1]

The title compound was prepared according to methods described for the synthesis of Intermediate 528, starting from Intermediate 530A and cyclopropylmethanol. $^1$H (500 MHz, CHLOROFORM-d) δ=11.44 (brs, 1H), 4.37 (q, J=6.9 Hz, 2H), 4.23 (br d, J=6.9 Hz, 2H), 2.16 (s, 3H), 1.40 (br t, J=7.0 Hz, 3H), 1.35-1.22 (m, 1H), 0.55-0.46 (m, 2H), 0.45-0.36 (m, 2H). MS (ESI) 225.0 (M+H)$^+$.

Preparation of Intermediate for Example 533. Ethyl 3-hydroxy-4-methyl-1-(oxetan-3-ylmethyl)-1H-pyrazole-5-carboxylate

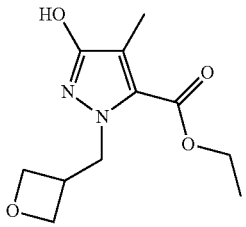 [SMILES: CCOC(=O)c1c(C)c(O)nn1CC1COC1]

The title compound was prepared according to methods described for the synthesis of Intermediate 528, starting from Intermediate 530A and oxetan-3-ylmethanol. $^1$H (500 MHz, CHLOROFORM-d) δ 11.2 (br s, 1H), 4.74 (t, J=7.2 Hz, 2H), 4.66 (d, J=7.2 Hz, 2H), 4.55 (t, J=6.3 Hz, 2H), 4.36 (q, J=7.2 Hz, 2H), 3.46 (td, J=6.9, 14.2 Hz, 1H), 2.13 (s, 3H), 1.40 (t, J=7.2 Hz, 3H). MS (ESI) 241.1 (M+H)$^+$.

Preparation of Intermediate for Example 534. Ethyl 3-hydroxy-1,4-dimethyl-1H-pyrazole-5-carboxylate

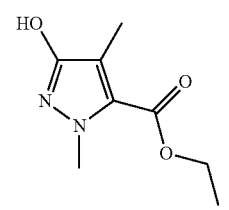

The title compound was prepared according to methods for the synthesis of Intermediate 528, starting from Intermediate 530A and methanol. $^1$H (500 MHz, CHLOROFORM-d) δ 11.3 (br s, 1H), 4.37 (q, J=6.9 Hz, 2H), 3.98 (s, 3H), 2.15 (s, 3H), 1.40 (br t, J=7.0 Hz, 3H). MS (ESI) 185.1 (M+H)$^+$.

Preparation of Intermediate for Example 535. Ethyl 1-(cyclopropylmethyl)-4-fluoro-3-hydroxy-1H-pyrazole-5-carboxylate

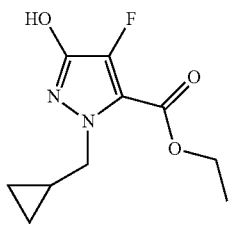 [SMILES: CCOC(=O)c1c(F)c(O)nn1CC1CC1]

A solution of ethyl 3-((tert-butyldimethylsilyl)oxy)-1-(cyclopropylmethyl)-1H-pyrazole-5-carboxylate (Intermediate 528B) (200 mg, 0.616 mmol) and Selectfluor (262 mg, 0.740 mmol) in Acetonitrile (3 mL) was heated at 90° C. in a sealed vial for 30 min. After cooling, the solution was mixed with 1 M hydrochloric acid and extracted twice with ethyl acetate. The organic phase was washed with saturated sodium chloride solution, dried over $Na_2SO_4$, filtered and concentrated by evaporation in vacuum. Chromatographic purification on silica gel (24 g silica gel cartridge, eluting with 0-100% EtOAc/Hexanes) to give the title compound (71 mg, 0.311 mmol, 50.5% yield) as a white solid. $^1$H (500 MHz, CHLOROFORM-d) δ 9.50 (br s, 1H), 4.50-4.30 (m, 2H), 4.27 (br d, J=6.9 Hz, 2H), 1.46-1.35 (m, 3H), 1.34-1.19 (m, 1H), 0.57-0.48 (m, 2H), 0.47-0.36 (m, 2H). MS (ESI) 229.1 (M+H)$^+$.

Preparation of Intermediate for Example 536. Methyl 3-(1,1-difluoroethyl)-5-hydroxypicolinate

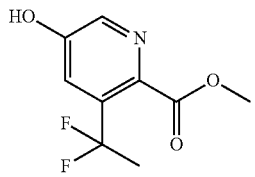

Step A. Intermediate 536A. Preparation of 1-(5-(benzyloxy)-2-chloropyridin-3-yl) ethan-1-one

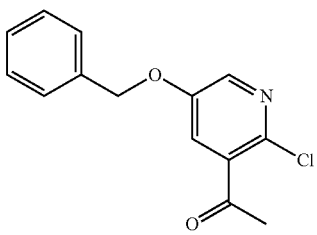 [SMILES: CC(=O)c1cc(OCc2ccccc2)cnc1Cl]

The title compound was prepared according to methods described in Bioorganic & Medicinal Chemistry Letters, 20(2), 679-683; 2010.

Step B. Intermediate 536B. Preparation of methyl 3-acetyl-5-(benzyloxy)picolinate

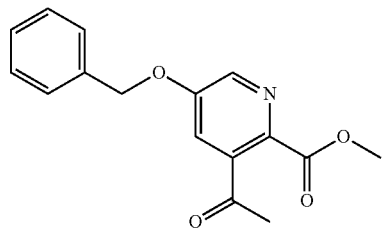 [SMILES: COC(=O)c1ncc(OCc2ccccc2)cc1C(C)=O]

A solution of 1-(5-(benzyloxy)-2-chloropyridin-3-yl) ethan-1-one (261 mg, 0.997 mmol) in MeOH (12 mL) was added [1,1'-bis(diphenylphosphino)ferrocene] dichloropalladium (II) (73.0 mg, 0.100 mmol), followed by $Et_3N$ (0.278 mL, 1.995 mmol). The reaction was heated under a carbon monoxide atmosphere (40-50 psi) at 85° C. for 16 hours. The reaction mixture was allowed to cool to room temperature, filtered through Celite and evaporated under reduced pressure. The residue was purified by column chromatography (24 g silica gel cartridge, eluting with 0-100% EtOAc/Hex) to give methyl 3-acetyl-5-(benzyloxy)picolinate (131 mg, 0.459 mmol, 46.0% yield) as a white foam. $^1$H NMR (500 MHz, CHLOROFORM-d) δ 8.53-8.40 (m, 1H), 7.51-7.36 (m, 5H), 7.19 (d, J=2.8 Hz, 1H), 5.19 (s, 2H), 3.99 (s, 3H), 2.55 (s, 3H). MS (ESI) 286.1 (M+H)$^+$.

Step C. Intermediate 536C. Preparation of methyl 5-(benzyloxy)-3-(1,1-difluoroethyl) picolinate

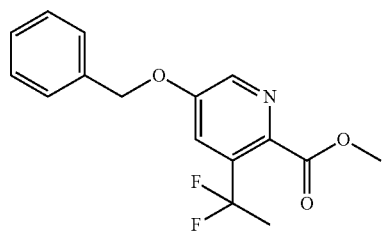 [SMILES: COC(=O)c1ncc(OCc2ccccc2)cc1C(C)(F)F]

A mixture of methyl 3-acetyl-5-(benzyloxy)picolinate (56 mg, 0.196 mmol) and 50% Deoxofluor in toluene (1 mL, 2.71 mmol) was heated at 80° C. for 2 h under $N_2$. The mixture was cooled to room temperature and diluted with DCM. The organic layer was washed with sat. $NaHCO_3$ (aq.), and brine, dried ($MgSO_4$) and concentrated. The residue was purified by silica gel chromatography (eluting with 0-60% EtOAc/Hex) to afford methyl 5-(benzyloxy)-3-(1,1-difluoroethyl)picolinate (42 mg, 0.137 mmol, 69.6% yield) as a white foam. MS (ESI) 308.1 (M+H)$^+$.

Step D. Intermediate 536

To a stirred solution of methyl 5-(benzyloxy)-3-(1,1-difluoroethyl)picolinate (37 mg, 0.120 mmol) in MeOH (3 mL) was added 10% Pd—C (30 mg, 0.028 mmol), followed by 2 drops of acetic acid. The reaction was put under the $H_2$ balloon for 16 hrs. The reaction mixture was filtered and concentrated. The crude product was purified by column chromatography (eluting with 0-100% EtOAc/Hexanes) to give title compound (21 mg, 0.097 mmol, 80% yield) as a white solid. ¹H NMR (500 MHz, CHLOROFORM-d) δ 9.30 (br s, 1H), 8.22 (d, J=2.8 Hz, 1H), 7.44 (d, J=2.5 Hz, 1H), 3.92 (s, 3H), 2.09 (t, J=18.4 Hz, 3H); MS (ESI) 218.0 (M+H)⁺.

Preparation of Intermediates for Example 539 and 541. Ethyl 1-cyclopropyl-5-hydroxy-1H-pyrazole-3-carboxylate & Ethyl 1-cyclopropyl-3-hydroxy-1H-pyrazole-5-carboxylate

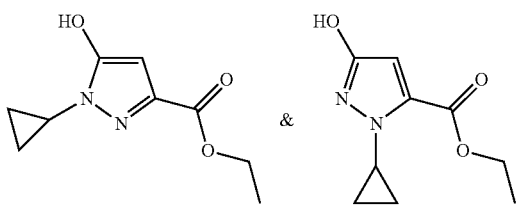

To a suspension of cyclopropylhydrazine dihydrochloride (0.515 g, 3.55 mmol) in THF (3.55 ml) was added Et₃N (1.089 ml, 7.81 mmol) and the mixture stirred at room temperature for 30 min. Then diethyl but-2-ynedioate (0.570 ml, 3.55 mmol) was added and the reaction stirred at 80° C. for 16 hrs. After cooling to RT, salts were filtered off and filtrate was concentrated. The crude product was purified by column chromatography (eluting with 0-100% EtOAc/Hexanes) to give ethyl 1-cyclopropyl-5-hydroxy-1H-pyrazole-3-carboxylate (Intermediate 539) (150 mg, 0.765 mmol, 21.53% yield) and ethyl 1-cyclopropyl-3-hydroxy-1H-pyrazole-5-carboxylate (Intermediate 541) (85 mg, 0.433 mmol, 12.20% yield).

Intermediate 539: ¹H NMR (500 MHz, CHLOROFORM-d) δ 11.01 (s, 1H), 6.16 (s, 1H), 4.35 (d, J=7.2 Hz, 2H), 3.90-3.80 (m, 1H), 1.37 (d, J=7.2 Hz, 3H), 1.13-0.97 (m, 4H). MS (ESI) 197.0 (M+H)⁺.

Intermediate 541: ¹H NMR (500 MHz, DMSO-d₆) δ=11.44 (s, 1H), 5.75 (s, 1H), 4.20 (q, J=7.1 Hz, 2H), 3.52-3.40 (m, 1H), 1.24 (t, J=7.2 Hz, 3H), 1.03-0.85 (m, 4H). MS (ESI) 197.0 (M+H)⁺.

The following Examples in Table 9 were prepared according to methods described elsewhere herein using appropriate starting materials, reagents and conditions.

TABLE 9

| Ex. No. | Structure | ¹H NMR, FXR EC₅₀ & MS (ESI) | Method |
|---|---|---|---|
| 524 | 2-(3-((4-((5-cyclopropyl-3-(3,5-dichloropyridin-4-yl)isoxazol-4-yl)methoxy)bicyclo[2.2.2]octan-1-yl)methoxy)-5-ethyl-1H-pyrazol-1-yl)acetic acid | ¹H NMR (500 MHz, DMSO-d₆) δ = 8.78 (brs, 2H), 5.47 (s, 1H), 4.19 (brs, 2H), 3.60 (brs, 2H), 3.16 (s,2H), 2.89 (q, J = 6.7 Hz, 2H), 2.32-2.22 (m, 1H), 1.42 (brs, 6H), 1.28 (brs, 6H), 1.19-1.09 (m, 5H), 1.07-0.99 (m, 2H). FXR EC₅₀ (nM) = 1497. MS (ESI) 575 (M + H). | Ex. 276 |
| 525 | 3-(((4-((5-cyclopropyl-3-(3,5-dichloropyridin-4-yl)isoxazol-4-yl)methoxy)bicyclo[2.2.2]octan-1-yl)methoxy)methyl)benzoic acid | ¹H NMR (500 MHz, DMSO-d₆) δ = 8.73 (s, 2H), 7.86-7.74 (m, 2H), 7.51-7.39 (m, 2H), 4.41 (s, 2H), 4.15 (s, 2H), 3.15 (s, 2H), 2.25-2.17 (m, 1H), 1.41-1.30 (m, 6H), 1.27-1.18 (m, 6H), 1.15-1.09 (m, 2H), 1.05-0.96 (m, 2H).). FXR EC₅₀ (nM) = 167. MS (ESI) 557 (M + H). | Ex. 104 |

TABLE 9-continued

| Ex. No. | Structure | ¹H NMR, FXR EC₅₀ & MS (ESI) | Method |
|---|---|---|---|
| 526 | 5-((4-((5-cyclopropyl-3-(3,5-dichloropyridin-4-yl)isoxazol-4-yl)methoxy)bicyclo[2.2.2]octan-1-yl)methoxy)-1-methyl-1H-pyrazole-3-carboxylic acid | ¹H NMR (500 MHz, DMSO-d₆) δ = 8.72(s, 2H), 5.94 (s, 1H), 4.20 (s, 2H), 3.65 (s, 1H), 3.58(s, 1H), 2.54(s, 3H), 2.34-2.22 (m, 1H), 1.55-1.41 (m, 6H), 1.38-1.26 (m, 6H), 1.18-1.09 (m, 2H), 1.08-0.99 (m, 2H). FXR EC₅₀ (nM) = 296. MS (ESI) 547 (M + H). | Ex. 276 |
| 527 | 6-(((4-((5-cyclopropyl-3-(3,5-dichloropyridin-4-yl)isoxazol-4-yl)methoxy)bicyclo[2.2.2]octan-1-yl)methoxy)methyl)-4-(trifluoromethyl)picolinic acid | ¹H NMR (500 MHz, DMSO-d₆) δ = 8.82 (s, 2H), 8.13 (s, 1H), 7.80 (s, 1H), 4.64 (s, 2H), 4.20 (s, 2H), 3.12 (s, 2H), 2.34-2.26 (m, 1H), 1.49-1.39 (m, 6H), 1.35-1.27 (m, 6H), 1.19-1.12 (m, 2H), 1.10-1.03 (m, 2H). FXR EC₅₀ (nM) = 86. MS (ESI) 626 (M + H). | Ex. 104 |
| 528 | 3-((4-((5-cyclopropyl-3-(3,5-dichloropyridin-4-yl)isoxazol-4-yl)methoxy)bicyclo[2.2.2]octan-1-yl)methoxy)-1-(cyclopropylmethyl)-1H-pyrazol-5-carboxylic acid | ¹H NMR (500 MHz, DMSO-d₆) δ = 8.78 (s, 2H), 6.05 (s, 1H), 4.33-4.09 (m, 4H), 3.55 (brs, 2H), 2.37-2.20 (m, 1H), 1.52-1.39 (m, 6H), 1.35-1.25 (m, 6H), 1.20-1.10 (m, 3H), 1.08-0.98 (m, 2H), 0.44-0.33 (m, 2H), 0.31-0.22 (m, 2H).). FXR EC₅₀ (nM) = 16. MS (ESI) 587 (M + H). | Ex. 276 |

TABLE 9-continued

| Ex. No. | Structure | $^1$H NMR, FXR EC$_{50}$ & MS (ESI) | Method |
|---|---|---|---|
| 529 | 7-((4-((5-cyclopropyl-3-(3,5-dichloropyridin-4-yl)isoxazol-4-yl)methoxy)bicyclo[2.2.2]octan-1-yl)methoxy)-1-ethylisoquinoline-3-carboxylic acid | $^1$H NMR (500 MHz, DMSO-d$_6$) δ = 8.83(s, 2H), 8.37 (s, 1H), 8.05 (d, J = 8.9 Hz, 1H), 7.59-7.29 (m, 2H), 4.23 (s, 2H), 3.77 (s, 2H), 3.35-3.18 (m, 2H), 2.41-2.23 (m, 1H), 1.63-1.52 (m, 6H), 1.45-1.27 (m, 9H), 1.18-1.11 (m, 2H), 1.10-1.04 (m, 2H). FXR EC$_{50}$ (nM) = 9.0. MS (ESI) 622 (M + H). | Ex. 276 |
| 530 | 3-((4-((5-cyclopropyl-3-(3,5-dichloropyridin-4-yl)isoxazol-4-yl)methoxy)bicyclo[2.2.2]octan-1-yl)methoxy)-1-ethyl-4-methyl-1H-pyrazole-5-carboxylic acid | $^1$H NMR (500 MHz, DMSO-d$_6$) δ = 8.77 (s, 2H), 4.24 (q, J = 6.8 Hz, 2H), 4.18 (s, 2H), 3.67 (br s, 2H), 2.31-2.19 (m, 1H), 1.96 (s, 3H), 1.51-1.39 (m, 6H), 1.35-1.26 (m, 6H), 1.22-1.10 (m, 5H), 1.08-0.99 (m, 2H). FXR EC$_{50}$ (nM) = 219. MS (ESI) 575 (M + H). | Ex. 276 |
| 531 | 3-((4-((5-cyclopropyl-3-(3,5-dichloropyridin-4-yl)isoxazol-4-yl)methoxy)bicyclo[2.2.2]octan-1-yl)methoxy)-1-isopropyl-4-methyl-1H-pyrazole-5-carboxylic acid | $^1$H NMR (500 MHz, DMSO-d$_6$) δ = 8.81 (s, 2H), 5.51-5.07 (m, 1H), 4.20 (s, 2H), 3.67 (s, 2H), 2.37-2.20 (m, 1H), 1.97 (s, 3H), 1.53-1.42 (m, 6H), 1.36-1.29 (m, 6H), 1.27 (d, J = 6.7 Hz, 6H), 1.18-1.12 (m, 2H), 1.10-1.03 (m, 2H). FXR EC$_{50}$ (nM) = 138. MS (ESI) 589 (M + H). | Ex. 276 |

TABLE 9-continued

| Ex. No. | Structure | $^1$H NMR, FXR EC$_{50}$ & MS (ESI) | Method |
|---|---|---|---|
| 532 | 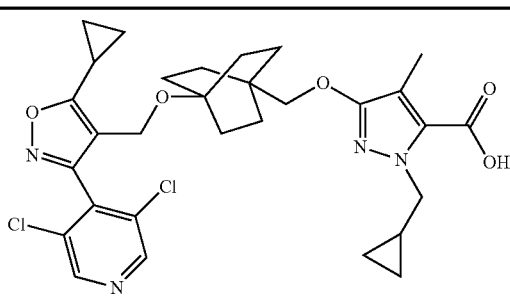<br>3-((4-((5-cyclopropyl-3-(3,5-dichloropyridin-4-yl)isoxazol-4-yl)methoxy)bicyclo[2.2.2]octan-1-yl)methoxy)-1-(cyclopropylmethyl)-4-methyl-1H-pyrazole-5-carboxylic acid | $^1$H NMR (500 MHz, DMSO-d$_6$) δ = 8.78 (s, 2H), 4.20 (s, 2H), 4.13 (br d, J = 6.5 Hz, 2H), 3.68 (s, 2H), 2.35-2.20 (m, 1H), 1.99 (s, 3H), 1.53-1.44 (m, 6H), 1.40-1.30(m, 6H), 1.20-1.11 (m, 3H), 1.10-1.00 (m, 2H), 0.45-0.35 (m, 2H), 0.30-0.20 (m, 2H). FXR EC$_{50}$ (nM) = 148. MS (ESI) 601 (M + H). | Ex. 276 |
| 533 | 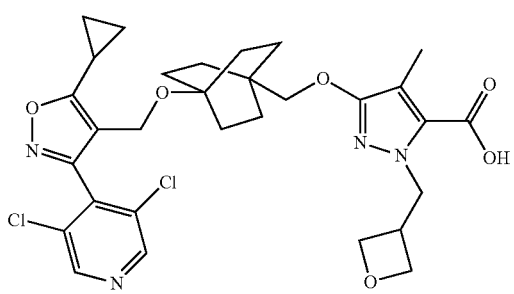<br>3-((4-((5-cyclopropyl-3-(3,5-dichloropyridin-4-yl)isoxazol-4-yl)methoxy)bicyclo[2.2.2]octan-1-yl)methoxy)-1-(oxetan-3-ylmethyl)-1H-pyrazole-5-carboxylic acid | $^1$H NMR (500 MHz, DMSO-d$_6$) δ = 8.81 (s, 2H), 4.63-4.50 (m, 2H), 4.40-4.30 (m, 2H), 4.20 (s, 2H), 4.14-4.01 (m, 2H), 3.64 (s, 2H), 3.40-3.30 (m, 1H), 2.28-2.18 (m, 1H), 1.96 (s, 3H), 1.57-1.41 (m, 6H), 1.39-1.27 (m, 6H), 1.19-1.12 (m, 2H), 1.10-1.02(m, 2H). FXR EC$_{50}$ (nM) = 1911. MS (ESI) 617 (M + H). | Ex. 276 |
| 534 | 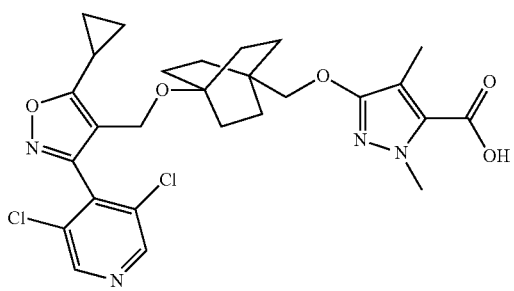<br>3-((4-((5-cyclopropyl-3-(3,5-dichloropyridin-4-yl)isoxazol-4-yl)methoxy)bicyclo[2.2.2]octan-1-yl)methoxy)-1,4-dimethyl-1H-pyrazole-5-carboxylic acid | $^1$H NMR (500 MHz, DMSO-d$_6$) δ = 8.75 (s, 2H), 4.17 (s, 2H), 3.82 (s, 3H), 3.61 (s, 2H), 2.28-2.19 (m, 1H), 1.94 (s, 3H), 1.52-1.36 (m, 6H), 1.34-1.21 (m, 6H), 1.18-1.10 (m, 2H), 1.07-0.98 (m, 2H). FXR EC$_{50}$ (nM) = 248. MS (ESI) 561 (M + H). | Ex. 276 |

| Ex. No. | Structure | $^1$H NMR, FXR EC$_{50}$ & MS (ESI) | Method |
|---|---|---|---|
| 535 | 3-((4-((5-cyclopropyl-3-(3,5-dichloropyridin-4-yl)isoxazol-4-yl)methoxy)bicyclo[2.2.2]octan-1-yl)methoxy)-1-(cyclopropylmethyl)-4-fluoro-1H-pyrazole-5-carboxylic acid | $^1$H NMR (500 MHz, DMSO-d$_6$) δ = 8.80 (s, 2H), 4.20 (s, 2H), 4.12 (br d, J = 6.7 Hz, 2H), 3.68 (s, 2H), 2.36-2.21 (m, 1H), 1.52-1.41 (m, 6H), 1.36-1.26 (m, 6H), 1.17-1.10 (m, 3H), 1.14-1.05 (m, 2H), 0.40-0.30 (m, 2H), 0.28-0.20 (m, 2H). FXR EC$_{50}$ (nM) = 50. MS (ESI) 605 (M + H). | Ex. 276 |
| 536 | 5-((4-((5-cyclopropyl-3-(3,5-dichloropyridin-4-yl)isoxazol-4-yl)methoxy)bicyclo[2.2.2]octan-1-yl)methoxy)-3-(1,1-difluoroethyl)picolinic acid | $^1$H NMR (500 MHz, DMSO-d$_6$) δ = 8.78 (s, 2H), 8.20 (br s, 1H), 7.31 (s, 1H), 4.22 (s, 2H), 3.68 (s, 2H), 2.35-2.20 (m, 1H), 2.04 (br t, J = 19.0 Hz, 3H), 1.59-1.48 (m, 6H), 1.41-1.33 (m, 6H), 1.22-1.10 (m, 2H), 1.18-1.04 (m, 2H). FXR EC$_{50}$ (nM) = 55. MS (ESI) 608 (M + H). | Ex. 276 |
| 537 | 5-((4-((5-cyclopropyl-3-(3,5-dichloropyridin-4-yl)isoxazol-4-yl)methoxy)bicyclo[2.2.2]octan-1-yl)methoxy)-1-ethyl-1H-pyrazole-3-carboxylic acid | $^1$H NMR (500 MHz, DMSO-d$_6$) δ = 8.74 (s, 2H), 5.97 (s, 1H), 4.18 (s, 2H), 3.93 (q, J = 7.2 Hz, 2H), 3.65 (s, 1H), 3.57 (s, 1H), 2.29-2.18 (m, 1H), 1.53-1.43 (m, 6H), 1.38-1.29 (m, 6H), 1.24 (t, J = 7.2 Hz, 3H), 1.18-1.10 (m, 2H), 1.12-1.01 (m, 2H). FXR EC$_{50}$ (nM) = 79. MS (ESI) 561 (M + H). | Ex. 276 |
| 538 | 2-((4-((5-cyclopropyl-3-(3,5-dichloropyridin-4-yl)isoxazol-4-yl)methoxy)bicyclo[2.2.2]octan-1-yl)methoxy)imidazo[1,2-a]pyridine-7-carboxylic acid | $^1$H NMR (500 MHz, DMSO-d$_6$) δ = 8.79 (s, 2H), 8.38 (d, J = 6.7 Hz, 1H), 7.84 (s, 1H), 7.46 (s, 1H), 7.28 (br d, J = 6.7 Hz, 1H), 4.20 (s, 2H), 3.73 (s, 2H), 2.33-2.21 (m, 1H), 1.54-1.45 (m, 6H), 1.37-1.27 (m, 6H), 1.19-1.10 (m, 2H), 1.10-1.01 (m, 2H). FXR EC$_{50}$ (nM) = 90. MS (ESI) 583 (M + H). | Ex. 276 |

TABLE 9-continued

| Ex. No. | Structure | ¹H NMR, FXR EC₅₀ & MS (ESI) | Method |
|---|---|---|---|
| 539 | 1-cyclopropyl-3-((4-((5-cyclopropyl-3-(3,5-dichloropyridin-4-yl)isoxazol-4-yl)methoxy)bicyclo[2.2.2]octan-1-yl)methoxy)-1H-pyrazole-5-carboxylic acid | $^1$H NMR (500 MHz, DMSO-d$_6$) δ = 8.77 (s, 2H), 6.01 (s, 1H), 4.45-4.27 (m, 1H), 4.20 (s, 2H), 3.56 (s, 2H), 2.30-2.20 (m, 1H), 1.53-1.40 (m, 6H), 1.37-1.29 (m, 6H), 1.20-1.11 (m, 2H), 1.08-1.02 (m, 2H), 1.00-0.94 (m, 2H), 0.88-0.80 (m, 2H). FXR EC$_{50}$ (nM) = 25. MS (ESI) 573 (M + H). | Ex. 276 |
| 540 | 5-((4-((5-cyclopropyl-3-(3,5-dichloropyridin-4-yl)isoxazol-4-yl)methoxy)bicyclo[2.2.2]octan-1-yl)methoxy)-1-ethyl-4-fluoro-1H-pyrazole-3-carboxylic acid | $^1$H NMR (500 MHz, DMSO-d$_6$) δ = 8.78 (s, 2H), 4.21 (s, 2H), 3.99-3.87 (m, 2H), 3.83 (s, 2H), 2.33-2.20 (m, 1H), 1.61-1.46 (m, 6H), 1.43-1.33 (m, 6H), 1.26 (t, J = 7.2 Hz, 3H), 1.18-1.11 (m, 2H), 1.09-1.03 (m, 2H). FXR EC$_{50}$ (nM) = 345. MS (ESI) 579 (M + H). | Ex. 276 |
| 541 | 1-cyclopropyl-5-((4-((5-cyclopropyl-3-(3,5-dichloropyridin-4-yl)isoxazol-4-yl)methoxy)bicyclo[2.2.2]octan-1-yl)methoxy)-1H-pyrazole-3-carboxylic acid | $^1$H NMR (500 MHz, DMSO-d$_6$) δ = 8.78 (s, 2H), 5.96 (s, 1H), 4.21 (s, 2H), 3.69 (s, 2H), 3.52-3.36 (m, 1H), 2.33-2.20 (m, 1H), 1.60-1.50 (m, 6H), 1.43-1.32 (m, 6H), 1.20-1.11 (m, 2H), 1.10-1.02 (m, 2H), 1.00-0.90 (m, 4H). FXR EC$_{50}$ (nM) = 59. MS (ESI) 573 (M + H). | Ex. 276 |
| 542 | 5-((4-((5-cyclopropyl-3-(3,5-dichloropyridin-4-yl)isoxazol-4-yl)methoxy)bicyclo[2.2.2]octan-1-yl)ethynyl)pyrazine-2-carboxylic acid | $^1$H NMR (500 MHz, DMSO-d$_6$) δ 8.92 (br s, 1H), 8.79 (s, 2H), 8.54 (br d, J = 11.3 Hz, 1H), 4.18 (s, 2H), 2.32-2.21 (m, 1H), 1.89-1.76 (m, 6H), 1.44-1.31 (m, 6H), 1.17-1.12 (m, 2H), 1.08-1.01 (m, 2H). FXR EC$_{50}$ (nM) = 4880. MS (ESI) 539.1 (M + H). | Ex. 130 |

TABLE 9-continued

| Ex. No. | Structure | $^1$H NMR, FXR EC$_{50}$ & MS (ESI) | Method |
|---|---|---|---|
| 543 | 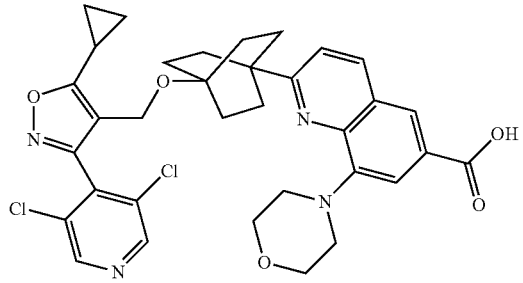<br>2-(4-((5-cyclopropyl-3-(3,5-dichloropyridin-4-yl)isoxazol-4-yl)methoxy)bicyclo[2.2.2]octan-1-yl)-8-morpholinoquinoline-6-carboxylic acid | $^1$H NMR (500 MHz, DMSO-d$_6$) δ 8.79 (s, 2H), 8.30 (d, J = 8.9 Hz, 1H), 8.10 (s, 1H), 7.57 (d, J = 8.9 Hz, 1H), 7.46 (s, 1H), 4.24 (s, 2H), 3.84 (br s, 2H), 3.66 (br s, 2H), 3.34 (br s, 4H), 2.34-2.23 (m, 1H), 1.99-1.84 (m, 6H), 1.52-1.38 (m, 6H), 1.18-1.11 (m, 2H), 1.10-1.02 (m, 2H). FXR EC$_{50}$ (nM) = 469. MS (ESI) 649.3 (M + H). | Ex. 410 |
| 544 | 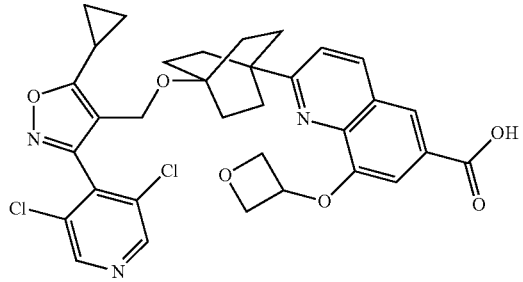<br>2-(4-((5-cyclopropyl-3-(3,5-dichloropyridin-4-yl)isoxazol-4-yl)methoxy)bicyclo[2.2.2]octan-1-yl)-8-(oxetan-3-yloxy)quinoline-6-carboxylic acid | $^1$H NMR (500 MHz, DMSO-d$_6$) δ 8.81 (s, 2H), 8.33 (d, J = 8.9 Hz, 1H), 8.12 (s, 1H), 7.62 (d, J = 8.9 Hz, 1H), 7.17 (s, 1H), 5.49 (quin, J = 5.3 Hz, 1H), 5.00 (t, J = 6.6 Hz, 2H), 4.68 (dd, J = 6.9, 5.0 Hz, 2H), 4.25 (s, 2H), 2.35-2.25 (m, 1H), 2.02-1.92 (m, 6H), 1.53-1.42 (m, 6H), 1.17-1.14 (m, 2H), 1.10-1.05 (m, 2H). FXR EC$_{50}$ (nM) = 118. MS (ESI) 636.3 (M + H). | Ex. 391 |
| 545 | 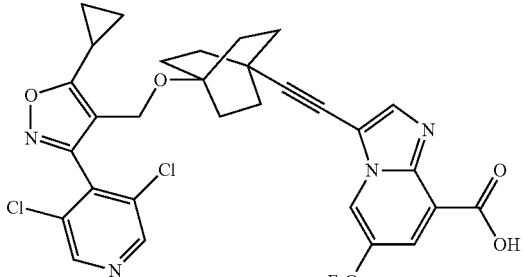<br>3-((4-((5-cyclopropyl-3-(3,5-dichloropyridin-4-yl)isoxazol-4-yl)methoxy)bicyclo[2.2.2]octan-1-yl)ethynyl)-6-(trifluoromethyl)imidazo[1,2-a]pyridine-8-carboxylic acid | $^1$H NMR (500 MHz, DMSO-d$_6$) δ 8.83-8.67 (m, 3H), 7.99 (br d, J = 19.7 Hz, 2H), 4.20 (s, 2H), 2.33-2.20 (m, 1H), 1.99-1.82 (m, 6H), 1.50-1.35 (m, 6H), 1.17-1.12 (m, 2H), 1.09-1.04 (m, 2H). FXR EC$_{50}$ (nM) = 5. MS (ESI) 645.3 (M + H) | Ex. 130 |

TABLE 9-continued

| Ex. No. | Structure | ¹H NMR, FXR EC$_{50}$ & MS (ESI) | Method |
|---|---|---|---|
| 546 | 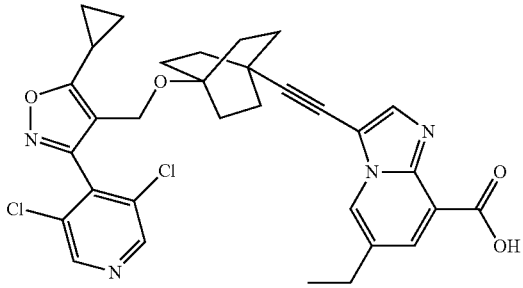<br>3-((4-((5-cyclopropyl-3-(3,5-dichloropyridin-4-yl)isoxazol-4-yl)methoxy)bicyclo[2.2.2]octan-1-yl)ethynyl)-6-ethylimidazo[1,2-a]pyridine-8-carboxylic acid | ¹H NMR (500 MHz, DMSO-d$_6$) δ 8.75 (s, 2H), 8.31 (br s, 1H), 8.05 (br s, 1H), 7.92 (br s, 1H), 4.19 (s, 2H), 2.77 (br d, J = 6.6 Hz, 2H), 2.24 (br s, 1H), 1.90 (br s, 6H), 1.40 (br s, 6H), 1.23 (br t, J = 6.8 Hz, 3H), 1.14 (br d, J = 5.8 Hz, 2H), 1.04 (br s, 2H). FXR EC$_{50}$ (nM) = 7. MS (ESI) 605.1 (M + H). | Ex. 520 |
| 547 | 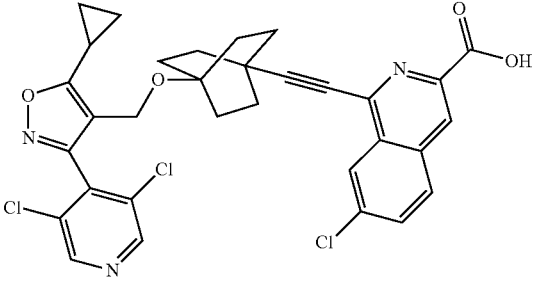<br>7-chloro-1-((4-((5-cyclopropyl-3-(3,5-dichloropyridin-4-yl)isoxazol-4-yl)methoxy)bicyclo[2.2.2]octan-1-yl)ethynyl)isoquinoline-3-carboxylic acid | ¹H NMR (500 MHz, DMSO-d$_6$) δ 8.81 (s, 2H), 8.46 (s, 1H), 8.18 (d, J = 8.5 Hz, 1H), 8.15 (s, 1H), 7.88-7.82 (m, 1H), 4.21 (s, 2H), 2.33-2.23 (m, 1H), 2.01-1.90 (m, 6H), 1.49-1.36 (m, 6H), 1.18-1.11 (m, 2H), 1.10-1.01 (m, 2H). FXR EC$_{50}$ (nM) = 251. MS (ESI) 622.4 (M + H). | Ex. 130 |
| 548 | 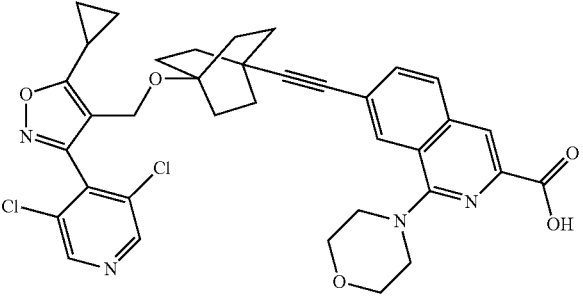<br>7-((4-((5-cyclopropyl-3-(3,5-dichloropyridin-4-yl)isoxazol-4-yl)methoxy)bicyclo[2.2.2]octan-1-yl)ethynyl)-1-morpholinoisoquinoline-3-carboxylic acid | ¹H NMR (500 MHz, DMSO-d$_6$) δ 8.79 (s, 2H), 8.11 (s, 1H), 8.03-7.94 (m, 2H), 7.62 (br d, J = 8.4 Hz, 1H), 4.21 (s, 2H), 3.84 (br s, 4H), 2.89 (s, 2H), 2.74 (s, 2H), 2.34-2.21 (m, 1H), 1.94-1.77 (m, 6H), 1.48-1.35 (m, 6H), 1.20-1.11 (m, 2H), 1.10-1.03 (m, 2H). FXR EC$_{50}$ (nM) = 13. MS (ESI) 673.0 (M + H). | Ex. 519 |

TABLE 9-continued

| Ex. No. | Structure | $^1$H NMR, FXR EC$_{50}$ & MS (ESI) | Method |
|---|---|---|---|
| 549 | 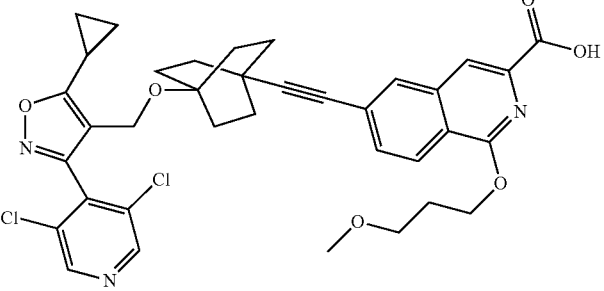 6-((4-((5-cyclopropyl-3-(3,5-dichloropyridin-4-yl)isoxazol-4-yl)methoxy)bicyclo[2.2.2]octan-1-yl)ethynyl)-1-(3-methoxypropoxy)isoquinoline-3-carboxylic acid | $^1$H NMR (500 MHz, DMSO-d$_6$) δ 8.78 (s, 2H), 8.14 (d, J = 8.5 Hz, 1H), 8.08 (s, 1H), 8.01 (s, 1H), 7.58 (d, J = 8.5 Hz, 1H), 4.57 (br t, J = 6.4 Hz, 2H), 4.20 (s, 2H), 3.54 (t, J = 6.3 Hz, 2H), 3.26 (s, 3H), 2.32-2.20 (m, 1H), 2.07 (quin, J = 6.5 Hz, 2H), 1.92-1.81 (m, 6H), 1.49-1.35 (m, 6H), 1.15 (br dd, J = 8.2, 2.5 Hz, 2H), 1.10-1.03 (m, 2H). FXR EC$_{50}$ (nM) = 126. MS (ESI) 676.3 (M + H). | Ex. 519 |
| 550 | 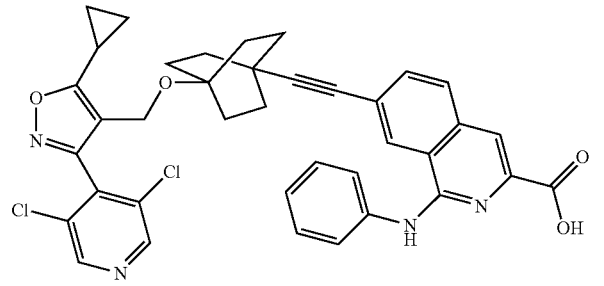 7-((4-((5-cyclopropyl-3-(3,5-dichloropyridin-4-yl)isoxazol-4-yl)methoxy)bicyclo[2.2.2]octan-1-yl)ethynyl)-1-(phenylamino)isoquinoline-3-carboxylic acid | $^1$H NMR (500 MHz, DMSO-d$_6$) δ 8.79 (s, 2H), 8.61 (s, 1H), 8.06 (br d, J = 8.0 Hz, 2H), 7.98-7.90 (m, 2H), 7.89 (s, 1H), 7.63 (d, J = 8.4 Hz, 1H), 7.32 (t, J = 7.9 Hz, 2H), 7.01 (t, J = 7.3 Hz, 1H), 4.21 (s, 2H), 2.32-2.22 (m, 1H), 1.96-1.80 (m, 6H), 1.52-1.36 (m, 6H), 1.20-1.12 (m, 2H), 1.10-1.02 (m, 2H). FXR EC$_{50}$ (nM) = 186. | Ex. 519 |
| 551 | 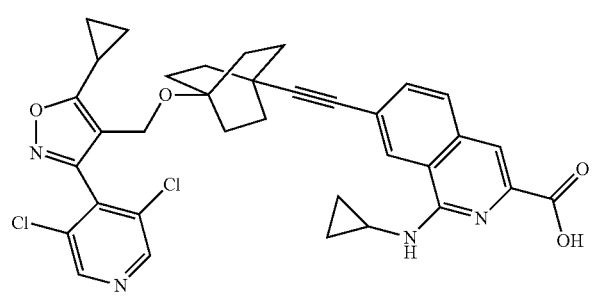 7-((4-((5-cyclopropyl-3-(3,5-dichloropyridin-4-yl)isoxazol-4-yl)methoxy)bicyclo[2.2.2]octan-1-yl)ethynyl)-1-(cyclopropylamino)isoquinoline-3-carboxylic acid | $^1$H NMR (500 MHz, DMSO-d$_6$) δ 8.82 (s, 2H), 8.29 (s, 1H), 7.85 (br d, J = 8.5 Hz, 1H), 7.70 (s, 1H), 7.56 (br d, J = 8.5 Hz, 1H), 4.20 (s, 2H), 3.22-3.08 (m, 1H), 2.34-2.23 (m, 1H), 1.83 (br d, J = 7.9 Hz, 6H), 1.46-1.31 (m, 6H), 1.15 (br d, J = 7.6 Hz, 2H), 1.08 (br d, J = 2.1 Hz, 2H), 0.77 (br d, J = 5.5 Hz, 2H), 0.61 (br s, 2H). FXR EC$_{50}$ (nM) = 406. MS (ESI) 643.1 (M + H). | Ex. 519 |

| Ex. No. | Structure | ¹H NMR, FXR EC₅₀ & MS (ESI) | Method |
|---|---|---|---|
| 552 | 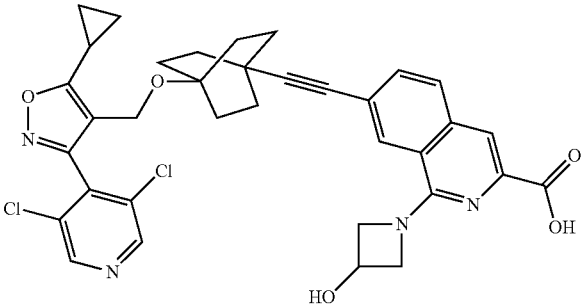<br>7-((4-((5-cyclopropyl-3-(3,5-dichloropyridin-4-yl)isoxazol-4-yl)methoxy)bicyclo[2.2.2]octan-1-yl)ethynyl)-1-(3-hydroxyazetidin-1-yl)isoquinoline-3-carboxylic acid | ¹H NMR (500 MHz, DMSO-d₆) δ 8.78 (s, 2H), 7.88 (br d, J = 8.5 Hz, 1H), 7.83 (s, 1H), 7.78 (s, 1H), 7.55 (br d, J = 8.2 Hz, 1H), 4.59 (br d, J = 4.9 Hz, 2H), 4.18 (s, 2H), 4.10 (br d, J = 5.5 Hz, 1H), 3.64 (br s, 2H), 2.32-2.20 (m, 1H), 1.90-1.73 (m, 6H), 1.43-1.28 (m, 6H), 1.14 (br d, J = 7.9 Hz, 2H), 1.05 (br d, J = 2.7 Hz, 2H). FXR EC₅₀ (nM) = 100. MS (ESI) 659.3 (M + H). | Ex. 519 |
| 553 | 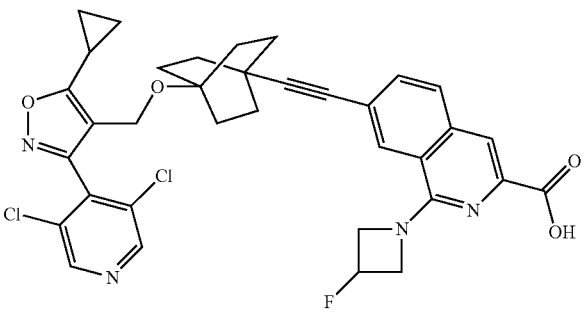<br>7-((4-((5-cyclopropyl-3-(3,5-dichloropyridin-4-yl)isoxazol-4-yl)methoxy)bicyclo[2.2.2]octan-1-yl)ethynyl)-1-(3-fluoroazetidin-1-yl)isoquinoline-3-carboxylic acid | ¹H NMR (500 MHz, DMSO-d₆) δ 8.78 (s, 2H), 7.91 (br d, J = 8.4 Hz, 1H), 7.83 (br s, 2H), 7.57 (br d, J = 8.3 Hz, 1H), 5.65-5.36 (m, 1H), 4.71 (br d, J = 17.6 Hz, 2H), 4.53-4.35 (m, 2H), 4.20 (s, 2H), 2.33-2.21 (m, 1H), 1.93-1.77 (m, 6H), 1.49-1.34 (m, 6H), 1.19-1.11 (m, 2H), 1.07 (br d, J = 4.5 Hz, 2H). FXR EC₅₀ (nM) = 12. MS (ESI) 660.9 (M + H). | Ex. 519 |
| 554 | 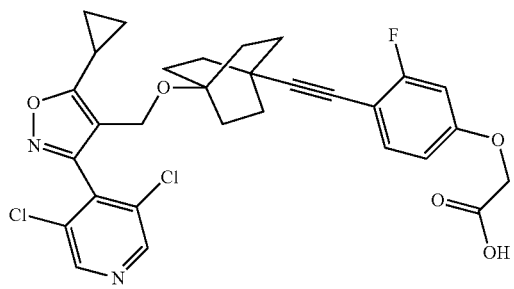<br>2-(4-((4-((5-cyclopropyl-3-(3,5-dichloropyridin-4-yl)isoxazol-4-yl)methoxy)bicyclo[2.2.2]octan-1-yl)ethynyl)-3-fluorophenoxy)acetic acid | ¹H NMR (500 MHz, DMSO-d₆) δ 8.81 (s, 2H), 7.22 (br t, J = 8.7 Hz, 1H), 6.71 (br d, J = 12.2 Hz, 1H), 6.63 (br d, J = 7.9 Hz, 1H), 4.39 (br s, 2H), 4.18 (s, 2H), 2.34-2.24 (m, 1H), 1.85-1.72 (m, 6H), 1.44-1.30 (m, 6H), 1.14 (br d, J = 7.9 Hz, 2H), 1.07 (br d, J = 2.7 Hz, 2H). FXR EC₅₀ (nM) = 3164. MS (ESI) 585.3 (M + H). | Ex. 130 |

TABLE 9-continued

| Ex. No. | Structure | $^1$H NMR, FXR EC$_{50}$ & MS (ESI) | Method |
|---|---|---|---|
| 555 | 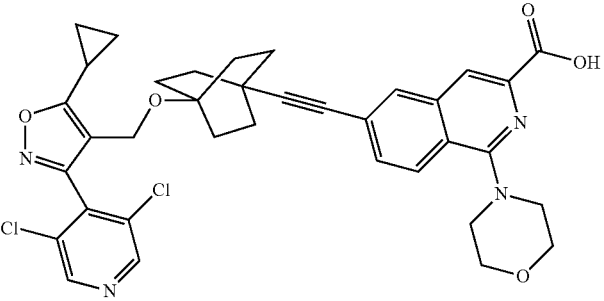<br>6-((4-((5-cyclopropyl-3-(3,5-dichloropyridin-4-yl)isoxazol-4-yl)methoxy)bicyclo[2.2.2]octan-1-yl)ethynyl)-1-morpholinoisoquinoline-3-carboxylic acid | $^1$H NMR (500 MHz, DMSO-d$_6$) δ 8.78 (s, 2H), 8.10-7.99 (m, 3H), 7.54 (br d, J = 8.6 Hz, 1H), 4.19 (s, 2H), 3.83 (br d, J = 4.0 Hz, 4H), 2.54 (s, 4H), 2.32-2.19 (m, 1H), 1.94-1.79 (m, 6H), 1.47-1.34 (m, 6H), 1.18-1.11 (m, 2H), 1.10-1.02 (m, 2H). FXR EC$_{50}$ (nM) = 87. MS (ESI) 673.0 (M + H). | Ex. 519 |
| 556 | 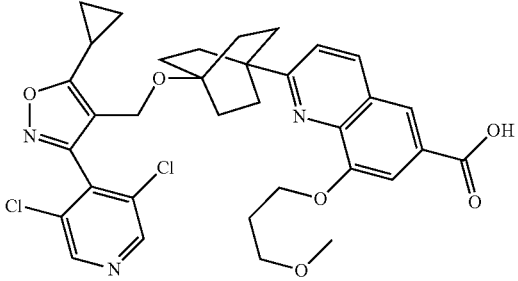<br>2-(4-((5-cyclopropyl-3-(3,5-dichloropyridin-4-yl)isoxazol-4-yl)methoxy)bicyclo[2.2.2]octan-1-yl)-8-(3-methoxypropoxy)quinoline-6-carboxylic acid | $^1$H NMR (500 MHz, DMSO-d$_6$) δ 9.26 (d, J = 9.1 Hz, 1H), 8.81 (s, 2H), 8.16 (d, J = 8.2 Hz, 1H), 7.63 (d, J = 9.1 Hz, 1H), 7.18 (d, J = 8.3 Hz, 1H), 4.32-4.28 (m, 2H), 4.27 (s, 2H), 3.62 (t, J = 6.4 Hz, 2H), 2.35-2.26 (m, 1H), 2.08 (quin, J = 6.3 Hz, 2H), 2.03-1.95 (m, 6H), 1.91 (s, 3H), 1.58-1.45 (m, 6H), 1.19-1.13 (m, 2H), 1.12-1.05 (m, 2H). FXR EC$_{50}$ (nM) = 30. MS (ESI) 652.1 (M + H). | Ex. 391 |
| 557 | 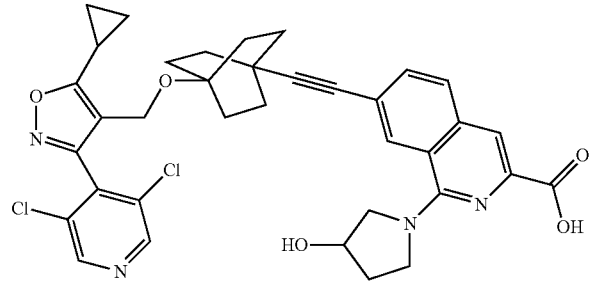<br>7-((4-((5-cyclopropyl-3-(3,5-dichloropyridin-4-yl)isoxazol-4-yl)methoxy)bicyclo[2.2.2]octan-1-yl)ethynyl)-1-(3-hydroxypyrrolidin-1-yl)isoquinoline-3-carboxylic acid | $^1$H NMR (500 MHz, DMSO-d$_6$) δ 8.83 (s, 2H), 8.14 (s, 1H), 7.88 (br d, J = 8.2 Hz, 1H), 7.78 (s, 1H), 7.55 (br d, J = 8.2 Hz, 1H), 4.39 (br s, 1H), 4.21 (s, 2H), 4.08-3.95 (m, 2H), 3.81-3.68 (m, 1H), 3.61-3.48 (m, 1H), 3.29 (br s, 1H), 2.34-2.22 (m, 1H), 2.04-1.94 (m, 1H), 1.92-1.76 (m, 6H), 1.49-1.31 (m, 6H), 1.15 (br d, J = 7.9 Hz, 2H), 1.08 (br s, 2H). FXR EC$_{50}$ (nM) = 188. MS (ESI) 673.2 (M + H). | Ex. 519 |

TABLE 9-continued

| Ex. No. | Structure | ¹H NMR, FXR EC₅₀ & MS (ESI) | Method |
|---|---|---|---|
| 558 | 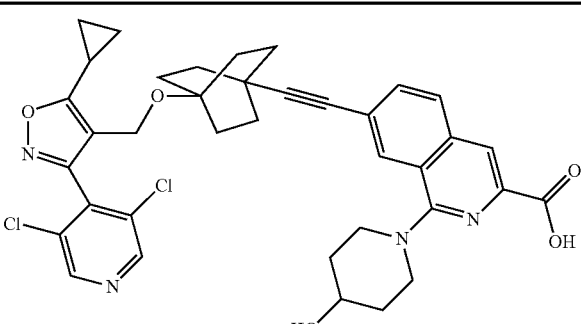<br>7-((4-((5-cyclopropyl-3-(3,5-dichloropyridin-4-yl)isoxazol-4-yl)methoxy)bicyclo[2.2.2]octan-1-yl)ethynyl)-1-(4-hydroxypiperidin-1-yl)isoquinoline-3-carboxylic acid | ¹H NMR (500 MHz, DMSO-d₆) δ 8.80 (s, 2H), 8.06 (s, 1H), 7.98 (d, J = 8.5 Hz, 1H), 7.89 (s, 1H), 7.60 (br d, J = 8.5 Hz, 1H), 4.19 (s, 2H), 3.80-3.56 (m, 2H), 3.54-3.39 (m, 1H), 3.06 (br t, J = 10.8 Hz, 2H), 2.33-2.23 (m, 1H), 1.99-1.89 (m, 2H), 1.88-1.76 (m, 6H), 1.69-1.57 (m, 2H), 1.45-1.31 (m, 6H), 1.19-1.11 (m, 2H), 1.10-1.01 (m, 2H). FXR EC₅₀ (nM) = 20. MS (ESI) 687.3 (M + H). | Ex. 519 |
| 559 | 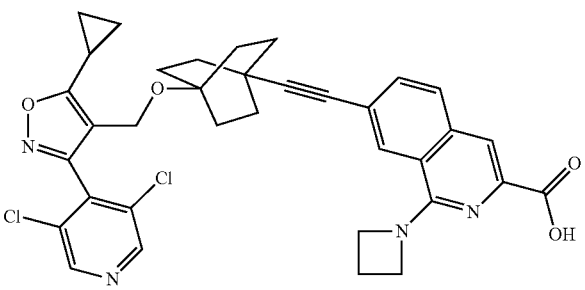<br>1-(azetidin-1-yl)-7-((4-((5-cyclopropyl-3-(3,5-dichloropyridin-4-yl)isoxazol-4-yl)methoxy)bicyclo[2.2.2]octan-1-yl)ethynyl)isoquinoline-3-carboxylic acid | ¹H NMR (500 MHz, DMSO-d₆) δ 8.78 (s, 2H), 7.92-7.83 (m, 2H), 7.75 (br s, 1H), 7.54 (br d, J = 8.2 Hz, 1H), 4.40 (br s, 4H), 4.20 (s, 2H), 2.39 (br s, 2H), 2.32-2.19 (m, 1H), 1.89-1.74 (m, 6H), 1.47-1.32 (m, 6H), 1.19-1.10 (m, 2H), 1.10-0.99 (m, 2H). FXR EC₅₀ (nM) = 20. MS (ESI) 643.3 (M + H). | Ex. 519 |
| 560 | 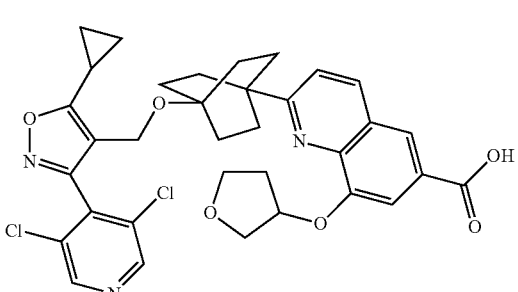<br>2-(4-((5-cyclopropyl-3-(3,5-dichloropyridin-4-yl)isoxazol-4-yl)methoxy)bicyclo[2.2.2]octan-1-yl)-8-((tetrahydrofuran-3-yl)oxy)quinoline-6-carboxylic acid | ¹H NMR (500 MHz, DMSO-d₆) δ 9.24 (br d, J = 8.0 Hz, 1H), 8.80 (d, J = 1.1 Hz, 2H), 8.15 (d, J = 8.2 Hz, 1H), 7.64 (d, J = 9.1 Hz, 1H), 7.18 (d, J = 8.3 Hz, 1H), 5.34 (br s, 1H), 4.26 (s, 2H), 4.02-3.97 (m, 1H), 3.97-3.89 (m, 2H), 3.81 (td, J = 8.1, 4.8 Hz, 1H), 2.38-2.23 (m, 2H), 2.18-2.06 (m, 1H), 2.03-1.91 (m, 6H), 1.58-1.40 (m, 6H), 1.20-1.12 (m, 2H), 1.09 (br d, J = 2.9 Hz, 2H). FXR EC₅₀ (nM) = 286. MS (ESI) 650.1 (M + H). | Ex. 391 |

TABLE 9-continued

| Ex. No. | Structure | ¹H NMR, FXR EC₅₀ & MS (ESI) | Method |
|---|---|---|---|
| 561 | 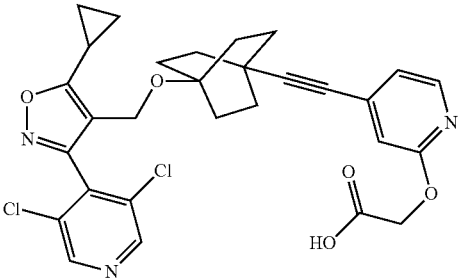<br>2-((4-((4-((5-cyclopropyl-3-(3,5-dichloropyridin-4-yl)isoxazol-4-yl)methoxy)bicyclo[2.2.2]octan-1-yl)ethynyl)pyridin-2-yl)oxy)acetic acid | ¹H NMR (500 MHz, DMSO-d₆) δ 8.78 (d, J = 1.4 Hz, 2H), 8.03 (br d, J = 5.1 Hz, 1H), 6.85 (br d, J = 5.0 Hz, 1H), 6.71 (s, 1H), 4.73 (s, 2H), 4.19 (s, 2H), 2.27 (br dd, J = 7.5, 4.1 Hz, 1H), 1.88-1.75 (m, 6H), 1.47-1.33 (m, 6H), 1.19-1.11 (m, 2H), 1.07 (br s, 2H). FXR EC₅₀ (nM) = 779. MS (ESI) 568.2 (M + H). | Ex. 130 |
| 562 | 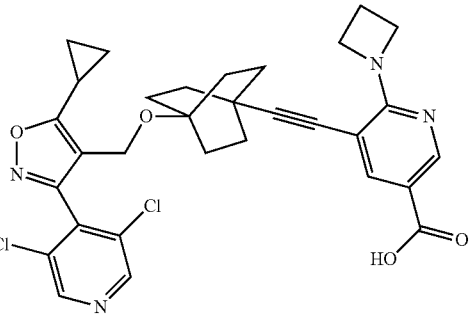<br>6-(azetidin-1-yl)-5-((4-((5-cyclopropyl-3-(3,5-dichloropyridin-4-yl)isoxazol-4-yl)methoxy)bicyclo[2.2.2]octan-1-yl)ethynyl)nicotinic acid | ¹H NMR (500 MHz, DMSO-d₆) δ 8.77 (s, 2H), 8.45 (d, J = 1.6 Hz, 1H), 7.70 (d, J = 1.8 Hz, 1H), 4.25 (br t, J = 7.4 Hz, 4H), 4.19 (s, 2H), 2.32-2.21 (m, 3H), 1.86-1.74 (m, 6H), 1.45-1.33 (m, 6H), 1.17-1.10 (m, 2H), 1.09-0.99 (m, 2H). FXR EC₅₀ (nM) = 21. MS (ESI) 593.4 (M + H). | Ex. 130 |
| 563 | 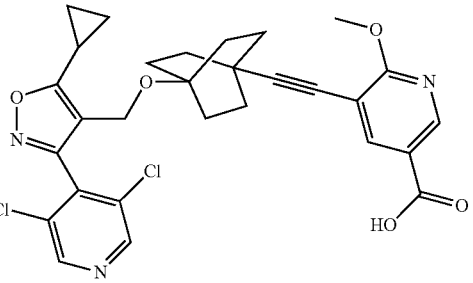<br>5-((4-((5-cyclopropyl-3-(3,5-dichloropyridin-4-yl)isoxazol-4-yl)methoxy)bicyclo[2.2.2]octan-1-yl)ethynyl)-6-methoxynicotinic acid | ¹H NMR (500 MHz, DMSO-d₆) δ 8.79 (s, 2H), 8.59 (d, J = 1.5 Hz, 1H), 7.99 (d, J = 1.5 Hz, 1H), 4.18 (s, 2H), 3.92 (s, 3H), 2.32-2.21 (m, 1H), 1.87-1.72 (m, 6H), 1.42-1.28 (m, 6H), 1.19-1.10 (m, 2H), 1.06 (br d, J = 2.4 Hz, 2H). FXR EC₅₀ (nM) = 16. MS (ESI) 568.2 (M + H). | Ex. 130 |
| 564 | 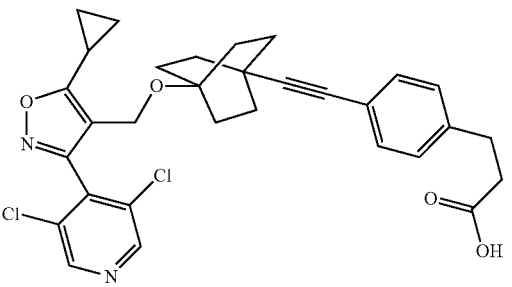<br>3-(4-((4-((5-cyclopropyl-3-(3,5-dichloropyridin-4-yl)isoxazol-4-yl)methoxy)bicyclo[2.2.2]octan-1-yl)ethynyl)phenyl)propanoic acid | ¹H NMR (500 MHz, DMSO-d₆) δ 8.79 (s, 2H), 7.21-7.16 (m, 2H), 7.16-7.12 (m, 2H), 4.17 (s, 2H), 2.77 (br t, J = 7.3 Hz, 2H), 2.47 (br s, 2H), 2.31-2.21 (m, 1H), 1.84-1.70 (m, 6H), 1.41-1.28 (m, 6H), 1.18-1.09 (m, 2H), 1.07-1.00 (m, 2H). FXR EC₅₀ (nM) = 175. | Ex. 130 |

TABLE 9-continued

| Ex. No. | Structure | $^1$H NMR, FXR EC$_{50}$ & MS (ESI) | Method |
|---|---|---|---|
| 565 | 2-(4-((4-((5-cyclopropyl-3-(3,5-dichloropyridin-4-yl)isoxazol-4-yl)methoxy)bicyclo[2.2.2]octan-1-yl)ethynyl)-3-(trifluoromethyl)phenyl)acetic acid | $^1$H NMR (500 MHz, DMSO-d$_6$) δ 8.78 (s, 2H), 7.56 (br s, 1H), 7.40 (br s, 2H), 4.15 (s, 2H), 3.56 (br s, 2H), 2.30-2.20 (m, 1H), 1.82-1.65 (m, 6H), 1.42-1.25 (m, 6H), 1.15-1.07 (m, 2H), 1.05-0.98 (m, 2H). FXR EC$_{50}$ (nM) = 115. MS (ESI) 619.3 (M + H). | Ex. 130 |
| 566 | 2-(4-((4-((5-cyclopropyl-3-(3,5-dichloropyridin-4-yl)isoxazol-4-yl)methoxy)bicyclo[2.2.2]octan-1-yl)ethynyl)benzyl)oxy)acetic acid | $^1$H NMR (500 MHz, DMSO-d$_6$) δ 8.81 (s, 2H), 7.27 (s, 4H), 4.50 (s, 2H), 4.19 (s, 2H), 4.01 (s, 2H), 2.34-2.22 (m, 1H), 1.89-1.70 (m, 6H), 1.45-1.29 (m, 6H), 1.21-1.11 (m, 2H), 1.07 (br d, J = 2.7 Hz, 2H). FXR EC$_{50}$ (nM) = 194. MS (ESI) 581 (M + H). | Ex. 130 |
| 567 | 2-(4-((4-((5-cyclopropyl-3-(3,5-dichloropyridin-4-yl)isoxazol-4-yl)methoxy)bicyclo[2.2.2]octan-1-yl)ethynyl)-2-fluorophenyl)acetic acid | $^1$H NMR (500 MHz, DMSO-d$_6$) δ 8.78 (s, 2H), 7.19 (br t, J = 8.1 Hz, 1H), 7.00 (br d, J = 8.5 Hz, 2H), 4.15 (s, 2H), 3.38 (br s, 2H), 2.25 (br d, J = 7.9 Hz, 1H), 1.75 (br d, J = 8.2 Hz, 6H), 1.40-1.26 (m, 6H), 1.15-1.07 (m, 2H), 1.06-1.00 (m, 2H). FXR EC$_{50}$ (nM) = 121. MS (ESI) 569.2 (M + H). | Ex. 130 |

TABLE 9-continued

| Ex. No. | Structure | ¹H NMR, FXR EC$_{50}$ & MS (ESI) | Method |
|---|---|---|---|
| 568 | 5-((4-((5-cyclopropyl-3-(3,5-dichloropyridin-4-yl)isoxazol-4-yl)methoxy)bicyclo[2.2.2]octan-1-yl)ethynyl)-6-(4-methylpiperazin-1-yl)nicotinic acid | ¹H NMR (500 MHz, DMSO-d$_6$) δ 8.81 (s, 2H), 8.57 (s, 1H), 7.89 (s, 1H), 4.20 (s, 2H), 3.83-3.60 (m, 2H), 3.51-3.24 (m, 2H), 3.16 (s, 2H), 2.92-2.69 (m, 2H), 2.54 (s, 3H), 2.33-2.22 (m, 1H), 1.80 (br d, J = 7.9 Hz, 6H), 1.43-1.30 (m, 6H), 1.18-1.11 (m, 2H), 1.10-1.00 (m, 2H). FXR EC$_{50}$ (nM) = 524. MS (ESI) 636.1 (M + H). | Ex. 523 |
| 569 | 2-((6-((4-((5-cyclopropyl-3-(3,5-dichloropyridin-4-yl)isoxazol-4-yl)methoxy)bicyclo[2.2.2]octan-1-yl)ethynyl)pyridin-3-yl)methoxy)acetic acid | ¹H NMR (500 MHz, DMSO-d$_6$) δ 8.80 (s, 2H), 8.44 (br s, 1H), 7.70 (br d, J = 1.9 Hz, 1H), 7.35 (br d, J = 7.9 Hz, 1H), 4.54 (br s, 2H), 4.18 (s, 2H), 4.06 (br s, 2H), 2.33-2.20 (m, 1H), 1.80 (br d, J = 7.6 Hz, 6H), 1.42-1.30 (m, 6H), 1.17-1.10 (m, 2H), 1.10-1.01 (m, 2H). FXR EC$_{50}$ (nM) = 1365. MS (ESI) 582.1 (M + H). | Ex. 130 |
| 570 | 6-((4-((5-cyclopropyl-3-(3,5-dichloropyridin-4-yl)isoxazol-4-yl)methoxy)bicyclo[2.2.2]octan-1-yl)ethynyl)-1-(4-methylpiperazin-1-yl)isoquinoline-3-carboxylic acid | ¹H NMR (500 MHz, DMSO-d$_6$) δ 8.78 (s, 2H), 8.17 (s, 1H), 8.12-8.02 (m, 2H), 7.58 (br d, J = 8.5 Hz, 1H), 4.18 (s, 2H), 3.58-3.50 (m, 8H), 2.88 (s, 3H), 2.31-2.21 (m, 1H), 1.90-1.78 (m, 6H), 1.44-1.33 (m, 6H), 1.18-1.09 (m, 2H), 1.06 (br s, 2H). FXR EC$_{50}$ (nM) = 201. MS (ESI) 686.1 (M + H). | Ex. 519 |

TABLE 9-continued

| Ex. No. | Structure | $^1$H NMR, FXR EC$_{50}$ & MS (ESI) | Method |
|---|---|---|---|
| 571 | 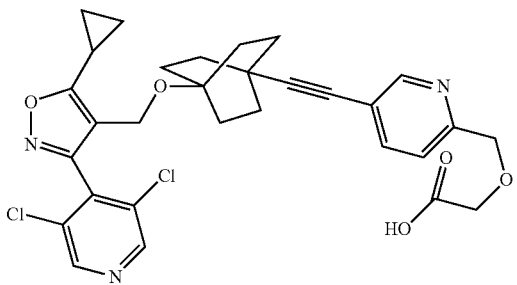<br>2-((5-((4-((5-cyclopropyl-3-(3,5-dichloropyridin-4-yl)isoxazol-4-yl)methoxy)bicyclo[2.2.2]octan-1-yl)ethynyl)pyridin-2-yl)methoxy)acetic acid | $^1$H NMR (500 MHz, DMSO-d$_6$) δ 8.78 (s, 2H), 8.40 (br s, 1H), 7.73 (br d, J = 6.1 Hz, 1H), 7.41 (br s, 1H), 4.58 (br s, 2H), 4.17 (s, 2H), 4.12 (br s, 2H), 2.31-2.15 (m, 1H), 1.78 (br d, J = 7.6 Hz, 6H), 1.34 (br d, J = 7.0 Hz, 6H), 1.17-1.09 (m, 2H), 1.05 (br s, 2H). FXR EC$_{50}$ (nM) = 272. MS (ESI) 582.2 (M + H). | Ex. 130 |
| 572 | 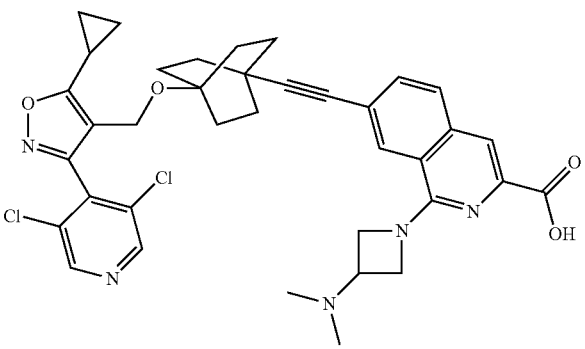<br>7-((4-((5-cyclopropyl-3-(3,5-dichloropyridin-4-yl)isoxazol-4-yl)methoxy)bicyclo[2.2.2]octan-1-yl)ethynyl)-1-(3-(dimethylamino)azetidin-1-yl)isoquinoline-3-carboxylic acid | $^1$H NMR (500 MHz, DMSO-d$_6$) δ 8.81 (s, 2H), 7.96 (br d, J = 8.5 Hz, 1H), 7.92 (s, 1H), 7.84 (s, 1H), 7.62 (br d, J = 8.2 Hz, 1H), 4.68-4.53 (m, 2H), 4.45 (br s, 2H), 4.20 (s, 2H), 2.70 (br s, 6H), 2.29 (br d, J = 4.6 Hz, 1H), 1.84 (br d, J = 7.6 Hz, 6H), 1.38 (br d, J = 7.0 Hz, 6H), 1.18-1.12 (m, 3H), 1.07 (br s, 2H). FXR EC$_{50}$ (nM) = 61. MS (ESI) 686.2 (M + H). | Ex. 519 |
| 573 | 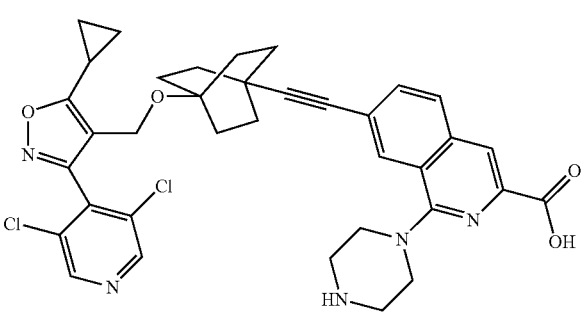<br>7-((4-((5-cyclopropyl-3-(3,5-dichloropyridin-4-yl)isoxazol-4-yl)methoxy)bicyclo[2.2.2]octan-1-yl)ethynyl)-1-(piperazin-1-yl)isoquinoline-3-carboxylic acid | $^1$H NMR (500 MHz, DMSO-d$_6$) δ 8.81 (s, 2H), 8.22 (s, 1H), 8.06 (br d, J = 8.2 Hz, 1H), 8.00 (s, 1H), 7.66 (br d, J = 8.5 Hz, 1H), 4.20 (s, 2H), 3.63-3.34 (m, 8H), 2.34-2.23 (m, 1H), 1.85 (br d, J = 7.6 Hz, 6H), 1.44-1.32 (m, 6H), 1.16-1.13 (m, 2H), 1.11-1.02 (m, 2H). FXR EC$_{50}$ (nM) = 1627. MS (ESI) 672.2 (M + H). | Ex. 519 |

TABLE 9-continued

| Ex. No. | Structure | ¹H NMR, FXR EC₅₀ & MS (ESI) | Method |
|---|---|---|---|
| 574 | 7-((4-((5-cyclopropyl-3-(3,5-dichloropyridin-4-yl)isoxazol-4-yl)methoxy)bicyclo[2.2.2]octan-1-yl)ethynyl)-1-(2-(pyrrolidin-1-yl)ethoxy)isoquinoline-3-carboxylic acid | $^1$H NMR (500 MHz, DMSO-d$_6$) δ 8.82 (s, 2H), 8.04 (s, 1H), 8.01-7.91 (m, 2H), 7.64 (br d, J = 8.5 Hz, 1H), 4.69 (br s, 2H), 4.20 (s, 2H), 3.15 (br s, 4H), 2.34-2.23 (m, 1H), 1.97 (br s, 4H), 1.91 (s, 2H), 1.84 (br d, J = 7.6 Hz, 6H), 1.38 (br d, J = 7.0 Hz, 6H), 1.20-1.11 (m, 2H), 1.08 (br s, 2H). FXR EC$_{50}$ (nM) = 1373. MS (ESI) 701.5 (M + H). | Ex. 521 |
| 575 | 7-((4-((5-cyclopropyl-3-(3,5-dichloropyridin-4-yl)isoxazol-4-yl)methoxy)bicyclo[2.2.2]octan-1-yl)methoxy)-1-ethoxyisoquinoline-3-carboxylic acid | $^1$H NMR (500 MHz, DMSO-d$_6$) δ 8.77 (s, 2H), 8.07 (s, 1H), 7.96 (d, J = 8.8 Hz, 1H), 7.52-7.35 (m, 2H), 4.59 (q, J = 7.0 Hz, 2H), 4.21 (s, 2H), 3.70 (s, 2H), 2.34-2.19 (m, 1H), 1.63-1.51 (m, 6H), 1.43 (t, J = 6.9 Hz, 3H), 1.40-1.30 (m, 6H), 1.21-1.11 (m, 2H), 1.10-0.99 (m, 2H). FXR EC$_{50}$ (nM) = 18. MS (ESI) 638.1 (M + H). | Ex. 357 |
| 576 | 2-(3-(((4-((5-cyclopropyl-3-(3,5-dichloropyridin-4-yl)isoxazol-4-yl)methoxy)bicyclo[2.2.2]octan-1-yl)methyl)amino)-1H-pyrazol-1-yl)acetic acid | $^1$H NMR (500 MHz, DMSO-d$_6$) δ 7.65-7.59 (m, 2H), 7.58-7.52 (m, 1H), 7.26 (s, 1H), 5.38 (s, 1H), 4.42 (s, 2H), 4.12 (s, 2H), 2.66 (s, 2H), 2.34-2.18 (m, 1H), 1.38 (br d, J = 8.2 Hz, 6H), 1.30 (br d, J = 7.9 Hz, 6H), 1.12 (br d, J = 8.2 Hz, 2H), 1.06 (br d, J = 2.7 Hz, 2H). FXR EC$_{50}$ (nM) = 2737. MS (ESI) 545.4 (M + H). | Ex. 362 |
| 577 | 2-(2-(((4-((5-cyclopropyl-3-(2,6-dichlorophenyl)isoxazol-4-yl)methoxy)bicyclo[2.2.2]octan-1-yl)methyl)amino)-4-methylthiazol-5-yl)acetic acid | $^1$H NMR (500 MHz, DMSO-d$_6$) δ 7.64-7.58 (m, 2H), 7.58-7.51 (m, 1H), 4.12 (s, 2H), 3.17 (br s, 2H), 2.99 (s, 2H), 2.86 (br s, 3H), 2.26 (br s, 1H), 1.46-1.34 (m, 6H), 1.29 (br d, J = 7.6 Hz, 6H), 1.12 (br d, J = 8.2 Hz, 2H), 1.05 (br s, 2H). FXR EC$_{50}$ (nM) = 860. MS (ESI) 576.4 (M + H). | Ex. 362 |

TABLE 9-continued

| Ex. No. | Structure | $^1$H NMR, FXR EC$_{50}$ & MS (ESI) | Method |
|---|---|---|---|
| 578 | 7-((4-((5-cyclopropyl-3-(2,6-dichlorophenyl)isoxazol-4-yl)methoxy)bicyclo[2.2.2]octan-1-yl)methyl)-5,6,7,8-tetrahydroimidazo[1,2-a]pyrazine-2-carboxylic acid | $^1$H NMR (500 MHz, DMSO-d$_6$) δ 7.67 (s, 1H), 7.63-7.57 (m, 2H), 7.56-7.51 (m, 1H), 4.10 (s, 2H), 3.99-3.90 (m, 2H), 3.73-3.50 (m, 4H), 2.80 (br s, 2H), 2.31-2.18 (m, 1H), 1.37 (br d, J = 8.2 Hz, 6H), 1.28 (br d, J = 7.6 Hz, 6H), 1.18-1.09 (m, 2H), 1.04 (br d, J = 2.7 Hz, 2H). FXR EC$_{50}$ (nM) = 903. MS (ESI) 571.4 (M + H). | Ex. 362 |
| 579 | 7-((4-((5-cyclopropyl-3-(2,6-dichlorophenyl)isoxazol-4-yl)methoxy)bicyclo[2.2.2]octan-1-yl)methoxy)-5,6,7,8-tetrahydroimidazo[1,2-a]pyrazine-2-carboxylic acid | $^1$H NMR (500 MHz, DMSO-d$_6$) δ 8.45 (s, 1H), 7.73 (br d, J = 8.5 Hz, 1H), 7.62-7.57 (m, 2H), 7.56-7.50 (m, 1H), 7.08 (br s, 1H), 6.50 (d, J = 8.9 Hz, 1H), 4.10 (s, 2H), 3.10-3.01 (m, 2H), 2.31-2.15 (m, 1H), 1.37 (br d, J = 8.2 Hz, 6H), 1.28 (br d, J = 7.6 Hz, 6H), 1.17-1.08 (m, 2H), 1.03 (br d, J = 3.1 Hz, 2H). FXR EC$_{50}$ (nM) = 70. MS (ESI) 542.1 (M + H). | Ex. 362 |
| 580 | 5-(((4-((5-cyclopropyl-3-(2,6-dichlorophenyl)isoxazol-4-yl)methoxy)bicyclo[2.2.2]octan-1-yl)methyl)amino)nicotinic acid | $^1$H NMR (500 MHz, DMSO-d$_6$) δ 8.19 (s, 1H), 8.11 (br d, J = 1.8 Hz, 1H), 7.64-7.59 (m, 2H), 7.58-7.52 (m, 1H), 7.31 (br s, 1H), 5.87 (br s, 1H), 4.13 (s, 2H), 2.73 (br d, J = 5.2 Hz, 2H), 2.33-2.17 (m, 1H), 1.49-1.39 (m, 6H), 1.32 (br d, J = 7.0 Hz, 6H), 1.12 (br d, J = 8.2 Hz, 6H), 1.08-1.01 (m, 2H). FXR EC$_{50}$ (nM) = 543. MS (ESI) 542.3 (M + H). | Ex. 362 |

TABLE 9-continued

| Ex. No. | Structure | ¹H NMR, FXR EC$_{50}$ & MS (ESI) | Method |
|---|---|---|---|
| 581 | 3-(((4-((5-cyclopropyl-3-(2,6-dichlorophenyl)isoxazol-4-yl)methoxy)bicyclo[2.2.2]octan-1-yl)methyl)amino)-1-methyl-1H-pyrazole-5-carboxylic acid | ¹H NMR (500 MHz, DMSO-d$_6$) δ 7.63-7.58 (m, 2H), 7.57-7.51 (m, 1H), 5.89 (s, 1H), 4.12 (s, 2H), 3.80 (s, 2H), 2.68 (s, 3H), 2.31-2.20 (m, 1H), 1.37 (br d, J = 8.5 Hz, 6H), 1.29 (br d, J = 7.6 Hz, 6H), 1.16-1.09 (m, 2H), 1.05 (br d, J = 2.4 Hz, 2H). FXR EC$_{50}$ (nM) = 265. MS (ESI) 545.3 (M + H). | Ex. 362 |
| 582 | 4-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-6-methoxypicolinic acid | ¹H NMR (500 MHz, DMSO-d$_6$) δ 8.06 (s, 1H), 7.89 (d, J = 7.9 Hz, 1H), 7.83-7.76 (m, 1H), 7.74 (br d, J = 7.6 Hz, 1H), 7.52 (d, J = 7.6 Hz, 1H), 7.43 (s, 1H), 4.09 (s, 2H), 3.94 (s, 3H), 2.27-2.18 (m, 1H), 2.03-1.93 (m, 6H), 1.57-1.46 (m, 6H), 1.13-1.09 (m, 2H), 1.05-1.00 (m, 2H). FXR EC$_{50}$ (nM) = 2024. MS (ESI) 611 (M + H). | Ex. 258 |
| 583 | 6-cyclopropoxy-4-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)picolinic acid | ¹H NMR (500 MHz, DMSO-d$_6$) δ 8.10 (s, 1H), 7.90 (br d, J = 7.6 Hz, 1H), 7.80 (br d, J = 7.3 Hz, 1H), 7.77-7.69 (m, 1H), 7.54 (br d, J = 7.3 Hz, 1H), 7.50 (s, 1H), 4.38 (br s, 1H), 4.11 (s, 2H), 2.31-2.17 (m, 1H), 2.04-1.95 (m, 6H), 1.61-1.49 (m, 6H), 1.17-1.10 (m, 2H), 1.08-0.98 (m, 2H), 0.81 (br d, J = 5.8 Hz, 2H), 0.72 (br s, 2H). FXR EC$_{50}$ (nM) = 955. MS (ESI) 637 (M + H). | Ex. 258 |

TABLE 9-continued

| Ex. No. | Structure | ¹H NMR, FXR EC₅₀ & MS (ESI) | Method |
|---|---|---|---|
| 584 | 3-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-methoxybenzoic acid | ¹H NMR (500 MHz, DMSO-d₆) δ 7.89 (br d, J = 7.6 Hz, 1H), 7.85-7.64 (m, 4H), 7.53 (br d, J = 7.6 Hz, 1H), 7.30 (br d, J = 4.0 Hz, 1H), 4.10 (s, 2H), 3.16 (s, 3H), 2.31-2.14 (m, 1H), 2.02-1.92 (m, 6H), 1.58-1.45 (m, 6H), 1.14-1.09 (m, 2H), 1.06-0.99 (m, 2H). FXR EC₅₀ (nM) = 296. MS (ESI) 610 (M + H). | Ex. 69 |
| 585 | 5-(5-(4-((5-cyclopropyl-3-(3,5-dichloropyridin-4-yl)isoxazol-4-yl)methoxy)bicyclo[2.2.2]octan-1-yl)-1,2,4-oxadiazol-3-yl)-2-methoxynicotinic acid | ¹H NMR (500 MHz, DMSO-d₆) δ 8.83-8.75 (m, 3H), 8.44 (br s, 1H), 4.22 (s, 2H), 3.96 (s, 3H), 2.33-2.21 (m, 1H), 1.99-1.92 (m, 6H), 1.49-1.38 (m, 6H), 1.18-1.10 (m, 2H), 1.06 (br d, J = 2.7 Hz, 2H). FXR EC₅₀ (nM) = 114. MS (ESI) 612 (M + H) | Ex. 253 |
| 586 | 6-(2-(4-((5-cyclopropyl-3-(3,5-dichloropyridin-4-yl)isoxazol-4-yl)methoxy)bicyclo[2.2.2]octan-1-yl)ethyl)-4-isopropoxyquinoline-2-carboxylic acid | ¹H NMR (500 MHz, DMSO-d₆) δ 8.97-8.53 (m, 2H), 8.07 (d, J = 8.5 Hz, 1H), 7.90 (s, 1H), 7.70 (br d, J = 8.5 Hz, 1H), 7.53 (s, 1H), 5.14-4.99 (m, 1H), 4.19 (s, 2H), 2.67-2.58 (m, 2H), 2.32-2.22 (m, 1H), 1.49-1.37 (m, 12H), 1.37-1.24 (m, 8H), 1.15 (br d, J = 7.9 Hz, 2H), 1.06 (br d, J = 2.1 Hz, 2H). FXR EC₅₀ (nM) = 30. MS (ESI) 650 (M + H) | Ex. 430 |
| 587 | (E)-2-(4-(2-(4-((5-cyclopropyl-3-(3,5-dichloropyridin-4-yl)isoxazol-4-yl)methoxy)bicyclo[2.2.2]octan-1-yl)vinyl)phenyl)acetic acid | ¹H NMR (500 MHz, DMSO-d₆) δ 8.94-8.45 (m, 2H), 7.26 (br d, J = 7.9 Hz, 2H), 7.20-7.08 (m, 2H), 6.17 (d, J = 17.0 Hz, 1H), 6.09 (d, J = 17.0 Hz, 1H), 4.28-4.14 (m, 2H), 3.64-3.42 (m, 2H), 2.32-2.18 (m, 1H), 1.65-1.46 (m, 6H), 1.43-1.33 (m, 6H), 1.19-1.11 (m, 2H), 1.09-1.00 (m, 2H). FXR EC₅₀ (nM) = 173. MS (ESI) 553 (M + H). | Ex. 516 |

TABLE 9-continued

| Ex. No. | Structure | ¹H NMR, FXR EC$_{50}$ & MS (ESI) | Method |
|---|---|---|---|
| 588 | (E)-6-(2-(4-((5-cyclopropyl-3-(3,5-dichloropyridin-4-yl)isoxazol-4-yl)methoxy)bicyclo[2.2.2]octan-1-yl)vinyl)quinoline-2-carboxylic acid | ¹H NMR (500 MHz, DMSO-d$_6$) δ 8.91-8.70 (m, 2H), 8.50-8.33 (m, 1H), 8.08-8.00 (m, 2H), 7.97-7.84 (m, 2H), 6.56-6.27 (m, 2H), 4.34-4.11 (m, 2H), 2.38-2.19 (m, 1H), 1.73-1.57 (m, 6H), 1.48-1.36 (m, 6H), 1.20-1.13 (m, 2H), 1.11-1.02 (m, 2H). FXR EC$_{50}$ (nM) = 88. MS (ESI) 590 (M + H). | Ex. 516 |
| 589 | (E)-4-(cyclopentyloxy)-6-(2-(4-((5-cyclopropyl-3-(3,5-dichloropyridin-4-yl)isoxazol-4-yl)methoxy)bicyclo[2.2.2]octan-1-yl)vinyl)quinoline-2-carboxylic acid | ¹H NMR (500 MHz, DMSO-d$_6$) δ 9.00-8.68 (m, 2H), 8.17-7.84 (m, 3H), 7.49 (s, 1H), 6.47 (d, J = 16.0 Hz, 1H), 6.38 (d, J = 16.0 Hz, 1H), 5.23 (br s, 1H), 4.23 (s, 2H), 2.35-2.27 (m, 1H), 2.13-1.99 (m, 2H), 1.96-1.86 (m, 2H), 1.86-1.74 (m, 2H), 1.73-1.66 (m, 2H), 1.65-1.58 (m, 6H), 1.44-1.32 (m, 6H), 1.20-1.13 (m, 2H), 1.09 (br d, J = 2.7 Hz, 2H). FXR EC$_{50}$ (nM) = 17. MS (ESI) 674 (M + H). | Ex. 516 |
| 590 | (E)-6-(2-(4-((5-cyclopropyl-3-(3,5-dichloropyridin-4-yl)isoxazol-4-yl)methoxy)bicyclo[2.2.2]octan-1-yl)vinyl)-4-methoxyquinazoline-2-carboxylic acid | ¹H NMR (500 MHz, DMSO-d$_6$) δ 9.03-8.69 (m, 2H), 8.09-7.89 (m, 1H), 7.76 (dd, J = 8.5, 1.6 Hz, 1H), 7.46 (d, J = 8.5 Hz, 1H), 6.33 (d, J = 16.0 Hz, 1H), 6.23 (d, J = 16.0 Hz, 1H), 4.23 (s, 2H), 3.45 (s, 3H), 2.35-2.23 (m, 1H), 1.69-1.55 (m, 6H), 1.45-1.37 (m, 6H), 1.19-1.13 (m, 2H), 1.11-1.03 (m, 2H). FXR EC$_{50}$ (nM) = 944. MS (ESI) 621 (M + H). | Ex. 516 |

TABLE 9-continued

| Ex. No. | Structure | $^1$H NMR, FXR EC$_{50}$ & MS (ESI) | Method |
|---|---|---|---|
| 591 | 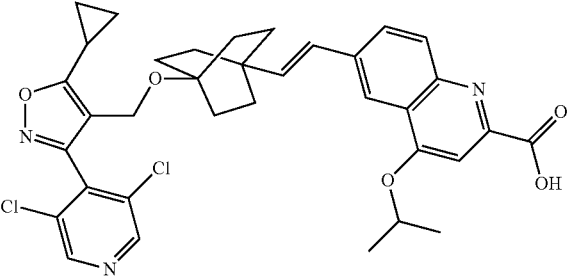<br>(E)-6-(2-(4-((5-cyclopropyl-3-(3,5-dichloropyridin-4-yl)isoxazol-4-yl)methoxy)bicyclo[2.2.2]octan-1-yl)vinyl)-4-isopropoxyquinoline-2-carboxylic acid | $^1$H NMR (500 MHz, DMSO-d$_6$) δ 8.85-8.81 (m, 2H), 8.04-7.88 (m, 3H), 7.53-7.49 (m, 1H), 6.44 (d, J = 16.0 Hz, 1H), 6.36 (d, J = 16.0 Hz, 1H), 5.08-4.99 (m, 1H), 4.26-4.20 (m, 2H), 2.34-2.26 (m, 1H), 1.68-1.56 (m, 7H), 1.47-1.42 (m, 6H), 1.40 (br d, J = 7.0 Hz, 6H), 1.19-1.13 (m, 2H), 1.09 (br d, J = 2.7 Hz, 2H). FXR EC50 (nM) = 16. MS (ESI) 648 (M + H). | Ex. 516 |
| 592 | 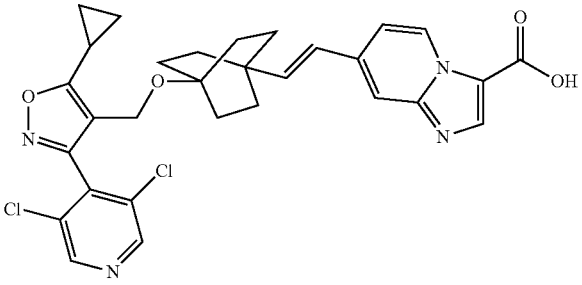<br>(E)-7-(2-(4-((5-cyclopropyl-3-(3,5-dichloropyridin-4-yl)isoxazol-4-yl)methoxy)bicyclo[2.2.2]octan-1-yl)vinyl)imidazo[1,2-a]pyridine-3-carboxylic acid | $^1$H NMR (500 MHz, DMSO-d$_6$) δ 9.31 (br d, J = 7.0 Hz, 1H), 8.84 (s, 2H), 7.93 (s, 1H), 7.50 (s, 1H), 7.20 (br d, J = 6.7 Hz, 1H), 6.37 (d, J = 16.0 Hz, 1H), 6.31 (d, J = 16.0 Hz, 1H), 4.23 (s, 2H), 2.32 (br t, J = 4.3 Hz, 1H), 1.64-1.56 (m, 6H), 1.43-1.37 (m, 6H), 1.16 (br d, J = 7.6 Hz, 2H), 1.09 (br s, 2H). FXR EC$_{50}$ (nM) = 194. MS (ESI) 579 (M + H). | Ex. 516 |
| 593 | 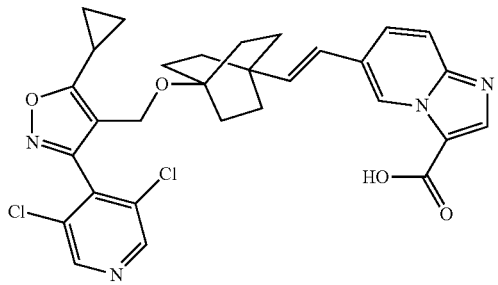<br>(E)-6-(2-(4-((5-cyclopropyl-3-(3,5-dichloropyridin-4-yl)isoxazol-4-yl)methoxy)bicyclo[2.2.2]octan-1-yl)vinyl)imidazo[1,2-a]pyridine-3-carboxylic acid | $^1$H NMR (500 MHz, DMSO-d$_6$) δ 9.19-9.07 (m, 1H), 8.82 (s, 2H), 8.17 (s, 1H), 7.79-7.62 (m, 2H), 6.33 (d, J = 16.0 Hz, 1H), 6.26 (d, J = 16.0 Hz, 1H), 4.22 (s, 2H), 2.34-2.26 (m, 1H), 1.63-1.56 (m, 6H), 1.42-1.33 (m, 6H), 1.19-1.13 (m, 2H), 1.11-1.06 (m, 2H). FXR EC$_{50}$ (nM) = 1129. MS (ESI) 579 (M + H). | Ex. 516 |

TABLE 9-continued

| Ex. No. | Structure | $^1$H NMR, FXR EC$_{50}$ & MS (ESI) | Method |
|---|---|---|---|
| 594 | 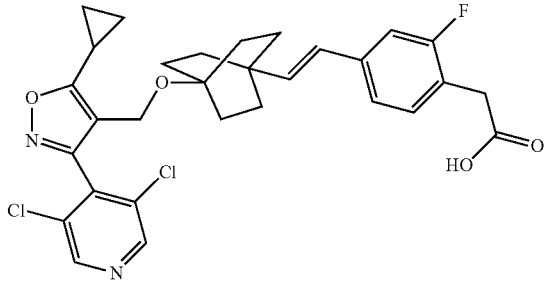<br>(E)-2-(4-(2-(4-((5-cyclopropyl-3-(3,5-dichloropyridin-4-yl)isoxazol-4-yl)methoxy)bicyclo[2.2.2]octan-1-yl)vinyl)-2-fluorophenyl)acetic acid | $^1$H NMR (500 MHz, DMSO-d$_6$) δ 8.82 (s, 2H), 7.25-7.19 (m, 1H), 7.16 (br d, J = 11.6 Hz, 1H), 7.11 (br d, J = 7.6 Hz, 1H), 6.18 (br s, 2H), 4.21 (s, 2H), 3.61 (s, 1H), 3.56 (s, 1H), 2.34-2.26 (m, 1H), 1.61-1.47 (m, 6H), 1.36 (br s, 6H), 1.19-1.11 (m, 2H), 1.08 (br s, 2H). FXR EC$_{50}$ (nM) = 153. MS (ESI) 571 (M + H). | Ex. 516 |
| 595 | 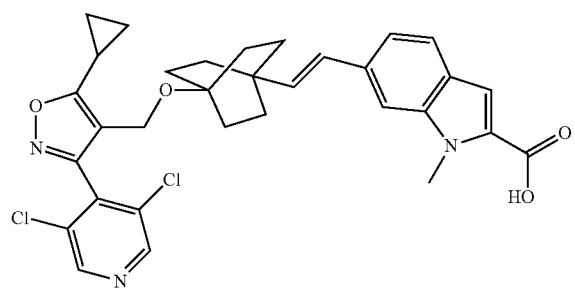<br>(E)-6-(2-(4-((5-cyclopropyl-3-(3,5-dichloropyridin-4-yl)isoxazol-4-yl)methoxy)bicyclo[2.2.2]octan-1-yl)vinyl)-1-methyl-1H-indole-2-carboxylic acid | $^1$H NMR (500 MHz, DMSO-d$_6$) δ 8.81 (s, 2H), 7.55 (d, J = 8.2 Hz, 1H), 7.45 (s, 1H), 7.18 (br d, J = 8.5 Hz, 1H), 7.13 (s, 1H), 6.32 (d, J = 16.0 Hz, 1H), 6.20 (d, J = 16.0 Hz, 1H), 4.22 (s, 2H), 3.98 (s, 3H), 2.33-2.25 (m, 1H), 1.64-1.52 (m, 6H), 1.42-1.31 (m, 6H), 1.15 (br d, J = 7.9 Hz, 2H), 1.08 (br d, J = 3.1 Hz, 2H). FXR EC$_{50}$ (nM) = 49. MS (ESI) 592 (M + H). | Ex. 516 |
| 596 | 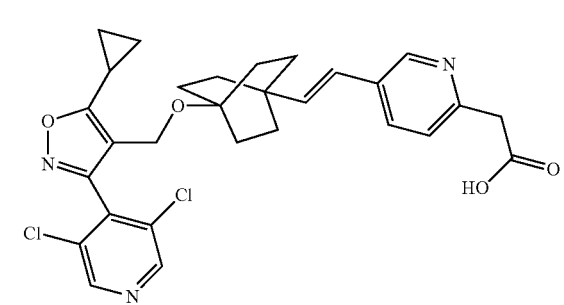<br>(E)-2-(5-(2-(4-((5-cyclopropyl-3-(3,5-dichloropyridin-4-yl)isoxazol-4-yl)methoxy)bicyclo[2.2.2]octan-1-yl)vinyl)pyridin-2-yl)acetic acid | $^1$H NMR (500 MHz, DMSO-d$_6$) δ 8.85-8.78 (m, 2H), 8.43-8.12 (m, 1H), 7.73-7.46 (m, 2H), 7.27-7.08 (m, 1H), 6.30-6.02 (m, 2H), 4.36-4.05 (m, 2H), 2.45-2.36 (m, 2H), 2.31 (br s, 1H), 1.56 (br d, J = 6.1 Hz, 6H), 1.44-1.31 (m, 6H), 1.15 (br d, J = 7.9 Hz, 2H), 1.08 (br d, J = 2.7 Hz, 2H). FXR EC$_{50}$ (nM) = 1350. MS (ESI) 554 (M + H). | Ex. 516 |

TABLE 9-continued

| Ex. No. | Structure | $^1$H NMR, FXR EC$_{50}$ & MS (ESI) | Method |
|---|---|---|---|
| 597 | 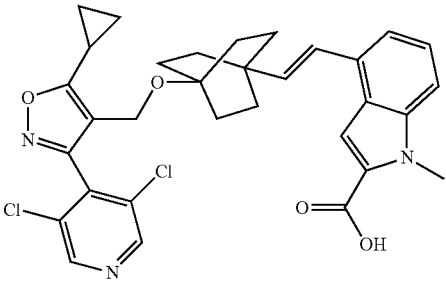<br>(E)-4-(2-(4-((5-cyclopropyl-3-(3,5-dichloropyridin-4-yl)isoxazol-4-yl)methoxy)bicyclo[2.2.2]octan-1-yl)vinyl)-1-methyl-1H-indole-2-carboxylic acid | $^1$H NMR (500 MHz, DMSO-d$_6$) δ 8.76 (s, 2H), 7.35 (br d, J = 8.2 Hz, 1H), 7.29 (s, 1H), 7.23 (br t, J = 7.8 Hz, 1H), 7.12 (br d, J = 7.3 Hz, 1H), 6.51 (br d, J = 16.2 Hz, 1H), 6.24 (br d, J = 16.5 Hz, 1H), 4.19 (s, 2H), 3.96 (s, 3H), 2.29-2.21 (m, 1H), 1.61-1.54 (m, 6H), 1.37-1.27 (m, 6H), 1.17-1.12 (m, 2H), 1.07-1.02 (m, 2H). FXR EC$_{50}$ (nM) = 208. MS (ESI) 592 (M + H). | Ex. 516 |
| 598 | 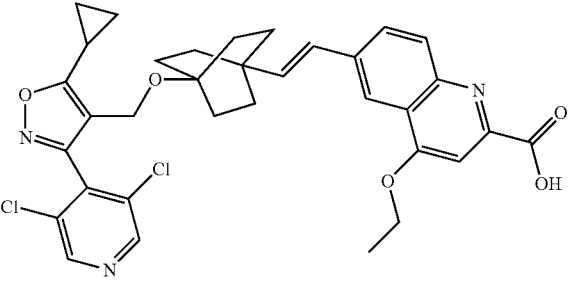<br>(E)-6-(2-(4-((5-cyclopropyl-3-(3,5-dichloropyridin-4-yl)isoxazol-4-yl)methoxy)bicyclo[2.2.2]octan-1-yl)vinyl)-4-ethoxyquinoline-2-carboxylic acid | $^1$H NMR (500 MHz, DMSO-d$_6$) δ 8.83 (s, 2H), 8.15-7.81 (m, 3H), 7.50 (s, 1H), 6.46 (d, J = 16.0 Hz, 1H), 6.39 (d, J = 16.0 Hz, 1H), 4.40 (q, J = 6.9 Hz, 2H), 4.23 (s, 2H), 2.34-2.27 (m, 1H), 1.67-1.56 (m, 6H), 1.50 (br t, J = 6.9 Hz, 3H), 1.43-1.34 (m, 6H), 1.16 (br d, J = 7.9 Hz, 2H), 1.09 (br d, J = 2.7 Hz, 2H). FXR EC$_{50}$ (nM) = 11. MS (ESI) 634 (M + H). | Ex. 516 |
| 599 | 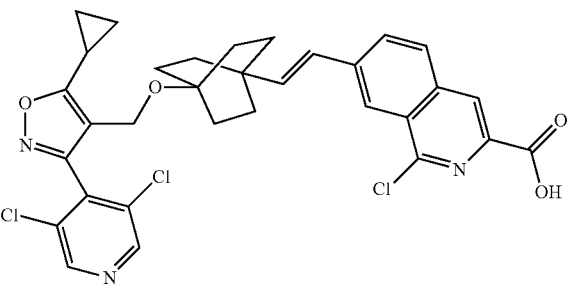<br>(E)-1-chloro-7-(2-(4-((5-cyclopropyl-3-(3,5-dichloropyridin-4-yl)isoxazol-4-yl)methoxy)bicyclo[2.2.2]octan-1-yl)vinyl)isoquinoline-3-carboxylic acid | $^1$H NMR (500 MHz, DMSO-d$_6$) δ 8.78 (s, 2H), 8.53 (br d, J = 1.9 Hz, 1H), 8.20-8.11 (m, 2H), 8.05 (br d, J = 8.7 Hz, 1H), 6.60-6.45 (m, 2H), 4.23 (s, 2H), 2.32-2.22 (m, 1H), 1.74-1.59 (m, 6H), 1.42 (br s, 6H), 1.20-1.13 (m, 3H), 1.07 (br d, J = 2.4 Hz, 2H). FXR EC$_{50}$ (nM) = 15. MS (ESI) 624 (M + H). | Ex. 516 |
| 600 | 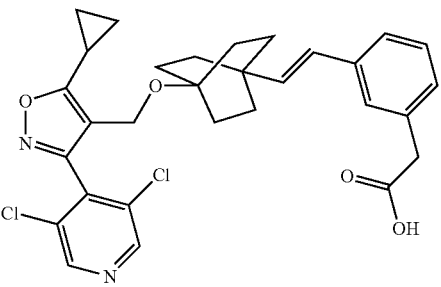<br>(E)-2-(3-(2-(4-((5-cyclopropyl-3-(3,5-dichloropyridin-4-yl)isoxazol-4-yl)methoxy)bicyclo[2.2.2]octan-1-yl)vinyl)phenyl)acetic acid | $^1$H NMR (500 MHz, DMSO-d$_6$) δ 8.83 (s, 2H), 7.25-7.14 (m, 3H), 7.06 (br d, J = 5.8 Hz, 1H), 6.24-6.06 (m, 2H), 4.22 (s, 2H), 2.55 (s, 2H), 2.37-2.21 (m, 1H), 1.56 (br d, J = 7.6 Hz, 6H), 1.38 (br d, J = 7.0 Hz, 6H), 1.15 (br d, J = 7.9 Hz, 2H), 1.09 (br d, J = 2.7 Hz, 2H). FXR EC$_{50}$ (nM) = 2038. MS (ESI) 553 (M + H). | Ex. 516 |

TABLE 9-continued

| Ex. No. | Structure | ¹H NMR, FXR EC₅₀ & MS (ESI) | Method |
|---|---|---|---|
| 601 | (E)-7-(2-(4-((5-cyclopropyl-3-(3,5-dichloropyridin-4-yl)isoxazol-4-yl)methoxy)bicyclo[2.2.2]octan-1-yl)vinyl)-1-(3-methoxypropoxy)isoquinoline-2-carboxylic acid | ¹H NMR (500 MHz, DMSO-d₆) δ 8.82 (s, 2H), 8.10-7.99 (m, 2H), 7.99-7.84 (m, 2H), 6.45 (d, J = 16.0 Hz, 1H), 6.37 (d, J = 16.0 Hz, 1H), 4.56 (br t, J = 6.4 Hz, 2H), 4.22 (s, 2H), 3.64-3.47 (m, 2H), 3.17 (s, 3H), 2.35-2.25 (m, 1H), 2.15-2.01 (m, 2H), 1.67-1.55 (m, 6H), 1.46-1.31 (m, 6H), 1.19-1.13 (m, 2H), 1.08 (br d, J = 2.7 Hz, 2H). FXR EC₅₀ (nM) = 18. MS (ESI) 678 (M + H). | Ex. 518 |
| 602 | (E)-2-(4-(2-(4-((5-cyclopropyl-3-(3,5-dichloropyridin-4-yl)isoxazol-4-yl)methoxy)bicyclo[2.2.2]octan-1-yl)vinyl)-3-fluorophenyl)acetic acid | ¹H NMR (500 MHz, DMSO-d₆) δ 8.81 (s, 2H), 7.50-7.32 (m, 1H), 7.13-6.87 (m, 2H), 6.36-5.95 (m, 2H), 4.29-4.08 (m, 2H), 3.55-3.39 (m, 2H), 2.35-2.19 (m, 1H), 1.62-1.49 (m, 6H), 1.43-1.31 (m, 6H), 1.18-1.12 (m, 2H), 1.07 (br s, 2H). FXR EC₅₀ (nM) = 81. MS (ESI) 571 (M + H). | Ex. 516 |
| 603 | (E)-7-(2-(4-((5-cyclopropyl-3-(3,5-dichloropyridin-4-yl)isoxazol-4-yl)methoxy)bicyclo[2.2.2]octan-1-yl)vinyl)-1-morpholinoisoquinoline-3-carboxylic acid | ¹H NMR (500 MHz, DMSO-d₆) δ 8.80 (s, 2H), 8.12-8.07 (m, 1H), 7.99-7.83 (m, 3H), 6.51 (d, J = 16.0 Hz, 1H), 6.39 (d, J = 16.0 Hz, 1H), 4.24 (s, 2H), 3.94-3.80 (m, 4H), 3.44-3.28 (m, 4H), 2.33-2.26 (m, 1H), 1.73-1.59 (m, 6H), 1.49-1.37 (m, 6H), 1.16 (dt, J = 8.1, 3.0 Hz, 2H), 1.12-1.05 (m, 2H). FXR EC₅₀ (nM) = 18. MS (ESI) 675 (M + H). | Ex. 516 |

TABLE 9-continued

| Ex. No. | Structure | ¹H NMR, FXR EC₅₀ & MS (ESI) | Method |
|---|---|---|---|
| 604 | (E)-7-(2-(4-((5-cyclopropyl-3-(3,5-dichloropyridin-4-yl)isoxazol-4-yl)methoxy)bicyclo[2.2.2]octan-1-yl)vinyl)-1-ethoxyisoquinoline-3-carboxylic acid | $^1$H NMR (500 MHz, DMSO-d$_6$) δ 8.78 (s, 2H), 8.11-7.99 (m, 2H), 7.96-7.85 (m, 2H), 6.41 (d, J = 16.0 Hz, 1H), 6.35 (d, J = 16.0 Hz, 1H), 4.56 (q, J = 6.8 Hz, 2H), 4.19 (s, 2H), 2.26 (br d, J = 4.3 Hz, 1H), 1.57 (br d, J = 7.6 Hz, 6H), 1.42 (br t, J = 6.9 Hz, 3H), 1.34 (br s, 6H), 1.15 (br d, J = 7.6 Hz, 2H), 1.05 (br d, J = 2.1 Hz, 2H). FXR EC$_{50}$ (nM) = 44.1. MS (ESI) 634.1 (M + H). | Ex. 518 |
| 605 | (E)-3-(5-(2-(4-((5-cyclopropyl-3-(3,5-dichloropyridin-4-yl)isoxazol-4-yl)methoxy)bicyclo[2.2.2]octan-1-yl)vinyl)-2-methoxyphenyl)propanoic acid | $^1$H NMR (500 MHz, DMSO-d$_6$) δ 9.03-8.65 (m, 2H), 7.25-7.05 (m, 2H), 6.85 (br d, J = 8.1 Hz, 1H), 6.09 (d, J = 16.0 Hz, 1H), 5.93 (d, J = 16.0 Hz, 1H), 4.23 (s, 2H), 3.77 (s, 3H), 2.75 (br s, 2H), 2.39 (br s, 2H), 2.29 (br d, J = 4.6 Hz, 1H), 1.57 (br d, J = 7.7 Hz, 6H), 1.41 (br d, J = 6.4 Hz, 6H), 1.16 (br d, J = 8.0 Hz, 2H), 1.08 (br s, 2H). FXR EC$_{50}$ (nM) = 432. MS (ESI) 597 (M + H). | Ex. 516 |
| 606 | (E)-3-(4-(2-(4-((5-cyclopropyl-3-(3,5-dichloropyridin-4-yl)isoxazol-4-yl)methoxy)bicyclo[2.2.2]octan-1-yl)vinyl)phenyl)propanoic acid | $^1$H NMR (500 MHz, DMSO-d$_6$) δ 8.77 (d, J = 1.3 Hz, 2H), 7.32-6.83 (m, 4H), 6.15 (d, J = 16.0 Hz, 1H), 6.04 (d, J = 16.0 Hz, 1H), 4.21 (s, 2H), 3.50 (br s, 2H), 2.78 (br t, J = 7.4 Hz, 2H), 2.31-2.20 (m, 1H), 1.63-1.47 (m, 6H), 1.43-1.31 (m, 6H), 1.19-1.11 (m, 2H), 1.07 (br d, J = 2.9 Hz, 2H). FXR EC$_{50}$ (nM) = 160. MS (ESI) 567 (M + H). | Ex. 516 |
| 607 | (E)-3-(4-(2-(4-((5-cyclopropyl-3-(3,5-dichloropyridin-4-yl)isoxazol-4-yl)methoxy)bicyclo[2.2.2]octan-1-yl)vinyl)-2-fluorophenyl)propanoic acid | $^1$H NMR (500 MHz, DMSO-d$_6$) δ 8.83 (s, 2H), 7.39-6.70 (m, 3H), 6.16 (s, 2H), 4.22 (s, 2H), 3.91 (s, 2H), 2.77 (br t, J = 7.3 Hz, 2H), 2.35-2.25 (m, 1H), 1.63-1.50 (m, 6H), 1.42-1.29 (m, 6H), 1.15 (br d, J = 8.2 Hz, 2H), 1.09 (br d, J = 2.4 Hz, 2H). FXR EC$_{50}$ (nM) = 269. MS (ESI) 585 (M + H). | Ex. 516 |

TABLE 9-continued

| Ex. No. | Structure | $^1$H NMR, FXR EC$_{50}$ & MS (ESI) | Method |
|---|---|---|---|
| 608 | 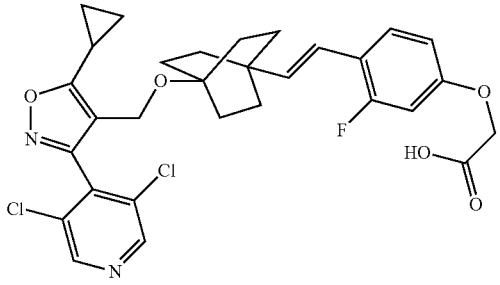<br>(E)-2-(4-(2-(4-((5-cyclopropyl-3-(3,5-dichloropyridin-4-yl)isoxazol-4-yl)methoxy)bicyclo[2.2.2]octan-1-yl)vinyl)-3-fluorophenoxy)acetic acid | $^1$H NMR (500 MHz, DMSO-d$_6$) δ 8.82 (s, 2H), 7.36 (br t, J = 9.2 Hz, 1H), 6.71-6.57 (m, 2H), 6.19-6.15 (m, 1H), 6.04 (s, 1H), 4.35 (br s, 2H), 4.22 (s, 2H), 2.35-2.25 (m, 1H), 1.54 (br d, J = 8.2 Hz, 6H), 1.40-1.29 (m, 6H), 1.15 (br d, J = 7.9 Hz, 2H), 1.08 (br d, J = 2.7 Hz, 2H). FXR EC$_{50}$ (nM) = 1033. MS (ESI) 587 (M + H). | Ex. 516 |
| 609 | 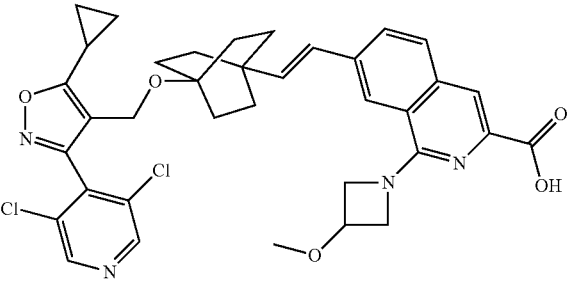<br>(E)-7-(2-(4-((5-cyclopropyl-3-(3,5-dichloropyridin-4-yl)isoxazol-4-yl)methoxy)bicyclo[2.2.2]octan-1-yl)vinyl)-1-(3-methoxyazetidin-1-yl)isoquinoline-3-carboxylic acid | $^1$H NMR (500 MHz, DMSO-d$_6$) δ 8.82 (s, 2H), 7.97-7.68 (m, 4H), 6.48 (d, J = 16.0 Hz, 1H), 6.34 (d, J = 16.0 Hz, 1H), 4.64-4.54 (m, 2H), 4.35 (br s, 1H), 4.23 (s, 4H), 2.55 (s, 3H), 2.34-2.26 (m, 1H), 1.61 (br d, J = 8.2 Hz, 6H), 1.39 (br d, J = 7.3 Hz, 6H), 1.16 (br d, J = 7.9 Hz, 2H), 1.08 (br d, J = 2.4 Hz, 2H). FXR EC$_{50}$ (nM) = 67. MS (ESI) 675 (M + H). | Ex. 516 |
| 610 | 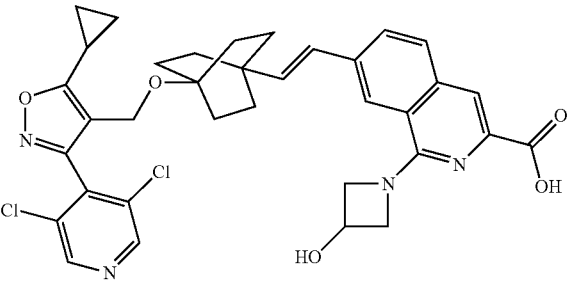<br>(E)-7-(2-(4-((5-cyclopropyl-3-(3,5-dichloropyridin-4-yl)isoxazol-4-yl)methoxy)bicyclo[2.2.2]octan-1-yl)vinyl)-1-(3-hydroxyazetidin-1-yl)isoquinoline-3-carboxylic acid | $^1$H NMR (500 MHz, DMSO-d$_6$) δ 8.81 (s, 2H), 7.96-7.65 (m, 4H), 6.48 (d, J = 16.3 Hz, 1H), 6.34 (d, J = 16.0 Hz, 1H), 4.66-4.57 (m, 3H), 4.25 (s, 2H), 4.16 (br d, J = 5.6 Hz, 2H), 3.90 (s, 1H), 2.34-2.26 (m, 1H), 1.69-1.55 (m, 6H), 1.49-1.38 (m, 6H), 1.16 (dt, J = 8.2, 3.0 Hz, 2H), 1.12-1.06 (m, 2H). FXR EC$_{50}$ (nM) = 77. MS (ESI) 661 (M + H). | Ex. 516 |

| Ex. No. | Structure | ¹H NMR, FXR EC₅₀ & MS (ESI) | Method |
|---|---|---|---|
| 611 | (E)-7-(2-(4-((5-cyclopropyl-3-(3,5-dichloropyridin-4-yl)isoxazol-4-yl)methoxy)bicyclo[2.2.2]octan-1-yl)vinyl)-1-(3-fluoroazetidin-1-yl)isoquinoline-3-carboxylic acid | ¹H NMR (500 MHz, DMSO-d₆) δ 8.84 (s, 2H), 8.01-7.66 (m, 4H), 6.49 (d, J = 16.0 Hz, 1H), 6.36 (d, J = 16.0 Hz, 1H), 5.61-5.45 (m, 1H), 4.77-4.64 (m, 2H), 4.53-4.43 (m, 2H), 4.24 (s, 2H), 2.36-2.29 (m, 1H), 1.66-1.57 (m, 6H), 1.44-1.34 (m, 6H), 1.16 (br d, J = 8.2 Hz, 2H), 1.10 (br d, J = 2.7 Hz, 2H). FXR EC₅₀ (nM) = 22. MS (ESI) 663 (M + H). | Ex. 516 |
| 612 | (E)-7-(2-(4-((5-cyclopropyl-3-(3,5-dichloropyridin-4-yl)isoxazol-4-yl)methoxy)bicyclo[2.2.2]octan-1-yl)vinyl)-1-(3-(hydroxymethyl)azetidin-1-yl)isoquinoline-3-carboxylic acid | ¹H NMR (500 MHz, DMSO-d₆) δ 8.81 (s, 2H), 7.88-7.63 (m, 4H), 6.46 (d, J = 16.0 Hz, 1H), 6.31 (d, J = 16.0 Hz, 1H), 4.46 (t, J = 8.5 Hz, 2H), 4.24 (s, 2H), 4.18 (dd, J = 8.5, 5.7 Hz, 2H), 3.90 (s, 1H), 3.65 (d, J = 6.2 Hz, 2H), 2.89-2.83 (m, 1H), 2.34-2.26 (m, 1H), 1.68-1.60 (m, 6H), 1.47-1.39 (m, 6H), 1.18-1.14 (m, 2H), 1.12-1.08 (m, 2H). FXR EC₅₀ (nM) = 108. MS (ESI) 675 (M + H). | Ex. 516 |
| 613 | (E)-1-cyclobutoxy-7-(2-(4-((5-cyclopropyl-3-(3,5-dichloropyridin-4-yl)isoxazol-4-yl)methoxy)bicyclo[2.2.2]octan-1-yl)vinyl)isoquinoline-3-carboxylic acid | ¹H NMR (500 MHz, DMSO-d₆) δ 8.84 (s, 2H), 7.96 (br s, 1H), 7.79 (br s, 3H), 6.49-6.23 (m, 2H), 5.57-5.32 (m, 1H), 4.24 (s, 2H), 2.39-2.26 (m, 1H), 2.14 (br d, J = 6.4 Hz, 2H), 2.01-1.92 (m, 1H), 1.81 (br s, 4H), 1.63 (br s, 6H), 1.40 (br s, 6H), 1.16 (br d, J = 7.9 Hz, 2H), 1.09 (br s, 2H). FXR EC₅₀ (nM) = 298. MS (ESI) 660 (M + H). | Ex. 518 |
| 614 | (E)-1-cyclopropoxy-7-(2-(4-((5-cyclopropyl-3-(3,5-dichloropyridin-4-yl)isoxazol-4-yl)methoxy)bicyclo[2.2.2]octan-1-yl)vinyl)isoquinoline-3-carboxylic acid | ¹H NMR (500 MHz, DMSO-d₆) δ 8.83 (s, 2H), 8.13 (s, 1H), 8.01-7.86 (m, 3H), 6.54-6.29 (m, 2H), 4.70 (br s, 1H), 4.23 (s, 2H), 3.90 (s, 1H), 2.33-2.24 (m, 1H), 1.61 (br d, J = 8.2 Hz, 6H), 1.43-1.37 (m, 6H), 1.16 (br d, J = 7.9 Hz, 2H), 1.09 (br d, J = 3.4 Hz, 2H), 0.83 (br s, 4H). FXR EC₅₀ (nM) = 51. MS (ESI) 646 (M + H). | Ex. 518 |

TABLE 9-continued

| Ex. No. | Structure | ¹H NMR, FXR EC₅₀ & MS (ESI) | Method |
|---|---|---|---|
| 615 | (E)-1-(cyclopentyloxy)-7-(2-(4-((5-cyclopropyl-3-(3,5-dichloropyridin-4-yl)isoxazol-4-yl)methoxy)bicyclo[2.2.2]octan-1-yl)vinyl)isoquinoline-3-carboxylic acid | ¹H NMR (500 MHz, DMSO-d₆) δ 8.92-8.56 (m, 2H), 8.04-7.78 (m, 4H), 6.57-6.24 (m, 2H), 5.75 (br s, 1H), 4.37-4.06 (m, 2H), 2.32 (br t, J = 4.4 Hz, 1H), 2.05 (br d, J = 4.9 Hz, 2H), 1.82 (br s, 4H), 1.67-1.58 (m, 8H), 1.43-1.35 (m, 6H), 1.16 (br d, J = 7.9 Hz, 2H), 1.09 (br s, 2H). FXR EC₅₀ (nM) = 52. MS (ESI) 674 (M + H). | Ex. 518 |
| 616 | (E)-2-((5-(2-(4-((5-cyclopropyl-3-(3,5-dichloropyridin-4-yl)isoxazol-4-yl)methoxy)bicyclo[2.2.2]octan-1-yl)vinyl)pyridin-2-yl)oxy)acetic acid | ¹H NMR (500 MHz, DMSO-d₆) δ 8.81 (s, 2H), 8.01 (s, 1H), 7.78 (br d, J = 8.2 Hz, 1H), 6.81 (br d, J = 8.5 Hz, 1H), 6.24-5.92 (m, 2H), 4.76 (s, 2H), 4.21 (s, 2H), 2.32-2.25 (m, 1H), 1.58-1.50 (m, 6H), 1.40-1.30 (m, 6H), 1.15 (br d, J = 7.9 Hz, 2H), 1.07 (br d, J = 2.7 Hz, 2H). FXR EC₅₀ (nM) = 3037. MS (ESI) 570 (M + H). | Ex. 516 |
| 617 | (E)-2-((4-(2-(4-((5-cyclopropyl-3-(3,5-dichloropyridin-4-yl)isoxazol-4-yl)methoxy)bicyclo[2.2.2]octan-1-yl)vinyl)pyridin-2-yl)oxy)acetic acid | ¹H NMR (500 MHz, DMSO-d₆) δ 9.03-8.62 (m, 2H), 7.96 (d, J = 5.3 Hz, 1H), 6.96 (d, J = 5.1 Hz, 1H), 6.74 (s, 1H), 6.39 (d, J = 16.0 Hz, 1H), 6.16 (d, J = 16.0 Hz, 1H), 4.69 (s, 2H), 4.22 (s, 2H), 2.32-2.26 (m, 1H), 1.63-1.53 (m, 6H), 1.43-1.36 (m, 6H), 1.18-1.12 (m, 2H), 1.11-1.04 (m, 2H). FXR EC₅₀ (nM) = 1465. MS (ESI) 570 (M + H). | Ex. 516 |
| 618 | (E)-2-(4-(2-(4-((5-cyclopropyl-3-(3,5-dichloropyridin-4-yl)isoxazol-4-yl)methoxy)bicyclo[2.2.2]octan-1-yl)vinyl)phenyl)-N-methylacetamide | ¹H NMR (500 MHz, DMSO-d₆) δ 8.79 (s, 2H), 7.85-7.68 (m, 1H), 7.36-6.98 (m, 4H), 6.31-5.73 (m, 2H), 4.22 (s, 2H), 3.89 (s, 2H), 2.57 (d, J = 4.6 Hz, 3H), 2.32-2.20 (m, 1H), 1.65-1.53 (m, 6H), 1.47-1.36 (m, 6H), 1.18-1.12 (m, 2H), 1.10-1.03 (m, 2H). FXR EC₅₀ (nM) = 393. MS (ESI) 566 (M + H). | Ex. 516 |

TABLE 9-continued

| Ex. No. | Structure | $^1$H NMR, FXR EC$_{50}$ & MS (ESI) | Method |
|---|---|---|---|
| 619 | 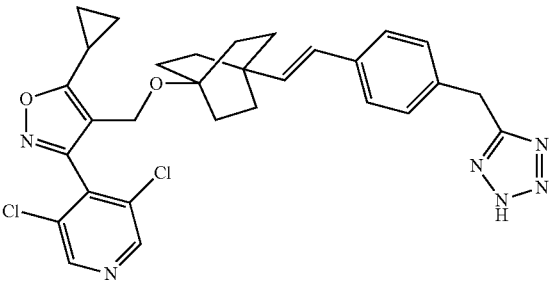<br>(E)-4-(((4-(4-((2H-tetrazol-5-yl)methyl)styryl)bicyclo[2.2.2]octan-1-yl)oxy)methyl)-5-cyclopropyl-3-(3,5-dichloropyridin-4-yl)isoxazole | $^1$H NMR (500 MHz, DMSO-d$_6$) δ 8.81 (s, 2H), 7.52-7.11 (m, 4H), 6.26-5.84 (m, 2H), 4.22 (br d, J = 9.2 Hz, 4H), 2.30 (br t, J = 4.9 Hz, 1H), 1.61-1.51 (m, 6H), 1.42-1.31 (m, 6H), 1.17-1.12 (m, 2H), 1.07 (br d, J = 3.1 Hz, 2H). FXR EC$_{50}$ (nM) = 213. MS (ESI) 577 (M + H). | Ex. 516 |
| 620 | 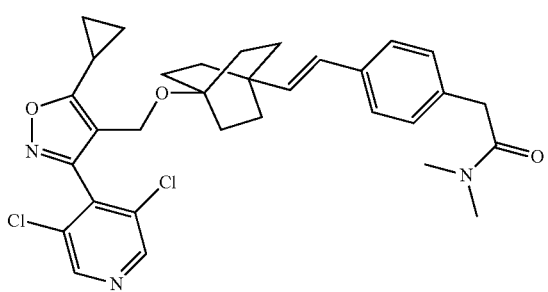<br>(E)-2-(4-(2-(4-((5-cyclopropyl-3-(3,5-dichloropyridin-4-yl)isoxazol-4-yl)methoxy)bicyclo[2.2.2]octan-1-yl)vinyl)phenyl)-N,N-dimethylacetamide | $^1$H NMR (500 MHz, DMSO-d$_6$) δ 8.82 (s, 2H), 7.26 (br d, J = 7.9 Hz, 2H), 7.11 (br d, J = 8.2 Hz, 2H), 6.14 (d, J = 16.0 Hz, 1H), 6.09 (d, J = 16.0 Hz, 1H), 4.22 (s, 2H), 3.63 (s, 1H), 2.96 (s, 3H), 2.81 (s, 3H), 2.54 (s, 1H), 2.34-2.25 (m, 1H), 1.59-1.51 (m, 6H), 1.39-1.34 (m, 6H), 1.15 (br d, J = 8.2 Hz, 2H), 1.08 (br s, 2H). FXR EC$_{50}$ (nM) = 382. MS (ESI) 580 (M + H). | Ex. 516 |
| 621 | 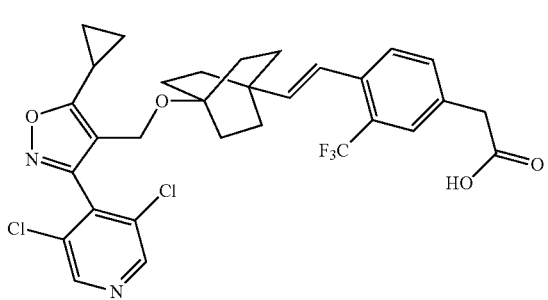<br>(E)-2-(4-(2-(4-((5-cyclopropyl-3-(3,5-dichloropyridin-4-yl)isoxazol-4-yl)methoxy)bicyclo[2.2.2]octan-1-yl)vinyl)-3-(trifluoromethyl)phenyl)acetic acid | $^1$H NMR (500 MHz, DMSO-d$_6$) δ 8.83 (s, 2H), 7.60 (br d, J = 7.9 Hz, 1H), 7.55 (s, 1H), 7.45 (br d, J = 7.9 Hz, 1H), 6.42 (d, J = 16.5 Hz, 1H), 6.18 (d, J = 16.5 Hz, 1H), 4.23 (s, 2H), 3.59 (s, 2H), 2.35-2.27 (m, 1H), 1.60-1.54 (m, 6H), 1.41-1.33 (m, 6H), 1.15 (br d, J = 7.9 Hz, 2H), 1.09 (br s, 2.4 Hz, 2H). FXR EC$_{50}$ (nM) = 43. MS (ESI) 621 (M + H). | Ex. 516 |
| 622 | 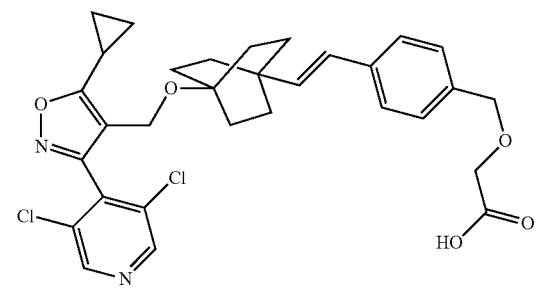<br>(E)-2-((4-(2-(4-((5-cyclopropyl-3-(3,5-dichloropyridin-4-yl)isoxazol-4-yl)methoxy)bicyclo[2.2.2]octan-1-yl)vinyl)benzyl)oxy)acetic acid | $^1$H NMR (500 MHz, DMSO-d$_6$) δ 8.81 (s, 2H), 7.31 (br d, J = 7.6 Hz, 2H), 7.23 (br d, J = 7.9 Hz, 2H), 6.17 (d, J = 15.5 Hz, 1H), 6.13 (d, J = 15.5 Hz, 1H), 4.47 (s, 2H), 4.21 (s, 2H), 4.02 (s, 2H), 2.29 (br dd, J = 8.4, 4.1 Hz, 1H), 1.55 (br d, J = 7.9 Hz, 6H), 1.36 (br s, 6H), 1.16-1.11 (m, 2H), 1.07 (br s, 2H). FXR EC$_{50}$ (nM) = 176. MS (ESI) 583 (M + H). | Ex. 516 |

TABLE 9-continued

| Ex. No. | Structure | ¹H NMR, FXR EC₅₀ & MS (ESI) | Method |
|---|---|---|---|
| 623 | (E)-3-(3-(2-(4-((5-cyclopropyl-3-(3,5-dichloropyridin-4-yl)isoxazol-4-yl)methoxy)bicyclo[2.2.2]octan-1-yl)vinyl)phenyl)propanoic acid | ¹H NMR (500 MHz, DMSO-d₆) δ 8.81 (s, 2H), 7.23-7.11 (m, 3H), 7.03 (br d, J = 7.0 Hz, 1H), 6.13 (br d, J = 3.7 Hz, 2H), 4.21 (s, 2H), 2.77 (br t, J = 7.5 Hz, 2H), 2.37-2.20 (m, 1H), 1.55 (br d, J = 8.2 Hz, 7H), 1.43-1.30 (m, 7H), 1.14 (br d, J = 7.9 Hz, 2H), 1.07 (br d, J = 2.4 Hz, 2H). FXR EC₅₀ (nM) = 843. MS (ESI) 567 (M + H). | Ex. 516 |
| 624 | (E)-2-(5-(2-(4-((5-cyclopropyl-3-(3,5-dichloropyridin-4-yl)isoxazol-4-yl)methoxy)bicyclo[2.2.2]octan-1-yl)vinyl)-2-(2,2-difluoroethoxy)phenyl)propanoic acid | ¹H NMR (500 MHz, DMSO-d₆) δ 8.82 (s, 2H), 7.23-7.08 (m, 2H), 6.89 (br d, J = 8.2 Hz, 1H), 6.51-6.23 (m, 1H), 6.14-5.86 (m, 2H), 4.39-4.04 (m, 4H), 2.76-2.62 (m, 3H), 2.37-2.26 (m, 3H), 1.54 (br d, J = 7.6 Hz, 6H), 1.36 (br d, J = 7.0 Hz, 6H), 1.15 (br d, J = 7.6 Hz, 2H), 1.08 (br s, 2H). FXR EC₅₀ (nM) = 438. MS (ESI) 647 (M + H). | Ex. 516 |
| 625 | (E)-4-(2-(4-((5-cyclopropyl-3-(3,5-dichloropyridin-4-yl)isoxazol-4-yl)methoxy)bicyclo[2.2.2]octan-1-yl)vinyl)benzoic acid | ¹H NMR (500 MHz, DMSO-d₆) δ 8.82 (s, 2H), 7.84 (br d, J = 7.9 Hz, 2H), 7.45 (br d, J = 7.9 Hz, 2H), 6.59-5.74 (m, 2H), 4.22 (s, 2H), 2.35-2.20 (m, 1H), 1.65-1.53 (m, 6H), 1.43-1.33 (m, 6H), 1.15 (br d, J = 7.9 Hz, 2H), 1.08 (br d, J = 2.7 Hz, 2H). FXR EC₅₀ (nM) = 350. MS (ESI) 539 (M + H). | Ex. 516 |
| 626 | (E)-4-(2-(4-((5-cyclopropyl-3-(3,5-dichloropyridin-4-yl)isoxazol-4-yl)methoxy)bicyclo[2.2.2]octan-1-yl)vinyl)picolinic acid | ¹H NMR (500 MHz, DMSO-d₆) δ 8.83 (s, 2H), 8.56 (br d, J = 4.9 Hz, 1H), 7.99 (s, 1H), 7.58 (br d, J = 4.3 Hz, 1H), 6.57 (d, J = 16.0 Hz, 1H), 6.31 (d, J = 16.0 Hz, 1H), 4.23 (s, 2H), 2.31 (br s, 1H), 1.59 (br d, J = 7.9 Hz, 6H), 1.39 (br d, J = 7.3 Hz, 6H), 1.15 (br d, J = 7.9 Hz, 2H), 1.08 (br s, 2H). FXR EC₅₀ (nM) = 879. MS (ESI) 540 (M + H). | Ex. 516 |

| Ex. No. | Structure | $^1$H NMR, FXR EC$_{50}$ & MS (ESI) | Method |
|---|---|---|---|
| 627 | (E)-5-(2-(4-((5-cyclopropyl-3-(3,5-dichloropyridin-4-yl)isoxazol-4-yl)methoxy)bicyclo[2.2.2]octan-1-yl)vinyl)nicotinic acid | $^1$H NMR (500 MHz, DMSO-d$_6$) δ 8.89-8.66 (m, 4H), 8.21 (br s, 1H), 6.41 (d, J = 16.5 Hz, 1H), 6.30 (d, J = 16.5 Hz, 1H), 4.21 (s, 2H), 2.30 (br s, 1H), 1.58 (br s, 6H), 1.37 (br s, 6H), 1.14 (br d, J = 7.0 Hz, 2H), 1.08 (br s, 2H). FXR EC$_{50}$ (nM) = 1153. MS (ESI) 540 (M + H). | Ex. 516 |
| 628 | (E)-2-(4-(2-(4-((5-cyclopropyl-3-(3,5-dichloropyridin-4-yl)isoxazol-4-yl)methoxy)bicyclo[2.2.2]octan-1-yl)vinyl)phenyl)thiazole-4-carboxylic acid | $^1$H NMR (500 MHz, DMSO-d$_6$) δ 8.83 (s, 2H), 8.40 (s, 1H), 7.89 (br d, J = 7.9 Hz, 2H), 7.50 (br d, J = 7.9 Hz, 2H), 6.46-6.15 (m, 2H), 4.23 (s, 2H), 2.37-2.22 (m, 1H), 1.59 (br d, J = 7.9 Hz, 6H), 1.38 (br d, J = 6.4 Hz, 6H), 1.15 (br d, J = 7.9 Hz, 2H), 1.09 (br s, 2H). FXR EC$_{50}$ (nM) = 72. MS (ESI) 622 (M + H). | Ex. 516 |
| 629 | (E)-7-(2-(4-((5-cyclopropyl-3-(3,5-dichloropyridin-4-yl)isoxazol-4-yl)methoxy)bicyclo[2.2.2]octan-1-yl)vinyl)-1-(4-methylpiperazin-1-yl)isoquinoline-3-carboxylic acid | $^1$H NMR (500 MHz, DMSO-d$_6$) δ 8.82 (s, 2H), 8.15 (s, 1H), 8.03-7.96 (m, 1H), 7.93 (br d, J = 8.9 Hz, 1H), 7.89 (s, 1H), 6.52 (d, J = 16.2 Hz, 1H), 6.38 (d, J = 16.2 Hz, 1H), 4.23 (s, 2H), 3.51-3.36 (m, 2H), 3.19-3.08 (m, 2H), 2.67 (br s, 4H), 2.54 (s, 3H), 2.31 (br d, J = 4.6 Hz, 1H), 1.61 (br d, J = 7.6 Hz, 6H), 1.39 (br s, 6H), 1.15 (br d, J = 7.6 Hz, 2H), 1.08 (br s, 2H). FXR EC$_{50}$ (nM) = 35. Mouse in vivo (3 mg/kg, @ 6 h): Cypa7a1 = −97%, Ffg15 = +7.1x. MS (ESI) 688 (M + H). | Ex. 516 |

BIOLOGICAL EVALUATION

The exemplified compounds of the present invention were tested in the transient human FXR/Gal4-luciferase reporter assay, and assay results were described in the EXAMPLES section hereinbefore.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/ml Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 µg of the pcDNA3.1-Gal4-FXR plasmid into 1.87 mL of Opti-MEM (Thermo-Fisher), and 40 µL of Lipofectamine 2000 (Thermo-Fisher)

into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% $CO_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an $EC_{50}$ value.

In Vivo Testing Example: Acute Mouse PK/PD

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

TABLE A

| | | Mouse PD | |
|---|---|---|---|
| Example # | Dose (mg/kg) | Cyp7a1 (fold change@ 6 h relative to Vehicle) | Fgf15 (fold change@ 6 h relative to Vehicle) |
| 27 | 30 | 0.10 | 2.8 |
| 101 | 3 | 0.06 | 21 |

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (IIa) or Formula (IIb):

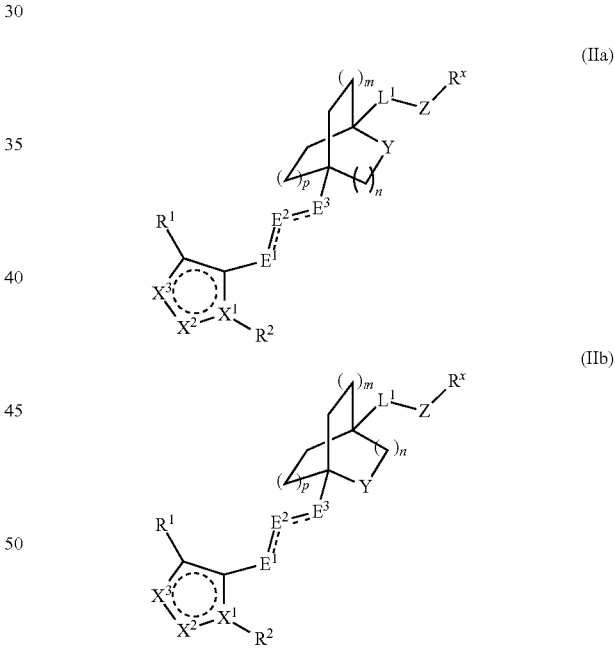

or a stereoisomer, a tautomer, or a pharmaceutically acceptable salt or solvate thereof;
wherein:
$X^1$ is C or N;
$X^2$ and $X^3$ are each independently CH, N, O, or S;
$E^1$ and $E^3$ are each independently a covalent bond, O, S, N, NH, CH, or $CH_2$;
$E^2$ is O, S, N, NH, CH, or $CH_2$; wherein ($E^1$ and $E^2$) or ($E^3$ and $E^2$) forms a single bond or double bond; provided that (1) the bonds between ($E^1$ and $E^2$) and ($E^3$ and $E^2$) are not both double bonds; and (2) at least one of $E^1$, $E^2$, and $E^3$ is not O, S, N, or NH;

Y is O, S, NH, or CH$_2$;

m, n, and p are each independently 0 or 1;

L$^1$ is a covalent bond, C$_{1-3}$ alkylene, C$_{1-3}$ heteroalkylene, C$_{2-4}$ alkenylene, C$_{2-4}$ alkynylene, or a 5- to 6-membered heteroaryl containing 1 to 3 heteroatoms independently selected from N, O, and S; wherein the alkylene, heteroalkylene, and heteroaryl are independently substituted with 0 to 3 R$^9$;

Z is phenyl or 5- to 10-membered heteroaryl, wherein the phenyl and heteroaryl are independently substituted with 0 to 3 R$^{10}$;

R$^X$ is —(CR$^{12a}$R$^{12b}$)$_e$—R$^Z$ or —O(CR$^{12a}$R$^{12b}$)$_e$—R$^Z$;

e is 0 or 1;

R$^Z$ is selected from —CN, —OH, —C(O)OR$^{13}$, —C(O)NR$^{14a}$R$^{14b}$,

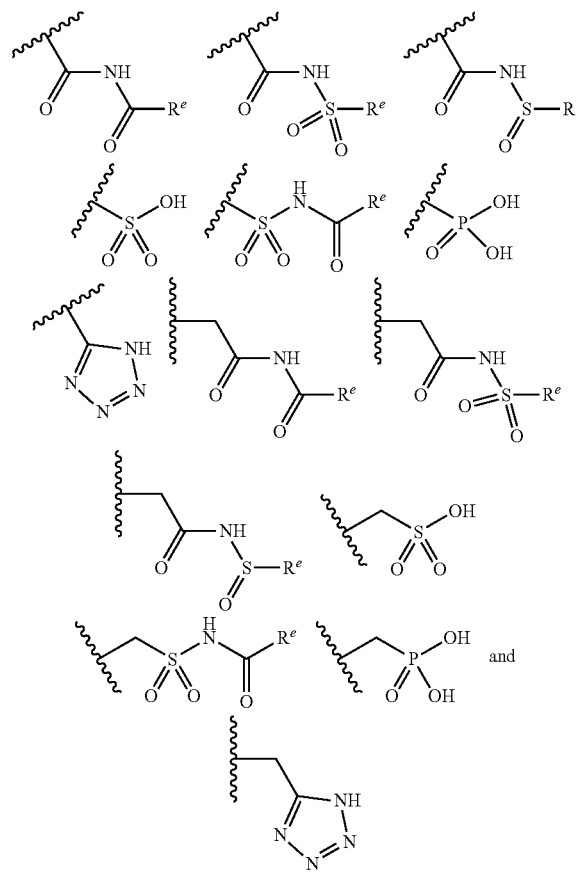

R$^e$ is C$_{1-6}$ alkyl, C$_{3-6}$ cycloalkyl, haloalkyl, hydroxyalkyl, aminoalkyl, alkoxyalkyl, haloalkoxyalkyl, or phenyl;

R$^1$ is C$_{1-6}$ alkyl or C$_{3-5}$ cycloalkyl, wherein the alkyl or cycloalkyl is substituted with 0 to 3 R$^{15}$;

R$^2$ is phenyl or 6-membered heteroaryl, wherein the phenyl or heteroaryl is substituted with 0 to 3 R$^{16}$;

R$^9$ is each independently halo, oxo, cyano, hydroxyl, amino, C$_{1-6}$ alkyl, C$_{3-6}$ cycloalkyl, C$_{4-6}$ heterocyclyl, alkylamino, haloalkyl, hydroxyalkyl, aminoalkyl, alkoxyalkyl, haloalkoxyalkyl, alkoxy, or haloalkoxy;

R$^{10}$ and R$^{16}$ are each independently halo, cyano, hydroxyl, amino, oxo, —OR$^a$, —SR$^a$, =S, —NR$^c$R$^c$, =NH, =N—OH, =NR$^a$, =N—OR$^a$, —NO$_2$, —S(O)$_2$R$^a$, —S(O)$_2$NHR$^b$, —S(O)$_2$NR$^c$R$^c$, —S(O)$_2$OR$^b$, —OS(O)$_2$R$^b$, —OS(O)$_2$OR$^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —OC(O)NR$^c$R$^c$, —NR$^b$C(O)NR$^c$R$^c$, —NR$^b$C(NR$^b$)R$^b$, —NR$^b$C(NR$^b$)NR$^c$R$^c$, C$_{1-6}$ alkyl, C$_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 R$^d$;

R$^a$ is independently selected from C$_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

R$^b$ is each independently hydrogen or R$^a$;

R$^c$ is each independently R$^b$ or alternatively, the two R$^c$ are taken together with the nitrogen atom to which they are bonded form a 4-, 5-, 6- or 7-membered heterocyclyl;

R$^d$ is each independently R$^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —OR$^a$, —SR$^a$, =S, —NR$^c$R$^c$, =NH, =N—OH, =NR$^a$, =N—OR$^a$, —NO$_2$, —S(O)$_2$R$^a$, —S(O)$_2$NHR$^b$, —S(O)$_2$NR$^c$R$^c$, —S(O)$_2$OR$^b$, —OS(O)$_2$R$^b$, —OS(O)$_2$OR$^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —NR$^b$C(O)NR$^c$R$^c$, —NR$^b$C(NR$^b$)R$^b$, or —NR$^b$C(NR$^b$)NR$^c$R$^c$;

R$^{12a}$ and R$^{12b}$ are each independently hydrogen, halo, cyano, hydroxyl, amino, C$_{1-6}$ alkyl, alkylamino, haloalkyl, hydroxyalkyl, aminoalkyl, alkoxyalkyl, haloalkoxyalkyl, alkoxy, or haloalkoxy; or alternatively, R$^{12a}$ and R$^{12b}$ together with the atom(s) to which they are attached, form a 3- or 4-membered carbocyclic or heterocyclic ring;

R$^{13}$ is hydrogen, C$_{1-10}$ alkyl, or glycosyl;

R$^{14a}$ and R$^{14b}$ are each independently hydrogen, C$_{1-6}$ alkyl, haloalkyl, hydroxyalkyl, aminoalkyl, alkoxyalkyl, haloalkoxyalkyl, alkoxy, or haloalkoxy;

R$^{15}$ is each hydrogen, halo, cyano, hydroxyl, amino, C$_{1-6}$ alkyl, alkylamino, haloalkyl, hydroxyalkyl, aminoalkyl, alkoxyalkyl, haloalkoxyalkyl, alkoxy, or haloalkoxy; and R$^{16}$ is each independently hydrogen, C$_{1-6}$ alkyl, haloalkyl, hydroxyalkyl, aminoalkyl, alkoxyalkyl, or haloalkoxyalkyl.

2. The compound according to claim 1, or a stereoisomer, a tautomer, or a pharmaceutically acceptable salt or solvate thereof; wherein:

X$^1$ is C, X$^2$ is N, and X$^3$ is O; or

X$^1$ is N, X$^2$ is N, and X$^3$ is N.

3. The compound according to claim 1, or a stereoisomer, a tautomer, or a pharmaceutically acceptable salt or solvate thereof; wherein:

Y is CH$_2$; and (i) L$^1$ is a 5- to 6-membered heteroaryl containing 1 to 3 heteroatoms independently selected from N, O, and S; and Z is phenyl or 6-membered heteroaryl;

(ii) L$^1$ is a covalent bond; and Z is 5- to 10-membered heteroaryl; or (iii) $L^1$ is $C_{1-3}$ alkylene, $C_{1-3}$ heteroalkylene or $C_{2-4}$ alkynylene; and Z is phenyl or 5- to 10-membered heteroaryl;

wherein the phenyl and heteroaryl are each independently substituted by 0 to 3 $R^{10}$.

4. The compound according to claim 1, or a stereoisomer, a tautomer, or a pharmaceutically acceptable salt or solvate thereof; wherein:

Y is O; and (i) $L^1$ is a 5- to 6-membered heteroaryl containing 1 to 3 heteroatoms independently selected from N, O, and S; and Z is phenyl or 6-membered heteroaryl;

(ii) $L^1$ is a covalent bond; and Z is 5- to 10-membered heteroaryl; or (iii) $L^1$ is $C_{1-3}$ heteroalkylene or $C_{2-4}$ alkynylene; and Z is phenyl or 5- to 10-membered heteroaryl;

wherein the phenyl and heteroaryl are each independently substituted by 0 to 3 $R^{10}$.

5. The compound according to claim 1, wherein:

$X^1$ is C;

$X^2$ is N;

$X^3$ is O;

$R^1$ is cyclopropyl;

$E^1$, $E^2$ and $E^3$ together form a moiety selected from

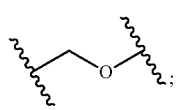 [SMILES: *CO*]

$L^1$ is

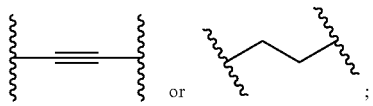

Z is benzo[d]thiazolyl, isoquinolinyl, phenyl, pyrazolyl, pyridinyl, or quinolinyl, each substituted with zero to 3 $R^{10}$;

$R^x$ is —C(O)OH, —C(O)NH$_2$, —C(O)NHS(O)$_2$CH$_3$, —CH$_2$C(O)OH, or —C(O)OCH$_3$;

each $R^{10}$ is independently F, Cl, —CH$_3$, —CH$_2$CH$_3$, —CF$_3$, —OCH$_3$, —OCH$_2$CH$_3$, —OCH(CH$_3$)$_2$, —OCHF$_2$, —OCF$_3$, —O(C$_{3-5}$ cycloalkyl), methylpiperazinyl, or cyclopropyl;

$L^2$ is covalent bond;

$R^2$ is phenyl or pyridinyl, each independently substituted with 0 to 3 $R^{16}$; and each $R^{16}$ is independently F, Cl, —CH$_3$, —CF$_3$, —OCH$_3$, or —OCF$_3$.

6. The compound according to claim 1, or a stereoisomer, a tautomer, or a pharmaceutically acceptable salt or solvate thereof; wherein said compound is selected from:

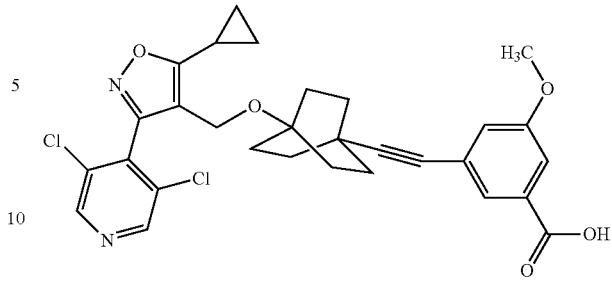

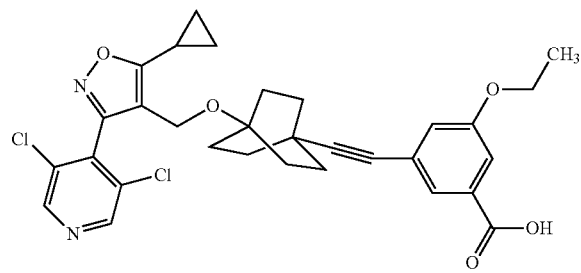

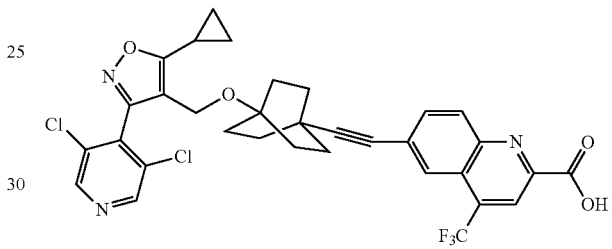

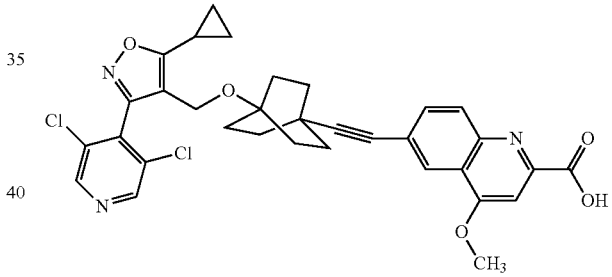

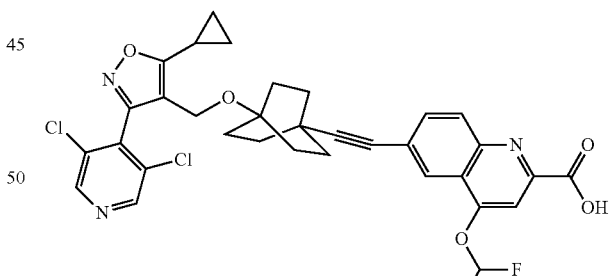

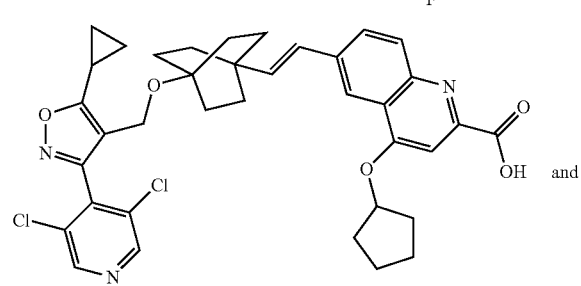

and

-continued

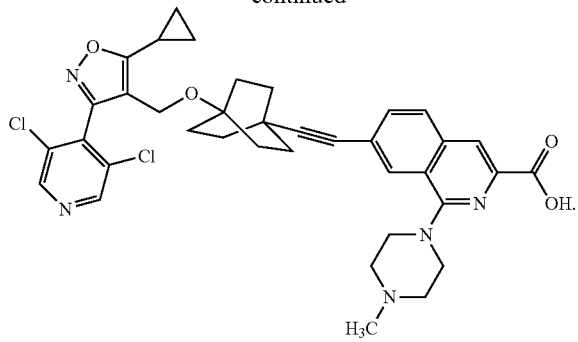

7. The compound of claim 1, which is selected from (E)-3-(2-(4-(((5-cyclopropyl-3-(2,6-dichlorophenyl)isoxazol-4-yl)methoxy) bicyclo[2.2.2]octan-1-yl)vinyl)benzoic acid (7); (E)-4-(((4-(3-(1H-tetrazol-5-yl)styryl)bicyclo[2.2.2]octan-1-yl)oxy)methyl)-5-cyclopropyl-3-(2-(trifluoromethoxy)phenyl)isoxazole (8); (E)-3-(2-(4-((5-cyclopropyl-3-(2-(trifluoromethoxy)phenyl)isoxazol-4-yl)methoxy)bicyclo[2.2.2]octan-1-yl)vinyl)benzoic acid (40-41); 3-((4-((5-cyclopropyl-3-(2,6-dichlorophenyl) isoxazol-4-yl)methoxy)bicyclo[2.2.2]octan-1-yl)ethynyl)benzoic acid (130); 2-((4-((5-cyclopropyl-3-(2,6-dichlorophenyl)isoxazol-4-yl)methoxy)bicyclo[2.2.2]octan-1-yl) ethynyl)isonicotinic acid (132); 2-((4-((5-cyclopropyl-3-(3,5-dichloropyridin-4-yl) isoxazol-4-yl)methoxy)bicyclo[2.2.2]octan-1-yl)ethynyl)-4-fluorobenzo[d]thiazole-6-carboxylic acid (133); 6-((4-((5-cyclopropyl-3-(3,5-dichloropyridin-4-yl)isoxazol-4-yl) methoxy)bicyclo[2.2.2]octan-1-yl)ethynyl)-1-methyl-1H-pyrrolo[2,3-b]pyridine-3-carboxylic acid (363); 6-((4-((5-cyclopropyl-3-(3,5-dichloropyridin-4-yl)isoxazol-4-yl) methoxy)bicyclo[2.2.2]octan-1-yl)ethynyl)-4-(trifluoromethyl)quinoline-2-carboxylic acid (364); 3-((4-((5-cyclopropyl-3-(3,5-dichloropyridin-4-yl)isoxazol-4-yl)methoxy)bicyclo[2.2.2]octan-1-yl) ethynyl)-5-(trifluoromethyl)benzoic acid (366); 5-((4-((5-cyclopropyl-3-(3,5-dichloropyridin-4-yl)isoxazol-4-yl) methoxy)bicyclo[2.2.2]octan-1-yl)ethynyl)-2-methoxybenzoic acid (367); 6-((4-((5-cyclopropyl-3-(3,5-dichloropyridin-4-yl)isoxazol-4-yl)methoxy)bicyclo[2.2.2]octan-1-yl) ethynyl)-4-(trifluoromethyl)picolinic acid (373); 6-((4-((5-cyclopropyl-3-(3,5-dichloropyridin-4-yl)isoxazol-4-yl) methoxy)bicyclo[2.2.2]octan-1-yl) ethynyl)-4-(trifluoromethyl)nicotinic acid (374); 6-((4-((5-cyclopropyl-3-(3,5-dichloropyridin-4-yl)isoxazol-4-yl)methoxy) bicyclo[2.2.2]octan-1-yl) ethynyl)-4-methoxyquinoline-2-carboxylic acid (375); 6-((4-((5-cyclopropyl-3-(3,5-dichloropyridin-4-yl)isoxazol-4-yl) methoxy) bicyclo[2.2.2]octan-1-yl) ethynyl)-4-(difluoromethoxy)quinoline-2-carboxylic acid (376); 6-((4-((5-cyclopropyl-3-(3,5-dichloropyridin-4-yl)isoxazol-4-yl) methoxy) bicyclo[2.2.2]octan-1-yl) ethynyl)-4-methoxypicolinic acid (377); 3-((4-((5-cyclopropyl-3-(3,5-dichloropyridin-4-yl)isoxazol-4-yl) methoxy)bicyclo[2.2.2]octan-1-yl) ethynyl)-5-(trifluoromethoxy) benzoic acid (378); 6-((4-((5-cyclopropyl-3-(3,5-dichloropyridin-4-yl)isoxazol-4-yl) methoxy)bicyclo[2.2.2]octan-1-yl) ethynyl)-5-fluoronicotinic acid (379); 3-((4-((5-cyclopropyl-3-(3,5-dichloropyridin-4-yl)isoxazol-4-yl) methoxy)bicyclo[2.2.2]octan-1-yl) ethynyl)-5-methoxybenzoic acid (380); 3-((4-((5-cyclopropyl-3-(3,5-dichloropyridin-4-yl)isoxazol-4-yl) methoxy)bicyclo[2.2.2]octan-1-yl) ethynyl)-2-methoxybenzoic acid (381); 6-((4-((5-cyclopropyl-3-(3,5-dichloropyridin-4-yl)isoxazol-4-yl) methoxy) bicyclo[2.2.2]octan-1-yl) ethynyl)quinoline-2-carboxylic acid (382); 3-((4-((5-cyclopropyl-3-(3,5-dichloropyridin-4-yl)isoxazol-4-yl)methoxy)bicyclo[2.2.2]octan-1-yl)ethynyl)-2-methoxybenzoic acid (383); 3-((4-((5-cyclopropyl-3-(3,5-dichloropyridin-4-yl)isoxazol-4-yl) methoxy)bicyclo[2.2.2]octan-1-yl)ethynyl)-5-(methoxymethyl)benzoic acid (386); 5-((4-((5-cyclopropyl-3-(3,5-dichloropyridin-4-yl)isoxazol-4-yl)methoxy) bicyclo[2.2.2]octan-1-yl)ethynyl)-4-methylpicolinic acid (387); 5-((4-((5-cyclopropyl-3-(3,5-dichloropyridin-4-yl)isoxazol-4-yl)methoxy)bicyclo[2.2.2] octan-1-yl)ethynyl)-3-methylpicolinic acid (388); 6-((4-((5-cyclopropyl-3-(3,5-dichloropyridin-4-yl)isoxazol-4-yl)methoxy)bicyclo[2.2.2]octan-1-yl)ethynyl)-4-isopropoxyquinoline-2-carboxylic acid (390); 3-((4-((5-cyclopropyl-3-(3,5-dichloropyridin-4-yl)isoxazol-4-yl)methoxy) bicyclo[2.2.2]octan-1-yl) ethynyl)imidazo[1,2-a]pyridine-7-carboxylic acid (393); 7-((4-((5-cyclopropyl-3-(3,5-dichloropyridin-4-yl)isoxazol-4-yl) methoxy) bicyclo[2.2.2]octan-1-yl)ethynyl)imidazo[1,2-a]pyridine-2-carboxylic acid (394); 5-((4-((5-cyclopropyl-3-(3,5-dichloropyridin-4-yl)isoxazol-4-yl) methoxy)bicyclo[2.2.2]octan-1-yl)ethynyl) pyrazolo[1,5-a]pyridine-3-carboxylic acid (395); 5-((4-((5-cyclopropyl-3-(3,5-dichloropyridin-4-yl)isoxazol-4-yl) methoxy)bicyclo[2.2.2]octan-1-yl)ethynyl) pyrazolo[1,5-a]pyridine-3-carboxylic acid (396); 3-((4-((5-cyclopropyl-3-(3,5-dichloropyridin-4-yl)isoxazol-4-yl) methoxy)bicyclo[2.2.2]octan-1-yl)ethynyl) imidazo[1,2-a]pyridine-8-carboxylic acid (397); 3-((4-((5-cyclopropyl-3-(3,5-dichloropyridin-4-yl)isoxazol-4-yl) methoxy)bicyclo[2.2.2]octan-1-yl) ethynyl)-1-methyl-1H-indole-6-carboxylic acid (399); 3-((4-((5-cyclopropyl-3-(3,5-dichloropyridin-4-yl)isoxazol-4-yl) methoxy)bicyclo[2.2.2] octan-1-yl) ethynyl)-5-isopropoxybenzoic acid (400); 5-((4-((5-cyclopropyl-3-(3,5-dichloropyridin-4-yl)isoxazol-4-yl) methoxy) bicyclo[2.2.2]octan-1-yl) ethynyl)-1H-indazole-7-carboxylic acid (401); 4-cyclobutoxy-6-((4-((5-cyclopropyl-3-(3,5-dichloropyridin-4-yl)isoxazol-4-yl) methoxy) bicyclo[2.2.2]octan-1-yl) ethynyl)quinoline-2-carboxylic acid (402); 6-((4-((5-cyclopropyl-3-(3,5-dichloropyridin-4-yl)isoxazol-4-yl) methoxy)bicyclo[2.2.2] octan-1-yl) ethynyl)imidazo[1,2-a]pyridine-8-carboxylic acid (404); 6-((4-((5-cyclopropyl-3-(3,5-dichloropyridin-4-yl)isoxazol-4-yl) methoxy)bicyclo[2.2.2]octan-1-yl) ethynyl)-1H-indazole-4-carboxylic acid (411); 8-((4-((5-cyclopropyl-3-(3,5-dichloropyridin-4-yl)isoxazol-4-yl) methoxy) bicyclo[2.2.2]octan-1-yl) ethynyl)quinoline-5-carboxylic acid (412); 6-((4-((5-cyclopropyl-3-(3,5-dichloropyridin-4-yl)isoxazol-4-yl)methoxy) bicyclo[2.2.2]octan-1-yl) ethynyl)-1H-indole-4-carboxylic acid (415); 4-((4-((5-cyclopropyl-3-(3,5-dichloropyridin-4-yl)isoxazol-4-yl) methoxy) bicyclo[2.2.2]octan-1-yl) ethynyl)-1H-indole-6-carboxylic acid (416); 6-((4-((5-cyclopropyl-3-(3,5-dichloropyridin-4-yl)isoxazol-4-yl) methoxy)bicyclo[2.2.2]octan-1-yl) ethynyl)-2-methylnicotinic acid (417); 6-((4-((5-cyclopropyl-3-(3,5-dichloropyridin-4-yl)isoxazol-4-yl)methoxy)bicyclo [2.2.2]octan-1-yl)ethynyl)pyridazine-3-carboxylic acid (419); 2-(4-((5-cyclopropyl-3-(3,5-dichloropyridin-4-yl)isoxazol-4-yl) methoxy)bicyclo[2.2.2]octan-1-yl)-7-(trifluoromethyl)quinoline-5-carboxylic acid (420); (E)-2-(4-(2-(4-((5-cyclopropyl-3-(3,5-dichloropyridin-4-yl)isoxazol-4-yl)methoxy) bicyclo[2.2.2]octan-1-yl)vinyl)phenyl)acetic acid (516); (E)-7-(2-(4-((5-cyclopropyl-3-(3,5-dichloropyridin-4-yl)isoxazol-4-yl)methoxy) bicyclo[2.2.2]octan-1-yl)vinyl)-1-methoxyisoquinoline-3-carboxylic acid (517); (E)-7-(2-(4-((5-cyclopropyl-3-(3,5-dichloropyridin-4-yl) isoxazol-4-yl)methoxy) bicyclo[2.2.2]octan-1-yl)vinyl)-1-isopropoxyisoquinoline-3-carboxylic acid (518); 7-((4-((5-cyclopropyl-3-(3,5-dichloropyridin-4-yl)isoxazol-4-yl)

methoxy) bicyclo[2.2.2]octan-1-yl)ethynyl)-1-(4-methylpiperazin-1-yl)isoquinoline-3-carboxylic acid (519); 3-((4-((5-cyclopropyl-3-(3,5-dichloropyridin-4-yl)isoxazol-4-yl)methoxy) bicyclo[2.2.2]octan-1-yl)ethynyl)-6-fluoroimidazo[1,2-a]pyridine-8-carboxylic acid (520); 7-((4-((5-cyclopropyl-3-(3,5-dichloropyridin-4-yl)isoxazol-4-yl)methoxy)bicyclo[2.2.2]octan-1-yl)ethynyl)-1-methoxyisoquinoline-3-carboxylic acid (521); 6-((4-((5-cyclopropyl-3-(3,5-dichloropyridin-4-yl)isoxazol-4-yl)methoxy) bicyclo[2.2.2]octan-1-yl)ethynyl)-4-methoxy-N,N-dimethylquinoline-2-carboxamide (522); 5-((4-((5-cyclopropyl-3-(3,5-dichloropyridin-4-yl)isoxazol-4-yl)methoxy) bicyclo[2.2.2]octan-1-yl)ethynyl)-6-(3-fluoroazetidin-1-yl)nicotinic acid (523); 5-((4-((5-cyclopropyl-3-(3,5-dichloropyridin-4-yl)isoxazol-4-yl)methoxy) bicyclo[2.2.2] octan-1-yl)ethynyl)pyrazine-2-carboxylic acid (542); 3-((4-((5-cyclopropyl-3-(3,5-dichloropyridin-4-yl)isoxazol-4-yl)methoxy) bicyclo[2.2.2]octan-1-yl)ethynyl)-6-(trifluoromethyl)imidazo[1,2-a]pyridine-8-carboxylic acid (545); 3-((4-((5-cyclopropyl-3-(3,5-dichloropyridin-4-yl)isoxazol-4-yl)methoxy) bicyclo[2.2.2]octan-1-yl)ethynyl)-6-ethylimidazo[1,2-a]pyridine-8-carboxylic acid (546); 7-chloro-1-((4-((5-cyclopropyl-3-(3,5-dichloropyridin-4-yl)isoxazol-4-yl)methoxy) bicyclo[2.2.2]octan-1-yl)ethynyl) isoquinoline-3-carboxylic acid (547); 7-((4-((5-cyclopropyl-3-(3,5-dichloropyridin-4-yl)isoxazol-4-yl)methoxy) bicyclo[2.2.2]octan-1-yl)ethynyl)-1-morpholinoisoquinoline-3-carboxylic acid (548); 6-((4-((5-cyclopropyl-3-(3,5-dichloropyridin-4-yl)isoxazol-4-yl)methoxy) bicyclo[2.2.2]octan-1-yl)ethynyl)-1-(3-methoxypropoxy)isoquinoline-3-carboxylic acid (549); 7-((4-((5-cyclopropyl-3-(3,5-dichloropyridin-4-yl)isoxazol-4-yl)methoxy) bicyclo[2.2.2]octan-1-yl)ethynyl)-1-(phenylamino)isoquinoline-3-carboxylic acid (550); 7-((4-((5-cyclopropyl-3-(3,5-dichloropyridin-4-yl)isoxazol-4-yl)methoxy) bicyclo[2.2.2]octan-1-yl)ethynyl)-1-(cyclopropylamino)isoquinoline-3-carboxylic acid (551); 7-((4-((5-cyclopropyl-3-(3,5-dichloropyridin-4-yl)isoxazol-4-yl)methoxy) bicyclo[2.2.2]octan-1-yl)ethynyl)-1-(3-hydroxyazetidin-1-yl)isoquinoline-3-carboxylic acid (552); 7-((4-((5-cyclopropyl-3-(3,5-dichloropyridin-4-yl)isoxazol-4-yl)methoxy) bicyclo[2.2.2]octan-1-yl)ethynyl)-1-(3-fluoroazetidin-1-yl)isoquinoline-3-carboxylic acid (553); 2-(4-((4-((5-cyclopropyl-3-(3,5-dichloropyridin-4-yl)isoxazol-4-yl)methoxy) bicyclo[2.2.2]octan-1-yl)ethynyl)-3-fluorophenoxy)acetic acid (554); 6-((4-((5-cyclopropyl-3-(3,5-dichloropyridin-4-yl) isoxazol-4-yl)methoxy) bicyclo[2.2.2]octan-1-yl)ethynyl)-1-morpholinoisoquinoline-3-carboxylic acid (555); 7-((4-((5-cyclopropyl-3-(3,5-dichloropyridin-4-yl)isoxazol-4-yl) methoxy)bicyclo[2.2.2]octan-1-yl)ethynyl)-1-(3-hydroxypyrrolidin-1-yl)isoquinoline-3-carboxylic acid (557); 7-((4-((5-cyclopropyl-3-(3,5-dichloropyridin-4-yl)isoxazol-4-yl)methoxy) bicyclo[2.2.2]octan-1-yl)ethynyl)-1-(4-hydroxypiperidin-1-yl)isoquinoline-3-carboxylic acid (558); 1-(azetidin-1-yl)-7-((4-((5-cyclopropyl-3-(3,5-dichloropyridin-4-yl)isoxazol-4-yl) methoxy)bicyclo[2.2.2]octan-1-yl) ethynyl)isoquinoline-3-carboxylic acid (559); 2-((4-((4-((5-cyclopropyl-3-(3,5-dichloropyridin-4-yl)isoxazol-4-yl)methoxy)bicyclo[2.2.2]octan-1-yl)ethynyl)pyridin-2-yl)oxy)acetic acid (561); 6-(azetidin-1-yl)-5-((4-((5-cyclopropyl-3-(3,5-dichloropyridin-4-yl)isoxazol-4-yl)methoxy) bicyclo[2.2.2]octan-1-yl) ethynyl)nicotinic acid (562); 5-((4-((5-cyclopropyl-3-(3,5-dichloropyridin-4-yl)isoxazol-4-yl)methoxy) bicyclo[2.2.2] octan-1-yl)ethynyl)-6-methoxynicotinic acid (563); 3-(4-((4-((5-cyclopropyl-3-(3,5-dichloropyridin-4-yl)isoxazol-4-yl) methoxy)bicyclo[2.2.2]octan-1-yl) ethynyl)phenyl) propanoic acid (564); 2-(4-((4-((5-cyclopropyl-3-(3,5-dichloropyridin-4-yl)isoxazol-4-yl) methoxy) bicyclo[2.2.2]octan-1-yl)ethynyl)-3-(trifluoromethyl)phenyl)acetic acid (565); 2-((4-((4-((5-cyclopropyl-3-(3,5-dichloropyridin-4-yl)isoxazol-4-yl) methoxy)bicyclo[2.2.2]octan-1-yl) ethynyl)benzyl)oxy)acetic acid (566); 2-(4-((4-((5-cyclopropyl-3-(3,5-dichloropyridin-4-yl)isoxazol-4-yl) methoxy)bicyclo[2.2.2]octan-1-yl)ethynyl)-2-fluorophenyl)acetic acid (567); 5-((4-((5-cyclopropyl-3-(3,5-dichloropyridin-4-yl) isoxazol-4-yl)methoxy) bicyclo[2.2.2]octan-1-yl)ethynyl)-6-(4-methylpiperazin-1-yl) nicotinic acid (568); 2-((6-((4-((5-cyclopropyl-3-(3,5-dichloropyridin-4-yl)isoxazol-4-yl) methoxy)bicyclo[2.2.2]octan-1-yl) ethynyl)pyridin-3-yl) methoxy)acetic acid (569); 6-((4-((5-cyclopropyl-3-(3,5-dichloropyridin-4-yl)isoxazol-4-yl)methoxy) bicyclo[2.2.2]octan-1-yl)ethynyl)-1-(4-methylpiperazin-1-yl) isoquinoline-3-carboxylic acid (570); 2-((5-((4-((5-cyclopropyl-3-(3,5-dichloropyridin-4-yl)isoxazol-4-yl) methoxy)bicyclo[2.2.2]octan-1-yl)ethynyl)pyridin-2-yl) methoxy)acetic acid (571); 7-((4-((5-cyclopropyl-3-(3,5-dichloropyridin-4-yl)isoxazol-4-yl)methoxy) bicyclo[2.2.2]octan-1-yl)ethynyl)-1-(3-(dimethylamino)azetidin-1-yl) isoquinoline-3-carboxylic acid (572); 7-((4-((5-cyclopropyl-3-(3,5-dichloropyridin-4-yl)isoxazol-4-yl)methoxy) bicyclo[2.2.2]octan-1-yl)ethynyl)-1-(piperazin-1-yl)isoquinoline-3-carboxylic acid (573); and 7-((4-((5-cyclopropyl-3-(3,5-dichloropyridin-4-yl)isoxazol-4-yl)methoxy) bicyclo[2.2.2]octan-1-yl)ethynyl)-1-(2-(pyrrolidin-1-yl)ethoxy) isoquinoline-3-carboxylic acid (574); (E)-2-(4-(2-(4-((5-cyclopropyl-3-(3,5-dichloropyridin-4-yl)isoxazol-4-yl) methoxy) bicyclo[2.2.2]octan-1-yl)vinyl)phenyl)acetic acid (587); (E)-6-(2-(4-((5-cyclopropyl-3-(3,5-dichloropyridin-4-yl)isoxazol-4-yl) methoxy)bicyclo[2.2.2]octan-1-yl)vinyl) quinoline-2-carboxylic acid (588); (E)-4-(cyclopentyloxy)-6-(2-(4-((5-cyclopropyl-3-(3,5-dichloropyridin-4-yl) isoxazol-4-yl)methoxy)bicyclo[2.2.2]octan-1-yl)vinyl)quinoline-2-carboxylic acid (589); (E)-6-(2-(4-((5-cyclopropyl-3-(3,5-dichloropyridin-4-yl)isoxazol-4-yl)methoxy) bicyclo[2.2.2]octan-1-yl)vinyl)-4-methoxyquinazoline-2-carboxylic acid (590); (E)-6-(2-(4-((5-cyclopropyl-3-(3,5-dichloropyridin-4-yl)isoxazol-4-yl)methoxy) bicyclo[2.2.2]octan-1-yl)vinyl)-4-isopropoxyquinoline-2-carboxylic acid (591); (E)-7-(2-(4-((5-cyclopropyl-3-(3,5-dichloropyridin-4-yl)isoxazol-4-yl)methoxy) bicyclo[2.2.2]octan-1-yl)vinyl)imidazo[1,2-a]pyridine-3-carboxylic acid (592); (E)-6-(2-(4-((5-cyclopropyl-3-(3,5-dichloropyridin-4-yl)isoxazol-4-yl)methoxy) bicyclo[2.2.2]octan-1-yl)vinyl)imidazo[1,2-a]pyridine-3-carboxylic acid (593); (E)-2-(4-(2-(4-((5-cyclopropyl-3-(3,5-dichloropyridin-4-yl)isoxazol-4-yl) methoxy) bicyclo[2.2.2]octan-1-yl)vinyl)-2-fluorophenyl) acetic acid (594); (E)-6-(2-(4-((5-cyclopropyl-3-(3,5-dichloropyridin-4-yl)isoxazol-4-yl) methoxy)bicyclo[2.2.2]octan-1-yl)vinyl)-1-methyl-1H-indole-2-carboxylic acid (595); (E)-2-(5-(2-(4-((5-cyclopropyl-3-(3,5-dichloropyridin-4-yl)isoxazol-4-yl)methoxy) bicyclo[2.2.2]octan-1-yl) vinyl)pyridin-2-yl) acetic acid (596); (E)-4-(2-(4-((5-cyclopropyl-3-(3,5-dichloropyridin-4-yl)isoxazol-4-yl)methoxy) bicyclo[2.2.2]octan-1-yl)vinyl)-1-methyl-1H-indole-2-carboxylic acid (597); (E)-6-(2-(4-((5-cyclopropyl-3-(3,5-dichloropyridin-4-yl)isoxazol-4-yl)methoxy) bicyclo[2.2.2]octan-1-yl)vinyl)-4-ethoxyquinoline-2-carboxylic acid (598); (E)-1-chloro-7-(2-(4-((5-cyclopropyl-3-(3,5-dichloropyridin-4-yl)isoxazol-4-yl)methoxy) bicyclo[2.2.2]octan-1-yl)vinyl)isoquinoline-3-carboxylic acid (599); (E)-2-(3-(2-(4-((5-cyclopropyl-3-(3,5-dichloropyridin-4-yl)isoxazol-4-yl)methoxy) bicyclo[2.2.2]octan-1-yl)vinyl)phenyl)acetic acid (600); (E)-7-(2-(4-((5-cyclopropyl-3-(3,5-dichloropyridin-4-yl)isoxazol-4-yl)methoxy) bicyclo[2.2.2]octan-1-yl)vinyl)-1-(3-methoxypropoxy)isoquinoline-3-carboxylic acid (601); (E)-2-(4-(2-(4-((5-cyclopropyl-3-(3,5-dichloropyridin-4-yl)isoxazol-4-yl)methoxy)bicyclo[2.2.2] octan-1-yl)vinyl)-3-fluorophenyl)acetic acid (602); (E)-7-(2-(4-((5-cyclopropyl-3-(3,5-dichloropyridin-4-yl)isoxazol-4-yl) methoxy)bicyclo[2.2.2]octan-1-yl)vinyl)-1-morpholinoisoquinoline-3-carboxylic acid (603); (E)-7-(2-(4-((5-cyclopropyl-3-(3,5-dichloropyridin-4-yl)isoxazol-4-yl) methoxy)bicyclo[2.2.2]octan-1-yl)vinyl)-1-ethoxyisoquinoline-3-carboxylic acid (604); (E)-3-(5-(2-(4-((5-cyclopropyl-3-(3,5-dichloropyridin-4-yl)isoxazol-4-yl) methoxy)bicyclo[2.2.2]octan-1-yl)vinyl)-2-methoxyphenyl)propanoic acid (605); (E)-3-(4-(2-(4-((5-cyclopropyl-3-(3,5-dichloropyridin-4-yl)isoxazol-4-yl) methoxy)bicyclo[2.2.2]octan-1-yl) vinyl)phenyl)propanoic acid (606); (E)-3-(4-(2-(4-((5-cyclopropyl-3-(3,5-dichloropyridin-4-yl)isoxazol-4-yl) methoxy)bicyclo[2.2.2]octan-1-yl)vinyl)-2-fluorophenyl) propanoic acid (607); (E)-2-(4-(2-(4-((5-cyclopropyl-3-(3,5-dichloropyridin-4-yl)isoxazol-4-yl) methoxy)bicyclo[2.2.2] octan-1-yl)vinyl)-3-fluorophenoxy)acetic acid (608); (E)-7-(2-(4-((5-cyclopropyl-3-(3,5-dichloropyridin-4-yl)isoxazol-4-yl) methoxy)bicyclo[2.2.2]octan-1-yl)vinyl)-1-(3-methoxyazetidin-1-yl)isoquinoline-3-carboxylic acid (609); (E)-7-(2-(4-((5-cyclopropyl-3-(3,5-dichloropyridin-4-yl) isoxazol-4-yl) methoxy)bicyclo[2.2.2]octan-1-yl)vinyl)-1-(3-hydroxyazetidin-1-yl)isoquinoline-3-carboxylic acid (610); (E)-7-(2-(4-((5-cyclopropyl-3-(3,5-dichloropyridin-4-yl)isoxazol-4-yl) methoxy)bicyclo[2.2.2] octan-1-yl)vinyl)-1-(3-fluoroazetidin-1-yl)isoquinoline-3-carboxylic acid (611); (E)-7-(2-(4-((5-cyclopropyl-3-(3,5-dichloropyridin-4-yl)isoxazol-4-yl) methoxy)bicyclo[2.2.2] octan-1-yl)vinyl)-1-(3-(hydroxymethyl)azetidin-1-yl)isoquinoline-3-carboxylic acid (612); (E)-1-cyclobutoxy-7-(2-(4-((5-cyclopropyl-3-(3,5-dichloropyridin-4-yl)isoxazol-4-yl) methoxy)bicyclo[2.2.2]octan-1-yl)vinyl) isoquinoline-3-carboxylic acid (613); (E)-1-cyclopropoxy-7-(2-(4-((5-cyclopropyl-3-(3,5-dichloropyridin-4-yl) isoxazol-4-yl) methoxy)bicyclo[2.2.2]octan-1-yl)vinyl)isoquinoline-3-carboxylic acid (614); (E)-1-(cyclopentyloxy)-7-(2-(4-((5-cyclopropyl-3-(3,5-dichloropyridin-4-yl) isoxazol-4-yl) methoxy)bicyclo[2.2.2]octan-1-yl)vinyl)isoquinoline-3-carboxylic acid (615); (E)-2-((5-(2-(4-((5-cyclopropyl-3-(3,5-dichloropyridin-4-yl)isoxazol-4-yl) methoxy)bicyclo[2.2.2] octan-1-yl) vinyl)pyridin-2-yl)oxy)acetic acid (616); (E)-2-((4-(2-(4-((5-cyclopropyl-3-(3,5-dichloropyridin-4-yl)isoxazol-4-yl) methoxy)bicyclo[2.2.2]octan-1-yl) vinyl)pyridin-2-yl)oxy)acetic acid (617); (E)-2-(4-(2-(4-((5-cyclopropyl-3-(3,5-dichloropyridin-4-yl)isoxazol-4-yl) methoxy)bicyclo[2.2.2]octan-1-yl) vinyl)phenyl)-N-methylacetamide (618); (E)-4-(((4-(4-((2H-tetrazol-5-yl) methyl)styryl)bicyclo[2.2.2]octan-1-yl) oxy)methyl)-5-cyclopropyl-3-(3,5-dichloropyridin-4-yl)isoxazole (619); (E)-2-(4-(2-(4-((5-cyclopropyl-3-(3,5-dichloropyridin-4-yl)isoxazol-4-yl) methoxy)bicyclo[2.2.2]octan-1-yl)vinyl) phenyl)-N,N-dimethylacetamide (620); (E)-2-(4-(2-(4-((5-cyclopropyl-3-(3,5-dichloropyridin-4-yl)isoxazol-4-yl) methoxy)bicyclo[2.2.2]octan-1-yl)vinyl)-3-(trifluoromethyl)phenyl)acetic acid (621); (E)-2-((4-(2-(4-((5-cyclopropyl-3-(3,5-dichloropyridin-4-yl)isoxazol-4-yl) methoxy)bicyclo[2.2.2]octan-1-yl) vinyl)benzyl)oxy)acetic acid (622); (E)-3-(3-(2-(4-((5-cyclopropyl-3-(3,5-dichloropyridin-4-yl)isoxazol-4-yl) methoxy)bicyclo[2.2.2]octan-1-yl) vinyl)phenyl)propanoic acid (623); (E)-3-(5-(2-(4-((5-cyclopropyl-3-(3,5-dichloropyridin-4-yl)isoxazol-4-yl) methoxy)bicyclo[2.2.2]octan-1-yl)vinyl)-2-(2,2-difluoroethoxy)phenyl)propanoic acid (624); (E)-4-(2-(4-((5-cyclopropyl-3-(3,5-dichloropyridin-4-yl)isoxazol-4-yl) methoxy)bicyclo[2.2.2]octan-1-yl) vinyl)benzoic acid (625); (E)-4-(2-(4-((5-cyclopropyl-3-(3,5-dichloropyridin-4-yl)isoxazol-4-yl) methoxy)bicyclo[2.2.2]octan-1-yl) vinyl)picolinic acid (626); (E)-5-(2-(4-((5-cyclopropyl-3-(3,5-dichloropyridin-4-yl)isoxazol-4-yl) methoxy)bicyclo[2.2.2]octan-1-yl) vinyl)nicotinic acid (627); (E)-2-(4-(2-(4-((5-cyclopropyl-3-(3,5-dichloropyridin-4-yl)isoxazol-4-yl) methoxy)bicyclo[2.2.2]octan-1-yl)vinyl) phenyl)thiazole-4-carboxylic acid (628); (E)-7-(2-(4-((5-cyclopropyl-3-(3,5-dichloropyridin-4-yl)isoxazol-4-yl) methoxy)bicyclo[2.2.2] octan-1-yl)vinyl)-1-(4-methylpiperazin-1-yl)isoquinoline-3-carboxylic acid (629); or a stereoisomer, a tautomer, or a pharmaceutically acceptable salt or solvate thereof.

8. A pharmaceutical composition comprising a pharmaceutically acceptable carrier and a compound according to claim 1, or a stereoisomer, a tautomer, or a pharmaceutically acceptable salt or solvate thereof.

9. A method of treating a disease or disorder, comprising administering to a mammalian patent a compound according to claim 1 or a pharmaceutically acceptable salt thereof, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), primary biliary cirrhosis (PBC), or idiopathic fibrosis (IPF).

10. The method according to claim 9, wherein the said disease or disorder is liver fibrosis, renal fibrosis, biliary fibrosis, or pancreatic fibrosis.

11. The method according to claim 9, wherein said disease or disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

12. The compound according to claim 5 or a salt thereof, wherein: Z is isoquinolinyl or quinolinyl, each substituted with $R^{10}$; and
$R^x$ is —C(O)OH.

13. A compound having the structure:

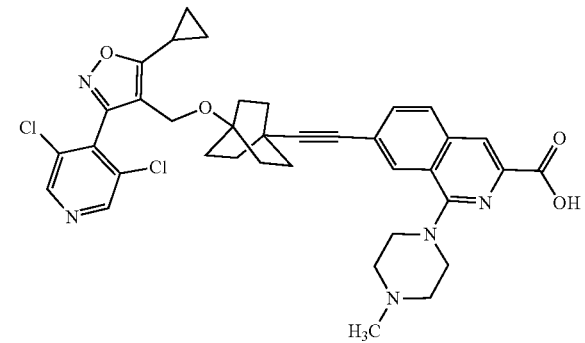 [SMILES: CN1CCN(c2nc(C(=O)O)cc3ccc(C#CC45CCC(OCc6c(-c7c(Cl)cncc7Cl)noc6C6CC6)(CC4)CC5)cc23)CC1]

or a pharmaceutically acceptable salt thereof.

14. The compound according to claim 13.

15. The compound according to claim 13 where said compound is said pharmaceutically acceptable salt.

16. A pharmaceutical composition comprising a pharmaceutically acceptable carrier and a compound according to claim 13 or a pharmaceutically acceptable salt thereof.

17. A method of treating a disease or disorder, comprising administering to a mammalian patent a compound according to claim 13 or a pharmaceutically acceptable salt thereof, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), primary biliary cirrhosis (PBC), or idiopathic fibrosis (IPF).

18. A compound having the structure:

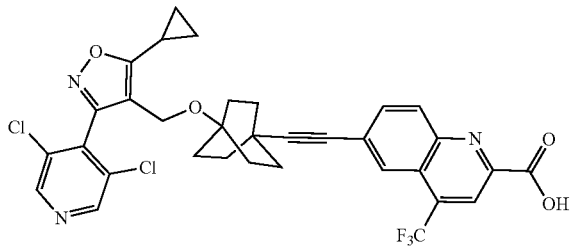 [SMILES: O=C(O)c1cc(C(F)(F)F)c2cc(C#CC34CCC(OCc5c(-c6c(Cl)cncc6Cl)noc5C5CC5)(CC3)CC4)ccc2n1]

or a pharmaceutically acceptable salt thereof.

19. The compound according to claim 18.

20. The compound according to claim 18 where said compound is said pharmaceutically acceptable salt.

21. A pharmaceutical composition comprising a pharmaceutically acceptable carrier and a compound according to claim 18 or a pharmaceutically acceptable salt thereof.

22. A method of treating a disease or disorder, comprising administering to a mammalian patent a compound according to claim 18 or a pharmaceutically acceptable salt thereof, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), primary biliary cirrhosis (PBC), or idiopathic fibrosis (IPF).

23. A compound having the structure:

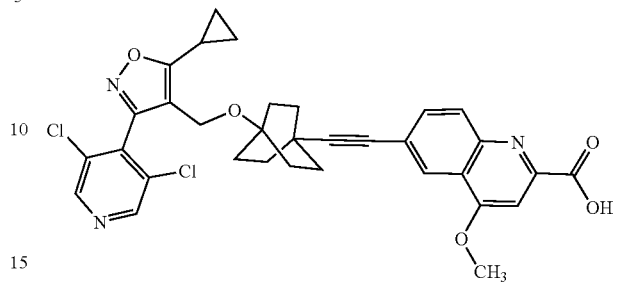

or a pharmaceutically acceptable salt thereof.

24. The compound according to claim 23.

25. The compound according to claim 23 where said compound is said pharmaceutically acceptable salt.

26. A pharmaceutical composition comprising a pharmaceutically acceptable carrier and a compound according to claim 23 or a pharmaceutically acceptable salt thereof.

27. A method of treating a disease or disorder, comprising administering to a mammalian patent a compound according to claim 23 or a pharmaceutically acceptable salt thereof, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), primary biliary cirrhosis (PBC), or idiopathic fibrosis (IPF).

\* \* \* \* \*

UNITED STATES PATENT AND TRADEMARK OFFICE
CERTIFICATE OF CORRECTION

PATENT NO. : 10,730,863 B2  
APPLICATION NO. : 16/175895  
DATED : August 4, 2020  
INVENTOR(S) : David Yoon et al.

Page 1 of 1

It is certified that error appears in the above-identified patent and that said Letters Patent is hereby corrected as shown below:

In the Claims

In Claim 5, Column 637, Line 42-47 (Approx.), delete "  " and insert

-- " " --, therefor.

In Claim 9, Column 644, Line 21 (Approx.), delete "patent" and insert -- patient --, therefor.

In Claim 17, Column 644, Line 66, delete "patent" and insert -- patient --, therefor.

In Claim 22, Column 645, Line 29 (Approx.), delete "patent" and insert -- patient --, therefor.

In Claim 27, Column 646, Line 26 (Approx.), delete "patent" and insert -- patient --, therefor.

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*